(12) United States Patent
Zwarthoff et al.

(10) Patent No.: US 11,220,714 B2
(45) Date of Patent: Jan. 11, 2022

(54) METHOD OF DIAGNOSING BLADDER CANCER

(71) Applicant: ERASMUS UNIVERSITY MEDICAL CENTER ROTTERDAM, Rotterdam (NL)

(72) Inventors: Ellen Catharina Zwarthoff, Rotterdam (NL); Annechiena Geertruide Van Tilborg, Gouda (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 136 days.

(21) Appl. No.: 15/076,544

(22) Filed: Mar. 21, 2016

(65) Prior Publication Data
US 2016/0273053 A1 Sep. 22, 2016

Related U.S. Application Data

(62) Division of application No. 13/265,376, filed as application No. PCT/NL2010/050213 on Apr. 20, 2010, now abandoned.

(60) Provisional application No. 61/170,928, filed on Apr. 20, 2009.

(51) Int. Cl.
*C12Q 1/6886* (2018.01)
(52) U.S. Cl.
CPC ...... *C12Q 1/6886* (2013.01); *C12Q 2600/118* (2013.01); *C12Q 2600/154* (2013.01); *C12Q 2600/16* (2013.01)
(58) Field of Classification Search
CPC ............ C12Q 1/6886; C12Q 2600/154; C12Q 2600/16
See application file for complete search history.

(56) References Cited

U.S. PATENT DOCUMENTS

| | | |
|---|---|---|
| 2002/0198371 A1 | 12/2002 | Wang |
| 2009/0054260 A1 | 2/2009 | Sidransky |
| 2009/0305256 A1* | 12/2009 | Pfeifer .................. C12Q 1/6886 435/6.12 |

FOREIGN PATENT DOCUMENTS

| | | |
|---|---|---|
| WO | WO-02/081749 A2 | 10/2002 |
| WO | WO-2005/082144 | 9/2005 |
| WO | WO-2006/088940 | 8/2006 |
| WO | WO-2008/083098 | 7/2008 |
| WO | WO-2008/140532 | 11/2008 |
| WO | WO-2009/036922 | 3/2009 |

OTHER PUBLICATIONS

Dulaimi (Clinical Cancer Research, 2004, vol. 10, 1887-1893).*
Smith (2007, Epigenetics 2:3, pp. 161-172).*
Tommasi (Breast Cancer Research, 2009, 11: R14, pp. 1-17).*
Friedrich (Europena J. Cancer, 2005, 41, 2769-2778).*
Hogue et al. , J. National Cancer Institute, 2006, vol. 98, pp. 996-1004.*
Aleman et al., "Identification of PMF1 methylation in association with bladder cancer progression," Clin. Cancer Res. (2008) 14(24):8236-8243.
Catto et al., "Promoter hypermethylation is associated with tumor location, stage, and subsequent progression in transitional cell carcinoma," J. Clinical Oncology (2005) 23(13):2903-2910.
Cortese et al., "DNA methylation profiling of pseudogene-parental gene pairs and two gene families," Genomics (2008) 91(6):492-502.
Cottrell, "Molecular diagnostic applications of DNA methylation technology," Clin. Biochem. (2004) 37:595-604.
Febbo, "Epigenetic events highlight the challenge of validating prognostic biomarkers during the clinical and biologic evolution of prostate cancer," J. Clin. Oncol. (2009) 27:3088-2090.
Feinberg, "The history of cancer epigenetics," Nature Reviews (2004) 4:143-153.
Friedrich et al., "Prognostic relevance of methylation markers in patients with non-muscle invasive bladder carcinoma," European J. of Cancer (2005) 41(17):2769-2778.
International Preliminary Report on Patentability and Written Opinion for PCT/NL2010/050213, dated Oct. 25, 2011.
Irizarry, "The human colon cancer methylome shows similar hypo- and hypermethylation at conserved tissue-specific CpG island shores," Nature Genetics (2009) 41(2):178-186.
Jones et al., "The fundamental role of epigenetic events in cancer," Nature Reviews (2002) 3:415-428.
Kim et al., "Epigenetic markers as promising prognosticators for bladder cancer," The Japanese Urological Association (2009) 16(1):17-22.
Kitamura, "Analysis of tissue-specific differentially methylated regions (TDMs) in humans," Genomics (2007) 89(3):326-337.
Lin et al., "Increase sensitivity in detecting superficial, low grade bladder cancer by combination analysis of hypermethylation of E-cadherin, p16, p14, RASSF1A genes in urine," Urologic Oncology: Seminars and Original Investigations (2009) 28(6):597-602.
Salem et al., "Progressive increases in de novo methylation of CpG islands in bladder cancer," Cancer Research (2000) 60(9):2473-2476.
Smiraglia et al., "Excessive CpG island hypermethylation in cancer cell lines versus primary human malignancies," Human Molecular Genetics (2001) 10:1413-1419.
Tada et al., "The association of death-associated protein kinase hypermethylation with early recurrence in superficial bladder cancers," Cancer Research (2002) 62(14):4048-4053.

(Continued)

*Primary Examiner* — Sarae L Bausch
(74) *Attorney, Agent, or Firm* — Morrison & Foerster LLP

(57) ABSTRACT

The present invention relates to a method of diagnosing cancer in a subject comprising detecting in the DNA of said subject at least one hypermethylated CpG island associated with said cancer, wherein an elevation in the level of methylation in said CpG island of said subject, relative to the level of methylation in said CpG island of a control subject, is indicative of said CpG island being hypermethylated.

9 Claims, 9 Drawing Sheets

Figure 2:
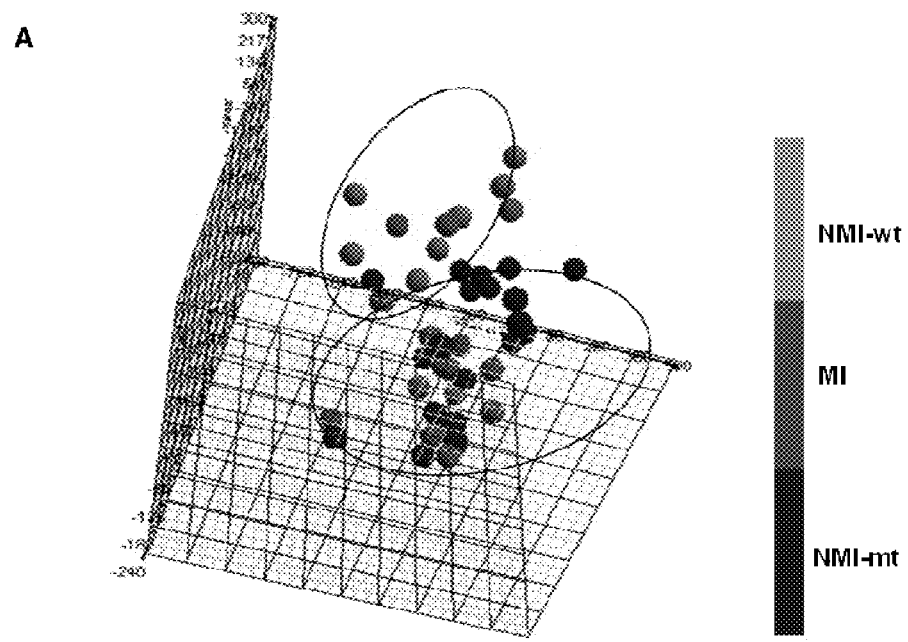
Figure 2:
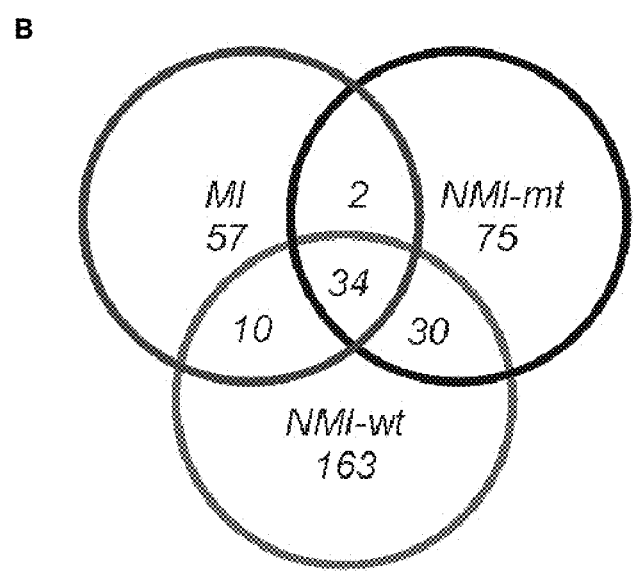

Specification includes a Sequence Listing.

(56) References Cited

OTHER PUBLICATIONS

Verma et al., "Genetic and epigenetic biomarkers in cancer diagnosis and identifying high risk populations," Critical Review in Oncology/Hematology (2006) 60:9-18.

Negraes et al., "DNA methylation patterns in bladder cancer and washing cell sediments: a perspective for tumor recurrence detection," BMC Cancer (2008) 8:238, 12 pages.

Pike et al., "DNA methylation profiles in diffuse large B-cell lymphoma and their relationship to gene expression status," Leukemia (2008) 22:1035-1043.

Rouprêt et al., "A comparison of the performance of microsatellite and methylation urine analysis for predicting the recurrence of urothelial cell carcinoma, and definition of a set of markers by Bayesian network analysis," in: Investigative Urology, Klocker et al. (eds.) The Authors Journal Compilation © BJU International (2008) 101:1448-1453.

Wu et al., "DNA methylation profiling of ovarian carcinomas and their in vitro models identifies HOXA9, HOXB5, SCGB3AI, and CRABPI as novel targets," Molecular Cancer (2007) 6:45, 10 pages.

\* cited by examiner

Figure 1 (ABC)
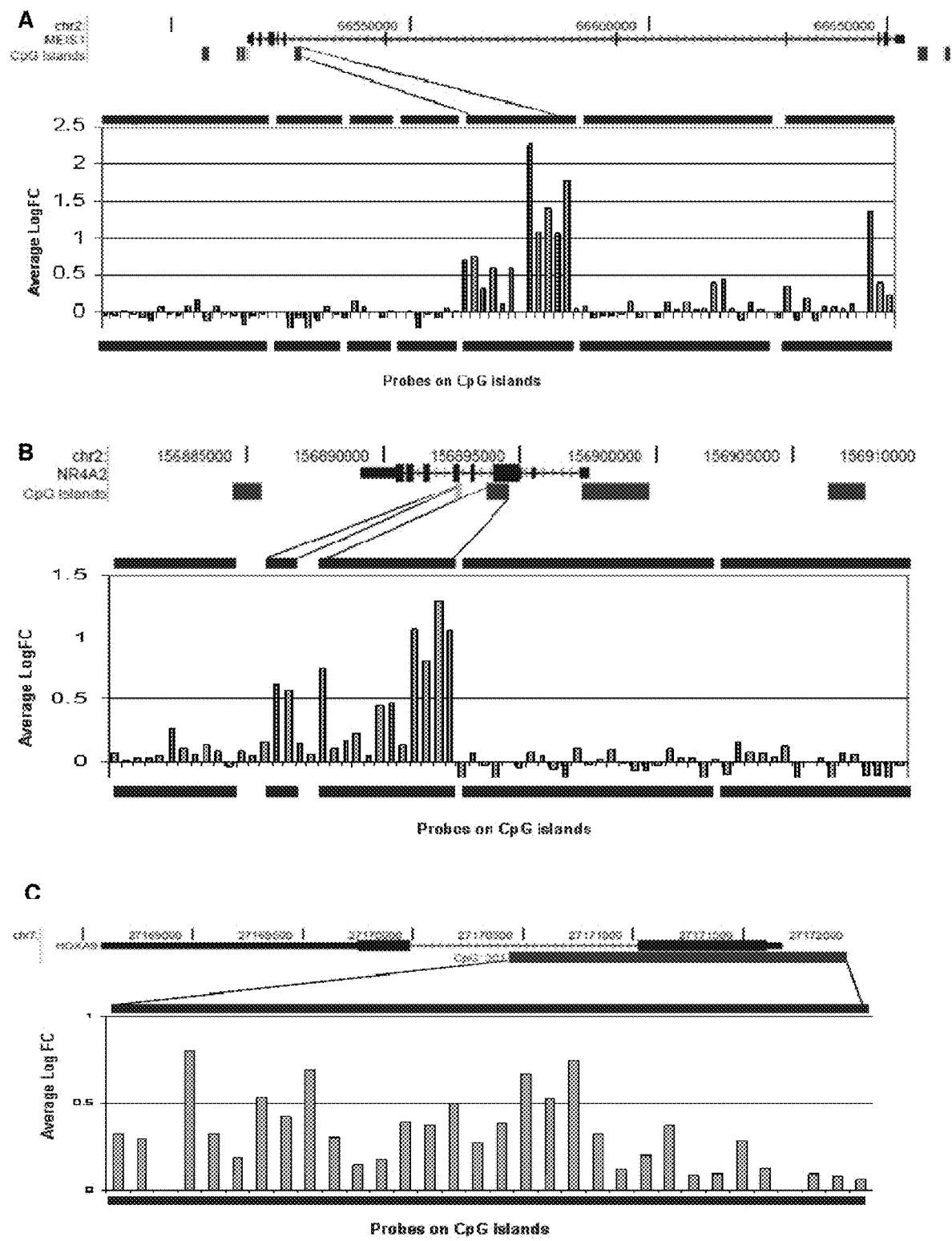

Figure 1(DEF)
D
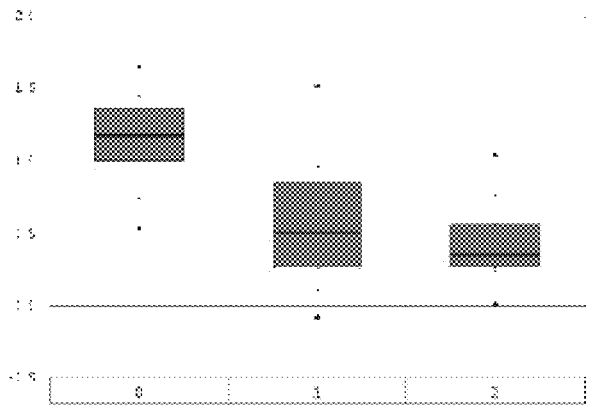
E
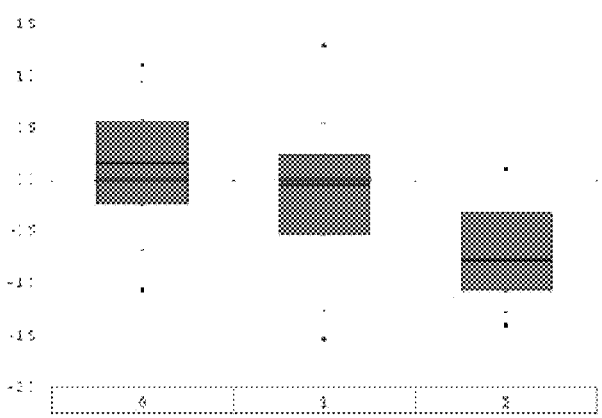
F
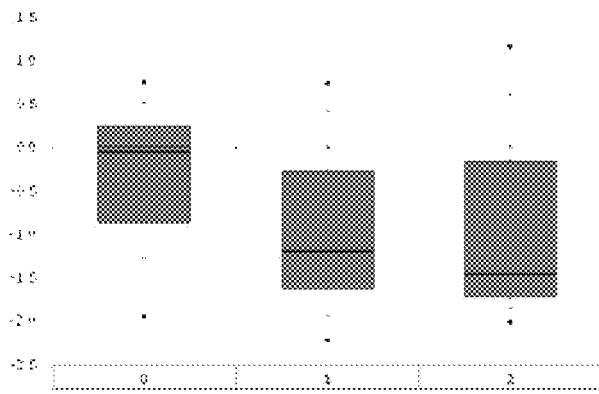
Legend: 0-Normal; 1-MI-BC; 2-NMI-BC

A

B

METHOD OF DIAGNOSING BLADDER CANCER

CROSS-REFERENCE TO RELATED APPLICATION

This application is a divisional of U.S. Ser. No. 13/265,376 having an international filing date of 20 Apr. 2010 (abandoned), which is the national phase of PCT application PCT/NL2010/050213 having an international filing date of 20 Apr. 2010, which claims benefit under 35 U.S.C. § 119(e) of provisional application U.S. Ser. No. 61/170,928 filed 20 Apr. 2009. The contents of these documents are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 313632019510_SeqList.txt, date recorded: Jun. 6, 2016, size: 539,273 bytes).

FIELD OF THE INVENTION

The present invention is in the field of bladder cancer diagnosis, and in particular the methods for predicting the progression of bladder cancer tumors. The invention provides diagnostic methods and diagnostic compositions for use in such methods. The invention further provides therapeutic targets for treating specific forms of bladder cancers.

BACKGROUND OF THE INVENTION

Bladder cancer is the fifth most common cancer in the western world with an incidence of 20 new cases per year per 100,000 people in the U.S. Unfortunately, these statistics do not include superficial pTa bladder cancer, which represents the most common type of bladder cancer. In the Netherlands, the incidence of both superficial and invasive bladder cancer is estimated as about 30 new cases per year per 100,000 people. This is in accordance with data from global cancer statistics for the western world. Superficial bladder tumors are removed by transurethral resection. However, up to 70% of these patients will develop one or more recurrences, and it has been estimated that 1 in 1,450 people is under surveillance for bladder cancer in the United Kingdom. Cystoscopy is an uncomfortable, invasive, and expensive procedure, but currently remains the gold standard for detection of recurrences. Because patients have to be monitored perpetually and have a long-term survival, bladder cancer is the most expensive cancer when calculated on a per patient basis.

Hence there exists a need for an inexpensive, noninvasive, and simple procedure for the detection of bladder cancer. Cytology done on voided urine is a noninvasive procedure with up to 100% specificity. Unfortunately, this method is limited by its sensitivity, which is especially poor for low-grade tumors. Because of this limited sensitivity, alternative methods need to be developed for the detection of tumor cells in voided urine.

SUMMARY OF THE INVENTION

The present inventors have found that the methylation of a number of specific CpG islands (CGIs) in the DNA of cells shaded in the urine of a subject is indicative of the present of a tumor, in particular a bladder tumor. Thus, aberrant methylation of these CpG islands in the DNA of a subject may be used as diagnostic and/or prognostic marker as well as a therapeutic target.

The present finding has been found to be particularly advantageous in the case of bladder cancer diagnostics (including disease prognosis and prediction of disease recurrence and progression), since the detection of methylation may occur in DNA (of cells) in a sample of urine obtained from the subject to be diagnosed. In particular urothelial cells present in said urine sample are used for this purpose. The skilled person will understand that diagnostic methods as indicated herein may make use of any body sample in which DNA comprising the aberrant methylations as defined herein can be detected, including biopsies of cancerous tissue, or tissue suspected of being malignant.

The present inventors have demonstrated the suitability of using methylation of specified CpG islands as diagnostic markers in bladder cancer diagnostics, such as for:
   detection of recurrent cancer in DNA isolated from patient urine, and
   detection of primary cancer in DNA isolated from patient urine.

Thus, in a first aspect, the present invention provides a method for diagnosing cancer in a subject comprising detecting in the DNA of said subject at least one hypermethylated CpG island associated with said cancer, wherein an elevation in the level of methylation in said CpG island of said subject, relative to the level of methylation in said CpG island of a control subject, is indicative of said CpG island being hypermethylated. The presence of a hypermethylated CpG island might indicate that the subject is at risk of, or suffering from, a cancer.

Preferably said CpG island is selected from the group consisting of the CpG islands listed in Table 1, Table 2, Table 3, Table 4, Table 5, Table 7, Table 9, Table 10 and Table 12.

In a preferred embodiment of methods of the invention, said cancer is bladder cancer.

In another preferred embodiment of methods of the invention, said method comprises detection of recurrent forms of cancer in DNA isolated from patient urine and wherein said at least one CpG islands methylation associated with cancer selected from the group consisting of the CpG islands listed in Table 1, Table 2, Table 3, Table 4, Table 5, Table 7, Table 9, Table 10 and Table 12.

In yet another preferred embodiment of methods of the invention, said method comprises detection of primary forms of cancer in DNA isolated from patient urine and wherein said at least one CpG islands methylation associated with cancer selected from the group consisting of the CpG islands listed in Table 1, Table 2, Table 3, Table 4, Table 5, Table 7, Table 9, Table 10 and Table 12.

In still a further preferred embodiment of methods of the invention, said DNA is obtained from a urine sample of said subject.

In another preferred embodiment of methods of the invention, said bladder cancer is non muscle-invasive bladder cancer. Alternatively, said bladder cancer is muscle-invasive bladder cancer. In a further preferred embodiment, said method provides detection of differential methylation of one or more of the genes provided in Table 7. Differential methylation of one or more of the genes provided in Table 7 is used to discriminate between subgroups of bladder cancer, such as between NMI-wt and MI and NMI-mt groups.

In a preferred embodiment of methods of the invention, general inflammatory cells in urine, preferably lymphocytes, are detected by methylation of at least one of the CGIs listed in Table 9. Table 9 indicates a number of CGIs methylated in blood but not in bladder cancer. The differential methylation of these CGIs, which can be detected in DNA (of cells) in a sample of urine obtained from the subject to be diagnosed, and in particular in urothelial cells present in said urine sample, are useful for the detection of lymphocytes in urine, or in general inflammatory cells in urine, which is indicative of cystitis. Positive detection of the presence of inflammatory cells in the urine can be used to diagnose infection or non-infective inflammation of the urinary tract and kidney.

In a preferred embodiment, said method comprises detection of recurrent cancer in DNA isolated from patient urine. This method entails the detection of specific CpG island methylations associated with recurrent forms of the cancer.

In another preferred embodiment, said method comprises detection of primary cancer in DNA isolated from patient urine. This method entails the detection of specific CpG island methylations associated with primary forms of the cancer.

The present inventors have further demonstrated the suitability of using methylation of specified CpG islands as prognostic markers in bladder cancer diagnostics, such as for:
prediction of disease course based on analysis of tumor-derived or urine derived DNA, including:
prediction of invasive potential of non-muscle invasive urothelial carcinomas;
prediction of urothelial carcinoma-specific survival, and
prediction of presence/absence of lymph node and distant metastases caused by urothelial carcinomas Thus, in a second aspect, the present invention provides a method for the prediction of the recurrence, progression or prognosis of cancer, in particular bladder cancer, comprising detecting in the DNA of said subject at least one hypermethylated CpG island associated with said cancer, wherein an elevation in the level of methylation in said CpG island of said subject, relative to the level of methylation in said CpG island of a control subject, is indicative of said CpG island being hypermethylated. The presence of a hypermethylated CpG island might indicate that the subject is at risk of cancer recurrence, progression of a cancer, and/or poor prognosis. A preferred method for the prognosis of a risk of cancer recurrence, progression of a cancer, and/or poor prognosis comprises detection of one or more methylated CpGs in CGIs of the genes listed in Table 12B, whereby the CGIs are preferably chosen from GPR103, DBC1 and/or GATA2 genes. Said cancer is preferably bladder cancer.

In a preferred embodiment of said method for the prediction of the recurrence, progression or prognosis of cancer, said CpG island is selected from the group consisting of the CpG islands listed in Table 1, Table 2, Table 3, Table 4, Table 5, Table 7, Table 9, Table 10 and Table 12, preferably from Table 5 and Table 10.

In aspects of the present invention the methylation of dinucleotide in or methylation level of a CpG island may be determined by any method available to the skilled person. Preferably said method comprises methylation-specific PCR (MSP). Alternatively, or additionally, use may be made of a multiplex ligation-dependent probe amplification (MLPA).

The present inventors have further demonstrated the suitability of using methylation of specified CpG islands as markers in bladder cancer diagnostics for prediction of therapeutic response, such as for prediction of failure or success of (neo)-adjuvant therapies.

The present inventors now envision as part of their invention the use of demethylating agents capable of specifically demethylating the CpG islands associated with tumor, in particular bladder cancer, as defined herein. They may also be of use as priming therapy for chemotherapeutic regimes.

Hence, the present invention provides a method for the treatment or prevention of cancer, in particular bladder cancer, comprising administering to a subject in need of such treatment a therapeutically effective amount of a demethylating agent capable of selectively demethylating at least one of the CpG islands methylations associated with cancer as described herein.

Clinical outcome of demethylating agents may depend on specific methylation profiles.

The present invention further provides pharmaceutical compositions comprising demethylating agents capable of selectively demethylating at least one of the CpG islands methylations associated with cancer as described herein.

The present invention further provides diagnostic compositions comprising PCR primirs and reagent or probes capable of selectively hybridising under stringent conditions to hypermethylated CpG islands as defined herein.

DETAILED DESCRIPTION OF THE INVENTION

As used herein the term "CpG island" refers to genomic regions that contain a high frequency of CG nucleotides. In mammalian genomes, CpG islands are typically 300-3,000 base pairs in length. They are in and near approximately 40% of promoters of mammalian genes (about 70% in human promoters). The "p" in CpG notation refers to the phosphodiester bond between the cytosine and the guanine. CpG islands are characterized by CpG dinucleotide content of at least 60% of that which would be statistically expected (~4-6%), whereas the rest of the genome has much lower CpG frequency (~1%), a phenomenon called CG suppression. Unlike CpG sites in the coding region of a gene, in most instances, the CpG sites in the CpG islands of promoters are unmethylated if genes are expressed.

As used herein the term "CpG island methylation" refers to a methylation of at least one CG dinucleotide in a CpG region as defined herein. Hence, the methods of the present invention include the detection of at least a single CG dinucleotide being methylated in a CpG island as defined herein.

As used herein the term "hypermethylated CpG islands" refers to a CpG island exhibiting an elevation in the level of methylation, relative to the level of methylation in the same CpG island of a control subject. Again, the level of methylation includes the presence of a single methylated CG dinucleotide in the CpG island as compared to the control situation, in which the same CpG island is unmethylated. Also, methods of the invention include embodiments wherein the methylation of a single CG dinucleotide in a CpG island as defined herein is detected among other methylated sites.

As used herein, "cancer" shall be taken to mean any one or more of a wide range of benign or malignant tumors, including those that are capable of invasive growth and metastasis through a human or animal body or a part thereof, such as, for example, via the lymphatic system and/or the blood stream. As used herein, the term "tumor" includes both benign and malignant tumors or solid growths, notwithstanding that the present invention is particularly directed to the diagnosis or detection of malignant tumors and solid cancers. Typical cancers include but are not limited to carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukemia, Hodgkin's disease, small cell carcinoma of the lung, melanoma, neuroblastoma, glioma, and soft tissue sarcoma of humans; and lymphoma, melanoma, sarcoma, and adenocarcinoma of animals.

The term "bladder cancer" as used herein refers in general to urothelial cell carcinoma, i.e. carcinomas of the urinary bladder, ureter, renal pelvis and urethra. The term includes reference to the non muscle-invasive (NMI) or superficial forms, as well as to the more dangerous muscle invasive (MI) types. Also included in the term is reference to the primary forms as well as to recurrent forms of the cancer.

The NMI types may further be subdivided into $FGFR3^+$ and $FGFR3^-$. Mutations in the fibroblast growth factor receptor 3 (FGFR3, indicated herein as $FGFR3^+$) occur in 50% of primary bladder tumors. It is known (e.g. Van Oers et al. 2005 Clin. Cancer Res; 11(21), pp. 7743-7748) that an FGFR3 mutation is associated with good prognosis, illustrated by a significantly lower percentage of patients with progression and disease-specific mortality. FGFR3 mutations are especially prevalent in low grade/stage tumors, with pTa tumors harboring mutations in 85% of the cases. These tumors recur in 70% of patients. Efficient FGFR3 mutation detection for prognostic purposes and for detection of recurrences in urine is an important clinical issue. Thus, in preferred embodiments of the present invention the method of diagnosis includes further the step of detecting an FGRF3 gene mutation. This additional step may be performed prior to, during or after the step of detecting the hypermethylated CpG island as indicated herein. The detection of the FGFR3 gene mutation as indicated in Van Oers et al (this reference is expressly referred to and incorporated herein by reference in its entirety for the methods and mutations to be detected as described therein) indicates the cancer is very likely of the non invasive type.

"Subject" as used herein includes, but is not limited to, mammals, including, e.g., a human, a non-human primate, a mouse, a pig, a cow, a goat, a cat, a rabbit, a rat, a guinea pig, a hamster, a degu, a horse, a monkey, a sheep, or other non-human mammal; and non-mammal animals, including, e.g., a non-mammalian vertebrate, such as a bird (e.g., a chicken or duck) or a fish, and an invertebrate.

A method of the invention can be performed on any suitable body fluid, such as for instance on abdominal fluid, pleural fluid, bronchial fluid, pericardial fluid, blood, serum, milk, plasma, sweat, tears, urine, peritoneal fluid, lymph, vaginal secretion, semen, spinal fluid, cerebrospinal fluid, ascitic fluid, saliva, stool, sputum, mucus or breast exudate. Preferably, a method of the invention is performed on blood, serum, plasma or ascitic fluid, more preferably serum. Depending on the methods employed, the skilled person will be capable of establishing the amount of sample required to perform the various steps of the method of the present invention. Generally, such amounts will comprise a volume ranging from 0.01 µl to 100 ml or more. Preferred samples are urine samples.

In even more preferred embodiments of aspects of the invention the cell fraction of urine, preferably tumor cell fraction, is used. Urine cell fractions may be obtained by filtration or centrifugation. The cellular DNA may subsequently be analyzed, for instance upon extraction of the DNA from the cells, although in situ methods performed on whole cells are also envisioned.

The skilled physician or biologist will be familiar with the various ways of providing a sample of a body fluid from a subject, in particular an urine sample. Urine collection and preparation of the sample for CpG island methylation analysis suitably comprises for instance the collection of a urine sample were collected into a 50 ml centrifuge tube. The sample may optionally be used for additional tests, such as dip stick tests for leucocytes, erythrocytes and nitrite as routinely performed in the art. The cells in the urine are suitably spun down for 10 min @ 3000 rpm; 4° C. An amount of supernatant is suitably stored at −80° C. for later use. The cell pellet may then be washed, for instance by adding a suitable amount of PBS (phosphate-buffered saline), such as 10 ml, to the cell pellet. After mixing and centrifugation (e.g. 10 min @ 3000 rpm; 4° C.), the PBS may be discarded. The cell pellet may then be resuspended in PBS (e.g. 1 ml) and transferred to a microcentrifuge tube. The suspension is then suitably centrifuged (e.g. 5 min @ 6000 rpm; 4° C.). The supernatant can then be carefully removed and the cell pellet may be stored in a −80° C. freezer until DNA extraction.

Commercial systems for DNA isolation from blood, urine and tissue are available form various suppliers of molecular biological reagents. Special reference is made to the DNeasy® Blood & Tissue Kit and DNeasy® 96 Blood & Tissue Kit available from QIAGEN GmbH, Hilden, Germany.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the polynucleotide or polypeptide compositions in the individual to which it is administered.

The present invention also pertains to pharmaceutical compositions comprising demethylating agents as defined herein.

A pharmaceutical composition can also contain a pharmaceutically acceptable carrier. The term "pharmaceutically acceptable carrier" refers to a carrier for administration of a therapeutic agent, such as a polypeptide, polynucleotide, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Once formulated, the pharmaceutical compositions of the invention can be (1) administered directly to the subject; (2) delivered ex vivo, to cells derived from the subject; or (3) delivered in vitro for expression of recombinant proteins.

Direct delivery of the compositions will generally be accomplished by injection, either subcutaneously, intraperitoneally, intravenously or intramuscularly, or delivered to the interstitial space of a tissue. The compositions can also be administered into the nervous system. Other modes of administration include topical, oral, suppositories, and transdermal applications, needles, and particle guns or hypossprays. Dosage treatment may be a single dose schedule or a multiple dose schedule.

Specific aspects of the present invention relate to the CpG islands indicative of certain forms of cancer emerging for instance from the following comparisons:

A) CpG islands hypermethylated in non muscle-invasive (NMI) bladder cancer (BC) that are FGFR3 wild type, herein referred to as NMI-BC wt, vs. muscle-invasive (MI) bladder cancer herein referred to as MI-BC (n=31)

B) CpG islands hypermethylated in MI-BC vs. NMI-BC wt (n=11)

C) CpG islands hypermethylated in all bladder cancers (n=62)

D) CpG islands hypermethylated in NMI-BC-FGFR3 wild type vs. NMI-BC-FGFR3 mutant (n=31), and E) Hypermethylated CpG islands predicting progression of disease or death of disease (resp. n=3 and n=11)).

The methods of the invention comprise the detection of hypermethylated CpG islands in the DNA of a subject. As indicated, hypermethylation is a relative term indicating that the methylation level of the respective CpG island is higher than or elevated with respect to the methylation level of the corresponding CpG island in a healthy control subject.

The methods of the invention comprise the detection of at least one hypermethylated CpG island in the DNA of a subject. Since there are many CpG island indicated herein whose hypermethylation is indicative of cancer, in particular bladder cancer, the method preferably entails the detection of at least 2, 3, 4, 5, 6, 7, 8, 9, 10, 11, 12, 13, 14, 15, 16, 17, 18, 19, 20, 21, 23, 24, 25, 26, 27, 28, 29, 30, or more, such as 35, 40, 45, 50, 55, 60, 65 or more hypermethylations in the DNA of a subject. In such instances, it is possible to speak of a CpG island methylation profile. In such a profile, the percentage of positively detected CpG islands is preferably at least 50%, more preferably at least 70%, more preferably at least 90%.

The CpG island methylation profiles may comprise of between 2-25 CpG islands for diagnostic purpose, such as determining whether a bladder cancer is present, and/or whether it is an NMI or MI type.

The CpG island methylation profiles preferably comprise of between 2-25, more preferably more, such as between 50 and 150, for instance about 100 CpG islands for diagnostic purpose, such as determining the prognosis of an NMI to develop into a more aggressive MI type of tumor. Thus, the present invention provides for a prognostic method for determining whether an NMI type bladder cancer can develop into an MI type.

It is also possible to use a method of the present invention to distinguish between a primary or recurrent form of the tumor.

The skilled person is well aware of the various methods that have been developed to analyze DNA methylation. Amongst these methods are restriction enzyme- and sodium bisulfite based approaches, as well as multiplex ligation-dependent probe amplification (MLPA) approaches.

Restriction-enzyme based methods are based on the inability of methylation sensitive restriction enzymes to cleave methylated cytosines in their recognition site. The identification of the methylation status relies on Southern hybridization techniques or PCR and is based on the length of the digested DNA fragment. The inability to digest methylated sequences results in longer fragments, indicating a methylated CpG dinucleotide. Restriction-enzyme based methods are simple, rapid and highly sensitive and are suitable for genome-wide methylation analyses as well as marker discovery techniques.

Preferred methods for application in aspects of the present invention is sodium bisulfite ($NaHSO_3$) based detection of DNA methylation. Such methods are essentially based on the fact that treatment of single-stranded DNA with sodium bisulfite results in sequence differences due to deamination of unmethylated cytosines to uracil under conditions whereby methylated cytosines remain unchanged. The difference in methylation status marked by bisulfite reactivity can accurately be determined and quantified by PCR-based technology. Bisulfite sequencing techniques (such as described in Frommer et al. Proc. Natl. Acad. Sci. USA 89 (1992), 1827-1831) provide qualitative data on the methylation status of 5-methylcytosines in the amplicon between the sequence primers and thus requires primers specific for bisulfite converted, but not specific for unmethylated or methylated DNA. This approach provides detailed information on the methylation status of all CpG-sites.

A methylation-specific PCR (MSP) assay for determining the methylation status of CpG islands may be used. Such methods are for instance described in Herman et al. 1996 (Proc. Natl. Acad. Sci. USA 93 (1996), 9821-9826) and Herman and Baylin (Current Protocols in Human Genetics 10 (1998), 10.16.11-10.16.10). The MSP assay is based on the use of two distinct methylation-specific primer sets for the sequence of interest. The unmethylated (U) primer only amplifies sodium bisulfite converted DNA in unmethylated condition, while the methylated (M) primer is specific for sodium bisulfite converted methylated DNA. Using MSP, 1 methylated allele may be detected in a background of 1000 unmethylated alleles. MSP is very suitable for analyzing the methylation status of CpG dinucleotides in a CpG-island. The method may also be applied for high-throughput analysis of clinical samples. The most critical parameters determining the success and specificity of MSP, i.e. bisulfite conversion, primer design and PCR as well as several post PCR validation approaches are discussed in Derks et al. 2004 (Cellular Oncology 26 (2004) 291-299). Methylation Specific PCR (MSP) is described in great detail in U.S. Pat. Nos. 5,786,146, 6,017,704, 6,200,756 and 6,265,171 and International Patent WO 97/46705.

Commercial systems for DNA methylation analysis using MSP are available form various suppliers of molecular biological reagents. Special reference is made to the EZ DNA Methylation-Startup™ Kit and EZ DNA Methylation-Direct™ Kit available from Zymo Research Corp. Orange, Calif., U.S.A.

Use can also be made, alone, or in combination with any of the above, of the MLPA technique. The MLPA technique is for instance described in great detail in Schouten et al., 2002 (Nucleic Acids Research 3(12) e57, 13 pp.).

Also, use can be made of a microarray chip to which DNA of a subject is hybridized. Such arrays for CpG islands are for instance commercially available from Agilent Technologies Inc., Santa Clara, USA.

Herein below are provided the following Tables:

Table 1. Coordinates of selected regions containing relevant CpG islands based on *Homo sapiens* full genome as provided by UCSC (hg18, March 2006). These CpG islands are aspect of the present invention as hypermethylation of these regions is associated with cancer, preferably bladder cancer and/or certain forms of said cancer.

Table 2. CpG islands differentially methylated in NMI-BC wt vs. invasive BC. These 42 CpG islands are aspect of the present invention as hypermethylation of these regions is associated with either NMI or more aggressive MI forms of the cancer. Hence, these regions are particularly indicated for use in diagnostic methods wherein typing of the cancer is relevant. The table provides data on CpG islands hypermethylated in non muscle-invasive (NMI) bladder cancer (BC) that are FGFR3 wild type, herein referred to as NMI-BC wt, vs. muscle-invasive (MI) bladder cancer herein referred to as MI-BC (n=31) as well as CpG islands hypermethylated in MI-BC vs. NMI-BC wt (n=11).

Table 3. CpG islands hypermethylated in (bladder) cancer. These 62 CpG islands are aspect of the present invention as hypermethylation of these CpG islands is associated with (bladder) cancer.

Table 4. CpG islands hypermethylated in NMI-BC FGFR3 wt vs NMI-BC FGFR3 mut. These 31 CpG islands are aspect of the present invention diagnostic markers for typing of (bladder) cancers and in particular indicate the relevance of FGFR3 mutations in bladder cancer. These 31 CpG islands may be used for diagnosis of FGFR3 wt primary and recurrent tumors in for instance urine. These 31 CpG islands may also be used for detection of FGFR3 wt tumors in patients with a FGFR3 mt (mutant) primary tumor. Alternatively, these 31 CpG islands may be used for the identification of recurrences that progressed to muscle-invasive disease or to stage pT1 or to high grade (WHO 2004 grading system) or G3(WHO grading system 1973). These 31 CpG islands may also be used to present specific targets for therapy in NMI-BC tumors that are FGFR3 wt.

Table 5. CpG islands potentially involved in progression and death of disease. These 14 CpG islands are aspect of the present invention as hypermethylation of these regions is associated with prediction of the recurrence, progression or prognosis of cancer of cancer, in particular bladder cancer.

Table 7 (including Tables 7A and 7B) indicates differentially labeled CGIs between subgroups of bladder cancer and/or between subgroups of bladder cancer and a reference sample (i.e. blood).

Table 9 indicates a number of CGIs methylated in blood but not in bladder cancer. The differential methylation of these CGIs, which can be detected in DNA (of cells) in a sample of urine obtained from the subject to be diagnosed, and in particular in urothelial cells present in said urine sample, are—apart from the purpose indicated herein for diagnosing bladder cancer—also useful for the detection of lymphocytes in urine, or in general inflammatory cells in urine, which is indicative of cystitis. Positive detection of the presence of inflammatory cells in the urine can be used to diagnose infection or non-infective inflammation of the urinary tract and kidney.

Table 10 provides a list of hypermethylated CGIs that show 3 or more CpG dinucleotides highly methylated in a specific CGI. This list comprises 82 CGIs representing 71 genes and 11 CGIs not directly associated with a gene. A preferred gene from Table 10 is MEIS1, showing the highest degree of methylation with a fold change of 4.8 and an average fold change of 2.2 across the 10 probes that were present on the array for this CGI.

Table 12 (including Tables 12A and 12B) provides a list of CGIs that are differentially methylated between tumors and urine from non-bladder cancer control. These genes represent potential biomarkers for urine tests.

LEGEND TO THE FIGURES

FIG. 1. Methylation pattern and expression of selected genes. (a) MEIS1, (b) NR4A2 and (c) HOXA9. (d), (e), (f) are Box plots representing the expression profiles which were taken from oncomine FIG. 2. Comparison of differential methylation between subgroups. (a) Unsupervised analysis performed on all probes present on the 244K array without selection: PCA showing the distinct bladder tumor groups cluster separately (Red-MI, Blue-NMI-mt and Green NMI-wt), (b) Venn diagram showing the number of CGIs that are differentially methylated FIG. 3. Semi-supervised analyses between bladder tumor subgroups involving hierarchical clustering and PCA. (a) Clustering and PCA of NMI-mt and NMI-wt tumors, (b) Clustering and PCA of MI and NMI-wt tumors, (c) Clustering and PCA of NMI-mt and MI tumors.

Figure 4:
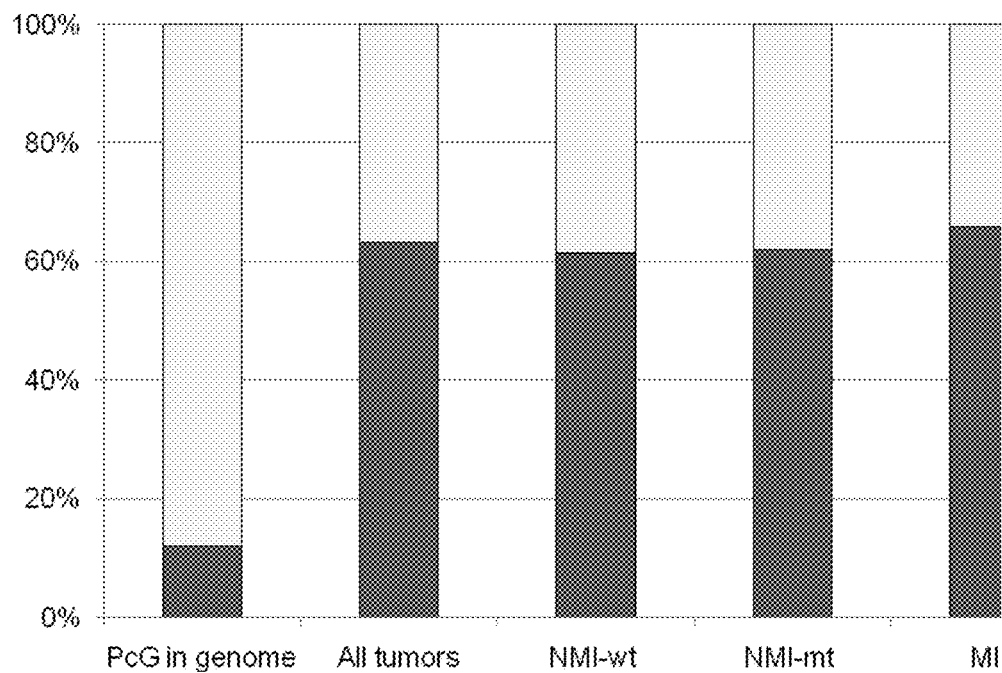
Figure 4:
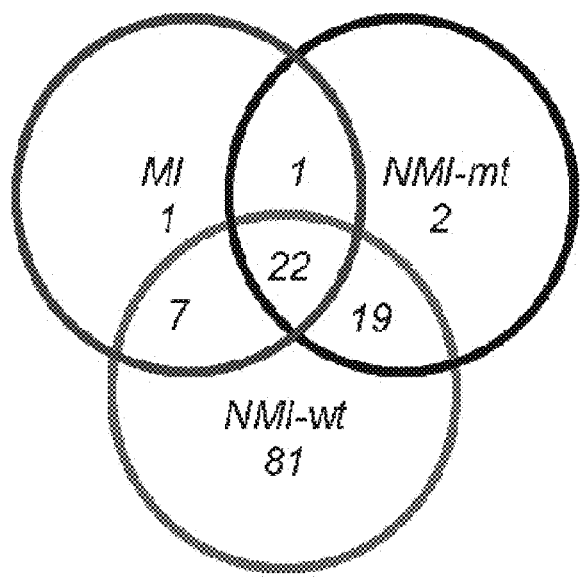

FIG. 4. Most methylated gene-associated CGIs are targets of polycomb complexes. (a) Overrepresentation of PcG genes in BC methylated CGIs. (b), Venn diagram showing the overlap in PcG target genes between bladder cancer subgroups.

Figure 5:
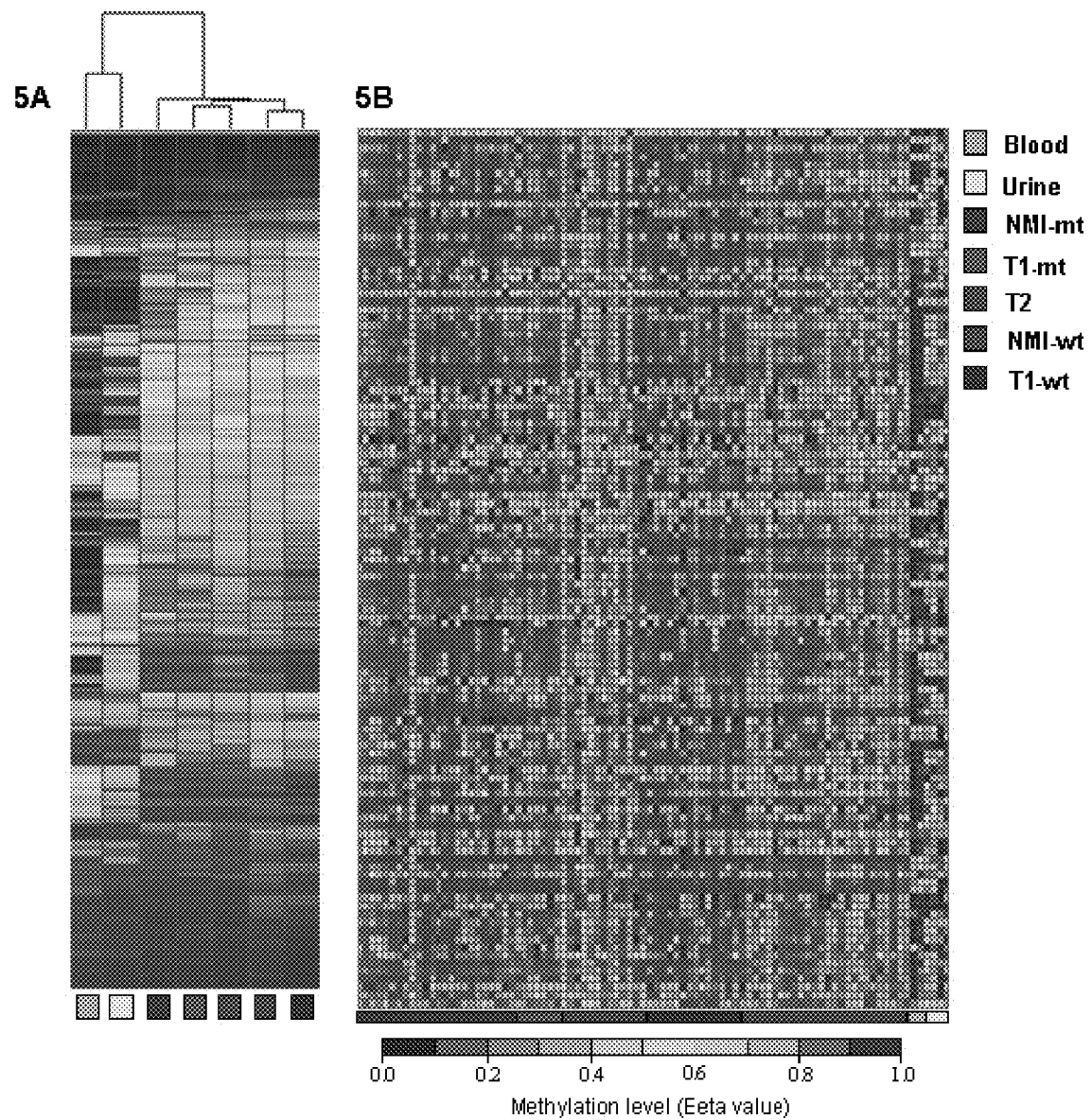
Figure 5:
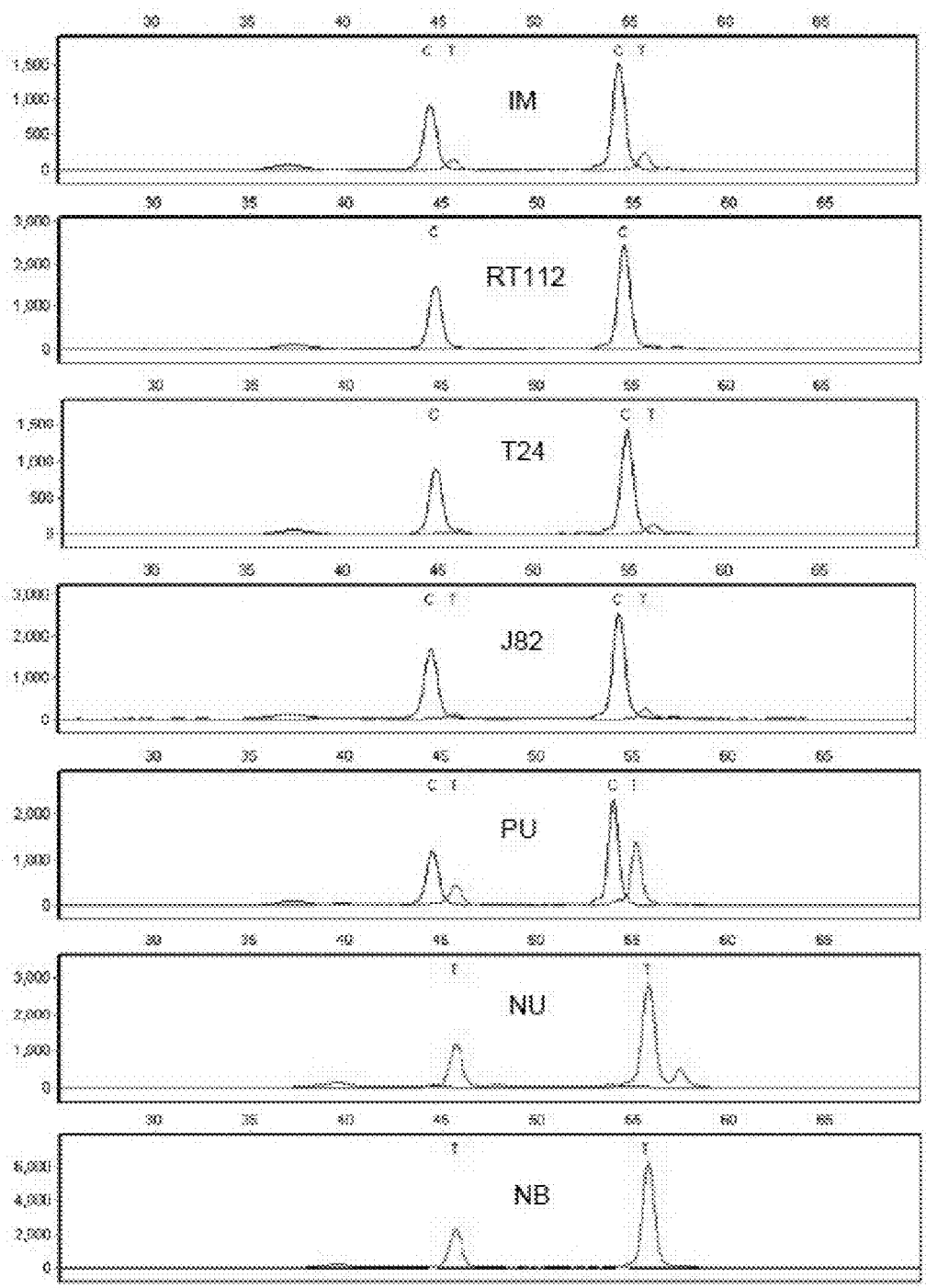
Figure 5:
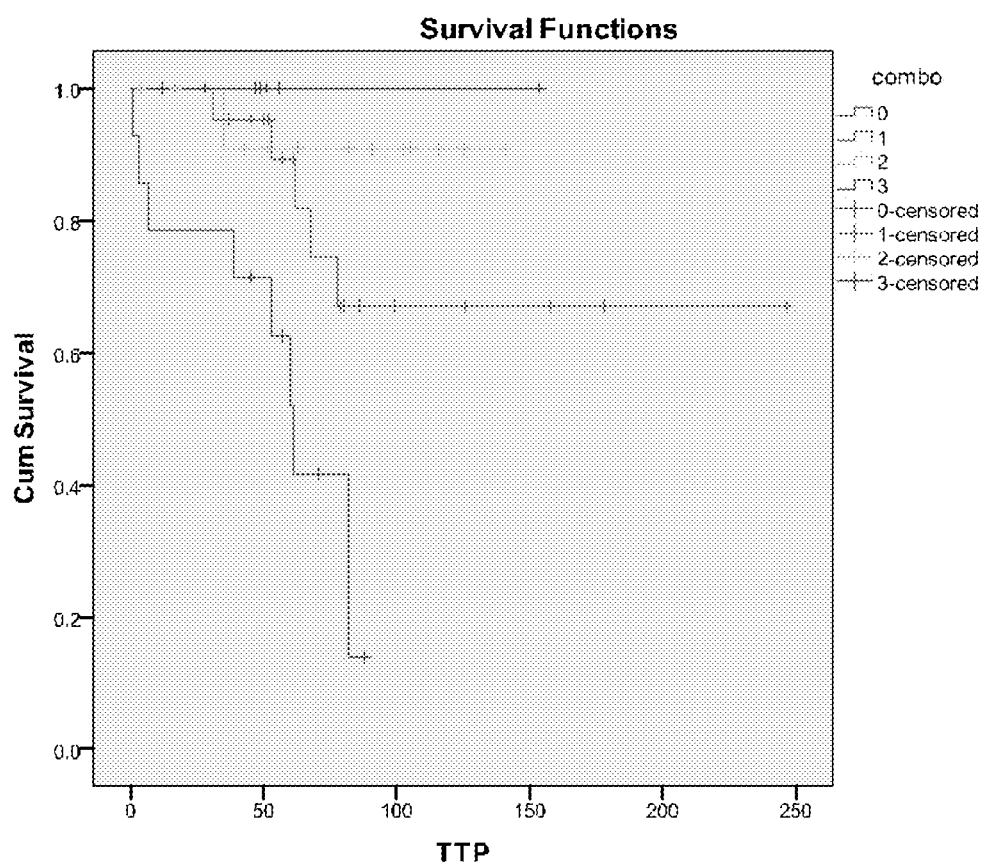

FIG. 5. A. Hierarchical clustering of GGMA data of all the investigated samples. B. Heat map showing the probes which are methylated in all tumor subgroups vs. blood and urine, C) Methylation of two CpGs in the MEIS1 CGI (black peaks: methylated CpG, red: not methylated. IM, in vitro methylated DNA; RT112, T24, J82: bladder cancer cell lines; PU: patient urine; NU: normal urine; NB: blood), D) KM curve for progression to muscle-invasive disease based on a combination of methylation of GRP103, DBC1 and GATA2.

TABLE 1

Coordinates of selected regions containing relevant CpG islands based on
*Homo sapiens* full genome as provided by UCSC (hg18, March 2006)

| | | |
|---|---|---|
| chr1: 119333484-119333719 | chr1: 149638545-149639227 | chr1: 160220156-160220709 |
| chr1: 178464743-178471598 | chr1: 2072175-2072389 | chr1: 2106293-2106715 |
| chr1: 232106869-232108183 | chr1: 33385564-33385979 | chr1: 41122328-41122880 |
| chr1: 47672249-47672972 | chr1: 68288825-68289104 | chr1: 71284766-71286392 |

TABLE 1-continued

Coordinates of selected regions containing relevant CpG islands based on
*Homo sapiens* full genome as provided by UCSC (hg18, March 2006)

| | | |
|---|---|---|
| chr10: 21828640-21829645 | chr10: 22804715-22807056 | chr10: 73437163-73438385 |
| chr10: 7449476-7449790 | chr10: 7489383-7495345 | chr12: 113657930-113659205 |
| chr12: 118612357-118612674 | chr12: 94776044-94776377 | chr13: 113930978-113931584 |
| chr13: 34950488-34951119 | chr13: 49595986-49600287 | chr13: 94152191-94153185 |
| chr14: 36205192-36206099 | chr14: 37746906-37747538 | chr14: 53488428-53488700 |
| chr15: 94688798-94689131 | chr15: 94696311-94696840 | chr15: 94705727-94706054 |
| chr15: 94712480-94712812 | chr16: 52873104-52882105 | chr16: 52873104-52882105 |
| chr16: 85098883-85102729 | chr16: 86294154-86294408 | chr16: 87372445-87372729 |
| chr17: 24303411-24303889 | chr17: 34157398-34159854 | chr17: 44074280-44075233 |
| chr17: 56827843-56838048 | chr17: 58865328-58865618 | chr17: 73932992-73933361 |
| chr17: 75377960-75381951 | chr17: 75531280-75531546 | chr18: 5186244-5187389 |
| chr18: 68359955-68362770 | chr19: 4059891-4060207 | chr19: 42586165-42586705 |
| chr19: 63420090-63420541 | chr19: 63784504-63785085 | chr2: 104835284-104839920 |
| chr2: 105864220-105865009 | chr2: 111591678-111597645 | chr2: 115635091-115637285 |
| chr2: 124498611-124499725 | chr2: 156892636-156892878 | chr2: 156893736-156894685 |
| chr2: 171384729-171385226 | chr2: 176737610-176738187 | chr2: 19424445-19425131 |
| chr2: 43251514-43251780 | chr2: 45249374-45251726 | chr2: 63134470-63134933 |
| chr2: 66525936-66527222 | chr2: 70984709-70985764 | chr2: 72224630-72228512 |
| chr20: 22505518-22507240 | chr20: 22510737-22514165 | chr20: 22514762-22515148 |
| chr20: 35582018-35583550 | chr20: 54012011-54014085 | chr20: 60061693-60062033 |
| chr21: 33316999-33322115 | chr21: 36990008-36995832 | chr21: 37857725-37858416 |
| chr21: 43350621-43351134 | chr3: 129688131-129694023 | chr3: 148591199-148594390 |
| chr3: 62330280-62330608 | chr3: 62331767-62332398 | chr4: 111780013-111780343 |
| chr4: 122520930-122521740 | chr4: 155881084-155881434 | chr4: 177159356-177159814 |
| chr4: 40134579-40135662 | chr4: 9756136-9756429 | chr5: 115810975-115811393 |
| chr5: 122461778-122463450 | chr5: 134390896-134393045 | chr5: 135442969-135443206 |
| chr5: 140724146-140724826 | chr5: 174091287-174092335 | chr6: 101023927-101024343 |
| chr6: 1549606-1560865 | chr6: 21704622-21705099 | chr6: 26312699-26313302 |
| chr7: 121727243-121727884 | chr7: 1481682-1482268 | chr7: 155266364-155266696 |
| chr7: 155288454-155292175 | chr7: 156895132-156895886 | chr7: 2082782-2083345 |
| chr7: 27164708-27165039 | chr7: 27219187-27220360 | chr7: 2724511-2724848 |
| chr7: 27251165-27252762 | chr7: 32768010-32768497 | chr7: 55040457-55041024 |
| chr7: 8449587-8450236 | chr7: 96488158-96489591 | chr8: 132985505-132986242 |
| chr8: 142288380-142288718 | chr8: 57520625-57522095 | chr8: 65661156-65662687 |
| chr8: 9798161-9799053 | chr9: 121170908-121172141 | chrX: 39749470-39754050 |
| chrX: 50040955-50041296 | | |

TABLE 2

CpG islands differentially methylated in NMI-BC wt vs invasive BC.
Provided for each are: ID; Comparision; Coordinates of selected regions containing relevant
CpG islands based on *Homo sapiens* full genome as provided by UCSC
(hg18, Mar. 2006);
Chromosome; GeneName; Location relative to gene Sequence.

7; I vs SW; chr1: 41122328-41122880; 1; chr1: 041122606-041122650; Unknown
CGGATGTGCGTGGACTCTGCGGGCGGGGCGCCCGTAGTCTCCCTCCTTCGCACCCCGGGCGCCTGGGAACCT
CCTCGCGCGTTTGGCCACTCGCTGCTCCTGGCAGTAGGGGCTTCGGGCCCCGCCGTGTCCCCACCCAGGTAT
GGGGATGCGGAGTTGATGGGTGCGGGGCGCTGGGAGGGGGCAGATGAAAGGGGCAGTCGAAAGGGGGCCA
TGCGCGCCGAGCGCAGCCGGGTCATTAGCCGCGGGTGTGAGCGGCGGGGCAGGCTTATCGCCCATCCAGGC
CTGGCGGGCGGGCGGTCCCCGACGCGCTGCCGCCGCCGCCCGCGGCAGAGGGCACGGCGGTTCCCACGCT
CGGGCCCTGGTTCGGGGGCGTTCTCGGGACGGCGTGGCCGCGCTCACCACCACCGCGGAGGCCGGGCTGTA
ATTAGGATAATTGCGCTGCTCCCAGCCTGGGGCAGCTCAGGACCCGGCTGCACCGCGCTGGCCCGGGACGGG
CGGGGGCAGGGGGTGGCGGGGCCCGAGCGATACAGCCCCTGGCGCAGTCCG (SEQ ID NO: 1)

61; I vs SW; chr10: 73437163-73438385; 10; CHST3; INSIDE
CGCCCAGACCGGCCGTGGCGGGGCCCGGCGCCACGTGCTGCTCATGGCCACCACGCGCACCGGCTCCTCG
TTCGTGGGCGAGTTCTTCAACCAGCAGGGCAACATCTTCTACCTCTTCGAGCCGCTTGGCACATCGAGCGCAC
AGTGTCCTTCGAGCCGGGGGGCGCCAACGCCGCGGGCTCGGCCCTGGTGTACCGCGACGTGCTCAAGCAGC
TCTTCCTGTGCGACCTGTACGTGCTGGAGCACTTCATCACGCCGCTGCCCGAGGACCACCTGACTCAGTTCAT
GTTCCGCCGGGCTCCAGCCGCTCCCTGTGCGAGGACCCCGTCTGTACGCCCTTCGTCAAGAAGGTCTTCGAG
AAGTACCACTGCAAGAACCGCCGCTGCGGCCCCTCAACGTGACGCTGGCCGCAGAGGCCTGCCGCCGCAAG
GAGCACATGGCCCTCAAGGCGGTGCGCATCCGGCAGCTGAGTTCCTGCAGCCGCTGGCCGAGGACCCCCGCC
TGGACCTGCGCGTCATCCAGCTGGTGCGCGACCCCCGGGCCGTGCTGGCCTCGCGCATGGTGGCCTTCGCCG
GCAAGTATAAGACCTGGAAGAAGTGGCTGGACGACGAGGGCCAGGACGGCCTGAGGGAAGAGGAGGTCAGC
GGCTGCGGGGCAACTGCGAGAGCATCCGCCTGTCCGCGGAGCTGGGGCTGCGGCAGCCCGCCTGGCTGCGG
GGCCGCTACATGCTGGTGCGCTACGAGGACGTGGCACGCGGGCCGCTGCAGAAGGCCCGCGAGATGTACCG
CTTCGCCGGCATCCCCCTGACCCCGCGGTGGAAGACTGGATCCAAAAGAACACGCAGGCGGCCCACGACGGC
AGCGGCATCTACTCCACGCAGAAGAACTCCTCGGAGCAGTTCGAGAAGTGGCCGCTTCAGCATGCCCTTCAAG
CTGGCCCAGGTGGTGCAGGCCGCCTGCGGCCCTGCCATGCGCCTCTTCGGCTACAACTGGCGCGGGACGCCG
CCGCCCTCACCAACCGCTCAGTCAGCCTGCTGGAGGAGAGGGGCACCTTCTGGGTCACGTAGGGGGGCCGG
GGCCCCGTATGCCCCTCCTCGTGAAAGGCCTGCCCCGTCTTTCTGCCGCAGCCCTCGCAGAGGGCGGGTGCA
CAGCGCCATGACGGGCAGCGCCTCCTGTAGCAGTAGGGCCCCCAGCCAGCGCTCCAGCCAA (SEQ ID NO: 2)

TABLE 2-continued

CpG islands differentially methylated in NMI-BC wt vs invasive BC.
Provided for each are: ID; Comparision; Coordinates of selected regions containing relevant
CpG islands based on *Homo sapiens* full genome as provided by UCSC
(hg18, Mar. 2006);
Chromosome; GeneName; Location relative to gene Sequence.

97; I vs SW; chr12: 118612357-118612674; 12; CIT; INSIDE
CGGGGTCCTCACGGCTCCCGCAGGCAGCCGGCCCCTGCTGCTGTCTTCAAACAGCCTCCCGGGGGACCGCTC
TCTCCGCGTGCTGAGCATCCGGCCGGGGGACTTCTCTCGCTCCAGGGGGCGGCCAGAGACTTGTCCCTGCGC
AGCTCGGTCCGCCCCTCGCGGTAGCGGTGGGGTGTGCTTGGCTCTCGCGGGTGGCTGGGGCCTTCGGGCGG
CGCTGGGCTGGAGGCCACGCGCTTGGTGATGTGCTCGTTGTACGTGGGTGGGCCTCGCTTGTTGGGGCTGCT
GGCGACACAAGAGAACGTAGGGAGCTGCG (SEQ ID NO: 3)

162; I vs SW; chr17: 34157398-34159854; 17; PCGF2-PSMB3; DIVERGENT_PROMOTER
CGAGAGGACCCGGACCCCGGCGGGGAAGGGCGCCCTCCCCCGGCCTCGCGGCCGCCCCAAAGCACATCCCC
TTCTGCCGGCCCCAAGTCCCCGCGCGTCCACGGCGCCCCTGTGCCCACGGGAGAGCACCCCCGCCCAGATGG
AAAAGGGGGTAGACCGGGCAGAGCGAGAGGCGGCTTTGGCTCGTGGGGAGCGGCGACCCAACCCAGCGCGC
ATCCCGCAAGCCCTCCCGGCTGCCCCGGACCTTCCCCCTCGCTACCTCGGAACAGGGTCTGCCCGGGGGCTG
CTGCACAAAGAGGGGTGGTCGAGGGAGACGCCAAATCGTTAAGACGGGAGCGGCCCGTTTCGGCCATCTTGGAA
GAGAGGAAAGGGAAAAAGGGACAGAAAAAAGGGAGAAAGAAAGGCGGACGGGGCAAGCTGGGCTAGGGACT
GACGGGGCGCGGGGGGTGCGAAGGCAGGATCGGCTCAGAGCCCCCCCTCCCATCGGGGCTTGCGAAGAACG
GCCGGCCCCCATCCCAATCCCCAGAGGGTTACAGGCCAGGAGAGGGAAAGGCAGGGGGAGTCCGCTCCGCT
TACCTGGGTTCGGGGTCCGGTGGGTCTCGGGGAGGGGGGGATGGGAGGGAGGGAAGGGAGGGGAGG
GGGCCGCAGCCGTGTCGCTCGCCCGGGCGGCGGGAGGGGAGAAACCTACGGTAAGAAAGGAGTTTGTGAAA
GCGGCTTGGGGTGGGAGGGAGAGGGGAGGGGAGGGGACCGAGGGGGGAGGGGAGGGACCGGAGTGTGGG
GGGGAGACAAAATGGCTTTTTTCCTCCAGACAAGGTAGGTCCCGCCCACCACTCACCCACGTGACCTCATTCC
TTCAGGATGCTGGCAGAGACGGGAAGAGGAGGGGGAGGCTGGCGCGGCGCTCCCCGCCACCGGCTGCCGG
GTCCCTAGCCAGGACGAGACCCCTCCCTTCCCATGCGGCCGCCCCGACCCCGGAGGATGGATCTCTTATGTT
ACCTTCCGCAGTTAGCCCCCCTCCCTTCAAAATATGGGTTCCCCCCACTGACACTGTGATGCCCATCCCTAAC
TGGGGCGCCTGGAAAATGGTGAAATGGGGACTGGGCTGAAAGGTGGCTCGTGGTCCTCCACGCCCCGGCCTA
GACCAAAGGGCGCGGGGTCCGGCGGGGGACGCGACGCCTTCAGCCAGGCGTCCGAGCGATTTTCATT
(SEQ ID NO: 4)

169; I vs SW; chr17: 56827843-56838048; 17; TBX2; INSIDE
CGGAGGCGGCACAGCTGGAGCCCGGATTGTGGCACGCCGTCACCGTGCTGCTCCGGGGAATCCCGACCCGC
TCCCTGCGAAAGCGTTTCCGAACGCGAACCCAGAGCCTGTGAACGCGCCGGCAAGCCCCCACTCCCCCACCG
CCGCCCGTCGCAGGTGGGCCCGTCCTAGGGGTCCTTCCTGCGCTCTACCCCGTCTCTCAAGTCACTCAGTCG
ATCGCCCCGTTCACGCTCCCGTGATCCCAGACATCCATAACCACGATCTCGCCTCCATGCACATCCAACGCAC
GACGGTGCACAACGTGCACCTGACTTCTGCGGACCAGGTGTCTCAAGCGTACAGCGGCCACCCGCGGAACCG
CGGCCCGGGGCCAGTGAGTCGTCTGCAGCTCCCCGGGTTAGGGGATTCCCCAGAACTCCGGGAAAGTCACCC
GAAGTCCATCCGGGATGCGGCCTTGGTTCTCGGCCGCGTATCTCGCCCTTAGGTGCAGAACGACGCCCTTCC
AGGGCCCACAGCTGCCAGGCTGGGCCTTGCCCTCGCATCCCCCGGGAAGACCAGGGACGGGGCCACACAGG
CCGTGGCTGCGGAGACGCTTCCCCGGGCCACCCCGCGACCAGGAGGGAGTCGAGCCGCCCGCTCTCCCGCG
TCCCCCGCCCCATCCCAGCCAGTTGGCCCCACCCTGCGCGGGATAATTGGGACGGGAGGGAGGCGACGGGA
GGGCGGCGGCTCCAGAGAGACTGCGCGCCTGTCAGCGGCAATTTGTTTAAGTGGACGGGACGGGCCGGGCC
GCTGCGGGCTGGGGTCACCGAGGCGCGCCCCACCCCAACCAGACCTGGGACCGCGGGGGAGCCCGGTCC
GGCCGCTAAACCGGGCTGGCTGGCGCCAGGGCTCCGGGAGGTGCGGTCCGGCGGGGAAGCCGTGATGGGAA
GCGACTCTGTCCAGGGAGTGTCCTTCACCACCACACTCCTCACGTCCAGGCAGTGATGACGGCCTGGCGGCA
CCCTCACAGCGGGCCCATAGCACGGGGCCACACACGTCCCCTGAGCTTAGCCTGGGCACATTCGTCTGCCAC
CGAGGGCTTAAGCCAGTCTGCAGCCCGCGCCCCGTCACTCGGACGCAAGTCCGTCGTCCGCTCTGCCACGCG
GCCGCACAGCCCGGCTTCCTGCTGCCCACTGCCCGCGGGTCACGCAACCCCGGCCCTGCACA (SEQ ID NO: 5)

270; I vs SW; chr21: 37857725-37858416; 21; chr21: 037857850-037857894; Unknown
CGATTTCCGCAGATTTCCTGCTGGAACGTTCTCTCGGGCCTCAAGTTTTCCTGAGAGGACGACGTGGAGAGTG
GAGACAAAGATGCTCAAAAGCCAGGAAATCGCAGGCTCGGAAGCCCCCACGCATCCTCTGAACGCAGCGCCA
TCTCGGGGCTGCGGCGGGACCAAGCGGGACGCTTGCAGGCTGTGCAGGCCGCGGGGCGCGCAGCCGCCGGCG
TAGGCCGCTCCAGCTGGAAGACCCCACCGCTAGGGTTCCAGGGGGCTGCGGACGCTTCCGAGGGGCCCAAG
GCGAAAGAACGCGCCCGCTTGTCGGCCACGTGACCGTCCCCGTCCGCGTCCGCAGCGACCACGTGACTGTGC
GTCCGCGGCGTCGATTGACTGGGAGCTCCCTGGCCACGCCCTAAGCGCCAGCCCCGGGCTTCGGGGGCGG
TGCTGCTGCGGTTGCCATGGCGTCTTCCGAGCGCGCAGGCGGGGCCCAGAGTAGCTTTTCGGGTATTTGCTA
CCGGCTCTCGGTAGGGCTGGTCACCTTTGCTTGCTGAGCTTCGCGCCCTGCGTCCTTTGGTCCCCAGCAACTT
GCAGGGCAGCCGTCCCTCATGAGGCCCTCCAGCGAATGCCCTAAAGCTCCGAAGTTGCTCCGGAGGAAACAG
GCTTGCTCCGAGGGTGCACGTCCTTACTGCCCGTGACGTCG (SEQ ID NO: 6)

271; I vs SW; chr21: 43350621-43351134; 21; CBS; INSIDE
CTGCTGCACTTGTAAAGTGGGTGCTTCTCAGCTTCATGGTTTGAGGGGTGCAGCCAGCTTCGGCCTAAGTGGT
GTTGAGGGTCGAGGACCCAGCACCCCCACACGGGAAGCGCGGTGTCCCGCCTTCAGGCTGGAGTACTCTGGC
ACCCTCTGGGGTCCCGAAGTGCCTGAGTACCTGTTTGAGCCGCGTTGGACTGCGCACCTGTTTGAACT
GCGTGTAGGTGACCGCGCACCTGTTTGAGCTGCCTGTAGCTGACCGGGCACCTGTTTGAGCTGCCTGTAGGT
GACCGCGCACTGTTTGAGCTGCCTGTAGGTGACTGGGCACCCGTTTGAGCTGCCTGTAGGTGACCGCGCACC
CGTTTGAGCTGCCTGTAGGTGACCGGGCACCCGTTTGAGCTGCCTGTAGGTGACCGGGCACCCGTTTGAGCT
GCCTGTAGGTGACTGGGCACCCGTTTGAGCTGCCTGTAGTGACCGCGCACCCGCTTGAGCTGCCTGTAGCTG
ACCGCG (SEQ ID NO: 7)

283; I vs SW; chr4: 40134579-40135662; 4; FLJ20273; INSIDE
CGCGTTGTAGGGGTAGCCGTAGTAGGCCAGTGTGTAGGGGTCGCAGGAGTACACGTAGCTGGGCTGCTGCG
CTGCCTCAGCCGCGCCGCCGCCCCTGGCTGCCTTCTGGTAGCGCGAGTACTGCTCCTGTCCACGGGCTTGGC
CAGCGTGACCTCCAGGCACGAGCCCTCCAGCTCAGTGCCGTTGAGGTTGTTCATGGCATGCACGGCATCCTC
GCGGCTGGTGAAGTGCACGAAGGCGTAGTCGCGGATCTTCTTGACGCGCTCCACGCAGCCGGGGTTGAACTG TABLE 2-continued CpG islands differentially methylated in NMI-BC wt vs invasive BC.
Provided for each are: ID; Comparision; Coordinates of selected regions contain-
ing relevant
CpG islands based on Homo sapiens full genome as provided by UCSC
(hg18, Mar. 2006);
Chromosome; GeneName; Location relative to gene Sequence.

GCCGAAGCTCTTTTGATGGTGTCCTCGGTGGTCTCGATCATGAGGTTGCGCACGTAGAGGATCTTCACGGTCT
CCATCACGTCCTCGTCCACGTCGATCTCAGGTTCGGCCCAGTCCACGGCGATCTGGTGGCCCCACAGCTGGA
TGCGGCCAGGCATGAGCTTGCGGCGAGCCATGGCAGCCGGCGGTGGCTCTCGTACTCCACGAAGGCGAAGC
CGCGGTTCTTCATCTTGTCGGCCGCGCTGGCGTAGACGATCACGTCCAGCACGCCCTCGGTGACCTTGGCAA
TCTCCTCCAGGATTTCCTCGCGCTTCTTCATCTTGGGGATCCCGCCGATGAAGAGGCGGCAGTTGTCCCGCTG
CAGCACACGCCGAGCAGGCGGCCCGGGCGGATCTCGTAGTTGTTGAGCTCACGCACTGCGCGCTTGGCCTCG
TGCTTGTGGCAGTACATGACGAAGGCGTAGCCGCGGTTCTTGCCGTCAAAGTCCATCATGAGGCGCAGCTCG
TAGATGCGGCCCACGGCCTCGAAACGGGCACCAGCTCGTCCTCGTACACGTCGCGCGGGATCTTGCCCACGA
AGACCTCGCAGCCACGCTGCGGGTGCGGGCCCTCCCAGCCGGGCGGTGGGCGCCCGTACTTGCGCTGCCCG
TTCTCTTGCACCATGCTGTAGCCCGTGCGCTCCATCAGCGCCAGCAGTGCTGCTCGTTGGGCGCGCCCGCCA
CGCCCTCGGGCACCTTGGCGGAGGACCCGGCGGCCGAGTCACTGCTCATGGCTGCGGTGGAATCCTCTGCG
(SEQ ID NO: 8)

357; I vs SW; chr7: 27219187-27220360; 7; chr7: 027219187-027219246; Unknown
AAGTCTGGAGATAATTATGTCGTACAGTCGCAAACATTATTCCGTTCTTACTGTAAACGGCCCCGGCCACCTT
TACGAGAAACCAGGAAACTTCTGAGAGTTACTAGCAGCGTTTACGCGGGCAAACGAGTTCTTTTTCTTTCTCT
CCCGGATTGTTCGAAGTATCTATCGGGCGGCTTCGATGCCAGGTTCAGAGGCGCGCCAGGGAGAGGGCGCC
CGCAGAGGAGCGCAGCGGAGAGGCCTACGCAGGTCCCCGGTGCCCGCGCCCTCGGAGGCCGGGCCCTGCG
TCTTGGCCAGCACTGGGTGGCAGCTGAGGCTGGTGGCCCGGAGCCCTCGCGGCCGCGGGCAGGCCCCTTCTT
GGGCAGGGTCGGGCACTCCCGCTGTCCAGGGCTCTTCGGCACCCTCCTTCCAATCAGGTCGCTCTCCCCTGC
TCCCCAGACTCAACTCCTCCGAAGCTGCTCCAGGTTGAATGTGACCGCTAGGCCGACTCCCTGGGCCCGCGA
GCAGTTCTCGAAAGGTGCGGACTGAGCCCTTTCTGGGGTGGGGTGCGGGTTGGTTCTCGCAAGTGTGACCCA
GGGTGAACTTGCTATTTCGGGTCCCGGGTGCTGCAGGGCAGGAGAACAGCTGGGATGGGGGACCCCGCCT
CCACCCTCGGGCCGGCACGTCCGCGCCCTGTCAGGTCCCCCTCCCTCCTCTATGATGGCCAAGGCGTGCGCC
AGGGCTATCCGGGAACCTTGTAAGGCCTCGTGCTGGCACCTAACCCCACTCGCGGCCACACTTCCTCTATGTAG
TCTGCGGCCCCGCCTGCCAAATAGAGTGACCAGTGCAGGGACAGAATGCCAGGCTGGTGGCCGACCGCCTGA
GGGACAAAGGCGAGCATTCACAAGCCAACAGCAGACCCCTGCCCCCCATATTTCCATTTCGCTCAGGCTTTTA
GGACAAAATCAACAAGGCCGCAGAGTGGTGCAGGCGCTCACCCCGGGTGCAGCCTGGGGAGCCACTGGTTC
CGCGACCCTGGGCATGAAACTCCTCAAGGGCGGCCCTCGAGACGCAGGGGAGAGGATGCTGCCGGCGCCTG
CCCGAGGGCTTCTCTGCGGGAAGCGGGCAGGCACCCCACCGGAGTCATTGCCGGGACCCTCAGCGCAACGC
GGGCCTGTTCCTCTCG (SEQ ID NO: 9)

373; I vs SW; chr7: 156895132-156895886; 7; DNAJB6; INSIDE
CGGAGATGGCGCGTCTGGATTCAGGGAGATCGTGCGGCCAGCTTCCCCTCTGCTCTGGATGGGGGCCGG
CCGCCGCCGCTCACTCACGGCTCTCTCTCTCCCGCTGTGCCTGCAGGTGTGGCCGCGACGATGCCCTCGCTG
AGGAGCGCATGCGGAGAGGCCAGAACGCCCTGCCAGCCCAGCCTGCCGGCCTCCGCCCGCCGAAGCGCCC
CGGCCTGCCTCGCTGCTGAGACACGCGCCTCACTGTCTCTCTGAGGAGGAGGGCGAGCAGGACCGACCTCGG
GCACCCGGGCCCGGGACCCCCTCGCGTCCGCAGCAGGTGTGCAAAGGGAGGCAGCCGTGGAGCAGGCGCAG
AGTGAGACTTCTCTGGGTGCCAGAGGACAGCGAGGACACAAACCGCGCCTGGGCTGCTGTGTTCTGACCTGA
GCGGGCGTGGGCGGTCGGGCGGGGCGGGAGGAGGTAGCCTCCTCTGCTCCTCTCCCGCTCGCGGCGCCCCA
CGCCACGGTGGCTCCGGGCCCCCCACCGTTAAAACGGGGTCCGCGTGTCCTGTACGCAGCGTGTTGCTCCGC
AAAGGATGACAGAGCTGCCACGGCAGTGCGAGGTGCTGCTTTTACCGTAGACGTGCCTTTTCGTAGCTTTAG
CGTAGAGCTTGAGGCCTGTGGCTTAGGCCGGGTGGTCTCGTGCTGGTGGGGTCTGCGTTTGCCCCTGCCCCT
CCGTCAGCTTCACCTTCTCGTGCCTTCTTCTGCG (SEQ ID NO: 10)

389; I vs SW; chr8: 132985505-132986242; 8; chr8: 132985506-132985550; Unknown
CGTAACGGGCGTGGGTCGTCCGTCGCGCCGCCCGGCGAGGAGTGGGCTGGCGGCGGTAGCTGTCGCCCGCT
TGGTTGCGTGACCGCGGGGTCCGCGTCCGCTCCCTCCACCCTTCGCCCTTCGCCCTCGCCTCGTTCCGGCCTC
CGCGGCCCAGCAACGGCCGTCATGGTGCCGTCGGCGCTCCCTGCGCGGCCCCGCTGAGCCTCGGTGCGGCG
GCGAGCGCGGTCGAGATCGCCATGCCTACCCGTGAGTGGCCGGCCGAGGGCCGGGGCGTTGGGAGGGCGAC
TGCCTGCGCGACGGCTTGGGCCGGGTACTCCTCCCGGGCGGCTGGGGAGGCTGGGCCGCGCTGAGCAGAGC
CAGGAAGTGTCTGCGAGCGGCGGAGTTAGTTTCGTTTCGGCTTAGCCTTCCGGAGATGGCGTGAGCCCGTTG
CACGGATCGGGAAACTGAGGCCCGAACGTTAAGGGAACTGCGGGACGCGCTGTTAGGAGGCGGCAGAGCTG
GTGGTAACCTGACCCGTGGGATTTCAAAGTTAAAGCCCTTTTCCCACGGCCACACGGCTTCGTGGGACTTTAT
GGAAATATTGAAAATAACTGCGGTACCATTGTCAGTCCCTTCTCACCTCGGGCCGGACGTCGCTAGTGGAGC
GCCGGCCCCGAGTCCCTTCCCGCGGCCGCCAGACAGACCCCCGACAGCCTAACTCGGCGTCCGTATCGCCGT
CGGGGCGGCTGAAGTCG (SEQ ID NO: 11)

12; SW vs I; chr1: 68288825-68289104; 1; DIRAS3; INSIDE
CGGAGGCACGAACCAAGCAGCCTAGAAGACAAATGCGCTGCTCGGAGAGACTGCCGCGGCAACCAACTGGA
CACCCCAAGAGCTCACTCCTCCGCGGTTTTATATTCCGACTTGCGCACAGGAGCGGGTGCGGGGGCGCAGGG
AGTGTGGGTAACAGGCATAGATTCCGCTTGCGCAATACGTGGTAAGAAACCAGCTGTGAGGGGCTGGCCCAA
CGCAGAGCGGCGCGAGGTCCGCTTGGCATCTACAACAATCGAGGGGCTAGTCCAGAAGTTCAAG (SEQ ID NO: 12)

15; SW vs I; chr1: 71284766-71286392; 1; PTGER3; INSIDE
GCTCAGCTAGTAAGTGAGGAGCTCAGCTCTGAAGCTGTAACCAAGACCGCGCGGGCAGGAGGAAAGGACACT
TCAGCGCTCTGCGGTTGCAAACACACCCCTGCGGGTGCTGCCACTTAGCAAAGTCTAGGTTCCCGCTTACTCG
CACACGCATCCTGACTTCCCCCAACCCTGGAACTACCTACCAGGAGCGGAGACCAGCAGACCGACAGCACGC
ACATGATCCCCATAAGCTGAATGGCCGTCTCGGTCGTGATGCGGCCCCACTGGGCACTGGACTGAGATGCCG
TGGCCTTGGCCGGCAGCGGGACACCAGGGCCTTAATGGTGGCCAGGTTGCAGGAAAAGGTGACTGTCAGCG
CCAAGAGCCCCAGGAAGGCAAAGGCAGAGGCGAAGAAAAGGTTGCCCCAGTTATGCGAAGAGCTAGTCCCGT
TGCCCCCTCGCCCGGTGCTGATGAAGCACCACGTCCCGGCCACTGGACGGTGTACTGGCCCACGCCCAGCAC
CGGCAGCAGGGCGAAGGCGAGCACGGCCAGCCACACGCCGAGCAGCACAGCGCGGGTGGCACGCGTCTTCA TABLE 2-continued CpG islands differentially methylated in NMI-BC wt vs invasive BC.
Provided for each are: ID; Comparision; Coordinates of selected regions containing relevant
CpG islands based on *Homo sapiens* full genome as provided by UCSC
(hg18, Mar. 2006);
Chromosome; GeneName; Location relative to gene Sequence.

```
TGTGGCTCGCATACCAGTGCGGCGCCCTGATGGCCAGCGCCCGCTCGACGGCCATGGCGCTGGCGATGACAA
CGAGGAGAGCCCGAAAACAGTCATGGTCAGCCCGAAAAAGGTGCAGAGCCGCCCCGACGGGTCGATGTGCT
CCCAACGCTGCTTGGACAGGTACACGACGATGACGACCGGGGTGGTGAGAAGCTGCCCGACCAGGTCGGTG
AGCGCCAGCCAGCCGATGCACAGCAGAAGGACTTCTTGCGCTTGCTCTCCCGGCGCCGGTAGCTGCGCGACA
CGAGCAGCATGGCCAGTGCGTTGCCCACGAAACCAGTGAGCAGCATGGTGATCGGGAAGGCCACGGACACC
GATCCGCAATCCTCGCCAGACCCTGGAGGGCGCGTGAGGTTGCCCCGCGCCTCGGGGAACGCTCGGGCGCC
CACATGCCTGTGTAGGAGTGGTTGAGGCGGGTGCAGAAGGGGGCATCCCCTCCGTAGCCCCGGGTCTCCTTC
ATGTTGGCTTCGAGGTGAGGAGGGGATGGCGTCCAGAGAGCCGCAGCGGGAGGGGGCAGACGCGGCGCGG
GCGGCGGCGGAGGTGGCGTTTACCGCGGCTGGGGCTGGGCTGCCCCCCATGGTGCGGGGCGCAG (SEQ ID NO: 13)
```

21; SW vs I; chr1: 119333484-119333719; 1; TBX15; INSIDE
```
ATTCTTAATTCCCACACCTCTTCCCAAGTTACGCCACCGGTCGAGGACGGCAGGAGACCCCCGAGTGCAGAG
AAAGCTCAAACCGGCAGCGAAGTCGGTCCTAGCCAAGCTGAAAAAACGTCTCGGATTCGCGGACAGCGGCCT
AGACACAGCCCGATCTTCCAGTCCTAGTGCCCTGGTCGAGACGGTTCTATCCTTTTGCAAAGAAGCCGGAAAG
AGCTGGGTCCCGGGGCG (SEQ ID NO: 14)
```

26; SW vs I; chr1: 178464743-178471598; 1; LHX4; INSIDE
```
CGGGGTGGGCTTCCCGCGCCTGCAGCCCGGAGGCGTCGAGCGCCTGATGGAGCGTCAGAGGAGACCTCGTC
CCAGCGTTGGGCCTTCTGTTGTATTTCTGCCAGAAACTCGCGTTGAGGAGAATTTGTTTAAGCGTTTCTCTAC
CTGTCCATGCATCTCGTAAATACAGTAAGCATGGCAAGCCCTTTCGCTGGTTAACCCCGGCGTCCGTGTGCTC
ACTGCCGCCCTGCACGCACGAGGTCGCGGATGGTTCAAAGCACCCGCGGTGGCAGCCGGAGAGGCAGAGCG
GGCTCTAGGGACTAAGACAGGGCCGAGCTGGACGACTGGTGGCAGGGCGGCCGGGGAGGCCCCGCCGCGGG
GAGGTTTGGGCCCCCTACCCTGCGGAACTGGAGGCAAGTGCGGACTCCGGCTGCAGGCCGCGGTCTGCGGG
GACGCGCGCGGGGGGCCTGCGTCCCGCCACCTCCGCGCACACCCCTGGTCCCCTTCCCCAGCCCGGGCCGG
CGCCGCCCGCCGCGTGACTCGCGCGTTCCGGGCCGAGTACGGGCTGTCCCTTGGCCCAGCCTCAGCCAGACG
CGGGGGAGAGAGAGCAGGGGCTGGGAAGTGCCGGCAGGAAAGGAATTGGCCAGGGGAAAGAGGAGGAGGA
GATAGATGGAGTCATCGGTTACGGAGCGCGCTCCGTCCGGCGGAGCGAAGCCGGGGACCGAGAGCGCGCAA
GGCGAAGACACAGCGACGCAGCCCCGTCCCCGGCCTCCGGACCGCCTGCCCCGCTCGGCCCCGGCTCGGCT
CCGCCCCGCCCCTGGGTCCGAACGGAGGAGGAGGAGGACACGAGCCGCGCGGGCTTGGAACCCACGAAGAC
CCGCAAACCCAGGGCGCCGCCGTCTCCGACCACCTGCTGCCGCGGCAGGCCATCAGCAGAATTTATACCCAG
GGCGCGAGCCCGCCACGGCTGGGCGGAGGCGGAGGCGGAGGCGGGGAGGGGGGGGGGGTCCGGCTTGCGA
GGCCCCGCCCCGCTCCCTGCCGCCCCGCCCCCCTCCGCCCCGCCGGCCTCACTCGGGGCGCCGGGACCCCCA
CTCCCTCCGGGGTCGGCTGCCCGCCGCCGGGTTGGGGGATGTGCCGAAGGGCGGGCCTCCCTGCGGAAAGC
GACGTCACGGCCGCTCCTCAGTGTGAATGAATCAAAACGCCCGGGTGACCGCGGCCTCCCGGCGGCC
(SEQ ID NO: 15)
```

40; SW vs I; chr10: 7449476-7449790; 10; SFMBT2; INSIDE
```
AAACCACTCTGAAAGAACTGTGAGACCTTTGCACTAAGACCATTAGGGATTCTACGCAAGGTTCTCTCTGCTC
CTTGCAAAATTACAGGCGTCATGAAGGATGGCGGCTCGTAAATCGAAGCCTTTGAACAGGGGCTCACCGTCC
GGCGGCATCAACACCTTGTTGTTCTGTGTGCACCACCCCACGGGGTGCAAATCCGCGATGACTACGTCACAC
CAGAAGTCGGCCCTGCGGTCCTCCCCGTAACCGCAGTAGCGCAGAAGCAGCAGCTGCCCGCACGTGGTAATG
ATCGTGGCCACCAGTACGTGTCCG (SEQ ID NO: 16)
```

41; SW vs I; chr10: 7489383-7495345; 10; SFMBT2; INSIDE
```
CGGCAACCGAGCCAGATCCAAGAGGGGTCGGCCTCGTCTAAATTGGTTTCCCACCAATGGCCTCGGATCAGC
CGCGGCTGTGCTGCGGGAGCCCTCAGGACGCGGCTGGGGTTGGTGCGCGGGGCCCGGAACCCCAAACCCGG
CTCGGTTCGGCAAGGTTCAGGGAGACAAGGTAGAGAAGGCTGGGGTGAGCGAGAAGTCGGGCGGCCGATCG
TCAGGGCCACGAGCCTCGCCTTGCCTTCTTGGAATCCCACCCAACTTTAAAGGCCCAAAGATCCTGAAAATTC
CGAAAGCGAAACGCGAGCTGGTCTCCAGAAGTTTGAGAACGGTCTCCCAGGCTTTCCAGCGTCGTCCCGGGA
TTCTCGGACACCACAAACGCCATCAACCACGAGCACCGGTGTCCGTGGCTATTGCCCCGAATGGTCCCCATCC
GCGTCCCCGGGAACTCCCTCGGCTTTTCGCGCATCCAGGCCCCAGCCCCAGCTACTGGTGCGCCCCGACCC
CTAGGTGCCAGAGCGGTGGTCGGCCGGGCTCCTGCCCAGTCTCGGCTCCTCCCTCCTCCCACCAGAAGGAA
AAACTTGGGCCCTTCGAGAACCCTGTGGAATGTTCTTTGTAATCAACTGTACATCCGCTTCCACGGCCGGCCT
CGTGCAAAATCGCGGGTTTCGGGGCCTTGGAGCAAATTGCGCTTGTCAGCGGCGACGTCAGGAGGACAAGGG
GAGGGGTTCGCGGCTGAAACTGCAGCTTCGCAGCACAGAGCCATTTTAGGCTGCTCCCCACCTCGCGGGGCC
CATGGGAAAGCCGGCCCCGGGAGGCGCGCCCAAACGCAGGCTGGAGGAGCCACGGACGCGTCCTGGCCGGC
GTGTCGCCATCGTTCAGCCTCGCTGCCCAGGTGGGAGGGGTCACCTGCCGCGGGGTCTCCAAGCCAGTGCCG
CTTGCTCCCGGCCCCACCCACTGACAGCACGGCGTCCGAGTGACCCTGTCAGCCTCGTTCTGCGCTCCTGC
AAACCACGTTGCTGCGCTAACTACAAACCTGGCCAACATGTCTTTGTAACCCTATCATTTAAAAACGCTTCCA
GGCACCTGGCCGCTGCCAGATCAGGTTCGCGGGCCCGGAGGAGGTCCTCCCACCTGCCCCCGCCAGCCCCG
GGGACCGGCGCGGCCTCCGTGTGGCCCCCGCCCACGAGGTCCCTCGGGCAGGAACCG (SEQ ID NO: 17)
```

112; SW vs I; chr14: 37746906-37747538; 14; SSTR1; INSIDE
```
CGGAAAAACTCGAATGTCGCCCTGCCGTTCCTGGGGTTGGTGACAGGTCTGGTCATCGCACGGCGGCAGCTC
CTCACCTGGATTTAGAAGAGCTGGCGTCCCGCCCGCCCAAGCCTTTAAACTCTCTCTGCCAGAACCCGCCAA
CTCTCCAGGGTACAAAGTACAGCAGGGACGCGGGTGGAGCCCTTCCAAGCGGCGCAGCCTTATCTTTCCCGA
GTGAACACCTAGGTGGATTCCCAACACCGCGCTGGCACGTTTCTGGAGGGAGTCTCAAGCTCCTCCAGAGC
TCCCAGCTGCCGTCCTCGTTTCTGCAGTCGATATTCCTGTGGGAGACACGGGGGCTCTGAGCGCTACGAGC
TTTATTAAGAGATTTGCGAATGGTTCACTCAGGTCCCTGAACACTCCCAATAGCCTAAGCTGCCTGCTGTGTT
ATAGCGCAGAAGCCCCTAACGCACGGTGGTTGTCCTTCTTCTCATAACGCTCGCAGCTTAGGGCCAGTTCCG
CGATTCTAAGAGTAATTGCGTGGGCACCTGTGCTGGGGCCAGGCGCAAAGAAGGGAGTTGGTCTGCGCGAAG
ATCGTCAACCTGCTAACAGACCGCACATGCACTTTGCACCGACCATCTACG (SEQ ID NO: 18)
```

TABLE 2-continued

CpG islands differentially methylated in NMI-BC wt vs invasive BC.
Provided for each are: ID; Comparision; Coordinates of selected regions containing relevant
CpG islands based on Homo sapiens full genome as provided by UCSC
(hg18, Mar. 2006);
Chromosome; GeneName; Location relative to gene Sequence.

118; SW vs I; chr14: 53488428-53488700; 14; BMP4; INSIDE
CGGTAAAGATCCCGCATGTAGTCCGGAATGACGGCACTCTTGCTAGGCTGCGGGCGGCGGCGCAGCCCAAAC
ATCTGCAGAAGTGTCGCCTCGAAGTCCCGCAGGAGCTCATGGCTCTGCCCTGAGCGCGTCCTCCCGCGTGGC
CCTGAATCTCGGCGACTTTTTTCTTCCCCGTCTCAGGTATCAAACTAGCATGGCTCGCGCCTCCTAGCAGGAC
TTGGCATAATAAAACGACCATCAGCATTCGGTTACCAGGAATCATGGTGTCTCTG (SEQ ID NO: 19)

147; SW vs I; chr16: 52873104-52882105; 16; IRX3; PROMOTER
CGCGAGGATGGGCGGGCTCCACGTCTGGGGGCGCTGTGAGCAGGGCCAGAGCGAAACCTCAGTCTGAGTTT
ACGAACTGGGAAGGAGCCTGAACCCCAGAAACACCGTTAACAAAGAGGGCGAACGCAGGGAGCCGAGGAGA
CGTCTCCTTGGCCTCTGGGGAAGGGGCTGGAGGAGCGAGCCAGCTGAGAAGCGGCTTTGCCGGGTGTCCACT
AGCGGTTCGCCAGCCCTCTGTGCGCCCGCAGAGTGACGCAGAGGCCGACACAGTCCCCTCCCCACTCGCCCC
TGGGGCGCCGCCGACCTTGATCACCCCCTTCGCGGAGGGAACTCCCAAGGCGCGGCGCTGGCCGCTGGGTC
CGCATGGCCCAGTCCTGTCGGGCTCCGCTCTGCTGCCGCCGAGCTTCGAAGGTGTGCAGTGTTGAGCCGTGT
CTTGTTCCGTGGCTTCGAGGGGTGTGCGCGCTTCCTATACCTCCCGGAACGCGCGAGATAGTCACACGCGCC
ACTTTGAGGGTCAAACACCCCGCATCTGGCCACACTGTACCTTTACTAACGTGGGGAGGGGGCAAAAAAATG
TGTCTCTCCTTCTTACCCCGAGGTGTCACTCGCCCAAACACTCCCTACAACTTCTTCAAGTCAAACTTGGCAA
GGTTGGCTGGCTGACTGCGAGAGGAAAAAGAGGGCGCGGAGGGGCGCGGCGCGGCGGGTGTAGAGG
CCACGGAGGCGAGGCGCCGAGCGTCCCCTTTGTCCTGTAGAGGGAGCTCCAGCCCCAAATTTCCCTGCTGCC
TCCCCCGGCCCGCCCACCCCAGGCCCGCTGGAGCCGGAATCCCGGCTGGAAAGGTGCGGCGGTCTGACACC
CCCGCAACCCCCGCGCCGGGGCCTTAGCAGGATGCCTCTTCTAGGGCACGTGGGAAAACCCACCAGGGTGCC
AAGACGCACAGATGCTCCCAGGACCCGGGCTCCCCAACTCTCAACTAGAGCTGGGCGTCACACATCATCTAG
AGGATTATGTACCCCTAGGCGACCCTCTTCTCCATATCCGCCTCCACCGTCACCCCACACCCTGGCATCTATA
AAGAGGGAAGGGGGGCAACCGGGTTGGAAGGAGGATGGAATCTGGGCTTGCACAGCCTCTTATAGGTAACA
GTGAGAAAGCCTAACTGTGTCGATCAAAGAATGGGGACGAAGGGAGTGATGAGAACACGACC (SEQ ID NO: 20)

151; SW vs I; chr16: 85098883-85102729; 16; FOXF1; PROMOTER
CACACACACACACACAAAAGTTGGGAGAGAATGTGAGAATGCTTGTGTTCGTGGACGCGTGCGCACGTATGG
AGCGGCGGTACCTATGATTATTTGCGCGTGGCGCCTGGCTATGCGTGGGCGAACGGCAGTGGAGAACATGTG
GGCGTGCATGAAGTGTGCACTTAAACCAAAGTGTGCCCTCCCCGTTGGGCAGGCCTGTGTGTTGGTCCAAGG
GTTGGGAGCGCCTGAGCTGTGTGAGGGTCGCTGGGAAGGGTGTTTGAGGCCGTGGGCGGTGCGGAGCGTGT
CTGTGTGCGCGGGGCTGAGCTGGTTGTGTGAAGTGGTAGCGGGTCTGCCAGAGAGCGTTTACCTGCGTGAAT
GCACAACCACACACTACGGGTCACGTCCCACACTCATTCTTTCCCTAGGCGGGCCAGGCTGTCTGCACGCGG
AGACCCAGAGAGGCCAGCGGAAGGGCAGCGCGGGAAGGCGCTCTCTTCTCCCGCGAGCGCAGATCTGGCGG
AGGAGGCGGCGACTGCCCGGCAGGCTGCGCCGGCGAGCCCCCCAGCTCCTCTCACCGACGTGCCAGGCGCC
CCGAAGGCGACAGGCGTCTCCCGCCGAAAATGAAGGCGTCCGAGCCAGGAAGGTGGGGGCGGGTAGTTAGG
GGAGACAAGGAGTCCGGAGAAAACCGAGAGGCGGGTAGGCTTTGAACGCGCCGCGCCGCGGGCCGTGCTGC
GAGCCCGGCACACGCCTCTCGCCCCAGCTCGCGCTGGGGCTTGGCCTCTAGGCTCTTCGCGATGACCCGCGA
AAACACCCCTCGCCCCCCTCTTCTCAACCGGAACCCTGGAGGGAGGAGGCCGCGCCCGGCCAGCAGTCGCTGC
GAGAGCAGCACTCACCTGGGTCTGTGCGCGCCGCGATGCGCCGGGGCTCCTGCGCTGTCCTGCGCTCCGCTC
TCGGCACCACCTTTCGTGGCTCCACCGCCCCCAGCCCGCACCCGAGCGCTGAGGTGCAAGGGCAGGTCTGCG
TGCGAGCCCCTGCGGGCTGGCAGCCAGGTGCGCGAGGGCCGCCCTTGCCGGCGCTCCCAGCCCGCGCTGT
CTGCTCTCAGGAACCTGGCCTGGCGCCAGTGTCAGAGGCCCCGCGGCGGCGGCAGGCCGAGCCCACAGGG
GCATTAGGCCAACTCCCCCTCCCGCCCTGCGCACGCGGAATTCTCTATTATTATTATTAAAGAA (SEQ ID NO: 21)

180; SW vs I; chr17: 75377960-75381951; 17; CBX8; DOWNSTREAM
CGAGCAGGAGCAGGCGCGGCCCCGGATGTGGAGCCAGGCTTTCGGAGAGCCCATTTCTACAGGGATTCGG
CCCGACGGGTGCCGGGCCGAGCTCGCTCGGCCTTTGTTAGTTTCGGCGCCGCTGATTGATCGCCTAATCCAG
TGGACCCTGAGAAGAACAGACTGGGCTGCCAATGGCCCGACCCCACGCCGCCGCGACCTGCCCGAGGGCAC
CGGGAGCGATGGGTGCGGAGGGGCTGGGAGGACGGTCATCCGGGCGGCTGGACCTCTCCTTCCTCCCCTCC
GCCTTCGTGGCTCGGCGCCGGGCCTCAGGGAGGACGCAGAGGGGGCGCCCGTGGCGGTGGGCGCCCAGCGG
TACCTTTGGGTCGGGGGGAGGTAAGGCTTTCTCAGCTCGGGTTCGGAACCAGAAAGCCACCGGCCCCCCGGG
GGTAAGGGGTGGGCGCCGGCGACCCGGGCCGACGCCGCCACCTCAGAGGGCGCGCGCGTCCCACCAAGGTC
GGCCGCCGGCCCTTCGGACGGACGAGGGAAAAGCCAGCCGCGGCTCCAGGGTGCCCGAGACTCAATCGCAC
CACCTGCACCCCGGCCACCTCCGCCTCCGAAGTCTCAGGAGGAAAGCCCCGACCCAGCCCGCAGCCTCTCTC
GCGCGTTCAGGACCCGAGGCTGCGGGCAGCCGCCTTCCACGACGGACAGCACGGAGTCCCGCCGGCCCCG
AGCCACGCCAGTCTCGGACTTCAGCTGGGTCCGAGGCTCCTCTGGGCCTGGAGGGCTTTTAGAGGAGAAGAG
GAAACCAGCACAGGAGCCCAGAGGGCCGGACAGGTCTGTGCGCCAGCGGCCCGGGCGCATGGCACAGTGC
CTGGATCAGGATTGGTGCGAAGCCAGCATCAAACGGACAGAAAATGAATCCGATCCGACACTCTAGGAAGAG
CATGAACCTTCCAATCCAACCAATGTTTGTGCGAGGCCAGGTTCCCCGCCCGGTGGCCCACAAGCCAGCCC
TGTCCTCGGGACGCAAGGTAACCAGTCCGGCTGGAGGCCGCCACGCACGCCTGGTCTCTGCAGTTGTGGCGG
ATTCCCAGGGACTCTGCCCAGGAAATGGAAACCCGTGAGGGCGCTCCTCAAAGCCGAGGGTGGTGATGGCCA
GCGAACCCGAAAAAGGGCAGGGTGGGCGCCCTCCCATCCGCTTAAGCAGTAGCCCATTCCACTGC (SEQ ID NO: 22)

187; SW vs I; chr18: 68359955-68362770; 18; CBLN2; INSIDE
CGCGCGCGCAGGTCCCCGCCCCTCTCCCCGGGCTGGGGCGGGTGGGCAGGCCGACGGCTGACCTGGTCG
AAATAGATGGTCATGGTGCGGTTGCTCATCTCGGACGGCTCGTGGTTGGTGCTCCGGTGGCGGAGAAGGCCA
CCTTGGCGCTGCCGGAGCGCACGGAGATGCCTAGGGAGGAGGTGACGGCGTCGTCGCCGACAGGCTGGAG
TCGCACACCACCAGGCACTTGCCCTCCAGCACGATGGGCTCCGTGTCGTTCTGCGCCCGCACGGGGCAGCAG
GCGGGCAGTAGCACAACAGCAGGGCCAGCGCCACCCCCAGGCAGGATCCGCAGCCGCCCGGCTCGCGCAGC
GCCCCCCGGCGCCCGGGCATCATCAGCCGCAGCCCGAGTGGCCCCGGCCGGGCGCCTGCATCGGGACTGG
TGGGAGGCGGCGCGCGGGGGTGGAGGCCGGCGCCGGCGCGAGCGCGCGGAAGGGCGCGAAGGAACGCGCG
GAGCTCGCAGCAGCCTCCGGGGGCCTTCGTCCCCGGCTCTGACGTTCAAGGCCAGGGTCGTTCTCAGAAGAA
AGGCGCCTGTGAACCTGTCAGGGCACAGAACCCAAAGCCTTACACCGGGAGGTGGAGCCACCGGGAAGAAG TABLE 2-continued CpG islands differentially methylated in NMI-BC wt vs invasive BC.
Provided for each are: ID; Comparision; Coordinates of selected regions containing relevant
CpG islands based on *Homo sapiens* full genome as provided by UCSC
(hg18, Mar. 2006);
Chromosome; GeneName; Location relative to gene Sequence.

```
GGGACTGGGAGCAGGTGCCTGCGGCTCGGGGGTTCTCCCCGAAGGCCACCCCCTTGGTCCCGCGCACAGCC
AACCCGCTTTCCGATCTGGCACAACAGGTCCGGAGAAACGCCCGGGCGCAGCTGGCAGCGCATCCCTGAAGG
CTCCCGAGCAGCGCGCGGGGCTGCGACGAGGAGGGGGCCGCGCTTCTGCAGGTCCTCGTCGCTAAGACGGG
CCCCGAGACCCTCAGAAGGCGTCACCGCCACCCCGCCCATTCACCAGCGCGGAGGGGGCTAAGACGCAGGC
AAAGAAAAACCTACGAATGCTTGCCTTCTCGCCTTCATCTCACAGCATTTCCTTGGAGCAGACCAAGGAACCC
TTTTCCTATCCCTTGTTTCCCTGCTATCCTCTATTTTTCAATCCTCGAGATGTTTTTAAAGTCCATTTAAGTCCC
TTTGGTACAGATTTTATCTGTTTTCCACCCACAGAACAAATCCCAGGAATCTCCTTGGGGCGAATAAGATTAC
TAGGGGGGAAATACACCACACACACACACACACACACACACACACACACACACACACACA (SEQ ID NO: 23)

200; SW vs I; chr19: 42586165-42586705; 19; ZNF569; DOWNSTREAM
GGAAGTATCTTGGCCTGCACGCGGTTTACATCATTGGGAGCACAGGCCTCGCCCTCCGAACTACGAGGCCCA
GAGCCCTTCGCGCCGAGCGTTTCCCGCCTTTCCCCTGTCTCAAGTCATTGCCCAGGGCCACTGCGGGCCGTTC
CTGCCTGTCCGTGGAGCTGCGCCCCCGTGTTCCCAGGGTGAACGAGCACGTGCGAGGCGGTGGTGCTTGTA
TCCGGGATAACCAGGTAGGGCGGCTGCATGCTTCATAGAGGCCAGCCTGTGCCGACCGGGAGCTGTAGGACG
GTCTGTGTCTGGGCTGCTTATGGGTATTCGCGTGCGTCTGCCGGTGCGCGGTCCGAGCCTACTCACGAGAGC
GTGTGTGTGTCTTCTGTCTCGTGTTGCTATGAGGTTTGCATCTGTGTGGCTGGAATAGCTTGTTTGTGGGGC
CCGCGCGTGACCTGTGTGTGCGTTACTGTGTGTGTCTAGGCAGGATAGTGACGGGCCGTGTGACTGTGACGC
CATCATCAGGTTGGTGAGATGGCGTGACCGCG (SEQ ID NO: 24)

207; SW vs I; chr19: 63420090-63420541; 19; ZNF274; DOWNSTREAM
CGAGGGAGGACGACAAGCGGGGACGTTGGCGGAGGGGTTAATGGCGGAGTCGCGATCCAGCCGAGCCCACA
ACTCTGGGAGGCTGGTTCTGCCTCTCTCCCGAAGCGTCGCCCGGCTAAGCTTCGAGACCAGGACACACAACC
GCCGACTATTCCAGAGCCCACAGTCGGCTTCACGCTGGAGGCCGGAAACGACACGTCCCCAAAGCCCGCGCG
CGCGGCCCGCCAGAACTGACCTACCCAATCACCGCACCGCTGCGATCAAGCGGCGACACACGTTGCCGGGTA
AGAGTCACGCTTGGCAAATAAGCAACCTGCCTCATCCAATCAGCGTCTCGCCTGCCCGGTTAGTTCCTTGTCT
TGCCCAACCAGATTCTTGCCTCCTCCATACCGCTACTTGCGTGTGCCGGTGCCTGGCCCAATCAGCGTCTTGC
GCCTCTTCTCGCTCCCG (SEQ ID NO: 25)

223; SW vs I; chr2: 72224630-72228512; 2; CYP26B1; INSIDE
CGCTTGTTGCGGTGGATGTCGCCAATGGAATTGGACACCGTGTTGGGGCCCAGCAACATGCGGGTGCTGCGA
GGCCACTCGGTGCTCACGAGGTGGTGCTCGCCCATGAGGATCTTGCGCACGTTCTCGCGCCGGTCACGCGTA
TCAGCGGCCGCCCCAACAAATGCGTCTTGAACACGTTGCCATACTTCTCCCTCCGCGACGACTGGAAGCCAG
AACCCTGCGGGAGCCACACCCGGGTCTCTCTCAGGGTGCACTTCTGCAGAGGGCCCGCGAGGGAGGGGCGG
CGGACCCCAACCGGGGTACAGTCACCTGCCCCCTCTCCCCACCAAACACACTCACACAGACGAGCACGCAGG
TTTTATTTTTCATAGCGTGCACAAGAACTGCGAAGTAGGGCCTAGAGGATAATAAATAATGCAAGGAGGCGGA
GGCCCAGGGGCACCCCAGGAGGCTGTTTTTTGGTAATGCTTTCGAGAGGAAAGAGGTATCCCGGACAGCTG
GACCCGAAGCGGGAGTCTCCGCCCCACCCCCACCCCCACACCCCCACCCCGCGCTCGGGAGCCTCTCGGAA
TAAATATTTCCAGGCTCCGGGCCACGGGCTGGCGAGACCCCGCGGGGTGGCCGCAGGCCAAAGATTATTATA
GCGGTAAGCGGTCGGTGCCCGGAGGCAGCAACTACAGATGGGGGTTGGAGTTTCCTCCGCTCTCCGGTGTGG
CCCGCGCAGGGACCCGGCGGCCCTCGGAGGACTCTGCAGGGCGGGGTCACGGGCCCAGAGCCGCGATTTTC
CTAATGCATTTTGCCCTGGAAATACGGAGACGGACTTTGGTTGCCGCCCTGGAGTTTGGAACCCGAGCGCGG
GGCGGGGCGGGACCGGGCAGGGCGACCCGCGCAGGTAACCAGATCCCCGGTGGTGGCGGCGCAAGCCGAG
GATGGCGGGGCCGGGCCGGCCGGACTCTCGAAACGGCTGGCGGAGCCGGCCGGCGCGGGTACCGGAAACC
GTGGAGACCTCAGAGGGGCGGGGCAAGGGCGTCCCGCTCACCTTTGACGTCGGCACTAGTTACCCCACCCC
ACGTTAACCCTTCTCCTGCCGGGGCAGCACCCGGCGCAAAGGGGAGGGGCGCCACCTGTCTAGCCGCCCCGC
CTGCCAGCCCAGAGCGTACCGACTCGGGCTCCAGATCTACCCGCTCCTGCACCCCCGAGGG (SEQ ID NO: 26)

227; SW vs I; chr2: 104835284-104839920; 2; POU3F3; PROMOTER
CGCTCGGCAGAGGCACGATACAGCGGGAGAGAAGGGCAGGCCCGTTCACATTTTAATCGGAGCGCACCGGC
GGCCGCTCCTCGGCTGCGTCCTGGGCTGCCGCTCGGGCTCGGGACTGCCAGATGCAGCTCTGGCTGGGGGC
GGCGGGCGCAAGCGGGCGCACCCGCAGCTAGGGGTGCGGGGTGCACGCACACGCACGCTCATTAAGAGCCA
TGTATTTATTGAATGTCCGAGTTGGGTTAGTTCATTGGAAATCCCCGAGGAGGGCTCAATTTGCCCTTGTTTT
CGTTGCCACTTTCCTTTTTTCTTGGTTCGCTGAGGTTCCTCTGTGCAGCGTTTCCGCTTGGCCGCGTCCCCCC
ACCCCACCCCACCCCACCCCCGCTTCTCTCGCCTACCGGGTGCACTCCCCCTCCCATCCCCCTTAACTCTTTC
AGCTGGGTTAGAGCTGAGAAAGCATTTGTCGCCGCCAGCCCATCCACCACGCAAATCCATCTGAGACAGAAA
GGAAAGAAAAAAAGCACCACCATGCCTAAGAATAGAGAGCGAGCAAACCCCCCACCGCTAATCACACACA
CACACACACACACACACACACACACGAGGAAGCGGTGGAGCAGAGAAGGGCGCGGCTAGCCGACCCG
GTTCTTTCGCCCGGCTCCTGCTGCCACAGGGAATTCCTAAAGCCATTGGGGTCGAATACACTTACGATGAATC
TATGGGGGAAGGTCGGACTGATTGCTTTTCAAATACATCGCACGGCTCCGCTGACCGGCACCCTCCAAACTCA
CAAGGGCACGCACGCTACTTGCCGAATCCCAGAGGAGGGAGGAGGGAGGGAAGGGAGGGGAGAGCGAAGGAG
GGAGAGAGGGGGTGGAGGAGCCAGGGAGCGGCGGCAGCGAGCGGTCCGTCTCGCACGCGCGGGCACCGCG
CTGGTCCTGGGCTGCAGGTTTCCCAGATGATGGCATCCGAGAACTTAAACAAAGGGGCTGCCGCCGGCGCGC
AACGGCTGCGGAAAGTTGCGGTGCGGATTTCCAAGGAGCGTGGCCACGACCAGAGCTCTTGGCGATGCGA
GCCCCCGCTTCCCACCCCCGCCGATCAGAGAAGGGGGCCGGCTGGTGAAGGGAAGAGGAAACTTTGAAACCA
CTGGGGACACACTGTCTATAGGTATTAGCTTGAATGGTACATCCGTGCCGCGCGCTTTACA (SEQ ID NO: 27)

235; SW vs I; chr2: 124498611-124499725; 2; CNTNAP5; PROMOTER
GACTCTCATCACTACCACACCCATGTGTCTTTCCTCTCTCCGTCTCCCTGAGACGCCAGTGAACCACCTGGGC
TTGGAATCCAGAGCCCCGGAACACCTTGCAGTACTTGCCCGAAGCAACGCGCCACAGCGGGAGGGAGACGCA
GACGCGAAGACCGGCGAGAGGATGTGCGGTGGGAGTAGCTGCGGGGTCTGCAAGCAGGGGAGCGCGCACAA
CGTTAAACCTTGAAACCAGAAATCCCGATCCTATCGAGACCCATCAGCTTTTCCCATTTGGGAACGAGCGCAG
GGGAAATTAATGCGTAATTCAAGCTCTGTTTTCCCCTCCCCTCCAAAGGTGAGGTGGGGGAACGCGTCTCGTT
AGCTCATTACAAAGCTTTCCGTGGGAAATTCCCTCTTCCTAATGCGTCTGTCTTGCAACTCCTATTAGCATCCT
```

TABLE 2-continued

CpG islands differentially methylated in NMI-BC wt vs invasive BC.
Provided for each are: ID; Comparision; Coordinates of selected regions containing relevant
CpG islands based on *Homo sapiens* full genome as provided by UCSC
(hg18, Mar. 2006);
Chromosome; GeneName; Location relative to gene Sequence.

```
TCGACAGCGGCCTTTGAAAATCTCCTTTAAATTTCATACCTCTACTCGTTTCCCAAATGGGGGAAGGGAAGA
GAAAGCCGGGGGGTAGAGAGAATTTCCTTCCCCTTTCCCTCCCAGGTAGCCAAAGCGCACCGCAGCGGCTTG
GCTTCCTGGAGGAAAAGCGCCCGAGCGGGGCAAAGACCCGCCCAGGCTGCTCTTATAGGCGACGCGGGGCG
GGCCTGGCTGGGGGCGGTGCCGCGCGGCCCCGCTCGCCTATAAGGAGCTGTCCGCCACCCGGGTGCTGATT
CCAGCTCTCGCGCCCGACGAGGTGGATTTGGCTGTCCACCGAGCTCCGGCGCCTGTCGTTCTAATTGGGTTT
GGATTTGCACCGTTAAGGAGGGGGAAGAGAAGGAAGAGGCGGGCGAGGAAGGCGAGTCCAGCTAGCGGCTG
TTGCGGGGACCGTAGCCCCAGCTGCAGCTCCGAAGAATCCCCCGCCACGGTTTCGGTGGAGCGTCTGGGCAC
GGGATGGAGTGAAAGAGCGAGTGCCTCTCCAAGCGGGGGTGGGAGGGGGCAGGCTGTGCAGAGGAGAGAGA
CAGCGAGAAGAAGCCGCGGCTGGCTACTGCGAATTTGGGATTCGATTGGGAGGGACCGCTCACTCGGGGGA
AATGGATTCTTTACCACGGCTGACCAGCG (SEQ ID NO: 28)

257; SW vs I; chr20: 22505518-22507240; 20; FOXA2/C20orf56; DOWNSTREAM
CGTACCCGGCTCTCAAAGGCACGGCACCTTTGAATTAGGTTGCGGAGTGGCCTGGGCGAGGGGACCCGGGG
CCATCAAAGGCCCGAGGGAAGGCCGTGGGGCGACACCCGTCTAATGACAAGTAATTAAGGATTCGACGCCGC
GCATTACCAGCGGAACGGGAGGCATTAATTATTTAAAAACGATTAGCCTTGCCGTGTGTCCTGCAGGCGTCCC
ATCATGTTCAGCGAAGATAACCAGCCACCCGAGGCGAGCCGGGGCTCGGAGGGCGGCGGGCGCGCTCCCCA
GCAGGCTTCGGGGCGGTGGACACGGGCGCACAGCCCAAGGCACCAGGGAAGGAGAGGAGGGGCCACCAAG
GGTCCCCACACAGGAAGGTGACTACATAACACTGACCCTGCTGAACAACGAAACAGATTTCTGCCCACTTGG
GTTCGAAGTCTGGTGACTGCGGCGCAGATGGGAAAAGCTTTCGGTCGGGGGTGGTGGGCAATTTCCATGTGC
CAGTTCCCTGTCGCATCAGACCAAAGACCCAAAGTAACCCAGCCAGGCACGGGCCTCTCACAGTGCCTGCTA
CCCAGGCGTTTAAAGAAAAGACCCCAGAGAGAATGTGGATCTGGCGTGGGGGCAGGGATTGGGGGGGGGCC
TGGTAGACACCTGGGGAAATACAACTTTATGAGGTTTCAAGGGGCAGCAGCAGAACTACTATTTTTCCGAGGT
CCACGCCTTTCCGCAGGCGGCGGAAAGACGCGGCTGGTTCTGTTGGGTCCTACAAACTCGCGTCCTCCGGAA
TTCCCGAGGGCAAGCCCGGCACGCGCAGCGTGCTCCTGCCCGTGGAAGGGGGGAAATCGGCGACTGGGTTG
CAGGGAGAATGCGATGATAAATGGCCCTGCGTCTGCTTTCTGACTTTCTCTCCTGGACCCAGCTCGTAACCCC
AGAGGCTCCCCAACCTGCCTGCCGCCAAGCACGGCTGTGCGCAAAAGGCCACCACCGCTTCCTGCAGCCAGA
GCTAAGGTTCACTCGCCTCTTAGAAAGGCGCGGCCCCTCCCCTGCTGCTGCTTGATGACGATCCCCATCGTCT
CCTCGGCCTGCCTGTCCGAGAAAGAGTTGAGACTGGACTCGAACCCCTGCGCGCCAAGGGGAGGGCGTCA
CCATGCTCCGCCTCAGCCTCTTCAAACTCCCATGCACCACGCACATCATTTTCTGCTGA (SEQ ID NO: 29)

262; SW vs I; chr20: 54012011-54014085; 20; CBLN4; INSIDE
CGACGTCCAGGGACCAGGTGCCCTTCGGCTCCCGCCGACCTGTTGCTCGAAACTTGCCCTGAGCTCTCGCTG
CCGGGCTCTGGGCTCCCAAGCCTCTCCCCCGCCGCCGCAGCAGCCTCTTTTAGGGCCCGGAAGAAATGGGAG
CCGGGGCTGGTGAGAGGGGTAGGAAGAGGGACGGTAGAAGTTTCAGACCCAGGCATATTTGGGAAGGCGAG
TGCTTTACATGATTCCCCATTTCCCAATCGGACCAGCTTAGCCTGGGCAGGCAGCCTCGTGCTGAGGTGCCTG
GAGACCGCCCACCCCTAGGTGCTCGCTTCCCCCCGGGTCTGACCTGATCGAAGTAAATGATGCGCGTCTTGTT
GCTCATCTCGGATGGCTCGTGGTTGGTGCTCCGCACCGCCGAGAAGGCGACCTTGGAGTTGGCCGCCCGGAC
CGATATCCCCAGCGGGAGGAAGAGGAGCCCTTGGAGTCCTGGCCCGGGTTCGAGTCGCACACCACCAGACA
CTTGCCCTCCAGCACGATGGGCTCCGTGTCGTTCTGTGCCCAGACGGGCAGCCCCGGCAGCGTGAGGACCAG
CAGCACGGCCGGCACCGCGGACAGCGCCCGGCGCCCGGAGCCCATGGTGAGCCGTGTGGGCAGCCGCGCCG
GCTGGCGCTGGTGCTCGCCCGCGTCGCCTCCTACCCCGGGATCCCGGTGCTCGGGAAGATGCTAGCGGCTAG
GTCGACAGCGCTGCAGGAGCGACGGCGGCGGCGGCGCGCACACTTCCACCAATTCTGTGGCTTGAAGTCAAA
GTCTCCCCTCGAGCTCTCTCGCTGCTCTGTTACCTTTGTCCTTTAAGGAGCTCATGCAGCACCCTTTACCCTAC
TCTCCTCCGCCCAAGAATCAGCCCTGCCTGGGGCCCCTGCACCCACTCTGGTTCCTAGACATCTGAAAGTCAT
CAAACCCTCACATTCACACCTCAAGGCAAAAAATAATAATAATAATAAATCTCACCCCAAACTCAAGCACCAC
CAGCTAAACCACGGAGCAGGAACAAAAAGAGGGGACTCAAAGAGAAGCCACAAGGGTGGCGGGTGCCCAGC
GGCGCGGGTGCCAGTCCTGTCTGGCTTGCGGCAGGGACGAGTTACAGAGGCAGAAGGTCCTTCCCAGGCTGA
GAAGACGCGAGGCTGTGTTCATGGCCAGGACGCCAGCGACTCCCACTTTCGCCTG (SEQ ID NO: 30)

268; SW vs I; chr21: 33316999-33322115; 21; OLIG2; PROMOTER
CGGTGCCGGGAGCCTTGCCTCCCGCCGCCACCCCTGGTCAGCTCTGCGCAAGAACGTCGTTCTGTTTGGCAG
CCAGGCCGAGACGCAGCCTGAATGTGAGCAGGAACTCGGAGAAGGGAAGGGAGAGATCAGAAAGAAGGCCC
GGGAGGGACCCGGGAAGCAGTGGGAGGTCTGCGCCCTGGAGCCCCGCGAGAGCCCGCCGGTTTGGCACGGG
CTCCTCCCGGGCCGCCCGGCGGTCCAACAAAGGCCGGCCCCGACACGCACCCGGTCTTTTGTGGGAGAGAAA
CACAAAGAAGAGGAAAAACACGGAGGAGGCCAACAGCACCAGCAGCACGGGGGCCAACCAGGAACTCCCGGA
GCCGGGGCCCATTAGCCTCTGCAAATGAGCACTCCATTCCCCAGGAAGGGGCCCCAGCTGCGCGCGCTGGTG
GGAACCGCAGTGCCTGGGACCCGCCCAGGTCGCCCACCCCGGCGCCGGGCGCAGGACCCGGACAAGTCCTG
GGGACGCCTCCAGGACGCACCAGGGCAAGCTTGGGCACCGGGATCTAATTTCTAGTTATTCCTGGGACGGGG
TGGGGAGGCATAGGAGACACACCGAGAGGTACTCAGCATCCGATTGGCACCAGGGCCAAGGGAGCCCAGGG
CGACACAGACCTCCCCGACCTCCCAAGCTACTCCGGCGACGGGAGGATGTTGAGGGAAGCCTGCCAGGTGAA
GAAGGGGCCAGCAGCAGCACAGAGCTTCCGACTTTGCCTTCCAGGCTCTAGACTCGCGCCATGCCAAGACGG
GCCCCTCGACTTTCACCCCTGACTCCCACTCCAGCCACTGGACCGAGCGCGCAAAGAACCTGAGACCGCTTG
CTCTCACCGCCGCAAGTCGGTCGCAGGACAGACACCAGTGGGCAGCAACAAAAAAAGAAACCGGGTTCCGGG
ACACGTGCCGGCGGCTGGACTAACCTCAGCGGCTGCAACCAAGGAGCGCGCACGTTCGCCTGCTGGTGTTTA
TTAGCTACACTGGCAGGCGCACAACTCCGCGCCCCGACTGGTGGCCCACAGCGCGCACCACACATGGCCTC
GCTGCTGTTGGCGGGGTAGGCCCGAAGGAGGCATCTACAAATGCCCGAGCCCTTTCTGATCCCCACCCCCCC
GCTCCCTGCGTCTCCGAGTGACAGATTCTACTAATTGAACGGTTATGGGTCATCCTTGTAAC (SEQ ID NO: 31)

276; SW vs I; chr3: 148591199-148594390; 3; ZIC4; INSIDE
GGCCGGCCGGCCTTCCTTCCTTCCGCCCTCGCCCTCTTCATGCCTCAGAAACGTGGCCTACTCTGCATTCGGT
GTGTGCGGAAGCAGCAATCACAGAGGCAGCCCTAATACCGGAGGCGGCGGCGGCGCAGCAGGGCCAGGTGG
TAGCTCGGGGCTGAGGATCGCGGCGGGGCAGCCGCTATGGGGCCCAAGCCCTGACACACGTACCATTCGCT
CAAGTCGGCGGTACGCGCCGCCACCGCCGCCGAGGAGGCCACCTGGGACTTGTGGCCGCAGTCCGACGAGG
```

TABLE 2-continued

CpG islands differentially methylated in NMI-BC wt vs invasive BC.
Provided for each are: ID; Comparision; Coordinates of selected regions containing relevant
CpG islands based on Homo sapiens full genome as provided by UCSC
(hg18, Mar. 2006);
Chromosome; GeneName; Location relative to gene Sequence.

```
GCGACACGAGGGAGACGGTGTAGCCGAATCGTAGCCAGAGCTGGGCGGCGGCGAGCGCCCGTGCACCTTCA
TGTGCTTACGCAGCGAGCTGGGGTGCGTGTAGCACTTGTCGCAGCCCCGCACCTTGCACGTGTATGGCTTGT
CGCTAGTGTGCACGTGCGAATGCTTCTTACGGTCGCTGCTGTGGCGAAGCGCCGCTCGCAGCCCTCGAACTC
GCATCTGAAGGGCTTCTCGCCTGGCGGAGGCAACGCAGAGACATTAGTGCTTGTGGGTCGTGTTCCCGTCAG
GTGCTTGCCACCCTCCCCCATTCGTCTCTCATTTTCTGGAAAAGAACTACAAAATATTTTCAGAAATCCTTTCC
ACGGCGCCTCAGGTCGAGCACCCCTTTCCCTCGTGCAGAGAGCGCCCCGGTGCCCTCTCTTGAACGCCTCC
ATCCCTCCCGCCTTCCTCCTCTGGGCTCATGGGGAGGGTATGGAGGAGGAGCGACAGTGACTCCATCTTAGT
CGAGTTTCCATCCTCGAAAATCCGATCCACTCGGGTTGTTTCCTCCAAATTTTCTCCACTTGGAACCAGAAGC
ACCTCTGCTCGGAAATACATTAACGGAGGAGCTCACAATATAGTTAACGGGGAAGCTCACATCTGCTCGATTT
AAAGTTGCTGTTTCAGACTAACTTCTCTGCCGCTACCCCGCCCAGCCGTCATCCCCCCCACCCACCCCCATCC
TGGCCCAAATTGTTTCCTAAAGTAGGTTTTGCGCAAACGCCAAAGCGATGAAATAATTTAAGGATGCGCAGCC
GATGCACATTGTGTGTGCATAAAGTGGATTCGTCTGCAGGGAGAGGTATTCTGAGCAATGATTCACTTCAGA
AGGATTTTTACAGGAATGGAGCCCCCTCCCTCTTTCCTTCTACCCCCTGAGG (SEQ ID NO: 32)
```

285; SW vs I; chr4: 122520930-122521740; 4; GPR103; INSIDE
```
GAAATGTTCTGGAGCATGGTGACGGGAATGCAGAAGAAGGTGATGAGCAGGTCACTGAGCGCCAAGGAGCA
GATAAAGATGTTGGTGACGGTGCGCATGGCCTTGCTGCGGGTCACCACGTAGAACACAGAGCATTGCCAAAG
AGCGCCAGGGCGAAGATGAGCACGCCGGTGAGCACGAGGGCCAGCTTGGCGCGTCCCGGCAGCTCTGGGGT
GTAGACGAGCGGTCGCAGCCGGTACAGAGCGATGAACTGCTCCCGCGTCAGGTTGTGGTCCCGCAGCAGCCG
AGAGAACTGCTCCGGGTAATGTTAAGCGCCTGCATTGCTGTGCGCTCCCGGGACGCGGGGCCACCGCCCGCT
ACTGGCTGGCCATCCGCATCTGCGGGGCAGCGAGGGCTTCGGGGGACCAGCCGGAGGCCGCCTCCCTTCCTC
TACTCTGGAGTCAGCCGCGCGGGAGGGCTCTAGGCTGCACCCGGGAGTTCGGGAAAGGAGGAGCAGCTCAG
GGATCAAACCCACGATAAAGAGGCGGGAAGCCAAAGCACTGGGAGACTCGATCTCAGTGACCAAAAAATGTT
CGCGGTTCAAATAAAGTTCTTCCCTTGCTCTTCCCTAAGGCGAGGCGCCGCCACGGTCTGGGGTGCTGGACG
CCACGCGAGGGTCCTGGCGCCTCTGGCTCCCCGCCTTCTGGCCATGCGATGCGGACGCCGGACCCGCTTGGG
GAGCGGTGGAGGGTGGGGCTGAACTCGGTGACGCCTCCCTCACACCCAGCTTCAGTGGCGCCAACGCCGCTT
CCCCGCACCCTCAGGGCG (SEQ ID NO: 33)
```

293; SW vs I; chr4: 155881084-155881434; 4; LRAT; PROMOTER
```
GAAGATGAGGTGCAGAAGTAAGCTGGGACCTGTGAGCCTCAATTTCGGCCTCTTCTGCGCTGAGACCCAAGC
GGATCTTGCTTGGCCTGTATGCGTTACTGGGGGAAATGGACGTGGGCCTGAGCGCGCAGGTGCGAGGGCGCT
GCCCCGGGGCCGACCACCCTGCGGGGACACTGTAGCTGTCATTCCTTCTTCTGCAGGCGGGTAGGGGAAGCG
GTGGCCAAAGTGGGAGTCGACCGCTCAGCACAGTCTGTCTGAGTGTTGACCAGGAAAGTCCAGGCTCTTTCT
AAATCTCGCCGCAGACCTGGTGACGCATTCGCATGTATTTAAGGCGTTTGCACGCAGAACG (SEQ ID NO: 34)
```

296; SW vs I; chr4: 177159356-177159814; 4; GPM6A; INSIDE
```
CTTTACTCTTGGAGAAATCCCTCACAACAAAGGACAAGGGAGAAGCAAGGGGGAGGGGCGCCCAGTGGACTT
GGCTGGAAGAAGTGAGCGGGCTGGGGTTGGAAGAGTAACTCGGGCTGCGGGCTGACGCAGTCGGCAACCGC
GGAAGAGCAGCATCTCCCCTGCGCCTGTGGATACGCCAGTCCAGGGATGGCGAGTGCTTTCTCCTCCCCAGC
TTCTCCCTCGCTCTTCGAGGTGACTCGTGGGACCCTGCGTCCTAGTGCTGGGTGTGAATCGGCTATTTCACAC
CCAGTTCTTCCCCCCTCCGCCACACGCAGTCACATTCCTGGAGCTATTCCAAGCTGCCTCCGCTAAGCACCGA
ATAAGCGGACCCTGCCTGGAAACTTGAGCGAAGCTGAACTGCGCCGAACTCCACCGTCCAGTGACCCGAGCC
AGTGTGGACGCCCTTTTAATCACG (SEQ ID NO: 35)
```

317; SW vs I; chr5: 140724146-140724826; 5; PCDHGA5; INSIDE
```
CGCTGTGCGAGCCAGGATCCGGGCAGATCCGCTACTCGATGCCGGAGGAGCTGGACAAAGGCTCCTTCGTCG
GCAACATAGCCAAGGACCTTGGGCTGGAGCCCCAGGAGCTGGCGGAGCGCGGAGTCGCATCGTCTCCAGAG
GTAGGACGCAGCTTTTTGCCCTGAACCCGCGAAGCGGCAGCTTGGTCACCGCGGGCAGGATAGACCGGGAG
GAGCTCTGCGCTCAGAGCCCACTGTGTGTGGTGAACTTTAACATCTTGGTTGAGAACAAAATGAAAATTTATG
GAGTAGAAGTAGAATAATCGATATTAATGATAACTTCCCGCGTTTCCGGGATGAAGAGTTAAAAGTAAAAGTT
AATGAAAATGCGGCTGCAGGGACACGGTTAGTGCTTCCCTTCGCGCGGGATGCGGATGTGGGTGTGAACTCT
CTCCGGAGTTACCAGCTCAGCTCCAATCTGCACTTCTCTTGGATGTGGTAAGCGGAACTGATGGACAAAGTA
TCCGGAGCTGGTGTTGGAACAGCCCCTAGACCGCGAGAAAGAGACTGTTCACGACCTCCTCCTCACAGCTTT
AGATGGCGGAGACCCGGTACTCTCCGGCACCACGCACATCCGTGTTACGGTCCTCGACGCAAACGAAATGCG
CCCCTGTTCACCCCATCCGAGTACAGCG (SEQ ID NO: 36)
```

333; SW vs I; chr6: 101023927-101024343; 6; SIM1; PROMOTER
```
CGAATCGGGAATTGGCATTCCGTAAGGGAGCGGAGGGCCTCAGGCCACTAGGCAGCTCCGAACGCGGGGAA
GCGGGAGCAAAGATGAGCTCAGAGCGAGGGTTGCCGGCGCCACCCTGGGCTGCGCATGAGGGGCCGTGGAC
CCGCCCCGAGACTCAGTGACAGTCGCAGCTTAACCCCGTTGGGGGCGCCGCCCCGCTGAGGTGGTTGCGTCT
CCAAGTCGTGAGCCTCCAATAGCTGCTCCCGCTTTCGCGTCGCAACCCCAGGACCCCGGGAATTACCACTGT
GCTCGTCTGGGCGGAGACCCGGTGCTTCGGAAGCCTGGGGCACATGCCTGGGTCCCACCCTAGACTCACCGC
CTCTGGGCCCGAGACATGGGAATCTGCCCTTGAATATCTGGGCGCCTTTGCTGTTA (SEQ ID NO: 37)
```

367; SW vs I; chr7: 121727243-121727884; 7; FEZF1; DOWNSTREAM
```
CGCTCCACAACCCGGAAGGAGCTCAGGCCGGACTTGGCGTGAGGGTCCCTGCGGGGCTGGGTCACCTACCC
GTCCGCGATCACCCCACAGGGGCTGTTAGTAATCTCCCTGCTTCCTAGGCCGTTGAAAGCACTCAGGTCACCC
ACTCTCGGTGACCAGAGCGGTCAGTCTTTCCCCGCCATGAAATGTGAGTTCGGGTGGCAGCCGCCGCGCCCC
TGCAGTGTCCCCTGCACATCTCCGGTCTCGGTCTCGCCTTTCTCAGCTCCGCGCCGCCTTTTCCTGGGCGCCG
```

TABLE 2-continued

CpG islands differentially methylated in NMI-BC wt vs invasive BC.
Provided for each are: ID; Comparision; Coordinates of selected regions containing relevant
CpG islands based on *Homo sapiens* full genome as provided by UCSC
(hg18, Mar. 2006);
Chromosome; GeneName; Location relative to gene Sequence.

```
CAGGACTCATGAAGTGAGGCGGGGCCACAGATTTAAGTTTATTCCCCGCAACTGTCGGGGCGGTCCCGGAGC
TGGTGAGGACGCGCTACGGTGGGTGCAGAAAGGAGATCCCTGGACTCTGTAGAACCTGGGCCCGCGGTGTG
GACCGATGGTGGATTCTCCGCGACAACAGCCCTGGAGGGGAGAGTGGGCCGGGGGAGGGGCCACGGGGCCC
CTGAGGCCTGCGGGGCTGGCCGCACTGGCCCCGGGCCTGGCGGGGTGGTGGAGTCCGAAGCGGCGAGGCGA
GGACCCCGGGGCCCGCTCCCCCCAGTCGCCCTCCCGGGATGTGGCCCCGCTGCAGTAGCACTACG (SEQ ID NO: 38)

376; SW vs I; chr8: 9798161-9799053; 8; hsa-mir-124a-1; PROMOTER
CGGGCTCCGGTGCGGGACAGGCAGCCGGAGGGAGCTCCAGACCCCTCCCCTCGCGCCCGCGGCCGCTGCGC
GGAGGTCTGCGGAGGGCGCCTGGCTCGGTCGGTCGCTCCTTCCTTGGCGGGCCCTCCCGACCCACGGTGCTC
AGCCAGCCCCATTCTTGGCATTCACCGCGTGCCTTAATTGTATGGACATTTAAATCAAGGTCCGCTGTGAACA
CGGAGAGAGAGGCCTTTCTCCTGAGGAAGGAAAGGAGGAAGGAAGGAAGGAAAGGTGAAAGAAAGGAAGAG
GGGTGGGTAGAAATGGAATAAGAAAACCAGGAAAAAGAAATAAAAAGCGGCGCGTGTGCGTGCGCACTGACA
GCGGGGAGAGGGATGGGGGTGGGGAACGCCGGAGGAAGGGACCACAGCATCCTCCCCGCCGCAGCTCCCCC
AATCACACAGACAATGAGATAACAGCGACGTCTTCCAAAGGTCTTTGTTCTCCCCCATCCTTTCGCATCCAGG
CTTTTTCCTGCAAAGCGGAGGGGTGGAGGGATGGGGGTGTGGGTGGAAGTGGGAGACGGAGGGGTGCCTC
CCCCGTGTTAATTACCCCGGCTCCCCTCGCCCCTTTCCCCGCGCCTCGCCTCCCCTGCAGCTCCAGACATGAA
AAAACAACATCGACCCCACCTCGCCCCAGCGCAGCAACCCACCCACCCATGTCGCCCTCTGCTTCGCCCAGG
AAACTGAAGGGGACTAGGAGGAGGAAGAAGAGAGCGAAGGACAAGGAGGCAGCGGGGACTCGGCAGCGG
CAGCCGGGGCAGGGCGCGCGGCCGCCCCTCTTTACCTCCATCGCTGAGTGGGGGCGCAGCCGGGCCGGGCG
TGCCGCAGGGGCGAGTTGCCGCGGTCCG (SEQ ID NO: 39)

380; SW vs I; chr8: 65661156-65662687; 8; BHLHB5; DOWNSTREAM
CGCGCGCGCGCGCACCCGCACGCAGTCTGCAATGCCCTCACCAGTCCCCGCAGCTGGGCAACCCCTCCAAGA
CCCTGTGTTACGCTTAAATTCCTCTCCCTCCTATCGTACCCACCATCCATCCTTAAGCAGGGAGGCCGAGACT
CACAGAATTCCCTTCTCCACCAACTCGCACTCTTGGTCTAGCACGCGGAAACCGAACCTTTCTACGCGGCCCG
ACCTTGCGATTGCTCCAGCATGAGTGGCATTGACTTTTCCAATGTAATGACTTATGAAAGATATAATCATGTG
TTAAATTGATCCTCCGTTTAACTGTTAATGGTGTGCTCTGGGCACATTTACGTATTTGATGCTATGGTAACTAA
TTACCACTAGAAAAAAGGATAATACACTTCCCAGACTTTGAAAAATAATCATGAGTTCACTTCCCGGCTCGCA
GCACATCGTGGCGGCCCTGCCGGGAGGAGCGAGAAACGAGTGGAAACCCGAAAGTGTGCTCATGGAATGCA
GGAGGTAATGAATCCTGGTCAGGTGAGACTACTTAGTCAAACCTTTAATGAAAACGTGATTCACATGGAAAGC
AGGAGTGGGAGGGAACAACTACACAAAGGTGCCTTTAAACAAAATTAAATGGCAAAACCTGCTATCAGAAAC
ATGAATAGGTTTCTTTCAATTAAAATGCAGGTAAGACTAAATTATCCACGTGCCAAGCAACTTTACATCAATTA
ACATTTTTTGTTGTGTGGGCAAAGTAAATGAGCCCGGCTCCTGCTCCTGTACTGCATATACAACTTGA
AAGTCTCTGGATTTCCAAGCCAATGAGCTGCAGGTTTATTTAAATTCGGCCTTTTAAATCAAACTTTAGACACA
GTAGGTGGAAGGAGGGAAAGAGAAGGAAAAACAAGGAGTCAGTAACTTCAGTTTAACAGTAGAAACAACTCT
TACGGTGAGAGTCTTTTTTGCCCGGCAAATCTCTGGCTCTCTGATCGACTGGTGTTTAGAACCAAGGTTCCAG
TAAACAGGGCTGGGTAGGATAACGAGGAGAGTGTTTGTGCTGGGACCTGGCAGGACTGGAGGAGGAAAGGA
GCCGCCTTCCAGCAGGTCCAGCATCCCTAGGTTGCAAACACACCAAATGACGTCCACGCAGCACTCGCCCCA
CCGCGCTGTTTTGCTTGCGCAGTGCTCCCGAAGGGATTCGGGATC (SEQ ID NO: 40)

398; SW vs I; chr9: 121170908-121172141; 9; DBC1; PROMOTER
CGTCGGGAGCGCGCGGGGACACACACGCCACTCACTCAAACCCGCAATTAGCCCTTTGAGCCCCAGGCACAG
GAACCCCCTCCCTAGAACTGGAGAAGACTTGGAGGCGGCGGGGCGGCCAGGTGAAAGCGGACAAGGGTGCC
GGTAGGGGGAGGGGCAGAGGAGCGCGGGGACGCCCCGAATGCGGCCCGGGGCCGGGTCCAAGGGCAGCGG
GGCTGCGGGGCGCTGCACCCGGCGCCGCCTTACCTGGAGTCAATGTCCGTCTTTGGCGGAGAGCTGCGGGA
GGACGCTTTTTATTCGCTCGGTGGGAACTTGGGAGAGCCCTGCGTGCAGCTCGCATTCCGGGCACGGCGCGG
GGACTGCAGGCGTGGGGGTACCTGGCTCCTAGCAGCCTGGCTCATACTCAGCCGTAAAGTCCCCTTCGCTGG
TCCCGAGGACAGGCATGAATCCCGGCTCCGGAAGGCGGTCACTCTCCCTCTGCCTCCCGGCTCTCTCGCTCT
CGCTCTCGCTGTTGCTCGCTCGCTCTCTCCCTCTCTCGCGGGTTCGCTCGCCTGCGCTCTCCTCCTCCCCGCG
CGCCAGATCAGTTTGCAGCCGTGGGGTCCGGGAGCGAGGCGGCTGGCGAATGGAGGGGAAGTCCAAGTGG
CCGCGGTCTCCGGGCGGGAGCGGCGGAGGCCGGGCTACGCCGGGGAGGGACTTAGCCGGCGACGGCCG
AAAATGAATGGGGAGCGGCGGCCGGGGGGCGGGAGGGAGGAGCTGAACGCCGGGGTTGCTTCCGAGGA
GTGTTTTGTACATCTTTAGGCGGAGGAGGAGAGAAGCGAGAGGAGGAGAGACGGGAGGCCGCCTCGAGGGA
AGGGCGGCCCGGGTGGGCTGGGGCTGAGCCGTAGGGAGTTTCGTGGGTCTGGGGCGTGTAGGGTGTTGTGT
CTATGCGCACGAGCATCCAAAGGGACCGCGCATACGCGCAAACCCGGAATCCTGGTGCCCTAAGCGTGACTG
TACTGTGTGTGTCGCGAGTACCTGAGTGTTTCTGGGGCGGCAGGTGTTTCCACGGCCGCGTGGATCCATCGA
GTGTGGGTTTTGTCTCGGGAGTTGCCCGTGTGGGTCCGTTTGTGTCTGCGCGTCTCTCTGTGAGTGTTTGACA
CTGTTTGTTTCTCTCGTGTGTAGGCGAGAGCCCACGTAACCTCCCAGAATGAAGCAAGAGCTTCTC
(SEQ ID NO: 41)

403; SW vs I; chrX: 50040955-50041296; X; CCNB3; PROMOTER
GCGTGTCGCAGCTGTGCACGCTGATTGGTCCTCTGCTGGCCAATCACCACTGCACTTCATGACGGCTGTAGTT
TTCAAAATCCCAACTGGGCTGGTGGAGGGTCGCAGGTGTCAGGTTGAGACGGACCGAGTCGCTATAGTAAGG
AGCTCCGTTCATTTCCTTGGCCTCTCCTGGTCTAGGGGTGCGTCGATGGTCTTTGCTGTCTGTCCTCGATCTC
GGTGTGAGGTAGGCGCCTTTGGGCAAGTACTGCTGGCTCCAGCGTCCGGCTCTGTCGCCTGCCAGTGGGTCC
TTGGGCGTCCTCCAGCCCCTTGCTGAATTCTGTTGCTGGGATGCGCGGCG (SEQ ID NO: 42)
```

TABLE 3

CpG islands hypermethylated in (bladder) cancer. Provided for each are: ID;
Comparision; Coordinates of selected regions containing relevant CpG islands
based on *Homo sapiens* full genome as provided by UCSC
(hg18, Mar. 2006); Chromosome; GeneName; Location relative
to gene Sequence.

2; ALL;; chr1: 2072175-2072389; 1; PRKCZ; INSIDE
CGGGCGCGGGAGCTACGCCAAGGTTCTCCTGGTGCGGTTGAAGAAGAATGACCAAATTTACGCCATGAAAGT
GGTGAAGAAAGAGCTGGTGCATGATGACGAGGTAGGTGCCGCTTCTCATGGGGCCGGGGGCCCGGGAACGC
GCTGCCCTGGGGCCTCCTCCGGGCTTTAGCGGAATTAATCCATGCACGAGAGACCTAGCCTCACGTTGACG
(SEQ ID NO: 43)

3; ALL; chr1: 2106293-2106715; 1; PRKCZ/FP7162; INSIDE
CGAGGAGTCGGTGTGAGGCCGCGTGCGTCTCTGTCGTGGACACGCGTGATTGACCCTTTAACTGTATCCTTA
ACCACCGCATATGCATGCCAGGCTGGGCACGGCTCCGAGGGCGGCCAGGGACAGAGCTTGCGCCGAGACCG
CAGAGGGAAGCGTCAGCGGGCGCTGCTGGGAGCAGAACAGTCCCTCACACCTGGGCCCGGGCAGGCCAGCT
TCGTGCTGGAGGAACTTGCTGCTGTGCCTGCGTCGCGGCGGATCCGCGGACCCTGCCGAGGGGGCTGTCAT
GCGGTTTCCAAGGTGCACATTTTCCACGGAAACAGAACTCGATGCACTGACCTGCTCCGCCAGGAAAGTGAG
CGTGTAGCGTCCTGAGGAATAAAATGTTCCGATGATGTGGAGCTCCTCTGATGCCTTTTTTC (SEQ ID NO: 44)

6; ALL; chr1: 33385564-33385979; 1; chr1: 033385935-033385979; Unknown
CGGACGTTAAGCCGCGTCCAGGGCTCCGTGCAGGCGCTGTACTGGTTGCCATCGTGCATCACGATGCAGTAG
AAGCCGCGGCTGGGCTGGATCTGGATGCTGCCCTTGCGGCTTGCGGCTTCGTGTGCAGCCCGATCACCCACT
GGGTCTTCTCCGCCACCACCACCTCCCAGTAGTGGACGCCACTACTGAAGGCTTCAGAACCCAGCACCGACA
CCTCCACATCGAAGCGCTTTGGCGAGTCCTGCAGTGGCTGTGGGTGCAGTTGCCGTAAGCCACAATGGTGCA
GTCGTCCGACAGGATCAGGCGCTGGTGGGCTGTGCCCGGGTCCAGGGTTAGGGCGGCTGGCACTGTGGGGG
TTGGAGGAGGGAGAGAAGATGAGTGGGGAGAAGGCTGTGGCCCACCATGCAGTG (SEQ ID NO: 45)

8; ALL; chr1: 47672249-47672972; 1; FOXD2/MGC12982; PROMOTER
CGCGCCGGCTTTGCCGCTTTCCCTGAGGGTGTCCAGTTTTGTGAATAAAATTAGAGAAATCTGCGGGCGTAGT
TCCCCAAGCCCAGCTCAGGCTTCCGTTTGCAGCCCGGCGCTGGCCGAGCTCGAACGCTGAAAAGGGCCGCGT
GCAATCGTTCCGCTGTGCCTCAGGACAAACTCCGCTTCAAGCCAGTGCCGCTCTCCGGCAGTTTCCTGATTGA
CTTAATTAGATCCGCATAATCGCTGGAGGGCTTTTCTTTCCCAGACCGAGAACAGCTCATTTATGGGGACCAA
AAGGAAGAGAGGGAGAGACGACCCGGACGCCACTGATAGCAACGTACTCTTCGCAAAAAACACTCAGTAACT
AGTGGAAAAGCCCAACAGGCATCCCCCTCCGCCCGCAACGCTTCCTCCCAATTGTTCTGGGCTGCACGAGGG
AGATGGCCGGGCCGTGGAACAGATGCAGAAGGAGGCCCGGCACGACCAGAGACGCTGTAACCAAGACCCGC
AGAGCCTGTGGCTTCCCGCTCTTTGGCGGTGCAGCAGGCATGGTGCTGGAGCCCAAGGCTTCTGGGAAAGAG
TCCAGGTTTTCGCGGAGGGAGCGACGGACTCACGCGGGATCGCAGGCACTGCTGCAAGACGCCGAACAGGC
TGAGCCGGTAGGCGAAAGAAGTAGGGTCACAGAAGAAGCAAAGAAAACGAAATAAATTCCGAATCCCGCG
(SEQ ID NO: 46)

50; ALL; chr10: 21828640-21829645; 10; C10orf114; PROMOTER
CGTCCGGGAGCCTCCGCAACTCGCATTTCCCAGTCGCAACCCTGGGTCATTCCTGCCTCCGTCCCAGCTCCCG
GACAATTCCCAAAGCCAAAGGCGTCGAGCGTGTTACTGGCTCCCACCAGCCCAATTAATAATCAGCTTAACTC
GTGGAGGCTTTGAGCCCCAGTGCTCCGTTCCCTGAAGCCTCCCAGTGCGGAGCCCGGCTCCTGCGAGGACAT
CCTTGGAGGGGGGCCGGGGCGCAGGGACGGATTTCCTGGGAAAAATGTCGCTGGCGTGTTGCACCTAGAGG
GCTGTGGGCAAGGAGGCACGCACCAATGTCCCAGTTCTGGGCTCTCAGATCGGGATTCCTCCAAAATCGCGA
CAGCCGCTCAGGTGCTGGGTGCTCACGTTGGCAGCACAAGCGCCAAATGCACGACCCCGCGCGCCGCGCGC
GACCTCCACGCACACTTAGAGCCGAGGTGACAAGGGAAGGCGGCGGGGGTGGAGCCGCTCTCTGGTGGAGC
ATGATCAATCACTTTAAAGGGTTCAAAAGTTCAAGTTCCCCTTTGGAGGGGGAGAGGTAATGCTTCCCGCGGCC
TGCTTCTCTCTGAGACCCGCGGGTTCCCGGCAGCCGCGCAACCACTGGGGATCTCGGCTGCCGCTTGCGGGA
GCCCCTTCCGGGGAACACGCTCTCGGGCCGCGCAGCCGGGCGAGGTTGACGCAGCTGCTAGGGGGCAGTTT
GGCTTCCCCGGGAGTACCGGAGTCGCTCGGCAAAAACGTGATCTCAGCCTGCAGGGCCCGGGGCGCGCGCTT
TTCCCTTTCTCAGCAACGGGAAAGGCCTGTTGGCAGAGGCCGGCGGAGTGCTGGCGGCCTGGCGGCTGGAG
GCTTCGGCGAAACCTGAGCTCCCTGCGACCTGTTCTGCTAGCAGGGGCGGGGAGAGCCCCAATAAGCCGC
CCCAGAGGCGACCGTGCAAATTCCTAAGAAAAAGCCCTCTAGAAAACACCAAGCCCTTCCAAAAG
(SEQ ID NO: 47)

54; ALL; chr10: 22804715-22807056; 10; chr10: 022806090-022806137; Unknown
CGTCGGCGCTAAGCAGCTCTGGAAACGGGCAGACCCAGCTGTGCAGCGATGTCCAGTGTCGCCGCATCTGCC
CCGCGGGGTGCAGCATGAGTCTTCCTTTGTGGCGTGCGGCTCCATCGGAACGCGCTTGCGACGACAAATTCC
TTTTTTCCCCCCGCAGTTAACAGTTCTGGGGCAGAGGCTGGTGGAGAGGTCCAGAGCCCACTCAGACCGAG
ATGAAGATGAGGAAAAGCATGAGCAGGAAGAGGCTGGCGGCTGCGGCGCCACAGGGAAGAGCTCGGTCGCG
GGCGCAGCCTCCCGCGACCGCGACTCCTGGGCTGCGTCGAGGAGCCGCGTTGCCATAGGAACCGTAGCGGC
GCCCCAGTGAAACCCTGCGTTCGGACAGGAGAAGCTAACCGGGCCGCCCACTCCCACCCGCGCTTCCTCCCC
GCCCCCACCGGCCGTGCGCGAAAAGCAGAGATCCGAGAACGCGTGCGGTACAAACGGCAAAAGCTTCGCG
CGCATTTTCCGGGAGTTGAGCGCGCGGCCGCAGGCGGGAACCTACCGCTCTCAGGCTCCCAGCCCGGGCGCT
ACGACCCTGTGGGCGCCGCCTGTCAGCCCCTCCTTCCAGCCCGCTCGGGCGCATCCCCCAGGCCGGGCCAG
CGACGCGGGCACCGGGAGCCCCTCCCCCGGTCCGGGCTTTGGCCCACACCCGGGGACCGCGGAGTGGGAAA
GGAACCAAAGCGCGGCGCCTGGCCGACCGCGGACGAAATTCGAGGCCGGAGGGCGTTTTCTTTTTTGCAAAA
TTGCCCCAAAGCCAGGGCCCATGTACCTACTGTCTCCTTTGCCCACATGCTCCAAGAAAATAAGACACATTC
TACCCCGAGTCCTAATTATTGGGCCATTTCCTTAACGCGCGGTCTGTCCCCGTGGGCAGAAACATACTGCGAG
ATGCAGTTTGGTAATTAACAAAGAGACGAGACCTAACTGGGCTTCCGAAATGCTGGATACTGCGGCCGGGTC
GCCCCGCATTCGGGCATCGCGCGGTTCCCGGCCTTCGGGACGTTCCGGCCCGGCCGGACTTTGACCGCTGGC
GAATTAGGAGAAACGCAGAAGGCGGACGCTCCCCAATTTCCCCATCGAGCCTTCTCCTCCCGAGTCTGCGAA
GCCCCTGGCTCAGGAGACACCGGCTCCGCGCCTGGGCCTGCAAATCCGCTTCCAGCGAGCGCAGGCCTGTCG
CTCC (SEQ ID NO: 48)

TABLE 3-continued

CpG islands hypermethylated in (bladder) cancer. Provided for each are: ID; Comparision; Coordinates of selected regions containing relevant CpG islands based on Homo sapiens full genome as provided by UCSC (hg18, Mar. 2006); Chromosome; GeneName; Location relative to gene Sequence.

87; ALL; chr12: 94776044-94776377; 12; SNRPF; PROMOTER
GTTACTTCCCAAAGGGCGTGTTCTCCAAGAACTGCATTTAGCATTTCAGATCAGAGTGACCCGAACTCAATAG
GATTACGACAAAAACTAGTGAGATTCAGATAACACCGTTACATCGAAAGTTTTATCCGTGACAGAGGAAATAT
TGCTTACGCCCTTAGGTAATTTCAAATGCACGTATGAAGGCCGTGCGGGTTTCTGCAGGCGAAGCAAAAGAA
AGGTGGGGCCGGCAGGGTCGTGGGGCGGGGGTGGGGCATGACACCTATCCCAGACGCAACTCGACCTCGTT
TGCAAGAAATTCTGTATCCAACTCTCTTCAGTGCGTTTCGCCG (SEQ ID NO: 49)

94; ALL; chr12: 113657930-113659205; 12; chr12: 113657930-113657987; Unknown
GTTCAGTGGTTTATAGAAAATTTCTTTCTCTCTCTCAGGTCCACTAAGACCGAGAGAGAGAGAGAAGTCGACT
CTGGCACACCCGGGCGAGGGGCTGCCGGGATTCGGGAGCTGGCGCGGTTGATTTTTCCGAGAATCCTCCACT
TGGGGTGACGTCGGGCAGCGCGCGCGGGCCGTGAGGTTAATGCCCAGGCTTTTCTCTAAAGCGTCCGGGAAT
GATCCGGCGAATAAAACGGGTGTCTGCAAAGTTAATGAATTGTACAGGAGGCTGAGGGTGGGGACTTCGACC
CGGGGAGCCAGAGGCGGTTCTGGTGGACGCTTCCCCGTGCGCCTAGGGGTGCGCTGGGCTTTCCCAGCCGA
GGTCTGCAGAGCGCACCGCGTGAGCTTCATCGATCTCATCTTCTTCCAAGTGGGAGGAGGTGGAGATGCTGG
GAGAGTTGTGGGGAGTTGGGAGTGGGTTGGAGGGGGACTGTCTAGATTCTACTCTGGAGGATCCAATCACGT
GGTGCTGTTCCCCTGCCTAGAACTTCAAGGTTTCCAACGGTTTGAATAAAACCCAAACGATGCCCGATGTCCA
ACGAACGAATGATCTAGCCTCGGCCTACTTCTCAGGACTTAGCTTTGTCCCTGCCCGCGACTTCCCGCTGGGA
ACGTCGTCCCCGCCACCACCGCTCTGCTTAGGTTCGAACTCTGGGCCACTCTTCCTACTCCCTCTGGTTTCCA
GCAGGAGAAGCGCTTCGGAGGAGGGGGCTAGGGGCGCTCAACCTCCCGGGTTAGAGGAAATGCAAGTTGGG
CCAATTTCGCCCTCCAGACTCCGAGGCGGATAGGCCCAGGGGGCAGCGGCCTTGCCCGGCGGCCACTGCCCT
CCTCCTCCCCCGCGCCCCTGGCTAGGCTTTGAAGAGCTCATTTTAAGAACTTTTCCATTTTCCTTTTGGAGG
CGTGTTGTTCTTCTCAGTCACCTCGCTTTTTTTTTTTTATGAGCTTCAGCGCTGATCTGCACGTTCTTCCCTC
CGTGTAATTTCAATTTGAACTCTCCCCAGAGCGGCCTTTTCCCTCTTGTTGCCTGCCAAGTCGTTTAAGGCTAA
GCAAACATTCTTCCTCCCGTCCGCGCGAGTCTCGGTCTACACCCGCGAGGGGAGGCGGAGGCGGTTAC
TCCGAGAGTTCCGGTGGGTTGGAGCCTTTCAGCAGCCGCCTTCAGACTGTTTGGGAGCCGAAAAGCG
(SEQ ID NO: 50)

99; ALL; chr13: 34950488-34951119; 13; MAB21L1; PROMOTER
CTTTGCCGTCATCGCGGGTGAATGCACCACTACCTTTTGGCAGTTGGAGGGGAGACCCATCAGAGCCGGAGA
ACCTGCAGCCACGACGGCGAGGATGTGCAGTGGTCTCTGGGGAAACGCCGCCTTCGCCCTCACCCGGCGCGT
GTGGCCCTGTGCCGTCCGCTCGCCGCCTCTCTCTCGCTGCTCCGCATTCCCGTGCCCTCTTACTTTCCTCTCT
GGGCTCAAGATCGCTACGCTTTATTTCTGCGTGAGCTTATTTGAAACCTTACTTGGTGTCCCGGCTTACTCTC
CACGTCTGCTCCAGACCACGGTCTGCCCACGCACCCCTCAGCCTGCACCGCCCACGTCCGGCCCAGGTGTGG
TCGCAGCCAAGCCCCAGCCGCGGGCCCTGCGCCCTGGCTCTCTCCCTTGGGTTCAGGCCAGAGATGCTTGC
CCCAAGACCTCGCCCCTTGCCTTCTTGGGCCACCTGCAGAACACCCTTGGTTGTCAAGGACGTGAGACAGCC
GAGGACGGGGAGGCCCCAGGGCTGTTCGGGGACCTTAAGTGGGTCCAACGGGAAGGACGCGGGCCTGCGAG
GGATGCCGGTCGGGCCTGGCTGGAGCCAGGCGCGCAGGTGGCGCATCTTCG (SEQ ID NO: 51)

102; ALL; chr13: 49595986-49600287; 13; chr13: 049599159-049599206; Unknown
CGGGCGGACGAATGGACGGATTCGAGCGAAGCTTATTTCCCTTCTCCTAACGCATCTACCTATAAATAGCGCT
CACCGCGCTGAGTCACCAAAACCCCGAGTTTCCCAAATAGCGCGTAACGACTGTGGGATCGCGTCCCTCGG
GGCTCTGTGACAGACTCCAACCACACACCCGCTGGGCTGGACTGCGGGCCCACACGGCCCAGCGGGTCTCTC
ACCACCCGGCGCCCAGGGACGCGGGCGAGGCCGCGGTGTCCGAGCGAGTCGACAGCGTCGGACTTCCCGC
GCGCGGACGGCGCTCTGGGGAAGGAGGAGCCGGCGGGCGGCTGGACCTGGCCTTGACTGCGCGGGGTCCGC
CCCCGCCCCCTCGGGAGCGCAGAGTTGCGGGGGGCCGGCACAGCCTCCGCCCTGCGCCGCCCGCTCACACA
ATGGGACGCGTCGGGAGGGGGCGGCCGCGGCTCCCATTCCGGTCCCAGGGCGGGGACTCCGGGCGGCGGA
GAAGCAGTCGGGCTGGGGCCAGAAGGAAAACCCCCTCTCCCTCTGCCCACTCAAACTGCGAAAGGGCTCCAG
CCGGCGGTGCCAGGGGCTGGGGAGCAGCTGGGGAGGGAGCGGAAGTGCCACCCCCTGCAGTCAAGGGTGGT
GACGTCACCCCTGCAGCCAGCCTGTAGGGGGGTGTCTGTACATCACATGACCCGGCCCCCCTCTCCCCGCCG
AAGCCCGCGCGCGCTCTCTCCCCAGCCCCGACTCCCACCTCTCCCCGCCCCCTCTCCCCAACTTTCGCC
CTCCCCGCTCCGGCACCGTGTCAACAGCGCCAGCTCCGCCCCCTCCCCGCGCCCTGTGGAACCGCCACGGCG
GCGCGGCGGGCGCTCGCGCTCAGGTCCGAGGCTCCGAGAAGCGAGCGTGCCCGGTTCCACCCTGCCCCCC
AGCTCAGTGCTGCTGGCTGCGTGGGCACCAGAGCCAGGGGGCACGGCGGCGTGCAGCGACAGCGCTTCTCT
GCTCCATCCTCCCACAGCAGTTAGAGGACGAAGCTGAGGCGCCGGGTCCGAGCTCGGAGGGAGCGAGGCGC
ATGCACGGCCTCCGGGCCCTGACGCGTAGCCTCCGGGGGTCGGCCCACGGGCGAGAGAAGCAGCCGGGAGC
CCCTCCTCGACCCCAGCAAGGCGGCCCGCGCCTCCGCTCTCCCTACCGCCCGGGTGGCGCACGCCAGTCCCC
GTCTTTGGC (SEQ ID NO: 52)

103; ALL; chr13: 94152191-94153185; 13; SOX21; DOWNSTREAM
CGGAAGCCTCATCCCGCCAAGCCTTCGCCTCCTCGCTGAGACTCTGAGCTGCCTGGGGTTGGCGGGCACCC
GATTCCGCCCCGGCCCAGACCGGTCACTCAGTGTGTGCATATGAGAGCGGAGAGAAGCGACCTGGAGGCCAT
GGGTGGGGGCGGGTGGTGAAGCTGCCGAAGCCTACACATACACTTAGCTTTGACACTTCTCGTAGGTTCCAA
AGACGAAGACACGGTGGCTTCAGGGAGACAAGTCGCAAGGGCGACTTTCCAAGCGGGAGATGGTGAAGTCTT
TGGACGTGTAGTGGGTAGGTGATGATCCCCGCAGCCGCCTGTAGGCCCGCAGACTTCAGAAAACAAGGGCCT
TCTGTGAGCGCTGTGTCCTCCCCGGAATCCGCGGCTTAAACATTCTTTCCAGCTGCGGGCCAGGATCTCCAC
CCCGCGCATCCGTGGACACACTTAGGGTCGCCTTTGTTTTGCGCAGTGATTCAAGTTGGGTAACCCTTGCTCA
ACACTTGGGAAATGGGGAGAATCTCCCCCCCCGCAACCTCCCGCACCCCAGGTTCCCAAAATCTGAATCTGTA
TCCTAGAGTGGGAGCAGCGTCTAGAAAGCAAAGAAACGGTGTCCAAAGACCCCGGAGAGTTGAGTGAGCGCA
GATCCGTGACGCCTGCGGTAGCTAGGGCATCCAGGCTAGGGTGTGTGTGCGGGTCGGGGGGCGCACAGA
GACCGCGCTGGTTTAGGTGGACCCGCAGTCCCGCCCGCATCTGGAACGAGCTGCTTCGCAGTTCCGGCTCCC
GGCGCCCCAGAGAGTTCGGGGAGCGGTGAGCCTAGCCGCCGCGCGCTCATGTTTATTCACGCGGCCTTGAGC
AGCCGAGCTCCAATCCATATTAATCAACCGCTCGACCTACACAAGTCTAAGTTTACGGGAGAAAACCTAGTCC
CCGAAAGGAAGAACAGCAATCCGGACAAGCAGTTGGCGCCTTTGTCCCG (SEQ ID NO: 53)

TABLE 3-continued

CpG islands hypermethylated in (bladder) cancer. Provided for each are: ID;
Comparision; Coordinates of selected regions containing relevant CpG islands
based on Homo sapiens full genome as provided by UCSC
(hg18, Mar. 2006); Chromosome; GeneName; Location relative
to gene Sequence.

107; ALL; chr13: 113930978-113931584; 13; chr13: 113931540-113931584; Unknown
CGACCCAGCCCCCGAGGAGAACCCAGAACCGACCCAGCCCCCGAGGAGAACCCAGAACCGACCCAGCCCCC
GAGGAGATCCCAGAACCGACCCAGCCCCCGAGGAGAACCCAGAACCGACCCAGCCCCGAGGAGATCCCAGA
ACCGACCCAGCCCCCAATGAGATCCCACAACCGACCCAGCCCCCGAGGAGATCCCAGAACCGACCCAGCCCC
CGAGGAGACCCCAGAACCGACCCAGCCCCCGAGGAGACCCCAGAACCGACCCAGCCCCCGAGGAGATCCCAG
AACCGACCCAGCCCCGAGGAGATCCCACAACCGACCCAGCCCCCGAGGAGACCCCAGAACCGACCCAGCCC
CCGAGGAGATCCCAGAACCGACCCAGCCCCCGAGGAGATCCCCAACCGACCCAGCCCCCGAGGAGATCCCAC
AACCGACCCAGCCCCCGAGGAGACCCCAGAACCGACCCAGCCCCCGAGGAGATCCCACAACCGACCCAGCCC
CCGAGGAGACCCCAGAACCGACCCAGCCCCCGAGAGATCCCACAACCGACCCAGCCCCCACGGAGAACCCAG
AACCGACCCAGCACCTGGGCAACATTCTGC (SEQ ID NO: 54)

111; ALL; chr14: 36205192-36206099; 14; PAX9; INSIDE
TCAGAGAATTTGGAAAGGCCTACTCTGAGGGGAGTAAAACTTCACCAGGCCCTGGGCTGGAAGCACAGGAGG
TCGCGGCTGGGCCCAGCGCCCTCGGGAGGCCAAGGGCAGGGAGCCGACCCAAGGTTAAGCCCTCCAGCTCT
CCGTCGCGGGTTTGGGTCCCGTCTCAAGAGTGGGGCGCGCGGGCTGGGCCTCCGGCCTGACACCCTCTCTTC
TCTCCATCAGTGAGCGACAGCTCCCCCTACCACAGCCCCAAGGTGGAGAGTGGAGCAGCCTGGGCCGCAACA
ACTTCCCCGCCGCCGCCCCGCACGCGGTGAACGGGTTGGAGAAGGGAGCCCTGGAGCAGGAAGCCAAGTAC
GGTCAGGTGAGGAGGCGAGGGTCAGGCCAGGTGGGCCGCGTGCGGCGGGGATTTAGGCGATGGAACACTTT
GTGATGGGTCCCTTTCTGAGCTTCCCGCGAGAGAAGCCCAGGCTGGCGTCCCTTTGCTGCTACGAGCCAGAT
CCTTCGTGGACTGGGGCGAAGCAGAGGCCTGAGCTTGGAAGGCGGAGCTGGGGCCTCGACCCCCGCCAGGG
GCCGGGAGCGCTCGTCAGGGCGCTGGGGGTCTGGGGCGGCAGCTCCCCGGGGCGAGGCTCTGGGAAGCGCC
TCCAGGCCTGTCGGCCTCCGGGAGCTTGGGAGGCGGCTCCCGAAGCCCTTTCGGCGGCTCTCGTTGGGGGTA
GAGTTAACCAAAGAAGGCGCTTCTGAAGGGCCGAGCGGAGCAGCCCTGGGGCCTCAGAGCCGCGCCTTCAC
GCCCGCGAAACGCGCGCCCCGGTCTCGGCCCCACGGTGCGACTGCGGCTGCGGGGTCCTCACGTTCGGACTT
TCTCTCCGGTGGCTCTCGGACAAACACGCTTGGCCAATCCTGCG (SEQ ID NO: 55)

130; ALL; chr15: 94688798-94689131; 15; NR2F2; DOWNSTREAM
CGCTACGAATGTAAGATGAATTTAGTGGCGCGGCTGCCTCCCTGAATCCGAACGGTAATGATGGATTTATCAA
CGGGGATTCGCCTTCAGCCCAGCGAGGGAGGTTTACTCAGCAAATATGTCGGCGGCACCCACCCAAATGCAA
TCATTTGACCCCCTGCGGACGATAGCTGCCGTGCCCCTTCCCACCGCTGGTCCTGCTTGGCCAGGGTCGCTG
GGGGCCAGAGGCCGGCCCGGATGACCAGAGAGGTGGCCTCACGGATCCTTGGCCTCTCGCCCCCTCCTCTGT
TTCCTCCTCTCAGCTTGAGGCTCTCCTGGCAAGGGGGATCGAT (SEQ ID NO: 56)

133; ALL; chr15: 94696311-94696840; 15; chr15: 094696796-094696840; Unknown
CGGGGGGGTGGGGCGTGGAGGGCGGCCTGAGTGCCGCGCCTGGCCCCTGCCCTGGGTCGGCACCAGGCCGC
GAAAGCCGGGGGCCGCCTTCTCGGCTGCTGAAGCCCGGGAGTCAGTCAAGCGCCCTTGGCACCGCGAGGGA
GGCGCACCTCGCCTGGTGCAGAGTTGCCGCGACCCGAGCGGGAGGAGGCACAGGACGCAGGGCTCCTGGCC
TGGCTGTGGGCTTGGCCTTGGCGCACTAAGCGCTCCCCATCTGCCCGAGCTGGCCTCCGCGGCCCTCTCGGC
CCAGTCTACGTTCGTTTAAGGACTTCAGCGCGAAGAAGAGCGAACGTGGCTAGAACCTGTTGACCTCTCCTCT
GGCCTGGAAGTCCGCACAGCTCGTGGCAACACTGGACGGACGGTTGTCAGGGGACGACCGCGGGCAGGTGG
GGAGGAGGCCTTGGTCTGGCTCCTGGATTCCACCCTGGGACGGAAGGGGAAGCGGAAACCTTGACCTCAGCC
ACACAAGGACACCTATCTGGCTGTCT (SEQ ID NO: 57)

134; ALL; chr15: 94705727-94706054; 15; chr15: 094705808-094705853; Unknown
CGCCTGCTGCCTGCCGTGGGGCCGCTCCGAGGTGCCAGGAACTCCGGTAAGGGTCCCGGCGGCGGCAGCCC
GGGAGTGGGCAAAGAGGGAACATGCGTGTATTTCAAAGAAACCAGCGCGGTCTCTGACTTCCCTGTCTTCGC
TCTCCACCCCCGCTCCCCCTCAACACACACATAATATAACAGACGCGAAGATAATCCTGCCATCTGGCAAATC
CCAAATTTGGTGACCAAGCTCGGAAAGCAACAGCGACGGCTCATCCCGGAGTAGGTGGCTGGTCCTGCCGGA
CTCTCCGGAGCTGGGGCAAGGGCCGTGGGCTCTGCCCG (SEQ ID NO: 58)

136; ALL; chr15: 94712480-94712812; 15; chr15: 094712480-094712531; Unknown
TAGGACCTGAAATTGCAGAGACATAGAAAATCAATACGTGGTCGGGAGTCAACTGCGCGCGACCAAGGGCTC
TGCCCTCCCTCTCTCCGTTGATTTGGACGCTGGGAAGCTGCCCGCCGTCCTTCCCACCCCCTTTGCCCAGCCT
TGGCAAGACCTCTCCGGAAACATACTCGCGTTAAGGAACTGGGAAAGCTTCCTGGCCCGGAGCTAGGAGCCC
GACGTTGGGGCTCCTTGCTGAGTGAGACGCTCAGTCCTGTGCTCCCGCCCCGCCCCAGGCGCCCAGTCCCGC
TGGGATCCATCTCCTCAGCCCCGGTTTCCCGCTCTGCGAGCG (SEQ ID NO: 59)

145; ALL; chr16: 52873104-52882105; 16; IRX3; PROMOTER
CGCGAGGATGGGCGGGCTCCACGTCTGGGGGCGCTGTGAGCAGGGCCAGAGCGAAACCTCAGTCTGAGTTT
ACGAACTGGGAAGGAGCCTGAACCCCAGAAACACCGTTAACAAAGAGGGCGAACGCAGGGAGCCGAGGAGA
CGTCTCCTTGGCCTCTGGGGAAGGGGCTGGAGGAGCGAGCCAGCTGAGAAGCGGCTTTGCCGGGTGTCCACT
AGCGGTTCGCCAGCCCTCTGTGCGCCCGCAGAGTGACGCAGAGGCCGACCAGTCCCCTCCCCACTCGCCCCT
GGGGCGCCGCCGCACCTTGATCACCCCCTTCGCGGAGGGAACTCCCAAGGCGCGGCGCTGGCCGCTGGGTC
CGCATGGCCCAGTCCTGTCGGGCTCCGCTCTGCTGCCGCCGACTTCGAAGGTGTGCAGTGTTGAGCCGTGTC
TTGTTCCGTGGCTTCGAGGGGTGTGCGCGCTTCCTATACCTCCCCGGAACGCGCGAGATAGTCACACGCGCC
ACTTTGAGGGTCAAACACCCCGCATCTGGCCACATGTACCTTTACTAACGTGGGAGGGGGCAAAAAAATGT
GTCTCTCCTTCTTACCCCGAGGTGTCACTCGCCCAAACACTCCCTACAACTTCTTCAAGTCAAACTTGGGCAA
GGTTGGCTGGCTGACTGCGAGAGGAAAAGAGGGCGCGGAGGGGGCGCGGGGTGGGCCGGGTGTAGAGGC
CACGGAGGCGAGGCGCCGAGCGTCCCCTTTGTCCTGTAGAGGGAGCTCCAGCCCCAAATTTCCCTGCTGCCT
CCCCCGGCCCGCCCACCCCGGCCCGCCTGGAGCCGGAATCCCGGCTGGAAAGGTGCGGCGGTCTGACACCC
CCGCAACCCCCGCGCCGGGGCCTTAGCAGGATGCCTCTTCTAGGGCACGTGGGAAAACCCACCAGGGTGCCA
AGACGCACAGATCTCCCAGGACCCGGGCTCCCCAACTCTCAACTAGAGCTGGGCAGTCACACATCATCTAGA
GGATTATGTACCCCTAGGCGACCCTCTTCTCCATATCCGCCTCCACCGTCACCCCACACCCTGGCATCTATAA TABLE 3-continued CpG islands hypermethylated in (bladder) cancer. Provided for each are: ID;
Comparision; Coordinates of selected regions containing relevant CpG islands
based on Homo sapiens full genome as provided by UCSC
(hg18, Mar. 2006); Chromosome; GeneName; Location relative
to gene Sequence.

AGAGGAAGGGGGCAACCGGGTTGGAAGGAGGATGGAATCTGGGCTTGCACAGCCTCTTATAGGTAACAGT
GAGAAAGCCTCAACTGTGTCGATCAAAGAATGGGGACGAAGGGAGTGATGAGAACACGACCCCGCCACCGCG
CAGGCTA (SEQ ID NO: 60)

153; ALL; chr16: 86294154-86294408; 16; KLHDC4; DOWNSTREAM
CGTGTGACACTTTGGAACGCTTCTCTCGTTACAAACCAGCGTCTTTACTGAAGGTCCTTCCGCTGCAGAGCTG
CGCAATGGATGTGTGGACAGAGCTAGTCGGCACGTGGAGGCTCTCCTGGTTTTCAGCAGGAAACGTGCTGTG
AGCAGGAATCGCGAGTGAGTTCCATGGCGTCCCCGGGTCAGCGCGCGTGCAGGAATCGCGAGTGAGTTCCAT
GGCGTCCCCGGGTCAGCGCGCGTGGGGTCCTGTCTCG (SEQ ID NO: 61)

155; ALL; chr16: 87372445-87372729; 16; chr16: 087372616-087372660; Unknown
CGGCGGGGAATCGGGTGGCCACGCACGTCGGCCTAAGGGGCCCTGGCAGCGCCCGGCAGGACAGCCGTCCA
CTGCACACCTCAGAGCCGGCACCCGGGACGGTCAGCGTCCCCATGGGCCCGGCACCGCAGCTGCCCAGATCC
TCACCCGCACACAGGAAGGGTCCCTGCAACCCAGCGTCCACCGTGGAGAAACATGAACGTGAGCAAAAATAC
GGCCTGCGGTGGGTGTGCGACCCCACACAGAAGGGCGAGAGGCTCGTGGCCATCCCACACACTGGGAG
(SEQ ID NO: 62)

165; ALL; chr17: 44074280-44075233; 17; hsa-mir-196a-1; PROMOTER
TTTCGCTAGATCATTTGTTAATTGTGGGAAGGAAGGACGCATCCGGGGAGGAGGAGATCCAGGGCTGGAAAAG
TGGGTGAGCGGCGCTGGCGCAGGCGGCCAGGAGAGAGCAGATGAACCGTTCGTTAGAGCAGCGAGGTAGTC
GTGAGCGCTGAGATCCAGAGACTAGGACCCACTCCCTCTCTGAGCAGCAAATTGGGAAGAAGATGCTCACTC
GGTAAGGGCGAGGGAGCCCGGCATGGCGCCCCACCACGGGCTCGGTCTTCTGCGCGCCAAGATCCCGCTTG
GGGCGAGGCGTTGGGTCAGCGTTTAGAGCCACTCCCTGCGCTGGTGGCTGGACATAGCCTCCCTATCCCACC
TCATCTTCCCCCATCCCCGACAGAGGAGGTTGTGAATCTACGGCCCTTGACGTTGAGGCGTCGGAGGGCGCA
CCTTTGTAATTGCGGCCTCCCTTCGCCCCTTAAGTGCCGCTTCTGGGCGCCTAGGCTGGATATGAAAGCCCCG
TTCCTAATCCTCTGCTCTGGTCCCCTCCTCTGACTGCTGGGACTCTAAGCTAGGCCCTCCCCAGGTTCCATCA
CTGCGGCGCCAACCCGCGGCTGGGCTGTCCGCAAGAGGGAGTTGAAGGCGCGCGGAATCCCGAGGTGCAGC
TGACCCTCCTCTCAACGCCGACTCGCCGCTCCCGCCCGGCCACCTCCCTGTCGGGCAGACTTCCTGTTCTCCT
GCTCACAGCAGGGAGGCAGTCGCCGAGCCGGTCAGCAGCGTGCACGGAGATCTTCACTCTGCGCCCAGCCCC
GGGACACAGGTGCAGTCTCCAGCGGAGCACTGCGGAGTGCGCGCCGTCGAGCACTAGGGAATCCTAGACGG
AGGACTTGGTCCATTCCACGCAGTCCCAGGCAGGTCCGCAGCGGAGGGACGCAGCGGTCTCCAACTCCTGGT
CACGACTTGGCG (SEQ ID NO: 63)

172; ALL; chr17: 58865328-58865618; 17; CYB561; INSIDE
AGAGGAGGCGGAGACCTGACCCCAGAAAGCAGCACTCAAACAGATGCAGCTGCACCCACGCGCCCGCCTGCT
GCCAGAGCCACTCTCCGGAGCCTGCAGTCCTGAAGACGCCTCAGCAGGGGCAGGCAGAAGACACCCCGCGA
ACCCCCAGGGCCGGCCGGGCGCATCACTGGGAGCCGGGGCTATCTCCCTCCGTCAGCGTCTTGAAGTCCATG
GAGAGGGCCTGCTCTTCCGCCTGGGAAGGCCGCTTCCAGTCGGCCCGGTCAAGATGTAGAGCACCGCCCCAC
CG (SEQ ID NO: 64)

176; ALL; chr17: 73932992-73933361; 17; DNAH17; INSIDE
CTTCTGCAGACAGACAAGAGCCCTCCTTACCTTCCATGAAGAGTCCGTACACGTAGGAGCCCTCTCGCGGAG
GAGCGGTCATGTCCTCTCGGTTTTTCTTGGTCACCTCGACAGACAGACACATCTTTCCAGGGGCCACTCGTTC
TTCCTGGCCATGGACTGCATGATGGCCGTGAGGAACGACTGGGGGTTGAAGAAGCCGGCCAGCCACACGGTG
GTGGGCAGGGCAAAGTCTGTCGTCCAGGCCTCGAGTTCCTGCAAGGCACACGAGCCGCTAGGAGGAGAGGA
CATAGAATGACATGGGAACGACCGGGCCTTGGCCGTTCTGAGCAGGGGTCACGCCAGAACCTTCCACGGGCC
ACTCAGCG (SEQ ID NO: 65)

181; ALL; chr17: 75531280-75531546; 17; TBC1D16; INSIDE
CGCCTCACGGGGCCTGCCAGCAACGCGCTGTGTGCAGCAGGAAGCCCACGCCAGGTCCTGACGGCTGCATCC
TGTGTGCTCTCCGGCCTGGCCGCCTCAAGACACGCCACCTTTGATGCACACGCGCTCCGGAGGCACAGGAAG
GACGGGGGCACTGGGAAGTCCATGTTTAGTCTCCTGACGTCGACCACACAAACCAGACGGAACGGTGTCCCC
GGCCCAGGCTGAGCGGAGCACACCATGAGGGCAGAGGCTACAGGTGATC (SEQ ID NO: 66)

183; ALL; chr18: 5186244-5187389; 18; chr18: 005186349-005186393; Unknown
CGTCGGACGTTCACAACGACCACGCTTTTCCCCGCTTCCTCGATTAGCCTGGCCTCCCTTGCTCCAGTGGGGC
GGACTCAAATGCGCACGCACGCACACGCCGCCAAGCCGGTCAACCGCAGACAAACTGACTCTTCGCCAACTA
GTAGCCACGGAGAGCAGCAAAGGGACCAAGGTCCTTCACCGCCTGCTCCAAAAAGACACGGCAACCTCCAGC
GGCGCCGCAGTAGCTGCCTCTGTGCTGCAGCCTCCGGTCGGAGTTTAGGTCTAATTCCTTAAGAAGTATCGCT
CCTCTGCCCTTCGTCCTACTCCCCTTGGCTTCGCCCACTTCGCCTCTTCTCCTCGGGAGGCCAGGAGGACCC
GGGTCACTTTGCCAATTCTGCGGAGGGGGAAGTAGCGTGAGGGAGATTCCCACGCAAGTAGCCCGAAGCCCA
CTACTCTTTGCCCCACCTCTCCACTCTCTTGCCCGTGTAGGTGCCGGTGCTGCTGGCGAAAGTCCCAGTTCTT
AAGGCTCCTGAGCTCGGAAGGGGTGTGAGGAGCCAGATGGGAAGAGAAGCAGCGGGACGAGGGCGAGGAAG
GGCTGGAGATTGTTAGAGGACAGATGGGGCGGGACTGGGGAGAGGGGCGAAGGCGACGCGCCGAGGCACTC
CTCCGCCCATGAGCACAGACGTAACTCCGAAACGCGCAGATGGGCGTAAGGTAAAGAGGCCTTTTTTCCC
TCTCCTCTCCGTCCTCTACCCTGCTCCCCTCCTAGACACTTGGTGAAAAAGCAAGGTGCGGTGTACCTGGAGC
GAACACCATGATTCTTCCAGCCGCTACGCCCCCAGATTAAGAGAGAAAGACAGGCAGACGGAGGATGGGAAG
AAGGCCGGACTTGGCGGGGTCCGGTGCAGGAGGGCGCGCTGGGCGGGCGGCGGGCGGGGCGGTCAGCACC
CCGGACGCTCCCGCCGCTAGATCCTGGGGCCGCAGCTCCAGCCGCCGCCGCGCGCTCTGCCTCCACAATGCG
GCCACAGCGGCGGCGGGAGGAGGAGGGTGAATCCCCGCTCAGTCCATCCCTCATTCCTGTGCCAGCTCGGGA
CGTACACTGCTGCTTAGGGAGCAAAGCACTTCCACCGCTTTCACGCGACGAAGGTCG (SEQ ID NO: 67)

TABLE 3-continued

CpG islands hypermethylated in (bladder) cancer. Provided for each are: ID;
Comparision; Coordinates of selected regions containing relevant CpG islands
based on *Homo sapiens* full genome as provided by UCSC
(hg18, Mar. 2006); Chromosome; GeneName; Location relative
to gene Sequence.

193; ALL; chr19: 4059891-4060207; 19; MAP2K2; INSIDE
GACCACAAAGCGCTTCCTCATCCTTTCCTCGCCCTTTGATGCCGCCGGCAACGTGACTCTGCGAGCAGCGGG
GCAGACGCCAGGTCTCCCTCGCAGGCGGGAAAGGGGCTCCAAGGCGGGTGCTGCCTGCTCGGGTCACATGG
CTACGTGGGGGCCTTGCTCAAATTCACTTCCTGCCTTCATTACAAAACTGTCAAAGGGGATCGCACGTTTGCA
GGGTGTCACCCAAGCATTCTGGTTTTGCAAACGACGCTGTGCGGCAGCGGTCTGATACCTGATGAGCTCGGT
GTGGCGGGGTCGGCAGCATTTCCTCCG (SEQ ID NO: 68)

209; ALL; chr19: 63784504-63785085; 19; MGC2752; INSIDE
CGGTGTCTGGAGGAAGCGGCGCGGACAGTCTCCCGCTCCACCGTGTCGGGCCTGAAGAGGCCGCTGAACGC
TCGCGATTACTGAGGCATCTGGTAGGATCGCAAGGCCATCAACCTACAGGTGAAGCCGAGGCGCTGTGGCGC
TTTGAAGCCGGAGAGAAGCTCAGTAGAATCGGGAAGGCGCTGGGGCTGTCCAACTCCACCTTGGCCACCATT
CGTGACAACAAGGAAAAGATCTGGGCGAGTTCCCAGGAGGCCACACTGAGGCGGCCACCAAGTTGACGCGTG
GCCGCAGCCTGGTGATGGAGAACATGGAGCAGCTGCTGAGCATGCGGATGGAGGACCAGAGCCAGCGCAAC
ATGCCCCTCAGTGTGGTGCTCATTCGGGAGAAAGCCCACAGCCGTTCGAGAACCGCAAGCAGGAGCAGGGCG
AGGGCGCCTAGCCCGAGAGCTTCGGGGCCGGTCGAGGGTGATTCGCTGGCTTTAAGGCGCGCCACAGCTTGA
GCAGCATCGGGGCCAGCGGCCAAGAACGCAGCTGCAAGAATCCAGCGTTAATGCGCAGGGTGATCCCGGA
GGGCG (SEQ ID NO: 69)

210; ALL; chr2: 19424445-19425131; 2; OSR1; PROMOTER
CGGCCGTTCGGTGCTGCGGTATCCCATCCCCCGCCTGTTTAAGAGAAATTGATCACGTTAAGCGGGCCCTGC
GTCGCTGCGCAGTGCCCGGACTACCGCTTGGATGGATTGACAAGGGAAGGACGCAGACACCTAAGAGCAACA
AGGGTACTTTTTAAGCGAGGTTACATGTGTTTAGGACTCGCGAGGCGTCACGTTTCGAATTTGGTAAAAGTC
CTCGGTAGCTAGGACCCAACAGTTCTGCCCTCCTGGAAACCCAATGAGGTGACAAAACTCCCATCTCATTACT
GGGAGTCCAGCGCACTCCGCCACCGCGGCTGCAGCTTCTGCTAGCTCGGAGCCTGCGGACTCCAGCCGGCGC
GAACTCCGCCGCGACTCTTTCTGGCTCTCTCGCTCACGCCTTCGGGGCGGAACCGCGGGCGCCGGAGTGGTC
CCAGACTCGGCTGGGACCGGGCAGCCTAGAAGAAGGGTCCCCTCAGTAGAGACCAGGCCTCCAGCTCTCCGT
CCGGCGCTCCGCTCCACAACCCGCCAGTCATGTGAGGTCCGTCAAGGGAGCGATCCCTCCGTCTGCCCGGGC
TTCCGGGCTGTGGACCGCACTGAACCCAGTCCCGCAGCAAGCCCTGCTGCCGCCTTTTCCTGGGCACGCCTG
CGGTGGTGACGGCCCGCTGCTATGTCTCCACG (SEQ ID NO: 70)

212; ALL; chr2: 43251514-43251780; 2; chr2: 043251514-043251559; Unknown
AAACACAGTGCCGCAGTGAAAGTGGGACAAACGCGCCTGTGTGCATCCTGGCCGAGGTGCCGGAGGAAGCG
TGGTCGGGGCAGAAGTGTTAATGGGCCTCCTTCCTGCCGTGCCCTGCCCGTGCCAGTCCTCGGTGCTCATCC
CGGCTCCCTGAAATGCTCGCTTCCACTCAGGGCCAGCGCACTCCCTCCACGTCCCTGGCCGCAGATCTGTCCT
GCTTTGACAAATAACCCGCTCAGCCTTCGGGTTTATGGTTTTTCCGTCG (SEQ ID NO: 71)

214; ALL; chr2: 45249374-45251726; 2; chr2: 045251412-045251456; Unknown
CGCTCCCTTTCCCGCACACGCATTGCTGCCTCCTCTCGGGCTTGGTTAATGAGTCTGTGCGCCAAGCCAGGTC
GCTCCGGGCAGTTCGCGCTTCCGCGCCTCGGCACTCGGATGACCGTGTCCTATTGTCTCTCTCGTGAATGTCG
CTGAAAAAAATAAAAGTTTGTTCTAAGCCCGTGGCATTTCCGCGCGCAGATGGAAAGGCAAGTGGGAGAGG
AGGGTGCAGGTGCGGGGCGGGCGCGGCGGCCCCTTCAGGCGCCGGGGCTGGGCTGCCCCCGGCCGGGAGC
AGCTCCGCTCCGCGCACGTGGCTGTGGGCGCTGCGGACGGGGACGGCAGGCGGGGACGGCAGGCGGGG
AGTGGAGGGTGCAGTGCCCGCAGGTGCCGACGGCTTCCTCCAGAGCCGTTCGCGCCGCGCCTTGCCTGGCTG
GTGGCGCGGGGAAACCATGGCAGCATTGCGGCTCCGGCGGGCGGGCTCTGCGCGGGCCCCACCGAGCTTT
CCGGGAGCCTCTCCCGCAGCCGATGGGCATCTAGGGCGCAGAACGAAGAGTGGGCGCCGAAACGGGTGTAG
GCGCTGGAGGCCGACGGGGAGGCCCGGGGCGGTCAGGCTTCTCGGTAGAGAGGGCCGTGCACCTCGCGGCC
TGCGGGCTAAGGCGGGGAGCCGCTCCTGGGCGGCCGGGCGCGCGGACTGGAGGGGAGGGAAGCGCCACGGA
CTGGGGAACCGGGGTGACGGGGAGACGGGGGGGCTGGTGGGGTGAGGTCGGCGGGCAGCAGCCAAGTGTT
CTGCAGCTCCGAACCCCGCCACCCCTGGGCGAACGGAATGGCACCCGCGGAGACGGGCGGGGACGGGCGAA
AGCGGGTTTGCTCCGACCCGAAGCTGAGCCCGGGTTGGAGGGCGAGACCGTAGGCGAGAATGGCCGCGCGG
GCTGGGAGACCCGGGCCGTATGGAGTGAGTGGAGCCGCCCGAGGTAGGGTAGTTGGGGATGGTAGTTGTGA
AGACAGTCGGAGTCTAGCTCCGGGCAGACGAAACACCGGGGCGCGCCAGGGTCCGTTTCCTCCTTCTCTCTG
CTTTCCCACCACCCTGTAGATACGGAGCCAGCAGTCGGGCTAGAGCGGAGGCTGAGGGTCGCGGTTCCAAGG
GCGGTCTCTCGCCCCGGGTCAGGCCCCACCCCGCGGTGGCGGTCGCGTGGCGCTGTCCTGGAGTTGAGCTGT
CCCGCGCCGCGGCC (SEQ ID NO: 72)

217; ALL; chr2: 63134470-63134933; 2; OTX1; INSIDE
CTCGAATCTTGGAGACACTGGCTTCTAGTCGCACATCTGCACTTTCTCCCACCTGTGGCCTCTCAGGCTCGGC
CGCCCGAGGGAGTTTCTTTTATTCCCAGTTCGGCTTTCTTTTGCAAGGCCGAGTCTGGGCCTGCCAGGGGCC
TGCCCGAGTCCTCTATCGCGGGTCCACGTGGCCACCAATGACCCGCGGCGCCCCGTGTCCCCGCAGCCA
CTCCGCGGAAGCAGCGGCGGGAGCGCACCACCTTCACGCGTTCACGCTGGACGTGCTCGAGGCGCTCTTCGC
CAAGACTCGCTACCCTGACATCTTCATGCGGGAGGAGGTGGCGCTCAAGATCAACCTGCCGGAGTCTAGAGT
CCAGGTGCGCACTCCCCGGGCTCCAGGGTCTGGGTAGGGAGCTGAGGCTGCTCGGGGAAGGTCTAGGAAGG
CTCTTGAGTAGTTCTTGAGGAGACCATC (SEQ ID NO: 73)

220; ALL; chr2: 66525936-66527222; 2; MEIS1; INSIDE
CGGTTTGGAGAGGGGAGCGCAAAGCGCTGGACGCATGCGGTACAGTGCCACGGCCGCCGGTGGGCTCCACT
GCCCTGGGGAGCTGAGGCGCGACGAATGAAGCACCAGGGCGCCTGGTGGGCGCCAGTCTCCGGTCTGGAGC
CTGCTGGCCTGTCCCTCCGGGGCGCTGAACCCCTAGTGCGGCGTCCTGGGGGCCGGGCAGGAAGGATGGCC
TCTCCACCTGTCTGCGAATGCAGCCCAGCCAGTTTGAGCCTCCGCAGAGGTGCGCTCCGGGACTGGGCGCTT
CTCGTGCTGTGAGAACGCTGGGCCTTGTTAGCTCATTAACCCCTCTGTCTCTAGGGCCCGTTGGCGGCACGGT
TTATTTTATTTTACCTGTTTTCCTCGGAGGGCGCGAAGACTCCACCCGCGCGGGGACCTGGGATCGACGACTT
TGATACTAGGCGGTATCCCGGAGGGCTAAGTCGGCGGAAATCCACTTGACCTTGTAGCGTTAGTCCTTTCTTT

TABLE 3-continued

CpG islands hypermethylated in (bladder) cancer. Provided for each are: ID;
Comparision; Coordinates of selected regions containing relevant CpG islands
based on Homo sapiens full genome as provided by UCSC
(hg18, Mar. 2006); Chromosome; GeneName; Location relative
to gene Sequence.

```
TCCTTTCCTTTCCTTTTCTTTCTTCTCTCTTCCTATTTATTTATTTATTTTAAAAATAGGATTAAGACACCAGT
AGAAGCTGTAATCCCGTTCCTTCCCCCACTCCCAGTCTTCCGGGCCGCCTGGAGGTCCCTGCCGGAGAGAGC
CACTTTGGCGGGCGCAAGCCCCTGGGCGCCCTCTCCTGACCGCCGCGCTCTCGGCTCGGCTTGGCTGTTCCG
GGCTCCCAGAGGCTAGGGGAAGCGAGGGGCGCCAGGGGCTTCCCGGCCTCAGCGTGGGGCGAGGTCCCGGC
TGCGACCCCGGAGAGAGGGAGAGGGGGGCCATGATGCTAGGCGTCGAGGCGAGGGTTGAGCCTGTTTGGCT
TCAGAGAACGATGCGGGTTCGACCGGAAGCGGGGCGCGTGTTCTAGGGGCCCTTGGGTGGATTAGGGGGCG
CCAAGAGGGTTAGGCGAGGAGAGGCCTGGCCACCCAGTTGCTAGACTTTAGGCCGCACTCCAGGAAGGAGCA
GTCGGCTTCCTTCCTAGGCCGCTTCTATTGCGCGCCACTCCTTGAATCTAAGCATTTTCCACTCCAAGAACCG
TTGGGAGAGAGGGGAGAGCGGAGCAGAGTCTCTAGGCCCCCAGGGCCGCCTCCCGGGGTGGCCACGCCTGC
CGGTAGCGAGCCGAGATTAGCTAGGTCTGTGCTCGGGCCTCAGCGGTGGCCCTGGCTCTTCCCTAAGCAGCG
GG (SEQ ID NO: 74)
```

222; ALL; chr2: 70984709-70985764; 2; VAX2; INSIDE
```
CGGGCGCATAACAGGCACCCCGCACATCGCACCGCGGACGCAGCGATCCTCCCATTTGTACCCTAAGGCCTG
AGAAGGCCGCTCCACACCTCCGCGTGCACAGTCCCTAGACCAGTGAGGGCGGGAGGGGAAATCCTTTTGTT
TTATATTGGAAACCTTACGCCAAAGGCAGGCAGGAAGCAACCAAAGGAACAACAGGCCGCCTGAGCCGTGGC
TCAAACAGCACAGGGCAGTGGCCGAGCACCAGGCTTTTCGGTGGAGCGGGATACCAGCAGGCAGAAGAGGT
GGACAACTCTGACCGCAGACTCCCTACAACCCCGCGATCGATGCTCCACCTGCACGCTCAAACGCACCTGTTT
CCCAAATTAATCCAGACGCGAATTTAACGACCGATTTTGTAGATCCGGGAAATTCTGTCCACCAGCGTCACCC
AACACAGCAACTTTTACAGACAATGCGTGGCGTCCGTTCCTGCTCACCCAAAGCGGCCTCTCTGGGCTGACAG
CCACCCCTGCGGGTCCTCAAACCCCACTCAAACCCTCCGAACCCCTGTGTCTGGGAGCAGTAGGGTGGGATG
ACTGCAGGATCCCTTGAAGAAGTGACTCGCTGCAACCCCACCACCAGCAGCAAAAACGCTTTCACCCGGGAG
CTGCATGGATGCGCGGATGGCGGGGGCTGAGGGGACGCGTGAAGCCCAGGCCTCTTGCTTGGGCTGGGCGA
TTCCCGCCGTGGGACGGGTGGGATTGACCTTAGTGGAGTCCAGTCCTTCGGAGAATCCGCGGGCAGTCGGGA
CCCACGCTCCGGAACACCCAAGTCCGAACTCGTACACACAGCACAATGGCGTGCAGCCGCCGGGGCCCTAAC
TCCCAGAGACGCGTCTGAAGAAGCCATACAAGGGGGCGCAGCTTCGGGGCTCTGGCTGGGAGGTTACTGCAG
GGACAGCGCCTCGCCTCCAGCAGCCGGGTCCAGGCTCAGGGCCGGCCGGCCTCTGCTCGCTTTCTGCTTGGA
TTACCAACAGCCACTGGGCTTGGGGAGATCGGCCGGGCCG (SEQ ID NO: 75)
```

230; ALL; chr2: 105864220-105865009; 2; NCK2; INSIDE
```
CGGCAAGACGCGCAGGAAGACCAGCGCGCGGGATGCGTCCCCCACGCCCAGCACGGACGCCGAGTACCCCG
CCAATGGCAGCGGCGCCGACCGCATCTACGACCTCAACATCCCGGCCTTCGTCAAGTCGCCTATGTGGCCGA
GCGGGAGGATGAGTTGTCCCTGGTGAAGGGGTCGCGCGTCACCGTCATGGAAGTGCAGCGACGGTTGGT
GGCGGGGCAGCTACAACGGGCAGATCGGCTGGTTCCCCTCCAACTACGTTTGGAGGAGGTGGACGAGGCGG
CTGCGGAGTCCCCAAGCTTCCTGAGCCTGCGCAAGGGCGCCTCGCTGAGCAATGGCCAGGGCTCCCGCGTGC
TGCATGTGGTCCAGACGCTGTACCCCTTCAGCTCAGTCAGTCGGCAGGAGGCTCAACTTCGAGAAGGGGGAGAC
CATGGAGGTGATTGAGAAGCCGGAGAACGACCCCGAGTGGTGGAAATGCAAAAATGCCCGGGGCCAGGTGG
GCCTCGTCCCCAAAAACTACGTGGTGGTCCTCAGTACGGGCCTGCCCTGCACCCTGCGCACGCCCCACAGAT
AAGCTACACCGGGCCCTCGTCCAGCGGGCGCTTCGCGGGCAGAGAGTGGTACTACGGGAACGTGACGCGGC
ACCAGGCCGAGTGCGCCCTCAACGAGCGGGCGTGGAGGGCGACTTCCTCATTAGGGACAGCGAGTCCTCGGT
AAGTGCGCTGCGCCCACAGCTCCGGCTGCAGGCAGTAAATGCGCCTTGCGCGGTGGGTCTGTGTGCCGCG
(SEQ ID NO: 76)
```

232; ALL; chr2: 111591678-111597436; 2; FLJ44006-BCL2L11; DIVERGENT_PROMOTER
```
CGACTCGGTGAAGGATGATGCCCGGAGGGTGATCTCGACCTTTAACATTCCACACACCTACCTCCACGCACCA
ATCGCCGGAATCTCCAACCCGCGGGCCGCGTGGGCTTTCTACCCTGCACCGCTGAGCCGCGGCCACGGGAAG
AGGCGCGCTCCCGGCGGCCCAAGCTGGGAGCCAAGCTCTAACGGGTGTGGCGGGAAGTGTGGTGGCCCGCC
AGCAGCTGCCACGACGCTCGCTCCACCGACGCCCAGAGCTGTGGCCGGGCCGGGGGCTGGCACCCGCTGGG
CCGCCACTCTCGGGGATTTTGGTGGCAAAGCGGAGGTCCCGCCGAGGCTGGCGAGGTGCGCGGCTGGCTGC
TAGGAAAGAGATCCAGACGGTCGCCTGGTGCGCTGGATCCCGTGCCCTTTCCCTGAAACCCAGCCTGGCCTG
ACTGCAACCTCTCCCAACTTCAGTGCCGGATCCCCTAGACAATCAGGGTGGGCTCCCCGCTGCGAGCGCGCC
CCACAGCCGGGTGCCGCCAAAGGTCTCCTGCTGTAGCGGTGACTCACATTCCCAGTGATTTAGAAAAACTGT
GGTGCCGAGTGAAAGAAAAAAAAAAAAGCAAACACCCTTAGACAAAAGAAAAAAGCTCCACTCTTTCCGCGA
GCGGGAAAAAAGGTTTGGTTCAGCAGTGATGCTATTTCAGTGAATCAGACGCTCTGGGGCTCTGCAAGGAAA
CGCACGGACTGGGAGAAGGAAGTGGGAGCCTAGAGTTTTGCTCTCGGCAAAACAAGAACTCGGCTTGTCCTC
CCAGGCCGGCGGTTTCCTACGGCAAGACAAGGCGCGGAAAACATTTTTACCATCTGACGCTGTAGTCTGTCCT
TTAGAAGAGAATAGGTGAAAAGTTTAATAAAGAAATTAAGCGATGTGAAGTCGTTCCCGCTGCTTGCAGAG
GGTGGGGAGCGGGCCTGGGCAATTTCGGAACTAGGAGAGACCACGTCGGCAAAGCCTGTGGTCCCGAACAA
GGGCCATGGATTTCCCATTTCTCAGATCCCGGCTGCCCGACTTCATTCTTGTTTCTTTCAGCACAAGCCATCC
CCCTTCTCCCTCCCTCCACGTCTCTTGGCAGAGACAGAAAGGGACACCGCTCTGCCCGCGTCCAGCGCGAAG
GAGGTGACCTAAAACCATGGGCCCTTCTCACACTGCGTTCTCTGCGCTCCGGCCCAGTTCCGGAGGACCTC
CCG (SEQ ID NO: 77)
```

238; ALL; chr2: 156892636-156892878; 2; NR4A2; INSIDE
```
CGGGTTGGAGTCGACATGGGCCCTGACGAGGGCACTGATCAGACTCACCGGGGCGAAGGGGAGAGGGCT
CCTGTGGGCTCTTCGGTTTCGAGGGCAAACGACCTCTCCGGCCTTTTAAACTGTCTTGCGAACCACTGCAAAG
GAAGAGCCCTGTTAGCGCCGCTTTTCCGAGCCCAGGCCCAGCTGCTGCCTCGGTCCCTCCCCGGGAAGGCC
GCAGCCGCGGGGCACCAGGCTGAGCG (SEQ ID NO: 78)
```

240; ALL; chr2: 156893736-156894685; 2; NR4A2; INSIDE
```
TCCTAACCAATTTCATTCTGAACAGGGAAGACAGCTCCTAGCACATGCAAATGACCCTCTTCCAACTCCGGCT
CCAGCAACTTCGGGCGGGGGCCAGCCGGGTCGGCTGAATGCGAGGGGATGCGACCTGGCCTCCCAGTCTT
TCTGCTTCCCTTTCTCAGACACCCGGAAGTCCCCGCCGCAGCCCATGGTCTCCTGCAGGGCAGCTTCGGCGG
ACCCCGGAGAGCTGGGCAGTCCCGGGAGAGCTGGGGCTGGGCTACTGCACCAAGGCAGAGGGCACACTCCG
```

TABLE 3-continued

CpG islands hypermethylated in (bladder) cancer. Provided for each are: ID;
Comparision; Coordinates of selected regions containing relevant CpG islands
based on Homo sapiens full genome as provided by UCSC
(hg18, Mar. 2006); Chromosome; GeneName; Location relative
to gene Sequence.

AGGTCCCGGGCACTAGGGGCTCCCTACCTGCCTACTCCGCTCCCGCCATTGCTCACCTTAAAGAAGCCTTTGC
AGCCCTCACAGGTGCGCACGCCGTAGTGTTGGCAGGCCGGTTGTCCCCACACACAGCGCACAGCCCCTCGTT
GGAGGGGGAGCCCCGCGACGGCGGTGAGGGCACCTGCGTGTCGAGCAGCTGAGACGCGTGGCCGATCTGCA
GGCCCGGGAAGCCCATGGACGCGGGCTTGCGATGGGGTTGGGCACAGCGAAGGTCTGCCCGTCCACCACGT
GGTGGCTGCCGGCGGGCTCCGGGTTCATGGGGACGTGCAGGGGCCCGTCGAAGCGCATCTGGCAACTAGAC
ACCGGGGTGCCAGGGGGCGATTGCTTAAGGAGAAGAGGGAGAGGCGGGAGACTGGCGTTTTCCTCTGCTCG
ATCATGTGCGTAGTGGCCACGTAGTTCTGGTGGAAGTTGTGGAGAGATCCCGGGTCGTCCCACATGGGGCTG
TGCTGCACCTGGAAGCCCGGGTGGTGGGCGTCGGGGGCGAGGAGGGCTTGTAGTAAACCGACCCGGAGTGC
GGCATCATCTCCTCAGACTGGGGGGGCAGGTGGCTGTGTTGCTGGTAGTTGTGCATCTGAATGTCTTCTACCT
TAATGGAGGAC (SEQ ID NO: 79)

245; ALL; chr2: 171384729-171385226; 2; GAD1; INSIDE
ATACAATTACCCACACAACAAAGAGGGCCTCGGGAGAGTCGCCAGCCCTGGTAGCATATGAACCAGGCACCG
GCGTTGGAGCTGGCCAGGGCAGGGCGGGAGGAACGCGAGGCCTGCGCGCCTTTGTTGGTGCTTTCGCCTTG
ATGGATTTCTTTTCTGACGCTTTCCACATTTCCCGCTCCCTTTTGCCGCCTCGGGGGTGGGGGTGGGGGTTAG
CGGGCAGTTGTGTTAATTTGCCCTCCACTCCCGGCGCCCTTACGGAATCCCGGTGGCCGCCAGTCGCCGGCG
CAAATGCCAAGTCACCGGTAGGAGACACAACAGAGGCGATGACCTGAATCCGCACGTGGCCTGGTTCGCCTG
GAAGCTGCCAAAGCGAAGGCAAGAGAGCCCGGGACCCTGTGTAAAACAGCAAGCAGCACGTGTCCCAGGCA
CACTGTTGCGGGCCCTTAGCCTAGCTACGCATCCGCACCCCAGGCTTCAAAGGCGCGCTGGGCG
(SEQ ID NO: 80)

254; ALL; chr2: 176737610-176738187; 2; HOXD3; INSIDE
GAAAGAGATCCGTGGGCTTCTGACCCTGGTTTAGGCAAAACAGGGGGAGGCGCCGAGACCAGCTCGAGCACT
AGCGGATTTTGAGAGAAACTGACCGCAACCTCCATCGCCTTCCCCCTCTCTTTCACTTGGATGGGCTGACTCT
ACCCGTCGGTGATTTACGACGATTGCAGCGCTAGTCACAGCCTGGCGCCTGGTGTCCCCTCCCTTCCCAAGCC
CCCTCAGCTTTTCCACTGCCACCGGCGTACAAGCAAGTGCCGAGCGGCCTCCGCAAGTCGGACTAGCCTCCC
GGCGTCCGAGGCCACCACGGGCAGCAGATTTTTGGTCCCCAGCGAGGCTGCGCGCGTTCGTCCCGCCTCCGA
CCGCCGAGCAGAGCTGCTAGCAGAAGCAGGCGCCGGTACTTTATATAATCCTGCTGCTCGCAGGGTGCAAGA
GCGGGAAAAGTGCGGAGTAGGGAATTCTTTTGCTGCGCTGCCTCCTACGCGGAGCCTGCTTTCCACTGCTGA
AAAGTGCCGGGCCTTGGGAAGTGTTTTTCTTTCATTCCTTACCGAAGCGTTTACTGCCGCCGTGGTCG
(SEQ ID NO: 81)

259; ALL; chr20: 35582018-35583550; 20; NNAT; PROMOTER
CGGCTGGCTACCGGTGCGCGGGGACCACACTCACAAACCGCATTCCGGTCTTCCCGCCCGAAAATCCGCGCT
GTGCGAGGGACCCACAAGACTGGCGGTCTAAAAGGGACCCGCCTCACTTGGAAACGGGCTGCGGTAGCCACA
ACCCTCCGGTAGCGGTAGCGTAACCCCGTTCGGTGATCCAGCCGCACAGCGCAACGGGTACAAAGAACCCCA
CTGGCTAAGGCCGACCTACCAGGGCTTGGGGGAGGGGAGCGGAAGACGAGGTCGAAACGACCTGTCCAGCA
GAAAACTATCCCCAAGCATATTCCAACCACTTCTCCGTAGAGCTCATTCCTTCCGTGCATACGAAGGGCGCCA
ATCCTTCCTGTATCCCTCCTACAGATACCGGGTGACTACGCTTTTGCGCCCAAAGCGCAGTGCTCTGGCTCAG
CTCCCTACAGTAAGCGACCTCCACCGCAGATTCTCATCTCCTCGCTACGTAAGAGAGATGTAAAGAATCAGAC
GGGTTACGCGCTCAGGCACCCTCATGAAGAGAGGACCTGGGCTTAAAACTCATTCAGTATCAGGAAAAGAGC
GCCGAGCACGGGCCTATTATGCCAAAGCTTCTGAAAGGGGCACCACGTTTTTTGCTCTATGGGGCAGATGAC
CCCTCCCTAATTTCGGTTTTCATCCATCCCCAAGGTAGGCTTTGGAGTGGCACCGGAGACTGAGCTCAAATTT
GCAGGCCAGGGACTGGGGAGAAGGGCGCCACACTAAGAGACCTGCACCCCCATTCTCGCCCTGTACTCTACC
CAGAGTCGTGGTCCCCTCCATTTTAAAGCAAAATCCAAAAGCAAGCACGGCGGAATCTTCTGGAAGGGGGCT
AAGATGGAACTCAGGAGGCGGGGGTCGGTATGGAAAGAGCAGATGGATTATTTTTTTCCTCTCCTGGCGAAT
GAGGGCGCCCCCAGCCACCCCTCCTCATAAACACCCCCCAAGGCGCGCATGCGCACTTAGGTGCGGGCGGG
TACTTAAGGCGCGGCCACCGCGGCTGCGGCAGTGCGCCCAACAGCGGACTCCGAGACCAGCGGATCTCGCAA
ACCCTCTTTCTCGACCACCCACCTACCATTCTTGGAACCATGGCGGCAGTGGCGGCGGCCTCGGCTGAACTG
CTCATCATCGGCTGGTACATCTTCCGCGTGCTGCTGCAGGTAAGTCTGACGGGGTTTCGGTGGGAGAGGGT
(SEQ ID NO: 82)

267; ALL; chr20: 60061693-60062033; 20; TAF4; INSIDE
CGTCTAATCGATGGTGGGGCGAAGGGAGAGCCACGGCGGCCCTGAGTGCAAGCACCATCCTGAAACCAGGA
GCCCATGAGGCCGCGGGAGCCGGAGGACCAGGACCGCCCTCGCACTGCCCTGTGACAGCTCCCGGCCCAGC
TCTCTGCCGCTCTGGATCCGTCACTAAGCAGCTCCATTAAGTGCCCGGTCGGCAGGAGCGGCAGGGAAACA
CTGGGGCACCCACATCTGAACAGAGAAGATGCCCACCTTGAGAAGGTACCTGGAGAAGGGAGCCACGAGCGA
CGTTTATGCTGAGAAGCGGCATCCGTGCACCTCACCTCCGCCCGTCCACGCCG (SEQ ID NO: 83)

281; ALL; chr4: 9756136-9756429; 4; chr4: 009756149-009756196; Unknown
CGCTCGGGTGGCCGAGTTACACCTGGCTATAAGTCATCCCGTGCACCTGACTAAATGCATCCCGTGCACCTGA
CTAAATGCGTCCCGTGCACCTGACTAAATGCGTCCCGTGCACCTGACTAAATGCTCCCGTGCACCTGACTAAA
TGCGTCCCGTGCACCTGACTAAATGCGTCCCGTGCACCTGACTAAATGCGTCCCGTGCACCTGACTAAATGCG
TCCCGTGCACCTGACTAAATGCGTCCCGTGCACCTGACTAAATGGTCCCGTGCACCTGACTAAATGCGTCCCG
(SEQ ID NO: 84)

284; ALL; chr4: 111780013-111780343; 4; PITX2; PROMOTER
CGCGGAGAGACACAGGGAGAGGGAAGGGAGTTGCGCTGAAAAGACGCAAAGATACGCGCGTGCAACTCCCT
CCCCCTTTCAGGTTTCAGAGGTTTGCAAACCAGGGCTGAGAGGAAGGGGCTCGGGAACTCACGTTCCTCTCGC
CCCCCTTCTGTCTGGAGTCTCGCCCCGCCAGAGGCTGGTTAACCCCAGTCCCGGCCGCCGCAGACACTGCGCT
GAGCTTTTGGGTCCTCGCCTTGCCCAGCGCCAGTGCAGCTGAAGTGAGAGCTGGTGGGAAATGCAAATGGCT
CCTGGAGAAATAGAAGATACAGAATGATTCTCATTCCCTCCT (SEQ ID NO: 85)

TABLE 3-continued

CpG islands hypermethylated in (bladder) cancer. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

302; ALL; chr5: 115810975-115811393; 5; SEMA6A; INSIDE
CGCGGCTGCCGCGGCTGGGCTTCCGCTTCTGCTGCAGCGTTGGGGTTGACTCTGGGGTGGGGAGGGCCGTC
AGGTCCAGGTGGTGCTGGTCTGCTTTAATGAGCATCTTGGCCGTGTTGCCGGGAGTGCGAGCTTGCCGTTGT
GCATGAGTGGCGTGAGGATGGCCTCCGGCTTTGGGTCTTTGGATTGAGTGTCCCCAAAGAGGCCGCTGAGCT
TGGTGACGCTGCTCATGGAGCCCCGGCGCGAGTGGGTGAGCTCCTTCTCTTGCGCTGCACCACAGCCACGTC
TTTGCGCCGATGATCACAGACGCAGTAGACGGTGATGCCCGAGAAGACGGCCCCCATGACGAAAGCCAGGAT
GACTGCAATGGCCAAGAGGGTGACGGGAACCAGCTGGTCGGGCCTTTGAGGTAACTT (SEQ ID NO: 86)

304; ALL; chr5: 122461778-122463450; 5; chr5: 122462228-122462286; Unknown
CGGCCAAGGCTGGCGGCGGCAGGTACCCGGGTGCCCCGAGGGCCACCCGCCGCCCCGCTCTGGCGCATCCA
TCAGTGGCCAGCTTTCACCGTGTCTGCCAGGCGGGACTCGCCAGGTGTCAGGCTCATGCCATAAGCCTGACA
CTTGCGCGGGGTCGCCGTGGCTCCTCAGGGAAGCTGGGCCAAGGAGGCTGGGTCGCGCCGGCGGGCGCCGA
GGCCACCTTCTCGGGGCAGGCCATCCGCGCTGAGGCGCAGACACGGCGGTCCTCCAGGCCCATTAATAACCC
GGAGGGCGCTGCGATCCGACAGCGCAGTCGCCACAGGCTCTATTTCCCGTGGCCGCCTGCCTCCTTCCAGCC
CAGTTCGAGTGGAGGGATACTGGGCGCCCACTACCGCCCGGCCGGAGGGTGGGGGTCCCTCTCGCGCAGGC
TGCTTTGGAGAGTGTCGGAGAGAGACAGCTTTATCTACAGCTTCACCCATTGTATAGCACAACAGAATCGCAT
TTAGCCTGGAGAACAGCCGTCGGGGCAGGAGTTGTGCCTTCTCTAACAATTAGGCTGATCGTTAAATTTGCTA
TTCCTTTCTTCCGGCGTCTAGGGAGAGCGTGCACACCAAACCCTCCAGAACAGCACCCCGGTCCCCCACCCC
GCCCCACCTGTCCCCGCCCTGCTTAGTGCCTGGAGGGAGAACTGACTGGTCGCTTGAGGGACCCCATTTCGG
GCGCGCCCTTGGAGTCCTGGGGCTGCGGCTCCTGCTCTACCGGGCTGCAGGCTTGCTCTGCCCCGTCCCGTG
GCGTTTGGGAGGCAGTGAGGAAGCCTCCGAGTCTCTGGGTCGAAGGAAGTGCGAATGGCACCCGCGATAGA
CTGGCCGTCTCCCCCACCCCGCCCCGTCTGGTGATTTTAAATCGTCTCCTGTGTAATTGTAAAAAGAGGAAAG
CTGAATACCAGACGACCAGTATAGAATCTCTTCGAGACAAGACAGATTGGGCAAGAGACGGGCTTTTTTTCGCAA
TACAAGGATAAACACATCCTGAAACTCCAGATAGAAACCTCAGGAATGGGCGAGAGGGTCAGAAGGAACGAA
GACAGTAGGGAAGAGAGAGAGAGACAGAGACAGAGGGAGAGATGCAGAGAGACTGAAACGGGAGGAAGA
AGCCTGGAACTGTCGGTTCCGTGGAGAGCGGACATGCTATCTGCGCCCAGATCCGAAGGCTTTTGGGGAGCC
TAG (SEQ ID NO: 87)

311; ALL; chr5: 134390896-134393045; 5; PITX1; DOWNSTREAM
CACAGAAGAAAAGGCAACCCCAGGCATAAAGAGGCTCTCAGCAGCCCTGCCCGAACGCTCCTGGCAGGCAA
GGGCCCCATAGCACCCTGGGGCCTCGAGGGTCACCGCAGACCCGGCCTGGGAAGAACCCGTAGAGTCCCGC
AGCCGCGGAGGGAGGGGGTTCTCGCTAAGGCGTCCCGCGGACAACGCCGAGAGGCACAGCTTAGCGGGTGC
GCACCGGACAGGCTCGCAACGCAGGACGGTGCCCTCATGGGAGCCAGGCGAGCAGGTCAAGAATGGTGGTG
GGGAAGCGGGGTAGGCAGACCTCGGCGGGGGCTGCCTCGGCGCTCTGCTCCTACCCAAGGGGCCCGGTTCC
CTTTCTACCCACAGTTCCCTTTCTATCCGCCTCCCTCCTCAGCCAATGAAGCAGTCGGGGCTCAGCAGTGCTT
AGCACGCTCGGACTATGGTTTTAATAGACGTACATGGACAAGTCGATATAGACAGATTTATTACAGTCAGTCC
AACATACACAGGGACGCTGTAAACAGGGGCGCGGCCGGAGAGCGGGTGTGCAAAGTGGGCGCAGGGCCCTG
GGGCCGCGCCCCTTGCTCTGCCGGCTCGACTCTTGCACGGCGGGCGGTGAGGAGGGGGCTGTTCGCCCAGA
CAGAGGGCCACCTCCTAGCCCGGGAGCGAGCAGAGGGCCTGGGCCTGCAGCTAAGCTCAAGGCTGGGGTGT
TCTGAGATGGACCTCCCCCACCTCCCGCCAGGCCCGCACTGCCCGCTGTCGCTCCGTGGCCTTAATATAGGG
CTCCGGGGCGCGGGGCCAGCAGGCTCTACCAGGCGCGCCGGGGCCGTGTGCGGCTCCACTGAGTGCCCGAT
CCTGGGCTGGGGGCACCGTCCCCCCAAACCCAACGCCCGCCCCAACACGGATCCGACTCGAGCTAAGGCGCT
CTCGGCCGGGCCTGCTCGGAGAGGGCAACTTGGTTTGTACGGGGTCGGGAAATCCTAGGCAAGTCCAGGCCC
CGCACATCCAGTCCGCAGGCCCGGCCACTCAGTCCGGATCCAGCGCGGCGGGGACGCGGGATACGAGGTCG
TCCTCCCCGGCCGCTGGGCCTCGGCGCTCGCCTACCGCGCCGCGTGCCCTCCGCGGAGTGGGCCTCCGGGG
CCCGTGGGAACACACACCACCACCCGCGCCATCCCGAGAGAAATTGCAACTCATCCATTTTTTCGCGGCACTTT
CTCCGACGT (SEQ ID NO: 88)

314; ALL; chr5: 135442969-135443206; 5; chr5: 135443148-135443192; Unknown
CGCGCGGGACCGGAGGCGCACACCGGAGGGGAGGTGCCCCCACCAAAATTTAAGTGCGGCGCAACATGCAC
CACAGGTAGGGCACTACCAGGGCAAAAAGACTTGGTGAATGCGAGGGCCGGGCCTATCAAAGGTGCGTATG
GTGGTACCAGAGCAAGGCGGAACAGCTGCTCAGTGGTCCGCAACCGGGTCAAGGGACAAGAAGACGATTCTG
GATTGTAGGCCGCCCGAGAGCG (SEQ ID NO: 89)

319; ALL; chr5: 174091287-174092335; 5; MSX2; DOWNSTREAM
CGGTGACTCGGAACAGAGGCAGAAAGGATGCGAGGACTTCTTGCTGCGTAAACAGCGCGGCGGGCAGATTG
GCACCTGGCACCTACCAGGACTGGCGCTTCGTCCCGCGTTTCCATTGTGCCCGCACCACTTTGAAAGTGGGC
GCCGGAAACTCCGTTTTTCTTATGGGGCCGGGGTCGGGCAACGTGGTTCAGAGGTTTCACAAGCTCCAGCAC
AGAAGTGATCCAAACCGAGGGGTCGGCTCGAAGTCGGAGGCTGATTTTTCTTGCTCAGTCGCTCCGCCGGAG
CTGAGCCGCTGGAACGACCCAAACCTACCTGAAAGCGCGTCTCTGCAGTCCCGCTGGACTTCTCCGGCTCGA
ACTCCTAATCTCAGCCCGGAATCCAGCCATATTCATTTAAGATTGCGTTTTCCAAAGGCCAAAGCCTTTCCCG
GTTTCGTCATCAGCCGCCAGGTTGGGTCCCTAATTAGCCTGTCCACCGAGCTTCCTTCCCGGCGCCGCTTGGA
CCCCGCAGCCCCGGGCGATCTCAGCCCGGGGGGAATCCGGAGAGCGCGGCTCCGGGTTAAGACTCTGCTC
GTCCCCAGGAGGACGGGGTCGCGATCCAGAGTGCGATCGGAGAAAAGGGCTGCATCTTGCGTGGCTGGCG
GGTTAGACTGGAATCCGTCTGGGGACTGCGCACCATCCCCATCGCTCCAGACGCCGAAACAAAACCTGAGGC
TCGGAGAGGGGAAAAGAGTTGTTCAGGCTGAACATACGCATCCCAGCCTCATAGGTGGATGGGGTTACCG
AGCTGAGAACCAAGCCGAGGTCCGCGAAGCCGGGCCGCCCCCTTGCTCTGGGCCTCCCTTCAAGCCTGCAGT
CTGGGGATGGGTTCCGAGTCACCGCGGTCCGGGCCTCGGTCAGGCTTGGTCGGGCACACAGGGCGTTTCAGA
GGCCAGATGACAACCTGTGGCGGCAAAAGGACTCTCCCTCACCAGGGACCCGCGAAGGCGCGCATTGCAAGA
TGTTAGCGTGCGGGCTTTAGATATCCTTGCGTCCG (SEQ ID NO: 90)

TABLE 3-continued

CpG islands hypermethylated in (bladder) cancer. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

324; ALL; chr6: 1549606-1560865; 6; FOXC1; PROMOTER
CGGGGTCCCACGCGGGCGGCGCGGTCTTCCCCAGGCCTCCTTCTCTGGAGACCCGGTTCCCAGGGGACGCTG
TGCGGGGACAGGCGGAGCCGGCCCTTGGAGCCCGGCGCGGGCAGAGGCGCCGCGGGACAACGCCTCCGACG
GCAGGGGGCGCTCGTAGCACGCGCAGTGCGCGGTGCGGGCGCCCAGGACGGCTGCCTGGCCCCGGGTTCCC
GAGGCGCGGGACCTGCCGGGGTGAGGTGCCCCCAGCCTGAGAGCCCCAGCTGGGTCGGCCAAGGGGCCTCC
GGGCTTCCACATCGTCCCTTTTTCTGCTGACGCTCGCGGGGAAGCGGCGGGAAGCCTGTGAGGGGCGGCCTG
GGAGCAGACGGACCACCAGGTCACCGGCGCGCGCTGCCAGGCCCGACCCACTCGCGAGGACCAGCGGTTCC
CGGAGGCGTCGGCCCTCAGGTCCTCGGGGGAGGCCGGCTGCACCGAGCCGGGTGTCGGCCTTGTCCCTGTC
CTGAGAGGTGCAAACACCGGCCCCGGCCCAGGCCCCGGGGCTCCTGCCCAGAAGGCTCAGAGCTGGGGGCC
GACCGCGCCTTACCCGCAGGAGGCCCGGCGGTGCGTCCGCGTTGGTGCCACTCCCCGGCCGGGGTGAGGGA
CGTCGGAAGGAAGGTCCCAGGGCGCAGGGTCCGCGAAGGGAGCACTCGGAAGGAAGGCTGGCTGCGGCCCC
GGCGCCTGGGTCCGCTGCGGCGCCGGGCCGGAGACCTGGGAACAGCCAGCCACCTGCAAGGTTGCAGCCCA
CCTCACCCCGCCGGCGGCTCCGGGCTGTCTGTGGGTCTGTCTCACGGGGCAAAGCCTTTCTTCCCACACCCA
CAGCCAAGGCGCGTCCGTGCAGGGGCACACGCCTTCTGCTCCAGCCCCAGGAAGGCGCTTTCGCCCTGCAGT
CCTCCGACGGCCGGCTCCGCCGCACCGCGCACCCTGGCTCCGGCAGACTCTGGGGCTGGGGACTCGCCCAC
CCTGCGCGGCGCGCCCCCACATGAGCCGAGGTTGGGAGGCTGCGGGGCCTCTGTCCTCCCAGGCCGTGGA
GTGCGGCGGCGCTCTGAGTCCGCTGGGGACCTGGATGGAGAGAAACTGGGGCTCGTTCGCGCACACATGCA
CCATTTTGTTCTTTCCGATCATCTATCCCTTTACGAATTTTATTTTTATTCCGGATTGTTAATGCAAGACGACAG
TTGAATCTCCA (SEQ ID NO: 91)

339; ALL; chr7: 1481682-1482268; 7; chr7: 001481829-001481873; Unknown
CGGCCTGCGGTGGGGAAGCGGGTACGGGAGGCCCAGCTCTCCCACCAGGGTCACTGGAGAGGAGCAGACG
CAGCCGTCCGCCAAGACCCGGGCACGAGTCCCCAGCAGCTGTCACTGCCCCAAACTAACGTGACCCCACGTC
CACCAGCAGGTGAACAGATAAACCAACGGCCGATCCACACAATGGCAGGCCACCCAGTGCCCACAACACCAC
GACTCTCCAGACTGTGCGAGCAGAGCACCCGCAAGCTCCCTCGGTATAAACTCAACGCAGACAAACCCACAG
GGCCACAGGGCGGCGCGGACTGGGAAGGGGCAAGAGGGGTAGCCGGCGATGGCCATGTACACTGTGGCCTC
CGCCCTCCCTCCCTGCCCGGCCAGGGCACCTGGGACGGCGGGGGGAGCGGCAGAGTTGCGCCCTCACCTTG
CAGACGCTGCTGCTGGCAGCCCCTTCGCTGTGCAGTAGGACCTCAGGCACGGGCACCCGCAGCTCCGGCCGC
TGTAGGTAGAGCTGCAGGAGAAGGTCTCGGCAGCCCTGCCCAGCACGCTGGAAGAGGTGGAGCAGGGCTCA
CCAGGCGGACG (SEQ ID NO: 92)

340; ALL; chr7: 2082782-2083345; 7; MAD1L1; INSIDE
AACACAGTTATGACACAGTGAGCCCACAGCACAGTTAGCCTGCAGCACAGTGAGCCCGAGACACAGGTATGA
CACAGCGAGCACATGGCATGGTGACCCTGAGACAGGGTTACGACTTGGTGAGCCCCAACATGGTGAGCCCAA
GACGGTTACGACATGGTGAGCTCACGGCACAGTGAGCCTGAGCCTTACGACACGATGAGCCCGCAGCACG
GTCAGCCTGAGACGGTTACAACATGGTGAGCCTGTGGCACGGTGAGCCAAGACAGGGTTACGACATAGTGAG
CCCACAGCATGGTCAGCCCGAGACAGTTATGGCACAGTGAGCCCGCGGCACGGTGAGCCCGCAGCATGGTGA
GCCCGAGACGGTTATGACACAGTGAGCTCACGGCACGGTAGCCCGAGACAGAGTTACGACTTGGTGAGCCCG
CGGCATGGTGAGCCCAAGACAGAGTTACGACTTGGTGAGCCCGCGGCATGGTGAGCCCGAGATGGTTACGAC
ATGGTGAGCTCGCAGCACGGTGAGCCTGCCATGGCCTCAAGGGTTAAGATGTAAAC (SEQ ID NO: 93)

345; ALL; chr7: 2724511-2724848; 7; AMZ1; DOWNSTREAM
CTTCTCAGCAAAGGCCAACACGTCTTTCTCGAGTCCAAGACCATCTCCCGTTCAAGGGCCCTCACCGCGCTTT
GTGAGTCTGTCTCGTGGGCCTCCTTCAGTGGTCTGTGACCAGCGGGAATGAATGGGACGTGTTTTGTTCAGC
CCTGACTCTTGGACGCTGGTGGCAGCCGCGGGCGCCCACTCACCTGGCACGTGGACGAAGGTGATGAGCGC
GGCTGACGGCTCCCGGGGGCAGTGTGGGGTCCAGTCTGAAGCCGACGCCCTCTCGGTCAGGCTTTCAGCAGC
AGAAGGCAGTGGACTCTTCACCATTTCTTCCAACACTTTCTCACGTAG (SEQ ID NO: 94)

349; ALL; chr7: 8449587-8450236; 7; NXPH1; INSIDE
AAACTGAGGCAACCAACTTATTCGCAAGAGTAAAACCCTATGGGGAGAAGCGATTCCTGCCCCTCTTCCCCCG
GCGAGGAACACGGCTGGAGCCACCCAGGCGCCTTCCAGGCTAAGGCGCCTTTAGGGCGCGCAGGGGTGAGG
GAGAGGGTGGGGAGAGTCCTAATTATTATGAATTTCTAAAGGCGCAGTAATTATTCACGGGGAGCAGGACAA
ACCATGGCTAGGCAGGGAAATCGATATATTTGCTATCGAAAGTTCCTGCTCGCCTTTAATGCAGACGAATGGG
GGATGCAGCCTCATTATTTTCCGTGGTTAGGCTCGCCAGCGTGGGGCCTGATGCAGCGTGAAATCTATCATCA
TTAGACCCGGGATGGAGCGGCGGGGGGGAGTTTCTCTTACTTACCAAACCGCAACAACAAACAAACAACGAC
GAACAACCGCCCCCTACAAACACTCATTCTCACACAACGTTGCCCTACCTCCCTCGCCGCTTGCCCTGGCCGC
TGTTGCACACTCCCCTGGGGGCTGTCTGACGCCCTAGAGCAGACACTGCGGTCACTTAAAGTGCGCCCAGTT
CCTCCACCGCAGCGGTCACACCGTTGATTTGATCCAGAAATAAGACGGATAGTACCGAGCGTTGGCG
(SEQ ID NO: 95)

354; ALL; chr7: 27164708-27165039; 7; HOXA7; PROMOTER
CGCCGCCGCCGTCTGTCTAGACTCAAGCGACTGAAGGGGCCAACAGAGCTGGTGTTTAAAGTAGAACCTGCC
CAGTCCAACAGCCCGAGCAGGGAGCGATTTCGGGGATCGCGGGAAGGAACGCACTCGCCAAGGGAGGGCCG
GGTGCCCTCGCCACCGGCTCATTCCTGCTCCGGTTTTGCCCGATGCGGTCCAGGAGGTTCTGGCAGGACGC
ACTGCCCCTCTGCCCCGGCCAAGGAGGATGCGGATACTGCCCGCAAGGTTCGGCCTTTATGGACCCAAGTCA
GCCAACTGGGCCGAGTCCTGCGGACACCGAAACCTCCCTTTCG (SEQ ID NO: 96)

358; ALL; chr7: 27251165-27252762; 7; EVX1; INSIDE
CGCCTGTGCTCTGGACTCGCTGTGCAGGGTCCGGCTCCGAGGCGCTGGTCGGCAGTCCGAACGGAGGGAGC
GAGACCCCCAAGAGCAACGGCGGCAGTGGTGGGGGCGGCTCGCAAGGCACCCTGGCTGCAGCGCCAGTGAC
CAGATGCGTCGTTACCGCACCGCCTTCACCCGAGAGCAGATTGCGCGGCTGGAGAAGGAATTCTACCGGGAG
AACTACGTATCCAGGCCGCGGAGATGTGAGCTGGCGGCCGCCCTAAACCGCCGGAAACCACCATCAAGGTAT
GCGGGGTCCAGGCTGGGGAGGCGGGTGTGCACCTATTTAGCGGGAAGTAAATGCCAACTGCCAACTCCCTGA TABLE 3-continued CpG islands hypermethylated in (bladder) cancer. Provided for each are: ID;
Comparision; Coordinates of selected regions containing relevant CpG islands
based on Homo sapiens full genome as provided by UCSC
(hg18, Mar. 2006); Chromosome; GeneName; Location relative
to gene Sequence.

```
AACGCAGGCCAGGAATCTGGGCCTGGGGTCTCCCTGCCCGGGCGTGCAGATTGACCCTCGTGACAGCTCCTA
GGCAGGCATTGCTGCCATGTGGCTGACTCTGTCCCTTTCCTGGTTAAATAGACAAGGGGTGGGCGTGGGGGA
AGGGGATAGAGTGCCTGTGCGGGTGACAAGGAATTTCTGGGGACACGCTCTCTGCGGCCGCAGACCAATTGA
GTCCATGTCCTTTCACTGCTCCTCCCATACACACACTGGCCTCTGGCACCCCGGGGGCCTGGCCACCTGGGCA
GAAGGAAGGAGGGAGCGGGCTGGATCACTCCCCAAACCTCTCTCGGAGGGATTCCAGCTCCAGGTGGTGGTG
GTGGGGTCGGTCTCTACCCGGCTGGTGTCTGCTTTGGCTGTTCCTGCCCTGCGAACACTGTCCCCGGAGCGG
GACCAGACTACTGGCCCTGAGCATCGGGCCAAGTCCAGCTACTGAACCTGCTCCGCTCCTCTCCCCAGGTGT
GGTTCCAGAACCGGCGCATGAAGGACAAGCGGCAGCGCCTGGCCATGACGTGGCCGCACCCGGCGGACCCC
GCCTTCTACCTTACATGATGAGCCATGCGGCGGCCGCGGGCGGCCTGCCCTACCCCTTCCCATCGCACCTGC
CCCTGCCCTACTACTCGCCGGTGGGCCTGGGCGCCGCATCCGCCGCCTCCGCCGCCGCCTCGCCCTTCAGCG
GTCGCTGCGCCCGCTCGACACGTTCCGCGTGCTGTCGCAGCCCTACCCGCGGCCCGAACTGCTGTGCGCCTT
CCGCCACCCGCCGCTCTACCCCGGGCCCGCGCACGGACTGGGCGCCTCTGCCGGCGGCCCCTGCTCTGCCTC
GCCT (SEQ ID NO: 97)
```

359; ALL; chr7: 32768010-32768497; 7; chr7: 032768257-032768301; Unknown
```
CGGACTTGTCCCCGCAGCCCTTGCGGACCTCCTGGTCGTCATGGCGACTGTGAAATGTGGGGTGGGGAGCAT
GCGTTCGAAGCCATTTGCGCGGGCAGTCCCTGCGTGTCCCCCCACGTGCTCCCCACACTCGCAGGACCCCCG
CCTCCGAGCTTCCCTGAGCGTGCAGCTTCCAGTGAGGGCAGCCCCACGCACAGCCCCCACACCCTCCCCAA
CGCCTTCAGCCCCCGGTGCGCGTAGTCCCCAAGCCCACACGTGCACTTCCACCTTGCGGCAGCTGCACGTAC
AGCCCCCCACACGCTCCCAGCCCCACTGGCGCAGAACCCATCACCGCTCGCCCTTCACGCGCTTCACTGGGA
GTGCAGCCCCCACCCCGAGCGCGCAGCTCCACGCAGCCTTCCACACTCTCCCCAGCGCCTGCAGCACCCCCA
GTGCGCACAGCTCTGCCAGTCGCTTCCCCGCGTGCCGCCCCTGCACCACTTCG (SEQ ID NO: 98)
```

362; ALL; chr7: 55040457-55041024; 7; chr7: 055040965-055041024; Unknown
```
CGAGCACGGCCTCGGAGGCTGAGAGGCCTGGGAGGCAGGGCCGCGTCCTGCGGGCTCCACGAGAGCCCTGT
GAAATGCCAGTCAGATCCTGGCCCAGTGCCCCAGGTCCTCCCGCAGCCTCGGCAAACCCTCCCCGGCGCTG
GAAACCTTCCCCTGCCAGGCGCAGAAGGCCGCGCGCAAGCACGCAGCTCACAGTCACCGCCACCTGCTCTGA
AACCCCAGGTTCAGCGCAGGATCAGAGTCCCCCATCCCCACCCCACGCAAGGGACGCAGGATTGACAGCGAC
CCTGAAGAAATGCAGTCGAGAGCTATTGTGAAAGGGCGCTGGCCCGGAGGCCCCCCAGCCCGCGCAGGACA
GGCCAGTTAATCGCCTTGGTCCCAGGCCCCTATTAGCGTGTCATCTGCGACAGCAGGACACGCCTTCCCATGC
CAGCCGCTTTGGGGCCCGTGCGGCCCTTTTTCCCTCGCAGCTGCTGCAACAAATAGCAGTTCTTTTGAGGGAA
GGAACAGTGTGGTCCTCAAAGTTCATAATGAAAATCTTGGAGAAAAGTCATAGTTGCTAA (SEQ ID NO: 99)
```

364; ALL; chr7: 96488158-96489591; 7; DLX5; INSIDE
```
CGAGCGGGACGAGCCCTGGGGCTCCCACACCGCTGGAGACTGCGGCGAGTTACACGCCATTGGGTCGCTGG
AGCTGGGACTGTGCTCCGGGGGCATCTCCCCGTTTTTCATGATCTTCTTGATCTTGATCTTTTGTTCTGAAACC
AGATTTTCACCTGAGTTGGGGAACAAAGGCACACGTTACCGGGACACTCAGAGGTCGCCCGCGCCTTCCCCG
GGGCGGCGACTGGAGGCATCTTCGGACCTCTGGGCGGCCCAGCCCTCCTGGCGTCTCCCCGCCGCTTGCGGC
CTACCGCCAAGAAGCTATGCCTTAGGCAAACCATGGAGCTCTGGCCCCAGAGGGCGCCCTGGCCGGCTCGGG
GCGCCCCGGCCCAGCGAGGCCACGACCCCAAGGCTTGTTTTTGTTTGGGCTGGGGGTGGGGGGACGCCAGCG
CGGCGGGTGTGCGCCCGAGTGTCCTCGGCGGCGGCGCGCCTCGTGTAAGCCTGCGCAGGACGCGCGGAACG
CGGCGAAGGTCTCCAAAACAATCGCGCGAGCCGGCGGGGAAGGGGCGTGGGGCGGGCTACGCGCGCCTGTG
GTCAGAAAAAGGAGCGAGCTCCCAACCCTCCCGTCCTACTCCCCTTCACTCCCTCTGCAGCTCAGAGAGGCCAG
AATCTGACTGCAGCTCTTGGCGGCGCTGAACATTCTTTATGCTTCCGTAGGCCCCAGCTGGGTTGGAGGAGT
AAAAGGAATGGGACAATCCAGGAAGACTTCTCACGTACAATAGCGCCCCCCACCTCGCGACCCTTCGGTGGC
CGTGGCCTGAAGCTCCGTAGGCTCAGGGCACGACCCTTCAGTTTCTCCGCTCCAGGCGACGTTCTCAGCCTTT
TCTTAGCCTGAGACCACCGCGAGAACACCAGGCCTTGCTCACCCCCGAGGAGGCTCTACATTGTTAAGAAAA
CCAGATACTGCTCTGGCTGCCTAGGCCGCCCTAGAAATAACCCTCCGCTTGCTTTCAACCCGCGAAATTGGC
CCCACAGCTCCGGAGGCCCGCTACGGGGTGGGGGCGGGGGGCGCGGTTAGTGGGAGGTATCTCCAGACCGT
GATGAATACCATCCCCACCGTCTCAAGGCCTGACTCACCGAGTTAAAGCATAGGGGCTGATGTCTTTGGGTCT
GTTAGTTTCTCACGGGTACTGTCAAAACAGCTCCAGTCCCATCGAGACTGAACCGCGCGACCAACCAGACGT
G (SEQ ID NO: 100)
```

369; ALL; chr7: 155266364-155266696; 7; RBM33; INSIDE
```
CGATTCAAAGATGCCGGCGTCCCGCAGTGTGCGGTTCGTGCCCTTAACCACCCGCTTCTTTGTTTCCCGCCCC
TCTGCTTTCGCAGGAGCTCTTGTGCTTGAGTTCAGTGTTAGTGGTAGCGTGGCTACTCCACTTGGAGGTGGCG
GCCGTCTGACCGTGTGTTACTGCTTTGCCGACGGGGCCTCCCGGCCCTGATGCGTGCTACACTCTGCGGGCTG
CACCGGGTGGCTCTGGTTGGGGGCGAAGCTGTGTTGACTGGGAGACGTTGGAAATTGAGACATGGAGAGATG
ACGGGAGTGCGTTTCTCTGGGTTTGATCTCCATCCTGTTTT (SEQ ID NO: 101)
```

371; ALL; chr7: 155288454-155292175; 7; SHH; INSIDE
```
CGCGGTGGCCCCCGCACCCGGAGCGTCGGCAGCACCTGGAGCGGTTAGGGCTACTCTGCCGCCGCCGCCCC
CGCGGTCCCCGCCGCCGCTGTCCCCGCCGCGGTCCGTGCGCGCGGGCGCCAGTGCACCAGGAGCGCGTGCG
CCAGGCGGAAGGGCGCGAAGGCCCGGTGCGCCCAGCTGTGCTCCTCGATGACCGCGTAGCACGAGGCCAGC
ACCCGGTTGATGAGAATGGTGCCCTGGGCCGTGAGCGGCGCGTAGGCGCCGCGGCCTCCTCGCTTAGGGTCA
CGCTGTGCACAGCGGCGGGCAGGAGCCGGCGGTCCCCGTCACGCTCGGCCACCACGTACACGCGCTGGCCC
GGGCGCACGCGGCTGGCGAACAGCGCCCGAGGCCCCAGTGCGCCCCGGAAGGCGGCCCCGAGCCCGAGGAC
GCCTCGGGCTCCCCGGTGGCCGAGTCGTTGTGCGGCGCCACAAAGAGCAGGTGCGCGGCGGTGAGCAGCAG
GCGCTCGCGCGGCTCCCGCGTCTCGATCACGTAGAAGCCTTCTTGGCGCCGTCGTCCGGGTCTCAGGAAAGTG
AGGAAGTCGCTGTAGAGCAGCCGGCCCTGGTCGTCCGCCGCCAGCACGCGGTCCCCGGGGCTCAGGTCCTTC
ACCAGCTTGGTGCCGCCCTGCTCCAGGTGACCGTGGCCGAGCCCGGGAAGCAGCCTCCCGATTTGGCCGCCA
CCGAGTTCTCTGCGGGTGAGGAGAAGGGAAGAAGAGAGGACAGGGCATTGAGTTCCGAGAGGGAGGCGCG
TCTCGGGGAGGAGGGCGCACGCTGGTGCCCGCGCTCCTAGGCCAGGGGTGCGCAAGGCGCGGGCGGGGC
GATTGATTCCAGGCGGGTCCCGCACACACCTCCCTCCCCCAACCCCACTGCCCCAGGGACAGGATTCCGACA
```

TABLE 3-continued

CpG islands hypermethylated in (bladder) cancer. Provided for each are: ID;
Comparision; Coordinates of selected regions containing relevant CpG islands
based on Homo sapiens full genome as provided by UCSC
(hg18, Mar. 2006); Chromosome; GeneName; Location relative
to gene Sequence.

CATTCCTTAACGACTCCTAAGTCTGGGCTGGCGGTCACAGAGGTTGGCTGGCGTTTCCTGCAGAGGCCGGTG
ACACTCTTTCCTTCCGCCTTCCTCCAACCCCACCCCCAGCTCCGCACACACCCGGCCTCGCCGCGAATCCATC
CAGAGGGGTTTGCTCTGCACTTGGATTCCTCAGGAAGCCTCCTTGAGCTCCCGCGGGCGCGGGCGCACCCT
CCTTCCCTCCCGCCCCGGCGCGGGGCGCGGCGCCTGCTCGCGCACTCAGCACCCGGGCTGCGCGGCGGAAA
CCCTGGCCCGC (SEQ ID NO: 102)

390; ALL; chr8: 142288380-142288718; 8; SLC45A4; DOWNSTREAM
CGCACGGCCTCCTCGTCCCTCTCGGGCAAGGCTATCAGCCAGAGCACCTCCCCTTTGACACTGACCGGCGTC
CCCAGCCCCGCCTTGTTACTGCATCCGTCTGAGGTACAAGGTTAGAAGCCACAGAACCCGAGCTGCAGCCTG
ACCCACACAAGCTGCGGGCGCAATGGCGCTTTGCAGACAAGACAGCCTGCCCGTCTGCCCTTCTTCTCGGCT
TCCCTTAAGACACAAGGTGACGACACGGACGGTTTCAAGTGAGTGCATCTGGAAATAATCTCAGTGCAGGGG
AGGGGTTGAGGCCAAAGATGTCGTGACCTGGTCCCCGCTGTGGCCAGGC (SEQ ID NO: 103)

402; ALL; chrX: 39749470-39754050; X; chrX: 039752648-039752692; Unknown
CGAGGTATAAAGACCAACGCACGACGGGCGCCGGGGCGCCGTCACCTGCCTGGGTTAACAGTTCCTGCCGCG
GGGGCAGGGAGAAAGGCGCTAGAGGGGCGCGGGTGCCGGCGGGGCCGAGCCCGGGCGCGGGCGAGCCCT
GGGTGCCAGGCCCTGCGCCGCACGCCACTCTCGCAGCGCTGCCGCGGGAAAGTGCCGGCGCTGGCTCTCC
CTCCCCTCCCGGGAATAGCGGGCGCAGGCACGCACATCCACACACATCCAACACACACACACCGCACACT
CACACACCCGGGTGGCCGCGCGGGGCTCCGAGCCGCGCAGGCCTCCTTGGCAGACATCTTCCTGTGTGGGAGG
ATTTCAAACGAGCCGTGAAAGCCAGAAACTACACGGGTTACAACTCCGGAATCCCTGGCCGGCCTCGGCCTC
CCTCCCCACCTCCGGCCCGGCCCCCTCCGTTCGGCCCGTGGCCAGGAGCCCCACCAAAGGACAAAGCTCACA
CGCCGAAAGCGCGGGGAGATCCGGGGGCGCAGAGATGCCCCGACGGCCCTTCTACCTTCTGACCCTGGGAC
CCACGGCCAAGTGCCGCGCAGCCGAGGTCGGCCTTGCTGATCTGTGGTGGCCCAGGGCGACCCGAAGCGCA
CCGGCTTCAGGGTGCGCCCTGGCCAGGGCTGGGGTGGAGGGTCACATAAGCCACCTGGCATCCGAGGGTGG
CCGCCTCGCCCCCTCAACGCCGCTCTCCAGGGAAGGAGGCGGCGGGGTCACCAGGGCGCAGCTGACAGCCC
CAGGCCCCGGCCAGGGCGCACCCAAAGAAGAGGGAGGCTGCTGCCTGAACTGGCCTGGGGGCAGAGGGAAG
TGGGCCCCGCGCTGTGGAAGGCCCCAGGCTGGAGCGCCGGGGACAGCTGTCAAGCGGCGAGGGCTAGGAG
TGGCCTCGCCTAGCGCTAGCCGGCCAGGCCCTGGAGGTGCTCCGCGCCTTCTCGGCCAAAAGCCAGCTCCGC
GCCGCTGGCGGAGTGGGAGGGAGGCGGCCAGGCGAGCGCCCCGCCTTCGTCGCCCGCGGTCACAGGGGCAA
TTACACTCCTGCTGCAGACGGTTACCAGCTCGCCCGCGCATCCCTCTCTCGGCTCCCCTCTCCTCCCCTCTCC
TCTCCTCCCCTCCCCTCCTCCGCGGAACTGCTGGCTCCATATTAGCGAGGGTGCCCTGGCAGCGCGACCGAG
GCAACTACCCCT (SEQ ID NO: 104)

TABLE 4

CpG islands hypermethylated in NMI-BC FGFR3 wt vs mut. Provided for each
are: ID; Comparision; Coordinates of selected regions containing relevant
CpG islands based on Homo sapiens full genome as provided by UCSC
(hg18, Mar. 2006); Chromosome; GeneName; Location relative
to gene Sequence.

4; SW vs SM; chr1: 2211959-2212429; 1; SKI; INSIDE
TAGGCAGGAGGAGGAGGAGGAAGAGGGCACCTGCTGAGATACTTCACTGGTCTGAGGGCCCCTTCTGCCCCA
GCTAGCGCTTGGGTGAGGGTTGGGCTTGCGGAGCCGTCCTGTAAAGCCGGGGATGCAGGACGCATTGTCACC
CCCTCCTGCCGCTCTTACGAAACACTCTTAATTGAGTCCGATTCTTGGTGAATCAGCCTTCCAAGAACCGCGA
CCGCAGCATCCTGTGCCGCTTCTGTGTTCCGCATTTTTCTCTTTCTGCAGCGTTTCCTCTCATTCTGGATGGAA
AGCCTGTTTGTCTCCCTCAATCTTTGGCGAGGGTGGCAGGCAGCCAGGCGGCCATTACGGGCCGCGCCTCCC
ACCAGCCAGTCGCTGGCAGGAGCGTCCGGGGAGGGAGCAGACCCCGTTCACCCTCACCCCAGAACTGAAGCA
GCGAGGGGACCCAGACGAGCTGGAATGCAGGCG (SEQ ID NO: 105)

5; SW vs SM; chr1: 2226303-2228929; 1; SKI; INSIDE
CGCGCTCCGCCAGCAAGACCTGGCGTCTGCAAAACACAGGCGTGAGGGGCGTGCTTACTAATGCCTGGTGTT
CCAGAAGGCGGCTCCCGCCAGGCCTCCCGAGTAGGAAGGAGAGGGCTCGGCCCGCCAGACACACACACACC
CACCTGCACACGCTGCTTCTCTGGGCTCTGCCTCACGGTTCTCACGCTGCAGCTCCGGTCTCGCGCCTCCTTT
TACGTTGTTTAGGTTTCTTTCTGACATGACTGAGGGAAGTGCGGTTCACAGGCAGAGCTGCCTGGGGAGAGA
GGTGGCAGGCGGCCCGTTGTTCACCGGGCCCCGGCCTCGCTAAATTCACACCTCGGCGGCGTCTGGCAGCTT
CCGCGGCGTGGGCTTTAGCACAACACAACCCCGTCGGCCCTCAGAGCTGCAGGGTTGCCGACGTGCCCTCCT
GCGCGTGCCAGTCCCTCGCCCCAGCCGTCCCCCGCCACTGTTGTCCTTGATTCTGGTTGGAGGTGTGATTTCC
CACATACATATTCATGTGGTGTGTTTGCAGCGTGGGGTGTGAGTCACACGGATATTTTAATGGGGAGAGTGG
GGGGGCTTGCGGAGGCGCCGGGCGGATGGACGTGTCCATCTGGCTCGTGGGGAGACCCGGGGCCCTCAGAT
GGTGCGATGTCTGAGGCTGCCCTCCTCACATTGATGGGAGCCAGGGCCTACTTGGCTTGCTGCCCCCAAGGG
GAACGTGGCCCTAGATACCGGGGGAGGCCCCGCCGCAGCCTCAAGTGACTGACTCAGGCCCCCAGGTTAGCA
CAGCTGCCACAGGCCTGGCGGAAACTCCGGATGGGGGTCTGAAAAGCCTTTGTGGGGTCGGGGCACCACAC
GGGTTGGGCTGATGGCGCGCTGGGGCGGGGCTCCAGGGCACATTGTCAGATAGATGACCCCACGGGGTGG
GCTGAGGACTGCTGGTCAGGTGAGGGGTGTGCTGGGACCGGCTGGGCAGTGACCCCGAGCCGCCTCCGGCC
CCCAGGAGCTGGAGTTCCTACGCGTGGCCAAGAAGGAGAAGCTGCGGGAGGCCACGGAGGCCAAGCGTAAC
CTGCGGAAGGAGATCGAGCGTCTCCGCGCCGAGAACGAGAAAAGATGAAAGAGGCCAACGAGTCACGGCTG
CGCCTGAAGCGGGAGCTGGAGCAGGCGCGGCAGGCCCGGGTGTGCGACAAGGGCTGCGAGGCGGGCCGCCT
GCGCGCCAAGTACTCGGCCCAGGTATGCGGGTGGGGAGACTGAGGCACGCAGCACGGTGGGCGTGAGCCGC
CGTGGGCCCCGGTGGCCAGTCCTGCCCAGCCGGAA (SEQ ID NO: 106)

TABLE 4-continued

CpG islands hypermethylated in NMI-BC FGFR3 wt vs mut. Provided for each
are: ID; Comparision; Coordinates of selected regions containing relevant
CpG islands based on Homo sapiens full genome as provided by UCSC
(hg18, Mar. 2006); Chromosome; GeneName; Location relative
to gene Sequence.

```
19; SW vs SM; chr1: 92718496-92725197; 1; GFI1; INSIDE
CGAGTGCACGGCTTTGTGCTGCTCCAGGCTCACCGCGTGCCGAAGGTCTTGCCGCACATCTCGCAGGCAAA
GGGTCTGGTACCGCTGTGGGACCTGCGCACGTGCACCTCGAGCCCGTGCGGCGTGAGAACACCTAAGGCGG
GTGGGGCCAGAGAGAAGGCCGCTGAGAGGGGCCGCGGGGCGCAGGCGAGGCGCGGGTAGGGGAAGCGGGC
GCACGGCAGGCGAGGTGGTGAGCTCGGGAGCCTCACCTTGCTGCACTTGATGCACTTGTAGGAGCCGCCGCC
CAGCAGCGGCGGGTGCACAGCAGCTCCGACTCCACCTTGACGCCAGCGCCCTTGTCTGCGTGCAGCCCGTGG
CCACGCTCGGGGTACAGCAAGCCCGCCGCTGCCGTGGGCCTCTCATACAGCCCGGCTGCCGCAGACCCGAAG
TCGCCGTAGAGCCCTAGGCCAGGGCCAGGGTGGCACCGGCCCCTGCGCTGCAGCTCCCTGGCGCCCCGGCC
CCCGCGCCGCCGGCAGCCCGCTTCGGGCCGTACAGCGCGGCGGGTGGCCAGGCTCCGGGGCGGGTTCGCA
GAAGAGGCCCAGGCCAGCGCCACGCTCCAGGGCCCCACACGGTCGGTAGCTTGCACCAGGTGCCGCAGGTC
AGAACCCGCCAGGCCGCTCCATGAGTACGGTTTGAAAGGCAGGGGGAAGGGCTGGGCTTCGTCAGCGATG
GGCACATTGACTTCTCCGAGGCTGTGGAGGCACAAGGGGAGCGTCCGGTCAGGCTTCAGACGGCAGAGCGG
AGGCGCCGGGCTGCGGCTGCGAGCGTGGCGTGTTCGCGGACTGCGGGGCACCCAGCGCTTGTAGAACACTG
CGTGCGCCAGGTGCCAGGCTCGCCCCAGGGTAAAACGTGGCCCGGGCCCTGGGGCCTCGCAGGCCACTATA
GGAGGCAGAACAGTAAACAGATCATTAAAAGACCTCGGGAGAGGAGGTCGTAAATTCTGTGCGAGTGCAGCG
GAGGCGCTCGGCGTTCCGAGGATCTTTTCTGGCTGGACCCGCGCACCTGGAGATCCTACAGGGAAGGGCGCA
TCTATAAATGCCCGTAGTTGAGCTGTTAAGAAGGAGAAGGTGGCGGCGTTCGGCCCCTCACAGCACTCAAGG
GCGGAAGGGTCCAGCCACCAGCGCAGGCACTCTCCCAGCCCCTACATGTTCCCATTCAATTCTTTTTCTTCCC
AGAATCCAAGAGGAAGGAGGGAGAAGGTCCATAAATGCGGCCCCGAACTACCCGAAAGGCTGCTGTCGAATA
AACCCGAAGGTATTAAGATTTCACGAAGTTAAGTGCC (SEQ ID NO: 107)

24; SW vs SM; chr1: 163590111-163590435; 1; LMX1A; INSIDE
CGAGAGGCCCGGCCACCGGCTCGGGAGCTGGGCCGGTCGCTTTGGGAGCGGATGAGGAAGGTTAGGAGAAG
CAGCGAGATAGATCCCAATTTTACAATTCTATTTTCTTTCGGTAGGGTCTCGGCGTCTGGGCCACGTTGAGAG
CGAACGTGGGCCGAGCGGAGGACACAGAGTAAAAAGCGACGCCCGCTGTATACATAAATCCGCACCCGCTGC
CCGCCCGGGTACTGCCTGCTCTGGCTTCCGCTCTCTTCCGAGGCTGGGCAAGTCCAAAAGTTCCCGAAAGGG
GGGTCAAAGAGGGGCGCTCAGTGCACGTGATTTCG (SEQ ID NO: 108)

29; SW vs SM; chr1: 219134035-219134808; 1; HLX1; DOWNSTREAM
TTCTTCCCTCTTTACTCCATTCCCTAACTCCTGCCTCGTAGGCAGCGGTGGGGAGCCGCAGGCTGCTCCCCGA
GTCCCAACGCTACTAGGGTGCTGTAACAGTGATGAGGCGGCGTTGCAGTCTGGCAGGCGCTGCAGCGGGCAC
CAGCTACGTTTTGCTGTCGGCGGCAGTTACCCGGACGCAAGTTAAGGGGTAGGCGCGCAGAGGCGGTTGGAG
GCGGGCGGCCGGCCCCTGACCTCGGAGAGCTGCGCCGAGCAGGGCGGAAAATTTATGGTCTGTGTACACTTT
CTGCTCCAGAGCCCCGCGCACCAGAAGGATGGGGCCCTGCGAGCGCGCCCCAGGCCGCGAGCTGGGGCCGC
AGGCGCCACGGCCATGTATAGTGCCCACCCGACTCTGTTCTGCAGCGCTGTGGTCATAAACCTTCCCTTAGAG
GGCGCGGCTGTAAACGAAAGTCCGGCGAGAGGTGGATGCAGGCCTTGCCGCCCGGACCCTCAGGTATAATTC
TGGAAACTTGCACGGAAGCCTGGGTCCCGCCATCTTCCCTGTTGTGGTGGGGTAAGAGGATAGTTTATACTG
GCTGTTTGGAATCCCGCGCGGTGGATGCAAGGTGGGATTCCAGCCAGCGACGCGCCGCGTGGCCGGGAGTG
CAGACAGGTCACCGGTCCCCGGGTGTCTGGACCGCGCCGCTTCCTACTGGGCTTACTTCGGGATCTAGACTT
CGGCCTCCGTCCTTGCAAGGGCCCAGATTTGATTCCGGTTCGTCGAGGCG (SEQ ID NO: 109)

35; SW vs SM; chr10: 845627-845967; 10; LARP5; INSIDE
CGAAACCCTCGAGGAGCGACCACATGACCCCCGCGCTGTGAGCTGCTGGCGGCCAGCGCCCTCGCCTCGATT
GTCTGCAGCCCTGTAGTGGGCCGCGAGGCACGCAAGCCGCAACTACAGCTCAACTGGTTTTGAAGCCTGAACTGCAGAGATCCTAATA
GCATGCACCACCACTACCCGTCGCCCGGATACACTGAACTGGTTTTTGAAGCCTGAACTGCAGAGATCCTAATA
TAGCAACGCAGGACGTTTACGGCCACCCGCCAGTGACAGCCGGTGATGTGATGACAGGAGGGCCTGGGTGAA
AATGCAAGACACTCACTCTCAGAGAACGACGACTCCACTTGAAATTCATGT (SEQ ID NO: 110)

38; SW vs SM; chr10: 3150889-3151107; 10; PFKP; INSIDE
CGGCCGGGTGGGGACCGGCGTGGCGTCCTGCGGACCGCGTGGAGTTTGGGGTGTCTGACATCGTTCTCCAC
GTGGCTATTTTCAGCGTTCTCCCGGGGAAGTACTTGGAAGAGATCGCCACACAGATCGCACGCACAGCATCA
ACGCGCTGCTGATCATCGGTGGATTCGAGGTACGTTACCGTTTCTCTCTTGCCGGTCTTGCAGGTGTGAGCCG
CG (SEQ ID NO: 111)

42; SW vs SM; chr10: 7489383-7495345; 10; SFMBT2; INSIDE
CGGCAACCGAGCCAGATCCAAGAGGGGTCGGCCTCGTCTAAATTGGTTTCCCACCAATGGCCTCGGATCAGC
CGCGGCTGTGCTGCGGGAGCCCTCAGGACGCGGCTGGGGTTGGTGCGCGGGGCCCGGAACCCCAAACCCGG
CTCGGTTCGGCAAGGTTCAGGGAGACAAGGTAGAGAAGGCTGGGGTGAGCGAGAAGTCGGGCGGCCGATCG
TCAGGGCCACGAGCCTCGCCTTGCCTTCTTGGAATCCCACCCAACTTTAAAGGCCCAAAGATCCTGAAAATTC
CGAAACGAAACTGCGAGCTGGTCTCCAGAAGTTTGAGAACGGTCTCCCAGGCTTTCCAGCGTCGTCCCGGGA
TTCTCGGACACCACAAACGCCATCAACCACGAGCACCGGTGTCCGTGCTATTGCCCCGAATGGTCCCCATCC
GCGTCCCCGGGAACTCCCTCGGCTTTCGCGCATCCAGGTCCCCAGCCCCAGCTACTGGTGCGCCCCGAGCCC
CTAGGTGCCAGAGCGGTGGTCGGCCGGGCTCCTGCCCAGTCTCGGCTCCTCCCTCCTCCCCACCAGAAGGAA
AAACTTGGGCCCTTCGAGAACCCTGTGGAATGTTCTTTGTAATCAATGTACATCCGCTTCCACGGCACGGCCT
CGTGCAAAATCGCGGGTTTCGGGGCCTTGGAGCAAATTGCGCTTGTCAGCGGCGACGTCAGGAGGACAAGGG
GAGGGGTTCGCGGCTGAAACTGCAGCTTCGCAGCACAGAGCCATTTTAGGCTGCTCCCCACCTCGCGGGCCC
ATGGGAAAGCCGGCCCCGGGAGGGCGCGCCCAAACGCAGGCTGGAGGGAGCCACGGACGCGTCCTGGCCGGC
GTGTCGCCATCGTTCAGCCTCGCTGCCCAGGTGGGAGGGGTCACCTGCCGCGGGGTCTCCAAGCCAGTGCCG
CTTGCTCCCGGCCCCCCCACTGACAGCACGGCGTCCAGTGGACCCTGTCTAGCCTCGTTCTGCGCTCCTGCA
AACCACGTTGCTGCGCTAACTACAAACCTGGCCAACATGTCTTTGTAACCCTATCATTTAAAAACGCTTCCAG
GCACCTGGCCGCTGCCAGATCAGGTTCGCGGGCCCGAGGAGGTCCTCCCACCTGCCCCCGCCAGCCCCGGG
GACCGTGCGCGGCCTCCGTGTGGCCCCCGCCCACGAGGTCCCTCGGGCAGGAACGCCGCGCGACCTCTGTT
CAGCGGCCGCGTCCTTGGCCACGGGCGACCCCTGTCGGGAACCCTGTTCCCGGCTAAGTGCGTTCCCGCATTC
CGGTGGCTCTCACCCGAGCTCGCGTTT (SEQ ID NO: 112)
```

TABLE 4-continued

CpG islands hypermethylated in NMI-BC FGFR3 wt vs mut. Provided for each
are: ID; Comparision; Coordinates of selected regions containing relevant
CpG islands based on Homo sapiens full genome as provided by UCSC
(hg18, Mar. 2006); Chromosome; GeneName; Location relative
to gene Sequence.

44; SW vs SM; chr10: 013553837-13554175; 10; C10orf30; INSIDE
TACAGTTGATACCCACCATCCCCATCATCGCTATTAGAATTGGGGTCAATACCCATCATCACTGTTAGACTTG
AGGCCGATACCCGTCATCACTGTTAGACTCGGGGTCGATATCATCATCACTGTTGACTCGGGGTCAATACCCT
TCATCACTGTTAGACTCGGGGTCGATACCCGTCACCACTGTTAGACTCGGGGTCGATACCCGTCATCACTGTT
AGACTCGGGGTCGATACCCGTCATCACTGTTAGACTCGGGGTCGATACCCGTCATCACTGTTAGACTTGGGGT
GATACCCATCATCGCTCTTAGACTCGGGGTTGATACTC
GTCATCG (SEQ ID NO: 113)

45; SW vs SM; chr10: 13556159-13556753; 10; C10orf30; INSIDE
CAACATCTGTCATCGCTGTTAGATTTCGGGTCAATATCCATCATCGCTGTTAGACTCGGGGCCGACATCCGTC
ATCGCTGTTAGACTCGGGGTCGACACCCATCATCGCCGTTGGACTCGGGGCTGAACCCGTCATCGCTGTTAG
ATGCGGGGTCGATATCCATCATCGCTGTTAAATTTGGGGTCGATATCCGTCATGACTGTTAGATTTGGGGTCG
ATATTCCTCATGACTGTTAGACTCGGGGCTGATATCTGTCATGACTGTTAGACTCGGGGCCGATATCTGTCAT
CCTGTTAGACTCGGGTCAATACCCGTCATCACTGTTACACTCGGGGCCGATACCCGTCACCGCTGTTGGACTC
GGGTCGATACCCGTCACCGCTGTTGGACTCGGGTTGATACCCGTCACCGCTGTTGGACTCGGGTCGATACCC
GTCACCGCTGTTGGACTCGGGCGATACCCGTCATCGCTGTTGGACTCGGGTCGATACCCGTCATCGCTGTTG
GACTCCGGTCGATATCCGTCATCAGTGTTGGGCTCAGGTCGATACCCGTCATCAGTGTTGGACTCGGGTCGAT
ACCCATCATCG (SEQ ID NO: 114)

47; SW vs SM; chr10: 15294510-15295293; 10; C10orf38; INSIDE
CGACAGCTTCACAGTAGGATTATTGTGATAAAAATGACTCAAGCGATGCAAAAAGTTTCATCTGTTCCCAGAA
TCCGAGGGAGAACTGAGGTGATCGTTAGAGCATAGCGACATCACGTGCGGTTTCTAATGTCCCTGGTGGCGG
ATACGCCGAGTCCTCGGAAGGACATCTGGACACCACTTTCGACCACCTCCTTGCAGGGGCGACATCCGCCAA
AGTCATCCTTTATTCCGAGTAATAACTTTAATTCCTTTCTAACATTTACACGGCAAACAGGAATGCAGTAAACG
TCACGTCCGTCCCACGGCTGGGCTGCCGTTCCGTTTCCTCCACGAACGGGTACGCGCTTCCATGAGAAAGGA
TATTTGGCAATTTTATATTCCACAGTCAGGTGGGTCTGCGATAGCTCATTTAATGTTAAACGCCATCAGGGGC
CTCTCCTCCCGTTTCTGCCAGGGCTTTTCTTGTCTTCTCCTTGGTCATCATCATCATCGTCTTCCTCTTCCTCG
TGGGCAGATCTTCTCTGGTGGGGGCTGGCTGCTGGCTCCGAGGGGGCATCCGCAGTCCGTCTGGTCGTCTCC
TCCTGCAGGCTGGGCAGCTGGCCACCACTTCTCCGACTCGCCCCTCCAACAAGCATCGCAGGGCACTGTCCT
CGGGGGTACAGACCGTGGTCCCACATTCGCTACCACTCTGTTCCACGTCATCCAGGTACACGAGCTGCGTGT
AGGCCGTGCTGTCTGGGGCTCGAGGCTCTTTCTGCTGGTGCTCTTGGACGGGCG (SEQ ID NO: 115)

64; SW vs SM; chr10: 88112905-88117344; 10; GRID1; INSIDE
CGTGAACGCCCTCGCCTCGCACCTGTGGCGCCTGCCGCGGGGCCCGACCGGAGGCAGTGGCTGTGGACAAG
GGCGGCCCCGGCGTAGGCCAGGATTTCCCCGCAGCCGGACCGGCCCAGCTCCGCTCTTTCCTGGGCGAACAG
CGCCCACCTCCGGCCCAGGCGGCGGCGCCTCCGCCCGCGGCGCGGACAGCGAGAGAGAAACCGGCTCCTCC
AAACCTGGTGGAGGAGCGCTGCAGAGAAGCGCCGGGCTGAGGCTCTGGGGGCCGCGGGGCGCGAAACGCCG
CGCCTACAGGTTATGCCCGGGAGAAGGAGACAGGTCGGGCTCCAGCCGCTGGGCGCTCCTCACCTCGAAGCG
AGGAAAACACCGGGCCACTGAGATCAGGGGAGGTGCGCCCGATACAGGTACCCGGCACGCAGACACGCCCA
CCCCCAAACACCGAGAAACAAAGACTGCCCGAGCCACGCACGCCTGCGCGGCCAGCGCTGGGCGCACACCC
GCGCCCACACAGCCCGAAGGGCGCCACGCAACCCGCAAGAACACCAGCTCCCCGCGCTCGCAGGCTCTCCGT
GCCGGCCCGCAGCGCAGAGCAGTCCCGGCGCCGCTGCCTAGGTGGGCCGGGAAGGCGCGCCACCGCGCATG
GCACCGCGGCTGCCGAGGAACAGAGGGTGCCCTGCGCAGCCCAGCTCGTCCCAACCCCTCCGGTGCCCACTG
CTGCGACGCCTCGCAGGCCGTGTCCCAGTGGGCCCTGGGCACAGCGGTCACTCACCTTCCTGCACAGCCTGG
ATGGGTTGTTGGCCTCGATGACCTTGATGGAGTAGGTGATCTTCTCGCTCTGCAGGATGTCATCGTTGAGGCT
CAGGTCGGATACCGCCAACTGGAACACCCTGTCGTCCTTGGCCGCGTTCTCCTGAAGATGGCACCTGGAGG
AGAGAAGGGATCAAGACCGGACTGGACAAGAACCCTCTCCCCGCTTCCCTTGGCCCGAGGGTCAAGGCACTC
GCAGACCGATGATTGCCGGGTGGTGGGAAGTCTGAACTGGGATTTCAGCTTGGCGGGGTAGATTAAGGCTCT
CCGATCTCCACCTGCACAGGAATATGTTCCCCTCCCCCCACCGCCCTCAGCGCACAGTGCACACAGTTGACA
TGAGTTACACATGCACATCCCACAGGCTGCCACCAGGTCACACACGTGTCTCACAACCAAGGCACCACATGTC
CTAGCCATGCTCCACACAAGGGACTAAGCCAAGCTGGGGTGGCCCCAGGCAGCGCCCAAATCCTTGACATGG
TTCCATAAATCCCATCCCAGGAGCCAGGAAG (SEQ ID NO: 116)

71; SW vs SM; chr10: 102986025-102986636; 10; LBX1; PROMOTER
CGGGGGGCGCCGGGCGCAGGCCGGGCATGGGGCCTGAGCTTAGGCCAGGTGGAAAGGTGGAAGGACCTAGT
GGGGACAGACGAAGAGACCGAGGAGCCGCCCGCCCGGCTAAATGGACACAGGAAAGCCTGAGTCAGGCTTC
TCATAATAAATAAACTGCACGTGAATAATTCAGCAGTCGCGCGGGGGCCGGTTGCATCAGCGCCGCCGCCGC
CGCGCGGCGCCCAATTCCCCGCGGAGGGGAGTAGCCAATTAAGGCACTTGAAAAGGGAGTCGGGTGGAAGA
TCCCCCGCCACCAGTATCCTGGATTTACCCAGGTCGAGTTCAGAGAGCCTCCCCGGTCCCAACCCCCTCGGG
CCCCATGGGTCAGGGGGCCGCCTGCTGGGAAGTGCTACCTCAGCTAAGCCGCTCAGGTGTCCCGAGACTCCG
GGCAAGGGAAGACAGGCGGCGAGACGGACCAGAATAAGGGATGCGGACGTCTGACCTGTGGAAAACCCAGC
ATCTGCAGTGCCCAGCCGCACAGGGAACGTGGGCGGCGTGGTTCCAAGCACAGTGAAGACGCCAGGCTCGG
ATCTGTGCTCAGAGCCGGGATCCCTCCGGGCTGCTTCG (SEQ ID NO: 117)

108; SW vs SM; chr14: 28317076-28317375; 14; FOXG1B; DOWNSTREAM
CGTAGCGACGACGTGGTCCTTGTAGGACCAAGCATTCTTGGCATTCTGTCGAGATTGAGATTCCAGAGCATCG
GATGAACGGGACTTATAGCTAAGGCGTACTCACCCACCCCTCCCTTCGTCTTTTACGCACGCAGCAACTCGTC
CTCACGTGCATAGGGGTAGTGGACAGTGTTGACTTGAATTGCTGTCCCTCGTTCCAAGCCTTTCCTGTGAATG
AACCCGAAAACACTCGACAGGTCGTGAATAATCGTTTTAATGAGTGTGCAAAGCGTGCGACGGGGTGCACCG
ACTGTCG (SEQ ID NO: 118)

TABLE 4-continued

CpG islands hypermethylated in NMI-BC FGFR3 wt vs mut. Provided for each
are: ID; Comparision; Coordinates of selected regions containing relevant
CpG islands based on *Homo sapiens* full genome as provided by UCSC
(hg18, Mar. 2006); Chromosome; GeneName; Location relative
to gene Sequence.

126; SW vs SM; chr15: 58079172-58079459; 15; FOXB1; PROMOTER
CGCTGGCGGGGGTAGGGGGTGTGGGTGGGTACGGAGTCCTTTCACTGCCCGTCGGCAGTTGGCACCAGAGC
GGAAAGTGTGTCCCCTCCCCCGCCTCTCTCCCTTGGGCAGTTTGATTTCCCGCCAGCTCAGTCGGAGTGGCCT
GGAAGAGCGGGCTCAAACTCCAAAGGCAGTCGTGGGAGAGTCGTAGCGGATACGTTTCCCCTGACATGCGCC
GGGTGCTCGTCTCTGCCCCCCACCCGCCCCAAAACCCAAACCTGCAAGTCGATGTTGTCCGGTGACCCCG
(SEQ ID NO: 119)

127; SW vs SM; chr15: 58083339-58085812; 15; FOXB1; PROMOTER
GTGCCTAAAGTTACCTAACGATACAAACCGGATACAACGCAGAGGAAACAGAATACCCCAGCCAAGCAATTTC
CATGTCAAACATCATCCGCGCGGCTGCTCCATCTGTGAACGTGAGTGGTCGCCTGCTCCCTCTTCCGCGGCG
GCCGCTTCCTCATACCTTCACACGGCGCACACCGGCCGGCGCGTCCAGCTGCCTGCCCAGTGGCCGAGGCTC
TTCCCCCTCGCCCAGTCTTGAGCTGGAAGTGATTCCTATTGGCCAAGGTGTCCATGTAAATAGGTGTGAAAGA
AACAGAGCTGGCCGGGCTCTCCCTTCTCGCTCAGTCCCCTCCCTCTGCAGCCCCCGCTCCCCCTCCTCTTCCT
CCTCCTCCCAAGGCGATTGTCATATGATAGCTAAGAAGTGGCACATTAATGAAGCGCCGCTACAGGGGTCTTT
TCTGCTCCTGTCACCGCTTAAACTATCAGATGGTTCGAGGGAGGACATGGAGGCAGCCACCTAGCTCAGCGG
AGACGCGGAGCCCACAGCAGCGCCCTCCGGAGCCCTAACACGTCGCTGCCACCATCCGCGCCGGGACTCCGC
AGCCGAGCTCGGCCGCCCGCAGGACGCTCCAGGAGCGTCGCGACCGGGCGGCACGGGACGCTGCGGGGCTG
AGCTCAAGAGCCCAGGTTCGCGCCGAGTCCAACCGGACCCGGACGCTGCGCGCGGAGTGCGCGTCGAGTGC
GCGCCGAGAGAGAAGCGGCGCGCAGCGGCGTCCTCCCGGATGCGGACGCGCAACTTGAAGCAACTTAAGGT
GAGCAGCTCTCTGTTCCGTCCCTGCCCCCTATTCTGGCCCCAGTACCGACTTACTTCCCGGCTATCCTCGCGC
CGTTCGCCGGCTTCCCCTCCCGCGCCCACTAAGCCCGCAAAGTTGCTGGCGAAAGAGTCCGGGCGCTGGCTG
ATCGAGCGCCGCAGCCCCACCCCCGACCCCCGAAGTCTGTTACTCGGTCTGGCTGACCCCGCCGGTGTCTCT
GTGCATCCATGCTACCTTTCCCTATTACCCACCCCCTTCCCAGATCCGAGCAGTCCGCCGGCCCGCGCGGACC
CAGAGCAAGAAGAGGGCGAGGAAGAAGATGCCTCGCCCGGCCGCAACACGTACAGCGACCAGAAGCCGCCC
TACTCGTACATCTCGCTGACCGCTATGGCCATCCAGAGCTCTCCCGAGAAGATGCTGCCGCTGAGCGAGATCT
ACAAGTTCATCATGGACCGCTTCCCCTACTACAGGGAGAACACGCAGCGCTGGCAAACAGTCTGCGCCACAA
CCTCTCCTTCAACGACTGCTTCATC (SEQ ID NO: 120)

167; SW vs SM; chr17: 47590175-47591465; 17; CA10; INSIDE
CGACGGGAAAACGGGGGGAAGGGGGGAGCCCGACACGGCACACACACATACACACTCGCACACACTTCCGA
GCGAGTGCACACTCGCACTCCCACCCGACAGCCGGCCAGGGACGCTGCACCCCCAAGTCAATATCGCAGTTTG
AATTGTTCCGGCAAATCTCCCCTCGGGCTCGACGGATGTGCGCCCCAGATGTGCTGACACATGTCCGATGCCT
CGCTGCCTTGGAGGTCTCCCCGCTCGCGTGTCTCTTCTCTTCGCACCAGCGGCGGAAACCGCACTAGCAGCG
GCGGGGCGGCGGCGGCAGCAGCCACCTGAAGCCACCAACACTGGGCTCTTCAGCAAAAACGAGACCC
CGATTCGTCTGGCGCCCAAGAAGACATAGACGATAGCCCCCCCGCCGGGCGTGCGCCGTGCAATTCCGGGCTC
CCGGGAGCGCGTAGCTCGCTGGCTAACCCAGGCAGTCCGCGGCAAGTTGCCCTCGAAGTCCGCCCCCCTCAC
CGGGGCATGGTCGGAGGGTGGCTGCTGCGCTCCGGGGCAGTTCTTCCTGCTTCCGGGGGGCGGGGAAGG
AGCAGACACAGCAGACACACAGAGAAAGAGAGGCAGGGATTATTGCCCAAACCGCCAGCCGCCGGCAGCCTC
CGCCGACCCTCCCTGCTCCCCAGGTCCGCGCGCAGCCTGCAGCCTCTCAGCCGGGTTCCGGCAGTGCGTCCA
GGGCGCCGAGGGGAAGGGCTGGGCCCCGGGGACTGGGGCGCGGTGGGGGCACACAGACTCTCCAGGTCGG
CGCGCCCTTCCTGCTCCTCTGCTATTTTCCTGAACTCCCCAGAACCCCCAGTTGCCTGGCTTCCATCGCCCGC
AACTAGCGCCGCTGTCGAGATTTTCCGCAATACAACTGCAGGGGTCGTTATTTCCTCGCCTACGGATCCCTAC
GCTTCCCAACTCAGAGAGAGGAGGACAGGTGGGGGCGGAGGGGGAGGAGGAAGGAGGCTTGGCCAGG
TGAGCGTCCTCGCCGCCGCCGGGCGTCCCAGCGTCAGCTCCGCAGCCCGGCACCCGGGGGCGGAGGCAGGA
GGCCCGGGCGGGAGGTGAGGCTGAGCGCGGCCATGAGGAGGGAGGAGGAGGCTGGGTGTCACAGCTTC
AGGCCACCTTGGCCGCCGCCTCGGCCCCAGTCCCTGGCAGCCGCCTCCGCACTCCGCCCCGCCTGGCTGCC
TCTGTTACCCTCCAGGATTTTCGAGTTTCTCTTCTTAAAAAGAACTTCGTGCTGCGGGTTCGGCGG
(SEQ ID NO: 121)

174; SW vs SM; chr17: 67623575-67623903; 17; SOX9; PROMOTER
CGTGGGTCCGCCTACCCCAAGCACTTTTTGTGACGTCACAGCTCCGGGACCATCCGGGGGCTTTACTCTCGC
GGAAGCCCAAAAGTTGGGGTTTGACCTCATGACCTTGGCCTTCCCGGGGGGCGGAGGCCCTCGGGACAGGAC
GCGCTGTCCCCGGAGTCCGGAGCTCAGGCCAGTGGCAGTCGACCCAGCCCCCGAGACTCCCTCACGCCGCTC
CAAAACCAAAACGGAGCCCAACACGAAGCTGGGTGAAGCCGTAGCTTGCAGGAGCCAGGGAGATGCGCTCTG
CCCGGACTTCCCGGGTCCTGTTGAGACGGAAAGGATCG (SEQ ID NO: 122)

175; SW vs SM; chr17: 67627870-67631593; 17; SOX9; INSIDE
CGACTCGGCTGACGTTTTTGACCCGGCCAGGAGGCAAAGACCAAAACGTCAGAGCAGTAGCCCTGTTACTGA
GGAGCGTCGGCAGGGTCGCGGGTAGAGGGGGCTGGAGAATGACTTGTCAGAGCTCAGGTCGATGTGGCGCG
GGGCGGCCTCGAGAGCGCCGGGCTCCTGCGTGGCCACGGCCGCCGCTGCCAACCTTCGCGGGGACTTAGCT
TTGCTTTCCATTGACTCCCTTTGCAAAAGCGCAGCAGAATCCTGACCAGCCGCACCAGCCCCGGCGAACCCGA
GCATGTAATCTATTTATATGGATTATTACGGAGGAACAGCGGGCGTTGAGTCACCAAAACATTTGCTTCAAAA
GACTATTTCTAAGCACTTTTGCAGGCAGGCAGGCTCGCTCCAGGCGCGTAAACTCGGCTACGCATTAAGAAG
CGGCTGCTTTTCGAATACTGCAAACCCAGCTAAGTCCCCGGTGCCGCGGAGAGAGCAGTGAAAAGAAATGTC
GGAGGTGGGGGTAGATCCTAGTCTAGACACACACACTTGCGCGCACACACACACACACACACAAGATTCG
CGCGGAGAAGGCACTAAAATTCTGGCATTCCGAGAGTACGACAAACTACACACTTGGAAGTCCCGGGTCCCC
CGCCTTCCCCGCAGCACCCCCCGCCCCCCCACCCTACCGTCCGCCCTTTGGCTGCGATCCCCTCCCCTCTCCT
CCCCTCCCGCCTCGTCACCCAGCCCAGTGCCACAATCCTCCTCCCTCCCCAAAATCGGGTCCAATCGGTGCTT
GCCAACCCTGGGACTGCTGTGCTGTGATTGGCGGGTGGCTCTAAGGTGAGGCGGAGTATTTATTAAAGAGAC
CCTGGGCTGGGAGTTGGAGAGCCGAAAGCGGAGCTCGAAACTGACTGGAAACTTCAGTGGCGCGGAGACTC
GCCAGTTTCAACCCCGAAACTTTTCTTTGCAGGAGGAGAAGAGAAGGGGTGCAAGCGCCCCCACTTTTGCTCT
TTTTCCTCCCCTCCTCCTCCTCTCCAATTCGCCTCCCCCCACTTGGAGCGGGCAGCTGTGAACTGGCCACCCC
GCGCCTTCCTAAGTGCTCGCCGCGGTAGCCGGCCACGCGCCAGCTTCCCCGGGAGCCGCTTGCTCCGCATCC TABLE 4-continued CpG islands hypermethylated in NMI-BC FGFR3 wt vs mut. Provided for each
are: ID; Comparision; Coordinates of selected regions containing relevant
CpG islands based on *Homo sapiens* full genome as provided by UCSC
(hg18, Mar. 2006); Chromosome; GeneName; Location relative
to gene Sequence.

```
GGGCAGCCGAGGGGAGAGGAGCCCGCGCCTCGAGTCCCCGAGCCGCCGCGGCTTCTCGCCTTTCCCGGCCA
CCAGCCCCCTGCCCCGGGCCCGCGTATGAATCTCCTGGACCCCTTCATGAAGATGACGACGAGCAGGAGAAG
GGCCTGTCCGGCGCCCCCAGCCCCAC (SEQ ID NO: 123)

199; SW vs SM; chr19: 42586101-42586705; 19; ZNF569; DOWNSTREAM
CGATTGGGGCCTCAGCCTTAGTTCTTCCAGCTGGACCCTGGGATGGTGCGGGGCTGTGGCTCTGGGAAGTAT
CTTGGCCTGCACGCGGTTTACATCATTGGGAGCACAGGCCTCGCCCTCCGAACTAGAGGCCCAGAGCCCTTC
GCGCCGAGCGTTTCCCGCCTTTCCCCTGTCTCAAGTCATTGCCCAGAGGCCACTGCGGGCCGTTCCTGCCTGT
CCGTGGAGCTGCGGCCCCCGTGTTCCCAGGGTGAACGAGCACGTGCGAGGCGGTGGTGCTTGTATCCGGGAT
AACAGGTAGGGCGGCTGCATGCTTCATAGAGGCCAGCCTGTGCCGACCGGGAGCTGTAGGACGGTCTGTGTC
TGGGGCTGCTTATGGGTATTCGCGTGCGTCTGCCGGTGCGGTCGAGCCTACTCACGAGAGCGTGTGT
GTCTTCTGTCTCGTGTTGCTATGAGTTTGCATCTGTGTGGCTGGAATAGCTTGTTTGTGGGGCCCGCGCGTG
ACCTGTGTGTGCGTTACTGTGTGTGTCTCAGGCAGGATAGTGACGGGCCGTGTGACTGTGACGCCATCATCA
GGTTGGTGAGATGGCGTGACCGCG (SEQ ID NO: 124)

204; SW vs SM; chr19: 57082579-57083180; 19; ZNF577; INSIDE
CAGCAGACCCCTTTTTAAGTACGCATGTGATAAGCAATGAACACGAACTGCCCAGAGCAGTCTCCAACACTGA
CACGATTCGCTTCCCCACCACGACGCCCTAGCGCTACTGTGCAACGAAGACCTCCAAGCACTGGTTCCAATGC
GGAGACCATGGGCTCCCAGACTCTGGGAACTCCAACACGACTGCGAAACGAACTCCCAGCGAGGACTCCCCG
AGAGCTCCCCGCAACACGGACCTCACGCGCTAGCGAACAACAGAAAAAAAAAAGCGCGCTCTCCCTGCCCCT
GAACATTCCCAGAAGCCCACGCAGACCAGACCGATGACCTGTCTCCACTGCTGGAGGCGAGTCAGGGACCCG
AAGTCTCTAAACACTCGCCTCTACCCGCCGCCCCGCGAACCCCACACACTGCAGACGCGACACTCGCAAGTTT
CGGGGATGGCGGCCGGCGAGGGCATACTGCGTCTTTCCGGAGACACGGAATACGGCACCAGCCGTCCCTTTA
TGATGCAATATGTCTGCGCCCAGGGGACGCTTGCTGGGAGCAGCCATTTTCAACCCTACTGCCGTAGAGCAG
GCGGAGTCCCTCTTTTCGCG (SEQ ID NO: 125)

233; SW vs SM; chr2: 119329502-119332035; 2; EN1; PROMOTER
CGAGGAGGCTGCAGGGACGCGCATGGAAGAGCCGGTGCGTGGGAGGGTTTGCGGGGGGGACATCGCGCCCC
CTAGGGGTGACCCCAGTGGGTCCCGTGTGCTCTCCGCGGAGCCGGCGGAGCCTTGTCTCTGCACCCGGCGCG
CAGCGGCCCCTTAAACAGTGGAACCGTGAGGCCGCTCTAAGCCGAAGGGCTGGAATCTGGGTTTCTCGGGTT
TTATTTTAGACCATTCGGCACCAAGCCCGAGCTCCCCCGCCGCACCGCTTCCAGTCCCCTTTCTTTCCATAGA
GCGACCGAAGCCGGCGGTGGCGCAGGGAGCCGAGTCTGATGAGCTCGCGGGCGGCTGAAGGCCGGCTTCCC
TGTGGGGAACGCGCCACCTGTCGGCGCCAGTGAGAACTGCGTCTGTGTGGCGCCCTCGGGGTATTCGGGGCT
GCGGGGAGATGTGTGCCTGAAGCCCTCGCTTGCGGTGGGGACGTCCGGCCTCTTTCCTGGCAATTGACCCCT
GAGGCGGGAGAGACAACGGAATTCCCACAAAGGGATCCTTCTCGGGATCTCCCCACCTCAAGACAGCTAAAG
CTGGAGGAAAAGCCCCTCCGGGGGTGGGGGTGCGGGTTTGCCCTGGATTCCGAAAGCAGAAAATACCCG
AGCCACACAGGGACGGGCGCCGCGTTGGTAGTCGGGGCTACGTTCCTACTCCCTCTACCTCCCCCGCGCTGT
GTGACCCTGGGCGGAACCCCGCTGCTCTCTGGGCCTCAGTGTTCTTATTCGTAAACTGAGGGCGTTGGAGAG
ATTGGTCCTCTCCCAACTCTGACCTTGAAACTGATACTGAATCTGAGCAGCGTCTGTAGACACCTGTGCCTTG
CCTTCTATTTCTAGCCTTGAATAAATCTGGACTTTTATGTGCATTTATATCCTAATCTCATATATATTTAATG
TATAACTGCTGCCATATTGTTTTCTCAATTGTCTAGGTTTTCATTTGGATGGGTTAGGATGGTCCAAATTATC
CCGATAAGTGCCCATTAACTTAAACCTTTTTAAAAAATGAAACCAGTAAAACTTCATTCACTTTGCAGTGTGGA
CACTGCTGGAGAGCACCCATGTCGTGGGTCCGCGAGGACACAAGGAGGGGCTTAGAGACATGCGGGAGGCT
TAGATGAGAAGACAGCACCCGGGCAGCGGTCAGTGTTAGAGAGAGGACCCGTAAGAAGGGCCGAGGCTAGA
GGGAGAGCGAAGACTGAGCCAACGACGCACCTGAGCCCTGGGGTGGGGGTGGAGCGTGGCTCCTAACCCAA
ATCTCCCTGCCAGGCAGTGTCCGAC (SEQ ID NO: 126)

264; SW vs SM; chr20: 54633629-54640196; 20; TFAP2C; PROMOTER
ACCATGAGCTTCCAGTTCCTACGGGTGAGAAAAGAGGTGTCTGTGTGGAGGGCAGGTGCGACCCCGGGGGCT
AGCAGAGAGGAGAGGCTGCGGGAGGACTCGCTGCGAAGGGCGAGGGGTGGCGCTGGTGGGACGGGCGCCT
GGGGCCGTGCAGGGTGGCTCCTGGGTGCTGCCCGGGCTGCCTGTCGCCCAGTACTGGCGCAGGAAGACGGG
TCCGCGCAGCGTCTGGCAACAGTGGCCTGCTCCACGCCTGGAGGCGACCAAGTTCTGAGTTAAAGGCGCCGG
GCTTAGCGGGAAGTGTATGGCGACCCAGAACACGGAGCGGAGAAGGCCTCAGGGGACACGAGGCTACCGCC
TTAGTCCTCGGGCCTGCGCTCCGAGCGGTTAGGGTGCGTACGGATGGGCTCCGGGATGTTAGTGGAGAGGTG
ACAGGAGTCTACCATCCCACGGCCAAGCGGTGAGGCCTCCGGCGGGCGGGGTCCCCCCGGGGCAGGGCA
GGGGGAGAGTCAGGCATGTCTCTAACGGGCTCCCTAGTAGAACCGCTAGGAAAGTGGCCTTCAACCCTAGGC
ACCTTTGTGGCTTTCAGGTAGTTGGGCGACTAAAAATTCACTTTTGTCGCTGAAATGGGACAGGTGGTTGT
CAGGTTAGAGACTGTGCCCACGAAGTCTCGTTTGGCGGGCCGGGACTGACGTGGACCCGGGCCCTCCTCGGA
AGCTTGGGAACCTGTGAGCCCCTCAGCTCCTCGCCTCACTTTGCCTGTTTGAAAAAAGGAGTTGTTTGAGAGA
AGAGTTAAGGCTCAAAAGGTTCTAAACGAAGAGCATGCGGCCTGACGCGGAGCGCAAAGAAGCGAGCAGTGA
ACTGAATCTGGTGGGACTGAGACCAGAGGCGTCTGTATGCGGCGGCCGCGCGCTTCGCGCCCTATTAAAGCAATCT
GTTATTTACGATAATCATTTTGTAATTATTTTGGAGTGGCTGTGACTTGATGTCTGTGGTGCCCCAGGGCATG
CCCTTACTGGACATAGATACTTCAGGGTGCCCTTTGACGCCAGTGTCGGTCCAGTGGGTGCCAGTGCCGCGA
AGGGAGGGTGGCGGGCGTGAATGCCCCCTCCTCCTGGGTTGCCGCAGGCCCCGGCCTTTCCACCTTGCTTGA
TCCTGGCGGGTCTGCCACTTACTGAGGTCCCTACCGGCGCTCACGTTGTCCCGAGAGGCGGGACAAACGTCC
GGCGCGTGGCGCGGAGTCTGCGAAAGCGCTCGGGGGCCTCCATCTTCTGCTCGGGAGTCCCTCCCTGGGGC
GGGAAGAGGAGTCGCAGATCTGCCCGAATCT (SEQ ID NO: 127)

280; SW vs SM; chr3: 148619483-148620015; 3; ZIC1; DOWNSTREAM
GAGTGCGTAAAGGGAAATTTTTGCATTGGTGGATTTATTGAAAGCATGGAAACAGTCTTCGGGGGTAGGTGT
AGGGGGTGCAACAGCGAGACTTCCCCACAACACCTCCACCGAAGGCTGGGTCGTCGCGTTTGAGGGACCCTC
CCGCCACCCCGCAGCCTGGCGGGGCGCTTTCCAAATCGTCGCGGCAGGCTCTGGCCGGGCAGGGCGAGATG
TGCGCATGCGCGGCCTGTGGCCCGAGGTTCCACGTGCTGATGAATATGCATGAGACTCCCCCGCCCTCGCGG
GCTAGGAGAGAACCAAGCAGAGGCTCCGGCCTGTGAAAGTCGCTGGCTAGGCTCCCAAAATAGTGCGGCGG
```

TABLE 4-continued

CpG islands hypermethylated in NMI-BC FGFR3 wt vs mut. Provided for each are: ID; Comparision; Coordinates of selected regions containing relevant CpG islands based on Homo sapiens full genome as provided by UCSC (hg18, Mar. 2006); Chromosome; GeneName; Location relative to gene Sequence.

```
GGTAGCTGCACGTGTTTGTTTTCAAACCGCGCTGGTTTAAGTGAGTTCACACTGCGGAGCCGACAGCAGAGG
GTAGAGCAACCTGGGGCTGCTGCCATTGAACGGCGAGTTGAGCGGGCCTGTCAGGGCCTCTCCGCCGAGGG
CCGGGGGCTGCATGGTGCTCGAGCCCCAG (SEQ ID NO: 128)

289; SW vs SM; chr4: 134288613-134289892; 4; PCDH10; PROMOTER
CGCGTTGCCCCTGCGCCTCCGGAAGGGGCACTCACAGCTGGTCAAGCGCGTCCTTCGGAACTCGGGGAGGCT
CCGTTGGGGCTTACACAGAGCTAAGCCCTGGGCCAGGGAGGATGGATGCAAGTACGTGCATGTGCAAACGTG
TTCGCAGATACCCGCAGCGGTGCACACTCGGGCCCCTCGTGTGCACGGGCCCTGCCCACCACCCCGCCCGCG
TTCGCCGCCGCCCCACTGTCCTCATCCCGCGGGCTGACCCCAGGATTGGCAGAAATCAGTGGTCTAATCTAG
CATGTGGGTAAAGGGATCGATCTCCAATTGCCAAAAAAAAAATAGAAAATAGCCGGTGTTCCCAGCCGCTGC
GTGGCACTTGGCCGCACAAGGCGCAGGGATATCAGAGGCGCTTTGCAGCGCTTGGCGGTGCTGTGTGCCGGA
TGCCCCAGAGCCCGGCGTTAGGATGCGGGCTTGTAGGAAGCGGCTCAAATCAACTCCTCAGTCACTGATGAA
CGCGCTCACGGCTCGAAGCTAGGTCCTCGAGTGAGTTAATCTACTTGGTAAGTATTTTGTGAATATGTATTTT
GGGAGGAAAGAAGCACGTCGAACGCGTCTGCCCGTCGTAAGCGCGTCATCCCCACATCCTTTAGCGTGAAT
TCCTCCGCTTTTTAGGAGTCACCTCCACCCCCTACTCCGTATGCTTCGCGCCTTTCCTCACGGCCCCGTCAGA
CCCCCTCACCTTTAGATTGACACATGCCATATAATACTCACTTTTAAAATGCCCTGCCAGTCTCTCTAGGGTCC
CTTAATTAGGTAACCCTTGCCAATTAGTGGGCCCTGCGCTACTTTTTCCCTTCTCGATGATTTATTTCCATGAT
GCGTATTAGGGAAAATACCTTAAAGGAAAAAGAATGTTAGCATCATTGGAAATCCCGCTCCTAGGAGAGGATA
TCGCAGCTGTGCTATTATGTTTTCGCATTTGCTGATGCAAACAGGGGAACCTCTCTATTCCCTCCCCATTACCT
GCGGCTGGGGACTGGGAACTTTCCGCGGCATTGTCCCCAGCCAGCGCCTCGGGACCTGCGGGGCTGTTCTCG
CTCTCACACTCACACTCACCCCGGCCGCCGGGCGAGAGTTCTGTCCCGCCCCGCCCGGCTGCCGCGTGACGT
GTCTGTTTGGCGGCCAGTTTGGCCAATCATCGGCAGCTCGGTGGGTGGTGCTCCTGGGCGATTGGTTGGCAG
AATGAGGGCGCTGCGCAAAAACGGAGAAGCCGAGCGCTCG (SEQ ID NO: 129)

290; SW vs SM; chr4: 134291113-134293078; 4; PCDH10; INSIDE
CGGAGCCAGACCTGACGGTGGAAATCTCTGAGAGCGCCACGCCAGGCACTCGCTTCCCCTTGGAGAGCGCAT
TCGACCCAGACGTGGGCACCAACTCCTTGCGCGACTACGAGATCACCCCCAACAGTACTTCTCCCTGGACGT
GCAGACCCAGGGGGATGGCAACCGATTCGCTGAGCTGGTGCTGGAGAAGCCACTGGACCGAGAGCAGCAAG
CGGTGCACCGCTACGTGCTGACCGCGGTGGACGGAGGAGGTGGGGGAGGAGTAGGAGAAGGAGGGGGAGG
TGGCGGGGAGCAGGCCTGCCCCCCCAGCAGCAGCGCACCGGCACGGCCCTACTCACCATCCGAGTGCTGGA
CTCCAATGACAATGTGCCCGCTTTCGACCAACCCGTCTACACTGTGTCCCTACCAGAGAACTCTCCCCCAGGC
ACTCTCGTGATCCAGCTCAACGCCACCGCCCGGACGAGGGCCAGAACGGTGAGGTCGTGTACTCCTTCAGCA
GCCACATTTCGCCCCGGGCGCGGGAGCTTTTCGGACTCTCGCCGCGCACTGGCAGACTGGAGGTAAGCGGCG
AGTTGGACTATGAAGAGAGCCCAGTGTACCAAGTGTACGTGCAAGCCAAGACCTGGGCCCCAACGCCGTGCC
TGCGCACTGCAAGGTGCTAGTGCGAGTACTGGATGCTAATGACAACGCGCCAGAGATCAGCTTCAGCACCGT
GAAGGAAGCGGTGAGTGAGGGCGCGGCGCCCGGCACTGTGGTGGCCCTTTTCAGCGTGACTGACCGCGACC
AGAGGAGAATGGGCAGGTGCAGTGCGAGCTACTGGGAGACGTGCCTTTCCGCCTCAAGTCTTCCTTTAAGAA
TTACTACACCATCGTTACCGAAGCCCCCCTGGACCGAGAGGCGGGGACTCCTACACCCTGACTGTAGTGGC
TCGGGACCGGGCGAGCCTGGCTCTCCACCAGTAAGTCGATCCAGGTACAAGTGTCGGATGTGAACGACAAC
GCGCCGCGTTTCAGCCAGCCGGTCTACGACGTGTATGTGACTGAAAACAACGTGCCTGGCGCCTACATCTAC
GCGGTGAGCGCCACCGACCGGGATGAGGGCGCCAACGCCCACTTGCCTACTCTATCCTCGAGTGCCAGATCC
AGGGCATGAGCGTCTTCACCTACGTTTCTATCAACTCTGAGAACGGCTACTTGTACGCCCTGCGCTCCTTCGA
CTATGAGCAGCTGAAGGACTTCAGTTTTCAGGTGGAAGCCCGGGACGCTGGCAGCCCCAGCGCTGGCTGGT
AACGCCACTGTCAACATCCTCATAGTGGATC (SEQ ID NO: 130)

309; SW vs SM; chr5: 133887842-133891327; 5; PHF15; PROMOTER
CGAGAGAAGGTGAGCTCGGCGGGCGCAGCGGGTTGGGTGGGTGTGGCCCGCGGCTCCGGGAACAGACCCAA
GGCCCCGCCACCGCCGGCTAGCAGCCCGACAGCCCGCCCGCCTGGCGAGCGCAGGCCTTCTTCCAGAAACTG
CGAGGATCCGAGCGTACTGTTTGTGCACCACAAGGTCAAGTCGGGAAGTGGAGCCGGAGGAGGAGGGGCGA
GGAGGCGAAGGGTGGGGAGAGGGGCGCCCCGCTTCCTCGCCATGTGCCAGCCTTTGGAAGTTACCCCTCGGT
TTTTAACTTTCGGGGTAATGGGAAGGAAGAGCAAGGAGGAAGGGGTCGCCCCGGGGCAAAATCCTGCTGGG
GCCAGGATGTGCAACCACCCACCCACCCGCTCATCACTGCCTTCTCCACCCCCCGGAAATGCGGGGCAGCGC
TAGGCGCCAGGAGGCACCCGGGAGGGGGAGGGGGCGACGAGCCCAATGGGGACCCTCTCTACGGACCGCCC
CTCTTTTCTTGAGGTCGCCTACAATTTCAAGTTCCCCGCCCGGAATGTTAGTTTTCCATTTGGAGTGGGTGC
GGGGAGGAGGGCCGCGCCCCTCCCCAAGACTCGCGTTCGCCCCTCCACCCCCTCCTGCCAGCACTTTCTGC
TCACTTCTGGTGCTGCAAAACGCCACGCAATTTATTCGATTCGCATTTTAAAACCAGCGATTCAGAAGCAGGG
CCTAGGGCGAGGGTCTTCCAGCGCTGGAGCCCCGGGGGGCGGGGTGCTCAGTGCAAACCTCGTTCCCTCGC
GAGTGTCGCCTCCAGGCTGTTATTTGCAAAGAAACGTCTTTTTGACGCAGGGAGAAATGGCAAATTTTAAGTA
CGTCATTAATATGGCGCCAAAAGATTTTTTTAAGTATAAGCTCGCTTTTTTTTTTTTTAAGGTTGCGGGGGGC
GCCGCCCGGGTCTGGGCGCGTAGGGGGCGGGGTGTGAGCAGAAAGTGTGAGTGAAAGAGTGGAGGGGCGG
GGTATGTGTGTGAGTGTGTGAAGTGTGAGCAGACCTGATGGGACTTGCCACGGGCGCAGCCGCCGCTCGGGCC
CGGCCCTGGGGACAGGGCGGGCTAGGGGCGCCCCAGAGTCATGGGGAGTCCGGGCCCAGGGTGCCAGCAGG
CGTGGTGGTGGGGCTGCGAGGGAGGGCACCCTTCCCCCACGGGGCCCGCAACGCTACCTGGACTCCCCGCC
GGAGCCAAACAACTGGGCGGGGGGTTGGGGGGCGGCGACGGGGTGTCGGGAGCGGAGATCGAGTGAAT
AAGAAAAAAGTGGCTACTCCCCCTCCCTCGCTCC (SEQ ID NO: 131)

328; SW vs SM; chr6: 5080084-5080849; 6; LYRM4; INSIDE
ATCCCTATTCCTTCTCCTTCCTCTCCCTTGGTAACGGCACTCCTAGGGCTGTGGAGGGTGCGGTTCACTCCTG
GGACTGTGGAGGGTGCGGATCACTCCCGGGACTGTGGAGGGTGCGGATCGCTCCCGGGCTGTGGAGGGTGC
GGATCGCTCCCGGGGCTGTGGAGGGTGCGGATCGCTCCCGGGGCTGTGGAGGGTGCGGATCGCTCCCGGGA
CTGTGGAGGGTGCGGTTCACTCCCGGGACTGTGGAGGGTGCGGATCGCTCCCGGGACTGTGGAGGGTGCGG
ATCGCTCCGGGGCTGTGGAGGGTGCGGTTCTCTCCCGGGGCTGTGGAGGGTGCGGTTCACTCCCGGGGCTGT
GGAGGGTGCGGTTCACTCCCGGGGCTGTGGAGGGTGCGGTTCACTCCCGGGACTGTGGAGGGTGCGGATCG
CTCCTGGGGCTGTGGAGGGTGCGGTTCATCCCGGGACTGTGGAGGGTGCGGATCGCTCCCGGGACTGTGGA
```

TABLE 4-continued

CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

```
GGGTGCGGATCGCTCCCGGGGCTGTGGAGGGTGCGGTTCTCTCCCGGGGCTGTGGAGGGTGCGGTTCACTC
CCGGGGCTGTGGAGGGTGCGGTTCACTCCCGGGACTGTGGAGGGTGCGGATGCTCCTGGGGCTGTGGAGGG
TGCGGTTCACTCCCGGGACTGTGGAGGGTGCGGATCGCTCCTGGGGCTGTGGAGGGTGCGGATCGCTCCAG
GTGTGATTTTCATGGGAATGGAACTGGCTCCCTAGGTGGTGTTCATTTC (SEQ ID NO: 132)

379; SW vs SM; chr8: 65653638-65653908; 8; BHLHB5; PROMOTER
CGAACGCCGGGGGAGGGACGGTGGGAGGGGTGCGGTGAGCGAGGGGCTGCCCTGCATGTAAACAGCCTCGG
GGTCCCAGACGAGACAAGTGGGACCGCTCAAGCCTGCAGAACCCCCGGTCTCGGTCCAGGCACAAGAGCCTC
CCGTAGCCCCGCCTGATCTTTCTCAGTCTTTAGGTTCCAGGACATCCAAAGGAGCGTAGGTAACCGACGTCTA
CGTAGTATTTCTGTCCCCGGAAGACTGGATCTCAGGGAATTATTATGGAAGATA (SEQ ID NO: 133)

386; SW vs SM; chr8: 72916429-72917309; 8; MSC; INSIDE
CGGGGCAAGGGCGCGTTCCCTATCGCAGGATCACTTGCTATGGTAAGCCGCCCACCCTGCGCGCTCCTCCGC
GCGGGGAAGAACCTGCGCGGCAGGACGTGGTGTTGGAGTTGGGGCGCCCGGAGCGGGAGTGGGGAGACCTG
ATGCAGAGAGTCTGGAGTCGGAGCTGGGGGTGCTGCAGGTAGGAGCAGGAGCGGGGCGGAGAGGGAGGCC
CGAAGAAGACCCCACACAGGTTGGCGCAGCGGGGCTTGGGGAGGCTTCAGCCCAGAAGTGGAGAGGGTTGA
CAGACGCCGCCTGATTAGAAAAAGCCGGGAGCTTGGGAAGGAGACGGGATTGAAGAAGCCACCCGGCAGGG
AGGCCGAACGGCCCAGAGCTCTCCGGGTAAAACCCGCCTGCGGTGATCTGGGAAGTGTGTCTCCACCTAGCC
CTGCGAGCAGCGGCCTTCCTCCCGCCCGTTGAAGGGCGCTGTGCTGGAGTACGAACCCGGCCCAGAGAAGCC
ACTCGCCCTTCTTTGTCACTTAAAACCCTGTCCCGACGCGGATCTCACGTCTAGACCTCTGTCTTTAAAGCGG
ATGTAGAGCGCGTTCTAACCGTTCCCTAACCATTGTGTCACCGCGAAAGGCGGGGCTGTGTGGAACCGTCCC
GCACGTGTGCGATGAATCTGGCTCCGCTGAGAACGGATCCGTGGGCTGTCTGGCGCGGGCTGGGGCAGCAG
CCGAGAGTTAGTCTACAGAGCTAGGGCCCGAGGGTGGACCTGCGTCCGCGTCTCGTCACGAAAGGAAGCTCT
TTTGGAGAGGCAAAACGTGGTCGCCCAGATCCGGCGCAGCTGTAGCCGTGGGCGCTGTGCAGTGACAGCCAC
ACCCGCCACCTGTCACG (SEQ ID NO: 134)

400; SW vs SM; chrX: 2845926-2846236; X; ARSD; INSIDE
TTTCTCATCAGGATACAGTTCCAGCGTCGCACAAACCCGAAGGAGGAGTACCAAGAGATGAAAAACAGGCAG
CCCACGCCGGCCATGCCGGTGACTGCTCTCGCGGAGACAGAGAAGAAACCGCAGGCTGGCCGGCAGCCAGG
GTGAGAATCCCCAGCGCCAGGAACTGGGTGTAACCCCAGAGCTGCGCCCTCAGGGCGGCGTCCACTTCGGGG
GGCCTGCCTGGGTCACAGTCGTTTGTGAGCGTGAAGGGCATGCCGTAGAAATAGTCAAATCCGTGGTTCAGG
GGGTGTGGCAGTGATCCCCGCG (SEQ ID NO: 135)
```

TABLE 5

CpG islands potentially involved in progression and death of disease. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

```
406; DOD/alive; chr2: 115635091-115637285; 2; DPP10; PROMOTER
AAAAAAGAAATGAGTATCAGAGTCTTATCATCATTACAGTTCTTATGGTTTTTAACCGACCTTTAGGAGTTCCA
CCGACGTGACCCAAGCAGCTGGTAGGAGAATCTGGGCTGGATTCGGAAGGCGCGCTACAGGACGCCCGCTG
CCCCGGATCGGAAGGCGCAGCCACCTCAGGCCACAATCTCAGACACGCCCTCGGGTCCCGACAGGTGTTGCCC
GCCTCCCACGGGGCTCCGGGACCCCGGTCCCCGGGCTGCCCCCTGCCTTCTGGGGCGCTGGAGCGCGCGCA
GTGGCGGAGCTGAGCCACCCAGTGCTTCGCACGGGCGCGCTCCGCTTCTCCGGGTTTTAGCGGAAGCCTGCG
GGGGGCGGGTAACCGCGGAAGCCGGCGGCCGTGGGCGCGCGGGTTGGGGCTCTCGCGCCGCTCCGGGC
TCTCCCCCCCCCGGCTGCGGTTGCCGAAGAGAGGCCGGAGGCGGCGCCCGGCTGCTCCACCTGGCGCGCT
GAGCACCGCGCGGGAGCCCCCGGGGGCGGGCGGTGGGGGGCGACTGCGGGAAGAAGGCACGAGGCG
TCGCCGCAGCTCGGTCAGGGGCCGGGGCCCCGCCGCTCGCCGCTGCACTAACTTGCCGCTTGGTCTCGCCTC
CCGCCGCGGCTCGCTGCGCTTTGGGTGGCGGGGGCGGGAGAGCGGGGAGTCAGAGGGTCTGCGGTGGCC
GAGGGAGGGACCCTACGACGGGGAGCCCGCCCGGTGCCGCTCTTCTTCCCCTCCCCGCCCCTCCGCTCCCCC
CACCCCGTCCCTTCCGCCGATTCCGGGAGGACGGGCGCCCGTGACCTGCGAACGCTGCCAAGTGACGGTCCC
CGAGTCTGAAGCGCCCGCGAGGAAGCGAGCGCCAGCGCGGGCCGCCGGCGATGACGGCCGCGAAGCAGGAG
CCGCAGCCCACCCCGGGGGCCAGGGCGAGCCAGGCGCAGCCGGCGGACCAGGTGAGAGCGGCAGCCGCGG
CCAGGCCCTCCCGGGAGGGGTGGCTCCAGTGCGCGCTCCGCCCGCCTCCCGCTTCCCAGGCTGGGCTCCCGC
GCCTCCCTCTTCTCACCCTCCCCCGCCCCGCCCCAGTTCCAGGCTCTCCTGCTTCTCCACGGACTCTGCGGGA
AGTTAGAGCCTCTGCTGCGCTCCGGGGCCCGGCGAGAGGATGCGCAAGGTGGAGAGCCGCGGGGA
(SEQ ID NO: 136)

407; DOD/alive; chr3: 62330280-62330608; 3; FEZF2; INSIDE
AAAATTGGTGCATTTAGGAAGGAAATGCTATAAACGCCTAATTCCTTCTCGTTCTTTGGGGTTGCTGAGCTGA
CCTCGCCGCGAGGGGAGAGGGGGAAAAAAACGCGCACTAATGATTCTGTTTATTAGTTATATATGTATATATT
CCGTGTTCGCTTGTACAGGAGGATTTACATGGCTGTATAAAGATGGCTAGGGGCGCCGCGCTCTTCTGGGGC
GCTCACGGTGACAGGCTGGGGTTAAAACTGGCTGCCCCAGGAGAAGCGGAGGCCTGGAATTAAATACGTTTC
GGCGCACTGATTTAAATAAGTTTCCTGAATATACAAA (SEQ ID NO: 137)

408; DOD/alive; chr3: 62331767-62332398; 3; FEZF2; INSIDE
AGAGCTTCCCCCTACACCAGGCACAACCCGATTCTAAAGAAATGCTGCGCCCGCGCCTGCAGATTTCGCCTTC
TCTCTCCAGATCCCTCTTTGCCTTCCTGCCAGCCAGCCGCGACCCGAGTCCTGAGTGAGGTGAGAAGAGAAG
```

TABLE 5-continued

CpG islands potentially involved in progression and death of disease. Provided for each are: ID; Comparision; Coordinates of selected regions containing relevant CpG islands based on Homo sapiens full genome as provided by UCSC (hg18, Mar. 2006); Chromosome; GeneName; Location relative to gene Sequence.

GCCTCGCCTGGCACGTTACCTTTTTGGTGAAAGCCTTTGCCGCAAAATTCGCAGACGAAGGGCTTGTAGCCCG
CGTGGATGCGGATATGCGTGTTGAGCGTGGAGCTGCGGTTGAACGCTTTGCCGCACTGGTTGCATTTATGTG
GCTTTTCCTAGGAAAGGGGCGAGTGCACAGTAAGGAGAGGCCACCTCGGGACACCTGGAAGGGACATCCCC
CCCACCCCCACTCAACCCTAGAGGGTAAGGGATAATCTTTGGCCATCGTATCCCCGGTGTTATCACTAAGATT
CTGGGGGTTGCGCGCGGGCTAGGCCCGACCCGGGGGCACGTACCTGGGTGTGGATAATTTTGTGCCTGCAGA
GCGTGCTGGCCTGGCGAAAGCCTTTGCCGCAGACTTTGCACACGAACGGTCTGGCTCCGGTGTGGACCGGCA
TGTGGCGGGTGAGATTATAGTGAGCGTTAAACACCTATGGAAAGACATGG (SEQ ID NO: 138)

409; DOD/alive; chr20: 22514762-22515148 20; chr20: 22514762-22515148; Unknown
ATCTTTTGCTGCTGAAATGCAGATGGTTTGGACACTTCATAAAGAGGGCATTAATAAGCCCGCCGAGTGAGCG
CCAGGGCGGGATTCTCCCACAAATTCAAGGTCTGTATCTCCGCGGAAGCCGTGCTATCGGTCCCCCGAGTGC
TGAAGGCTCCCACGAGGGGCAGGCCAGCCCGGTGCGCCAGGGAAGGAGCTTGATGGTGTGTACGGCTACGT
AGTGAACGTGGAGGTGTGCGCAGCGGAGTCAGAGGGGCTAGATCCCCAGCATTTCCCACGGGGTCCCACCTA
GCGCGTGGATGGAGCAACTTCATCACTCCACCGAGGGCAGGGAAAGAGGAGTAAGCATTGGAGCTCAAAGAA
TGAGCAATTTTTCAAAGCTTTCTCC (SEQ ID NO: 139)

410; DOD/alive; chr20: 22510737-22514165; 20; FOXA2; PROMOTER
CGGGTGGTTGAAGGCGTAGTGGTGTTCCGGCTTCAGGTGGGCCTCAGGCGGCAGGCCCGGGTGGTGGGGCG
GGCCCAGCAGGTGGGCGCGGCCTGCTGCTGCTGCCCGGGAGAGGGCGCCGGCTCTGGGGGCTCAGCGCCG
CAGCCGGCGTCCCCTTCAGCTCTCCCAGGCCCCCTCGCTTGTGCTCCTGGCACGGGGAGGCGCTCGAGTGAG
GCGACTCGGTGCCCGCCGGAGTCTCGGAGGCCGGCCCGGCGGCCTCCCCGAGTTGAGCCTGTGAGGCCTGG
GCTCCGGCGGCCGCTTCTTGCCGCTGCCGGCGGCGCCTGCGGCCTCCTTCAGCGCCAGCTGCTTCTCGCACT
TGAAGCGCTTCTGGCGGCGCAGGTAGCAGCCGTTCTCGAACATGTTGCCCGAGTCAGGGTGCAGGGTCCAGA
AGGAGCCCTTGCCGGGCTTGTCGGGCGAGCGGGGCACCTTCAGAAACAGTCGTTGAAGGAGAGCGAGTGGC
GGATGGAGTTCTGCCAGCGCTGCTGGTTCTGCCGGTAGAAGGGGAAGAGGTCCATGATCCACTGGTAGATCT
CGCTCAGCGTCAGCATCTTGTTGGGGCTCTGCTGGATGGCCATGGTGATGAGCGAGATGTACGAGTAGGGCG
CTTTGCGTGCGTGTAGCTGCGCCTGTAGGTCTTGGGGTCGCGGGCGCGGCTCAGGCCCGCCTGCCCGTACAT
GGGGCTCATGGAGTTCATGTTGGCGTAGGGGGCCAGGCCGCCATGGCCCCGGCCGCCTGCCCCCCGAGCG
GGCTCAGGCTGGGACTCAAGTGCGGCCCATGCCCGCCACGCCGGCCGCCCCGGCCGAGCCGCCCATGCCCG
CCATGGCGCCCGCGCCGGGGGACATCCCCGCCAGGGACGGGCTCATGCCAGCGCCCACGTACGACGACATG
TTCATGGAGCCCGCGCTCATGTTGCCCGAGCCGCTGCCCATGGCGGCCGCCGACATGCCATGTACGTGTTCA
TGCCGTTCATCCCCAGGCCGGCGTTCATGTTGCTCACGGAGGAGTAGCCCTGCGGACAGAGCCCCGGGAGGG
AGGCGACAGCGTTAGCACCGCGGCTGGAGGGTGCCCAGACCTCCCACCCACCGCCCAGGCCTCCGCGTCCG
GGGAGGCCTCCGGGGGCCCTTTCGTCCCCGATGGCCCAGTCTCCGGACTCCGAGTCTGTTTCATT
(SEQ ID NO: 140)

411; DOD/alive; chr8: 57520625-57522095; 8; PENK; PROMOTER
ACAGAGGACTTCTCGGGGTTCCCGAATTCCCAGGGTTAAAACAAACTTGGTTTGTGCGGCGACACCGCTACC
CTTACCGGTCCCCAGATAGTCGCGGATCCCCGAAGCTAAGAGCCAGGGCAGGACTCAGTCAGTGTTCCAGGA
ACAGCTGAGACACCCAGGTCACCACGGGCTCGCGCCGCTGCCGCTTGAGACCCGGTGCGAACCGCCATACGCG
CCGCGCGGTGGGCCGGAGGCAGTCCGCGTACTGTTGCGGAAACTCTGTCTCACAAGGTGCGCAACACTCGCC
GCGCGCAACACCACCAGGAAGTTGATGTCGGCCGGGCGCACTAGGCGGTAGCTGCACGTCGCGCAATCCTGG
CTGCATTCGGCCCGCACGGTCGCCAGGAGCCCGGGGCCGAGCAACAGCAGCCAAGTGCAAAGTGTCAGGAA
CCGCGCCATGGACTGCGAGGAGAGAGGGACGCGTGCTTCGGCCTGCCTGGGCGCAGACGGGGTCCCTCGG
CAGGACCCTCGCCGCGACAGCCTCAGCAGGGGATCGTCGAGCAAAAGCCCGCAGGAATGCTCCTTTCTGGGG
CCCCGCCCTCCCGGCCGACAGCTTTTAGGTAGACGTGGAGGCGACTCAGATCGCCTCGCGGTTCCCGGGTGG
CGCGGTCGCCCCAACGCGAGGCTGCCTGGGGCACCCGGCTCTTTTCCTGGGCGTCCGCGGCCCAGGGCAA
GATTCCGGAGAGAACGCCGCAGACCAGGGGCGAGAGAGCGGGAGCCAGGGCAGGCAGGACATTGACTGGG
GTCACAAAGAAGAACCAGGGAACGCTGTGGGGAACCCATGCAATGAAATGTGAAGGGAAAGAGGGCGGGCA
GACGTCCCCAAACCCGCTCAGCAAAGACAAGCTTCGGGCAAATTCACTCACGTTGACGCTGTTCGGATGGAG
CAGGCCAATTGGAAAAGCCGGGTTCAGACACGACTCTAGAGGGAAGAGAAGAAGGCAGTGTGAGGAGGGCG
GGCGTCGGGGAGAAGCGGGCCCGGGTGTGCTGGCGGACGTAGGGCCTCACCGTCGCGGTCCTCAGCGTCTC
TGCGGGGTCACGGGCCAGGCTGCGGGGCTCTGAGCGCCTGCCTCGCCGTCCCGGGGCTTAACGGCTGCTGG
AGCCACTTTATAATTACCCCAAACCGAAGGAGGCGCGCGCGCCCCAATCGCCGGCGGGCTGCAGCT
(SEQ ID NO: 141)

412; DOD/alive; chr17: 24303411-24303889; 17; PHF12-SEZ6; DIVERGENT_PROMOTER
GATCTGCTCTTCAAGAGGAAGCCTAAAGTGGAGAGTTTGTAATCCTGACAACGCCCAGCTACCTGCGTACCCC
GGACTCCAACTCCCAGTTTGCAACGCCAAAGGGTCTAAAGGGCGAACGGGGGCGATTGCATCCTGGGAGCAA
GAATCGCGATAGGTCTGATGGATTGTGGGAACTGTAGTTCCATGTGCGTGCGATGCACTCTATGGTAGGATA
GACCCGGGAAGAGTCATTTGCCGGCCAGGAAGGGATACTTTTGAGGACGTCAGTGCTGCATGCCGGGATTT
GTAGTCTGAGGCCCGCCTCGCATTCTGGGCGGGGATTCATGCTCCTTTTCAGGGCGCCCGCTCCTCCCCTTG
GTATTGCCGTCAGAGATGGGCGGTTGGTTATTGCTGCCTGATGGTGGATGAAGCAGTGGAAAAGAGAATTGT
ATCGTTGTGCTTGACACTAGGGGTTTAGTTGGAATTGTGCTTC (SEQ ID NO: 142)

413; DOD/alive; chr1: 149638545-149639227; 1; PSMB4; PROMOTER
TAGGATTACTGCATGTTCAGCTACGACCTCATCAACATGGCTGCTGGAAGTCGTCTACAGGAAAAAGAAAGAA
ATGACACTGAAGGATCACTTCCGCTTCCGTTGGCGCAAGCGCTTTCATTTTTTCGCTACCGTGACTAAGATGG
AAGCGTTTTTGGGGTCGCGGTCCGACTTTGGGCGGGGGGTCCGGCCCCAGGACAGTTTTACCGCATTCCGT
CCACTCCCGATTCCTTCATGGATCCGGCGTCTGCACTTTACAGAGGTCCAATCACGCGGACCCAGTAAGTTCT
CGGCGCTTCGTTTGCGTAGCGGGAGGGACCGTGGGGCCTGGTGCTGCCGGCTGGTTTTGAGAGCCCGGGAA
GGTGAGGCGGGGACCCCGGGGGCGCGGAACGGCAGGGGAGCTCAGGGCGCGGAGTCCTGGAGAATGCAG
AATAATTGGAAGGAATTATAGAAAATCAGAAGCGCAGCTAGTGCGCGGAAAGAGGGCGCAGTCCATCCCCCC
TCTCAGCTCCCACCGTTCTCACTCTTTAGGAACCCCATGGTGACCGGGACCTCAGTCCTCGGCGTTAAGTTCG

TABLE 5-continued

CpG islands potentially involved in progression and death of disease. Provided
for each are: ID; Comparision; Coordinates of selected regions containing
relevant CpG islands based on *Homo sapiens* full genome as provided
by UCSC (hg18, Mar. 2006); Chromosome; GeneName;
Location relative to gene Sequence.

```
AGGGCGGAGTGGTGATTGCCGCAGACATGCTGGGATCCTACGGCTCCTTGGCTCGTTTCCGCAACACTCTCG
CATTATGCGAGTCAACAACAGTACCATGCT (SEQ ID NO: 143)

414; DOD/alive; chr21: 36990008-36995832; 21; SIM2; PROMOTER
TCCTTAGTGACAAGGTCTCTGATCTCCTGCTGCCACTGCAATAGCCTCTCCCATCCCGCGGGGAACGGCCGGA
GTTCTTCCCTTGATCTCTCCCGAGTCGGCTTCCGCTGGGGATGGATCGCAGGTAGCGCCGGCGCGGCCTGGG
GAAGAACAGTTGCGGAGCATCTGAAGCGGAAAATCCAAGCAGATGTGAGGCGATCCGGGCCCGCCTCGTTCC
TCTTGGGGCCTGAATTTCTTCCAGATAAGTTTCCTAATGGAACATTTCTAAGAGGTGGGGTACGAGGCGGCTT
GCTCGCACGGCAGTGGGACAGACTGCGGGTGGGGACGTACTGAGAGGTCCGGACCTCAATGCGTCCGACCC
GTCTCCACACCGCCCTTTTCCAGCCCCCAGTCTCCTTTCATTCCCTACTCTTCAGGCTCCTTTGGGGCCAGTG
GGTGAACCGCCATTTAGAACGGTGCCTCGGACTCGGGGTCGTGCGCTCCATCTCTGCCTCCCCCCTGGGGCC
CGCGAGGCTGGTCCGGGCTTTCTGAGCTGGGCGTTCGGCTTTAGGCCCAATACCTGGACCAGGAATTTCTTC
TCCCCGCGCCAGAAGGGAAAGACATAGGAGGTGTCCCAATCTGCGGTCACCGCCGATGCTCCTGACACTCTA
GTGAGCACCTGCCCGGTACTTTTCCATTCCAACAGAGCTTCCAGCTTCATACTAACTATCCCACATACGGCCT
GTGGGTATTAGCTCTAAGTGTCCTTTTCCGAGGGCCCGAGGCTCCCCCTCCAGCAGGGAGAGCTCCGGGACG
GCCCCCACCAAGGGTTGGGTTCTTCCTTCACAATTCCACAGAGGCATCCCTGTCCTTCCTACCTGGGAAACCT
CGAGGTGCGGTGCCCGTGTACTTCTGGTACTTTGCGTGGTGCCATCAGGGACCCCAGAGCCACAGCTGCGTG
TGTGTGTGGATGTGTGTGTGTGTGCGCGCGCGCGTGTACGGCGAAGGATGTGCTTGGGGGAGCCGAG
TACACAACGTCTGCTTGGGCAGCTGCTGGGCAGGCGTTGGGCCTGGAGGTATCTCACACCCACGTATCTTCC
AGTCTTCAAACACGGCATTGCTCTGCCTCCCGTAGCGCGCTTCGAACCTGCCTCGCGGACACGTGAACAGAG
GCTGCCCTGGGAAGATAAGTGCGCTTTCCCGTAAAATCCGGGAAATTTGCCTTG (SEQ ID NO: 144)

415; DOD/alive; chr1: 232106869-232108183; 1; SLC35F3; PROMOTER
AAGTACTGAACTGGGAGCGGCAGGGTTTGAGTCAAAAGAGAAGGGTGGAGGAGCGCGTCCGGTGCCCCAAG
GCTTCCAGGCGGAGCGCGGGCGCGAGGTGCGGGCTCCGGGGCGGAGCGCACGCCCGGAGGCGGGAAGTGG
GCAGCAGCGCCCCCGCCTGGCCCCTGTGCGCCCCGACCCGACGCCTCCCCGCCCGACCAGGTGCCTCGAGAG
CGCACAGCTGGGAGGGCTCTCCCGGTCGCGGCGAGACTCACGCCTGCGGTGTGCTAGGGCGGCGGCGACGG
TGACGGGCGTGGGGCCGGCGCTGCCTCGGCTGCCGGGTCGTTGCGGCGAGCGCGCGGGCCGGCCTGGAGTC
ACCGGGCTGAACCGCCGCGCCTGCATCGTGCCGCACGCCGCGGAGGCGCTCGGGTACAGACCGCGCGGGCG
CGCACAAAGCGGCCCGGGGCGGCCGGCGCGGCGCAGACCCTCGGTGGCAGCGCACTCCAGTCTTCCCAGGC
TAGCGGCTGCAGGGAGCTCCGGCCCGGCGCCCCTCCGCCTCAAGTCTGGGAGCTGCCGGTCCCACTCTGTCT
TTGCCTATGGGGATTCGAGAGTTTCCCAGCGGCGCACCCAGGGGCAAGAGCATTGCCGTGTGAGTAGCGCCC
CGGCGTGGGTGAGCGAGCCGGCGGGCGGGAGGCCGGAGCGCCGGGGTAGCCCTTTGCAGCTGGGACACTGG
GCAGTCTGAGGCTCGGGGAAGGGCGGCGCGCGCGGTGGAGCTGCTCGGGAAGTTTCAGTCATTCTTTCCCTC
GCCACTCGCCCCAACCCGCACTGCCCCGAGAGCCCAGGATAGGGCACTGGGGACAGCTGCCCGGGGAAGTG
GGTGAGTGGCGGCGGAAGGGAGGAGCGCGGGCTCTGCCGCGGCGCTCGCCCCCGGAGGGCCCCGGCCGC
GCTCTTGCTCTCGCCCTGGGATCTGCTCCTCACGAATCCCCTCCTCTCTGTCCATGCTCCCCTGCCCACCCAC
CTGCCCGTGGCGCCTGCGACCGCAGTGGCATGAGGAGGTCACCGGACGTCAGCCCCCGGAGACTGTCCGAC
ATCAGCCCCCAGCTCCGGCAGCTCAAGTACTTGGTGGTGGACGAGGCGATTAAGGAGGATCTGAAATGGTCG
CGCTCCGTGGAGGATCTCCCAGCGGGCCGGTGGGGCTCACGTCCATCGAGGAGCGGATCCTGCGCATC
(SEQ ID NO: 145)

416; DOD/alive; chr6: 21704622-21705099; 6; SOX4; INSIDE
TGCATCACCACCTTGGTTTTGTTTTATTTTGCTTCTTGGTCAAGAAAGGAGGGGAGAACCCAGCGCACCCCTC
CCCCCCTTTTTTTAAACGCGTGATGAAGACAGAAGGCTCCGGGGTGACGAATTTGCCGATGGCAGATGTTTTG
GGGGAACGCCGGGACTGAGAGACTCCACGCAGGCGAATTCCCGTTTGGGGCTTTTTTTTCCTCCCTCTTTTCC
CCTTGCCCCCTCTGCAGCCGGAGGAGGAGATGTTGAGGGGAGGAGGCCAGCCAGTGTGACCGGCGCTAGGA
AATGACCCGGAACCCCGTTGGAAGCGCAGCAGCGGGGAGCTAGGGGCGGGGGCGGAGGAGGACACGAACTGG
AAGGGGGTTCACGGTCAAACTGAAATGGATTTGCACGTTGGGGAGCTGGCGGCGGCGGCTGCTGGGCCTCC
GCCTTCTTTTCTACGTGAAATCAGTGAGGTGAGACTTCCAGAC (SEQ ID NO: 146)

417; p-np; chr1: 160220156-160220709; 1; OLFML2B; INSIDE
TTGGGGTTGTAGTCTATCTGGGTCGTATAGGAATACTCATTCTCGAACAGCAGCCTGGGGACGATCTGTGTGT
TGGTGTGGGTGTCGAAAGCGTAGGAGATGTTGGCATTCCGCTGGTTGTAGCTATCACGGCATACAGCACCCC
ACAGATGACGAAGCAGTTGCCGTAGAAATTCCTCCGGAGCCCCGTGCGCCATGTGGTCTCCTTCTGTGTGCTC
AGGTCCGCGGCATTGAGCTTGCTCAGGACAATGACCTCCTGGCTGAAGCCCTCATCGTCCAGGGCCGGGTAG
ATGAGCCATGGCCATTCTCGTCCACAGCAAAGTCCACGTCTGAGTGGCCCTGCCATCGCCAGGGGGTGGCCT
CCTCGTAGGCCACGTCATGCAGCATGGCCCAGGCAGCCACGTAGCGCTGCTTCAGGTCGTACTTGATGATGT
TGCGGGTGAAGGCGCGATTGTAGTAGAAGGCGCCATTTATACCACGTGGCCTGTGCCGATCCAGCTGTACGG
GAGCTTGTAGGAATTGCTCCAGCGACCTGCAGGTGGGGAGAAAAC (SEQ ID NO: 147)

418; p-np; chr3: 129688131-129694023; 3; GATA2; INSIDE
TCACAGGCCAGCTGGAAGTGGGCAGAAACCCTGTGGGTCCCAGACCCTCCCCAATCGGCCGCTGCTCCCACC
TCTCCCGCCCCAATTTTTCAGCAGCTCGATTCCTGCGGATCCTACATCCGGGAAGAAGCAGACGGGCCCTCCT
CCCCTCCCTCGCCTGGCGCGCGGCGCCTGGGTTCTCATCACCACGGGCCCAGTGCTCACCGTGCGCGGGGCT
GTAGGAGACGCGCGCCCGCGCGTGAGCGGGGTTGGCATAGTAGGGGTTGCCCTGCGAGTCGAGGTGATTGA
AGAAGACGTCCCCTCGTCTGGAGGCAGCAGCTGCGCGGGTTCCATGTAGTTGTGCGCCAGGCCCGGGTGGTG
TGAGTCGGGGTGCTGCGCATTCAGCACGGCCGGGTGCGCCATCCAGCGCGGCTGCTCGGGCGCCACCTCCAT
GGCCGGCGGCGGCGGCTCAGGGTCTGGGTGCAGACGGCACGGCCTCTGCGCGGGAAGGGGGAGTGAGGCG
TGCCGCCAGCGCCTGACACCCCCCAAAGTCCCACCACGAGGTGTCCCGCACGCCACGGAGCCCCAGCCCAGA
TCCGGCGAGAAAGAGCACCAGTCCCGGGTGGGAGGAAAGCCCAAGGCTCAAAACGAAAGGAAGGCGGGGAG
GGGGTTCAGCCACGCACACTCACGTGGTGACCCGCGGCTCCAGAATCACACACCCGTGCACATGGGGTCACG
CCCGGGGACGGGTCCCGACACCAGTGACCCCAACAAACGCACAGAGCAGCACTTCAGTCAGACACTCACACT
GAGCCCCCCCGCCCGGTAGACAAACAATGAACACAGACTCAAAAGTTGGAGACAGGCGCCCGGGCACCCAGT
```

TABLE 5-continued

CpG islands potentially involved in progression and death of disease. Provided for each are: ID; Comparision; Coordinates of selected regions containing relevant CpG islands based on Homo sapiens full genome as provided by UCSC (hg18, Mar. 2006); Chromosome; GeneName; Location relative to gene Sequence.

```
GTGGCACTTGATCCCAGCGACACGCACACACCCACACTTGGCGCCAGATACACATACTGATCTCAACCCCGAA
AACATGCACACGCAGCCCCTGAGCGCAGTACTAAGCGGCACAATCAGGACCTTCAACAAAGCACACCAAAG
CAGTCGCCCGCAGCCTGGCCCCCCGCCCTAAGTCCCCCCAGAGTCCCCTCAAAGCTAGGAGCGCCCCAGGCC
CCCAGCCGGCTCTCAAACCCCAAACTTACACACGCAGCCGTGGGGAGGGGAGGGACTCGGCCTCTGAGAGTG
AAGGAGTTCGGCGGGAGCCCCGAGGGCGACGGGCCCAGGGACAGCACGTCCGGAGGCTG (SEQ ID NO: 148)

419; p-np; chr6: 26312699-26313302; 6; HIST1H4E; INSIDE
GTCTGATCTGTGAAGGGTAGGGCCAGCAGGCAGCACCAAAGTTCCCGTATGCGCGTTTTCAGTCTTCATTTAG
GTCCGAATTCCCGGCATATAAGAATACTACCGTCGCTTGTTTTTCAGATTTTTGGGCTATTTTCGTTGGTGTGT
TGGTCATGTCTGGTCGCGGCAAAGGCGGAAAGGGACTGGGTAAAGGAGGCGCTAAGCGTCACCGTAAGGTC
CTGCGAGATAACATCCAGGGCATTACCAAGCCTGCCATCCGGCGCCTTGCTCGTCGCGGGGGTGTCAAGCGC
ATTTCTGGTTCATCTACGAGGAGACTCGCGGGGTTCTGAAGGTGTTTCTGGAAAACGTGATTCGTGATGCTGT
GACTTACACGGAGCACGCCAAACGCAAGCAGTGACAGCGATGGATGTGGTCTACGCGCTGAAGAGACAGGG
ACGCACTCTTTACGGCTTCGGCGGCTAATGCTACCGTTAAACGACTCAGCATCTCGACTTCCCAAATCAAAGG
CCCTTTTCAGGGCCGCCCACAGTTTTCCGCAAAAGAGCTCATGACTTGTTAGACGATTGGTTGGTCTCTTTAT
AAGTTAATTGTTCCTGTCAA (SEQ ID NO: 149)
```

TABLE 6

Primers and probes for MEIS1 MS-SnapShot.

BSP Primers (MEIS1)

Fwd. 5'
GGGTTTTTAGAGGTTAGGGGAA 3'
(SEQ ID NO: 150)

Rev. 5'
CAACTAAATAACCAAACCTCTCCTC
3' (SEQ ID NO: 151)

TABLE 6-continued

Primers and probes for MEIS1 MS-SnapShot.

MEIS1 A/B SNAPSHOT Probes

| Probe | Sequence (5'-> 3') | Size (bp) | Strand | UM | MT | µM* |
|---|---|---|---|---|---|---|
| MEIS1 A | T21 GGAGAGGGGGGTT ATGATGTTAGG (SEQ ID NO: 152) | 45 | sense | T | C | 0.2 |
| MEIS1 B | T14 GTTTGTTTGGTTTT AGAGAA (SEQ ID NO: 153) | 34 | sense | T | C | 0.2 |

TABLE 7A

Differentially labeled CGIs between subgroups relative to blood

| CGI | Gene Name | Probe location | Subgroup |
|---|---|---|---|
| chr01-2072175-2072389 | PRKCZ | chr01: 002072146- 002072190 | NMI-mt vs Ref |
| chr01-2106293-2106715 | PRKCZ | chr01: 002106497- 002106541 | MI vs Ref |
|  | PRKCZ | chr01: 002106664- 002106715 | NMI-wt vs Ref |
| chr01-47672249-47672972 | FOXD2 | chr01: 047671905- 047671953 | NMI-wt vs Ref |
|  | FOXD2 | chr01: 047672191- 047672235 | NMI-mt vs Ref |
|  | FOXD2 | chr01: 047682633- 047682689 | MI vs Ref |
| chr1: 63554983-63563059 | FOXD3 | chr01: 063559476- 063559520 | NMI-mt vs Ref |
|  | FOXD3 | chr01: 063559476- 063559520 | NMI-wt vs Ref |
| chr01-68288825-68289104 | DIRAS3 | chr01: 068289060- 068289104 | NMI-wt vs MI |
|  | DIRAS3 | chr01: 068290072- 068290116 | NMI-wt vs Ref |
| chr01-71284766-71286392 | PTGER3 | chr01: 071284980- 071285024 | NMI-wt vs Ref |
| chr1: 90955098-90955445 | BARHL2 | chr01: 090955137- 090955181 | NMI-mt vs Ref |
| chr01-119333484-119333719 | TBX15 | chr01: 119333484- 119333528 | NMI-wt vs MI |
|  | TBX15 | chr01: 119333569- 119333613 | NMI-wt vs Ref |

TABLE 7A-continued

Differentially labeled CGIs between subgroups relative to blood

| CGI | Gene Name | Probe location | Subgroup |
|---|---|---|---|
| chr1: 163590111-163590435 | LMX1A | chr01: 163590167-163590226 | NMI-wt vs Ref |
| chr1: 173258989-173259419 | MRPS14 | chr01: 173259418-173259462 | NMI-mt vs MI |
| chr01-178464743-178471598 | LHX4 | chr01: 178470479-178470532 | NMI-wt vs Ref |
| | LHX4 | chr01: 178470597-178470641 | NMI-wt vs MI |
| | LHX4 | chr01: 178470597-178470641 | NMI-wt vs NMI-mt |
| chr1: 196153712-196154414 | LHX9 | chr01: 196154203-196154247 | NMI-wt vs Ref |
| chr1: 219117072-219117487 | HLX1 | chr01: 219117515-219117568 | NMI-mt vs Ref |
| | HLX1 | chr01: 219121301-219121352 | MI vs Ref |
| | HLX1 | chr01: 219134113-219134157 | NMI-wt vs Ref |
| chr1: 241719037-241719368 | SDCCAG8 | chr01: 241719439-241719492 | NMI-wt vs Ref |
| chr02-19424445-19425131 | OSR1 | chr02: 019415391-019415435 | NMI-mt vs Ref |
| | OSR1 | chr02: 019424965-019425009 | NMI-wt vs Ref |
| chr02-45249374-45251726 | SIX3 | chr02: 045013420-045013464 | NMI-wt vs Ref |
| | SIX3 | chr02: 045015982-045016033 | MI vs Ref |
| | SIX3 | chr02: 045015982-045016033 | NMI-mt vs Ref |
| | SIX2 | chr02: 045085251-045085298 | NMI-wt vs Ref |
| chr2: 54536404-54537878 | SPTBN1 | chr02: 054536311-054536361 | NMI-wt vs Ref |
| chr02-63134470-63134933 | OTX1 | chr02: 063134470-063134515 | MI vs Ref |
| | OTX1 | chr02: 063134470-063134515 | NMI-mt vs Ref |
| | OTX1 | chr02: 063134803-063134847 | NMI-wt vs Ref |
| chr02-66525936-66527222 | MEIS1 | chr02: 066525898-066525942 | MI vs Ref |
| | MEIS1 | chr02: 066526023-066526067 | NMI-mt vs Ref |
| | MEIS1 | chr02: 066526791-066526835 | NMI-wt vs Ref |
| chr02-70984709-70985764 | VAX2 | chr02: 070985519-070985563 | MI vs Ref |
| | VAX2 | chr02: 070985519-070985563 | NMI-wt vs Ref |
| chr02-72224630-72228512 | CYP26B1 | chr02: 072227412-072227461 | NMI-wt vs Ref |
| | CYP26B1 | chr02: 072227537-072227583 | NMI-wt vs MI |
| chr2: 73004709-73005568 | EMX1 | chr02: 073004783-073004827 | NMI-wt vs Ref |
| chr2: 85213468-85216104 | TCF7L1 | chr02: 085215511-085215555 | NMI-wt vs Ref |
| | TCF7L1 | chr02: 085216153-085216212 | NMI-mt vs Ref |
| chr02-105864220-105865009 | NCK2 | chr02: 105864372-105864417 | NMI-wt vs Ref |
| | NCK2 | chr02: 105864443-105864487 | NMI-mt vs Ref |
| | NCK2 | chr02: 105864906-105864950 | MI vs Ref |
| chr02-111591678-111597436 | FLJ44006-BCL2L11 | chr02: 111592037-111592081 | NMI-mt vs Ref |
| | FLJ44006-BCL2L11 | chr02: 111593125-111593170 | NMI-wt vs Ref |
| chr02-115635091-115637285 | DPP10 | chr02: 115636612-115636656 | NMI-wt vs Ref |
| chr2: 119329502-119332035 | EN1 | chr02: 119330694-119330738 | NMI-wt vs Ref |
| chr02-156892636-156892878 | NR4A2 | chr02: 156892639-156892683 | MI vs Ref |

TABLE 7A-continued

Differentially labeled CGIs between subgroups relative to blood

| CGI | Gene Name | Probe location | Subgroup |
|---|---|---|---|
| chr02-156893736-156894685 | NR4A2 | chr02: 156894489-156894533 | NMI-mt vs Ref |
| | NR4A2 | chr02: 156894576-156894620 | NMI-wt vs Ref |
| chr02-171384729-171385226 | GAD1 | chr02: 171384729-171384773 | MI vs Ref |
| | GAD1 | chr02: 171385019-171385063 | NMI-mt vs Ref |
| | GAD1 | chr02: 171385019-171385063 | NMI-wt vs Ref |
| chr2: 172653235-172653630 | MAP1D | chr02: 172653288-172653332 | NMI-wt vs Ref |
| chr2: 174907710-174910885 | FLJ46347 | chr02: 174910857-174910905 | NMI-wt vs Ref |
| chr2: 176652334-176656692 | EVX2 | chr02: 176655532-176655591 | NMI-mt vs Ref |
| | EVX2 | chr02: 176656139-176656183 | NMI-wt vs Ref |
| | EVX2 | chr02: 176656517-176656563 | MI vs Ref |
| chr2: 176720618-176720921 | hsa-mir-10b | chr02: 176720535-176720594 | NMI-mt vs Ref |
| | hsa-mir-10b | chr02: 176720535-176720594 | NMI-wt vs Ref |
| chr02-176737610-176738187 | HOXD3 | chr02: 176737609-176737653 | NMI-mt vs Ref |
| | HOXD3 | chr02: 176737609-176737653 | NMI-mt vs MI |
| | HOXD3 | chr02: 176738050-176738094 | NMI-wt vs Ref |
| | CENTG2 | chr02: 236438664-236438711 | NMI-wt vs Ref |
| chr3: 11721578-11721824 | VGLL4 | chr03: 011721492-011721547 | NMI-wt vs Ref |
| chr3: 12983649-12984210 | IQSEC1 | chr03: 012983600-012983644 | NMI-wt vs Ref |
| chr3: 25680561-25681574 | TOP2B | chr03: 025681366-025681410 | NMI-wt vs Ref |
| chr03-129688131-129694023 | GATA2 | chr03: 129692644-129692688 | MI vs Ref |
| | GATA2 | chr03: 129698463-129698509 | NMI-wt vs Ref |
| chr03-148591199-148594390 | ZIC4 | chr03: 148592447-148592499 | NMI-wt vs Ref |
| chr3: 148613030-148613264 | ZIC1 | chr03: 148613058-148613102 | NMI-mt vs Ref |
| | ZIC1 | chr03: 148619483-148619541 | NMI-wt vs Ref |
| chr4: 4910534-4911092 | MSX1 | chr04: 004910620-004910670 | MI vs Ref |
| | MSX1 | chr04: 004910620-004910670 | NMI-mt vs Ref |
| | MSX1 | chr04: 004910620-004910670 | NMI-wt vs Ref |
| chr4: 30330303-30333940 | PCDH7 | chr04: 030333744-030333788 | NMI-mt vs Ref |
| | PCDH7 | chr04: 030333834-030333878 | NMI-wt vs Ref |
| chr4: 41678680-41678940 | WDR21B | chr04: 041678597-041678646 | NMI-wt vs Ref |
| chr4: 85636684-85639823 | NKX6-1 | chr04: 085637474-085637518 | NMI-wt vs Ref |
| chr4: 94974810-94975333 | ATOH1 | chr04: 094974874-094974918 | NMI-wt vs Ref |
| chr04-111780013-111780343 | PITX2 | chr04: 111780048-111780092 | NMI-mt vs Ref |
| | PITX2 | chr04: 111780288-111780343 | NMI-wt vs Ref |
| | PCDH10 | chr04: 134291474-134291518 | NMI-wt vs Ref |
| | NR3C2 | chr04: 149586403-149586447 | NMI-wt vs Ref |
| | TRIM2 | chr04: 154436244-154436288 | NMI-wt vs Ref |
| chr04-155881084-155881434 | LRAT | chr04: 155881084-155881128 | NMI-wt vs Ref |

TABLE 7A-continued

Differentially labeled CGIs between subgroups relative to blood

| CGI | Gene Name | Probe location | Subgroup |
|---|---|---|---|
| | LRAT | chr04: 155881330-155881378 | NMI-wt vs MI |
| | HAND2 | chr04: 174687934-174687985 | NMI-wt vs Ref |
| chr4: 184255825-184258373 | FLJ30277 | chr04: 184255924-184255968 | NMI-wt vs Ref |
| chr5: 360287-360592 | PDCD6 | chr05: 000360593-000360637 | NMI-wt vs Ref |
| chr5: 1161803-1162051 | SLC12A7 | chr05: 001162056-001162100 | NMI-wt vs Ref |
| chr5: 3647468-3656054 | IRX1 | chr05: 003654466-003654525 | NMI-wt vs Ref |
| chr5: 5192442-5193941 | ADAMTS16 | chr05: 005192514-005192558 | NMI-wt vs Ref |
| chr5: 6790705-6791004 | POLS | chr05: 006790682-006790728 | NMI-wt vs Ref |
| chr5: 54554812-54555385 | UNG2 | chr05: 054555175-054555219 | NMI-wt vs Ref |
| | UNG2 | chr05: 054555391-054555442 | NMI-mt vs Ref |
| chr5: 114542616-114544119 | TRIM36 | chr05: 114542773-114542817 | NMI-wt vs Ref |
| chr05-115810975-115811393 | SEMA6A | chr05: 115811349-115811393 | NMI-wt vs Ref |
| chr5: 127899858-127900162 | FBN2 | chr05: 127900012-127900056 | NMI-wt vs MI |
| | FBN2 | chr05: 127900012-127900056 | NMI-wt vs NMI-mt |
| | FBN2 | chr05: 127900101-127900154 | NMI-wt vs Ref |
| chr05-134390896-134393045 | PITX1 | chr05: 134390896-134390940 | MI vs Ref |
| | PITX1 | chr05: 134390896-134390940 | NMI-wt vs Ref |
| | PITX1 | chr05: 134391093-134391137 | NMI-mt vs Ref |
| | TRPC7 | chr05: 135720277-135720321 | NMI-wt vs Ref |
| chr05-140724146-140724826 | PCDHGA5 | chr05: 140724562-140724606 | NMI-wt vs Ref |
| chr5: 140780945-140781256 | PCDHGA11 | chr05: 140781192-140781236 | NMI-wt vs Ref |
| | PCDHGA12 | chr05: 140791316-140791360 | NMI-mt vs Ref |
| | PCDHGA12 | chr05: 140791441-140791494 | NMI-wt vs Ref |
| chr5: 141235749-141238152 | PCDH1 | chr05: 141237048-141237094 | NMI-wt vs Ref |
| chr05-174091287-174092335 | MSX2 | chr05: 174091297-174091341 | NMI-wt vs Ref |
| | MSX2 | chr05: 174091410-174091454 | MI vs Ref |
| | MSX2 | chr05: 174091473-174091517 | NMI-mt vs Ref |
| chr6: 1326743-1330210 | FOXF2 | chr06: 001329813-001329866 | NMI-mt vs Ref |
| | FOXF2 | chr06: 001329813-001329866 | NMI-wt vs Ref |
| chr06-1549606-1560865 | FOXC1 | chr06: 001551371-001551415 | NMI-mt vs Ref |
| | FOXC1 | chr06: 001551429-001551473 | NMI-wt vs Ref |
| | FOXC1 | chr06: 001551500-001551559 | MI vs Ref |
| chr6: 5947471-5950124 | NRN1 | chr06: 005947569-005947613 | NMI-wt vs Ref |
| chr6: 10498025-10498551 | TFAP2A | chr06: 010498473-010498517 | MI vs Ref |
| | TFAP2A | chr06: 010498473-010498517 | NMI-wt vs Ref |
| | TFAP2A | chr06: 010498811-010498870 | NMI-mt vs Ref |
| chr6: 22677564-22678684 | HDGFL1 | chr06: 022677587-022677632 | MI vs Ref |
| | HDGFL1 | chr06: 022677587-022677632 | NMI-mt vs Ref |

TABLE 7A-continued

Differentially labeled CGIs between subgroups relative to blood

| CGI | Gene Name | Probe location | Subgroup |
|---|---|---|---|
| | HDGFL1 | chr06: 022677587-022677632 | NMI-wt vs Ref |
| chr6: 25834434-25834701 | HIST1H2AA | chr06: 025834650-025834695 | NMI-wt vs Ref |
| | HIST1H2BA | chr06: 025840937-025840981 | NMI-wt vs Ref |
| chr6: 41176454-41177326 | NFYA | chr06: 041177112-041177165 | NMI-wt vs Ref |
| chr6: 50895246-50896050 | TFAP2B | chr06: 050896068-050896112 | NMI-wt vs Ref |
| chr6: 75968300-75968853 | COL12A1 | chr06: 075968669-075968713 | NMI-wt vs Ref |
| chr06-101023927-101024343 | SIM1 | chr06: 101024299-101024343 | NMI-mt vs Ref |
| | SIM1 | chr06: 101024299-101024343 | NMI-wt vs Ref |
| chr6: 101953488-101953856 | GRIK2 | chr06: 101953514-101953560 | NMI-mt vs Ref |
| | GRIK2 | chr06: 101953514-101953560 | NMI-wt vs Ref |
| chr6: 108592365-108597232 | NR2E1 | chr06: 108595517-108595561 | NMI-wt vs Ref |
| chr6: 126122028-126122524 | HEY2 | chr06: 126122132-126122176 | NMI-wt vs Ref |
| chr6: 166499964-166503413 | T | chr06: 166502963-166503011 | NMI-wt vs Ref |
| chr6: 169801163-169801511 | WDR27 | chr06: 169801059-169801108 | NMI-wt vs Ref |
| chr7: 1029023-1029492 | hsa-mir-339 | chr07: 001029489-001029533 | NMI-wt vs Ref |
| chr07-2082782-2083345 | MAD1L1 | chr07: 002083155-002083200 | MI vs Ref |
| | MAD1L1 | chr07: 002083155-002083200 | NMI-wt vs Ref |
| | MAD1L1 | chr07: 002121288-002121332 | NMI-mt vs Ref |
| chr07-2724511-2724848 | AMZ1 | chr07: 002724511-002724555 | MI vs Ref |
| | AMZ1 | chr07: 002724511-002724555 | NMI-wt vs Ref |
| | AMZ1 | chr07: 002724629-002724673 | NMI-mt vs Ref |
| chr07-8449587-8450236 | NXPH1 | chr07: 008449587-008449636 | NMI-mt vs Ref |
| | NXPH1 | chr07: 008449587-008449636 | NMI-wt vs Ref |
| | NXPH1 | chr07: 008450192-008450240 | MI vs Ref |
| chr7: 19113449-19113833 | TWIST1 | chr07: 019113860-019113907 | NMI-wt vs Ref |
| chr7: 27149139-27152087 | HOXA5 | chr07: 027150566-027150625 | MI vs Ref |
| | HOXA5 | chr07: 027151311-027151355 | NMI-mt vs Ref |
| chr07-27164708-27165039 | HOXA7 | chr07: 027164869-027164913 | MI vs Ref |
| | HOXA7 | chr07: 027164869-027164913 | NMI-mt vs Ref |
| | HOXA7 | chr07: 027164944-027164988 | NMI-wt vs Ref |
| chr7: 27170441-27172987 | HOXA9 | chr07: 027170467-027170515 | NMI-mt vs Ref |
| | HOXA9 | chr07: 027170467-027170515 | NMI-wt vs Ref |
| | HOXA9 | chr07: 027170998-027171042 | MI vs Ref |
| chr7: 27198331-27199622 | HOXA11 | chr07: 027198283-027198327 | NMI-wt vs Ref |
| chr07-27219187-27220360 | EVX1 | chr07: 027245650-027245694 | NMI-wt vs Ref |
| chr07-27251165-27252762 | EVX1 | chr07: 027251482-027251527 | MI vs Ref |
| chr7: 35263447-35264743 | TBX20 | chr07: 035263668-035263712 | NMI-wt vs Ref |
| chr7: 96469320-96469736 | DLX6 | chr07: 096469212-096469266 | NMI-mt vs Ref |

TABLE 7A-continued

Differentially labeled CGIs between subgroups relative to blood

| CGI | Gene Name | Probe location | Subgroup |
|---|---|---|---|
| | DLX6 | chr07: 096469526-096469572 | MI vs Ref |
| | DLX6 | chr07: 096469776-096469827 | NMI-wt vs Ref |
| chr07-96488158-96489591 | DLX5 | chr07: 096489129-096489173 | NMI-mt vs Ref |
| | DLX5 | chr07: 096489475-096489520 | MI vs Ref |
| | DLX5 | chr07: 096489536-096489591 | NMI-wt vs Ref |
| chr7: 119702299-119702721 | KCND2 | chr07: 119702676-119702723 | NMI-wt vs Ref |
| chr07-121727243-121727884 | FEZF1 | chr07: 121727241-121727285 | NMI-wt vs MI |
| | FEZF1 | chr07: 121727336-121727380 | NMI-wt vs Ref |
| chr07-155288454-155292175 | SHH | chr07: 155291537-155291581 | MI vs Ref |
| | SHH | chr07: 155291593-155291637 | NMI-mt vs Ref |
| | SHH | chr07: 155291751-155291795 | NMI-wt vs Ref |
| chr7: 158509937-158510390 | VIPR2 | chr07: 158509989-158510033 | NMI-wt vs Ref |
| chr08-9798161-9799053 | hsa-mir-124a-1 | chr08: 009798455-009798508 | NMI-wt vs NMI-mt |
| | hsa-mir-124a-1 | chr08: 009798593-009798644 | NMI-wt vs Ref |
| | hsa-mir-124a-1 | chr08: 009800023-009800077 | NMI-wt vs MI |
| chr8: 10624024-10624296 | SOX7 | chr08: 010624244-010624300 | NMI-mt vs Ref |
| | SOX7 | chr08: 010624319-010624366 | NMI-wt vs Ref |
| chr8: 11597006-11600365 | GATA4 | chr08: 011599544-011599588 | NMI-wt vs Ref |
| chr8: 25955253-25955609 | EBF2 | chr08: 025955446-025955495 | NMI-mt vs Ref |
| | EBF2 | chr08: 025955446-025955495 | NMI-wt vs Ref |
| chr8: 55532724-55535078 | SOX17 | chr08: 055533948-055533992 | NMI-wt vs Ref |
| chr08-65661156-65662687 | BHLHB5 | chr08: 065661235-065661282 | NMI-wt vs MI |
| | BHLHB5 | chr08: 065662258-065662302 | NMI-wt vs Ref |
| chr8: 72916429-72917309 | MSC | chr08: 072917197-072917241 | MI vs Ref |
| | MSC | chr08: 072917336-072917380 | NMI-wt vs Ref |
| chr8: 140700279-140700514 | KCNK9 | chr08: 140700520-140700564 | NMI-wt vs Ref |
| chr08-142288380-142288718 | SLC45A4 | chr08: 142288398-142288442 | NMI-mt vs Ref |
| | SLC45A4 | chr08: 142288610-142288657 | MI vs Ref |
| | SLC45A4 | chr08: 142288610-142288657 | NMI-wt vs Ref |
| chr8: 145014900-145015187 | EPPK1 | chr08: 145015195-145015240 | NMI-wt vs Ref |
| chr9: 959530-963276 | DMRT3 | chr09: 000959621-000959665 | NMI-wt vs Ref |
| chr9: 21979774-21980108 | CDKN2A | chr09: 021979951-021979995 | NMI-wt vs Ref |
| chr9: 23812413-23812667 | ELAVL2 | chr09: 023812373-023812424 | NMI-wt vs Ref |
| chr9: 37024136-37028341 | PAX5 | chr09: 037024964-037025008 | NMI-wt vs Ref |
| chr9: 101621613-101627382 | NR4A3 | chr09: 101627386-101627439 | NMI-wt vs Ref |
| chr10-7489383-7495345 | SFMBT2 | chr10: 007491431-007491476 | NMI-wt vs Ref |
| | SFMBT2 | chr10: 007491576-007491626 | NMI-wt vs NMI-mt |
| chr10: 13556172-13556753 | C10orf30 | chr10: 013556159-013556211 | NMI-wt vs Ref |

TABLE 7A-continued

Differentially labeled CGIs between subgroups relative to blood

| CGI | Gene Name | Probe location | Subgroup |
|---|---|---|---|
| chr10: 15294605-15294858 | C10orf38 | chr10: 015294592-015294641 | NMI-wt vs Ref |
| chr10-21828640-21829645 | C10orf114 | chr10: 021828885-021828929 | NMI-wt vs Ref |
| | C10orf114 | chr10: 021828954-021828998 | NMI-mt vs Ref |
| | C10orf114 | chr10: 021829373-021829417 | MI vs Ref |
| chr10: 76825135-76839606 | ZNF503 | chr10: 076834917-076834976 | NMI-wt vs Ref |
| | ZNF503 | chr10: 076837381-076837425 | NMI-mt vs Ref |
| chr10: 88112905-88117344 | GRID1 | chr10: 088115612-088115656 | NMI-wt vs Ref |
| chr10: 94441310-94441717 | HHEX | chr10: 094441395-094441439 | NMI-mt vs Ref |
| | HHEX | chr10: 094441744-094441795 | NMI-wt vs Ref |
| chr10: 99068802-99071038 | FRAT1 | chr10: 099070245-099070298 | NMI-wt vs Ref |
| | FRAT1 | chr10: 099070376-099070420 | NMI-mt vs Ref |
| chr10: 101277153-101277910 | NKX2-3 | chr10: 101277900-101277957 | NMI-wt vs Ref |
| chr10: 102974173-102980053 | LBX1 | chr10: 102975940-102975999 | NMI-wt vs Ref |
| | LBX1 | chr10: 102976227-102976273 | NMI-wt vs MI |
| | LBX1 | chr10: 102976227-102976273 | NMI-wt vs NMI-mt |
| chr10: 106389558-106392802 | SORCS3 | chr10: 106392567-106392611 | NMI-wt vs Ref |
| chr10: 124891898-124892607 | HMX2 | chr10: 124892023-124892067 | NMI-wt vs Ref |
| chr10: 128863581-128864054 | FLJ45557 | chr10: 128864100-128864145 | NMI-wt vs Ref |
| chr11: 22319439-22319953 | SLC17A6 | chr11: 022319657-022319701 | NMI-wt vs Ref |
| chr11: 31776637-31777992 | PAX6 | chr11: 031776609-031776653 | NMI-wt vs Ref |
| chr11: 68274244-68274755 | MTL5 | chr11: 068274304-068274348 | NMI-mt vs Ref |
| chr11: 117983446-117987106 | PHLDB1 | chr11: 117984800-117984844 | NMI-wt vs Ref |
| chr12: 1844001-1845219 | CACNA2D4 | chr12: 001844114-001844158 | NMI-wt vs Ref |
| chr12: 40253533-40253742 | PDZRN4 | chr12: 040253480-040253529 | NMI-wt vs Ref |
| chr12: 52726910-52727810 | HOXC4 | chr12: 052727781-052727833 | NMI-mt vs Ref |
| | HOXC4 | chr12: 052727781-052727833 | NMI-wt vs Ref |
| chr12: 79634857-79635257 | MYF5 | chr12: 079634813-079634857 | NMI-wt vs Ref |
| chr12-94776044-94776377 | SNRPF | chr12: 094776044-094776094 | NMI-wt vs Ref |
| chr12: 95164929-95165298 | ELK3 | chr12: 095165171-095165220 | NMI-wt vs Ref |
| chr12-113657930-113659205 | TBX5 | chr12: 113325125-113325174 | NMI-wt vs Ref |
| chr12: 113609113-113609535 | TBX3 | chr12: 113609153-113609207 | MI vs Ref |
| | TBX3 | chr12: 113609259-113609303 | MI vs NMI-wt |
| chr13-34950488-34951119 | MAB21L1 | chr13: 034950488-034950532 | MI vs Ref |
| | MAB21L1 | chr13: 034950709-034950765 | NMI-wt vs Ref |
| | MAB21L1 | chr13: 034950955-034950999 | NMI-mt vs Ref |
| chr13: 35817738-35819004 | SPG20 | chr13: 035817882-035817927 | NMI-mt vs MI |
| chr13: 57101588-57102323 | PCDH17 | chr13: 057101685-057101729 | NMI-wt vs Ref |
| | PCDH17 | chr13: 057105585-057105629 | NMI-mt vs Ref |

TABLE 7A-continued

Differentially labeled CGIs between subgroups relative to blood

| CGI | Gene Name | Probe location | Subgroup |
|---|---|---|---|
| chr13-94152191-94153185 | SOX21 | chr13: 094152286-094152330 | MI vs Ref |
| | SOX21 | chr13: 094152463-094152507 | NMI-mt vs Ref |
| | SOX21 | chr13: 094152463-094152507 | NMI-wt vs Ref |
| chr13: 105943410-105943788 | EFNB2 | chr13: 105943362-105943406 | NMI-mt vs Ref |
| | EFNB2 | chr13: 105943488-105943532 | NMI-wt vs Ref |
| chr13: 111763361-111764235 | SOX1 | chr13: 111764262-111764315 | NMI-wt vs Ref |
| chr13: 112249708-112249928 | TUBGCP3 | chr13: 112249984-112250030 | NMI-wt vs Ref |
| chr14: 19992581-19993863 | APEX1 | chr14: 019993551-019993604 | NMI-mt vs MI |
| chr14: 23710894-23712060 | REC8L1 | chr14: 023711936-023711980 | NMI-mt vs Ref |
| chr14: 28317076-28317375 | FOXG1B | chr14: 028317289-028317343 | NMI-wt vs Ref |
| chr14: 33338698-33340189 | NPAS3 | chr14: 033339869-033339913 | NMI-wt vs Ref |
| chr14: 36122289-36122589 | NKX2-8 | chr14: 036122225-036122274 | MI vs Ref |
| | NKX2-8 | chr14: 036123184-036123232 | NMI-wt vs Ref |
| chr14-36205192-36206099 | PAX9 | chr14: 036196442-036196486 | NMI-mt vs Ref |
| | PAX9 | chr14: 036205602-036205647 | MI vs Ref |
| | PAX9 | chr14: 036206112-036206171 | NMI-wt vs Ref |
| chr14: 37137198-37138958 | FOXA1 | chr14: 037137114-037137159 | NMI-wt vs Ref |
| | FOXA1 | chr14: 037137543-037137587 | NMI-mt vs Ref |
| chr14: 56347822-56348040 | OTX2 | chr14: 056347712-056347756 | NMI-wt vs Ref |
| chr14: 60045486-60047933 | SIX6 | chr14: 060046995-060047041 | NMI-wt vs Ref |
| chr14: 60173732-60174416 | SIX1 | chr14: 060173710-060173754 | NMI-mt vs Ref |
| | SIX1 | chr14: 060179528-060179574 | NMI-wt vs Ref |
| chr14: 98781593-98783184 | BCL11B | chr14: 098782637-098782681 | NMI-mt vs Ref |
| chr15: 50867751-50870991 | ONECUT1 | chr15: 050870481-050870525 | NMI-wt vs Ref |
| chr15: 58083428-58085812 | FOXB1 | chr15: 058084349-058084393 | NMI-wt vs Ref |
| chr15: 62984853-62985116 | ANKDD1A | chr15: 062984784-062984834 | NMI-wt vs Ref |
| chr15: 65902540-65909629 | LBXCOR1 | chr15: 065908791-065908850 | NMI-wt vs Ref |
| chr15: 72206924-72210097 | ISLR2 | chr15: 072206870-072206914 | NMI-wt vs Ref |
| chr15: 74414579-74414893 | ISL2 | chr15: 074414745-074414789 | NMI-wt vs Ref |
| chr15: 88158407-88159577 | ANPEP | chr15: 088158433-088158477 | NMI-wt vs Ref |
| chr15-94688798-94689131 | NR2F2 | chr15: 094688839-094688885 | NMI-wt vs Ref |
| | NR2F2 | chr15: 094688901-094688949 | MI vs Ref |
| | NR2F2 | chr15: 094689087-094689131 | NMI-mt vs Ref |
| chr16: 727072-727328 | NARFL | chr16: 000727383-000727427 | NMI-wt vs Ref |
| | CBLN1 | chr16: 047869472-047869516 | NMI-wt vs Ref |
| chr16-52873104-52882105 | IRX3 | chr16: 052879704-052879750 | NMI-mt vs Ref |
| | IRX3 | chr16: 052879918-052879974 | NMI-wt vs Ref |
| | IRX3 | chr16: 052880382-052880426 | MI vs Ref |

TABLE 7A-continued

Differentially labeled CGIs between subgroups relative to blood

| CGI | Gene Name | Probe location | Subgroup |
|---|---|---|---|
| | IRX5 | chr16: 053528320-053528364 | NMI-wt vs Ref |
| chr16: 66071900-66072846 | ATP6V0D1 | chr16: 066071973-066072017 | NMI-mt vs MI |
| chr16-85098883-85102729 | FOXF1 | chr16: 085098933-085098977 | NMI-wt vs Ref |
| | CNTNAP1 | chr17: 038089272-038089316 | NMI-mt vs Ref |
| | CNTNAP1 | chr17: 038089272-038089316 | NMI-wt vs Ref |
| chr17-44074280-44075233 | HOXB5 | chr17: 044026017-044026069 | MI vs Ref |
| | HOXB5 | chr17: 044026017-044026069 | NMI-wt vs Ref |
| | hsa-mir-196a-1 | chr17: 044074404-044074448 | NMI-wt vs Ref |
| | hsa-mir-196a-1 | chr17: 044074457-044074501 | NMI-mt vs Ref |
| chr17-58865328-58865618 | CYB561 | chr17: 058865281-058865326 | MI vs Ref |
| | CYB561 | chr17: 058865281-058865326 | NMI-wt vs Ref |
| | CYB561 | chr17: 058865512-058865556 | NMI-mt vs Ref |
| chr17: 67627870-67631593 | SOX9 | chr17: 067630891-067630945 | NMI-wt vs Ref |
| chr17: 71582000-71585125 | GALR2 | chr17: 071583191-071583235 | NMI-mt vs MI |
| chr17-75531280-75531546 | TBC1D16 | chr17: 075531439-075531483 | NMI-wt vs Ref |
| chr17: 75936057-75936582 | C17orf27 | chr17: 075936313-075936368 | MI vs Ref |
| | C17orf27 | chr17: 075936313-075936368 | NMI-wt vs Ref |
| chr17: 76404186-76404427 | KIAA1303 | chr17: 076404103-076404162 | MI vs Ref |
| | KIAA1303 | chr17: 076404103-076404162 | NMI-wt vs Ref |
| chr17: 77537903-77538626 | ASPSCR1 | chr17: 077538538-077538583 | NMI-wt vs Ref |
| chr18: 894579-899574 | ADCYAP1 | chr18: 000899042-000899087 | NMI-wt vs Ref |
| chr18-5186244-5187389 | ONECUT2 | chr18: 053259508-053259552 | NMI-mt vs Ref |
| | ONECUT2 | chr18: 053259508-053259552 | NMI-wt vs Ref |
| chr18-68359955-68362770 | CBLN2 | chr18: 068361299-068361343 | NMI-wt vs MI |
| chr18: 74837994-74842232 | SALL3 | chr18: 074838538-074838582 | NMI-wt vs Ref |
| chr18: 75565313-75565933 | CTDP1 | chr18: 075565319-075565363 | NMI-wt vs Ref |
| chr19: 898548-898981 | ARID3A | chr19: 000898650-000898694 | NMI-wt vs Ref |
| chr19-4059891-4060207 | MAP2K2 | chr19: 004059891-004059935 | NMI-wt vs Ref |
| | MAP2K2 | chr19: 004060122-004060166 | MI vs Ref |
| | MAP2K2 | chr19: 004060122-004060166 | NMI-mt vs Ref |
| chr19: 9131907-9132918 | ZNF317 | chr19: 009132692-009132736 | NMI-wt vs Ref |
| chr19: 12985960-12986259 | NFIX | chr19: 012986040-012986084 | NMI-wt vs Ref |
| chr19-42586165-42586705 | ZNF569 | chr19: 042586544-042586592 | NMI-wt vs Ref |
| chr19: 55553586-55553895 | NAPSA | chr19: 055553837-055553881 | NMI-wt vs Ref |
| chr19: 57082654-57083180 | ZNF577 | chr19: 057082979-057083023 | NMI-wt vs Ref |
| chr19: 60283718-60285792 | EPS8L1 | chr19: 060285492-060285536 | NMI-mt vs Ref |
| chr19: 60907042-60907388 | EPN1 | chr19: 060907107-060907151 | NMI-mt vs Ref |
| | EPN1 | chr19: 060907320-060907364 | NMI-wt vs Ref |

TABLE 7A-continued

Differentially labeled CGIs between subgroups relative to blood

| CGI | Gene Name | Probe location | Subgroup |
|---|---|---|---|
| chr19: 62043096-62043807 | PEG3 | chr19: 062043010-062043054 | NMI-wt vs Ref |
| chr19: 63321122-63322053 | ZNF329 | chr19: 063321824-063321868 | NMI-wt vs Ref |
| chr19-63420090-63420541 | ZNF274 | chr19: 063420437-063420481 | NMI-wt vs Ref |
| chr19-63784504-63785085 | MGC2752 | chr19: 063784639-063784683 | NMI-wt vs Ref |
| | MGC2752 | chr19: 063784804-063784848 | MI vs Ref |
| | MGC2752 | chr19: 063784804-063784848 | NMI-mt vs Ref |
| chr20: 9444472-9444893 | C20orf103 | chr20: 009444951-009444998 | NMI-wt vs Ref |
| chr20: 21433933-21444714 | NKX2-2 | chr20: 021439947-021439991 | NMI-wt vs Ref |
| chr20-22505518-22507240 | FOXA2 | chr20: 022505822-022505866 | NMI-wt vs MI |
| chr20-22510737-22514165 | FOXA2 | chr20: 022505888-022505938 | NMI-wt vs Ref |
| chr20-22514762-22515148 | FOXA2 | chr20: 022507864-022507908 | NMI-wt vs NMI-mt |
| chr20: 23294035-23294650 | GZF1 | chr20: 023294489-023294536 | NMI-wt vs Ref |
| chr20: 25011839-25013525 | VSX1 | chr20: 025011908-025011952 | NMI-wt vs Ref |
| chr20-35582018-35583550 | NNAT | chr20: 035582918-035582969 | NMI-mt vs Ref |
| | NNAT | chr20: 035582918-035582969 | NMI-wt vs Ref |
| chr20: 36785545-36790786 | SLC32A1 | chr20: 036787891-036787941 | NMI-wt vs Ref |
| chr20: 38749965-38753401 | MAFB | chr20: 038753128-038753174 | NMI-mt vs Ref |
| | MAFB | chr20: 038753269-038753318 | NMI-wt vs Ref |
| chr20: 49542203-49542863 | NFATC2 | chr20: 049542266-049542311 | NMI-wt vs Ref |
| chr20-54012011-54014085 | CBLN4 | chr20: 054013134-054013178 | NMI-wt vs Ref |
| chr20: 54411932-54412178 | CSTF1 | chr20: 054412143-054412187 | NMI-wt vs Ref |
| chr20: 55680656-55681057 | TMEPAI | chr20: 055680906-055680952 | NMI-wt vs Ref |
| chr20: 56860125-56860442 | GNAS | chr20: 056860480-056860524 | NMI-wt vs Ref |
| chr20-60061693-60062033 | TAF4 | chr20: 060015181-060015225 | MI vs Ref |
| | TAF4 | chr20: 060062094-060062139 | NMI-wt vs Ref |
| chr20: 62371744-62371958 | PCMTD2 | chr20: 062371900-062371944 | NMI-wt vs Ref |
| chr21-33316999-33322115 | OLIG2 | chr21: 033318624-033318681 | NMI-wt vs Ref |
| chr21-36990008-36995832 | SIM2 | chr21: 036991619-036991663 | NMI-wt vs Ref |
| | SIM2 | chr21: 036999107-036999151 | MI vs Ref |
| chr21-43350621-43351134 | HSF2BP | chr21: 043902052-043902096 | MI vs Ref |
| | HSF2BP | chr21: 043902052-043902096 | NMI-mt vs Ref |
| chr21: 45511336-45511549 | POFUT2 | chr21: 045511551-045511595 | NMI-wt vs Ref |
| chr21: 46892946-46893236 | PRMT2 | chr21: 046893181-046893225 | NMI-wt vs Ref |
| chr22: 18453364-18453931 | DGCR8 | chr22: 018453720-018453764 | NMI-wt vs Ref |

TABLE 7B

Sequences of differentially labeled CGIs between bladder cancer subgroups relative to blood

```
CGI: 561 range = chr1: 63554983-63563059
CGGGCAGGCCCAAGCTGCGATGTGGAGAATTCGATGTCCGAGCGACCTCCTCGGAGGAGTGGGTCGAGTTAAATA
TAACCGCGCGAATGGAATGGCGCTAAAAATAAGGCAGCAGCTGGCCTGTCCACAGCCCTGTCCCGGGAGGGGCGG
GGGCCCCAGTGGTCTTGGGCAGGAAGGCCGCGTCCGGCCCAGGGGCGAGAAGGCTGCGGCGTCCGCAGCCAGGGC
TGGAAGGCCTGGGAGGCCGCGCTCTGTGGGCCCCGGGGCCTCCATTCGGGCTGGGTCGCGGGCCTGGACGGGGAC
TGTCCAGAGGCATCCGAAAGCCAGGCCAACTTGCCTGGACGTAACAAGACGGAAGGGCTGGGCGCTGAGGTCCTG
CCAGCCCGGCCGCCAGAGGGAGCTGAGCGCCAGAGGAGGACAAGCCGAACCCTTCAGGAGGCCGGGCGTCTCCGG
AGACCGAAGCGCCGGAGGACCCGAGGAGGTCTGCCCCGCGCGCTGCTCTGGAGACTCCCGGGGCGGGTGGCGCTC
GGCCTTTCCGCTCCCTTCCTTCCCACAAGTCCCTTCCCGCGCGCCCCACGGCCCTGCCCGCCCTCCCGCGTCA
GCGCCCCAACCGTCAAGCCAGCAATTGAAACGTTTCCAAAACGGTCTATTTATTTGCTCCCAATAAATCGATCGG
CGGTGATTAAAGAATCGATGTGGCCTGGGTGGGCGAGTCGCTTGAGGGGAGGGATTGGGGGCTTTCGCCCGGCGC
CTGCAGGGAGGCCGAGGGCGGGCGCGGGCCTGAGGGAGGCGTGTCCCGCCCGGGCCACACCCGAGGACCCGACAC
CTGGGCTGGCAGGCCCCGGCAGGCAGCGTTCCCTCCGGCGGAGAGGGGCGCGCGCCCGCCGCCTGCTTTCCTCGG
CCCCTCTCGCCTTTCTCGCGCGCCGGGGAGGCTGTGGCCGCCAGTGGCTGCGGAGCTGCTCAGAGGCTTTTGTTG
CTCCTCGGCCGGCTGAATGGGGATTTTGTAAAGCGGGACAGATAAAAATGAGCAGCATCATATTGTTTGACAGAA
TGATCTCGCATGATGAAGTGTCGGCTCCAAGGGGGTGAAAATGGTGAATTCCTAAAAACCCAGCCCTGGGCTCC
TCCTCGAGCTGCCGGTAGCCTGGAGGGACCCAGCGGACAGCCGGGCCTGGCCGCATCGCTCCAAACGGTGTCAGA
AAGACTCCGGCTTTCAATGCCAAGTCATTTTTAAGCCCCGATCCTGTCCAGGACCTTTCTCCTCGTCGTGGATGAAA
GAACAATTTTCGAGAGAAAGGCTCGTTTTTATTAAATCCGACATGCTGCTGATAACTCCATGCTAATGTGAAATA
ATTAACATAATAGCCATAATTAAAAGCACGCTAACAATGCCATAAATTTATCACACAATTTTACTAGCTTTCTGC
CCCTAACTGCTCTCTCATCGTTAATTAAACGTGTTGCCTTTTACAGAATGGATGTTTATATATTTCCAATATAAA
TAAATTCGAAACCATCCTCTCTCTTCCTCTTTCTCTCCTCCTTTCCTTTTGGTCTCTCGCCATTTACAGGCAC
GCCTTGGCGTGGACCCTGAGTGGCAGACATCTTGAAAATAAATGAAGTTTTGAGATGCAAATCCAAACAAGAACA
TTAAAATAGCCTCTTTTTTTCCACCCCGAAAAGATCCGGAGAGGTATACAAGGGGGTAGTGGTGGGTAAGAGAGT
TGAAAATCCCCCGCTTTGGGAAATGGAAGTAATCTGGGTGGGTTGGGGCCTTGGGTACCACCTCTGCCCTTTCCC
ACCTTCCTTGGTGGCGGCCATCCAGACAAAGAGGCCGGTAATAGTTTAACAAATCTATGAAGATTTTCAAGAAGC
AGCAGACTTTGATTGTTGCGGGCGCGGGGGTGTTGGGGAGAAAGGAGGGGAATTTTTCTAATAGTCCCACCCACG
TTTTGCTCCCTCTTGGACAAAGAGTAACTACTCTTGGTGGGGGACGCGCCCTTCACTCCGCGGAACCTGGTCCCA
ACTCCCCGTATTGTAAGAAAAGTGCACCCGCGCGCGGGCATGATGATTCTATCTCACATCGCGCCAACGACTTAT
TCAAGCCACTGGCACTGTCTCTGACTTAAAAGAGGAGAAAAGAGGCATATGGGTTCACTTGGGCCTGGTGAGGGG
TAGGTGGGCAATTCCCGCCTTCCGCACTCTAACCGTGCCCCTCCTCCAGTGTTGACCACCTAAGAACCCAAAATG
AGCTGTAATTAATTTCCCTTTCTCCATCATAAATTTTTCTATCCATTTCTTCCCCCCCATCCCCCCACTGGACGC
ACACACTAAATCTCCCCTCCCCTGGAGACGTCTCAATTTCCTTCCTATCGATCCGGACTCCATTCTTCTTGCCTC
CTGTTGCTAGAACCTAGATCCCCACTCCCCGCACCCCTCATTCCCACCGCGTCCAGGTGGCTTTCCCAGCGGGGT
ACCATGTACTCTGCCCGCTCCAGAGGAACCGAAGGGGTTTCATTCCATTCTCCTTTGGTTGAAACATTTCAAACA
TTTGAGCAGGTGAGGCAGCTGGCTGCCATCTTCCTTTTTAAATCTCTCCTGGGAAGTTCGCTTGTTGAGACTCAA
AGAGTCACTCAAACTCATAATTGCGTGTGTGTGTCTACTCATTCTCCCTCTATCTCTCCAATAACCCTTTGAGAC
TCAGAAACTTTTTATCCACATACACCCTTTATCACATTTTCTTCCCCCCACTACATGTGTCTCACTTTCTCTCTG
TATCTGTCTCGCTTCTTCCGTCTCTGTCCTACAGCTTGGCGGTAACTGACGACCTGTGAGCTTTTAGCTGCAAAC
TGCAACTACGCGGCAAACAATTTATTTAGCCCGACATCTAGCCGGTCTTCCGGCAGGACCCTGCACCGCGTCGGGA
TCGGACCCTTCCGCTGGGGCGGCCTCCTGCGTCAAGGCCAGCAGGAACCTTCCTGTCGCCCTCCCCGGCCGCCGC
TTCGCCTCCTTCCCGCCCCCGGAGGTTGTGCAGGCGCTATGGTCCGCCTGGAGGGGAGAAAGCCGGCGGCCGGTTC
CTGAGCCGAGAGCGGCCGCGGAAAAATCCTCTGCCTCCGCTGGAAATCGATATTAGGCCGGCGCGGGCGCGGGAC
GTCGGGGCCGCAGCCAGTAGGTTGTGCACGTCTCATCATTTAGCTAATCGAGTCGAAAAGTTTCTGTAAGGGCCG
GACCCAGCATCAGATGGTAACACTGATTGAACAAGAGATTAGCACAATAGATCTCTAACCGAGGGGAAGCGTTGC
TTTTCACGCTACGCGCCGTAATTAATGGTATGAATCAATTAATTTGACTTTTATTGTGTCGAAGGAAAAAAGCGC
AACAAATGGAACCGGCAGCTGGGAGTTGTTCGTCCTCCACCCCCTTCCCCAGGGAGGTTCCAGGAGGACACCGGG
GAATGGACGGATCAGGCTGGGCCGTGGCAGAGGGAGGGTAGGAGGCAGCGACCAGCAGCGTGGAGGGAGTCCAGA
GAGCTAGCCTCTGCGGACGGCGGAATCGAAATTAGGCTCATTTGGAGACTACTTCGAGACCGGTGAGGGGAGCCC
TGTAGCCACCATCCTCCGGCGCGCATCCACACATACTAGTCCACGCGGGCCCAGCCACCAAGGCCGCGGCAGGGC
CAGCGCTGCGCCCCGGGCCCCTGCCTTTAGGGCTGGGCAACCCAAGCAGAGCAAAGGAGGTTCCTGAATGTGTAA
ATTTCCGCTTTTTAGCTTTTTTTTTTTTTTTTTGGACCTTCCGACACTTCGGTTGCTGAGGCAGTTGCAGACG
CGACCTCTGCAGTCCTGGGCGATGGCCAGCCAGCTCAGCTCGGGTCGGTTTCGCGGAAAGCTGTCTAGACGGCAT
TGTAAACGGTTCGGAGCCTGCGGGCCACAAAGCTGTGGAGCTACGGAAATCAACTCTGAGATGCGTTTTAGGGCC
GTGTGCAACCTCGGGATCATTTAGATAAAGAAAAACTGTGGAGGTTGGCGGGCGTCTCAGGATAGTGTCACCACC
CCCTACCCTGCTCCCAGCCTCAGATGAGTAGTGTTATATCCTGGGAAACTGTCTAATGGGGATGAAAGTCAATCT
GTGTGTCTCAATGCCTGTAATGAAGCAAGTTTACAGATTTTTAAATTTTTATTTTTATTTTATTGAATTATTTTT
GGTGTGTCTAGGCCAAGGAAAGAGGAGATCGTGGGTGGGAAACAGACTGAGGGAATCAGAAGCACCACTGTCCA
TCCGGAATTAAATCCACATCCCAGCATCTTCTGCAAATATTTCACTAATTATTTCCTCTCGGAACTCCTCCCCTC
GTGCTCCTTCCTCTGGTGAGGCCGGCGCTCCCCTCCCAGGCCGCAGCGGACAGACAGGGATTGGGTTCCGTGTGC
CTGCCACACCAGGCAGGCTCTTGCGGCTCCCAACTAGGCGGCCTAAATGAGGGAGGAAAAGAGGAGGCGCATCGCT
GATTCACCGCGTCAAGAGCACTGACTTTCCTTGGAGGTGTGAGGTCCACGCACCCCAGCCACGCACTTGGGGGTC
GGTTTGCGGTGCCTCCCCCTCCAGTCCCAGTGAAATCCCCACAGTTTTTCCTACTATCACTGACTTGCCTTGCAC
TCCGCGTGCATTGGCCACACATCCTCGCCTCCTCCACCCGCTCCGCCGCCGGTTTTCTTGGAAGTTAAATCTTGG
AGGATTTGTCCACACCTTAAGAGAAGAAAATCCACGTTAGCTGGCAGCAACGGAGATCCCAGCATGCTGGCATGC
CCAAGTCTGCCCAGGTTCCCCAAGGCCATGCCCGCCGCCCGGGAAGTCACTGCCCGCACCCCTCACGTTTCTTC
AGCCGCCCCTGGGCGCTGCGTCTAACCTGAAGACACCAGGCCTCTTCCCGGATCCACTCGACTTACCCAGGCCGC
TGCCAATCCCAGCTCCTTCCCCAGCGCCTCATTTCCGATTTTTTCATATGCTAAGTCGTTTAACAACTCCAAGTA
GCCAGTTATGGCTTCTTTATTTATAGGTTCCCTGCTATTTTACGTCGTTTTTTATTTCTCGGCAACTATTCTAG
TAGATTAATCAATAGCCATTTTCTGACCTTCGGGAACCCCAGCTGATGCTTTTTGTGGCCGCACGAAAAAATACA
TACAGGAAAACACGCCCGCATCAAGCCGGGAAAGAGCAGGTAGGACCTGAGTGGTTTGGTTGGGGGAGGGGAAA
AAGACATCTCAGCAGGTGTCTTCCCCGGAATGAGCACTGAGGCAGGGGAATCTGAAATCTAATTAATTAGCAGGAG
GGAGCCGGGTGCGCTGCTCTTACTCTTTAAAGCTAAAAACAATGAAACAAAAAGCAAAACAGAGACTAAGTTTTG
CTTTTTAAAACACGATATGGGAACCTCGTTCTAGGTCGCCCAGTCCCTGTCAAGGAGTGTGACAAAGTGGGGGG
GAGAAGGGCGGAAGGGAGAGGGGGCGGGAAGGCAGGGCAGCGACAGTCGCACAGTCCCGCGGACGCTCCCAGGC
CCACGCCCTGACTCGCTCACACCCACCCACACTCACACCCACCCGCTCCCTGGGCCCAGGGCCCGGATCCAGCC
TGGGTGGGGGGTCTCCGGGCGGGCCGCAGCGCCCTCCGTGCCCCGGGGATGCTGGCGCACAGTGCGGAGCGGAG
```

TABLE 7B-continued

Sequences of differentially labeled CGIs between bladder cancer subgroups relative to blood TTGCGCGTCTCTCGTCCCTTTGTTGACAATTCCCTGAACCAACTTGAGTTTGGCCGGCTCGGCCGCGGCCCTGAC
GTCACGCACGGTCACGTGGCCCCGCCTCCCGCTGGATCTTTAAGTAGAAAGTAATCTATCAGGCCAGTCCTTAAA
ACGGGACTTTCGACTACCGGGGCTTCGGCGTCCCTGACACCCAGCCCCCTGCCCCCCCGCTACTGTCCCTGCCCG
CGCCCTCCCGAGCTGCTCGGCGCCCGGCGTCCCGCGCCCGCCTGGACCGCTCCTGCGCCCCACGCCAGGGCCAGA
GGCCGAGGGAAGGCGGGCTAAGTGAGGGGGCGCGGCGTGGAGAACCGCCGGGGCCGGGAGCGGTAGCGAGCGCCTA
GTACCGAGCGCCAGGGACGGCAGGAGTTCGCGGAGCGCGGCCGCTGGGGGCGGACGGCAGAGCCCGCGCCACGCG
ATGCGGGGCCGCCGAGTGTGAGCTGAGCCCAGCGGGCCCCAAGCCACCTGCGGCCCCCTCCCCTCTCCCTGCCCC
CCATCTTTCGGGGGCACTCAAACCCTCTTCCCCTGAGCTCCGTGGCAGCCCCCGAACACCCTCATCGCCCGCTGC
CCCCTCCCGCCGCCGCTACCAACCCCGAGGAGGGATGACCCTCTCCGGCGGCGGCAGCGCCAGCGACATGTCCG
GCCAGACGGTGCTGACGGCCGAGGACGTGGACATCGATGTGGTGGGCGAGGGCGACGACGGGCTGGAAGAGAAGG
ACAGCGACGCAGGTTGCGATAGCCCCGCGGGGCCGCCGGAGCTGCGCCTGGACGAGGCGGACGAGGTGCCCCCGG
CGGCACCCCATCACGGACAGCCTCAGCCGCCCCACCAGCAGCCCTGACATTGCCCAAGGAGGCGGCCGGAGCCG
GGGCCGGACCGGGGGGCGACGTGGGCGCGCGGAGGCGGACGGCTGCAAGGGCGGTGTTGGCGGCGAGGAGGGCG
GCGCGAGCGGCGGCGGGCCTGGCGCGGGCAGCGGTTCGGCGGGAGGCCTGGCCCCGAGCAAGCCCAAGAACAGCC
TAGTGAAGCCGCCTTACTCGTACATCGCGCTCATCACCATGGCCATCCTGCAGAGCCCGCAGAAGAAGCTGACCC
TGAGCGGCATCTGCGAGTTCATCAGCAACCGCTTCCCCTACTACAGGGAGAAGTTCCCCGCCTGGCAGAACAGCA
TCCGCCACAACCTCTCACTCAACGACTGCTTCGTCAAGATCCCCCGCGAGCCGGGCAACCCGGGCAAGGGCAACT
ACTGGACCCTGGACCCGCAGTCCGAGGACATGTTCGACAACGGCAGCTTCCTGCGGCGCCGGAAACGCTTCAAGC
GCCACCAGCAGGAGCACCTGCGCGAGCAGACGGCGCTCATGATGCAGAGCTTCGGCGCTTACAGCCTGGCGGCGG
CGGCCGGCGCCGCGGGACCCTACGGCCGCCCCTACGGCCTGCACCCTGCGGCGGCGGCCGGTGCCTATTCGCACC
CGGCAGCGGCGGCGGCCGCGGCTGCTGCGGCGGCGCTCCAGTACCCGTACGCGCTGCCGCCGGTGGCACCGGTGC
TGCCTCCCGCTGTGCCGCTGCTGCCCTCGGGCGAGCTGGGCCGCAAAGCGGCCGCCTTCGGCTCACAGCTCGGCC
CGGGCCTGCAGCTGCAGCTCAATAGCCTGGGCGCCGCCGCGGCCGCTGCGGGCACAGCGGGCGCCGCGGGCACCA
CCGCGTCGCTCATCAAGTCCGAGCCAAGCGCGCGGCCGTCGTTCAGCATCGAGAACATCATAGGTGGGGGCCCCG
CGGCTCCTGGGGGCTCGGCGGTGGGCGCTGGGGTCGCCGGCGGCACTGGGGGTTCAGGGGGCGGCAGCACGGCGC
AGTCGTTTCTGCGGCCACCCGGGACCGTGCAGTCGGCAGCGCTCATGGCCACCCACCAACCGCTGTCGCTGAGCC
GGACGACTGCCACCATCGCGCCCATTCTTAGCGTGCCACTCTCCGGACAGTTTCTGCAGCCCGCAGCCTCGGCCG
CCGCCGCTGCTGCGGCCGCCGCTCAAGCCAAATGGCCGGCGCAATAGGGACGCGCCAATGGCCGGGACCCAGGGT
CCGGCGGCGGCCTCGAGCAACAAATGCACCTCCAGGCTGCGCGCCCTGTCCCAAGCCCGGTCCCGGTCCCGCTGC
CCAATCCTGGACTCTGCCTCTCCCAATTTCCTTTCCCCTGAGCCCCAACGCCTACCTTCCGCGGCCTCCATCC
CCTCGCGCACACCTAAGCTGGTCGAGCAAACTCACCGCGCGCCCGCCGGGGATAGCTTTCCATACAGGTAAAACC
GAAAACCGAATTTTCCAAAAATGCACCCCGACGGCGCCTGCTCTTAGTACCG (SEQ ID NO: 154)

CGI: 26 range = chr1: 90955098-90955445
CGCGTCTGCTACCAGATGCGGCTCCGGGGGCTCCATGGTGACTGAGATAGGAGAAGAAGGCGCCGTCCCTACGGT
ATCAATCTCCGAACAGGGAGATGGGGTGGCCTGACTCCTAAAATCCGCGGTCCTGGCCTCACCGAGCGGGCGGAA
ATCTCCATTCATCATGCCTGGGCTGCCTGAACTGGCACTGGACAAAATCGTGTCTATTCCAAAACTCGACCCGCT
GGCCCCTTCCATTGTCATTGCTACATGAGGTCCACGCCACTCCGCGTTCAGCAGCCGCCCCGAACCAGCGAAGA
AAGCTATCGATCGTAAAACAAAATAAACACCAAACAATGTTGCCGCCG (SEQ ID NO: 155)

CGI: 29 range = chr1: 163590111-163590435
CGAGAGGCCCGGCCACCGGCTCGGGAGCTGGGCCGGTCGCTTTGGGAGCGGATGAGGAAGGTTAGGAGAAGCAGC
GAGATAGATCCCAATTTTACAATTCTATTTTCTTTCGGTAGGGTCTCGGCGTCCTGGGCCACGTTGAGAGCGAAC
GTGGGCCGAGCGGAGGACACAGAGTAAAAAGCGACGCCCGCTGTATACATAAATCCGCACCCGCTGCCCGCCCGG
GTACTGCCTGCTCTGGCTTCCGCTCTCTTCCGAGGCTGGGCAAGTCCAAAAGTTCCCGAAAGGGGGGTTCAAAGA
GGGGCGCTCAGTGCACGTGATTTCG (SEQ ID NO: 156)

CGI: 32 range = chr1: 173258989-173259419
CGCGGAAGAGGGCGGAAGGAGAACCCCTGGACTGGTCCTCACCGAGCACTACAGGTGGCAGAGCCGTGGGGACC
CGTGGGTTATGAGATTCAGCGGTGAGGGGTAGCGGTGTGGATAAAAGTAGAGGCCTGACCTGCTTGAACGTCCGC
AGCAGCGAGCCCAGCATGAAGGCCGCCATGTTGTCCGCTACAAACTACAAACCGCTGAAACTTTATTGACACTGC
CGAATAGCGCAGGACACGAGGGGCGGGCCTGGGCCGCCTGGGGCGGAGCTGGGAGGTGGGTGGGAATGTGGCCT
ACAGGAAAGCGGGGTTAGTTTTGGGATCGGAGCTCTCGCGATATTTCACGGAACTTGGGCAAATGACAAATCTGA
AGGCGCCGCGTTGATGCTGATGGCGCAGCCAGACCCGCCCCGTGTGTTGCAGCCCG (SEQ ID NO: 157)

CGI: 58 range = chr1: 196153712-196154414
CGTCTGGCCAAAGGCGCCCAGCTCAACGGCCGCGACGCGGTAAGGAAGGGCTCCGCCGCGGCGGTAGCCGGGCAC
CCCTGCGCCCTCTGTTAAACCAAGCCGACTCCCTGGCCGGTGGAGAACCGGAGCGGCGGGTCGTAGAGACGTCCG
CTTGAGGGTGGCGGGTGAGTTTTCTCCCGTCCACCTATGCCTACAGGGCTAAGAAACGGTCGTTTTTCTGAATCG
AAATGTCTGCAGCTGGCTATCCTCCGTCGCAGCTGATTCCGAAAGAGCAGGGAGAGGAACTGGGAGGAGGTGGGA
TGGGGGGTGGTGGCATTCTCTTCTACAGACCTCAAGGTTCCCTTGATTCCGGGGCAGGCGTCTCCCCGGCGAGGA
TCCGCAGCTCCGAGGGCAAGCTGGGCATAAGCAATAGGAGGACGGCGCGCTGCCGAGGCGTCCGAGCCAAGCAGG
AGCCCAGGTGGCCTTAGTCTCTGGGCCTGATGACCGGACCTGTGGAGTAGATTCCGACGCACGCTGGGTCATTTCC
AGTTCTCTAGACGCTCGGGGCTTGGGACCCCTAACCGAGAGAATCTCAGGGTTTCTGGCATCCCGACTCAGTCCC
TCTAAGGAGACAGCACTACGTTTAGCGCCAGGACCCGGCGGGTGTCATGTGTAGGGGGAAATCAAATAAAACATA
CGGAGGAGCGCGGCACCCAGTCGAAACG (SEQ ID NO: 158)

CGI: 43 range = chr1: 219117072-219117487
CGGCGGGGGTCGCTCCAAAGACTTGTATTTCGCGTTTGCCTCCGGGAGCTGGGAGTAAGGCCTTGGATGGCGCCG
ACGCGGTTGCGAGGAAGCTGAGGCCTGGGAGAGCAAGGGGCGCGCAGGCGAAGTTGCAACTTGCACTCCAGCCGC
GGGCCTGCGGAGAAAGGGAGGCTCGCGGCGCCGCGAGGAGTCGGCGGGCCTCGGGGCCTCGCTTTCGCCGCATC
TGCCCAGCGCTCCGGGCCTTGAATCTCGGCAGATGCGAGTTGTGGGCACCTAGGGAACCCTGAGGACTCGCATTC
CCCCGGGTCTGTATCCCGTGCCCACCCCGGAGCGTCGCAAACCTTGGAAAGGGTGAAAGCTGATAGGGGAGTCTT
ATTTCTTAAGAGAGAGGGTGAGGGCGCGCGGCGCTGCCTCG (SEQ ID NO: 159)

TABLE 7B-continued

Sequences of differentially labeled CGIs between bladder cancer subgroups relative to blood CGI: 25 range = chr1: 241719037-241719368
CGGAAGAGGTGGACCGGCTGCGGACCCAGGTACTGTGCAGAACGCGGCGCAGGTGGGAGTCCTTGGGCGGGCGTC
TACAGGTGGATCTTTTATGCACCTCAACAGGCCGGCTTTCTCACGGATCACATCGGTTAGCAGTAAGCTGGGAGG
GAGGTCCCGAAGACTGTGCTGGGCACAGTGCAGGACCCAGAGAAGCGGAGCCATGGGCCCGTCCTGGTGAGGGAG
TTAAAGTCCGTGCAGGTGAACAGACCCCGGCCCGCGAATCAACGAACCACACCGAGTGCCAAGTTGCGCCGTGCA
GGCTGCGGAGGGTGCGAGAGCAGGGAGAAGCG (SEQ ID NO: 160)

CGI: 132 range = chr2: 54536404-54537878
CGAACGCAACATCAAGGGCGAAAAGAGGCTGCACAAATCACGTAGAAAATTAGACCGCCTCTTTCCATGGCGATA
ATCGAATTAGCCTCAAATTAAACGTGAAATTGGCCCTCTCCGGCTGTGGAGACAAAGCCCCTATTGTCCTGCTCG
GGTAGCGGCAGCAGCAGTGCCCACCCCGCCCCGGCCAGCCTGGTCGGTCCCCGCCGCTGGGAGGATGAGGTCCGG
GCTGGACCCGGGAAGAGCCTCAGCTGGAGAGGACGTGGACGCGCCCGAGGCTCGGCTCCCTGGGCGGCTGCGGGG
CTCCGGGCAGGAGGAGGAGGGCGGGCGAAGCAGAGGGAGCGGGCGGGAGGCTGGGAGGGAGGAGGTGCGGAGGGCGGA
GGGCGTGCGGGAGGGATCCCGGGAGTGCGCTTGTGTGTGTGTGCGCGCGCGCCCGCCCCGCGCGCTCCTCTCCCC
GCCCCTCGCCCCCTCCCTGCGAGCGCCCTCCTCTCCTCCTCCCCCCGCCCCCGCGCTCCCGCCCAGCCCCCGGA
ATCAGTGCCGCTGTTGCCGTGCAGGCTGCGGATTCCTCCAGTCCCTCCCTCGGCCGCCTCTCCTCCCGGAGCGAG
CGCGCAGCCCTGCGCAGCAGCGCCCACTGGTCCCGTCCTGTGAGCCCCGGCCCCAGCCGCGGACAGACCCGCGGA
GTCGCCTCCCGGCCCACCCGCCCGGCCGCCGAGGAGCGGGAGGAGGACGGGACCCCGGCGCCCCCACCCCATCCC
CGGGAGGTAGGTAGGGGGCCCGAGGCAGGGAGATGCCAACTCACTGGGGCTGCCTCCCGGGTGGGCTCCGCGGCG
GCGGACGGGCGGGAGGAGGGGCGCGGGCCCAGGGCCGGAGGACGCCGCTGCCCGCCTGCCCTGCGCCCGGGGAGC
CGCGTGGGGCAGGGAGGCTGCAAAGCCCAGGCGGTGGGGGAGCCCGGGTCGCGGGTGCTCATTGGTA
CTCGGATGATGCGGGACGAGGGGCGGCAGGCTCTGCGGTGAGGCGGCAGCAGACCCGCCGTGCGCACCGCTGCCG
TCCGGCCCCAGCCCCGGCGCGGCGCGGCGATTCCTCCTCCCTGCCTCCGCCGGCGCCTCCCTGCAGCCGGGCGCG
GCGGCCCCTGACGCGGAGGCCCCTGGCGCGGAGGTGGGTGCGGAGCGGACAGCGGACAGCCGGAGGGTCTATTTT
CAGGTGCCCTCTCTGTGGCCCCGCGGGTGGGGAGCGGGGGCGGGCGGTGACAGGGCCGGGCTCTGCGCGTAGCGGT
GCAGGGGATGCGGCCAGGCGTGGTCCCGGCTGCGCCGCGCTGCAGCTGAGCCGGAGGCGGCGGCCCCGCGCCCCC
ACCTCCGCCCCATCCCTGCGCTTGCTACCCTCGTGCGCCCGCCCCCCCCCCGCCCTTTCTGCCGTCCCCACTCTC
CCAGGGCTGGGCGTGAGCCGCCTCCGGGCGCCGAGCCGCCGCTGCGCCCG (SEQ ID NO: 161)

CGI: 77 range = chr2: 73004709-73005568
CGCGTTCCCCCGCGGAGTGGCTCTCGAGTGCGGGGAGGTGTTGCGGAGGGGAGTGGACTTAGGGAAGGGGCGGCA
AAAGGGCAAAGGGAGAAATGGCGTGTGTGCGTGTCAAGGAATGGAGAGGGCAGGGCGCTTGGGAGCAGGGCGC
GAGGCCAGGCTCTGTTGGGCCCCGGCTCACGGCGCCCCTTCTCTCTGTCTGTACCTGCGTGTGTTGCCGTCGGCG
GCGGGGCCGCAGCCAGCGACGTGCCCCAGGACGGGCTGCTTCTGCACGGCCCCTTCGACGCAAGCCCAAGCGGA
TCCGCACGGCCTTCTCGCCCTCGCAGCTGCTGCGGCTGGAGCGCGCCTTCGAGAAGAACCACTACGTGGTGGGCG
CCGAGCGGAAGCAGCTGGCCGGCAGTCTCAGCCTCTCCGAGACGCAGGTAATCACCCCCGGTCGCGGCCTGCCCT
GCGCCCGGAGCCCGGGTGGAGGTGAGGGTGCGCGGGTGCAGGAGAGGCCCTGAGCCCGCCCCAGCCCAGCCCTGC
TGGGTTCCAAAAGGCCCCCATTCCCCGCGGCGCTGCGGTCAAGCCCGTCTTTAGAGCCTCTTCCTCGAGACTGCG
TGCAGCCTGCTGAGCCCGCAGGACTTTTGTCAAGCGCTAAAGACCTAGCAGGAGGCAGAGTAAATGCAAACTGTA
TCCCGAGCCCGGCTCCCAAAGCTCCTCACGGGGGGACCAGGTTCCCTGGAGGAAGCGGGTCGCCTCGGGAGCGGG
CAGCGCAGGCAGCACCGAGGCCACTGGAGCTGGCTCCAGCCCTGGCATTCCTGCAGCCCTTTTCCCGCCACTGTG
TCGGGGCGCTCATAGTCCTGCGGGGAGCCGGTCCG (SEQ ID NO: 162)

CGI: 221 range = chr2: 85213468-85216104
CGGGGGTCGCGTTGGAACCCCACAGGAAAAGGCGCGGAAAGCCGCCGGGCATTTTCCGGGGTTCCATAGATGTC
CCCAGTGTCCTAGTCCGTGCATCAGCTCGCGCACTCGGAGGGACTCTAGGCAGGGGGAGGGGCCCGCGGCCAGTA
TGTGCGTCCGAGGCTTTCCCGCAGGGGGCAGTGCCGCCCGCCCGCGCGCCGATACGGTGGGAGGGGGTGGGAACC
TGCGCGGAGTTCTGGAGGTTCTTTGGGAGAAAGTTAGGGGATGCGGAGGGGTGGGCGCAAGACTTCCAGGACTCC
AGGGAGGCCGTGGGGAGGGCCGCCGAGGGTGCAGTGTGAGGCGCAGGAGGGGGTTGGGGCGGTGCACGTTGCAG
GGAGACGCAGCCCCTGGAAGATGCGAGTGTGAACGTGTGAGTGCGTGTGTATGTGTGTGTGCGCGCG
CACCGCAGCTCTCCGGGTTCCGCGAGGCGCGCGGGTGTCAGCTTGCAGCCGGGGCTCCTCCCTCCGGCCCCCTG
CCCAGCCCGGCGGTCCCTCCTCCCTCCCTCCCCGCTCGCCCCTCCCCGGCGGGCCAGGGGCTGGGACGCCCCGGC
GGAGCAGGCGGCGGCGGTGGCGAGTTGGGGAGCCCTAGGCTCGGCGCTGCCGGAGGGGCCCGAGCCGAGCCGCCT
GCGCCCCGGCCGGGCAGCGCCGGGCCCGCTTCCCGCGGGCCACGCCCTGTCAAACTTTGTTGCGGCGGCTAGCG
CAGCGGGCCCGCAAGCGGGCGGGAGGGGCGCCGGGCCGGGCCGGGCAGGGCGCGGGCGGCTAGGGGCTCCGAGAG
CGGCGGCCCCGGCCCGCGGCCCCACCATGCCCCAGCTCGGCGGCGGGGGCGGCGGCGGCGGCGGCGGCAGCGGGG
GAGGCGGCGGCTCCAGCGCCGGGGCGGCCGGCGGAGGGGACGACCTCGGGGCGAACGACGAGCTGATCCCCTTCC
AGGACGAGGGGGGCGAGGAGCAGGAGCCGAGCAGCGATGACGGCCTCGGCGCAGCGGGACCTAGACGAGGTCAAGT
CGTCCCTGGTCAACGAGTCGGAGAACCAGAGCAGCAGCTCGGACTCGGAGGGTAAGGAAGCACCGCGGCCACCCCC
GGGGGATCCCGGCCCTGCGTCCGCTCACCCGCTCTTGCCTTTGTGTCTCCTCCGCAGGCGGAGAGGCGCCCGCAG
CCCGTCCGGGACACTTTCCAGAAGCCGCGGGACTATTTCGCCGAAGGTATGTGCCCGCTGGGACAGCCCCCCACT
CTCGATTCCCGCTGCGCTCCGCTGCTCAGCCCGGGCGGCCCACCGTCCCCCTTGCTTGGGTGGACGCACCCTTGC
CCTCCGCCTTTATTGGCGGCAGCCCCCGTGGGGCGCGTGGGGGCGCCGGAGCCGGCCCTCAGCTCCCGCCCTCGAGC
CCCCTGCCGCGGCGCTGTCAGTCCCGGGGCTGGGCCTCACCTCGCCTTGGTCTTGTTCGCAGTGAGAAGGCCT
CAGGACAGCGCGTTCTTTAAAGGACCCCCGTACCCTGGGTACCCCTTCCTGATGATCCCGGACCTGAGCAGCCCG
TACCTCTCCAACGGACCCCTGTCTCCCGGAGGAGCGCGCACCGTGAGTGCCCGTCGGGCGCGCCGGGAGGGTGG
GAGGCCGCGGCCCGCAGGATGCGCCCCCGGGCTTGGCCATGGAGTGGGGGATGGGGCCTTCTGCGCCGATCCAA
GCAGAACTTGTTTGCGGAGTTGAACTACTCTCTGGCGGCCGAGCGCGAGGCTGCGCTGGCCAGTGCCTGGATGAA
AGTAAAGTTACTTTAACTTTTCCCCTCTTGCGGGTTGAGGTTTTGGAGTCCACCTCTGGGATCTTCCTTGGCCTC
CAGAATTCTTCGCCTGCACCGAAGGAAACTTGGATTTGTGCCCGCTTTGGGGGGGTCTCGCTTTCCTTCTTGGAA
ATCGGTCAGCTTTCTCTGGCAGTGGGGCAAGGGGCCTAGGGAGCTGGGTTGCGACGTTGCTCCGACTCCGGG
TTCACTGGGCGGCTGCAGGCTGGTTCCTAAGAAACCCAGTTTTCGTGGCGGGTTATTCACAGCCCCCGTTCCCAC
CCCCAGCCCTCGCACCGGGGCCTCAGCTTTTCTGCGGAGCTAGCTCCGAATTTTAAACTCGCGTAGATGATTTCG
AGGCGACCCAAGGCATTCTTCAAGTTGAGGAACTTGGCTTTTTCCCCTTTTGTCGCCTGCTTTTCTCATTTAAA
GCGAGCGCTGCGACACTTTAAACCTGTTAATGGGCGCGTATTGTGTGCTGCCCGCTGGCATTTAGAGCGGTGATT
AAGCAAATTGACCGGGCCCCAGACGACGTGCAAATGAGGGCGGATTCCTTCGCCCCCTCTCTCTGGCTCTAAACT TABLE 7B-continued Sequences of differentially labeled CGIs between bladder cancer subgroups relative to blood CCCGCCCCCGCGTTGCGAGGGGCGCAGCTGGGGGCTGGCGAGGCCTTTGTGTCCCCCAAGCCGCCACTCCACCC
CTAGGCTCCCTGCCCAGGTGCTGGGTCCGATGACAGATGTTGGGTGAACGCCTACCTACTGTGTGCCAGGTTCCC
GCGTGCTGCTGCTTGGGCGCGATGTGAATCGTAGTAGTTCTTTGCTTCCCGCCCAGATTCCCATTGCCTGCCACT
TCGCTGTCGACG (SEQ ID NO: 163)

CGI: 173 range = chr2: 119329502-119332035
CGAGGAGGCTGCAGGGACGCGCATGGAAGAGCCGGTGCGTGGGAGGGTTTGCGGGGGGGACATCGCGCCCCCTAG
GGGTGACCCCAGTGGGTCCCGTGTGCTCTCCGCGGAGCCGGCGGAGCCTTGTCCTCTGCACCCGGCGCGCAGCGG
CCCCTTAAACAGTGGAACCGTGAGGCCGCTCTAAGCCGAAGGGCTGGAATCTGGGTTTCTCGGGTTTTATTTTAG
ACCATTCGGCACCAAGCCCGAGCTCCCCCGCCGCACCGCTTCCAGTCCCCTTTCTTTCCATAGAGCGACCCGAAG
CCGGCGGTGGCGCAGGGAGCCGAGTCTGATGAGCTCGCGGGCGGCTGAAGGCCGGCTTCCCTGTGGGGAACGCGC
CACCTGTCGGCGCCAGTGAGAACTGCGTCTGTGTGGCGCCCTCGGGGTATTCGGGGCTGCGGGGAGATGTGTGCC
TGAAGCCCTGCGCTTGCGGTGGGGACGTCCGGCCTCTTTCCTGGCAATTGACCCCTGAGGCGGGAGAGACAACGG
AATTCCCACAAAGGGATCCTTCTCGGGATCTCCCCACCTCAAGACAGCTAAAGCTGGAGGAAAAGCCCCTCCGGG
GGGTGGGGGGTGCGGGTTTGCCCTGCGATTCCGAAAGCAGAAAATACCCGAGCCACACAGGGACGGGCGCCGCGT
TGGTAGTCGGGGCTACGTTCCTACTCCCTCTACCTCCCCCGCGCTGTGTGACCCTGGGCGGAACCCCGCTGCTCT
CTGGGCCTCAGTGTTCTTATTCGTAAACTGAGGGCGTTGGATGAGATTGGTCCTCTCCCAACTCTGACCTTGAAA
CTGATACTGAATCTGAGCAGCGTCTGTAGACACCTGTGCCTTGCCTTCTATTTCTAGCCTTGAATAAATCCTGGA
CTTTTATGTGCCATTTATATCCTAATCTCATATATATTTAATGTATAACTGCTGCCATTATTGTTTTCTCAATTG
TCTAGGTTTTCATTTGGATGGGGTTAGGATGGTCCAAATTATCCCGATAAGTGCCCATTAACTTAAACCTTTTTA
AAAAATGAAACCAGTAAAACTTCATTCACTTTGCAGTGTGGACACTGCTGGAGAGCACCCATGTCGTGGGTCCAG
CGAGGACACAAGGAGGGGCTTAGAGACATGCGGGAGGCTTAGATGGAGAGAGCACCCGGGCAGCGGTCAGTGT
TAGAGAGAGGACCCGTAAGAAGGGCCGAGGCTAGAGGGAGAGCGAAGACTGAGCCAACGACGCACCTGAGCCCTG
GGGTGGGGGTGGAGACGTGGCTCCTAACCCAAATCTCCCTGCCAGGCAGTGTCCGACGAGCATCGACGGCAGGCG
TCGAGACCAGTGCAGGGTAGCTCAGACCTCAAGCCACGCTTGACCTTTCCATGAAATGAATAAAACTCGAAAGCC
AGGGAAAGGGGACAGTACTTTGATCCGGAGATCGCTTATAACCTCTGCTTGGAGTTCCGAGTTCGTGCGGCTCAA
GGGAGGCTACAGTCCAGCAAGCTCTGGGCTCCAAGCGTGGGGACGGCAGCCCCCAAGCTTGGCGCACCCCTCGGG
AAGCCCCGGAACGGTCCTCGCCAGACATAGCCGGCTGTCCTGGTCCTTAGCTTCAGGCTGGCGGCGCAAGGCCAG
AGCGGCTGCCTTCTAGGCACCTGGGTGGAGGTCTCGCATAGCATTCCCTGAGAAGCGAAACTGCCCTTGGGGCCG
CAGCGAGCCTGCCACATCGAACTGGAGACCCTCTGCTTTCGGGATAGATGGGACGTTTCTGCTCTGTCCTTCTTG
GAGTCCCGGAATCGTTCTGGGGCGCGTGCTGCCTGGAGGCGGTGAATTTCAGGGTCTTGAGAAGCCGCGCACAC
ACGGGATTCTGGGCGAGCGTCCCGTCTCTTAATTCCTATTAAGAGACGGGAAAATCGAGGGACTGGAGGTCCCAT
CATTGTCGCGTGAGCAGCCTCCTGAACACCAAGCGAGACCTGAGGGTTCCGCTGGGGCCTCGCCCTGACACCCGG
GCCCTCCGTGTGGTCGAGAGTTTGCGCCCGCTCCCGCTAGGGCAGCGAGGTCCCACTTGCGGCCGGCTGGGGCAT
GGTGGCACCGGTTGTCTACTCCCCACTTGTGACACCGACAGCTTCCAACTCCTCCACCCCACCCCGTGGAATTCT
GGACTTTGTGAGGGCCGCCGGGGTCCTGGCCCTGGGGTCAGCTGCCATCTGACTAAGCCAGGACGGCGGAGCTCC
AGGCCTTGCTCCAGCACTGCCGGTGCGTCGGGGCCCGCGGAGAGCCCAGGGCGGGAGCTGTGGGCTGAGCCGGGT
GGCCGCGTGGACACAGATGCCCGGCCGGACTGAGCGGCAGCCAAGACTCTCCGTCCATCCCGCCGCTGGACTCGA
CTCTCCCAGACCCGCCACGGAACCCAGATTTGAGCACGCAAGATAAAGACGCCAGAGGCGAGTGCGCGGCGGAGA
ACTGGCCGCGACACGGGAAGCTTCTGGGGCGCAGAACGCTGGCTCCGACTCGCGCGGCG (SEQ ID NO: 164)

CGI: 36 range = chr2: 172653235-172653630
CGACGGCGCGCTTGTGGCCCGGCCGGAGCTTGCGTGCGCGTTCTGACGGCTGGGTGCTGTGTTACAGGTCGGCGC
AGTTCGAGCACACGGTTCTGATCACGTCGAGGGGCGCGCAGATCCTGACCAAACTACCCCATGAGGCCTGAGGAG
CCGCCCGAAGGTCGCGGTGACCTGGTGCCTTTTTAAATAAATTGCTGAAATTTGGCTGGAGAACTTTTAGAAGAA
ACAGGGAAATGACCGGTGGTGCGGTAACCTGCGTGGCTCCTGATAGCGTTTGGAAGAACGCGGGGGAGACTGAAG
AGCAACTGGGAACTCGGATCTGAAGCCCTGCTGGGGTCGCGCGGCTTTGGAAAAACAAATCCTGGCCCTGGACTC
GGTTTCCCAGCGCGGTCAACG (SEQ ID NO: 165)

CGI: 295 range = chr2: 174907710-174910885
CGCCCTCGCCCCCCCCCGCAAGTATCCCCCACTACTCCCCCCCACCCCCGCGGCCCTAGCTAGCTGACTTGACT
GGCACGCGCCGGGAGCCCGGGCTCGGGCCCCTCGGAGCGTCTGATTGGCTGCGGGGCAGCTCCGGTCTGCTCTGC
CTGCGCCCTCATTGGGCGAGAGGCGCAGCCAGCGGCACTTCAAAGCGGGTGCTCCTCGCACTTAGGCTGAGTTTA
GCCGGCGGGAGCCTGGAGTCCGCTCGGCACGAGCGCGGGGACGCGGGAGCCGCGCGGGACCCAAGCAGTTTTTCC
GAGCAGCCGCCAGGCTCAGCCCCGCTCCCAGCCTCGCTGCGCAGCCAGAGACCTGCTATGGCCACGTCTATACTC
GGGGTAAGTCGCAAGCGCGGCAACGCATTTGCTTGTTTTAACCGGAGTAATTTTTCGTTATGGCTTCTGGGGTCT
GCGGCTCCGGAGAAACTGTTGCTGCTAGACTGCAGCTTCAGCTTCTATTAGCACTTTCCACATTTCTGGGACTGA
TTTTTCCCCAAGTTTTTGGAACCCAGAAAGATGCCTTTGCAAGAAAAGGCCTTCTTAATCAAGTCCTTTTTCATT
TGGTTTCAAAAAAAAGCTAGAGGTTTCTTTTCTTCCCCTCGTGATTTATACCCCATCCCCCGCATTGCTTTGGGG
ATTTTGTTGCAATTATGCGACAATGGTGTTTCCAGAAAACAGTCTTAATCGTTTTGCAGTCCATCTAGTCACGCT
AATAAACATTTACATTTCCGCGGCTCCCCAATTCGCCCATGACTTTGAAATCTGTCTCTGGCCGCTTATCCTCGG
ATTATTGTTTTCATAATCGCTGTTTTTGTGTGTATGTAAACTTTAAAACCAAACGTTTTCTATTAAAAAAGAAAA
GTCAAGTCGTAGCCACCCTGGGAGAGCTGCAAGTTTCGCCCGTCCCTGGCAGCTGTTTCGGCCGCCTCCGCCCTC
ACCCGGTGTTTGTTGTCTCTGGTCTCTGTGTTTACCTTCGCGCTTCACCCCGAAGGGCGACTTGGGGTCTTCTGG
GAGATGAGCCGGTTTACGCGACAACCCAAGTCCGGTTGTAGGCAGGGTTGCAGCGGGGAACACGGAGGCATCTT
TGATTTATAGCCTCAGCGAAGTGCAACTTTCCGGCGCCTGGACCTTGCCCGGGTGATCGCCCCTGCTCCGCGCC
CGGTGCGGCGACTCCTCCGCGGGCGCGTGGGAGGAGGCGCGAGGCGGGGAGCCAGGACCCCCGGGAGCAGCCG
CAGGGGACGAGGCTGCTCACGGGTGCACTTTGTTTCTTCCCCCACTTCCTCTTGCCCTCCTCCTTCTTTGCTCCCT
CCCCCATCCCACCCACTCTAGGAAGAGCCGCGCTTCGGAACGACCCCCTTGGCCATGCTGGCGGCGACCTGCAAC
AAGATCGGCAACACGAGCCCGCTGACGACGCTGCCAGAGTCGAGCGCCTTCGCCAAAGGCGGCTTTCACCCCTGG
AAGCGCTCCTCGTCCAGCTGCAACCTCGGCTCCAGCTCTCGGGCTTCGCGGTGGCCACCGGGGCCGTGGCTCG
GGCGGCCTGGCGGGCGGCTCGGGCGCCGCCAACAGCGCCTTGTGCCTGGCCTCCAGTCGCCCCACGTCGTCCGCC
TTCAGCAGCGACTACGGCGGCCTCTTCTCCAACTCGGCGGCTGCCGCGGCGGCAGCGGCCGGGGTGTCCCGCAG
GAGGCGGGTGGCCAGTCGGCCTTCATTTCCAAGGTGCACACGACGGCAGCCGACGGGCTGTACCCGCGCGTGGGC
ATGGCGCACCCGTACGAGTCCTGGTACAAGTCGGGCTTCCATTCGACGCTGGCGGCCGGCGAGGTGACCAACGGC
GCGGCGTCGTCGTGGTGGGACGTGCACAGCAGCCCGGGCTCGTGGCTGGAAGTGCAGAACCCCGCTGGGGGGCTC
CAGAGCTCGCTGCACTCGGGCGCCCCCCAGGCCTCGCTGCACTCGCAGCTGGGCACCTACAACCCCGACTTCAGC TABLE 7B-continued Sequences of differentially labeled CGIs between bladder cancer subgroups relative to blood TCGCTCACGCACTCCGCCTTCAGCTCCACGGGCCTCGGCTCCTCCGCCGCCGCCGCCTCCCACCTGCTCTCCACC
AGCCAGCACCTGCTGGCCCAGGACGGCTTCAAGCCGGTGTTGCCCTCCTATTCGGACTCCAGCGCCGCCGTGGCA
GCCGCCGCCGCCAGCGCCATGATATCGGGCGCCGCGGCTGCCGCCGCCGGGGGGAGCTCGGCACGCTCTGCCCGC
CGCTACTCGGGCCGCGCCACCTGCGACTGCCCCAACTGCCAGGAGGCGGAGCGGCTGGGCCCGGCCGGGGCGAGC
CTGCGGCGCAAGGGCCTGCACAGCTGCCACATTCCGGGCTGCGGCAAGGTGTACGGGAAGACGTCGCACCTGAAG
GCGCACCTGCGCTGGCACACGGGCGAGCGGCCCTTCGTGTGCAACTGGCTCTTCTGCGGCAAGCGCTTCACGCGC
TCGGACGAGCTGCAGCGGCATCTGCGGACTCACACGGGCGAGAAGCGCTTCGCCTGTCCGGTGTGCAACAAGCGC
TTCATGCGCAGCGACCACCTGAGCAAACACATTAAGACGCACAACGGGGGCGGCGGGGGCAAAAAGGGCAGCGAC
AGTGACACGGACGCCAGCAACCTGGAGACGCCCCGTTCCGAATCCCCCGACCTCATCCTGCATGACTCCGCGTC
AGTGCCGCCCGGGCGGCGGCAGCGGCGGCGGCGGCAGCGGCGGCGGCGGCGGCGGCTCCGCGGGAGGCAAG
GAAGCAGCGTCTGGCCCCAACGACTCTTAGAGGCCGGGCGAGAGGCGGCGAGCACACAAGCGAGTAGAGACACCGA
GAACGAACGAGAGGTTCGGAGGGCGAGCGAGCGGGAGGCGGGAGGGCAGGGGCTTCAGTGACGCCCCAGGGCCC
GGGCTGGGCGCGAGGTGGAGCCGCTCAGGGCTCCCGGGCTGCGGTTCGCCCGCTGTGCGAGGAGCTCCCCTCTGC
CTTCCGCGCCCGGATAAGAATCGAACGCGTGGTCCGGAAACAAAAGCGAACCATCCTCCGACACAAACACTTTAA
AAACTGTACTCCCAGACGTACACATACACCGGAGACCTACAACCACAAGCACGCACACTCGCGCGCGCACACACA
TACCACTCGCCCAAACTTCTCGAGCG (SEQ ID NO: 166)

CGI: 289 range = chr2: 176652334-176656692
CGAAAAGGAGGCGGCGCAACGGCCACCCCTTCCAGCACCTCGGCTTTGTCCTTCCCGGGGAAGGCGGCCACATCC
CTACCCGCCTTGCTCCTGAACGTAGTAAACAATCTCACAAACAACCACCGCTGCCCACGCTCTCCATCCGTCCTC
CCGGCCTTATCAGACCTCCGTTCTCCCGCACTCTTCGGGCAGGGTCCCTAATAAGCTCAGGCTGAAAGAACGTTT
GCCACCTCCCCCACCCTCGTTGAAAGAAAAGGAAGAAAAACAGCAGCAGCAGCAGCAGAAACCTCCGGGGCGACTCCTCC
CCCGCCCCCAAGCACCAGCGCACAGCATCCCCCTCTGTCTTTGTTGTGGTTCTCCGTTGCTTCGGGCCACGCCGT
TCAGCCAAGCAACCCGGACCTGAGAGTGCACAGCCAGGACTAGCTTAGGGGGCGAGGGGTTGGTCTTTGGGAAAC
CAAGCGCTCAGGACAGAGGTGGAAAGTGGGTCCCGGGAGCCAGAAAAGAGAGAGAAGGGCAGACGGCTGGGTGGC
AAATACAAAAATAGAAATAATTTAGGGGGATGCCCGCCAGGCTTTTGCCCTTCCTTCTCCCCCAATTCGGAG
CAGGTTCCCTTCGGCCTCCCGCGCCCGGGGCGCCCCCTGGCGGCAGCGGCAGCAGCGGGCAACGCGCGGAGGGC
TCAGGGGGCGCACAGGGGACTCCCGGGCACACTCAGAGAGGCGGGCGCGGCCCCCTGGCGGTGGCGACGTAGTTA
TCTGGTGAGCGGAGCCTCGTCCCTCTGGTCCGGCGGGCTCACGGCCGTCTTACTAAGCACCGCGGCCGAGTAGGG
CAGGAAGCCGCTCTCGGAACGCGGCGCCGCCGCGCTGCAGCCGAAGCCGAGCCTCCCCCGGCCCCGGCGCCCCC
GCCGCCGCCGCCACCACCACCACCGCCGCCGCCACCGCCACCCCGGGAACCCAGGGCTGCGGCAGCTGCTGCCGC
GGCTGCCGCCGCCGACTGACTGCTGTGGCAACTGAGGCACGAGCAGGGTGCAGAGCCGCCGCTGGGGGGCGCGCC
GGCCGCCGCCGCCGAGGAGGCCGCAGCCGCTGCGGCTGCCGCGGCTGCCGCGGCAGAGGCCGCGCTGTTGAGCCC
CGCGGCGGCCGCGGGAGCCTGGTAGAGACCAGGGTGGCGGAAGCTACACAGCAGCTCCGGCCGAGAGTAGGGGTG
CGAGAGGGCGCGGAAGGTGTCCAGTGGCCGGATGGAAGTAGCGAAGGGCGACGAAGCCGCGGCCGCCGCGCGCTGA
GGCTGCAGCCGCGGCCGCCGCCGCCGTGACGCCCACGTGCGGGTAGTAGTGCAGCGGCACGTGCGAGTGGAAGGG
GTAGGGCAGGCTTCCGGTGGCGGCCGCGTGCGTCATCATGTAGGTGTAGAAGCTGGGGTCGGCTGGGTGCGGCCA
GGACATGGCCAGGCGCTGCCGCTTGTCCTTCATGCGCCGGTTCTGGAACCACACCTGCGGGGAGAGACGCGCCGC
AGCCTGGGTTAGGGAGCGCCCCGTGTTCCGACTCCTGTCCCAGGACCTCTGCCCCTTCCGGACCTCTGAATGGC
TTGGTCTACTTCTCTCCGACCAAGCCCAACCCCGAGTACCCTGTGGTCTCCCAGCTGGGAAAGTGTGGACGGCAG
TGTGTGGACCGCCGTGGGCACACCGTCCTCAACGAAGAGGGTCCTCTCCCCCGCGTCCGGCTGCTGCTGCTCCTC
AGGCTTTTATTCCCTTACTTCTTGCTGCACTTTTTTGTCCCAATCCAACCTTTCCTCTCCCTCCCGCCACCCACC
AGTGCCGGTCTCGCTGAGCACCCGTCTCTCAATCCCAGGATTTGTACGGGGATTCTGGGCAGCCTTTGAAGAGAG
GCTGCCGCTCAGCTTTTCTGAGAGGTCGCCGCGCGAAGTCTTGAGCCCTCCGAACTGCAAGGACCTGCCCCTAGG
GGCACGGGTCCGATTTTGATATTGAAGGGATGATTTTGTTGGAATCGTTTGCCTTAAATGAGTGGGTAGAGCAAT
GTCTCCATAAACGGGGAAGGGGACGTTTCCACCCCTCCCAACACTATCTAATAAAGACATCATTCGTCACAACTC
TAAATTAAAGAAAGCCCGATCAAACCAGAGGGAGACTTCCACACTCCTCCCCTACCCCGTGGAGATTTTTTCTTT
TTTCTGCAGTGTCGAACGCTCCATGAAGGGCTCACCAAATCGCCTAACCTCCCGGCTATCTCTCCCAGACGTATA
ATAAAATTAATAACCTAAAGTTATATATAAATAAGGACAATTTCGTTGCATTTTTCCCCGCAGGAGGTTGCCCTT
TTTTCGTTGCCCAAGAGGAAAATGTTCAGGAAACTACTGTCTCAAACCAATCGATTTTAAAGATACAGTATCCTT
TTCTCCGTGTAACGATTTATGCGGAAAATAAATCTCCAAGCTCAAGAGCAAATGAAAAGTTTCACCTCTGGTTCC
TGCTTGAGGAACAAAGACCAACTGGGCTTGCCGCCTAGGGGAAAGTGGGGCCGTGGGTATGGGCGAGGGGGCATC
TGGCCAGGCGTTGGGCACAATGGAGCAGGGGCGAGTGCTTTCAGCATTGGAGTCACCATTCGGGGGCCTTCTTAG
ATCCGTCAGGCCGGACAACCGTTCGGATTCGGTGGCCGGGAAATAAATAAGCCAATTCCTTTGGTGACTACCCCC
CGCGGATTTCAGACCCTTAGCTAAATCTAGCCACCCAGAAAGGGGAAAGGGGAAAAAGAAACAATCAACCCAGA
TGCCCCCGGGGAGGCCAGAGCAGGCATGCACTGGAATTGATACCTTGATGGTGGTTTCGGGCAGGTTGAGTGCCG
CGGCCAGCTCGCACCGGCGGGGCCGCGACACATAGTTCTCCCGGTAGAACTCCTTCTCCAGGCGCGCGATCTGCT
CGCGGGTGAACGCCGTACGGTAGCGCCGCACTTGATCCGCGCCAGAGCCGGAGCCACCCAGCGCCGCGCTCCCGC
CGCTGCCTCCGCTGCCTCCATGCAGGCTTCCGAGGCCTGAGCCCGACGCCGACGTCGTGGTGCCGGCAGCCGAGC
CGCTCTCTGCGTACCCTGGCAAACAAACGACCAACAGCGCATGAGTGGCTGTAGGACCAACAGCCCGGCGCTGGC
GCTGCGCGCGGATCGGGGAAGCCCCGTCAGGAAGGAGAGTCGCTGCCGGAATTGATGGGGTCTGTCATGCTTACA
AATTGCTGCCGTTAATGGAATCAATAAAGTTTGGGGAGCCCTTCATAAGCAAATAATAGAAACGGAATTAGGAGA
TTTCTTTTTTAATAATTAGAAATTTTCAACCAAGGAGGAAAAGTGGCCGAGGGAAAATGCCTACCTCTGGGCGCA
GTTTGGGAAGCTCTGGGTTTCCCATGGTCTGGAGACCGCAGGGCAGCTTTTTATACGGCCTCTAACCTTTATCTG
AGTCTTCGGGGTTTCAAATATTTTAAGAGTTCCAACACAGCAGTAGCTCAAACCCAAGCCAATAGGGGGTGAAAT
ATACTTTTCAACTCTTTCTCCCGCTGACCTAAACAGAGACGCCGGCGAGGCTTCCTCCGACTTACCCAGAAGAAT
GCCCCCTCCAGCCCTGAGGGCACAGGGGCAGGGGAGTTCAGAGTAGTTGCCCAGGGTACCTTTCCCAAAAGCAAC
TCGGCTGCTGACTAGGGGTCTACCGGCTCGCTCGGGCTCTTAGACACGAGCGCAGAAACATTTTCTCGGACTCAG
GAGCGAGGGCGGGTGGGCCTGGTGTTCCAGGCTCCGCAGGCCTGAGCCTGGCGGGAAAGCTCAAGGAGCAGAACT
GGAAGGCACGGTCCCAGACATGCGTCCCGCCCCCGCCCGTGCTAGCTCGGTGTAGCTTGCCTGTGGAGGGTCTGA
GAGGGGAAAAGGCACCGGGAAAGGCTGGCGGGGGCCGCGAGGAGCAAAGAGGATGGGACTGGAGAGCGCGGTGC
GGCCGGCGCGGTTACCTTTGCCATTGTTTTCCTTAAGCTGAGCGGCGCCAGGGCAGGCCCCCGGGGGAGCGAGGCGG
AGCAGCCCACCTCCACGTCGCTGCTCATGTCGGCCTCAGCGGCCGCCTCTGAATAATGGCCCGGCTTCTTGCGGC
TCTCGGCGGCGGAGGAGATTTCGGAGGGAGACGGTGCTTTCGCTGCCCGTGTGCTGCAGGTTGAACAAAGTGTCTA
TTTCGAATTTGCCCTTGGCGGGGAGTTCTCCCAGAGCGCTGTGCAGGGGGGCAGACGGCAGGCGCGGGCTTAGGC
GAGCCGGGTGCTGCGAATTTTCCAGGGCCTCGAGCACAGCATTGCCAGCCGAGTTGGACAAATTGGAGAATCTCT
TGCCCGCCG (SEQ ID NO: 167)

TABLE 7B-continued

Sequences of differentially labeled CGIs between bladder cancer subgroups relative to blood CGI: 25 range = chr2: 176720618-176720921
CGCCGCTGTAAGTACCTTCCCGCTTCTTCCGAATCGCGAAGAGACGGTACTGATCGCGGGGAAGTGGTGGGCTAA
GGGGCCAAGCCAGCGGAGTGGGCGGATAGAAGAAAGGCCCTGCCTCCCCCACCCCACCCCCACCCTCCACCCCCG
GCCTCGCTCTGCGAGGTTAGCCCGCTTCGGGAGGTGGAGGCGCTAAATCGAGGTCCCGGAAAGCTTTTCTGGGGC
CTGGTTCACAGACACCTGCCTGAGAGAACGGTCCGCGGGGTCTCGCCCTTGTCTCCTTGGGCCTCCCTAGACCTT
CGCG (SEQ ID NO: 168)

CGI: 20 range = chr2: 236438623-236438823
CGAATCCAGTCCCGGCCGGCGCTTTGAAGCCTGTGCTGTGCGATTTTCTCAGCAGTGAGGTAGGAATAGACGCGG
CTAATGACAGGAAGGTCGCGCGGGTGAGCTGACCTGTGTGTGGCGCAGCCTTGGGTTCCGCAAATAGGGCACCCA
CAGTAACACGTGTGGCGCCGACCCCGCCGTGCGCAATCGGGGCTTTATACG (SEQ ID NO: 169)

CGI: 22 range = chr3: 11721578-11721824
CGATGGGACCGCGGCTTGACACGCATTAAGGAGCCACTGAAAACTCCATCTAAGCAGAAAAGCGGCTTAGTCATC
CATGCGTTCTGGGCAAGTTATCCTGGCCGCACCACGTGGAACGGAGTAGATAGAGCTCGGGAAGCTGAGCGCAGG
GCGGACAACGGGAAGGCCAGAGCCGTGGGCAAGCACGCGGAGGGCAGCGAGGGGCACTGGCACCGGAGCCGCGGG
GAGGCAGGAAAACGCAGAGGCG (SEQ ID NO: 170)

CGI: 68 range = chr3: 12983649-12984210
CGCTCCTGTCCCAAGGGCGCGTCTCTCTCTCCCACGCACAAACTCGGGTCCTGTTTGCTCTTCTCTCACCCAAAC
CCACAGTCTGGCGGACGCACCCCGCCCCGCAGGCAGCTTTCTCTGCACGCCGGGCGCCCGGTCCCGACGGTCAC
CCGCACTCCCGCACAGGCATCCCCACAGCCTGCGCCAGCCCACCGCTCAGCACCCGGGAAGGCCGCTCGCCCCGC
GCCGCGCCCTCACCCGCTGTCAAGCTCTAGCTCCAGAAGGGACTGGGTCCTCTCCGAGTTGCAGTGCAGGCACCA
CATGGCGGCCGCAGTGGGAGCGGGCCGGGCCGGGAGCCGGGACCCAGGCCCAGCAGAGGCCGCCGACTCCCGCCA
GCGAGCCGCCGGATCCCGGGGCCGACACCCGGCCACCCGGAGACCCGCCACCCGCCACGCGATCACGTCGGGGC
TCCTGGTCCAGCGTCCGCCGGCTCCCGCGGCTCCGGCCCCAAGTCCGAGCCCCAGGCCAGCCAAGCCCGCCCCTC
CGCCGCCGCCCGCTTGGCGCAGCGCGAGGCCGGGCCG (SEQ ID NO: 171)

CGI: 120 range = chr3: 25680561-25681574
CGCGGGGAGCGGGCTGGAGGATTCTGCAAGCACAGGCCCCTATGGAGCGCCCGTTCGGGGGACGGGATTTCCCTC
CCTTTCCCCTCCCCCGCCCGTTCGGAATTCCGCCCCCGCCGCGGGCCGGAACAATGCAGCCGCCCGTCCCGGGG
ACCAGCCACTTACCACCCAGGTCAGTGCCCCGTTGCCGCCGCCCACGCCGGCTCCCGCGCCGCAGCCACCCGACT
TGGCCATGGCGAGTGCCTCCAGCTCACAGGCCCTGAGGCCGCAGCCGCCGCTCCCGCCTCCCTGCGGGCCGCTGG
GCCCCGCCGCTCCGCACCCACCGCTCCACTCGCCGCACTCCTAGCCGCCGCGACCCCCGCGCCCCATCGCGAAGA
TCCGGAGCGGACGTCCAGCCGAGCCCGCTGAGGAGGCCGCGCGCCGCCGGCTGCCCTCAAACTCGAGGCGCGGCGTC
CGCGTCGCCCGGGCCTAGCGCGGCGGCTGAGGAGAAAGCAGGGAGCGACCGGCGGCGGCCGAGCGGCGGCGTTGC
CTTCTCGCCCGCCCGCGGGCGCCGCTGCAGGCCGGGCTGAAGCCCGGGCGTGCGAGCGCGAGGGCGGCCGGGGA
GCCGAGGCGCTCGGACGTGGCGAGGACGCAGAGGTGCCTTGTCCTTCTCACACTCCGCGAAGGCCAGCCACTCG
AGTCGCCAGAGTAGTCGTCCCGGTCGCCGCCGCTGCTTCAAAGGCAGCCTTAGCCTCGCTGCAGCCCCGATTTCC
TCACACACACACCGAGAGGGACAATAAACAGAGCCGCCGCCGCCGCCGCCACGGTCACCTCCCTCTTGTCCGG
CATAACACCGCACACACATTTGCACACCGGGGAGAGAGGGAGGGCGCGGCGGCCGCCCCCGCTGTCAGTCAGC
GCCATGCTGTCCAATCCGGGCCTTGTCGCCACAGCCTCTCGGCCAATCCCAAAATTCCAAGCCCCCTGGAGGGGC
GGGACCCGAGGGGGGAAACGTCATTGCGGGTAGCAACCG (SEQ ID NO: 172)

CGI: 23 range = chr3: 148613030-148613264
GACCGGCGCTTCGCTAACAGCAGCGACCGCAAGAAGCACATGCACGTGCACACGAGCGACAAGCCCTATCTTTGC
AAGATGTGCGACAAGTCCTACACGCATCCCAGTTCGCTGCGCAAACACATGAAGGTAATCGCCGCACTCTCGTCG
CCCCCTTTGAGGCAGGAGCTCTCTTGGCTCTCGGCTTGGGGTCGGCGGCGAGTGGCAGACAGGCGGTGGCGGGA
GCCAGAGGAA (SEQ ID NO: 173)

CGI: 41 range = chr4: 4910534-4911092
CGGGCAAACCTCCGGAGGCCCCGGTGCACCGCGCGTCCAGCCGGCCCAACTCGAGCTAGAAGCCCCAACCACTGC
CCAGTGCCTGAGTTGCAGTCTTGGGTCCTTTAGAAACCTGGAGATGTGCGTAAAATTCAGATGCCGGTATTCCCG
AACTTCCCCAGGCCTCAGCATATCTCGGCGGCCTGTGGACAGATGGGGAGGCTACCAATCGCTCCGGCGTCGCAG
CCCGACCCCTGCCGCCAGACCCCGGACGTCTTCCGGATAATAAAGTTCCCGCTCTAATTCATTTTCCCTAATCTG
GACGCCCCTAATCTACAGCTTTTATTGCGCCCAGTTAAAAGTCGAGGGAATTCGCTGTCCCTCCGCGCTCGGATA
ATTACCCCTAAATGGCCACGGCAGCCCCTTGTGTTTCCTGGAGATTAGAACCCCGCAGTCATCAATGGCAGGGCC
GAGTGAGCCGCCAATCACCTCCGCTCACTCCCTGAGAGCCGCTGGCCTGGGCCGCAGGAGGAGAGGCCATAAAGC
GACAGGCGCAGAAAATGGCCAAGCCCCGACCCCG (SEQ ID NO: 174)

CGI: 300 range = chr4: 30330303-30333940
CGAGCGCGGCGGCTGGCTGACGCTCCCTCCCGCCTCCTTATCCCGGGCCCTCCTCCCTCGCTCTCTCCTAGTGTG
TAGTTTCGGCGGCTCGGCTGCTACTGCCGCCGCCGCTGCAGCGAGCAGCGTCAGGGACAAGCCTGATCCGTGAGCG
AGCGAGCACCCAGCAGCAACCACCACTTTGGGCAACTTGCGGGTTTCCTGCTCGCGGGTAGCGAACGGGAGATTC
CCACTAGCGGTTCAGTGTCTCCGAGCCGCTGCAGCCCGAGGGGCGGCGGGAGCGCCCGCACCAGACTCTCCCAGA
CGCGAAAAGGGACGAGACAACTGCGGAATTCACCAGCCGTGCCAGGGCACTTCCGAGGCCACAACCGACTGACAC
TTTTTCTCCCCTTGGCAAACTGGATTTTTTTTTTTTAAGCTACTTGGCAGCTGTCTCTGACTCCACCTCCCCCTCC
ACCCCCGCCCGAAAGCCTTTGGCTTTTCTTCGGAAATCCAGACAGAATTGGGCATCTTTGTTAATTGCCGTTGGG
GACGCCCGGCCGTGCGCTTTCGCCGGCTAACGTCGCCTGTGCTCCGAGCCTGGTTTGCTCACCTTTGAACTGCAA
AGGGATCAAGTTCAGCTTGAGTTCCCTGCATTGGGAAGGAGAGAGAGCGTGCAAGAGAGCGAGTGGGAGAGGGGG
AAAGGGGAAAGGAGAGGAGGGAGGAGAGAGGAGGAGAGAGGAGAGGGTGGAGAGAGGATCGAG
AGAGAGCGGGGAGAGAGAGGCTGCAATCTCCTCCCTGAATCGCGCACAGCGCTGCAGATCCCACTGCTCCGACAT
GCGGGCCGAATGCAGGTGAGAAAAGGCACGGACTCTGCGGCTGCGAACCCAAACTTGGGCACCGCACGGTGCGCA
CTGCTCAGCCTTCGCCCCCGTGGGCGAAAGGCTGCTGCGGTTTCAGGCGGCTGCTTCGTGACTAATGACCTTGCG
CAGAGTTGTTAAGAAAAAAGAGAAACCCGCGCTCTCCGGGGTGAGAAGGGACTGACTCTGGGCGTCTCTGAAGAT
GGCTCGGGCTTCTCTTTGGCGCGCCGGGGGGACCCTGACACTGACCGCTCTGTGACGCGAGTAGTCTCCCCTGCA TABLE 7B-continued Sequences of differentially labeled CGIs between bladder cancer subgroups relative to blood CCGTGCCCGAAGCGACGTGCCGGGGGATTTTTCATTCTCGATCTGTTGACTGGCTCCCCCGCTGCATGAGCAGAG
TCGGAGTTGAGACTGGCTTGTTGCTGGCCCCAGCGCCTGGTGCAGGAAGCGACTCACGTTTGTCTGGGTGGCCGG
AGCCGGAGCAGAGCCTGGGTTTGGAGTGAGTGCCTGGAACGTGAATTGGACTCAACTCGAGTAGCAGCAAAGACC
AGCGGGCTGGCAGGCGGGGGAGGCTGCAGGCTCATTCCCCACCTCTTCCCAGCCCCACTGCCCGTCTGCCGGAGC
GGTTCTGGCCCCTTCCGACAGAGCGGGGACTAGAGCCGGGGATTCTCCGCCCGCTGAGGGGGATGACTCTGGGTTG
GGGGAGCGCCGAACCCGCGGCGCGCAGTGTCCCGTGAACTGTGAGTACTGCGACTGAACGGCGGCAGGCGAGCGG
GCGATTAGCACCCATTGCATGAATTATGAAACAATAACTTTCGGAAGAAGCAGGAGGAAAAAAAGAAGCATCTAT
CGCTGCCCTCCCACCCCATTCCCGGCCAACTCTCCACGCCGCTTTTGCCCCCTCCCTCCCCTCCCTCTCGCTCC
TTCCTTTCCGGGAGAGGGGAGAGGACTCGGGGGAGGGCAGGCGGCCGGCCCCGGAGGAGGGGGCGCCGAGGGGG
CTGTGGTTAGAAGGAGCAGTAGCAGCAGCAGCAGGAGAAGATGCTGAGGATGCGGACCGCGGGATGGGCGCGCGG
CTGGTGCTTGGGCTGCTGCCTCCTCCTGCCGCTCTCGCTCAGCCTGGCGGCCGCCAAGCAGCTCCTCCGGTACCG
GCTGGCCGAGGAGGGCCCCGCCGACGTCCGCATCGGCAACGTGGCTTCAGACCTGGGCATCGTGACCGGATCGGG
TGAGGTGACTTTCAGCCTGGAGTCCGGTTCCGAGTACCTGAAGATCGACAACCTCACTGGCGAGCTGAGCACGAG
CGAGCGGCGCATCGACCGCGAGAAGCTGCCCCAGTGTCAGATGATCTTCGACGAGAACGAGTGCTTCCTGGACTT
CGAGGTGTCGGTGATCGGGCCCTCGCAGAGCTGGGTGGACCTGTTTGAGGGTCAGGTCATCGTGCTTGACATCAA
CGACAACACGCCCACCTTCCCGTCGCCCGTGCTCACGCTCACGGTGGAGGAGAATCGGCCGGTGGGCACACTTTA
CCTGCTGCCCACAGCCACCGACCGCGACTTCGGCCGCAACGGCATCGAGCGCTACGAGCTGCTCCAGGAGCCCGG
AGGCGGCGGCAGCGGCGGCGAGAGCCGGCGCGCCGGGGCGGCGTGGTCCTTGACAGCGCCCCCTACCCCGGGGGCGGCGGGAA
CGGCGCGAGCGGCGGCGGCTCGGGAGGCTCCAAGCGGCGGCTGGACGCATCAGAGGGCGGCGGCGGCACCAACCC
CGGCGGCCGCAGCAGCGTGTTCGAGCTGCAGGTGGCGGACACCCCGGACGGCGAGAAGCAGCCGCAGCTGATCGT
GAAGGGGGCGCTGGACCGCGAGCAGCGCGACTCCTACGAGCTGACCCTGCGAGTGCGCGACGGCGGCGACCCGCC
TCGCTCCTCGCAGGCCATCCTACGGGTCCTCATCACCGACGTGAACGACAACAGCCCCCGTTCGAGAAGAGCGT
GTACGAGGCCGACTTGCTGAGAACAGCGCCCCGGGGACCCCCATCCTGCAACTGCGCGCAGCCGACTTGGACGT
GGGGGTCAACGGGCAGATCGAATACGTGTTCGGGGCGGCCACCGAGTCGGTGAGGCGGCTGCTGCGCCTTGACGA
GACGTCCGGCTGGCTCAGCGTCCTGCACCGGATCGACCGCGAGGAGGTGAACCAGCTGCGCTTCACGGTCATGGC
CCGCGACCGCGGGCAGCCCCCAAGACCGACAAGGCCACCGTGGTCCTTAACATCAAAGACGAGAACGACAACGT
GCCGTCCATTGAAATCCGCAAGATTGGGCGCATCCCCCTCAAGGACGGGGTGGCCAACGTGGCCGAGGACGTTCT
GGTCGACACCCCCATCGCTCTGGTGCAGGTGTCCGACCGAGACCAAGGCGAGAACGGGGTGGTCACCTGCACCGT
GGTGGGCGACGTGCCCTTCCAGCTCAAGCCAGCCAGCGACACCGAGGGCGACCAGAACAAGAAAAAGTACTTCTT
GCACACCTCGACCCCTCTGGACTATGAGGCCACCCGGGAGTTCAACGTGGTCATCGTGGCGGTGGACTCAGGCAG
CCCCAGCCTCTCGAGCAACAACTCCCTGATTGTCAAGGTGGGAGACACCAACAGACAACCCGCCCATGTTCGGCCA
GTCGGTGGTGGAGGTTTACTTCCCTGAGAACAACATCCCGGGCGAGAGGGTGGCCACGGTGCTGGCGACAGACGC
AGACAGCGGTAAGAACGCCGAGATCGCCTACTCGCTGGACTCCTCTGTGATGGGGATCTTTGCCATCGATCCCGA
TTCTGGGGACATCCTGGTCAATACCGTGCTGGACCGCG (SEQ ID NO: 175)

CGI: 21 range = chr4: 41678680-41678940
CGTCACCCAGTTACTCCCGTTTAGCCAACGAGCTGCGTGTGAGCTGCATGGAGCGGAAAAAGGTCCAAATTCGGAG
CTTGGATCCCTCCTCTTTGGCGAGCGACCGATTTAACTTCATTCTGGCGAGTACCAACAGCGACCAGCTCTTCGT
AGTGAACCAGGTCGAAGTCGAAGGCTCCAAGTACGGCATCATCAGCCTGCGAACTCTGAAGATCCCTTCGTTCCA
CGTGTACGTGCTCAGAAACCTCTACGTCCCCAACCG (SEQ ID NO: 176)

CGI: 217 range = chr4: 85636684-85639823
CGCAACTTCCCGCAGTTACTGCCGCTCAGCCGCACTAAGGAGGTCCGGAGACTTGGAAGAAACTTCGGAGACTCG
CTGAAAGGCGAAGAACTGAGCGAGAAAAGGACCCCAGGCTGGGCCCTGAAGTCCACCTGGAAGGCTGGGAGCCTC
CGCGGCGCTGCGGCCTACTACCCCGAAGCTAGCGTGATCTTGGGGCAACTCAGTTTGCCTCAAGCAAGGTCTTT
GCGGGATGGTACATTTTCCCCAGGCCGTGTCCCTTCATCTCACTCTTCTCCTGGCTCGCTCTTGTGTTAGGGTGT
TGAGCTCCACGATGTCCCCAAATGTGCCCGGACGCAGCGTGTGCCAGCCCCCAGAGTGGAGGCAGGTGGGAAAGC
GCGGGCCCAGCGCTGGTGAGCGGCTGGAAGCGCTCGCCCTGCCCTGGGGACGCTGGACTGTCTTCAATGGGCTCA
CCCAGGCCGAGTGTACTCGGGCGGCGAGGGCGAAGAGGTGAGGTGGGACACCCCAGGCGGAGACGTGCATGCAA
ATACACTCACTTCCCGGGCGGTGGAGGGCTCACCGCTGCCGGGCCTCACTGCTTCGAAGAGAGGCAGCGGGTTAG
GCTGGCGAAGGCGGAATGGGGCGCTGGACGACAGGGAGGAGGCCGGGAAGGACTGCAGTGGCCTCTCCTCCC
CTCTCCTCCCCATCTTTCTAATCCAGGCCAGGCCTGCGGTCCTGGCCAGGCCGTTTCAGGAACAGCCAGGGCCTC
GGACGAGACACACGTCCCTCACCGCGTTGTGGTCCACACGAACACACACACACCGGCTCAGCCCAGGCGTACTCA
AGACTTAGAGAGAGGGAGGCGCTTGGATACAGCCACGCGAGCTCAGAAAAGCGAGAATCCCTTTCTGGAAGCCCT
GGCCCAACCTAACTGGTGTGATTCCGGCGCTGTCAAACTACTGGGGCGGGCCACAGGATGGACTGAGCGGCATGC
ACACCAGGGGCCGCGACCCGGGAGTGGGCAGAACAGGCACGGCAGGCAGGCATCGGGGCGCGGGTGGTAGTACTC
ACGAGGGGTACAGGCCAGGCGTGCGTCCCTCCAGGGCGGGCTCTGCATCACTCCGGGCCAGAAGATGGGCGTCCG
GCCAGGCAGCTCAGCCAGCGGCTTGGGGTACCGGCCCACGGCGGCCACGGCGCGGCGCTGGGGCTGAAGTAGAG
CCCGGGCGGCGGCGGCGGCGGGCTCAGGCTGCTAAAGCGTGGCAGTCCGGCCAGCAGCCCCGCCGGGGATGAGGC
GGCGGCTGCGGCCGGCAGCAGCCGCGGCGGCGGCAGAGGCGGAGGAGGCAGAGGCGGCAGGAAGAGGAGGA
GGAGGAACCGGAGGGCGAGGCGGAGGGCAGGGCGGCCCCGAGGCCACGGGCATGGAGGGCCGGCTCAGGATATC
GTTGATGCCGTGTGGGGTGGCGGCCGAGAGCTGCTGCGGGGGGCTGCCGAGGGATGAGAGCCCCCCGTGGCCGG
GGGCTTCAGGCCGCCTGGGTTGTGGGTGCCCAGAGGCGGGGAGGGCGACGAGGAGGACGACGACGAGGACGAGGA
GGAGGGGGGCGGCAGGCAGCGGGGGATACGCGGCAGGGTACAGCGGGGTCTTCATCTCGGCCATGCTGTGCAG
GGCGGCCAGGGGAGGGCTGCTGAGCAGGAATGCGCTCTGCCGGGTGCCCTCCATTGCCCCCACCGCTAACATCCC
ACGGCCACGCCGGAGACCGTAGCCTTGCAGCGAGGGCGCTGGCTGGTGCCCCCCGCGGGGCTCAGAGGAGCCGGA
AGCGCCGAGGGCGCGAGCGGAGAGGCACTCGGCGCGCCCGGAGGCGAGCTGCCAACTGAACCAAAAATGCCGCTG
CCGGGAGTTGCTCGCCTAGCTGCGCAGCAGAGATGTCCAAACCCTCCACGCGGGGAGGCGGCAGCTCGCCGAGAAA
AGCAGGCGTCCCGGCGGGCTAGGCAGTCCTTTCGTTCCGCGAGTCCTAGATTCGATCCCTGGCTATTCTCTCTTC
CTCACTTTTCCTAGCTGTTCAAAGTGCGCTACTTCTCATCTTCTGCCCCCGGGAAATAAGCAAACAAAACCCAG
GCTGGCTCCGGAGAGTTTGTAGCAAAGTTAGTTGCCGAATCTCCACTTTGAAGTTGGAGGGTGGGGGTGGCTTGC
TTTCTTTGGGGAGGTTCAAAGGACGCCTTGTGCAGCCCGTGGCGCTCCTCTGATCTTACTGGGATGCTCTGCTCT
TTCGGTCGCGCGGCTGATTCGCATTCGACGCTCACTGTGCCCGGGAGAAAGCGCATCCAGCCCGCGGGAGATCT
AGCCTCTGTGCGGGCTTCCTCCGCCCACGCTGCCCCGGGCTGCTGCGCCAGAAAGGGCAGTGCCACGGATCCCCG
CGGCTCCCAGGTCCTCACCTCCACCCGCCTTGCCCTCTGGCCCACGGGGCACTGGAGTTGCAATATTGAAAAGAA
AAAGGGGGAGGAAAAACACAGAAAAACAAAAGACTAAGTGTGAAAAGTCTGACGGCTGGGTTTCGGCGCCGCTCG
TCAGTCCACTTCTGCAAACGGGCCCGGCGACCCCCGCCCCACCCCCGCTCCCTCTCTCCCTCTCACTCTCAGCCT TABLE 7B-continued Sequences of differentially labeled CGIs between bladder cancer subgroups relative to blood TTGACTCTCCTCTCTGGCATTTTCTTCGCGGCTTCCCAGGCTTCGGTCTTCTAAGTCCTGTCCTCTGGCCAAACT
GACCCTCTCCGCGGCTCCTCCGCTCTTTCTCTCCTTTCCTCTCTCCCTCCGGGCCTGACAGTTCAGATGAAGCTC
TCAAAGGTAATAAAACATTTGCATCACTCCCTACCCCTCTTTAGCTGGGGGACGAAAGGGAGGGGGAAGTGGGGG
ACCAAAATGAGAACTTTGAGGGACGTCACTCCGAGGCTGCGGGGGCCGGCGAGCCGGGCGCAGGCCGGGGGCGTA
ACCACCGTGTCCAATAGCTCGCCGCCTCGATCCTTGCGTCGCCCCTGGGGCTCGCCCACTCGGGGGCGCCGCACC
CTCTGATTGGCTGAGGCGGGCCAGGCGTAGGGCCGCGCCCGCCTAGTCCCCTCCCGCTCCCTACTTCTTTCTCCT
GTGGGCGGGGCCAGGAGGGGCGGGAGCTGGTGAGTGGTGCGGTTCCGCGCTGGGGCCAGTGGCCG
(SEQ ID NO: 177)

CGI: 39 range = chr4: 94974810-94975333
CGCGGTGCGGAGCGTCTGGAGCGGAGCACGCGCTGTCAGCTGGTGAGCGCACTCTCCTTTCAGGCAGCTCCCCGG
GGGAGCTGTGCGGCCACATTTAACACCATCATCACCCCTCCCCGGCCTCCTCAACCTCGGCCTCCTCCTCGTCGAC
AGCCTTCCTTGGCCCCCCACCAGCAGAGCTCACAGTAGCGAGCGTCTCTCGCCGTCTCCCGCACTCGGCCGGGGC
CCCTCTCCTCCCCCAGCTGCGCAGCGGGAGCCGCCACTGCCCACTGCACCTCCCAGCAACCAGCCCAGCACGCAA
AGAAGCTGCGCAAAGTTAAAGCCAAGCAATGCCAAGGGGAGGGGAAGCTGGAGGCGGCAGAGGCGGCGGCGGGAG
AGCTGTGGGGTTGTTCAGGAAAAGTTGGGCTGGGGGCTGAGGCACCTGAAGCAGTGAACCAGGACTAGGTAGGAA
GCAAGAGCATCCTCCTGCGCAAGCGGAGACGCAAACGCGCTCCTGAACCCATGCAACCGCCCGGCCCAGCGCCG
(SEQ ID NO: 178)

CGI: 162 range = chr4: 134291113-134293078
CGGAGCCAGACCTGACGGTGGAAATCTCTGAGAGCGCCACGCCAGGCACTCGCTTCCCCTTGGAGAGCGCATTCG
ACCCAGACGTGGGCACCAACTCCTTGCGCGACTACGAGATCACCCCCAACAGCTACTTCTCCCTGGACGTGCAGA
CCCAGGGGGATGGCAACCGATTCGCTGAGCTGGTGCTGGAGAAGCCACTGGACCGAGAGCAGCAAGCGGTGCACC
GCTACGTGCTGACCGCGGTGGACGGAGGAGGTGGGGGAGGAGTAGGAGAAGGAGGGGGAGGTGGCGGGGGAGCAG
GCCTGCCCCCCCAGCAGCAGCGCACCGGCACGGCCCTACTCACCATCCGAGTGCTGGACTCCAATGACAATGTGC
CCGCTTTCGACCAACCCGTCTACACTGTGTCCCTACCAGAGACTCTCCCCCAGGCACTCTCGTGATCCAGCTCA
ACGCCACCGACCCGGACGAGGGCCAGAACGGTGAGGTCGTGTACTCCTTCAGCAGCCACATTTCGCCCCGGGCGC
GGGAGCTTTTCGGACTCTCGCCGCGCACTGGCAGACTGGAGGTAAGCGGCGAGTTGGACTATGAAGAGAGCCCAG
TGTACCAAGTGTACGTGCAAGCCAAGGACCTGGGCCCCAACGCCGTGCCTGCGCACTGCAAGGTGCTAGTGCGAG
TACTGGATGCTAATGACAACGCGCCAGAGATCAGCTTCAGCACCGTGAAGGAAGCGGTGAGTGAGGGCGCGGCGC
CCGGCACTGTGGTGGCCCTTTTCAGCGTGACTGACCGCGACTCAGAGGAGAATGGGCAGGTGCAGTGCGAGCTAC
TGGGAGACGTGCCTTTCCGCCTCAAGTCTTCCTTTAAGAATTACTACACCATCGTTACCGAAGCCCCCCTGGACC
GAGAGGCGGGGGACTCCTACACCCTGACTGTAGTGGCTCGGGACCGGGGCGAGCCTGCGCTCTCCACCAGTAAGT
CGATCCAGGTACAAGTGTCGGATGTGAACGACAACGCGCCGCGTTTCAGCCAGCCGGTCTACGACGTGTATGTGA
CTGAAAACAACGTGCCTGGCGCCTACATCTACGCGGTGAGCGCCACCGACCGGGATGAGGGCGCCAACGCCCAGC
TTGCCTACTCTATCCTCGAGTGCCAGATCCAGGGCATGAGCGTCTTCACCTACGTTTCTATCAACTCTGAGAACG
GCTACTTGTACGCCCTGCGCTCCTTCGACTATGAGCAGCTGAAGGACTTCAGTTTTTCAGGTGGAAGCCCGGGACG
CTGGCAGCCCCCAGGCGCTGGCTGGTAACGCCACTGTCAACATCCTCATAGTGGATCAAAATGACAACGCCCCTG
CCATCGTGGCGCCTCTACCAGGGCGCAACGGGACTCCAGCGCGTGAGGTGCTGCCCCGCTCGGCGGAGCCGGGTT
ACCTGCTCACCCGCGTGGCCGCCGTGGACGCGGACGACGGCGAGAACGCCCGGCTCACTTACAGCATCGTGCGTG
GCAACGAAATGAACCTCTTTCGCATGGACTGGCGCACCGGGGAGCTGCGCACAGCACGCCGAGTCCCGGCCAAGC
GCGACCCCCAGCGGCCTTATGAGCTGGTGATCGAGGTGCGCGACCATGGGCAGCCGCCCCTTTCCTCCACCGCCA
CCCTGGTGGTTCAGCTGGTGGATGGCGCCGTGGAGCCCCAGGGCGGGGCGGGAGCGGAGGCGGAGGGTCAGGAG
AGCACCAGCGCCCCAGTCGCTCTGGCGGCGGGGAAACCTCGCTAGACCTCACCCTCATCCTCATCATCGCGTTGG
GCTCGGTGTCCTTCATCTTCCTGCTGGCCATGATCGTGCTGGCCGTGCGTTGCCAAAAAGAGAAGAAGCTCAACA
TCTATACTTGTCTGGCCAGCGATTGCTGCCTCTGCTGCTGCTGCTGCGGTGGCGGAGGTTCGACCTGCTGTGGCC
GCCAAGCCCGGGCGCG (SEQ ID NO: 179)

CGI: 308 range = chr4: 149582663-149586506
CGGATTACGCAGCCACTTCTCCCTGCAAAGTGCACGCTCCCGCGCCGCGGCCGCACGCCGAGCACGGCAAGCGGT
GCCCCGCCGCGCGCCCCTACACACCTGCCTCGGCCGGGGTCCGTCTCTCGCCGTCTACCTGTTGCAGCGCTTGCC
ACCGCCACGAAACCCCTGCTGCGGAGCCCCCCTAAATCCAACCACATCCAGGCCAGCGAGTGCCGCTCTCCCTGC
AGCGGGAGAGCCCGAGGCAGCAACGCTCTTGCACCCAGGTGACTGACTGCACGGGCTTCCTCTGAGCAGCCTGAA
GTTGGCTCCCGTCTCCCGGCCCAATGACACCCCGGGCGCGGAGGGGCTGAGAGGAGGGGCAGGGGCAGGGGCA
GGGCCAGGGCGGGCAAAAAGGGAGGGAGAGAGGGCGGGCGAAAGCCCGGAGGGGGAGGTGGGCCAGCTGGAGGGC
TGGCCCTTTTAAAAGCGGGTCACATGTCCAGATAAAGTTCAGGTTGCTATCCCGCCCCCCTGAACCCTTCCTATT
GGCCCGAAGAGAAGCAAGGCTCCACGCCGCACGGGTCAGGCGGGCTTCTTATTGGACAATCCAGGCTGTCAGTCA
CCAGGCGGGCGACATGACTGATACAAAGTTGCTGCGACACACGCCTGGACTCGGCAGCTTCCTTAAAGCCGCAGCC
GCGGCGGGAGCTTGGGGTGCCGGGCGGTGGCTACATCAGGCGGCCTCCGCACGCTGCCCCCACCCCCATCGCTCG
GCCGCCCCAAACTTGCTTACGTCCACCCTGCTCTCCTTCTGACCGACCCCAGGATATCTGGAGAGATGTGAAAAG
TGTGCTGACGCGGAAGAAGTCGGTTTTTCCGCGAGCAAAGTGTCGTCCCCTCACGCTCTCCACCTGCAGCTCCAG
GTGAGCTGCAGCCCAGACCCTGGCGCCGCCCAACAGCGTCCGCGCGGGGAGGACTCTGGGTGGGCTTCACCCG
ACCCTCGAGGTTCCTCTCCCAGCCCCTTTCCACTGTCTCCAGAGTTACCTCTCAGCAGAGCAGCAGCAGCCTTCG
CTGCCAGCGAGCAAGACGATCACGTTCACTCGATTTGAATTTAGTTGTTTTAACCGTGCTGGAAAAACCCTTTAA
ACACAGCTTTCCTCCCATCCCTTAGACCCCTAACACCAAAAAAAAAAAAAAAAAAAAAAAAAAAAAAGAGAGA
GAGAGAAAGATAAATGAAAGAAGTGGCAGGGTCAAGAGCTGCTCCTCTACTTCCTTATAATTTTGTCACTGTACT
TACTACTTTAGTATTGGATTTTTCCACTAGTTCAATTTGAAAGCAAGCTTACCATCGAGGATATTCACGTTATAA
TGGGTGGAGGGGGTGGGTCACATAAGTGGGAGAAACAGACAGGAGGGGGAGGGAAGGAACCAAACTGTTTTCTAAGGA
TCGGTTGTCTGCATGAAGAAATTTCGGTTTCCCTCCAACCGCCCCCTCCTCGATTCTCCTCCCGCCCACCCAAAT
GCTGCAGTTACTAAGCAAAGGATGGGGTTCCTAACTTTGATTTCTAAGGACTTTTAGGCTTCTCATGTAAGGCC
CCGTTTTAGGCTCCCCGCTGGCCCGGAGTCAGCATCAGTGACGTATACACCTAAATCTGGTCCCCCGGCCCTCGG
CGACCCGCAGCCCGGCGGCGGCAGCTGTGCGGCCTCCGCCTCACCCTCGCTTCGCGCCGCCAAAGCCCGAGGC
GGGGGACCGGGGGACACCCTGTGCCCAAAGGCCCCTCCTCTCCTTAACAGTTAGTTAAGCTCCGGGATTCCGGAC
CCCTAACCCAGGGCTGAGACTTGAACTCTCAGCCGCTCCAGTCAGGAACTCCCTGGAGATAGGGGCGACAGCGGC
AGCGCCGCGAGCTGGTCCTGACCCCAGACTCTAATGCCCCTCGGTCCCCAGCTTGGAGCTGCCCCGGCGTCCCC
GCAGCCAGGAGTCCCGCCGAGCGTCCCAACTTTCCCGCGGGGCCCACCGTCACGCGCACTCTCCCGGCCCAGCG
AACTGGGCATCGATCTCACGTCGGCAGAGCGCGGGCGGCGGGCGGGAGCAAGGGGAGTCCCGGACCTAGAGCCTG TABLE 7B-continued Sequences of differentially labeled CGIs between bladder cancer subgroups relative to blood GGCACGCGAGGCGGCGGCGGCTCCGCAAGCGTTGCCGAATTATTCATTATTAAAGGAATGGACGTGTCTCTTTTA
CTAAGTTTTTATCTCCTTTGAGGAGGGCCGGTCTTGCCCTGGATCTCAGCTTCTTGCAAAATCTAGGTTAGAACC
GTGCAGGGGCAGCCGCCGCGATCACTCGCCCGCCACCCAGCACCCTTGCCCCAGGGCCGCCAGCGGGCAACTCGT
CTCCTGCCCGCATCCCACCTCCGCTCGCCAACCCGCGCCCTCTGCCCTGGGCGCGCAACCTGCCTTGCCCGGGGC
CGCCCCTGCGCTCTCCGGACCCCCTCTCGCCGCTGTCAGCGCAAAGTGACTGTCGCTGCACTCACCTTTTCTAGG
ACATGGTGGGGAGGCTGGGGCGGGGAAGGGGAACGGCTAGACTCCCGCCGCCGCTGCTGCCGCCGCCACCAGCA
AGTCCAATATTGGCTGATCGGCGGTGAGGATGGAGAGGATGATAATCCCGGCAGTGGCAGTCGCCCTGCTGACGG
TGGGTAGAGCAATAGTGCTGTTACCCTACAAGAGGCGGCGAGGCAGCGGCGCCAAATCGCGCAGAGGGGGACGCG
GGCACCCGCCCGCCCCCAGCGGCGGCGGCCGGGCCTCTGGCGGGCCCCTCTCCCGGGGCTGCGCGTCCGCTCGGC
GTTGACAGCGGCGTCCCTGGGAGCCGGGAAGTCCGGCAGGAGGATCCCGCGCCCGCCGCTCCGCAGCGCCACTCT
CCCGCGCCCCTCCCCGGGCCCTGGGTGGCCGGTGACAGCTCCGGCGGCCGAGCGCGTGTGTGAGGGGGCGGTCGC
AGGGGGAGCCTGCGCCCCCCTCCCCGGGTCACGCCCTCACGAGCGGGAGGAGGCGGCACCGCGTCCGGCCACCCG
CGGGTGGGAAACGGGCAGGGGCGCCGGCAGCCGCCCTCCCACTACGGCCACTGACAACCTGGAGGCCAAAGGAAA
ACTGAGCCCAAATGCACGCACCCCCTTCAGCCCTGCCCGCAGCCCTCCAAAGTCCGGCCCTGACCTCGCGCCCGG
CTTCAGGTGCAGTTCCCACCTGCGGGGGGAGGCGAGGGCTGGGGACCTCGCGCGGGGGGCGGGAGGGAAAAGTTT
TCTTTTCCTGCTCCTCGGCTGCCCACCCCGCCAGGCTGCTCCTCTCCCCGCCCCTCTCGGGCTCGCCGCGCCTCT
GCCCCACCCCCGCCGTGGGGGGCGCCGAGGAGGGAGCGGGCGTCTGTGCGCGGAGGCGTGCGGGGAGCTGGCTG
GGGCGCTGCGGTCGCGACCGGTCCCCTCGCTCTGACGGCGGCTCAGACGCCCGCGGAGGCGGCTCGGCGGGGCAA
GCCGAGGAAGGGGCCGAGAGCCGGGACCCCTCCTCCTCCGCTCGCGGCGCGCGCGCCCCCGCGTCTCCTGGC
GCGCCCCGCGCCCTCGTGCCCGCTCGGGCAGACACCTACGCAGACGCGAAAGTGAAAGGGGGGCGACTGGGCCC
GGCAGGCGGGCGGCCGGCGGCGCGGGCACGCGGCAGGGGACAGAGGATGGATGGGTGAACCCGGATCCCGGGA
TTCTCCCGCGCCCGCTGCCCCTCTGCGGAGCCTCCCCGGAGTCCCACGCCCCCACCCCGGCCACGGAGATCACCA
CGTCAGGAGATATGTATGCGTGTGCATGTGTGTGCGCGCGTGTTCACGCGCGTGTGCGAGGTACGCTTCTGCCCC
AGACTCTTCCCCCGCACCG (SEQ ID NO: 180)

CGI: 44 range = chr4: 154436043-154436665
CGAGAAGCTGAACGAGCTGGCCGACCAGGACTTCCCCTTGCACCCGCGGGAGAACGACCAGCTGGATTTCATCGT
GGAAACCGAGGGGCTGAAGAAGTCCATCCACAACCTCGGGACGATCTTAACCACCAACGCCGTTGCCTCAGAGAC
AGTGGCCACGGGCGAGGGGCTGCGGCAGACCATCATCGGGCAGCCCATGTCCGTCACCATCACCACCAAGGACAA
AGACGGTGAGCTGTGCAAAACCGGCAACGCCTACCTCACCGCCGAACTGAGCACCCCCGACGGGAGCGTGGCAGA
CGGGGAGATCCTGGACAACAAGAACGGCACCTATGAGTTTTTGTACACTGTCCAGAAGGAAGGGGACTTTACCCT
GTCTCTGAGACTCTATGACCAGACACATCCGAGGCAGCCCGTTTAAGCTGAAAGTGATCCGATCCGCTGATGTGTC
TCCCACCACAGAAGGCGTGAAGAGGCGCGTTAAGTCCCCGGGGAGCGGCCACGTCAAGCAGAAAGCTGTGAAAAG
ACCCGCAAGCATGTACAGCACTGGAAAACGAAAAGAGAATCCCATCGAAGACGATTTGATCTTTCGAGTGGGTAA
GGAGAGGGCTTCTGTGCCCGACG (SEQ ID NO: 181)

CGI: 122 range = chr4: 174686622-174688044
CGGCGGGTACGTTGGGGATGCACTCGCGCAGTTCGGCGAAGGCGCTGTTGATGCTCTGAGTCCTGCGCCGCTCCT
TGCGGTTGGCGGTGCCTCGGCGCTTCACCGGGCGCGGCCCCCCCAGGCCCGGGGCCCGGCGCCCGGCGCACCC
CCCCGTAATGGGAGTGGTCCAGGCCGGCGGCGCCGCTGGCATACTCGGGGCTGTAGGACAGGGCCATGCTGTAGT
CGGGGGGCGACATCTCGGGGTGGCCGATGAGCCAGCCATGGAAGTAGGGGTTCTCCTCATGGCTGCAGCGGCTGG
CGGCGGCGGCGGCAGCTGCGGCGGCGGCGGCGGCAAACGGGTAGCCCTCGTGGTGCACCACCGGGTGGTGGGGAA
AACCACCTACCAGACTCATTTCGCCCTCCGCGCCCCTCCACGCGCCCCAGCGTGCGCGCAGCCCCGCCGCGCCCTT
CGGCCCGGGCCCCTGCCTCAGCGCTCGGCGTCCTCCCCCACCCCCACCCCCAGCCCCCGGGCGCCCGGGCCCG
CCCGGCAGCCGCAGAGGGGCTGCTGCAGCCCGGGCCCCGTCCCCCGCCTGGCCAGCCGGGCCCGCCTCAGCAG
CGCTGCGGCCGCCGGCTCCCCATGGGGCGCGGCGAGCTGGTCCTGGCACCGTGCGCCCCTGGCCGCCGCCGCCGC
CGCCTCCGGTTCCCGCCTTGCTCCACGGCCCGCGCTTCGGCTCCTGCTTTCCCGGGCTGCTGCGCGGAGGCAGAAT
CCTCTCGTGCTCATACAAAGGTGCCGGGGCTCCCGCGAGGCTGGTACGCGGAGTCTCGGGAATCCAAGCCCGGGC
CGCGGTCCTGGCACCGAAGCTAACCCGGAATCCAGGGGCGAGTCTGAGCCGCGGCTGGAGGAGCCGGTCCAGCTG
TGCCGGGGGCGGCGGGGTCGACTGCTCACTGCAAAGCTACCTCCGTGCGACCCTCCCCTTCCCGCCTCTTCCCC
TCCCCCCACCAGCCCGATCTGGGTTCTTGGGCGCTTATTGTTTTAATGAAATTTTTGGTTGTTGTTTTGGTC
CTTAAATGTGATTTTAGCTGCGAGTAACGTGTCCTCGCTCCTCTCGCGCTCTCTCGGAGGGTTTTCAGAGAGGTC
TCAGTGCATCCATTTTCTCAGATCCTCTCCTTTCGGGGCAAGGATCTGGGGCCCTGAATGAGCCTTGGAGCTCGA
AGACCGCGGCTCGGGCTCTCGGAGGGCTCTGCGCGGTGGCCGAGGAAGCTCCGGGGTGACGGCGGTGGTTCTCCT
GGGCTGGACGACGTGAGGGGAGCAAGCGGATTTTCCCAGCAAGATCTCCATGTACAGCTACATCTTTAGGGCCGC
TCGGGTTAATATATGTCGTCAGAGGCTCCTCACGCCAATCCCGGGGCGGCAGGGGCGGCGCCTCGAGCTCTCG
(SEQ ID NO: 182)

CGI: 245 range = chr4: 184255825-184258373
CGAGATTGGCCGCAGATGCCCCGACGGGATGGCCTGGGGAGCCGAAAGCTGTCCCCAGCCCCGGACAGCTACTGC
CCACGCCGCGCAGGCCAGCCTCACACAGTAGCGAATCTCCTTCACGCGACTTCCTCGCAGGCCTGTGAACCCGCA
GGGGAGGCGGAGGTCGGTTCAAACCCTGCGAGAGCCCCTGCCCAGCGCGGAGTCCTGCACACGGTGGAAAGTCCT
TACGCATTAGCGGGCAGGATTAAACGACTTCACACCACGAGGTGCAAGACTGGGCTTCGGGGCCTTCCTCGGTGT
TGCTATTTTAAAAGAAGCTGCTCAGTAACCCAGAAGAAGATGACGGGGGACCGGTGGTGTAGACCCGGCTGGAGAG
GAGTCCAGGGCCTGGGAGGCGCCCCCTCTGACTGAGGGGCTGGGGACCCTGAAGCTTGGCGTCCAGGCCCCGCCA
GCGCTGCACCCGGCATTGTCCCGCTGGGGCAGGCGTCCGGTCCCTCGGCAGTGCGGGCCAGCACGTACGTAGTA
GCTGCTGAATAAATAAATGCCTATGCAACAGGGAACGTCCCGGCCCACCCCGGCCGGGCCAGGGCCTAGGAAGGG
CGGGCGTCCGGCGCCGCCGTGGGTCCCTCCGGCGTGGCCGCCCACACCTCCTGGCCACGGCGGGGCTGCGGTGGG
GGGACATCCTGGGGCGGGCGGCTGGACGGAAGGGACTAGAGTCGGGGCGCGTCCACGGCCAACCGCCCCGAACCA
AGCAGGGGAGGCCAGGGACCAGGAGCTTCCGGGGCCCCGCGGCTGGAGCGCCCGGACGCGAAGGGGCGGCGGGTG
ACGGGGCGCGGTGCGGGCGGCTACAGGGCCGGACGGGAGTTCCTCCGCTTTCCGCCGCGCGGCTCGCGGTCTCAG
CCGAGGTCATCGAGGGCCAGGAGCCCTGGCGAGGCCCCGCGTCCCGGACCCACCCAGCACGCACTCCCAGGGCTTG
GCGCTTTCCCACCACCCCGGACCGCCCTTGGGGTGCCGGAGGGGCTCGGGGCGGCGGCGTGGGGAGCCTTTGTGCC
CTCTCCGCTTGTTGAGGTTTTTTCTCGGAGGAGAGCTCCCCGCCCGCCACCCCTTTCCTCTCGAAAGTTTTGTG
GTTTCCCTAGAAGACGAAAGAGGTTGAGAAGGTTGCGGAGACTTTTGCAATCTTCCCCGTCCAGAAACTCTAAAA
CCTCTCGGCGTTTGGCCCAGGGGAGCTATCTGGGGTCAAGGGGAGGGAGCTGGCCGCACATTCCTTCGCCCGCCT
TCCTCCCACCTGGAGCCGCGGCCCCGCGGGGCAGTGCGTCCGAGCTGGTGCGGCGACGCCGGCAGCGGCGGGGTT TABLE 7B-continued Sequences of differentially labeled CGIs between bladder cancer subgroups relative to blood AAGCTCAGGAATGCGGCGCGAGGAATGCGCATGCAGATGAGGCGGGCGGGCGCATGCTAATCGCATGCAAATGAG
GGGCCCGCCGCTGCCGCGGCAGCGCCGCAGCTTCCCGGATCCGAGCCCAGACGGCGGCGGCTCCGGCAGCCTGGG
CGCCGCGACCCTCGGCGGCCAGAGGGGGACGGGGCGGAGGAGGAGGAAGAGGCGGAGGCAGCGGCGGCGAGGGGG
AGGAGGGTTCGCTCGCCGGCTCCGACGCAGACATGGTGGACTGATCCGCAGCGGGGCCGCGAACAGCGTTTCCTG
AGGCACCTCCCGCGCGTGGTTCCGCCGCGCCCCGCGCCCTGCGCCCCTCAGCCCCTCGCCGGCGCCCGCGTCGCG
GGTTGGCAGCCTAGCCCGGCAGCCGCGTTCCCGCCGCGTCCCGCGCCCGGTACCTATGGAGGCGCCGCTCGCCGG
CGAGGCCGCCGACCATGCCTAGGAGGGCCGGGAGCGGTCAGCTGCCGCTGCCCCGGGGCTGGGAGGAGGCCAGGG
ACTACGACGGCAAGGTCTTCTACATTGACCACAACACCAGGAGGACCAGCTGGATCGACCCCCGGGACAGGTGGG
CGCCGGCCGCGGGGGCGCGGGCCCGTTCGGACACGGCGGCTGTTGTCCCGGAGACCCGGCCGCGCGGGGGGCTGG
GGCGGCGCCGGCCCGCGGTGCCCCGAGGGGTCCCGGGAGGGATGTGGGGCTGGCTGCTCCGGCGGGGCCGAGGAG
CCGCCCGTACCCGGGCTCCTCCGCCCACCGGCTTCCCGACGCCCCTCCGGGGACCCGGCCCCGAGGCAAGGCTGG
AGTCGCTGCCCCGGGCCGACGCCGCGCGCCAGGCTAACGGACCCGAGGGGCCACCTGAGCCCTGTTAGGAACTTC
CCTAGGCTTCGAGGTGCCCACGTGGAGGCTGCAGGACACCTTCGGCCTCTGGGCGGCGGGGGTGGGCTAGGGCCT
CACTGCCAGTTGGGGAACGAGCCCTCCGGGCCACCTGTGGCATCCCTCCAGGCCGTCCTTGGCGCGGGAGCCTGGG
CTGCGAGCTCTTTGGCGGGGGCGCCCAGACTGGCCGGAGGTCCCGAGCTGGGAAGGGGCTCCCGCCCCCCGCCGGG
CCCTGCTAGTGGGTGTGACTGACTTTGCCCCTCAGAGTTTAAAAACGCGCGTTTGGGGGTTTCGCTGTCTGTCG
(SEQ ID NO: 183)

CGI: 33 range = chr5: 360287-360592
CGTGCGCCTCAGAAGGGGCGTTAGGCAGAACGCGTGCCCATTCTCAGGTGTGCTCGGCGTGTGTGTGCTCGGCGT
GTGTGTGCTCGGCGTGTGTGTGCACACGTGTGCCGTGCGCCTCAGAAGGGGCGTTAGGCAGAACGCGTGCCCATT
CTCAGGTGTGCTCGGCGTGTGTGTGCTCGGCGTGTGTGTGCACACGTGTGCCGTGCGCCTCAGAAGGGGCGTTAG
GCAGAACGCGTGCCCATTCTCAGGTGCGCTCAGCGTGTGTGTGCTTGACGCGTGTGCACACACACATGTGACGGT
GTGCCG (SEQ ID NO: 184)

CGI: 18 range = chr5: 1161803-1162051
CGACCGGCGTGCACCGTCTCGCCATTCCCAAGGGCAGTGCAGAGCATGGCACCCAGCACCCGACAGGCGAGGACG
GCCCAGGACAAAGCGGCAGCTCTAGCTGTCCTCAGATTTTGGGAGGGGGCTCCCAACACGGACACGGTAGGTAGT
TGGAGCAGGAGGGACGGGCAGGCCACTGACCACGCAACCGGGCCTCTGTCAGCGGCCAGGGGCAGAGGGAGGCAG
GACCGCCCCTGGACAACCGACACG (SEQ ID NO: 185)

CGI: 584 range = chr5: 3647468-3656054
CGAGGCTCCGTGAAGAGAGGGAAGCGAGGCAGGGGGTGAAGGGACCGCCTGGCCGGTGTCCAGGATACGGGTGGC
TCAAACCACCAGCAGAACAGCATGCCGACTCTGGCCCGATGGCCGCCTTCATCCCGTAGCCCCAACCCGGCCTAA
AGCCGAGAAGACGCCAGAGTGCGCTGCTGAAATTCCCGCGGAGTCCGGTGTGCTGGAGAGCCGCAGCGGGGTGAA
CTCCCGGCCCCGTCTCTGCGTAGGAGGTGGTTCGCAAAGTGGCCCCGGGAGCCGGGACTGGTACCCGGTTCCCCA
CGGCACCGTCCGGAGCTCTCCAGCCACGAGGCGCAGAAGTGGCCTGCCAGCGCCTTCCCAGGCTCAGGGAGGCGA
GGAGGCCCGTGCACTTGGCATCTTCTCCCGGGAGCCGACACGGCCAGGGCCGCGGCGAAACGGAGCCCATCTCAAG
TGCGCCGCGCCTGGCCGCGTCCTGTAGCCCGACGAGGCTGAGGATGGAGGAGGGGAGACGCAGGGAGAAGAGGAC
GCGGGACTTGGACCCAAGAGGCCGCTCCGTTGCCGGTCTGGCGGCGGCGCCGACTCGGGTTCGCGCGTTCCACAC
AAGTTTCCTGTCTGCCTCTGCACACCTGGTGGACAAACCGGGCGTCCAGGCCACACCGTCTTCCCCCTTCGCGGG
GGCGCGGGGATGTTTCCCTCCGGCTGCCAGGGGGCTTTCTGGGTGAAGAGAAAGCCCCTCCCCCCGCGTCTCCCC
CCACCCCTCCCTCCGAGAACCCGCGGCGCCGACTGCGCCTGCTTCCCCCGAGCTGGCGACTTCTTCCGCGGGATTT
GCCCTCGCTCAAAGTTTGCACAATTGAAAGAGCCCGCAGAGCTCGGCCGCCGCTCCCCGCTTCCCCAAGGGCGGCGAG
GCCGGTCATTGGCAGACGATCGGTTACTACCCAGTAGGGGCCCACGGGAACCCGCATCTGGAGTCGGGGTGTCA
CGCCACGCCGGTTCAGTGGCTCGCGGAGAGCGTCCGGGTGCACTTCTGCCAAAGATGTCCCCTGGAGGCCCCGGC
CGCGCGGGACTCGGGGGAGAGGCCGCTCCCCCCTCGCTGTCACCAGCGTCCAGGCCGCCGGCCCCTTCCCCGCTG
CCCAAACAGTAGAAAAGCAGGCGCCAAGTTGTTTTTGTTAAAAAGGGGACACACCTCGGCCGCGAAACTGCAAAC
CCGGTGTCAGACAGCTGTAAACCCGTGTCGACAGGTTGTCAGACAGCTGCGGGGCTGGTCGGGAAGGAGCCCAC
GGCCTCCGGGCCCACACCCCGCCGCCCCGACGCGCGCGCCCACCGCGAGAGTAGCTGGCCGGGCCGGCACGGGGC
ACCACGTGCTCGCGGGAGGGGCGGGAGCGGCCGGCGAGGGCGGGCAGGAGGGGAGGGGGCGGGAGGGGAGCC
AGGGGCGGGGCCTGCGCTCAAGGGGATGCCAATCAAAGCATCAACTTCAAATTGTGTCTGAAAGCCCCGCCGCCG
AGCGGAGGGCGGCCGCCGCAGTCGGCGCGCGATTGCGGATCCGGGCGCAGCCGGGAGCCGGGCGCCTGCGAGCAC
CGGGCAGAGGAGCCGCGACCGGCCTCCATCTCCCGGCCCGCCCGAGCGCGCCCGGCCGGCCGCCCGCTCCTCCCT
AGACCCCTCGCGGCGCCCCCTGCAACCCCTCCGGCCGGCCTCCGCCTCCCCTCCCCGCGCCTTTAATACTCGCCC
GCTGCGGCGGTCGCCGAGTCCGCGGACATGTCCTTCCCGCAGCTGGGCTACCCGCAGTACCTGAGCGCCGCGGGG
CCGGGCGCCTACGCGGCGAGCGCCCGGGGGTGCTGGCCGCGGCCGCTGCGGCGGCTGCCGCCGCCTCGTCGGGC
CGACCGGGGCCGCGGAGCTGGGCGGCGGGGCAGGCGCGGCTGCAGTCACCTCGGTGCTGGGCATGTACGCGGCG
GCGGGGCCGTACGCGGGGCGCGCCAACTACAGCGCCTTCCTGCCCTACGCCGCGGATCTCAGCCTCTTCTCGCAG
ATGGTGAGTGCGCCCGGCCTCCCCCGCTTCTCCTCTGTCTCACCCGCGCCAGGGCAAGGGTGGCGGGTCGCCCGG
GAGGGAGAGACTACGGGTGGACCTGGTCCGGAAGAGGAACTAGAAAGGTCCGGGGGCAGGTTCCCGGTGGCCGAG
GCCGCGGCCCCCGGGGACGCAAGAGGGCTGGGAGGCCGGGCGGGTGACGGCTGGCCATCTCGGCCTGGGAAAGC
GGAAGGCCCGGGCCAGGGAGCGGGTAGCGAGTGAATTCAGAGAGGCCGCAGAAGCAGGCCCGTGGAGCGGTGCCC
GCGCTGGAGGTCGGGGGCAAACTCGCCTGGCTCGGCCAGGGCGCCCAGGGCCACCAGGGGTTCCTGCAGGTCG
GCCCGGCGTAGCGTAGCAGGACTTCCCTTCCTGGCCGCGGGTTCCACTCGCGCGGCCTCTTTAGTTTTCGAACCG
AGTCTGAAAACTTGGTTTTCTCCCTCTTTAGCAGCTCCGAGATAGTTGTATCCGAGTTTGCCAGACAGACCCCT
TCTAAGCCTGGTAGAGTCAATCAAAATAATCTTAACAATAGAGGTCCAAAGGGATGGAGAGGTCTCTCCACGGCG
TGAGTGCGAATTTGAGATTAAACAAAAATTAAGTTGCAGTAATGTGCTGGTGTCTGAAACGGTGTTTGATTTTAC
TTTTGTAAGTTGCCCAAGTTTTCATTTCATTTGCACAGAAAGAAAAGCACTTTTCTTCCTGCGTTACATAATGGA
GGATTAAAGAAAACAGTGTCCCTTGGCTTAAAACAAATGGTGTCCTCTTAGTCTCCCGTCCCAGTGGGCGTTAGA
TGTCGGGGCAGGCGGCTGCACACTTAATTCTCCGCGGGGCATTGGCCTGTCTGCCGGTCCAAATCATCCATTTT
CCTTGGTCTGACTGCAAGGTCGGTGCTTAAACTTCGGACGGCTGGTGAATTGTGCGGCGGGCGCGGGGCCCTGGG
AGGCAGCCCCCTCCTGGGTCGCTGCCCGCGGGATAAAGCAATTTCCAAGCACCCGCGATATCTCCCCGCTCCCCG
CAGGAGAAGCGGGGAGTAAACGCCCCTCAAGTGTGCACAAGCAAAGAGCGGGTTTCCCTGTAACTTTTCTTGTAG
TTTTGAAAGAAAGCGGCCCGGCTGCCTTTCAGGTCTCTTACTATCGAAAAAGATCAGCCCCCATTTTGTTCAGGC
GGCGGGGAGGCCGGGACGCGATGAGAGATTTACAAGGTGTCCTTTCAAAAAGAATTCCCAGTGGAGACGAGGCTG
AAACGTCTTCTTTACAATTACAACCAAAATAATTAGAAAAGCGCAAAGTACATTTTGGAACGATTGGGCAAAAAC TABLE 7B-continued Sequences of differentially labeled CGIs between bladder cancer subgroups relative to blood

```
GAAATCTAGCCGCAGAAATGTTTTCTCTGCGGCCTCAGTCACCAAACTAATTAGTCCAAGAAATCTTCTGGTCTT
TACAACTTTCTCAGAGTCCGGAACTCCCTTTGCTAACATTGCAACTAGACCATTTTTTCAGAGGATGAATATTTT
TTACAGAAATTGCGAATGCAGTTGTGTGCCATTTGGGAACCCTGCCTGTGTTTGCGGGGGAGGGAGAGAGCTTCA
GTGTGAGGACCTGCACCCTTTGTGGAGAGCTGGGGAAGGGAGATGTTTGCTGTTCTGAGTTGTTTTTCCCACCTA
GAGGGATAATATGTAAAAATTATTCCCACCCAAAAGGTGTGTTTCTCCCACTGGTTCTGAGAGAG
TAAACTCAAACCCAAACCCTGATTCTAGGCCTAGGTTTCCAAGCCATTATAATTGGGTGTTTGGAAGTCAAAAGA
TAAAATTGTATTTGAATGTCTGTCTGCGCAATTTATGGTAATAATGAGGCCTAATGAGGTTGTTAGAAAGATAAA
ATGTTATTTACCAAAAAACCTGATGGGATAATTTGACTTGCTGTGTTTTACTACTGATTATAAAAAGAATATCGA
TTGCAAATAAATCAGCGCCTCTAAATGCCTGCAAACAGCTAGTGTTTGCTCCCTCCAGATCAAAGTCAAACTTAA
GAGATGAAGTAACTGAGAAGAGGCCTAGGATACTGAACCGGTTCCCCTCCTGGCCGCCGGTGGCTCCCAGCCCTT
GCGTTAATATTTTACAGGCTAAGCCTTCCTTTTGTATTAAAAAAAAAAATGGTGTTTTTGTTATTGTTGTCGATG
ATGGCCGGGATTAAAATTTTAAATTACCTGTCACCTCTAAAGACCTTTTAATGTGGGTAAACCATTATATGCAGA
TTAATTTGGAAGGCAAAGGACTGTGCTTTCGTTTTAAATTGCTGGCGGATTTAGACCGGTAGAAAACCCGGGATG
GTTTATTTTGATTGAGCCCCCTCTGGGTGGCAGAGAGGAGGCTTGGGCTCTGGGCCCTTTACGTTTGGAGAAATG
GCTTTATCAGCTCAGTTGAAAGGTTTTTCCCTCTAGCTAGTGAAAGATAAACTTGGAAATGCAGGTTTCTCCAGC
GGTTGGTGGTGGGGACAGGGGTCGCCTAGGGAACTTGCAGGGGCCGCGGCCTCTGTTGTGCTCTTCTGGAGAGTG
CACTGTTTGTGGAACTTTTCTAGAGTGGCAAAAACGATCTCCACTGTCGGTGAAAGGGCAGTTCCTGAAGTCAGC
TCATGGTCTCGGCTCCCCTTCTCCCCAGCAGTGAACTGGGGGTGACTTCCTGATCTGCCCAGCACAGGAGAGCCC
CGCAAAGCGCCTGGGAGGCCCTCGAGTCCATTGAAGCGGCTGCTTCCCACTCTCCCGTCTTGGGGACTCATGTCT
CTCTCTCTCTCTCCCTTTCTCTCTCCACTTCCCTCCTCTCTCTCCTCGATGGATCTGCCCTGTGGCTTCAGGGCT
CGCAGTATGAACTGAAGGACAACCCTGGGGTGCACCCCGCCACCTTCGCAGCCCACACGGCGCCGGCTTATTACC
CCTACGGCCAGTTCCAATACGGGGACCCCGGGCGGCCCAAGAACGCCACCCGCGAGAGCACCAGCACGCTCAAGG
CCTGGCTCAACGAGCACCGCAAGAATCCCTACCCCACCAAGGGCGAGAAGATCATGCTGGCCATCATCACCAAGA
TGACCCTCACGCAGGTCTCCACCTGGTTCGCCAACGCGCGCCGGCGCCTCAAGAAGGAGAACAAGGTGACATGGG
GAGCGCGCAGCAAGGACCAGGAAGATGGAGCGCTCTTCGGCAGCGACACCGAGGGCGACCCGGAGAAGGCCGAGG
ACGACGAGGAGATCGACCTGGAAAGCATCGACATTGACAAGATGCACAAGACGATGGCGACCAGAGCAACGAGG
ATGACGAGGACAAGGCCGAGGCTCCGCACGCGCCCGCAGCCCCTTCTGCTCTTGCCCGGGACCAAGGCTCGCCGC
TGGCAGCAGCCGACGTTCTCAAGCCCCAGGACTCGCCCTTGGGCCTGGCAAAGGAGGCCCCAGAGCCGGGCAGCA
CGCGCCTGCTGAGCCCCGGCGCTGCAGCGGGCGGCCTGCAGGGTGCGCCGCACGGCAAGCCCAAGATCTGGTCGC
TGGCGGAGACAGCCACGAGCCCCGACGGTGCGCCCAAGGCTTCGCCACCACCACCCGCGGGCCACCCCGGCGCGC
ACGGGCCCTCCGCCGGGGCGCCGCTGCAACACCCCGCCTTCCTGCCTAGCCACGGACTGTACACCTGCCACATCG
GCAAGTTCTCCAACTGGACCAACAGCGCATTCCTCGCACAGGGCTCCCTGCTCAACATGCGCTCCTTCCTGGGCG
TTGGCGCTCCCCACGCCGCGCCCCATGGCCCTCACCTTCCTGCACCTCCACCACCGCAGCCGCCGGTCGCTATTG
CCCCGGGGCACTCAATGGAGACAAGGCCTCGGTCCGCAGCAGCCCCACGCTCCCAGGTACAGCTCCAGGCCGCG
TCCACCTGTCCCCTAGCTGGGAATGCAGAGGCCTGGCTAGGTGTGGTAGCGTGGGGTGCAGCATGAGCCGGGAGG
GTACCAGGCAGTGGCCGCTGAGCCCTGGGGCTGCGCTTAATCCCTGCTTCAATTTAGAAAGCCAGACAAGGCCCT
AGGGCTCTCCCAAGAGAGCTTTGCCCTACCGGCGGGCCTGCTACGGGGTGGTGGTGGGGTGAGGGGTGACGTTTT
TCGGCGAATCTGCCTGGGCAGCCGGCAGAAGTTGGTGGGAAGGAGGCCTGGGACCTCTCCCGCCCGTCTCTCCGT
CCTAACTCTGCCTCTTCCGATCTCTCGCAGAGAGAGACCTCGTCCCCAGGCCAGATTCGCCGGCACAGCAGTTAA
AGTCGCCCTTCCAGCCGGTACGCGACAAGTGAGTGCTGTTTGCTTTTGCTATGGGAGAAGGCGGTGGGGAGGGGG
GAGGAGGAGTGGTCGGGACCCGGGCGGAGCTGGCTGGGTGGCGGTGGGGGTCGCGCAGTCCTAGTTGAAGGAGCG
CTCCCCGCCAGCCCTGGGCGCCGGGCGAGCCGAGGAGACTGGAGTTTCTCCCCAGCCGGGAGCCGCGCTGGCTGT
CGACCCCGCCCCCAGGGCTCCGCTACTGGAACCGGCGTCGCCCGGCGCTGCGTCCCCCACTCACAGTGCCCCTGT
CTTCTTGTCTCGCTGTGTTTCCCATGCAGCTCTCTGGCCCCGCAGGAGGGAACGCCGCGGATCCTAGCAGCCCTC
CCGTCCGCCTGATTAAGGGTCTTCTTTTACTTTTGCGGGGGGAGGGGGAGGAGTTGGGAGGGAGGGAATGTG
GGAGGAATTAAGACAAATATTTCAGACTGGTGTAAAGGACAAATATGACAACGACGTCAAGGACTCGCATCCGTC
GCTTTCTGCAGAAAGGGGCTTCTTCGGTCCCGAGCTCGCGTCCAGGTGGCCAGGGCCTCTGCCGGCGGCTCCAGTG
GCTGCGATTATCGGGTTCGGTAAATGCCCCCACGTGCTTGTGTCTCTTTCCCCCCTTTTCTGTATATAGAGTGGT
TTCAGATTGTAAATAGCGCGTCAGCGAACTTGTCTAAATCATATATTTTTGTCTAATAAACTAAATGAAATGACA
CCCCCTCCCCGCTCCTGCTGCTGTGTGCCTGTCCAGCGTGTGTGTGAGTGTGTGTTTGTGTGTGAATGTGTGTGT
GTGAGTGTCTGTGTGGCAGAAACAGAGACAGAGAGAGAGAAGTGGGGATACCTGGAACCCTGGGTGG
GACCCAAGGGTCTGTGGCTGGGGGAGATGGGCTTCTCAATGGGGGCCTTTAGAGACTGTTGCCACCCAAGACGCA
GGTGCTTTAAACATCTCTTCGTTGTTTGTGGTTGTTGTTGAATTTTTAAATATTGTCACTGTGGCAGTTTCTTGC
TGGCAGTTCAATTGCTTTCACGAACATTTTTCTGAGACATAATTTTCTCAGGACATAAATAAGTTCAATTTGAGG
CAGTTTTACAAAACGATTTTATAACGTCGGTAAAAACAGAGGAAAAAGAATTTTTATTGCGACCCCAGAGGAGAA
CTTCGGATTAGAAACCAGTTTACAACTAGTTGTCTCAACGGCGCATCGTGGCGCCTGGTCGTTTTCTGAGTTGAG
TGTGAAAATAATGGAGTATCGCTTTGCATGTATTTTTAGTGATTCGGTTAAATCAAACACGGGAAGAAATTGGAA
GGCTCTTTAAAACTCCACAGATGGGCCAGCCGGGATGCGGTGCGGGCTTCTCTGCGGTGTGAGGTGTGAACGAG
GGGCTGAGGCTGTGGTGGGAAGCGAGAAAGAGGAGGTGGCTTTGGTCTCCCAGGGAAGCCCCTTTACACTTGGGC
TCCACGGACTGCGTCCTTTGCCCTCAGGCGCGCGCACCGCGGGAGTCCAGAGCAAATTGCCCTTAGATGGCCGCG
GCCGGGCAGCGGGGAGGCAGCTGGGAGCAGCGATGTTGGGAAACACTCGCAGCGGGGCTGGCCTCGGGCGCGCGC
GAGTGGGGAAAGGCCTAGGAGCCTGGACATCGCTGCGGATCCGGGACATCAGCATCAGTGGGTTCGGAGCGGGAC
GCGCGCCACGCGCCGCAGCAGGCACCTTCAGGAGGCTTTGCGGACCCGGCGCGGGGCCTTCAGGGCGCAGGCGAC
TCAGCGTTGAATGCGTGAAAACTGAGCCAGCAAACATTTCAGGATCGGAGGATGTGGGCTGCCGGGAAA
AACGGTCTAGTGGGACAGGGCCGAGTCCCGAAGTCAGAGCCGAGTCCCGAGGTCAGAGCGGCCGTCCTCCGCTC
GCACCCCAGCCTGTGACCCGCCCTTCCCGGCTTGCTCGAGACCCACTGGCGCCAGTGCTGCGCGTGGGGACTCC
GTGCATGGCCGAAGCGAGGGGGAAAGTCGGGGCGCTGGTGTCTTTTCAGAGGTTCCAGGAAAGAGGGAGGCTCGC
GTTAGGACTAGGAGGTGCCAGTCCACGGCTCCTACCCGCTCCCGACGCCCGCATCCTTCTACAGCCCTCCACCCC
GTTCCTGGTCCCTGTAGAGGGGAAGGTCCTCTCCCTGCCCCGAGGCGGGAGGAAAAGCGGCGAAGAGGAGGCTCG
AAGGGCGCCGCGTAGGGCAAGTGGGCCGAGGACACCG (SEQ ID NO: 186)

CGI: 140 range = chr5: 5192442-5193941
CGTGTACTCGCGCACACGCAGTCAGGTGTGGATGTACACCCGCGCACACCCAGGCACATGTACACCCGCGCGCTC
ACACACCCCATCCAGCTACAGCAGAATTCTGGCCAGGCTGTTGACCGCACACCTGCTGCCTCCTTGGCCACCCTG
TCCACACAGTAGCCCGATCGACCCCCGTGGCGGCCGAGACCCAGGCCCATCCGCAGCCCTGAGACCTCCCTAGGG
ATTGCACCCAGCAGCCAGTCACCGGCTCCGCGGCCTGGCCAGTTGAGGGTGGCCGTGACCGCGGGGCCAGGAGC
GCCGCCACATCTCGGGGCAAATGGCGCGGGGGAAGAGTTTCCTCCTCAGCCTCCCCGTCTCCGATCGCTCCGCAA
```

TABLE 7B-continued

Sequences of differentially labeled CGIs between bladder cancer subgroups relative to blood ACTCCAGAGCGAGGCACGCGCCTTTAAAGGCAGGTCCGCGGCTCTCCCACGTCCTGGCGCCCGGTTTTCCGCACC
CAGTGTCCCCACAGCTGTGCCCGGGCACAGAGGCGCGGCCAGACCGCACTCCGCGGGCTGCAGGTGTCCCGGCCT
CTGGCGGCGCCGGTGCGGCCCGGAGGTGGGAGCCCGCGGAGCCACTGCAGTAGCTGGAGTCCCGCCGAGTCCCCA
GCCCCAAGGCAGGGCAGGAGCGCGCACCGGCCGGAGGTCCATGCTGAGCATCGCCCGCGCCGGTGCCCGGCAGCC
TCTCCAACTGTGTGGTCCCCGCGCGGGCAGAGAGGCACGGACTGCAGGCCGTGGGCAGCTCCATCTTCCCGCGTC
CTCCTCCTCTGGCGCTGCCCGCTGTCTCCCGCCTTCCCTCTGCTCCCCGCTCGCCTCCGCCTCAGCGCCCCGCTG
ACCTCGCCTCCTCCCCTCTGCTCTTTGTCCCTGCACTCTCCCCTCCTCGGTCCTCTGACCCCCCCGCCCTCACCT
CCTCCCCTCCTCTCTCCCCTGCCCGCCCCGCGCTCTCCCACCGCTCCCGCCGCCCCGCCGCCGCGGCTGCCACT
CCGCCCCCGCGCCGCACGGAGCTTCAGTAATAACCCCGGCGCGGCGGCGGAGTCGCTGTGGGGAATCCTCCCGC
GCTCTGCCTGGGTCGGGTCCTCCCTGCCCGCTCGCACGCTGCCGGCCGGGGACCCTCCGGTGGCCCCTAGCCCCT
CGGAGCGCTCCTGGATGAAGCCCCGCGCGCGCGGATGGCGGGGCTTGGCGGCGCTGTGGATGCTGTTGGCGCAGG
TGGCCGAGCAGGTGAGTCCCGGGCGCTCCCACCAGCGCGGAAACCGCGGGTCCGGACAGCTGGAGGCGAGTCCCC
CGCGGCTCCTCTCCCGCGGACCCCGCCGTCTCACCGCGATGTCGCCGCTGTTTTCCGCAGGCACCTGCGTGCGCC
ATGGGACCCGCAGCGGCAGCGCCTGGGAGCCCGAGCGTCCCGCGTCCTCCTCCACCCGCGGAGCGGCCGGGCTGG
ATGGAAAAGGGCGGTAAGTCCGTGAGGTGGGGGCTTCTAATCCTTGCCATTTAGCAGCTCGTAATCTCCGTGCCG
(SEQ ID NO: 187)

CGI: 21 range = chr5: 6790705-6791004
CGGATCGAAACTGTGGTGAAAGACCTTTGGCCGACGGCTGATGTGAGTATGTTCTTTGGAGTTCTGTGTCGCACG
TCACGTGCGAGTAAATTTAAATACCCTGTGATGATGATGTGTCGGCTAGATCCACACAGACCTTTTCTCGTTGGC
CCGAGGCAGCAGTTCTCCAAGTGTGCTTTGAGAAGGCCTCCGTTGCCTGGAATGCATGGCCCCGGCGCACCTGC
ACCTGCTGTCTTAGACACCTGCGGTGGCCGCACATCTTCGTGATGCTGGCGCGCACTCAAGTGCGAAGACCATCG
(SEQ ID NO: 188)

CGI: 54 range = chr5: 54554812-54555385
CGGGCTCGGCGGCGGTCTGCTCGCACTTACGTCGCCAGCCCAGTCTCGTACCCGAAAATTCAAGCCCCATCCGAG
ACAGGGAACCCAGCAGGCTTGCACTGCCACGGTGGGGAGCGGGACGCACGGAGCACGACACTGACTGGGGGAAGG
GGGCAGCAGTTCGCGGCTCCTGCAGAGCAGCTGCGTGGCGGGAATGGGTCCTTCCACCGGCGGTGCGGCGGCCCT
GCGCCGGCTCCGGGCAGCCGAGTAGCCCGCCACCCACCAACTAGCTAAGCAGCCGCCTCTGTGAAGCTCGGCGGT
TCCCTGTGCGCCTGCGAAATTTTGACTCCGACTCACCAGCGACCGGCCACCGAGCCGCCGCTGTAGGAGCTGAGA
GCACGTCTTGAACACCGGATCTTTCCACCCAAGACCCGACAGCGTGCAGGGGCCTCGAGCAGTAATTTGAGGCCG
CGTTTCCCGCCAAGGTTTGGCCCCAGCTAACCGCCCCACCCATGCAACCGAGCGGGAAGAAAGCTGTGATTCGAG
GGGCCAGGAGAATACGGGAAAAGCTTCTGTTCTGCGCACAGCCAGTGCG (SEQ ID NO: 189)

CGI: 129 range = chr5: 114542616-114544119
CGCGCACAGGGAGTCGAGTGCTCCTTTGTGCCATCACCTCTTCTCGAAGCTCCAGGCGCAGAGGGCAAACGCTGA
CGCCCTTTCCCGCCTTCTCTCCGTCTGCGAGTTCCGGAGGGCAGTGCACTGTGCAGCCTCCGTACTTCCCGACAC
GTTCCGCCTGCAAACCACTTAGGAGCTTCTGCCGGCAATTTCTCGGATGCAGCGCGGAGCCCAGCCTCCCGCACT
GACTCAGGCCCGGCACCACCCGCCTGCTGAGGGCGTCGTCGCGGGCGCACCGACGGCGCCAGCCTGCGTTCCT
AAAGGCTCCAGGACAGGTGTGGGGCTGAAATCCCGCTCCTCCAGCATCTTCCCCTCCCTACCAAAAGAAGGCTGC
TTTAAATATTCCCGGCCTGGAGCAGCAGCAGCTAAGGACCTGGAAAGAGGCCCGAAAAGGCCAGGGCAGGGCGAA
CGAACGTGCTGTCCCTATTTACCGGCCACACGCTCTGACTGCGGCGTGACCCTGATCGCACACTTCGAGCCTGTT
CACTCGCTGGGCGGACCCTCCCTCCACGCTCCGCGCCCAGGCAGGCGAGGTCACCCACTCGAAGTCACCACGTTT
GAGTAGCCCTGGTTGGTGGGGCAGCGCCCCCTTGGCCAACGCCCCGCCCTCCTCTCCATCTTCCGACGCTGGGCT
CTCGCCCTTCGGCGTCCGAGAGCCCCTATTGCTGCCCAGCTGGCCCCAAAAGCGTCCGAAAGTCCCCTCTTGGCT
TATTTCAGAGATGCCACGCAATAAAGAAAAGGCGGCTACTTTGCATTCCGCAGCTGCTGGGACGCCCGGGCTGCG
AGCGCGGCTCCTGGATTCCAGCCTCCCGCCCTTCCCAGGCGCTGGAATGGACACGGACGCCCACAGTGGCGGGCC
AGGTAGTGCCGGAGTCGGGGGCCCAGGCCGCGGCGCCCCGCGCCTCATCACTTACCTTGCCTTTAGCTATCAATT
CCATGATGTAGCCAAATTCACTCATCTCCCCAGACTCCGACATGTTTACACCCCTTCACAAACTCTGGAGGACCG
ACGCGGGTGTATCGAATTTGTCCTTTCTTTTCTCTTTTTCTGTTTTTAGTCTGAGTTTTGCCGAGCTCCCCGCCC
ATAAGCTGTTAACCAGGAAAAGAGGGGAAGCGCCGGGGAAAGCAAGAAGCGGGCTTGGGTGAAATGAAGGCCATC
GAGGGCTCCCGGGCAGCCTCGCCCGGCTTGCTAGGATCCGGGTGCAGCGGTCGGGGCTGCGCGATCTAACGGAAC
AAACGAGGGCGGCGGCGGCGGCAGCAGAGGCCGTGAAACCCTCACCAGGCGGAGCCGGGCGCGCGGAGGCCCCGC
CTCCTCGGGGGTCGCGGCAGCGGTTCGGACCGCAGCGGAGACAAACAAACGCGCACACAAAGCGGGTCCGCACTC
GGCTCAGCGCGGCCCCAGCTAGACATTCCCCGGCCTTTATCGCATGCCGGCAGGTTGGCCGTCCCCGGCTCTCGG
CGCG (SEQ ID NO: 190)

CGI: 21 range = chr5: 127899858-127900162
CGCGTCCCGATTATCAGTGCAATGTGATCACTTGATTTTAAACGCAACTATGCGTCCAAATGGCTGAGTGCAAGA
GGTCGGCCGGAGATAGGGCCGAGTGCGCTGCCCCAAGCTGCGATCCCTGCCAAGCACTCACGGACAATGCACTGG
TTTCCTCCAGGGAGCGTCTTCCATCCAGGGCAGCAGTAGGAGTGGAATCTGGAGCCGCACACGTTGGGCCTGTGA
TGGACAAGCGCGGTCACGTAACAGATAGGTAGAGGGATGCAGCAACATATAAACGGTCTTCGTAAGCAATGCCCC
GAGCG (SEQ ID NO: 191)

CGI: 56 range = chr5: 135720297-135720941
CGCCAGTCCTTTGTAGGCGTTCATGCGCGAGCGCGAGTGGCTGAAGGAGTCTTTCCGCTGTTTCTCGGTGCACTC
ATTGCACTTGCAGAAGTAGTCGTGGGGCCGCTCGATGCGGGCGCCCTTGAGCAGCAGGATGTGCACGATCTCATA
CTCCTGGCAGTGCGCCGCCAGGATGATGGGCGTGATGTCGTGGGAGAAGCGCGTGCCGTCTCGTCGTAGGCATA
GAAGTCGTCGTCGCGCAGCTCCTGTTCCAGCGGGCTGAGCGTCAGGCGCTGGCCCTGCGCGAAGGCCGGGTGGTT
GAGGATGGCCTCCACGATGCGCACATAGCCCTTGCTGATGGCCAGCAGCAGCGCGTCCCCCACCCGTGCCAGGTT
CTCCTTCTTCAGCAGCAGCTCCGTGACCTCTAGGTGCTCGTTGCCCACGGCCAGCTGCAGAGCGTTCTGCCCCAT
GTAGTCCACACAGTTGAAGTTAAGGGTCTTGGACTCCTCCAGCATTTTCCGGACCACCGGGATGTTGCCATACTC
AGCCGAGTCCAGGAAGCGCTCCTCCTCGGGCGTCAGACTGGTGCCCTTCTCGTTGAACATGTAGGCGGGACCCCG
GATGGCCTGGCGACGGCCCTTCTCCCTCAGCGTTGTGTGCCGGCG (SEQ ID NO: 192)

TABLE 7B-continued

Sequences of differentially labeled CGIs between bladder cancer subgroups relative to blood CGI: 29 range = chr5: 140780945-140781256
CGAGAAACCGCGGAATATCGGCTTAGAGCCTGCCATGGCGAATCGGCTACAGCGCGGGGACCGCAGTCGGCTGCT
GCTGCTGCTGTGCATTTTCCTGGGGACGCTGCGGGGGTTCCGGGCCAGGCAGATCCGATATTCGGTGCCAGAAGA
GACCGAAAAGGGCTCCTTCGTGGGCAATATCTCCAAGGACCTGGGGCTGGAGCCCCGGGAGCTGGCGAAGCGCGG
AGTCCGCATCGTCTCCAGAGGGAAGACACAGCTTTTCGCTGTGAATCCGCGAAGCGGCAGCTTGATCACGGCAGG
CAGGATAGACCG (SEQ ID NO: 193)

CGI: 182 range = chr5: 141235749-141238152
CGCGGCGTCTTCCTGCACGAAGCGACCCAAGCAGCCCCAGTCCGCACCGCCTTGGTCAGCGGGCGCTCCCAGCAC
ACACCCAGCGCGCGGAGCGACTCCTCCCAGAGGACGCCGAGTGTGTGTGTGTGTTGCGGAGATTAGGGGGTGGCG
GGGGGGACGGCGGCAGTTTCTTGGGCTCTGGCGGCCCCACCCCCACCCCGGCAGCGCCCAGCCTCCAGGAACCCA
AGGCAAGGCTAGGGCGCGGCGTGGTGAGAACGCGCTTCGGCTAGTGGGGGGAGCCCTTGCGCCCCCCGCACCCAG
GCCACCGCGGGGAATCCCTCCTCCCCGGCATCTCCGGCCTCGGCCTAGGGTCCCCCGCAAGCCGGAGCCGGCGCG
AGCGGCGCAGCGGGCGCCAGGAGGGGGCGGGAGGGGAGCCGGCGCCGGAATCACAAAGCCGCGAACCCGGCTAGG
CGGGGACATTCTCATAAAACCGACCCTCTCGTGGCGAGCAGAGGGGGTTTTTGCCCTACGCTCAATCCTCCAAG
GCCTCAGTGCCGCCCCAGTCTTTCCTGGCAGAAGAAATAGTAGCCGACCACTGTTGGGGAAACTGAGGCCAGAA
TTCTGACTTACAGAGGGTAGCTGGGGGGAAGGGGTGCGAGACCACCTTCGCCTACAAATTCTGCTCCTTAGCCTGC
CGCGATCTCCGTTCTGGCTCCAGGGCCTGCCCGCGCACACACTGGCCTACAGCGGGGACCAGGCGGAGGGGGCGC
TCAGGTGTGAGACGAACCCAGGTGTGCGGGACCCACCAAGGTGTGTGGGACCCAGGTGTGCTGGAGACCCAGGTG
GCTCAGAAAACTCAGCTAAATGGCTGGAAGAGGGTCGCAATCACCGTCCCAGGCTAGCACCCTCTACAAAGGAAC
CTGGGGCCCAGAGCTCCGGGGAGGCGGGATGGCTTGGCCAGCCAGGTCCAGGTCAGCTTGTTCCCGGAACACCAGCCGG
TTCGGCCCGGGAGTGGGGGTTGGGGAGGCGCCGACTGGGAAGCCGGCAGGCCGGCCCAGCCTTCCCGCTGTGCCG
ATATTTACAATAATAATGTCGCGATTAACGTGGCGGGGCGCTTGGGGCTCGCCGAACGACCCCGGCGGCTTCTCC
TGCCTGAATCTGGACTCCGAGAGAGAGGAACGGAGTGTGTGTGTTTGTGTGTATGCGCTGCAGGGTGTAATGTAA
TGTGACACTGTTGGTTTAAGGTGTGTGACACCCAGTGTTAGATGGGTGAAGCAGTGGATTCTGTGTTTGTGA
CCGTGAGGCGCTGCTGTAGGTGCCAATTCCTGTGTTAGAGTGTGTGCCATCAAGCGTGTGCTGAGATACTGGGTT
GTGTGTTTGTGTGGGTGCAGTAGAGGGGTGCAAGGAGACCTGTCTGTGTACCTATGTTCTGGCCAAGAAGTGGG
TAAGATGATATATGCTAGGGTGTGTTCCTTAAAGGAATGTGGGGGGTGGCTAGGTTTTGAGGGTTCATCTAGTGA
ACTGTGGCTGTGACACTCGTACATGAGGGCACGAGATTGTGTTTGTGTCCACGTCGCGGGGTGTCACACCCGG
TTGTGTTATTGCTCTGTAAAGCCACGGGTTGTGTGTCGGTGCTGCTGATCGTGCAGACACTGAAGCGGATTCTGA
GCTGGCGACGGTGCCCCAGTGGGCGCTGGTGTGCGGGAGGTATGTCTGTGTGCACATATGCAGGGATGTATGTAT
GTGTGTATATATGTCCACGGTCTGGCCCTCTGGGTGCCCGCGAGAAGCTGGAAGCGGCTGAGTGAGCCGAGGTAG
TTGCCCAACAAGTGTGTATGTATGTGTTGTGGACAACGGTCCTTGCTTGCTCCGTCCTCCGGGAGACCCCCACCA
AACTGGGGGCCGCGCGCTTCCCCAAACCCATCCTCCACGCCGCGCGCTCCTGGAGTCTCCTTATCCCCGTCTCTC
CGAGCGCGCCCAGGTTTGGGACGCGGGGACTAGGGTTCTGCTCAGCACCCCCTCCCCTCCCTCGGCTTCTCGCCG
CGGACCTGGGAGGACGGAATCCCTCAGCCGCATCCCCTGCTATGGGCTCCCAGCAGCCCCCACCTCAGCCCCCTC
GCGCCGAGCTCGTGTTGGGCCCCGCGGCCTCGCTCCGCCGAGCGCCCTCCCTCAGCTCCCGCCGGCCATGACC
GCTTCGGGCCCCAAGCCGCTGCTGCCTCCACCGCCGCCGGATCCTTACCCGCCTCCGGGCAGCGCCGGCCGCCG
CCCCGCTGTCCATGAGCCGCCGCCGGCCCCGGCCTGGGCTGCGGCTCCGCACGGCTGGGGCTGGAGCTGCAGTTC
GGGCTCCGGCTCCGGCTCCGGCTGGCTCTGGGCGCAGCAGCCCGGCGGCTTTGCGTCCGCGCCGCGCTCCCGCTC
CCCG (SEQ ID NO: 194)

CGI: 263 range = chr6: 1326743-1330210
CGCCGCGCAGAGTCGGCCGAATCCAGCTTCTCCAAGGGCGGGCGGGTGGGATGATTTGTTGATTTGCTTGTTTTC
CACCAAACCGCAGGGCACCTCCAGGAGCTCCGGGACAACTTACAAATGAAGACACAGAGCCCCCGTCCCTTGCTT
CAGAGAACCAAATAACGGAACTGAATGATCGTTTCTTCAGCAAAGCCTAAATGACGCTTGCGTCCCGCGGAGAGGT
GCCCACGCGCGACTCGGCTGCCCCCTCTTCTTGCGGGTCCGGGTAGGGTAGGGCGGGAACGCGGGACGTGCCCTA
AGCGGGCCAGCCGAGCGCGAGACAGGCGGATGCTGCAGAAGCCTGCCCGCCTGCGGGTCACACACCGGCCGGCCTC
GGCTGCAGGGGTTGCGGGGCCACGGGTCGCGGGGCGCCGGGAGCCGCGAGCAGGTGACGGCCGCGCCGGGCAGCC
CCGCGGGCCGCGATTCCCGAGAGCCTGGCGCCACCCCGCGGAGCCGGAGGAACTGCGGCTTCTTCCCGCTCCCG
CGCGGAGGGGAGAGGGAGGCGCAGCGCGGAGGGGAGAGGGAGGCGCAGCGCGGAGGGGAGAGGGAGGCGCAGCGC
GGAGGGGAGAGGGAGGCGCAGCCCGCACCGCGCAATCCCGGGGCTCTGGCGGGAGGGAAGGTGACTTGCGTGGGA
CGACTCCAAGAGGCCAGGCCCGGCCTTCGCAGTTCACCCACGAGGATACCGCGACCAAGCCACCAAAGCACTCTC
TGGCCAGGCCGAGACCCCTTTTCCCCGGGCCCCAAGAGAAAAAAGCACTTTCTCCTAAAACACGAACTCCCCGC
GGAGGGGCCCGGGGCTGCCTGGCACGGGGCAGGGTGTGCGGCTGCCGTGCGGGCGCGGGCCAGAGTCACGTGGAG
GCAGGCGGAGAGGGCGAGGGGGCCCCCGTAAATCATCCTGAGGGATTTTTGGCCCAAGTCCCTGTTTCCGAAAGG
TTGCGGGACGGCTTTGACGTTGATTATGTAGCTGTTCTCTTTTCAAGTGCGCGCCCCTCCCCACCGCAGCCCGTC
TGGTGTGCGAGGATTGTGTTTGAAAGGGAGGAAGCATCCTTGAAGTGGTGGGTGATGGATTGTCTAAACCCTTCT
GGGACGTTCTGGGTGGGGGTTTTCGAGGCAGCTCATCAATAAAGACCCCCCTGGAGAGAAGGGGCGGCTGGAGAC
CAGCCCCCGCCGCGCAGCCCCGAGGCCCCAGGCCTGGAACACAGTCCTCGGTGTGGGGCACAGGGCGTGAGGGGA
GGATGAGCTCCCCCTGAGCAGATGGAGATTTCTCCTTGCCTGGGCCGTTTGACCCCCAAAGCCTTGCAGACTGGC
CGCGTGGGTGCCATGGGGCGATTTCTTGGGAAAGGAGGGCAGCAGAAAGGCCCGTGGGCTCTCAGCGCCTTGGAG
TCAGGGGAGCAGGAAGGGGAGTGGAGGTGCGGACACGCCTCCAGCCACCGTGCTCCCCTAGGAGGATCTCCCTTC
AGCCCCTGTAGAACCCTGCATCTCAACCACCCTCGTGCATGTGGTTTACCTTGGCATAGATTTCCAAGCCGCTAC
AGAAAACCTGTCCACCTCCCCAAGGTGGAGGCGGGAGTTGGGAGGCAGGGGTGCTGGAAAGGGTCACCTGGCTC
AAGCCGACCCCAGGTCTGACGGGCGGAGAGCCTCGAGGGCCACGCCCCAGGCCAGTGGTGTCCTCTGAGGCCGCA
AAGCCGACTGGCTTCTGGAGGAGCAGCAGCTCGGCCTCAGCCTCGGCTGGGAAAAGACGCAGTCGGGGCCTCC
GTGCTCCAAACTTGAACTACTCTGGGTCCCCACGAGGAGGAGGCTGCCCTGGGGTCAGAAACTCCGACGGAAATG
AAGGGGAGGGGGCGTAGGTTCCCTGGCACAGCTCGGCCTGGAGAGGCAGCCTGGGGGCCCAAACTCATCTAGGGC
GCGCCCGGAGCTTCCCCGGCCTCTCTTGGCCCATCGCGAACGAGCTCCCCTCCCCGACTGGGTCGGCCTCGGGCG
CCTTTCGCCTTCGCAGGCCGCCGGGGTTCCGCGGAGGGCTTGTGCTCCCTCCCGCCGCCGCAGCCCGCCCGA
AGGTCAGGCCGCATCCGGGGCCCGGGGCCTTTGGCCAGGCTGCGGGGAGGGGTGGGGTTGGGGGCTCCCCAAAG
CAGCTTCTCGGAGGCGGCGTCGGGGCGCCCTGAGGTCCCTAGTCGGCCTCTGGGCGCCGAGCACGTTTTATTTAT
CCCCACAGAGGATGCTGGAGGACAAAAGAAATATTTGGACGTCAGAGCTGATTTATATTTTTGGAAGAGCTACGT
TTCCTTTTCTGAAGAGAAGCGAGCGCGCCCCATATCCTGAGCTCGGCGGGGAGGACGAGAGGGGAGTTTTGATGC
GCCAGGAAGTTCATCTATCGCCCAGGCGCTCAGGACCCGGCGCCCCGCCGAGTTCGCCGCCCTCGGAAATATTTA TABLE 7B-continued Sequences of differentially labeled CGIs between bladder cancer subgroups relative to blood TTTATTTGGGGGAAGGGAGGGCAGCGGGGAGGAGACCAGCCAGACGGGAGAAGAAAGCCCTGCCCGGGCTGGGTT
GGGACCTCCAGGGCGCTTCCCCGCGCGGCCGCAGCCGGCCAGCCTCTGGTCTCGGTTGGAGGGCATCGCAGGCGC
GGCCTGGCGACCTCCGGGCGCCTTTGGCTGGTGTCTTCCGTAGCCCTCGGCGCGCACCCTCCCGCGTGCAGTGCC
CGGAGTGACCTCTTCAGGCCCCGCGGGCGCCTCCTGGGTGGGCCCCGCGGCCCCTCCAACCCTGCCCAGCGTGTG
TGCGCGGCCTAGCCATCTTTCTCCCCAGCCTGGGAAGGCGGGCGGAGGAGGGGGATCCGAGGCCGGGGGCCGCGG
AGCAAAAGGCACGCGGACCCCTAAACGACCCCCGAGCGTTGCCACAGCCGGGAGGGCGGAGGGAAGGTGTGCAGA
GCTCGGGGGTCTCCCAGGACGCAGCTTGGCTCCTACCGGTTTCCAAGGCATCTGCAAGCTCTGTCCTGCGACCTA
AAGCATGGGGACGTCCCTTCCAGCAGCATCAGTGGGCGAAAAGTTAACATGCTGAGGGCACCGGCACCCACACT
TGCTTCCAGGAATACTTGCGGTACAGGCTTCCTGACTTATTTTCTTTAGCCGCTGGGTGCCCCCCCTTCTTCCCC
CGTTGGGAGACGCAGACCGACTCTGTTCCAACCTAAGCCCCTTCTCTCTGCCTTTTGGACAAAGCGGGCCGCCTC
TGCTCTCCACTCACTCCCCGCAACCCCGCAACTCGCCACCCCTAAACGCAGCGGGCTGTAGGCGAAGTCGAAGAG
GTGCTCCGCCTGGTACCGCGGCCTGCGCACTGGGATCGGGGCCTGCAGGCCGCTGGGCTGGCTCCTGGGATCATC
CCAAGGTTTTGGTCTCGCAACCGAGGGGACCCGCGCCCGGCAATTTGGGAAGTGCGGAAATGGGGTGAGGCCGGT
CTTCGCTTGAGGGTCTCG (SEQ ID NO: 195)

CGI: 190 range = chr6: 5947471-5950124
CGATGCGGATTCGCGCTGGCGCTGAACGCTGAGCGCAGGCGGGGAGGCTCGGCACTCTCCGACCTCAGTAGCGCC
CCCAAAACCGAAGTCCAGCCGGCCAGAGAGGACACTTACGTGCACACGGTCTTGATGTTCGTCTTGTCGTCCAGG
CCCTGCGGGTAGTTGGCCATGCTGTCGCCCAGCTTGAGCAAACAGTCCGAAAAGCCCTTGAAGACCGCATCGCAC
TTGCCCGCTGCTCTCACGGCCTGCACCAGATACGCTGCGGGGAGGAGGGAACACCGGTCAGCAGCGCCACGACCC
CGCCCTGCCGCCCACTGCCCTTTCCTGCGAGACCCTGGCTCCGCGCGGCCTCATCGCATCGGGCGGCCTCTCCCA
GCGCCCAGCCTCGGGGCTCGCCAGTGTTAAAGGTGAATGAAAGACGTGACCCAGGAATGCCCGACCTGCAGCTAA
CGCTGCGTCTAGTGCAAATTGTCGGTGTGTGAGCAGGTGTGGGTGGGTGGGAGGTAGGTGAGTCCATTCCTTTCC
TCCAGCTCCCTCCCGCATCTCGCTCCGTATCTTTTTCTGTTTCCATCGCCCCCTCTTCTCACCTCCCTCATCCCT
TTTATTTCTCTTTCTCCTCGCTCCCTCCTTCGTCTCCCAACACTTCCCCAGCAAGCCCTGTCACAGCTCTCGCAA
TGCGATCTTCCATTTTGAGGTGACAGAAGGGGTCTCGGCTGCAGCGTGCGGGGCGAGAACGGGGTGGGGAGACG
ACAGGGCGTGGGGTCACGCAGCTGAACCCAACGCCACATCACGAGAATAAGCCTCAGGCTTGGCGCTCTGTCCTT
GGTGGGCGCTCAGCAAACACTGCTGAATGAATGAACGAATATAGTCCCTGGAAGCCACCAGCAGTTACCGAAATG
GATTGTTTCATTATAAAACCGATTGCCTACCGTGGACTCTGTATTCCGAGTGAGACCCTCGGATGCACCCTCTCC
CGCCCCGCTGGAAAGAGGGCAGCCTGGCGTCCTGAGACCTGGCGCGGATGATGAGTGGTCTGGAGAGGAGAAGG
CCAGAGGCCGGGCGGGGTCACGGATGAGTCTGCCTGGGTCACCTCCGCAAAGGCAAATCCACGAACCTCGGGCC
TCTTTCTCTCCTCCTCCCCTGTCCGCCACTCGGCTCCCCAGACACCCTTAACAACCCACCCGCCCGCCAAAAAGC
CCGCCTACACTCCGGACGGCAGCGGGGAGAGGCTGTTCTTCTCCAGGTGCCAGCCCTGCTGCTGAAAGTGAGCTC
GCCGCGGCCCGGGGCTCCTGGCCCCAGCTCAGGACTCCCTGCAGAGAGCAGGCAGGGATAAAAGCTGAGCGGCGG
GAGGAGGAGGAGGAGGAAACACAGGCCGCACGAAGGTCCAAGCCCCAAGCCCCCAAGCCCCCCGGCCTCTGGA
CGGCCAAACCCCGAGGCGCGGGACTGGAAGGACAGGTACCAGGCTGCGGGCGCGCGGCTGTGGCCATCTCTTTCC
GCCCTGAGGCCGACGAACCCGGCTGGAAGCTGAGTGCCTAGCGGCCAAAGCAGCCCGGGCGCCGGGAGGGCGCC
AGAGAAGCACAGCGTTAGGGCGGGGAAGAAAGGGTGAATCTCAGAATCGAAATCCGCACTGGCGCCCACGACCCT
GGGCGCCGGCCTGGTCCTCGGCAGCTTTCTGGCGGCTGCGCTTGTGTGTGAATGTGTCCCGGGAGGACCGGACAC
CTCAATCCCCCGGCCCCAACGCGGGCGCCTGTCCGCGAGCGCCGGGCCAGACGCCGAAGAGGAAGGTGACCGAA
CCCGTAGCAGCTTCCGAGAGCGTACCCGTTTGCAAATTGCTGCAGGAAGAGCGAGGCGGGCCTTGCGCTTTTTAA
TCCGGAACGGGAAGCACTGGGGAAGGGACCGAGGTTAACTTCGACCTCCGCTGGGGCAGATACGTAAACCTTCTC
AAACCTCCGAGTTCACCTTACAGCGAACATTAAATACCCTTGCACTACAATACTAACAAATCGAACACTGACGTT
AAAATCTTAAGAATAAACGAATCTTTGTTCTGATAGAGCTCGTTCAAATGGAAATACACTCCACACATCTTCCT
CTATAACGCATGTCACAAATACAGCTTTGCAGAGAAGAAACGAAATAAAATAAAGTCCAATCTCCCCGTCCACGT
CTCTCCCCACCCCTTGCCTACACCCCCAAAACTCAGTGGCGAAAGAAGCCCCTAAAATGCATTGACATTTTTAA
GGGGAATTGGGGCTCGCCGGGGGCGGGAGCGCTCTTGTCACGTTATCTTCCCAGGCGCTGCTGGAGAAGACCCTG
CACACCGCGCATGTGTGAGTGTGTGCTGTGTAAAATAAGTCGTGAACATTTCTGTCTTTTAAAACTGTGACTCCT
TGGACTCTAGCCTTCTCTGGGAGGCCGGGAGGCTGCGCGCGGGACGGATTTTGCAGGCGCACGCGTCCCAGCAGG
TCGCAGCCCGTGGGTCCCTCGCTGTCCTTCCTGAACCCCGCTTAGGCGAGACTCTAGCGGGTGACCCTGGCTCCT
TCCCTGTCCTCTCTGCCGTCCCCTTCTTTGTGCGGTTTCCATCCGTTCATTCATTCGTTCGACCTCTCATTCATTC
CGAACTTCCTCCTGCTGCGTCTTCTTTCG (SEQ ID NO: 196)

CGI: 40 range = chr6: 10498025-10498551
CGTTTCGGGTGCGGGGTGCTGATGCTGCTTTTTTGTTGTTCGTTTGCGCTCGCGCTCGCTCTCGCTCTCTCTCTG
CATCCCCCTCACCCCCTTTCTCGGAGACTGAACTAAGTGAAAAGTTGTTTCAATAATCGCAGCTCTCTGCTCCGC
CAGGGCCGAGGGAGGCGGGCGGAACACGGAGGGTGTTTTGTTAAATGCTCCCGTCGTTCGCAGGGGCTGGGACTT
GATAAAAGGAGACAGTTTTCTGAAAAGATTTGATTGAAATGGCGTGTGCCAGGGCTGATGGGAGCCAGCGAGGGA
CAAAGCGCCGAGAATCCATGGACACTCGAGCAATTATGCCTCCACGCTGAAGGTGGATTAGCGCGCTGGAAAGAA
GCATATGTTTGGCCCGGGGCGACACTTCCCCCCGGCTGAGCTTAGAGAATGGGAGCGCGGAGAGCGGCTGGACCC
GGAATATCAACTATCTGCGAAGCCCCCCCTTCTAGCCCAACTCCGCCAGCCTCCCCGCCCCCGCCGGGGAAAAGT
CG (SEQ ID NO: 197)

CGI: 100 range = chr6: 22677564-22678684
CGTCCGAGGGTGGGTCCAACGGGCTTCGAGTGTTCGGGAGATAATGCACACTTCGCAGTGGATCTTCTCGGGGCC
CCGAGCGTTGCCCGCCCATTAGGTGGCGCCGGTCCCCTCGAACAGGTCGCTCAACAACTCCCGCCCAGCAGCCGC
CCTTACTGCGCGCGCGCAGACTTCGGCGTCTACTTCCGGTGTGGCCCAGGCGGGGTCCGCAGAACCAGCTATGTC
GGCCTACGGCATGCCCATGTACAAGAGCGGGGACCTGGTGTTTGCCAAGTTAAAGGGCTATGCCCACTGGCCGGC
GAGGATAGAGCACATGACCCAGCCCAACCGCTACCAGGTGTTTTTCTTCGGGACCCACGAGACGGCCTTCCTGAG
TCCCAAACGCCTGTTCCCGTACAAGGAGTGCAAGGAGAAGTTCGGCAAGCCCAACAAGAGGCGCGGCTTCAGCGC
GGGGCTGTGGGAAATCGAGAACAACCCCACGGTCCAGGCCTCCGACTGCCCATTAGCCTCAGAGAAGGGCAGCGG
AGACGGGCCTTGGCCGGAGCCCGAGGCCGCAGAGGGCGACAGGAGCAAGCCGACCCACGCTGGTGGCGGCGGCGA
CGAATTGGGGAAGCCGGACGACGACAAGCCCACTGAGGAGGAGAAGGGGCCGCTGAAGAGGAGCGGAGGCGAGGGCGGC
GCCGGAGGACGCCCCCAAACGACCCAAGGAGGCAGCCCCCGACCAAGAGGAGGAGGCGGAGGCGGAGAGGGCGGC
GGAAGCGGAGAGGGCGGCGGCGGCGGCGGCGACGGCCGTCGACGAGGAGAGTCCGTTCCTCGTGGCGGTGGA
GAACGGCAGCGCCCCTAGCGAGCCGGGCCTGGTCTGCGAGCCGCCTCAGCCAGAGGAGGAGGAGCTCCGGGAGGA
AGAAGTCGCGGACGAGGAGGCCTCCCAGGAGTGGCATGCCGAGGCACCGGGCGGCGGAGATCGCGACAGCCTGTA TABLE 7B-continued Sequences of differentially labeled CGIs between bladder cancer subgroups relative to blood GTTACCAGCGTTTCCAGAAGAGCCCCTGCCCCGTTCCTGCTGCGGCCTGGCCGTTCTTGGGGAATCTGACCACGG
CGTGCAAACTGGGACTGCCTTTCCCTCTCCTCAGCCCGTCCTCCTCCAACCCGCGCTCCTTTGCCCTGCCG
(SEQ ID NO: 198)

CGI: 20 range = chr6: 25834434-25834701
CGCCGCCCAAAAGCTTATTGAGTTCCTCATCATTGCGGATCGCTAGCTGCAGGTGGCGGGGAATAATGCGAGTTT
TTTTGTTATCGCGAGACGCATTGCCTGCCAGCTCAAGGATTTCTGCTGTGAGATACTCTAACACTGCCGCCAAAT
ACACTGGTGCGCCTGCCCCTATCCGCTCTGCATAGTTTCCCTTACGAAGCAGACGATGGATCCGGCCTACGGGAA
ACTGCAAACCCGCTCTAGAAGAGCGAGACTTAGACTTGGCGCG (SEQ ID NO: 199)

CGI: 71 range = chr6: 41176454-41177326
CGGCTTTATCGTAGGAGCGTCTTCGCCTCCCCCGTTTCCAGTAGAAAAGACAGCTTTGCTCCTTTGAAAGCGCAG
ACCGCCGCACCTCCAGCCCCTTCTCCCCGGGGAAGTAGGCCCCGCTAAGAATGTGGGAAGGTGGTGGGGCGGCGA
CTGAAGTCGCTTCCGATTGGCGTTGTCCCAAGGAAGCCTGCGCGGATTGATCGGCGGCAGGCCTCCAATAGAGCC
TGCTAGGCGGATTGGCTGCTACGCGGCTGGGCCCTGTTTCCGGTACCTAGGCGGGCAGCCATGGTGACCGGCGAG
CGGCATGCGACGCCGCCTCTGTGGCCTGTGGAGGCCCGCTTGGCGGCGCTGCTTCCCGACCTACTGGTCTTTCGG
AAGCCTCGGGGATGGGAACCCGAGCTCGCCACGGCCCAGGGCGTCCTCCTAGGCGTCCATGTGACGGGTGAGGGC
GACGGCCGGCACTTGCACTTAAGTCTCTCTGGCCTGCGGGAGAGGCGGCCGTTGGGTCTAAGCCCCTGGAGGCCTC
GACGGTTACAGGCCTAGCCTCCCGCGAGCTAAGGCACAGTTTAACTTCGTGCTGCGGCTTCCTTAGGAAACTTTG
AGTATCTTCGTTTTAGCGTGGGAGGACATCTTTTGGGATGAACCGGCTCAGTCCTTGAGCTCACCCCAAAGATGA
TGAAATTGAAACTCAGAGGAAAGGATTTTTACAGGACCACGCCCCGGGCTTTGAACCCGTTTTTCCCAACCCCGA
GCATTTTCTATTAAGCGTTCTGTTTCAATTATTTTATTCGTTCAGTTAATTCGTTCTTGGCGTCATAAGTATATG
CCCGCCGTTGTTCTGGCCGTAGCTATCTAGCAGCCACTCCGCGAGTCG (SEQ ID NO: 200)

CGI: 68 range = chr6: 50895246-50896050
CGTCCGAACAGAAATCGCAGCCGCCTCCTGTGTGGGCATCTTTCACGGAAATTTCTGCCCACGTTCAATGCGTAC
GGGTCTCTAGCACTGAGGCTAGCTCAACTCTTCGGGGCAGGAGAAGTTGCGCCCAGCCAGGAGGACGCCAGCCGC
CTCCGGGGCCCGGACCGCGCTCGCCAAAGCCCTTTTCCGGCTCGGGCGAGGGCTGACGCGGCCAGACGGCTCCGC
TACTCGCGGGCGAGGCGGACTAGGCGGACGAGGCGGCCGAGGCGGGCGAGGTGGGAGAGGCGGGCGAGGTGGGAG
AGGCGGCCGAGGCGGGCGAGGCGCGGGGCGCGGCGGGCCAGGCTGGGGACCGGGAAGCCCGCGGAGCCTCGCT
TTTAAGCGGAATGGTCTGGGACAGCCCCAGGTGGTTGCCAGGGGAAGGGAGGAAGGGAAGGTTCTGCTGAGACGT
CGAGGTTGGAAATAAAAACTTCGGAAAGGCGAAGCGGATTTAGAAAAGGAGGGAAGTCGAGGCGGGCGAAGCGGG
CCATGGAGATTGCTAAGAGGAAAAGTTGGAGAGAAAAGGAAGGAAGAGAAGCAGACTCCCGGGTGGCGGGCGCGG
GCCGCTAGGTCAGACGAAAGGTGGAGGGATGCAGAGGCTCCCCAAAGAGCCGAGAAAGACACGCGACCCCTCCGG
ATCGGGACAGCTCCTGAAAGCCCGGCGCAGAGCCGCCTCGAAGATCCTAAGAGTGGGCGACTCACAGGCGCGGCC
GGCAAGCTCCTGGGGGACTCGGGCTCGGACGAGCGCCCACAGGCAGCGCCTGGCG (SEQ ID NO: 201)

CGI: 43 range = chr6: 75968300-75968853
CGGCGCCGTTTTGGAAACCCATCTCGGAGCGCCCCACTGCCTCCGCGGGAAGGTCCGACGCACCCGGCTGTCCCT
GAGGGAGGCAGGATGGAGCAAGGGCAGGACACTGGAGGTGGTGCCCAGCAACTCCGGCGCGCGCTTGCTTCCCAG
GCTGGAAACCTTGGCCCAGGCTCAACCTGTCTGAGCTGGACCAGTCCAGGCCACGCGCCTTGGAGCCCTGCTAAC
CAACAGGGACAGCCGCGACCCTAGGTCGTGCGAACACCTGGGGTCCCGGATCTCCGCTTGCCTGCCATCATCCCC
CAGGCTGCTTGGCTGCTGGCTCATCTGCCCGCACCGTCCGCCCCGCCGACTGAGCTCCCCACAAAGCACACAGAG
GCGCAGAGCCAGCGCTGTTGGAGTCTTTTATTGTGTTCTGTCACCGAGGTCGCAGCCCCGAGCCAGGTGGTTGGT
TACCAGCCAAGCGAGCGAGTGCGCCCGCTCTTCGGGGCTCCTGGGTGCCACCCGGAGGTGTCCTGTTGGTTGCGC
TGATTAGAGCCGTCGCCCCCTCTCGGGCG (SEQ ID NO: 202)

CGI: 27 range = chr6: 101953488-101953856
CGCCTTTTGTGCCGGGCTGTGGCTCGCTATCGACATCTCGTCCGTTACCAAGGCTGGGTTTCCTACTGATTTCCC
TCCTCCTCTGCTTTCACAGGCTCGCGCGGCCGGACATTGTGGGTGTGCGTGCTGGATTTCTCCCGGATGCTCTCC
GACTAACATGGATGTCCCACCATTCCTTGCAGTGGAAGGTTGTTCCTTGGCGCTGGTGAGGAACATGCAGCG
ATTGCTAATGGGTTTGGGAAGCGGAGACTCCTTCCTCTCTCTATGACCATGCCGTGATCGTGTCTGCGGTCACCA
CTCGACGCATCCTCATTTCTACCCGAACCCAGGAGCCGAACGCTAGATCGGGGAAGTGGGTGCCGTGCG
(SEQ ID NO: 203)

CGI: 318 range = chr6: 108592365-108597232
CGCCGAGTTCGAGAAAGCGCTACGCCGCCGGTCGGGCTAGCTCCACAAGCGGCTGTACAAGTTGGCTGTCAAAAA
ACGCTGATTTCTCCTCCTGTCACCTAATAAACCCCTACGCGCTTATGGCCTCGTCCCACAATCCCCCAATCTCGT
CCCAATTCGAAAAACCGAGGAGGAGGGAATAAACTGAGAGATAAAGATCCCCCCATCTTGCTCTTTCCCCGGGAC
CCCAGCCTTGGTCGCGGCGCCCCACTAAGGAGGACACAGGCTCTGGTGTGTGGTGTGCGAGACCCCGAGCTCG
AGGCCGAGCCAAGGCTGGGCAGAAAGTTGCAATCACGTGCTGTCGGAGCCCACTGGAGCGCACAGCCCGCTCCCC
CTGGGACGCCCAGGCGGAGGACCTGCTGCGCCCTCCCAGGGCTCGGGGACTCCAGCATTCACTTGCACGCACAG
GCGAACTCTGATTGAAAGCCCGGGATGACACCGAGTCTGGAGAAAGAGGGACCGGGGGGTGGGCTGGCGGAATTG
CAGAGCGCCGGCCACAGCTCCCCTCCCCGCGAACGTCGAGCGGAGGGCGGGAGGTGTAACCTCTGACCTCTGGCC
GGGTCCACGCCCTGAGGAGGGACTGGCAAGCTCTTGTTCGACAAGTTCAAGCTGCCGAGAGAGCTTAAATAGAAT
TAATCTCTTAGAGATCGGGGATCATCGCTCCCTCGGCATGCGCTCTCCCAGCGCCGCGCACAGAGCAAGGCGCGA
GAGAGCTCAGGAATCGCGGGAAGGCAAGCGGAATGGGAGGGGGTAGGGGATGAGGGCCTCTCTTCACTATTCCT
CCGCCCGGAGAGCGGGAGCCCGCAACGCCCGCCGAGGACGAGCGGCGGGAGGAGGGAACGCTCTGCCCTCCAGCCGCC
CCGGTGCAGATAATGGAGGCGACAAGAGATTCGCTCAGCGTCGGATGGGCCAGCTCTGCTTGGGGAAGCTGGCGG
CATCCTCCCCTCGGCTGGTGCCCAAACCCACTGCGCGAAGGCCGAAGGAACGCGAACCTCCAGAAGACCCCATC
CTCAGCCCTGACTTTCCGTAGATATGTGCAAAATGAGTAAATTACTCACCTCGGGCCAGATCCAAGTTTTACCCA
ACAGAAGGGGCACCGGACCAAGAATGAACCAACTCACATGGCCATGTCCGGCGGCACAATCACACGCCAGCACA
CAGCCACCCCAATTTCTTCCGCGAATCTATCTGGCACTCTGGAGAGAGGGGAAAAGCGTTTTGAGAAAGCCCCGT
CACCCCTCCCCTTCCTTCTTGCCGTGAAATATACGAATTCATTTTTATTACGAGCCGCACCGTCCTCACCATCAC
GCACGCACAGAGCCACACTCCCATATTCACACTTTCTAACTCGTAAGCTCCGACAGCGCCTGCATTTTCTTTGGG
AGCCGCTTGGAGGTTCATTAATATCATTAGCATTTAACCCCCTCCCTCTTCCCATCCCCTCCCCGCACATGGCTG
ACGTCAGACCCCGCCAGGAGTTGGGGGAAAAGCTAAGTGGGCCAGGGACGCCCTATTCCCCTCCCCGCGGCTGCC TABLE 7B-continued Sequences of differentially labeled CGIs between bladder cancer subgroups relative to blood

```
TGTCAGAGCGCTTCTGGAGATATTACAGGGGACCCAGCCCGCAGCGACAGGCACAAAGTCACGGGGTAATGAACT
TCGGGGACCCTTCGCCGCTGCGTGCGCGGCTCTCCCCGGAAACCCGGACCTGGCCGCCTCTTCCCTCGGAAGATT
TCCCAGCAATCTAGTTTTCCCACTCTGCGCTTGGGTTCCGGCAGCGCGGAGCCCGTCTGCCTCTGAGACTGCGGT
AGTGTTTTCCTTCTTTCCTTGGGAGACCAGCGGTCGGCAGAGATTGCCCACACTCTGCATGCCTATGTAGAGGGA
GAGATCGAAGACTGAGTGACAGGAATGGGGAAAAAGAGGGATTTCGCTCCGTAGGAAGGCCATTTTCGTGTCTCC
ATCTCTGTCTTTCAACATCCCTCTCTTGCTGTTCTTCCTTCTTCCTCAGTCTTCCTGTCCATCTCTCCATCTGTC
TGTCCATGTGTGTGTCCATATCAAGCAGCATTCCCAGCAGCTGCGGTTTTGCAAGAGCCGGGAAGAAACTTAAGG
ATGCTTAAATTTCCACTGTTGGACGAATTCTGAGCGCCCAGGGAGCAGCGCAGCGCGCGACTGACACCCACCTGT
CCCGCCCAGGAGCCTTGCAGGCTGGAGGGCAGCTGGAGAGCGGCGGCGCCCGGCGGCGAGGCGGGCGCTGCCGGC
CGGGACTCGGGCAGCGCCCACCAACCGCTCCGCCCCGGGACAGCCAGCATGAGCAAGCCAGCCGGATCAACAAGT
GGGTACCTCTCGGGCCGCCGTGGGGCCTAGGCGCGCAGCCTGGGGCGAGCGAGCGGGGAGGCTGGGGGAGGTCCT
GCCTGGAGCGCTGCGAATCTGAGCCCCTGAGAGGGATTCCAGCGGGCGTGTGCGTTCGGCCCAGACCTGTAGACC
GTGAGTTGGAGCATTTCGTGGAGAGGGGAGAGCCGTTTCGTTGCCTCTGGATTGCTTGATCCCCCTGTCTGGTG
CGGTGAGAAGGTTACGACCCGCGCAGCCCACCAGTCGGATGAGTTGTCTCCATTTAGCCGCCAGGTGCTGGATGG
GGGGGCCATGGGGGCGGGAACTGGGCCGCAGCTCCAGGCGGTAGCACAATAACACACTCGCTCAAAACTCCGAGC
TCCAGCGCGCAAAAGCAACTCTGTGCAAAGCGGATTTTGAATGGAATGCTTTGCACCCCGTTTCTAGCTATTTCA
AATAATCCTGCAAACTGGGAAGCAGAAACAATTTAAAAGTCACATTTTCCTTAATCCTAAATCCGCGTAGGTCAT
AACTGGGGAATTTAAAGTATGGCGAACCACTCTAGCAAAGAGAGGACCAAATCCCTAATCCCAAGGACTTTTCGA
GCCGGAGCCCAGCAGAGGCAGGAGTGCGCGGCCTGCTCCCTCCGTGCGCTTCTCTCCTTCCTCGAACTTCCTTAG
CTGCCGGCTCTCCGAACGCCAGGCCGCAGCTGACCTCTCACCACCCCGAGACTCACGAGCGCAGGGCTAAGTGTG
TGTGCGAGGGCATTTGCTTGCACCCTGCCTGCGGAACCCAAGAATGTGCAGGCCCGAGCCAGCGTTGAGCAGGCG
CGGTCACGGTGCTCAGATCTCCCGGGGGCATTTCAGTTCCCGCCATTGGCCCACGGCTGCGGGCTCCAGGG
TCTGAGGCTGGGGACTACCGTTGCCGCCGCAGTCCCCATATCCCGAAGTTGCCTTGCTGCTTGTGTTGTTTTCGC
AGATAGCATTTTGGCGCTCTGTGCGTTCCTTCCCTCCCCCTCCCCCTTTCACTCGCCCTCATTGTCCTGAGTCT
TTGAAAGTTGGGAGAATCGGAGATACTTCTGAGGACTGGTAATGAAGTCTCACTTAAGTGGGATGCAATTCCCGC
CCTCCTACCCCCCTCCAAGAAGGAGGTTGTGTTTTCATTTTGTTTTGCTTTGGGTGCTGACCTTTAAAAATTAG
AGCAAAATGAACGTGAACAAAAAGAAAAGGAGAAATGTTTCGAGCTGGGGCAGAGGGAGCAGAGAAGGAGCCCTC
ACCGCGGCCGGAATGCAGAGCGGACCCTGGCCCAGGACTGGGTTTCCCTTTAGGCTCGGGCCTACCCTGGCCCTC
GCTGTTGGAATCTCCAGGAGGTAAAGCGACCTCGATTTTTGTTGCCCGCATTCCCGGGCGTGAGTGTCCTTCCCA
GGAGGCTCAGGAGGCCGTTTCTGTTGCATTCTGAGCCTCCGTTGCAAAAACTGAAGCCCGTGGGTCTCGGCAGGC
CTCCTAGCTCGCTCGCCCCGGGACAGGCCCTCGCCTACACCCCTGGAAGTAAGGAGCCCCGGGCTCTTTCGTCCT
TTTCGGGGTGTGGAGCCCCTGGGGCCCTTGAAAGGTGAGGCCTCAGAGGCGAGGGAGGGGTGAGCGGGGAGCTCT
GCCCGCCTGCGGCTGCGCCCCGCTGTGGACTAGGAGGCAGGCCAACCCTCCGGACTTTGGGGGAAAAACCACAG
CGGGCTCCTTGCGGAAACTTTGGCCGTTCTAACTTGCCAAGAGCCTGAGTGAGGCCTTGGAAGCCTCCAGCCCCG
GCTCAGGTCGGGACGCGGCTGCTGAGCTTTCTCAGGCCCGCAGGACAGCGGCCCCCGCCGGTGGCCGCCGCTGCAT
TTAGGCCCTTTCCAGACCGGTGGCGGCAGCCAACCCGAGACTTGCGTCCCTCGGGCCCGGGGCAGCTAGGAGGTC
GGCGCGCAGCGGGCCGGGTCAGGACTGGGTCGAGCAGACAGAGCTGCAGCCCCCGCCTTGCCCGGCTTCTCGCGG
CTGGAGAGCAGAGCGATGTCACCCGGAGCCCCGCCTGGGTGGTAACGAGACCCTGGCCAGTCACCCCTGCAGCCC
AGACTAACTTCTTTCAACAGCCTCTGATGGTAATTACAGTAATCGAAGCTGCCATATATCTTTAGGCAATTATGA
CACACAAAAAGCCCCGAGGGGACCCCCTGGCGAGGGAAGTTAAGAACGGTTTTCCAGCTTCAGGAAACTCCGGCT
CGCCTCACGTCGGAGCTCGCTCGGCTTGCTAAATGAGAGGAGCTTTGCAACGGGGTCAACCAGCTTGTCTCGTGA
CCCCAAGTCACCTTAACGTGGCTGGGTGGCGGAGTCTGAGGCACAGGCCCGCTATGCCCCGGAATTTTCGCGTCC
CTCCCTCCTGGGCCCGCCCCAGCCCGGTTGCCTGTTTCTAATCTGCCCCGGGAGCCGCGGCTCAGAGGTCTGCT
CAGAGGCAGGACTCGCACTGGTGGTGGCCTAGAGGGCAACAGTCCGGAAGCTCGGGCGGGGAATCCG
(SEQ ID NO: 204)

CGI: 38 range = chr6: 126122028-126122524
CGCGGTACCTGAGCTCCGTGGAAGGCCTGGACTCCTCGGATCCGCTGCGGGTGCGGCTTGTGTCTCATCTCAGCA
CTTGCGCCACCCAGCGGGAGGCGGCGGCCATGACATCCTCCATGGCCCACCACCATCATCCGCTCCACCCGCATC
ACTGGGCCGCCGCCTTCCACCACCTGCCCGCAGCCCTGCTCCAGCCCAACGGCCTCCATGCCTCAGAGTCAACCC
CTTGTCGCCTCTCCACAACTTCAGAAGTGCCTCCTGCCCACGGCTCTGCCCACGGCCCACGGTTGCCCATG
CGGATTCAGCCCTTCCGAATGCCATCCACGGGCAGCGTCGCCCCCTGCGTGCCACCTCTCTCCACCTCTCTCTTGT
CCCTCTCTGCCACCGTCCACGCCGCAGCCGCAGCAGCCACCGCGGCTGCACACAGCTTCCCTCTGTCCTTCGCGG
GGGCATTCCCCATGCTTCCCCCAAACGCAGCAGCAGCAGTGGCCGCG (SEQ ID NO: 205)

CGI: 270 range = chr6: 166499964-166503413
CGTCGCCTCCCGTTCAAGCAGCGTCCCTTCCCACAACCCCCGTGCAGAAGGCGCAGCGCGGCCCCCTCCTCGCTG
GTCCCAGACCTGGCGGGCTCCTCACACCTACCTGGCCCCCTCCGTTGAGCTTGTTGGTGAGCTTGACTTTGCTGA
AGGAGACGGGAGCCTTCATCCAGTGGGCCCCGAAGTTGGGCGAGTCGGGGTGGATGTAGACGCAGCTGGGCGCCT
GCGGCTTCCGGCTTGCCCCCCGGCACCCATTCCCCGTTCACGTACTTCCAGCGGTGGTTGTCCGCCGCCACGAAGT
CCAGCAGGAAGGAGTACATGGCGTTGGGGTCCAGGCCAGACACGTTCACCTTCAGCACCGGAAACATCCTCCTGG
AAAACACGGGGCGGGCGCAGGAGGACCCCGACACTGACCAGGTAGGCCGGAGGCAGAAGCTGGGCACAGAGGCCT
CAGTTATTTCGGGGCACAGAGGAGCCCCTGGGGAACGTCCGAGGGTGACTCCCAAGCTCCCCCTTCCCCGAGCC
CTGCCAGGTCCAGGTGGCCTCCTCACCATCTCCACGGCCTGGGAGGGAGGGAGGAGGACCTGGCGAAAGGGT
TTCAGTGCAGGAGGCCACATCCCGCGGGACAGGCGGGGACCAGGGCGCGCCTCGCGGGTCCCGGGATGCCTCCG
AGGTCGGGACACCGAAGTGCGCGTTCCTCCTCCCAAGCTTCCGCGGAGAAAGCCCCAGAAGAGGGGCTTGTAGA
AATGCACTCGAGGGAGTTAACCAGAGCGGGAACAAACACAAAGCCCTCCTCCAGGAGAAAAAGGGTTCGACCTCC
GGGAACTTGCCAGGTCCCCCAGGCTGCCCAGGCGCTGGAGAGCGCGGCGCGCGGGCTCCGGACGCGCACCCAC
CTGCCGTTCTTGGTCACGATCATCTCATTGGTGAGCTCCTTGAAGCGCAGCCACAGCTCGCTCTCCTCCAGGCCC
ACGCGCAGTTCGCGCTCTGTGGGGTCGCCCTTCTCGCTGCCCGCCTGCAGCTCATTCTCCACGGCGCTCAGCAGG
TGGTCCACTCGGTACTGCAGGCTCTTTCCCGCGCTCTCGGTGCCAGGGGAGCTCATCCTCCCGTCCGGCTCCCCT
CCCCGCGTCCCCGAAGCCCAGACTCGCTACCTGAGATCCACCTTCCCTGCTCTTGGCCGCCGCCCTTCCGAGAA
AAGGGGCCCCTTGGACCGAGACCTGCGACGGCTCCCGGGTCCCGGGTCCCGGCACAGACCCGGGAGGAGGGCGCG
GACCAAGACTTGGGGGAGGGACGGGGCAGAGGGGTGGGAGAAGTTATTCCACTTGAACTCCCCAAGGCTCT
ACTAGTGTAGGTCTCTGGGGACCGAAATTCAGTGCCCTCCCCATAAATAGAGCCGCGGCGGCAGCGCTGGGGTGC
TCGGCGGATTGGGCCGCGCACGCTTTGAAGTGCCGGGCAGCCTCCCATTGGCCGAGAGCGGCCATATCAGACCCA
GCCGGGCGGGTCTGGGAGGCCGGGGGCCAACAATGGGCTCCCGCACGCCTGTTTCATGTAAATCCGGGGCCCCAG
```

TABLE 7B-continued

Sequences of differentially labeled CGIs between bladder cancer subgroups relative to blood CCCTGCGAGCCCCGGCCCAGCCCCTACACCCCCGCCCTTCTCCAAATGTTTGCACCTCCATCAAAGCGGCGGGGC
AAGCCCCGGAGGAAGGTAAGCTGGACGCCCCGGCCTGCCCCAGCCCGCCCCAGCCCGCCCCAGCCCGCACTTCCG
CGAGGGGCTGCCCGGCAGCCTGCGATGCTCCCTGATTCCCGCGCGGGGTCCTCCTCGCTTTCCCAGCGCGCCCGG
ATCCCGCAGCCGCGCCAGGCTGGAACGTTCGCGCGGCCTCACCTGTCCCCGCTCCAGGCGCGCCTCCCTCCCCTC
CCAGGGACGAGCGCATTTGGCCGGGCTTTGGGATGCGCCGCGCTCGTCTCGCCGCAGTAGTAGTGCTGTTCTCGC
GCCTCCGATGCCTCAACTCTCCAGTCTGGCAGTTTCCGGTGCACCTGTCCCCACACGTCCCTCGCCCACGGAGCC
CCAGGCGGCGTTACGCACACCCAGGATCGTGGATCAGCCTGCCCCGGCGTCGGGTGTCCCCGCGGCTCTCACCAT
CTGGAAAAGGAAGGTCCGCGCGCAGAGAGGGAAATGGACGGAAATAAGCAAAAGCAAAACAACCCCTTCTGAGAA
GTGTCCTCCTCGCTCTCTTATAAAAACAGGACTTGTTGCCGAGGTCAGCGCGCGCATCGAGTGTGCCAGGCGTGT
GCGTGGTTTCTGCTGTGTCATTGCTTTCACGGAAGGTGGGAGAAGGTCGGGGCTGGCGGGGTGGTCCGGACTAGT
GGGACTCGGGGCGCTTTCCCCGCCCGGCCCAGCGCCAAGCGGTGTCGGCAGCGGTTGTTTTATTACCTTTCGGTG
AGAACTTACGCGAGGAGAGCGAAGGAGAGGTGACAATGAGCAGGAAATAGTTCAGTGGGGTCTCTTTAAACAGTA
ACATTCCTCCTAAAACGGGAGCCCAGGAAGGGGGAAGGAGGCAGAAGCTCCCCCTTCCAAGGCCTGGCTTTGCGC
TTCTGCACACCTCGCCCATTCGCTGGACGAGGGCCTGCCTCGGGTAGCAGCCTCTGTTTCCCGGTCTCCTGAGCG
GGCACCCCAGCCCCAACCCCTCTAGAGAAAGCCTGCGCATCGGGTGGGGCAGCGAGTTCAGAGGAGTCTTGCGCC
CTAGCAAGGGGGCTTTCCCGCGGACATGGTATCTGCGCCCCGCGCTAAGTCTCCCCTGCCCCCTGCCCCCTGCCC
CTCGCCCCTCGCCCAGCCGGGCTCGCTCCGGGGTCGGGAATTGCTGGGGAAGCCGAAGGAGGGATCCCCGCCCGG
GACTCGAGGGATCGACCCGCCTCGCGGTATGCGGAGGGCTGCAGGGACGCAGTCCCGGGGAAGGGTGCCTGCCGC
CCGTGGGGACAGGGCTCCTTCTCTCCCTTCTCCAACTTACACCGACGAGTCAGGAAGCCGGAGCGTCTAGTCCC
TGTCCGCATTTCTCAGTGTCTTTTGATGTCTGGGATGCATGGATATTCCCAGGGGGCTGACCCGAGGTGGGGAAG
TTTCCTTCTAGAAAGAGGCACCAAAAGGACCTCATTTGCTCCTGACGCCGGACCCTCCTGACACGCCTTCACTGG
CTCATCGGGTCCTGGGCTTTGGGGGAGAGCGTGGTGCGTGTTACTCTCCTTACTCCGGGTATTAAAATGTCTAAG
AGGTCATCGCTTTGGCCCAAGGCCTCCCGAGGATAAGATAAAAGGGAAAAGTGGAGGGGAGGTGAAGGAGGAACG
AGGGTGGGTCCCAGGCAATTGAGGGCCTCGGAACCCTAGGCACGGGAGCGAAACCTCTCCTGCGGCTTCAGGGCA
AAGGAGTCCCGAAGGCTGGATCCCTCCCCTGCGCTCGGACGGCGTCGCGGCCGCTTTTCCCACAGTCGGGAAGCG
(SEQ ID NO: 206)

CGI: 25 range = chr6: 169801163-169801511
CGCGGCCGGGTTGATCTCCAACACGGCAATCTTCCCGCCAAAGAGGGAGGCCAGCAAGCACAGCACCTGCAGGGA
CGCGGTTTCAACATCGTTAGCGACACCACCCAGTAAAAGCAGACGAAACGTGCATCCGCACACGTATCCTAACAG
CTGCTTCATTCTCATAGCAGCGACATCGCCCTGTCACTCCTAAAACGTTTTTACACACAAAATCCCGTTTACTCA
GCCAGTCGTTACAGGATCACTCTGAAGAAAGAAGAAATCAGAGGCACGTCTCATAGACAGGGAGGGCCGCGTCTC
AGGACTGACCTTTTGATCCGCAGTGCGGTTCCTCAGGGCACACGATCCG (SEQ ID NO: 207)

CGI: 40 range = chr7: 1029023-1029492
CGCATACGAGTCCAGGGGCTGCTACAAAGCGCGGCGACGTCTCCGCGGCGAGCTGGCCACTCCATGGTCCCGGCG
CAGACACTGGGGCAGGCGCCGGCTCTGTCGTCGAGGCGCTCACAGGCAGGCACACGTGAGCTCCTGGAGGACAGG
GAGAGCGGCCGCCCCGCCCCTGCGGAGCACAGGACGCTTCCTGCCACCCCTGCAGAGCATGGGACGCTTCCTGCC
ATGGTGCCGTGGCAATGGGTGGCACCTGCCTGTGGCCCCTTCTCAGAAGGACGTTTTAAACGCGTGAGGTCTGAT
GCACAGCCACAGGGAGACACAGACGAGCAGATGTGGGCATCCGAGTATTTACAAGGTCTGGTGGCTCCTGCAGCC
GCGACACGGGCTGAGCGCAAGTGATGTGTGAGGTGTCCCCAACAGATGGCACGGGGAGCGCCCACACCCGCCACC
GCGGGGTCTGCGGAAGCTCG (SEQ ID NO: 208)

CGI: 26 range = chr7: 19113449-19113833
CGCTTCTAAACCCAATACGCTTTTCTGGAGTCCTCGGAACAGCTGGCCGGGGCTTTTAGCACACGGGACGGGACC
TTCGCCTTTGCCTGTTTTTTTTCGACCAGGAGAAGCAGGTGCGAGAGTCTGGGGCTTAGGAGGTGGAAGGCGGG
GAAAGAGAATCCACTAGGTCCTCGTGTAGAGAACAACAGTCGCTCTTAGATATTACTCCAGGACGGAAACCTGA
TTGCAAACCGCTGTTCCTTCGAAACTTGCAAAACCCGGAACAGAAAACTCCCGCCCAGCCAATTTTAGCTCTCGC
TGAACTCTCCCGCCTGCGTTACGTTTGCACAGCAACTCTTTGTAAATGTCCGAGTCCTCTCGGAGGAAAGATCGT
TAGGGCGACG (SEQ ID NO: 209)

CGI: 207 range = chr7: 27149139-27152087
CGAGAGCCGCGTCCCCGCGGTCGCGTGGATTTAGAAAAAGGCTGGCTTTACCATGACTTATGTGCAGCTTGCGCA
TCCAGGGGTAGATCTGGGGTTGGGCGGGCGGCGCCGGGCTCGGCTCGCTCTGCGCACTCGCCTGCTCGCTGCTGG
CAGGGGCGTCCTCCTCGGCTCCGGACGCCGTGCCAACCCCCTCTCTGCTGCTGATGTGGGTGCTGCCGGCGTCGG
CCGAGGCGCCGCTGGAGTTGCTTAGGGAGTTTTTCCCGCCGTGGTGGCTGTCGCTGCCGGGCGAGGGGGCCACGG
CGGAGCAGGGCAGCGGATCGGGCTGAGGAGAGTGCGTGGACGTGGCCGGCTGGCTGTACCTGGGCTCGGCGGGCG
CCGCGCTGGCGCTGGCAGCGTAGCTGCGGGCGCGCTCTCCGGAGCCAAAGTGGCCGGAGCCCGAGCGGCCGACGC
TGAGATCCATGCCATTGTAGCCGTAGCCGTACCTGCCGGAGTGCATGCTCGCCGAGTCCCTGAATTGCTCGCTCA
CGGAACTATGATCTCCATAATTATGCAACTGGTAGTCCGGGCCATTTGGATAGCGACCGCAAAATGAGTTTACAA
AATAAGAGCTCATTTGTTTTTTGTATATGTGCTTGATTTGTGGCTCGCGGTCGTTTGTGCGTCTATAGCACCCT
TGCACAATTTATGATGAATTATGGAAATGACTGGGACATGTACTTGGTTCCCTCCTACGTAGGCACCCAAATATG
GGGTACGACTTCGAATCACGTGCTTTTGTTGTCCAGTCGTAAATCCTGCCTGATGACCTCTAGAGGTAAACTCGT
GCACTAATAGGGGAGTTGGGTGGAGGCGAGGGGGGTGGCGCGCGCCCCGGGCGCGTGCCCGCCGCAGTTGCC
GCCGTTCAGCCGGACTCGAGCGCCACCCGCTGGAGGCAGGGCTCATCGCCCAGCTTCCGACCGGGGCTGCAAGG
GCCGGGGTCGAATTGAGGTTACAGCCCATTATGGCAAAATTATTGCATTTCCCTCGCAGTTCCATTAGGATGTAC
CAATTGTTAGGCCGTCAGCTGCCGATCGCGCGCCCGGCGAGGATGCAGAGGATTGGGGGAGGTGGTGACTTGCA
TTTTATTTACAACAACTTTATTTCCCCGTTTTGCAGCCCCTCTTATTTTTGTGTCGAGGTTGGGGTCGGTACTG
ACCGTCCTGCCAGCAGCTCTGAATTTTGAAAATACAGATATCACCTTCGGGGAAGGGGGAAAGCCATTTAGCCAA
TTGGAGAAATAAATCCTGCCCGCAGCAGCAGCAGCTACAATTACGGCTCTGTTTTTGCGAGCGCATGAGGGACAG
TGTCCCTGCCGCTCTTAAATGACAGGCGTCTATTAAAGATAGCTTTTGTGTAGTGTTTCTCCAAGGCGAGGTCAA
ATTCCATACACTTTTATAACCGTAGTCGATTTTTCTTTCGTGTGTGAATATGAGTTTTCATTAGTTTGCGATT
TGATTTGCTTACGTATCCAGCCTGGAAAATCTTCATCACAGGGTCCGGTTCCTCGAGCCAGCCGGGCCCAAGTC
GGAGGGTTCTCCTTGAACCCAGCGAGTGGGCCCAGGCTCCCTGCAGCCACAGAGGCTGCCTGGGGTCTGGGATC
CGTGGGGCGGGTTACTGGGGTCTTGCTTAGACCTCCAGGAGTAAAATGAGGGCGATAATGGAAGCATTCCTTGGC
AGTGCCTAGTATCTCTGTAGTTATTTTCCACGGCTCCGAAAGACTCAAGTAAATCACAAATATAGCTGAGAGGCA
AGTGGAGTCTCCCCGCTGGAGGCCCGGCGTTGCAGGCGCCCCTGGCACGTCTGGAAGCCAGGACTCTGGCGGCTC TABLE 7B-continued Sequences of differentially labeled CGIs between bladder cancer subgroups relative to blood CCATGGCCCTGGGCCCCTCGTTGGGTCCTGAACGCTGCTGTGGCGGCGACGCGGGCGCTATCGGAGGCTGGGAGC
GGGAATCCGGAGCCGGGAGCCTACCCCGGGCTGTAATGTTCCACCCGCGCCCAGGTTAACTCGCCTCGGCTGAGG
CTGCTTCTCTTCCACTGACGGTTGCACACGCGGGACCGAGAGACTGGGCTCTGTTGGGGCCCCCTTTGTTCCTCG
AGCTTCCTTCCTGTTCTGGGAGGCGGCTTGGGAGGCCGCGACAAGGCCGGGCTCCAGCTCTTAGACCCCCTCTTT
CCACTGGCCAGAGATGATTTGATGATGCCCTTCGGGACTTACTGGCGGAGGGACTTAGGCAGAGACGCCCAGACAC
GAAACGGGGCTCGGCCCAGGGGCTCTTTCCTCCCCAGCAGCCCCGCGTCCCGAGGTCGGGGAGCTCAGAGACACTA
GCACAGGAGCCCCAGACGCATTCAGGGCGCACCCCAGAACTCCGGAGCCGGTTTGGGCATCCTTGTGGAGCGGGA
CTGGGTGTGTGCAGTGCGCCCCGCTCCACCGCTGGTATTGGCTGTGTGTGAGGTTTTGTTTTGTTTTGTTTTGTT
TTGTTTTGTTTTGTTTTGTTTTGTTTTGTTTTGTAAGAAATAAATGCACAGACGCTTGCAAAGCTCCGGGCTCCCCTGAA
GCTGCGGAAGCCCCCAGATGGGAGCAGGCGGGGAGAAAAGTTGGGGAACAGGCGAGGGCAAGGGGGCAAAGCCGA
AGGAGGTTGCAGCGCTGGCCTGGTCCCTGCCCAGGCATCTACTCGCCGCCTTTGCCTCTGAGTCCTCCCCGCTG
GGCTGCGTGGAATTGATGAGCTTGTTTTCCTTTTTCCACTTCATGCGGCGGTTCTGGAACCAGATCTTGATCTGG
CGCTCGGTGAGGCAGAGCGCGTTGGCGATCTCGATGCGGCGGCGCCGTGTCAGGTAGCGGTTGAAGTGGAACTCC
TTCTCCAGCTCCAGTGTCTGGTAGCGCGTGTAGGTCTGGCGGCCTCGGCGCCCATGGCTCCCATACACAGCACCT
ACGAGCAGAAACGGCCGGGCGCCG (SEQ ID NO: 210)

CGI: 201 range = chr7: 27170441-27172987
CGGAGCTGGGCAAGCCGTCAGGGCGCCCTAAGGCCGCTGATCACGTCTGTGGCTTATTTGAATAATCTGTCATGG
GGACCCTTGTGGCCCGGGTCGCCCGCAGCCTCATCTTGGCAGGATTTACGCCGCCACTGGCCGAAGGCAAGAAGT
GGAAGGAATCGGCCGTCTCCCCCAGCGTCCCAGCTCCGGCTGCCCTGGCTGCCGCCGCTCACGGACAATCTAGTT
GTACAAAAGGCTCTCTGGGCTGCACTGCTTTCGAAGAACGGCCCAAAGTATCTCGGTCCTGGGCCTGGGCAGCCA
AGGAGAGGGGCGGCCAGTCTTGGCTCGTCCCGAAGTGCCCGCCCCGCCCCCTCTCGCTGCAGCAGCCGCCTCCTC
TCCCGTAGCCCTGCGGGCCGCTCTTCACTGCTCTCCAGACTTGGGGCCCTATCTGAGGCGTCCCAAACACCAACT
TCTGGCTCCTGGCCCCAACTCGAGAGGCTTCCAGCGAGGACGAAGGCAGGCTCGAGAGAAACCTGGCGGGCCAGC
AGATCCGGGAGGCCGGCGTGGAGGCGGCGGCGGATTTGAAGGGAGGAGACACTTACTGGGATCGATGGGGGGCTT
GTCTCCGCCGCTCTCATTCTCAGCATTGTTTTCAGAGAAGGCGCCTTCGCTGGGTTGTTTTTCTCTATCAACTGG
AGGAGAACCACAAGCATAGTCAGTCAGGGACAAAGTGTGAGTGTCAAGCGTGGGACAGTCACCCCTTCTGGCCGA
CAGCGGTTCAGGTTTAATGCCATAAGGCCGGCTGGAGGGCAAGCCCGCGAAGGAGAGCGCACCGGGCGTGGGCTC
CAGCCAGGAGCGCATGTACCTGCCGTCCGGCGCCGCCGCCGCCACGGGCGCCTGGGGGTGCACGTAGGGGTGGTG
GTGATGGTGGTGGTACACCGCAGCGGGTACAGCGTTGGCGCCCGCCGCGTGCACTGGGTTCCACGAGGCGCCAAA
CACCGTCGCCTTGGACTGGAAGCTGCACGGGCTGAAGTCGGGGTGCTCGGCCAGCGTCGCCGCCTGCCGGGGAGG
CTGGCCCAGGGTCCCCGGCGCATAGCGGCCAACGCTCAGCTCATCCGCGGCGTCGGCGCCCAGCAGGAACGAGTC
CACGTAGTAGTTGCCCAGGGCCCCAGTGGTGGCCATCACCGTGCCCAGCGCCTGGCCCGCCCGGCCCGACCCACG
GAAATTATGAAACTGCAGATTTCATGTAACAACTTGGTGGCACCGGGGGGGGAAGTACAGTCACCTAATAAGTTGC
CGGCGCCCGCGCCCCATTGGCCGTGCGCGTCACGTGCCCGTCCAGCAGAACAATAACGCGTAAATCACTCCGCA
CGCTATTAATGGTCCGATGTTTTGCAGTCATAATTTTTATAGCAAAAGCCATATGTTTTTATGTAAAGGGATCGT
GCCGCTCTACGATGGGGTTTGTTTTAATTGTGGCAACGACGATTAAAAGATCAAATCTAGCCTTGTCTCTGTAC
TCTCCCGTCTCCCCCCCCATACACACACTTCTTAAGCGGACTATTTTATATCACAATTAATCACGCCATCAAGAA
GGCGCGGGTCCCGTGCGAGTGCGGCCAGCGGAGCCCCTCACATAAAATTAGACAATAATTGAAGCCATAAAAA
AGCAGCCAAATCGCATTGTCGCTCTACTGTATTTAAATCTATATTTATGATATTTCATAAGGAGTTATTGTTTCA
GAAGCCACACAGGCTGGCGGGAAGTCGGAAACGACCAACAGATTCGTTTGCCTCGCCGTGGCTCCCAGCTGTAAA
AATTTACGAGGACTTGGAAAGGTTAGACTGTTGTGTTTGGTTGGCGAGCTCCCTGTAAATAATCCCTGCGGTCCC
CGGGAGAGGCGAGTTTACCCGCGGCCGCCCTCGAAAAGTCAAATTCAACGCAGGATTCCGTCCCAAACGGAGCCGC
CGCCGGCCCTACCAGGGCACTCCAGGCAGGGACCGGCCGCTCAGGGAGTACCGCGGGTGTAGGTCCCCACAGCTA
CCCGCCTGGAGCGAGGGGCGCCCGGGCAACCCTTAAATTCGCCTTTGCTACGAGGACCCCACGGAGGAGCTGGCC
AGGAGGGAGCGGCCAGCCGCCACCAGGGCGAAGGTTTTGAGGGCCTGGTTGGTTGTGCGGCGCGCTCGGTCCCCG
GCCCTCGACCCCACGCACACGCGCGCCCAGCCCGCCTTTCTCATCAGCTGGCAATCAGGATTCCCAGGCGCAGGC
GGCTGGCGACCCAGCCCTGTGCTCCAGCCTCAGAGGCTCTAACCATGAGCGCTGCAAGCCTGGTTGCGCTCCGTG
AATCCCAGCTGGGGAAAAACTACAAGTGGCATGAATGGAAGGCAAGTTCGGTTTGGGAAAAGGCAGCCTCGCCT
AAGAGACCCCGCAGCTCCGGAACCTGGGAGGCCCGCACCGATGTGGCCTGTCCCGGGGCGCGTGAGCCTTTCAG
GGCTCCTTCCTCCCTTTCCAGCTGCTACTCCGGGCCTCGCCTTGGTTACCTACGGGGCCCGGAGACTCGGCG
(SEQ ID NO: 211)

CGI: 114 range = chr7: 27198331-27199622
CGGCGGCAGCGATCGGCCCTGACCATAGAGGCGGCCGTGGCGCGGAGGACTTGACCTTTACGGCACGAGAGGAGG
GCGCTGGCTGAGCCGCAGGGAGGGGGACGCTGCTCTCTCCAGCCTCCTCCACCCAATAGCAGTTCCGCTCGACCCA
CGCCAGCTGCGCGCTCACCCCCTTTCCCCCTCCATTTTGTGCAGTGTCCGCAGACCCGCGGCCGGAAACAAAGCC
CCCAGCCCTGCTCTCACCACCCTTCTTGCAAGCTGCTGTCGCCAACCCCCCAGACCAGAGGCTCAGAGCTAACGC
TAAGCCCCTTAAGGCCCTCTCCAGGGCCCTCTTCTCTCGCCAGCCGCCCTCAGCCAGCTCCTGACCCCAGCCGCC
CTCAGCCAGCTCCTGGGTACCACTCTGGGTGCCAACCGGGACCTGCCGGTGCCACGGTCCCGTGCGCCGGGTCCC
GGCCTCGGGCTGCGGCGGCTTCGGGGCCTACAGCCCAGCGGCGGGAGCGTGGCAGAGGCGCGGGGCGCAGCGC
AGCCCGAGGCTGCCTCCCGCCGGGCGGACGGCGCGGCCGCTGGGTGCACAGCGTAGCCCCGCGTGCCCGGCTC
GCTCTCCGTTCCCTCGGATAGCTCCCACCGCTCGGCTCCGGGCTCAGAAAGCGGAAGTATTTGGTAGAGAAAAC
ACGGTTTCTTTTCAGCTCGTCTCAAAATCCCTTTTAGAGAAAATGCTTCCTGTCAAGTTTTATTTCCCGTTGCAAA
CCACCTTCCACGCTGCCAAGAATTAAGACCGGGAGAGATTAAATACCCGATTATTCTCCTGGGGAGGGCGGGGCG
GGGCCGGGAAGTGGGCACCCACACCAAACATTCCTTGAAGTAGGCTTGTCCTGATCCAGCGCGCCCGGGGAGCC
CCACGAAGGCCCGCGCGGCCTGCGGTGACGTCAGCCTGCAGTTGCGGGCCACTCACCCGCACAGACACGGCCCT
TGCTGTTCCGCGCCGGGACCTCCGCCAGCCGTCCTGCCGCAGCCCCGACTGGCCCGCGTGCCGTCAGAGGGAGGC
CCGCTTTACACCGGCCTGAGCCTCCATTTTGAGTAGGGGGTTCTTGTAGAAGCGTGGAGGGTTTGGGGCGCGCC
TCTGTCCCCGAGGGGCGCGACATCAGGTAGCTCTCCGAGTTCACACCCCAGTACCTGGGGAGGACCTATGTCGC
CGCATAACCGCCCGCAGAGGTTTGGAAATCTCTGAGACCCGTTGTAATTATTTCTGCCCAGTGGATCCGGCTCTT
CAGCGTCACGAGAGCCG (SEQ ID NO: 212)

CGI: 111 range = chr7: 35263447-35264743
CGGTTTCCGGCTTTTGGACAATGGTCCCTCGCTTAACGAATGCTAACGAATGCTCCCTTAGCTGGGAGCTGCAGG
GACCGGTCCCGGCAGGTCTAACCAACCGTCCGCAGGCGCCGTGGTCGAGAGCAGAGCCGAGACGGCGGGGCAGGG
TGCCAAGCGGAGGGCACAGCCTGGCAGCCACCGTTGGCGGCAGGAGAGAATGGGAGAAGGGAGACCCGCTTCTCA

TABLE 7B-continued

Sequences of differentially labeled CGIs between bladder cancer subgroups relative to blood GCACAAGGGCATCTGTCTACTCCCGAACATGGCCGGAGATTCCTGTCCACAGCCTCCCTCCAGCTCTTTCTGGTA
GACACTTTAAAAGCGACATTAACGGGCTTCGGTGCCTTTGGATTCCTAAATTAGGTTTACGGAAAAGGAAAGACT
TCCCAAGAACAGTGAGAAGAGGAACTGCAGCCCCTCCAAGGCCGCTGCGGCGCGTTCCCGGGGCGCGCCGAGAGC
AGCGCGCGGCTCCGTGCCCCGTGGGGAGCGCGCGGCGCGGCCTTGGATTTCACCGCGAGTCGGGAGGGCGGGTCT
GAGCCTTGCCTCCCAGGATCCTTCCGACGAACACCCCGCGGGTTTTAGTTTATCGAGCCAAAGTGGTCCCGGAGA
AGCGCTCCCTCGCAGCCAAGCTGCAAGAAGTGGCCGGGAACCTACAGGCCTCGGGCCGACCCAGGAAGCCTCCGC
ACCAGAAAGCTCGAGGAGCCCTTACCCAAGTCTTGCTCGAAGGGCAAAGCAAAGAGCCAGCACCCCTGAGTGTCA
CTGAAGTTCCTGGATGGGGTGTGAGTGCGCGCGTTCCGTCCGAGACCTCAGTCTCGCCCAGCTATAGAGCCGATA
AAGGGATGTCTTGTGGGCGTAAGGCGCTTCGCGCCCATCTCCAAGGCCGATGTGGTCAGGAGGTGAGGGGAAATG
TCCTTCTGGCAGAAGCCCGCGGTGCTGCGACGTTGACCCGCCTGGCCTCAGGCTCAGGGCGGCGGGCAGCCCAGG
GCACATGTAGTTTCAGCAGCCGCGCTACGTGGGCGGGGGACCCCAGGCCACCCCACGTGTCCGCCCTGGGCCTCC
TCCGGGTCCCAAGGCGCGGCGCCTCCAGGCCTTGTAGCGTCTTCCCCGGGTCCCCGCGCGCCAGGCCCCGCAGCC
TGCTCACAGGACAGCCCTCGGGGCTGCGACCCTCTCGCTCCTCCCCGCGGCCACTCGCTCCCCGTTCATCCCCCA
CGAGCTCACTACCGCAGGGACCGGCCCTCAGAGCCCCGGGCCTCCTCCCGGCAGTGGAAGAATCAGCGTGCTAAC
ATTGTGTGCAAAACTCGCAGCG (SEQ ID NO: 213)

CGI: 30 range = chr7: 96469320-96469736
CGAGGGCCTTGCCCGCCCTCCTCCTCCCACCCGCAAGGGTTGGCCCGCGTTCCCCTGCGGGCGAGACAAAGAAGC
AGGAGCCAGGACCCGGCTGGCGCCTAACCCGGCGCCGGGGCCTTGAGCCCCTGAGGTGTGCGCCTTCCTGCAAGG
CCCCAAAGAACCCGAGTTTTTGCCCCTTGCTGAAGGGTTGGAAGTGCGGGCTGGACTAGTGCAAACAAGAGTGAC
TCCAACCGCCTTACTTCAGCTCATTACCGTCACCCATGAAAACGGAATGAAGGACTGGGAAGCCAATCTGCCGCG
TTCAATTGGAGAGAAATGACTGTCGGAAGAGGCCCTGCGGTAAATAGCCTCTGAGCCGCGAACTCTATGCGCCGT
GGCCGGTGGCAGAGGCCACACCTGGCAGCCACTCGTGGCGCG (SEQ ID NO: 214)

CGI: 32 range = chr7: 119702299-119702721
CGGAAATCATCGGCGACTGCTGTTATGAGGAGTACAAGGATGCAGGCGAGAGAACGCCGAGCGCCTGCAGGACG
ACGCGGATACCGACACCGCTGGGGAGAGCGCCTTGCCCACCATGACTGCAAGGCAGAGGGTCTGGAGGGCCTTCG
AGAACCCCCACACCAGCACGATGGCCCTGGTGTTCTACTATGTCACGGGGTTTTTCATTGCCGTCTCTGTCATCG
CGAATGTGGTGGAAACAGTGCCGTGCGGATCAAGCCCAGGTCACATTAAAGAACTGCCCTGTGGAGAGCGGTATG
CTGTGTGGCCTTCTTCTGCTTGGACACGGCCTGCGTCATGATCTTCACAGTTGAGTATTTGCTTCGCCTGGCTGCAG
CGCCTAGTCGTTACCGTTTTGTGCGTAGTGTCATGAGTATCATCGACG (SEQ ID NO: 215)

CGI: 42 range = chr7: 158509937-158510390
CGTCCTCCGACGCGAGATGGCTGTGTGCCACCGACTGTCCAAATGCCCTGCCAATGCCATCGTGAAGCATCCGTG
TGAAGGAAAAAGTCCACCTTACCGTGCGCTGTGGCATCGATCAGGCGTGTGGACAGTCGCAGGCACGCAGCGGTC
TCCCAACATCAGGGCACACCGCGATCAGGTGTGTGGACAGTCGCAGGCACGCAGCGGTCCTGCAGCAGCAGGGCG
CACCGCGATCAGGTGTGTGGACAGTTGCAGGCACGCAGCGGTCTCCCAGCATCAGGGCACACCGCGATCAGGTGT
GTGGACAGTCGCAGGCACGAAGCGGTCCTGCAGCAGCAGGGCGCACCGCGATCAGGTGTGTGGACAGTTGCAGGC
ACGCAGCGGTCTCCCAGCGTCAGGGCGCACCGCGATCAGGTGTGTGGACAGTCGGTGGGCACGCAGCGGTCTCCC
AGCG (SEQ ID NO: 216)

CGI: 20 range = chr8: 10624024-10624296
CGCAGGAGGGCTCGGCCTGGGACCCCCTCTGCGGGCCTGCGGCTTTAGCCAGCAGAAAGAGGGGCGTCAGTCCTA
TCCCCAAAGTTCCGCCTCGGGAAAGAGCCCTGAGCTCTGAACTCCGACGAAAAAAGGAAGGGCTCTGTTCCGGAC
CGGGTGGGGTTTGGGAAGGGTAGAGCCGGCCTCGGGTGCCCTTCTTACAGGGCCTGTCTCCCGCTGCGTGCACCA
AGTGCTTTGAAAGTTTTTCGCGGATTAAAACGAATAAAAACCTCGTCG (SEQ ID NO: 217)

CGI: 221 range = chr8: 11597006-11600365
CGAGGGTGAAGGATCGCCGCAAGGCACCGCACCTCCCGCTGCAGCCCATCCCGCACTACTAGGAGAAGCCGGCGT
AGGAGCGCCGCCTGTGTCCTTGGCTGTGGGGAGGACGTCAGATGGCACCCCGCCAGACACTAAGCCCCAAGCCCC
TGGCTTGTTGCTAAGAAAATTCACTGCCCGGTCCAGACTCAGCCCTTTTCGCCCTTTAAGGGTCGCGCGTGGGAG
GCAGCTCTGAGACCCCGGGTAGCGCTGGAGCCACAGATTTCCTCCGAGAAAAGAAAGGCCGGGATAGCTTCCCGC
TCGCCCAAGCCCAGATTTTCCACTCTCCAGGAAGGCCTTGCAGGTCCCTGCCGCAGGCCTTGGCTTCGCGCCTCT
CTCGCTCGCCCCCACGAAGATGATTGCCGGTTTCAAACCGGGAGCAGGGAGTCTGCTTCCTTCTCCGCTGAGTC
CGAAGGATCGCAGATTGGAGCGTGCTCCGGAGACCGCTTTTCCGCAGCGCCGGCCTCCGAGATCCCCAGCACCCC
TTCAGCCTTAAGTTCCCACGTTTCGGGTCCGTGGCGCCAATTCTGCTAAGTAGCAGGCTAGGAATTGGGGGAAGT
CGGAGAAGAAACCCTAAGTGTGTCGCCCCCAGCTTCCGGGATGCAGGCCCGCCGGGGTCTAGAGGGGCGGCTGCC
GTGCGTCCAGCCTGTGCGCAGGCCTTTCGCCGCTCGGCGCCCCAGGCAGCCTCAGTTTCCTTTCCTCTGTTTGCG
CCCCAGTGAACCTCCGCACCTCTCATTCAGGGAAGAGAATTCCCCGCGCAGCCGCGCTCGTTTCTTCCTCTGGGA
TTTTCCTGAGAATCCCCAGGAGTTGGCCACGATCCCATGGGGGGTTTCCTTCTACCCAGCCCCGCGTCCTGGCCT
CGTCCTTAACCCCCGGGTTGCCTTCACTCAGGCTGGGAATCCACGATTGATTTCCTACTACGGAAGCGGGTGGCG
TTCCCAGCCTGCTTTCGGAGCAGCACGGGTTTCGTGCAGGGTGTTATCCCGACCCCTTCCCCATCCCTCTAATC
TGGCTTGAGAAGCCCGTGCTGGAGAGAAAAACGCGGCCTTAAAAAAAAAAAAAAGTTTAACCGAAAGCGTGAGAG
CCACCCGCCGGCTGTTATCTGGGGCTGAAGGCTGCGGTAATCGATGGGTTATTTTTACGCGGTAATAGGGCCCTG
TGATTGCTCTATTAACCTTTAGACCTGTCTGAGGGACTCTCCGGCTCGCAGCCCCGCTGCGCTGGGGCCTCCAGG
CTCTGACGCCGACTCCCAACTCAGGCCTGACACATTCCCCTCCCCCATACCCTGGAAGAGCCCCCTCCATGAAGA
AGCTCCCCTGGACCGCCTGGCTCCCCAGCCCTTGCCACGTCCCTTGGATTGGTGCAGAGCCGCCGCAGGCTGCAG
AAAAAAGGGGAAAGATTAGAAGAGAGGAGGCCACAGGAGATGGGAAGTGTCGCCAGGAAGGGATGCAGATTGCA
TAAATACATAAAATTGAGGCTGAGGCCTGGGCTCCCGACCATCTCCCTGGGATTTTGGGAAGGCAAAAGGGAGGC
TTCGGTCTCTACGCTCTGATTTTAGGAGGCAGTCTGGGTGTCTCCTGAACCTCCAAGGAATCCGGGCTGGGAGG
ATCCCCACTACCCCTGCCCAGGAACTAGCATCCAGCCGGGCACCCCGGGTGACCCAGTGCCCCACACAAGATCGA
GAGTTGAGCCCAAGAGGTCACCTTCTTCTCTACTGGCCCCGCCCCTCGCCCGCCGCTGCGGGATGAGGACCACAG
GAAGGGGGGCGGGAGGGAGAAAGGGAACTCATTAATAAAGCTGACCCTGGGCACCACAGCGAACCCAATCGAC
CTCCGGCTGGGTTGCGGTGATTCCCCGCTCCCTGGCGGTAGCACTTGGGCATTTTCCGCGGAGACCCCAGAGCC
TGGACTTTGCCTGCTGGGGGAGCTTTCCGCACAGTCCCGCAGCCTGCGCCCAGCGGAGGTGTAGCCGGGGCCGCG
CACCCCCGCCCCGCCCTTGCACGTGACTCCCACAGGCCAGTCAGCGCCCTAGGGCCGAGTTGCTGGGCCGGGGAC
CCGAGCCGCGAGCTGGGGACTTGGAGGCGGCCGGCGCAGGGGCCGCGAGAGGCTTCGTCGCCGCTGCAGCTCCGG TABLE 7B-continued Sequences of differentially labeled CGIs between bladder cancer subgroups relative to blood GGGCTCCCAGGGGAGCGTGCGCGGAACCTCCAGGCCCAGCAGGTAGGGCTTTTTTCTTCCCTTTCTTTGCTCCTT
CCCGCGGTCCCCCAAACTCGGAGCTTCTCCGCCTTTGCTTGTCTGGAGGTAGAGAGGTAGCTAGTGGGAGGAAAA
GAGACGTGCGCTACTCACTTCACCGAAATTGCCCAACCCCTGCTCTGCTTTTGACTTTGCCTTAGCAACTTCTTT
AAGTCAAAGTAAGACTTGGGGGCAAAACAGAGAAATATTGGAAGCGCCTTTGGATTCTTTCCGTGTGAACTTGAA
CGCTTTCAATCCCTGTCCCCGTGTGCACATTCTCCAACCCTTGTTTGCATATCGCAGGCCGGGGCCTGGGTGGTG
ATGGTGGCCGCGTGAAGTTACCGGGACTGACGGGCCCGGGACAGGCTGCACGGCAGCTCGCACATGGAGGGAAGT
AGACGGAGGCTTGTCGCCCACCAGCGACTCCGGGGACGCAGGGTGGCAGTGCCAGGCAGCTCCGCTGGGCCTCAG
GGGCCCCCGGGAGCCGCTCTGAGGTGCGGAGAGGCTGCTGAGTGGCGGAACTATTCATGCCCTTTCTGGCCGGCC
TCCTCGCCCTCGGGGCTGGGGTCCAGGGACTGAATGCTCCTCTGGAAGCTCACCACCCCACCTGCCCGCGCTGCT
TCTACCTGAAACTGGCCAAGGGCCCGAGCCCGGACCGGAGCCGTGACTTCCCTCCGCCGGCCACGGGGCTGCCCG
GATCCGCCGGGTTATGTCGCTTGGCTTTGGGCTCAGGGGTCACCGTGGGCAGAGGGGGTGCCGGGGTCGCGGAC
TGCCACCAGGTTGAGGAAAGGAGGGGCCTTTTGGCTGGGGAAAGAGCGTGGTGGGGGACCCGCGGCCGATGGAAT
CCCTGGGGCAGCGCGGCCCGCACCGTGGAGGTTGGGGAAGCGCCTCGGGGAAGTGTTTCCTGTGTTCCCAGAAAA
GGAAGACAACCGAGAGCAGGTTTCAGGCTTTTAAAGAAAGCCTGGGGTGTGGAGGTGATGCTCCGCACACGTCTG
TGTCTCCTCCCCTGCTGCGGCCGGCTTGGTTGTGCCGGCTAGCGTGCGACCGTCCTCCTCGCTGCAGGCCGAGAG
CGGAGGCGTAAACCCAGGCCAGCGAGGAGTGTCCTATAAAGGGACGGGGACTTTTCGGCG
(SEQ ID NO: 218)

CGI: 25 range = chr8: 25955253-25955609
CGTTTGCTCCGCCGTCAGTCCATAACCAGGCGCTACTAAGGCCTCCAGGCTCGGTGCGCAGAGCCGGGAGCGCTC
CTCCAGCTCCAGGTTGGGGGAGTCGGGGTGGGAGGAGGTTCGGGAAATCGACTGATTTAGAGGCTGGGGGTGAGT
AGCCTCGATTTATCATCCCTGATGGTGAGAGTGGAAAAGTGTCGCGAGAGTGACAGATGGAATCTTTAGTGCTTC
GCAAGAGGGAGTTATTAGGCCGCGGGGTTTGGGGGGTACTTTCCGCTTACTTTGTCATTCTCCACAAAGTCCACG
AAGGCCGTCCGCTCGATCTCCACCGGCTGGCCCTGCCTGTCATAGAGCGCCAGGACG (SEQ ID NO: 219)

CGI: 233 range = chr8: 55532724-55535078
CGCTCGGTATGTTCATCTAAACGACCTTGGGCAAGTACGTCGATTCCAAGGTACAATCAGCCCTCCCAGACGGCT
TTTCGAGTCTCCCTAACCCCGGTGGGAGAGGACGCGGCGCCAGAGCCCAGCTCCGGCTAGTTTTCCCGGGGGCAG
GTGTAGCCTTGGGCGCGGGGCCGGGGGAGGGGCAAGGGGCGGGCGTGGGGTTGGACTGGGACGTGGGACTCGGAC
CACGGCCTGGGCGTGGGCCTAACGACGCGGGACCGGCCCGCCCTCGCCGCTCCATTGGCCACATCTGTGCAGAAA
AGGCCCCGCGGCCCAGGGGCGCCCGCAGTGTCACTAGGCCGGCTGGGGGCCCTGGGTACGCTGTAGACCAGACCG
CGACAGGCCAGAACACGGGCGGCGGCTTCGGGCCGGGAGACCCGCGCAGCCCTCGGGGCATCTCAGTGCCTCACT
CCCCACCCCCTCCCCCGGGTCGGGGGAGGCGGCGCGTCCGGCGGAGGGTTGAGGGGAGCGGGGACCAGGCCTGGAGC
GCCATGAGCAGCCCGGATGCGGGATACGCCAGTGACGACCAGAGCCAGACCCAGAGCGCGCTGCCCGCGGTGATG
GCCGGGCTGGGCCCCTGCCCCTGGGCCGAGTCGCTGAGCCCCATCGGGGACATGAAGGTGAAGGGCGAGGCGCCG
GCGAACAGCGGAGCACCGGCCGGGGCCGCGGGCCGAGCCAAGGGCGAGTCCCGTATCCGGCGGCCGATGAACGCT
TTCATGGTGTGGGCTAAGGACGAGCGCAAGCGGCTGGCGCAGCAGAATCCAGACCTGCACAACGCCGAGTTGAGC
AAGATGCTGGGTGAGTCCGAGTCGCAGACCCAGGCGGCCGGGCGCGCTGGCGCGAATCGCTAGGCCGATTTCTTA
AACCCCCAAACTGTTCTTTGCGAGCCTGACGCCCAAAACCAGGGGTGTGTAGCGGCCACGTCCTTTCTTAAGGCTC
TGGGTTCCCTTCCCGCTTCCCGCCCTCCGACCCTCCAAAGCAGCTTTCCGCCTTGCTCTCCGGCTCCCGGATTCC
CCAGGTGGCCGGGGGCGCGGGTCCAACGGCTCTGGGAAGGCGACTTCCCGGCACCTCCGGGCGGCGCGAGAGCAC
CCTTGGCCCTGAACTGGGCCGGTTGTGTCCATCCCTCGACCCCTTCCCTAGTTAGGTGTCCTTTTCTGTTTTTCG
AACGACCGGGTGATGGGTGAGCGGAAAGCCGCTTCCAGGAGACCAAAAGAAAGGGGTGCCTTTAGAGGACGGGTG
TTCCCCAAGGGCTCGGACTCAGGAGTCCCAGATCTCCCTCTTTAACTTCACCCCGGTTGCGCAATTCAAAGTCTG
AGGGGGGAGGTGCGTCCAGGTGGGGCCAGGTGGGGCCTGGAGCGGGAGCGCAGCCGATAAGCCCTGCGCCCCTCT
CCCCCTTCCTTCCACTGTGCAGGCAAGTCGTGGAAGGCGCTGACGCTGGCGGAGAAGCGGCCCTTCGTGGAGGAG
GCAGAGCGGCTGCGCGTGCAGCACATGCAGGACCACCCCAACTACAAGTACCGGCCGCGGCGGCGCAAGCAGGTG
AAGCGGCTGAAGCGGGTGGAGGGCGGCTTCCTGCACGGCCTGGCTGAGCCGCAGGCGGCCGCGCTGGGCCCCGAG
GGCGGCCGCGTGGCCATGGACGGCCTGGGCCTCCAGTTCCCCGAGCAGGGCTTCCCGCCGGCCCGCGCTGCTG
CCTCCGCACATGGGCGGCCACTACCGCGACTGCCAGAGTCTGGGCGCGCCTCCGCTCGACGGCTACCCGTTGCCC
ACGCCCGACACGTCCCCGCTGGACGGCGTGGACCCCGACCCGGCTTTCTTCGCCGCCCCGATGCCCGGGGACTGC
CCGGCGGCCGGCACCTACAGCTACGCGCAGGTCTCGGACTACGCTGGCCCCCGGAGCCTCCCGCCGGTCCCATG
CACCCCCGACTCGGCCCAGAGCCCGCGGGTCCCTCGATTCCGGGCCTCCTGGCGCCACCCAGCGCCCTTCACGTG
TACTACGGCGCGATGGGCTCGCCCGGGGCGGGCGGCGGGGCGCGGCTTCCAGATGCAGCCGCAACACCAGCACCAG
CACCAGCACCAGCACCACCCCCGGGCCCGGACAGCCGTCGCCCCTCCGGAGGCACTGCCCTGCCGGGACGGC
ACGGACCCCAGTCAGCCCGCCGAGCTCCTCGGGGAGGTGGACCGCACGGAATTTGAACAGTATCTGCACTTCGTG
TGCAAGCCTGAGATGGGCCTCCCCTACCAGGGGCATGACTCCGGTGTGAATCTCCCCGACAGCCACGGGGCATT
TCCTCGGTGGTGTCCGACGCCAGCTCCGCG (SEQ ID NO: 220)

CGI: 74 range = chr8: 72916429-72917309
CGGGGCAAGGGCGCGTTCCCTATCGCAGGATCACTTGCTATGGTAAGCCGCCCACCCTGCGCGCTCCTCCGCGCG
GGGAAGAACCTGCGCGGCAGGACGTGGTGTTGGAGTTGGGGCGCCCGGAGCGTGGAGTGGGGAGACCTGATGCAG
AGAGTCTGGAGTCGGAGCTGGGGGTGCTGCAGGTAGGAGCAGGAGCGGGGCGGAGAGGGAGGCCCGAAGAAGACC
CCACACAGGTTGGCGCAGCGGGGCTTGGGGAGGCTTCAGCCCCAGAAGTGGAGAGGGTTGACAGACGCCTGCCTGA
TTAGAAAAAGCCGGGAGCTTGGGAAGGAGACGGGATTGAAGAAGCCACCCGGCAGGGAGGCCGAACGGCCCAGAG
CTCTCCGGGTAAAACCCGCCTGCGGTGATCTGGGAAGTGTGTCTCCACCTAGCCCTGCGAGCAGGGCCTTCCTC
CCGCCCGTTAGAAGGGCGCTGTGCTGGAGTACGAACCCGGCCCAGAGAAGCCACTCGCCCTTCTTTGTCACTTAA
AACCCTGTCCCGACGCGGATCTCACGTCTAGACCTCTGTCTTTAAAGCGGATGTAGAGCGCGTTCTAACCGTTCC
CTAACCATTGTGTCACCGCGAAAGGCCGGGGCTGTGTGGAACCGTCCCGCACGTGTGCGATGAATCTGGCTCCGC
TGAGAACGGATCCGTGGGCTGTCTGGCGCGGGCTGGGGCAGCAGCCGAGAGTTAGTCTACAGAGCTAGGGCCCGA
GGGTGGACCTGCGTCCGCGTCTCGTCACGAAAGGAAGCTCTTTTTGGAGAGGCAAAACGTGGTCGCCCAGATCCG
GCGCAGCTGTAGCCGTGGGCGCTGTGCAGTGACAGCCACACCCGCCACCTGTCACG (SEQ ID NO: 221)

TABLE 7B-continued

Sequences of differentially labeled CGIs between bladder cancer subgroups relative to blood CGI: 17 range = chr8: 140700279-140700514
CGGCCGCCCCGATGCACAGCGTCCCCATGCAGGAGAAGAAGCCCACAGTCACCATGTTCTCCATAGACACGTCAG
TGTTGCGCATGCCACAGCACTTCTTAATGCGCTTCAGCAGGTAGCGCACGAAGGTGTTCATGCGCTCGCCCAGGC
TCTGGAACATGACCAGTGTCAGCGGGATGCCCAGCACGGCGTAGAACATGCAGAAGGCCTTGCCCGCATCGGTGC
CAGGTGCAGCG (SEQ ID NO: 222)

CGI: 21 range = chr8: 145014900-145015187
CGCTGACCACCTGCCGCAGGGCCGCAGCCCTCCCAGACCGACAGAGTGCCACCAGCTCCCGCCGCTTGTCAGCGC
CAACGTATTCGGAGAGCAGCAGGTCCCAGAGTGACACGCTACACCCCTTAAACCTCCCTGTGCTGACGGGCACCT
TCATGGCCCTCAGAGCCACCGCGGTGTGGTCGTCCACCTCAAGCACTGTGTCTGAGGGCAGTGGCAACAGCAACA
ATCCGGTCTCGGAGTCGCACACGCAGCGCTCCCTGAGCTGCTGGTAGGTCACCTGGTCCCGCG
(SEQ ID NO: 223)

CGI: 260 range = chr9: 959530-963276
CGTGTGCCCTTCGGCGGGCGGCTGTAGCTGTAGCTGTTGTGACGGCTACGGCGGAGGCTGCGGCCGCGCGGGGAA
TGGAGCCGGACCGCGGAGTCGTCACCTCCAAGGTGTTTCTAGTGGCCTCCTGGAAGATGATCCCGCGCCCACCTT
GCCGGCGTGTTCGCGGGCCCCTGCCCACTGCCCCCCCTCTTTCTTTAGGTCTGGCTTTTGAGGATCCCGGAGTCT
TGCAGCTCCCGCCATTCCGCAGATAACCTCCGCACACTTAATTGTGACCCGCGGGTGGTCGGAGAAGCTCCGCA
CGCGTCCTCAGTGGGAAAGTGTCCCCTCTCAGCACTGCCCCCTTCAGTCCCCTGCATTTCTGGAAAGTCAGGCA
AGGCCCAGGTAGGCTGCCAGTGCACTCTCAGCCTTGACTGAGCACCTTTCGGGCCTCTGGTGAGCCCCGAGAGCC
AGGTTTGGCTCGGCAGAGCGGGCTTGGGCTGCGCAAGCAATGCGCATCGTGGCCGCCTGCACCCTGGGAACTAGG
CCTGTCCAGTGGGCAGCATCCTCATTTTTGAAAAGGCCCTTCTAAACCCACCGGCCTCGCCTAACGCCGTTTGGT
GCTGCATCCGAGCGGCCTCACGCGGTCCCCTGGAAGGGCCACTCCCAGCGGGAGGGCGGGGCCCGGGACCTGCGC
TGGCCACGCAGGGTCTCAAGCTGACCGGAAGACCCGGCTTTTGGCCTGTGTCCAATAGCCCCAGAAGAGAGGGGT
CTGGAGCCTTCCTCCCACGCGTAGTGACGCTCAGGTGTCCTCGGGTTGTTAGTCTTGACCCAGGAGAGTGCAAGA
CAGGCCCAAGGCCTGGGGGGATTGCGTTATGAATGTCCAATTCTAAACACAAGGTAGAGCACAGACAGTACATCC
TCACGGCTGGATTTTAACCGTATTTTAATAAACACATTCGAGGGGGTGTCAGTTTCCCCAAGCTCTGCCCCCTTC
CGCGGGCGGGATCCATGGTGTGTGCAGTGTAAGAGTGCGCAGAACGCGTGTGTTCAAGTGTGGGCGTGGCAGGCG
TCGTGTGCTCGCCCCGCGCACTGTGCGGATCGCCCAGACAGCCTTGACAGGTTTTTGCAGATGTTTGGGTGCTAC
GGTGTGGGGAAACCCAGGCAGGAGCGCCAGGCCTAATTCTCCTGGACTCTTGGTGAGCGGCCGCTACTCCACGAG
GGGCTAGAAGCAAAGGGGGCACGCGCTTTTCCCCAGGCCGCCTCTTGCTGCCGCAGTGGCTGAGGGCGCTGATGA
CCCCTCCCCGCTTCCAGCGGACTTGACCCGCGGGCTGACAACCCACCGCGACAAGCAGGCGGCTGGGTTCGCGCC
GCCGCCCCGGGGCCCTTGGCTCAAATTTCACCTCGAGTCCTGCAGACCCTGCGCCACTGAATTGGGGCCCAGGAC
GCCCTTGGTGACACTCGCCTTCTTGCTGCCACAACCACCGTCATACCCCGCAGCCGGGGCTCCCTCCGCTAACCAC
GCTTGGAGACCCCAATCGGGACAGAGGTGGGAGTCAGACCCCCCCTGGCCTGCACTGCCGTTTCCCTCGATTCT
TGCGGAAACAAGACTCCCGCCCACACATAAAAATGCAGCTCCCGGCCACCGGGCGCCGGTGGCTCACGCCTGTAA
TCCCAACACCTTGGGAGGCCGAGGCGGGCGGATCACTTGAGGTCAGGAGTTCGAGAGCAGCCTGACCGACTACTA
AAAATACAAAAATTAGCCAGGAGTAGTGGTGCATGCCTGTAATCCCAGCTACTCGGGAGGCTGAGGCACAAGAAT
CGTCTGAACCCGGGAAGCGGAGGGAAGCAGCGAGTCGAGATCGCGCCACTGCACTCCAGCCTGGGCGACAGAATG
AGATTCCGTCTCAACAAATAAATAGAAATAAAAATATGCAGCCCCCTCCGCTCCACTTGAACTTTAATGCTGAAC
CGGTTTCCCACGTATACGTGTATCGCACCGCATTTTGACGCTTTGCATCGAGTCGCATTAATGGCGCTTTTGAGA
ACGCGTCGTCGCGCTTTACAGAGAAACCCTACGGGCAGCCTGTGGAGGGGTAGGGGATATTCATTGGCTTTCCCT
GCTGGGCCCCGTCCGCCGGGCGGGTTAGGGTCGTGGCAGCCTGCCCGCGCGCGCTGACTCTGGAATTTTGTCCG
GGAAACTGGCGTAGGGCCCTGGCTCTCCCTTGCCCTCCGCGCACACGCGGACGAGGCCTTAGATCCACAGCCTT
TTCTAGGCCCTGCGCCTTTGAAGCTGGGCCACTGCCAACCGCTCGCGATTCTCACCTTCAACAGTCGCCCCCTTA
CCCCTCCCCCACCCGCCTGCCCTCGGGAGCGGGTCGCCTCCACTCCACCACCTGTTTAAGTTCCTCCCCCTCGGC
GCCCCTCCAGTCCCCACCCCGGCCCCGGTCCAAAAAACCAGCAAACGGAACTTTTCCACAGTTGAAAGCCGCGGC
CCGCGAGGCCGGGCTGGGAGGGGAAAGCGGGGCGTGTCTGGGGGGCGGGGCCCCGAGCACTCCGGAAGTTGCCCC
GCCCAGGAGGCTCCTGGGAAAGTGAGGAGAGGGCCCGGGCCTACTTTCGTCCTGGTGTGGCGCCCCTCAGCCTCC
CCTCCTCCCAGTTCCCGCGCCTCCGCAGGGCGCCTCGGCCTGCCTCCAGCAAAGTTCGCGCCCCCTGTTCCTG
GGGTGTCGGCCGCGCGGGCCGTTTCCCTTCATTACTCCCGGGCCCCTGAATCCGAACGCTTTCCCAGAAGCGCGC
AAATCCGCTTGCTTTCCCCGCGGCTGGGCTTTGTTCAGGGACAGCAAAGGAGGAGGCGGGAGGCTGGTGAGGTTT
TCTGGAAAAGGGGCTTGTCCCGAGGAGGAAGTGCCCCAGATCCCTGAGAGCCAACGCTCTGGGGAGAAGAAACTT
TCCTTCTCCCTTGAATGTTGCTCAGATTACCTAAAATTATTTTTTCAGCCCTTGTGTTCTAAAGTCGCAGGGTAA
AGGTTATCTTAAGACTTAACATCAGCGCTGCTCATTTGTACGTTGGTGGAGACGTGCCTTTTTTCCTTTGCACTT
AAGGTGGACAGGGTCTGCGACGCTCCCTTCCAGGACGGTGTGGGGAAGCGGCCGACGTCCCAGCCGGACTCACG
CCCTCCTACTACTGGGCGTCGGCTCCGCCGCGGGCGCTCCCGACAGGGAGCTGGAGTCGGACGAGCGGCTGCCCC
CAGGGCCTCCAGGAACCGCGGCCCAGCGGGGAGCGCCCAGGCTAGCGCTTTTCCAGTTCCCTTCGAAAGCGCGG
GGCTGAGGTCGCGGCGCTGGGCCCTCGGATGAAGCCGTGCTGTAGCTACACCTGAACCCCGCGAAAGGCTGGCGC
GGTCGTGTATCCAGGCTGGGTCTGAGGAATCCGCAAGCGGGAGAGCGCTAACTCCTAGGCGTGAGCCGCTGCTGG
CTTCGAGAGTTCGAGAACATGAAGGACCTGGCTTCTCCCGCCCGGTCGGCTTAGGGCAGCGAGGTCACAGGCCG
TTCTGCTCTCCCTGTTTGTCCCCAAAGGCCTCGGCACGTGGGGATCTGGAGCAGGCCTCAGGCTGCGACCCGTCT
CTTCCCCTACCAAAATTATGTGGGAACAGCGGTCCAGGACCTTCCCCTGTTCAGCGGTATCCCCGGGCCGGTGAC
CCCGGGGTTCAGTCGTCTCCCCGACCCCAAGCGGCCTCTGCTTTCCACCCCTCGCCCCGGAGGGCGGCTTCG
(SEQ ID NO: 224)

CGI: 25 range = chr9: 21979774-21980108
CGCGGCCAGTGAAATCCCAATCGTCTTCCACGTGGAACCCCAGGTCCGCAGTTATGATAACGGATCACATCGCTC
CTGCGGAAAGTGCGCGCGGTGGAGTGATAATTGGACCTAGCGTCTAAATTCTTGTTGGAGGACCTCGTTCCAGCT
GCCAGTTAAGCCTCTGGGATCCGCAGCGTCTCTAGGAATTGAGAGAGTGGGGAAGTTAGGATCCAGGAGGAGGAT
GGTGGGGGCTGAGGAGTGGAGGAGCAGCGTGCATCTCATCTCTTGTCGCCGGGCGGGCGCTCTTTCGGGTCCAGG
GCCCTTGCACCCCCAGCGTGGCTCCGGAGGCGGCG (SEQ ID NO: 225)

CGI: 20 range = chr9: 23812413-23812667
CGACTATGCAAACGCTTGCCGCTAGCCGCATCCTTCTATCGCCCCCCAACTCAAGACCCGAAATGGCCAACTCTT
CACCGAGGGGGCGTCCCATCGCTGCCTTGCCTTGGCCCGCCCCTTCGCCAAGCTCAATCCCTTTTCCCCAGAAAA TABLE 7B-continued Sequences of differentially labeled CGIs between bladder cancer subgroups relative to blood ACCTGTGCCTGTCCTCAGACCCGGCCCCACGGCTGGAAGTCAAAACCCACCCCGGAGCCACGCGGCTGGAGCACG
TTTTTACACCTGCTCGGCCGCTTAATTACG (SEQ ID NO: 226)

CGI: 278 range = chr9: 37024136-37028341
CGCTCACAGGTCGGAATAATTCAAGCCTTCCGCTCCCCCGCCGAGCTGGGGTAGCTGATCACTGAGCTGAAACTA
AACGTTTTAGGTGGAAAAAAAGCGTCCGAAGGCACCGTGAAATGATTAAGGAACTAAAGAGCTTCTCGCCATGTG
AGATCATGTCCTGTTCTCGCCAACATCACAAGATGTCCCCAGACACGCCGCGCCCCAGCGCGCCGCCCCACACT
GCCGGCCCGGAGCGAGGAAAGGGTAGGCGCTGCGCGGCCGGGCCTGCTCAGCGCGCCAGACGTGGCGGACCCGGC
CCGGCCGGAGTAGAGCGGGAAGCCGGGAGAGCAGCAGTGCTGCTGCCGCGCCGCCCCAGACTTTTATAGGGGTTG
GGGGGAGGGAAGGAAGGCTTCAGCCTGCGCCGGGCGCTAGCCAGCGCACCTACGGGAAGGGGCAGACCGAAGCGG
AGCCCGGGAGCCCGGGTCTTCCAGCCGCACCTTCTATTAAGACATGCGCTTGGGGGTCGCGGCCCTCTGCGCTGT
GCGCGGGGCCTGTGACATCTCCATGTGCAAACCCCGCTGCTTAGACGAGCGCAGGCCGGGTTTTTGTTTTTGAAG
AAATTAACTGCTCGGCCAAGCAGGTGCTTTTGAAAGGGGTTGCAAAGGCTGGCAGTGTTGCCAGGCACCGAGGCG
ACGTTCCGGTTTACTCCGATTCACCCCTAGGGCGGCGCCCGACCCCAGGGTTCCCAGCCATCCAACCCCCACCCC
AATTTGTTGGGGTCCTGACTATTGCTGGGCCCCTGACCCTAGGGCAGCGCCAGATCCCTAAAGCCCCCAGGTCCC
ATCCAGTCTTCTAGTCCCAGAACCCCTCCCCACATCAAGTTCCATTCTGGCCCAGAGCATGGAGGTTAAGCTGTG
AAATACTGGAGATGAAATCCGGGCTTCCGCTTTGGAGCACCCGGGCAGAGCAGAACATCTCAGTAGTTTCTGGAG
ATTGGCGGGAGTTCCAGACACCTTACCCCGGCCCATAAGTGGAATCGCATTTGCCCTCGAGCCCTGAGACGTTGTG
GAGTCCCAGAGCCCCAGGACTTGATTCCAGAGAGGAAATCAGATCTCACAGAGACCGAGCAGAGGTGTGGCATGTC
CAGCCCTCTCTCTTCGGGCCAGACTCAAGCCTCCCCTCCCTGTTCCCCTCCCCAGCCTTGAGTTAGTTCAGCTGC
TGGGCCTAGCCACTGAAAGCCTGTGGGGCCCTGCAGCGGGGTGGTCGCAGGGGAAAGGTTCTCCAGGGCGGGGGA
GCGCTCCGTAGGAGGACTCCTGGCCCGCCGGACAATGGCAGTTTTGGAGAGTGAATCGTCCTCAGCAAGAGTGTT
GTTTGTTTTTTGGAGGGGGTGGTCACGAGGCTGGGTCGCAACCTAGGGGGAAGAGCCTAGAGCTCGAGGAAAGGG
GGGCCCCGGCGGCAACTGGACATCACATATCCACTGAGCAGATTTCGCCACAATCGGAAATGTGGCTGTGGATT
CCCGGGCGGCCCCCCACCAAGTGGTCTGCGCAGTTCCCCAGCGCCGCCTCCTCCCTGCAGCCTGCGGGCCCGTG
TCCCTACCCCGAGATTTGATTTTTGGCCATCTCCGAGTGCTCGACTCTTTCCCTCCGCAGCCCAGCCCCAGCCCA
GGCTTCCCGCCCTCCCGCCTCGCCCGCGCCGGGAGGCAGCGCCTGGGAGGAGCGGCCTGTCCGCGCCTGGAGATC
AAAAGCCCTCCCGGAATTGACATTTCACCCCGGGCTGGGGGCGGGGGGTGTTGGTGTTTTGTTGTTGTTGTTGTT
TCCATTTAGAGGGCTTGTTTTGTTTTTGTTTGTTTTCTGTGAGTTTTCATTTTTCCATGGGATATTCTTTTGTTT
CGGGTGTTTTGCGTGTTGTTTTTTCGTGGGATTGATTTTAGCGGGTTTTGCTCTGTAAGTCCTGGTCTTTGGGGT
GAGTTTTGATTTTGTGTAATTTTGTACTTTGTCCTTGTAGGCTGTCTTTTTGTGTGTCGTTTGTAAGGCTTTTCC
TTCTCCGCGGTGTTTAGATGTGTTTTGATTTGGTGTGAGTGGGTGTCGTCTGTGTGTGTTGCCTTAGGGAATT
TCGTGTTGTGTGTGTTTGTTTCCTTCGATTTGAATTTTATTTTTTTGAACTGTACGTTTTGGTGGGGGATCGGG
TTATATTTTCATGTGTTGTCTTTAGTTTTTGTGTTTGTGAGATGCGCTGGTGAGAGTTTGCGTGTGTATTTTGGC
TTTTGTGGGGCTTTGGGATTAGGGAGGGGACATCAGCCGCTACTCCGTTCCTGCCCGCACCCATGAAGGGCAGAG
GATTAGGCCAAGCATCACGAATCGTAGGTTCGCCGTGCTCCGCCGCTTCGCGCTCTGGACGCTCGAGACCAGCGG
GAAACAAATGTGGTTCCCGAGGGGGCGCCCGCTGGTCGTCAAAACCTCGCGGGCCCGGAGGCGCCGCTGCTGGGT
CAGAATCGCAGAGCCCCCTCGCGGGGTACCGAGGCCCAGCCGCCGTCCCCTTGCCCACCCTCTCCCCTGTGAGT
CGGTCTCCCCTTGCGCTTGGCCAGCATGCTTCGGACCGTCCGGACTCCCGCAGCGTTGGCCCAAGGGGCGGCTCC
CCTCGGCGGAGCAGGTGACGAACCACTTCGGAGGACACGGAATTGACACTGCGGCCCTAGAGATACGGGACAAGG
GGCCAGAACGCGGGGAGTCTAGGCTCAGATCGGAGTCGGGATCCCGGGAAAATCCCCCATCTCCCTTGCCCGCAG
CCCTAGAATCCCAGAAACCCAACTCCGCGCAGCTTTCGGTTTGGAGAGCCCGCCCTGGTTTGCAAGCACAGATAC
ATGTGCCCACACCCGAACACACGCAGACACCGCCAGAGAGCGAGACGCGAGCGGGCGCCTCCGTAGCAGCGGCT
TGCGGGCGGAACCGGAGCTGGCGCCGCCTCAAGGGGAAACCGAACTGTAGTGACCGGAAATGTCCCCAGGACAG
AATAAGCCATTCCTTCTGTCCACGTTGCCAGGACTTCTCCAGCTCAACACACCTTGGTTTGTTTAATGTTACACG
AGGGAGAAGATTTAGAGGCAGAGACACATGCTGGCTCAATCGGCGAGGAAATACGAGCAGAGTCTAAACAGAAAG
AAATATGGAACGGGGGGAGACTAGACTGTGGGGAAGGCAAATTGGAGGCCCAGAAAAAGGGGCTGGTGCGGAAGCT
CCTCCAGGCCCCTGGGCGCTCTGGCATTCTGTGAGAAGGAGAAAGCAGAAGCCGAGAACAGAGAGTGACAGGAAA
AGAAAAGAGACGCAGAAGGGGTTGGCCTAGGCACGCTGCGAGCTGCCCTCCAGCTAAGACGCTGCGGGCAAGGGA
GGGGGAGGCCGACATCGCCAGGCGAGGGGCCAAGGTCGGGCTCTTTAACTCAGCCAGGAAACATCGTTGGGGGCT
CCAGGGCTCGTGGAGCCCGAACTGGGGCTCATTTCCGGCCCGATGCCCCTCTTCCCCAGACCCCTAGCCCGGAAT
CCAGCAAAGGCTGGGCATCGCCGTCCGCCACTGGGCCTCCCTCTGTGCGAGCCCTGGGAGAAGCCTCAGGGAAC
GACTCTGGCACTGGGGCTCGGCCCCGGAGCTAGCGCAGAGCGTGGGTGGGAGTCGACATCCAGGCAGGAGGCAAA
GAAGAGGCCCCGCCCTAAAGCCGAGGGCCCAGTTCTTCGAAAGCCTGTGGCCGGAGCTGGACTCACAGGATTCGG
GGTCCGTACAGCGCGCACGTGGTACCGCATCTTCGGCAGGCGGCCCCTAATGCCCAGCCCCGCCCTGCTTCGT
TTGCCGGGCCTGAACTGTGTCAGCATTGAGGGTGGACGCCGAGTCGCGGCGAGTTGGTCCCTTGCGGTATAAACT
TGGGGCTTCCCTAGGGGCGGTGCCGGGATGGATGGGGGCGCCTCTCCACCTGCAACTCCCCAGCGCAGAGCGCA
AAAAGTGCACATCGCGGGCCAGCCGTCGCCTCGGGGTTTCAGGCGGCGCCCGGGGCAAAAAGGAGCTGAGGATTG
GTTTGGGTCAAAACACCCATTTCAGTTGGCAGTGGGGTCCTCTGCGCCTACAGGGCTTCGAGCTCCGGGTGCGGG
CTCACTGGGGCACCATGTGCCAGCGACTCGCCACCCGGAAATACTTGGGTTGCGCTAGAATACGCAATGGGTCTG
TGTTCG (SEQ ID NO: 227)

CGI: 392 range = chr9: 101621613-101627382
CGGGCCGCCACCGCCGCCTCGGCTCCTCCGTGACGTCCGGGAAGGGTATCCCCGGCACTCAGGAAGTGGTGGCCG
CGGGCAGCTCCGCCCCACGCGACTCGGGGCTGGCCGAGCTGCCGGGTGGTAGAACCGCCGGGCCTTCCGCAGGG
CGGGCGGGGATCACCGTCTCCCCACCTCCGTGCGCACACACATGCACGGGCCTCGCGCCCCGCTGTCGCCCGCGC
CTCGCCCTGCTCACTTCTCACAGCCCGCGCCGGACGAAGAGAGCCGCCAGCGCCCCCCTCTCTCCCACGGCTCG
CACCCACTCACCCCGACCCCCGCCCGCGAGCCCGGCCCCTCGTCGCCGGTCACCAGACCTGGTCGAACGAGTCC
AAGATGGCGACTCCGCCCCCGCCCCTCCGCACTCCCGGCGGGGTCAGGGCGCCCCTCACGCGGCGGGCTCGCG
CCCGAGACCCGGCTAAAAATAGCCAGGCCCGACTATATTTGGTTCGGCCGGATCCTGGCGCGGCCGCGCGCTCCC
CGCCCCGCCCCGCCCCGCCCCGCGCGCCCTGCCCCGCCCCGCGCGGCGTTGAATGGAGAAGGGGCGGGGGTGACC
GAGGGGAACCTACTCCGCTATCTGCGGCGCGCGCCGGCGGCGGGTCCCGGCTCCCGCCAACCGCCGAATTTAGTAACATCG
CCTGCGTCAATCACGCGCCTCGCGTGCGTCAGCGCGCGCGGGTCCAGGTCCTGCTCCCCCCCTTCAAGCCTTTG
AATGGATACAATGTAGCAGCGCCCTCCTTCCTTCCGAGGCTGGATTGGAACCCGCCGCAGTGCAGAGACTCGGTT
GCTCTCGGCTGGGTCAACTTTCGGGGCATTCTCCCACGATCCTCTCCGCACCACCGTGTCTGAATTGGAAGTGGA
GGCGAAGAAAGATATACATGCCATATTTACCTATATGTAGTTTGTTTTCAAGTTTCTGGTCCTAGCTCGAACCTT
CTTCGATTCTGAAATGTGTGCTGTCTACAAAGGAATCTTGTATCTCCCCTCGGCGCAGCGCCCCCCGCCCCCGCC TABLE 7B-continued Sequences of differentially labeled CGIs between bladder cancer subgroups relative to blood ACACACACACAAATTGGGACAGGTCAAACATATAAAACGGTATTTGTGATTCAAGCGGACCACATGGGGACCACT
CTATCTGCATTGTTTCACTCAAATATTTTCTCCTGTCCAAAAATTCATTTCTGAAAGAGACTGCGTTCACTCAGC
AGCAACCTTTGGGACTAGGGGTCTTTAACTCTGATAAATTTTGTTTTCATCAAGAAATTTACACTTAAATTTATC
ATTTCCAGGAAGAAATTGCTCTCCTTCATACAGTCACCCAGGCTTTCGGCACACCATTTCATGACAAATGTGTCC
GAGGAGACCAAAGCAAATCCCCTAGCGAGGGACTGACTAATAAGTCCTGTTGATTGATTTCGAAATGTTTAATTT
GGGAGATGTGGGCGGAGGGCATCTACAACCATCAAAAAGTGAAAGTGCTAGTTGAGAGTTCCATTTCTGACCCGG
TGCCGGGGAGGAGGAATGATTTGCAATAGTCAGACCCGCTCAGCTGTTCAACACGTGTGTGTTTGTTTTACACAC
AGAGTAGTTTCTGCTGCAGCGCGCGTGTGCATGATGGATGTGCACTTCGCTGGGTTATAACGTGTCCAGTTAAGA
AACCCACGCCGTACGTGTAAAGAAATCAAACCTTATCCCCGGAACCATCTGCATCCCTGTGTGAAACACGCACCC
AGTAAATGATGCGGGGAGGGGGGATTAGCCTGGGCGCAGAGGACCGGAGCAACGTAAACAGCTTTAGAACCTATG
CAAGAGGAAAGTGCAGCTGCACCTCAGGGCGTCTTCGGGCTGGTGCCAGACGCCTTCTGCACCGGCTGCCAGGTC
ACTGGAGCTGGTCAGAAGCTGGCTGGCGGAGCCTTCCCTTTCGGAAGAGCTGTCCTCTCCCTTACCCCCTCGCC
CTGGCTCCGTGCCTCGGGGCAGCCTCGGAGGCGCGCCAGCAGCACTCCTCCAACTCTACTCCACCCGAGCCTGAC
AGCTGGGCGGTCCCGCCTGACCCGTGGGCAGGCCGCTGCACCCTCCCGCAGACGCACGCCCTGGCGAGCGGTTCC
GCTGCAAAAAGAGAAGCCCCCAGGCCGGGGCCGGCCGTGCGGCGGAGTTTCCATTGTGCGGCCGTGCGACTGGCC
GAGGAACGCGCGCGCGCGCGCGCACACGAACACACACACCCTCCCTCGCACACGCGGAACCGGCTGGGCCAGG
GGAGGGAGGAGGAGGGTGACGTAGCGTCCCATGGCGTCACATTGACGTCTCGCATTCCAGGCACTCTATGGAGAG
GCCGCTAGGGCTCCTGTGGCATAAATGACGTGCCGAGAGAGCGGAGCGGAACGCGCAGCCGGGAGCGGAGTCTCC
TGCCTCCCGCCCCCACCCCTCCAGCTCCTGCTCCTCCTCCGCTCCCCATACACAGACGCGCTCACACCCGCTCC
CTCACTGCACACACAGACACAAGCGCGCACACAGGCTCCGCACACACACTTCGCTCTCCCGCGCGCTCACACCC
CTCTTGCCCTGAGCCCTTGCCGGTGCAGCGCGGCGCCGCAGCTGGACGCCCCTCCCGGGCTCACTTTGCAACGCT
GACGGTGCCGGCAGTGGCCGTGGAGGTGGGAACAGCGGCGGCATCCTCCCCCCTGGTCACAGCCCAAGCCAGGAC
GCCCGCGGAACCCTCTCGGCTGTGCTCTCCCATGAGTCGGGATCGCAGCATCCCCCACCAGCCGCTCACCGCCTCC
GGGAGCCGCTGGGCTTGTACACCGCAGCCCTTCCGGGACAGCAGCTGTGACTCCCCCCAGTGCAGATTTCGGGA
CAGCTCTCTAGAAACTCGCTCTAAAGACGGAACCGCCACAGCACTCAAGTACGTATGAGATTCGCCCAGTTAATA
AGGGGACTTGCTAAAAAAGTTGGCTTGCTGGGAAGCGTCGCTCCTGAAATTGACAACTTTGAGTGTGGGGTTCCC
TCCCCTGACCTTGCCGCCCGGCTCCGGCTTTGCTAGCCCAGCGGCCCGTAGGTTCTGATCTGAAACTTTTCCCCT
GTAGTGGGCCCGCGGGGATCTCTGGAGCTCGTGGGATTCCTCCCCCCCACTCGAAGAGGCGAAAAGCCTCTAACAA
AGAGGAGGACCGGGATTTGTGCTATAGCGGCTCCAGCGATGTAATTCAGGGTATTTCGGCTCTAGTTGTCATGGT
AATGATGCTCTCGGCGGCGGCGGCGGCGGCAGCGGCAGCGGCAGGGAGTTGCAGCTCCGGTGATGAACGGCA
GTAATTTTCCTGCCTTTTAAGTAGGATTGAAAATAGGAGCTCTGGTGGGTCCAAGTAAATGTTGCTAATGGTGGC
ACCGAGCTGGTTCTCTGGAAGGAAGCTTAGGAGGGAAAGGGCCTAGGCAGCGACGGCCAGAGTTTGCAGACGCACT
CGGAGGACCTCAGGAAAGAGGGCGTAATTGTAGGAATGTGGCTTATTGTATTGAAATGAGCCTGGGGTTCCACTA
GGCACGTCTGCCTGTCGTCGCTGACATGCCGGTTTACACTTTTCCCTTAGGAGGTAAATCGGGTGTAATTGGCGA
CTCCCGCACACTGACACGTGTGGGGACGGTGTCCCTCTCCTCTGGACGTTGGCTCGGTGTGGGAAAGGCATGCTT
TTTCACGGACAGAACTCGCGCTTTTGGAGAAGTTGCTCCGAGTGTTTTACTCTTAGTAGAAATGAAAGTTCTCGG
TGGTGAGACGAGACGGTCATGCGAGCGCAGCCTGCGGAGACTGACTTCCAAAGGCACCTCTCCAACCTGTTGGA
AGCCTCGGGGCAGTGGTGAGGAAGAACGCATTTGTCCCTTGATTTCCAAAAACGTTCTTGGAGATTGCCTTTTAT
TTATTTATGCGTCCGGATTCTCCAGAGGGAAGAGCTGCGAGGAGTTAGTAATCAGAAATGTCGGGCTGTGATCCC
AGGGCCTTGTGGTGCTGGGAGAGAAGAACAGGGAGCCGTCATTCCATCGCGAGTCCAGTGCCGGATCTCCTTTTC
CCACGACCGGGAAATATTTTATAGAATCAAGTTAGGGAAAGAAAAAGCTGCCTAACGTGGCTGATGGGCACAATG
AATGAAGTTACTTTATTCGAGTTATTTTCGCTGAACAAGATGCTCAGAGTTAGTATCAAAGCCTCCTTAGGCC
ACAGCAACCTCCACGTCCGCTCCGCCCCCCACCCCCCGGCACCCATCCACCCCTTTGCCTGGGACCGTGCGCTCA
CAGAAATTCTTCCCCGCGTTTGTCTAGTCTCCCTCGGTCTTTCTGAGAATCTCAGTCTTTCCCTTTCTGTCAGT
CTCTCCCTCGCTCCTCTTGCCCCCGCCCAACCTCCGCCCCCGCTCCCCAGGGTTGGAAACTCCGCAGAGGAGCCC
CGGTCACAATGGTGCGTTTCACGGTTTCCTCCACACACTTCACCACCGGGAGGGGAACACGGGGGTGTTCCTTTC
GTCTGCCCACGAGAAAGAAAGGGGCTTTGACAGAGGTAGTTATTTCTTCCTAATTTACAACCCCAAGGCTCTGTG
CTCCCGGCCCCGGCGGCCGCAAGCAGGAGCGGCGGAACGTGTTTCCAGGCACTGAGGCTTTGCCTAGGTAACCGG
CCGCTTGTGGGGTGGAGAGAGCGGCGGGGCGCTGGGCTGGGCTGGAGGGAAAGGCTGTGTGGGTCCCTCCCGCGAA
CGCTGGGCGCTCGAGGGGAACTCCTTCGTTGGGGAGAGGCGGTCCCCGCCCACCCGAGTTCTGAGGCCTCCTCTC
AGAGAACGACTCCGCTTGAAAGGCCCTCAGGGAATGCGGGACGGGAATGCGGGCACCCACTGAAGGGCGGGTGG
GGGATTGCTGGAGACCCCCATTGAAGATGCGGGGAGACGGGAAGCACGTGCTACAGCCGTGGGAAGATCCGCTTC
TACCCGCGCTACATCGAGCGCAAGCTTTCCGTCCGAGCAGCTCCAGCTGGGGCTGGGGGTGGCAAGGGAATCCCC
CATTTCCTGGTCGTCGAGGGTTTCCTGGACCTGGGAGCCCCGAGTCCCTTTCTCTCTTCCTGCAGGCAAGCCCCG
GGCTCAGGGGCGCCAGGAGATGACCCTCGTGGCCCCGCGCACCTCGGAGGTTTTTGGTTTGGTTTGATTTGGGGT
TTTTCGGTCCCTGTTCCCACTCTTCGAGCTGCGCCCACCCCGGGCAAAGGGGGCGCTATAGGCCGGAGTTTGGGC
ACCCAGTTCCTTCCCTGAGGCCTGCTGAGCTGCGCTTTCAGCTACAAAGTTTCGCTGAGGCTGTGGGCTGAGACG
CTGGTCCCGGAGCTGCGCTCGGCGCCCTCAGGAATGTGCCCCCGCTAGGCCGCTGGGTGGCCAGGAGCCTCCAAG
CCGCCCACCCTCGAAGACACCGCCCTCTGGGTGCAGGGGACCTGCCTCCGCTCGTCCCATCAGCCGCTAACGCCG
TCCGCTTCGTCCCCTTGCTTCCAGCGCCAGCCTTCTCATCGCTGTGCCCTTTTGTTTGCTTGACCCCTGGCCCTC
GAAACTCGCGGCTAATAGAAGCGAAGCTCCATTAGCATTTAGAATGAAAAGCGCAGACTTTCTTAATTCCTCGGG
GCATTCATGCATTCGTTCCGGACCTTGTGCATTTCCTATGCAACGTGTAAAATTTGTATTTGAGGGGTGGGGCG
GGCGGAGCTGGAAAATGGCTTTTTTCCGCTGGTGAACACTCACTGACCCCCGTATTCGGGCGGAGCTCG
(SEQ ID NO: 228)

CGI: 56 range = chr10: 13556172-13556753
CGCTGTTAGATTTCGGGTCAATATCCATCATCGCTGTTAGACTCGGGGCCGACATCCGTCATCGCTGTTAGACTC
GGGGTCGACACCCATCATCGCCGTTGGACTCGGGGCTGATACCCGTCATCGCTGTTAGATGCGGGGTCGATATCC
ATCATCGCTGTTAAATTTGGGGTCGATATCCGTCATGACTGTTAGATTTGGGGTCGATATTCCTCATGACTGTTA
GACTCGGGGCTGATATCTGTCATGACTGTTAGACTCGGGGCCGATATCTGTCATCACTGTTAGACTCGGGTCAAT
ACCCGTCATCACTGTTACACTCGGGGCCGATACCCGTCACCGCTGTTGGACTCGGGTCGATACCCGTCACCGCTG
TTGGACTCGGGTTGATACCCGTCACCGCTGTTGGACTCGGGTCGATACCCGTCACCGCTGTTGGACTCGGGTCGA
TACCCGTCATCGCTGTTGGACTCGGGTCGATACCCGTCATCGCTGTTGGACTCCGGTCGATATCCGTCATCAGTG
TTGGGCTCAGGTCGATACCCGTCATCAGTGTTGGACTCGGGTCGATACCCATCATCG (SEQ ID NO: 229)

TABLE 7B-continued

Sequences of differentially labeled CGIs between bladder cancer subgroups relative to blood CGI: 22 range = chr10: 15294605-15294858
CGTTAGAGCATAGCGACATCACGTGCGGTTTCTTAATGTCCCTGGTGGCGGATACGCCGAGTCCTCGGAAGGACA
TCTGGACACCACTTTCAGCCACCTCCTTGCAGGGGCGACATCCGCCAAAGTCATCCTTTATTCCGAGTAATAACT
TTAATTCCTTTCTAACATTTACACGGCAAACAGGAATGCAGTAAACGTCCACGTCCGTCCCACGGCTGGGCTGCC
GTTCCGTTTCCTCCACGAACGGGTACGCG (SEQ ID NO: 230)

CGI: 987 range = chr10: 76825135-76839606
CGCTCCCAAAGCCACGCGAAAGTGGAAGCGCGGGGCCTCGGGATGCCCATCCAGCCGGCTGCCCGCGCGCTGGCC
GGGGTTCCAGGACTCCTTCCTGCTCCGCCGGGCTCTGCAGCGCCGCCTGGTGGACACGCGGCGCTCCGCCCGGGC
TCCAGCCGCCAGCCGGCGCGCCGGGGATCCCGCGGCTGTTCGGGAAAAAGCTGGAGAGAGTCGGGGGGCGCGCCT
TGGGGAGGGGCATTTGTCCCTCCGAGGAGGCTCGCACCTCGGCCTGGACACGCAGCAGATACTGGCACCCACCCT
TCACTTACCGCGCGCCCGGGGTGACTCGGATCCGTCCAACACGTCGGGGAATCCTTTCTGTCCTCACCCCCGGGC
GCCCCAGCGCCGGAACGCTGCTGCCTCTGTGTAGCTGCTCCCGGAAGGAGTTTCATCAAACTTTTAAGGGGCTTT
GGTTTTGGGTTGTGTTGATAAAATACCAAGAAGGGGCATGAAGGCACGAACGTCCCGGGTTCGTCTCCCTGCTGG
TCCCAAGCCTGAATCCCAGGGCGGGGGAATGTCTAGGTCCTTCCGGGCCGGCAAGGTGTGGTCGCTCAGGGACCC
CTGTCCGAAGACGCTAGGGAAAAGAGGCACAGCCTGTGGGTCGCAGTGGCCAGGAGCGCGTGGCCGCTGCTGGTG
AGAGAGTGGTAGACGCCTGGCTTTCAGGTCCTGAGCTGCGGGCACCGGAGCGTGGGACCCCGGCTGCAGCACCGC
CACGCGCTCCCGCCCTCCCACCTGCAGGGCGGGGGATGTCTGTCCAAGAGGCCGGGGCGACAAGCCCGCCGGCCA
GGATTCTCAAGGAACCAGGCCCAGCTCAGCCTCTCTCGGCGGGACCAGAGTGGGACCGGGGCCGCGGCGTCCGAA
GACGCTGCGGGCCAGGGGTCCTCCTCGGCGCCAGCTCCGTTTCCTGGGGTCTCGCGACGTCCGGACATCAGGGTC
GGGGGTGTGGAGACGGCGGCGGAGCCAGAGTCCCCACCAAGTCAGTTCCAGGAGGCGGCCCGCGCGCTTCCCGCA
GTGTCCGGGAGGTCGCTGGGGGTGGCTTTGCGTGCAACCCGGGTAAAGGCCCTGCAGCCGTGAGGCTGGCGCTGG
GAGGAGGGTGGAAAATCTCAAAGTCACCAATCCCGGTGCAAATGGCGGCAGGGGCCGCGGGCTGTCGGACGCAGG
CGAGAGGCCAAAGGCTGACTTCGCGCGGCCGTGAGTCCCCAGAGGCAACAGGGGTACCTGAGCGCCGAGGGGATC
CCGAGACTCGGAGAAACCGGAAGAGCCTGACCCCAGGGAGCGGAGAGTTTGGGGTGCGCTCTCAGAGCTGTGACT
CCACGGTCCCGGAATCCTTGGAAAGGGCGCTCTGGGCTCAGAGCTCCCAACTAGCCGGAGGACCTGGGCTAGCGC
CCAGGCCTGGAGCGTCTGGGAGGGGGCGCTGGGTCTCGGCCCCCCTCCCCCCAAAAGGGACTGAGACTTTTTTCT
GCGTGCTTCCTTCGGCGCTTCGGGCAGCTCTGTCCTGCGGCCCAAGCTGGGGAGAAGACAGCGGCCCGCGCCACA
GGGAGCTGCGCCCGGACCCAGACTCCCGCCGCGCTTCTGCAGAGCGGAGCCCTAGGTGCCCACCTGGTAGCCCCA
GAAAGGCCGGACCTGGGCGCCGGGACGCTCGCGGGGCCGCACTTGGAGGGGCTTTCCGGGTCCTGGCCGGGCGGG
CTCTCCTGCGGCGCGGAATGGAATAGAGCGCCGGCTGCAGAGCCACCCGGACGGGGAAAAGCAGCGGTGGCGCCG
GCCAGCCCCGGGTCCCGACTCTGGAGGGAGGAAGGAGCGGGCGGGTGGGGGTGGGGTGAGGGCGAGGGTTGCGG
GGAGCGTTTAGAAGGCCCTGGGCAGCCAGAAGAAGAAAAGAGGACGCACTCTCCCCTAGGGACCAGAGGGTCCCT
GCGTACTCCCCCCAGGCCCGGGACACAGGTTCCCCCAGCGCCCCTCCGCCTCCCAGTCTATTCGGCTTGCCCCAG
CGCGCTGCCCCACGTCCCCGAGGCCCCGGCCCAGGCCCAGCCGGCGAGTCCCGGCCTGCTCCACTCTGCACAAAA
CGAAACCCAAATGCCCAAAAAGCTCAGGAGGGAAATTTAACAAAAACCCTGTCCCCCGCCCCACACCCCCTTTCA
CTTTTAACAAGCCAGCTGCCAAGAGAAAATTGAAATAAAAACGAAATGATAGATAGCGGAGGACACTATTTTCCA
AATGGTGAAATATCCTCTAAAAATATGTTCCCCAAGGCCAACTTCGCGGCTGGTAGCCCCTTCCGACGCCTTTGC
CTCCCAGAAAATCACAACAAAGCGATCGGAAATTCAGCCACGGTCCCGGGAAGAAGGAGTAGCAGTGAGGCCCCG
GAACCCACTGCGGCCGAAACTGCCATGCTCTCTTTAACCAAAATAAAAAAGATAAGAAGAAGAAGTAAAACCCTT
TAATACATCAAATATACGGAATTTTAATCTTTAAAGCGATACATTGTCTATTATTTTAGTACATGACGTAAACCT
TGTCCCCTTCTCAGCGGGTGGACTTAAAAATTAAAAATAGTTAAGTGTTCCTTTTAAAGAACAAAATAAGGCAAA
TGAGGTTTTGGAATAGAATTTTTTCTTTTTCTTTTTTTTTTGTTGTTTTCTTCCAGAATACATACAAAAAAATA
CCCATTCTCTTCGATGGTATACACCTTAAAAATAATTGCAATTTGAAATCAGAGCTGACAAATTGTGACTTTTTT
TTTCATTTTTTTGTAACAAACATGCATGTAAATTTGTGTTTCAATCAGACATTAAATAACGTACAATACAATCA
TAGCAATTTTAAAGTAACATTAAAGAGAAGACCTCTAGTTCTGTGGCGGTTTGCTTTTATTTATAATCTACAAG
GGATGGGAGGGTTTGTTTTCCACATTTTTACCCTCAAGTTTTAAAATTTTTCCCACCTCCTTTTTACCTACAGAG
CTCAAACTAAATAATGCACTTTTGAACCACCGGTCCGCTTGGAGCTAACATAAATAAATACCAGTGTCCACCGAT
GCAGTCCTCAGATGAACACTTTCTCAATTATTTTTTCCTTTTTTTTTCTATAAAAAGTCAAATGATATTTTTTCA
ACTTTTATAAAGTTTGGGTGGGGAGGTGAAAGTGGGGAGAAGGGGAGTTGTCCACCGGGTCTCGGTCGCTGCTGT
CGGGTAGATAGATACGGTATACATTTCTTTCCTTTCGTGGCCCGAGTCCTCCCCACGCGCGGGTGTCAGCAGCCT
GGGCCGTGATCCCGCCTCTCCCTGGACTCCTCCCCTCCCCCTCTCCCTCCTCTCCCTCGCTCGCCCTCCCGGCCG
CCCTCACTGATACCCCAGCGCCGAGGCGGTGGTCAGTCTCTGTCCGTAGAGGGCGTAGGGGGAGTAGTACGGTCC
GGTGGCGGCGGGCACCGGCACGGGGGCGCCAGGCGTGGGAAGCGGGCTCTTGGAGTAGGGGTGGTAGCGGCTGCT
GAGTCCCAGCGCGTGGTGGGGGCTGCGCAGCGCCAGCGTCCCAGGGCTGCCCGGTGCGCCCGAGGTGGGGATGTG
CATGTGGCAAGCCATGGCGGCCGCGGCAGCGCTGGCCAGAGACGACGAGCTGGGGTAGCCCGACAGCAGTTTGTC
TGTCCCGGGAAATGCCGTATGGGTCCGCAAGTGGCTCAGCAGCTCTTCGGACGTGGCGAAGCGCTTGTCGCACGG
CCCGTTGGCCGACACCCAGTTGCAGATGTGGGGGAGTGGGTCGTTAGGGAGCATAAAGCCGTAGGGGTAGAGGGG
GTGGCCGGCCAGGGAGGGCGGTGTGGCGCCAGCAGCCGCGGCGGCCGCGTTAGCGAGGAGTGCACACCGTGCAGCA
GTGCGTGGGGTACACCAGCGGGTATCCGGACTTCAGCGCCGCAGCCGCAGCAGCCGGATCATGTGCGCAAGAAGC
GCTGGCGGCCGCCGCCCCTGCCAGGTGGCTAGCGCAGTGGTAGCTGAGGCAGTAAGGGTCCCGGCACAAACTGGC
TGTCATCACGGACGGCGGAGACGCTCCGGCCAAAGGGCTGGAGCCGGCCGGCTTACTGCAGCCCAGAGACCCGGC
CGCCGCCGCCGCCAGCTGCGCCCCCACCAGGCTGCCCGGCTTGGTGGGGTCAAGTGCCACGCCGTGTGGCAGGAA
CTGGGGCGGGTAGCCGGCGTAGGCCCCGGCCAGGCTGCCTGGGTAGGTCATACCCGCGGGAGGCAGAGGGAACAC
TGTCTGCCCGGCTTGTAGGGTGACACGGGAGCCACCAGCCCAGAGCCCAACACTGAGGAGGAGGTGGGCGCGCT
GGGGCCGGAGCCGGAGCTGGAGCCCGATGAACCGCCGCAGTCCGAGCCCAGAGCCTTGCCTCCCGGGCCCCATC
CGGATGCTGGTTCACATCCACATTAATCCCGCCGCCGCAGCTAATCCGGCCGTGTGCCAGCCCCGTGGGTCCCCC
TTCGGCCGAGGCGCCCCGGTGCCCTTGCCACCGCCGCCCACGTCGGTGTCTTTCTTGTCGTCCTTGCCCTCCGG
GGCACCCCGGCCGAGGACAGCATACCTCCCGGCGAGCAGGCCGAGGCGCTGGAGCTCGGGCTGCCTGTCCTGGG
CGTGAATGGCTGGCAGGTGGCGCTCGGTACCCGGAATCCCGACTTCTCCGACGAAACACCCCGCCGCCGCCCCC
GCCACCGCCACCGCCTCCACCGCCGCCTCCCGGCTCCTTCTTATCCGGCGCGGGTTTGGAGTACGGCTTGAAACT
CGACTTGTCCTCCACGCCGATGTCGCTCAGCTTCAGGGGCCCGATTTGGTGTCCTTGTCGCCCGCAGCACCGCC
GCCGGCACCGCCCGCGCCGCCCCCGTTGGAGGCAACCGAGGAGAGTTTGGAGGAGGGCGAGGGGTCGGGCTTCCC
GATCTGCGAACATGTTTGCGCCAACAGCGCCAGCGGGCTCTTCTTGGCATCGAGCTGCGGGGTCAGACGATGGGG
GGGGAGCGTCACACAGAGAAAGAAGTGGAAACCCTTTAGAATCCTGGCTTCTGGGGTTCAAATGCCTCTCCGCAA
CAGCCCACGAAGATCCTCCCAGCCCCAAGGCGCAATTCTAGGCGGCACCCCCTCTTCAACACCCACTCACAAACA TABLE 7B-continued Sequences of differentially labeled CGIs between bladder cancer subgroups relative to blood TTCTCGCCGTTGGGAAAGGCAGCAGATTGCTCCCCCCGCCCAACCACCACCCCCAGCAGCATCTTTCCTGCCCTC
TCTGAGCGCTAACTAGATTTTTAAAGAGCAAAATGTTTTGGTTTTCGGTTCCTAGACCCAGAACTGTACCCCCTC
CCCACAAACACTCCTTAATTCTTCAGAGTAAGGGCTCGGGCGGCTGGCGCCTCAGAGGCTGTGTGCACACACTGG
CTTCTGCGGATACGAAGGACGGCGACTTTGGAACCGTATTTCAGACCTCCGCCTGCCTTCGGTGCCGAGTGAAGG
GGCCTGGGTCGGGGTAGGGGCTTTCATATCGAAAGGAGAAACAAGTATTGGCAGCCTTGCTCCCTAGCATGCACG
CCCCATTCCACTTCCTCCCCCTTTTCCGCCCTAGTTTTGAGGTACGGAAGCAGTAGCCTCTTCCCCCATTCGGGA
GCTGAATCACTCCGACCCCCCCACCTCCGCCCAGATCCCGAGAAAAGAAAGCCCTAGGGTGGCAGCCAGGGTAG
TGGTCCCAGTGCGATCCAGAGAGAGGGTCCTTACCTCGATGGGGCTGACCGGCGTGGAAGGCAGGGGCTGCAGGT
ACTCGGGGTGCAAAATGTGGCCAGTTCGTGCCGTCAGCATCTTCAGCACCTTGATTGGCAGGCGGTTGGCCTGGC
GCAGGGGGTCAGAGGGGGGCACGGCGTGCACAAAAGGCTTGGTGCTGCCGGCCGGGGACGAGCCTGGGCCGGGGC
CGGAGCTATTTCCAGAGAGCGCGCTGGTCCAGGCAGGGTCTGCACCGCCGCCTCCGCCTCCGCCGCCGCCGCCGC
CGCTGTGCTTACTGCTTCTTAGGGCAGAAAGCGAGGGCGCTGTGCTCATGACCCACCCGCGCGCATGGGAGCAGC
GGGGGGGAGGGCTCCGGGAGGCGCGGGGCGGGCTCGGGGCTGCGCGCTCGCCCGGGAGCAGGAGCAGCGGGAGG
AGGAGGAGCTGGCGCGGCGGCCACGGGCGCCCAGCGCGCCTTCTCGGCGCGTGGAGCCAGACGCGAGTAATCCTG
GGTGGCCCGCAGCGGAGCCGTGGCCGGGCTAGAGGAGCCGGCTGGACTGCGGGAGTGCCGGGCGGCTCGCGGTGT
CCGCCTCGGGCTGCTCCCCTGCGCTGCGTTCTCGCGGCCCCGCGCCGGCGCTGCGCTCTGCGATGCGAGCCGCTG
CGTGTCCAGCCGGGGCTCTGGCGAGGAAACTCACTTCAAAAGCAGCTGCACCAAGGGGGAGATTAAAGCCTTTGC
CGCCTTCCAATCAAATGGGAGCCCGAGGTGATTGGAGGGTCAAGGGGATGTGACGCGTCCCGCGCGCGCCGCCGC
GCCGCTGCCAGGACTCTCAGTGCCGGTTTTAATGGGCAGCTCCCTCTTCGCCGCCCCCCTGTGTGTCCCCTCCCT
CGATTTCGCTGGGAGGACGAGATGGACATTTATTCTACGTTTGCCATCCGCCGCCTCCCTCTTTTTTCCTCCTCG
TCGTTCTTCCTTTCCCCAGCTCGAAAATAAACTGAAACCTTCTTTTGAAGGGGGGTGCGCGTGAGGAACAGACTG
CGGGGGGTGTCCAGAAGGAGCACCGGTGGGAGTGTGGACACCGGCCGGACTGTCAACTCCAGGGGCGAAGGGAAC
CTGCACACCCAGTGTTTTTTCCTTCGCAGTAATCGAGATCCCGCGCGGCGCAGCGCAGCCACCAGGGTAAGAAGG
CAAGGTGGGGAGCCGGAGCTGGAAGAAGCCCGCCCGCCCGCTCTAATTTCCTCAGATTCCGCGGCGGAGAAACCA
GAAGCTAGATGGGCAGTCGCAGCGGCGGCGGCTCAACACCGCGAGGAGCGCTGGGCTCTCCGCCCTTCCCGGCCA
CGTGACGCCCGGGGACGCGTAGATTGGGGCAGCAGCGGGGGTCACATGTTTCCTCTGTTTCACCCTCAGTCTGTC
CCCCAACCCCCCATTCTTACTCTCCCACCCTGTTTTCCTCCCTCCCCCCCTTCTTTGGGCATCTCCACCCCTCCA
TCAATTGTCAATGTTCCTCGACCGCAATCAATCAGTTATTTGTCAGCTCTTGTCAATCCTCCCGTGATTTATGTC
AGCTTTTGTTGCTGATTACAAGGCGGGTGCGACTTGAAGGGAAAAAGAGAGAGGGAGAGAGAGACGGAGAGGAAG
GAGGAGATTGAGAGGGAACTGGAGGAGGGGAAAAGAGGAGCGGCCTCCTGGATGGGGGTGGGGTGGGGGCTCTA
AGAAAAAGAATGAAAGAGGCGCACGGTGTCAGGAAAATGAATAGCGAGAGTAAAGTGCGCAGGTGCGCCCAGGGC
GCCGAGAGGGCGCGCAGGCCTGGAGTGTGCGCCTGCCCTCGGTGTCGGAGAGACGCCCTTCCACCTCTGGGA
GCCTCGGTCTGTTGGGGTCGCGGAGTTCGGGCGCGGCTCCGGGTACCCGAGACCAGCGGCGGCAACTTCTAACAC
GGGAGATTTCCCGCCACCCCACCCCGCCGCCGCGAGTCCTCGCGGGGCGTGTTGCGTGCGGAGGTCAGGCTGCCA
CCCTCTGTAGTTCCCTAACCCCAAACTCGGAGACTTCTAAGAGCCACACCACCAAGGAACTTCTAGTCCTGGAGG
TCAATGGTGGGGCAAACCTCGCCTCAATTCTTTGACCCCCTCGGGTCGTAAGCAGGGCTAAGAGGCTGCGAAGAA
GAGGCCTGGCCATGGGTGTATGGGGGAAGAAACATCTCAGGCTCACTCATGCCCCTCCCCGACCTTCTCCCACC
TGCCGCCATCCCCGCAGGCTGGGGAGCCAGGGTAACTCGGGGCTGCTCTCTCGAATTTATTGGAACGCCGAGTCG
GAATGAGCTGCGCTAGGAGAGCCGAGGGAAGGAGCGAGAGAGGGAGGGGGCGGCTGCCTGTGGGAACGCGGGTTC
TTCCAGGGAAGCGGAGCGGGACTGCCGCGTTCCCCTCGATTTGCACCGTCACTCGGGTTGTTTGGGAAGAAAAG
GGAGGCGCTGTGCGTGCCACCGGGTACCTGGACCTGGATGCCCAGTGTGTATGCATGCCTGTGGCGCTGCGTGAG
TTATCGGGGCTCTGATAGCGTCCGGAGCGGGTTCGAGGGTCTCCTCCAGGAACTCGCAGAAATTAGAGGGGGTGG
GGAGGAGGACACACCCCCTTCCTCGGAACGACTTAGAAGACTTTGAATCTCCCCTCCTCCGCTTTTCCGCCCGG
CTCTTCTTTTGTTGTCAAGTCCTTTTGATAAATGGTGGGGCTGGGAGCTCTGGGAGTCGGGAGCCAGTCTGTGCC
CGCGTGGGGGGCGGGGCCGAGCCTGGAGACCCGGTTTCGACCGGCGCGCACCTGGGGCTGAGCCGGGTGCGCGC
GGGGGTCGGGTCTGGAACTGCCCTTGGTATGCTCGCCCTCTCCTCTTGGCCCATCTCACTCCCTCCCCCACCTG
ACTCCCCTCCCCGGCTTCTTTCTCTGTCTCCCACTCCGCACGGGTACCGAGAACTTTCCGGGGTGAGTTTTAGAA
TTTGCTCCTAGGCATTCTTTTTCTGCGTTTGGATTTTATCCCTTGATTCTTTGGGTTGGTAAACTTTATGAAATG
GTAACTTGACTGAAGCTCATTTGGAGAGAAGAGGGGAGTGAGGCGGTGTGTGCTTGGGCGTGGTGTTTGTCAGTG
TGAGCGTGTAAGAGCACACCTGCATTCAAGGGGGTTTGTAGTGTCCGTGCGACATCTGAGGGAGGTGAGTCGGCG
AGCGGGTGGCGAGGCCCCACGCTGAGGGAGGCGGTTGTCTGGTCTCAGGGAGACAAGTCCCAGGTGCGCGTTTCG
GAGGGCGGGACAGTCCTACGCTGTCTCTGCGGGGCAGCGCGTCTGTGAAGCACTCTTATCCTTCGGGTGTGTCCA
TGTGTGCCTGGTTACTGAGTCGCGGCCGTCTAGGTGTCGACCCAACCAATGGTAGTGCTCCTAACGCCGCGAGC
CCACCTTTGGGCCGCTATCGCCGCGGCCTCCCCGCGAGGCCCGGGCACTGAAATTCTGGGGCCTGCGACAGGGCC
GGGGGGGACGCAGCCAAGGGCGTCCCTCCCCAGCCTCCAGACTCAGCTCTTCCCCCTCTCCTCTAATTCCAGCAG
CTTATTACGCCGGCGGCTCAGGGGAGGCAGCCTCAGCACCTGAAGCCTGGGGGGCCGTGGAGTGGCTCCTGCGT
CCCCCGGTGTGGCCACACACGCTCGTGGGGCTGCGCTGTGCTGCGTGGGTGCGGGTCGTGGTCAGCGTGCGTTCG
CTTTTCTCAAAACTCCACTCCGAGGGTCCGAGCGCATGGGGGCGCCTGGGGCCTGCGCGCCCGGGGCTTTTGGG
AGGCGCCAGCGTCCGAGCCTGCGCACCTCGCGCAGGAGGCCAAACCCCCGAAGGCCGGCGCGGGCCCCGGGAGTGG
GGGCCATTAATTACTCTGCGCCAGGCCTAAAGCCTCCAACCCCCAGCAGCAGTTGGCGTGGATGTCCTGCGGATT
TTATTTGCAAACAATGGAAATGATTTGTTTTCTCTAAAAAAGGAGTGGGCAAGGCAGATATTGGAGGAGGGGGTG
GGAGGAGGAGAAGGAAGGGGAAAGAGCTGAGGAAAAAAGTTTGAAAATGCCTTGAACTATTCACTGTCGAGATGG
CTAATCAGTATTGAGGCCGGAGGGCAGGCGGGCCGCCTTTCACCGCCGCTTCCCTTTCATCTCGGGCTCGGCGGA
GGCGCTCAATTAAAAGCCTATCAGTTTGTAAGTAAATCAACGCTATCAGAGTTGTCACATCAAACAAAACGATT
ATTATTGCAGCCCGCCTCCCCTATTAATCTCCCTCGAAGATAATCCGCCTGACAGGTCAGGCCCGGCGAGCTGGA
AAGCCTGGCCCAGAGCACCCAAACAGTCCCGGACTGGCGCGCGCCCCGGGGGCCTCCCCACCCCTGTCCTGCCC
CGCCTCGCGGTCCCTGGGAGCGGGGAGAGAAAGCGCGCGGAGGCCTCTGCACCCAGGTCCGCCCCACCTGACT
GGGAGCAAGGCCCAGATTCGCGGGCGCAGTAGGGGACAGTCCCGCGGCCCCTCGCCGCTGCTCGGGGCAGGGGA
GAAGCCTGGCGTGCAGGAGCGCGGCCCGGCCCGGGGTCTCGCCACGGCCTGCGCTCTCCTCGGCTCTCATTTAT
TTTCTTCCTCCCTTCTTTTGTTTTCTCTCCCGCGTCTTTCTGGGCTCCCCCATCTTTTTCCTTCATTTCCTTTT
CCTTTTCCCTTTTTTTACTTGCCAGGGAGTATTTCCCATTCTGGCTCTCTCTTCTTGGTGTGCCGTATAAACCT
TTCTTGCGCAGCCACACTGCCTGGAGTAGGATGTTCTCAGGGCCCGGGTTATTTCTCCCGGGTTGCCCCAGGAGT
GTGCAGTTCCCAGAAACTCATGGCAAAGTCCTCTATAATCTCTTTCCGAGCAGGGGCTCTGAGAAGCTCTGCGCC
TGTTTAAGGGTTGGGTGGGTTTGGAGGGGTGAAGAGGAAAAAGAGGGAGAGAGACTGGTGGACAGTTGTCCTATT
CTGGAATTAGTATTTTGCCTTGGAATTTCATAGCTGTAACGTTGCCGACCTCGCTGTTGGCGTTGCCCGGGCTTT
TCAAATATGTAGATAAGACTCAAGGGGGCATCCAGGCCTCAGTAGTGACTATGTGTGTGTGGGTGGGTGCCTGAT
ACAAGTAAATACACCCAGATAACTGCCTCTGTGGCCTCAAGTTAGTGTCCCAAGAGTTTGGGTGGGGCCTCGCTT TABLE 7B-continued Sequences of differentially labeled CGIs between bladder cancer subgroups relative to blood CTAGAAGGCGCAAAAATCGTGGCCTTCTTCCCAGTGGCCTCCGGCTTCCTGCTTTGGGATGCCTCGGAATCGAGC
CGGACCCGCCTTTTTCTGCGCTCTTCCTCCACATCTGTAGGCCCAAACGGCCACTGCCGGAGCCAGGTGGAGCCA
GGATTGAGGGGTAGCTGAAGTGTCTGTGACGAAAGGGCTGCCCGAGGGAGCCCAGGCCTGCCACCTCATATGTCG
GGTTCAGTGCGCCGCGAAGGCTCTCCGCGCCTGTATCTCGGAGGACCCCCAGAGCGCTGCAGTATTGGGCGTCAG
GGCCGAGCCTCTCGCAGCAGTCACGCCGCAGTCCGAGGCCACGGACATCCAATAGAGCCCACTTCAACTTGCATG
GTGCATGGGGTCCAGGACCGGTGGCCCCCACACAGGGTTTCCCAAAGCCTCTCCATTTGTCTGCACTCTCCACTG
CCGACCTTGTAGGAAATTTATTTCCATGCCCAGAAATATTGTTTGGACACAGTGGCTCGGTTATCTTCGCGCCTG
CTTTTCTTAAATACATTTATTTCACCTCTGCCACGCTGCAGATATTTAAAGATCTGTAGATACCGTAACCCTCAG
CGATGCGGGACTCACTCTGGTTATAGATAATATTCTCTGGGTGGTTATTTGAACATAAGTTCTATCTCCAGCCCA
GATGACACCCAAGCAGGGGCTGTAAAGGACACTTGCTCTAGAATGTTTTCAACTGAAATATATGTCCACACACGG
AGAATTTAAGAGTATTTTTATATTTCTCTCTAGATCTAAATATTCAGATGTGTTAATTACATGCCCTAGAAGCTG
GAAGCGATCAGTGGTGTTCACACTGGACGTGGAGCTGTTTGTATAATTTTCATCTCCCTGCACTTAAACATGACT
CTCAGTCTAATAAATTCAACCTTGTCATTTTTAGAATCGACGGGATTTCTCTGGCTGTCGTTTGCGCTGCATTTA
TCCGAATACATCCAGCTCGCAGGCATCCTGCAAGAAACGGCTTCCCGGCTCGCGTGTACGCCGACACCTCGGCCCA
ACGCAGGACTCGAGGTGGTTTCTAGTGCCCGGGTGGCTGCAAGTCTGCCCTCCGAGGGAGGCTGGACAAGCGGCG
CCCCCAGGTCGAGCGGCCTCTCGCTGCCTGGCAGTGCCTGGCAGCCCCCACCTCTGCCAGTGCTTCGGAAACCCG
CCTGGCCAGGTTCGCCCGCGGTGAAAAATGAAAGCAAATTCCCCAACAGAGGTAGCCGGAACTTTCCTCGACGAA
GGCTCCCTCCTGCCGCTGTGTCTGGAGAACCCCCAGAGCGCTGCAAGTTAGCAAGAGAGATTCGATGGCGGCTCT
GGAAGGCGCACGAAGGGTGGGGCGGGGGAGCAAAGAGGCCACTGGGTGACCCAGCCTGGTCCGGGGTGAAACGCT
AGAGAAGGCGCCTCGCCTTCCTTATTTCAATGCAACTCCTCGGCCCCAGACGGTAAAAATAGTTTCCAAGCTGCC
GCGGACGCCCAGGATGTGTTTGCAGAGATCAAACTGGGGAGGAGGCAGCTTTGTAAAAGTTGCAGAAAGATTAGC
CGAGAAGCGTCCGCCCGGCGGGGCTCAAGAAAGCTTGGGGACAGCTCCATGTTCCTTGGGGCGGAATGGCCCAAG
AATTTGGCCTGGGTAACCCCCTGCCCAGTTCTCTGTCCTCACTTCGAGCCAGTGCTTAAATAACTTCCCGCCGCCT
GCCCTGCAAACTTCCCGGCGCGGCGCCGTTGAGGCCAGGACACAGCAAAGGCTAGCAAAACCCCGCCGCGGCGCG
CTCGGCCCCGGCCCTGAGAGGCTGCGCGGGTGGGAGGACCAGTGTGGTTTCTGCTCCCACTCGGCTGCCCAGACC
CTCAAGACCGATCCCCCAACTCCTGGGGACGGGTGCTTCCCTCTGGGAGCCGAGATCTTGCGGGGCCAGCGAGGG
CGCAAAGTGCGCGCGCTGGCCCGCGCGGGGGCGGCCGCGCGTCTCTCCGCGGGGCCTGTCGCCAGGCCGGCCGCG
GCGCGTGAGTGATGAGGGCAGAGAAGGGCGCCCATAAATCGCGGGTGTCAGGGCGAAAAACTCTCTTTATTGTCT
GCGTGATGGATGGGCCCGGGGACGAGACACCCAAATACTTCGTATCGCCTTTAAATGGGAACACATTTTCCGCGGC
CATAATTCATGTTTTTTAAATAGAAAGTTTGAAATGTTGCCTATATTTCACCAGCCCTGACATATTTATGAATCG
CTCCCTGCATGCAAATATCATTACTTAAAGCGCCGGGGAGAGCGCGGGGGAGGGGAGGAGGCGCGGTTCCCGGGG
CGTGGGGGTGGTGAACCGGGGAAATATCGGTGGAGGGGGGCCATCTCCCTAAAGGGCAGAGGGTGAGGTGCGGTG
AATAGCCGTATCCGGAAACCGAGCGTGCCCCGGGCTTCTTTCCCGCCGCCAGACCCCGCACAGCCGCCCTGGGAC
GTTTTTCGAGGCTTGGGACCTAAGACGGGTCCCCGGACCCTGCTGGGAAACCAGGGGGCGTTTTTCGTCCCTCTC
TGAGGCCATTATCCAAGCTGAAACCACCTTTTATAAGAAAAAGTTTAAAGAAAAAAATTTAACAAACACAAAT
AATAATAATAACCCAACATGTTTCGCGTTCTTTGCCACTGCATCGATTTTATTGATTTTCATTCTGCAAACCTGG
GAATGTGCGCGCTCGGGAGGGGAGGCTGTCAAAACCCAGTCATCGCGGGGACTGGATGGGGGACAATTCTCCGAC
GCCGCGGCCTGGACCCGCCCCCACCCAACCGGCGCACCACCTCCCAGGCACCACGGAGCCTGCGCAAGCTGCGGG
GCCGTAAAGGAACCGGCCCCCAATCTCCGGGGCTTCAGTCCCGCCCCTCTCTCCCCCCAGTGCCCTGCAGCGCTC
CCAGGGTCCGTGTCTGCCCCTCCCCAAGCCCCCACTGTCAATACAATCCCTGTTAAAAAAAAAAAATCTTTTTAGA
GCCAGGCACGTGCCGTCGGCCTCTCCCCTGCCCGCCTGGCCCAGGAGGCGCCCACACCTGCGCCCTCACTTGCCG
AGACTTTTACCTGTGCAGTCCCCGGCGGCGCCTGCAGCCGCGCAGGTAACCGAGAAATGGAAGGGAGGGCTGGGG
AGTGAGAAGGACAGAGAGCACCGCCCGACACAACCAGACGCGCGACGCCTCCTCTCTGGACCGGTGCTG
GGGCCCTGGTAGAACCAGCTCCGGGAGCCGAAATTGAGCCATGAAGAGTGGGCCGAGGGAGGGGCGAGGGGAACG
GGCCTCAGGAGGGAGGGGCGGGCCCGGCGGCACTTCCGTTGGGGGTGGGGCTGCGGGCTGCCGCGCCGGTCCCGC
CCCTCCGCCGCGGGCCCGCCCGCTCCAGGCCAGGCTCCGCCCCCACCGACTCGGAGCTGGATCTCAGGCCACG
GCGCCCCCCAGTCGCGCCCCCAACCCCGGAGGCCTCGGGCTGAACCGGGTTTCGCAGGAGGGCACAGGGCG
(SEQ ID NO: 231)

CGI: 356 range = chr10: 88112905-88117344
CGTGAACGCCCTCGCCTCGCACCTGTGGCGCCTGCCGCGGGGCCCGACCGGAGGCAGTGGCTGTGGACAAGGGCG
GCCCCGGCGTAGGCCAGGATTTCCCCGCAGCCGGACCGGCCCAGCTCCGCTCCTTTCCTGGGCGAACAGCGCCCA
CCTCCGGCCCAGGCGGCGGCGCCTCCGCCCGCGGCGCGGACAGCGAGAGAGAAACCGGCTCCTCCAAACCTGGTG
GAGGAGCGCTGCAGAGAAGCGCCGGGCTGAGGCTCTGGGGGCCGCGGGGCGCGAAACGCCGCGCCTACCAGGTTA
TGCCCGGGAGAAGGAGACAGGTCGGGCTCCAGCCGCTGGGCGCTCCTCACCTCGAAGCGAGGAAAACACCGGGCC
ACTGAGATCAGGGGAGGTGCGCCCGATACAGGTACCCGGCACGCAGACACGCCCACCCCCAAACACCGAGAAACA
AAGACTGCCCCGAGCCACGCACGCCTGCGCGGCCAGCGCTGGGCGCACACCCGCGCCCACACAGCCCGAAGGGCG
CCACGCAACCCGCAAGAACACCAGCTCCCCGCGCTCGCAGGCTCTCCGTGCCGGCCCGCAGCGCAGAGCAGTCCC
GGCGCCGCTGCCTAGGTGGGCCGGGGAAGGCGCGCCACCGCGCATGGCACCGCGGCTGCCGAGGAACAGAGGGTG
CCCTGCCAGCCCAGCTCGTCCCAACCCCTCCGGTGCCCACTGCTGCGACGCCTCGCAGGCCGTGTCCCAGTGGG
CCCTGGGCACAGCGGTCACTCACCTTCCTGCACAGCCTGGAATGGGTTGTTGGCCTCGATGACCTTGATGGAGTA
GGTGATCTTCTCGCTCTGCAGGATGTCATCGTTGAGGCTCAGGTCGGATACCGCCAACTGGAACACCCTGTCGTC
CTTGGCCGCGTTCTCCTCGAAGATGGCACCTGGAGGAGAGAAGGGATCAAGACCGGACCTGGACAAGAACCCTCT
CCCCGCTTCCCTTGGCCCGAGGGTCAAGGCACTCGCAGACCGATGATTGCCCGGGTGGTGGGAAGTCTGAACTGGG
ATTTCAGCTTGGCGGGGTAGATTAAGGCTCTCCGATCTCCACCTGCACAGGAATATGTTCCCCTCCCCCCACCAG
CCCTCAGCGCACACGTGCACACAGTTGACATGAGTTACACATGCACATCCCACAGGCTGCCACCAGGTCACACAC
GTGTCTCACAACCAAGGCACCACATGTCCTAGCCATGCTCCACACAAGGGACTAAGCCAAGCTGGGGTGGCCCCA
GGCAGCGCCCAAATGCCTTGACATGGTTCCATAAATCCCATCCCAGGAGCCCAGGAAGTTCCCCGGGAGGGTGGTG
TCCCCCACCCAAATCCCAGGACAGAATGATGGGTCCTTCTCCATGCACGTCCCCTGCTGAGTGGAGCTGAGCGAA
GCAGGTCTACAGTTGGCTTTCCTGCGCAGAGGGGTCTTCCTTAGGCAGGGGCTTCGGATGGCCTGCAGCTTGGAT
GACTGTGACGCTGCCCGGCCTGGCGCCCTGAGCTCAGCCTCCTACTCTCCATCCTTCCCCACTCCCATTTCCTGT
ACGTCTGTCGAGGGGAGTGGGGGAAGGGGACTTGTGTCTAGGCGCCTCCACGTTCAGATCTAGCGGAGCTGGGG
GTCCCAGAAGGAGCTGCTCTTGAAGGGCTTTCTAGAACCGCGGACAGCTCCTCCAGGGCGCCCTCCGGCTGGCGC
TTTGTGCGCCTAGCACAGCTTCCACGGACCCTGCGCTTCCAGCCGAGATCAGTGCGACCAGCCCGAGCCTAGTCC
TGCAACCTGGACAGCTCTGGAGTCAGCCACCCACATCCCGCCTCACCAAGCCTCGAGGGTCCCTGAGGTCCCGGA
GCTAGGCCCAGTGATCCCTCGAGCTGGGGGCTGGGTAGGAGGAGGGAGGCCCGGATTCCTCACTACACCCGGAGC
CGGCGCCGCAATGCTGACCGCGAGACCCGCACCCCTCCAGGGCGGGAAGCAGGTTTGGTCACGGGCCCCTGAGGA

TABLE 7B-continued

Sequences of differentially labeled CGIs between bladder cancer subgroups relative to blood GGAATCGTAGCTCTCCGAGCCCAGGCCTAGTCCTCACCACCCCACTCCACCACCCACCCTCCCGCCTTGTCCCGT
CCTCCTCGCCTTCAACACCTCCCAACCCCCAGTTTCCCTGTGCTCGCTGGTCTTTCCCAACTTCCGGAAAGACGA
CTGCGGAGGGACTCCCCCAAAGCGACCGCTGTCAGCCCCCCAACTCGGCCCAACTTCCCGAGATTCCTCCCGTGT
TGCTCCCAACTCCCACCCACTCCCCCTCGGCGCGCCCACTCCCCCTCGGCGCGCCCCCTCCTCCTCTGCGCTTTC
ATCTTCTCTCCCGGTTCTCTCTCTCTATCCATCTCTTCCCGCTCAGCATCCCCCTACCCCCCGCTGCCCACGCTT
CTTCCCTCGGCTCCCACCACCCAGACCGTCTGGGCCCCCAAGACTTGGACCACGCAAAACTCTAGGACTGTCCAG
GATGGGGATGCAGTCGCCACAACCAGATACACACGCACTCACACATACACCAAGGGCTACACAGACACACACCGG
AGAAGCAGGCAGACACTGTGTCCACTCTAACAGGCTGACAGACAGTCGTGCACGCACCAACACACGCTCAGATGG
CCCCACACACCCCAACACCCTCTCACAGTAACACCGACACCGTGCCAGGCGCACACAGCGACACACGCTGACAAC
ACGCACCCACACACATTCACACACGGTTCCGGTCCGGCCTCTTTGATCTTGCCCTGCCAACTTGGCGAGCCCCCC
GCTGTACCTCCCCCTGCCCCCCGCTGCTCTGAGCTGCGCAGAAGGGCCCTCCCGACCCGCCGACGGCCCCGCTAA
GGGCGCGGGTCTCGACGCGCGTCCATCCCGGTGTTCCCCGAAGCGTCGGCCCTAAGTGTCGGTAGAGGCCGCGGG
GCCCCGCGCGGAGATCGGAGCCCCGGGGAGCGGCAAGCAGCCAGCGGGAGCGCGGCGCGGCCGGTGCACAGCTCC
TCCGCCGGGCGGCGCGGCGCGGCCCTTCGGGGGAGCACCGCCCGCCGCCGAGCCCCTCGGCCCCAGGGAAACGCCAAGT
TTGGACGCCGCGCACCCCCTGCCCCGTTGGGGCCCCCGCCCAGCCTCGGCCCGGCCTCCAGCGCGCTTACCGAT
GTGGATGATGGAGTCGGCCCGCACCGACACGCACTGGCATATCCAGGGGAGAAGCCACAGCGTCAGCGCTTCCAT
GTCCCCCGGGCGCGCGGCTCATCCACCCGGGCCCGGGGCGAGGCCGAGGGCAGCGCGAAGCGGGGAGGCGCTGGT
CCCGGTGCAGTCCCGGGCGCTCCCGGGAGAGCCGAGCCCGCCCGTGCGTCTTCCCCCGCGCGCCCGCCCCCTGC
GCCCTGCGCCCGCCCCAGCCCAGCCCAGCCCAGCCAGCGCGGTCGGGCTCCCGCTCCGGCTCCGGTGGCGGCTG
CGGCGGTGCTGGCAGCTTGAGCCCAGGCCGGCGCGGCGGGGGCGGCCCGCGGCTGTGGCAGCGGCGCTTCCCGCG
GCTAGAGCGGCTTCGGGGGAGGCTGAGGCGGTGGCGGCGGCGGCCGGGCCGGCGTGGCGGCTCTGGGCTGGCTGT
GTGTCTGAGCCCCGGCGAGGAGCGAACTGCGGAGGACGCCCCCTCCCCTCCCCTGGGGTCCTCCCCCTGCGCTCCCC
CTCCCCTCCCTGCCCGCCTCCCTCCCCTCCGCCCGCCTCTCTACCACGTGACTGCGGAGCCTCAGCCTCGCGCG
CGGCTCTCGCCCGCTCGCGGCTCGGAGGGGGCGCCGGGTGCTCCACGCTCCCGGCTCGGGGGACGCTCGGAGACC
GGCACAGCGGCGGGGACCGGCCTGGGCTGCGGCGCGCCGAGCTCTGACGGTTCGGGCCTCCTTCTCCGGTTCGCC
AGGGGCGGGAGAATGGAGGAGGGCCGGCCGCTAACTGCCCTCGAGGGGCTCCCGAAGCGCCCTGGCGACCTCAGC
AGCCGCGCGTCTCGGGTCATGTCCCCGGCCGAAACAGACCGTTCCTCGTGGAGTGGGACCTGGGGAGCAAGAAGA
GAGACCGGGGCGGGGCGCCGGGCCAGGCCCCAGGACAGCTGGGGAGCCAGAGGGGGCCGGCCGCGCAAGCATCT
CAGAGTAGAGCCCGGGCCGTGGGCTCGAACCCTGGCTGGCCGCGCGGACCTCGGCGGGCGCCCATCCCCCGCTCC
ATGGGCAGCGCGCTCAGCCGGGAGTCGGGCAAGAGGCTCGGACTCTGAAGCCCAATTCATGGCCGGAAACCAGCG
CAGCCGTGACCGCGGCGCCTGGACGTGAGGAGCCTTCCAAGCGGCCGGCGGGCTCAGACTCCGACCCTGCACGGA
GCTTTCATGTGCGAGCCCGGGCGAAGAGCCCGCTCCTCGCGGCCACAGCGGAACAGGGCTCCCTCCGCCTCCGGT
GCCTGCCTCGGGCCG (SEQ ID NO: 232)

CGI: 34 range = chr10: 94441310-94441717
CGAGGGTTTGATGATGCGGCCCGAGCCTGGCTGTGGTCGCCTGTCGGGGCTGGAGCGGGACCCTCAGCCGGGCCG
GGCCTGGGGGCTAACGTTTTCACAGTGCGCCCTGAGTTTCCTTGGGTTACTGCTGGGACCGCGCAGGAGGAAGCA
AAGAGTTTTTCGAGCTAGACCAACAGGAAACACATTGACGGAAATGTTGCCATAGCCCATGGGGTGGCTTTAACT
GGCCGCCCCCGCGGGCTGGGTGTGAAATCAGAGGAGGCCGCGGCTCCCCCGGCCAGGATTGGAGGCTCCTCGCGC
AACCTAATGCGGGTGTCCGGGCCCGAGCGCTTCCCGCGCAGCCAGGCCTTGTCGGTGCAGCAGCCCCGCTCCTCC
CCAACACGCACACACCCGGTGTTCGCAAGTGCG (SEQ ID NO: 233)

CGI: 182 range = chr10: 99068802-99071038
CGCGCCCGACTGCGGGAGCCAGGATCAGGTCCCCAGGGCGCCCTTGCAGACAGCACCCTGAGCGAAGGAGCTCAG
AAGGCAGTCCGGCTTCACCCAGACCCCCAATCCCACAGAAGCGCCGTCCCCAGCGGCACAGCACCCCCTCCCCG
GCGCGGTGGTAGGGCCCGACGTGACGTCACCCATTGTTTACAAATCAACCCGAGCCGGCAGGATTCCGGCTCCCG
CGGCTGCAGGCGCGCGGCTAGAGTGCCTGGCGGGCTCCGGCTTCCGCGTCCGCCCCGGCCCGGTCCAGACTTAG
TCTTCAGCTCCGCGCCCGCTCCGCCGCGGCCCACCGCGCCCGCCGGCAGCCGAGCCCCCAGCGACGCCCGCACAG
CTCCGGGTGCCCAGACAGGGGGCCATGCCGTGCCGGAGGGAGGAGGAAGAGGAAGCCGGCGAGGAGGCGGAGGGG
GAGGAAGAGGAGGAGGACAGCTTCCTCCTACTGCAGCAGTCAGTGGCGCTGGGCAGCTCGGGCGAGGTGGACCGG
CTGGTGGCCCAGATCGGCGAGACGCTGCAGCTGGACGCGGCGCAGCACAGCCCGGCCTCGCCGTGCGGGCCCCCG
GGGGCGCCGCTGCGGGCCCCGGGGCCCCTGGCTGCGGCGGTGCCGGCGGACAAGGCCAGGTCCCCGGCGGTGCCG
CTGCTGCTGCCGCCCCGCGTTGGCGGAGACTGTGGGCCCGGCGCCCCCTGGGGTCCTGCGCTGCTGCGCCCTGGGGGAC
CGCGGCCGCGTGCGGGGCCGCGCTGCGCCCTACTGCGTGGCCGAGCTCGCCACAGGCCCCAGCGCGCTGTCCCCA
CTGCCCCCTCAGGCCGACCTTGATGGGCCTCCGGGAGCTGGCAAGCAGGGCATCCCGCAGCCGCTGTGGGTCCG
TGCCGGCGAGGATGGCTCCGGGGCGCCGCCGCCTCCCGCCGCCTGCAGCAGCGACGCGGGTCCCAACCAGAAACC
CGCACAGGCGACGACGACCCGCACCGGCTTCTGCAGCAGCTAGTGCTCTCTGGAAACCTCATCAAGGAGGCCGTG
CGAAGGCTTCATTCGCGACGGCTGCAGTTACGTGCAAAGCTTCCCCAACGCCCGCTCCTGGGACCTCTGTCGGCC
CCGGTGCATGAACCCCCTTCGCCTCGCAGCCCTCGCGCGGCCTGCAGTGACCCTGGCGCCTCCGGGAGGGCGCAG
CTCAGAACTGGCGACGGCGTTCTTGTGCCTGGCAGCTAACACGCCGGGGTGGCCACAGCGCCAGCCTCAGACTG
GAGGGCAAGGGGTTCCCTTGAGGGCTGCAGTTCTACTCAGGCTGGTGGAGAACTCTGGCTTTTGGAAGCGAGAGT
AAAAAGCTAATGACGAGGAACCGAAAAATCGCGAGTGTTTCGCGGGTAACTGGGGTTGAGGGCCAAAATATTTGG
AATGAAGGACTTTGGCCCTATTTAAGGCAGATTTTACAGGACGCACCTCAAACGTACAAGTCAGTAGGACTCCTT
ATTTGGCGTGACCCGACCTGGCCGCGGAGCCTGCATTTCCTCGCAGCCTCTCAGTGCCCTCCAGCCCCGCGACCA
TGTGGCCACAATCCACGCTTCTCCGGATCGCGGTGCGCCGGAACCACGGAGGATGATGCCAGTTACTTGCTTTAC
CTTTTCAGGGCTGGCTCCTGATCCACTTTGGGGGAGGAGAACATGAGTAGATAATTTCAGGGTGCAGCCCAATCT
GCCAGACTTAAAAAAACCATCTTGTGTCTTTGGAGGTGCTGCTTAATACCAAACATGCGGTGCCATGAAGGGACC
CTTTGGGGGTTGAATAGGAGTTAACCCCTGCGCTCTCTTTGCAACTGTCTCTTCTCAGATGGTGGGGGAAGG
CTGTACGACACGGTGGGGAAAGGAGGTGGGGGCGGGAGTATTGAATGGTGGTGGAAGGGTAGAGAGGCGCGGA
GTGAACCCCACGCCCTGTCTAAAGTGTATTTTCAGAGCCGGCCCGCCTCTCCTCGGTTCAAGGTCACTGTTTCCT
GGGCACGCACTGGGTTGCGGGACAGAGTAGCCAGGTTCTGCCGGTGCTCGGAGAAGAGCGCAGTGTTTTGCAAGT
GCTGGAGTCTCCTGAGGACACGCGCGTCGCCGCCACCGCGGGTGTGGGAAAGCGCGGACGTGCTGGGCGGCTGTG
CTTCGGTAGGCGACCACCGCCCCTGGCCGCGCTCCGGGCTTTCACGGAAACTCCCGAGACCG
(SEQ ID NO: 234)

TABLE 7B-continued

Sequences of differentially labeled CGIs between bladder cancer subgroups relative to blood CGI: 56 range = chr10: 101277153-101277910
CGTGCACGGGCTTGGAGACGGGGCGCCAGTACCAGGCAGGGCACAATGAGGCTTGGGGCCCTTACAGTCGCTGCA
ACCTGGAGGTACCGAACCGGGGACTCCGACCTGACATGCAGGCGAGGCTGCGAGGTCCAGAGCCTGGACCTGGTT
CCTAGGGAGCGCCACTCCTTCTGACCCCTGTGGCGTGCGTCCTGGCGCGCCGCACCCGCCTGGTGCCTCGGCCCT
CTCTGCTGTTCCCTGGCTGATTCTGAGCAAGGCCAGCAGCCCACGGCCCCACCCGACCCCCACATCTCCGCAGGG
TCAGGCGAGCCGAGCAGGAACTGCGCCGGGGCAGTGGTGATGGCTGGGCGTCCCTGCAGCTTCAGGGGCCAAGGG
CAATCGGGGGGCTAGGCCCGCAGACCTGGCCGTCCGCTGACGCAGCGAAGGTCTAGCGGAACCTTGGGGATCGCT
CTCCCAGTGCCGACCGAAGGCCCGGACCTCCAGGCTGGACGCGGCGAAGGCCGCATAAGACGTTACTTAAACATG
TTACTTAAACAAGACTGCAGTAAACGTTTCTTTCCAAGTGAGAAAGGTCTTTTTCGTTCTCAGACGGTTTGAAGG
TGTTTGTGCCAACGTGACCCCCGGGGAGATTTGGAGGAAGCTTTCTACGTCCTAGGAGGCTGAGATCCCACGGAG
CCGGTTTACGGTTGAGAGCAGACAGTTTCGAGTAGATAGCGCTGGAAGAGACACGAAGAATCTCTCTTGCTTCTT
GGAACGCG (SEQ ID NO: 235)

CGI: 403 range = chr10: 102974173-102980053
CGCTTTAACTAGACGGGCGGATAAATGGCCCCGTTTCTCCTCAGCCCCGACGCGCCTGCTTAGCTGCGCGCCCCG
CGGGCGCCGCAGCTCGGGTGGGCTCAGCCCTGGGGCGCCGCCCCCAGCCCAAAGGGACCCAGCGGGGCCAGGCC
CAGGGCCGCGAAGCAGAGAGCGGCCGGAGGTGCCAGGGCCGCTTCATTGGGATTCATGAGCGTGTTGGGCGGGCG
GCCTGGGGCTTCGGGCGCGGGCGGGGGCCGAGTGGGGGGTGCGCACGGCGGGCGCAGATGCCCGGGTGACCGA
CCCGCCGTGGTCCCTGCGCCGCCTTTGTGCCGAGGAGGCGCGCGGGGACCTAATCCATCAAATTGTCTACAAA
TTGTGAAGAAAATTCAAAAACCATATGGTCGCCAGCGCCGGCGCGCTCTGGGCTGCGGAGGGCCGCGGCCGTGCC
CGCACCGGGAGCCGCGGGGGCTGGGCCCGGCTATTGTCGCCTGTCAGCGGCCGCCAGGCCCATTCGTCCCGGC
CTTCATGGTCCGCGCTCCGAATTACAGACCCATCCATCCTAAGAGAGGGCAATTTTTGTCGCCCGGGAGGAACCA
GCCGCACGCCTGCCCCGCTGCCCTGCCGTCTCCTTCCTTCTCTGCTCCTTCTCTCTCTTCTCCTCTCTTCCCATT
CTTTTTTTCTCCCTCTGTCTCTGTCTCCCTTTCTCCGTTTCTCTGTTTCTCTCTCTTTTTCCTCTTTTTCTCCGT
CCTGTCTCTGTGGCTCTCCGCTTTCTCTCTCTGCTTTTGGAGTGTCTTTCTGTGCTCTAGTAAAATGCAAAGACTTTATTTATT
TCTCTCTGTCTCTTCGTTTCCTCCTGGACACGCACGTTCCTGGCTCGGGCCCGGGGCCCCATCGCCGCCCGAGA
CCAGATGCGCATTTCTCACATCAATTTTGCGGAGAAAGAGAGCCCAGCGGCCCGGAGGCGGGACCCCACTCCGGT
GACAGCGGCTACTCGCCAGCCCAGCGACAACAAAAGCCCGGAGAGAAACCCGCTCTGTCCAGGAAAGTGAAAGCG
GCCTCAGCCCCCGCCCCAGCCGGCCTTGGGGCGCCGCAGACCCGCAGAGAGTCCTTGCAAGATCCATACCTCTGCC
CCCAGCGGTGTGCCGGGGTGTGGAGGCAGAATTGGTTAATGTTGCCAGAAATTCACACCAGCTCCCAGACGCTTG
GGCTTACAGTTCCAGGTGCCCACATTGAAATTCAGCCTGGCCTTGATGCCTTTAGCCTTTGGCCCCCGACTCCCC
AAGGATGAGGCCCTCGGGGCTAGAATCGAAACTTGGGAACCCAAGGCTCCACCCCGCGTCTGACTGAGTGATACC
TGCAGCGCTCCCGGGGCTCAGCCCTGTTTTCGGGGAGTGCAGGGAGAATGCCCTTGGGTCTGGGGTGGGATGCAG
GAAATGCAGGGCAAGACCCCCTCCCACCCTTTGTTCAACACAAATTAATGTTGTACTGTGGTGTGCCCCCACATA
CACAGGCATTTTCTCCCAGCATTTCACGGCTCGTTTTTTACCCCGACCTGGCGAAGCCCGCTTCTCTCCCGATTT
AGCAGCTGCCTCAGGTTTATGGGCAAGAGGCGCCTCCTCCTGCTGCTTCCCCCTCGCCCTTCACTCTTAAGCCTG
TCCTGAAAATCCCCCCCAAATCTCCAAGGCTAGGGCGACCGGCACGAAGAGCGGCAAGAAGCCCAGCCTGCCGCT
GCTTCTCGGAAACGGGCCCACCACTCAGACACGGTCGCCGCCGGTTCTAGTAAAATGGCAAAGACTTTATTTATT
GGAGAAAGAGGCCTTGGGTACAGTCTAGGGAGGAGAGGGGAAGGGAGGAGCAGGGAAGGGGCACTCGCAGCCCAC
TCACATCCAGCCACCCTCCTCGGCCAAGTCGGGTAGGAGTGGGGTGTTCGAAGTGGCAAGAGAGACCCAGAGCT
GTGGAGGAGGTGAGGTGAGGGCTTGGGTCGGCCTCCTCTCTGTCTCTGTCACATGCAAAAAAATTCTAAAAAGAG
TACAAAATAATTATAGGGCTTTGGGTTCTGTTTTCGATAGTTGGTTGGTTGGATTTCCCCCTGCATTGTCCCTAA
GAGCCGGACTCCAACAGTCAGTCCGAGGAAATGCGGGAGGGAGGGAGGAATCTTAAAAACAGCATTAGTGGGCAT
TAGGAGGCAGAAATGGCATCGAAAACAGACTTTTCTCTCAGAGGGTGGGGAGGAAAGATCGATTTTGAAACTTGC
AAGTCAGGACCTGACTGCCCACCTCTTCCCCTCCCACATGAGGAAAAAAGGCCCGAGGAAATAGAAGTCAACTGC
AATAAGGCCGAGGGAGGCGAGGAAGGAGCGGGCGCGGTGCATTCGCCACATGCAGAGAAAATCAAAACAGCCGGA
GCTGCCACTCCCCTAGACCGCAGGGTTAGTGTTCCCCGCCCTGGTTTCTGTCTCGCCCTCAGCAAACCCGGCAGC
CCGAGAGCTTTGAAAACATCGAAATCTCCGAGATTTAAAAAATAATAATAAAAGAAAGGAAAAATCAGGCTGCGG
TGGGAAGAACCCGCTATATAGGTTTAAATATTTATATAGAAGCCATACAGAATTGCACGGCGAGGGCTTCCGGGG
CGGCGGAGGCCGCTGGTGGCGGCCGGCCCGGCCGGCCAGCCTGGGTTTATTGCTTCGAGAGGGAAGGAGGCGGCTG
CCAGGAGCCGAGTCCGGGGCCGGGACAGGGGAGGAGGCGGGAGTTGGCAGAGGAGGTCCCAGCTCCCCTCGGCG
GTCCGGTCCGGGAGGCGTTGGGCTTTCGAGCGCTAGGAGCCCAGGGCGGCGGAAGACCCGGGGCGCCGCTCAATC
GTCCACGTCGATCTCTTCGTCTTCCTCGTCCTCCGAGCAGTCCTGGCTGCTGGCCGGCTGGTCCGTGAGCGGAGA
GGCAGGCGAGAGCTGCAGGGCGCCAGCGCCCGGGGCCTTCGGGGCGCCTGGGGGGAGGGGACCGGAGGCGCGGGCCT
CGACTTGGCCCTGCCGCAGCCGCCGCCACCGCCGGCTGTGGCCTCCGAGTTCTGCTCGAGTTCGGCCAGCGCCAC
GATGTCCATCTGCCCGCTGGGGCCCAGTTTCTTGGCGGACTCTACGTCGGCCTTCATCTCCTCCAGGTCCCGCTT
GAGCTTAGCGCGCCGATTCTGGAACCAGGTGATGACTTGCGCGTTGGTGAGGCCCAGCTGCTGCGCGATTTGGTC
GCGATCGGCGGGGACAGGTACTTCTGGTATAGAAAGCGCTTTTCCAATTCATAGATCTGGTGGTTGGTGAAGGC
CGTGCGCGACTTTCGCCGCTTCTTAGGGGTCTGCCGCTGCCCAAAGATGGTCATACGTCGCGGCCTGGGAGGAA
AGGACAGTGTAGGCTCGCGTTGGGAGAGAGGGAAGCCCACCCTGGCTCTCGCCCCCGTAACTCCGTAACCCACCCA
GGCCTGTCCGGCCTGCAGTCTACCAATGTTCCCTTCTCAGATTTAATTCAGCCTCCAGGACCAGGGCAAGTCTTG
GCTATGGCAAACCATCTCCTGTCTTTGGTCTCCCAGAAGTCCCTAGGAAAATTGTTTTGGTCTCTGCCCCCTAC
CTAAGAGTTGGTTTGAAAGACCCAAAGTCTCTAAGGGTATGAGAAGCAGCAGAAGACACCCTAATTGCCCTAA
GAATGTTGGTTCTCCATCCCTTCCCAATCACTTCAACTCTACCCTACCCATAAGGTCCCCGGCAAAAGACTCTCG
ATTCCCCACGCCGAGTAGCCGGGCTAAGAGCGCCCAGGACACTGGGAACGCAAGGGAGCCCGGCAAAGCAAGCAG
ACTGCGAAAGAGCTTGGCCACCCTTCTCCTGCCACCCCCAGCTCTGGCCTACCCAGAGGTCCCTGGGAAATAA
GGATTGGGTCCCGTCCACATATCTTCACTCCCATAAGCAGCTGCTCAGGCTGGAAGGCCCTGGCGGCCGGAGAG
GGCAGAGGCGAGCAGAGGCATAGGGGACGAAGCGCGCAGGGCACAGGGCGCGAGGCGCTGGGTGCAGGGGAACCC
AGCAGCTGCGCCTACCTTCGGCTGCCTGCAGAACGCTGACCTCCAGCCCCTTAAACGTCTTGCTGGCGAGCTCCT
CCAGCGCGCACAGCGGCGAGGTCTGCGAGAGCAGCGCGCGGCCCGCCAGGGGCAAGCCGCCCTGCGCGTGCTTGT
GGCGCGGCCAGCAGGTGCGCGCCCCGCACAGCGAGTAACTTCTCCGCACAGACGGCTTGTTGAGGATGTCCT
CGATGCTGAACGGCGTCAGTGGCTTGTTGGAGTTGGCAGGCGGAGGCAGGTGGTCCAGCGGGCTGCGCCGCCGCT
CCTCCCCCGGCGCCGCCTTGCCGTCCTCCTTGGAAGTCATCTCGGCCTTGTTCGGGGTCCCGGCCGGGGCGGCTC
GGGCCGCGGGGACCCAGCCCGCGGGCAGCTCGGGCGCCGACGGCGCGGGCAGGCAGCGGCGGGTGGAAAGGAGG
CCGCACTGGGCAGGGCGCGGGCCGGGCGCGGGGCCGATTAGCGCGGCGGCTGAGGAGGGGAGAACAGCGCGGGGC
CCCGGGAAGAGGGCGCTGACGCGGGCGCCGCTGCTGCTGGGGCTTCCAGCAATCCGGGGCCGGAGCCGGGGCGCG TABLE 7B-continued Sequences of differentially labeled CGIs between bladder cancer subgroups relative to blood CTGCGCGGGGCTCCAGTTTCGCCAACCCCGGTGCTATTTAAAGGTGTCAGGTGGCTCGGCAGTGGCTCCTGGCCC
CGGGTCCTGGCGGCCGCAGTTGGAAGAGCCGAGGCGAGGGCGCCGATCCCGGACTGCGAGGGAGGCGGAGAGACG
GGGCAATTGACTATTGCTAACAAGTTAGCCTTGATCGCGGTGTAATCAATTATCTGCAGCGGCACTTCTTTCTCT
TTCTCTCTCCTTTCTCCCTTTTTCCTCTCTTCTTTGCCTCTGTTCTCTCCTCCTGTTCTCGCTCTCCCTCCCTCC
CTCTCTCTTCTCTCTTCTCTGCTCCCCCCTTCTCTCTCCTTCTCCCCTCCCTCGCCCTCTCTTTCACTCTCT
GTCTGTCCAATGCAGGCGGCTGTAAGTTGGGAAGCTCATTAATTAGCGGGCGGGGGTAGGAGGAGCCGGCTGGA
ATTAGCCTGCCTAATGCGCCTGTCAGTCCGGGCGCTGCGCTGCGTTCGGCCCGAGCTGTTTGTAAATTACATTAG
CTGCTCCTTTATTGCACCCGAACCTCGGGCGACTGAAAAGCCACCGCCCCCACCCCAAACTGCAGCCGCGCTCC
TGGCGCACCCGCCTCCCGCCGGCCTAGCTGCAATGACCGCACCGGCCCGAAGGTCTCGGTCTCTCCGACCCGGGA
TGTGGAGCCCGAAAGAGTGGTGGGAACCCCAGCCCGGGAGGGACGCGGCCGCCGCTCGGGCCAGGTAGGACCAGG
AGCCCGGGTGGGCCCCGCTGCCACCCAGAGTGGACTTTGCGGAGCTGAGATCAAGAGCCCAGCGCCTCTACCTCT
GACCCTCTTGCCCTCACCCCACTGCCTGGGCGACGCGCCTGGGGAGAGGGAATCTGAAGCCCTCCTGCGCTGGC
CCGCAGGAGGTCAGAGCCGGCTGCGCAGCCTTGGGTGGGCGACGCGGGAAGGGGGTGGAGGACCCCAGGGGTTGG
GGGAGGGGGCTAGTCGGAGAGCTCAGCCTTCTCCACGCGGAGAGGCGGAGGAGGGAATTGTTGGCGGCTCTGGAC
GCCTCTCCCCGGCCTGATTCCGAAGCGGCCGCCCTACCTCCTCCGGCAATCTTGCTCACTTTCCTCCGGCAGCCG
CTCCCCAGGCTGGCTGGGGCCACCAACGGCCTGATGATGGGCGTCTGAAGAGTAGCCAGGCCAGGTGCCGGGGCT
AACGGGGCCGGCTCCGTGCCTCCCTGCTGCG (SEQ ID NO: 236)

CGI: 295 range = chr10: 106389558-106392802
CGGTCACGAAGGATCTCAGCTGCACCAAGCGCGCAGGCTACACTCCTGCAGTAGCGGATTGGGGACCAGATAAGC
CCACGCGGCTCCCGCCTGAGTACCCTCTTAACTGGCGGCCGACACTTTGAAACAATTGAGTCCGTTCAGAAACGG
ACTGGGGAGAGTGAGGGCACGACCTCAAAATCCTAGGCAGCAAAATGAGGTCTGGATCCTCCCTGGAAGAACAGA
CATCTCGACTACTCTCTCGCCCCACCTCTGGCCGGGAGGTCGGGGCAAGGAGAATCCCTCAACCGAGAAGATCTG
GCAAGTCCCCGATCCCACCGGGGCCTTCCGCCTCTTTTCCCTCATCCCCTAGGAGGCTTTATCAGGTTCTAACCG
CTTGTAGTGGGGGCCGTGGGTGCTCGGGGCGCCAAGAGGAGGGGGCTGCCGAGAGCGGCCTGCCTAGTTCTCAGC
ATTGCCTCTTTGACCACTCGCAGGCTCCTGGAAATGCAAACACAGCCCGTGCGTGATCCGCACGCGACCAAAAGC
CGAGCGCACACCTCCCGCCCCCGCCCCACTTGCCATCGCTCACACTAACGTGCACACATGCTCGTGCAAACGCGC
ACGCACGGAACCGCGCGCCCCCTCACACCCAGCCGCGCTCCCGGCCCGGCTCAGCCAGGTGCCCCCACGCGGCAG
CGCCCGGTCTGCCCGCCGGCCCCTGCGAACCCCTCGCCTCACGCCCGCCTGCCTGCGCGCACGCACGCGCACGC
ACGCATTCCCCACGCCCCCGCGCGGGGGCGCAGGCCTTGGGTGGCGGGGTTTGGCCGGGAGCCGGCCGGGCCAGG
GAGCGGCGAGCAGAGTCCAGGGTGCATCCCGCGCTTGGCTTCCGTGCGCAGCCTCCCCGCGCGGAGGCACCTGGC
TCCCTCTCGGCTCTAGAACGCGAACAGTTGGCGTTGAGCACACAACTCCTCCTCCTTCTCCCCCGAGACCCCTGT
ACCCTCCCCGCGCGCCATCTCCCGCCCCTCATAACAGGCCCGAAGAGTAAACCCCCAAACGCGTCCAGAAGCGGC
TCCCAACTCTTCGCCGGGAGCACGTTGGAGGCTGGATTTCGGAGAGACTCGGGATTGGGGTCTATTGCCGGCCCC
TCCTGGATCCGGCTTGATTTTCATATTTTAAGAAGATTTTCTTATTACCTTTGATTACTCCTTTTTTACCAAATTT
CTGGAGGAGCTCAGTGGGGAGGATTGGGGGGAATCTGATTTTAAGAAAGAAAGCACCGAAGGGGCAATTATTAAT
TTTCCTCGGGTTTGGAATCACCCTCTGGACAAGAGAACGGGCGAGCGGGAGCTAGGAGGGAAGAGTGGAGAGGAC
CGGCGAGGCGCGCCAGCCGGAGCCACCTCCTTCCCGGCCGCCCCTCCCCACTCCCCCTACACACACGCTCGC
TCGCTCGCCGGCGCGCACACCCCCCGCGCCGGACCCGCACCTCGGCGGGCGCCACACACTCGGCAGCCCGAGC
CGCGGTAGCCGCAGCGGGATGGAGGCGGCGCGCACGGAGCGCCCCGCAGGCAGGCCGGGGGCGCCGCTTGTCCGG
ACGGGGCTCCTACTCTTGTCGACGTGGGTCCTGGCCGGCGCCGAGATCACTTGGGACGCGACAGGCGGTCCCGGA
CGCCCGGCGGCCCCGGCTTCGCGGCCACCGGCGTTGTCTCCACTCTCGCCGCGGGCAGTGGCCAGCCAGTGGCCG
GAGGAGCTGGCGTCGGCGCGGAGAGCCGCCGTGCTGGGGCGCCGGGCCGGACCAGAGCTGCTGCCCCAGCAGGGC
GGCGGCAGAGGCGGTGAGATGCAGGTGGAAGCCGGAGGGGACATCACCGGCAGGCGAGCGGCGGGGCCGGGGCATC
CCAGCTCCTGCCAAGCTTGGCGGCGCGAGGAGGAGTCGCCGGGCGCAGCCCCAATCACCCAGGAACGCGGGGAC
GCCTGGGCCACTGCTCCGGCCGATGGTTCCAGAGGAAGCCGTCCCCTTGCTAAGGGTTCCCGGGAGGAGGTGAAG
GCGCCGCGGGCTGGGGGTCGGCGGCTGAAGACCTCCGGCTGCCCAGCACCTCCTTCGCGCTGACCGGGGACTCG
GCCCACAACCAAGCCATGGTGCACTGGTCGGGACACAACAGCAGCGTGAGTACCCACCCGGCGGCGGGTCCGCCT
GTTTCCTGACACCGAAGGGGAATGGGGGGGTGGGTGGGAGCGAGGGACAGATAGTTGCTCGGGGGTCGAGGCGGG
GGACGCCTCGACTTTTCGAGATAACAGGTTTGTCCGATTCCCCCACGCCCCAACAGGTTAACGGAGTTTGTTG
TTAGACGCTGTGTGTGTTTGTTTACTGGAGACCCTAGGCTTCGGCCGCCGGGAGGGGAGTGAGGAAGGGGCTTC
TTAAAGATGAGTGGGGGAGGGATCTGTGCTCACTTTCTCCAATACTTGGCTTGGAGGGTCAGTTTTCCTGTTTGC
GGGGTGCTTGAATTCTTGGATGAGAAAAAGGGCTGACTTGGGGCGGGAGCCGCTGAACAGACCGATTCCTGCGGC
TGCCGGGCTCCCCCTACCCCCACCCCACCCCCACCCCCCCTCCCGTCACGCGAAAGGGAACCCGGAAGGCCATTC
GGACTCCCAGCCTCCTGCTCGCCTCGGGGTCGCTGCTATCCGCTCCAGGCGCGCAGTCCTCCAGCCCAAGAGGGA
GGCTCGGCCAAGTCGGCCCCCAGCCTTGGCCTTCAGGTAACCCCGGTTCCTCCTTCAAAGTCCAGGGAGCGGCCC
TGGAAAGCCGTAGCAGAGGCCGTAAAAAAAAGTTTAAAGCGTGAAGCGAAATTCCACACCCATCCAGCGCTCATG
CCACACCGCTCGCCCTCACGCACGCACAGGCACACGGAAGTCGCTCAGCAGAAAACTCTCGACTTCACCATTGCG
TCCTGCGCCACAAACGGCTCCCTGAGCGGAGTTGGGTGCCTGAGCTTCCTGCACACCTCTCCACCCGCTTTTCCC
CGCCACCGGGTTCTCCTGGACAAGGATGTACCGAGAGGTGGCGTCGTTGAGCCCGGTCTGGCCTACTCCGGCATT
CCGAACTGGGCGCCCGACTGAGCATCGCGCCTGCCTGGCAGCTGCAGCGGCCCGCAGCGCGTGCCCGGAGGGGCT
CCCCCTACCTCGCCGGCACCCAGCGCTGTGCAGCCAAGCAAAGAAAAGGCGGGGACAGGTTCCCACCATCTCCC
CGACTTCCCTCCCTCCCGCG (SEQ ID NO: 237)

CGI: 56 range = chr10: 124891898-124892607
CGGGCGCTCATTCTGAGCCGCGACGCCCCTCAACAGGCTCCCGGCACCGCAGAGCCAGAGGCCACGCGGTGAGA
ACCCAGTGCGTGCGCTCTTCTTGTGTGAGAGGCCGGAGGTAGAGTTGGGAGAAAGAGGAGCCGGCGAAAAGGTT
AGTGGGATCTGCTTTCCCTTCTGCGGCCTTCTGGGCCAGCTAGGGCCTGGGAGATGGGGACCAGGGTCGGAGGCT
TGGGGGCGGGAGGGCGGTGCTGCCGGCTGCTTCCTGCAAGCGGTTTGAAGAGGCATCGCGTTGTCCGGCCGCCTG
CGCAAGGGCCACGCGCTGCTGCTTTCACCCCCTTGCGCCCGCGGGGCACCTGGACTCCCCTTAAGAGTCCCCGTG
GGGCCTGAGCTTCTGCTGGGCGCTACGCTGCCCTCCACGATTCCATTTTGCCCCATTTACTCGGGTCGTCCACTT
CCCGCGGCTCAGTGACCCAGCCAGGGGGCGTCTTCCGCTAGCGGTCCAAATGTAGACTCCGCAAAGAGGCTAAGA
AGACCTGTCTACCCGGGTGCGCGCGATGGGGTCAGGGTGTAAGAACCAGGAGCCTCATAGAAACCTCTGCTTGGG
GTCCAAAGCCCAGCCGGGCACTCCCAGAGGACAACATCCGCCCCCGCATGTACACGTGGCCCCGCAGGACCCAGC
CGCAGGGCTCCCACGCTCGGCTCCCCGCCCTCTCG (SEQ ID NO: 238)

TABLE 7B-continued

Sequences of differentially labeled CGIs between bladder cancer subgroups relative to blood CGI: 32 range = chr10: 128863581-128864054
CGACCACTTCCGTATGAGGCACGATTCGTTGGCATTCTTCACCTGCAGCAACCGCTGTGGGACTAGGCTGGTTCC
CCAGCCCCGGCGGGGTGTGAGTCTGCGACGGCTGCTCACTACATTCGGGGGACAGGCACTGCATCGGGGGTGAGC
AGGCCAGGGCAGTTTCCGAGGGCGCCTGGAGCCCGTTGAGATGTGTGGCTCTCCTCCGCTCGTCATCTGCCGGGC
AGAGTGACCACTGGCTGGCGGCTGCAGAGTCTGACAAACCAGGCTCGGGGGCCCTGGCACTGAGGGCAGGTGCGT
AAACGGTGGCAACCTCCGTTTTAAACACCCTCCTGAGGGCAGGTGGAGCGGGCTCCTCGGAGTTTGGCCTCCCCC
GGTCCTGCTTGGCCCTCCCGAGCAGCTGGTAATCGGGCTCTTCGGATGGAGGCCGAGTGGAGTTTTGGAGCGCAG
CTTCTCCATAGCTGAGCGGCTCCG (SEQ ID NO: 239)

CGI: 38 range = chr11: 22319439-22319953
CGCCGCCGCCGCGGCCAAGGGCACCTGCAGAATGTGAGAGAGCCTGGGAGGTCTTGCAGCTTGGTGTCACCCCAC
CACCCTAATCCCCGAGGGTGGGGGGAGGTCGACGGCCCTCCTCCCAACCCCGACGGGTCCTGAAAAATGGGAATG
GGTCAGCATCGGGGGTACCTAAGCCGCCAAGTCCTTGACTCGCCCCTGCTCTGCCGCGCAGGGTGCTGGAGAAGA
AGCAAGACACCGGGGAGACAATCGAGCTGACGGAGGATGGGAAGCCCCTAGAGGTGCCCGAGAGGAAGGCGCCGC
TGTGCGACTGCACGTGCTTCGGCCTGCCCCGCCGCTACATTATCGCCATCATGAGCGGCCTGGGCTTCTGCATCT
CCTTCGGTATCCGCTGCAACCTGGGCGTGGCCATTGTGGACATGGTCAACAACAGCACCATCCACCGCGGGGCA
AGGTCATCAAGGAGGTGGGCAACGTCTGGCCGCCCTGGCTCCTGCCCTTCGGCCATGCGGCCTCG
(SEQ ID NO: 240)

CGI: 98 range = chr11: 31776637-31777992
CGGGAACGTGAAGCGAAGCTCACCACCGGTGCCCGCTACCCCCACGCCGGCAACTCTGTGCTTCGTTTGGCCCAC
GTGTCCTCCCCACGCAACTAGGGGCGACGGTCCTGTGCCTGAGGTGACAATCACCCCCCAAAAACCTCACTTGCG
GGTGGGGGGGTGTGATTGCCAGTTGACCCAGAATTTTCTAGCAACTAGGCGCGTTAAAGTGAAAAGCCCCTGGA
CTAGCTCCACCTCCGGCCCCAACCATCACAGGCGGACCCTAGCTGATTTGACTCTCACTTCCCGCCCTCAGACTG
CCGGCGACGAAAATCCGCCCGAATCGGGCGCCACCTCTGGTGGAAGCTGCTGTCCTCGGCTTCTGCCCAACTCCA
AGAAGCGGAAGGGGGGTGTATCCTGCGCCCCAAGCTCATGGGAGCCCACGCACCGGGGAGAGCCCGGAGTGGAGG
CTCTGGGCTCAGCCCTCCCAGGCCTAGGCCACCGTGCCCTGAGTCCCTCCCCAAGACTTCTCGGACTAAGTGGGC
CAGACTCTTGTCAGGGGAGGGATCACCAGGACCTCAGATTGCTGGGGCGGAGGGGTGGACGCTCGTGAGTGCGA
AGTTCGGGTGTCACTTGGGTGTGTCCAGTGTCTACAAGTGGGAATCCTACGGTTTCAAAAGTCAGGCAGGGATGG
GGTTGCCTACACTCGGTGGGGTCAATCGCTAGTCTCACCAGAGGCGGGAGCGGGCCTGGGGGCCCTCTGAGCTCG
CGGAGGCGGCGGGTTCGGGGCCCGTGCGGGCGGGGTCGCCCAGGGGAGCCCGGGCCCCGCGCGTCAGGAGGCCTC
CGCCGGCCGAGCGGCCGCGCTGGGAAACAAGAAGCGAGCGCTTTGCTCCCTATCTTCCCAGTGTCCGTCCTATAT
TGTTTTCTGCTCTTAAAACTGACATGTCTAATTGGCAATTGGTGCCGAATCGTGTCCAGAGGTCTCTTGTGGAAC
ATTTCTACAGCTGTCTCCTTCAACTAGACGCTTATTCATGTGCCCTTAATGAGAAACAAAACGTTCTCTAATGAG
CAATTACAGAGCGACAGGATTGTTCCCATAACAAATTCTTGCGAGTGACAGAAGCATCCTTTGTACCAGATATTT
CGCATACTGTTACCGATTTTCCCTTCCCTCGCCCGACTCCATGGAGGCGCCGGGCATCCGGAGCCGGTCCGAGAG
CTCACGGATGCGCCGGCAGCCTCCTCGCAGTCCCGCGCGCCGCCCCTGGCCCCGAGCCCCTCGGCTCCGTTGTGC
TCCTGGGAGTGAGACGCCACGTCCCATTATCCCGCATATTATCTCCTTGTCACGAGGACAACAAATACCGATTAA
TCTTCG (SEQ ID NO: 241)

CGI: 61 range = chr11: 68274244-68274755
CGGACGCCCGGGTGGGAGGCTCCTTCCAGGACCCAGGCGCCCAGGGGCAACACCGCCGGGCTGCGGTGCGCGGGT
AGCAGCGAGGACAGGAAGTGCACGTTGCAGGCGGGCGGCTGCGGGGCCTGCAGGAGCGCGACGTCCTCCAGCGCG
CTGAGCTCTGGGATCCCGGGGTACTCCCCGAGGAGCTCCCCGCCGTCGCTGTCGCCCCCCGCGAGCTTCGCCTTG
ACCTGGCCCTTGCAGTCGGCGCCCAGCGCGGGGTTGAACGCGTGCAGGACGGGTTCCTTGGGGTCCGCCGGGCCC
AGGTACGCTTCTTTGAAGACGTGGAACTCGTCCTCCTCGTACTTCACGGGGGCCTTCAGGCCGATGTTCTCCGAA
GCGAACGGACCCTCGGGGCTTAAGAGCTCCGTCACCATCGCATCCTCGGGGCTGGGCAGCCCGCCCGGCAGAGGG
CCCTCCTCCATGGCGCAGGGCGGCGGGGCGGGATGGCGGGGGCCGCGCACCTGCAACACGCG
(SEQ ID NO: 242)

CGI: 269 range = chr11: 117983446-117987106
CGGACGGGACGGGGGACGGGGGCGGGGACTGGCGGGAGGGGGCGGGACAGGCTCGCTCTCCTCCTACTTAGCGA
GCTCCCGGGGAAAAGCAACGGTGTCCTCCTAAGCCTGAGGCCACCGCGACCGAGCCGAGCCAGGCTAAGGGACCA
GTGTCTCCCTGCCCCCCCCCACCTCTAGGTAAGAGCGCCCCGTCCCACTACACTTGCGGGTCCCATTCGCTGCG
GTGCTAGGACTGGATAAGGGGAAGTCCCCGGGGCCTGGCGAGAGCCCTGAGATCAGCTCTAGGCTAGGGAGCTCG
GCAGAAACCCGTGGGGGAGAGAGGGCACCCCAGGTGAGTGCGTGGGGGCGAAAGGAGCGTTATGGGGAGTTTTCC
TGTGAGCCTCTTGCTTTTGCCTTCCTCGGCCGCTGCCAACGCCACCGCCAGAGGGGGCCGTGACGCTCTCCCCCC
CTTGGAGAAACTCTGATCCTGGCCCTATCCAGACTCTCCCGCCGGCACCCAGGCGGCCGGGCGGACACTCGCGGG
GTATCGGGCGGCGAGCGCGCGCGCGGGTTTTCGTCCTCCAGCGCCCCACACCTCCCCCTCTCCGCCACAGCAGG
ACCTTGGGCGGGGGTATCTCCTGTGACGTCTCCCCGCCTGTCCCCAGGCCGGCCGCCTTGATGGCACAGGAAGG
GATTCGGAGTCCGGCTCAGAGTCTTGAGCGTCTAGGAGGGCTGCCTGGGGGTGTCCAGGAGATGGGAAGCCCGCC
TGGGGCCTCCCAGGCACTCCCCAAGGCCCCACGTCCTCGGGGGCCGGGAGGCCGCCTGGGGCGCCTTGCCACGC
CCGCGCGGTCCCTATTGGAATCCCTAGCGGAGTTCCCCGAGCGGAGGCTGACCCAAGTCATTCCGGGCTCCCCGG
GATAGGGAAGTGCGGGCGGGCGGCTGGGTAGGGGCGCCGGCGCAGGGTGGCCGAGTCGCCCGCTAGCGCTTCCGC
CGAGGCAGGCTCGAGTGGGGACTTGGCCGGGCGACCGCACAGCCCTGCCGGGGACCCACGGCTCTGGGCGGGGC
TGCATTCTGGGCCGTTAGCTCAGCGGTCCTGGAGCCTCCCGAGGCTGACTCATCGGGCGGCGGGCTCACCCCCCA
GCCGTCAAACGCAAACGCAGGCGCCCCACCACGCCCGGGCTCCCACGGCACACGCACGCCTCCGCGACACTT
CGCACACCTACGTCCCTGCGTCACGCCACCCAGACACACCCGGACCCGCCCACACGCCGAGGCCTTCCCACGCAC
TCCATGCCTTACGCCTCACAGGAAAGCGCCCCGCGCTCACGCAGCCCCTCACACCCGCAGCCCCGCTTACACGCG
CCCCAGCTCACACATGCACCCCAGTCACACAGCCTACCTCACACACGCACCCCAGTCACACACACAACCCAGCTC
ACACACGTACCCGTCACACATGAGGCCCCAGCTCACACACGAAGCCCAGCTCACACACGCAGTCCCAGCTCTCAC
ACACACACCCCAGTCAAACACGAGGCCCCAGCTCACACACGAAGCCCAGCTCACACACACTGCCCCAGTTACACA
GCCCAGCTCATGCAAGCAGCCCGTCACACACACAGCCCAGCTCACACACACAGCCCAGCTCACACAAGCAGCCCG
TCACACACACAGCCCAGCTCACACACACAGCCCCAGTTATACACACACAGCCCAGCTCACACACGCAGCCCGTCA
CACACACAGCTCAGCTCAATACACAGCCCAGCTCACACACACAGCCCCAGTTACACACACAGCCCAGCTTACACA
CACAGCCCAGCTCACACACACAGCCCCATCACACACACAGCCTATCACACACACAGCTCAGCTCAATACACAGCCC

TABLE 7B-continued

Sequences of differentially labeled CGIs between bladder cancer subgroups relative to blood AGCTGACACACGCAGCCCAGCTCACACATACACTCCAGCTCACACACGCAGCCCGTCACACAGCCCCAGCCACAC
ACACAGCCCAGCTCACACACGCAGCCCAGCTCACACATGCAGCCCCCTCACACATGCAGCCCCAGTCACACACAC
AGCCCAGCTCACACCGCAGCCCCAGCTCACACACGCGGCCCCTCACACACATTCAGCCGCCCTTCCCGCAGCTGC
CAGGGCTCGGAACGGGCGGTGTCTGTGGGGGCCGCCCCGTTTCCCGGCCGCGCAAACAAGCGGCTCCTTCTCTCTG
CCCCGCCAAAGAAAGGCCGCTTGTCAGGGGCGGGCGGGCAGGCGGCAGCGGCAGGCGCCCAACACTGCGGCCTTG
TCCCACGCGGGCAGCCTGGGCAGGAGCAGGCCGAGGGGTGCAAGGGGCCGCTACCTTGCGGAAACCTCCCTCCCT
CGGCCCTGCGGACCGCGGAGAGGCACCTTTCCACCACCGGACACCCAAGCAACAGCCCTCGCTCCATCCGCGCTC
TCCCGGCTCCCCCTCTCCTCGGGCCGCCCATCTCTCCTCTCTTCCGCCTTTGGGGTCCCGGTGGGCCCCAGCCTC
CCTCTCCTTCGCCCCATCTCCCCGCCCGTCAGCCTCCCCTCCGCTGCCCTCGCGCATCCCCAGTGTTCCCGTCTG
TCGTCGCCTCCACTTGAGGACCCGCCTGTCCTTTCTTCCCCCGACCCCTCCACCTCTGTGTTCTTCAGTCTCCCC
GCATCCTCTGCCCTCGGTCTTCCCCTCCCCAGCTTGCATTTTTTCCCATCTCTTAGTCTGCCTTTCATTTTCCCC
TTCACATCCCGGTGGCTCCCCTTCCCCGCCCCGTCCCTCTGCACACCCCCATTCATCTCTGTCAGGTTTTTCTCA
TCCTTAAGTTCTCTCGTCCCCCTCCCCACTCGGGCGTCCCCGCTGGGCTCCCCGCCTCAGTTTCCTTCCCTTCC
TGACTCCTTCCTCTGACGGCGGCCCTTTCTCGAGGGCGGATGTGCGCCTGGAGGGCGAAGGCGGCGGCCGAGAGG
ACCCCAGCTCGGCCTGGCGGGCCTCTGGCCACAGCCATGCACCGCTTGGGCCGAGGCCGAGGCCGACCCCCAGGG
ACACAGGTGAGGCCGGGCGACCCGCGGGGCTCCGGGGAGCGCCCGAGCAGTGGCCCCGCGAAGGGCCGGGTCTGG
TGCTCTGGGGCTGGCTTTGGACCTCTCGTCCTGGGACTCCGTGGGAGCCCGGGAGCTGTGTCAGTGCCCGTTGGT
GCTGGAGCCAGTCGGCCCTTCCTTGGCCTCCTTCAGGCGGGGGCCAAGACCCCCGAGAGTTCACTCTGGGTGCTC
CACTCGGCGGAGAGGGCTTCAGACTGGTGTCCCGCGTGGCTGGGGTGTCGGCGCATTCCCGCGGGGAGGAGGCC
GAGGGCCCGGGCCGGGTCACCTGCCGGCGCCCCGGCCTTGCGCACAGAGGGCCTTGCCTGTCGCTCGTCAAATC
CAGACACCTGGGCCTCCGCCACTCGGCTGCCGGGGCGGCACTGGGGCGTCTGTACCCAGCGTGCGGGAGGGCACC
CAGGGCCGGACGCGCACCGCAGGGGTCTTTTTTTGGCCGCGGGGCCGGGCGGGCGGGTGGTAATGACAGCCGGGTTGC
TGGGGAGCCGCGGGCCAGATGGAAGCGGGGCCGCAGGTGAGGGACGTCCCTCGCGTAGCGCCACTCAGCCGCCGG
GGCCAGAGCGGGAGTCAAGGTGAGGGCGCCCCAGGTGGCCGCTCTCGGCCGCGGCGATCG
(SEQ ID NO: 243)

CGI: 97 range = chr12: 1844001-1845219
CGTGCGGGTGACTCCTCTTCCTGCCGACAAGGTGGGCGATGAGAACGAGGAGGCCCAGTCCCACCAGGGCGCCGC
CGACGGCGATGGGGATCGGCGTGTTGTTCTCGCCCAGCAGACGCTCCTCCGCAGATCCGAACTGGTTGCCTTCCA
CCTTGAAAGCCTGGCCCCACACTGGGAATATGTTGATTGAAAACGCCTTCGTGCCGCGGACACGCTCCGCTCCGG
CTGTAGAATTGCCGATGGCTGCCCGCAATGCTCGCAGGGAGTCGTTGGCAGCTTTAAAAGTGGGGTCTCTGGGGT
CAGGAAGAGTCGTATTCAGCTGGATTCCTCGTAGGAAAATCCGGCTAGAACCTGCATTCATCCCCAACCGGAAGC
CCAGGACCGTGGTGCCCTCGCCGCGCCGCTCCCGGGTCTCCAGGTGGGCGCCGCGCTCCCGCTGGCTGAGGTCAT
GCCCAGGTCACCGTCGCGTGGTCCCTCCTCTCTGGGTGAGGTTCAGCTGCAGTCCCGCGCTGGCCGGCAGGCAGG
CCCCGTGGGTGCCGCTCACGCTGTACCTGGCCACGGAGGGGAGGAAAGGGGCTCTCGGCGCCGCTGGCGGGAAGGCG
CGTCTTGCTCGTGGCGCGTCTCTCCCTTGCTGAAGCTGCTGTTGGAAATCTAGGCCTGGATCGGGGCACCGCGGA
GCCTGATGGTCTCGCTGTTCGTGCGGACCTGGGGGCCTTGATATCTGGTAGAGATTCCACAGTCCTGATTTCCTT
GGAGCTTGCACTGAGGAAAATGTGTGTGTCTGACAAGTTGTAAACAAAACTCATGAGCTGGACGCTGTCACGTGT
CGCACTTCTTGTGAAATGGAAGGTCAGTGTCTGTCTTCCTCCAAAGCACAATCGCGTGCCTGGGGTCGGAAGTGT
TCTCTTTACTGCAAGAGCCACTGTCAAGCACTTCCGCATTGGATGGCAGGTCAAAGGTCACATTCTTAGAGCCAC
TCTTAGAGTCGTAGTTCATCGAGAAGGCAGCGAAGCTGGCCATTACGCAGGCTGTCCCGTTGCCCTTTTTCACCG
CATCCGCTGCGGCTGCACCACGCACGAGGCCCAGCAGCAGCAGCAGCACCAGGGGCAGCCGGGGGCTCCACCAGA
TGCAGCCCGGGCGGCAGGCGCGAGGGGAGCCGGTGTGTGGGGAACCGGGCGCGGGGAGGCGGTTGCGGGGCGCT
GGCCTGAAGGACGGTGGCG (SEQ ID NO: 244)

CGI: 16 range = chr12: 40253533-40253742
CGACGGGACACGGTACATCACAAAGAGACCCGTGCGAGACCGAATCCTGAAGGAACGTGCCTTAAAGATCAAGGA
AGAGCGGAGTGGCATGACCACAGACGATGACACCATGAGCGAGATGAAAATGGGGCGCTACTGGAGCAAAGAGGA
GAGAAAGCAGCACCTGGTTAGGGCCAAAGAGCAGCGCCGTCGCCGTGAGTTCATGATGCG
(SEQ ID NO: 245)

CGI: 79 range = chr12: 52726910-52727810
CGTGTTCCCGGGCGGAGGTGCGCGCAGCCACCCCAGGCTGCTGCCAGGTGCCCGCTGGGGCTGCCAGGGCGAGGA
GGCCTCTGGGCTGTGGAGCGAAAGTCAGATCCACCGCCTACTGCGGGGTAGGGGCCGCAGTGGGGACCGCCAGCC
CTGTGGTCCCTCTCGCGCTGACTGGCGTAAAGTTGTGGCCGAATTCGCATCTCTTCTGGTGCTTCTCGCCCGCCA
GCGCAGGGCCCAGGTGTTTGAGGCGAAGGGGCTCTAGCTCCCCGCAAGCCTGGAGCCAGGCGTCGCGCTTCCTCC
GGGCTTAATCCAGACCTTTCAACACACACCTCATTCGGGGAGGAGAAAAGCACAGGACCGCGGAGAGCCCAGCT
TTGAGGCCAGGCCTGAAGGGATAACCCACACAGGGAACGTTTTCCTATCAGAGAATAATGGAGCACAAAATAATT
CAGAAAGCGAATGGGCAGGACCACAGCCTGAGAGTCCCGCGCCGCGGGCCTGCAGAGCCGGTCTCCCGAGCA
CCGCGGCAGGACCATTTCGTTGGAATGTAGGGCGAGGCCGAAGCCCGCCCCGGACCCAGGCCGCGAGGTGCGCGC
CGGCCGCCGAGGGGCCGCCTGTAAATTACAGCCCGCGGGAGGACTCGGAAATACACAAAAGGAGCCGAAAGATT
TAAACAGTCGGAGGCAGAGGCGTCCCGAGGCGGCCAAAGCGGAAATCAATCACGTAATTAAAACAGGGAGGGGAC
GAAGCCCAAGGCTGGGGGTCCCGGGTTCGGAGGAGGCGGCCAAGGTGCAGGCCGAGGCTGGCGAGCGGCTTAGGG
ACGTGGCTCGCCCGCCAGGACCAGAGCGCGCGAGGGGCTTCGGGGAAGTTTATAACACATCGCTATTGATTCCC
G (SEQ ID NO: 246)

CGI: 32 range = chr12: 79634857-79635257
CGGAGCGACAGACTAGGGAGCTCCGCCCGGGATTTGCCCATCGGCGGAGGCGCCAGGCTCCCGTTTCTCCCCATC
CCTCTCGCTGCCGTCCAGGTGCACCGCCTGCCTCTCAGCAGGATGGACGTGATGGATGGCTGCCAGTTCTCACCT
TCTGAGTACTTCTACGACGGCTCCTGCATACCGTCCCCCGAGGGTGAATTTGGGGACGAGTTTGTGCCGCGAGTG
GCTGCCTTCGGAGCGCACAAAGCAGAGCTGCAGGGCTCAGATGAGGACGAGCACGTGCGAGCGCCTACCGGCCAC
CACCAGGCTGGTCACTGCCTCATGTGGGCCTGCAAAGCCTGCAAGAGGAAGTCCACCACCATGGATCGGCGGAAG
GCAGCCACTATGCGCGAGCGGAGGCG (SEQ ID NO: 247)

CGI: 30 range = chr12: 95164929-95165298
CGCGGTGGAGATCAGCCGGGAGAGCCTTCTGCTGCAGGACAGCGACTGCAAGGCGTCTCCGGAGGGCCGCGAGGC
CCACAAACACGGCCTGGCCGCCCTCAGAAGCACGAGCCGCAACGAATACATCCACTCAGGCCTGTACTCGTCCTT TABLE 7B-continued Sequences of differentially labeled CGIs between bladder cancer subgroups relative to blood CACCATTAATTCCCTGCAGAACCCACCAGACGCCTTCAAGGCCATCAAGACGGAGAAGCTGGAGGAGCCGCCCGA
AGACAGCCCCCCGTGGAAGAAGTCAGGACTGTGATCAGGTTTGTGACCAATAAAACCGACAAGCACGTCACCAG
GCCGGTGGTGTCCCTGCCCTTCCACGTCAGAGGCTGCGGCGGCGTCCGCCTTCCTGGCCTCGTCCGTCTCG
(SEQ ID NO: 248)

CGI: 35 range = chr12: 113609113-113609535
CGCGCGAAGCAGAGAACGAGAGGAAAGTTTGCGGGGTTCGAATCGAAAATGTCGACATCTTGCTAATGGTCTGCA
AACTTCCGCCAATTATGACTGACCTCCCAGACTCGGCCCCAGGAGGCTCGTATTAGGCAGGGAGGCCGCCGTAAT
TCTGGGATCAAAAGCGGGAAGGTGCGAACTCCTCTTTGTCTCTGCGTGCCCGGCGCGCCCCCCTCCCGGTGGGTG
ATAAACCCACTCTGGCGCCGGCCATGCGCTGGGTGATTAATTTGCGAACAAACAAAAGCGGCCTGGTGGCCACTG
CATTCGGGTTAAACATTGGCCAGCGTGTTCCGAAGGCTTGTGCTGGGCCTGGCCTCCAGGAGAACCCACGAGGCC
AGCGCTCCCCGGACCCCGGCATTAGGCGCCAGCTGCCGGCTATCTGCG (SEQ ID NO: 249)

CGI: 121 range = chr13: 35817738-35819004
CGCAATAATGCTGCGTCACGAAACTGCGCATTCCAAGAGAAACTTTTCTCAGGCCCAGAATTAAGTCGGAGGGAT
CCGCCCGCGCAGCTCAATCCCTAGGAAGCATGAAAGAATGTATTGTAAAGAGTAAAATCACGCGCAATCCATCCCA
ATATAACCGCAGTTGTTCGTGGGCCTTCTTGCAGAGAAAGGCTGCCCAACCTTGACGGGGCCATGGGCGCTGCGG
GAGGGCAAAAGACCACAGAGATCTGCGAAGCCAAAGTAAACAACGGGGTTGGGGCGGCGAGAATGATCAATAGCG
ATGCTCCGAAAGGACTCCGCGATAGGAATCGAGCGGGAAGGATTCCCTCCATCCTAACAGTCCATGGGTTAAGAG
GCCGAAGCTTCCCTAAATACCACACTCCCGCGAGAGAAGGGACTGAGAACAACTTCTCAAACTATTCTCTCTCGA
AATCGCTCCCTTCCTCGAAAATTCCATCTCTGAGACTCGGATGAGGTCCCCACCCCCTCCACCCTTGTCCCGTGA
CCGTCGCCCGCTCAGCCTCCCAGCCGAGTCCGCGGGGCCTGGGGCGCCACCCCGCCCACCCAAGGGACCGCGCA
GGGGTGAACTCCCCCGCGCCCCACCTGCGCCTTCCAGACCTCGGGCGCCCCGGCGTTGCCTCGAGAGCTCCCTGC
GCGGCCGCCGCGGCACGGACCAGCTCCCACTCCCTTACACTGGGCGCCGCTGCGCTCGCCGGGGCCGGTCCCGA
GGTTCCCAAGGCCTCGCGCGCGCGCTTGCCGTGGCAACCAAGACGTTCCACGACGCGCGCTCTCGAACGCTTCGC
GTCACGCGGCCGCGCGGCCCCGCCCGTCGGCCTCGCTCCCGCCACAGAGCCCGCAGCACGCCGCCGCCGCAGCCT
AGGTCACGTGAGTACCCACGCGCGCGTCTTGCCAGCGGATTCATCACCGGCCTGCTCAGACTAGGTTCTGCCCAC
TCTGACCTTCTAAATGGTACGTGGGAGGACGTCCGTCCCCTTCGGACCCAAGAGTCACCGTAACACTCTAGAAGG
GGAGAAAAGGAGCGAGGGCGGCAGGCGACAGAGAACCTCGCGAGTCAGCGGCCCCGCGCAGACCCCCCAGGCAC
GGTCCCCTGCGGCCACGTCGGCTGCTCGGCGCCTGCGCAATCTCTTTCTCTCCAGCGAAACCGAGGCCTCCGGAG
AGCCTAGTAGAGAGTGTGGGCAGTGAGCGCTTGTAGCCGCTAGAGGGAGCGCTGGGCACAGTGCACG
(SEQ ID NO: 250)

CGI: 58 range = chr13: 57101588-57102323
CGCGGCATGTTCGTACCAGCGCGGGCAGAAACGGGCTCACGAGCGCCCTCGAATTCACACACACTCACCGAAATA
CACATCTCAGCCCGTGGAAGCGCATTCACACACACCCACGTACACTCCTCCGCACCTCATTCAGATGGGTCCACG
CGGAGTCAGGGCTGCGCTTCCCTTGGCATGGGCGTGTGTGCGGCGAGGGCGTGTGTGCGTGCGTGTGTGAGAGTG
TGTGTAGAGAAACCCTTTAGGCAGACCGCAGCTACGTTATTCTGCAAGCATACTGCGATTCCCGATTCCGTGTAT
GTAGGACCACAAAAAAATTAAATCGCTGTTAAACTTTTTTTTGTAAATTCTCTTTTCCGAAGGAAGGCGCTGGAA
GAGCTACTCCCGGTGGTTAAAGGCCCGGGAGACCTGGTGGCGAATCCTGGGGCGCGTCCGCTTTGGCGGAGCGCT
GGGCTCCGCTAGCCGGACTGGTTCCCCATCTAACTGATCTAATCAATGACTCCGAAGAGCCGGGGCTCCTGGCCC
CGCCCCCGCCATCCTCTTCTCCGCCTCCCATTGGACGCGGGCCGAGAAGGCAGGGCCTTGCTCCTCGCTCGGATT
GGCTGACAGGGAATCAGTATCAATGTTTAAGCGGCGGCGTGAGGTGAATAGAGTCAGTCAGCAAGAGACGCTGGG
GAGAGAGCAGGGATCGCGAGCCCGGCGGATGCGGCAGCGGCGGAAGGCGGCTGGGGAGACG
(SEQ ID NO: 251)

CGI: 30 range = chr13: 105943410-105943788
CGCCGGGCTCTGCGGGGGCATCTCCTGGACGATGTACACCGGGTGCCCGTAGTCGCCGCTGACCTTCTCGTAGTG
AGGGCAGAAGACGCTGTCCGCAGTCCTTAGCGGGATGATAATGTCACTGGGCTCTGAGCCGTTGTTGTTGCCGCT
GCGCTTGGGTGTGGCCAGTGTGCTGAGCGACAGCGTGGTCGTGTGCTGCGGCGAGTGCTTCCTGTGTCTCCTCCG
GTACTTCAGCAAGAGGACCACCAGCGTGATGATGATGACGATGAAGATGATGCATCCTGAAGCAATCCCTGCAAA
TAAGGCCACTTCGGAACCGAGGATGTTGTTCCCCGAATGTCCGGCGCTGTTGCCGTCTGTGCTAGAACCTGCAGA
CGCG (SEQ ID NO: 252)

CGI: 74 range = chr13: 111763361-111764235
CGCTCCCAGCCGGCAGCCGCTCTGGGCGTGCACCCGCCACGCGAAGCCAGAGGTTGGACGACGCAGCCGGCCAGG
CGCGGCTCCCGGGGGACCCCGAAACCGCCTGTGGCTCAGGCCCTACTTGGCAAGAAGAGACTGGGGAGTGAGAGG
AGGGGTCACTCTTGCTCTCTCGCACAATAGACTTCCCGCAGGCGAGTGCGAACGGCCTTTTGCTTCCTCCTTCTT
TTCCAGGACCCTTAGCGACAGGAGAGGAAGAGAAGCGGCCCGGCGGTTTAATTGCCAATTTCCTGATGCAGCCAC
AGGGCCCAGCAGCGGCTCAGCCTAGGCCACCGGGTCCAGGCCTCTAGGCAATAGGCCCGGCGCCCCTCCAAGCA
CCGTTTCCCGCCGACCCCGCAGTCATCACTGTGAGCTCGAGAGTATGGGCAGCCTGTGGTGCCCTGAGGCGCCGG
GCGCTCGGCGCATCCGCCGTGCCCACAGCGCTGAGGACCAACTAGGGCTGCCCTCGGCCAGGGGCACTGTGCCCG
TTTGAGTGGCACTCGGACCTGGCGAGGGGTGGAAGCCCAGGTAGAGCTCGCGTCTTTAAGAGCCCACCCGACAGAA
CTGCGCGCTACATCTGCGCCAGCTGGGCTGGGTGGGAACAGCGCAGAAATACTCCCGTGCCGGGGCGTACAGGGC
AGGTAGGCCCAGCAGAGAGTCTTCTCGGAAAGTTTCCCACAAAAGAAGGGCCGGGCAGGCCGAGCGGCAGGAAAA
GCCGGTGCTCAGCGGCGAGGCCCGAGAGGTCTGGCATCCGGCGGCCTCCCAGCTTTGCTCGGGTCTCCCGCCGCC
TCTCTCCAGAGCCGCCCGTAGCTCCGTGGGCGGAGGGCGCAATGCCCCG (SEQ ID NO: 253)

CGI: 28 range = chr13: 112249708-112249928
CGATTCCTATCGAATCAACACGGCCATTAAGGACAAAAACGGGCAGGACACAAAAGCAAGCCTGGATGGCGCACC
CTACAAACGAGTTCTGAAACAAAGCGAGTGCCAGACGCGCGTGGGAAAGACGCGCGTGGGAAAGACGTGCATGGG
AAAGTCGCGCGTGGGAAAGTCGCGCGTGGGAAAGTCGCGCGTGGGAAAGACGTGCGTGGGAAAGACGCGCG
(SEQ ID NO: 254)

CGI: 87 range = chr14: 19992581-19993863
CGTGACGTAAGTCCGCCGCGGGTTCGCCAGCACCTTGCCATCCCGCACCACGCCCACGCCAATCTTATTGGCGCT
GCCTTCAAAACCCAGCACCGCCGGCATGGCGGAGGCTGGGAGAAAACGCCGACAGGACTCCTGGCAATGTCAGGA TABLE 7B-continued Sequences of differentially labeled CGIs between bladder cancer subgroups relative to blood GCTGTGGAGGTCCTCACTAGTCCGCGCTGGGCCGCAGCTTTCCGGAGCGCAGAGGAAGCTGGCCAGCCTGCAGAT
AGCACTGGGAAAGACACCGCGGAACTCCCGCGAGCGGAGACCCGCCAAGGCCCCTCCAGGGACCTGTCTTCCTAA
CTGCCAGGGACGCCGAGCCAACTCTGTGCCTTACATTCGTATCCGTTTTCCTATCTCTTTCCCGTGGTCCAGCCC
AGCCTTCTCCACTGTTTTTTTCCCTCTTGCACATAGTTAGAATCTTAAGTCAGTGTCACACAATGTGCTGTGCAT
CTGGCACAACGATAAACAGCCCGAGGGAGGGTTGGGGACCTAAGTGTCCTAGAGAATTAGAGGAGGGAGGCGAGG
CTAAGCGTCTCCGTCACGTGGTGTCAGACAGACCAATCACGCGCATTCTTCGGCCACGACAAGCGCGCCTCTGAT
CACGTGACCAGGTCCGCTACCCACGTGGGGGCTCAGCGTGCACCCTTCTTTGTGCTCGGGTTAGGAGGAGCTAGG
CTGCCATCGGGCCGGTGCAGATACGGGGTTGCTCTTTTGCTCATAAGAGGGGCTTCGCTGGCAGTCTGAACGGCA
AGCTTGAGTCAGGACCCTTAATTAAGATCCTCAATTGGCTGGAGGGCAGATCTCGCGAGTAGGGTACAAGGCACT
ATGAAATGATCTAGTTTCGTGGGTGAGGGGCTGAAGGGCCTATGATGCACGGAGGCGGGGAAAGGATTTAGAGAT
AACGTGGTTTGAAAGGCGGGACCTGGTGCGGGGACGCTCTTGGGAGGAGTCTTCTCCCCAGCCTTAGCTGGTTTC
ATGATTTCTTTGCGTCTGTAGGCAACGCGGTAAAAATATTGCTTCGGTGGGTGACGCGGTACAGCTGCCCAAGGG
CGTTCGTAACGGGAATGCCGAAGCGTGGGAAAAAGGGAGCGGTGGCGGAAGACGGGGATGAGCTCAGGACAGGTA
AGGGAATGAAATCAGCCCTTCTTCCTAGAAGCTGCGGCGGGGGTGTTTGTCATTCCCTTGATGTACGGTAAGTAC
GGGCCGACTCATTTTTGCAGGGGTTTGTGAAGAAGTCGCAGGAACCGTAGGCTTTCGTTGGGTCTATAGTTAACG
CCGGATCG (SEQ ID NO: 255)

CGI: 79 range = chr14: 23710894-23712060
CGCCTGTTACTAGAGGCGAGAACCGGAGCCCATTGGTCGGAACACCTCACAATGGACCCCAGCGGCGCGCAAAAT
CCTTATGATTGGTTTGCTGGCTGCCTCGGGAGACCCTGTTGCCAGGATACTTGGCGTTCCCGACCCGACCCCCGT
TCCCCATTGGCTGTCAGGGCAAAAGCCGCCATCTAATGAGGAGCGAGGTGCGGTGCCCCGAAGCGCTCGCTTCCC
GCGGTGCGATCTAGTCCTGCAGTAGGCGGCCCGGGGCCACACCGCGGCCGCCCAAGCCAGTGCAAGGCCCAGGGG
CCTGACATCGCTCCCAGCGCTCGAGGACCGAGGCCTGCTGTGGAGGACACCGTGCTCCCTCGGGACCTGCTCTGG
ATTCCGGCCCGGACGTCCCCTTGGAGCTCTGCATCTCCAACCTGGAACCCAACCCAGAAGTCTCAAGTTTGACGC
ATCACGTGGCGTGCGGATCCACTGAGGGTCCACAGAGAGGGGCGCCCATCTCCTGCGTCTCAGTTATCCTGGTAA
TTGTGTATCTGCCCATTGTTCGTTGCCTCATTAACTTGGCTTTCTAGGTGCACCCACCTTGCCACCAGAGAAGTC
CAAATCCTGACTTCTCTCCAAGGTGTTGGGAATTCTGTGCCCTAAAGAATTCCGACTCAGATCCGAACGGGGATC
TGGTGGAATCGAGGGTGAAAGACCAGAGGGACAATGTTCTACTATCCCAACGTGCTTCAGCGCCACACCGGCTGC
TTTGCCACCATCTGGTAAGGGCGGGGCCCGTTGGCGCGCGATGGCGGACGCTGCCCGGGATCCCAGCCTGACAGC
TCCCCCTCCATCCCCATTCTCCCACCTTCCCCACCCACTTCAGGCTGGCGGCGACTCGCGGCAGCCGGTTGGTGA
AGCGCGAATACCTGAGGGTGAATGTGGTGAAAACCTGGTAAGGCCCAGAAAAGGGAAGGAGGGCCTGGTGCGGGG
GGTGAGTTAGGGGATGGGGTGGCCAAGACTGTGGGCCCACTCCTGGACGCAGCGGTAATCAGGGCGCATTGTTCC
CCAGCGAGGAAATCCTCAATTACGTGCTGGTACGAGTGCAACCCCCGCAGCCCGGCCTGCCGCGGCCCCGCTTCT
CCCTCTATCTCTCAGCCCAACTTCAGATCGGTGTGATCCGCG (SEQ ID NO: 256)

CGI: 23 range = chr14: 28317076-28317375
CGTAGCGACGACGTGGTCCTTGTAGGACCAAGCATTCTTGGCATTCTGTCGAGATTGAGATTCCAGAGCATCGGA
TGAACGGGACTTATAGCTAAGGCGTACTCACCCACCCCTCCCTTCGTCTTTTTACGCACGCAGCAACTCGTCCTC
ACGTGCATAGGGGTAGTGGACAGTGTTGACTTGAATTGCTGTCCCTCGTTCCAAGCCTTTCCTGTGAATGAACCC
GAAAACACTCGACAGGTCGTGAATAATCGTTTTAATGAGTGTGCAAAGCGTGCGACGGGGTGCACCGAGCTGTCG
(SEQ ID NO: 257)

CGI: 147 range = chr14: 33338698-33340189
CGAGAACTCCAAGTCCGACGAGAAGGGGAACCAGTCCGAGAACAGCGAAGACCCGGAGCCCGACCGGAAGAAGTC
GGGCAACGCGTGTGACAACGACATGAACTGCAACGACGACGGCCACAGCTCCAGTAACCCGGACAGCCGCGACAG
CGACGACAGCTTCGAGCACTCGGACTTTGAGAACCCCAAGGCGGGCGAGGACGGCTTCGGTGCTCTGGGCGCGAT
GCAGATCAAGGTGGAGCGCTACGTGGAGAGCGAGTCGGACCTGCGAGAACTGCGAGTCACTCACGTCCGA
CAGCGCCAAGGACTCGGACAGCGCAGGCGAGGCGGGCGCGCAGGCCTCCAGCAAGCACCAGAAGCGCAAGAAAAG
GCGGAAACGGCAAAAGGGCGGCAGCGCCAGCCGCCGGCGCCTGTCCAGCGCGTCGAGCCCAGGCGGCCTGGACGC
GGGCCTGGTGGAGCCCCGCGGCTGCTGTCCTCCCCCAACAGTGCCTCGGTGCTCAAGATCAAGACGGAGATCTC
AGAACCCATCAATTTCGACAATGACAGCAGCATCTGGAACTACCCGCCCAACCGGGAGATTCCAGGAACGAGTC
CCCCTACAGCATGACCAAGCCCCCCAGCTCTGAGCACTTCCCGTCCCCGCAGGGCGGCGGCGGTGGGGGTGGCGG
TGGCGGGGGGCTGCACGTGGCCATTCCCGACTCGGTCCTCACCCCGCCCGGCGCCGACGGCGCGGCCGCCCGCAA
GACTCAGTTCGGCGCCTCGGCCACCGCGGCCCTGGCCCCCGTCGCCTCCGACCCGCTGTCACCCCCGCTCTCGGC
GTCCCCGCGGGACAAGCACCCCGGGAACGGCGGCGGGGGCGGGGCGGGGCGGCGGCGGCGGGGGGCGGCGGCCC
CAGCGCGTCCAACTCCTTGCTGTACACTGGGGACCTGGAGGCGTCTGCAGAGGTTGCAGGCGGGCAACGTCGTGCT
CCCGCTGGTGCACAGGGTGACCGGGACCCTGGCCGCCACCAGCACGGCCGCGCAGAGGGTCTACACCACGGGCAC
CATCCGCTACGCGCCCGCCGAGGTGACCCTGGCCATGCAGAGCAACCTGCTGCCCAACGCGCACGCTGTTAACTT
CGTGGACGTTAACAGCCCCGGCTTTGGCCTCGACCCCAAGACGCCCATGGAGATGCTCTACCACCACCGTGCACCG
GCTCAACATGTCAGGACCGTTCGGCGGCGACAGTGAGCGCAGCTAGCCTGACGCAGATGCCCGCGGCAACGTGTT
CACCACGGCCGAGGGACTCTTCCTCCACGCTGCCCTTCCCCGTCTACAGCAACGGCATCCACGCGGCACAGACTCT
GGAGCGCAAGGAGGACTGAGGCGCCGCCCGTCCTGGGCCCGGCCAGGCCCCGCTTGAGGAGGCATCGTCGGCAT
TTTCGTTTAGACCTTTAATTCTAGCACTTTGAATTCGAGCAGGTCAGCGTCTTCTCTCGCCACGACG
(SEQ ID NO: 258)

CGI: 22 range = chr14: 36122289-36122589
CGCCCGGCCGCTGCCGATCTCGGAGCTCGGAGGCCGAGCTCCACAAATTTGGGTCCAGGCCCGCTTTAGAGCCCC
TGGGCGGGGGCGCTTCTCAGGGCATCCTGTGAGGGCTTTGAGGCCTCCTTGGAGTCGCCAGATGAACTGGTGCCG
CCTGTGCGCCTTGGCCCCATAGCCTCAACGGCACTCTCACTGCCTGGGCTTTGGTCTTTGCCCAGGAGCCTGCCC
ATGGCCTACGCTCCCCGCTCGCAGCATGGCAGACCCTGACGAGGCTGCCCGCCTTGGTCCGGGAATGGACCGATC
G (SEQ ID NO: 259)

CGI: 123 range = chr14: 37137198-37138958
CGGGGCAGGGTACCCGCGAGGGCAGGCACGTGGCGGCTCCTGCGGTGTCCCGGGTTAAACTTGCCTGTGTTTAAG
ACGGGTCTGCGACAGCTTGGGGCGGTCCAGGTCGCGGGGAGGGCGGGCTCCTCAAGTGGGGGATCCGCGGCAGTG
AGGACTGTAGGGTGCGCGGGTACTCCGGGTAGCCGCCAGCGGAGGAAGCGGCTCCGCCCTTCCCGGAAGCTGCCC
TTGCTACACCCGTGGGGCCTGCTCCCGGCGCAGTCCCGCAGTACCCTGAGCGGCACTCGGTCCTTTGACCACGCTT TABLE 7B-continued Sequences of differentially labeled CGIs between bladder cancer subgroups relative to blood GGCTGCCTCAGCTTACACTTCCCAGCAGGATCTGGCTGGGAGCCCCTTCCTCAGATATTCACCAGGCAGGTAGAA
GCAGAGGGAGACGACGGCGAAAGGTGGAAGGAGAGGCCGCGGCCTCGGGCCTCGGGCCCCGGGCCCAGACGGCGG
CCTCTCGCGGCGACAGGGTCCTTCCTATTTAGCAGGACCGCAGGGTTGGCAGACAGCAGGGCCTGGGCCGGCGGG
GCTCTGCGGTGCCCATTCGAGTCTCTCCAGGGCTTCCCTCTGTGGCTGTCCCTCGCCTGCCCCCTTTCCTTGCCT
ACCCTTCCCTGGACGGGGTTGTTGTCAGGTGACGGCTTCAGCAACCCAGCCATGCTTGGTGTGGAGTGGTTCGAG
TTCCTCCGCGGGCCCCACCCCCCACCCAGATAAGAAGCTTAAGTCCTCCTTCTGCAGGGGAGAATCGGATGCAA
TGAAACTAAGACCTGTGGTCGTTAACGCGGTTCAAAGCCGACCCCAACTGGGACACGGCTCAGCTTAGAAGTGAG
GAAGGCCTGGGACGCTGGAAACAAGGGGTCACACGTGCGTGTGCCTGGCCTTCGCAGGTGGATGTGTGCGCCGAG
CTGGGGAAGGGGCCAGGGAGCCGCGAGACTGCGGTCCCCCGCGAGAGAGAAGTATGGGCCTGGCCAGGGTTCGAA
CTCCGTTCCTTCGCTGCCTTCCTTTTATTTTTCTTCCTCATCTTCCTTCCTCTCTCCCTTGGTTCCATCATTAAA
TCTTTAAGGGATTAATTCACAACTCTGTAGTAGGTAGGGGCCCTGGGACCACTTGACGGGCCTTTGCAGGCAGTT
CTGTACAGAGTCCTAACCCGTAACGGGCCTCAACCCCGGCTGTGTGTGCGTGTGCTTGTGTCTGTGTGTCTTTGT
GTGTAAAAGCAACGCATAAACATACCCAGGGCTTTCACTTATTTTATTGAAGCAAACAAACAAAAACAGCCACTG
GGTTTGTCTTTTCCCCTACTCCTGCCTGAGCGCCGCCGGGTTTCTGAGCTGCTCCGGGCGCGGACCTAGCTCACC
CGCAGCCGGATGTCGGAGCCGGAGCTGCTCCCCACCCGGCCTCGCCCGCGGGCGACAAAACCGTCCCTCTGGCCA
CGGGAGAGCATCGCCTTGCCAAAATCAACTCGCATTTTCATGTATTCAAATGAGAAAGACTGAGAAGGGCGATTT
CCCCTGCTGGGCAGTCGACAGCGTTGGAAGGAAGAAGTGCCCCCTAGGGCCTCGCGGAAACGGGAACAAACCTCC
CTCGAGGCCCCGGAACCGATATGGCGACCCCGCCCAGACCTGGGTCCCCGCGGCCGCGCGCGTCTCCCGCCGTT
GTGGCCCCCGAGTTACTGACTTTTGTTCACACCGGTCAGCGCCTGTTGGAGGACGTGCTCAGCCCCAGCCGGTCC
CTCCTCATCCAGCCGATCCCCTCCTGGGGAGCGCG (SEQ ID NO: 260)

CGI: 20 range = chr14: 56347822-56348040
CGGGCCTCGAGGATGCGAGTGTGAGGTCGACAAGATATCGTGGAAGAGAGCGAACGAGGGAGGCCCCCGTTGGAA
ACAGTTTCTGTGTTAGAACAAACGCCACCAAACGACCGACACTGCGAGGCCTGGAGCTACCTGGGCTGGCGCCGC
CCGAGCCCCGGGCTGCGAGCCCAGAGGCTGGGAAGTGATGGGACCTGGGGGCCCGAGCCGGAGAGTGCG
(SEQ ID NO: 261)

CGI: 178 range = chr14: 60045486-60047933
CGGCGGGCGCTGTCGAGCACGGGGAGGTGCTGAAATAGTCCTGGCGTGCTGATTCAAGCTTTGATTGGCAGAGCC
ACCCGGTGACTGACAGGGGGTCTCCATGGCGCCCGCGCCGCCAATCCGCCCACCCCAATAGCGGAGCCAGCTCGC
CTGCCGGCGTGCCTGAGCCGAGCCGAGCCCGAACCCCAAGCCGCGGAGCCAGCACCTCCTCCAGTCGGGGTCGTC
CGCTCCCGGCCGTTGAGCCACCGCCGCCACCCGGTAGTGTGTCCCGCTGCCCCAATCCGCCTCATCAACAAGCGC
CTGGCACACTCAGCCAGGCCCGCGGGCATCTGCTGCGTGTCCCGCTCCGGGCTCAGTGCCCTCGCCGCCGCCGGC
ACTGCCTCGATGTTCCAGCTGCCCATCTTGAATTTCAGCCCCCAGCAAGTGGCCGGGGTATGTGAGACCCTGGAA
GAGAGCGGCGATGTGGAGCGCCTGGGTCGCTTCCTCTGGTCGCTGCCCGTGGCCCCTGCGGCCTGCGAGGCCCTC
AACAAGAATGAGTCGGTGCTACGCGCACGAGCCATCGTGGCCTTTCACGGTGGCAACTACCGCGAGCTCTATCAT
ATCCTGGAAAACCACAAGTTCACCAAGGAGTCGCACGCCAAGCTGCAGGCGCTGTGGCTTGAAGCACACTACCAG
GAGGCTGAGAAGCTGCGTGGAAGACCCCTGGGACCTGTGACAAGTACCGAGTAAGGAAGAAGTTCCCGCTGCCG
CGCACCATTTGGGACGGCGAACAGAAGACACACTGCTTCAAGGAGCGCACGCGGCACCTGCTACGCGAGTGGTAC
CTGCAGGATCCATACCCTAACCCCAGCAAAAAACGTGAGCTCGCCCAGGCAACCGGACTGACCCCTACGCAGGTG
GGCAACTGGTTCAAAAACCGCCGACAAAGGGACCGAGCGGCTGCAGCCAAGAACAGGTCGGTACCTAGAGGCCTC
CGCGCTTTGAGCGCACCGGGGAGGAGGCGGGTGGAGGCACCTCTGGCGCCCTTACCCAGTCCCTGGCGACTCCAA
TTCAGCAGGAGTTGGGAGCGCGGTCTGTCTTGGGTTAAGAGCCCTGCGTTCTGGGCTCCTGGCCGGGAGTTCCCT
TGCCGGCTCTGCTTCCCCACCCGCTGGCTCCCCACGCCTGCGGGCAGCTGCAGCAGCTGGTCCCGGTCACCAAAC
CAAGGCTTCACTGGGACGGAGAGGGGAAGAGAAATAAAAAATTAAAATCCTACAAACAGTTAGGGACCCCAAGAC
CCAAAGCTAATTCTTGTCAGCCTGGGCACAGGCTCCTACTATTAATCGAAGCCTGGCTTATTAGCAATGTGTCGG
TTTCATGTTAATTATCATTTTCAAAGCCCAGGTATATCCCTCCTAATGCTTTGAAAACAGTTTTCAATGGACTT
TTGAGAAATGGGAAGTCGAGTTTTCCTCTTCCCATGCGCTGCCTGCCACTCTTGTCTCAAAACAGCAAACTAGTC
CGTGGGCCGAGGCTTTTCGTTTCCCGGAGTGTGGATCTCGATTAGCCAAACATTTTGCGGAAGAGCCCGGCCTCA
TCCCCCAGGCCCAAATGCTCCTTACAATCCTTTTTGCCTTTAGGTCGGGCCGACCCGATCCAACGCGATCGCGGG
AGCACTTGCTCAGGCGTAAGCCCCAGGCAGACGCACCGTTAGAAATGGTATCCCATGTCCCTGGGACCGATCTGT
CCTTGTCACCCACACTTCGTTTATTTCCTGACAGTCCTGTAAATCTCCCAAAAGTGCACAACAAACAGGGAGGAC
ACTGCAAGCCCAGTATATAAAAGACCTGGGAGCTGCGGCGCTGAGAAAGGGCGCGAATCATGGTGGGGCACAACA
GTAGGGACCCGCGGAGGGGCGGCCGCGGACTCCTGCCCGACCTCTGTCGCCTTGCCGAGTAATCCTCGCCTTAAC
TGCTGGGGTCTTCGGAAGAACCTCTAGCCGCCGGGCTGGAGGGACCGCAGGAGGTGGTGGGGGCGGCGACGGGCG
GCTGTGTTACGAGCTGTGACCCGTGTTCCCTTTCTTCCCCGTAGACTCCAGCAGCAGGTCCTGTCACAGGGTTCC
GGGCGGGCACTACGGGCGGAGGGCGACGGCACGCCAGAGGTGCTGGGCGTCGCCACCAGCCCGGCCGCCAGTCTA
TCCAGCAAGGCGGCCACTTCAGCCATCTCCATCACGTCCAGCGACAGCGAGTGCGACATCTGAGTTGCCCATCCA
GGATGCTCAGAAGCAGATTCCAGTGTAAAAACGAGAAAAACAAATGAAAGAGGGGAAGAAGATGAGAGACCTGC
AAATCCAGCGCCACAGAAGCCAGGTGACCAGGGACCCGCGGGCTCGGGTTGCCGTTTCCCGCCCCACCCCGCGGC
CGGCCTGGCTTCACTGGCGCCCTTTGGCCGCGACCACGGGAACCAGCC (SEQ ID NO: 262)

CGI: 54 range = chr14: 60173732-60174416
CGGCTAGGCTGCGCCTGCATCAGGCGTGGTGATTGGCAGGCGCCTACGGCCCACGCAGAGATGGCCGCGTGGGGG
TCGGAGCGCCAACTTCTCAGCTCCCCTTCTCCCATGACCCTCACCCCCCACACCATCTTCAGCCGCCCACTGGGA
GCTTCCTCCACCCCTACCCCCCAGTGCCGGCGAGGCCCCTGGCAGATGGAAGCTGCTGACTGATGGGGCTGCC
GAGCGCGAGGGAGCTGAGTGAGGCCCTTGCGCCCTAGGCGGTTGCACCCCGGACCCCTGCAGCTGTGGACGCCGG
AGCTGTGCGCAGTCATCCTGAGCCAGCCCGCGGGGCCCGATCGGAAGGGACGCCTCTCCTAAGAGCTGGCCTGGA
GTCCTGGAGCCTCCAAGCGGGCAAGTAGGGGCCGCAAAGGCTGGGCTGGGCCTCCGCTGAGGCCCTCGGGGGCCT
CTGGGCCCTCATGGCCTGGAGGCCGCGCGGCCCAAGCCCCTAGAGCAGAGGCCGCGCTAGCCTGCAGGGGTCGAC
GCAGGGCCGGAGGCAGCGGCTTTTCCTTCCCACTCCGGGTTGACCCTAAAGACACGATTTAACGTGGCGGCGGCA
GCTGCCCACGCTGTCTGGAGGAGCAGGGCGCCTGGGATGCGCGGCGAAACTGGCCCGGAGGGGGGCCCAGGCCT
CACGCGCCCG (SEQ ID NO: 263)

CGI: 133 range = chr14: 98781593-98783184
CGGAGGCTCCTTCCGTCCCGGCCTCACCTGGATCCCGGGAACCGCCCGCTCTGTCCCGCCAAGGTGGGCTGAGGA
AGACGGCGCCACTCATCAGGGCAATGGCGGCGGGCGGAAGAGGGATCCCCGTGCGCCCCCAGCACCCGGGACGAA TABLE 7B-continued Sequences of differentially labeled CGIs between bladder cancer subgroups relative to blood TGCCACCCCGGCGAAGCGACCCGACCGGCGCGCACGGTTTCGGGGAGGGGACCACTTCCACATTCCCCATGCCCG
AGAAGGTCACCCACCCGGGAGAGCGCCCAAGGGCCAGAGAGGAGGCGACTGGTGGAGGAGGGGCGGCCCCGTGCG
CACAAAGGGGCCCGGGGCCGGCAGGCTCCCCGCCCTTGACCTTGGGTCTCCGCCTCCATCCATCTCCGCCGGCTG
CCAGGGAAGGGGGCTGGCCCGGGGCCAGAGGCGTGCTCGCTGGGCTGCTGCTGGGCTGGGGACCGACGGGGGCGG
GGGGGAAAGGAGCCGGGAAAAAAGACTCCAGGGCTGCAGAGTGCTCCGAGGAAGCCTGCATTCCACCACCTTCAG
GAGCCGGTCCCGAGGCGGCTCCGATTCACTGCATGCCCCCCGCCCCCAAAGCAAAAGTTGCACGGATGCACGAG
GGAAACCCCTTCCCAAAGCTAGCCCTTCGACTCGCCCACCCCCCGCCTTCCTCGGACCCAGGCCGAGTGGGGGAG
GGGAGTGTCAGGGGAGGAAGAAAGGAGCGCGCCTTCCCAGCGAGGCCAGACGCGGGCTGGGTCAGCTGCGCCTCC
GCCCGCCCCTCGCCGCCCGGCTCAGGCAGCTGCTCCATTAAGCCCCCGAATTATGCATGGACCTTGAGCCCTCTC
GGCCCTCCCGCCCCACCAAGGCACAATCAACGTGCGCAGCGGGCGCGGGTCAAAGAGAGAGGGAAGGAGGTGGAC
GATGGGCGCAAGGCCGTGGGCGAATCAGAGGCCGGCGGCCAGGCGGGGGCCAGGCGCGCCCGCAGGCCTGGGAAC
AGTGCCGAGGAGCCTCCCGACCCGGCCAGGGCCAGCCGGGAAAGGGGCACCGCTCGCAGGGGAGGCCCCCGCGCA
GTTTTGAAGTTGCCAAAGTGTCCGCGCCGTGCCGGGTGCGGGGTCCGGGAGATGCAGCCGCCCCCGCGGAGCTCT
GCGCCCCTGGCCTCGGGGAAGGCCATTGTGTTCTCCTGTGTGGCAATGAAGGGGGCTATGGACCCCAACCATTGA
GCCCTTGGAGGGAGGGGCCTGAAGACCCCTCGGGCAGGGCGGGGGAGGCTGTCTTGCGGGCGGCGGAGAGGATGG
GTATGATTTGCTCGGGATAGGCACCGTCGCGGGGAGGGAGGAGGCCAAGCTTGAGGAGGGGCTGCTGGAGATGG
AAGGAAGTGAGAGGAGACTTGCAAGTTGCAAACGTCGGGGAAACCGGAAAATTGCAGTAGCGGGGAGGCAGGTGG
CGCCCAGAGGTTCGAAAGCAGAATTGGGAGGACTTCGATGTCCACCTCGCAGACAGTGACCCAGGCCCCAGAGGG
CTCCGCAGCCTGGAGCCTCGCGTCCCGCCTCCCCGCAACACGTGTTTTCAGCGTTCCAGACCACAGCGCTGCAG
TCTACGCTGCCCTGACG (SEQ ID NO: 264)

CGI: 248 range = chr15: 50867751-50870991
CGCCAAAAGAATGAGCGCGGGAGGGGGTCACAGCAGCCAGTTCGGCCAAACATCGACGCTGCTCCGGCACGCTCC
AGCCCAGCGCCTGGGATGTGTCAGAGGTACCTGCGAGGAACATTTGCGTGCGATTCCACGCACGCGTTGCATCCC
TCTTCCCAAACCCGGATCGCTGAACTGAGAGGTGGCGCAGAGTGTCTCACCAGGTGCGGGGATTTCTCTCCGCCT
CAGGCCGTACGAGCTTCCCTCGCTGTCCCTGAGCGCAAATGACCTCTTCAGTCGCCGAGGCCCGGCCGCTTAGC
TCTCGGAGCCTTCCACAGCCCAACACCCTGAGCCCTGGAGTAGGCAATTTGCTCCCACAGCCCTGTGCTGGCCCT
TCCAGGCACAGGGAGTCCCCCTTCTAGGGGTAGGGGCGGGCGGGATGAAGCGCACCCAGCCCTCTCTCCTACCCT
TCCTCCTTTGGTCCCTTCGGCTTTCGTGTACCTTATCTCCCGCGCGCCCAGCTCCTTGGCCGGCTCACCTGCTAA
GCGGAGCGCGGACATGCGCTGGAACTCCGGCTCCTGCAGCCACTTCCACATCCTCCGGAAGGTCTCCCGGCCGGA
TTTGAGTTTGCTCCAGGGTTTGGGGTTGCGCAGCAGGTCCGAGAGGGTCCCCTGGGAGCGGCAGAGCACCCTCTG
CGCGAAGATGGCCTGTGGGATGCTGTAGCGCTTGAGCTCGGTGGTGATACGCTGCGCCACCTCTTTGGTATTGAT
CTCTTCCATCTGCCCTGAATTACTTCCATTGCTGACCTGCGCGCCGGTCACCGAAGGGTTGGGCTCCCGGGCTGT
GCCCAGGAGTTGCCCGTGGCCCTGGGCGTTCAGGTGGGCGTGGGGATGGTGCGGAGGAAGGCCGTTGATGGGCAC
CATGCCGGCCGAGGTGGGCGTGAGGTGCTGCTCCCCGTGGCGGCCGAGCATGGCCGGGTGGTGGGCTTCGAAGCC
GTTGGGGGTGAGCATCTTGTCGGTGGGCATGGCGGCCCCCGGGTGGGCATAGTGGGGGAGCCCTTGCTGGGAGTT
GTGGATGCTGCCCAGACCGGACTGGAGAGGGCGAGAGGCTCTGGCCCATGCCGGCCACGTCCTTGTGGTAGGG
GGTATAGAGGTTATTCATGGAGGCCAGCCCGCGCTCATCCCGCATGAGCGTGAAGCTACCGCTCACGTTGCCCGC
CAGGCGCTGGTGGTGGTGCGGGTGGTGGTGATGGTGGTGGTGGGAACTTGTCCGAGACTGT
GGAGATGGGAGGCAGCGGCTGCAGAGGGGTCAAGGTGGTGTAGGTGGTGGGCATGCTCATACCTGGGGGAGTCTC
GCAGGCCATGGTCATGGTGGGATGCAGGGGGCCGGCCAGGCTGTGCTCAGGGGCCCGGTGGTGGTGGTGGTAATC
TCCGCCGCCGCTGCCGCCGTCCAGCAGGGACGCCATGCCCATGGAGCGCGGGTGCGCGGGGGGCAGGTGGCTGCC
GCGGTGCGCCACGGAGCTGCGCGCGTGGGGGCTGCCGCCCAGCAGGTCGGCAGGGGCGGGCACCGGCTCATGGCT
CACCCCGTGCAGCTCGCCGATCGCTTCCATGGTCAGCTGCGCGTTCATCGTGATCCGGGCGAGCAGGCGGCGGAC
ACAACATCGATGTGGCCAGGCAGAGGCGGCGAGGGGCGCACGGAGTCCGGTCTTCACATCGGCTGCTGGCGACTG
TTGCCTTCCTTCCTCTCACTGTGGGCTCTGTCTCTCTCTCTCTCTCCGTGTGTGTGTCCGTGTGTGCG
TGTGCGTGTGTGTGTGTGTGTCTCGCCTTCCCTCTTACCCCCCACCTTCCCCTCTGCGTCCTCGGCTTTTT
TTTTTTTAATATTAATTTCCAAAGAGGATCCGCGCCGTTGGGAGAGCGCAGTGCCCCAGCCCGCCCGCCTCGGCC
ACCTCTCGCCCCTCTCTTTCTTAAAATTCTGAGGTCTCCGGCTCCCCTGCCGCGGCCCGCGCGCCTGCCGCGTCT
GCTGCCTGCCCGCCCCGCTGGCCAGCTTGAGCCATGGCTCTGTTACTGTTACAGACTCTGTGGCCGCGGTTCGGT
AGCCGCCGCCGCCGCCGCCAGCGGCCCGCCCTCACGCCCGCCAGCGCGCATGCGCAGGGGCCGGAGGCCCGCCCC
CGCCCCCTAGGTCGCGGCGCGCCAGGCCCTTGGCGTCCCGGTACAAATGAAGGAGGGGGCCCAGCGCCTTCCCTG
CGGCGCTGGATGGCCAGGGAGCTGCGGGCACGTGCGAAAGATTGGCGCAGAGCGCGACCTGGGCCGCCGCTGCA
ATCCCAGGAGACTCGCGCCTGGCTCGCTCGCCTCCCTTGCTTGAGTGGGCTCTGTCCTCCCAGCCCGGGACGCT
CGTGTCGGGCTTCTAGCGGCTGGAGTGCTGTGCTTGGAGACATCGCCCCTCTCTCCAGTTGCTGCTTCCCGGT
GCAGCTTGCCCGGGGAGCTGGGGACTGTGTCATCACCCCTTCGGCTCTAGCCCACTAAGCTTTATTTCCCGGGGG
GCTGCTGGGAGTGCGCTTTCCCACCCTTGAATTCACGGCCTATTGGGGGATGGGGGTTGGGGTGGGGTGGGGTGC
AGATTGCTTAAAGGGCTGGGTCCGTTTGGCGGCCGTTGACCCGGCACCCTTCGTCCTCCCAGATACATACTTGCC
CACCCTTTCTCATCCATGCCCTGGGGAGAGGAGTAATCAGTGCCAAGAATCCCAGTTCGGGCCATACCTCACTGT
CCCCCGCCGCCTGGCTCCTTCTCCCGCTCAGCTCATAATTAAGGCTGTGCGTCCGCTTCGCCGATGACTCCACT
GTGGAGGGGGCGAGGGAGAGCGGAGGGAGTGCCCTGGAGGGTACCCATGTTAACTTCCGGGTGCTGGTGGGGCC
GTGGAGGCTCGGGCCGTCCCTGCGGTTACTCCCAAGGCCCTCCTGCTAAAGCACCCGGAGGCGGTTGCTTTCCAG
AAGTACTGACGCAGACAGGGTGGACGCCGGCGCGCGGGTCTCCGCTTGGCCCCTAGGGACGCCCTTTTCCCGGCG
TCCCCGAGAGACGCCTCCAGATTTGAAAATCAATTCAGCTTCGGGAGTAATTTCGCCCTTTCCCACAGTCACGCTC
CAATCTGGAATCGAACCTGGTCTTTGGGCCTGGTGGGACGTGTGCGGAGGCCCCCAGTTTGAGACGTACACCCG
GCCGCCACATGCCGCG (SEQ ID NO: 265)

CGI: 226 range = chr15: 58083428-58085812
CGCGCGGCTGCTCCATCTGTGAACGTGAGTGGTCGCCTGGCTCCCTCTTCCGCGGCGGCCGCTTCCTCATACCTT
CACACGGCGCACACCGGCCGGCGCGTCCAGCTGCCTGCCCAGTGGCCGAGGCTCTTCCCCCTCGCCCAGTCTTGA
GCTGGAAGTGATTCCTATTGGCCAAGGTGTCCATGTAAATAGGTGTGAAAGAAACCAGAGCTGGCCGGGCTCTCC
CTTCTGCTCAGTCCCCTCCCTCTGCAGCCCCCGCTCCCCCTCCTCTTCCTCCTCCTCCTCCCAAGGCGATTGTCATA
TGATAGCTAAGAAGTGGCACATTAATGAAGCGCCGCTACAGGGGTCTTTTCTGCTCCTGTCACCGCTTAAAACTA
TCAGATGGTTCGAGGGAGGACATGGAGGCAGCCACCTAGCTCAGCGGAGCACGCGGAGCCCACAGCAGCGCCCTCC
GGAGCCCTAACACGTGCTGCCACCATCCGCGCCGGGACTCCGCAGCCGAGCTCGGCCGCCCGCAGGACGCTCCA
GGAGCGTCGCGGACCGGGCGGCACGGGACGCTGCGGGGCTGAGCTCAAGAGCCCAGGTTCGCGCCGAGTCCAACC
GGACCCGGACGCTGCGCGCGGAGTGCGCGTCGAGTGCGCGCCGAGAGAGAAGCGGCGCGCAGCGGCGTCCTCCCG TABLE 7B-continued Sequences of differentially labeled CGIs between bladder cancer subgroups relative to blood GATGCGGACGCGCAACTTGAAGCAACTTTAAGGTGAGCAGCTCTCTGTTCCGTCCCTGCCCCCTATTCTGGCCCC
AGTACCGACTTACTTCCCGGCTATCCTCGCGCCGTTCGCCGGCTTCCCCTCCCGCGCCCACTAAGCCCGCAAAGT
TGCTGGCGAAAGAGTCCGGGCGCTGGCTGATCGAGCGCCGCAGGCCCCACCCCCGACCCCCGAAGTCTGTTACTC
GGTCTGGCTGACCCCGCCGGTGTCTCTGTGCATCCATGCTACCTTTCCCTATTACCCACCCCCTTCCCAGATCCG
AGCAGTCCGCCGGCCCGCGCGGACCCAGAGCAAGAAGAGGGCGAGGAAGAAGATGCCTCGGCCCGGCCGCAACAC
GTACAGCGACCAGAAGCCGCCCTACTCGTACATCTCGCTGACCGCTATGGCCATCCAGAGCTCTCCCGAGAAGAT
GCTGCCGCTGAGCGAGATCTACAAGTTCATCATGGACCGCTTCCCCTACTACAGGGAGAACACGCAGCGCTGGCA
GAACAGTCTGCGCCACAACCTCTCCTTCAACGACTGCTTCATCAAGATCCCGCGGCGGCCGGACCAGCCAGGCAA
GGGCAGCTTCTGGGCGCTGCACCCAAGCTGCGGGGACATGTTCGAGAACGGCAGCTTCCTGCGGCGCCGCAAGCG
CTTCAAGGTGCTTAAGTCCGACCACCTGGCGCCCAGCAAGCCAGCCGACGCGGCGCAGTACCTGCAGCAGCAGGC
CAAGCTGCGGCTCAGCGCGCTGGCGGCCTCGGGCACGCACCTGCCACAGATGCCCGCCGCCGCCTACAACTTGGG
CGGCGTGGCGCAGCCCTCGGGCTTCAAGCACCCCTTCGCCATCGAGAACATCATCGCGCGGGAATACAAGATGCC
TGGGGGGCTGGCCTTCTCCGCCATGCAGCCGGTGCCCGCTGCCTACCCGCTCCCCAACCAGTTGACTACCATGGG
CAGCTCGCTGGGCACCGGCTGGCCACACGTGTATGGCTCCGCCGGCATGATCGACTCGGCCACCCCCATCTCCAT
GGCGAGTGGCGACTACAGCGCCTACGGCGTGCCGTTGAAGCGCTGTGCCACGCGGCGGGCCAAACGCTGCCCGC
CATCCCCGTGCCCATTAAGCCCACGCCGGCCGCCGTGCCCGCTGCCTGCGCTGCCAGCGCCCATCCCCACCTT
GCTCTCGAACTCGCCGCCCTCGCTCAGCCCCACGTCCTCGCAAACAGCCACCAGCCAAAGCAGCCCCGCCACCCC
CAGCGAAACGCTCACCAGCCCGGCCTCCGCCTTGCACTCGGTGGCGGTGCACTGACCCGCAGGAGCCCACGCCCC
CTCGTTCTCCTCCCCACCACCTCACTCGCCTTCCCTGGCTCCCAGTCCTGCCGGCCCCCACCTGGGACCGCCA
CCCTAACTTGTTCATTTCACCTTCGGCCAACCCGCCTTGCCCCAAGAGAACTTTGTTTTGGACCCAGGAGACCAA
ACACAAACTTGCAGATGGGCCGAGAGGCGCGTGGGAGTTGTCCTCGCCCCACATCAAGGAAGGCCGGGGCCACC
TGAGCCGAACCATCCCCTCCCTGAGGCCCCGAAACCCCCTCCTATTTGACCGGCGGGGGAAACCCTGTCACCCCC
TCTTCGCCGAGAAAAGCGCGTCTTCCCTCCGCCCAGATCGGCGGAGCCCCGAACTCTGCG
(SEQ ID NO: 266)

CGI: 22 range = chr15: 62984853-62985116
CGCGCCCCTCTGGCCTCCATCACTGTCGTGCCGGTCGTGGGGACAGATGGGAGGGAATTACGGTATTTACAGCTG
CTCTTCGCCGGCTCTTGCTCCCCCGCGTGTCGACAACCGAAACTGCAGCGAGGCCCAGAGGCCTCTGCCCACTCC
CCTCGGAGTTCCAGGAGGACGCTAAGCGCGAGAAGCCAGGCTCAGGGAAACTGAACGCCCATACGCTCCTAGTCC
CTCTCACCTGGATCCTCTGCGTCAGGTTACGTGCTTGCG (SEQ ID NO: 267)

CGI: 541 range = chr15: 65902540-65909629
CGGGACGCAGGTGCAGGGTGCTGGACGCAGGTGTGCGGCCGCTTACCTGGGGCGTGCAGGCCTTGGGCTGCGGGG
AGGCGGCGGGCGCCGCGTGGCCCGCGGGCGGGCGGACCCGGGAGGGGCGCTAGCGACTGCGCGGGCGGTGGGT
GTGGCGCCCCGGCTCTCAGCTGTCAGGCGCGCCTGCCCCGCCACTCGGGCTGTGACCGCGCCGTCCCCGCCGCCG
CGCCATGCGCTCCAGGCTTCGGCCTCTTCTTCCGGCCAGTCCCCGGCCTCGGGTCAACGGCTCAGGGTTCGCAT
CTCCGCGCCCGGGGTCCCGGCGCCCCGTGCCCGCTGAGAGCGGGAGGGGCCGCGGGTGGGAGCGCGGAGAACCAG
GGAGCACGGCTGTGCGCGCGCGGGGAGGGGCCCGCGTCACCCGGAGAGCCCGGCGGATCCCGGACTCCCGC
CCGCCGCTCCTCCCGCCGCGCACCTCCGCTCACCGCTCGCCCGGCTCCAGCCGCCGCCGCACTGTGAGTACCCAC
GTCCGGTAGCCCGCCGCCCCGCGCTCTGCTCCTGCAGCTTTTTTTTCGTTTAGTTCTGATTTGGGCTCCTGTGG
CTGTTGTTTTTATGATTATACCTAAAGACACCACCGCCTCGCTCCCACCACTGCCAGTCTCCCGCTTCGCTGCCC
TCCCCAAGCTCGTCCATCTAGCTCCGGGAGCCGACGGGGGTTCCTCAAGCTGCTCTGGCTGCTCCTTGTCGC
TGCATATGGCTCTTCGCCTGTGCTTTCCGCTTTGGCCCCCGAAATTCCGTTCCTTTCCTAGGGACCCCCTTCTTC
TGACTCGGGCCCGGACCCCCCTCCTCTCACTCAGGGAAACCGCGCAGGGACCCAGGACCCTCAACTGGGGTAC
GCTCTCGGCTCGGGCGCTGTCTTCACTGTATGCGGGCCAGGCATAGTTGCCGATTTCGAGAAACCGAGAAGCTGT
CATTTCCCAGCGCTGCGCGCCCTCCAGCCACCTCCAGGAGGGCGCGAGGCTTGTCAGCCGGGGAGTTAGGACAGT
GTTTTTGCCTCCTACAATGATATAAAGGACTTCAACGCGAAATAAGGGTCAACTTATTTTAGTTCGATCCTCGGA
GATAAAGATGAAACAGACAGATAATACATAAATAGCTTGATACTTGAAGAAGGTACAAAACAGATGAGAGAAAGA
GGAACGAGCCGGCAGAGACAGCTCAGGGACAGATAAGATCGACAAATGAGGGTCTCCTAGACAAATAGAGAAGAA
GGGAGAGAGACAGATAAACAGAAGATTCCAGTCTCCTTGCTGAAGGCTTTTGAACTGGGATCCCCTGTCTGGAGC
TGCCCCTCTGAAAACGGAGTTACATTCAGGGCCGACTGCAGGGGAGGAGCCCTCAGGGTTGGGCTGCCCTGGCCG
CAGGAGCGCCTGCAGCCTTGGGCCGGATGGGAGCCTGGCTTGTCTGAGGACATGTGGCTGGGTCAGGCGACCTAG
AGGGCCCCAAACATCAGTCCCCAAGTACCCCCGCTGCTGAGGTCTGCCTGCACAGCTCCCTCCCTGCCTCAGCCA
GAAAGCAAAGTGCAAGGACCAGCAGCAACTTGTGTGCCTGGAGCCTTGCAATGGCTACGAAGATGGCTGAGATTC
CTTCTAGCCCATATGAGCCGGGACAGCGAGGCATGAAGGATACTCAGAGAGGTGATGCCCCTCAAAGAGGAAGCC
CAGAGCCCCGAATCCTGCAGTTGGCCCGAGTGGGAAACGTATATCTGAAGGAGGAAAGCTCAAGGAGTGGGCGAC
TGGAAGCTAAGAAGTGGATCCCAACAAAGTTCCTTGAGAACCTCTCTGTCCCACACGTTGACCTCGGTGGAAACC
AGCTTTGGTCTGGAATACAGCTAAAAATGCAGAAAATGTGGTTAGAACTGCAGGATCCTGGTCTCACTAATAGCT
GGAAAGAAAACGGTTTATATATCCAGCCGAAATCTTTCTGCTCAACGAACGCGGGCGCCAGCCGTGAGAGGAGAA
GCTCGGGTTTGTGGAAACTGGCAATGTTGTCCCCTGAAGCCGGCTCGGGCACCAAGCTGGGTGCGGTGGGGGCCG
CGCTAGGTCCGGGTGCGCACCGAGCGCTTTGGAGAGGGTCAGGTTCAGCACCGCGAACAGCGGTAGCCTCCGCCT
CTCTCCTTCCCTGGCAGACACGGTTCCCTCCTCCTTCTCCTCACCCCCCTCCTTCTCTTCACCCCCCTCTACCCC
CTGCTGTCTGGAGATGGGCAGTGACCGCCCCTCCCCCCTCCCCACCCCTCCTTGCACTGCCCCCGCCCGCCGCG
TGCATGCGCGACTGAGCAGAGGGGCGGCCGATCCCCGAAGTCCGGGCTTCAGGACCCGGGCCGGCAGCACCGGCT
GCGAGGGTTGCCGAAGGCGCACGGATCTGGGCGCTGAAAAAGCCAGGATTTGGCAATGGCTTTGCTGTGTGGCCT
TGGGCAAGTCACTCTGCGTATCTGGGTTTCACTTCCTTCCCAATCCGAAAACGGGATTGGGTTCCTTGCAGCCCG
GGCATTCCTGAGGTCTCCTTTACCCCTTCTCCTCCCCAAGCCCCGGGGGCTGTTGTTAACGGCGCCAACATGGG
TCTGAGTAACAAAAGACGCCTGTCCAGGGGGTGAATGAGTTTGGACTCCCCACTGCCAAGTATCCCCCGCGCGCC
CAACTCGGAGCGCCCTGCTGGGCGGGCCCGAGCCTCGGCGGCGGCGCTGAAAATGGCTCATCTGCTCTCTGCTTT
CTCTATTTCGCAGGAGCGGCGGCATGGAGGCTCTCACCACTCAGCTGGGGCGGGGCGCGAGGGCAGTTCCTCGC
CCAACTCCAAGCAGGAGCTGCAGCCGTACTCGGGCTCAGCGCTCTCAAACCCAACCAGGTGGGCGGAGACGTCGC
TGTACGGGTGCCCATTGTGTCGCTGGTCATCGACGGCCAGGAGCGCCTATGCCTGGCCAGATCTCCAACACCC
TCCTCAAGAACTACAGCTATAATGAGATCCACAACCGCCGCGTGGCCCTGGGCATCACGTGCGTGCAGTGCACGC
CGGTACAGCTGGAGATTCTGCGTCGGGCCGGGCCATGCCCATCTCGTCGCGCCGCTGCGGCATGATCACTAAGC
GAGAGGCCGAACGCCTGTGCAAGTCGTTCCTGGGCGAGCACAAACCACCCAAGCTGCCCGAGAACTTCGCCTTCG
ATGTGGTGCACGAGTGCGCGTGGGGCTCGCGTGGTAGCTTCATCCCTGCGCGTTACAACAGCTCTCGTGCCAAGT
GCATCAAGTGCGGCTACTGCAGCATGTACTTCTCGCCCAACAAGTTCATCTTCCACTCGCACCGAACACCCCGACG TABLE 7B-continued Sequences of differentially labeled CGIs between bladder cancer subgroups relative to blood CCAAGTACACGCAGCCCGATGCCGCCAACTTCAACTCCTGGCGTCGTCACCTCAAACTCAGTGACAAGTCGGCCA
CAGACGAACTGAGCCATGCTTGGGAGGACGTCAAGGCCATGTTTAATGGCGGCACGCGCAAGCGGACCTTCTCCC
TACAAGGAGGCGGCGGAGGCGGTGCCAATGGCGGGTCGGGTGGGCAGGGGAAGGGTGGTGCTGGCGGCGGTGGCG
GCGGTGGCCCAGGGTGCGGTGCAGAGATGGCCCCAGGCCCGCCGCCCCACAAAAGCCTGCGCTGTGGCGAAGATG
AGGCTGCCGGGCCTCCGGGGCCACCTCCACCCCACCCGCAGCGGCGGACTTGGCCTGGCGACTGGAGCTAGTGGC
CGGCGGGCCCAGGAGGGCCCGGTGGCGGCGCCGGCGTACGAAGCTACCCGGTGATCCCGGTGCCCAGCAAAGGCT
TTGGGCTCCTGCAAAAGCTGCCCCCACCACTTTTCCCCCATCCTTACGGCTTCCCTACGGCCTTCGGCCTATGCC
CCAAAAAGGACGACCCGGTTTTAGGCGCGGGCGAGCCAAAGGGCGGTCCTGGCACTGGGAGCGGCGGCGGCGGCG
CGGGGACAGGCGGGGGTGCGGGGGGCCCGGGAGCCAGCCACTTGCCCCCGGGGGCAGGGGCGGGCCCGGCGGCG
GCGCCATGTTCTGGGGGCATCAACCCTCCGGGGCAGCCAAGGACGCAGCGGCAGTGGCTGCAGCGGCCGCCGCCG
CCACTGTGTACCCGACGTTTCCCATGTTCTGGCCAGCAGCAGGCAGCCTCCCGGTACCGTCCTACCCCGCTGCTC
AGAGCCAAGCCAAGGCCGTGGCGGCAGCCGTGGCGGCGGCAGCGGCGGCGGCAGCGGCAGCTGCTGGCAGCGGTG
CCCCAGAGCCCCTGGACGGTGCCGAGCCAGCCAAAGAGAGTGGCCTCGGCGCGGAGGAGCGCTGCCCGAGCGCTC
TGTCCCGCGGGCCCCTGGACGAAGACGGCACGGACGAGGCGCTGCCACCGCCCCTGGCCCGTTGCCCCCGCCGC
CCCCGCCGCCCGCACGCAAAGGCTCCTACGTGTCGGCCTTCCGGCCGGTGGTCAAGGACACCGAGAGCATCGCTA
AGCTCTACGGGAGCGCCCGGGAGGCGTACGGCGCGGGGCCTGCTCGGGGGCCGGGACCCGGCGCTGGGAGCGGCG
GCTACGTGAGCCCGGACTTTCTGAGCGAGGGCAGCTCCAGCTACAATTCCGCCTCGCCCGACGTGGACACCGCGG
ACGAGCCCGAGGTGGACGTGGAATCCAACCGCTTCCCCGACGACGAGGACGCGCCAAGAGGAGACCGAGCCCAGCG
CACCCAGCGCAGGGGGCGGCCCAGACGGTGAACAGCCCACTGGACCCCCTTCCGCCACCTCCTCTGGCGCGGACG
GTCCCGCAAACTCTCCCGACGGCGGCAGCCCCGCCCCGGCGCCGCCTCGGGCCACCCCAGCTGGCCGGCCCG
CATTTGGGGACTTGGCAGCCGAAGACTTGGTGCGGAGACCTGAGAGGAGCCCGCCAAGCGGCGGCGGCGGCTACG
AGCTGCGAGAGCCTTGCGGGCCCCTAGGAGGCCCCGCGCCGCCAAGGTGAGCCCCGCGCCCGCCCCGCCCAGTGG
CGCCTTCCCCACCCTACCCTGTGCGCGGCAGGGCTGCGGGGCCGGGCGGGGAGAACGGGAATTTTGTTCCGCGCAGGCG
TGGGAGCAGCAGGCCTCGGCCACTCTCCGCAGGCCCAGCCTTGGGCGCGCTGCGAAACTGGGCCCACCCGCACCC
TCCAGTGAGGGTTTCGAAGGGAAGGGAAGCTGGGGGCGGCGGGAGGACTGGGGAACTTGTGTGCTTTGTTTTTGT
TGATGGGAATGGGGAGGGAGACCGGCTGAGACTGCCAGACACAGGACAGAAAAGGGGTGTGGAGAAAGAAAGAGG
AGGTAAGAAAGGAACCCAGAGCCAGAGAAAAGCGCTCGCCCGGGTGGGCATCAGAGCCCCAAGGAAGAGGAGAAG
AGAGGACAGTGTGGCCTCTCCCTGAGTCGGGCCCAGCAGTACCGGGTCCCCGGAATCTCCCACCACCCCAACTC
GCAGTTTTCCGAGTCTCTTCGCACTCCCGCCTTGGGAACCACAGGGTTCGTTGCTGGGAAGCTGTCTCGGGACCG
CGTGCGGAGCGGGAGGGGGGCTCTCAAGCTGGCAGGGCCGGGGCTTGAGGGGCAGGATGCAGCCAGGCTGGAGTC
GTTGGCCATTTTGAAAGTGAGTGCGCATACCTGTACATTCGGTTCATTAAAACACGAATCATTAACCGGATGCGA
AAGGCGTCATTTATGCCGCGGACGGGGCACTGGCGGGAGGGAAAATGCCTAAAAGGAGGCGGGTGCAGAGGGTGG
AGGACACTTTGAACGCCCCTCGGCTTGGGAGCCGCTTTGTGTTTAGAGTAATTTTCCCGAGGGCGCTAACAATTA
CCCTGAATCTACAAGGGGGCAAGGGTGCGCCGCGTGCGTCACTGTGCCCGCTCAAGTCCAGCGGGCGCACCAACC
TTTGCCACTCCGTCGGCTTTCCCTCTTGGCCGCGGGGTAGGGCTGGGCGTCTTTGGGCCGCCGCAGGGCGCCACC
CTAATCGCCTGTCATTTCTCGGCCGTCGCAGGTGTTCGCGCCCGAGAGGGATGAGCACGTGAAGAGCGCGGCGGT
GGCGCTGGGGCCCGCGGCCTCCTACGTCTGCACCCCCGAGGCCCACGGTAACGCCTGTCGCGGCCGCTGGCCACT
GTAATGGGGGAACCGCAGACAGAGGGCCGGGGTCAAGGAAGGCCTGCGAAGGAAGACAAGGAGAGAGAGACGCAGAG
AAAGAGGGAGAGGGAAAGAAAAATAATGAAAACAAGGAAGCTAAGCTAGTACTCCCAACAACTTCCAATCTTTAG
TTACTTAAAAACAACAGTGACAACGCCCTCTCCACCACACGCACACACATGCTGCAGTACACCCAGACACGGCGT
TAAACCCTTAACAAAATCACGCCCGACACGGCCTTCAAATCCTCTCATTTATTCAGCAAGTGTGTTTGGCCGCGG
GGTCCCCTTTGGCTAGGCCGGATCGGGGCGGAGGATGGGGGCACATGGCCGCGCGCTTGGGTACCCCAGAAGCGC
CAGGGTAGCTGAGGCCCATCGCGGGGTGGTGGGGGCCGCCCTGCACTTGCGCGCCTTACCAGGTTCCTCACAGAG
GAGGGGTTGGGGGCAGCGGAAAATCGGGCAGGTCGAGGCAGCCGAACCCCGGACGATGTCCCCCCACCCACCCCG
AAGGTCGCAGCCTGGGCCGCGTTCTCAGCAGGAGTCGGGCGGACAGACCCGGCGGCCACGCGCGCTCGCGGTGCC
CCAGTATCTGCGCGCGATGTAGGTCGCTCGTCCCTGGTGGGCTCGGCTGCTCGCCTAGCTCTTTTCCAAGGGGCT
GGGGCGGGGGCCTGAAGCCCGGAGATGAGCAGACCAGGCGCGGGGGTGGGGGGTGCCCGGCCCAAAGCCTCAGGG
CGCGCTCCTGGGCGCACAGCCGGGAACCAGAGGCGGCCACGACGCTTTTAATTAGGGCTGGGGCGCCCCGACCGC
GGCAGCTCCGGCAGTATCCGGGTCACGGTTTCTTTGCCTCTCTTGAAATTCGGTTTGTTGCCTTCAAGAGCCAGA
TAAGGAAGACAATCACTCGCCCGCCGATGATTTGGAAACG (SEQ ID NO: 268)

CGI: 216 range = chr15: 72206924-72210097
CGGGAAGTAAAGCCTCGGGACTTTGGTTAAGCGCGCCCCACTGGCGTATCGCGCCGCGGGACTGCAGAGCCGTGA
GCAGCGGTCGCCTTGGTGCAGGGTTCCAGCCACATCTTCCTCGCCCAGCCAGCACCCTCTGCCGTTGACCCGCCT
CTGCGCCCGGCAAGCGGCTTCCAGCAGGGGGCGCGCGGCGGACCAGGCTTGGGCCCTAGAACAGCGCGGATGGAGT
CGCTGGAGCAAGTCCCCAGATCCAACCGGTTTCAACCCTCCCCACCCTCCCGACGCTCCGGGTTCGCGACGTTGA
AGTTAAGGGTCGATCCGCAGAAAGCGGCCAGGGGCTCCAGCTCTCCATTCCTGGGTCTGTCTGGGGTCGGCTCCA
GCCTGGTTAGAAGCCTTAGTCTGGATTCGGCAGATTCTGAATCTGGGACCCTCTGCGCTAGCGGCTTGGAACCTT
GTCACCCTCCCCTCCCCACCCCTACTTCCACACACCTGATTAGTTGTCTGTTTCTTTAATGATCAAAGACGTGG
GCGGCGGCGGGATGAGGTCTTGGTTCCCGGCTCCACAGCCCTCCCTAACTGTCATTATTAACGTTATAAACATTA
GACCCGCTTCTGCGCGCCGGACGGCGCCGGACGAGGTGCGCGCAGTCTTCTAGCTGAGCTCGGAGGCAGATCCAG
AAGTCGCGGCTCCCACCCCAGGCCTCGGCGGACTCTGCCTGGGGCGACTCGGGCTCCAGCCCTGCCCGGGCGGGC
ACTGGGCTCTCCAGGGTCGAAGGCAGGGTAAGGGGCGTCTTTCCCCAGGGCAGCCTCCGGGAACAAAAGCATT
TGCTGTAGAGTGAGCTAGAGCCTCCGGGCCCGCGGGAGTCAGCTCCCGCCCAGGGGTGGTCACCGCGTCCTTAAC
CACCCCAGGAGCCCCGTCTCCCTGCCGAACTCCTTGGCTTCTGCAACCCTGTCAAGACAGCAAGGAAAGGGGGTC
TTCCCTGGTCCTCGGGCCCGAAGTTTCGGGGTTGCTTATAGGACGGGTTCCTGCAGTCCAGGGAAGCTCTGGGC
AGATAGCGAGCCCATTCTCCCTTCCATTACCCAGATTCTGCCTCCCTGCGGAAGGCAAAAAAGAAAGAAAGAAAA
TAGGTAAAAACCGGCGGAGGGCCTTGAGCCTCCCCGCCTGGCGCCCCTCACTCAGTCCCGAAAAGTCCCCTGGAC
ACGCCATGCCGGACCGGACTCAGCTCCCGCTGCTGGGCCCCTGCCTCCAAATATCCTTCCCAGGCACAGGCTCCC
AAGACCGCCCCCTCAGGGTTCCCAACACCCGGACAACTGCCCAAGACGCCGCTCCCCGCCCCCACCCCCACCTTG
TTCGGCAGACAAAGAAGGGTGTGCTGGCCCCGCCGTCTGCCTCCTTCTCCCGACCCCACAAGGCCTAGAAACCTC
AGGGACTCACCCCGGGCTAGGGACCCAATCCTGGCTGTCCCACCACAGGATCCCCGGCAGGGACGGGTCACAGTG
CTCTCACCCCTCGACCATTTTCGAAGACACCTTCCCTGAAAGGCGCCTTGCGCCCTCCCCATGGGTCGGCGGGGG
GGGACTCCAGGCCCGAGCAGGCGGTGTGAAGTTCTGTGTTCGAACTGGGGCTGAGCAAGATGCGATGGTCTCAG
CCCGCTGGGCCGCCCGTAGCGACGGCAGGAGTAGGGGAGAGGGAGGGACGCTTGGAGTGTGAGCGCACCAGTCTG
TTCATATTTAATTTACAAAGCAGCCTCGGAACCCCGGGCCGGTGGTCTCTTTAGAGCGCTGCGCTCTTAGCCTGT
CTCTCTTCCCCACCCCCTCCCCTAGCTCATTAAGATGCTCAACACTCAAATCGGGGTATTGATCTCCACGGAAGC TABLE 7B-continued Sequences of differentially labeled CGIs between bladder cancer subgroups relative to blood CCCAAACCCTCGCCATCGAGAGACCCCCATGGCCCGGGGTGATGGCTGTGGGGCTTGGTGCTCCCAGAGAGCTCA
GTGGCTACAGAATGGGTGGGGATTCTGCGTGTCTCCCGGAGCCTGAACCCCTTTCCTGGTTATGGCCGGTAGCTG
TCTCCAGGGCTAACGTGGGCAGCGCAGGGGGGCGGAAACCGGGTTTTAGCCAAATGCCTCGACATCGCCGCGCCT
CCGCCTCCTCGTCGCTGAAAGAAATGTCGGGGTTTCATCAGAGCTAGGGAGCGACAGTCGGGAACAGCGAGTCTG
CCGAAGCCGGCTGTTGTGTGAGGGTGTGAGACGGCGGGGCGGTGAGGACGCCACCGCGGCTTGGGGGATAGTGCGT
GTGGGGTTGACCGTGTGTCTGCTTGAGAGGCTGTGAAGATATGGGGGGCAGATATGGGAGAAATGCTCGGGCCTG
AAGTCCCCAGCCCACCGTGCTCAAGAGTAGCGGACGTTTTGCCACCATCCTTGTCTGTGCTACTGTCTGCTGCAG
CTTCCGTGCCCCGTTCTCCTGGAGCAGGCAAGACCTGGAGTGAGGTGCTTGGGTGCGCTCGAGAGAGCTTCCCCC
TGCTCCACCTGTCCCGCGGTGCGCGCAGGCCAACGCGTCGGGCAGTGGGCTTCAAGCGCTGGTTTAGCCACAAAA
GACCAGAAGTAAAGAGTTCCGGCTTAAGAGGCTGGGCAGGGCTGCGGTGGGCTGGGGAGGGGGGTGTCCCTTCCC
AGCACGCCCTGCAGGGCTGTGCGTTCTGGTGTCGGGTTAGACTAGCAGGCGGGGCGGGGGGGTTGGGGCGGCGGG
GCGGGGGAGACTAGGGCTTATATCAGCCCAGATCCAGGCAAAATGGTAGGGAGGGTGCGGCGCTCTGCTAACAC
TATCAATTATGCATCATGTTGAACGTGGCTTCGGGGAGGAGGCGGCTAGCAGCGGGGGGTGCGGGAGGGAAGGGT
CCGCGCGAGCTCGGCTGCGCGCAGCTCAGCGGGTCCCGCTCGAAGTCTGTCGGTGCCACCGCCTGCATTTGCAAA
AAGAGTTTAAAGGCAAAGACACGCCTTCCCCCCCCACTTCAGCCGCGCGCCTTTCCTTCCCCCAAATTCCTCAAA
GATGGTTTGTCTCACGTGTTGCAGGGCGTAAAAGCGGCTTGCATTCAATTAGCAGCGAAGCTCGCGGGCGCTGGC
GGGACAGGCGCGTGAGGGTGAGTTCGCGTGAATGTGTGTATGCGTGTGCGAGAGGAGAACGGTAAGTGTCCCGGG
TGCAGGTGTGCCCGTGAAAATGCG (SEQ ID NO: 269)

CGI: 32 range = chr15: 74414579-74414893
CGGAGCTCAAAAGCCGGACGCTACTGGACGAGGCTTAAAGCGCTCGCCCCAGCGCGGGGCCGGTGAGGAACGTTC
ACCGTGGACCATGGTCGAATAATGTTAGCGTGCACTCGGGGCCTCGCCTTAGCCTTCTGCAAAGCCTCGGCCTGC
GCCCTCGGCTGCATCCGTTTCGACGCCAACCAACCTCATGCTCTTAGTAGAACGGCAGTAGCGACCGCGCCCTCA
GGCCCACAAGCCCGAAGGTCTGGGCAGGGTCTGGAATGGCGGTGGAGACACTTTATCCGCAGGCGTTTCACCTCG
CGCCCCACCCAGGCG (SEQ ID NO: 270)

CGI: 109 range = chr15: 88158407-88159577
CGGCATCTTGGCCGGGTTGTAGGAGCGAGGGAGAACGCGACTGTAACGCGGGCGTTGAGCACCTAGAGTTCCCCT
TCCTCTTCACTGAGAGCTGCGGCGGAGGCTTTAGACCGAGGAGCGAGATCTAAGGTTAAAGAAAGGGCCTCTGAG
CCCAGTGTTGGCCAGAGACCCCACAGGCGGGCCGGGTTCGCCCTTTGCCTTCGGCCGCGCCCCACCCACCAGGGA
CAGAGTGGCCGCGGCCGAGCCGGGTCCACCCGCCGCAGCTTAGCTCCGCTCCGCCGCCTCCCCGTCCGTCCTCC
CCAGGCTCCCGTCGCCCTCGCCCACCCTGGGGCCCCCTCCCCAGATGGGAGCCCCTCCGACCCCTGCGAGGCCCG
CTGGGGACCCACTTGACCGCGAGATCGTAGTGGGAGCTCGGCCAAAAGAATTCTTCGCTTTCCCTGGCCCTCAGT
TTACCCATCTGGGAAGAGGGGCGTCGCGGCCGCAGAAGTCCAGCTCCGCACGCGCCAAGCGCTGGGTCTGCAGCT
CCCTCGGTTCCCGCGCACCCAACTGCCCCACGACCCCTACCCGCGCCGCAGCCCCCGCCCTCCCGCCCACTTG
CCTGGGCCGCCGGGCGCTGGAACCTGGACCCTGGACCCTGGCGGGTTCCGAGCTGCGCCGCCGCCGTCCCTGCCC
CTCCAGCACTGGACTCCTCCTTTCCCGTCTTTTTAAAGGGAAGTAACCGGACCCGACCACTACTCCACCCGATTC
ACCCCTAGCGGGCCGCCCGCCCGCAGCTCCGCCCGGGCTCCTCCCCCGTCCGCCCGCGGCTTCCCGGGAGCCCCC
CAGGGCTCCTCCGCTCCTCCGACGGCCCGGCCTTCCCCCCCGGGGCCTGGGATGCACCAGGGCTCCTGCTGCCCCC
GACGGGGTCCCTGTCGCCGCAGCCCGCGGGACCCGCCGGCCACATCTGGACGGCATCTGCCGCGGGGGAGGGGCT
CAGAGCCTCGCCCTGAGTGTCCCGCAGGGAGCCTTGTGCATCCGGGGCAGGAAGCCAGCGCATCCCGTGCAGACG
GGTGGTGCAGATAACGGACCCGCCACAGCACGCAATTCAACTTTCTTGGTACCTGGGACTCGTAGTTCAGAAGGC
GCAGTAGCACGACCTTGCGAAAAAGCACCGGAGTCGGGAACACGCG (SEQ ID NO: 271)

CGI: 21 range = chr16: 727072-727328
CGCCACCCGCACGACGGACGTCGGCACCACACGAGCTGCCCTTGGCAAAACGCGTTGTCGGCTGCTGGGATGGAT
TTCAGGTTAAAGCAGAGTCACCAGGCCGACCACTGCTTACCTTGTTAGCATCTAGAACCTTCTTCAGCTCCTCGT
GGCTCTGCTGGGTGATAAGCACGGTCTCTGCGGAGGTGATGCAGCCGCTGCACGCCAGGCAGTCGTTTAGCGAGA
CCTTGGCCTTCTCCAGCCTCCGGGTCCCGCCG (SEQ ID NO: 272)

CGI: 61 range = chr16: 47868915-47869809
CGGGTCCACTCCTCACTCGCGAAGTCCCTATCTATCTCTGTGGGTCCCGGAGGCACAGGGCTGCAAGGGCGCCCG
CTAGAGCTGCTCCACGGCTTACCGGATTGCATGCGGAGAAGAAACGGGCCCGGGTTTCAACAGAGGCCCCGTGCT
CCGTGAATTTCTAACTCGAACCAGCCGCTGGGATAAATCCGAGAAACGTTGTTTATTGTGCTATTATTAACTTTC
CCTTCTCCCCACGCCCCTAGAGGGAAATAAAATTCATTCCTGAATATTGGGCCAGGAAAACGTTTCTCTGAAAGGA
ACCACAACTGCAGGGGACCACCCGGCTGCAGCTCCCAGCTCCCGGCCCTTCGCCCTAGGCTGCCCACTCGCTCCG
GCTCCCGACCTCCCCGCTGCCGAAGCAACTGGGTCAGCCTTTCAGACTTAAAACGAAGTCGTTTATTTCATTTTT
GCTTTCACATTATGTTCCGATACAATCAAAACTCCTGGACGAACCTCTTGAATAAAGTCCTGTGAATGAGCGGAA
TCATAGGTCCTGGGCGCCCGAGTATGCGGCGGGTGGACTCCGGATTCAGAGGCGGTGTATAAAACATACGCTGCT
TCGGGAACTGCGAGGGGGACGCGGTGGGAGACATCCGGGGACAGAAGGCCTGAGGAGTCTGCCGCTCCAGGCAGG
GTCGTTTGGGTCCTCAAACTGGGACTATTCCTGATGCATTTGGAATGCAAAGAAAAAATCAAACTTCGCTCCTG
GGCCGGCGGCCGCGCCTGGCCTAGCAAGATTTCGGCCACATTTCTTACGTTTCCGCCAAAGCTGTGAACACAGGC
GAATGCAGTGCTGGTCCCCGGCCTGGCGCAGGAAGGAGCGCAAGGCCGGCTTTGCAAGGAAGCCCTCGCG
(SEQ ID NO: 273)

CGI: 179 range = chr16: 53527803-53530347
CGCGAAGGCTCGGGGCTGCGAGCCGAATGCCCGCCGAGCTGCCTGGGAACGGGAACCGCGCACCCGGGAACGCCA
GGCGTTTCTCTTCATCCAGGAACGGCGCGGAGAGCCTCCGGCTGGGGAGCTAAACCGCTGGGGACTCCGCGGCTG
CTGCCTGAGTCGCTGTCCGCTGCCCGCATCCCTTCCGCCCTGGGCCTCTGCACGGTCTGCGGTTTTCTGTGCGCA
CTTGGTCTTCAGTACTAGCACCCAATTACGTCTGGGTTTTTCTTCTTTACAGAGCTGGGTTTCGGTGGCCACCAG
CTTTTCTGGTGTTTAGTGACTCTGAGTTTGGAGGTGGCCTACCAGGCAAACGGGGATTCAGGGCATTTAGGAAAC
GTCTTCCGCGCTTAATCCCAGAAGTGGTTGCGTGTCCGTACGATCCCAAGTTCCTCCCGGAGCCTCTTCTTTGCT
GCGTCTCGGGCCCTCCAGCAGGCGAAGCCTCTTAGACGCGCTGGGGAAACTTCCGGCGTGTTCGGGGCTCAGGGT
TTCTTCTCAGGCATGGATTGGGGCGCAGAAGTTGCGCGAGGCAGCGCCTAAGGTCCCGAGGTGCTGAGACTGTGC
TGGCGTTTGCCACCTGCCCCTGGCTAGGCCGTTTCTGGGCCCAAGAAACGCCTACCTTGGCACTTAGGGACCAG
AAGCCTCTGGATGTCTAGCAACAGGGGTCACGGGATCACTGCGTGGGGTCTCTGTAAGCAGTCCCCTGAGGCAGT
GCAAAACCGGAAACCTGCTCTGTGCGGGGCCGAATCAGTTCATGGGATTTGGGAGTCAGGAGAGACGTCTTTCTC TABLE 7B-continued Sequences of differentially labeled CGIs between bladder cancer subgroups relative to blood CTCCCAGCTCCTACACTCCGGGTACCAAGGCCCGAAATGCCGTTCCCCCAGCCCGGGTGCGGGGTCTGCAGCAAG
GCCTCCTGATTTGCAAACCCCTCCGGGCTGCTTATTCCTGGTGCCATGCGCAGCCCTTGGGACCTAGAAGATTGT
GGGGGAGGGAAGGTCGCACGTGCGGTTTTGGCACCGACCGTGCCTCCTAGTCCACCTGTCCCCCACAGCTAGCTG
CCAACTCGGACGGAAGCGCGGAACAGCGCAATGCAAACCGCCCAAAGTGAAAGGAATGTAATTGCGCTCCCATGA
CAGAGCCAGACGCGGATGCAGTTTAGGAAGGGCGCCGCCTACCGGCCCCTGGGAGCCATGCGATTCGAAGGGAGG
GGGACCTAGAGGAGACCCCCGCTATCCCCCCACCCACCGTGGGGCCTTAGCTTTGAACTCCGGCCCGGACAAACT
TAAACTGCTTCGCCACCCCAACGCGCCACAGCCCTGGACCTAAGACCCAGTTAGCATTGGGAATTTGGGGAGCAG
GGCCCACGACTAGAACAAAGTTAACCCTACCGGTTCCCGCCACGGCTTCGGCACATTTCAAAAAACCAGGCGCAG
GCAATTGAGAAATACGCTGCCGGCTGAAACAGCCTGCGGGTGGGGGCTGCAGCCGTGCGCGCCCGGCAGTTCCCG
TCCCGCATCAGGTGTACGCACTTCCACTCCTGCGGGCCCTTCCACGCTCCAACTCTGGACCCCGCGCAGTTTTAA
TCTGCGGTTTGGGAAATGGGGGTGCTACCGTGCAACCGCGCCCTGAAAGACCGTTTTGGTCTTAAGAGCTTTTGG
CCTGTGGGGTGGACATCTGTAGAAAAAGGAAAAACAAAACAAAAGTAACCTCCCATTGCGTCGAACCCTCCTATT
CCGAAAAGAACTTTAATGAGGTTGGCTTGGCAAGGCCTGCGGTGCTTACCTCGGCTTCGCCCTACCCCGCCAGAA
GCCCTCATAGGTTGTATCCACTGGTCTCCCCCAGGTGCAGGGTTATTAGGGGAAAGGGGGCGCGCCTCGGGCT
GGATCTTTGTTTCCCTCGTCGCCCGGTCATCAAACAGGAGGGAAATCGGGCCCGACTGGGACCTTGCTGCCCGCC
TTCCCCTTAAACTGGCTAAAGCTTCAGGACTGTCCCTAGACCCACCCCGCGGGTCTTCCTTTGTGTCCAGGGCAT
AGCCGATCTCCTTTTCGTTTTCACGAGAACTGCGACTTGGGCCTCGGGCACTAGGCGAGCCCAGGTTGTGGCCTA
ACAGCAGATCGCCTCGGGAGCTTGGCTGCAGCTCTGCCCGCACCTCCAGCGCTGGGCGGCCTCTCGGGGCCAGTG
GGGATCTCTGGCCTCGTGTAGGCCACGGGCCCAGCCCTGGGTCCCCAAGGCCGCTCGCCGGGCAGCGCTCGTTT
CCGGCACCGGGACGAGCCCAGCGCGCTCAGACACCACTTTCCCGGTGAAATCTGCTTTTATTTGCTCCGAGCAAA
CCTCGGGCTCTCAGCGCTCCCGCCTGATGGATGCAAATGTAAATGTGCACTTATTTAATTGGATCAGGCCCCAAG
ATAAAAGAGATAAACGGCTCCCCGCTTGCTAACTTATTTTCCTAGGCATGCAGCGCCGCGTGGAGGGGAAGCTAA
TGAAGGAGCAGCGCGGTGCTGGGCACTCGAGCTCTCCGCAGCCGTGGCACGCTGGCCGGCCGGCCCCGCG
(SEQ ID NO: 274)

CGI: 78 range = chr16: 66071900-66072846
CGCAGGCCAACGCGAAGACACGATGATCCCAAAGACCTTAGTGTCTTGGCGGGGGGAGGGGAAGAGGTGGGGGA
CTTTTCCGCTTAGCTTCCCTAAGGGTTGCTACGCGACAGCTCTCGGGCTACGTCAGGGTAAAGAGGTTTGTATGG
CCACACCTCGCACCGACCAACTACCCCCGAAACACCCCCTCCTCCCAAACTGCAGGGTGAGCACAGCGAGAGAAA
AGGTGGCCCAAGCAGAGGCGAACAACTGCGGTTCTTAAAGCCTTGTTTGAGTTTGGGCCCGCGCCGAGCCACAGC
TAGAGGTAGATCCCGCTCCTGCGCGTCCGCTATCAGCCCCAGGATTCCCAGAGAGGCCTCTCAGGCCCTTCAAGA
CCCCCCCTTCCGGCTTCCCGGCCTACACCTCTGAACCCTCAGGCCCCGGACAGCCTCTATCCCCGCCTTTCGCGG
CCCCGGCTCACCCTCTAGCGTCTCGCACTGCACCAGGTTGAGGTAGTCGGCCTGGCTGAGCACCCCGGCCTTCAG
GCCGCGCACCAGTCCCTCCAAGTAGCCATTGTCCACGTTAAAGTAAAGCTCCGGGAAGAACGACATGGCTGCTGC
GGGAGCGGCGGGACCGGAGAACCAGGACCGGCCGGCACGAATCGCGACTCCCCAGGCAGCTGACGCTGCGTCCT
CAGCGGGCTGTCAAGTGCGTCAGGTGACGCGCAAGCGCCTCACGTGACCATAAGGGGCGTGGCTCTGAGCGGTG
CCCGGCTTCCGGGTGGCTGCGCGGAAGCGCGGTGCAGGCGTGGGCTGGCCCTGCGGCGCCTGCGCGCTAAAAGA
GGAAGTTTGAGGCCGGCCGCTTGGTGGCGCCTGTGGCCGCAGGGATTTGACTGGGCCTTCTCTAGCTTTCCCCGG
TTTGCTGCACTTGACGCTGCAGGGCGGGCGGGGTAAAGAAGGGAGCG (SEQ ID NO: 275)

CGI: 39 range = chr17: 38089258-38089793
CGGGGGTTGGGGGCACGGAAGGGGAAGCTTCGGTCGCTAAGTGGGCCGGCCTTTGGAAGGGTCTGGGAGGGGCCA
GCGCTGACTAACAGTCGGTTTCCCTACCCTAGACGGCTGCGACGAGGAGCTGGTGGGTCCCCTGTATGCACGCTC
CCTGGGCGCCTCCTCCTACTACAGTCTCCTTACTGCGCCGAGATTCGCCAGGCTGCACGGTGAGCTCCGCGGAAC
ATCAGCTGCCAACTGGCAGCGCACCGCGGAAGGGTGGGGGCCTCCGGAGGACTTCGGGGAGAGGGATAGCCGGTT
AAAGCTCCTGTCCTTTCTATAGGCATAAGCGGGTGGTCACCACGGATTGGGGATCCGAATCCCTGGCTCCAGATA
GACTTAATGAAGAAGCACCGGATCCGGGCCGTGGCCACACAGGGCTCCTTTAATTCTTGGGACTGGGTCACACGT
TACATGCTACTCTACGGCGACCGAGTGGACAGCTGGACACCGTTCTACCAGCGAGGGCACAACTCGGTACTCTGG
GCGCCAAGGCG (SEQ ID NO: 276)

CGI: 69 range = chr17: 44074360-44075233
CGGCGCTGGCGCAGGCGGCCAGGAGAGAGCAGATGAACCGTTCGTTAGGAGCAGCGAGGTAGTCGTGAGCGCTGA
GATCCAGAGACTAGGACCCACTCCCTCTCTGAGCAGCAAATTGGGAAGAAGATGCTCACTCGGTAAGGGCGAGGG
AGCCCGGCATGGCGCCCCACCACGGGCTCGGTCTATCTGCGCGCCAAGATCCCGCTTGGGGCGAGGCGTTGGGTC
AGCGTTTAGAGCCACTCCCTGCGCTGGTGGCTGGACATAGCCCTGCCAACCTTCGCAGGGGACTTAGCTTTGCTT
CAGAGGAGGTTGTGAATCTACAGGCCCTTGACGTTGAGGCGTCGGAGGGCGCACCTTTGTAATTGCGGCTCCCT
TCGCCCCTTAAGTGCCGCTTCTGGGCGCCTAGGCTGGATATGAAAGCCCCGTTCCTAATCCTCTGCTCTGGTCCC
CTCCTCTGGACTGCTGGGACTCTAAGCTAGGCCCTCCCCAGGTTCCATCACTGCGGCGCCAACCCGCGGCTGGGC
TGTCCGCAAGAGGGAGTTGAAGGCGCGCGGAATCCCGAGGTGCAGCTGACCCTCCTCTCAACGCCGACTCTGCCG
CTCCCGCCCGGCCACCTCCCTGTCGGGCAGACTTCCTGTTCTCCTGCTCACAGCAGGGAGGCAGTCGCCGAGCCG
GTCAGCAGCGTGCACGGAGATCTTCACTCTGCGCCCAGCCCCGGGACACAGGTGCAGATCTCCAGCGGAGCACTG
CGGAGTGCGCGCCGTCGAGCACTAGGGAATCCTAGACGGAGGACTTGGTCCATTCCACGCAGTCCCAGGCAGGTC
CGCAGCGGAGGGACGCAGCGGTCTCCAACTCCTGGTCACGACTTCGGCG (SEQ ID NO: 277)

CGI: 269 range = chr17: 67627870-67631593
CGACTCGGCTGACGTTTTTGACCCGGCCAGGAGGCAAAGACCAAAACGTCAGAGCAGTAGCCCTGTTACTGAGGA
GCGTCGGCAGGGTCGCGGGTAGAGGGGGCTGGAGAATGACTTGTCAGAGCTCAAGGTCGATGTGGCGCGGGCGG
CCTCGAGAGCGCCGGGCTCCTGCGTGGCCACGGCCGCCGCTGCCAACCTTCGCGGGGACTTAGCTTTGCTTTCCA
TTGACTCCCTTTGCAAAAGCGCAGCAGAATCCTGACCAGCCGCACCAGCCCCGGCGAACCCGAGCATGTTAATCT
ATTTATATGGATTATTACGGAGGAACAGCGGGCGTTGAGTCACCAAAACATTTGCTTCAAAAGACTATTTCTAAG
CACTTTTGCAGGCAGGCAGGCTCGCTCCAGGCGCGTAAACTCGGCTACGCATTAAGAAGCGGCTGCTTTTCGAAT
ACTGCAAACTCCAGCTAAGTCCCCGGTGCCGCGGAGAGAGCAGTGAAAAGAAATGTCGGAGGTGGGGGTAGATCC
TAGTCTAGACACACACACTTGCGCGCACACACACACACACACACACAAGATTCGCGCGGAGAAGGCACTAAAATT
CTGGCATTCCGAGAGTACGACAAACTTACACACTTGGAAGTCCCGGGTCCCCGCCTTCCCCGCAGCACCCCCCG
CCCCCCCACCCTACCGTCCGCCCTTTGGCTGCGATCCCCTCCCCTCTCCTCCCCTCCCGCCTCGTCACCCAGCCC
AGTGCCACAATCCTCCTCCCTCCCAAAATCGGGTCCAATCAGCTGCCTGCCAACCCTGGGACTGCTGTGCTGTG
ATTGGCGGGTGGCTCTAAGGTGAGGCGGAGTATTTATTAAAGAGACCCTGGGCTGGGAGTTGGAGAGCCGAAAGC TABLE 7B-continued Sequences of differentially labeled CGIs between bladder cancer subgroups relative to blood

```
GGAGCTCGAAACTGACTGGAAACTTCAGTGGCGCGGAGACTCGCCAGTTTCAACCCCGGAAACTTTTCTTTGCAG
GAGGAGAAGAGAAGGGGTGCAAGCGCCCCCACTTTTGCTCTTTTTCCTCCCCTCCTCCTCCTCTCCAATTCGCCT
CCCCCCACTTGGAGCGGGCAGCTGTGAACTGGCCACCCCGCGCCTTCCTAAGTGCTCGCCGCGGTAGCCGGCCGA
CGCGCCAGCTTCCCCGGGAGCCGCTTGCTCCGCATCCGGGCAGCCGAGGGGAGAGGAGCCCGCGCCTCGAGTCCC
CGAGCCGCCGCGGCTTCTCGCCTTTCCCGGCCACCAGCCCCCTGCCCCGGGCCCGCGTATGAATCTCCTGGACCC
CTTCATGAAGATGACCGACGAGCAGGAGAAGGGCCTGTCCGGCGCCCCCAGCCCCACCATGTCCGAGGACTCCGC
GGGCTCGCCCTGCCCGTCGGGCTCCGGCTCGGACACCGAGAACACGCGGCCCCAGGAGAACACGTTCCCCAAGGG
CGAGCCCGATCTGAAGAAGGAGAGCGAGGAGGACAAGTTCCCCGTGTGCATCCGCGAGGCGGTCAGCCAGGTGCT
CAAAGGCTACGACTGGACGCTGGTGCCCATGCCGGTGCGCGTCAACGGCTCCAGCAAGAACAAGCCGCACGTCAA
GCGGCCCATGAACGCCTTCATGGTGTGGGCGCAGGCGGCGCGCAGGAAGCTCGCGGACCAGTACCCGCACTTGCA
CAACGCCGAGCTCAGCAAGACGCTGGGCAAGCTCTGGAGGTAGGACCCGGCGGGGGCGGCGCGGCAGGGTGGGCA
TCGCGGCGGCTGGGGCGCTGGTCAGGGCTGATTTGCCCCGCCCCGCCTCCCATCGCCCGGGAGTTGCCGTTCCG
GGAGCCGGCGGGATGGGGTTGGGAGTGGGAATGGGGTGTAACTGTGGCTCAGAGTTTGACAAAGTTCTTGGGCTG
CTCGCGGGGACGCGGAGGAGGGGGGTGGTAAGTGGAAGAGGTGAGGAGGTAGCTGGAGGATGGACGAAGACTGG
TGGGAGACGGAAGGAGGGGGCTGCCAGCCTGCTCTCCAGTCGCCTGGAAGCTCAATCGGGGCGGGGAAGTGAAAC
TTGCCTCCCTCCTACCCGGCCTCTTAAAACTGCACTCTCTCGTGCAGCCCCACTGTCCACGGAGATGGGGCAAGG
GAGAAACCGAGGTTGGAGGAGACCCTTGGCAGGAACTGGGAGGCGGGAGGAGGGAGGCTACTGGAAATAGGTGGG
AGTGTATGGTGGGGGGTGAGAATTGGGGACCTTCTTGCAGCTTAAGTAATTTGGGGGAAAGTTTTCAAAGGGGGT
TGGGGTTGGGGGCGGTAAGTCGAGCAGCAAAGGCGTTTAGGGGGCAGCACCGGGAGTCGTTTTCATCTCCAGCGT
TTCCAAAATAGAAATAGAAGGGGAGGGGAGGGAGGGGGCGGGGAGTGACCGCTCAGGTCAGACTGCAATAACTTA
TTTATTTATTTATTTTTAAGAAAAGTTATGAGCTGTGGTTGCAGGCAGGAGGGAAGATGGAGTTGTGTGCAGAGG
AAGCCGAGTGGTCTGGGTCGCCGCCTCCTCCCCGCCGACCTGACAGTTTGGCGGATTTCACTGACCCCTCTCCCT
CTTTTTCTCTGTGCCCCCCGCCCCGCCCCGAGCAGACTTCTGAACGAGAGCGAGAAGCGGCCCTTCGTGGAGGAG
GCGGAGCGGCTGCGCGTGCAGCACAAGAAGGACCACCCGGATTACAAGTACCAGCCGCGGCGGAGGAAGTCGGTG
AAGAACGGGCAGGCGGAGGCAGAGGAGGCCACGGAGCAGACGCACATCTCCCCCAACGCCATCTTCAAGGCGCTG
CAGGCCGACTCGCCACACTCCTCCTCCGGCATGAGCGAGGTGCACTCCCCCGGCGAGCACTCGGGTGAGTCGCCC
CTCGACCCCACCGGACAAGCTATCTCCGTCCCGCCTGGCACACCCCCTGCCCTCCGCCTGGGAGATTCTTCGTGG
GGACTTTATGCTTCCCGGGAGGGACACACTGCCCTTTGCGCCCGTCCCGCTCCCCTCTCTACCCAGAGCCTAAGA
GGCATCCAAACAACACACACAAACACACACACCCCAACTCAATCCCAGCATCCGAAGAGATTAACTTTTTTAT
TGGGAGGTAAAATGCCCTTAACAGCCTTACAAGACCTCTCCCTTCTTCTCTGCTCCCCCACCCCAAAAGCACACA
CAGGGCTCTTACACAAGTAGCAATTAGGTCTTCCGGACCCTCCGGGCCCCAGACCCTCCCCTGATAAAAGGGGGC
TGTCCAGTGTGTACCGGCGGGTTAATCATTGGGCGACTTATCTCCGGTGCAGCGCGCCTCTTGCGCGGGTGCGGG
CCCTTATTACACTTTAGCAGCGAGGGAGGGTCCCCGGAGGGTGCCTAAGACTAGGGCGTCTGCACAGCCCTTGTT
GATTTTCTCGTGCTTGTTCTTTTATTGTCCACAGGGCAATCCCAGGGCCCACCGACCCCACCCACCACCCCCAAA
ACCGACGTGCAGCCGGGCAAGGCTGACCTGAAGCGAGAGGGGCGCCCCTTGCCAGAGGGGGGCAGACAGCCCCCT
ATCGACTTCCGCGACGTGGACATCGGCGAGCTGAGCAGCGACGTCATCTCCAACATCGAGACCTTCGATGTCAAC
GAGTTTGACCAGTACCTGCCGCCCAACGGCCACCCGGGGGTGCCGGCCACGCACGGCCAGGTCACCTACACGGGC
AGCTACGGCATCAGCAGCACCGCGGCCACCCCGGCGAGCGCGGGCCACG (SEQ ID NO: 278)

CGI: 260 range = chr17: 71582000-71585125
CGCCTCCGCCCCGCGTTTCCTCCCCCCGATCTCCCAGGGGTCCTCTTTTGAGGGCACCCCAGCCCCTCGACGGTC
CCGGGATATCCTGCACCCCTGCCAGGCTGCAGGGAAGCGCCGAGGCGCGCGGAGTGCGAGGTCCGTGCTCCCTGC
GGCGCGGCGCACACGCAGGGTCCGGGGTCGACCCCTCCACCGCTCCGGCGTCTGCCGGGGAAGTCAGTCCGCCTG
GTCAGCCCAGAACCCCCGACTGCGGGGGCTGGAGCTCGGAAGCAGGTACAAGCGCCACTCTCCGCCTGCGCCGTG
GAATGCGCGCCGGGACCACTCCGCAGCCCTTCCCCCAGCGCCGCCGGCCGCTGCTGGGGACAACCTCGCCCTCCT
GTCTCTTGCTCCTCCTCCTGACCCCAGCGCACCCCCATCCCCGCCCCAGATGAGGCAAGGCTCCCTCCGCCTTCA
GCCCGGCCAGAGTCGCACTAGGAGTTGCAGCGGCCGCAGCCCCGGGAGCTTCCCGCTCGCGGAGACCCAGACGGT
GCAGGAGCCCGGGCAGCCTCGGGGTCAGCGGCACCATGAACGTCTCGGGCTGCCCAGGGGCCGGGAACGCGAGCC
AGGCGGGCGGCGGGGAGGCTGGCACCCCGAGGCGGTCATCGTGCCCTGCTCTTCGCGCTCATCTTCCTCGTGG
GCACCGTGGGCAACACGCTGGTGCTGGCGGTGCTGCTGCGCGGCGGCCAGGCGGTCAGCACTACCAACCTGTTCA
TCCTTAACCTGGGCTGGCCGACCTGTGTTTCATCCTGTGCTGCGTGCCCTTCCAGGCCACCATCTACACCCTGG
ACGGCTGGGTGTTCGGCTCGCTGCTGTGCAAGGCGGTGCACTTCCTCATCTTCCTCACCATGCACGCCAGCAGCT
TCACGCTGGCCGCCGTCTCCCTGGACAGGTGAGCCAGCGCCTTGGCCTCCCTGGGAGATGGGCATCCACGCGGGG
GATGGAGCGGGAGGCGGGACTGGGGACCAAGAAGGGACGCGCAGAGTGGGACAGGACACTAAGAAGGCAGTGGAA
GACAAGCGGGCGCGGAGGAGGAAAAAGAGGAATAAGAATGGGGGACCGTGGTGTCCCTCGGTTAGATGCGTCCTG
GGGCCTGGAAGCCTGGAGAATGTGGCTCTCCAGCGCCGCCCGTGCCTGACAACGCGCAGCGTTTCCCAGTACGAC
GCGTTTGTGCGCGTTCATCTCGCTTGAGCTTAATGCCCTCCGTGAGGGTGGGATAGGACAAAGTGCCCAATATAC
AGAAGAGTTGAGTTCCTAAGTAACTCGCTCAGAGTCGCCAGCCAGGGATCGGGTGCGTGAAGTGACCGTCTGTCT
CCTGCAGCCAACTTCAGGCGCCTCCACTGCGCTCGCCTCCAAGCCACGGTTTGGTTGGTTGGTGCAGCTGGCTCA
GGTCCAGGCTGTGGATCTTGGGTCCTTTGCAAGGATCCACTCCGGAGTCCCAGCGAGCGTGCCTAAAGGTCCCTA
GCTCAGTCCCAGCCCACTCTGCCTCTCGCCTCCAAACAAAACAAAACAAAATAAAATCCAAAACAAGTCGGGGCC
GGGAGAGGAGCGTGCCCTGGGGTTCTTCCTCCCAGCCAGAGGAGAGCGAGAGACGCACATTCGGGAGAGCGCGG
GACTCAGGTGGAGCTTGAAAGGACACTGGGATGGTTCCTGGGGAGGAAATCCGGGTATTTCCCCTCTCCATCCTC
TGGAAAAACAGAGAGCGAGGCCAGACTGCCCCCACACCTCCTGTAGCCACTGAGCGCGAAGTGCGTTGGTTCCG
AGCGCGCTGGTGGGATCCACAAAGCTCGCATTCTCTCAGGAATCCCCTGAGAAATTAACTGTCCCTTGCCCAACA
TGTCTTCTCCAGGCTGTCTGCTAGAGCCTCAGGCGCCTCCGCCCTCCCTCCCGCGGCACCGTCACCAGTGGGTAG
TCACAGCCTCCCGGAGCCCATAGCCGGTTCTCCAACCCTTTAGTCTTCAGTGGCTTTGGGGTGCCCTCTCAGTGGA
GACTGTGGTTGCAGTCCCCGGGGGCAGCGGGAGAATGGCTTGAAGGCACACCTTTCCTGCTGCCGGGCCCGCCCG
ATTTCCAGGCTCCGCTGAGTGCTGGGACACGCTGGGAGGCCCCCACCTCCGCCCTCACGCCGAGCCTCACCCCC
ACCTCCTCTGTGTGCGGTGTAACCATGCGCTAAGGACCTTCCTGAGAGCAGCCTTGGGACCGAGGTGCAGGGGT
CGCGGCCCTCCAGCATGAATGTGCCCGCTCAGCCGACGTCTCCCTTCCCGGTCTGACCGCAGGTATCTGGCATC
CGCTACCCGCTGCACTCCCGCGAGCTGCGCACGCCTCGAAACGCCTCGAAAACGCCATCGGGCTCATCTGGGGCTG
TCGCTGCTCTTCTCCGGGCCCTACCTGAGCTACTACCGCCAGTCGCAGCTGGCCAACCTGACCGTGTGCCATCCC
GCGTGGAGCGCCCCTCGCCGCCGCGCCATGGACATCTGCACCTTCGTCTTCAGCTACCTGCTTCCTGTGCTGGTT
CTCGGCCTGACCTACGCGCACCTTGCGCTACCTCTGGCGCGCCGTCGACCCGGTGGCCGCGGGCTCGGGTGCC
CGGCGCGCCAAGCGCAAGGTGACACGCATGATCCTCATCGTGGCCGCGCTCTTCTGCCTCTGCTGGATGCCCCAC
CACGCGCTCATCCTCTGCGTGTGGTTCGGCCAGTTCCCGCTCACGCGCGCCACTTATGCGCTTCGCATCCTCTCG
```

TABLE 7B-continued

Sequences of differentially labeled CGIs between bladder cancer subgroups relative to blood CACCTGGTCTCCTACGCCAACTCCTGCGTCAACCCCATCGTTTACGCGCTGGTCTCCAAGCACTTCCGCAAAGGC
TTCCGCACGATCTGCGCGGGCCTGCTGGGCCGTGCCCCAGGCCGAGCCTCGGGCCGTGTGTGCGCTGCCGCGCGG
GGCACCCACAGTGGCAGCGTGTTGGAGCGCGAGTCCAGCGACCTGTTGCACATGAGCGAGGCGGCGGGGGCCCTT
CGTCCCTGCCCCGGCGCTTCCCAGCCATGCATCCTCGAGCCCTGTCCTGGCCCGTCCTGGCAGGGCCCAAAGGCA
GGCGACAGCATCCTGACGGTTGATGTGGCCTGAAAGCACTTAGCGGGCGCG (SEQ ID NO: 279)

CGI: 38 range = chr17: 75936057-75936582
CGAGAGCCTCTACGACGCACTCAACCAGTACTACGTCCACCTCGGCGGCCAGAAGTACGTGGACCTCGGTCTGGG
GACCCACCGCGTCAAATGTCGGGTTCACCCCAACTTCCGCCTGATTGTCATTGAAGAGAAAGACGTCGTGTACAA
ACACTTTCCCATCCCCCTCATTAACCGGCTGGAGAAGCACTATCTGGATATCAACACGGTGCTGGAGAAATGGCA
GAAGAGCATCGTGGAGGAGCTCTGTGCGTGGGTGGAGAAGTTCATCAATGTCAAAGCACATCATTTCCAGAAGAG
GCACAAATACAGCCCCTCTGACGTCTTCATCGGCTACCACTCGGACGCCTGCGCGTCTGTGGTGCTGCAGGTCAT
AGAGAGGCAGGGTCCCCGGGCCTTGACGGAGGAACTTCACCAGAAGGTGTCTGAGGAGGCCAAATCGATCCTGCT
GAACTGCGCTACGCCCGATGCCGTGGTCCGGCTGAGCGCCTACTCGCTGGGCGGGTTCGCAGCGGAGTGGCTGTC
G (SEQ ID NO: 280)

CGI: 22 range = chr17: 76404186-76404427
CGTCACGTGCAGAGCATCCTCCCGACTGGCGAGGTGGCTTCCACGTGCCCCGTCAATCAGGGCTGGACAGTCCGT
CACGTGCAGAGCATCCTCCCGACTGGCGAGGTGGCTTCCACGTGCCCCGTCAATCAGGGCTGGACAGTCCATCAC
GTGCAGAGCATCCTCCCGACTGGCGAGGTGGCTTCCACGGAGCGATTCTCGAGACCCGAGGGGCGTGGACACAGC
TTCTACGCAGGCAGTCG (SEQ ID NO: 281)

CGI: 53 range = chr17: 77537903-77538626
CGCGCGTCGGGCGCTGGGAAGGTGACTGTGCGTTGGGCGCGCTTGGTGGCCCCAGGGCTGGGCCTGCTCCCGTCT
GACAGTAGTGCCGCGCTGCATGGCACGGGTGTTGCGTTCGTGGGTGAGAGCGCTGAGGTCTGCACGTCGGGTCTC
AGTGGTCATGGGGATGGAAGCCACCCCAGTGGCTGTCGGGGTGAATGGAGGCCCCTGGAGATGGCAGCGGGTTAA
GCACGAGCACGGAATTCTCCCTCCCAAAACGGAACTCAGACAACAGTGACGGAGCCTAAGAGCAAAGCCAAAGCC
ACGGGCAGGGGTGAGCGGGACCCGAGGCAGGAGATGACGGAGCCTAAGAGCAAAGCGAAGCCACGGGCAGGGGTG
AGCGGGACCCGAGGCAGGAGGTGACAGAGCCTAAGAGCAAAGCGAAGCCACGGGCAGGGGTGAGCGGGACCCGAG
GCAGGAGATGACGGAGCCTGAGAGCAAAGCGAAGCCACGGGCAGGGGTGAGCGGGACCCGAGCCAGGAGTGGCGC
CGGGCAGGGAGGCAGGCAGCCCCAGGCGCTGTGTGGGCACTGGGTGAGAAGCAGGGATCCCGGCGCCCTGGCTCT
GTGCTGCTTCCTGAGACGAGAGTGGCAGAGGGCAAGAAGAAAACCAAACAGCGCGGGGAACAGAAGTCAGGAAAG
ATGAACGTCTGGAAGGAAATGCCCCTGGGCCGGGCGGTGCCCCCGGGCG (SEQ ID NO: 282)

CGI: 330 range = chr18: 894579-899574
CGGAGAGACCTCGGAGCAGAGAAGGCGCCGCCGACCCTCGCGGCTGCCTGGCCCGCGGCTCCTACAAAGGCGGGC
TAGCCGCCCGCCCTCTCCCTTGCCTTCCTCCCCTTCTTTTCTGACTTTCCCTCTTTCCCTTAATCGCCTGCTTCT
TCCTCCGGGTGGACTTACGGCCACCTTGCTCCTCCGCGCTTCACCTCATCGCCCCCTCTTTCTTTCTTCTGCCTC
TCTCTCTGCGCCCCCTTCTCTCCGTGTCACGCTCCCTCCTGGTTCTGCGCGTCTACAAACTTTTGAGCAGAACAC
GAGCCTCGGCAAACGAGTCCCGCAGCTCCTCCTGCTGCTCCCGCTGGTTCCTGCGGCTTCTGCTCAGACACCAAC
GCCAGACGGCGATGCCTCTCGGTGGTGACTCCAGCGCAGGAACTTGAAGAAGCGCTTTGCCCGCCGTCCTACCT
GGCAGCTCTCCTGGCAGCGGGAGGAGTTGAAGGGTAAGGGAGGGAAAATCTTACCAAAGCGACCGGCTCACTCGA
CTGCTGATTCTTTCGCTTGGCATCGCGTCAGGGGAGTTAGCTTTCCTTCAGCCGGGTCTGGCTAGTTATTGGGCG
CCGGGTAGATGCATATATATATATTTTTTCTAACTATAGCAAGCAAGAAGTGGCAGGGCGCGCACCGGCTGTCG
CCAAGTGCTGTTCAACTCAGGGAGCCGGGGCTTCGCTCCGTCCCTCCCCCGGCTTCCAGAGCTTTTTGGGGTTGG
AGGGTGGGAGGCCAGGGGCGTTCTCACAGCTGTGTGTCCTCTTTCCCATCCTGCGCAGAATGACCATGTGTAGCG
GAGCGAGGCTGGCCCTGCTGGTCTATGGGATAATCATGCACAGCAGCGTCTACAGCTCACCTGCCGCCGCGGAC
TCCGGTTCCCCGGGATCAGGTAGGTGCTGGCTGCCTGGCCCAAGCAGGAGCTGGGGCTTCCCAGGCACAGACGCT
TCCTCACGGTCTCCTTCCTGCAGTCCTTTGGGTCCAGACTACTAGCATCGCCCTCTGCGCCCCCGGTGCGCCTCC
GCCAGCCTCGGCTGGACAGCGGGTCCCCATTCTAGCCGAGGGTCTGGCAGGCTCCGCGACTGCTCGGACGCCTCC
CCCAGCCCTAGGCAGCTCAGGGTCCCGGGTAGAGCCAGTGAGCTTCTGGCCGCTGGAGAACCCCCCCTCCCCCAA
CCCGGCCCACAGGATGGGGGCAGGGCACGGCCCCTAGCTTGGTTTCTTTTACCTATTCTTGGGACGAGTTAGGAG
AACTTCAGCTCTGGAGCCTGGCCGGGGGTTGAGCGTGAAGCTCCCTCGGACTTTGCTTTGTTACTGCTTGTTCTG
GACTATCCGGGTGGGGTCTCTCTCTCCTCCACCCTTTCTTTTCATTTCATTCCAATTCTTTCCCCTGAAGAGC
TTTCTTTCAAGTGATCCGTGTTCCAACTGCATTTTGAATCCCAGGCTGTCTTGGGGGGCGTGCGGTGGGGAGGGT
GTTGGCCCGGTGTGATTGAGGAAAAGCGACTTAAGAGAGGGAAGAACAAGGACGAGACTGCGAAGGAGGGGGAAA
AACAGGCGCAAAGGAGGAGGAAGGGAAAGCCAGCAGGCAGGCAGGACCGGGAGAGCAGCCCTGCCTGGCCCGGGA
TGGAGGAACCTTGGCTTTTTTCTTAACCCCGGGTTTCTAACCGGCAGGCGCGGCCCAGGTTCCCGGAGGCAGCCC
CAGAGTCGCGGACCGATGTGCCAGGCTGTGGATGAGCCCTGGGTAGGGAGGGTTCGTACCAGCGGCGCCTGGGG
CAGCGAGGAGCGCGCGTTCTGCCTGCGAAGCTGCCTTCTCCGAGCCCCGCCCAGGAACATTAGCTCTGGGGGGCC
GCTGATCATTGATTTGGACGGAGAGATGGGTTCTGGGTTCTGTATTAGGATTCCAGCATCTGGGCTCGAGGCAGG
GCAATATCCAGAAAGACCCCAGGGTTCGGGGTACCCGGGCCAGGGCTGAGGCGCATCGCCGAGCAAAGGCTGGGT
GCGAGGCGTGCGGAATGATGCGCTTGCCTTGCCCGGGCCTCTCCAAGGATGGAGAAAAGGCGAGTGAAGCAGCGA
AGTACGACTCCAACCCCGCCCAGAGAGTGCTACTAGCGCTGGCTGCACGCCAAGTCTCTCCAGGGGTCCAAGCG
AGAGGGATTTGTTTTAACCCATCTCTACCCGTCCTGTGTCAAGAACGGAGGCTGTAGAGGGCGACTGCGAAGTCG
CCAGGCACTCGCTGGATCTCGGTCCCCTCCTCGTGCTCTGGGGTTGAGATGGGCACCGCCATCGATAACAGAT
CAGCGCGAACTATTCGTTTAGTGGCCTTAAAACACCCTGGTTTCACCCTCAGCTATTTTCAAGTTCCCGTGTGCC
TGGCACTTTCTCCGTGCGAGAAGCACCGGAGGGTGCGGACGCGCCACAGTCTGAGCCGCCGCCGAACTGGCTAAG
TTTAGGGGCATTTATTATTCATGTTCCTGCCAGATCCTCGCCTGCCCAAAATAGAAACCGAGGTTCTCCGTGACC
TACATCTGCTCGGAGAAGGGCTCCCCTGGGCTCGGAGGCTGGGGTGGGGGTGGCTGAGGAGTTGGCCCCCGCACG
CCCCACGCATCCTCTCCTTTGCTTTCTGGGCCTCCCCATTCGGGTCTTCGCGTGGGTCAGCGCCCGGTCTCCCAG
GGCCTTTCTCGTCCCCGCCCGTTGCTGCTTTGGGGAGGCTCGGGAGCCAGGCGGGAGGGGGGGGGGCCTCTTTTCC
GTAGACAGGTGTGCGCGATCGGCGGAGACGCCTCGGTTTCCCAGCGCTTGTTGAGGCCGTGGCCCGCAGGACGAC
CCTTTACCCGCGAAGGGGGGTGGGCGGCGCCCGGCGGGTAGGAGTGGTTGGGTGTCGTTGCCTCCTCCTTA
CCTCTGCTCCCACCCCCAGTCCTGGGAGAAGAGACAATTCTCAGCGGAGGACTTTTATCACCTGTGAAAATCCGC
GCGAGCCCCTTACTTTGGATCCTCGCCGAGCTGGGGAGGAACTTGCACTGACCACACCTTCTGTCCCCGGCCACC
CCGCAGGCCAGAGGAAGAGGCGTACGGCGAGGACGGAAACCCGCTGCCAGACTTCGATGGCTCGGAGCCGCCGGG TABLE 7B-continued Sequences of differentially labeled CGIs between bladder cancer subgroups relative to blood

```
CGCAGGGAGCCCCGCCTCCGCGCCGCGCGCCGCCGCCGCCTGGTACCGCCCGGCCGGGAGAAGGTGAGATTCGCG
CGGCCTCGCGCACACCCGCGGCTGGGAGCTCGGGACTGCGGTGACGGGAGGGGCAGTGTGGTGACCCACCCAGGA
TTTTTTTTTTTTCCCGTGAAAGTCCTCAAGCCTGTCCTCTCCCTGGCCCGATCCTATTGCAGCGACAGAAAATC
AGCAGCGGGCGGGTCTGTGTGGACCTGAGGGCGCGTGGGGACCGAGGGGGGCTGTGGCCCAAAGAGTGGCAGTG
AGTGGCGTCAAGGAACCCACACTCCGCATCTGCCACTCCTAGAGCCGGGACTAGCTCCCGATCCTAGCAGTTGCT
CTCGAGATCATCCCGGGAGTTATTGGCGAGTTCTGGGCCTCTGGAGGTTTCCCTGTCAGCCTCCCCGGCCGCCGA
GGGGGCGCGCGCCCAACAAGGGGGTCTCTAGCGGCCACCTGGGGACAGAAACAGTGACCCTGGGCGCGCACTTTG
CCTCCCCGTTAGAGATGTCGCCCACGGGATCCTTAACGAGGCCTACCGCAAAGTGCTGGACCAGCTGTCCGCCGG
GAAGCACCTGCAGTCGCTCGTGGCCCGGGGCGTGGGGTAAGAGTTTGTGGAAGGATTAACCTGCGCGCGCCGGGG
TGGGTGCCTGTGCGGGGCGCGCGGGGCGGGCGGCGGTGGGTGCCCGTGGGGGCCAGGGTGAGTCTGCGCCCCTGG
GTCTGGGGTGGGCATCCGCCACGGGTCGCAGTTGGAGATTTTGAAGTGGCACTTTAAATTTGCCCAGAGAGCTCT
GGAAGAGGCAAAAAGGGAACGCGAGCCAGGGAGTTTGATCCGTTTTGAATGAAAAGAAAGAGAAACCAAACCAAA
CCTCTCAGTCATCCAAAACCTTCAGGCTTCCAGGGAGGTTTTGCTATAATTTTCTCTAAGCATGACTGTTTCTGG
GGGAGGGGAAAGGGGTGGTTGTATTTACTGAAAATTCAAATCGAAATAATAAATGGCCAAATGTGGACACTTATG
GACCCAAACAGTTTTGCTCACGCCAGAGAAACTGAGAGCACAGGGCTTGTGTGAAGCCTATCTCGGCAGAAGGCA
ACATTCTAATAAAGCCCGTGGGAAAACAGATTACATTTTCGCCATGAATAAGTCATGCAGTGAAAAATATTGCCT
ACAGCCTGTCGACTTATATTATTATCACGTTTTTCAACTCGGCGTGAGGAGGGAGAGGAGTGTTCATATTTGACT
AGGAATTGCAGGATCGATGCAAACTCCAGGGCAGCAGCCAGACTGGCATATGTAGGGCTCTCCGGTTACTTTCTC
TGTATGTCGCGGGTGAGAGGAACAGCGAGGACAATTTAGCGCAAACACACGAAGGGTCGGATCTCAAGGGGGCAG
CGCTGGGAGAAAGGTTAGGCTTGAAGCGCGCGTCGCCTGCCCGGATCTTATCCCGGGCCCCTCCGCAGGGTTTG
GTGCCAGGAGATCCTGCGTGGGGAGGGGGGCATCGAGGGGCTGCCGTCTCGGCCCTCCCCACGGCTGCTTCCAGG
CAGAGGCGGGCGACGCGGTGGGCAGTGCGAGCCCCGGGCCTCCCCGAAGGCTCCCGCGTGGGGTGGGGCCCGCC
TGCTCCCCGCGGCGATTGAACCTGTGTCTCCCGCCCCGCCACCCTCTTCCCGACCCCTTTGCTTGCAGTGGGAGC
CTCGGCGGCGGCGCGGGGACGACGCGGAGCCGCTCTCCAAGCGCCACTCGGACGGGATCTTCACGGACAGCTAC
AGCCGCTACCGGAAACAAATGGCTGTCAAGAAATACTTGGCGGCCG (SEQ ID NO: 283)

CGI: 338 range = chr18: 74837994-74842232
CGCAGAAATTACTCGTGCGCACCATTTCCGCTGTGGGGGCATTCGTACAAGTTTCCGCTGCACACACAGCCTCCC
GGGCCCTCTCCTCCAAGGCTCTGCCGGATCTTCCAACGAAATCCCAGAGCAGCCTGCGCTGGGGAGCCCGCAAGT
CTCTCCAGATCTCTGCACCCCGCACCGCCCGGAATCTGGGACGGCGCCCACGCAGGGCTGGGCCAAGGGCAGAGC
TCGCACCCTGCCTTCACGCCCGGTTCACTTGCGTCCACGAAAGCAGCGTGCCGGCCTCCTCCATCTTCCCACTCG
CGCAACGCACGGCGACCCGCGCGACACTTCTGCAATCTGAAGGCTTGCTTCTTACAAATAAAGGGCCAGAGTCTC
ACACTTGCCTTCGTTGGAGGGACTTAGAAGATCCTCCCCACGTCCACACCTTGTAGGAAATGCAAAACAGATCGA
TGAAATTAAACAGTTGCATTTGGAAGCCCCAGAAAGACCTAAAGACATCGTGCCGGTTTGTTGGAGAGAGGGTTG
CGGGACAGGGGGAGCGGGCCTTACGCAACAGAAAAGGTGGGCACAGCGCGCTCAAAATGACCCAGTGAGGAGTTG
GTGCCGCCGGGCCAGAGGCTGCGAGTCCAGCTGGCTCTGGACTTGCTCCGCAGGCGTCAGACGCCGTGGGAACCT
GTGTCTGCTTCTTCTCTCCAAAGTGTATCGGTTAAAAAAAAATAAAAGTAGTAGTAGTAGTAGTGGTAAGGAAAA
AAATAAAAATAAAAAGGAGACACAATTAACCAGGTCATAAAAGCTAGGGCACCTTCGACCAGGGCTCTGGCCCTC
CAGCGATCGTTTTGCGTTGTTTCTCTTCTCAAAAGTAGTCTCAGACCCCTGCCTTTCCGCTGCAGCTCTGCGACT
TCCCCAAACTCCTTAATCCTGTAAATTCTGCAAGAAACTCCCATCCTGCAAGCTGCTTTTCCCCCTCCCCCCTGC
GTTCCTTTTTCTCTCCCCACCCGCGCCGCCTCTCTATGCCCCTCTCTTCTCAGAAAAATTCCTGCCCCCCGCGC
GCCCCAAAGCCCGGGCTGCAAACTTTTCCCCGCCGGGCGCCTCTGCGCCAGATGCCGGAGCGTCTCCACAAAGCC
TGAGCATCTGCACAAGTTCGCAGCCTAACTGCGGGATAAAGACGTTTCCCCCGTAGCTTAACTAGAAAAGCGCCA
TCGATGGGTGTGTTAAACGGGATAACTAGAGATTTCAAACACCTTTTATTTGCCTGTCTTGAAAAAAAAATCTAA
ATGAATACGCCCGCTACCAAAAGGCAAATAAAACCAACCTTAAGGGTTTTTGTTGTTTTTTTTTTTTTCAAAA
GTGGCGATAGGGACTGTTTGGACCTGACTCCAACCTGCGCCCTCCCTTCCTCTATGACCCTCCTGCGCTTTTCCT
GGAACCCAAAGCTCTGACTTCGTCAAACTTACACAATTAAAGGCAGGCGGAAGAACGCGGGCTGGGAAGCAAGCG
GGAAGATTCTAGAATGGAAGGGAGCCCGCCGAGCGCCGCGAGCCGCGCCAGGCCGGGTCCGATGGAGCAGGCGGG
GATTCCTCCCCAGGCGGACCCCCGCCACCAGCCCTGCCGGGAGCTCGCGGCCTGCGGAGCGCCCGGGCTGGCCG
CTCACCGCCCGCTTCCCCCAGCGAACGACTCGGGGAAGCTCCAGGAGGCCATCTGTGCTGACGGTTCACACCAGA
CAGGACCACTTGCAAGGACAAAAATAAGAAATTTAGGAAACGAAAAAAGACGTACTGGGGCGAGGGGCGCGGGCG
CGGCGACGACGGGGCCGGGGGCACATCCTGGCGGCCGCTCGGGGAGAGAGGACACGCGCGGGAAGGAGCGCGGCG
GGTGCACGGCCGCGGGTGGGAGTACGCGCCTGTGCGCGCGGGGCGAGGGCGAGGGCGCGTGCGTGTGACCGCGGG
GAGGGGGCGGGCGCGTGTGCGGGGAGCGCGCCGCGCCAGGGGCCGAGTGTGTGGGGCCGATCCAGAAGTGCGCAG
CCCCCTCACCTGGCCCCCGTGTCATCCCCGAAATCCCGGGAAAGGGTGGGCCGCGCGCAGGGGGACTTAGGGTGGGGA
GGAACTTTCGGTCGCGCTCGCTGCCCACTCCGCTGGCGCCCGGTGGCCCGTGGTGAAGGGGGACTAGGGTGGGGA
ACACCGGGGCCCTGCGGTCCCCTCCCTTTCCTGTATTTAAGAAGCCGCCGGCGGCGCAGAGGCCCAGGCGGGCTG
GCGCGGGGGCGAGGCGGCCCGGTGGCAGCAGCGGGCGGGGCGGGCGCTCCGGAGTCGGTGGGGCCCGCGGGTTGG
GGGGCGGGAGAGGGGGGAGTGGAAGGGAGGGGGAACGCAGGGGAGGGAGAGGAGGGGAGGAGCCGCGCGGCCCCG
CGCCGCTTCCGAACCGGAAAGTTGGTCTTGCCGAAGTCCTGCCACCCCGGCGTGCGCACTCCGCTCCGCTCCGGC
CGCGAGCCTCCGAGCCCGGCCGGCCGCCGGGGGAAGCCCGCGGAGGGGACGCGGGGCCGGGCGAGAAGGTCGGA
GAGCGGGGGCACCTGAGCCCGGGCGGGCCCGCCGCGCTGAGCGGCGCTGAGAGCCGCGGCGGAGCAGCGAAGGC
GGCCGGCCGACCCCGCGCGCCCGGAACAGGAGGCGCGGCGCCCGAGCGGCCCGGGCGAGACAAAGGCGCGGGTC
GGAGCCCTGCCCGCGGCCGCTCGCTCCGGGAGGGGCCGCCCGGCGGCGACGGGGGGCGCGGGCGGCGGCG
CAGACACTCTATAAAGGGGCGAGCCCGGCGCGCCGGCGGAGACGGCGCCGCGCGGACGCCGCCAAAGTTTGCTGC
CTGCGCCCTGCGGAGGGACGGCCACCGCGGCCCGCGCCGCACCCGGGCCCCGCCACAGCCGCACCCGGGGCGGCC
GAGGAGCGCGGCGCCGGAGCCCGCGATGTGAGGCGGCGCGGGCAGCGCGCGCCCCGGTCCCGAGGCGCCGCGGC
CCCCTCCTCGTCGGCGCGGCCGCTAATTGCGAGCGCGGCCTCATTTGCATAGGCCGCCGGAGTCCGCTGGAGCCC
GGCCAATCGGCGCGGCCCTCCGCTAATGGCCATGCATTATTCACCAGCCTAATTGCTCAGCCCCATGCGCGGCCC
GCGCAGCCGCCGCCGCCCCGCGCCCCGCCGCGCGCCCGCCAGGCCGCCCGCGCCGTCCCCGCCGGCCGCCC
GCTGATGCCGCTGCCCCGCGCGGGGCCCGAGCGCCGCTAGCAGCATGTCGGCGCAAGCAGGCCAAGCCCCAGC
ACCTCAAGTCGGACGAGGAGCTGCTGCCGCCTGACGGGGCTCCCGAACACGGTGAGGGCCGGGCTGCGGGGTGG
CCGGGGGGTCTGGGGCTGCCCGTCCGGGCTGGGGAAGCGCGTGCGGCGGGAGCGGATGCGCGGTCCGGGAGCGG
GAGAAAGTTCCCTGCTTCCTGCGGGCAAGCGTCCGCCCCGCGCCAGGCCGGCCGCGGGCCCGGGTACTTCGCC
GGAGCGCGCGCGGCCGCCGAGAGAGTTGTGGGCGAAGTAAACTTGGCTCCTCTCCTCGGAGTCGGGGAGCTGCCC
GCGAAGGGCGCCGAGGCGCGCGCCGGCTCGAGGACGGCTCGGAGGCCGGGCGGGAGGGAGTCCACGGTGCCTCC
GCCGCCGCGCCGCCCCCCAGGGTCTCTGCGCCAGGACGCTGAGGCCGGCGGCGGCGGGGAAGGCGACCGCAGCCC
```

TABLE 7B-continued

Sequences of differentially labeled CGIs between bladder cancer subgroups relative to blood ACCTACCGCTGGACGCGGGTTGGGGACCCCGCCGCCCGGCCAGCTTTGTTCGGGGGCCCGCGGCCCCTCCCGGGC
CCCCGCACCGCCTCGGGTGACCCGCGGTGTCCCAGCGCGTTGACGCAGCCTGTGATCCCTCGCGAGGCGAGGAGA
AGGTCGGGGGCTTGGCTCTGCCTAATGGCCGCCCGGGGAATTAAGCTGGGGGTGAGCGCAGCGGCGGCGGCCTGG
GCCTGGCCCCTGCTCGCGGCGTGTTTCCGGGGCGTTCGTTGCAGCGTCTGCGCGGGCCTTTTCTCTCCCGTCTTT
TTGGATCCGCCGAGGCCGGGCGCTGGAGACCTCGGCTTTGCAGTCATTTCGCTGGTAGGAGCGTCCTCTTCGAAA
CATCCAAGAGCAAAGGGCAGGCGCCGCGAAAGTTAAGAGACTGGCAAAGGGCTGGACTTCCCAGAGTGGCGCCTT
AGCCCCGCAAAGTTTGGGGCGCCCCCACCCCCTTCGTCG (SEQ ID NO: 284)

CGI: 43 range = chr18: 75565313-75565933
CGGGTGCAAACGCATCCTCTGTCCCACGTGGAGTGGTGTGTCCACACGCATGTCCTCTGTCCCATGCCCACGTGG
AGGGGCGTGTACACACGCATGTCCTCTGTCCCGTGTGGAGGGGCGTGTACACGCACACGTGTCCTCTGTCCCGTG
TGGAGGGGCGTGTACATGCTCACATGTGTCCTCTGTCCCGTGTGGAGGGGCGTGTACATGCAAACGTGTATCCTC
TGTCCCATGTGGAGGGATGGGCACATGTGTGTCTTCAGGACGCCTGTCTCAGGCACCCGTGTGTCTTCAGGACGC
CTGTCGGGCACACGCGTGTCTTCAGAACGCTTGTCTGGGGCACACGTGTGTTCTCAGGATGCCTGTCTCGGGCAC
ACAGGTTGCGGGGGCGGCCGGGGCTCCTCAGGCCTTTTCTCCCGACTGTTGCTACTATTCTTTTTAGGGCATCTT
TCACTTCCAGCTGGGCCGGGGTGAGCCCATGCTGCACACGCGCCTGCGTCCACACTGCAAGGACTTCCTGGAGAA
GATCGCCAAGCTGTACGAGCTGCACGTCTTCACCTTCGGCAGCCGGCTGTACGCACACACCATCGCAGGTCAGTC
AAGCCGCAGCCGAAGAGGCCG (SEQ ID NO: 285)

CGI: 33 range = chr19: 898548-898981
CGGGACCGTTTCACAGATGAGAAGACCGAGGTGCCAGGGTGGCGATCGCACGAAGGGCCCGTCACGGGAGAATGA
GGAGGGTCTGGCGTCAGCAAGCTCCCCCGGAATCTCGTGATCTGGAANTCCACAGAGAAGCACCTTCACCACGCC
AGCTTCCCGGGCCGCGCTTCATTGTCATTTCTGGAGAGTGTTATTAATATCCGCCCCGTGGGTGCGGCGCTGTGT
ATTTCCAGAGAGGGGACTCGGGGCCCATCAGGGCCGGGGAGTGGAGCCGGCAGATGTTCGGCCCTGCCCAGAAT
CACTTCCCCAATTTCCCCACGCCCGGCGGGGCTCTCAGCATCTGCATCCGCCGAGGCCTGGCTGTGCTGACGGGA
ATTGAAAGGACCTCGTGGCTTAGGCAGGCGGGGGAGCCCCCCGGCTGGTCAGGTGCACG (SEQ ID NO: 286)

CGI: 70 range = chr19: 9131907-9132918
CGCCGCGACTATGGGGTAGCGTTCAAGGGCAGGCCGCACCTCACTCAGCACATGAGCATGTACGACGGGAGAAAA
ATGCATGAATGTCATCAGTGCCAAAAAGCCTTCACCACGAGCGCGTCCCTCACACGGCACAGGAGAATCCACACC
GGGGAGAAGCCTTACGAGTGCAGCGACTGCGGGAAAGCCTTCAACGACCCTTCAGCCCTTAGGAGCCACGCAAGA
ACTCACCTCAAAGAGAAGCCCTTTGACTGCAGTCAGTGTGGAAATGCATTCCGGACCCTCTCGGCCCTGAAAATC
CACATGCGAGTTCACACTGGCGAGAGGCCTTACAAGTGTGATCAGTGCGGGAAGGCTTACGGCCGGAGCTGCCAC
CTCATCGCACACAAGAGAACGCACACCGGAGAGAGGCCCTACGAGTGTCACGACTGTGGGAAAGCTTTCCAGCAC
CCCTCCCACCTCAAAGAGCACGTGAGGAATCACACGGGGGAGAAGCCCTACGCGTGCACGCAGTGCGGCAAAGCC
TTCCGCTGGAAGTCCAACTTTAATTTGCACAAGAAGAACCACATGGTGGAAGACCTACGAATGTAAAGAATGC
GGGAAATCCTTTGGCGATCTCGTGTCCCGGAGGAAACACATGAGGATTCACATCGTCAAGAAACCCGTGGAATGT
CGGCAGTGCGGGAAGACCTTCCGAAACCAGTCCATCCTTAAGACTCACATGAACTCTCACACTGGAGAGAAACCA
TACGGGTGCGATCTCTGCGGGAAAGCTTTCAGCGCGAGTTCAAACCTCACCGCACACAGGAGATACACACGCAA
GAGAGACGCTACGAATGCGCCGCCTGCGGGAAAGTCTTCGGTGACTATTTATCCGGCGGAGGCACATGAGCGTT
CACCTTGTAAAGAAACGAGTTGAGTGTAGGCAGTGTGGCAAGGCCTTCAGGAACCAGTCAACGCTGAAGACGCAC
ATGCGAAGCCACACGGGGGAGAAACCGTACGAATGCG (SEQ ID NO: 287)

CGI: 25 range = chr19: 12985960-12986259
CGGAAAGCGCGCTTTTCGGCAGAGCTGGTTAGTTTTTAATGCGGGCTTTTTTTTTCTCACCCGCCGTTCCCTCCG
CTCCGGTCTGATTCGCAAATCCCCAAACTGGCACAAACCGGGAAACTTGCGGCCGGCCGTTCTTCTCCCCGAGTT
GGAGACAGCCCTCTCCTCTTCCCTCCCCCGCCTCTGGGCCCTGACCCACTGCCTGGTTTGCGCTAGAGCCGTTTA
AAAAAGAAAGAAAGGAAGAAAGGAGCCGGGCTCTGGTACCCCGATGCCAGCCGAGGGCGCGTTTCCCAGGCGGCG
(SEQ ID NO: 288)

CGI: 35 range = chr19: 55553586-55553895
CGCGACCACCCGCTGCGCATGCGCTTCACTTGGGCGTCACCCGGGGAACTGCGCCTGCGCAGTCTCTCCCCATCC
GAGGTCCGCTCCGCGGAGTGCGAGCGCGCGCCAGGCCCACCCGGGCGCTGCTCTTCATGTCCCCGCGGTCGAAGAC
GGCCACATACGTCCCCAAGAAGACGTCACCGAGGATCCAGAAGGGCCCTGCAGGCGGAGGGACATCCAGGGCCTG
GAAACCGGACAAGCAGAGGCGGACGCCATTTCGAGTAGTCTGCAAGGCAACAAGACGACAACTGGGTGTCGCGGC
CACAAGGACG (SEQ ID NO: 289)

CGI: 47 range = chr19: 57082654-57083180
CGATTCGCTTCCCCACCACGACGCCCTAGCGCTACTGTGCAACGAAGACCTCCCAAGCACTGGTTCCAATGCGGA
GACCATGGGCTCCCAGACTCTGGGAACTCCAACACGACTGCGAAACGAACTCCGAGCGAGGACTCCCCGAGAGCT
CCCCGCAACACGGACCTCACGCGCTAGCGAACAACAGAAAAAAAAAAGCGCGCTCTCCCTGCCCCTGAAACATTC
CCAGAAGCCCACGCAGACCAGACCGATGACCTGTCTCCACTGCTGGAGGCGAGTCAGGGACCCGAAGTCTCTAAA
CACTCGCCTCTACCCGCCGCCCCGCGAACCCCACACACTGCAGACGCGACACTCGCAAGTTTCGGGGATGGCGGC
CGGCGAGGGCCATACTGCGTCTTTCCGGAGACACGGAATACGGCACCAGCCGTCCCTTTATGATGCAATATGTCT
GCGCCCAGGGGACGCTTGCTGGGAGCAGCCATTTTCAACCCTACTGCCGTAGAGCAGGCGGAGTCCCTCTTTTCG
CG (SEQ ID NO: 290)

CGI: 159 range = chr19: 60283718-60285792
CGAGGTGGGGCGAGGAACCACCCGGACTGGGTCTCCATGGGCGGGGTCGTGGCTTAGGGCAGGGACAGGTGTAG
GGCGAGGGGTGAGTTCGGGGCGTGGACGTGCGTGGGTTCACAGGTGTGAACGGTAGCCGCACGTGGGCTGGGACT
GAGCTGAAAAATCGGCCAGGGGCGAGGCCCGGGTAGGAAGTGGGTGCGGCGTGGGGAGGCGTGGCCTGACGGTGT
GATTGGCAGGCGGAGCTGATCCGAGAGGACATCCAGGGGGCTGTGCACAATTACCGCTCGGGCCGCGGGAGCGC
AGGGCGGCGGCGCTCAGGTGAGAGGGAAGAAGTTGGCAGGGTCTCTGGGAAGCCGGTTTCCCCTCCTTGTGCCTC
AGTCTACAACACCAGCCTGGAACAGAACAAGAGTTTTGCATGGAGTCAAGCACACCCTAGTCGAGTCTTGTCTGT
ACCTCCCAGACGAGCTGACCCCTTCTCCAGAACTCTGCTTCTTTTCTCTGTTCCCTGTCCAGGCCCTCAGTTTCA
CTCTAGAGAGGTGCTATCCCTCCGTATATCGGATTTCTCCCTACCTCGTTGAACTTGTTCACTCCCTTTGAGCCT
TTTGAGCCTGTGTGTCTCGTTCTGCGCCCTGGATTTCCCCCTCCCTGGACCCCTCAGTGGACCCAGTCTTGGTGT TABLE 7B-continued Sequences of differentially labeled CGIs between bladder cancer subgroups relative to blood CCCCGTCGCCCTCCGCAGGGCCACGCAGGAGGAGTTGCAGCGCGACCGCTCGCCCGCCGCTGAGACCCCGCCCCT
GCAGCGCCGCCCGTCAGTCCGCGCAGTGATCAGCACCGTAGAGCGGGGCGCGGGCCGCGGACGACCCCAGGCGAA
GCCCATTCCCGAGGCAGAGGAGGCGCAGAGGCCTGAGCCGGTGGGGACCTCGAGCAACGCTGACTCGGCCTCCCC
GGACCTGGGTCCCCGGGGTCCTGACCTGGCGGTTCTGCAGGCGGAGCGGGAAGTGGTGAGCCGCTAAGGAAGGGG
TCTGGGGGCAGGGCCAGGCGACTGGAGGCGGGGCTAGGGCGTGGAAGGGCGGGGCCGGCTGCGGGACGGGCGTTC
TCTGGTCAGACTTCTGCGTTATGGAAGAGGGGCTGGGTCGGGGGCGGGGCTTGGTTGTGGGGCGTGGCCAGGTGT
TTGGGGCGTGGCCTGATCTGGGGAAGTGTATAGGTGCTCAGGTTCAGGGCTTCGACGGGGATGGTTTTGGAACTC
GGGAGCCCTGAGCGTCCCCCTCCTCTGTCCCCTAGGACATCCTGAACCACGTGTTCGACGACGTAGAGAGCTTTG
TATCGAGGCTGCAGAAGTCGGCGGAGGCGGCCAGGGTGCTGGAGCACCGGGAACGCGGCCGCAGGAGCCGGCGCC
GGGCGGCTGGGGGTAAGGGGCACCCTGGCGTGGGATCTGAACCCCCTCCCGATCTCTTCCAAATGTCCCCGCTCT
CCCCAGGCTCTCCCCTCCCGCCACTTGCCAGGGCTGACCTCACCGCCATCTTAACCGGGTGTCCACCTCTCTCTG
CCTGCCTGGTGCTGGCCCCGCGTCCCCATCGCCGCGCCCGTCTGCTCCCCTCAGAGGGCTTGCTGACGCTGCGGG
CCAAGCCGCCCTCGGAGGCCGAGTACACCGACGTGCTGCAGAAGATCAAGTACGCCTTCAGCCTGCTGGTGAGGA
CGCGCCCGCCCCTGGGCCGGGGCGGGCACGACGAACCTGTCCCGTCCCCGCACCCACGCCAACCACCTCCCTC
CCCACGCCCCAGGCCCGGCTGCGCGGCAACATCGCCGACCCCTCCTCTCCGGAGCTGTTGCACTTCCTTTTCGGG
CCTCTGCAGATGGTGAGACCCGCCCCAGGCCCTCGGGCCCCCCTGCAGCGGGAGGAATCGGGTTCGACTTGTAGA
AGGTGTGGCGGCACAGCCTGCCCCTCCTGCTCCCCTGACAGATTGTGAACACGTCGGGGGGCCGGAGTTCGCGA
GCAGTGTGCGGCGGCCGCATCTGACATCGGATGCCGTGGCGCTGCTGCGGGACAACGTCACTCCACGTGAAAACG
AGCTCTGGACCTCGCTGGGGGACTCGTGGACCCGCCCCGGGTGAGGGGCG (SEQ ID NO: 291)

CGI: 34 range = chr19: 60907042-60907388
CGCTCCCCTGCGTTTCGGCTGCTGGCCCAGCAGAGGGCGCCGGAGAGCGGACGGAGCCGCAGGCGGGGTTGTGGG
AAGACGCTGGGATCCCGTGCGCGCTTGTGCTCCTTCCTTCTGGGCCAGCGCGCAGACTATCAACCGAGGTATTCA
GTCCCTCGGAAACCCAGTTCCTCCGTTTCCAGGCTTCTCGCCCACACGGAGACAGTCGCTCTCACACGTACCTCT
CGCGGGCTCTTACTCGTGGTCCCGGTCTCCTCCTGGTCCCCACCTTCCAGCCCAGCGCGCACACTAGACGGCACG
TGCTCTCCACGCTCTTTCTCCAGCGCCCCTTGCTCACCCGCCCCCCG (SEQ ID NO: 292)

CGI: 61 range = chr19: 62043096-62043807
CGCAGCAAGCCTCAGCCGCCCTTATTTAAGATACCGCCCGAGAGGGCGGGGAAAGAAAACCCCTACAGGCAGGAC
AGCCCTTCGCCCCTCCCACCACCACTGCGGCAAACAAGCCCCGCCCCCAGAGGGTAGCCGGGCACGCCGGCGCCG
CGAGGCCGATGGCACCCCGCAGGAAGGGGCATTTTCGCAGCCCCCAGACCCAGCCCAGGAGGCCCAGGGCTCCCG
AGAGCCGCATTCCGCCGTGGCAACAGGGATAGCATTGGTGTCGACCTTGCTGGACTTGCCGTGGCAGAGCCCCCG
GCTGTCTGCCCTAATGCCCCCGGTTTGCTGCGGTGGCCCCCGGCCAGTCAGAAAGGCGCGGAGACCCTGCAGCAG
CCCCTCAGACCCCGGACTGCAAGATGGCGGCACCAACGCAGCAGCCCGGGCTGCGCCCACCCCTGCCCCAAAAG
GCACCAACCATCCACAGCCTGGCCGCCACTGTGCCCACTCTCGGACTGGGCAGCGGGCGGCCAAGTACCATGTCC
GCCAGCCCGCCCTGCCACAAGGGTCGCTGGCTTGCCGCGGGGTCTTGGGCTTGCGCAAGCAGGCCACTCTGGCC
CAGAGCCGTCGCGACACCAAGGTCCCGCGGGCAGGAGGCGCGCGGGGCGGCCGAAGGCGCACTCACCTCACCTCA
GTGCTGCGCAGCCTCGGGCACGAACAGCCGCCTAGCG (SEQ ID NO: 293)

CGI: 94 range = chr19: 63321122-63322053
CGCCCAACGAAGAGGAGGGAGTAGGGGTCCGCGCCCACCACGAAAGGAGAGTAGAGGGCTCGCGCCCTGCGGGG
AGAGGCGTTAGGGGGTCCGCGCCCGGCGAGGAGATGCGCGTACCAGCCCCGCACGCCAAGGGGAGAAGACACGCG
GGACGGTCCGCGCCTGGCGGAGAGAGTTCCTCACGCCCGCCCCGCCGGGAACCACAAGCCAGCGCCCCTAACAAG
CCCCTGCCCAGAGCAGGGCTGCCGCGTACCCTCACAGACAGAAAGAGCGACCACGCAGCCACCGCCCAGCCCCAG
CCGCTCTGGAGTCCTTGACCCCACCCTCACTAGGCCTTGGCTCCGCGACCGGTGGGCGGGAACGGAGGAAACAGA
CCCGAGAGGCCGCGAGAGGACGGAACTCACTTCCCGCCGCCGTAGCGTCCTCGTCAGCTCGCCCTCCGACTCTCC
GCATGGGCGCGCAGAGTTCCCGGATGCGATATTCCGGTGACACCGGACGCTGGGGGCGGGGCCTAGTGCGACGAG
GGCGGGGCCGGGGCCGGCCCGGGGCGGGGCCGTGGCCGCAGCTGCCTGGCAGCCAGAACCTGGGAGCGCTCGCAG
TGCTGCCTTTCGGGGTTCTTTGTCCTTCGCTTCTGCTGGTAGGTGAGGTTTAACAGACGGAAAGACGCCGGGAGC
GCACGTGGGCTGCCTTGAGCCGCTGCGGACGAGCACCTTGTCTCTCAGGTTGACCAGCCGTATATCCGCTTGCGA
GCCTGCACCACCCTGGGCGCGCGTGGTCTCGGCAGAATCTCGTTCACACGGGTCCCACTCGTAGGCTGCTGTGTC
TCCTTCCTCTCACGGCGTCGGGGACTGGGGCCTGGAGTCACTCCTCTACAGGGGTGTGGAACGCGCCAATGGACG
CTGACACCTTCATGCGGTCGTTTAACGCTCCG (SEQ ID NO: 294)

CGI: 35 range = chr20: 9444472-9444893
CGCTTCCCTATCGGGGCTGCACGTAGAGCATCTAACCGCATGTTCCCGGAACCTGGGATGCGCGCGCGCAAAGGA
GCGCCCAAGCGTGCAACCCAGAGTTTGGACGCGCCGCCCTTTACAGCCCCCGCCCCGGGGCGGGCGAGCTGAGG
GGGCGCGGGGCGTCTGTGTTCCCAGCTGATCACAGAACAGGCCGATATCGCATTGACCCGGGGAGCTGAGGTGAA
GGGCCGCTGTGGCCACAGCCAGTCGGAGCTGCAAGTGTTCTGGGTGGATCGCGCATATGCACTCAAAATGCTCTT
TGTAAAGGTAACTCCGAGCCCAGCGGGCAGAGGGGCCGCAGGCTCCGCGTGGGTGTGGGAAGTGGCGGCCCCTAG
GTTTAAGAACCCAGACGCTGCGGGACGATTGAAGCGCACCTCCCCG (SEQ ID NO: 295)

CGI: 671 range = chr20: 21433933-21444714
CGCGGAGACATCTCGAGTCCCGCAGGTGTCTGAGCTGCGCTGCGCGCCCCAGCCGGGAAGCCTTTTCTTATCCAA
CCGCGCCGCCCCGCGGAAAGCCTGGGTACTGCAGACGCCCTCACCGGCCCACCGACAGCTGGTTTTGAAGCGGGG
GCTTAGAAAAGTAAAGGGGACAGTGTTTGGAGCCACGATGCCTTTGATGTGAGGCGGTTCCACCCAACAATCAAC
GAATCAAGCTGGAACTGCAGGCCCTACTTTTGTTGGGGGAGGACCTTAAGGAATGTCACCCCCTTGTCCCCTAC
CCTCTGCCCCACGCCCAGCCTCTCAGAAGGCACCAGGCGTGAGTAGAGTGCGAGGCGTCCACACCCTCGTGTCCC
TTCCATTCCCGGACACCTTTGTCACCCTAGCCGAGGCCTCAGCACGGAGTGAGGGTTGCCTGGGGTGCCCTGCTGT
GTGTGGGGCGTTCTTGCCTCCCGGGCCCTGACCCCACGGTCTGGGTCGGCGAGGCGTCTCTCCCTGGCGTCTGGA
CTGTGCGCCTGCCCCGCTTCCAGGCGACGAACGGCAGGAGCCGGGGTCCGGCGGGACCCGGATCCAGGGCGGGC
GGAAGGCGAGGGTCTCTCCTTCCCGGAACCCCGCCCGGAAACCTGCAACCAAACCGGGTCCCTCCTCCGCATC
GCTCCCGCGCTCCCGGCCGCCTCCCCACGCGGGCACCCACTCTCCGGGCCCTCGCAGCACCGCCCCTCTCCGCGT
CCACCCGCGCGGCCGCCGACGCCGCGCAGGGGCCCTGAGATCGCGGAGACAGCGCGCCCTGGCGCCTGGTGGGCCCTC
CCAGTGGCCAGAGCGCTCCTGGACCAGTCGGCTGTGGTCTGTGCCCAAACACGATGGAAACCGGGGCTGGGACGG
GCGGTGGTACGCACGTGGAGGAGAAGAGGCATGGCGGGAAAACCACAGCCGAACACAGGTCGACTCGCACCTCCC
AGGCACCCGCCGCCGTCTGACTCGCGGCTCTCCCCAAGGTTCCGACTCGCCGCCACCTCTTGGCACCACTCACCG TABLE 7B-continued Sequences of differentially labeled CGIs between bladder cancer subgroups relative to blood

```
GGCTCCGACCCGGGCCGCGAGTCCGCTGATGCGCAGCTGCCTCCGGCGGCTCCCGGGCTCTGCCCGGACCCGCGC
GCAGAGACGCTCGGGAACGCTGGGCTCGGGCGCCTCCTGGCGGCGGCAGCACGCGGCACACGCTCGGTTCTCCGG
CCCGAGGGGGCGCGTGGAGCGTACGCGGGATCCGCGCGCGGGCCTGGGCTGCTGGCCCACATTTCCCCGCTTGCT
CGGATGGCGGCGCTGAGGCCTATTCGCCTCTTTATTAATAACGATGCCTCGGGAGGGAAAAAATAGAGCCTTTAA
AAATCAGAGTGCGAGAGAGGAGTGTGTGTGTGTGTGTGTGTGTGTGTGTGTGTGTGTCTCGGGGCGTTGGTGA
AAGCAATAAAACTCAGATCGCTTCCTTGGCGAGATAGCGGCGGCTATAATGCGCCGGGGGGATCAGGGGTTTATT
TGCAGATCCTGGATAAAAGATGATATATCGACACGGTTTAGAGTGTCACTGCGCTTGGCCTCTCAGGGAGCCACA
AGTACATATTTCCTGAAATACCGCCCAGCACAGTATCTAATCCGCCCGCCACTTAACACCGGGAGGGGAACTTCA
GCAGCGCACAAGCGCGCTCCCGGTTTCCTGGTTCTGGGTGGGGAGAGCCCAAATGAGAAGGATCTGGTATGCCTA
GACGCCCCCTCCCCTGGCCTTTGTCTTCAGTCCAAGTAATCACTTAGCGATGGGCCTTAATAAATACGTCTGAGA
ACTGTCCTTATGCTCGGTAAATATTGGATTAGCTTTTCAATGACCAGGCTCTTGAAAAGGCTCGAGAAATACACA
CCAGGTCTCAACTAAGCCCAACAGTCAATAGGTAAGGAAATAAGTTATTTCCCCATCTGAGGTGGGGAATGTTGG
GAAGGGGGACTTCCACTCTTACCAAATTATCTGATTCTACTAAATATGACCGTTGTACTAAATAGGAAAGGGGGC
GCATCCAAGTTTCCCATTAGTCGGAATTTCCACCAGCTCAGTTCTGCTCATTAAGGGCCGAGTGACTTTGTGGGG
AACATATCTGGGTTCCAGTTTTTATTTCCACAGAGCTCAGCATAAACTATTTTTGTTTAGTACATATGGTTTATT
TGGGGACTGCTTATGGGAGTTTTGACCTGGCAATTGCAGGGGAGAAGGCATGACCCAAATTATTTCCGACTGCCT
CGCGCCAATTTGGACCGCTTAGAGGAGGCAAAAAATGGGCAAATTCCTTGGAAGCCCTGCTGTGTCTCCCTGGTA
CTGAATTTTGTAAGCACGCGATACAGGAGACATTGAAAATTAAAGAGGAAGTATCTCCCTCCTCCAACATGGGGA
GAGACGCTGTTGGAAGAAGTTTCTGAAGTGGTTTCCCATCGCACCAAGAGGCCAGTGGGATGGATCCCCGCGCAT
AATTCAAAGGAACGCGCGCGTCTTTAGCTCTTCGGGGTTGGTAACCAAGTGGTCCGGCCGGGCGCAAGTCGCCTT
GGAACCGGCTGCAGCCCAAGTCTAGCTGGGCCCGGGACTGAGCGGCACCCTTGGCCTCTCAGAACCTTTCTCGCG
GTGAGTGGAAGGGCGGCTCCGCGCGCGGGCGCTTCGGGGCCGGTCGGTTGCGAAATCAGGGGGTGGATTTTCATC
TACCCAGGAGCCGCTAAGCCCGTAGGGGACCGAGCATCACCCAGGCCCTGGGTACCCTGAGTTGCCTCCTGAGCC
CCAGGACGGTCCGATGGTGCAGAGCTCCCAGGCAGAAGTTAGTTTCCTGATACACACACAGCAGTGAGCAAAGTG
CGCACAAGTGAGCCAAACCCTGAAGACGCAGGTTCGCGGACTCCCATCCCAGCGTTAGAGTCAAGGAGACAGAAG
AGAGGAAGGAGAAGTGAGGAAGGGAGAGAGATTATGAGAAAAAGAGATTATGAAAGTAGAGAAAGAGATTATG
AGAGCGAGATTATGAGAAGAGAGAAAAAGAGAGATTTTGAGAGAGAGAGACAGAATGAGAGAGATCCAACTTTCA
GTGTCACGGGGCCTAGGCGGGGCAAGCGCCCTCCGAAGCCATCAAAGACAGGGGTGGCTTTTTCTCCCCTCCTCC
AGCCTCCTCCCCAATAGATATAGCACGAATTTTTAATGCGTCTTCCTTTCACAGACAACAATACAGGGTTTGAAA
GCCGGACACAATTTAGGTTTTGTGCGGGTCCCTCCTCGCGCTCCCTCGGCCCAGCTGGCCATATGGAATCCAGCA
TGGAGCCCGTGGATGACAAAGGGACCCAGTGACAGGCCCAACAAAACCCCAAGGAGACTTCTGCCTGACTCCGGG
ATTCACTGCCGGCGATAAGCGCGCTGAATGGTGCGGGGTGGGGCGGGGGTGGGGGGGCGGGCCCCTTCTCCTTCT
TCCCCTCTCTCTGTCCCCGCGATCCTTTCTCTGTCCCTTTTTAATATGCACGCCTCTAACATCTCCGGCTCCCAG
CTTTCCCATTGTGCGGTTTTGTACCGCCCGCTGTAGATTGGGCGAAGATAGACTGCTGAAGCGGACCCCGCGCCG
GGTGCGCTCCCAGGGCGCTGGGGTTAGGGCCACACAGGGCTCCGCAGGCGCTTTTATTGACTCCATGGGGACCCG
AGGACAGAGAGAGCGGGCGCCGGGTCCACCTCCCGGGCTCCCGGCCGGCCACAGGAGCGCACACCCAGATTGCA
GGCCCGCGGTCCTGGCCACAGCTCCAAATTTGTCCTCAATGAGCAAGTGGTGGAAGCCTGCCAGGGTGAGGACCT
TCCACGCTTCCCCCTTCCTCTCTGGAAACCTGAGGGTCTCTTGTGATCATTCTCACCCTGGAAGCCCTGGGGCCT
GGAAAAGTCAAAATGGCCTCAGGCCTTCTGACAGCTCCGCTCCAAGAGACTTGAAACCCTCACCTTTCCTCCCAA
GAGGATTTTGGGATTAGGGGAAGTTGCAAGTGGATGTTGAGTGGTTAGTACCAGGGCAGGTTGGGCGTTCAATTA
TTGCACAACAAACTATTTGGGAGAAATTCGTTGGCCTTTAAAAACAGTAAGACATAAGCCCCCAAACATTGCCAA
GCTAGTGTGGAGAACAAAGGGAGACCTTTTAGCATTTAGAAAAACTGCCCTTTCCCCGAGGATGAGCCCGGAGAT
GGGAAAGGACCTTTACTGGGGTATTAGAAAGACTTCCGAGCCCTCAATTATCCAGGGGCGGTGTGGAACGCGGGA
ATAAAGTGTCATCGCGTCCCTGGGCTGCTGCGCAGAGTGCTATCGACGCACAGATTTGGTCGCACGGATAATCAT
GTTTGCTTTAGATATTGAATTAAACCTGATCATCAACTACAGGGAGCGAGAAAGTCAGCTGGGACCGCTCCTTTT
GCCCGGCCTCCTCACTGCCACCCAACCCCCCAGCCTTGATGGTGCAGCTTCGGAGAGAACAGAGATACAATTTCC
AAATGCGCCGACGTTCAGTCCCTCAGCGTCTGCAGCACCCGCTGGGCTCTGAGCTAGAGTCCCAAGTATTTTTAG
AAACCCGCGAGATAGAGGAGAAAGGCTCATCCTCCAGTTGGCCAGGCTTCCTAAGACGCTCCCCCGCGTGGCCAA
GTGTGCGCCAGCATCTGCCAAGGAGATCTTCCTCCAGCAACAAGGGTGGGACGGAATCCGTTCCCCGCCGGAAAG
ATGGATGCGCCCTTCCCGGGCGTGCCCGGGCTGTGTGCCCACTTCCCATCCGGGGAGCTCACCCCACCCCCAAA
CCTCTACTTCCTAGCAATCCACCCAGTTCCACGCTCAAGGGCTGACTGGGGGGACCGCAGGGCGGGGGTGCGGAC
CGCCGAACGCTGGAGGGAAGGAGGCCCGGGATCCAGTCCCCGGAGAGAGGCCTGGAAGCCCGGAAAGGATGGGAG
CGTAAGGGAAGGGAGAGGCATGGTTTGCTGGGATTGCCAAAGATTCTCGCTCCCTGGCTTCCTGGGGCCAAAGAT
CCTAGGGAGGGCTGCAGTATCCCCTCCCTCCCCCGAGCCCAGAACCCCGCGTACTTCCCCCAAGCCCCCTAAGCC
AAAGCCTCGCGCGCCCTGACCGTTCCCACCCCCAGCCTTAGCGGTCTCCTAGGTCAGCACCAGCCCGCAGATTTT
GAAAAGGAGTGGGGAGTGGGGAGAAGGCAGCCAGTCTTAACCTCAGACCCCCACCCACCCACTTTCTTAGCGTGA
GGTAAGTCAAATGTAACAAAGTGAAAGTCATCGAGTGTAGTGGCTTCAACAGCTTCTCAGGCTGAAGGAGCCACT
CATAGATTTGGGCCAGCGAGGGGGGTTTGCTCTCCTCGCCTTTGCGGCTCCCGAAGTCACTTTTCCTCCCGTAGC
CGGACGCTGCCGCCCGGGGTTCAGACAGCGCGCGAGACCAGGGGAGATGCGGGGGAGGGTGGGCGGCCCTGGGCT
TCCGGCCGACCGCTCGCAGGCCGGAGGCCGGAGCGTTCTCCTCCCCGCCCCAATCCTAGGCGCGGGGTGCAGCCTG
TGGTCGGAGGGGCCTGCACCGGGAGCCCCGCCCGCCCCAGGGCCCCGGTACCCCCGGCCTCCCCGCCCGAGAGGA
ACCGCCTGTGGGAGCCCCGCGGGCGGCCGGGCCCGGCTCCCAGGCCCAGGCCTCCGGCCCGGCGCAGTAGGACAA
ACGGGAGGGCAGGGATTTTTTCTTTTTTCTTTTTTAAACACAGGATTTTTATTAAAATTCTTATTTAAAAAATC
GAAAGCTTTCTGCGCCCGGCGCTGTTGGGGAACCGCGCCGAATAGCTGAGCTCCAAGTTCGGGGCTGAAGGCCCG
GAGGACAGGGCAGAGGGCTCCCTGCCTACAGGGTTTTCTTTTCCATATTTGAGAAATGTTTGCACAATAAAATAA
AAAGAGAAAGGAAGAAACAGGGGAAAACGCAAAAACAAAAACAAAACAAAAACAAACCCAAACAAGCCACAAA
GAAAGGAGTTGGACCCAGACGGGAAACAGGCCGGTCCTGAAGGTCATTTTGGCAACAATCACCACCGATATTTAC
AACGAAAAGCGAAATCTGCCACCAGTTGTCAGAACGTTTACATGGCCATAAATATTTAGCATTTTCTTATTTTTT
TTTAAAAAAAGGAAGAAATTCTCTGTATTTTTAAAGTGTTCTCCACTTGCTTTAGAAGACGGCTGACAATATCGC
TACTCACACAAACATATTTACAAAATGCACGAAAGCAGGGGTGGGGGGTCGGTCTTTTTCTCGTTTTCAAGTGA
CGACATTAACGCTGGGACGGTTTGGTCCCCCCGGGGAGAGGCAAAGAAGCGAAGCTGCGCAAACATTCTGTAAAC
ACGGCGTAGAGTTCAGCCCTCTCCCAAGGTTCAGAAGGAGAGGCATGGGCAGAGCTGGGTGGGTGGGATCTGCCA
CTCCAAGGAGACGCAGGCAACCTCCCGGCGCCTCCCTAGTGGAGCCGAGAGTCAACTCGACTCCATAATAATAAT
TATAATAATAATAATAACCACCATAAGGACCGAGGCCTCCTCGCCGCCACCGCCGCGGGGTGGGCCTGGGCCT
GGGGCCGCGAGTCTCGTTGGGGCGGCGCTCACCAAGTCCACTGCTGGGCCTGGACCAGGGGGTGTGCTGTCGGGT
ACTGGGGGTGCTGGCCGAGCTGTACTGGGCGTTGTACTGCATGTGCTGCAGCGACTGCGCGCTGTAGGCAGAAA
AGGGAATGCCCGCCTGGAAGGTGGCGGCTGCCAGGTCCTGGGCTTTGAGCGCGTGACATGGTTTGCCGTCCCTGA
```

TABLE 7B-continued

Sequences of differentially labeled CGIs between bladder cancer subgroups relative to blood CCAAGACGGGCACGGCCACCCGGCGCGGCGAGGGCAGGGGCGTCACCTCCATACCTTTCTCGGCCCGGGCGCGCT
TCATCTTGTAGCGGTGGTTCTGGAACCAGATCTTGACCTGCGTGGGCGTGAGGCGGATGAGGCTGGCCAGGTGTT
CGCGCTCGGGCGCCGACAGGTACCGCTGCTGCCGAAAGCGCCGCTCCAGCTCGTAGGTCTGCGCCTTGGAGAAAA
GCACTCGCCGCTTTCGCTTCTTGCCGGCGTCCCCCCCGCCGCCCGGGGTCTCCTTGTCATTGTCCGGTGACTCGT
CGGCCGAGGGCTCCGGGGACTTGGAGCTTGAGTCCTGAGGGGGCGCCCCGGCAGCCAGACCGTGCACTGGGGGGA
GGGGGAGAGAGAAGCGCGTCAGGCGTCTGGAGGCCGCGCGCAGCCTGCACCAGACTCGGAGCACCCTGGATCCTC
CGTGCGACCCTGGACCTCCGCGCCTGGCAGCCCAGCCCCGCTGCCTTTGCCATGACCCCTGCCTTCCTCTACGCC
TGACGAAGACGTCGGGACCTCCCAGGGTAAAGAGGGAAATCCGTAGGAGTGGGGGCTAGGGGCTCGCCTTTCAAG
GGGCTCACATAGTGTGGGTGAGAATTTGGGGGGGGAAGTGGCACTGAAGATCATCGCGGGTTAAGGGCTCCGGCG
CCCTTAAGCGGTTTCCTCTCCGGCGAGACGTGGGCAGATTTTTAAAAGAAATACCCCACAATCCCAGCATTGATC
GGCTCGGCCATTTAAGGCAGGTTTTTGGGGGCTTTCGTTTCTGCTTTCGGGCCTTCTAGACACCCCTGCACTGC
ACAAAGCGTCCTCTATGATCGCGCAGGGGGCAGGGTGAGCTATTTATACCCGGGCCACCCGAAGCCTCCCCACCC
TCCACCCGTACCCGGACGAGGCTCGCTGGCTACCTCCAGGGCGCCAGGCCAGTCCCTCCCAGCGGCCGGAGTCCG
GGGGCTGCGGCTGGAGCCATCGGTCCGGGTTGACATCATATACCAGCCCCTGGAGGTATAGCCCTTCTCCCTCT
TTCTCCTTAACTTCTCGCATTGAAAAAAATTTTGGAGACCAAGTTCTTTCCCGGAACTAAGGAGGCTTGAAGAGG
AGGGCAGAGGACATCCTATACAGGTGTTAAAAATCTTTCTACGGATCCGAGTGAGGGGTCCGGGCTTACATGGC
CCCTTCCCCTTTCACTCCCAGCGTCCAACCCGGGCTGCGGCTGCAGGAATGGAGGGGACCACGGCCTCGGCAGCC
AAGTTTTGCTACTTACGGGAGTACTGAAGGCCTCGGTGCTGGCCAGCCAGCGCGTGTACGGGTTGTCGCTGCTG
TCGTAGAAGGGGTTCTTCAGGGGCAGGCTCTGCACCGCGTCCAGGGCGCCCTGCCCCAGCGGCCCGGCCCTCTTG
GCTGGCTCGGGCCCCTCGTTCTCTTCCTCCGGACCTTCGGCCACAGAGCCCTCCTCATCGTTGGTGTCCGGCAGG
TCTAAGATGTCCTTGACCGAAAACCCCGTCTTTGTGTTGGTCAGCGACATGGTTCGAGACCCCAAAATTTATGTC
GCAAAGTTGTAGCTTCACTTGGTCAATTCGTGGCGCTCCCCTGCCCCGGCGGGCGGGGAGGGGGAGGTTGGGGG
GAGGGACTGGGGGAGGGGAGGGGGGAATTGGCTTTAATTATTGGGATAATTATTATTTTTAAAAAGAGAAAGAAA
CTGGGGATGGGGAGGAAAAAAATGAAGCCCAACCCAGTGCCTCTCTCTGTCTTCTTTGAAAGCACGCGGAAATGG
ACGCAGGAAGCCGGGCGGCCTGCGCGCCGAGCGCCGCGGGCCCCGGCCTTAGTTTCTAACTCCAGGAGGGGTGCC
AAGGCGGCGTCAGCTCGGGCTCCGGCGGCCGCTCGGCGCGCGGTGGCGGCTGGTGGCGAGGAAAAAATGGGCCAT
TGCCCGAGCGATCAGTCCATATAAGGCTGGGCTCCACTCACGAACCTGGGGAGGCGGGGAGAGGGGGAGAAAGAG
AGGGAGGGAGGGAAAGAAAGGGGAGGGAGGGGGAGCGAGAGAGGGAGCGGGAGAAGGGTGGAAAAAAGGGGGAA
GAGACATTAAAAACGCAAAGGTTGGCCACGTGTGGGCGGGTCTTGGGAGTCAAGTGGATGAAGACAGTATTTGCA
GATGTGAAATTGTGGGTTTGGGGAGCTCCGCGCTCCCAGCCAACGGCCCTCTAGAGCAAGATGAGAGGTGTAAC
GTGTCAATTAATTGCAAAGACGGGGCGAGCCTTTTTTTTTTAAACCCAGTATTTACATACAAAGGGCCACGCG
TCGCTCGCGAGTCCACACACTTGAAAGGGCCGTTTTAACAAATTGCATCTTAAAAAAGGTGGGGGTGGGGAGGAG
GAGGGGAGAAAACAAAACAGAAACCAGGAGGAGGGAAAAAAATCCTCTTTAACATTCACCGGTTCCTACCTCCCG
CCCCCGCGCGCCCACCCCCGGCAAGCCGGAAAATTGGCGATTTGTGGCGCCTTTGGAAAAGGGGGAGGGGGCGAA
GGCCGAGCTGCGGAAATCTCTCCTTTCCATCGTTGGTGGTTGCCTAAACAAGATCCGGTTCAAATGGCAAGAGCC
CAACTTCTGTAAGCCTCCTAGGTCAATATTTTGGTTGAGGCTTAAGGATGAGTGCTAGAAATGACAAGGCAAGTA
ATTGATTCCAGTTAACCGCGAGAGAGCCCAAAACCCAGGAGAGAGCTCCGCTCCGGGCCGGCCAGAGCCACCACC
AAGCGACCCGCCCCCTTCCAGCCGCCCTTTATTTGCTAAAGACTCATTTATTTCCTTCACTCCGCCTCCCCCCAC
CTCCCACCCCCAACCCCCCGCCTCCACCTCTCTGCGGCCAAGGAGGACGCGCAGTTCACTTTCTGCTTTGCGGGC
GGTCCCGGGGAGGGCGGGGTAAGAGTGAGGAGCTCCAACTTCGTCTGGGGTCGGACCCTGGCCCTGCTGCCTCTG
GGCTCTGCGGGCCTCTTTCCCGGGTGGAGGAAAGGGCAGACGGCCCTGCTCTTTCCTGCCCTCTATTATCCCTC
CCTCTCCGGCCCCTCCCTCTCCAGCCTCTGGCTAGAGGTGGAGCAGCGGGAAGGCGGCGGGGCGGGATTGCGGG
GGTGGGGGTGGGGTTGTGTCTCCAGCCTGGGTGAAGACCCAGAAAGCTGCGGGGGAGGGGGGTCGCTGGGTGGC
CCGACGATGCCTCGTTTTCTCCCCAGTTTTCTTCTCCCACGCGAGTTCTTTAGTGTGGTCTCTTTTTGGACGCCT
TGGGTGCGTTCGGAGTACGCGCTCCACGTTTCCAGGTTAAGTCAGGTTAGTGTGAAGTTTCCAGCCACTCTCGGC
TCTGGGAACTGAACTTTCCCGGGACTTGCACTTCCTCCTCGGCGCTGGGGTTGGAAAAGACCACGCCGCATTTGC
CACCCCTTCTTCTAGTTAAAACTTTTTTGGGGGGGGGGTGCAGGGGTGTAGATTGGCTACCTGATGCTCGTTCGC
CCCAGAGGAGTGTCAGGAAGGAGCTTTGTCTGGGGGCGGGAGGGGCACAAAGGCCACCCCTGCGGGGTCCAGG
TCTAGTCTTCCCACAACCTGGGCTCCTCCGCGCGGGCCAAGCTGAGCGCGCGGGCACCGGGTCCTCCTCGCGCGC
AGCTGCAGCGGACGCCGCCGCGCCCCAGCTGCCCCGGGTTGCCAGCGCTGGGTGAGGGCACCTCTCCCCGAGCC
GCTCGGCGGCTTTCTGCAGCCCTAGCTGCCTCGCCCCCAGTATGTGACTGGGTGACAATGGCCCAGGTTAGAGC
AAGCCCCTCGTCGGCGCGTCCTGGGTGGTCGGACCCGGGCAAACACAAATACAAACCGATTGCTAAGCTGCGGAC
AATGAGCGAAATGTAGACAAATGTCCCGCTCCCGTTGGAAGCCTTTGTCCCGGCTCG (SEQ ID NO: 296)

CGI: 61 range = chr20: 23294035-23294650
CGCCACGGCGTGGCCACCGAGGTGGTGTACCGCTGCGACACCTGCGGCCAGACCTTCGCCAACCGCTGCAACCTG
AAGAGCCACCAGCGCCACGTGCACAGCAGCGAGCGCCATTTCCCATGCGAGCTGTGCGGGAAGAAGTTCAAGCGC
AAGAAGGACGTGAAGCGGCACGTGCTGCAGGTGCATGAGGGCGGCGGCGAGCGGCACCGCTGCGGCCAGTGCGGC
AAGGGCCTGAGTTCCAAGACAGCGCTGCGGCTGCACGAGCGCACACACACGGGAGACCGGCCCTACGGCTGCACC
GAGTGCGGCGCCAGGTTCTCGCAGCCGTCCGCGCTCAAGACGCACATGAGGTGCGCGGGGAGCCGTCCGGAGGGG
TCCCTGCGCACTGGAAGGGTGTGTCAAGCACTGAGGTCGTCCTGGGATTTGATGTCTCACTGCTTAATTTCTCCG
CTCCAAACCTGGGGGCTTATTTCGAGACAGCGTTTAGTTCTCTGTCAAGGTACAGGGGCTGCGAGTGATGGCTCT
GCTCCCTTGTTCTGAGACCCCTGGGGCGCCCCTGCTGGCCGGGACGTCCCTCTGGTGGGACCGCGACAGCGGCCG
CGGGCTCGCCCCACCG (SEQ ID NO: 297)

CGI: 118 range = chr20: 25011839-25013525
CGCGCTTTGAACCCAACCAGCCCTCATCGCTCGGAGCCCTGCGTCCCCCGCTTCCCAATCCCAGAACCCCGGAAG
CAGATCTCCTCAGTCCCACTCCCTGAGGGTCCTACAGTCCGAGGTCCCGCAGCGAGGGAGGAGCAAACGCCTGAG
CTCCGCGGGAACCCGGCGCGGCTGCCTGCGCGCACGCAGGGACGCGGAGCCCGAGCCTGGGCCCTGCAAAGTGGGT
CTCCCACTCGCTGCGCGTTCGAGTGGGGCCTCCGCTAAACATGCAGATTAAACAAGGGGCTTCCGATAAGGATAA
TTACAGGAGGCTGCGCATTGACTTTCCGTTACTAAAGGAAGACCCAAATCTCCCCCTTGCAAGCTGTTCCCGGGA
TTACCAAAACAATCACTTTCTTTTGAGATCATTGTCTTTTGAACCACTCCAGCTCGGGGCAGAACGCTTTAGACG
CTGGCGTTGTTTTCCGCTCCGCGAGGAATTTTCCCCAGATTTATCTCTGGGTTTAGGGAAGGCGTTGGGCATTC
GGGACTGCGTAGTCGTTTGTAAATCCGAATTTGGGGTAGCAGTTAAGTGAGATACCTACGCTTCCACACAGTTTG
TAGCCCGAGACCAGTCAGGCAGGCAGGGTAGTCGATTCTAAGGTGGCCCGACCGGGGTCGCCCGCGAATGGAAAG
CCTAAGGGGCGAGGGCGGACGCGGGCGCCGTGCCTGCAGCCCCGGGTGCCGACCAAGTGGCCTCACCTGGGACAG
GTCTTGGGGTCTCCCTCCCCTAGGTCTCCCTGGAAGGTAGGCGATCACGGGAGTGACAGACCCCGAGTAGATAGC TABLE 7B-continued Sequences of differentially labeled CGIs between bladder cancer subgroups relative to blood CAGTGATCCAAAGACACCAAAAGGCCAGGCGGTAGGAGCCCAGCCTCAGACACTCTCTATAGTGACCGCGGCGCC
TCGGGAAGGATCGTCTTAAACTCATTTTGCAGGTGAGAGCAACTGGGACTTATTAACCCAGTCACATCGGACACA
GAGACGTGGCGAGGGCGACACAGAGCAGGAGACTCAATCAAGGAGCCCGTATTGGAGCTCTAAGGGGACTCAGAG
ATGCAGAAGGAACGAACTTCTAAGGGGTCTTGCAATTCCTGGACTGGGGCGTTCCTAATGCATCCCGGGACCCCA
ATGCCAGGGAGGGGCCTGCAGGACCCCAGCGGTGGGCGAGTTGTGTCCTGGGTCACCTTGTGTTTCGCAGCGTGG
CGGTGGCAGGAGCCCAGCGCGGGAGGACATTTTCATAGCCTCCTACAGTGAGAAACGCCCCCCACCCGACGCTGC
GCTCATCTGTGTCCCCGCTGTTGCCGGGGCTCTGGTATCCACTTGCGCGCCCTATGTGGTGGGGATCCACCCAGA
GCCCAGCGTCAAGTTATACGGGCGCTTCACTCAGCGTCAGCCAAGACCAGGGAAGCGCTTCTTGCCGTTTAGGAG
ACGTCTGCAAGAGATAAAAAGCTAGCCCACGATCCACCCACAATCCTCGTGTCCCCGGGGTGCCCTCGCAGTTGC
CAAACCTACGGGCCGCGTTTAGGGGAAGCCTCCGCGTCCTGGCGGCCAAAAGAATGGGCTCCTTCCAGCTTCCCC
CTACCGGATACCACCTGCAAATCTATTGCCAGAGGCGCAGCTCCCGCGAACGTTCCCGCCCCGGGCGGCCCCCAG
GAGTCGTTTTGGGTCCCTAAATCCGTTGAGGGTTCCG (SEQ ID NO: 298)

CGI: 380 range = chr20: 36785545-36790786
CGGCCGTCGGAGCAGGGCCCCAGCGCACCGCGAGCCTCTGCTTCCTCCGCCTTGCAGCGCCGCGAGCCCTTCTTT
CCTCCGCGCCTGGCCCCGTCTGCGCCCCTCTCGGCGTGGGCATTCGCAGACCCGCTAGGAGGCTGACGAGAGGTG
TCCTCATAGAGTCCTGCCTTCTTCCAGACCCCCAAACGAAAAGAAAGAGAAAAGCCAACCTTTCGCCTCCATTCT
GCACGCATTTGGAGAGCGGCTGGTGGCGAGCGATCCGCACAATCGCTTCCCTCGCGGCGTCCCTGGACGGGCGGA
GAGAACCCGGGTGACTGAGCCTGAGGCTGAGCTTCCTTGGGAGCGATCCATGCCAGCCACTTCTACCTTCAAGGG
GGACTCGCGGCCGGGTTTACGCGCGAAGGATGGGTGCCAGGGGAAACTGACTTATAGACGACCCGCTCCGCGAGAG
ACTGACAACTCAGTCCTGCGGGCTTTCGGGGCGCCCAGACCAGTCCTTAGCCAGAGGATCTGGGGCTGCACAGCT
CCCGGACCCTGGAGGGGGTGGTCCGGGGGTGGGAGACTGCGAGCATCAGCCCACGCCGGCCCCCTCCCACCCTGC
GGCGGCGAGGTGGGAAGGGCCAGGATGCGAGCTTAGCACCCTCCCCTAGAAATGCAGCACTTCGCCCCCCCACCTC
CCCTGCCCTCGGCGCTCCCTCTTTCACGCGCTCCCTCCCGCCTCCTTCCCAAGGGCGCCCTTCTTCTGCCCCCAG
CTCACGTCTGAATCCCTCGGCGCCCCCTTTCTCTTCTCCTAGCCCCTTCCTCACGTCCCCTGCCTCCGGGTATTT
CCTCTCTCCAATCCCCCACCCCCGCACCGCCTGATTCCGAGGGGCGGGAGCGCATTGGGCTGCGCACGGGTGGGG
GCGCCGCGCCAGCTTCGCGTAGCTGCTCTGACGCCGCTGCCGCCGCCGCCGCCGCCGCCGCCTTCCGCAGCCCAG
CTCGCGCCCCGCGGCAGCTCCGCAGTGCACTAGCCACCACCGCCGCCGCCGCCGCTCCGCCAGACCTGCTGCCAG
CTTGCCCGGTCCAGCCCTGAGAGAGCCTCGAACGCCAGCTGCGAGGGTCATGAGCCAGAGAGCCCCGGGGCGCCG
CGCGGAGAGCAAGCGGAGATAGCGACTTTGCGCCCCCAGCCCTCGCCTTCTTGCATCGCGTTCCCCGCATCCTC
GGGTCCTTCTGTCCTTTCCGCTGTCCCCACCGCCGCCATGGCCACCTTGCTCCGCAGCAAGCTGTCCAACGTGGC
CACGTCCGTGTCCAACAAGTCCCAGGCCAAGATGAGCGGCATGTTCGCCAGGATGGGTTTTCAGGCGGCCACGGA
TGAGGAGGCGGTGGGCTTCGCGCATTGCGACGACCTCGACTTTGAGCACCGCCAGGGCCTGCAGATGGACATCCT
GAAAGCCGAGGGAGAGCCCTGCGGGGACGAGGGCGCTGAAGCGCCCGTCGAGGGGAGACATCCATTATCGCGAGG
CAGCGGAGCTCCTCTGCCGCCCTCCGGCTCCAAGGACCAGGTGGGAGGTGGTGGCGAATTCGGGGGCCACGACAA
GCCCAAAATCACGGCGTGGGAGGCAGGCTGGAACGTGACCAACGCCATCCAGGTAAGCGCGGGATTCCCAGTTCT
GCCTGTCCTCCCCCCTCCCAGCTCAGCGTGCCGGGCTCTGCCCCCGACAGTCGCCCGGTGATCTCGGCCTGGAGA
CCCCCTCCTGTACCCAGGAATCTCCCTTTCTCCATCCCTCCCAGCCCTGCGCGGGGACCTACGCCCCAGGCGGT
GTTTTCCGCCCTAACCCACGCTCCCTCCCAACGGCACCAGCTGCAAGACCGCTAGGCTGAAGTTCGGTCTGAGAC
ACCTGTCCGGAGACACTGCAAAAGTGAAGGAAATGGGGGGAGGGAGCAGGAAGCGATGAGAAAGAAAGAAAATCA
GGATTGGAGGGCACGGTTTGGTCTTGGACTCTGGAACGGATTCACAGCTGCATTTTTGGGAGGAAAGAAGAAGGG
GAAATCGCTGAGGTCGGAGTCTCCTCCCCCCGCACACACGCATAGACACGCACACGTATATAGGCAGGCACACCA
CATGCCCACAGCCCCCCTTCCCACGAACAAAGGCGCAGGCACAGGCGCACACGCATGTATCTATATATAGACCA
CAGTACTATCCCCAAATGCACCTGCGTACACCCCTACAGCTCCACAAACAAAAGCATATACCTGCACATACCAAA
CACACGAATATTCGTTTGAACATATGCACACACACATGCACAGATGCATGCAGACAGGAACCAGCCTGCTCCCTT
GGGTGCGGCCCTGTTGGAGACATACAGGTATACACACACGAAAGCACACACATGCTCCCACACAAACACATTTAG
TCCGCAATAATCCAGCATTACCTGTGCACAGATCGCCCCTCTCGCCCGAAATCCCGGCTGCACCGCAAAGAGGC
GGCCAGCTCCTCCCCGTGTGACCCTGGCGAAGCCCTCTCCAGAGGCTAAGAATGGCCCCTGCTCTCTAGGCCCTC
TCCCCTTATTCCTAACCCCCCACTCCCCACCAGGCGGCGCAGGACTCCTACATAGGGAGCAGGTTTGGAGTCTTG
GCAACGACCTCCGAGCTAGCAGGGGCTGGCAGGCCGCAGCTTTCTGGGCCGAAGGAGACTTCAGCTCTAGGCAAC
CCCGGTCCCTTACAGCTTGGCCCCGCGGCGTCCTGGAGCGCACTATCACTGGGGATGTTCCTCCACGGAAGGCAGGTTTTCT
GGGAGCAGAGGCCTCCCAGGGGTTGTTCCATGTATCGGGGTAAGCAGGACTTCCACCGGGCCCCGAACACCAGATG
GCCCGACCCAAGGCGCTTTCCGCTCCGGGGCCCGGCGAGACGGCCTTGCTGGATCACGGACCCGGGGCTGCTCCC
GCCTTCGCTGTGCCCCGCGACTTCCCGGGGCGTCTTTCAAGGCTCCGTTTGATAGGCCCCAAGGGAGGCCAGGGC
AGGAGGCTGGAGGCTCGTAGGCCTCCGGGACCCTGGATTTCGTTAGCTCTTAGTCCCCGTGTGGATTCTAAACCC
TACAGCCCTGTCCGCCTGACCCTGAAGCTTCTGGTTCTAGACTCTTGCTCGGTTCGGCTTTCTGGCCTCCCTGGC
GCCTTCCCGCCAAGCTCCTCCTCCTGCTTGCCTCCCCAGCCTCCACTTAGTCCCCTTCCTTAGGTCTCGCCCTCG
CCTCACTCTAACTCCAGCCTTGTCCTAAGACTCTCAATTTCCAGCCCTGCTTCCTCCTCCCCGCGCGCTGCTCCC
CAAGCGTCTTCACATTGTCTCTGTTCTTGCCTCCCAGGGGCTTTGCCCCACCTTCAGCCCCTCTCCCTCTCTACC
CTATTTCCTTTTCGCCTCACAACTGCAGCCTTTAACGTTTCCTCCTCTGGTCTGAGCCTGAGACGCCCGAGTTTT
CCTCTTTAGCTCCCGTGCCCCATTCCAGCCCCACCACAAATCCCGTGCCCACTCTTTCCACTGGCCCAGGCCCAG
CTCACTACCTTTCTTAGAGCCCCTTTCCGACTACGCTCCCTTCTGTCCCTTCTCATCTCCTCCCCCAACTCCTCA
TTCTGTTCCTGTCCCCAGAAACCATCCCGAAGTATCTCCCTTCCCTCCTGTGGCTTCTCCCTATTCTCAGCCCTC
TCCCACCCTAGCCTCTCGCTATCACCAGCCATTAGCGCACCTTTCCTTCTCAGATCCGTCCATACATCCCTCCC
TCTCCATCTCTGGCTCGACACCCGGGCTCACTATTAGTTCCCCTACATCCACCCCGCAGCCTGCTCTTAACCTCT
CCTCCCCGGCGGCTCAGACCCAATTCTCAGTGTCCTTAGCGCCCCCTTCGGGCCACAGCGTTAAGCACGCCCCC
CGGGCCCCTCATCCGTTGCCAAGTTCGCTGAGCGTCCGCGTCTGGTTGCCTCTCCGCCCCACAGGGCATGTTCGT
GCTGGGCCTACCCTACGCCATCCTGCACGGCGGCTACCTGGGGTTGTTTCTCATCATCTTCGCCGCCGTTGTGTG
CTGCTACACCGGCAAGATCCTCATCGCGTGCCTGTACGAGGAGAATGAAGACGGCGAGGTGGTGCGCGTGCGGGA
CTCGTACGTGGCCATAGCCAACGCCTGCTGCGCCCCGCGCTTCCCAACGCTGGGCGGCCGAGTGGTGAACGTAGC
GCAGATCATCGAGCTGGTGATGACGTGCATCCTGTACGTGGTGGTGAGTGGCAACCTCATGTACAACAGCTTCCC
GGGGCTGCCCGTGTCGCAGAAGTCCTGCTCCATTATCGCCACGGCCGTGCTGCTGCTAGGCTTGCGCCTTCTTAAGAA
CCTCAAGGCCGTGTCCAAGTTCAGTCTGCTGTGCACTCTGGCCCACTTCGTCATCAATATCCTGGTCATAGCCTA
CTGTCTATCGCGGGCGCGCGACTGGGCCTGGGAGAAGGTCAAGTTCTACATCGACGTCAAGAAGTTCCCCATCTC
CATTGGCATCATCGTGTTCAGCTACACGTCTCAGATCTTCCTGCCTTCGCTGGAGGGCAATATGCAGCAGCCCAG
CGAGTTCCACTGCATGATGAACTGGACGCACACATCGCAGCCTGCGTGCTCAAGGGCCTCTTCGCGCTCGTCGCCTA
CCTCACCTGGGCCGACGAGACCAAGGAGGTCATCACGGATAACCTGCCCGGCTCCATCCGCGCCGTGGTCAACAT TABLE 7B-continued Sequences of differentially labeled CGIs between bladder cancer subgroups relative to blood CTTTCTGGTGGCCAAGGCGCTGTTGTCCTATCCTCTGCCATTCTTTGCCGCTGTCGAGGTGCTGGAGAAGTCGCT
CTTCCAGGAAGGCAGCCGCGCCTTTTTCCCGGCCTGCTACAGCGGCGACGGGCGCCTGAAGTCCTGGGGGCTGAC
GCTGCGCTGCGCGCTCGTCGTCTTCACGCTGCTCATGGCCATTTATGTGCCGCACTTCGCGCTGCTCATGGGCCT
CACCGGCAGCCTCACGGGCGCCGGCCTCTGTTTCTTGCTGCCCAGCCTCTTTCACCTGCGCCTGCTCTGGCGCAA
GCTGCTGTGGCACCAAGTCTTCTTCGACGTCGCCATCTTCGTCATCGGCGGCATCTGCAGCGTGTCCGGCTTCGT
GCACTCCCTCGAGGGCCTCATCGAAGCCTACCGAACCAACGCGGAGGACTAGGGCGCAAGGGCGAGCCCCCGCCG
CGCTTCTGCGCTCTCTCCCTTCTCCCCTCACCCCGCCCCCACCAGCCCAGTGCGCCCTGCCGCCGCG
(SEQ ID NO: 299)

CGI: 315 range = chr20: 38749965-38753401
CGCTGGTGGAGCCCGCCTCCCTGAAGCCGGAGTTGGCGAGTTTCTCGCACTTGACCTTGTAGGCGTCTCTCTCGC
GGGCCAGCCGGGACACCTCCTGCTTAAGCTGCTCCACCTGCTGAATGAGCTGCGTCTTCTCATTCTCCAGGTGGT
GCTTCTGCTGGACGCGTTTATACCTGCAAGACTGGGCGTAGCCCCGGTTCTTCAGGGTCCGCGCTTCTGCTTCA
GGCGGATCACCTCGTCCTTGGTGAAGCCCCGCAGGTGGCGGTTCAGCTCGCTGCGCACGGACATGGACACGAGCTGGT
CGTCGGAGAAGCGGTCCTCCACGCTGCCGTTGCCGCCCGCCGCCGTCGCCGAGGCCGTCGCGTGCGGCCCGGGCC
CGGGGTGGCTAGTGGGCAGCTGTTGCGCGGGCTAGCGGCGCTGGACGGCGGCGGCGACGCTTGGTGATGATGGT
GATGGTGCGGGTGAGCGTGCGGGCCCAGCTCGTCGTGGGCCACGCCGGCGCCCGGGTACGCGTGGTGCGGGTGAG
GGTGGTGGTGATGGTGGTGGTGAGCGCCGCGAAAGCTGTCGAAGCTTTGCAGCGGCTGTGGCACTGGGTGCG
AGCCGATGAGCGCTTCCACCGCGTCCTCGGGCGTCAGGTTGAGCGCCTCGGGGTTCATCTGCTGGTAGTTGCTCG
CCATCCAGTACAGATCCTCGAGGTGTGTCTTCTGTTCGGTCGGGCTGAAGCTGGGCGACGAGGGCACGGAGCTAC
ACGGAGTGCTGAGCGGTGTGGAGGACACCGAGCCGGCTGGCTGCAGGCGTGTGCAGGGCCTGCCCGGACGCTCCG
CGCGCCCCAGTGGCTCCTTCTTCACGTCGAACTTGAGCAGGTCGAAGTCGTTGACATACTCCATGGCCAGCGGGC
TGGTGGGCAGCTCTGGCCCCATGCTCAGCTCCGCGGCCATCGCTGAAGCGAGGCGCAGCCGCGCTGCCGCCCGG
GAAACTTTGCGGCCGGCCGGAGCGCGCCGAGCCAAGCGCGGGGGGGAAGAGCGGAGAAGAGCTGGGGAGGCGGGG
AGCGAGGGCGCAGCGGGCCGGGGCCGCCGGCCAAGCCTTTGTCTGGGGACGCGGCGGCGCGCCGGAGAGTCCCGA
GGCTGCCTGCACCGCCCCAGAGTCTGGGCTGTGCCCGCGCAGGGACCGGGCCGGGCGGGTAGAGTCGGGCGGGGTGGA
GAGGCAAGCGGAGCGCGCGGTGGGGCTGAGGGGAGGCGTGGGGCGAGTGCCCGTTGCTCGCTCTCTAGCTCTCTT
GCTCTTACGCTCTCTCGCTCGCAGCCGCTCGCAGCTCGGCGGTGCAGCTGTGCTGGATCCGGCGGCGCCGCAGCC
TTTTATCGCCTCCTGATGTCACTGGGGTGCGGGGGCCCGGGCGGCCCGGTGCGCGGGCCAATAGCTGCACGGCCT
CCGCGGCCCAGCGGCGCAGGGCGGGGCGCGCCTGACAGCTCCCCCGCCCCCGCGTCAGCTGACTGGCGGCCCGA
GCGGCCCCGGAGCGGCGGAGGCCTGGCGGAGCGCTGGAGCGGAGTGGGACGGCCAGCCTGGGCCCACCCCCGTAC
CCTGCAGGTCCCGGCCCACGCACGCTCGCCTGGAGTGCGCGCCCCACCTCTAGGCCAAATCACCGCTTTCCCCTC
CTCGCGCACTCTCCTCCCTCAGTTCCCTTTGCACCCCACCCCCATCCCGTGTCACCCCAAGGAGGCTCAGAATG
AGCGCCGGGACAACGCCTCCTGGGCCCTTTGTTCCCAAGCGGCCCCCGCCCAGTGGGCGACGCTCTGTGTGTCCT
CGCGGCTTCTGGCCGTGTGTGTCGTGCGTTCCTGTTTCTGGAGATCTGCGCGTATTTGTATGTTGGGGAGGGCGG
GCTCGAGGCTCCGAGAGTTGTGTTCAGACCCAACTCTTAACCTCAGGGGACCTTTCTCAGGCCAAGCGAGGGCCC
CTCCTGGCGGGTGCAGTCGCAGAGCCCTGAGGTTCGACTCCACTGGCCCCGCCGCTCCCCGCGTTCACCCCACCG
CACAATGTTCACAGTGAAGGCGACGGGAAAAGCAGCAGCCCAAAGGCTCTGAATTCCTCTTCCCCGCCACACGCA
CGGAATCCTGAGCCCCCGGAGCCTCGGGGCCGAGGCCGGCCCGGGCACTGGGTGAGTGAGTCCCGGCCGCTGT
GGAGCCGGCCCTGTTTTTGTTTGAACGTTTTGTAACGATTAAGCAGATCCCGGCGTCAGCCGCCGCGGAGAGGC
TCAAACAGGCATAAAGTGCGACCCCAAGTGGCCACTGTGCGCAAAGGCGCCGCGACCGCCCGGCCCACGGCCGGA
AGGCTTGGACGGCGCCTCGTACCCAGCCAGGTCTCCCCTACCTGGCCCAACCCAAGCCAGCCCAGAACGCATACT
ATGTGTGCACCAGAGCCCAGGACAGGTTCCCCTCGAGCGATGTACAGGTCCTCGGGTCCCGTCTTCGTACTCAGC
CGCGAGCCTCGAGCCGCGAGCTCCGCTCTGGTCGCCCCGTTGAAATTCCGTGCCCCAGCGTTCGGGGGTGCCCGT
CGGCTGCTCCCTGGGCCGGAAGGTCCTGGGCGGAGGAAGGCCGGTAGCCAAAAGTGGAAGCGCCACAGTGAAGCG
GCCCAGGGCCACCGGGTGAGAAACCTCCCCGGAGGGCAGACGGGGAGACCGAAGCACACCGCACTAGGCATCCAG
ACTGGGCTTGGGAGCCGCGCACCCTCCCTACCCAGATCCAGGATGGCTAGAATTAACGGGTTCTTTCTGAGACCT
CGGCTCAGGCGCCGAAACCGGATAGATCGCGAATTCGCTGGACCCGGAGACCCGACCCGCCTCCCGCGTCACCTT
CTTCTTTCTAGCTTTGGGCGCGCGCAGCGAAAGGCAGGAGAGGCGCCACTGGGTGAGTGAGTCCCGGCCGCTGT
CTGCGCTGGACCAGCCCGACTGACCTCGCGCGTAGGGGTCGCGTGAGCCACACCGGTGCAGACGCGCCTAGATTA
TTTTTAAATGTTAGAAGGTAAAATATTTGCCTCCAATTAATCTGAAAACTCTCTATTCTCTTGCGCCCTCGGAGA
GGCTGGGGTACGGCGTGGTATTGGGCGCCTATTTTTAATAAAATGAGTGTATTTTAACTAAAACTTAACTCAAT
CTTGTGGGGTGGCAAATTAAATGCTGGAAGAGCGCGTCTACAACCCTCTTCGAGAAGCGTGCTCTCCGCAGAAAT
GAGTCGGCCGCTGGAGAGAGAGCCTGGGCGGTGCCGCTGCGCAGCCCCTGCCAGTAGCTGGGGGTTGGGGACTC
GCACCTTGTAAATGTCCTCGTCTTGTTTGAACGCAGTGAGAGCACACTCGTTTCCAGATCACTCGGGACCGGGTG
TCTCGGATCTGTGCAGACTATGTATGGCTCCGGCCTCAGGCGGCCAGGGCGGGACAAGCACG
(SEQ ID NO: 300)

CGI: 43 range = chr20: 49542203-49542863
CGCTGGCACCACCGAGCCCCGCCGCACCCCGCCGCTATTCTCAGGACGACCTGGGCAGCCCCCAGCTTCTAGAA
AAGACACAGAGGAGACTGCGCAATCAACAGGCAGGAGTGTGCGTGAGTGCGGCATGACATGGGCACGCCACCCCA
GAGAAGTGGGCGCCTGCTGCGCTAAACGTCATCCGTCATCCTTTCGCTGAAAAGTTGGAAAACAAACAACAAAAA
CCCCGCCCAGCCTCATTTAATGCGAACCAAACACAAAAGCCACAGGGGAAAGCTTTTCCTCTCTGTGCTTCCCTT
TTCCGGCCGAGGAACACCACCAGCCAAGATAAGGGGACTGTGCGGGGCCCTCTGCGCGGCTTCAAAGGGCTGGCA
CCCGCCCGGGCCCGCTCCCACTCCCACTGGCTAATGGGCTCCCCGCTCCAGCCCTTGGGGAGCAGGAGGCGGCCG
GGGCTCCATGCCAGGCGACTTGGAAGAGGTTTAAGGCTCACGCACCAAGGGAGGAAGCTCGGCCTGTCAAGAG
GCGTGATAAAGCAGCCCCTTATCGCAGTTTTCCTTTCAACTGCCTCCAAGTGAGCGCCGGCCGGGCTGGGCCTG
TCAAGGCCAAGCGTGTTCCTTTCATGTCGCCCTGGGTTCCTCGGTCAGCGACGTATCCACG
(SEQ ID NO: 301)

CGI: 20 range = chr20: 54411932-54412178
CGCGGGTTTAAGTGGACGCCAGGTGCACCGGACACAGGCTGTGTTTAACCACACCGGAGGACTATGTGTTGCTGCC
CGACGAGAGGACGATCAGTCTTTGCTGCTGGGACTCGAGGACAGCCGAGCGGAGAAACCTGCTGTCGTTGGGGCA
CAACAATATTGTACGCTGCATAGTGCACTCCCCCACCAACCCCGGGTTCATGACGTGCAGCGATGACTTCAGAGC
GCGGTTTTGGTACCGGAGATCG (SEQ ID NO: 302)

TABLE 7B-continued

Sequences of differentially labeled CGIs between bladder cancer subgroups relative to blood CGI: 30 range = chr20: 55680656-55681057
CGCACGCGCACGTGTGTGCCTGCATGCACTCACATGTGTGTTTCCAACCGGCCGACAGTGACGCACGTATGCCCT
CGCCACTCGGCAAGCACCTCGTGCTCCTTGGTAACCAGCAGATGTTTCTCTCAATTACTGATTTTCAAGAGCCTG
GTGTTTCCTGACATGAGCCAGGATGGCGGGCGGCGCCCAGGGGAGGGGAAGTGAACCGGGGCTCCGTTTCCAAGG
CTCTTGGACAAAAAGCGAAGCCCTGGATCAGGAAGCACAATGCGGCTGGTATTTAGCCGCTTCTCAATAGTGCCT
CATTCAATCCCCGGGGCCTCATTGATGCCCGCCGCGTGCTGGAGAGCCTCTGAGGGTCAGTCGGCGACGGGCACC
GTCTGGAGGGGTCTCGCCGCTAACCCG (SEQ ID NO: 303)

CGI: 26 range = chr20: 56860125-56860442
CGCAGCATGGTAGCGGGAGCGCAGCTGCGCGGGCAACCGCCGGGTTTGTGGCCGGTTGGCGGGCTCAGTGCCGCC
TCAGTGGGCTCTAGCAGTAGAAAAGTAAAGCGACTACCCTAAGATACCCAGAGCGAGAGGAGAGGGGCTAGAAGG
GTGCTGGAGGCAGGCTGTAGTGGGGCTAAAGGAGCTGACTGACCAGCGCTGCGGCCGGTGCCCGAAGCAGCGAGC
AGCGCACCTCAGCTCCGGTTGCCGCGCGGCATGGTATTTATCTGTGGGTTCAGTGCGCACAGCGTTGTCCAGTCT
CGAAACCACCCTAAACCG (SEQ ID NO: 304)

CGI: 18 range = chr20: 62371744-62371958
CGTGAGTGAGGGCGTGCACGGTGTGGGGTCCTGTGAGTGCGGGTGTGCACGGTGTGGGGTCGTAAGTTCAGGCGT
GCACGGTATGGGGTTGTGTGAGTGCATGGCGTGGGGTCTTGTGAGTGCGGGCGTGCACGGTGTGGGGTCTTGAGT
TCAGGCGTGCACGGTATGGGGTCGTGTGAGTGCATGGTGTGGGGTCGTCAGTGCGGGCATGCACG
(SEQ ID NO: 305)

CGI: 22 range = chr21: 45511336-45511549
CGCAGGGCCCACGCTCCCGGCCTCTGGGACGCTCACGGCAGCCCCACGAGAATGATCACACGAGGGCCCACGCTC
CCGGCCTCGGGGACGCTCACGGCAGCCCCACAAGAACGATCACACGAGGGCCCATGCTCCCAGCCTTGGGGACGC
TCATGGCAGCCCCACGAGAATGATCACACGAGGGCCCACGCTCCCGGCCTCGGGGACGCTCACG
(SEQ ID NO: 306)

CGI: 24 range = chr21: 46892946-46893236
CGCGGCCTAGAGCGGTGAGTGGGGTCTCGAGCGCATCCCGGGTGTTTGTGCCGAGGCTGGTGACGTCCGAGGTGG
CCTCTGAGTGTGCTGACTTGTGACCCTGAGCTGTTGGGGGCTCACCGGTGACTCCATGGTCTTGTTGAGCACCCT
GCACGTGGGGCTCAGGGTCGGTAAAATAGCAGTGCGTGGAGACCGCGTGCTAGAGGCCGTGGCGCCCGCGTACAA
TGAGTCGCAGACAGCACAGACGGGAGTAGGGCAGAATAGACAATATCCCGTGAATTGCGTGGGGCG
(SEQ ID NO: 307)

CGI: 38 range = chr22: 18453364-18453931
CGCCAGCGCACAGCGCGGCAGGACGCGCCCGGGTCTCAGCGGACTTGTGCATGTTAGCTGTGTAGATTTATGTGA
GGGCTTGTAAAACTCTGGTCTTGTAAACTAGTCTTAAGCGCTTTTAATATGGAGACAGATGAGAGCCCCTCTCCG
CTCCCGTGTGGGCCCGCAGGAGAAGCGGTGATGGAGAGCCGAGCTCGCCCCTTCCAAGCGCTGCCCCGTGAGCAG
TCTCCACCACCTCCCCTGCAAACGTCCAGTGGTGCAGAGGTAATGGACGTTGGCTCTGGTGGTGATGGACAGTCC
GAACTCCCTGCTGAAGGACCCCTTCAACTTCTACGGAGCTTCTCTTCTCTCCAAAGGATCCTTCTCTAAGGGCCGC
CTCCTCATAGACCCGAACTGTAGTGGCCACAGCCCGCGCACCGCCCGGCACGCACCTGCGGTCCGGAAGTTCTCC
CCTGACCTTAAGTTGCTTAAGGATGTAAAGATTAGCGTGAGCTTTACCGAGAGCTGCAGGAGTAAGGACAGGAAG
GTGCTGTACACAGGAGCAGAGCGCGACGTGCGGGCGGAGTGCG (SEQ ID NO: 308)

TABLE 8

PcG target genes methylated in all bladder tumors or specific subgroups.

| All | NMI-wt only | NMI-mt only | MI only | NMI-mt and NMI-wt | MI and NMI-wt | MI and NMI-mt |
|---|---|---|---|---|---|---|
| DLX5 | ADCYAP1 | BARHL2 | TBX3 | CNTNAP1 | EVX1 | HOXA5 |
| DLX6 | ATOH1 | BCL11B | | EBF1 | GATA2 | |
| FOXD2 | BHLHB5 | | | FOXA1 | HOXB5 | |
| GAD1 | C20orf103 | | | FOXD3 | MSC | |
| HLX1 | CACNA2D4 | | | HHEX | NKX2-8 | |
| HOXA7 | CBLN1 | | | HOXC4 | SIM2 | |
| HOXA9 | CBLN4 | | | HOXD3 | VAX2 | |
| IRX3 | CDKN2A | | | MAFB | | |
| MAB21L1 | COL12A1 | | | ONECUT2 | | |
| MEIS1 | COL27A1 | | | OSR1 | | |
| MSX1 | CYP26B1 | | | PCDH17 | | |
| MSX2 | DMRT3 | | | PCDH7 | | |
| NR2F2 | DPP10 | | | PITX2 | | |
| NXPH1 | ELAVL2 | | | SIM1 | | |
| OTX1 | EMX1 | | | SIX1 | | |
| PAX9 | EN1 | | | SOX7 | | |
| PITX1 | FBN2 | | | UNG2 | | |
| PRKCZ | FEZF1 | | | ZIC1 | | |
| SHH | FLJ46347 | | | ZNF503 | | |
| SIX3 | FOXA2 | | | | | |
| SOX21 | FOXB1 | | | | | |
| TFAP2A | FOXF1 | | | | | |
| | FOXG1B | | | | | |

TABLE 8-continued

PcG target genes methylated in all bladder tumors or specific subgroups.

| All | NMI-wt only | NMI-mt only | MI only | NMI-mt and NMI-wt | MI and NMI-wt | MI and NMI-mt |
|---|---|---|---|---|---|---|
| GATA4 | | | | | | |
| GNAS | | | | | | |
| GRID1 | | | | | | |
| GZF1 | | | | | | |
| HAND2 | | | | | | |
| HEY2 | | | | | | |
| HMX2 | | | | | | |
| HOXA11 | | | | | | |
| IRX1 | | | | | | |
| IRX5 | | | | | | |
| ISL2 | | | | | | |
| ISLR2 | | | | | | |
| KCNK9 | | | | | | |
| LBX1 | | | | | | |
| LBXCOR1 | | | | | | |
| LHX4 | | | | | | |
| LHX9 | | | | | | |
| LMX1A | | | | | | |
| LRAT | | | | | | |
| MAP1D | | | | | | |
| NFIX | | | | | | |
| NKX2-2 | | | | | | |
| NKX2-3 | | | | | | |
| NKX6-1 | | | | | | |
| NPAS3 | | | | | | |
| NR2E1 | | | | | | |
| NR3C2 | | | | | | |
| NR4A3 | | | | | | |
| NRN1 | | | | | | |
| OLIG2 | | | | | | |
| ONECUT1 | | | | | | |
| OTX2 | | | | | | |
| PAX5 | | | | | | |
| PAX6 | | | | | | |
| PCDH1 | | | | | | |
| PCDH10 | | | | | | |
| PHLDB1 | | | | | | |
| PTGER3 | | | | | | |
| SEMA6A | | | | | | |
| SFMBT2 | | | | | | |
| SIX2 | | | | | | |
| SIX6 | | | | | | |
| SLC32A1 | | | | | | |
| SNRPF | | | | | | |
| SORCS3 | | | | | | |
| SOX17 | | | | | | |
| SOX9 | | | | | | |
| T | | | | | | |
| TBX15 | | | | | | |
| TBX20 | | | | | | |
| TBX5 | | | | | | |
| TFAP2B | | | | | | |
| TRIM2 | | | | | | |
| TRIM36 | | | | | | |
| TWIST1 | | | | | | |
| VIPR2 | | | | | | |
| VSX1 | | | | | | |
| ZIC4 | | | | | | |

TABLE 8 Continued

TABLE 9

CpG islands (CGIs) methylated in blood but not in bladder cancer. Provided for each are: ID no.; Coordinates of selected regions containing relevant CpG islands based on Homo sapiens full genome as provided by UCSC (hg18, Mar. 2006); GeneName; Location of the probe used; the Fold Change; and the sequence of the CGIs.

| No | CGI | Gene Name | CGI probe location | FC |
|---|---|---|---|---|
| 1 | chr19: 53930240-53930625 | RASIP1 | chr19: 053930330-053930374 | 2.66 |
| 2 | chr7: 72883371-72883981 | CLDN4 | chr7: 072883457-072883501 | 2.64 |

TABLE 9-continued

CpG islands (CGIs) methylated in blood but not in bladder cancer. Provided for each are: ID no.; Coordinates of selected regions containing relevant CpG islands based on Homo sapiens full genome as provided by UCSC (hg18, Mar. 2006); GeneName; Location of the probe used; the Fold Change; and the sequence of the CGIs.

| No CGI | | Gene Name | CGI probe location | FC |
|---|---|---|---|---|
| 3 | chr22: 26522794-26528592 | MN1 | chr22: 026525238-026525282 | 2.21 |
| 4 | chr7: 5614184-5614510 | FSCN1 | chr7: 005614143-005614190 | 2.15 |
| 5 | chr16: 66239477-66241425 | RLTPR | chr16: 066241103-066241147 | 1.93 |
| 6 | chr5: 551112-551430 | SLC9A3 | chr5: 000551380-000551424 | 1.86 |
| 7 | chr19: 6426223-6426998 | DENND1C | chr19: 006427051-006427102 | 1.82 |
| 8 | chr3: 32836146-32836433 | TRIM71 | chr3: 032836466-032836511 | 1.78 |
| 9 | chrX: 129301145-129301626 | SLC25A14 | chrX: 129301313-129301357 | 1.76 |
| 10 | chr9: 124027565-124030907 | LHX6 | chr9: 124029663-124029718 | 1.74 |
| 11 | chr10: 129424401-129427356 | FLJ46831 | chr10: 129426989-129427033 | 1.71 |
| 12 | chr1: 3147370-3148160 | PRDM16 | chr1: 003147944-003147988 | 1.65 |
| 13 | chrX: 128941527-128945710 | BCORL1 | chrX: 128944842-128944886 | 1.64 |
| 14 | chr17: 7584523-7585036 | DNAH2 | chr17: 007584859-007584908 | 1.63 |
| 15 | chr1: 27548507-27550603 | SYTL1 | chr1: 027550188-027550232 | 1.6 |
| 16 | chr19: 10304689-10307022 | ICAM3 | chr19: 010306004-010306051 | 1.56 |
| 17 | chrX: 129132628-129134108 | AIFM1-RAB33A | chrX: 129133196-129133244 | 1.55 |
| 18 | chr21: 45648960-45650662 | COL18A1 | chr21: 045663489-045663539 | 1.53 |
| 19 | chr10: 134864694-134865392 | KNDC1 | chr10: 134865054-134865098 | 1.48 |
| 20 | chr9: 129556229-129557670 | SH2D3C | chr9: 129556146-129556190 | 1.48 |
| 21 | chrX: 47305347-47306043 | ARAF | chrX: 047305953-047305997 | 1.45 |

Sequence of the CGIs of
1 chr19: 53930240-53930625
CGTGCGGGGCTGGGGCGGCGGTTACCTGGGCGTCCTGGTAGCCCTGGAGCAGCAGGAAGTAGGGGCGGTTGCTGGG
GGCCTGGATGAGGCACTGAGTCAACTGATCGAAGTCCCCGGGGTCTGCAGTTCCGATTTGGGCGTCGGCTGCCCCTG
GGGCCATGCTAAGTGCCTGCTGTCTCCGCTCCTGCTGCCGCCGCCGCCGCCCCTGAAGGCTAAGCTCCGACACGCTG
CGCCGCAAAGACAAGTTTTCTGAGCGCTCCTTGCCTCCAGACCCAGCTGGGGCCCCTGATCCGGTCCCCGGGCCAGG
ACTGGCCAGCGCTGCCCCACCCGACGCCGCCCGGGAGCGGTTCTTCTGTGGCCGCCACGAAGGGGCGCCGGTGCCT
GCG (SEQ ID NO: 309)

2 chr7: 72883371-72883981
CGAACGTTAAGTCCGTCCCCAGCGCTTGGAATCCTACGGCCCCCACAGCCGGATCCCCTCAGCCTTCCAGGTCCTCA
ACTCCCGTGGACGCTGAACAATGGCCTCCATGGGGCTACAGGTAATGGGCATCGCGCTGGCCGTCCTGGGCTGGCTG
GCCGTCATGCTGTGCTGCGCGCTGCCCATGTGGCGCGTGACGGCCTTCATCGGCAGCAACATTGTCACCTCGCAGAC
CATCTGGGAGGGCCTATGGATGAACTGCGTGGTGCAGAGCACCGGCCAGATGCAGTGCAAGGTGTACGACTCGCTGC
TGGCACTGCCCGCAGGACCTGCAGGCGGCCCGCGCCCTCGTCATCATCAGCATCATCGTGGCTGCTCTGGGCGTGCTG
CTGTCCGTGGTGGGGGGGCAAGTGTACCAACTGCCTGGAGGATGAAAGCGCCAAGGCCAAGACCATGATCGTGGCGG
GCGTGGTGTTCCTGTTGGCCGGCCTTATGGTGATAGTGCCGGTGCCTGGACGGCCCACAACATCATCCAAGACTTC
TACAATCCGCTGGTGGCCTCCGGGCAGAAGCGGGAGATGGGTGCCTCGCTCTACGTCGGCTGGGCCGCCTCCG
(SEQ ID NO: 310)

3 chr22: 26522794-26528592
CGCCAACGTCTTGTCGTCGTCCGCGCTGTCCACCAGGGCCTTGTCAGCGGGCATGTACCAGGCAGCGCTGTGCTCTG
CCATCAGCGAGTCCAGGTCAATGGTGCTCATGGCGCTCTTGACCGCCTCGGAGCAGCAGCTGCCCAGCTCGCTGTCG
CCATTCTGCGCCCCTGAGGCCCCGACGGCGCACTCACCCTTCTTGCCACCCTTCAGCCCCAGAGGCTGGTCCTCGGA
GATGCTGAACTGCTGCCTCTGTAGCTGGATCTGCGCCTGAAGGATCTCCAGGGGGTGGATCTCGTCGGGTGGCGGGG
CGCCGCTGCTGCTCGTCGGGGTGCGGACCTGCTCCAGGCCCGGAGTGCCCGGATGGCCCGGGCCCCACCGCCGCC
GTAGCTGTCAGGGGTCGAGGTAGAGTTAGACATGATGCCCAGGCCGAGGGCGGCGGGGGCGCCTTCGGTCCGTGT
TCCCCGGCGCCTACCCCACGGGGAGGGAGTTTGGGCGAGCCGGTCACCAGGGGACTCCTGCTCGCTTTAACTAGTGC
CTGGGGGTTGTCAGAGCTGGACGACACCTCGTCCTCATTGGCGTAGCTCGTGCTCACCTCGTCCGAGGCGAACTCAC
CCACGTTTGGCGAACTACTGTCCGACTTGGCCCCGCCGTCCAGGGACCCAATGAGGTCCGGCTGATCCCCCAGGAGC
AACTCAGCCCCCTTCCCCCAGGATGGCGACGTGAGCGCCTTTTCGTGGGGCGTCGGTGCCCCGCGCGTCTCGCCTGC
GGAGCTTCCCCCGACGGCTGCGCCTGACGCTTGCTGCTGCCCTGGGCTCACCCCAGGTGCGCCCCCGCTGTCCGGAG

TABLE 9-continued

CpG islands (CGIs) methylated in blood but not in bladder cancer. Provided for each are: ID no.; Coordinates of selected regions containing relevant CpG islands based on Homo sapiens full genome as provided by UCSC (hg18, Mar. 2006); GeneName; Location of the probe used; the Fold Change; and the sequence of the CGIs.

| No CGI | Gene Name | CGI probe location | FC |
|---|---|---|---|

CCGCCGAGTACTTGTCAAAGAAGGTGCCAGGGCTCACGTGACCACTGTCCCTTTTTCTGCGACCCCGTCCCCGGCCG
CCGCCCCCGGAGACCGGCTTGCCGTCATTCCCCGACGTGGATTCCAGGGTGTAGTTGGGGGAGAGGCTGGTGCCGTC
CCCCTGGGCTGGAGGGTTGGGCGGCCCCGAGGCTTTGGAGCCGCTGCTACTGGTCCCGGACGGGCCTCCGGGTCCT
GGGGCCCCAGGAGCAGTCCCTCCTGGGAAGTAATCCGAGCCCGGGTTGCCGGCCACTGCCGCGCCGTCGGTCTCGTT
CTGGCTCAGTTTCCTCTTGCCCTCTGGCGGGTTCTTCTTGTTGAAGGTCACGTTGAGGTTGGGGGCCCCGAGGCTGG
CGATCATGTTCTGGCAAGCGGTGGAGAGCGCAGCCAGGCAGCTCTGGCCGAACAGGTTGTCCTTGGAGCTGGGCTTG
TTGAAGGAGCCCAGCGAGAGCGCGCCCAATTTACTGGCCGAGGTGCGCTGGCTGGGCTGGAAATCAGGCTGCGGCG
GGTAGGCACCCCCGCCACCGCCGCCACCAGAGCTGCCACCGCCCCCTCCCGCGCTGGGGGGCGAGTTCACGCCTGG
ACCGCTGTCGGCGTGGACTGCCGGCCGGCTGCACCAAACGGAAAGCCCGGCTGGCCCCGAGCGCAGACGTAGCA
AAGTCCGGCGGCGGGGCCGGCGCTCCGAAGCAGCGCTGGGGAGCCCCACGCCCGCCCCGGGCGACTGCAGCTGAC
CCAGGCCTCCCAGACTGCCCCCGAACTGCAGGCCCGGTGAAGGCAGCGCGGGCACGTGGCCCTCTCCGGGCATCCT
CATCGGCTCCTGCAGAGGGCCCCGGAACAGCACCCCCGAGCCACCAGGCGGAGGAGGGGGCGCCAGGCTGGGGTCG
TGCCGGGCCACAGTCAGCGGGCAGACCCGAGCCGCCCATCCTACGGGGCAGCAGGTCTCCGGGCGGCGGATGCGGAC
CTGAGAACCACGCGCTCTCTTGCGCCAAGTGCGGCGCCTGCTGCTCGAAGGTGCCCAGACGCCCGGCGCCCGTGCTG
CCGCCTTCGCGCTCAAAGTTCGGCTGGGCCAAGCCGCCCACCGGGCCGCCATGCACCAGGCCGCCCTGGCCCACGTC
CCCGGGGTGGCCTAGCTGAGCCAGGTTGGGCTGGCGCAGCCGCTGCTGCTGATTCCGCGACGCCATCTGCTTAATCA
TGAGGGCCGCGTTTTGGCGCTGCTGCTGCTGCTGCTGTTGCTGTTGCTGTTGCTGCTGCTGCTGCTGCTGTTGCTGCT
GCTGCTGCTGCTGCTGCTGCTGTTGCAGGGACTGGTGGTCCGGGGCCGGATGCTGCAGGGGCGGCCCCGAAGGGAA
GCTGTCGGGCACAGGCGGTGTGAACTCGCCGGGTAGGCCTGGGTAGGCGGAAGGGGAGAGGTGATTATCCAGAGCG
CCGTTGTGCATGCTGCCGTTCCACGAAGCGCAGCGGTCCACTCCCGCGCTGCCCGGAAAGTCGAAGCGCGGCCTCTT
GGCCACGTTCATGTAGGGGGGCGCGTCGAAATGCTGCAGCCGCTGGTTGGGCGCCTGCTGCGGAGGAGGATGCTGC
ATGCTGAAAACAGGCTCGGAATAAGGGTGCATGCTCCGGTTCTCCAGCCGGTGGATGGGATACTCGAATTGCGCGTG
CTGGCTGGGCAGCATGGGGCCTCCGTCCTGCAGGCCGCCGCTGGGCGTGCCCGCCTCGCCCTGCTGGGGCCGAGGG
AGCGCAGGCGGGCACGAATTTTGTCGGACTAGAAGCCCGGGTGGCGGCGGCGGCTGCTGCTGTGGCGGCTGCTGCG
GGGGCTGCTGCTGAGGGGGTGGCGGGGCCTGCTGGGGAGGCTGCATTAACGGGTGCCTGGAGCCCACTGAGGGCTC
CAGACCCACAGGCATCTTTCTGGCCCCACTGAACCTCTCAAAGAACACACCATGCTGCTGCTGCTGCTGGGGCT
GCTGCTGCTGCTGGGGCTGCTGCTGCGGTGGCTGGGCGTGCATTTTGGACAAGCCCACCATGCCCGCAGCTCTGGGC
ATGGCCGAGGCGCCCGGGAAAGCGCCCCAGGAACCTGGCGACCCGCTGCATAATGAGGCAGCTGCCCTTCGGAGT
CAGAGGGCGAAAACATGTCAAAATGTCCCGAGGGCGCCTCGCCCGGGTAATTGTATTCCAGCGAGTCGACGGCTCCT
TGGTTCGTCACCCTCCGTGGCTCCAGACTGTGGGAATCGGAGCCGCTGGAGGACGGCAGGCCGTGGAAGGAGGCGG
CTCGGTTAGGGCTCTGGTCCAGCGGCAGGCATGGGGCCGGCACGGCGTGGCTGGAGGCACCTGAACTGTGGAAGTC
CGGGAGGTTCCCCGGTCGCTGCGGGCCGAAGCTCTCAGGCCCCTGGCTCTCCGCCATGTGCTCATAGCCCTCGGCGA
AGGGCGGCTGGCTGCCCAGGCCTCCGGCTGCGCCGCCGTAGCCGAGCAGGCGACCCCCGTGCAGGCACGAGGCCCC
GGGGTCCGGGCCACCGAAGTTGCCCCCAAAGTGGGGGTGATGCTGGTGGGGATGATGACTTCCCGGGTGGCCGTGG
TGAGGCTGCTGGCCGCCAAAGAAGCCGTGCACAGGCTGCGCTTGCAGCCCCCCTGCGTGCAACTCCGAGTGGCCGC
GCGCGTGGAAGCCGTAGGGCTCCATGTTCATGCCCAAGATCGGGGGTTCGCCCAGCGCGCTCATAGCAGGATCCACA
GGGCCAGGGGGCCCCCAGTGTGGAAAGCCGGGGCCTTAAAGTGGGTGTTCATGCTCAGTCCGGTCTCGTTAAAGTT
CCTCTCGCCCTGGCCAGCGTTCCTGCTGTTGACCTGGGGCTCGAATTGGTCCAGCCCAAACATACTTGGCGGGGGC
AGAGGGGGATCAATAGGGCATGACAGCCGGCTCTCCGGGCGCGCCTCCGGCCAGCTACTCGTTCCAGCCCAGGATT
GGGCGCTCCGGGACGCTCAGCACCGCGGGGGCTCAGCGCGCACCTCCACCCCGCCTGATGTGAGGGACGGGGGCG
GGGTATTAGCTCCTCTCCTGAAGCTCCGATTCTGCCCGGGGAGGGCCTCTCACATCTTGCGAGGCCGCGGGCCTCT
AGGAGCCGTGTTGGGGGGCCCATGCCCCGGGCGGTTGTCACAGCCGCGGGTGGGTCTGCGGGGAGGGGACGAAGCC
GCGGATGAACGGAGACAAAAAGTTAAGTGGGGGGAATGGGGAGGGAAGGGGGTTGGGAGAGCAGAGCGATCACCTT
CTCAAGTCCGATTGGGTCTGCTGGGGAGCCCTCAGGACGCCGCCCGCAGCCTCCCGGAGTCCGTGGCAGAGCTGCTA
AGGGCAGGGGAGGGAGACCCTTCAAAGCCGCGGCTGGCGCCGGGCACCGACAGAGCGGTCCCTCCCCCCGCCCCCC
GGAGTCCCCGCGCCCCGCAGCCCGAGCCTCCACCGAGCACGATCCGCTCGCACAATCCCCGTAGGCTCCGGGCGAG
CGGCTGCTGCTTCTTCAGCGGGTCGGAGGACTGGAGGCTCCGCTCGGCATCGCCGGTGCCGGCCCCCGAGCCGAGG
ACGCAGAGGGGCTGCGAGGCGGCAGGCGCCGGGGGCTGGAGCCGAGGGTCGGGGAAAGGCGCGGCTCCTCTGCTC
GGCAGCGGGTGCGCTGCGTTCGGCGCGCAGCTTCGCGGCCACGTCCGCCGCCTGCCGCTTCTGTTCTCCGCCGTTGG
GTGTCTGAGTTCGCCGGAGTCTCCGCGCACCGTTGCAGGCGCGGGAGGGCAGCGAGACGAGGGTTGGGTCGCTCC
AAGGCTCCGGTTCCCTGCCTCCGCGCTGAGGTGCTTCGCGAGTCCCTCTCGGACCTGAGGGAGGGGGGCGTACGCG
GGTCGGGGGCCACGCCGGGCGAGCAGGCTAAGGCGTTCCCGCTGCGCTCTCAGAGCCCGGAATGGGGGAGGGG
GGCGCGGGGCAGCTCTGGGGGGTCTGCGCACCCCTCTCCCGACTAGCGGGGGGGCTCTGCGTGGGGCGTTCCGAG
GGTCTCGGCTCCCCTCTCTGTGTCTGCCTCTCGCCCAGCGCCGGGAGAAGCAGCAACAAGTTTTGCATTTCAGCAATC
AATTTCAGCCATTACATTTGCACCAATCAGCGCCGCCCAAGTTCCGGGCTCGGGGCGGGGCTCGCTCTTAAGGTGGT
CCGGGGTCCTGGCTGCCGAAGCCCCCGCCACGAACCCGCACTACCCCAGCTCTGGGGTCCCCTGCGCCCGCCTCTCC
TCGGGGTCCGGCGTCAGTGCGCTGGGGGCGCGCCCCGGCCTCCGGGCGCATGAGCTGGAGAGGGTGCAGGCGGA
GGAGAATGGCGGGAGCTTGGCTTTGTTCACCCCCTTCCCATTCACACTGTTCCCAACTCCCCACCCCCAACTGGAGCG
AGACCCACCGGGTGGGCAGGGGGCGGGGAGGTGGGCGGTGAGGCTGCAGACAATGAGGTCGCCAG
GCAAAGACCCTAGACTCGCCACGGAAAGTCGCTAAGTGTCTACTGCACTTCGGCTCCGGGGTGAACACTCCGTTCTC
CGCTAGCGGCGCCCAAGTTAGCCGGCCCTGGGATTTTCTTGGAGGGTAAAGCAGACGGGGAACCTCGAAGTTAGGGT
TCTCCTCGAGAGACCTGGGCGCTTGCTCACTCCTCCGTCACTAGGGCGTTCACAATTGTTCCCCTTCCCCACTGCCTG
GGGTTCCCGGTTCTCACCGGCCGGCGTGGGCTCCAAGGAGTCACAGTCACTCAGCCACTTTATGGGGAGCACATCG
GTTGAGCCCAGTAACCGGAGCGACTTGCGAGGCGGCTGGGAACCCCGAGAAGACACGCACGAAGAGGGCGCACCCG
CCGGGCCGCACACCTTGCCCTGGGCCACCCGGTCCAAGACCCAGACCCTCTGCGGGTGCG (SEQ ID NO: 311)

4 chr7: 5614184-5614510
CGCCTACCACGTGGCCGAGATTCCCGAGGCTGCAGCCAATGAGCAGCATAGTCCGATGGGGAGGCTGGAAGGGCC
GTTCACGAGATCTCTCGGGAGGAATCGGTAGGAGCTGCCCAACTGAAAGGGACGGGGAATAACCCGGGCGAGGG
ACCTGCCCAGGCCCTGCCCTCTGGGGGAAGCCAGGCCAGGGGCCGGGGCATCTCTGGGGTCCCAGGTGAGATGC
GGGTCGAGGGAGCCAGGCCACGGTTCTCCAGACTCGCGTGGAGGCCACGAGCGTCTTCTGGAGGAGCGGGCACTGC
GCGGACCGGCAGACTCTGGGGCG (SEQ ID NO: 312)

TABLE 9-continued

CpG islands (CGIs) methylated in blood but not in bladder cancer. Provided
for each are: ID no.; Coordinates of selected regions containing relevant
CpG islands based on Homo sapiens full genome as provided by UCSC
(hg18, Mar. 2006); GeneName; Location of the probe used; the Fold
Change; and the sequence of the CGIs.

| No CGI | Gene Name | CGI probe location | FC |
| --- | --- | --- | --- |

```
5 chr16: 66239477-66241425
CGTCCTAACGTACTGTCGTTCCTGAATCTCGCAGGCACCGACACTGCCCTGGACACTGTGAGGGGGTGCTCCGTGGG
GGGATGGATGACCGGCAGGGCGGACTGGAGGGCGGGACGGGGAGGGCTCGGTCCCCCCGCGGGTGTAGCCAACAG
CCTCCCCCCGCAGCTCTTCGCAGCGGTATCCCGAGGCTGCTGCACCAGCCTTACCCACCTCGACGCTTCGAGGAACG
TCTTCTCCCGCACGTAAGGGGGACCTGTCGGGGCCGGGGGAGGCTGCTGGAACCGCCTCCTTGCGGCCCCAGGCC
CACCTTCCCACTTCCCCAGGAAGTCCCGCGCCGCGCCGGCCGCGCTGCAGCTCTTCCTCAGCCGCGCGCGGACGCT
GCGGCACCTGGGCCTGGCGGGCTGCAAGCTGCCGCCCGACGCGCTCAGGTCAGTGTCGGACCCCGGCCACGCCCCC
GCGGGCGCTCCCACCCTGCCCTGGCCTTCGCCCCTCCCCGCTCCTGCTTCTGTCGCTCCCACAACCTCCCCCAGATCC
TGGCCCTGCCTCCTTCGTTCGCACCCTGGAGCCCCCTGTCCCAGCTCCCGCCACCCCGTGTAACGTCCTCTCCCAGAG
CCCTTTTGGATGGCCTCGCGCTCAACACGCACCTCCGCGACCTGCACCTGGACCTCAGCGCTTGCGAGGTGAGCGCC
GGCCCCCAGAAGAGACCACACATTGGGAGAGGCGCTGGGAGGCGGAAGGGCAGGGCCGTGGGCCGCCTGCCCCTCC
CCACTCGCGGCCTAAGTGGGTCCCACTTCCCACCTCCCACCTCCCACATACAGCTGCGCTCGGCCGGCGCCCAGGTG
ATACAAGACTTAGTGTGCGACGCAGGCGCTGTGAGCTCCCTGGATCTGGCGGATAACGGTGAGGCTGCAGGAGAGCC
CATCCTGCATCATCCACTCGATTCCCAATCCCCACCCTACCCTTGCAACTTCGCCTCGTGCGTGACCCGAGTCACCC
CCAGGCTTCGGCTCAGACATGGTGACTCTGGTGCTGGCCATCGGGAGAAGCCGGTCCCTGAGACATGTGGCGCTTGG
AAGGAACTTCAACGTCCGGTGCAAGTGAGCCCCCACCCTACTCCTGGGCCTCCCAGACAACACCCCACCACCCCTGT
CCCCCACAACTGCGGCCCCTGCCCACAGGGAGACCCTGGACGACGTCCTGCACCGGATTGTCCAGCTCATGCAGGAC
GACGATTGTGTGAGTTCACGGGACCTTGCAGGGCCTCGGGCAATTAGACCACTTTGGTCCTCCTTTCTCTTGTTCCCT
CAGACCCTGTGACCTGCCCTCACTGACCCCTGACTCCAGCCATCAATGGCTTTCTCTTAACCCCAGCCTCTTCAGTCT
CTGTCGGTGGCTGAGTCTCGGCTGAAGCTGGGTGCCAGCGTCCTACTCCGGGCCCTAGCCACCAATCCTAACCTGAC
CGCGCTGGATATCAGCGGCAACGCCATGGGGGACGCGGGCGCCAAGTTGCTGGCCAAGGCGCTGCGGGTCAACTCG
AGGCTCCGGTGGGCGGGGTCAGAGGGGTGGGACCAGCGGGCAGGGGGCGCGGTGGAGAGGAGGGCACCGGGCTAA
GGGGAGGGACTGAATGAGGCGGAGCAAATGGAGCAGGCTGACGAGGCGAATGGACTAGGCCGAGGGTTGGGTGGG
GCGTTGGGAAGCTCCGTCCCCGACTGAAGCCAGGCCCGGCCCAGGTCTGTGGTCTGGGACCGGAACCACACATCTGC
TTTGGGTCTGCTGGACGTGGCGCAGGCGCTGGAGCAGAACCACAGCCTGAAGGCCATGCCTCTGCCACTGAACGACG
TGGCCCAGGCGCAGCGCAGCCGCCCGGAACTGACAGCACGTGCAGTCCATCAGGTGGGCGTCCCCCTCTTCCCTTGC
CCTTCTCTGCACGGTAACTCCGTCCCTCG (SEQ ID NO: 313)

6 chr5: 551112-551430
CGGATGCCGGCCTCCTGCCTCGGCCACCGCCCTCCTCTTCAAGGATGCTGTTTTGCCTCTGGTCGCTCTATCTTATCT
TTTTTCTCCGCACTCCTGGACGTCTCTCGGACCTTTCGCTCTGACAGTGGCTTGAGCCTCGGCCGCCACTTCCGCCCC
TGCTACTTCGGGGCCACGTCTCGGTCCGACGCTGAGGGGTGCTGCCAACCGTGTCTTCTCTGTGAACGTCCTCACGA
TGAACGCCCCCGTTCCACTTCCCACCCTGGAGCTGCTGCTTCCGTGACTCACATTCCGGCCATTTCCGTGGTGTGAGG
TACGGGCG (SEQ ID NO: 314)

7 chr19: 6426223-6426998
CGTTACATTGCGATTCATTCAGGAACCCACGAGACCTCTCCCCGCAGCGTCCCCGCTGCTCACCGGGCTGCAGACGAG
TGCGTCGCGGTACCCCCCGAAGAGCAGGGCCTGGGCTTTGAGGAAGAGACGGGACACCCCTTCCCCGGGGGCCAGG
GCGACCTTCCTGAGCCGGAGCCTCAGCAGGGACACCTGAAGCACAAGGGAGTGGCCCTGAGTGGGCAGGTGTGGGC
CCCTCGCCTCCCGGGGCAGGAAGGTGGGAGGGGCGACACTGACCACGTCTGGAGGCAGCGCCTGCACGTCGTTAAA
GGTCGTCTCCAAGGTATTGGCGTCCACGTTCAGCACCACGACGTCCTCCAGGGCTTTTTCTCGTACTCTCTGCGGAAA
AGCGGGGTCGGCCGCTCAGAGCCCGGGAGTCCTTGGCAGAGGAGGGCATCTGGGGATGTAGAGGAAGGGGGAACCC
TCACGTCCCCGTCGTCGGGTAGATCCACGCTCACCTCGGCGAGACTGGCGTGCACTCCAATGAGGTAGGGCATGGG
CGCGCTGCGGACCGAGGGGACGGGGTCATGCAGGCACCGCCCCCAGGGCCTGCCCACAGGCCCTGCCCCTCCCAGC
TGCCCTGCTCACCAGCAGTAGTCCAGCAGGTGTGGGGGCAGCGTGGGGATCAGCACGTGCTCCCAGCGCATGGGG
TACAGGAGCGCGCAGGACGCGTGGACGCACGAGGTCAGCTGGGGAGCGATGGCGGGGCGTGGAGTCAGGGCCTGG
ACCCTCTAGCGCG (SEQ ID NO: 315)

8 chr3: 32836146-32836433
CGTGAAATCGCCGTTCGTGGGCCCACGGCTGCACCCCGAGATAGAAGCGGAATAAAGGGACGACGTTACCTTCACCA
GCCTGAGTCTCTTGGGCCGCGCCCGCCTGCCCCGACTCCAAGCCCTACAGGAACCGGTTTCCCTGGTTAGGAGGTAT
CCACCCGGCTCAACCAGGGTCTCGACTTCCTTGGAAAAGACCAAGGCAGCCGTACGCTGCTGGAACGCCGGAGTGCA
AAGGCTTTTAGGGCTACATTGCAACCCTCGGGCTCGATTTCGCCCTTTGGGCTGTCG (SEQ ID NO: 316)

9 chrX: 129301145-129301626
CGTTGCCGCCTTTTTCGTACTGAGCGCGCAGGGCACTACGCCCACCACTCCCCTTGACCCACTCCTCAAGCCCTGATA
CCGGGGCGAGGCCCCTTCCTTTTCTAGTCCTTCTACGCGCCAGGTGGGTGGGTTTCGCGGTGACGAGGCGACACCTC
TTTCCCCTCTGGCGAGCACGTTAACTGGGGAAGCTACCAAATTCTCACGCCTTAGCCTCCCTGCCTCCACCTCCCGCA
AGTCCGGTTGCCCCTCTAGGCTTCTGCGCCTGCAGTGGTTCCGACCCTCGCCTTTAGAACTCTGCCGCTTCCGCCTCT
TATTTCGCGCCTTTGTTTTAGTTTTGGAAGGGGCGGAGTTGAAATGGCTGCGCCGCGGTTGCCGAAGCAACGCTTTG
GTTACTTCCGTTGGTTTCAATGCTTCCGGGTTGGCGCTGCAGTGGCGTTTCCGACTGTGGGAGCCTCAGCTTCCCAGT
CGTCCGATGAGCCCG (SEQ ID NO: 317)

10 chr9: 124027565-124030907
CGAGGCCCAGGCGAGTGGCCAAGACGCGGCAGGACAGGAGGATGCGCCTGGCTGCTCTCGGCTGCTGGACGCGGCC
TGCAGTAGGGAGAGCGCAGCCCGGGGTAATCCCACTCAGGGCTCCGGGTGCCCAGTTCTCCCACTTCCCATCCTGGC
GGCCTAAAGGCAAGGCCTAGACCCTGGAGAGGCCAAAGTCGGGCCAAAACAGCGAAGCTGGGACTGGAACAGG
CGCTGGGGGCCTGCGCATGACCCCAGGCTCAGAATGCGACACTCCAGTGACGCCGGGGAATGAGTTGAGATGGAGC
CGGAGACAGAGGTTGGGGTTCAGGACGAGGCGCTTGGGTATGGGATCGGATCTGAGACGGTTGCGGCGCTGGTGCT
TTGGGCTGGACCAGACTCGAACCCAGAGCGGAGCGAGGGTCAGAGCCAGGGCAAGAGTCCGAAGCCCAGCTCAGCG
TCCAGCCCGCGAGAGACCCCACCATGAATGACGTCCGAGTAGGGTTGGAACTCGAAGCCCGAACGCACTGGAAATGC
```

TABLE 9-continued

CpG islands (CGIs) methylated in blood but not in bladder cancer. Provided
for each are: ID no.; Coordinates of selected regions containing relevant
CpG islands based on Homo sapiens full genome as provided by UCSC
(hg18, Mar. 2006); GeneName; Location of the probe used; the Fold
Change; and the sequence of the CGIs.

| No CGI | Gene Name | CGI probe location | FC |
|---|---|---|---|

AGCCGGACGACGGCTGGGATCCGAGTGGGTCCGGGCCAGAAATGGGGACCTCAGAGCTCCACCGAGGCGCTCGAGG
TCAGAACTGAAGCCTGAGACTTAGGCAGGACCCGAGACAGAGCCAGAGACGATACCGAAACCCAATGGACCGCGAG
GACCGAAGGCAGATCCGGGGCGCAAACCTGTGCAGGCACTGGCGCGCTGCCTGGAGCTCTGGGTTCGCGCCGCTGA
GCGCCGGCAGGTTGGACCAGCGCTGCGCGCCGGAAGTGCACTCGGGACGCCGGGGTTCTGGAGGAGAGACCACACG
CCGCAAAAGTGGCCTCCGAATGCGCCCGGGGCCTGCCCTCGGCGACACTGCTGGCTCGGCGGCCGCAGCCTACCTG
AAGTAGTCCATCTTGCAGAAGATCTCCTTGTTCTTGATGTAGCAGCTGTTCTGCTGCCTCAGCGACGTGCGACACACG
GAGCACTCGAGGCACCGCACGTGCCAGATGAGGTTGTTGACCTGGGGACGGGGCGGGACGGAGGTCGGCTCAGCG
CGGGCCTCTTTCACTCCGGGCCCCAGCCTTCCCGGTCTCATTTACAGTCAGAGGCGCTGAAGCTCAGAAGGTGCATG
CGATTCCCCTATTTTTCTCCCGTAATACTGAGACTCAGGGAAATGGAAATAAACTCTTCTTATTTTTCAGACGGAACCC
GGGGGCTCAGGCAGACCCTAAGTCTTGCCCAAAGCTTCGCAGTCGGGCAGCAGTGGAGCCAGGATTTGGAAGTAAGA
GGACCTGCGGTGCTTCCCTGCAGTCTCCTGCGCTGCGTCCCACGCCCCGACAACACGCACGCAACACCTACCCCTGT
CTCACCTTGAGCAGATATCGGTCCAGGATCTCGAGGCCGCAGCTGGAGCAGATGTTCTTGCCTGCAGACGGCACGGA
GGAGGCGGCAGAGGGCGGTGAGCAGACAGATGGCGTGCTGGGCGTACATGGGGAGGCCTGACCCTCGTCCTTGTCC
AGAGCTCCTGCCAGGGCCTCGGCGTCAGACTGAGCCTGCGGCGGGGAGAGAAGGAGAGGAGCGCTGATCCGGGCA
CCCAGAGTTGGGGCTGCCTTGGAGACAAATCTGGGGCCCCGAGCACCAATTGACAACGAAATCTCCCCAGGACAAT
GCGCCGTAGACTGAAGGACAGGGATGGAAGGGCCTATTGGAGAGGAAGGGACGGCCCCAACTTTTAACACGCGCAT
TCTGGGTGCTGGGAGCGGTTAAAGCCAACATTCCCTGCCGGAAAACCGAGGCTCAGAGAGGGGCGGCGCCCGCCGG
GAGTCCCCCAGAGCGTGAGCAGCAGTTCGTGGCCGGAAAACCTGGCCAGGTCCCCAGGGCCGGGCCGCTGGAGGAC
TGGGCACCGCAGGCAGGGCCAAACGGACTCACCATGGCGGGCGGCGCGGTCCCTTCAAGACAGCGGGTGGTCGCTT
TGCAGCCGGACCCTGGCTGGGCCATCACCTGGGGGAGGGGGGAGGGAACGCAGGCGGCGGCGGCTGCTGAACTG
GCTCCGCACAGCCTGAGCCCAGCGCCTCCCCGCGCCTGTTATATAAACCGGCGCCGAACAATGAGTCCTAACTTTGT
AGTGGGCATTTAAAGCCCTTCCCCACAAAAGCGGTGTCTCTCTAATGAAGCAATTTGAATTTGGATTGGATTTTTTCC
CTCTCTCTCCCCCTCTCCCTGCACTTAACCCGTGGCTCTTGAAGTAATCGCTTAGTTCCCTTGCAATCCAAGCCTCTGA
GGGGGGAAGAAAAACACGCGCACACACACAAACTACCTGCAATTAGAAATTGTCGTGAATGCCCAAGATAAGAGG
TAGCCAGAGTGTCAATTCCAACTGTCAATCAGTGAGATCCATCAGGCGCCCAAAGAATTGCAAATTTGATTTTTTAA
TGGTAGTAATTAAAAATCGAATTTTTTCTCTCTCCACCCGCCCCCCCACCCCACTCCCCTTCCTCGCTCCCTTCTCCTC
TCGGCACAAAATGCAAAAGGAGAAAAGAGAGAAAGAAAGAAATAAAAAAGAGATGGGTGAGGGGCGGAGGGTGG
TTGAAGAAAAGAAAACCCCGAGCGCGGTGAGCACCCGCCCGCCCGCCCGCCTGACACGCGCGGCGAAATTGAAGCA
GCTATATTGACACGGATTCAGGCGCCTTTCGAGGGCCAGTCGGAGGGAAACCCGGAGCAAAAAGAGAGCGAGATCG
GGGCGAAACGGGACCAAAAAGAGAAAAGAGAGGCGCTCAAGGGGAGGAAAAAGCACCCTCCAGCCCCTCGGCGCGC
CGGGTACCGGCCCCGCGTCGGGATTCTCAGCGCTGCGCCGGCACAACCCCGGCGCATCGGCGCTATCAGCGCCTAT
TCAGACGGACAATACCGGCCTCGCCTCCTCTTGATTCGCCTGTGTCTTTACTAAATCGCTTTTTGAGAAATTCCTCCAA
CATTTGCATAATGTGTTCCCGCTTTCCGCGACCCCCCCCCCCGCTCGCGCGCGCGCTCCCACACTCACAAGCACACA
CTCACAGGCGCACCCTCGTACCCCTCCTTCCTGCAACCGCCCGCCACCCTGCTCGGCCCGGCTGGGTCCCGGACCCT
GCCCGACCCCGGCCCGGGCGCTCACCCAGTCGTTCGCCGGCTCACCTGGTCGGTGGCGGGGCCGCCCTCGGCCGG
CAGCCGGCAGCCCTCGGGCAACGCCGGGGCGGCGTTCTCATGCTTCCAGTACATGGGCCGGGGAACCTCGGGCTCA
GCGGGCGCGCAGCGCGGAGAGCTGCGCCGAGGGGGACCACAGCCG (SEQ ID NO: 318)

11 chr10: 129424401-129427356
CGCCTCTTTCGCACAGGTGCCCGACTCGGAGTCCGGGAGGCGGGCCCTCTTTCCAGGTACCCAGCCCAGCGTCAGCC
TGGGTCCATCCTCCGCCACCCCACAGCGCGGGGAGCAGGGGAGGCCGAAAGCCGGGCAGCTTGGGGGGCCGGGATA
ACCCGGGCTGCAGCAACCCCGGGCGGCAGCAGGACTGGAGAGCTGGTGTCGGACGCCACTGCAGAGACGTCCCTGTT
TTCGGCGCGTCCTCCGACACCCAGCAGAGAGCTTGGCGCTCTCCGCTCTGCGCGCCCGAGGTCACAGCGCGGAGAAA
CCTGGCGGGGCCCCGGACTCCCCGGCTTGGGAAAAGCGATGACTGCCCTGAACTGCTGGGGCGTTCGAAATTTCCAG
GGTCCCGACCCTCCGTGGGGTACGCGCGACTTCGGCGCAGATGTCAGTCCGCTGCCTTCCGGGTTGAGGGAGCGAG
GACTCCAGACGACCCCAGGGCCGCTGTCCAGGCCCAGCCCCGCGTTCTCCACCTCGCCACCTCGCTCTGCGGCTCCA
GCCTGGAGATCTACGGACTTCATTGCGATCTCTTGCCAGTGTAGTCGCCCTCTATCCCTAGCCCCGAGTCCCGGGTA
ACCCAGGGGCCCCGGCGAGGCGAGTTTCTTTGGGGCGAGATGTCCCGAGCCGAGCAAAGGGGCCGCGCATTGGACG
GGGCTCCCAAGCCACAGCCCTGGGGGCCTTGAGGAGTCGTGGTACGGTCCAGGGCAGTCGGGGCTGCGGGGCCCGT
GAAGCCAGACGAGGCTACGGACTTAGGGTCCCTGCAACCAAGACGGCGAGCGACTGTGGACTCGGGACGGATCGCA
CAAAGGAGGAAGGGGGAATCAGAGGGGCGTCCGGTCCAGGACGTGTCAGGCCTGGGCGGGGCGGAAAACTGACACC
AGGGCGAGGACAAGGATTTCGCTCCTCCAGGGCTGCCAGGGGAGGGGCTCGCCACCGTCACTCTCCATGGGCTCTG
GCCCCGACGGTGTTTAAAGGGCGGAGGGCTGGGCCGGGCTGGTCGCACCCGGGCGCTGCTGGCGGCCAAGCTGGAT
GGGTCGCCAGTGAGTTTCGGTGCGGCACCGCTGGCCCAGGCCCGGGCGCGGCTGGACATGGCCACCTACTGCGACG
ACCTGGGCCCCTCCTCGGCCCCGCCCGGCCAGGCCCAGGCCAGCCACCGCGCACCCCCGGGCTATGAGCCAGGGGATCT
GGGCGCGGTGGGCGGGGCCCCCTCCTGTGGGTGAACGCGCCAGCGCTCAGCCCCAAGTCCTACGCTTCGGGTCCC
GGGCCTGCGCCGCCCTACGCGGCCCCGAGCTACGGGGCTCCCGGCCCGCTCCTCGGCGCCCGGGCGGCCTGGCGG
GCGCCGACCTCGCCTGGCTGAGCCTCTCCGGCCAGCAGGAGCTGCTGAGGCTGGTGCGGCGCCCTACTCCTACTCG
GCGCTCATCGCCATGCGCATCCAGAGCGCGCCGTGCGGAAGCTGCTCAGCCAGATCTACCAGTACGTGGCTGG
TAACTTCCCTTTCTACAAGCGCAGCAAGGCGGGCTGGCAGAACTCCATCCGCCACAACCTGTCGCTCAACGACTGCTT
CAAGAAGGTGCCCCGCGACGAGGACGACCCAGGTAACAGCGGCGCGCCGGCTCGCTCCGTCCAGGACTCCCCATCTT
CCCGCCGGGCCGCGGGCACTCCGGGGTGGGAGCACCTTAGACAACCTAATTTCTCCCTGCGCGGTTGGGGATACCC
GGGGAGGGAGGGAGAAGGGGAAGAAGTGCTTGGGCATGGACAGGTTCTCAGACAGCGGCTGAGCCCACCACAGGCCC
GCGTTTACAGTGCGGCGGTCCCGGGGCTCTCAATCTCTGTGCGCTCCTTCGGAGGAAGAAGCGGGAGAGCCAGCAAG
CTGGGTGACCTTGGGAGTGACTCAACTTCCCTGGGCCTCAGTGCCCTACCTGGTAAAATGGGGAAGACAGCGCCTAC
CCCAAGGATGGGCAAAACAAATAGGATGCCCGTTTGGAAAGCTCTGGAGCCTACCTGGGGGCCTGGCGTGGTCTGCG
CTGTCCTTGGCAGAGCGGCTGGCGGAGTCCCACCATTAGCATCTCGCAGGCCTTCCTTCACCTTAACGGGGCTCGGC
CTTTCCCAGGGCTCCCTTCCTCCTCCTTTCTGGATTGTCACTTTCTTCCCAGTCCTGCTGTGGAGGCCCATCGGGTAC
AGAGTGCCCGTCAAGGGTGGAATGGGGGCGAGGACTCAGACCCTCTGTAAGGGCCAGCAGGGGATCTTTCTGAAGC
TGACCTCCTCGCTGGCTCACACCACGGCCCGTCAAAGCTCGAACCTTCTGAACTGGGCTGTTTCTTCTTCTGCAGGTA
AAGGCAATTACTGGACCCTGGACCCCAACTGCGAGAAGATGTTTGACAACGGGAACTTCCGAAGGAAGAGGAAGAGG
AGAGCTGAAGCCAGCGCGGCCGTGCGCTCGGGAGCCAGGAGCGTGGGAGGGGCCGAGGCGCCAGCGCTGGAGCCC

TABLE 9-continued

CpG islands (CGIs) methylated in blood but not in bladder cancer. Provided for each are: ID no.; Coordinates of selected regions containing relevant CpG islands based on Homo sapiens full genome as provided by UCSC (hg18, Mar. 2006); GeneName; Location of the probe used; the Fold Change; and the sequence of the CGIs.

| No CGI | Gene Name | CGI probe location | FC |
| --- | --- | --- | --- |

```
CCGAGCGCGGCTTGCCTGGACCTGCAGGCCTCGCCCTCTCCATCCGCACCCGAGGCCGCCACCTGCTTCTCCGGTTT
CGCTTCTGCTATGAGCGCTCTGGCTGGCGGCCTTGGCACCTTCCCCGGGGGCCTGGCGGGCGACTTTTCTTTCGGGA
GGCGGCCACCGACAGTCGCCACCCACGCTCCCCAGACCCTTAACCCCTCCCCTGGCTTCGCCCCTGGCCACCAGACC
GCGGCCGCCGGCTTCCGCCTCAGTCACCTCCTCTACAGCCGGGAAGGGACCGAAGTTTGAAGGGAGGCTGGAGGCT
AGCCGGGTGCGGGTCCAGAGGTGCTGAGCTCAGGCCTCCGGTTTCCCCTGGTGACAGCCCCACGTGTTGGCGTTGAA
GGCCTTGGTGCCCTGGGAGGAAGCGCAGAGCCGGGGGCGGCTCG (SEQ ID NO: 319)

12 chr1: 3147370-3148160
CGGGGTGCGGGGAGGTTGAGAGCGCGGCGGCCGCTGCCAGCAATCGAGGAGCCAGCGGCGCGTGTGCTGAGGGCC
CAGCTAGCAAAATAAAGAGGGTTTTCAGCGGAGCGGCGGCTCAGGCGAGGCTGGGGGAGCCGGGGAGCGCGTCCCG
CCATTTTTCCAGCCGAGGTCAGCAGCGGGTGAAGGGGCGGAGTCCGTGGTGTTCCCAACTGCCCAGGCGGGCGGTG
AGATGGGGCAGGCGGTTCCGCAACGCGGCTCAGGCCCCAGCGCCCTGCCTGCAGGAGGCCGCTTCTTTCTCTGTTGC
CATCGGGCGCCGGTTTCCTCTTCCGGGGATGCAGGGCAGCTGGGGGGGCTCTGCCTCTGTGCGGCTCTTCCGTGGTT
CCACGCTGGGCTCCGGGGTGACCACAGTCCTCAGCAGCCCACACCCTCAGCCCGAAGGGGGCCCAGGCCCCGTGCC
CAGAGGATCCAGAGAGACAGCCGGGAGCCCAGCAGCTGTGGCAGCTGCCCCCACCACCACCCCGGGGCTGGCCAGG
TCCCACCTCCTGACGCCACACGGTATGACTGGGCCCTCCTGGTCAGTGCGTCGCATGTAACGCCTTCAACTATTGGG
GCCGGTGTTGGAGCATCCGTCTCTGCGTCCCCACCTGATGACAAGCTCCGGGGAGCAGGAGTGCTGGCCAAGCCCAC
GCACGGACCAAGCCCACGTCAGACTCCGCCAGAAAGGCAAGAAGGGCCTCCGCATGGCGTGACGGATGGGTTTATG
GGGGCATTCCATCCCACCCGGACGCTCG (SEQ ID NO: 320)

13 chrX: 128941527-128945710
CGGAGCTTGAGCGCCAGAACCACGCACTGAGGTCGCCCAGGGTGGGGAAGTGGGGGGCCGGGGGAGGGGCGGGGC
ATCCGGCGGGGAGGTCTCCCCCACCGCATGCAAGACCCTTTGCCCCCCCACAACATACACTGAGGCTAAAACGGGGA
TGAGAGTCACACAGAGCAGGAGCGAAATCTTTCGCTCTCCGACCCGAACGGCGCGTTGCTCGACCCCCCCCTTCCTG
GAGCCAGGGGCTGGCCGAGGAAGGTGGCTCCGTTCTTCCCCCGTGGCCAGTGCGGGGTCTGCGGCTGCCCGGCGAG
GTTCCGGCTTCCCCGGGACTGGCAGGGGGAGCCCCGAGAACTGCAGGCCCGCCCCCCTTCCTCCTCCTCCTTCCCC
TCCTCCCCCACGTGTCCTCCCTGAGCCCAGCAGCCTGATCCCAGCACCCCCCGCCACCTCCCTCCTCCCGCTTCGCCC
GCTTCCCCGGCGGCGTGGAAGAGCAAAGTTGCGACAGCGGCCGGGGGCTCTGCCCAGGTAAAGGGGGCGCCGTG
AGGCGGGGTGGTGGGGGAACGGTGCGGCCCTGCGGCGGGGGCGGGGGGAGGATAAAGAAACTTGCTTCCCGCGG
CCCCCACCCCGCGTGGGTTCCGATCTTGCGTGGAACGAGCCCGCGTGGCGAGTCGGCAACACTGCCGGGACCGA
GGCCGGCACCTGGACCCGGACCCGGACCGCGCGCTTGGGCCGGCTCGGCGGGCGCAGGCAGCGGGCCAGGCCAGC
ACCCAGGCAAGGGCGGGTGGGTGGCCGTACACCGGACCGAATCGGGGACTCCGGTGGCGTGGGCGCGGGCCGAA
CCCCGACCGGGCCGAGTTGGGTGGCGAAGTAGGACGTGGATTCGGGGGCGGGGCGCGGCGGGAGGGGGAAACCAG
GCCTGGCCAGACTGGCCTGGGCGTGGGGGCGGGGGCGAGTTCGGGGCACTTGCTGGGCTCTGGACCGAGCGGTAG
GGCGGGGCGGCGCTAGGGGCTGGGCCGGACCCGCAGGGAGAGGGCGAGGGGAGGGAGAGCCGGGGGTGGAGTAG
GGGCGTGGAGTTGTGAGCGGGGTCTGGCCTCGGCCGGGGCGAAGGTAGATCGGCGGGCGCGCGAGCGGAGGGAG
GGAGGCCCGCGGCGGCGCGGCGGCAGCGAAGGCCAGCTTCCGCGGAGTTTGTGCCCGGGCTTCCCGGGCTCTGGCC
GCCTCACGCGCACAAATGGGGCTAGGGGACTGAGTGGTAAGCAACTCCGAGTGTTAGACGGTGATCGGGCGGCGAT
TCCGGGAAAAGCGAGGAAAGACACAGTCTGCGATTGTGCCGCACCCCCCCACCCACCTCTTAGCATCTGGATTCTGCT
CTCGTAGTGGGGGCCGCGGACCCTCCCCGCCACAGTCCTTTTTACTCTCCAGCACTCCCACCGCCTTCCCCCTTCTTCA
GCCATCTGACTCTCCTAGGGGTATGTGTTTTTGGGGGTGGACGGCGACGGGGGTGGGGGATACTTTCCTTCCCGTGG
CGGCAACCTAGTTCGTATCTTATTCCTACAAGGTAGCGTCGCTTCGAGTCGCATGGACATTGGGGTTTAGATAATTTA
CCCCCCACCCAAGCGATTTAATGGCTTTTAAGCAAAAGGCGAATACCTGGATTTCCATGGGAGGGATGAGGTTTGAA
GATTGGGATTCACCCCTAGCTCACTTCCACTACCAACCCCTCTTTCTTGTGAGCCACTTCCACGGGTATTCAAATCTG
GGGGGGAGGGGGACGGGAGTATTAATATGCTTCTCTATTTCTACACAGGGTCGGCGTGGCGAAGGACGGCTAGCCT
TGGAGGGAAAGTAGCCACCAGTCCAACTCGGGTCGCCCCCACCATTATTTCGGTGAGGGGGCAACGCTAAGAAGGGG
ATACTGGTGGGTAGGGGCCCAGTATAAGGGAGGGGGCTGGGTAGTCGTCCCCAGAAGGACTCCGTGTCTTGGCGGG
GAGAGAGAGAGGCGAGCCCCGGCTTCAGGGGAGGGGTTCCGGGGAGGGAGATGGGGGGTGGCGACGACGGTGGG
GGGGGGAGCGGGAAGAAGGGGGAGTCACGCCCTGCCTGCAAGGGGAGCCTCCCTCAGGCCCCTGGGAGAAGGGGA
CTGAATGCGTCTGTTCTCCGCTGCCCGGCAGAGGAGATCTGGGGTCTCGAGATTTGCACACTGGATCGGCACCAGTG
GCCTGAGAAAGTCAGGTCGGGGCATAAGGTGGAGAACGTGGAAGAAAGAGAGAGAACCCTTTGGCCGCGGCTCAC
TGACCCTCTCCCTTCCTCAACCTCCCCCTTCGAGGGGCGTCGAGGTGGGGGGGACGTGGGGCTCCTGCAGCCCCGC
AGATTGAGCGCCTCCGCCTCTCCCAGGAGTCTAGCTTTTTGCCCGGCTTGCTGCAGCCACTGCTGCCTCCCTCTCCGG
AATCCGCTCGGTCCTCTCAGCGATCCCCTCCTCCTCTCCTCCCCTCCCAGTGTCACCGGGGCTGCTTGGCTCTGCCCC
CTTCGCCGCCGCTTGCTCCCTGCTTTCGTCCCTCCCTCTCTTGTCTGCTCCCTCCCTCTCCCGCCTCCTCCTCCCCATTCCC
CCCCACCCGCGTAGGCCGCATTCTGGGAGTTGTAGTCCGGTGGAGCGGGGGTTGGCGCCGCCCGCGGACCCAGCCG
GACTCCACTTCCCGTCGAGCCCTGCGACCGGCACCCACTCCACCAGGCTTGCTCGCACACAGACACACACACACAC
CGCTCTCCCCCTCACTCTTTCGCTCGCCGCGGCTGCTGCCAGTGTGTGGCTCTGTCTCTCCTCCGCTTTGCTGAGCCC
TCCCTTCTTCCTCTCAGTTCCTAGAGTCGACCGCCGCCGCCCGCCGAGAGAGAGGAGAAGGAGGTCGGTGGCGATAA
GGGGCGGAGGGGGGCATCAGATCGGGGCAGTATTAGGCGGGTGGCGGTTAAGAGGGAGTAAGAGGGAGCCCGGGT
GGCGGCTGAGCCTCCCCGCGGAGCCGACCCGGGAACAGGTGCGTCTTTTTTCTCTCTCCCCAATCCTCCACCCC
TTTTGACTCCCCGGCTTTTTCGTATCCCCCCACCCGCTTCTTTCTATCTTAAGCCTTTCTCCAACCCTGTTCCTTCTTTT
CCCTGCGGCCGCTCGGCTTGCCCCCGGGGGCCGCGTCCTCTTCGTGTGCCCCGGACGTAGCGCTCCCTGGAGCTGGG
TATGTCTTCGCCCCTCCCTTCGGGACAGCTCCCTTCCACTTCCCACCTTCGTACCCCATCCCCTGACTTGCCCTACCCC
CTTCTCGACCCCCTTCTCTCTTAGCCAGGTGAGACTCGTTCGCCACGATCAAGAGAGTCTTCTTCCCGGCTGGGCGG
GGGTCTCCATGGAAACGGGGGTCGGTTGATCCTGGGGGGGAAACCATAGGAATTACCCCACTCCTCGGAAAGGGAG
GTGGAGGCTATGGTCTTGTTAACTACCTGACTCCAACCCCCGATCCAAGGATCCGACGATCCGAAGGGAGGCTGGCT
AGCAGGGCAGGGCGAGAAAAGGCTTTTTTTGGGGGGGGGGGTGTCCGTGATGAAGTGTTGAAGAGACCGGGAGA
AAATGCCCTCCAACCTCAGAGGGGAGGTGCGACGGGTGCTCTTCAGGGCTGCTTTCTTCCCGGCGCTGGGGTGCGGG
AATCGTAGGGTAAGGGGTACCCCTAGGTGGCGGCGGGGCCTGGGTTCGGGAGTGGGAGTGCTGTGATGGGGCAGG
GGCAATTATCCGAGTCCCTGGAAAAAAGGCGGGGGATGACTTCGGAGCGCCCTGGCTCCGCTGCCCTCGCTCTAGGG
GCGGGGGCCGCCGGGCCGGGCGCGGCGGGGAGGGGGCTTAAATTGAAGGAAGATGAGATCGGGGGCAATTCATACT
```

TABLE 9-continued

CpG islands (CGIs) methylated in blood but not in bladder cancer. Provided
for each are: ID no.; Coordinates of selected regions containing relevant
CpG islands based on Homo sapiens full genome as provided by UCSC
(hg18, Mar. 2006); GeneName; Location of the probe used; the Fold
Change; and the sequence of the CGIs.

| No CGI | Gene Name | CGI probe location | FC |
| --- | --- | --- | --- |

AGCACCGGCAAGCCAGAGGGGAGATCCGGCGTGCAAGCCCTCCACCCGCTTCGCGCCAGGCCTGGAGGCAAGGGGT
CGGCGAGCGAAGCCGAGGGCTGGAAGGAGGGAGGCTCCGGTTACGGGGCCGGGTTTCGGGATCAGGGGCAATCCCC
CGGCCCTTGGAGAAGGAGGGAGAGGGATGGCCGCGAACCCCAGGGCTCCCCCACCCCGGGTCCTAAGGGGCGTGAG
GGACGGACAGCAGGCCCAGCGGAGCTGGATTCGAGCGGATCGCGGCCG (SEQ ID NO: 321)

14 chr17: 7584523-7585036
CGAGTTGGTGCGGGACGTGCCGCACGGCGTGCTTCTGCTGGACACCTTCCACAGGCTTGCCTCCCGCGAGGTGCGGC
TGCCCCGCGGCTTCCTCGGCTTCCCGTCCCGCGTGCTTTCCTGGAGTCCCTCCTTCCGGAGGCCCTCCTGCCTCCACG
TGTGCCCTTCTCCATGTCCAGCATTCGGGCGCCTCTTGTCTTTCTTCTGTTCCCTGGCTTCGGCGTCCCCGGGAGTGT
GACTCCCGCAGCGGGGTGCAGCTTTCCTCTGGGATGAGTGACCGGAGGGAACCCGCCTTCCCGGGCACGTCGCCAG
CCTCTTCCTCTTCTTCCCTAGGCTATCAAGCGGACTTATGACAAGAAGGCGGTGGATCTCTACATGCTGTTCAATAGC
GAGCTGGCCCTGGTGAACCGTGAACGGAACAAGAAATGGCCAGACCTGGAGCCCTACGTGGCCCAGTATTCCGGAAA
GGCGCGCTGGGTGCACATCCTCCGGCGTCGCATCGACAGAGTCATGACCG (SEQ ID NO: 322)

15 chr1: 27548507-27550603
CGAGGAGGCTGACCCGGAGCTGGAGCCCGCGTCGGGGGGAGAGCAGGAGCCGCGGCCCCAGCAAGCCCAGGTAGG
CGGGAGTGGCCCGTGGCTGCTCTCAACATCCGGAGCGGACTCCGGGCGGGGAGCGCTCCTGCCCAGGGCTGCGAGC
CGCCCGCGACCCAGGGCGCTCGGGGCAGGGGTGGGGAAAGAAGGGGCGCCCCGTCACTTGCCCCCTCTGCAGACCA
AGGCCGCGTCCCAGATCCTGGAGAATGGGGAGGAGGCCCCGGGGCCCGACCCCTCTCTCGACCGCATGCTCAGCAG
CAGCTCCTCGGTGTCCAGCCTTAACTCCTCCACGGTGAGGCGGGAGGGAGGGGACCCGGGCGGCCGGGGGGTGGAC
CCGTTCCGATGCGTAGCCCCTGCCTGCCCCTCCCTCGCCGCGGGACCCACCGCTGCAGCCCCCCAGCCTGCCACCTA
TGACCCGGGTCTGAAGCCTCCGCGCTGCCCGCGGCCCCGACGTGAGCCCTGCGAGCGGCCCTGACTCCCACCCACTC
CCGTCCGCAGCTGAGCGGCAGCCAGATGAGCCTGTCAGGCGACGCGGAGGCGGTGCAGGTCCGCGGCTCCGTGCAC
TTCGCGCTGCACTACGAGCCGGGCGCCGCCGAGCTGCGCGTGCACGTGATCCAGTGCCAGGGCCTGGCCGCCGCCC
GGCGCCGCCGCTCGGACCCGTGAGTGCCCCGCCGGCCAAGCGGGGCGGCTGTCACAGCCCAGCCCACCATTCAC
AGGGTCTCGGCCTCCTCGTCCTCATCTTCAAAATGGGAACAACAGCGTTATTGGGAGGCGTGCGATTAAGCGAGACA
ATCCCTGTAAAGCGCTTAGCACGAGGCCTGGCACGTGTTCGGGATGGTGGCTGGGGGAGCCCACAGGCAGGGGAGA
AGGCTCTGGGAGGGCCCCTCCTCACCTCGGGTTCTCACCTCCCCAGCTACGTCAAAAGCTACCTCCTCCCGGATAAG
CAGAGCAAGCGCAAGACGGCGGTGAAGAAACGGAATCTGAATCCGGTTTTCAACGAGACTCTCCGGGTGAGGCTGTG
ACCACGATGCGGTTCCCCGTTAATGAACTGGACGCCCCCTTCCTGCGGGGCTAGGTGGCAAGGGCAGCCAGTAACGT
CATTGCCCGGAGGATCGGCGGAGGGGGCCCATTAACTCGTTATCCAGTGTTGTCAGCCTCGTGGTGGGCGTGGTGAT
AGTGCAGGTCCCCATTAATGCCCTTAGGGGCTCCCCAGAATTCCATCATGGTAGGAACGCGGTAGGACCTGCCTCAG
CCAACTCGCGCAGCATCTACGCGGGCCACCAGCAGTGCTCCACTAAAGCTCACCTCCTGTCCTCAGTACTCCGTCCCG
CAGGCCGAGCTTCAGGGCCGCGTGCTGAGCCTGTCTGTGTGGCACCGCGAAAGCCTGGGTCGCAACATCTTTCTGGG
CGAAGTTGAAGTGCCCCTGGACACGTGGGACTGGGGCTCTGAGCCCACCTGGCTCCCCCTGCAGCCCCGGGTGAGG
CAGCCAGGCCGCGTGGGAGACCTGCGGCCCGGGTCTCCTGCATTTACCCCACCAGGCTCTCCCGCAGCCCCCTCAC
ACCCCGCCTTCGACAGAACCTCCCCTCAACCTCTTAACCTCATGGCCCCAGGCGAAGCCCGGCCGGCCACGGCCCCT
TCCCCGAGGGCGCTAGGACCCCTAGGTTCTGCCCCTGCAGGCCCCGCCGTCTCTTCTAGCCGCACCCCATCCGGGTC
TGCAGACCCCACCCTCCTGAGGCCCCTTTCCATTAGCCCCTGCTCCACGATAAGCCCGCCTCTCGCAGGTCCCACCCT
CTCCCGACGACCTTCCGAGCCGCGGGTTACTCGCCCTGTCCCTCAAGTACGTCCCCGCCGGCTCCGAGGGTGAGTGA
CAGCCGGAGAGGCCAAGCTGGACACGCCCTGAAAAGCGGGAGACTCCAGTCCCCGGGTTTGGGGGCGGTGGACTCC
ATCCGTGTGCGGGCCTGAGCCGAGCCTCTCCGCAGGCGCAGGACTGCCCCCGAGCGGGGAGCTGCACTTCTGGGTG
AAGGAGGCTCGGGACCTCCTGCCGCTGCG (SEQ ID NO: 323)

16 chr19: 10304689-10307022
CGCCCCCTTCCATTCCCCGCCCGCTTCCATCACTTGGTGTCGCCCAAGCCTGTGGTCGCCCCTAGCAACGCCCTCCCT
CACTTCGCAGTCGGTTTCCCCTTTCATCATCGCCCCCCCACGTCCCGCTCTTGGTCTCTCCCGATCCCGCGTGGATCC
GGTGCTTGGGCGCCCCCGCCAACGACCCCCGCGCACCTCAGCGTTGGTGTCGCCCGGTTCCCCCCGCGCACGCGCAC
CGTGGTATTTCCCGCCACGCTCCTACACCGCCCCCCCCAATACCTGGTTGGTCACGTCCCCGGGAGGCCCCGGATC
AGTATCTTGCGGCGGTTACGGAACTGGCGCTCGGTGTGTTCCAGGCGTTTCCGGATCTCTTCTGGATCTAGAGGCGG
CAGCTCTTCTTCCGGCGCCCGGCGCTCCGCGGCATCGCCGGCTTCGACTTCGGCCCCAGACTTAGGGCTCAGCGGGG
GCCGGTGAGTAACGGACACGTCCGCCGCCATCTTGGGAAACCCGGCGCCTTCTGGGACCAGCGAGCCGGGCGGAG
CGGCATAGAGCGGCAACGAGGGCGCGCCCGTCGATTGGCTGGGAGAAACCCCACCTCCTTCCCGCCCCCCTTGCCCC
GTTGGCTAAGCCCCAGCCCACCTCTCAAGAGTTCAAGCTGCGTCTGCGCGCCACAGGCCCCGCCCCCTTCCGTCGCA
GCGACGCTACTCAGTGGATGTGCACCTGGGTGGGAGAGACTTGCAGCGCGGGTGGAATCAAACCACAGATTAGGGA
GTTTGAAGGCTTTATTGGTGCGGAATCTGAGGGCACAGCCAAGCCCCGCCAACTTTGATCCCGGATCCCAGCGTCA
CTCAGCTCTGGACGGTTCTTCCCCATTGCTTCTGTCGGCTGCATAGACGTGAGGGGCAGATAGGTGCTCTCCTCCCT
AACATGGTAACTGCCGCTCCGTTGGTGCTCCCTGAAGACGTACATTAAGGCCAGTACGATAGTCACCACGCCCAGGG
TCAGTAACACCGCCACGAAGACGGGGACAAAGTGGGAGCTCCCAGCTGTGCAGAGAAAGCGCTAAGTCAATATGCGT
CCCTTCTGTCTCCAACCCCCCGCCCCCGGCTTACCGGTCCAGACCCGCAGCCCCGTGTTAGCTCACCCTCAATGTC
CATCACCACGACCAGGGTGTATTTGCCTCGTGAGCTGGACGCTTGGCACTGATAAGTACCATTATGTGTTACGTTGAC
GAAGAACGGGATCCCCACCGGCACCTCCCGGCTGGAGCCTTCCTTCAAACACCGCAGCTCGGGGTACGGGTTGCCCC
TGGCTTGGCACTGCAGGACGTGTCTCGTTTTATCTTTCCATTTCAAGTGCTGGGGGCATGTGGCTCGGTCAATTTTGG
GACCATCTGTGGAACCACCATGTGTGATCAGACACCCAACACACCCGAGGCACAGTGGTGCAGAGGAGCGTCTAATC
TTTCAGGGCAGGGTGGAGGGATTAAAGGTCAGGGTGACCGACTCACACAGGACTCGCAGCTGGACGTACTGTTC
CTGTGCAAGAACTCGCCGTCCACCTCGAGAGTGGCACTGCAGAAGAAGCTGCGTCCGTCGTCACTCTCGGTAGCATT
TAGCTGAAGTTGAGCTGGCTGCCCCGGGCCGCGGCCGGAACTCCGTCCAGCGTGACCTGGACTCGAGCCCCAGCC
ATGCAACTCACGGTCACTGTGGACCCCTCATGGGCGGTGGGCTCGCTGAGGTTCACAATGGGTCCTAGGAAGCCTAA
AGGCGGGGCATTGCCCAGGAGCTTAATGAACAGGACCTTCCTGTGGGTCAAGCCGCTCCCTCCGCCCTCCCCTTTCC
TCTCGGGATATCCGGGCCACGCTTTCGGCCGTTCAAGCCTCGCCCTCTTTCCGCGCTGTGTCCAGCTTCGGGCACTCA
GGCCCAACCCACGTTGCAACTGCTATTGGGGCAAGCCAGGCCCCACCTTTTCGGCTAGTCTCCGCCCCCTCTGCCAC
GCCCCCAGACTGCTGAGGCCGCGCCCCCTTCCCACGCCTCCTCTTACTAAAGACCGTCAAGTTCTCCCGGGCCTCCC TABLE 9-continued CpG islands (CGIs) methylated in blood but not in bladder cancer. Provided for each are: ID no.; Coordinates of selected regions containing relevant CpG islands based on Homo sapiens full genome as provided by UCSC (hg18, Mar. 2006); GeneName; Location of the probe used; the Fold Change; and the sequence of the CGIs.

| No CGI | Gene Name | CGI probe location | FC |
|---|---|---|---|

GTCTCTCGCCCCCTAGGGTCACGTTGCAGACGATCTCCCGGGCACCCTCCTGATCCGCGCGCGCCGTGGCTGTGGCT
GTGGCCGTTAGCGTGTCCCCGTGGTTCATGACTGTCGCATTCAGCATCTGGTCCCCAGCGCCAGGTAGACCTGGGC
CTCTGAGGCTGGAAAAAGCCCGTCTAGGGTGCAGTCCACCGGCCACGACGTTTCCACCTCCAAGAACCGGGGGGCCA
CGAGGCGCGGGGGGGTCACG (SEQ ID NO: 324)

17 chrX: 129132628-129134108
CGCGGCGGGCCTTCCCCATTGGCCAGCCAAACACAACCGACTGCGGCAGCCAATAGGAGCCGCTCTCCTGAACATTC
AGAGGATGGGTGCGCGTGGTGTGATAAGGGGATGTTGGCGCCTGGTACGCGCCCCCCTACATCTGGCAAGTCTGTAA
CAGAAACAGTTACACCCCCTACACACGCACACGCGTGCCCGCTGGCTCCCTCCTCTCAGCTGTACAGGCCCCGGACA
ACCCACTGCGTGTCTTGGCAGCGGCCTCCCAGGCTGCCTGGGGCCCGCGAGTGCACCTGCTCACTCATTAAGACAGA
GCATCCCTTTATCCCAAGGCGCGGGTCGGGTAGAGGGTGGGGGTAGAGGGGACGGGGTAGCGGGGACCGGGAAGG
CGCGGCTCAGCTGCCCGCTGCTCCCGAGGTGAAAGAGGTGCCTCCGCCCCCACCCCATCCCCGCAGAGTTGCGTTGC
TCCAGGGAGGCCGAAGTGATCCAGTGATGTCTTAAGGTGCAGCTCTTTGTCCTCCCCAGCTGTGCTCCCTGCCCGCT
GACCCCGTGCGCTCGAGCCAGTGGGGGTGGGGAGCCCGAAACCTATAACATAAACGGGGGCAAGGAGAAAGAAGTC
TATCCCGGGGTGGCGTGTGCCGCTGTCCCCACCCCGTCTCTTTCCTCCTGAGGCTTCTTCCCTCGGGTCCGTCCCGGG
AATGCAGGCAGGGGAGGGTGTGGGCCGAGGCGCGGCGGCGGCTGGAGCAGCGCGGTAGGGTCCTTCGCCAGAGCA
TCCGGTCCGAGGGCGCACACAGGCAGAAGGCTCGCGGCTCGTCCACTCTCCTCCCTCTCTCCTCCTCTCCCTGGCTTT
TGTGTTGGTGCCTCCGAGCTGCAAGGAGGGTGCGCTGGAGGAGGAGGAGGGGGCCCGGAGTGAGAGGCACCCCCT
TCACGCGCGCGCGCGCACACGGTGCCGGCGCACGCACACACGGGCGGACACACACACACGCGCGCACACACACACG
CACAGAGCTCGCTCGCCTCGAGCGCACGAACGTGGACGTTCTCTTTGTGTGGAGCCCTCAAGGGGGGTTGGGGCCCC
GGTTCGGTCCGGGGGAGATGGCGCAGCCCATCCTGGGCCATGGGAGCCTGCAGCCCGCCTCGGCCGCTGGCCTGGC
GTCCCTGGAGCTCGACTCGTCGCTGGACCAGTACGTGCAGATTCGCATCTTCAAAATAATCGTGATTGGGGACTCCAA
CGTGGGCAAGACCTGCCTGACCTTCCGCTTCTGCGGGGGTACCTTCCCAGACAAGACTGAAGCCACCATCGGCGTGG
ACTTCAGGGAGAAGACCGTGGAAATCGAGGGCGAGAAGATCAAGGTGATCCAGGGGGTCAGGTCCAGGAAGGGTGG
GACCCGGGAGGGGAACCTCGCCCGAGGCATAGCTCTAGCGGTTGTCGTCGTCCAGCGTCCAGCGCGTGGCGGTTTCG
CCTCTTGCTGAGCCGAGGACCCTCG (SEQ ID NO: 325)

18 chr21: 45648960-45650662
CGCACGCCCCTCCTGTCTCGCGTCCGTCCCTCCGTGCAGCCGGGGCAGGACCCTGCAGGGGCCTTGCGGGCCGGAG
GTGCCGGCTTCCTCCTCCGTCCCGTCCCCCCCGCGGTGACTCTATTCAAATCTCCCCCCTTCCCGCTGCCCCACCGGA
CTCAGGGGCTGGGGTCGTAGCCCGGCGGGCAGCGGTGTTCACCTTCCGCATAAACCTGGGCTTCCTCGCGGGGCAG
CCCCCGGGCCCTGTGCTGGGTCGCAGCCTCGGGCGGTTCCCTCGGGGCGGGACGTGTCCCCGTCCGTCCTCGCCCGT
CCCCGCCGCCCCCGGGTCCCGGCCCGCCCCGTCCTCGCAGCCGCAGGTCCGCTGCGGCGCCCGCCCCCCTCTCCCCT
CCCCGGGCCTTGCCCTGCTCGTCGCTCCGCCCCCTGCCCGGCCCCTGCCCGCCCCTGCCCGGCCTCCCAGCGGCGGCGGC
CGCGCCCGCCCCGCCCCCTGCCCGGCCCCTGCCCGGCCCCTGCCCGCCCCTGCCCGGCCTCCCAGCGGCGGCGGC
TGCAGCGCGGCGGTCCGAGCGGGTGCACCGCGGCGGAGGAGGCAGCATCCCGCGGCGCTGACGGTCCTGGGGAGA
GCATGGCGCCGAGGTGAGGCCGGGGCTGCGGGCAGGGGTTGGGGGACGCCAAGATGCGGCTGCGGGGGTCGCGGG
GGTCGCGGGGCTCGACCCGGTCCTGCGGGGGTCGCGGGGGTCCTGCGGGGTCTGACCCGTGCCTGTCCCCGCGCAGG
TGCCCCTGGCCATGGCCGCGGCGGCGGGGCCTCCTGGACGTGCTCGCCCCCTGGTCCTGCTGCTGCGGGGTCCGCG
CGGCCTCCGCGGAGCCAGGTAAGACCCGGGCGGGACGGGAAGGTTCGCGCCGGTGCCCGCCGGCCTCGCCGCCCTG
GCTGGGGTCCCCGCCCGGCTCCCTCACCCCCGCCCCGGCCGCTCTGGGTTCAGCCCCGGCCCTGCCCACGCGCGCAG
GAGGCGCCGGAGCCGGACGGAGCGGGGCGGGGTGGCCGGAGTCCCGCCGCGGGGACCGAACCTCCGCGGCCGGCGGGGTCGTCGGT
GGGAGGGGTGCGCGGTGCGAGCGGCCGGAGTCCCCGCGCGGGGACCGAACCTCCGCGGCCGGCGGGGTCGTCGGT
GCCGGGAGGGCTCGGGGCGGGGCCGCGGGGTCTCGGGAGACGCGGCCTCTGTCGCCGTCACGGCCTCGTCCCCGCA
GCGCCGGGTCCCGGGACTGACCGCGGGCGGAAGGCGGCGGAGCGCGGGGCGTCGTCTCCGCGTTTCCAACCTGTTG
AGGCTCCTCGCCGCGGGCCGGGCCTTGTGCGCCTCTGTCCCCGCCGCCCTCAGGCCTCTGTCCCCGCGCCCGCCGTG
GTGTCGGGTTGCGCGGTCCCCTTTGATGCCAACCGAGCGCCGCGCGGTCCGAGAACAATGCCCAGAAGCCGCTGCCC
CGCCGGCCTCGCCGCTTCCCGTGCGCGGCAAACGGTGCGCGGGGCCCGTGGGGACCTTCCTGCCTCCAACCCCGGG
ACCCAGTTCCCCACCACCTGCTAACCGGGGCCTCCTGCCTCCAGCCAGCCCAGCAGAGGCCGGGGGAGGCGGCGG
GGACGCGGACCCCAGGGGAGCCCCGCCCAAAGGGCCTGGGTGCCTTGTCGCGGGTGGAATCCACCCGGGGGTCCA
CGCAGCCAGCGCCTGCCTCCGACTCG (SEQ ID NO: 326)

19 chr10: 134864694-134865392
CGAGGACAGGGCCCGGCCCCACCCCGGGGCGAGTACGAGTTTGGAAGCAGTGAGGGCGCAGAGTGGGGCTCCATCT
GGGGAGAGGGCCTCTCTCTGTCACCCGGCCCCGTGCGGCAGTTCAGGGTCCCAGCATCTCCCCTGCACTGGGAGGCGG
CAGCCGTGCCCGGGGGGCGCCCGTGGTGGGCGGGTGCAAGAGAGAAGGGCGTCGGGTGTGCAAGCACCACCGGCCT
CCCATTAACAGCCTGCCCGGGCTCCGCCCACAGGAGCCACTGTCCACGTAACCTGCGTCTCTTTCTTTCAAGGAAAAG
AGAAGCCAGCCATGGCCAGGACCAGCAGCAGGGCCCCCTGCTCACCCACCTCGGTGTCGGATGTGGACTCGGACGC
ACTGTCACGGGGAAACTTCGAGGTGGGGTTTCGGCCTCAGAAGGTCCGTAAAAGCCGAGAGAGCGCAGCAGCCTGAG
GCTGGCGAGGACAGACGGCCAGCTGGCGGGGCCTCAGACGTGGAGGCAGTGACCCGATCGGCCAGGTCCAAAGGGG
TCGGCCCAGCCTTGTCCCCCGGCCCAGCCGGATTCCAGAGCTGCAGCCCCGGCTGGTGCAGCGCCTTCTACGAGGCC
GACTGCTTCGGGGCCGACGTCCACAACTACGTGAAGGACCTGGGGCGGCAGCAGGCGGACGGGGCCCTGCCCGACG
CCCAGAGCCCG (SEQ ID NO: 327)

20 chr9: 129556229-129557670
CGAATGCAGCATCCCTGCGCTCGGCGCCCTGCTATTGGCCAGAGATGATCTCACCGCCTCCCGGCCTGCGCGCGCCT
GATTGGCCGGTGCGGGGATGCTGCGCTCGCCGCCGGCGGGGCAGTCTTCAGGCGGGTCCGCGAGCGTGTGA
GCCTGGGGGAGCGAAGAGCCGACGCGCCTGGCATCTCCCAGGGGGCTCAGGGGGCAGGAGCGCGGAGACCCCGG
ACAGGGTCTTAACCCCTTCCCGCCAGCCCGAGCCCAGCATCCCCTCCAGCTCCCCTCGGCGTCCCAACCCCAAGCAA
AGCCATCCCCAAAGGATGCTCCGCAGAGAGGCGGGGTCCGGGTCCTCCCCTCCACCCCCTTCCGTTTAACCCTCTCA
CCGCCGCGGCGCGCCGTCTGCACTGCCCGGCCAGCTGGGCTGGGAGAGACCCGCGCCCCAGGCATGTCCAAGCCCAC
CTAGAGGGCGGGAGGGTGGCGGGCGCTCTGGCCCCAACCCCTGGCATCCGAAGCATCCCCCGCGTTTCCTGCTCCTCA TABLE 9-continued CpG islands (CGIs) methylated in blood but not in bladder cancer. Provided
for each are: ID no.; Coordinates of selected regions containing relevant
CpG islands based on Homo sapiens full genome as provided by UCSC
(hg18, Mar. 2006); GeneName; Location of the probe used; the Fold
Change; and the sequence of the CGIs.

| No CGI | Gene Name | CGI probe location | FC |
|---|---|---|---|

```
CTCAGTCTTCAGATCCCAGTCCGGCGCCCCCGGTACAATGGGGAGCCAGGGTGCCCAGGTCAGCCGCAAGGGCCAG
CGTACCAGGCGGAGGACCGGCAGGACGCCGGAGACCCCATCTCCCAGTCCCCCTGCCCCAGCTCTCTCCCTCCTGC
GGAGGAGGCAGAAACGGACCGGCATCTACCGCAGCCCAGAGTCCCAGGAGTGGCCGCCGAACCCTCACCCCGCGGA
GCGCCTGGGCGCCCAGAGGTGAGGCTGGGGTGACCCCGCCCCCTCCCCGGGTCGGCCGGGCCCAGCCCAGCCCGAC
CCTGCCGGGCGCCGCTGAGCTGCAGCTCCCCGGCTGGCTCTAGGGCCCCGGGCGGAGCGGCCGGGGGTCCCAGCCC
GGCGCGCGTGGCGGGGGCCGAGCCGCCCCCTCACCTGCACCTGCACGAAGGAGCCGCGGTAGAAGCAGCAGGCGGC
GGCCGACAGGGCACTCCACAGGCTGCACCGCTCGGTCATGGTGGGGCCAGGCTGCCGGGGCCGGGACGGTGTGGGG
GGGCGGTGGCCGGCGGGGCAGGGGCGCAGGGACCAACCGGCTAGGCACCGGCTGCGCGTGCCTCTCAGCGGCGCG
ATTACCTCATCGCCTTGTCGGGGAGGAGCGGGGAGGCGGGGCGGGGAGACCCCACCCTCCAGCCGGCCAGGGGAG
GGGAGGGGGCCATTGTTCCTCCCTCCGCCCGCCCCCGCTCCCAGCCCCTCGCCCCCGCCCTCCAGTTCCGCGCGC
TCGGGCTGCCTGGAGCTGCGGGCGCGGAGCGGAGGACCTGCCAAGGAGGGTATTACCGGGGGCAGCGGGATCGGGT
GGGGACCCATGGGCCAGCGAGGGGAGGTTCTGCCTCCCCCACTCGCCGCACCTCTAACAGACCGGGAGCG
(SEQ ID NO: 328)

21 chrX: 47305347-47306043
CGCCTGCGCGAGTCAGGACGAGCGCTTGCCCCAGATCTTGACGTTTCAGGCGGCCCCTCCTAATCCGGAACACGACT
CACATTCCGTTGGTCTTGCCTTGACAGACGTGACCCTGACCCAATAAGGGTGGAAGGCTGAGTCCCGCAGAGCCAAT
AACGAGAGTCCGAGAGGCGACGGAGGCGGACTCTGTGAGGAAACAAGAAGAGAGGCCCAAGATGGAGACGGCGGCG
GCTGTAGCGGCGTGACAGGTGAGGGCGGGCCCGGGAGGGCTCGGTTTCTGGAGCGGCTGCCGGGCACGGGCAGGG
AGCCCGGACCGAAAGCTCAGCTCCAGGATGGCTGCGCTTGGGCCCCGGCGTTCCCTGCCCGGAACCGGAGGAGTGG
TTTGACCCGGGGCGAGACCATCGTCGACAGCGGGGTGGGTGGGTAACAGGAATAGGCGGGCAAGGCTGCGGGTG
ATGGTTTCGCCCGCTGCTAGTGGTGGTGCGCCTGCGCAGAGCCGGAAGCCCTTTGGTAGGCGGGACCCGACCGAGT
GGTGCCGGGATTCCGTCTTAACCCCCGCTAAGGTGTCCAATGACCTTTCCTTACCAACTGCGGGAGTGTGTGGAAA
CGCGGTTCACTCCCCGGTTTCCTTATTCTGGATCAGTGTCTGACCGCCCCGCCGGGAGAATGTCAGGATTCTCGCCT
CT (SEQ ID NO: 329)
```

TABLE 10

Hypermethylated genes and CGIs in bladder cancer.

| Symbol | CGI | Fold Change |
|---|---|---|
| MEIS1 | chr2: 66525936-66527140 | 4.76 |
| NR2F2 | chr15: 94688798-94689034 | 2.93 |
| SOX21 | chr13: 94152191-94153185 | 2.8 |
| MAB21L1 | chr13: 34950554-34951119 | 2.68 |
| OTX1 | chr2: 63134539-63134851 | 2.67 |
| MGC2752 | chr19: 63784504-63785085 | 2.64 |
| IRX3 | chr16: 52873104-52882105 | 2.63 |
| PAX9 | chr14: 36205265-36206099 | 2.62 |
| FOXC1 | chr6: 1549606-1560865 | 2.5 |
| DLX5 | chr7: 96488158-96489487, chr7: 96489900-96490182 | 2.45 |
| NR4A2 | chr2: 156892636-156892878, chr2: 156893804-156894601 | 2.45 |
| CNTNAP1 | chr17: 38089258-38089793 | 2.35 |
| FOXF2 | chr6: 1338049-1339169 | 2.35 |
| HHEX | chr10: 94441310-94441717 | 2.33 |
| PRKCZ | chr1: 2072175-2072389, chr1: 2106293-2106661 | 2.31 |
| HOXA7 | chr7: 27164708-27165039 | 2.27 |
| MSX2 | chr5: 174091287-174092335 | 2.26 |
| SLC45A4 | chr8: 142288380-142288627 | 2.22 |
| FLJ44006-BCL2L11 | chr2: 111591678-111597436 | 2.21 |
| MAP2K2 | chr19: 4059920-4060207 | 2.2 |
| SHH | chr7: 155288454-155292175 | 2.19 |
| chr13: | chr13: 49605587-49606020 | 2.19 |
| MAD1L1 | chr7: 2082894-2083307 | 2.18 |
| hsa-mir-196a-1 | chr17: 44074360-44075233 | 2.17 |
| NXPH1 | chr7: 8449658-8450236 | 2.17 |
| chr18: | chr18: 5186244-5187389 | 2.12 |
| C10ORF114 | chr10: 21828640-21829594 | 2.1 |
| SIX3 | chr2: 45014932-45016562, chr2: 45013398-45013616 | 2.08 |
| TFAP2A | chr6: 10530308-10530634, chr6: 10498025-10498551 | 2.08 |
| ISL2 | chr15: 74414579-74414893, chr15: 74419318-74422570 | 2.05 |

TABLE 10-continued

Hypermethylated genes and CGIs in bladder cancer.

| Symbol | CGI | Fold Change |
|---|---|---|
| VAX2 | chr2: 70984709-70985764 | 2.04 |
| AMZ1 | chr7: 2724531-2724783 | 2.01 |
| CYB561 | chr17: 58865386-58865618 | 1.99 |
| HOXD3 | chr2: 176737660-176738187 | 1.97 |
| SIM1 | chr6: 101003802-101004273, chr6: 101002495-101002783 | 1.95 |
| EFNB2 | chr13: 105943410-105943788 | 1.91 |
| GAD1 | chr2: 171384799-171385226 | 1.91 |
| MSX1 | chr4: 4915358-4915735, chr4: 4910534-4911092 | 1.9 |
| FOXA1 | chr14: 37137198-37138958 | 1.88 |
| HDGFL1 | chr6: 22677564-22678684 | 1.85 |
| chr13: | chr13: 49595986-49600287 | 1.84 |
| chr16: | chr16: 87372445-87372706 | 1.84 |
| EVX1 | chr7: 27251165-27252762 | 1.83 |
| UNG2 (CCNO) | chr5: 54554812-54555385 | 1.83 |
| ONECUT2 | chr18: 53254153-53259851 | 1.81 |
| HSF2BP | chr21: 43902100-43904249 | 1.8 |
| chr1: | chr1: 119350668-119352843 | 1.8 |
| FOXD3 | chr1: 63554983-63563059 | 1.79 |
| FOXA2 | chr20: 22514822-22515055, chr20: 22510737-22514104, chr20: 22505518-22507240 | 1.77 |
| GRIK2 | chr6: 101953488-101953856 | 1.77 |
| chr2: | chr2: 45249374-45251690 | 1.77 |
| SIX1 | chr14: 60178708-60179539 | 1.76 |
| HOXA9 | chr7: 27170441-27172987 | 1.75 |
| FOXD2 | chr1: 47671713-47671985, chr1: 47682300-47683607, chr1: 47672249-47672972 | 1.73 |
| NKX2-8 | chr14: 36122886-36123441 | 1.72 |
| ZNF274 | chr19: 63420090-63420541 | 1.72 |
| TAF4 | chr20: 60061693-60062033 | 1.71 |
| SIX2 | chr2: 45085286-45086054 | 1.7 |
| chr8: | chr8: 145909302-145910517 | 1.7 |
| PCDH7 | chr4: 30330303-30333940 | 1.69 |
| PITX2 | chr4: 111774415-111774953 | 1.68 |
| TCF7L1 | chr2: 85213468-85216104 | 1.68 |
| chr6: | chr6: 10492952-10493478 | 1.68 |
| SOX7 | chr8: 10624024-10624296 | 1.66 |
| HOXC4 | chr12: 52726910-52727810 | 1.65 |
| PITX1 | chr5: 134390992-134393045 | 1.65 |
| PCDHGA12 | chr5: 140790679-140792801 | 1.64 |
| chr6: | chr6: 170422815-170423038 | 1.64 |
| EPN1 | chr19: 60907042-60907388 | 1.63 |
| DLX6 | chr7: 96469320-96469736 | 1.62 |
| hsa-mir-10b | chr2: 176723195-176723460, chr2: 176720618-176720921 | 1.62 |
| SIM2 | chr21: 36990064-36995761 | 1.61 |
| CACNA2D4 | chr12: 1844001-1845219 | 1.6 |
| HOXA5 | chr7: 27149139-27152087 | 1.6 |
| NCK2 | chr2: 105864220-105865009 | 1.6 |
| OSR1 | chr2: 19424445-19425131 | 1.58 |
| C17orf27 (RNF213) | chr17: 75936057-75936582 | 1.57 |
| chr6: | chr6: 169051743-169052507 | 1.56 |
| EVX2 | chr2: 176652334-176656692 | 1.53 |
| ZNF503 | chr10: 76825135-76839606 | 1.52 |
| chr5: | chr5: 92931996-92934631 | 1.52 |
| KIAA1303 | chr17: 76404186-76404427, chr17: 76390187-76390410 | 1.48 |

TABLE 11

Genomic distribution of methylated probes in bladder cancer.

| Probe location | % on array | % in bladder cancer |
|---|---|---|
| divergent promoter | 2.5 | 2.4 |
| downstream | 3.9 | 4.0 |
| inside | 52.4 | 52.3 |
| promoter | 26.0 | 25.9 |
| intergenic | 15.3 | 15.3 |

TABLE 12A

Overview of the CGIs differentientially methylated between tumor and control urine.

| Symbol | CGI | Fold Change |
|---|---|---|
| HOXA9 | chr7: 27170441-27172987 | 16.53 |
| PENK | chr8: 57520681-57521969 | 14.69 |
| PCDH7 | chr4: 30330303-30333940 | 12.00 |
| KCNA1 | chr12: 4888847-4891432 | 11.89 |
| HLX1 | chr1: 219134071-219134808 | 10.46 |
| POU4F2 | chr4: 147778656-147781351, chr4: 147777682-147778033 | 10.17 |
| LHX4 | chr1: 178464743-178471598 | 9.79 |

TABLE 12A-continued

Overview of the CGIs differentientially methylated between tumor and control urine.

| Symbol | CGI | Fold Change |
|---|---|---|
| FOXD2 | chr1: 47682300-47683607, chr1: 47672249-47672972 | 9.67 |
| LBX1 | chr10: 102986025-102986636 | 9.44 |
| chr11: 115956893-115956940 | chr11: 115955870-115957122 | 9.03 |
| LMX1A | chr1: 163590111-163590435 | 8.86 |
| BHLHB5 | chr8: 65662303-65662699, chr8: 65661156-65661382 | 8.61 |
| OTX1 | chr2: 63134539-63134851 | 8.22 |
| GAD2 | chr10: 26544390-26547440 | 8.02 |
| EVX2 | chr2: 176652334-176656692 | 8.02 |
| FLJ44006-BCL2L11 | chr2: 111591678-111597436 | 7.89 |
| ONECUT2 | chr18: 53254153-53259851 | 7.75 |
| ZIC1 | chr3: 148619591-148620015 | 7.33 |
| FOXA1 | chr14: 37137198-37138958 | 7.24 |
| DSC3 | chr18: 26875488-26877115 | 7.19 |
| SIM2 | chr21: 36990064-36995761 | 6.78 |
| MEIS1 | chr2: 66525936-66527140 | 6.74 |
| FEZF1 | chr7: 121727243-121727884 | 6.62 |
| ZNF503 | chr10: 76825135-76839606 | 6.57 |
| SLC35F3 | chr1: 232106922-232108080 | 6.34 |
| FEZF2 | chr3: 62331811-62332352 | 6.26 |
| NR4A2 | chr2: 156893804-156894601 | 6.20 |
| EN1 | chr2: 119329502-119332035 | 5.59 |
| PCDH10 | chr4: 134291113-134293078 | 5.53 |
| OSR1 | chr2: 19424445-19425131 | 5.23 |
| ZIC4 | chr3: 148591199-148594390 | 5.00 |
| CBLN1 | chr16: 47868915-47869809 | 4.92 |
| HMX2 | chr10: 124891898-124892607 | 4.89 |
| FOXB1 | chr15: 58083428-58085812, chr15: 58079172-58079459 | 4.76 |
| chr19: 057648585-057648629 | chr19: 57648469-57649057 | 4.58 |
| DPP10 | chr2: 115635208-115637235 | 4.55 |
| chr7: 032768257-032768301 | chr7: 32768010-32768497 | 4.48 |
| C10orf114 | chr10: 21828640-21829594 | 4.44 |
| FOXD3 | chr1: 63554983-63563059 | 4.39 |
| chr5: 092933638-092933682 | chr5: 92931996-92934631 | 4.25 |
| TCF7L1 | chr2: 85213468-85216104 | 4.21 |
| VAX2 | chr2: 70984709-70985764 | 3.99 |
| CBLN2 | chr18: 68359955-68362770 | 3.97 |
| PCDHGA12 | chr5: 140790679-140792801 | 3.94 |
| chr21: 037857850-037857894 | chr21: 37857725-37858416 | 3.89 |
| HOXA7 | chr7: 27164708-27165039 | 3.79 |
| GRIK2 | chr6: 101953488-101953856 | 3.77 |
| NKX2-8 | chr14: 36122886-36123441 | 3.65 |
| SOX9 | chr17: 67627870-67631593 | 3.64 |
| chr18: 005186349-005186393 | chr18: 5186244-5187389 | 3.50 |
| SOX21 | chr13: 94152191-94153185 | 3.43 |
| SNRPF | chr12: 94776152-94776377 | 3.39 |
| MSC | chr8: 72916429-72917309 | 3.18 |
| PITX1 | chr5: 134390992-134393045 | 3.05 |
| SOX7 | chr8: 10624024-10624296 | 2.99 |
| chr2: 042182832-042182879 | chr2: 42182944-42183157 | 2.97 |
| TBX15 | chr1: 119333515-119333719 | 2.96 |
| SIM1 | chr6: 101003802-101004342 | 2.91 |
| PFKFB1-APEX2 | chrX: 55043085-55043710 | 2.89 |
| GATA2 | chr3: 129688183-129694961 | 2.86 |
| chr5: 122462228-122462286 | chr5: 122461778-122463450 | 2.82 |
| GPR103 | chr4: 122521018-122521740 | 2.81 |
| SIX2 | chr2: 45085286-45086054 | 2.80 |
| SFMBT2 | chr10: 7489383-7495345 | 2.79 |
| NXPH1 | chr7: 8449658-8450236 | 2.73 |
| CA10 | chr17: 47590175-47591465 | 2.71 |
| CNTNAP5 | chr2: 124498723-124499725 | 2.66 |
| ZNF274 | chr19: 63420090-63420541 | 2.62 |
| HOXD3 | chr2: 176737660-176738187 | 2.61 |
| PITX2 | chr4: 111774415-111774953 | 2.55 |
| OLIG2 | chr21: 33316999-33322115 | 2.54 |
| FOXA2 | chr20: 22505518-22507240, chr20: 22510737-22514104 | 2.53 |
| DBC1 | chr9: 121170908-121172035 | 2.49 |
| PAX2 | chr10: 102497473-102499636 | 2.45 |
| MAB21L1 | chr13: 34950554-34951119 | 2.35 |
| CYP26B1 | chr2: 72224630-72228512 | 2.31 |
| CBLN4 | chr20: 54012011-54014085 | 2.26 |

TABLE 12A-continued

Overview of the CGIs differentientially methylated between tumor and control urine.

| Symbol | CGI | Fold Change |
|---|---|---|
| GAD1 | chr2: 171384799-171385226 | 2.25 |
| HHEX | chr10: 94441310-94441717 | 2.22 |
| chr9: 013268499-013268548 | chr9: 13268313-13269805 | 2.20 |
| FOXF2 | chr6: 1338049-1339169 | 2.17 |
| DLX5 | chr7: 96489900-96490182 | 2.08 |
| TBX3 | chr12: 113589232-113589931 | 2.04 |
| MEIS2 | chr15: 35174679-35174906 | 2.04 |
| PTGER3 | chr1: 71284813-71286392 | 2.04 |

TABLE 12B

Overview of CGIs associated with progression of NMI-BC.

| Symbol | CGI | FC |
|---|---|---|
| GPR103 | chr4: 122520930-122520974 | 1.81 |
| chr2: 042182832-042182879 | chr2: 042182832-042182879 | 1.96 |
| KCNA1 | chr12: 004890074-004890118 | 2.01 |
| HLX1 | chr1: 219134113-219134157 | 2.14 |
| DBC1 | chr9: 121171898-121171944 | 2.59 |
| GPR103 | chr4: 122521031-122521075 | 4.17 |
| TBX3 | chr12: 113609259-113609303 | 2.76 |
| GATA2 | chr3: 129693434-129693486 | 2.20 |
| TBX2 | chr17: 056833879-056833928 | 2.15 |
| TBX2 | chr17: 056835246-056835290 | 2.10 |
| ZNF577 | chr19: 057082979-057083023 | 2.08 |
| MSC | chr8: 072916695-072916739 | 1.82 |

EXAMPLES

Example 1

The CpG island hypermethylations as indicated in the Tables 1-5 are the result of comparative studies using well characterized patient samples. Both tumor samples and controls were analyzed. The DNA was extracted directly from the tumor and control tissue. DNA samples were analyzed using a CpG island microarray comprising 200.000 CpG islands (Agilent Technologies Inc.). The results obtained are indicated in the various Tables 1-5 as listed herein.

Example 2

Materials & Methods

Patient Samples, Ethics Statement and DNA Isolation

Samples from 44 fresh frozen bladder cancer tissues were collected, representing 29 non-muscle invasive tumors (19 with FGFR3 mutation (NMI-mt) and 10 without (NMI-wt)) and 15 muscle-invasive tumors (MI). Tumor tissue of patients was obtained from the Department of Urology of the Erasmus MC, Rotterdam. The medical-ethical committee of the Erasmus MC Rotterdam approved the project. All patients gave written informed consent. For validation, 90 formalin-fixed, paraffin-embedded (FFPE) bladder cancer samples (27 Ta NMI-mt, 13 Ta NMI-wt, 10 T1-mt, 14 T1-wt, 26 MI) were collected from the Department of Pathology. Usage of these samples was performed according to standards presented in "The Code for Proper Secondary Use of Human Tissues in The Netherlands" (http://www.federa.org). Tumor samples were included only if at least 80% of the sample consisted of cancer cells, as verified by H&E staining. DNA from tumor tissue was isolated with the DNeasy Tissue kit (Qiagen, Hilden, Germany), according to the instructions of the manufacturer. Commercially available normal human genomic blood DNA (Promega, Madison, Wis., USA) was used as a reference in the genome wide analysis and the GGMA. DNA isolated from cells present in normal urine of four healthy persons of more than 50 years old was used as reference DNA in the GGMA validation assay.

Differential Methylation Hybridization (DMH) and Data Analysis

DNA amplicons were prepared for hybridization according to the DMH (differential methylation hybridization) protocol described by Yan et al [Yan et al. 2002.) Methods Mol Biol 200: 87-100]. Briefly, 0.5 µg of genomic DNA was digested with the four base (T^TAA) restriction enzyme MseI, which restricted genomic DNA into fragments less than 250 bp in length, while leaving the GC-rich CGIs relatively intact. Subsequently, the sticky ends of the fragments were ligated to linker primers. Samples were then digested with the methylation-sensitive restriction enzymes HpaII and BstUI to increase the genome coverage and to ensure complete digestion. Reference samples were treated in the same way to generate amplicons. PCR reactions (20 cycles) were performed using the purified, digested, linker ligated DNA as template to generate final target amplicons, followed by coupling to fluorescent dyes (Cy3 in case of human genomic reference DNA and Cy5 in case of tumor samples) before hybridizing to the Agilent 244K CpG island microarray. The pooled amplicons were co-hybridized on the array. Using this approach, genomic DNA fragments containing unmethylated CpG sites in one sample (e.g. the human genomic reference DNA) were degraded by restriction digestion and not amplified. However, corresponding DNA fragments in the other sample (the bladder tumor) that contain methylated restriction sites were protected from digestion and subsequently amplified by PCR. Differentially methylated sequences were identified by comparing hybridization signals between fluorescently labeled tumor (Cy5) and reference (Cy3) amplicons.

All microarray data generated are compliant with current MIAME standards according to Brazma et al [Brazma 2009. Scientific World J 9:420; Brazma et al. 2001. Nat Genet 29:365]. Normalization, preprocessing of raw data and statistical analysis were done using Bioconductor packages in an R programming environment (http://www.r-project.org/). Raw hybridization signals were normalized by applying the within-array global "lowess" normalization method [Yang et al. 2002. Nucleic Acids Res 30: e15], which assumes that the bulk of the probes on the array are not differentially expressed. The normalization also includes a pre-processing step, as a result of which the normalized intensities were log 2-transformed. The log 2-transformed intensities were then subjected to further statistical testing to determine which loci were differentially methylated. The linear model "limma" was applied [Smyth 2004. Stat Appl Genet Mol Biol 3: Article3]. We performed the following comparisons: All tumors vs. Blood, NMI-mt vs. NMI-wt, NMI-mt vs. MI, and NMI-wt vs. MI, to find genes that have different methylation profiles across the groups compared. These comparisons are analogous to a classical two sample t-test analysis.

The p-value threshold was calculated using the Benjamini and Hochberg method [Benjamini et al. 2001. Behav Brain Res 125: 279]. The loci corresponding to p-values less than 0.05 and a log fold change of either greater than 0.5 or less than −0.5 with more than 2 probes representing the same CGI were classified as differentially methylated. We left chromosome Y probes out of the subsequent analyses.

Illumina Custom Golden Gate Methylation Assay and Statistical Analysis

We designed a custom Golden Gate Methylation assay interrogating 384 CpG containing probes representing 238 CGIs, 184 genes, and 46 intergenic regions. The selection of the probes was based on the differentially methylated loci in the genome-wide analysis. Probes were included to detect methylation in all bladder subgroups, but also probes that appeared to be specific for a certain subgroup compared to others, and some probes specific for progression or death of disease. The methylation assay is an adaptation from the Illumina high-throughput SNP genotyping assay described by Fan et al. [Fan et al. 2003. Cold Spring Harb Symp Quant Biol 68: 69]. In short, non-methylated cytosines (C) were converted to uracil (U) by treatment with bisulfite. Sodium bisulfite modification of genomic DNA was carried out using the EZ DNA Methylation Gold Kit (Zymo Research Corp, Orange, Calif., USA) according to the manufacturer's protocol, using 0.8 µg of FFPE DNA. The conversion efficiency was monitored by PCR with universal BS specific primers provided with the kit. Arrays were run at Service XS, Leiden, the Netherlands according to the manufacturer's protocol and as described by Bibikova et al. [Bibikova et al. 2006. Genome Res 16: 383].

Data were analyzed with Illumina's BeadStudio Methylation module software. All array data points were represented by fluorescent signals from both methylated (M) and unmethylated (U) alleles. The average methylation value $\beta$ was derived from approximately 30 replicate methylation measurements for each locus. The methylation level was given by $\beta=(\max(M, 0))/(|U|+|M|+100)$. The $\beta$-value ($0 \leq \beta \leq 1$) reflects the methylation level of each CpG site where 1 represents fully methylated and 0 represents unmethylated. At each locus for each sample, the detection p-value was defined as 1-p-value computed from the background model characterizing the chance that the signal was distinguishable from negative controls. Using this as a metric for quality control for sample performance, 6 FFPE samples (6%) were dropped from the analysis, because they either had very low overall signal intensities or >25% of loci failed. The significant differences were assessed by comparing the average $\beta$ value per locus per group. Significant loci were selected on the basis of an average $\beta$ value ratio larger than 1.4 and a difference between the average $\beta$ value ($\Delta\beta$) larger than 0.3.

Validation of Methylation of Individual CGIs

We used the MS-SNAPSHOT method described in [Gonzalgo and Liang 2007. Nat Protoc 2: 1931; Lurkin et al. 2010. PLoS One 5: e8802] to investigate methylation in urine DNA quantitatively. The method involves the bisulfite conversion of genomic DNA and the subsequent amplification of interested genomic region. This is followed by the methylation specific single nucleotide primer extension with CpG specific probes and finally the fragments are visualized on a ABI sequencer. To test the method, methylation of MEIS1 gene was investigated using normal, patient urine samples along with bladder cancer cell lines. In vitro methylated DNA was used as a positive control. A list of primers and probes used is given in Table 6.

Results

A Genome Wide Methylation Profile for Bladder Cancer

To investigate global DNA methylation in bladder cancers, we analyzed 44 bladder tumors on Agilent 244K human CpG island microarrays using differential methylation hybridization. We found that 729 different probes were significantly more methylated in bladder tumors compared to blood with a log fold change greater than 0.5 and a p value of <0.05. To select the most hypermethylated CGIs, we used as an additional criterion that 3 or more CpG dinucleotides should be highly methylated in a specific CGI. This selection generated a list of 82 CGIs representing 71 genes and 11 CGIs not directly associated with a gene according to the Agilent information file. These are shown in Table 10. The gene showing the highest degree of methylation was MEIS1 with a log fold change of 4.8 for the most highly methylated probe and an average log fold change of 2.2 across the 10 probes that were present on the array for this CGI (FIG. 1). We observed that for most of the significantly methylated CGIs, the adjacent CpG dinucleotides within a CGI were co-methylated. In contrast, CGIs neighboring a methylated island were usually not methylated.

Methylation of Intronic CGIs is Associated with Reduced Gene Expression

The 244k array contains probes for CGIs as displayed in the UCSC genome browser (http://genome.ucsc.edu/cgi-bin/, build 19). Of the CGIs represented on the array, 26% is located in promoter regions. Many studies have shown that aberrant methylation of CGIs in promoter regions represents one of the most frequent epigenetic events associated with gene silencing in cancer. In our analysis we observed that there was no specific preference for methylation of promoter regions. Instead, methylation was distributed proportionally over CGIs in promoter regions, within genes and in intergenic regions (Table 11). Examples are shown for CGIs in two of the selected genes, MEIS1 and NR4A2 (FIG. 1). To investigate whether methylation outside promoter regions also repressed gene expression, we next compared genes with methylated CGIs with available genome-wide expression profiles of bladder cancer using the Oncomine database [Blaveri et al. 2005. Clin Cancer Res 11: 4044; Dyrskjot et al. 2004. Cancer Res 64: 4040; Dyrskjot et al. 2003. Nat Genet 33: 90; Lindgren et al. 2006. Oncogene 25: 2685; Modlich et al. 2004. Clin Cancer Res 10: 3410; Sanchez-Carbayo et al. 2006. J Clin Oncol 24: 778]. This information could be obtained for 54 genes. Out of these 54 genes, 22 showed promoter CGI methylation and a positive correlation with low expression was observed in 17 genes (77.3%). The remaining 32 genes showed methylation of CGIs within introns. Interestingly, 23 of these genes also showed low expression (71.9%) in bladder cancers. These data suggest that not only promoter CGI methylation but also methylation of intronic CGIs leads to reduced gene expression. The expression profile box plots of MEIS1, NR4A2 and HOXA9 are shown in FIG. 1.

Analysis of Individual Subgroups Shows NMI-Wt Tumors to have a Highly Methylated Profile To explore whether global DNA methylation can identify subgroups of bladder cancer, we performed an unsupervised analysis by means of a principal component analysis (PCA) using all probes on the array (244K) (FIG. 2A). The first three components of the PCA explained 42.4% of the variability between the samples suggesting that there is a reasonable discrimination between the subgroups. This unsupervised analysis indicates the presence of two clusters of bladder cancer patients. The NMI-wt tumors (in green) clustered closely together and separate from the NMI-mt (in blue) and MI tumors (in red). Furthermore, we looked at the individual subgroups of bladder tumors. NMI-wt tumors showed a 2.7 to 4.6 times higher number of hypermethylated probes compared to the NMI-mt and MI groups (FIG. 2B). A list of genes differentially methylated between subgroups is given in Table 12.

Figure 3:
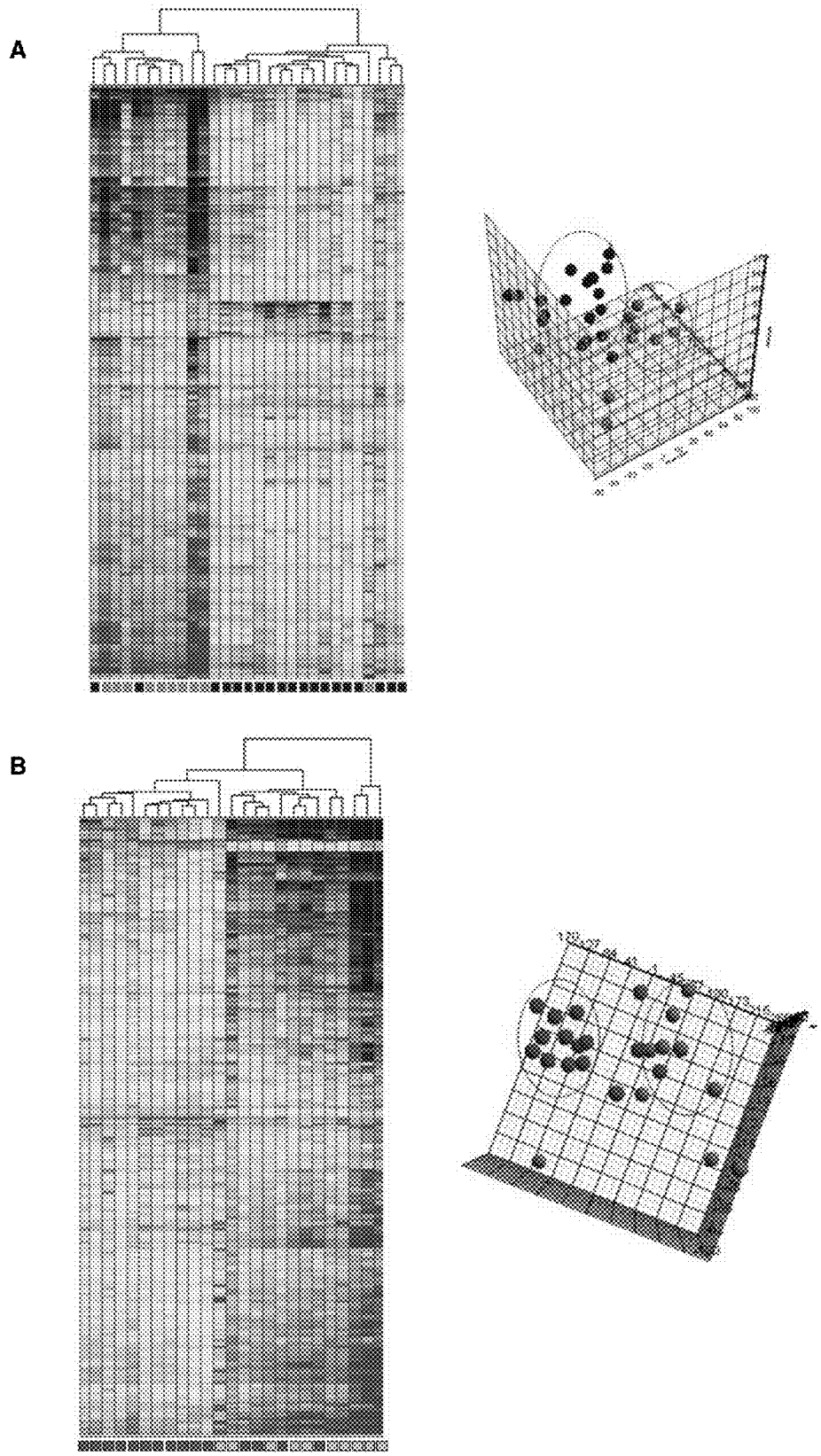
Figure 3C:
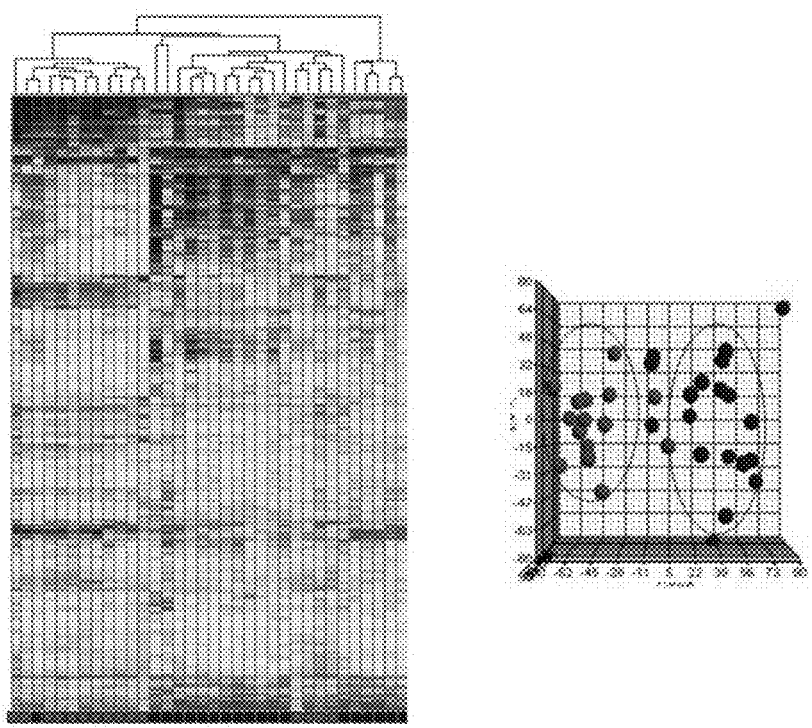

We next clustered the different subgroups of bladder tumors based on all probes that were differentially methylated between two groups with a p value of <0.05, regardless of the log fold change. For clustering of probes differing between NMI-mt and MI tumors, we had to use a p-value <0.5 because not many differences exist between these two groups. We employed a hierarchical clustering algorithm choosing Euclidian distance and complete linkage to organize the three different comparisons (FIG. 3). We then performed principal component analysis on the same data. The probes along with gene names and p-values are listed in Table 12. These semi-supervised analyses showed clearly that the different bladder cancer subgroups can be identified based on their methylation pattern.

Genes Hypermethylated in Bladder Cancer Often are PcG Target Genes

Polycomb group (PcG) proteins function as transcriptional repressors of genes that have been implicated in stem cell self renewal and differentiation. These PcG target genes have been shown to be particularly prone to DNA methylation in cancers [Ohm et al. 2007. Nat Genet 39: 237; Widschwendter M et al. 2007. Nat Genet 39: 157; Schlesinger et al. 2007. Nat Genet 39: 232]. We investigated whether DNA hypermethylation in bladder cancer was more present in PcG target genes by matching our list of 71 genes from Table 10 with recent studies showing that 8-14% of all genes in the genome to be PcG regulated [Bracken et al. 2006. Genes Dev 20: 1123; Lee et al. 2006. Cell 125: 301]. Notably, we found that 63.3% of the hypermethylated genes in bladder cancer were PcG target genes, with a representation factor of more than 3 (http://elegans.uky.edu/MA/progs/representation.stats.html) (FIG. 4A). This was approximately the same for all different tumor subsets. Twenty-two PcG regulated genes were methylated in all three subtypes, while a striking 81 genes were specific to NMI-wt tumors (FIG. 4B). A list of the PcG target genes methylated in bladder cancer is given in Table 8.

Genes Methylated in Blood Compared to Bladder Cancer

We also observed 21 CGIs that were methylated in blood but not in bladder tumors. These are listed in Table 9. We compared our results with a study based on methylated DNA immunoprecipitation (MeDIP), in which the genome-wide methylation pattern in blood was investigated [Rakyan et al. 2008. Genome Res 18: 1518]. We found a 90% correlation with their study.

Validation of Hypermethylation and Markers for Diagnosis and Progression

Next we set out to validate the selected significant CGIs on a custom Illumina platform based on bisulfite conversion of tumor DNA. The following CGIs were included in the custom array:

1) Differential methylation between tumors and blood (Tables 9 and 10);

2) Probes that could be of use as biomarkers to distinguish the subgroups. There were 7 CGIs representing 6 genes found to differentiate between NMI-mt and NMI-wt tumors. In the MI versus NMI-wt comparison, we found 17 CGIs representing 13 genes to be significant. No significant probes were found between the MI versus NMI-mt subgroups at a p-value <0.05. Therefore we decided to include probes from 6 CGIs representing 6 genes with a p-value <0.5;

3) CGIs that were associated with progression and survival. In all cases the CGI to be validated had at least 3 CpGs that were highly methylated.

We employed a hierarchical clustering algorithm on the average beta values per subgroup with all 384 probes on the array choosing Euclidian distance and complete linkage. The analysis clearly separated the bladder tumors from normal urine and blood (FIG. 5A). We were able to validate more than 70% of the probes hypermethylated in all bladder tumors. For example, in the custom 384-plex GGMA, there were 205 probes which were methylated in bladder cancer but not in blood based on our Agilent array data. Of these, 147 probes were also methylated in bladder cancer but not in blood in the GGMA. These probes are shown in the heat map (FIG. 5B). We also included DNA isolated from cells present in urine of healthy individuals, which most likely are derived from normal urothelial cells. Eighty % of the probes validated against blood were also not methylated in urine. For the different subgroups of bladder tumors, the number of probes validated varied between 65-75% of probes compared to blood and 76-83% compared to urine.

CGIs that are differentially methylated between tumors and urine from non-bladder cancer controls represent potential biomarkers for urine tests (Table 12). We validated several of these using a bisulfite specific PCR followed by a Snapshot assay for the CpG. The results of these analyses are shown in FIG. 5C. We were able to detect methylation in urine DNA quantitatively using this method. We investigated MEIS1 gene methylation at two CpG sites using different probes (MEIS1 A and B). The black peak (Cytosine) represents methylation and red peak (Thymine) represents no methylation. In vitro-methylated DNA (IM), BC patient urine sample (PU) and bladder cancer cell lines (RT112, T24, J82) showed a strong methylation signal while normal urine (NU) and blood DNA (NB) were not methylated.

Next we analyzed the CGIs that were included on the GGMA as potential markers for progression. To this end the 6 best CGIs that were methylated in non-progressors vs progressors and similarly, 6 CGIs that were methylated in progressors vs. non-progressors were analyzed separately and in several combinations (Table 12B). The Kaplan-Meier curves depicted in FIG. 5D show that a combination of CGIs in the GPR103, DBC1 and GATA2 genes can significantly predict progression (p=0.001). Interestingly, methylation of the GPR103 and DBC1 CGIs was inversely correlated with progression and methylation of GATA2 was strongly indicative for progression. The DBC1 associated CGI overlaps with the promoter of this gene, whereas the GATA2 and GPR103 CGIs are located in introns.

Discussion

We report an investigation of bladder cancer-associated aberrant DNA methylation. To our knowledge this is the first study that addresses genome-wide methylation in bladder cancer. The major goal of this work was the identification and validation of methylated CGIs that could serve as biomarkers for the early detection of primary and recurrent tumors as well as markers that are predictive of disease course. The genome-wide screen resulted in the selection of 177 CGIs that significantly differed in methylation in tumors when compared to blood. About 70% of these CGIs could be validated in a custom GGMA assay. This analysis also showed that most of these CGIs were not methylated in urine-derived DNA from age matched non-bladder cancer controls. This group of CGIs represents markers for urine based assays. Methylation of some of these markers was confirmed on urine samples. Another important finding is that a combination of CGIs from the GRP103, DBC1 and GATA2 genes is able to predict progression to muscle-invasive disease. Loss of heterozygosity or homozygous deletions of DBC1 (also called DBCCR1) gene (deleted in bladder cancer 1) have been observed in many bladder tumors, as well as methylation of the promoter. Methylation has so far not been correlated to disease course. In our study methylation of the promoter CGI of the DBC1 gene was associated with a decreased risk of progression. The role of the GATA 2 transcription factor in cancer is contradictory. Decreased expression was found to be correlated with proliferation in monocyte progenitors, whereas high expression seems to poise prostate cancers for a more aggressive phenotype and gain-of-function point mutations have been found in chronic myeloid leukemia. In bladder tumors a lower expression of this protein has been observed in MI vs. NMI-BC, which correlates with methylation and the positive association with progression. The GPR103 (QRFPR) gene encodes a G protein-coupled receptor and hence the protein is involved in signal transduction, however, but no further data about the gene or its product can be found in the literature.

Most genes discovered in the present study have never been shown to be methylated in bladder cancer or in other types of cancer. Some of the previously described methylated CGIs in bladder cancer that are associated with the SOX9, CDKN2A, TERT, DAPK1, EDNRB, and LAMB3 genes were also found to be methylated in our study, although only SOX9 and CDKN2A made it to the list of our 177 highly methylated CGIs.

To our surprise we observed that NMI-BCs with a wild-type FGFR3 gene have more methylated CGIs and the intensity of methylation is more profound than in the FGFR3 mutant NMI-BC and MI-BC groups. The difference in methylation presents additional evidence that the two subgroups of NMI-BC develop along different pathogenesis pathways. WT NMI-BCs also have more wide spread chromosomal aberrations than FGFR3 MT NMI-BCs. The extensive methylation in WT NMI-BC is reminiscent of the CpG island methylator phenotype (CIMP) that characterizes a subset of colorectal cancers (CRC). CIMP in CRC also identifies a subset of CRCs as it is associated with BRAF mutations, microsatellite instability and occurs more often in elderly females. No large-scale genome-wide study on DNA methylation has been performed for CRC, however, CIMP has been studied using a 1536-plex GGMA array.

When comparing the genes methylated in this study with those found by us, there was hardly any overlap. This confirms that CGI methylation is tissue and tumor type specific.

In line with previous reports in solid tumors, a high proportion of the genes we find de novo methylated in bladder cancer are repressed by polycomb complexes (PcG) in embryonic stem cells. PcG target genes are as much as 12 times as likely to be silenced by DNA methylation in cancer as non-PcG target genes. The association between DNA methylation and PcG has further been substantiated by the finding of interactions between DNMT1, DNMT3A, DNMT3B and several PcG complex subunits like EZH2 and BMI1. Another recent study showed that 49% of the genes methylated in colon cancer are polycomb targets in embryonic stem cells, agreeing with other reports showing that genes prone to tumor specific hypermethylation in colon cancer were more likely to be marked by H3K27 methylation in normal tissues than genes lacking H3K27 methylation. Another study reported that many genes hypermethylated in a prostate cancer cell line were bound by PcG in normal cells but lost PcG binding upon acquiring DNA methylation in cancer. In this perspective we found that 60% of the hypermethylated genes in bladder cancer are PcG targets in embryonic stem cells. These epigenetic alterations occurring in early development specifically in stem or progenitor cells might be bladder cancer specific and this strengthens the further understanding of bladder cancer tumorigenesis. Besides finding 92 commonly PcG regulated genes in bladder cancer subgroups, a group of 336 genes regulated by PcG complexes are found to be specific to NMI-wt tumors. Besides a possible CIMP phenotype being the cause for the extensive methylation in this group, another possible explanation for this finding could be that the cell from which the WT NMI-BCs originate is more closely related to the embryonic or bladder stem cell than the founder cells of the MT NMI and MI-BCs. In general it is thought that lineage-specific genes are activated during subsequent differentiation steps and during this process the PcG complexes will be replaced by cell fate specific transcription factors. Hence, fewer possible methylation targets will remain after every differentiation step.

Our data clearly shows that adjacent loci within a certain CGI are co-methylated, while neighbouring CGIs of a certain gene can have a very different methylation level. Significant association among the methylation states of adjacent CpG sites and a high frequency of short-range co-methylation was reported previously. Another interesting finding in this study is that our data shows no preference for methylation of CGIs in promoter regions compared to gene bodies, since the location of the significant CGIs is distributed over the genome in accordance to the distribution of CGIs on the array. The effects of promoter methylation on chromatin organization and gene expression have been well documented in various types of cancer. In our study, besides promoter methylation, we found more than 50% of all significant probes to be located in CGIs located within gene bodies. The influence of this on gene expression in not fully known. Previous reports in *Arabidopsis* have shown that gene body methylation was low in genes transcribed at low levels, higher in highly transcribed genes, and absent in genes that were not transcribed. By comparing our methylation results with gene expression studies, we show that for 70% of our genes there is an inverse correlation with gene expression, suggesting that intragenic methylation also contributes to gene silencing.

In summary we have identified hypermethylated CGIs in bladder cancer. The aberrant DNA methylation in bladder cancer seems to be very selective and could be the first step in tumor initiation, especially for the WT NMI-BCs. The study also illustrates an interesting biological finding: besides the promoter methylation intragenic methylation observed to the same extent in bladder cancer and it also appear to influence the gene expression. Many discovered methylated CGIs represent putative biomarkers for early detection in urine-based assays. The combination of CGIs from the GRP103, DBC1 and GATA2 genes predicts progression to muscle-invasive disease. Thus, the CGIs identified in this study will be of considerable interest for further investigation of their clinical and functional relevance and will provide advance insights into the pathogenesis of bladder cancer.

The invention claimed is:

1. A method for diagnosing non-muscle invasive (NMI) bladder cancer in a test human subject suspected of having NMI bladder cancer comprising:
   (a) measuring DNA methylation levels of at least one CpG island in OTX1 in a test sample of urine from the test human subject suspected of having NMI bladder cancer; wherein the at least one CpG island in OTX1 is located in chr2:63134539-63134851 of the human Genome Assembly hg18 of March 2006; wherein measuring comprising treating the DNA with sodium bisulfite under conditions whereby unmethylated cytosines are converted to uracil, and methylated cytosines remain unchanged and further comprising methylation-specific PCR (MSP) using at least two distinct methylation-specific primer sets for the sequence of OTX1;
   (b) comparing the level of methylation of the at least one CpG island from the test sample to the level of methylation of the at least one CpG sequence of OTX1 from a control sample from a healthy control subject; and
   (c) detecting an increase in the level of methylation of the at least one CpG island in the test sample relative to the control sample, thereby diagnosing the test human subject as having NMI bladder cancer and performing a transurethral resection on the test human subject.

2. The method of claim 1, wherein the step of measuring DNA methylation levels is preceded by the step of extracting DNA from a urine cell fraction obtained from the test sample of urine.

3. The method of claim 2, wherein the urine cell fraction is obtained by filtration of centrifugation of the test sample of urine.

4. The method of claim 2, wherein the method further comprises the step of obtaining the cell fraction by filtration or centrifugation of the test sample of urine.

5. A method for predicting the recurrence or progression of a non-muscle invasive (NMI) bladder cancer in a test human subject diagnosed with NMI bladder cancer comprising:
   (a) measuring DNA methylation levels of at least one CpG island in OTX1 in a test sample of urine from the test human subject diagnosed with NMI bladder cancer; wherein said at least one CpG island in OTX1 is located in chr2:63134539-63134851 of the human Genome Assembly hg18 of March 2006; wherein measuring comprising treating the DNA with sodium bisulfite under conditions whereby unmethylated cytosines are converted to uracil, and methylated cytosines remain unchanged and further comprising methylation-specific PCR (MSP) using at least two distinct methylation-specific primer sets for the sequence of OTX1;
   (b) comparing the level of methylation of the at least one CpG island from the test sample to the level of methylation of the at least one CpG sequence of OTX1 from a control sample from a healthy control subject; and
   (c) detecting an increase in the level of methylation of the at least one CpG island in the test sample relative to the control sample, whereby an increase in the level of methylation of the at least one CpG island in the test sample relative to the control sample indicates that the NMI bladder cancer in the test human subject is likely to progress or recur and performing a transurethral resection on the test human subject.

6. The method of claim 5, wherein the test sample of urine is a urine cell fraction.

7. The method of claim 6, wherein the urine cell fraction is obtained by filtration or centrifugation.

8. The method of claim 1, wherein the test human subject is tested for the presence or absence of an FGRF3 gene mutation.

9. The method of claim 5, wherein the test human subject is tested for the presence or absence of an FGRF3 gene mutation.

* * * * *

SEQUENCE LISTING

```
<160> NUMBER OF SEQ ID NOS: 329

<210> SEQ ID NO 1
<211> LENGTH: 550
<212> TYPE: DNA
<213> ORGANISM: Homo sapiens

<400> SEQUENCE: 1
cggatgtgcg tggactctgc gggcggggcg cccgtagtct ccctccttcg cacccgggc       60 gcctgggaac ctcctcgcgc gtttggccac tcgctgctcc tggcagtagg ggcttcgggc    120
cccgccgtgt ccccacccag gtatgggat gcggagttga tgggtgcggg gcgctgggag    180
ggggcagatg aaaggggcag tcgaaagggg gccatgcgcg ccgagcgcag ccgggtcatt    240
agccgcgggt gtgagcggcg gggcaggctt atcgcccatc caggcctggc gggcgggcgg    300
tccccgacgc ggctgccgcc gccgcccgcg gcagagggca cggcggttcc cacgctcggg    360
ccctggttcg ggggcgttct cgggacggcg tggccgcgct caccaccacc gcggaggccg    420
ggctgtaatt aggataattg cgctgctccc agcctggggc agctcaggac ccggctgcac    480
cgcgctggcc cgggacgggc gggggcaggg ggtggcgggg cccgagcgat acagcccctg    540
gcgcagtccg                                                           550

<210> SEQ ID NO 2
<211> LENGTH: 1209
<212> TYPE: DNA
<213> ORGANISM: Homo sapiens

<400> SEQUENCE: 2
cgcccagacc ggccgtggcg gggccccggc gccacgtgct gctcatggcc accacgcgca       60
ccggctcctc gttcgtgggc gagttcttca accagcaggg caacatcttc tacctcttcg    120
agccgcttgg cacatcgagc gcacagtgtc cttcgagccg gggggcgcca acgccgcggg    180
```

```
ctcggccctg gtgtaccgcg acgtgctcaa gcagctcttc ctgtgcgacc tgtacgtgct      240
ggagcacttc atcacgccgc tgcccgagga ccacctgact cagttcatgt tccgccgggc      300
tccagccgct ccctgtgcga ggaccccgtc tgtacgccct cgtcaagaa ggtcttcgag       360 aagtaccact gcaagaaccg ccgctgcggc ccctcaacg tgacgctggc cgcagaggcc       420
tgccgccgca aggagcacat ggccctcaag gcggtgcgca tccggcagct gagttcctgc      480
agccgctggc cgaggacccc cgcctggacc tgcgcgtcat ccagctggtg cgcgaccccc      540
gggccgtgct ggcctcgcgc atggtggcct cgccggcaa gtataagacc tggaagaagt      600
ggctggacga cgagggccag gacggcctga gggaagagga ggtcagcggc tgcggggcaa      660
ctgcgagagc atccgcctgt ccgcggagct ggggctgcgg cagcccgcct ggctgcgggg      720
ccgctacatg ctggtgcgct acgaggacgt ggcacgcggg ccgctgcaga aggcccgcga      780
gatgtaccgc ttcgccggca tcccctgac cccgcggtgg aagactggat ccaaaagaac      840
acgcaggcgg cccacgacgg cagcggcatc tactccacgc agaagaactc ctcggagcag     900
ttcgagaagt ggcgcttcag catgcccttc aagctggccc aggtggtgca ggccgcctgc     960
ggccctgcca tgcgcctctt cggctacaac tggcgcggga cgccgccgcc ctcaccaacc    1020
gctcagtcag cctgctggag gagaggggca ccttctgggt cacgtagggg ggccggggcc    1080
ccgtatgccc ctcctcgtga aaggcctgcc ccgtctttct gccgcagccc tcgcagaggg    1140
cgggtgcaca gcgccatgac gggcagcgcc tcctgtagca gtagggcccc cagccagcgc    1200
tccagccaa                                                                1209

<210> SEQ ID NO 3
<211> LENGTH: 316
<212> TYPE: DNA
<213> ORGANISM: Homo sapiens

<400> SEQUENCE: 3
cggggtcctc acggctcccg caggcagccg gcccctgctg ctgtcttcaa acagcctccc       60
gggggaccgc tctctccgcg tgctgagcat ccggccgggg gacttctctc gctccagggg      120
gcggccagag acttgtccct gcgcagctcg gtccgcccct cgcggtagcg gtggggtgtg      180
cttggctctc gcgggtggct ggggccttcg ggcggcgctg ggctggaggc cacgcgcttg      240
gtgatgtgct cgttgtacgt gggtgggcct cgcttgttgg ggctgctggc gacacaagag      300
aacgtaggga gctgcg                                                       316

<210> SEQ ID NO 4
<211> LENGTH: 1209
<212> TYPE: DNA
<213> ORGANISM: Homo sapiens

<400> SEQUENCE: 4
cgagaggacc cggaccccgg cggggaaggg cgccctcccc cggcctcgcg gccgccccaa       60
agcacatccc cttctgccgg ccccaagtcc ccgcgcgtcc acggcgcccc tgtgcccacg      120
ggagagcacc cccgcccaga tggaaaaggg ggtagaccgg gcagagcgag aggcggcttt      180
ggctcgtggg gagcggcgac ccaacccagc gcgcatcccg caagccctcc cggctgcccc      240
ggaccttccc cctcgctacc tcggaacagg gtctgcccgg gggctgctgc acaaagaggg      300
gtggtcgagg gagacgccaa atcgttaaga cgggagccc gtttcggcca tcttggaaga     360
gaggaaaggg aaaaagggac agaaaaaagg gagaaagaaa ggcggacggg gcaagctggg      420
```

```
ctagggactg acggggcgcg gggggtgcga aggcaggatc ggctcagagc ccccccctccc    480
atcgggcttt gcgaagaacg gccggccccc atcccaatcc ccagagggtt acaggccagg    540
agagggaaag gcagggggag tccgctccgc ttacctgggt tcggggtccg gtgggtctcg    600
gggagggggg gatgggaggg agggagggaa gggaggggag ggggccgcag ccgtgtcgct    660
cgcccgggcg gcgggagggg agaaacctac ggtaagaaag gagtttgtga aagcggcttg    720
gggtgggagg gagaggggag gggaggggac cgaggggggga ggggagggac cggagtgtgg    780
ggggagaca aaatggcttt tttcctccag acaaggtagg tcccgcccac cactcaccca    840
cgtgacctca ttccttcagg atgctggcag agacgggaag aggaggggga ggctggcgcg    900
gccgctcccc gccaccggct gccgggtccc tagccaggac gagacccctc ccttcccatg    960
cggccgcccc gaccccggag gatggatctc ttatgttacc ttccgcagtt agccccctc   1020
ccttcaaaat atgggttccc cccactgaca ctgtgatgcc catccctaac tggggcgcct   1080
ggaaaatggt gaaatgggga ctgggctgaa aggtggctcg tggtcctcca cgccccggcc   1140
tagaccaaag ggcgcggggt ccggcggggg acgcgacgcc ttcagccagg cgtccgagcg   1200
attttcatt                                                          1209

<210> SEQ ID NO 5
<211> LENGTH: 1209
<212> TYPE: DNA
<213> ORGANISM: Homo sapiens

<400> SEQUENCE: 5
cggaggcggc acagctggag cccggattgt ggcacgccgt caccgtgctg ctccggggaa     60
tcccgacccg ctccctgcga aagcgtttcc gaacgcgaac ccagagcctg tgaacgcgcc    120
ggcaagcccc cactccccca ccgccgcccg tcgcaggtgg gcccgtccta ggggtccttc    180
ctgcgctcta ccccgtctct caagtcactc agtcgatcgc cccgttcacg ctcccgtgat    240
cccagacatc cataaccacg atctcgcctc catgcacatc caacgcacga cggtgcacaa    300
cgtgcacctg acttctgcgg accaggtgtc tcaagcgtac agcggccacc cgcggaaccg    360
cggcccgggg ccagtgagtc gtctgcagct ccccggggtta ggggattccc cagaactccg    420
ggaaagtcac ccgaagtcca tccgggatgc ggccttggtt ctcggccgcg tatctcgccc    480
ttaggtgcag aacgacgccc ttccaggggcc cacagctgcc aggctgggcc ttgccctcgc    540
atccccccggg aagaccaggg acggggccac acaggccgtg gctgcggaga cgcttccccg    600
ggccaccccg cgaccaggag gggagtcgagc cgcccgctct cccgcgtccc ccgcccatc    660
ccagccagtt ggccccaccc tgcgcgggat aattgggacg ggagggaggc gacgggaggg    720
cggcggctcc agagagactg cgcgcctgtc agcggcaatt tgtttaagtg gacgggacgg    780
gccgggccgc tgcgggctgg ggtcaccgag gccgcgcccc caccccaacc agacctggga    840
ccgcggggga gccggtccgg gccgctaaac cgggctggct ggcgccaggg ctccgggagg    900
tgcggtccgg cggggaagcc gtgatgggaa gcgactctgt ccaggagtg tccttcacca    960
ccacactcct cacgtccagg cagtgatgac ggcctggcgg caccctcaca gcgggcccat   1020
agcacggggc cacacacgtc ccctgagctt agcctgggca cattcgtctg ccaccgaggg   1080
cttaagccag tctgcagccc gcgccccgtc actcggacgc aagtccgtcg tccgctctgc   1140
cacgcggccg cacagcccgg cttcctgctg cccactgccc gcggggtcac gcaacccgg   1200
ccctgcaca                                                          1209
```

<210> SEQ ID NO 6
<211> LENGTH: 688
<212> TYPE: DNA
<213> ORGANISM: Homo sapiens

<400> SEQUENCE: 6

| | | | | | |
|---|---|---|---|---|---|
| cgatttccgc | agatttcctg | ctggaacgtt | ctctcgggcc | tcaagttttc | ctgagaggac | 60 |
| gacgtggaga | gtggagacaa | agatgctcaa | aagccaggaa | atcgcaggct | cggaagcccc | 120 |
| cacgcatcct | ctgaacgcag | cgccatctcg | gggctgcggc | gggaccaagc | gggacgcttg | 180 |
| caggctgtcg | gcggcggggg | ccgcgagccg | ccggcgtagg | ccgctccagc | tggaagaccc | 240 |
| caccgctagg | gttccagggg | gctgcggacg | cttccgaggg | gcccaaggcg | aaagaacgcg | 300 |
| cccgcttgtc | ggccacgtga | ccgtccccgt | ccgcgtccgc | agcgaccacg | tgactgtgcg | 360 |
| tccgcggcgt | cgattgactg | ggagctccct | ggccacgccc | taagcgccag | ccccgggctt | 420 |
| cgggggcgg | tgctgctgcg | gttgccatgg | cgtcttccga | gcgcgcaggc | ggggcccaga | 480 |
| gtagcttttc | gggtatttgc | taccggctct | cggtagggct | ggtcacccttt | gcttgctgag | 540 |
| cttcgcgccc | tgcgtccttt | ggtccccagc | aacttgcagg | gcagccgtcc | ctcatgaggc | 600 |
| cctccagcga | atgccctaaa | gctccgaagt | tgctccggag | gaaacaggct | tgctccgagg | 660 |
| gtgcacgtcc | ttactgcccg | tgacgtcg | | | | 688 |

<210> SEQ ID NO 7
<211> LENGTH: 511
<212> TYPE: DNA
<213> ORGANISM: Homo sapiens

<400> SEQUENCE: 7

| | | | | | |
|---|---|---|---|---|---|
| ctgctgcact | tgtaaagtgg | gtgcttctca | gcttcatggt | ttgaggggtg | cagccagctt | 60 |
| cggcctaagt | ggtgttgagg | gtcgaggacc | cagcaccccc | acacgggaag | cgcggtgtcc | 120 |
| cgccttcagg | ctggagtact | ctggcaccct | ctggggtccc | gaagtgcctg | agtacctgtt | 180 |
| tgagccgcgt | gtaggtgact | gcgcacctgt | ttgaactgcg | tgtaggtgac | cgcgcacctg | 240 |
| tttgagctgc | ctgtagctga | ccgggcacct | gtttgagctg | cctgtaggtg | accgcgcact | 300 |
| gtttgagctg | cctgtaggtg | actgggcacc | cgtttgagct | gcctgtaggt | gaccgcgcac | 360 |
| ccgtttgagc | tgcctgtagg | tgaccgggca | cccgtttgag | ctgcctgtag | gtgaccgggc | 420 |
| acccgtttga | gctgcctgta | ggtgactggg | cacccgtttg | agctgcctgt | agtgaccgcg | 480 |
| cacccgcttg | agctgcctgt | agctgaccgc | g | | | 511 |

<210> SEQ ID NO 8
<211> LENGTH: 1078
<212> TYPE: DNA
<213> ORGANISM: Homo sapiens

<400> SEQUENCE: 8

| | | | | | |
|---|---|---|---|---|---|
| cgcgttgtag | gggtagccgt | agtaggccag | tgtgtagggg | tcgcaggagt | acacgtagct | 60 |
| gggctgctgc | gctgcctcag | ccgcgccgcc | gccctggct | gccttctggt | agcgcgagta | 120 |
| ctgctcctgt | ccacgggctt | ggccagcgtg | acctccaggc | acgagccctc | cagctcagtg | 180 |
| ccgttgaggt | tgttcatggc | atgcacggca | tcctcgcggc | tggtgaagtg | cacgaaggcg | 240 |
| tagtcgcgga | tcttcttgac | gcgctccacg | cagccggggt | tgaactggcc | gaagctcttt | 300 |
| tgatggtgtc | ctcggtggtc | tcgatcatga | ggttgcgcac | gtagaggatc | ttcacggtct | 360 |
| ccatcacgtc | ctcgtccacg | tcgatctcag | gttcggccca | gtccacggcg | atctggtggc | 420 |

| | |
|---|---|
| cccacagctg gatgcggcca ggcatgagct tgcggcgagc catggcagcc ggcggtggct | 480 |
| ctcgtactcc acgaaggcga agccgcggtt cttcatcttg tcggccgcgc tggcgtagac | 540 |
| gatcacgtcc agcacgccct cggtgacctt ggcaatctcc tccaggattt cctcgcgctt | 600 |
| cttcatcttg gggatcccgc cgatgaagag gcggcagttg tcccgctgca gcacacgccg | 660 |
| agcaggcggc ccgggcggat ctcgtagttg ttgagctcac gcactgcgcg cttggcctcg | 720 |
| tgcttgtggc agtacatgac gaaggcgtag ccgcggttct tgccgtcaaa gtccatcatg | 780 |
| aggcgcagct cgtagatgcg gcccacggcc tcgaaacggg caccagctcg tcctcgtaca | 840 |
| cgtcgcgcgg gatcttgccc acgaagacct cgcagccacg ctgcgggtgc gggcctccc | 900 |
| agccgggcgg tgggccgccg tacttgcgct gcccgttctc ttgcaccatg ctgtagcccg | 960 |
| tgcgctccat cagcgccagc agtgctgctc gttgggcgcg cccgccacgc cctcgggcac | 1020 |
| cttggcggag gacccggcgg ccgagtcact gctcatggct gcggtggaat cctctgcg | 1078 |

<210> SEQ ID NO 9
<211> LENGTH: 1167
<212> TYPE: DNA
<213> ORGANISM: Homo sapiens

<400> SEQUENCE: 9

| | |
|---|---|
| aagtctggag ataattatgt cgtacagtcg caaacattat tccgttctta ctgtaaacgg | 60 |
| cccccggcca ctttacgaga aaccaggaaa cttctgagag ttactagcag cgtttacgcg | 120 |
| ggcaaacgag ttcttttct ttctctcccg gattgttcga agtatctatc gggcggcttc | 180 |
| gatgccaggt tcagaggcgc gccagggaga gggcgccccg cagaggagcg cagcggagag | 240 |
| gcctacgcag gtccccggtg cccgcggccc tcggaggccg ggcctgcgt cttggccagc | 300 |
| actgggtggc agctgaggct ggtggcccgg agccctcgcg gccgcgggca ggcccccttct | 360 |
| tgggcagggt cgggcactcc cgctgtccag ggctcttcgg caccctcctt ccaatcaggt | 420 |
| cgctctcccc tgctccccag actcaactcc tccgaagctg ctccaggttg aatgtgaccg | 480 |
| ctaggccgac tccctgggcc cgcgagcagt tctcgaaagg tgcggactga gccctttctg | 540 |
| gggtggggtg cgggttggtt ctcgcaagtg tgacccaggg tgaacttgct atttcgggtc | 600 |
| ccgggtgctg cagggccagg agaacagctg ggatggggga ccccgcctcc accctcgggc | 660 |
| cggcacgtcc gcgccctgtc aggtccccct ccctcctcta tgatggccaa ggcgtgcgcc | 720 |
| agggctatcc gggaaccttg taaggcctcg tgctggcacc taaccccact cgcggcacac | 780 |
| ttcctctatg tagtctgcgg ccccgcctgc caaatagagt gaccagtgca gggacagaat | 840 |
| gccaggctgg tggccgaccg cctgagggac aaaggcgagc attcacaagc caacagcaga | 900 |
| cccctgcccc ccatatttcc atttcgctca ggcttttagg acaaaatcaa caaggccgca | 960 |
| gagtggtgca ggcgctcacc ccgggtgcag cctggggagc cactggttcc gcgaccctgg | 1020 |
| gcatgaaact cctcaaggc ggccctcgag acgcagggga gaggatgctg ccggcgcctg | 1080 |
| cccgagggct tctctgcggg aagcgggcag gcacccacc ggagtcattg ccgggaccct | 1140 |
| cagcgcaacg cgggcctgtt cctctcg | 1167 |

<210> SEQ ID NO 10
<211> LENGTH: 751
<212> TYPE: DNA
<213> ORGANISM: Homo sapiens

<400> SEQUENCE: 10

| | |
|---|---|
| cggagatggc gcgtctggat tcagggagat cgtgcggcca gcttccctcc ctctgctctg | 60 |

```
gatggggcc ggccgccgcc gctcactcac ggctctctct ctcccgctgt gcctgcaggt    120
gtggccgcga cgatgccctc gctgaggagc gcatgcggag aggccagaac gccctgccag    180
cccagcctgc cggcctccgc ccgccgaagc cgccccggcc tgcctcgctg ctgagacacg    240
cgcctcactg tctctctgag gaggaggcg agcaggaccg acctcgggca cccgggcccg    300
ggaccccctc gcgtccgcag caggtgtgca aagggaggca gccgtggagc aggcgcagag    360
tgagacttct ctgggtgcca gaggacacg aggacacaaa ccgcgcctgg gctgctgtgt    420
tctgacctga gcgggcgtgg gcggtcgggc ggggcgggag gaggtagcct cctctgctcc    480
tctcccgctc gcggcgcccc acgccacggt ggctccgggc ccccaccgt taaaacgggg    540 tccgcgtgtc ctgtacgcag cgtgttgctc cgcaaaggat gacagagctg ccacggcagt    600
gcgaggtgct gcttttaccg tagacgtgcc ttttcgtagc tttagcgtag agcttgaggc    660
ctgtggctta ggccgggtgg tctcgtgctg gtggggtctg cgtttgcccc tgcccctccg    720
tcagcttcac cttctcgtgc cttcttctgc g                                   751

<210> SEQ ID NO 11
<211> LENGTH: 734
<212> TYPE: DNA
<213> ORGANISM: Homo sapiens

<400> SEQUENCE: 11
cgtaacgggc gtgggtcgtc cgtcgcgccg cccggcgagg agtgggctgg cggcggtagc     60
tgtcgcccgc ttggttgcgt gaccgcgggg tccgcgtccg ctccctccac ccttcgccct    120
tcgccctcgc ctcgttccgg cctccgcggc ccagcaacgg ccgtcatggt gccgtcggcg    180
ctccctgcgc ggccccgctg agcctcggtg cggcggcgag cgcggtcgag atcgccatgc    240
ctacccgtga gtggccggcc gagggccggg ggcgttggga ggcgactgcc tgcgcgacgg    300
cttgggccgg gtactcctcc cgggcggctg gggaggctgg gccgcgctga gcagagccag    360
gaagtgtctg cgagcggcgg agttagtttc gtttcggctt agccttccgg agatggcgtg    420
agcccgttgc acggatcggg aaactgaggc ccgaacgtta agggaactgc gggacgcgct    480
gttaggaggc ggcagagctg gtggtaacct gacccgtggg atttcaaagt taaagcccctt    540 ttcccacggc cacacggctt cgtgggactt tatggaaata ttgaaaataa ctgcggtacc    600
attgtcagtc ccttctcacc tcgggccgga cgtcgctagt ggagcgccgg ccccgagtcc    660
cttcccgcgg ccgccagaca dccccgac agcctaactc ggcgtccgta tcgccgtcgg    720
ggcggctgaa gtcg                                                     734

<210> SEQ ID NO 12
<211> LENGTH: 279
<212> TYPE: DNA
<213> ORGANISM: Homo sapiens

<400> SEQUENCE: 12
cggaggcacg aaccaagcag cctagaagac aaatgcgctg ctcggagaga ctgccgcggc     60
aaccaactgg acaccccaag agctcactcc tccgcggttt tatattccga cttgcgcaca    120
ggagcgggtg cggggcgca gggagtgtgg gtaacaggca tagattccgc ttgcgcaata    180
cgtggtaaga aaccagctgt gagggctgg cccaacgcag agcggcgcga ggtccgcttg    240
gcatctacaa caatcgaggg gctagtccag aagttcaag                          279

<210> SEQ ID NO 13
```

<211> LENGTH: 1209
<212> TYPE: DNA
<213> ORGANISM: Homo sapiens

<400> SEQUENCE: 13

```
gctcagctag taagtgagga gctcagctct gaagctgtaa ccaagaccgc gcgggcagga      60
ggaaaggaca cttcagcgct ctgcggttgc aaacacaccc ctgcgggtgc tgccacttag     120
caaagtctag gttcccgctt actcgcacac gcatcctgac ttcccccaac cctggaacta    180
cctaccagga gcggagacca gcagaccgac agcacgcaca tgatccccat aagctgaatg    240
gccgtctcgg tcgtgatgcg gccccactgg gcactggact gagatgccgt ggccttggcc    300
ggcagcggga caccagggcc ttaatggtgg ccaggttgca ggaaaaggtg actgtcagcg    360
ccaagagccc caggaaggca aaggcagagg cgaagaaaag gttgcccag ttatgcgaag      420
agctagtccc gttgccccct cgcccggtgc tgatgaagca ccacgtcccg gccactggac    480
ggtgtactgg cccacgccca gcaccggcag cagggcgaag gcgagcacgg ccagccacac    540
gccgagcagc acagcgcggg tggcacgcgt cttcatgtgg ctcgcatacc agtgcggcgc    600
cctgatggcc agcgcccgct cgacggccat ggcgctggcg atgacaacga ggagagcccg    660
aaaacagtca tggtcagccc gaaaaggtg cagagccgcc ccgacgggtc gatgtgctcc      720
caacgctgct tggacaggta cacgacgatg acgaccgggg tggtgagaag ctgcccgacc    780
aggtcggtga cgccagcca ccgatgcac agcagaagga cttcttgcgc ttgctctccc       840
ggcgccggta gctgcgcgac acgagcagca tggccagtgc gttgcccacg aaaccagtga    900
gcagcatggt gatcgggaag gccacggaca ccgatccgca atcctcgcca gaccctggag    960
ggcgcgtgag gttgccccgc gcctcgggga acgctcgggc gcccacatgc ctgtgtagga   1020
gtggttgagg cgggtgcaga aggggggcatc ccctccgtag ccccgggtct ccttcatgtt   1080
ggcttcgagg tgaggagggg atggcgtcca gagagccgca gcgggagggg gcagacgcgg   1140
cgcgggcggc ggcggaggtg gcgtttaccg cggctggggc tgggctgccc ccatggtgc    1200
ggggcgcag                                                           1209
```

<210> SEQ ID NO 14
<211> LENGTH: 235
<212> TYPE: DNA
<213> ORGANISM: Homo sapiens

<400> SEQUENCE: 14

```
attcttaatt cccacacctc ttcccaagtt acgccaccgg tcgaggacgg caggagaccc      60
ccgagtgcag agaaagctca aaccggcagc gaagtcggtc ctagccaagc tgaaaaaacg    120
tctcggattc gcggacagcg gcctagacac agcccgatct tccagtccta gtgccctggt    180
cgagacggtt ctatcctttt gcaaagaagc cggaaagagc tgggtccgg gggcg           235
```

<210> SEQ ID NO 15
<211> LENGTH: 1209
<212> TYPE: DNA
<213> ORGANISM: Homo sapiens

<400> SEQUENCE: 15

```
cggggtgggc ttcccgcgcc tgcagcccgg aggcgtcgag cgcctgatgg agcgtcagag      60
gagacctcgt cccagcgttg ggccttctgt tgtatttctg ccagaaactc gcgttgagga    120
gaatttgttt aagcgtttct ctacctgtcc atgcatctcg taaatacagt aagcatggca    180
agcccttttcg ctggttaacc ccggcgtccg tgtgctcact gccgccctgc acgcacgagg   240
```

```
tcgcggatgg ttcaaagcac ccgcggtggc agccggagag gcagagcggg ctctagggac    300
taagacaggg ccgagctgga cgactggtgg cagggcggcc ggggaggccc cgccgcgggg    360
aggtttgggc cccctaccct gcggaactgg aggcaagtgc ggactccggc tgcaggccgc    420
ggtctgcggg gacgcgcgcg gggggcctgc gtcccgccac ctccgcgcac accctggtc     480 cccttcccca gcccgggccg gcgccgcccg ccgcgtgact cgcgcgttcc gggccgagta    540
cgggctgtcc cttggcccag cctcagccag acgcggggga gagagagcag gggctgggaa    600
gtgccggcag gaaaggaatt ggccagggga agaggagga  ggagatagat ggagtcatcg    660
gttacggagc gcgctccgtc cggcggagcg aagccgggga ccgagagcgc gcaaggcgaa    720
gacacagcga cgcagccccg tccccggcct ccggaccgcc tgccccgctc ggccccggct    780
cggctccgcc ccgcccctgg gtccgaacgg aggaggagga ggacacgagc cgcgcgggct    840
tggaacccac gaagacccgc aaacccaggg cgccgccgtc tccgaccacc tgctgccgcg    900
gcaggccatc agcagaattt atacccaggg cgcgagcccg ccacggctgg gcggaggcgg    960
aggcggaggc ggggaggggg ggggggtccg gcttgcgagg ccccgccccg ctccctgccg   1020
ccccgccccc ctccgcccCg ccggcctcac tcggggcgcc gggaccccca ctccctccgg   1080
ggtcggctgc ccgccgccgg gttgggggat gtgccgaagg gcgggcctcc ctgcggaaag   1140
cgacgtcacg gccgctcctc agtgtgaatg aatcaaaacg cccgggtgac cgcggcctcc   1200
cgggcggcc                                                          1209

<210> SEQ ID NO 16
<211> LENGTH: 313
<212> TYPE: DNA
<213> ORGANISM: Homo sapiens

<400> SEQUENCE: 16
aaaccactct gaaagaactg tgagaccttt gcactaagac cattagggat tctacgcaag     60
gttctctctg ctccttgcaa aattacaggc gtcatgaagg atggcggctc gtaaatcgaa    120
gcctttgaac aggggctcac cgtccggcgg catcaacacc ttgttgttct gtgtgcacca    180
ccccacgggg tgcaaatccg cgatgactac gtcacaccga aagtcggccc tgcggtcctc    240
cccgtaaccg cagtagcgca gaagcagcag ctgcccgcac gtggtaatga tcgtggccac    300
cagtacgtgt ccg                                                      313

<210> SEQ ID NO 17
<211> LENGTH: 1209
<212> TYPE: DNA
<213> ORGANISM: Homo sapiens

<400> SEQUENCE: 17
cggcaaccga gccagatcca agaggggtcg gcctcgtcta aattggtttc ccaccaatgg     60
cctcggatca gccgcggctg tgctgcggga gccctcagga cgcggctggg gttggtgcgc    120
ggggcccgga accccaaacc cggctcggtt cggcaaggtt cagggagaca aggtagagaa    180
ggctggggtg agcgagaagt cgggcggccg atcgtcaggg ccacgagcct cgccttgcct    240
tcttggaatc ccaccaact  ttaaaggccc aaagatcctg aaaattccga aagcgaaacg    300
cgagctggtc tccagaagtt tgagaacggt ctcccaggct ttccagcgtc gtcccgggat    360
tctcggacac cacaaacgcc atcaaccacg agcaccggtg tccgtggcta ttgcccgaa    420 tggtccccat ccgcgtcccc gggaactccc tcggctttc  gcgcatccag gccccagccc    480
```

| | |
|---|---|
| cagctactgg tgcgccccga gccctaggt gccagagcgg tggtcggccg ggctcctgcc | 540 |
| cagtctcggc tcctccctcc tccccaccag aaggaaaaac ttgggccctt cgagaaccct | 600 |
| gtggaatgtt ctttgtaatc aactgtacat ccgcttccac ggccggcctc gtgcaaaatc | 660 |
| gcgggtttcg gggccttgga gcaaattgcg cttgtcagcg cgacgtcag gaggacaagg | 720 |
| ggaggggttc gcggctgaaa ctgcagcttc gcagcacaga gccatttag gctgctcccc | 780 |
| acctcgcggg gcccatggga aagccggccc cgggaggcgc gcccaaacgc aggctggagg | 840 |
| agccacggac gcgtcctggc cggcgtgtcg ccatcgttca gcctcgctgc ccaggtggga | 900 |
| ggggtcacct gccgcggggt ctccaagcca gtgccgcttg ctcccggccc ccacccactg | 960 |
| acagcacggc gtccgagtga ccctgtcagc ctcgttctgc gctcctgcaa accacgttgc | 1020 |
| tgcgctaact acaaacctgg ccaacatgtc tttgtaaccc tatcatttaa aaacgcttcc | 1080 |
| aggcacctgg ccgctgccag atcaggttcg cgggcccgga ggaggtcctc ccacctgccc | 1140 |
| ccgccagccc cggggaccgg cgcggcctcc gtgtggcccc cgcccacgag gtccctcggg | 1200 |
| caggaaccg | 1209 |

<210> SEQ ID NO 18
<211> LENGTH: 630
<212> TYPE: DNA
<213> ORGANISM: Homo sapiens

<400> SEQUENCE: 18

| | |
|---|---|
| cggaaaaact cgaatgtcgc cctgccgttc ctggggttgg tgacaggtct ggtcatcgca | 60 |
| cggcggcagc tcctcacctg gatttagaag agctggcgtc cccgcccgcc caagccttta | 120 |
| aactctctct gccagaaccc gccaactctc cagggtacaa agtacagcag gacgcgggt | 180 |
| ggagcccttc caagcggcgc agccttatct ttcccgagtg aacacctagg tggattccca | 240 |
| acaccgcgcc tggcacgttt ctggagggag tctcaagctc ctccagagct cccagctgcc | 300 |
| gtcctcgttt ctgcagtcga tattcctgtg ggagacacgg ggggctctga gcgctacgag | 360 |
| ctttattaag agatttgcga atggttcact caggtccctg aacactccca atagcctaag | 420 |
| ctgcctgctg tgttatagcg cagaagcccc taacgcacgg tggttgtcct tcttctcata | 480 |
| acgctcgcag cttagggcca gttttccgcga ttctaagagt aattgcgtgg gcacctgtgc | 540 |
| tggggccagg cgcaaagaag ggagttggtc tgcgcgaaga tcgtcaacct gctaacagac | 600 |
| cgcacatgca ctttgcaccg accatctacg | 630 |

<210> SEQ ID NO 19
<211> LENGTH: 272
<212> TYPE: DNA
<213> ORGANISM: Homo sapiens

<400> SEQUENCE: 19

| | |
|---|---|
| cggtaaagat cccgcatgta gtccggaatg acggcactct tgctaggctg cgggcggcgg | 60 |
| cgcagcccaa acatctgcag aagtgtcgcc tcgaagtccc gcaggagctc atggctctgc | 120 |
| cctgagcgcg tcctcccgcg tggccctgaa tctcggcgac ttttttcttc cccgtctcag | 180 |
| gtatcaaact agcatggctc gcgcctccta gcaggacttg gcataataaa acgaccatca | 240 |
| gcattcggtt accaggaatc atggtgtctc tg | 272 |

<210> SEQ ID NO 20
<211> LENGTH: 1209
<212> TYPE: DNA
<213> ORGANISM: Homo sapiens

<400> SEQUENCE: 20

```
cgcgaggatg ggcgggctcc acgtctgggg gcgctgtgag cagggccaga gcgaaacctc    60
agtctgagtt tacgaactgg gaaggagcct gaaccccaga acaccgttta acaaagaggg   120
cgaacgcagg gagccgagga gacgtctcct tggcctctgg ggaagggcct ggaggagcga   180
gccagctgag aagcggcttt gccgggtgtc cactagcggt tcgccagccc tctgtgcgcc   240
cgcagagtga cgcagaggcc gacacagtcc cctccccact cgccctgggg cgccgccga    300
ccttgatcac cccttcgcg gagggaactc ccaaggcgcg gcgctggccg ctgggtccgc   360
atggcccagt cctgtcgggc tccgctctgc tgccgccgag cttcgaaggt gtgcagtgtt   420
gagccgtgtc ttgttccgtg gcttcgaggg gtgtgcgcgc ttcctatacc tcccggaacg   480
cgcgagatag tcacacgcgc cactttgagg gtcaaacacc ccgcatctgg ccacactgta   540
cctttactaa cgtggggagg gggcaaaaaa atgtgtctct ccttcttacc ccgaggtgtc   600
actcgcccaa acactcccta caacttcttc aagtcaaact tggcaaggtt ggctggctga   660
ctgcgagagg aaaaagaggg cgcggagggg gcgcggcgcg cggccgggtg tagaggccac   720
ggaggcgagg cgccgagcgt ccccttttgtc ctgtagaggg agctccagcc ccaaatttcc   780
ctgctgcctc ccccggcccg cccaccccag gcccgctgga gccggaatcc cggctggaaa   840
ggtgcggcg tctgacaccc ccgcaaccccc cgcgccgggg ccttagcagg atgcctcttc   900
tagggcacgt gggaaaaccc accagggtgc caagacgcac agatgctccc aggacccggg   960
ctccccaact ctcaactaga gctgggcgtc acacatcatc tagaggatta tgtaccccta  1020
ggcgaccctc ttctccatat ccgcctccac cgtcaccca caccctggca tctataaaga  1080
gggaagggg gcaaccgggt tggaaggagg atggaatctg ggcttgcaca gcctcttata  1140
ggtaacagtg agaaagccta actgtgtcga tcaaagaatg gggacgaagg gagtgatgag  1200
aacacgacc                                                        1209
```

<210> SEQ ID NO 21
<211> LENGTH: 1209
<212> TYPE: DNA
<213> ORGANISM: Homo sapiens

<400> SEQUENCE: 21

```
cacacacaca cacacaaaag ttgggagaga atgtgagaat gcttgtgttc gtggacgcgt    60
gcgcacgtat ggagcggcgg tacctatgat tatttgcgcg tggcgcctgg ctatgcgtgg   120
gcgaacggca gtgggagaaca tgtgggcgtg catgaagtgt gcacttaaac caaagtgtgc   180
cctccccgtt gggcaggcct gtgtgttggt ccaaggggttg ggagcgcctg agctgtgtga   240
gggtcgctgg gaagggtgtt tgaggccgtg ggcggtgcgg agcgtgtctg tgtgcgcggg   300
gctgagctgg ttgtgtgaag tggtagcggg tctgccagag agcgtttacc tgcgtgaatg   360
cacaaccaca cactacgggt cacgtcccac actcattctt tccctaggcg ggccaggctg   420
tctgcacgcg gagacccaga gaggccagcg gaagggcagc gcgggaaggc gctctcttct   480
cccgcgagcg cagatctggc ggaggaggcg gcgactgccc ggcaggctgc gccggcgagc   540
cccccagctc ctctcaccga cgtgccaggc gccccgaagg cgacaggcgt ctcccgccga   600
aaatgaaggc gtccgagcca ggaaggtggg ggcgggtagt tagggagac aaggagtccg   660
gagaaaaccg agaggcgggt aggctttgaa cgcgccgcgc cgcgggccgt gctgcgagcc   720
cggcacacgc ctctcgcccc agctcgcgct ggggcttggc ctctaggctc ttcgcgatga   780
```

```
cccgcgaaaa caccccctcgc cccctcttc tcaaccggaa ccctggaggg agaggccgcg    840
cccggccagc agtcgctgcg agagcagcac tcacctgggt ctgtgcgcgc cgcgatgcgc    900
cggggctcct gcgctgtcct gcgctccgct ctcggcacca cctttcgtgg ctccaccgcc    960
cccagcccgc acccgagcgc tgaggtgcaa gggcaggtct gcgtgcgagc ccctgcgggg   1020
ctggcagcca ggtgcgcgag ggccgcccTT gccggcgctc ccagcccgcg ctgtctgctc   1080
tcaggaacct ggcctggcgc gcagtgtcag aggccccgcg gcggcggcag gccgagccca   1140
caggggcatt aggccaactc ccctcccgc cctgcgcacg cggaattctc tattattatt   1200
attaaagaa                                                           1209

<210> SEQ ID NO 22
<211> LENGTH: 1209
<212> TYPE: DNA
<213> ORGANISM: Homo sapiens

<400> SEQUENCE: 22
cgagcaggag caggcgcggc cccggatgtg gagccaggct ttcgggagag cccatttcta     60
cagggattcg gcccgacggg tgccgggccg agctcgctcg gcctttgtta gtttcggcgc    120
cgctgattga tcgcctaatc cagtggaccc tgagaagaac agactgggct gccaatggcc    180 cgacccacg ccgccgcgac ctgcccgagg gcaccgggag cgatgggtgc ggaggggctg     240
ggaggacggt catccgggcg gctggacctc tccttcctcc cctccgcctt cgtggctcgg    300
cgccgggcct cagggaggac gcagaggggg cgcccgtggc ggtgggcgcc cagcggtacc    360
tttgggtcgg gggaggtaa ggctttctca gctcgggttc ggaaccagaa agccaccggc     420 ccccggggg taagggtgg gcgccggcga cccgggccga cgccgccacc tcagagggcg     480
cgcgcgtccc accaaggtcg gccgccggcc cttcggacgg acgagggaaa agccagccgc    540
ggctccaggg tgcccgagac tcaatcgcac cacctgcacc ccggccacct ccgcctccga    600
agtctcagga ggaaagcccc gacccagccc gcagcctctc tcgcgcgttc aggacccgag    660
gctgcgggca gccgccttcc acgacggaca gcacggagtc ccgccgggcc ccgagccacg    720
ccagtctcgg acttcagctg gtccgagct cctctgggc ctggagggct tttagaggag      780
aagaggaaac cagcacagga gccccagagg gccggacagg tctgtgcgcc agcggcccgg    840
gcgcatggca cagtgcctgg atcaggattg gtgcgaagcc agcatcaaac ggacagaaaa    900
tgaatccgat ccgacactct aggaagagca tgaaccttcc aatccaacca atgtttgtgc    960
gaggccaggt tccccgccgc ggtggccccac aagccagccc tgtcctcggg acgcaaggta  1020
accagtccgg ctggaggccg ccacgcacgc ctggtctctg cagttgtggc ggattcccag   1080
ggactctgcc caggaaatgg aaacccgtga gggcgctcct caaagccgag ggtggtgatg   1140
gccagcgaac ccgaaaaagg gcagggtggg cgccctccca tccgcttaag cagtagccca   1200
ttccactgc                                                           1209

<210> SEQ ID NO 23
<211> LENGTH: 1209
<212> TYPE: DNA
<213> ORGANISM: Homo sapiens

<400> SEQUENCE: 23
cgcgcgcgca ggtccccgcc cctctccccg ggctgggggc ggggtgggca ggccgacggc     60
tgacctggtc gaaatagatg gtcatggtgc ggttgctcat ctcggacggc tcgtggttgg    120
tgctccggtg gcggagaagg ccaccttggc gctgccggag cgcacggaga tgcctaggga    180
```

```
ggaggtgacg gcgccgtccg ccgacgggct ggagtcgcac accaccaggc acttgccctc    240
cagcacgatg ggctccgtgt cgttctgcgc ccgcacgggg cagcaggcgg cagtagcac     300 aacagcaggg ccagcgccac ccccaggcag gatccgcagc cgcccggctc gcgcagcgcc    360
ccccggcgcc cgggcatcat cagccgcagc ccgagtggcc cccggccggg cgcctgcatc    420
gggactggtg ggaggcggcg cgcggggtg gaggccggcg ccggcgcgag cgcgcggaag    480
ggcgcgaagg aacgcgcgga gctcgcagca gcctccgggg gccttcgtcc ccggctctga    540
cgttcaaggc cagggtcgtt ctcagaagaa aggcgcctgt gaacctgtca gggcacagaa    600
cccaaagcct tacaccggga ggtggagcca ccgggaagaa ggggactggg agcaggtgcc    660
tgcggctcgg gggttctccc cgaaggccac ccccttggtc ccgcgcacag ccaacccgct    720
ttccgatctg gcacaacagg tccgagaaa cgcccgggcg cagctggcag cgcatccctg    780
aaggctcccg agcagcgcgc ggggctgcga cgaggagggg gccgcgcttc tgcaggtcct    840
cgtcgctaag acgggccccg agaccctcag aaggcgtcac cgccaccccg cccattcacc    900
agcgcggagg gggctaagac gcaggcaaag aaaaacctac gaatgcttgc cttctcgcct    960
tcatctcaca gcatttcctt ggagcagacc aaggaaccct tttcctatcc cttgtttccc   1020
tgctatcctc tattttcaa tcctcgagat gttttaaag tccattaag tccctttggt    1080 acagatttta tctgttttcc acccacagaa caaatcccag gaatctcctt ggggcgaata   1140
agattactag gggggaaata caccacacac acacacacac acacacacac acacacacac   1200
acacacaca                                                             1209
```

<210> SEQ ID NO 24
<211> LENGTH: 538
<212> TYPE: DNA
<213> ORGANISM: Homo sapiens

<400> SEQUENCE: 24

```
ggaagtatct tggcctgcac gcggtttaca tcattgggag cacaggcctc gccctccgaa     60
ctacgaggcc cagagccctt cgcgccgagc gtttcccgcc tttccctgt ctcaagtcat    120 tgcccagggc cactgcgggc cgttcctgcc tgtccgtgga gctgcggccc ccgtgttccc    180
agggtgaacg agcacgtgcg aggcggtggt gcttgtatcc gggataacca ggtagggcgg    240
ctgcatgctt catagaggcc agcctgtgcc gaccgggagc tgtaggacgg tctgtgtctg    300
ggctgcttat gggtattcgc gtgcgtctgc cggtgcgcgg tccgagccta ctcacgagag    360
cgtgtgtgtg tcttctgtct cgtgttgcta tgaggtttgc atctgtgtgg ctggaatagc    420
ttgtttgtgg gggcccgcgc gtgacctgtg tgtgcgttac tgtgtgtgtc taggcaggat    480
agtgacgggc cgtgtgactg tgacgccatc atcaggttgg tgagatggcg tgaccgcg      538
```

<210> SEQ ID NO 25
<211> LENGTH: 450
<212> TYPE: DNA
<213> ORGANISM: Homo sapiens

<400> SEQUENCE: 25

```
cgagggagga cgacaagcgg ggacgttggc ggaggggtta atggcggagt cgcgatccag     60
ccgagcccac aactctggga ggctggttct gcctctctcc cgaagcgtcg cccggctaag    120
cttcgagacc aggacacaca accgccgact attccagagc ccacagtcgg cttcacgctg    180
gaggccggaa acgacacgtc cccaaagccc gcgcgcgcgg cccgccagaa ctgacctacc    240
```

| | |
|---|---|
| caatcaccgc accgctgcga tcaagcggcg acacacgttg ccgggtaaga gtcacgcttg | 300 |
| gcaaataagc aacctgcctc atccaatcag cgtctcgcct gcccggttag ttccttgtct | 360 |
| tgcccaacca gattcttgcc tcctccatac cgctacttgc gtgtgccggt gcctggccca | 420 |
| atcagcgtct tgcgcctctt ctcgctcccg | 450 |

<210> SEQ ID NO 26
<211> LENGTH: 1209
<212> TYPE: DNA
<213> ORGANISM: Homo sapiens

<400> SEQUENCE: 26

| | |
|---|---|
| cgcttgttgc ggtggatgtc gccaatggaa ttggacaccg tgttggggcc cagcaacatg | 60 |
| cgggtgctgc gaggccactc ggtgctcacg aggtggtgct cgcccatgag gatcttgcgc | 120 |
| acgttctcgc gccggtcacg cgtatcagcg gccgccccaa caaatgcgtc ttgaacacgt | 180 |
| tgccatactt ctccctccgc gacgactgga agccagaacc ctgcgggagc cacacccggg | 240 |
| tctctctcag ggtgcacttc tgcagagggc ccgcgaggga ggggcggcgg accccaaccg | 300 |
| gggtacagtc acctgccccc tctccccacc aaacacactc acacagacga gcacgcaggt | 360 |
| tttattttc atagcgtgca caagaactgc gaagtagggc ctagaggata ataaataatg | 420 |
| caaggaggcg gaggcccagg ggcaccccca ggaggctgtt ttttggtaat gctttcgaga | 480 |
| ggaaagaggt atcccggaca gctggacccg aagcggagt ctccgccccc accccaccc | 540 |
| ccacaccccc accccgcgct cgggagcctc tcggaataaa tatttccagg ctccgggcca | 600 |
| cgggctggcg agacccgcg gggtggccgc aggccaaaga ttattatagc ggtaagcggt | 660 |
| cggtgcccgg aggcagcaac tacagatggg ggttggagtt cctccgctc tccggtgtgg | 720 |
| cccgcgcagg gaccccggcgg ccctcggagg actctgcagg gcggggtcac gggcccagag | 780 |
| ccgcgatttt cctaatgcat tttgccctgg aaatacgag acggactttg gttgccgccc | 840 |
| tggagtttgg aacccgagcg cggggcgggg cgggaccggg cagggcgacc cgcgcaggta | 900 |
| accagatccc cggtggtggc ggcgcaagcc gaggatggcg gggccggggc cggccggact | 960 |
| ctcgaaacgg ctggcggagc cggccggcgc gggtaccgga aaccgtggag acctcagagg | 1020 |
| ggcgggggca agggcgtccc gctcacctt gacgtcggca ctagttaccc caccccacgt | 1080 |
| taaccttct cctgccgggg cagcaccccgg cgcaaagggg aggggcgcca cctgtctagc | 1140 |
| cgccccgcct gccagcccag agcgtaccga ctcgggctcc agatctaccc gctcctgcac | 1200 |
| ccccgaggg | 1209 |

<210> SEQ ID NO 27
<211> LENGTH: 1209
<212> TYPE: DNA
<213> ORGANISM: Homo sapiens

<400> SEQUENCE: 27

| | |
|---|---|
| cgctcggcag aggcacgata cagcgggaga gaagggcagg cccgttcaca ttttaatcgg | 60 |
| agcgcaccgg cggccgctcc tcggctgcgt cctgggctgc cgctcgggct cgggactgcc | 120 |
| agatgcagct ctggctgggg gcggcgggcg caagcgggcg cacccgcagc tagggtgcg | 180 |
| gggtgcacgc acacgcacgc tcattaagag ccatgtattt attgaatgtc cgagttgggt | 240 |
| tagttcattg gaaatccccg aggagggctc aatttgccct tgttttcgtt gccactttcc | 300 |
| tttttttcttg gttcgctgag gttcctctgt gcagcgtttc cgcttggccg cgtccccca | 360 |
| ccccacccca ccccaccccc gcttctctcg cctaccgggt gcactccccc tcccatcccc | 420 |

```
cttaactctct tcagctgggt tagagctgag aaagcatttg tcgccgccag cccatccacc      480
acgcaaatcc atctgagaca gaaaggaaag aaaaaaaagc accaccatgc ctaagaatag      540
agagcgagca acccccccca ccgctaatca cacacacaca cacacacaca cacacacaca      600
cacacgagga agcggtggag cagagaaggg cgcggctagc cgacccggtt ctttcgcccg      660
gctcctgctg ccacagggaa ttcctaaagc cattggggtc gaatacactt acgatgaatc      720
tatgggggaa ggtcggactg attgcttttc aaatacatcg cacggctccg ctgaccggca      780
ccctccaaac tcacaagggc acgcacgcta cttgccgaat cccagaggag ggaggaggga      840
ggaagggagg gagagcgaag gagggagaga ggggtggag gagccaggga gcggcggcag       900
cgagcggtcc gtctcgcacg cgcgggcacc gcgctggtcc tgggctgcag gtttcccaga      960
tgatggcatc cgagaactta acaaagggg ctgccgccgg cgcgcaacgg ctgcggaaag      1020
ttgcggtggc ggatttccaa ggagcgtggc cacgaccaga gctcttggcg atgcgagccc     1080
ccgcttccca ccccgccga tcagagaagg gggccggctg gtgaagggaa gaggaaactt      1140
tgaaaccact ggggacacac tgtctatagg tattagcttg aatggtacat ccgtgccgcg     1200
cgctttaca                                                             1209
```

<210> SEQ ID NO 28
<211> LENGTH: 1109
<212> TYPE: DNA
<213> ORGANISM: Homo sapiens

<400> SEQUENCE: 28

```
gactctcatc actaccacac ccatgtgtct ttcctctctc cgtctccctg agacgccagt       60
gaaccacctg ggcttggaat ccagagcccc ggaacacctt gcagtacttg cccgaagcaa      120
cgcgccacag cgggagggag acgcagacgc gaagaccggc gagaggatgt gcggtgggag      180
tagctgcggg gtctgcaagc aggggagcgc gcacaacgtt aaaccttgaa accagaaatc      240
ccgatcctat cgagacccat cagcttttcc catttgggaa cgagcgcagg ggaaattaat      300
gcgtaattca agctctgttt tcccctcccc tccaaaggtg aggtggggga acgcgtctcg      360
ttagctcatt acaaagcttt ccgtgggaaa ttccctcttc ctaatgcgtc tgtcttgcaa      420
ctcctattag catccttcga cagcggcctt tgaaaatctc cttttaaattt catacctcta      480 ctcgtttccc aaatgggggg aagggaagag aaagccgggg ggtagagaga atttccttcc      540
cctttccctc ccaggtagcc aaagcgcacc gcagcggctt ggcttcctgg aggaaaagcg      600
cccgagcggg gcaaagaccc gcccaggctg ctcttatagg cgacgcgggg cgggcctggc      660
tgggggcggt gccgcgcggc cccgctcgcc tataaggagc tgtccgccac ccgggtgctg      720
attccagctc tcgcgcccga cgaggtggat ttggctgtcc accgagctcc ggcgcctgtc      780
gttctaattg ggtttggatt tgcaccgtta aggagggga agagaaggaa gaggcgggcg      840
aggaaggcga gtccagctag cggctgttgc gggaccgta gccccagctg cagctccgaa       900
gaatcccccg ccacggtttc ggtggagcgt ctgggcacgg gatggagtga aagagcgagt      960
gcctctccaa gcggggtgg gagggggcag gctgtgcaga ggagagagac agcgagaaga    1020 agccgcgggct ggctactgcg aatttgggat tcgattggga gggaccgctc actcggggga   1080
aatggattct ttaccacggc tgaccagcg                                      1109
```

<210> SEQ ID NO 29
<211> LENGTH: 1209
<212> TYPE: DNA

<213> ORGANISM: Homo sapiens

<400> SEQUENCE: 29

```
cgtacccggc tctcaaaggc acggcacctt tgaattaggt tgcggagtgg cctgggcgag      60
gggacccggg gccatcaaag gcccgaggga aggccgtggg gcgacacccg tctaatgaca     120
agtaattaag gattcgacgc cgcgcattac cagcggaacg ggaggcatta attatttaaa     180
aacgattagc cttgccgtgt gtcctgcagg cgtcccatca tgttcagcga agataaccag     240
ccacccgagg cgagccgggg ctcggagggc ggcgggcgcg ctccccagca ggcttcgggg     300
cggtggacac gggcgcacag cccaaggcac caggaaggga gaggaggggc caccaagggt     360
ccccacacag gaaggtgact acataacact gaccctgctg aacaacgaaa cagatttctg     420
cccacttggg ttcgaagtct ggtgactgcg gcgcagatgg gaaaagcttt cggtcggggg     480
tggtgggcaa tttccatgtg ccagttccct gtcgcatcag accaaagacc caaagtaacc     540
cagccaggca cgggcctctc acagtgcctg ctacccaggc gtttaaagaa aagaccccag     600
agagaatgtg gatctggcgt gggggcaggg attgggggg ggcctggtag acacctgggg     660
aaatacaact ttatgaggtt tcaaggggca gcagcagaac tactattttt ccgaggtcca     720
cgcctttccg caggcggcgg aaagacgcgg ctggttctgt tgggtcctac aaactcgcgt     780
cctccggaat tcccgagggc aagcccggca cgcgcagcgt gctcctgccc gtggaagggg     840
ggaaatcggc gactgggttg cagggagaat gcgatgataa atgggcccgc gtctgctttc     900
tgactttctc tcctggaccc agctcgtaac cccagaggct ccccaacctg cctgccgcca     960
agcacggctg tgcgcaaaag gccaccaccg cttcctgcag ccagagctaa ggttcactcg    1020
cctcttagaa aggcgcggcc cctcccctgc tgctgcttga tgacgatccc catcgtctcc    1080
tcggcctgcc tgtgtccgag aaagagttga gactggactc gaaccctgc  gcgccaaggg    1140
gagggcgtca ccatgctccg cctcagcctc ttcaaactcc catgcaccac gcacatcatt    1200
ttctgctga                                                            1209
```

<210> SEQ ID NO 30
<211> LENGTH: 1209
<212> TYPE: DNA
<213> ORGANISM: Homo sapiens

<400> SEQUENCE: 30

```
cgacgtccag ggaccaggtg cccttcggct cccgccgacc tgttgctcga aacttgccct      60
gagctctcgc tgccgggctc tgggctccca agcctctccc ccgccgccgc agcagcctct     120
tttagggccc ggaagaaatg ggagccgggg ctggtgagag gggtaggaag agggacggta     180
gaagtttcag acccaggcat atttgggaag gcgagtgctt tacatgattc cccatttccc     240
aatcggacca gcttagcctg gcaggcagc  ctcgtgctga ggtgcctgga gaccgcccac     300
ccctaggtgc tcgcttcccc ccgggtctga cctgatcgaa gtaaatgatg cgcgtcttgt     360
tgctcatctc ggatggctcg tggttggtgc tccgcaccgc cgagaaggcg accttggagt     420
tggccgcccg gaccgatatc cccagcgggg aggaagagga gcccttggag tcgtggccgg     480
gttcgagtcg cacaccacca gacacttgcc ctccagcacg atgggctccg tgtcgttctg     540
tgcccagacg ggcagccccg gcagcgtgag gaccagcagc acggccggca ccgcggacag     600
cgcccgcgc  ccggagccca tggtgagccg tgtgggcagc cgcgccggct ggcgctggtg     660
ctcgcccgcg tcgcctccta ccccgggatc ccggtgctcg ggaagatgct agcggctagg     720
tcgacagcgc tgcaggagcg acggcggcgg cggcgcgcac acttccacca attctgtggc     780
```

```
ttgaagtcaa agtctccct cgagctctct cgctgctctg ttacctttgt cctttaagga    840
gctcatgcag caccctttac cctactctcc tccgcccaag aatcagccct gcctggggcc    900
cctgcaccca ctctggttcc tagacatctg aaagtcatca aaccctcaca ttcacacctc    960
aaggcaaaaa ataataataa taataaatct caccccaaac tcaagcacca ccagctaaac   1020
cacggagcag gaacaaaaag aggggactca aagagaagcc acaagggtgg cgggtgccca   1080
gcggcgcggg tgccagtcct gtctggcttg cggcagggac gagttacaga ggcagaaggt   1140
ccttcccagg ctgagaagac gcgaggctgt gttcatggcc aggacgccag cgactcccac   1200
tttcgcctg                                                          1209

<210> SEQ ID NO 31
<211> LENGTH: 1209
<212> TYPE: DNA
<213> ORGANISM: Homo sapiens

<400> SEQUENCE: 31
cggtgccggg agccttgcct cccgccgcca cccctggtca gctctgcgca agaacgtcgt     60
tctgtttggc agccaggccg agacgcagcc tgaatgtgag caggaactcg gagaagggaa    120
gggagagatc agaaagaagg cccgggaggg acccgggaag cagtgggagg tctgcgccct    180
ggagccccgc gagagcccgc cggtttggca cgggctcctc ccgggccgcc ggcggtcca    240 acaaaggccg gccccgacac gcacccggtc ttttgtggga gagaaacaca aagaagagga    300
aaaacacgga ggaggccaac agcaccagga cgcgggggcc aaccaggaac tcccggagcc    360
ggggcccatt agcctctgca aatgagcact ccattcccca ggaaggggcc ccagctgcgc    420
gcgctggtgg gaaccgcagt gcctgggacc cgcccaggtc gcccaccccg gcgccgggcg    480
caggacccgg acaagtcctg gggacgcctc caggacgcac cagggcaagc ttgggcaccg    540
ggatctaatt tctagttatt ctgggacgg ggtggggagg cataggagac acccgagag     600 gtactcagca tccgattggc accagggcca agggagccca gggcgacaca gacctccccg    660
acctcccaag ctactccggc gacgggagga tgttgaggga agcctgccag gtgaagaagg    720
ggccagcagc agcacagagc ttccgacttt gccttccagg ctctagactc gcgccatgcc    780
aagacgggcc cctcgacttt cacccctgac tcccactcca gccactggac cgagcgcgca    840
aagaacctga ccgcttgc tctcaccgcc gcaagtcggt cgcaggacag acaccagtgg      900
gcagcaacaa aaaagaaac cgggttccgg gacacgtgcc ggcggctgga ctaacctcag     960
cggctgcaac caaggagcgc gcacgttcgc ctgctggtgt ttattagcta cactggcagg   1020
cgcacaactc cgcgccccga ctggtggccc cacagcgcgc accacacatg gcctcgctgc   1080
tgttggcggg gtaggcccga aggaggcatc tacaaatgcc cgagcccttt ctgatcccca   1140 ccccccgct ccctgcgtct ccgagtgaca gattctacta attgaacggt tatgggtcat    1200
ccttgtaac                                                          1209

<210> SEQ ID NO 32
<211> LENGTH: 1209
<212> TYPE: DNA
<213> ORGANISM: Homo sapiens

<400> SEQUENCE: 32
ggccggccgg ccttccttcc ttccgccctc gccctcttca tgcctcagaa acgtggccta     60
ctctgcattc ggtgtgtgcg gaagcagcaa tcacagaggc agccctaata ccggaggcgg    120
```

```
cggcggcgca gcagggccag gtggtagctc ggggctgagg atcgcggcgg gggcagccgc    180 tatgggccc aagccctgac acacgtacca ttcgctcaag tcggcggtac gcgccgccac     240
cgccgccgag gaggccacct gggacttgtg gccgcagtcc gacgagggcg acacgaggga    300
gacggtgtag ccgaatcgta gccagagctg ggcggcggcg agcgcccgtg caccttcatg    360
tgcttacgca gcgagctggg gtgcgtgtag cacttgtcgc agccccgcac cttgcacgtg    420
tatggcttgt cgctagtgtg cacgtgcgaa tgcttcttac ggtcgctgct gtggcgaagc    480
gccgctcgca gccctcgaac tcgcatctga agggcttctc gcctggcgga ggcaacgcag    540
agacattagt gcttgtgggt cgtgttcccg tcaggtgctt gccaccctcc cccattcgtc    600
tctcattttc tggaaaagaa ctacaaaata ttttcagaaa tcctttccac ggcgcctcag    660
gtcgagcacc cctttccctc gtgcagagag cgcccccggt gccctctctt gaacgcctcc    720
atccctcccg ccttcctcct ctgggctcat ggggagggta tggaggagga gcgacagtga    780
ctccatctta gtcgagtttc catcctcgaa aatccgatcc actcgggttg tttcctccaa    840
attttctcca cttggaacca gaagcacctc tgctcggaaa tacattaacg gaggagctca    900
caatatagtt aacggggaag ctcacatctg ctcgatttaa agttgctgtt tcagactaac    960
ttctctgccg ctaccccgcc cagccgtcat ccccccccacc caccccccatc ctggcccaaa   1020 ttgtttcccta aagtaggttt tgcgcaaacg ccaaagcgat gaaataattt aaggatgcgc   1080
agccgatgca cattgtgtgt gcataaagtg gattcgtgct gcaggagag gtattctgag    1140 caatgattca cttcagaagg atttttacag gaatggagcc ccctcccctct ttccttctac   1200 cccctgagg                                                           1209

<210> SEQ ID NO 33
<211> LENGTH: 807
<212> TYPE: DNA
<213> ORGANISM: Homo sapiens

<400> SEQUENCE: 33
gaaatgttct ggagcatggt gacgggaatg cagaagaagg tgatgagcag gtcactgagc     60
gccaaggagc agataaagat gttggtgacg gtgcgcatgg ccttgctgcg ggtcaccacg    120
tagaacacag agcattgcca aagagcgcca gggcgaagat gagcacgccg gtgagcacga    180
gggccagctt ggcgcgtccc ggcagctctg ggtgtagac gagcggtcgc agccggtaca    240
gagcgatgaa ctgctcccgc gtcaggttgt ggtcccgcag cagccgagag aactgctccg    300
ggtaatgtta agcgcctgca ttgctgtgcg ctcccgggac gcggggccac cgcccgctac    360
tggctggcca tccgcatctg cggggcagcg agggcttcgg gggaccagcc ggaggccgcc    420
tcccttcctc tactctggag tcagccgcgc gggagggctc taggctgcac ccggagggtt    480
cgggaaagga gagcagctca gggatcaaac ccacgataaa gaggcgggaa gccaaagcac    540
tgggagactc gatctcagtg accaaaaaat gttcgcggtt caaataaagt tcttcccttg    600
ctcttcccta aggcgaggcg ccgccacggt ctggggtgct ggacgccacg cgagggtcct    660
ggcgcctctg gctccccgcc ttctggccat gcgatgcgga cgccggaccc gcttggggag    720
cggtggaggg tggggctgaa ctcggtgacg cctccctcac acccagcttc agtggcgcca    780
acgccgcttc cccgcaccct cagggcg                                       807

<210> SEQ ID NO 34
<211> LENGTH: 349
<212> TYPE: DNA
<213> ORGANISM: Homo sapiens
```

<400> SEQUENCE: 34

```
gaagatgagg tgcagaagta agctgggacc tgtgagcctc aatttcggcc tcttctgcgc    60
tgagacccaa gcggatcttg cttggcctgt atgcgttact gggggaaatg gacgtgggcc   120
tgagcgcgca ggtgcgaggg cgctgccccg gggccgacca ccctgcgggg acactgtagc   180
tgtcattcct tcttctgcag gcgggtaggg gaagcggtgg ccaaagtggg agtcgaccgc   240
tcagcacagt ctgtctgagt gttgaccagg aaagtccagg ctctttctaa atctcgccgc   300
agacctggtg acgcattcgc atgtatttaa ggcgtttgca cgcagaacg              349
```

<210> SEQ ID NO 35
<211> LENGTH: 457
<212> TYPE: DNA
<213> ORGANISM: Homo sapiens

<400> SEQUENCE: 35

```
ctttactctt ggagaaatcc ctcacaacaa aggacaaggg agaagcaagg gggaggggcg    60
cccagtggac ttggctggaa gaagtgagcg ggctggggtt ggaagagtaa ctcgggctgc   120
gggctgacgc agtcggcaac cgcggaagag cagcatctcc cctgcgcctg tggatacgcc   180
agtccaggga tggcgagtgc tttctcctcc ccagcttctc cctcgctctt cgaggtgact   240
cgtgggaccc tgcgtcctag tgctgggtgt gaatcggcta tttcacaccc agttcttccc   300
ccctccgcca cacgcagtca cattcctgga gctattccaa gctgcctccg ctaagcaccg   360
aataagcgga ccctgcctgg aaacttgagc gaagctgaac tgcgccgaac tccaccgtcc   420
agtgacccga gccagtgtgg acgcccttttt aatcacg                           457
```

<210> SEQ ID NO 36
<211> LENGTH: 677
<212> TYPE: DNA
<213> ORGANISM: Homo sapiens

<400> SEQUENCE: 36

```
cgctgtgcga gccaggatcc gggcagatcc gctactcgat gccggaggag ctggacaaag    60
gctccttcgt cggcaacata gccaaggacc ttgggctgga gccccaggag ctggcggagc   120
gcggagtcgc atcgtctcca gaggtaggac gcagcttttt gccctgaacc cgcgaagcgg   180
cagcttggtc accgcgggca ggatagaccg ggaggagctc tgcgctcaga gcccactgtg   240
tgtggtgaac tttaacatct tggttgagaa caaaatgaaa atttatggag tagaagtaga   300
ataatcgata ttaatgataa cttcccgcgt ttccggatg aagagttaaa agtaaaagtt    360
aatgaaaatg cggctgcagg gacacggtta gtgcttccct tcgcgcggga tgcggatgtg   420
ggtgtgaact ctctccggag ttaccagctc agctccaatc tgcacttctc ttggatgtgg   480
taagcggaac tgatggacaa aagtatccgg agctggtgtt ggaacagccc ctagaccgcg   540
agaaagagac tgttcacgac ctcctcctca cagctttaga tggcggagac ccggtactct   600
ccggcaccac gcacatccgt gttacggtcc tcgacgcaaa cgaaatgcgc ccctgttcac   660
cccatccgag tacagcg                                                  677
```

<210> SEQ ID NO 37
<211> LENGTH: 415
<212> TYPE: DNA
<213> ORGANISM: Homo sapiens

<400> SEQUENCE: 37

| | |
|---|---|
| cgaatcggga attggcattc cgtaagggag cggagggcct caggccacta ggcagctccg | 60 |
| aacgcgggga agcgggagca aagatgagct cagagcgagg gttgccggcg ccaccctggg | 120 |
| ctgcgcatga ggggccgtgg acccgccccg agactcagtg acagtcgcag cttaaccccg | 180 |
| ttggggcgc cgccccgctg aggtggttgc gtctccaagt cgtgagcctc caatagctgc | 240 |
| tcccgctttc gcgtcgcaac cccaggaccc cgggaaatta ccactgtgct cgtctgggcg | 300 |
| gagacccggt gcttcggaag cctggggcac atgcctgggt cccacccctag actcaccgcc | 360 |
| tctgggcccg agacatggga atctgccctt gaatatctgg gcgcctttgc tgtta | 415 |

<210> SEQ ID NO 38
<211> LENGTH: 639
<212> TYPE: DNA
<213> ORGANISM: Homo sapiens

<400> SEQUENCE: 38

| | |
|---|---|
| cgctccacaa cccggaagga gctcaggccg gacttggcgt gagggtccct gcggggctgg | 60 |
| gtcacctacc cgtccgcgat caccccacag gggctgttag taatctccct gcttcctagg | 120 |
| ccgttgaaag cactcaggtc acccactctc ggtgaccaga gcggtcagtc tttccccgcc | 180 |
| atgaaatgtg agttcgggtg gcagccgccg cgccctgca gtgtccctg cacatctccg | 240 |
| gtctcggtct cgcctttctc agctccgcgc cgccttttcc tgggcgccgc aggactcatg | 300 |
| aagtgaggcg gggccacaga tttaagttta ttccccgcaa ctgtcggggc ggtcccggag | 360 |
| ctggtgagga cgcgctacgg tgggtgcaga aaggagatcc ctggactctg tagaacctgg | 420 |
| gcccgcggtg tggaccgatg gtggattctc gcgacaaca gccctggagg ggagagtgggg | 480 |
| ccggggagg ggccacgggg cccctgaggc ctgcggggct ggccgcactg gccccgggcc | 540 |
| tggcggggtg gtggagtccg aagcggcgag gcgaggaccc cggggcccgc tcccccagt | 600 |
| cgccctcccg ggatgtggcc ccgctgcagt agcactacg | 639 |

<210> SEQ ID NO 39
<211> LENGTH: 888
<212> TYPE: DNA
<213> ORGANISM: Homo sapiens

<400> SEQUENCE: 39

| | |
|---|---|
| cgggctccgg tgcgggacag gcagccggag ggagctccag acccctcccc tcgcgcccgc | 60 |
| ggccgctgcg cggaggtctg cggagggcgc ctggctcggt cggtcgctcc ttccttggcg | 120 |
| ggccctcccg acccacggtg ctcagccagc cccattcttg gcattcaccg cgtgccttaa | 180 |
| ttgtatggac atttaaatca aggtccgctg tgaacacgga gagagaggcc tttctcctga | 240 |
| ggaaggaaag gaggaaggaa ggaaggaaag gtgaaagaaa ggaagagggg tgggtagaaa | 300 |
| tggaataaga aaaccaggaa aaagaaataa aaagcggcgc gtgtgcgtgc gcactgacag | 360 |
| cggggagagg gatgggggtg gggaacgccg gaggaaggga ccacagcatc ctccccgccg | 420 |
| cagctccccc aatcacacag acaatgagat aacagcgacg tcttccaaag gtctttgttc | 480 |
| tcccccatcc tttcgcatcc aggcttttc ctgcaaagcg gaggggtgg agggatgggg | 540 |
| gtgtgggtgg aagtgggaga cggaggggtg cctccccgt gttaattacc ccggctcccc | 600 |
| tcgccccttt ccccgcgcct cgcctcccct gcagctccag acatgaaaaa acaacatcga | 660 |
| ccccacctcg ccccagcgca gcaacccacc cacccatgtc gccctctgct tcgcccagga | 720 |
| aactgaaggg gactaggagg aggaagaaga gagcgaagga caaggagagc agcggggact | 780 |
| cggcagcggc agccggggca gggcgcgcgg ccgcccctct ttacctccat cgctgagtgg | 840 |

| | |
|---|---|
| gggcgcagcc gggccgggcg tgccgcaggg gcgagttgcc gcggtccg | 888 |

<210> SEQ ID NO 40
<211> LENGTH: 1209
<212> TYPE: DNA
<213> ORGANISM: Homo sapiens

<400> SEQUENCE: 40

| | |
|---|---|
| cgcgcgcgcg cgcacccgca cgcagtctgc aatgccctca ccagtccccg cagctgggca | 60 |
| acccctccaa gaccctgtgt tacgcttaaa ttcctctccc tcctatcgta cccaccatcc | 120 |
| atccttaagc agggaggccg agactcacag aattcccttc tccaccaact cgcactcttg | 180 |
| gtctagcacg cggaaaccga acctttctac gcggcccgac cttgcgattg ctccagcatg | 240 |
| agtggcattg acttttccaa tgtaatgact tatgaaagat ataatcatgt gttaaattga | 300 |
| tcctccgttt aactgttaat ggtgtgctct gggcacattt acgtatttga tgctatggta | 360 |
| actaattacc actagaaaaa aggataatac acttcccaga ctttgaaaaa taatcatgag | 420 |
| ttcacttccc ggctcgcagc acatcgtggc ggccctgccg ggaggagcga gaaacgagtg | 480 |
| gaaacccgaa agtgtgctca tggaatgcag gaggtaatga atcctggtca ggtgagacta | 540 |
| cttagtcaaa cctttaatga aaacgtgatt cacatggaaa gcaggagtgg gagggaacaa | 600 |
| ctacacaaag gtgcctttaa acaaaattaa atggcaaaac ctgctatcag aaacatgaat | 660 |
| aggtttcttt caattaaaat gcaggtaaga ctaaattatc cacgtgccaa gcaactttac | 720 |
| atcaattaac attttttgt tgtgtgggca aagtaaatga gcccggctcc tgtgctctct | 780 |
| gtattggcat atacaacttg aaagtctctg gatttccaag ccaatgagct gcaggtttat | 840 |
| ttaaattcgg ccttttaaat caaactttag acacagtagg tggaaggagg gaaagagaag | 900 |
| gaaaaacaag gagtcagtaa cttcagttta acagtagaaa caactcttac ggtgagagtc | 960 |
| tttttttgccc ggcaaatctc tggctctctg atcgactggt gtttagaacc aaggttccag | 1020 |
| taaacagggc tgggtaggat aacgaggaga gtgtttgtgc tgggacctgg caggactgga | 1080 |
| ggaggaaagg agccgccttc cagcaggtcc agcatcccta ggttgcaaac acaccaaatg | 1140 |
| acgtccacgc agcactcgcc ccaccgcgct gtttttgctt cgcagtgct cccgaaggga | 1200 |
| ttcgggatc | 1209 |

<210> SEQ ID NO 41
<211> LENGTH: 1209
<212> TYPE: DNA
<213> ORGANISM: Homo sapiens

<400> SEQUENCE: 41

| | |
|---|---|
| cgtcgggagc gcgcggggac acacacgcca ctcactcaaa cccgcaatta gcccttгgag | 60 |
| ccccaggcac aggaaccccc tccctagaac tggagaagac ttggaggcgg cggggcggcc | 120 |
| aggtgaaagc ggacaagggt gccggtaggg ggaggggcag aggagcgcgg ggacgccccg | 180 |
| aatgcggccc ggggccgggt ccaagggcag cggggctgcg gggcgctgca cccggcgccg | 240 |
| ccttacctgg agtcaatgtc cgtctttggc ggagagctgc gggaggacgc tttttattcg | 300 |
| ctcggtggga acttgggaga gccctgcgtg cagctcgcat tccgggcacg gcgcggggac | 360 |
| tgcaggcgtg ggggtacctg gctcctagca gcctggctca tactcagccg taaagtcccc | 420 |
| ttcgctggtc ccgaggacag gcatgaatcc cggctccgga aggcggtcac tctccctctg | 480 |
| cctcccggct ctctcgctct cgctctcgct gttgctcgct cgctctctcc ctctctcgcg | 540 |

-continued

```
ggttcgctcg cctgcgctct cctcctcccc gcgcgccaga tcagtttgca gccgtggggt      600
ccgggagcga ggcggctggc gaatggagag ggaagtccaa gtggccgcgg tctccgggcg      660
gggagcggcg gaggccgggc tacgccgggg gagggactta gccggcgacg gccgaaaatg      720
aatgggggag cggcggccgg ggggcgggga ggaggagct gaacgccggg gttgcttccg       780
aggagtgttt tgtacatctt taggcggagg aggagagaag cgagaggagg agagacggga      840
ggccgcctcg agggaagggc ggcccggtg ggctggggct gagccgtagg gagtttcgtg       900
ggtctggggc gtgtagggtg ttgtgtctat gcgcacgagc atccaaaggg accgcgcata      960
cgcgcaaacc cggaatcctg gtgccctaag cgtgactgta ctgtgtgtgt cgcgagtacc     1020
tgagtgtttc tggggcggca ggtgtttcca cggccgcgtg gatccatcga gtgtgggttt     1080
tgtctcggga gttgcccgtg tgggtccgtt tgtgtctgcg cgtctctctg tgagtgtttg     1140
acactgtttg tttctctcgt gtgtaggcga gagcccacgt aacctcccag aatgaagcaa     1200
gagcttctc                                                             1209
```

<210> SEQ ID NO 42
<211> LENGTH: 340
<212> TYPE: DNA
<213> ORGANISM: Homo sapiens

<400> SEQUENCE: 42

```
gcgtgtcgca gctgtgcacg ctgattggtc ctctgctggc caatcaccac tgcacttcat       60
gacggctgta gttttcaaaa tcccaactgg gctggtggag ggtcgcaggt gtcaggttga      120
gacggaccga gtcgctatag taaggagctc cgttcatttc cttggcctct cctggtctag      180
gggtgcgtcg atggtctttg ctgtctgtcc tcgatctcgg tgtgaggtag cgccttttgg      240
gcaagtactg ctggctccag cgtccggctc tgtcgcctgc cagtgggtcc ttgggcgtcc      300
tccagcccct tgctgaattc tgttgctggg atgcgcggcg                            340
```

<210> SEQ ID NO 43
<211> LENGTH: 214
<212> TYPE: DNA
<213> ORGANISM: Homo sapiens

<400> SEQUENCE: 43

```
cgggcgcggg agctacgcca aggttctcct ggtgcggttg aagaagaatg accaaattta       60
cgccatgaaa gtggtgaaga aagagctggt gcatgatgac gaggtaggtg ccgcttctca      120
tggggccggg ggcccgggaa cgcgctgccc tggggcctcc tccgggcttt agcggaatta      180
atccatgcac gagagaccta gcctcacgtt gacg                                  214
```

<210> SEQ ID NO 44
<211> LENGTH: 420
<212> TYPE: DNA
<213> ORGANISM: Homo sapiens

<400> SEQUENCE: 44

```
cgaggagtcg gtgtgaggcc gcgtgcgtct ctgtcgtgga cacgcgtgat tgacccttta       60
actgtatcct taaccaccgc atatgcatgc caggctgggc acggctccga gggcggccag      120
ggacagagct tgcgccgaga ccgcagaggg aagcgtcagc gggcgctgct gggagcagaa      180
cagtccctca cacctgggcc cgggcaggcc agcttcgtgc tggaggaact tgctgctgtg      240
cctgcgtcgc ggcggatccg cgggaccctg ccgaggggc tgtcatgcgg tttccaaggt      300
gcacattttc cacggaaaca gaactcgatg cactgacctg ctccgccagg aaagtgagcg      360
```

```
tgtagcgtcc tgaggaataa aatgttccga tgatgtggag ctcctctgat gcctttttc      420
```

<210> SEQ ID NO 45
<211> LENGTH: 413
<212> TYPE: DNA
<213> ORGANISM: Homo sapiens

<400> SEQUENCE: 45

```
cggacgttaa gccgcgtcca gggctccgtg caggcgctgt actggttgcc atcgtgcatc       60
acgatgcagt agaagccgcg gctgggctgg atctggatgc tgcccttgcg gcttgcggct      120
tcgtgtgcag cccgatcacc cactgggtct tctccgccac caccacctcc cagtagtgga      180
cgccactact gaaggcttca gaacccagca ccgacacctc cacatcgaag cgctttggcg      240
agtcctgcag tggctgtggg tgcagttgcc gtaagccaca atggtgcagt cgtccgacag      300
gatcaggcgc tggtgggctg tgcccgggtc cagggttagg gcggctggca ctgtgggggt      360
tggaggaggg agagaagatg agtggggaga aggctgtggc ccaccatgca gtg            413
```

<210> SEQ ID NO 46
<211> LENGTH: 719
<212> TYPE: DNA
<213> ORGANISM: Homo sapiens

<400> SEQUENCE: 46

```
cgcgccggct ttgccgcttt ccctgagggt gtccagtttt gtgaataaaa ttagagaaat       60
ctgcgggcgt agttcccaa gcccagctca ggcttccgtt tgcagcccgg cgctggccga      120
gctcgaacgc tgaaaagggc gcgtgcaat cgttccgctg tgcctcagga caaactccgc      180
ttcaagccag tgccgctctc cggcagtttc ctgattgact taattagatc cgcataatcg      240
ctggagggct tttcttttccc agaccgagaa cagctcattt atggggacca aaaggaagag      300
agggagagac gacccggacg ccactgatag caacgtactc ttcgcaaaaa acactcagta      360
actagtggaa aagcccaaca ggcatccccc tccgcccgca acgcttcctc ccaattgttc      420
tgggctgcac gagggagatg gccgggccgt ggaacagatg cagaaggagg cccggcacga      480
ccagagacgc tgtaaccaag acccgcagag cctgtggctt cccgctcttt ggcggtgcag      540
caggcatggt gctggagccc aaggcttctg ggaaagagtc caggttttcg cggagggagc      600
gacggactca cgcgggatcg caggcactgc tgcaagacgc cgaacaggct gagccggtag      660
gcgaaagaag tagggtcaca gaagaagcaa agaaaacgaa ataaattccg aatcccgcg      719
```

<210> SEQ ID NO 47
<211> LENGTH: 999
<212> TYPE: DNA
<213> ORGANISM: Homo sapiens

<400> SEQUENCE: 47

```
cgtccgggag cctccgcaac tcgcatttcc cagtcgcaac cctgggtcat tcctgcctcc       60
gtcccagctc ccggacaatt cccaaagcca aaggcgtcga gcgtgttact ggctcccacc      120
agcccaatta ataatcagct taactcgtgg aggctttgag ccccagtgct ccgttccctg      180
aagcctccca gtgcggagcc cggctcctgc gaggacatcc ttgaggggg gccggggcgc      240
agggacggat ttcctgggaa aaatgtcgct ggcgtgttgc acctagaggg ctgtgggcaa      300
ggaggcacgc accaatgtcc cagttctggg ctctcagatc gggattcctc caaaatcgcg      360
acagccgctc aggtgctggg tgctcacgtt ggcagcacaa gcgccaaatg cacgaccccg      420
```

| | | |
|---|---|---|
| cgcgccgcgc gcgacctcca cgcacactta gagccgaggt gacaagggaa ggcggcgggg | 480 | |
| gtggagccgc tctctggtgg agcatgatca atcactttaa agggttcaaa agttcaagtt | 540 | |
| cccctttgga ggggagaggt aatgcttccc gcggcctgct tctctctgag acccgcgggt | 600 | |
| tcccggcagc cgcgcaacca ctggggatct cggctgccgc ttgcgggagc cccttccggg | 660 | |
| gaacacgctc tcgggccgcg cagccgggcg aggttgacgc agctgctagg gggcagtttg | 720 | |
| gcttccccgg gagtaccgga gtcgctcggc aaaaacgtga tctcagcctg cagggcccgg | 780 | |
| ggcgcgcgct tttcccttc tcagcaacgg gaaaggcctg ttggcagagg ccggcggagt | 840 | |
| gctggcggcc tggcggctgg aggcttcggc ggaaacctga gctccctgcg acctgttctg | 900 | |
| ctagcagggg cggggagag ccccaataag ccgccccaga ggcgaccgtg caaattccta | 960 | |
| agaaaaagcc ctctagaaaa caccaagccc ttccaaaag | 999 | |

<210> SEQ ID NO 48
<211> LENGTH: 1226
<212> TYPE: DNA
<213> ORGANISM: Homo sapiens

<400> SEQUENCE: 48

| | | |
|---|---|---|
| cgtcggcgct aagcagctct ggaaacgggc agacccagct gtgcagcgat gtccagtgtc | 60 | |
| gccgcatctg ccccgcgggg tgcagcatga gtcttccttt gtggcgtgcg gctccatcgg | 120 | |
| aacgcgcttg cgacgacaaa ttccttttt ccccccccgca gttaacagtt ctggggcaga | 180 | |
| ggctggtgga gaggtccaga gcccactcag accgagatga agatgaggaa aagcatgagc | 240 | |
| aggaagaggc tggcggctgc ggcgccacag ggaagagctc ggtgcgcggc gcagcctccc | 300 | |
| gcgaccgcga ctcctgggct gcgtcgagga gccgcgttgc cataggaacc gtagcggcgc | 360 | |
| cccagtgaaa ccctgcgttc ggacaggaga agctaaccgg gccgcccact cccacccgcg | 420 | |
| cttcctcccc gcccccaccg gccgtgcgcg aaaagcagag atccgagaac cgcgtgcggt | 480 | |
| acaaacggca aaagcttcgc gcgcattttc cgggagttga gcgcgcggcc gcaggcggga | 540 | |
| acctaccgct ctcaggctcc cagcccgggc gctacgaccc tgtgggcgcc gcctgtgcag | 600 | |
| cccctccttc cagcccgctc gggcgcatcc cccaggccgg gccagcgacg cgggcaccgg | 660 | |
| gagcccctcc cccggtccgg gctttggccc acacccgggg accgcggagt gggaaggaa | 720 | |
| ccaaagcgcg gcgcctggcc gaccgcggac gaaattcgag gccggagggc gttttcttt | 780 | |
| ttgcaaaatt gccccaaagc cagggcccat gtacctactg tctcctttgc cccacatgct | 840 | |
| ccaagaaaat aagacacatt ctaccccgag tcctaattat tgggccattt ccttaacgcg | 900 | |
| cggtctgtcc ccgtgggcag aaacatactg cgagatgcag tttggtaatt aacaaagaga | 960 | |
| cgagacctaa ctgggcttcc gaaatgctgg atactgcggc cgggtcgccc cgcattcggg | 1020 | |
| catcgcgcgg ttcccggcct tcgggacgtt ccggcccggc cggactttga ccgctggcga | 1080 | |
| attaggagaa acgcagaagg cggacgctcc ccaatttccc catcgagcct tctcctcccg | 1140 | |
| agtctgcgaa gcccctggct caggagacac cggctccgcg cctgggcctg caaatccgct | 1200 | |
| tccagcgagc gcaggcctgt cgctcc | 1226 | |

<210> SEQ ID NO 49
<211> LENGTH: 332
<212> TYPE: DNA
<213> ORGANISM: Homo sapiens

<400> SEQUENCE: 49

| | | |
|---|---|---|
| gttacttccc aaagggcgtg ttctccaaga actgcattta gcatttcaga tcagagtgac | 60 | |

| | |
|---|---|
| ccgaactcaa taggattacg acaaaaacta gtgagattca gataacaccg ttacatcgaa | 120 |
| agttttatcc gtgacagagg aaatattgct tacgccctta ggtaatttca aatgcacgta | 180 |
| tgaaggccgt gcgggtttct gcaggcgaag caaaagaaag gtggggccgg cagggtcgtg | 240 |
| gggcggggggt ggggcatgac acctatccca gacgcaactc gacctcgttt gcaagaaatt | 300 |
| ctgtatccaa ctctcttcag tgcgtttcgc cg | 332 |

<210> SEQ ID NO 50
<211> LENGTH: 1226
<212> TYPE: DNA
<213> ORGANISM: Homo sapiens

<400> SEQUENCE: 50

| | |
|---|---|
| gttcagtggt ttatagaaaa tttctttctc tctctcaggt ccactaagac cgagagagag | 60 |
| agagaagtcg actctggcac acccgggcga ggggctgccg ggattcggga gctggcgcgg | 120 |
| ttgattttc cgagaatcct ccacttgggg tgacgtcggg cagcgcgcgc gggccgtgag | 180 |
| gttaatgccc aggcttttct ctaaagcgtc cgggaatgat ccggcgaata aacgggtgt | 240 |
| ctgcaaagtt aatgaattgt acaggaggct gagggtgggg acttcgaccc ggggagccag | 300 |
| aggcggttct ggtggacgct tccccgtgcg cctaggggtg cgctgggctt tcccagccga | 360 |
| ggtctgcaga gcgcaccgcg tgagcttcat cgatctcatc ttcttccaag tgggaggagg | 420 |
| tggagatgct gggagagttg tggggagttg ggagtgggt ggaggggggac tgtctagatt | 480 |
| ctactctgga ggatccaatc acgtggtgct gttcccctgc ctagaacttc aaggtttcca | 540 |
| acggtttgaa taaaacccaa acgatgcccg atgtccaacg aacgaatgat ctagcctcgg | 600 |
| cctacttctc aggacttagc tttgtccctg cccgcgactt cccgctggga acgtcgtccc | 660 |
| cgccaccacc gctctgctta ggttcgaact ctgggccact cttcctactc cctctggttt | 720 |
| ccagcaggag aagcgcttcg gaggaggggg ctaggggcgc tcaacctccc gggttagagg | 780 |
| aaatgcaagt tgggccaatt cgccctcca gactccgagg cggataggcc caggggggcag | 840 |
| cggccttgcc cggcggccac tgccctcctc ctccccccgcg cccccctggct aggctttgaa | 900 |
| gagctcattt taagaacttt tccattttcc ttttggaggc gtgttgttct tctcagtcac | 960 |
| ctcgcttttt ttttttttat gagcttcagc gctgatctgc acgttcttcc ctccgtgtaa | 1020 |
| tttcaatttg aactctcccc agagcggcct tttccctctt gttgcctgcc aagtcgttta | 1080 |
| aggctaagca acattcttc ctccctcccg tccgcgcgag tctcggtcta cacccgcgag | 1140 |
| gggaggcgga ggcggttact ccgagagttc cggtgggttg gagcctttca gcagccgcct | 1200 |
| tcagactgtt tgggagccga aaagcg | 1226 |

<210> SEQ ID NO 51
<211> LENGTH: 628
<212> TYPE: DNA
<213> ORGANISM: Homo sapiens

<400> SEQUENCE: 51

| | |
|---|---|
| cttttgccgtc atcgcgggtg aatgcaccac taccttttgg cagttggagg ggagacccat | 60 |
| cagagccgga gaacctgcag ccacgacggc gaggatgtgc agtggtctct ggggaaacgc | 120 |
| cgccttcgcc ctcacccggc gcgtgtggcc ctgtgccgtc cgctcgccgc ctctctctcg | 180 |
| ctgctccgca ttcccgtgcc ctcttacttt cctctctggg ctcaagatcg ctacgcttta | 240 |
| tttctgcgtg agcttatttg aaaccttact tggtgtcccg gcttactctc cacgtctgct | 300 |

| | |
|---|---:|
| ccagaccacg gtctgcccac gcacccctca gcctgcaccg cccacgtccg gcccaggtgt | 360 |
| ggtcgcagcc aagccccagc cgcgggcccc tgcgccctgg ctctctccct tgggttcagg | 420 |
| ccagagatgc ttgccccaag acctcgcccc ttgccttctt gggccacctg cagaacaccc | 480 |
| ttggttgtca aggacgtgag acagccgagg acggggaggc cccagggctg ttcggggacc | 540 |
| ttaagtgggt ccaacgggaa ggacgcgggc ctgcgaggga tgccggtcgg gcctggctgg | 600 |
| agccaggcgc gcaggtggcg catcttcg | 628 |

<210> SEQ ID NO 52
<211> LENGTH: 1226
<212> TYPE: DNA
<213> ORGANISM: Homo sapiens

<400> SEQUENCE: 52

| | |
|---|---:|
| cgggcggacg aatggacgga ttcgagcgaa gcttatttcc cttctcctaa cgcatctacc | 60 |
| tataaatagc gctcaccgcg ctgagtcacc aaaaccccga gtttcccaa atagcgcgta | 120 |
| acgactgtgg gatcgcgtcc ctcggggctc tgtgacagac tccaaccaca cacccgctgg | 180 |
| gctggactgc gggcccacac ggcccagcgg gtctctcacc acccggcgcc ccagggacgc | 240 |
| gggcgaggcc gcggtgtccg gacgagtcga cagcgtcgga cttcccgcgc gcggacggcg | 300 |
| ctctggggaa ggaggagccg gcgggcggct ggacctggcc ttgactgcgc ggggtccgcc | 360 |
| cccgcccct cggagcgca gagttgcggg gggccggcac agcctccgcc ctgcgccgcc | 420 |
| cgctcacaca atgggacgcg tcgggagggg gcggccgcgg ctcccattcc ggtcccaggg | 480 |
| cggggactcc gggcggcggg agaagcagtc gggctgggc cagaaggaaa accccctctc | 540 |
| cctctgccca ctcaaactgc gaaagggctc cagccggcgg tgccaggggc tggggagcag | 600 |
| ctggggaggg agcggaagtg ccaccccctg cagtcaaggg tggtgacgtc acccctgcag | 660 |
| ccagcctgta gggggggtgtc tgtacatcac atgacccggc cccctctcc ccgccgaagc | 720 |
| ccgcgcgcgc gctctctccc ccagcccga ctcccacctc tcccccgccc cctctcccca | 780 |
| actttcgccc tcccgctcc ggcaccgtgt caacagcgcc agctccgccc cctccccgcg | 840 |
| ccctgtggaa ccgccacggc ggcgcggcgg gcgctcgcgc tcaggtccga ggctccgaga | 900 |
| agcgagcgtg ccccggttcc accctgcccc ccagctcagt gctgctggct gcgtgggcac | 960 |
| cagagccagg gggcacggcg gcgtgcagcg acagcgcttc tctgctccat cctcccacag | 1020 |
| cagttagagg acgaagctga ggcgccgggt ccgagctcgg agggagcgag gcgcatgcac | 1080 |
| ggcctccggg ccctgacgcg tagcctccgg gggtcggccc acgggcgaga gaagcagccg | 1140 |
| ggagcccctc ctcgacccca gcaaggcggc ccgcgcctcc gctctcccta ccgcccgggt | 1200 |
| ggcgcacgcc agtccccgtc tttggc | 1226 |

<210> SEQ ID NO 53
<211> LENGTH: 988
<212> TYPE: DNA
<213> ORGANISM: Homo sapiens

<400> SEQUENCE: 53

| | |
|---|---:|
| cggaagcctc atcccgccaa gccttcgcct cctcgctgag actctgagct gcgctggggt | 60 |
| tggcgggcac ccgattccgc cccggcccag accggtcact cagtgtgtgc atatgagagc | 120 |
| ggagagaagc gacctggagg ccatgggtgg gggcgggtgg tgaagctgcc gaagcctaca | 180 |
| catacactta gctttgacac ttctcgtagg ttcaaagac gaagcacgg tggcttcagg | 240 |
| gagacaagtc gcaagggcga cttccaagc gggagatggt gaagtctttg gacgtgtagt | 300 |

| | |
|---|---|
| gggtaggtga tgatccccgc agccgcctgt aggcccgcag acttcagaaa acaagggcct | 360 |
| tctgtgagcg ctgtgtcctc cccggaatcc gcggcttaaa cattctttcc agctgcgggg | 420 |
| ccaggatctc caccccgcgc atccgtggac acacttaggg tcgcctttgt tttgcgcagt | 480 |
| gattcaagtt gggtaaccct tgctcaacac ttgggaaatg gggagaatct cccccccgc | 540 |
| aacctcccgc accccaggtt cccaaaatct gaatctgtat cctagagtgg aggcagcgtc | 600 |
| tagaaagcaa agaaacggtg tccaaagacc ccggagagtt gagtgagcgc agatccgtga | 660 |
| cgcctgcggt agctagggca tccaggctag ggtgtgtgtg tgcgggtcgg ggggcgcaca | 720 |
| gagaccgcgc tggtttaggt ggacccgcag tcccgcccgc atctggaacg agctgcttcg | 780 |
| cagttccggc tcccggcgcc ccagagagtt cggggagcgg tgagcctagc cgccgcgcgc | 840 |
| tcatgtttat tcacgcggcc ttgagcagcc gagctccaat ccatattaat caaccgctcg | 900 |
| acctacacaa gtctaagttt acgggagaaa acctagtccc cgaaaggaag aacagcaatc | 960 |
| cggacaagca gttggcgcct ttgtcccg | 988 |

<210> SEQ ID NO 54
<211> LENGTH: 603
<212> TYPE: DNA
<213> ORGANISM: Homo sapiens

<400> SEQUENCE: 54

| | |
|---|---|
| cgacccagcc cccgaggaga acccagaacc gacccagccc ccgaggagaa cccagaaccg | 60 |
| acccagcccc cgaggagatc ccagaaccga cccagccccc gaggagaacc cagaaccgac | 120 |
| ccagccccga ggagatccca gaaccgaccc agccccaat gagatcccac aaccgaccca | 180 |
| gcccccgagg agatcccaga accgaccag ccccgaggagaccccagaa cgacccagc | 240 |
| ccccgaggag accccagaac cgaccagccc cgaggagat cccagaaccg acccagcccc | 300 |
| cgaggagatc ccacaaccga cccagccccc gaggagaccc cagaaccgac cagcccccg | 360 |
| aggagatccc agaaccgacc cagcccccga ggagatcccc aaccgaccca gccccgagg | 420 |
| agatcccaca accgacccag cccccgagga ccccagaa ccgacccagc ccccgaggag | 480 |
| atcccacaac cgacccagcc cccgaggaga ccccagaacc gacccagccc ccgagagatc | 540 |
| ccacaaccga cccagccccc acggagaacc cagaaccgac ccagcacctg gcaacattc | 600 |
| tgc | 603 |

<210> SEQ ID NO 55
<211> LENGTH: 902
<212> TYPE: DNA
<213> ORGANISM: Homo sapiens

<400> SEQUENCE: 55

| | |
|---|---|
| tcagagaatt tggaaaggcc tactctgagg ggagtaaaac ttcaccaggc cctgggctgg | 60 |
| aagcacagga ggtcgcggct gggcccagcg ccctcgggag gccaagggca gggagccgac | 120 |
| ccaaggttaa gccctccagc tctccgtcgc gggtttgggt cccgtctcaa gagtggggcg | 180 |
| cgcgggctgg gcctccggcc tgacaccctc tcttctctcc atcagtgagc gacagctccc | 240 |
| cctaccacag ccccaaggtg gagagtggag cagcctgggc cgcaacaact tccccgccgc | 300 |
| cgccccgcac gcggtgaacg ggttggagaa gggagccctg gagcaggaag ccaagtacgg | 360 |
| tcaggtgagg aggcgagggt caggccaggt gggccgcgtg cggcggggat ttaggcgatg | 420 |
| gaacactttg tgatgggtcc ctttctgagc ttcccgcgag agaagcccag gctggcgtcc | 480 |

| | |
|---|---|
| ctttgctgct acgagccaga tccttcgtgg actggggcga agcagaggcc tgagcttgga | 540 |
| aggcggagct ggggcctcga cccccgccag gggccgggag cgctcgtcag ggcgctgggg | 600 |
| gtctggggcg gcagctcccc ggggcgaggc tctgggaagc gcctccaggc ctgtcggcct | 660 |
| ccgggagctt gggaggcggc tcccgaagcc ctttcggcgg ctctcgttgg gggtagagtt | 720 |
| aaccaaagaa ggcgcttctg aagggccgag cggagcagcc ctggggcctc agagccgcgc | 780 |
| cttcacgccc gcgaaacgcg cgccccggtc tcggcccac ggtgcgactg cggctgcggg | 840 |
| gtcctcacgt tcggactttc tctccggtgg ctctcggaca acacgcttg gccaatcctg | 900 |
| cg | 902 |

<210> SEQ ID NO 56
<211> LENGTH: 332
<212> TYPE: DNA
<213> ORGANISM: Homo sapiens

<400> SEQUENCE: 56

| | |
|---|---|
| cgctacgaat gtaagatgaa tttagtggcg cggctgcctc cctgaatccg aacggtaatg | 60 |
| atggatttat caacggggat tcgccttcag cccagcgagg gaggtttact cagcaaatat | 120 |
| gtcggcggca cccacccaaa tgcaatcatt tgaccccctg cggacgatag ctgccgtgcc | 180 |
| ccttcccacc gctggtcctg cttggccagg gtcgctgggg gccagaggcc ggcccggatg | 240 |
| accagagagg tggcctcacg gatccttggc ctctcgcccc ctcctctgtt tcctcctctc | 300 |
| agcttgaggc tctcctggca aggggatcg at | 332 |

<210> SEQ ID NO 57
<211> LENGTH: 527
<212> TYPE: DNA
<213> ORGANISM: Homo sapiens

<400> SEQUENCE: 57

| | |
|---|---|
| cggggggtg gggcgtggag ggcggcctga gtgccgcgcc tggcccctgc cctgggtgcg | 60 |
| caccaggccg cgaaagccgg gggccgcctt ctcggctgct gaagcccggg agtcagtcaa | 120 |
| gcgcccttgg caccgcgagg gaggcgcacc tcgcctggtg cagagttgcc gcgacccgag | 180 |
| cgggaggagg cacaggacgc agggctcctg gcctggctgt gggcttggcc ttggcgcact | 240 |
| aagcgctccc catctgcccg agctggcctc cgcggccctc tcggcccagt ctacgttcgt | 300 |
| ttaaggactt cagcgcgaag aagagcgaac gtggctagaa cctgttgacc tctcctctgg | 360 |
| cctggaagtc cgcacagctc gtggcaacac tggacggacg gttgtcaggg gacgaccgcg | 420 |
| ggcaggtggg gaggaggcct tggtctggct cctggattcc accctgggac ggaaggggaa | 480 |
| gcggaaacct tgacctcagc cacacaagga cacctatctg gctgtct | 527 |

<210> SEQ ID NO 58
<211> LENGTH: 326
<212> TYPE: DNA
<213> ORGANISM: Homo sapiens

<400> SEQUENCE: 58

| | |
|---|---|
| cgcctgctgc ctgccgtggg gccgctccga ggtgccagga actccggtaa gggtcccggc | 60 |
| ggcggcagcc cgggagtggg caaagaggga acatgcgtgt atttcaaaga aaccagcgcg | 120 |
| gtctctgact tccctgtctt cgctctccac cccgctccc cctcaacaca cataataat | 180 |
| aacagacgcg aagataatcc tgccatctgg caaatcccaa atttggtgac caagctcgga | 240 |
| aagcaacagc gacggctcat cccggagtag gtggctggtc ctgccggact ctccggagct | 300 |

```
ggggcaaggg ccgtgggctc tgcccg                                          326
```

<210> SEQ ID NO 59
<211> LENGTH: 331
<212> TYPE: DNA
<213> ORGANISM: Homo sapiens

<400> SEQUENCE: 59

```
taggacctga aattgcagag acatagaaaa tcaatacgtg gtcgggagtc aactgcgcgc      60
gaccaagggc tctgccctcc ctctctccgt tgatttggac gctgggaagc tgcccgccgt     120
ccttcccacc cccttttgccc agccttggca agacctctcc ggaaacatac tcgcgttaag    180
gaactgggaa agcttcctgg cccggagcta ggagcccgac gttggggctc cttgctgagt    240
gagacgctca gtcctgtgct cccgccccgc cccaggcgcc cagtcccgct gggatccatc    300
tcctcagccc cggtttcccg ctctgcgagc g                                   331
```

<210> SEQ ID NO 60
<211> LENGTH: 1226
<212> TYPE: DNA
<213> ORGANISM: Homo sapiens

<400> SEQUENCE: 60

```
cgcgaggatg ggcgggctcc acgtctgggg gcgctgtgag cagggccaga gcgaaacctc      60
agtctgagtt tacgaactgg gaaggagcct gaaccccaga acaccgttta acaaagaggg     120
cgaacgcagg gagccgagga gacgtctcct tggcctctgg ggaaggggct ggaggagcga    180
gccagctgag aagcggcttt gccgggtgtc cactagcggt tcgccagccc tctgtgcgcc    240
cgcagagtga cgcagaggcc gaccagtccc ctccccactc gccccctgggg cgccgccgca   300 ccttgatcac ccccttcgcg gagggaactc ccaaggcgcg gcgctggccg ctgggtccgc    360
atggcccagt cctgtcgggc tccgctctgc tgccgccgac ttcgaaggtg tgcagtgttg    420
agccgtgtct tgttccgtgg cttcgagggg tgtgcgcgct tcctatacct ccccggaacg    480
cgcgagatag tcacacgcgc cactttgagg gtcaaacacc ccgcatctgg ccacatgtac    540
ctttactaac gtggggaggg ggcaaaaaaa tgtgtctctc cttcttaccc cgaggtgtca    600
ctcgcccaaa cactccctac aacttcttca agtcaaactt gggcaaggtt ggctggctga    660
ctgcgagagg aaaagagggc gcggaggggg cgcggcgcgc ggccgggtgt agaggccacg    720
gaggcgaggc gccgagcgtc cccttttgtcc tgtagaggga gctccagccc caaatttccc    780
tgctgcctcc cccggcccgc caccccggcc ccgcctggag ccggaatccc ggctggaaag    840
gtgcggcggt ctgacacccc cgcaacccc gcgccgggg cttagcagga tgcctcttct    900
agggcacgtg ggaaaaccca ccagggtgcc aagacgcaca gatctcccag gacccgggct    960
ccccaactct caactagagc tgggcagtca cacatcatct agaggattat gtaccctag   1020 gcgaccctct tctccatatc cgcctccacc gtcaccccac accctggcat ctataaagag  1080
gaaggggggc aaccgggttg aaggaggat ggaatctggg cttgcacagc ctcttatagg   1140
taacagtgag aaagcctcaa ctgtgtcgat caaagaatgg ggacgaaggg agtgatgaga   1200
acacgacccc gccaccgcgc aggcta                                        1226
```

<210> SEQ ID NO 61
<211> LENGTH: 254
<212> TYPE: DNA
<213> ORGANISM: Homo sapiens

<400> SEQUENCE: 61

```
cgtgtgacac tttggaacgc ttctctcgtt acaaaccagc gtctttactg aaggtccttc    60
cgctgcagag ctgcgcaatg gatgtgtgga cagagctagt cggcacgtgg aggctctcct   120
ggttttcagc aggaaacgtg ctgtgagcag gaatcgcgag tgagttccat ggcgtccccg   180
ggtcagcgcg cgtgcaggaa tcgcgagtga gttccatggc gtcccgggt cagcgcgcgt   240
ggggtcctgt ctcg                                                      254
```

<210> SEQ ID NO 62
<211> LENGTH: 283
<212> TYPE: DNA
<213> ORGANISM: Homo sapiens

<400> SEQUENCE: 62

```
cggcggggaa tcgggtggcc acgcacgtcg gcctaagggg ccctggcagc gcccggcagg    60
acagccgtcc actgcacacc tcagagccgg cacccgggac ggtcagcgtc cccatgggcc   120
cggcaccgca gctgcccaga tcctcacccg cacacaggaa gggtccctgc aacccagcgt   180
ccaccgtgga gaaacatgaa cgtgagcaaa aatacggcct gcggtgggtg tgcgacccca   240
cacagaaggg cgagaggctc gtggccatcc cacacactgg gag                      283
```

<210> SEQ ID NO 63
<211> LENGTH: 947
<212> TYPE: DNA
<213> ORGANISM: Homo sapiens

<400> SEQUENCE: 63

```
tttcgctaga tcatttgtta attgtgggaa ggaaggacgc atccggggag aggagatcca    60
gggctggaaa agtgggtgag cggcgctggc gcaggcggcc aggagagagc agatgaaccg   120
ttcgttagag cagcgaggta gtcgtgagcg ctgagatcca gagactagga cccactccct   180
ctctgagcag caaattggga agaagatgct cactcggtaa gggcgaggga gcccggcatg   240
gcgcccacc acgggctcgg tcttctgcgc gccaagatcc cgcttggggc gaggcgttgg   300
gtcagcgttt agagccactc cctgcgctgg tggctggaca tagcctccct atcccacctc   360
atcttccccc atccccgaca gaggaggttg tgaatctacg gcccttgacg ttgaggcgtc   420
ggagggcgca cctttgtaat tgcggcctcc cttcgcccct taagtgccgc ttctgggcgc   480
ctaggctgga tatgaaagcc ccgttcctaa tcctctgctc tggtcccctc ctctgactgc   540
tgggactcta agctaggccc tccccaggtt ccatcactgc ggcgccaacc cgcggctggg   600
ctgtccgcaa gagggagttg aaggcgcgcg gaatcccgag gtgcagctga ccctcctctc   660
aacgccgact cgccgctccc gcccggccac ctccctgtcg ggcagacttc ctgttctcct   720
gctcacagca gggaggcagt cgccgagccg gtcagcagcg tgcacggaga tcttcactct   780
gcgcccagcc ccgggacaca ggtgcagtct ccagcggagc actgcggagt gcgcgccgtc   840
gagcactagg gaatcctaga cggaggactt ggtccattcc acgcagtccc aggcaggtcc   900
gcagcggagg gacgcagcgg tctccaactc ctggtcacga cttggcg                 947
```

<210> SEQ ID NO 64
<211> LENGTH: 289
<212> TYPE: DNA
<213> ORGANISM: Homo sapiens

<400> SEQUENCE: 64

```
agaggaggcg gagacctgac cccagaaagc agcactcaaa cagatgcagc tgcacccacg    60
```

| | |
|---|---:|
| cgcccgcctg ctgccagagc cactctccgg agcctgcagt cctgaagacg cctcagcagg | 120 |
| ggcaggcaga agacacccog cgaaccccca gggccggccg ggcgcatcac tgggagccgg | 180 |
| ggctatctcc ctccgtcagc gtcttgaagt ccatggagag ggcctgctct tccgcctggg | 240 |
| aaggccgctt ccagtcggcc cggtcaagat gtagagcacc gccccaccg | 289 |

<210> SEQ ID NO 65
<211> LENGTH: 368
<212> TYPE: DNA
<213> ORGANISM: Homo sapiens

<400> SEQUENCE: 65

| | |
|---|---:|
| cttctgcaga cagacaagag ccctccttac cttccatgaa gagtccgtac acgtaggagc | 60 |
| cctctcgcgg aggagcggtc atgtcctctc ggttttttctt ggtcacctcg acagacagac | 120 |
| acatctttcc aggggccact cgttcttcct ggccatggac tgcatgatgg ccgtgaggaa | 180 |
| cgactggggg ttgaagaagc cggccagcca cacggtggtg ggcagggcaa agtctgtcgt | 240 |
| ccaggcctcg agttcctgca aggcacacga gccgctagga ggagaggaca tagaatgaca | 300 |
| tgggaacgac cgggccttgg ccgttctgag caggggtcac gccagaacct tccacgggcc | 360 |
| actcagcg | 368 |

<210> SEQ ID NO 66
<211> LENGTH: 265
<212> TYPE: DNA
<213> ORGANISM: Homo sapiens

<400> SEQUENCE: 66

| | |
|---|---:|
| cgcctcacgg ggcctgccag caacgcgctg tgtgcagcag gaagcccacg ccaggtcctg | 60 |
| acggctgcat cctgtgtgct ctccggcctg gccgcctcaa gacacgccac ctttgatgca | 120 |
| cacgcgctcc ggaggcacag gaaggacggg ggcactggga agtccatgtt tagtctcctg | 180 |
| acgtcgacca cacaaaccag acggaacggt gtccccggcc caggctgagc ggagcacacc | 240 |
| atgagggcag aggctacagg tgatc | 265 |

<210> SEQ ID NO 67
<211> LENGTH: 1138
<212> TYPE: DNA
<213> ORGANISM: Homo sapiens

<400> SEQUENCE: 67

| | |
|---|---:|
| cgtcggacgt tcacaacgac cacgcttttc cccgcttcct cgattagcct ggcctcccutt | 60 |
| gctccagtgg ggcggactca aatgcgcacg cacgcacacg ccgccaagcc ggtcaaccgc | 120 |
| agacaaactg actcttcgcc aactagtagc cacgagagc agcaagggaa ccaaggtcct | 180 |
| tcaccgcctg ctccaaaaag acacggcaac ctccagcggc gccgcagtag ctgcctctgt | 240 |
| gctgcagcct ccggtcggag tttaggtcta attccttaag aagtatcgct cctctgcct | 300 |
| tcgtcctact cccccttggct tcgcccactt cgcctccttc tcctcgggag gccaggagga | 360 |
| cccgggtcac tttgccaatt ctgcggaggg ggaagtagcg tgagggagat tcccacgcaa | 420 |
| gtagcccgaa gcccactact cttttgcccca cctctccact ctcttgcccg tgtaggtgcc | 480 |
| ggtgctgctg gcgaaagtcc cagttcttaa ggctcctgag ctcggaaggg gtgtgaggag | 540 |
| ccagatggga agagaagcag cgggacgagg gcgaggaagg gctggagatt gttagaggac | 600 |
| agatggggcg ggactgggga gaggggcgaa ggcgacgcgc cgaggcactc ctccgccca | 660 |

| | |
|---|---|
| tgagcacaga cgtaactccg aaacgcgcag atgggccgta aggtaaagag gccttttttc | 720 |
| cctctcctct ccgtcctcta ccctgctccc ctcctagaca cttggtgaaa aagcaaggtg | 780 |
| cggtgtacct ggagcgaaca ccatgattct tccagccgct acgccccag attaagagag | 840 |
| aaagacaggc agacggagga tgggaagaag gccggacttg gcggggtccg gtgcaggagg | 900 |
| gcgcgctggg cgggcggcgg gcggggcggt cagcaccccg gacgctcccg ccgctagatc | 960 |
| ctggggccgc agctccagcc gccgccgcgc gctctgcctc cacaatgcgg ccacagcggc | 1020 |
| ggcgggagga ggagggtgaa tccccgctca gtccatccct cattcctgtg ccagctcggg | 1080 |
| acgtacactg ctgcttaggg agcaaagcac ttccaccgct ttcacgcgac gaaggtcg | 1138 |

<210> SEQ ID NO 68
<211> LENGTH: 315
<212> TYPE: DNA
<213> ORGANISM: Homo sapiens

<400> SEQUENCE: 68

| | |
|---|---|
| gaccacaaag cgcttcctca tcctttcctc gcccttgat gccgccggca acgtgactct | 60 |
| gcgagcagcg gggcagacgc caggtctccc tcgcaggcgg gaaaggggct ccaaggcggg | 120 |
| tgctgcctgc tcgggtcaca tggctacgtg ggggccttgc tcaaattcac ttcctgcctt | 180 |
| cattacaaaa ctgtcaaagg ggatcgcacg tttgcagggt gtcacccaag cattctggtt | 240 |
| ttgcaaacga cgctgtgcgg cagcggtctg atacctgatg agctcggtgt ggcggggtcg | 300 |
| gcagcatttc ctccg | 315 |

<210> SEQ ID NO 69
<211> LENGTH: 578
<212> TYPE: DNA
<213> ORGANISM: Homo sapiens

<400> SEQUENCE: 69

| | |
|---|---|
| cggtgtctgg aggaagcggc gcggacagtc tcccgctcca ccgtgtcggg cctgaagagg | 60 |
| ccgctgaacg ctcgcgatta ctgaggcatc tggtaggatc gcaaggccat caacctacag | 120 |
| gtgaagccga ggcgctgtgg cgcttttgaag ccggagagaa gctcagtaga atcgggaagg | 180 |
| cgctggggct gtccaactcc accttggcca ccattcgtga caacaaggaa aagatctggg | 240 |
| cgagttccca ggaggccaca ctgaggcggc caccaagttg acgcgtggcc gcagcctggt | 300 |
| gatggagaac atggagcagc tgctgagcat gcggatggag gaccagagcc agcgcaacat | 360 |
| gccccctcagt gtggtgctca ttcggggaaa agcccacagc cgttcgagaa ccgcaagcag | 420 |
| gagcagggcg agggcgccta gcccgagagc ttcggggccg gtcgagggtg attcgctggc | 480 |
| tttaaggcgc gccacagctt gagcagcatc ggggccagcg gcccaagaac gcagctgcaa | 540 |
| gaatccagcg ttaatgcgca gggtgatccc ggagggcg | 578 |

<210> SEQ ID NO 70
<211> LENGTH: 682
<212> TYPE: DNA
<213> ORGANISM: Homo sapiens

<400> SEQUENCE: 70

| | |
|---|---|
| cggccgttcg gtgctgcggt atcccatccc ccgcctgttt aagagaaatt gatcacgtta | 60 |
| agcgggccct gcgtcgctgc gcagtgcccg gactaccgct tggatggatt gacaagggaa | 120 |
| ggacgcagac acctaagagc aacaagggta cttttttaagc gaggttacat gtgtttagga | 180 |
| ctcgcgagga cgtcacgttt cgaatttggt aaaagtcctc ggtagctagg acccaacagt | 240 |

| | |
|---|---|
| tctgccctcc tggaaaccca atgaggtgac aaaactccca tctcattact gggagtccag | 300 |
| cgcactccgc caccgcggct gcagcttctg ctagctcgga gcctgcggac tccagccggc | 360 |
| gcgaactccg ccgcgactct ttctggctct ctcgctcacg ccttcggggc ggaaccgcgg | 420 |
| gcgccggagt ggtcccagac tcggctggga ccgggcagcc tagaagaagg gtcccctcag | 480 |
| tagagaccag gcctccagct ctccgtccgg cgctccgctc cacaacccgc cagtcatgtg | 540 |
| aggtccgtca agggagcgat ccctccgtct gcccgggctt ccgggctgtg gaccgcactg | 600 |
| aacccagtcc cgcagcaagc cctgctgccg ccttttcctg gcacgcctg cggtggtgac | 660 |
| ggcccgctgc tatgtctcca cg | 682 |

<210> SEQ ID NO 71
<211> LENGTH: 265
<212> TYPE: DNA
<213> ORGANISM: Homo sapiens

<400> SEQUENCE: 71

| | |
|---|---|
| aaacacagtg ccgcagtgaa agtgggacaa acgcgcctgt gtgcatcctg gccgaggtgc | 60 |
| cggaggaagc gtggtcgggg cagaagtgtt aatgggcctc cttcctgccg tgccctgccc | 120 |
| gtgccagtcc tcggtgctca tcccggctcc ctgaaatgct cgcttccact cagggccagc | 180 |
| gcactccctc cacgtccctg gccgcagatc tgtcctgctt tgacaaataa cccgctcagc | 240 |
| cttcgggttt atggtttttc cgtcg | 265 |

<210> SEQ ID NO 72
<211> LENGTH: 1226
<212> TYPE: DNA
<213> ORGANISM: Homo sapiens

<400> SEQUENCE: 72

| | |
|---|---|
| cgctcccttt cccgcacacg cattgctgcc tcctctcggg cttggttaat gagtctgtgc | 60 |
| gccaagccag gtcgctccgg gcagttcgcg cttccgcgcc tcggcactcg gatgaccgtg | 120 |
| tcctattgtc tctctcgtga atgtcgctga aaaaaaataa agtttgttc taagcccgtg | 180 |
| gcatttccgc gcgcagatgg aaaggcaagt gggagaggag ggtgcaggtg cggggcgggc | 240 |
| gcggcggccc cttcaggcgc cggggctggg ctgcccccgg ccgggagcag ctccgctccg | 300 |
| cgcacgtggc tgtgggcgct gcggacgggg gacggcaggc gggggacggc aggcggggag | 360 |
| tggagggtgc agtgcccgca ggtgccgacg gcttcctcca gagcccttcg cgccgcgcct | 420 |
| tgcctggctg gtgcgcgggg aaaccatgg cagcattgcg gctccggcgg gcgggctctg | 480 |
| cgcgggcccc caccgagctt tccgggagcc tctcccgcag ccgatgggca tctagggcgc | 540 |
| agaacgaaga gtgggcgccg aaacgggtgt aggcgctgga ggccgacggg gaggcccggg | 600 |
| gcggtcaggc ttctcggtag agagggccgt gcacctcgcg gcctgcgggc taaggcgggg | 660 |
| agccgctcct gggcggccgg gcgcgcggac tggaggagg gaagcgccac ggactgggga | 720 |
| accggggtga cggggagacg ggggggctgg tggggtgagg tcggcgggca gcagccaagt | 780 |
| gttctgcagc tccgaacccc gccacccctg ggcgaacgga atggcacccg cggagacggg | 840 |
| cggggacggg cgaaagcggg tttgctccga cccgaagctg agcccgggtt ggagggcgag | 900 |
| accgtaggcg agaatggccg cgcgggctgg gagacccggg ccgtatggag tgagtggagc | 960 |
| cgcccgaggt agggtagttg gggatggtag ttgtgaagac agtcggagtc tagctccggg | 1020 |
| cagacgaaac accggggcgc gccagggtcc gtttcctcct tctctctgct ttcccaccac | 1080 |

| | |
|---|---|
| cctgtagata cggagccagc agtcgggcta gagcggaggc tgagggtcgc ggttccaagg | 1140 |
| gcggtctctc gccccgggtc aggccccacc ccgcggtggc ggtcgcgtgg cgctgtcctg | 1200 |
| gagttgagct gtcccgcgcc gcggcc | 1226 |

<210> SEQ ID NO 73
<211> LENGTH: 461
<212> TYPE: DNA
<213> ORGANISM: Homo sapiens

<400> SEQUENCE: 73

| | |
|---|---|
| ctcgaatctt ggagacactg gcttctagtc gcacatctgc actttctccc acctgtggcc | 60 |
| tctcaggctc ggccgcccga gggagtttct tttattccca gttcggcttt cttttgcgaa | 120 |
| ggccgagtct gggcctgcca ggggcctgcc cgagtcctct atcgcgggtc cacgtggcca | 180 |
| ccaatgaccc gcggcgcccc cgcgtgtccc cgcagccact ccgcggaagc agcggcggga | 240 |
| gcgcaccacc ttcacgcgtt cacgctgac gtgctcgagg cgctcttcgc caagactcgc | 300 |
| taccctgaca tcttcatgcg ggaggaggtg gcgctcaaga tcaacctgcc ggagtctaga | 360 |
| gtccaggtgc gcactccccg ggctccaggg tctgggtagg agctgaggc tgctcgggga | 420 |
| aggtctagga aggctcttga gtagttcttg aggagaccat c | 461 |

<210> SEQ ID NO 74
<211> LENGTH: 1226
<212> TYPE: DNA
<213> ORGANISM: Homo sapiens

<400> SEQUENCE: 74

| | |
|---|---|
| cggtttggag aggggagcgc aaagcgctgg acgcatgcgg tacagtgcca cggccgccgg | 60 |
| tgggctccac tgccctgggg agctgaggcg cgacgaatga agcaccaggg cgcctggtgg | 120 |
| gcgccagtct ccggtctgga gcctgctggc ctgtccctcc ggggcgctga acccctagtg | 180 |
| cggcgtcctg ggggccgggc aggaaggatg gcctctccac ctgtctgcga atgcagccca | 240 |
| gccagtttga gcctccgcag aggtgcgctc cgggactggg cgcttctcgt gctgtgagaa | 300 |
| cgctgggcct tgttagctca ttaaccccctc tgtctctagg gcccgttggc ggcacggttt | 360 |
| attttatttt acctgttttc ctcggagggc gcgaagactc caccccgcgcg gggacctggg | 420 |
| atcgacgact tgatactag gcggtatccc ggagggctaa gtcggcggaa atccacttga | 480 |
| ccttgtagcg ttagtccttt cttttccttt cctttccttt ttctttcttc tctcttccta | 540 |
| tttatttatt tattttaaaa ataggattaa gacaccagta gaagctgtaa tcccgttcct | 600 |
| tcccccactc ccagtcttcc gggccgcctg gaggtccctg ccggagagag ccactttggc | 660 |
| gggcgcaagc ccctgggcgc cctctcctga ccgccgcgct ctcggctcgg cttggctgtt | 720 |
| ccgggctccc agaggctagg ggaagcgagg ggcgccaggg gcttcccggc ctcagcgtgg | 780 |
| ggcgaggtcc cggctgcgac cccggagaga gggagagggg ggccatgatg ctaggcgtcg | 840 |
| aggcgagggt tgagcctgtt tggcttcaga gaacgatgcg ggttcgaccg gaagcggggc | 900 |
| gcgtgttcta ggggcccttg ggtggattag ggggcgccaa gagggttagg cgaggagagg | 960 |
| cctggccacc cagttgctag actttaggcc gcactccagg aaggagcagt cggcttcctt | 1020 |
| cctaggccgc ttctattgcg cgccactcct tgaatctaag catttccac tccaagaacc | 1080 |
| gttgggagag aggggagagc ggagcagagt ctctaggccc ccagggccgc ctcccggggt | 1140 |
| ggccacgcct gccggtagcg agccgagatt agctaggtct gtgctcgggc ctcagcggtg | 1200 |
| gccctggctc ttccctaagc agcggg | 1226 |

<210> SEQ ID NO 75
<211> LENGTH: 1049
<212> TYPE: DNA
<213> ORGANISM: Homo sapiens

<400> SEQUENCE: 75

| | | | | | |
|---|---|---|---|---|---|
| cgggcgcata | acaggcaccc | cgcacatcgc | accgcggacg | cagcgatcct | cccatttgta | 60 |
| ccctaaggcc | tgagaaggcc | gctccacacc | tccgcgtgca | cagtccctag | accagtgagg | 120 |
| gcggggaggg | gaaatccttt | tgttttatat | tggaaacctt | acgccaaagg | caggcaggaa | 180 |
| gcaaccaaag | gaacaacagg | ccgcctgagc | cgtggctcaa | acagcacagg | gcagtggccg | 240 |
| agcaccaggc | ttttcggtgg | agcgggatac | cagcaggcag | aagaggtgga | caactctgac | 300 |
| cgcagactcc | ctacaacccc | gcgatcgatg | ctccacctgc | acgctcaaac | gcacctgttt | 360 |
| cccaaattaa | tccagacgcg | aatttaacga | ccgattttgt | agatccggga | aattctgtcc | 420 |
| accagcgtca | cccaacacag | caacttttac | agacaatgcg | tggcgtccgt | tcctgctcac | 480 |
| ccaaagcggc | ctctctgggc | tgacagccac | ccctgcgggt | cctcaaaccc | cactcaaacc | 540 |
| ctccgaaccc | ctgtgtctgg | gagcagtagg | gtgggatgac | tgcaggatcc | cttgaagaag | 600 |
| tgactcgctg | caaccccacc | accagcagca | aaaacgcttt | caccccgggag | ctgcatggat | 660 |
| gcgcggatgg | cggggggctga | ggggacgcgt | gaagcccagg | cctcttgctt | gggctgggcg | 720 |
| attcccgccg | tgggacgggt | gggattgacc | ttagtggagt | ccagtccttc | ggagaatccg | 780 |
| cgggcagtcg | ggacccacgc | tccggaacac | ccaagtccga | actcgtacac | acagcacaat | 840 |
| ggcgtgcagc | cgccggggcc | ctaactccca | gagacgcgtc | tgaagaagcc | atacaagggg | 900 |
| gcgcagcttc | ggggctctgg | ctgggaggtt | actgcaggga | cagcgcctcg | cctccagcag | 960 |
| ccgggtccag | gctcagggcc | ggccggcctc | tgctcgcttt | ctgcttggat | taccaacagc | 1020 |
| cactgggctt | ggggagatcg | gccgggccg | | | | 1049 |

<210> SEQ ID NO 76
<211> LENGTH: 785
<212> TYPE: DNA
<213> ORGANISM: Homo sapiens

<400> SEQUENCE: 76

| | | | | | |
|---|---|---|---|---|---|
| cggcaagacg | cgcaggaaga | ccagcgcgcg | ggatgcgtcc | cccacgccca | gcacggacgc | 60 |
| cgagtacccc | gccaatggca | gcggcgccga | ccgcatctac | gacctcaaca | tcccggcctt | 120 |
| cgtcaagtcg | cctatgtggc | cgagcgggag | gatgagttgt | ccctggtgaa | ggggtcgcgc | 180 |
| gtcaccgtca | tggagaagtg | cagcgacggt | tggtggcggg | gcagctacaa | cgggcagatc | 240 |
| ggctggttcc | cctccaacta | cgtttggagg | aggtggacga | ggcggctgcg | gagtccccaa | 300 |
| gcttcctgag | cctgcgcaag | ggcgcctcgc | tgagcaatgg | ccagggctcc | cgcgtgctgc | 360 |
| atgtggtcca | gacgctgtac | cccttcagct | cagtcaccgg | gaggagctca | acttcgagaa | 420 |
| gggggagacc | atggaggtga | ttgagaagcc | ggagaacgac | cccgagtggt | ggaaatgcaa | 480 |
| aaatgcccgg | ggccaggtgg | gcctcgtccc | caaaaactac | gtggtggtcc | tcagtacggg | 540 |
| cctgccctgc | accctgcgca | cgccccacag | ataagctaca | ccgggccctc | gtccagcggg | 600 |
| cgcttcgcgg | gcagagagtg | gtactacggg | aacgtgacgc | ggcaccaggc | cgagtgcgcc | 660 |
| ctcaacgagc | gggcgtggag | ggcgacttcc | tcattaggga | cagcgagtcc | tcggtaagtg | 720 |
| cgctgcgccc | acagctccgg | ctgcaggcag | taaatgcgcc | ttgcgcggtg | ggtctgtgtg | 780 |

```
ccgcg                                                                  785
```

<210> SEQ ID NO 77
<211> LENGTH: 1226
<212> TYPE: DNA
<213> ORGANISM: Homo sapiens

<400> SEQUENCE: 77

```
cgactcggtg aaggatgatg cccggagggt gatctcgacc tttaacattc cacacaccta      60
cctccacgca ccaatcgccg gaatctccaa cccgcgggcc gcgtgggctt tctaccctgc     120
accgctgagc cgcggccacg ggaagaggcg cgctcccggc ggcccaagct gggagccaag     180
ctctaacggg tgtggcggga agtgtggtgg cccgccagca gctgccacga cgctcgctcc     240
accgacgccc agagctgtgg ccgggccggg ggctggcacc cgctgggccg ccactctcgg     300
ggattttggt ggcaaagcgg aggtcccgcc gaggctggcg aggtgcgcgg ctggctgcta     360
ggaaagagat ccagacggtc gcctggtgcg ctggatcccg tgccctttcc ctgaaaccca     420
gcctggcctg actgcaacct ctcccaactt cagtgccgga tccctagac aatcagggtg      480
ggctccccgc tgcgagcgcg ccccacagcc gggtgccgcc aaaggtctcc tgctgtagcg     540
gtgactcaca ttcccagtga tttagaaaaa ctgtggtgcc gagtgaaaga aaaaaaaaa      600
agcaaacacc cttagacaaa agaaaaaagc tccactcttt ccgcgagcgg gaaaaaggt      660
ttggttcagc agtgatgcta tttcagtgaa tcagacgctc tggggctctg caaggaaacg     720
cacggactgg gagaaggaag tgggagccta gagttttgct ctcggcaaaa caagaactcg     780
gcttgtcctc ccaggccggc ggtttcctac ggcaagacaa ggcgcggaaa acatttttac     840
catctgacgc tgtagtctgt cctttagaag agaataggtg aaaagtttaa taaagaaatt     900
aagcgatgtg gaagtcgttc ccgctgcttg cagagggtgg ggagcgggcc tgggcaattt     960
cggaactagg agagaccacg tcggcaaagc ctgtggtccc gaacaagggc catggatttc    1020
ccatttctca gatcccggct gcccgacttc attcttgttt cttcagcac aagccatccc     1080
ccttctccct ccctccacgt ctcttggcag agacagaaag ggacaccgct ctgcccgcgt    1140
ccagcgcgaa ggaggtgacc taaaacccat gggcccttct cacactgcgt tctctgcgct    1200
ccggcccagt tccggaggac ctcccg                                        1226
```

<210> SEQ ID NO 78
<211> LENGTH: 242
<212> TYPE: DNA
<213> ORGANISM: Homo sapiens

<400> SEQUENCE: 78

```
cgggttggag tcgacatggg ccctgacgag ggcactgatc agactcaccg ggggcgaagg      60
gggagagggc tcctgtgggc tcttcggttt cgagggcaaa cgacctctcc ggccttttaa     120
actgtcttgc gaaccactgc aaaggaagag ccctgttagc gccgcttttc cgagcccagg     180
cccagctgct gcctcggtcc ctccccgggg aaggccgcag ccgcggggca ccaggctgag     240
cg                                                                   242
```

<210> SEQ ID NO 79
<211> LENGTH: 943
<212> TYPE: DNA
<213> ORGANISM: Homo sapiens

<400> SEQUENCE: 79

```
tcctaaccaa tttcattctg aacagggaag acagctccta gcacatgcaa atgaccctct      60
```

```
tccaactccg gctccagcaa cttcgggcgg gggccagccg ggtcggctga atgcgagggg      120
gatgcgacct ggcctcccag tctttctgct tccctttctc agacacccgg aagtccccgc      180
cgcagcccat ggtctcctgc agggcagctt cggcggaccc cggagagctg ggcagtcccg      240
ggagagctgg ggctgggcta ctgcaccaag gcagagggca cactccgagg tcccgggcac      300
taggggctcc ctacctgcct actccgctcc cgccattgct caccttaaag aagcctttgc      360
agccctcaca ggtgcgcacg ccgtagtgtt ggcaggccgg ttgtcccac acacagcgca       420 cagcccctcg ttggaggggg agccccgcga cggcggtgag ggcacctgcg tgtcgagcag      480
ctgagacgcg tggccgatct gcaggcccgg gaagcccatg gacgcgggct tgcgatgggg      540
ttgggcacag cgaaggtctg cccgtccacc acgtggtggc tgccggcggg ctccgggttc      600
atggggacgt gcaggggccc gtcgaagcgc atctggcaac tagacaccgg ggtgccaggg      660
ggcgattgct taaggagaag agggagaggc gggagactgg cgttttcctc tgctcgatca      720
tgtgcgtagt ggccacgtag ttctggtgga agttgtggag agatcccggg tcgtcccaca      780
tggggctgtg ctgcacctgg aagcccgggt ggtgggcgtc gggggcgagg agggcttgta      840
gtaaaccgac ccggagtgcg gcatcatctc ctcagactgg gggggcaggt ggctgtgttg      900
ctggtagttg tgcatctgaa tgtcttctac cttaatggag gac                        943

<210> SEQ ID NO 80
<211> LENGTH: 495
<212> TYPE: DNA
<213> ORGANISM: Homo sapiens

<400> SEQUENCE: 80
atacaattac ccacacaaca aagagggcct cgggagagtc gccagccctg gtagcatatg       60
aaccaggcac cggcgttgga gctggccagg gcagggcggg aggaacgcga ggcctgcgcg      120
cctttgttgg tgcttcgcc ttgatggatt tcttttctga cgctttccac atttcccgct       180
cccttttgcc gcctgggggt gggggtgggg ggttagcggg cagttgtgtt aatttgccct      240
ccactcccgg cgcccttacg gaatcccggt ggccgccagt cgccggcgca aatgccaagt      300
caccggtagg agacacaaca gaggcgatga cctgaatccg cacgtggcct ggttcgcctg      360
gaagctgcca agcgaaggc aagagagccc gggaccctgt gtaaaacagc aagcagcacg      420
tgtcccaggc acactgttgc gggcccttag cctagctacg catccgcacc ccaggcttca      480
aaggcgcgct gggcg                                                       495

<210> SEQ ID NO 81
<211> LENGTH: 574
<212> TYPE: DNA
<213> ORGANISM: Homo sapiens

<400> SEQUENCE: 81
gaaagagatc cgtgggcttc tgaccctggt ttaggcaaaa caggggagg cgccgagacc        60 agctcgagca ctagcggatt ttgagagaaa ctgaccgcaa cctccatcgc cttccccctc      120
tctttcactt ggatgggctg actctacccg tcggtgattt acgacgattg cagcgctagt      180
cacagcctgg cgcctggtgt ccctcccctt cccaagcccc ctcagctttt ccactgccac      240
cggcgtacaa gcaagtgccg agcggctccc gcaagtcgga ctagcctccc ggcgtccgag      300
gccaccacgg gcagcagatt tttggtcccc agcgaggctg cgcgcgttcg tcccgcctcc      360
gaccgccgag cagagctgct agcagaagca ggcgccggta ctttatataa tcctgctgct      420
```

```
cgcagggtgc aagagcggga aaagtgcgga gtagggaatt cttttgctgc gctgcctcct    480
acgcggagcc tgctttccac tgctgaaaag tgccgggcct ggggaagtgt ttttctttca    540
ttccttaccg aagcgtttac tgccgccgtg gtcg                                574
```

```
<210> SEQ ID NO 82
<211> LENGTH: 1226
<212> TYPE: DNA
<213> ORGANISM: Homo sapiens

<400> SEQUENCE: 82
cggctggcta ccggtgcgcg gggaccacac tcacaaaccg cattccggtc ttcccgcccg     60
aaaatccgcg ctgtgcgagg gacccacaag actggcggtc taaaagggac ccgcctcact    120
tggaaacggg ctgcggtagc cacaaccctc cggtagcggt agcgtaaccc cgttcggtga    180
tccagccgca cagcgcaacg ggtacaaaga accccactgg ctaaggccga cctaccaggg    240
cttgggggag gggagcggaa gacgaggtcg aaacgacctg tccagcagaa aactatcccc    300
aagcatattc caaccacttc tccgtagagc tcattccttc cgtgcatacg aagggcgcca    360
atccttcctg tatccctcct acagataccg ggtgactacg cttttgcgcc caaagcgcag    420
tgctctggct cagctcccta cagtagcgac ctccaccgca gattctcatc tcctcgctac    480
cgtaagagag atgtaaagaa tcagacgggt tacgcgctca ggcaccctca tgaagagagg    540
acctgggctt aaaactcatt cagtatcagg aaaagagcgc cgagcacggg cctattatgc    600
caaagcttct gaaagggca ccacgttttt tgctctatgg ggcagatgac ccctccctaa    660
tttcggtttt catccatccc caaggtaggc tttggagtgg caccggagac tgagctcaaa    720
tttgcaggcc agggactggg gagaagggcg ccacactaag agacctgcac ccccattctc    780
gccctgtact ctacccagag tcgtggtccc ctccatttta aagcaaaatc caaaagcaag    840
cacggcggaa tcttctggaa gggggctaag atggaactca ggaggcgggg gtcggtatgg    900
aaagagcaga tggattattt ttttcctctc ctggcgaatg agggcgcccc cagccacccc    960
tcctcataaa caccccccaa ggcgcgcatg cgcacttagg tggcgggcgg gtacttaagg    1020
cgcggccacc gcggctgcgg cagtgcgccc aacagcggac tccgagacca gcggatctcg    1080
caaaccctct ttctcgacca cccacctacc attcttggaa ccatggcggc agtggcggcg    1140
gcctcggctg aactgctcat catcggctgg tacatcttcc gcgtgctgct gcaggtaagt    1200
ctgacggggt ttcggtggga gagggt                                         1226
```

```
<210> SEQ ID NO 83
<211> LENGTH: 339
<212> TYPE: DNA
<213> ORGANISM: Homo sapiens

<400> SEQUENCE: 83
cgtctaatcg atggtggggc gaagggagag ccacggcggc cctgagtgca agcaccatcc     60
tgaaaccagg agcccatgag gccgcgggag ccggaggacc aggaccgccc tcgcactgcc    120
ctgtgacagc tcccggccca gctctctgcc gctctggatc cgtcactaag cagctccatt    180
aagtgcccgg tcaggcagga gcggcaggga aacactgggg cacccacatc tgaacagaga    240
agatgcccac cttgagaagg tacctggaga agggagccac gagcgacgtt tatgctgaga    300
agcggcatcc gtgcacctca cctccgcccg tccacgccg                           339
```

```
<210> SEQ ID NO 84
<211> LENGTH: 292
```

```
<212> TYPE: DNA
<213> ORGANISM: Homo sapiens

<400> SEQUENCE: 84
cgctcgggtg gccgagttac acctggctat aagtcatccc gtgcacctga ctaaatgcat    60
cccgtgcacc tgactaaatg cgtcccgtgc acctgactaa atgcgtcccg tgcacctgac   120
taaatgctcc cgtgcacctg actaaatgcg tcccgtgcac ctgactaaat gcgtcccgtg   180
cacctgacta aatgcgtccc gtgcacctga ctaaatgcgt cccgtgcacc tgactaaatg   240
cgtcccgtgc acctgactaa atggtcccgt gcacctgact aaatgcgtcc cg           292

<210> SEQ ID NO 85
<211> LENGTH: 329
<212> TYPE: DNA
<213> ORGANISM: Homo sapiens

<400> SEQUENCE: 85
cgcggagaga cacagggaga gggaagggag ttgcgctgaa aagacgcaaa gatacgcgcg    60
tgcaactccc tcccctttca ggtttcagag gtttgcaaac cagggctgag aggaaggggc   120
tcgggaactc acgttcctct cgccccccctt ctgtctggag tctcgcccgc cagaggctgg   180
ttaaccccag tcccggccgc cgcagacact gcgctgagct tttgggtcct cgccttgccc   240
agcgccagtg cagctgaagt gagagctggt gggaaatgca aatggctcct ggagaaatag   300
aagatacaga atgattctca ttccctcct                                     329

<210> SEQ ID NO 86
<211> LENGTH: 416
<212> TYPE: DNA
<213> ORGANISM: Homo sapiens

<400> SEQUENCE: 86
cgcggctgcc gcggctgggc ttccgcttct gctgcagcgt tggggttgac tctggggtgg    60
ggagggccgt caggtccagg tggtgctggt ctgctttaat gagcatcttg gccgtgttgc   120
cgggagtgcg agcttgccgt tgtgcatgag tggcgtgagg atggcctccg gctttgggtc   180
tttggattga gtgtccccaa agaggccgct gagcttggtg acgctgctca tggagccccg   240
gcgcgagtgg gtgagctcct tctcttgcgc tgcaccacag ccacgtcttt gcgccgatga   300
tcacagacgc agtagacggt gatgcccgag aagacgcccc ccatgacgaa agccaggatg   360
actgcaatgg ccaagagggt gacgggaacc agctggtcgg gcctttgagg taactt       416

<210> SEQ ID NO 87
<211> LENGTH: 1226
<212> TYPE: DNA
<213> ORGANISM: Homo sapiens

<400> SEQUENCE: 87
cggccaaggc tggcggcggc aggtacccgg gtgccccgag ggccaccgc cgccccgctc     60 tggcgcatcc atcagtggcc agctttcacc gtgtctgcca ggcgggactc gccaggtgtc   120
aggctcatgc cataagcctg acacttgcgc ggggtcgccg tggctcctca gggaagctgg   180
gccaaggagg ctgggtcgcg ccggcgggcg ccgaggccac cttctcgggg caggccatcc   240
gcgctgaggc gcagacacgg cggtcctcca ggcccattaa taacccggag ggcgctgcga   300
tccgacagcg cagtcgccac aggctctatt tcccgtggcc gcctgcctcc ttccagccca   360
gttcgagtgg agggatactg ggcgcccact accgcccggc cggagggtgg gggtccctct   420
```

| | |
|---|---|
| cgcgcaggct gctttggaga gtgtcggaga gagacagctt tatctacagc ttcacccatt | 480 |
| gtatagcaca acagaatcgc atttagcctg gagaacagcc gtcggggcag gagttgtgcc | 540 |
| ttctctaaca attaggctga tcgttaaatt tgctattcct ttcttccggc gtctagggag | 600 |
| agcgtgcaca ccaaaccctc cagaacagca ccccggtccc ccaccccgcc ccacctgtcc | 660 |
| ccgccctgct tagtgcctgg agggagaact gactggtcgc ttgagggacc ccatttcggg | 720 |
| cgcgcccttg gagtcctggg gctgcggctc ctgctctacc gggctgcagg cttgctctgc | 780 |
| cccgtcccgt ggcgtttggg aggcagtgag gaagcctccg agtctctggg tcgaaggaag | 840 |
| tgcgaatggc acccgcgata gactggccgt ctccccacc ccgccccgtc tggtgatttt | 900 |
| aaatcgtctc ctgtgtaatt gtaaaaagag gaaagctgaa taccagacga ccagtataga | 960 |
| atctcttcga gacagcagat tgggcaagag acgggctttt tttcgcaata caaggataaa | 1020 |
| cacatcctga aactccagat agaaacctca ggaatgggcg agagggtcag aaggaacgaa | 1080 |
| gacagtaggg aagagagaga gagacagaga gacagaggga gagatgcaga gagactgaaa | 1140 |
| cgggaggaag aagcctggaa ctgtcggttc cgtggagagc ggacatgcta tctgcgccca | 1200 |
| gatccgaagg cttttgggga gcctag | 1226 |

<210> SEQ ID NO 88
<211> LENGTH: 1226
<212> TYPE: DNA
<213> ORGANISM: Homo sapiens

<400> SEQUENCE: 88

| | |
|---|---|
| cacagaagaa aaggcaaccc caggcataaa gaggctctca gcagcccctg cccgaacgct | 60 |
| cctggcaggc aagggcccca tagcaccctg gggcctcgag ggtcaccgca gacccggcct | 120 |
| gggaagaacc cgtagagtcc cgcagccgcg gaggagggg gttctcgcta aggcgtcccg | 180 |
| cggacaacgc cgagaggcac agcttagcgg gtgcgcaccg gacaggctcg caacgcagga | 240 |
| cggtgccctc atgggagcca ggcgagcagg tcaagaatgg tggtggggaa gcggggtagg | 300 |
| cagacctcgg cggggggctgc ctcggcgctc tgctcctacc caaggggccc ggttcccttt | 360 |
| ctacccacag ttcccttct atccgcctcc ctcctcagcc aatgaagcag tcggggctca | 420 |
| gcagtgctta gcacgctcgg actatggttt taatagacgt acatggacaa gtcgatatag | 480 |
| acagatttat tacagtcagt ccaacataca caggacgct gtaaacaggg gcgcggccgg | 540 |
| agagcgggtg tgcaaagtgg gcgcagggcc ctggggccgc gccccttgct ctgccggctc | 600 |
| gactcttgca cggcgggcgg tgaggagggg gctgttcgcc cagacagagg gccacctcct | 660 |
| agcccgggag cgagcagagg gcctgggcct gcagctaagc tcaaggctgg ggtgttctga | 720 |
| gatggacctc ccccacctcc cgccaggccc gcactgcccg ctgtcgctcc gtggccttaa | 780 |
| tatagggctc cggggcgcgg ggccagcagg ctctaccagg cgcgccgggg ccgtgtgcgg | 840 |
| ctccactgag tgcccgatcc tgggctgggg gcaccgtccc cccaaaccca acgcccgccc | 900 |
| caacacggat ccgactcgag ctaaggcgct ctcggccggg cctgctcgga gagggcaact | 960 |
| tggtttgtac ggggtcggga atcctaggc aagtccaggc cccgcacatc cagtccgcag | 1020 |
| gcccggccac tcagtccgga tccagcgcgcg cggggacgcg ggatacgagg tcgtcctccc | 1080 |
| cggccgctgg gcctcggcgc tcgcctaccg cgccgcgtgc cctccgcgga gtgggcctcc | 1140 |
| ggggcccgtg ggaacacaca caccaccccgc gccatcccga gagaaattgc aactcatcca | 1200 |
| tttttttcgcg gcactttctc cgacgt | 1226 |

<210> SEQ ID NO 89
<211> LENGTH: 237
<212> TYPE: DNA
<213> ORGANISM: Homo sapiens

<400> SEQUENCE: 89

| | | | | | |
|---|---|---|---|---|---|
| cgcgcgggac | cggaggcgca | caccggaggg | gaggtgcccc | caccaaaatt | taagtgcggc | 60 |
| gcaacatgca | ccacaggtag | gggcactacc | agggcaaaaa | gacttggtga | atgcgagggc | 120 |
| cgggcctatc | aaaggtgcgt | atggtggtac | cagagcaagg | cggaacagct | gctcagtggt | 180 |
| ccgcaaccgg | gtcaagggac | aagaagacga | ttctggattg | taggccgccc | gagagcg | 237 |

<210> SEQ ID NO 90
<211> LENGTH: 1042
<212> TYPE: DNA
<213> ORGANISM: Homo sapiens

<400> SEQUENCE: 90

| | | | | | |
|---|---|---|---|---|---|
| cggtgactcg | gaacagaggc | agaaaggatg | cgaggacttc | ttgctgcgta | aacagcgcgg | 60 |
| cgggcagatt | ggcacctggc | acctaccagg | actggcgctt | cgtcccgcgt | ttccattgtg | 120 |
| cccgcaccac | tttgaaagtg | ggcgccggaa | actccgtttt | tcttatgggg | ccggggtcgg | 180 |
| gcaacgtggt | tcagaggttt | cacaagctcc | agcacagaag | tgatccaaac | cgaggggtcg | 240 |
| gctcgaagtc | ggaggctgat | ttttcttgct | cagtcgctcc | gccggagctg | agccgctgga | 300 |
| acgacccaaa | cctacctgaa | agcgcgtctc | tgcagtcccg | ctggacttct | ccggctcgaa | 360 |
| ctcctaatct | cagcccggaa | tccagccata | ttcatttaag | attgcgtttt | ccaaaggcca | 420 |
| aagcctttcc | cggtttcgtc | atcagccgcc | aggttgggtc | cctaattagc | ctgtccaccg | 480 |
| agcttccttc | ccggcgccgc | ttggaccccg | cagccccggg | cgatctcagc | cggggggga | 540 |
| atccggagac | gccggctccg | ggttaagact | ctgctcgtcc | ccaggaggac | ggggtcgcga | 600 |
| tccagagtgc | gatccggaga | aaagggctgc | atcttgcgtg | gctggcgggt | tagactggaa | 660 |
| tccgtctggg | gactgcgcac | catccccatc | gctccagacg | ccgaaacaaa | acctgaggct | 720 |
| cggagagggg | aaaaagagtt | gttcaggctc | gaacatacgc | atcccagcct | cataggtgga | 780 |
| tggggttacc | gagctgagaa | ccaagccgag | gtccgcgaag | ccgggccgcc | cccttgctct | 840 |
| gggcctccct | tcaagcctgc | agtctgggga | tgggttccga | gtcaccgcgg | tccgggcctc | 900 |
| ggtcaggctt | ggtcgggcac | acaggggcgtt | tcagaggcca | gatgacaacc | tgtggcggca | 960 |
| aaaggactct | ccctcaccag | ggacccgcga | aggcgcgcat | tgcaagatgt | tagcgtgcgg | 1020 |
| gctttagata | tccttgcgtc | cg | | | | 1042 |

<210> SEQ ID NO 91
<211> LENGTH: 1226
<212> TYPE: DNA
<213> ORGANISM: Homo sapiens

<400> SEQUENCE: 91

| | | | | | |
|---|---|---|---|---|---|
| cggggtccca | cgcgggcggc | gcggtcttcc | ccaggcctcc | ttctctggag | acccggttcc | 60 |
| caggggacgc | tgtgcgggga | caggcggagc | cggcccttgg | agcccggcgc | gggcagaggc | 120 |
| gccgcgggac | aacgcctccg | acggcagggg | gcgctcgtag | cacgcgcagt | gcgcggtgcg | 180 |
| ggcgcccagg | acggctgcct | ggccccgggt | tcccgaggcg | cggacctgc | cggggtgagg | 240 |
| tgccccagc | ctgagagccc | cagctgggtc | ggccaagggg | cctccgggct | tccacatcgt | 300 |
| cccttttttct | gctgacgctc | gcggggaagc | ggcgggaagc | ctgtgagggg | cggcctggga | 360 |

```
gcagacggac caccaggtca ccggcgcgcg ctgccaggcc cgacccactc gcgaggacca    420
gcggttcccg gaggcgtcgg ccctcaggtc ctcgggggag gccggctgca ccagccggg     480 tgtcggcctt gtccctgtcc tgagaggtgc aaacaccggc cccggcccag gccccggggc    540
tcctgcccag aaggctcaga gctggggcc gaccgcgcct tacccgcagg aggcccggcg     600
gtgcgtccgc gttggtgcca ctccccggcc ggggtgaggg acgtcggaag gaaggtccca    660
gggcgcaggg tccgcgaagg gagcactcgg aaggaaggct ggctgcggcc ccggcgcctg    720
ggtccgctgc ggcgccgggc cggagacctg gaacagcca gccacctgca aggttgcagc     780
ccacctcacc ccgccggcgg ctccgggctg tctgtgggtc tgtctcacgg ggcaaagcct    840
ttcttcccac acccacagcc aaggcgcgtc cgtgcagggg cacacgcctt ctgctccagc    900
cccaggaagg cgctttcgcc ctgcagtcct ccgacggccg gctccgccgc accgcgcacc    960
ctggctccgg cagactctgg ggcctgggga ctcgcccacc ctgcgcggcg cgcccccac    1020 atgagccgag gttgggaggc tgcggggcct ctgtcctccc aggccgtgga gtgcggcggc   1080
gctctgagtc cgctggggac ctggatggag agaaactggg gctcgttcgc gcacacatgc   1140
accatttgtt ctttccgatc atctatccct ttacgaattt tatttttatt ccggattgtt   1200
aatgcaagac gacagttgaa tctcca                                        1226

<210> SEQ ID NO 92
<211> LENGTH: 583
<212> TYPE: DNA
<213> ORGANISM: Homo sapiens

<400> SEQUENCE: 92
cggcctgcgg tggggaagcg ggtacgggag gcccagctct ccccaccagg gtcactggag     60
aggagcagac gcagccgtcc gccaagaccc gggcacgagt ccccagcagc tgtcactgcc    120
ccaaactaac gtgaccccac gtccaccagc aggtgaacag ataaccaac ggccgatcca     180 cacaatggca ggcccaccag tgcccacaac accacgactc tccagactgt gcagcagag    240 cacccgcaag ctccctcggt ataaactcaa cgcagacaaa cccacagggc cacagggcgg    300
cgcggactgg aaggggcaa gaggggtagc cggcgatggc catgtacact gtggcctccg    360
ccctccctcc ctgcccggcc agggcacctg gacggcggg gggagcggca gagttgcgcc    420
ctcaccttgc agacgctgct gctggcagcc ccttcgctgt gcagtaggac ctcaggcacg    480
ggcacccgca gctccggccg ctgtaggtag agctgcagga gaaggtctcg gcagccctgc    540
ccagcacgct ggaagaggtg gagcagggct caccaggcgg acg                      583

<210> SEQ ID NO 93
<211> LENGTH: 560
<212> TYPE: DNA
<213> ORGANISM: Homo sapiens

<400> SEQUENCE: 93
aacacagtta tgacacagtg agcccacagc acagttagcc tgcagcacag tgagcccgag     60
acacaggtat gacacagcga gcacatggca tggtgaccct gagacagggt tacgacttgg    120
tgagccccaa catggtgagc caagacggt tacgacatgg tgagctcacg gcacagtgag     180
cctgagatgg ttacgacacg atgagcccgc agcacggtca gcctgagacg gttacaacat    240
ggtgagcctg tggcacggtg agccaagaca gggttacgac atagtgagcc cacagcatgg    300
tcagcccgag acagttatgg cacagtgagc ccgcggcacg tgagcccgc agcatggtga    360 gcccgagacg gttatgacac agtgagctca cggcacggta gcccgagaca gagttacgac    420
```

```
ttggtgagcc cgcggcatgg tgagcccaag acagagttac gacttggtga gcccgcggca    480
tggtgagccc gagatggtta cgacatggtg agctcgcagc acggtgagcc tgccatggcc    540
tcaagggtta agatgtaaac                                                560
```

<210> SEQ ID NO 94
<211> LENGTH: 336
<212> TYPE: DNA
<213> ORGANISM: Homo sapiens

<400> SEQUENCE: 94

```
cttctcagca aaggccaaca cgtctttctc gagtccaaga ccatctcccg ttcaagggcc     60
ctcaccgcgc tttgtgagtc tgtctcgtgg gcctccttca gtggtctgtg accagcggga   120
atgaatggga cgtgttttgt tcagccctga ctcttggacg ctggtggcag ccgcgggcgc   180
ccactcacct ggcacgtgga cgaaggtgat gagcgcggct gacggctccc ggggcagtg    240 tggggtccag tctgaagccg acgccctctc ggtcaggctt tcagcagcag aaggcagtgg   300
actcttcacc atttcttcca acactttctc acgtag                             336
```

<210> SEQ ID NO 95
<211> LENGTH: 646
<212> TYPE: DNA
<213> ORGANISM: Homo sapiens

<400> SEQUENCE: 95

```
aaactgaggc aaccaactta ttcgcaagag taaaacccta tggggagaag cgattcctgc     60
ccctcttccc ccggcgagga acacggctgg agccacccag gcgccttcca ggctaaggcg   120
cctttagggc gcgcaggggt gagggagagg gtggggagag tcctaattat tatgaatttc   180
taaaggcgca gtaattattc acgggagca ggacaaacca tggctaggca gggaaatcga    240
tatatttgct atcgaaagtt cctgctcgcc tttaatgcag acgaatgggg gatgcagcct   300
cattattttc cgtggttagg ctcgccagcg tggggcctga tgcagcgtga aatctatcat   360
cattagaccc gggatggagc ggcgggggg agtttctctt acttaccaaa ccgcaacaac     420
aaacaaacaa cgacgaacaa ccgcccccta caaaactca ttctcacaca acgttgccct    480
acctccctcg ccgcttgccc tggccgctgt tgcacactcc cctgggggct gtctgacgcc    540
ctagagcaga cactgcggtc acttaaagtg cgcccagttc ctccaccgca gcggtcacac    600
cgttgatttg atccagaaat aagacggata gtaccgagcg ttggcg                   646
```

<210> SEQ ID NO 96
<211> LENGTH: 330
<212> TYPE: DNA
<213> ORGANISM: Homo sapiens

<400> SEQUENCE: 96

```
cgccgccgcc gtctgtctag actcaagcga ctgaaggggc aacagagct ggtgtttaaa     60 gtagaacctg cccagtccaa cagcccgagc agggagcgat ttcgggatc gcgggaagga   120 acgcactcgc caagggaggg ccgggtgccc tcgccaccgg ctcattcctg ctccggtttt   180
gcccgatgcg cgtccaggag gttctggcag gacgcactgc ccctctgccc cggccaagga   240
ggatgcggat actgcccgca aggttcggcc tttatggacc caagtcagcc aactgggccg   300
agtcctgcgg acaccgaaac ctcccttcg                                      330
```

<210> SEQ ID NO 97

<211> LENGTH: 1226
<212> TYPE: DNA
<213> ORGANISM: Homo sapiens

<400> SEQUENCE: 97

```
cgcctgtgct ctggactcgc tgtgcagggt ccggctccga ggcgctggtc ggcagtccga      60
acggagggag cgagaccccc aagagcaacg gcggcagtgg tggggcggc tcgcaaggca     120
ccctggctgc agcgccagtg accagatgcg tcgttaccgc accgccttca cccgagagca    180
gattgcgcgg ctggagaagg aattctaccg ggagaactac gtatccaggc cgcggagatg    240
tgagctggcg gccgccctaa accgccggaa accaccatca aggtatgcgg ggtccaggct    300
ggggaggcgg gtgtgcacct atttagcggg aagtaaatgc caactgccaa ctccctgaaa    360
cgcaggccag gaatctgggc ctggggtctc cctgcccggg cgtgcagatt gaccctcgtg    420
acagctccta ggcaggcatt gctgccatgt ggctgactct gtccctttcc tggttaaata    480
gacaaggggt gggcgtgggg aaggggata gagtgcctgt gcgggtgaca aggaatttct      540
ggggacacgc tctctgcggc cgcagaccaa ttgagtccat gtcctttcac tgctcctccc    600
atacacacac tggcctctgg caccccgggg gcctggccac ctgggcagaa ggaaggaggg    660
agcgggctgg atcactcccc aaacctctct cggaggatt ccagctccag gtggtggtgg      720
tggggtcggt ctctaccggg ctggtgtctg ctttggctgt tcctgccctg cgaacactgt    780
ccccggagcg ggaccagact actggccctg agcatcgggc caagtccagc tactgaacct    840
gctccgctcc tctccccagg tgtggttcca gaaccggcgc atgaaggaca agcggcagcg    900
cctggccatg acgtggccgc accggcggga ccccgccttc taccttacat gatgagccat    960
gcggcggccg cgggcggcct gccctacccc ttcccatcgc acctgcccct gcctactac   1020
tcgcggtgg gctgggcgc cgcatccgcc gcctccgccg ccgcctcgcc cttcagcggt     1080
cgctgcgccc gctcgacacg ttccgcgtgc tgtcgcagcc ctaccgcgg cccgaactgc    1140
tgtgcgcctt ccgccacccg ccgctctacc cggggcccgc gcacggactg ggcgcctctg  1200
ccggcggccc ctgctctgcc tcgcct                                       1226
```

<210> SEQ ID NO 98
<211> LENGTH: 485
<212> TYPE: DNA
<213> ORGANISM: Homo sapiens

<400> SEQUENCE: 98

```
cggacttgtc cccgcagccc ttgcggacct cctggtcgtc atggcgactg tgaaatgtgg     60
ggtggggagc atgcgttcga agccatttgc gcgggcagtc cctgcgtgtc ccccacgtg    120
ctccccacac tcgcaggacc cccgcctccg agcttccctg agcgtgcagc ttccagtgag    180
ggcagcccca cgcacagccc cccacaccct ccccaacgcc ttcagccccc ggtgcgcgta    240
gtccccaagc ccacacgtgc acttccacct tgcggcagct gcacgtacag ccccccacac    300
gctcccagcc ccactggcgc agaacccatc accgctcgcc cttcacgcgc ttcactggga    360
gtgcagcccc caccccgagc gcgcagctcc acgcagcctt ccacactctc cccagcgcct    420
gcagcacccc cagtgcgcac agctctgcca gtcgcttccc cgcgtgccgc ccctgcacca    480
cttcg                                                              485
```

<210> SEQ ID NO 99
<211> LENGTH: 564
<212> TYPE: DNA
<213> ORGANISM: Homo sapiens

<400> SEQUENCE: 99

```
cgagcacggc ctcggaggct gagaggcctg ggaggcaggg ccgcgtcctg cgggctccac      60
gagagccctg tgaaatgcca gtcagatcct ggcccagtgc cccaggtcct cccgcagcct     120
cggcaaaccc tcccccggcg ctggaaacct tcccctgcca ggcgcagaag gccgcgcgca     180
agcacgcagc tcacagtcac cgccacctgc tctgaaaccc caggttcagc gcaggatcag     240
agtccccat ccccacccca cgcaagggac gcaggattga cagcgaccct gaagaaatgc      300
agtcgagagc tattgtgaaa gggcgctggc ccggaggccc cccagcccgc gcaggacagg     360
ccagttaatc gccttggtcc caggcccta ttagcgtgtc atctgcgaca gcaggacacg      420
ccttcccatg ccagccgctt tggggcccgt gcggcccttt ttccctcgca gctgctgcaa     480
caaatagcag ttcttttgag ggaaggaaca gtgtggtcct caaagttcat aatgaaaatc     540
ttggagaaaa gtcatagttg ctaa                                            564
```

<210> SEQ ID NO 100
<211> LENGTH: 1226
<212> TYPE: DNA
<213> ORGANISM: Homo sapiens

<400> SEQUENCE: 100

```
cgagcgggac gagccctggg gctcccacac cgctggagac tgcggcgagt tacacgccat      60
tgggtcgctg gagctgggac tgtgctccgg gggcatctcc ccgttttca tgatcttctt      120
gatcttgatc ttttgttctg aaaccagatt ttcacctgag ttggggaaca aaggcacacg     180
ttaccgggac actcagaggt cgcccgcgcc ttccccgggg cggcgactgg aggcatcttc     240
ggacctctgg gcggcccagc cctcctggcg tctcccgcc gcttgcggcc taccgccaag      300
aagctatgcc ttaggcaaac catggagctc tggccccaga gggcgccctg gccggctcgg     360
ggcgccccgg cccagcgagg ccacgacccc aaggcttgtt tttgtttggg ctggggtgg      420
gggacgccag cgcggcgggt gtgcgcccga gtgtcctcgg cggcggcgcg cctcgtgtaa     480
gcctgcgcag gacgcgcgga acgcggcgaa ggtctccaaa acaatcgcgc gagccggcgg     540
ggaaggggcg tggggcgggc tacgcgcgcc tgtggtcaga aaaaggagcg agctcccaac     600
ctcccgtcct actccttca ctccctctgc agctcagaga ggccagaatc tgactgcagc      660
tcttggcggc gctcgaacat tctttatgct tccgtaggcc ccagctgggt tggaggagta     720
aaaggaatgg gacaatccag gaagacttct cacgtacaat agcgccccc acctcgcgac      780
ccttcggtgg ccgtggcctg aagctccgta ggctcagggc acgacccttc agtttctccg     840
ctccaggcga cgttctcagc ctttctctag cctgagacca ccgcgagaac accaggcctt     900
gctcacccc gaggaggctc tacattgtta agaaaaccag atactgctct gggctgccta     960
ggccgcccta gaaataaccc tccgcttgct ttcaacccgc gaaattggcc ccacagctcc    1020
ggaggcccgc tacggggtgg gggcgggggg cgcggttagt gggaggtatc tccagaccgt    1080
gatgaatacc atccccaccg tctcaaggcc tgactcaccg agttaaagca tagggggtga    1140
tgtctttggg tctgttagtt tctcacgggt actgtcaaaa cagctccagt cccatcgaga    1200
ctgaaccgcg cgaccaacca gacgtg                                         1226
```

<210> SEQ ID NO 101
<211> LENGTH: 331
<212> TYPE: DNA
<213> ORGANISM: Homo sapiens

<400> SEQUENCE: 101

| cgattcaaag atgccggcgt cccgcagtgt gcggttcgtg cccttaacca cccgcttctt | 60 |
| tgtttcccgc ccctctgctt tcgcaggagc tcttgtgctt gagttcagtg ttagtggtag | 120 |
| cgtggctact ccacttggag gtggcggccg tctgaccgtg tgttactgct ttgccgacgg | 180 |
| ggcctcccgg ccctgatgcg tgtacactct gcgggctgca ccgggtggct ctggttgggg | 240 |
| gcgaagctgt gttgactggg agacgttgga aattgagaca tggagagatg acgggagtgc | 300 |
| gtttctctgg gtttgatctc catcctgttt t | 331 |

<210> SEQ ID NO 102
<211> LENGTH: 1226
<212> TYPE: DNA
<213> ORGANISM: Homo sapiens

<400> SEQUENCE: 102

| cgcggtggcc cccgcacccg gagcgtcggc agcacctgga gcggttaggg ctactctgcc | 60 |
| gccgccgccc ccgcggtccc cgccgccgct gtccccgccg cggtccgtgc gcgcgggcgc | 120 |
| cagtgcacca ggagcgcgtg cgccaggcgg aagggcgcga aggcccggtg cgcccagctg | 180 |
| tgctcctcga tgaccgcgta gcacgaggcc agcacccggt tgatgagaat ggtgccctgg | 240 |
| gccgtgagcg gcgcgtaggc ggccgcggcct cctcgcttag ggtcacgctg tgcacagcgg | 300 |
| cgggcaggag ccggcggtcc ccgtcacgct cggccaccac gtacacgcgc tggcccgggc | 360 |
| gcacgcggct ggcgaacagc gcccgaggcc ccagtgcgcc ccggaaggcg ccccgagcc | 420 |
| cgaggacgcc tcgggctccc cggtggccga gtcgttgtgc ggcgccacaa agagcaggtg | 480 |
| cgcggcggtg agcagcaggc gctcgcgcgg ctcccgcgtc tcgatcacgt agaagccttc | 540 |
| ttggcgccgt cgtcgcggtc caggaaagtg aggaagtcgc tgtagagcag ccggccctgg | 600 |
| tcgtccgccg ccagcacgcg gtccccgggg ctcaggtcct tcaccagctt ggtgccgccc | 660 |
| tgctccaggt gaccgtggcc gagccccggga agcagcctcc cgatttggcc gccaccgagt | 720 |
| tctctgcggg tgaggagaag ggaaagaaga gaggacaggg cattgagttc cgagagggag | 780 |
| gcgcgtctcg gggaggaggg cgcacgctgg tgcccgcgct cctaggccag gggtgcgcaa | 840 |
| ggcgcggggc ggggcgattg attccaggcg ggtcccgcac acacctccct cccccaaccc | 900 |
| cactgcccca gggacaggat tccgacacat tccttaacga ctcctaagtc tgggctggcg | 960 |
| gtcacagagg ttggctggcg tttcctgcag aggccggtga cactctttcc ttccgccttc | 1020 |
| ctccaacccc accccagct ccgcacacac ccggcctcgc cgcgaatcca tccagagggg | 1080 |
| tttgctctgc acttggattc ctcaggaagc ctccttgagc tcccgcgggc gccgggcgca | 1140 |
| ccctccttcc ctcccgcccc ggcgcggggc ggggcgcctg ctcgcgcact cagcacccgg | 1200 |
| gctgcgcggc ggaaaccctg gcccgc | 1226 |

<210> SEQ ID NO 103
<211> LENGTH: 337
<212> TYPE: DNA
<213> ORGANISM: Homo sapiens

<400> SEQUENCE: 103

| cgcacggcct cctcgtccct ctcgggcaag gctatcagcc agagcacctc ccctttgaca | 60 |
| ctgaccggcg tccccagccc cgccttgtta ctgcatccgt ctgaggtaca aggttagaag | 120 |
| ccacagaacc cgagctgcag cctgacccac acaagctgcg ggcgcaatgg cgctttgcag | 180 |
| acaagacagc ctgcccgtct gccttcttc tcggcttccc ttaagacaca aggtgacgac | 240 |

```
acggacggtt tcaagtgagt gcatctggaa ataatctcag tgcaggggag gggttgaggc    300
caaagatgtc gtgacctggt ccccgctgtg gccaggc                            337

<210> SEQ ID NO 104
<211> LENGTH: 1226
<212> TYPE: DNA
<213> ORGANISM: Homo sapiens

<400> SEQUENCE: 104
cgaggtataa agaccaacgc acgacgggcg ccggggcgcc gtcacctgcc tgggttaaca     60
gttcctgccg cgggggcagg gagaaaggcg ctagaggggc gcggggtgcc ggcggggccg    120
agcccgggcg cgggcgagcc ctgggtgcca ggccctgcgc cgcacgccac tctcgcagcg    180
ctgccgccgg gaaagtgccg gcgctggctc tccctcccct cccgggaata gcgggcgcag    240
gcacgcacat ccacacacat ccaacacaca cacacaccgc acactcacac acccgggtgg    300
ccgcgcgggg ctccgagccg cgcaggcctc cttggcagac atcttcctgt gggaggattt    360
caaacgagcc gtgaaagcca gaaactacac gggttacaac tccggaatcc ctggccggcc    420
tcggcctccc tccccacctc cggcccggcc ccctccgttc ggcccgtggc caggagcccc    480
accaaaggac aaagctcaca cgccgaaagc gcggggagat ccggggcgc agagatgccc     540 cgacggcct  tctaccttct gaccctggga cccacggcca gtgccgcgc agccgaggtc     600 ggccttgctg atctgtggtg gcccagggcg acccgaagcg caccggcttc agggtgcgcc    660
ctggccaggg ctggggtgga gggtcacata agccacctgg catccgaggg tggccgcctc    720
gccccctcaa cgccgctctc cagggaagga ggcggcgggg tcaccagggc gcagctgaca    780
gccccaggcc ccggccaggg cgcacccaaa gaagagggag gctgctgcct gaactggcct    840
gggggcagag ggaagtgggc cccgcgctgt ggaaggcccc aggctggagc gccggggaca    900
gctgtccaag cggcgagggc taggagtggc ctcgcctagc gctagccggc caggccctgg    960
aggtgctccg cgccttctcg gccaaaagcc agctccgcgc cgctggcgga gtgggaggga   1020
ggcggccagg cgagcgcccc gccttcgtcg cccgcggtca caggggcaat tacactcctg   1080
ctgcagacgg ttaccagctc gcccgcgcat ccctctctcg gctcccctct cctcccctct   1140
cctctcctcc cctcccctcc tccgcggaac tgctggctcc atattagcga gggtgccctg   1200
gcagcgcgac cgaggcaact acccct                                      1226

<210> SEQ ID NO 105
<211> LENGTH: 468
<212> TYPE: DNA
<213> ORGANISM: Homo sapiens

<400> SEQUENCE: 105
taggcaggag gaggaggagg aagagggcac ctgctgagat acttcactgg tctgagggcc     60
ccttctgccc cagctagcgc ttgggtgagg gttgggcttg cggagccgtc ctgtaaagcc    120
ggggatgcag gacgcattgt caccccctcc tgccgctctt acgaaacact cttaattgag    180
tccgattctt ggtgaatcag ccttccaaga accgcgaccg cagcatcctg tgccgcttct    240
gtgttccgca ttttttctctt tctgcagcgt ttcctctcat tctggatgga aagcctgttt    300
gtctccctca atctttggcg agggtggcag gcagccaggc ggccattacg ggccgcgcct    360
cccaccagcc agtcgctggc aggagcgtcc ggggagggag cagacccgt tcaccctcac    420 cccagaactg aagcagcgag gggacccaga cgagctggaa tgcaggcg                468
```

<210> SEQ ID NO 106
<211> LENGTH: 1324
<212> TYPE: DNA
<213> ORGANISM: Homo sapiens

<400> SEQUENCE: 106

| | | | | | |
|---|---|---|---|---|---|
| cgcgctccgc | cagcaagacc | tggcgtctgc | aaaacacagg | cgtgaggggc | gtgcttacta | 60 |
| atgcctggtg | ttccagaagg | cggctcccgc | caggcctccc | gagtaggaag | gagagggctc | 120 |
| ggcccgccag | acacacacac | acccacctgc | acacgctgct | tctctgggct | ctgcctcacg | 180 |
| gttctcacgc | tgcagctccg | gtctcgcgcc | tccttttacg | ttgtttaggt | ttctttctga | 240 |
| catgactgag | ggaagtgcgg | ttcacaggca | gagctgcctg | gggagagagg | tggcaggcgg | 300 |
| cccgttgttc | accgggcccc | ggcctcgcta | aattcacacc | tcggcggcgt | ctggcagctt | 360 |
| ccgcggcgtg | ggctttagca | caacacaacc | ccgtcggccc | tcagagctgc | agggttgccg | 420 |
| acgtgccctc | ctgcgcgtgc | cagtccctcg | ccccagccgt | ccccgccac | tgttgtcctt | 480 |
| gattctggtt | ggaggtgtga | tttcccacat | acatattcat | gtggtgtgtt | tgcagcgtgg | 540 |
| ggtgtgagtc | acacggatat | tttaatgggg | agagtggggg | ggcttgcgga | ggcgccgggc | 600 |
| ggatggacgt | gtccatctgg | ctcgtgggga | gacccggggc | cctcagatgg | tgcgatgtct | 660 |
| gaggctgccc | tcctcacatt | gatgggagcc | agggcctact | tggcttgctg | ccccaaggg | 720 |
| gaacgtggcc | ctagataccg | ggggaggccc | cgccgcagcc | tcaagtgact | gactcaggcc | 780 |
| cccaggttag | cacagctgcc | acaggcctgg | cggaaactcc | ggatgggggt | ctgaaaagcc | 840 |
| tttgtgggggt | cggggcacca | cacggggttgg | gctgatggcg | cgctggggc | ggggctccag | 900 |
| ggcacattgt | cagatagatg | accccacggg | gtgggctgag | gactgctggt | caggtgaggg | 960 |
| gtgtgctggg | accggctggg | cagtgacccc | gagccgcctc | cggcccccag | gagctggagt | 1020 |
| tcctacgcgt | ggccaagaag | gagaagctgc | gggaggccac | ggaggccaag | cgtaacctgc | 1080 |
| ggaaggagat | cgagcgtctc | cgcgccgaga | acgagaaaag | atgaaagagg | ccaacgagtc | 1140 |
| acggctgcgc | ctgaagcggg | agctggagca | ggcgcggcag | gcccgggtgt | gcgacaaggg | 1200 |
| ctgcgaggcg | ggccgcctgc | gcgccaagta | tcggcccag | gtatgcgggt | ggggagactg | 1260 |
| aggcacgcag | cacggtgggc | gtgagccgcc | gtgggccccg | gtggccagtc | ctgcccagcc | 1320 |
| ggaa | | | | | 1324 |

<210> SEQ ID NO 107
<211> LENGTH: 1324
<212> TYPE: DNA
<213> ORGANISM: Homo sapiens

<400> SEQUENCE: 107

| | | | | | |
|---|---|---|---|---|---|
| cgagtgcacg | gctttgtgct | gctccaggct | caccgcgtgc | ccgaaggtct | tgccgcacat | 60 |
| ctcgcaggca | aagggtctgg | taccgctgtg | ggacctgcgc | acgtgcacct | cgagcccgtg | 120 |
| cggcgtgaga | acacctaagg | cgggtggggc | cagagagaag | gccgctgaga | ggggccgcgg | 180 |
| ggcgcaggcg | aggcgcgggt | aggggaagcg | ggcgcacggc | aggcgaggtg | gtgagctcgg | 240 |
| gagcctcacc | ttgctgcact | tgatgcactt | gtaggagccg | ccgcccagca | gcggcgggtg | 300 |
| cacagcagct | ccgactccac | cttgacgcca | gcgcccttgt | ctgcgtgcag | cccgtggcca | 360 |
| cgctcggggt | acagcaagcc | cgccgctgcc | gtgggcctct | catacagccc | ggctgccgca | 420 |
| gacccgaagt | cgccgtagag | ccctaggcca | gggcagggg | ggcaccggcc | cctgcgctgc | 480 |
| agctccctgg | cgccccggcc | cccgcgccgc | cggcagcccg | cttcgggccg | tacagcgcgg | 540 |

```
ccgggtggcc aggctccggg gcgggttcgc agaagaggcc caggccagcg ccacgctcca      600
gggccccaca cggtcggtag cttgcaccag gtgccgcagg tcagaacccg ccaggccgct      660
ccatgagtac ggtttgaaag cagggggaa gggctgggct tcgtccagcg atgggcacat       720
tgacttctcc gaggctgtgg aggcacaagg ggagcgtccg gtcaggcttc agacggaga      780 gcggaggcgc cgggctgcgg ctgcgagcgt ggcgtgttcg cggactgcgg ggcacccagc      840
gcttgtagaa cactgcgtgc gccaggtgcc aggctcgccc cagggtaaaa cgtgcccgg      900 gccctgggc ctcgcaggcc actataggag gcagaacagt aaacagatca ttaaaagacc      960
tcgggagagg aggtcgtaaa ttctgtgcga gtgcagcgga ggcgctcggc gttccgagga     1020
tcttttctgg ctggacccgc gcacctggag atcctacagg gaagggcgca tctataaatg     1080
cccgtagttg agctgttaag aaggagaagg tggcggcgtt cggcccctca cagcactcaa     1140
gggcggaagg gtccagccac cagcgcaggc actctcccag cccctacatg ttcccattca     1200
attctttttc ttcccagaat ccaagaggaa ggagggagaa ggtccataaa tgcggccccg     1260
aactacccga aaggctgctg tcgaataaac ccgaaggtat taagatttca cgaagttaag     1320
tgcc                                                                    1324

<210> SEQ ID NO 108
<211> LENGTH: 323
<212> TYPE: DNA
<213> ORGANISM: Homo sapiens

<400> SEQUENCE: 108
cgagaggccc ggccaccggc tcgggagctg ggccggtcgc tttgggagcg gatgaggaag       60
gttaggagaa gcagcgagat agatcccaat tttacaattc tattttcttt cggtagggtc      120
tcggcgtctg ggccacgttg agagcgaacg tgggccgagc ggaggacaca gagtaaaaag      180
cgacgcccgc tgtatacata aatccgcacc cgctgcccgc cgggtactg cctgctctgg       240 cttccgctct cttccgaggc tgggcaagtc caaaagttcc cgaaaggggg gtcaaagagg      300
ggcgctcagt gcacgtgatt tcg                                              323

<210> SEQ ID NO 109
<211> LENGTH: 770
<212> TYPE: DNA
<213> ORGANISM: Homo sapiens

<400> SEQUENCE: 109
ttcttccctc tttactccat tccctaactc ctgcctcgta ggcagcggtg gggagccgca       60
ggctgctccc cgagtcccaa cgctactagg gtgctgtaac agtgatgagg cggcgttgca      120
gtctggcagg cgctgcagcg ggcaccagct acgttttgct gtcggcggca gttacccgga      180
cgcaagttaa ggggtaggcg cgcagaggcg gttggaggcg ggcggccggc ccctgacctc      240
ggagagctgc gccgagcagg gcggaaaatt tatggtctgt gtacactttc tgctccagag      300
ccccgcgcac cagaaggatg gggccctgcg agcgcgcccc aggccgcgag ctggggccgc      360
aggcgccacg gccatgtata gtgcccaccc gactctgttc tgcagcgctg tggtcataaa      420
ccttccctta gagggcgcgg ctgtaaacga aagtccggcg agaggtggat gcaggccttg      480
ccgcccggac cctcaggtat aattctggaa acttgcacgg aagcctgggt cccgccatct      540
tccctgttgt ggtggggtaa gaggatagtt tatactggcg gtttggaatc ccgcgcggtg      600
gatgcaaggt gggattccag ccagcgacgc gccgcgtggc cgggagtgca gacaggtcac      660
```

| | |
|---|---|
| cggtccccgg gtgtctggac cgcgccgctt cctactgggc ttacttcggg atctagactt | 720 |
| cggcctccgt ccttgcaagg gcccagattt gattccggtt cgtcgaggcg | 770 |

<210> SEQ ID NO 110
<211> LENGTH: 339
<212> TYPE: DNA
<213> ORGANISM: Homo sapiens

<400> SEQUENCE: 110

| | |
|---|---|
| cgaaaccctc gaggagcgac cacatgaccc ccgcgctgtg agctgctggc ggccagcgcc | 60 |
| ctcgcctcga ttgtctgcag ccctgtagtg ggccgcgagg cacgcaagcc gcaactacag | 120 |
| ctcgccacgg ggcacacaga caggcatgca ccaccactac ccgtcgcccg gatacactga | 180 |
| actggttttg aagcctgaac tgcagagatc ctaatatagc aacgcaggac gtttacggcc | 240 |
| acccgccagt gacagccggt gatgtgatga caggagggcc tgggtgaaaa tgcaagacac | 300 |
| tcactctcag agaacgacga ctccacttga aattcatgt | 339 |

<210> SEQ ID NO 111
<211> LENGTH: 218
<212> TYPE: DNA
<213> ORGANISM: Homo sapiens

<400> SEQUENCE: 111

| | |
|---|---|
| cggccgggtg gggaccggcg tggcgtcctg cggaccgcgt ggagtttggg gtgtctgaca | 60 |
| tcgttctcca cgtggctatt ttcagcgttc tcccggggaa gtacttggaa gagatcgcca | 120 |
| cacagatcgc acgcacagca tcaacgcgct gctgatcatc ggtggattcg aggtacgtta | 180 |
| ccgtttctct cttgccggtc ttgcaggtgt gagccgcg | 218 |

<210> SEQ ID NO 112
<211> LENGTH: 1324
<212> TYPE: DNA
<213> ORGANISM: Homo sapiens

<400> SEQUENCE: 112

| | |
|---|---|
| cggcaaccga gccagatcca agaggggtcg gcctcgtcta aattggtttc ccaccaatgg | 60 |
| cctcggatca gccgcggctg tgctgcggga gccctcagga cgcggctggg gttggtgcgc | 120 |
| ggggcccgga accccaaacc cggctcggtt cggcaaggtt cagggagaca aggtagagaa | 180 |
| ggctggggtg agcgagaagt cgggcggccg atcgtcaggg ccacgagcct cgccttgcct | 240 |
| tcttggaatc ccacccaact ttaaaggccc aaagatcctg aaaattccga aacgaaactg | 300 |
| cgagctggtc tccagaagtt tgagaacggt ctcccaggct ttccagcgtc gtcccgggat | 360 |
| tctcggacac cacaaacgcc atcaaccacg agcaccggtg tccgtggcta ttgccccgaa | 420 |
| tggtccccat ccgcgtcccc gggaactccc tcggctttcg cgcatccagg tccccagccc | 480 |
| cagctactgg tgcgcccga gcccctaggt gccagagcgg tggtcggccg ggctcctgcc | 540 |
| cagtctcggc tcctccctcc tccccaccag aaggaaaaac ttgggccctt cgagaaccct | 600 |
| gtggaatgtt ctttgtaatc aatgtacatc cgcttccacg gcacggcctc gtgcaaaatc | 660 |
| gcgggtttcg gggccttgga gcaaattgcg cttgtcagcg gcgacgtcag gaggacaagg | 720 |
| ggaggggttc gcggctgaaa ctgcagcttc gcagcacaga gccattttag gctgctcccc | 780 |
| acctcgcggg cccatgggaa agccggcccc ggggaggcgc gcccaaacgc aggctggagg | 840 |
| agccacggac gcgtcctggc cggcgtgtcg ccatcgttca gcctcgctgc ccaggtggga | 900 |
| ggggtcacct gccgcggggt ctccaagcca gtgccgcttg ctcccggccc cccccactga | 960 |

```
cagcacggcg tccgagtgac cctgtctagc ctcgttctgc gctcctgcaa accacgttgc    1020
tgcgctaact acaaacctgg ccaacatgtc tttgtaaccc tatcatttaa aaacgcttcc    1080
aggcacctgg ccgctgccag atcaggttcg cgggcccgag gaggtcctcc cacctgcccc    1140
cgccagcccc gggaccgtg cgcggcctcc gtgtggcccc cgcccacgag gtccctcggg     1200
caggaaccgc cgcgcgacct ctgttcagcg gccgcgtcct ggccacgggc gaccctgtc     1260 gggaaccctg ttcccggcta agtgcgttcc cgcattccgg tggctctcac ccagctcgc    1320 gttt                                                                1324

<210> SEQ ID NO 113
<211> LENGTH: 337
<212> TYPE: DNA
<213> ORGANISM: Homo sapiens

<400> SEQUENCE: 113
tacagttgat acccaccatc cccatcatcg ctattagaat tggggtcaat acccatcatc      60
actgttagac ttgaggccga tacccgtcat cactgttaga ctcggggtcg atatcatcat    120
cactgttgac tcggggtcaa taccttcat cactgttaga ctcggggtcg atacccgtca    180
ccactgttag actcggggtc gatacccgtc atcactgtta gactcgggt cgatacccgt    240 catcactgtt agactcgggg tcgatacccg tcatcactgt tagacttggg gtgataccca    300
tcatcgctct tagactcggg gttgatactc gtcatcg                             337

<210> SEQ ID NO 114
<211> LENGTH: 592
<212> TYPE: DNA
<213> ORGANISM: Homo sapiens

<400> SEQUENCE: 114
caacatctgt catcgctgtt agatttcggg tcaatatcca tcatcgctgt tagactcggg     60
gccgacatcc gtcatcgctg ttagactcgg ggtcgacacc catcatcgcc gttggactcg    120
gggctgaacc cgtcatcgct gttagatgcg gggtcgatat ccatcatcgc tgttaaattt    180
ggggtcgata tccgtcatga ctgttagatt tggggtcgat attcctcatg actgttagac    240
tcggggctga tatctgtcat gactgttaga ctcggggccg atatctgtca tcctgttaga    300
ctcgggtcaa tacccgtcat cactgttaca ctcggggccg ataccgtca ccgctgttgg     360 actcgggtcg atacccgtca ccgctgttgg actcgggttg atacccgtca ccgctgttgg    420
actcgggtcg atacccgtca ccgctgttgg actcgggcga tacccgtcat cgctgttgga    480
ctcgggtcga tacccgtcat cgctgttgga ctccggtcga tatccgtcat cagtgttggg    540
ctcaggtcga tacccgtcat cagtgttgga ctcgggtcga tacccatcat cg            592

<210> SEQ ID NO 115
<211> LENGTH: 780
<212> TYPE: DNA
<213> ORGANISM: Homo sapiens

<400> SEQUENCE: 115
cgacagcttc acagtaggat tattgtgata aaaatgactc aagcgatgca aaagtttca      60 tctgttccca gaatccgagg gagaactgag gtgatcgtta gagcatagcg acatcacgtg    120
cggtttctaa tgtccctggt ggcggatacg ccgagtcctc ggaaggacat ctggacacca    180 cttcagcca cctccttgca ggggcgacat ccgccaaagt catcctttat tccgagtaat     240
```

```
aactttaatt cctttctaac atttacacgg caaacaggaa tgcagtaaac gtcacgtccg      300
tcccacggct gggctgccgt tccgtttcct ccacgaacgg gtacgcgctt ccatgagaaa      360
ggatatttgg caattttata ttccacagtc aggtgggtct gcgatagctc atttaatgtt      420
aaacgccatc aggggcctct cctcccgttt ctgccagggc ttttcttgtc ttctccttgg      480
tcatcatcat catcgtcttc ctcttcctcg tgggcagatc ttctctggtg ggggctggct      540
gctggctccg aggggcatc cgcagtccgt ctggtcgtct cctcctgcag ctgggcagc       600 tggccaccac ttctccgact cgcccctcca acaagcatcg cagggcactg tcctcggggg      660
tacagaccgt ggtcccacat tcgctaccac tctgttccac gtcatccagg tacacgagct      720
gcgtgtaggc cgtgctgtct ggggctcgag gctctttctg ctggtgctct tggacgggcg      780

<210> SEQ ID NO 116
<211> LENGTH: 1324
<212> TYPE: DNA
<213> ORGANISM: Homo sapiens

<400> SEQUENCE: 116
cgtgaacgcc ctcgcctcgc acctgtggcg cctgccgcgg ggcccgaccg gaggcagtgg       60
ctgtggacaa gggcggcccc ggcgtaggcc aggatttccc cgcagccgga ccggcccagc      120
tccgctcttt cctgggcgaa cagcgcccac ctccggccca gcggcggcg cctccgcccg      180 cggcgcggac agcgagagag aaaccggctc ctccaaacct ggtggaggag cgctgcagag      240
aagcgccggg ctgaggctct gggggccgcg gggcgcgaaa cgccgcgcct acaggttatg      300
cccgggagaa ggagacaggt cgggctccag ccgctgggcg ctcctcacct cgaagcgagg      360
aaaacaccgg gccactgaga tcaggggagg tgcgcccgat acaggtaccc ggcacgcaga      420
cacgcccacc cccaaacacc gagaaacaaa gactgcccga gccacgcacg cctgcgcggc      480
cagcgctggg cgcacacccg cgcccacaca gcccgaaggg cgccacgcaa cccgcaagaa      540
caccagctcc ccgcgctcgc aggctctccg tgccggcccg cagcgcagag cagtcccggc      600
gccgctgcct aggtgggccg ggaaggcgcg ccaccgcgca tggcaccgcg gctgccgagg      660
aacagagggt gccctgcgca gcccagctcg tcccaacccc tccggtgccc actgctgcga      720
cgcctcgcag gccgtgtccc agtgggccct gggcacagcg gtcactcacc ttcctgcaca      780
gcctggatgg gttgttggcc tcgatgacct tgatggagta ggtgatcttc tcgctctgca      840
ggatgtcatc gttgaggctc aggtcggata ccgccaactg gaacaccctg tcgtccttgg      900
ccgcgttctc ctcgaagatg gcacctggag gagagaaggg atcaagaccg gactggacaa      960
gaaccctctc cccgcttccc ttggcccgag ggtcaaggca ctcgcagacc gatgattgcc     1020
gggtggtggg aagtctgaac tgggatttca gcttggcggg gtagattaag gctctccgat     1080
ctccacctgc acaggaatat gttcccctcc ccccaccgcc ctcagcgcac acgtgcacac     1140
agttgacatg agttacacat gcacatccca caggctgcca ccaggtcaca cacgtgtctc     1200
acaaccaagg caccacatgt cctagccatg ctccacacaa gggactaagc caagctgggg     1260 tggcccagg cagcgcccaa atccttgaca tggttccata atcccatcc caggagccag      1320 gaag                                                                  1324

<210> SEQ ID NO 117
<211> LENGTH: 609
<212> TYPE: DNA
<213> ORGANISM: Homo sapiens

<400> SEQUENCE: 117
```

```
cgggggggcgc cgggcgcagg ccgggcatgg ggcctgagct taggccaggt ggaaaggtgg      60
aaggacctag tggggacaga cgaagagacc gaggagccgc ccgcccggct aaatggacac     120
aggaaagcct gagtcaggct tctcataata aataaactgc acgtgaataa ttcagcagtc     180 gcgcggggc cggttgcatc agcgccgccg ccgccgcgcg cgcccaatt ccccgcggag       240 gggagtagcc aattaaggca cttgaaaagg gagtcgggtg gaagatcccc cgccaccagt    300
atcctggatt tacccaggtc gagttcagag agcctcccg gtcccaaccc cctcgggccc     360
catgggtcag ggggccgcct gctgggaagt gctacctcag ctaagccgct caggtgtccc    420
gagactccgg gcaagggaag acaggcggcg agacggacca gaataaggga tgcggacgtc    480
tgacctgtgg aaaacccagc atctgcagtg cccagccgca cagggaacgt gggcggcgtg    540
gttccaagca cagtgaagac gccaggctcg gatctgtgct cagagccggg atccctccgg    600
gctgcttcg                                                            609

<210> SEQ ID NO 118
<211> LENGTH: 298
<212> TYPE: DNA
<213> ORGANISM: Homo sapiens

<400> SEQUENCE: 118
cgtagcgacg acgtggtcct tgtaggacca agcattcttg gcattctgtc gagattgaga      60
ttccagagca tcggatgaac gggacttata gctaaggcgt actcacccac ccctcccttc    120
gtcttttacg cacgcagcaa ctcgtcctca cgtgcatagg ggtagtggac agtgttgact    180
tgaattgctg tccctcgttc caagcctttc ctgtgaatga acccgaaaac actcgacagg    240
tcgtgaataa tcgttttaat gagtgtgcaa agcgtgcgac ggggtgcacc gactgtcg      298

<210> SEQ ID NO 119
<211> LENGTH: 287
<212> TYPE: DNA
<213> ORGANISM: Homo sapiens

<400> SEQUENCE: 119
cgctggcggg ggtaggggt gtgggtgggt acggagtcct ttcactgccc gtcggcagtt      60
ggcaccagag cggaaagtgt gtcccctccc ccgcctctct cccttgggca gtttgatttc    120
ccgccagctc agtcggagtg gcctggaaga gcgggctcaa actccaaagg cagtcgtggg    180
agagtcgtag cggatacgtt tccccctgaca tgcgccgggt gctcgtctct gcccccacc    240 cgcccccaaa acccaaacct gcaagtcgat gttgtccggt gaccccg                  287

<210> SEQ ID NO 120
<211> LENGTH: 1324
<212> TYPE: DNA
<213> ORGANISM: Homo sapiens

<400> SEQUENCE: 120
gtgcctaaag ttacctaacg atacaaaccg gatacaacgc agaggaaaca gaatacccca     60
gccaagcaat ttccatgtca aacatcatcc gcgcggctgc tccatctgtg aacgtgagtg    120
gtcgcctgct ccctcttccg cggcggccgc ttcctcatac cttcacacgg cgcacaccgg    180
ccggcgcgtc cagctgcctg cccagtggcc gaggctcttc cccctcgccc agtcttgagc    240
tggaagtgat tcctattggc caaggtgtcc atgtaaatag gtgtgaaaga aacagagctg    300
gccgggctct ccctttctcgc tcagtcccct ccctctgcag cccccgctcc ccctcctctt   360
```

| | |
|---|---|
| cctcctcctc ccaaggcgat tgtcatatga tagctaagaa gtggcacatt aatgaagcgc | 420 |
| cgctacaggg gtcttttctg ctcctgtcac cgcttaaact atcagatggt tcgagggagg | 480 |
| acatggaggc agccacctag ctcagcggag acgcggagcc cacagcagcg ccctccggag | 540 |
| ccctaacacg tcgctgccac catccgcgcc gggactccgc agccgagctc ggccgcccgc | 600 |
| aggacgctcc aggagcgtcg cgaccgggcg gcacgggacg ctgcggggct gagctcaaga | 660 |
| gcccaggttc gcgccgagtc caaccggacc cggacgctgc gcgcggagtg cgcgtcgagt | 720 |
| gcgcgccgag agagaagcgg cgcgcagcgg cgtcctcccg gatgcggacg cgcaacttga | 780 |
| agcaacttaa ggtgagcagc tctctgttcc gtccctgccc cctattctgg ccccagtacc | 840 |
| gacttacttc ccggctatcc tcgcgccgtt cgccggcttc cctcccgcg cccactaagc | 900 |
| ccgcaaagtt gctggcgaaa gagtccgggc gctggctgat cgagcgccgc agccccaccc | 960 |
| ccgaccccg aagtctgtta ctcggtctgg ctgaccccgc cggtgtctct gtgcatccat | 1020 |
| gctacctttc cctattaccc accccttcc cagatccgag cagtccgccg gcccgcgcgg | 1080 |
| acccagagca agaagagggc gaggaagaag atgcctcgcc cggccgcaac acgtacagcg | 1140 |
| accagaagcc gccctactcg tacatctcgc tgaccgctat ggccatccag agctctcccg | 1200 |
| agaagatgct gccgctgagc gagatctaca agttcatcat ggaccgcttc ccctactaca | 1260 |
| gggagaacac gcagcgctgg caaacagtct gcgccacaac ctctccttca acgactgctt | 1320 |
| catc | 1324 |

<210> SEQ ID NO 121
<211> LENGTH: 1283
<212> TYPE: DNA
<213> ORGANISM: Homo sapiens

<400> SEQUENCE: 121

| | |
|---|---|
| cgacgggaaa acgggggaa ggggggagcc cgacacggca cacacacata cacactcgca | 60 |
| cacacttccg agcgagtgca cactcgcact cccacccgac agccggccag ggacagtcac | 120 |
| ccccaagtca atatcgcagt ttgaattgtt ccggcaaatc tcccctcggg ctcgacggat | 180 |
| gtgcgcccca gatgtgctga cacatgtccg atgcctcgct gccttggagg tctccccgct | 240 |
| cgcgtgtctc ttctcttcgc accagcggcg gaaaccgcac tagcagcggc ggggcggcgg | 300 |
| cggcggcagc agccacctga agccaccaac actgggctct tccagcaaaa acgagacccc | 360 |
| gattcgtctg gcgccccaag aagacataga cgatagcccc ccgccgggct gcgccgtgca | 420 |
| attccgggct cccgggagcg cgtagctcgc tggctaaccc aggcagtccg cggcaagttg | 480 |
| ccctcgaagt ccgccccct caccggggca tggtcggagg gtggctgctg cgctccgggg | 540 |
| cagttcttct cctgcttccg gggggcggg aaggagcaga cacagcagac acacagagaa | 600 |
| agagaggcag ggattattgc ccaaaccgcc agccgccggc agcctccgcc gaccctccct | 660 |
| gctcccagg tccgcgcgca gcctgcagcc tctcagccgg gttccggcag tgcgtccagg | 720 |
| gcgccgaggg gaagggctgg gccccgggga ctggggcgcg gtgggggcac acagactctc | 780 |
| caggtcggcg cgcccttcct gctcctctgc tattttcctg aactcccag aaccccagt | 840 |
| tgcctggctt ccatcgcccg caactagcgc cgctgtcgag atttccgca atacaactgc | 900 |
| aggggtcgtt atttcctcgc ctacggatcc ctacgcttcc caactcagag agaggaggac | 960 |
| aggtgggggc gggaggggga ggaggagaag gaggcttggc caggtgagcg tcctcgccgc | 1020 |
| cgccgggcgt cccagcgtca gctccgcagc ccggcacccg ggggcggagg caggaggccc | 1080 |
| gggcggggag gtgaggctga gcgcggccat gaggaggga ggaggaggct gggtgtcaca | 1140 |

```
gcttcaggcc accttggccg ccgcctcggc cccagtccct ggcagccgcc tccgcactcc    1200
gccccgccct ggctgcctct gttaccctcc aggattttcg agtttctctt cttaaaaaga    1260
acttcgtgct gcgggttcgg cgg                                            1283
```

<210> SEQ ID NO 122
<211> LENGTH: 327
<212> TYPE: DNA
<213> ORGANISM: Homo sapiens

<400> SEQUENCE: 122

```
cgtgggtccg cctaccccaa gcacttttg tgacgtcaca gctccgagga ccatccgggg      60
gctttactct cgcggaagcc caaaagttgg ggtttgacct catgaccttg gccttcccgg    120
ggggcggagg ccctcgggac aggacgcgct gtccccggag tccggagctc aggccagtgg    180
cagtcgaccc agccccgag actccctcac gccgctccaa aaccaaaacg gagcccaaca    240
cgaagctggg tgaagccgta gcttgcagga gccagggaga tgcgctctgc ccggacttcc    300
cgggtcctgt tgagacggaa aggatcg                                        327
```

<210> SEQ ID NO 123
<211> LENGTH: 1324
<212> TYPE: DNA
<213> ORGANISM: Homo sapiens

<400> SEQUENCE: 123

```
cgactcggct gacgttttg acccggccag gaggcaaaga ccaaaacgtc agagcagtag      60
ccctgttact gaggagcgtc ggcagggtcg cgggtagagg gggctggaga atgacttgtc    120
agagctcagg tcgatgtggc gcggggcggc ctcgagagcg ccgggctcct gcgtggccac    180
ggccgccgct gccaaccttc gcggggactt agctttgctt tccattgact cccttttgcaa    240 aagcgcagca gaatcctgac cagccgcacc agccccggcg aacccgagca tgtaatctat    300
ttatatggat tattacggag gaacagcggg cgttgagtca ccaaaacatt tgcttcaaaa    360
gactatttct aagcactttt gcaggcaggc aggctcgctc caggcgcgta aactcggcta    420
cgcattaaga agcggctgct tttcgaatac tgcaaaccca gctaagtccc cggtgccgcg    480
gagagagcag tgaaaagaaa tgtcggaggt gggggtagat cctagtctag acacacacac    540
ttgcgcgcac acacacacac acacacacaa gattcgcgcg gagaaggcac taaaattctg    600
gcattccgag agtacgacaa actacacact tggaagtccc gggtccccg ccttccccgc    660 agcacccccc gccccccac cctaccgtcc gcccttttggc tgcgatcccc tccctctcc    720 tccctccg cctcgtcacc cagcccagtg ccacaatcct cctccctccc caaaatcggg    780
tccaatcgct gcctgccaac cctgggactg ctgtgctgtg attggcgggt ggctctaagg    840
tgaggcggag tatttattaa agagaccctg gctgggagt tggagagccg aaagcggagc    900
tcgaaactga ctggaaactt cagtggcgcg gagactcgcc agtttcaacc ccgaaacttt    960
tctttgcagg aggagaagag aagggggtgca agcgccccca cttttgctct ttttcctccc   1020
ctcctcctcc tctccaattc gcctcccccc acttggagcg ggcagctgtg aactggccac   1080
cccgcgcctt cctaagtgct cgccgcgta gccggccacg cgccagcttc ccggggagcc   1140
gcttgctccg catccgggca gccgagggga gaggagcccg cgcctcgagt ccccgagccg   1200
ccgcggcttc tcgccttttcc cggccaccag ccccctgccc cgggcccgcg tatgaatctc   1260
ctggacccct tcatgaagat gacgacgagc aggagaaggg cctgtccggc gccccagcc   1320
```

```
ccac                                                                  1324

<210> SEQ ID NO 124
<211> LENGTH: 602
<212> TYPE: DNA
<213> ORGANISM: Homo sapiens

<400> SEQUENCE: 124
cgattggggc ctcagcctta gttcttccag ctggaccctg ggatggtgcg gggctgtggc      60
tctgggaagt atcttggcct gcacgcggtt tacatcattg ggagcacagg cctcgccctc     120
cgaactagag gcccagagcc cttcgcgccg agcgtttccc gcctttcccc tgtctcaagt     180
cattgcccag aggccactgc gggccgttcc tgcctgtccg tggagctgcg gccccgtgt     240 tcccagggtg aacgagcacg tgcgaggcgg tggtgcttgt atccgggata acaggtaggg     300
cggctgcatg cttcatagag gccagcctgt gccgaccggg agctgtagga cggtctgtgt     360
ctggggctgc ttatgggtat tcgcgtgcgt ctgccggtgc gcggtccgag cctactcacg     420
agagcgtgtg tgtgtcttct gtctcgtgtt gctatgagtt tgcatctgtg tggctggaat     480
agcttgtttg tgggggcccg cgcgtgacct gtgtgtgcgt tactgtgtgt gtctcaggca     540
ggatagtgac gggccgtgtg actgtgacgc catcatcagg ttggtgagat ggcgtgaccg     600
cg                                                                    602

<210> SEQ ID NO 125
<211> LENGTH: 599
<212> TYPE: DNA
<213> ORGANISM: Homo sapiens

<400> SEQUENCE: 125
cagcagaccc cttttaagt acgcatgtga taagcaatga acacgaactg cccagagcag      60
tctccaacac tgacacgatt cgcttcccca ccacgacgcc ctagcgctac tgtgcaacga     120
agacctccaa gcactggttc caatgcggag accatgggct cccagactct ggaactcca     180 acacgactgc gaaacgaact ccgagcgagg actccccgag agctccccgc aacacggacc     240
tcacgcgcta gcgaacaaca gaaaaaaaaa agcgcgctct ccctgcccct gaacattccc     300
agaagcccac gcagaccaga ccgatgacct gtctccactg ctggaggcga gtcagggacc     360
cgaagtctct aaacactcgc ctctacccgc cgccccgcga accccacaca ctgcagacgc     420
gacactcgca agtttcgggg atggcggccg gcgagggcat actgcgtctt tccggagaca     480
cggaatacgg caccagccgt cccttttatga tgcaatatgt ctgcgcccag gggacgcttg     540
ctgggagcag ccattttcaa ccctactgcc gtagagcagg cggagtccct cttttcgcg     599

<210> SEQ ID NO 126
<211> LENGTH: 1324
<212> TYPE: DNA
<213> ORGANISM: Homo sapiens

<400> SEQUENCE: 126
cgaggaggct gcagggacgc gcatggaaga gccggtgcgt gggagggttt gcggggggga      60
catcgcgccc cctaggggtg accccagtgg gtccgtgtg ctctccgcgg agccggcgga     120
gccttgtctc tgcacccggc gcgcagcggc cccttaaaca gtggaaccgt gaggccgctc     180
taagccgaag ggctggaatc tgggtttctc gggttttatt ttagaccatt cggcaccaag     240
cccgagctcc cccgccgcac cgcttccagt ccccttttctt tccatagagc gaccgaagcc     300
ggcggtggcg cagggagccg agtctgatga gctcgcgggc ggctgaaggc cggcttccct     360
```

```
gtggggaacg cgccacctgt cggcgccagt gagaactgcg tctgtgtggc gccctcgggg      420
tattcggggc tgcggggaga tgtgtgcctg aagcccctcgc ttgcggtggg gacgtccggc      480
ctctttcctg gcaattgacc cctgaggcgg gagagacaac ggaattccca caaagggatc      540
cttctcggga tctccccacc tcaagacagc taaagctgga ggaaaagccc ctccgggggg      600 tgggggggtgc gggtttgccc tggattccga aagcagaaaa tacccgagcc acacagggac      660
gggcgccgcg ttggtagtcg gggctacgtt cctactccct ctacctcccc cgcgctgtgt      720
gaccctgggc ggaaccccgc tgctctctgg gcctcagtgt tcttattcgt aaactgaggg      780
cgttggagag attggtcctc tcccaactct gaccttgaaa ctgatactga atctgagcag      840
cgtctgtaga cacctgtgcc ttgccttcta tttctagcct tgaataaatc ctggactttt      900
atgtgccatt tatatcctaa tctcatatat atttaatgta taactgctgc catattgttt      960
tctcaattgt ctaggttttc atttggatgg ggttaggatg gtccaaatta tcccgataag     1020
tgcccattaa cttaaacctt tttaaaaaat gaaaccagta aaacttcatt cacttttgcag     1080 tgtggacact gctggagagc acccatgtcg tgggtccgcg aggacacaag gagggggctta     1140 gagacatgcg ggaggcttag atgagaagac agcacccggg cagcggtcag tgttagagag     1200
aggacccgta agaagggccg aggctagagg gagagcgaag actgagccaa cgacgcacct     1260
gagccctggg gtgggggtgg agcgtggctc ctaacccaaa tctccctgcc aggcagtgtc     1320
cgac                                                                 1324

<210> SEQ ID NO 127
<211> LENGTH: 1324
<212> TYPE: DNA
<213> ORGANISM: Homo sapiens

<400> SEQUENCE: 127
accatgagct tccagttcct acgggtgaga aaagaggtgt ctgtgtggag ggcaggtgcg       60
accccggggg ctagcagaga ggagaggctg cgggaggact cgctgcgaag ggcgaggggt      120
ggcgctggtg ggacgggcgc ctggggccgt gcagggtggc tcctgggtgc tgcccgggct      180
gcctgtcgcc cagtactggc gcaggaagac gggtccgcgc agcgtctggc aacagtggcc      240
tgctccacgc ctggaggcga ccaagttctg agttaaaggc gccgggctta gcgggaagtg      300 tatgcgacc cagaacacgg agcggagaag gcctcagggg cacacgaggct accgccttag      360 tcctcgggcc tgcgctccga gcggttaggg tgcgtacgga tgggctccgg gatgttagtg      420
gagaggtgac aggagtctac catcccacgg ccaagcggtg aggcctccgg cgggcggggg      480 tccccccccgg ggcagggcag ggggagagtc aggcatgtct ctaacgggct ccctagtaga      540
accgctagga aagtggcctt caaccctagg cacctttgtg gctttcaggt agttgggcga      600
ctaaaaattc acttttgcct gcgtgaaatg ggacaggtgg ttgtcaggtt agagactgtg      660
cccacgaagt ctcgtttggc gggccgggac tgacgtggac ccgggccctc ctcggaagct      720
tgggaacctg tgagcccctc agctcctcgc ctcactttgc ctgtttgaaa aaaggagttg      780
tttgagagaa gagttaaggc tcaaaaggtt ctaaacgaag agcatgcggc ctgacgcgga      840
gcgcaaagaa gcgagcagtg aactgaatct ggtgggactg agaccagagg cgtctgtatg      900
cggcggccgc ttcgcgccct attaaagcaa tctgttattt acgataatca ttttgtaatt      960
attttggagt ggctgtgact tgatgtctgt ggtgccccag ggcatgccct tactggacat     1020
agatacttca gggtgcccctt tgacgccagt gtcggtccag tgggtgccag tgccgcgaag     1080
```

| | |
|---|---:|
| ggagggtggc gggcgtgaat gcccctcct cctgggttgc cgcaggcccc ggccttttcca | 1140 |
| ccttgcttga tcctggcggg tctgccactt actgaggtcc ctaccggcgc tcacgttgtc | 1200 |
| ccgagaggcg ggacaaacgt ccggcgcgtg gcgcggagtc tgcgaaagcg ctcggggggcc | 1260 |
| tccatcttct gctcgggagt ccctccctgg ggcgggaaga ggagtcgcag atctgcccga | 1320 |
| atct | 1324 |

<210> SEQ ID NO 128
<211> LENGTH: 530
<212> TYPE: DNA
<213> ORGANISM: Homo sapiens

<400> SEQUENCE: 128

| | |
|---|---:|
| gagtgcgtaa agggaaattt ttgcattggt ggatttattg aaagcatgga aacagtcttc | 60 |
| gggggtaggt gtaggggggtg caacagcgag acttccccac aacacctcca ccgaaggctg | 120 |
| ggtcgtcgcg tttgagggac cctcccgcca ccccgcagcc tggcggggcg ctttccaaat | 180 |
| cgtcgcggca ggctctggcc gggcagggcg agatgtgcgc atgcgcggcc tgtgcccga | 240 |
| ggttccacgt gctgatgaat atgcatgaga ctcccccgcc ctcgcgggct aggagagaac | 300 |
| caagcagagg ctccggcctg tgaaagtcgc tggctaggcc cccaaaatag tgcggcgggg | 360 |
| tagctgcacg tgtttgtttt caaaccgcgc tggtttaagt gagttcacac tgcggagccg | 420 |
| acagcagagg gtagagcaac ctggggctgc tgccattgaa cggcgagttg agcgggcctg | 480 |
| tcagggcctc tccgccgagg gccggggggct gcatggtgct cgagccccag | 530 |

<210> SEQ ID NO 129
<211> LENGTH: 1273
<212> TYPE: DNA
<213> ORGANISM: Homo sapiens

<400> SEQUENCE: 129

| | |
|---|---:|
| cgcgttgccc ctgcgcctcc ggaaggggca ctcacagctg gtcaagcgcg tccttcggaa | 60 |
| ctcggggagg ctccgttggg gcttacacag agctaagccc tgggccaggg aggatggatg | 120 |
| caagtacgtg catgtgcaaa cgtgttcgca gatacccgca gcggtgcaca ctcgggcccc | 180 |
| tcgtgtgcac gggccctgcc caccaccccg cccgcgttcg ccgccgcccc actgtcctca | 240 |
| tcccgcgggc tgaccccagg attggcagaa atcagtggtc taatctagca tgtgggtaaa | 300 |
| gggatcgatc tccaattgcc aaaaaaaaaa tagaaaatag ccggtgttcc cagccgctgc | 360 |
| gtggcacttg gccgcacaag gcgcagggat atcagaggcg cttttgcagcg cttggcggtg | 420 |
| ctgtgtgccg gatgccccag agcccggcgt taggatgcgg gcttgtagga agcggctcaa | 480 |
| atcaactcct cagtcactga tgaacgcgct cacggctcga agctaggtcc tcgagtgagt | 540 |
| taatctactt ggtaagtatt tgtgaatat gtattttggg aggaaagaag cacgtcgaac | 600 |
| gcgtctgccc gtctgtaagc gcgtcatccc cacatccttt agcgtgaatt cctccgcttt | 660 |
| ttaggagtca cctccacccc ctactccgta tgcttcgcgc cttttcctcac ggcccccgtca | 720 |
| gaccccctca cctttagatt gacacatgcc atataatact cacttttaaa atgccctgcc | 780 |
| agtctctcta gggtcccctta attaggtaac ccttgccaat tagtgggccc tgcgctactt | 840 |
| tttcccttct cgatgattta tttccatgat gcgtattagg gaaaatacct taaggaaaa | 900 |
| agaatgttag catcattgga aatcccgctc ctaggagagg atatcgcagc tgtgctatta | 960 |
| tgttttcgca tttgctgatg caaacagggg aactctctcta ttcctccccc attacctgcg | 1020 |
| gctggggact gggaactttc cgcggcattg tccccagcca gcgcctcggg acctgcgggg | 1080 |

```
ctgttctcgc tctcacactc acactcaccc cggccgccgg gcgagagttc tgtcccgccc    1140
cgcccggctg ccgcgtgacg tgtctgtttg gcggccagtt tggccaatca tcggcagctc    1200
ggtgggtggt gctcctgggc gattggttgg cagaatgagg gcgctgcgca aaaacggaga    1260
agccgagcgc tcg                                                       1273

<210> SEQ ID NO 130
<211> LENGTH: 1324
<212> TYPE: DNA
<213> ORGANISM: Homo sapiens

<400> SEQUENCE: 130
cggagccaga cctgacggtg gaaatctctg agagcgccac gccaggcact cgcttcccct      60
tggagagcgc attcgaccca gacgtgggca ccaactcctt gcgcgactac gagatcaccc     120
ccaacagtac ttctccctgg acgtgcagac ccaggggat ggcaaccgat tcgctgagct      180
ggtgctggag aagccactgg accgagagca gcaagcggtg caccgctacg tgctgaccgc     240
ggtggacgga ggaggtgggg gaggagtagg agaaggaggg ggaggtggcg gggagcaggc     300
ctgccccccc agcagcagcg caccggcacg gccctactca ccatccgagt gctggactcc     360
aatgacaatg tgcccgcttt cgaccaaccc gtctacactg tgtccctacc agagaactct     420
cccccaggca ctctcgtgat ccagctcaac gccaccgccc ggacgagggc cagaacggtg     480
aggtcgtgta ctccttcagc agccacattt cgccccgggc gcgggagctt ttcggactct     540
cgccgcgcac tggcagactg gaggtaagcg gcgagttgga ctatgaagag agcccagtgt     600
accaagtgta cgtgcaagcc aagacctggg ccccaacgcc gtgcctgcgc actgcaaggt     660
gctagtgcga gtactggatg ctaatgacaa cgcgccagag atcagcttca gcaccgtgaa     720
ggaagcggtg agtgagggcg cggcgcccgg cactgtggtg gccttttca gcgtgactga     780 ccgcgaccag aggagaatgg gcaggtgcag tgcgagctac tgggagacgt gcctttccgc     840
ctcaagtctt cctttaagaa ttactacacc atcgttaccg aagccccct ggaccgagag      900 gcggggact cctacaccct gactgtagtg gctcggacc ggggcgagcc tggctctcca       960
ccagtaagtc gatccaggta caagtgtcgg atgtgaacga caacgcgccg cgtttcagcc    1020
agccggtcta cgacgtgtat gtgactgaaa acaacgtgcc tggcgcctac atctacgcgg    1080
tgagcgccac cgaccgggat gagggcgcca acgcccactt gcctactcta tcctcgagtg    1140
ccagatccag ggcatgagcg tcttcaccta cgtttctatc aactctgaga acggctactt    1200
gtacgccctg cgctccttcg actatgagca gctgaaggac ttcagttttc aggtggaagc    1260
ccgggacgct ggcagccccc agcgctggct ggtaacgcca ctgtcaacat cctcatagtg    1320
gatc                                                                1324

<210> SEQ ID NO 131
<211> LENGTH: 1324
<212> TYPE: DNA
<213> ORGANISM: Homo sapiens

<400> SEQUENCE: 131
cgagagaagg tgagctcggc gggcgcagcg ggttgggtgg gtgtggcccg cggctccggg      60
aacagaccca aggccccgcc accgccggct agcagcccga cagcccgccc gcctggcgag     120
cgcaggcctt cttccagaaa ctgcgaggat ccgagcgtac tgtttgtgca ccacaaggtc     180
aagtcgggaa gtggagccgg aggaggaggg gcgaggaggc gaagggtggg gagaggggcg     240
```

| | | | | |
|---|---|---|---|---|
| ccccgcttcc | tcgccatgtg | ccagcctttg | gaagttaccc | ctcggttttt | aactttcggg | 300 |
| gtaatgggaa | ggaagagcaa | ggaggaaggg | gtcgccccgg | ggcaaaatcc | tgctggggcc | 360 |
| aggatgtgca | accacccacc | cacccgctca | tcactgcctt | ctccaccccc | cggaaatgcg | 420 |
| gggcagcgct | aggcgccagg | aggcacccgg | gaggggagg | gggcgacgag | cccaatgggg | 480 |
| accctctcta | cggaccgccc | ctcttttctt | gaggtcgcct | acaatttcaa | gttccccgc | 540 |
| ccggaatgtt | agttttccat | ttggagtggg | tgcggggagg | agggccgcgc | ccctccca | 600 |
| agactcgcgt | tcgcccctcc | acccctcct | gccagcactt | tctgctcact | tctggtgctg | 660 |
| caaaacgcca | cgcaatttat | tcgattcgca | ttttaaaacc | agcgattcag | aagcagggcc | 720 |
| tagggcgagg | gtcttccagc | gctggagccc | cgggggcgg | ggtgctcagt | gcaaacctcg | 780 |
| ttccctcgcg | agtgtcgcct | ccaggctgtt | atttgcaaag | aaacgtcttt | ttgacgcagg | 840 |
| gagaaatggc | aaattttaag | tacgtcatta | atatggcgcc | aaaagatttt | tttaagtata | 900 |
| agctcgcttt | ttttttttt | taaggttgcg | ggggcgccg | cccgggtctg | ggcgcgtagg | 960 |
| gggcggggtg | tgagcagaaa | gtgtgagtga | aagagtggag | gggcggggta | tgtgtgtgag | 1020 |
| tgtgtgaagt | gtgagcagac | ctgatgggac | ttgcacgggc | gcagccgccg | ctcgggcccg | 1080 |
| gccctgggga | cagggcgggc | tagggcgcc | ccagagtcat | ggggagtccg | ggcccagggt | 1140 |
| gccagcaggc | gtggtggtgg | ggctgcgagg | gagggcaccc | ttcccccacg | gggcccgcaa | 1200 |
| cgctacctgg | actcccgcc | ggagccaaac | aactgggcgg | ggggttgggg | gggcggcgac | 1260 |
| gggggtgtcg | ggagcggaga | tcgagtgaat | aagaaaaaag | tggctactcc | ccctccctcg | 1320 |
| ctcc | | | | | 1324 |

<210> SEQ ID NO 132
<211> LENGTH: 762
<212> TYPE: DNA
<213> ORGANISM: Homo sapiens

<400> SEQUENCE: 132

| | | | | | |
|---|---|---|---|---|---|
| atccctattc | cttctccttc | ctctcccttg | gtaacggcac | tcctagggct | gtggagggtg | 60 |
| cggttcactc | ctgggactgt | ggagggtgcg | gatcactccc | gggactgtgg | agggtgcgga | 120 |
| tcgctccggg | gctgtggagg | gtgcggatcg | ctccggggc | tgtggagggt | gcggatcgct | 180 |
| cccggggctg | tggagggtgc | ggatcgctcc | cggactgtg | agggtgcgg | ttcactcccg | 240 |
| ggactgtgga | gggtgcggat | cgctcccggg | actgtggagg | gtgcggatcg | ctccggggct | 300 |
| gtggagggtg | cggttctctc | ccgggctgt | ggagggtgcg | gttcactccc | ggggctgtgg | 360 |
| agggtgcggt | tcactcccgg | ggctgtggag | ggtgcggttc | actcccggga | ctgtggaggg | 420 |
| tgcggatcgc | tcctgggct | gtggagggtg | cggttcatcc | cggactgtg | gagggtgcgg | 480 |
| atcgctcccg | ggactgtgga | gggtgcggat | cgctcccggg | gctgtggagg | gtgcggttct | 540 |
| ctcccggggc | tgtggagggt | gcggttcact | cccggggctg | tggagggtgc | ggttcactcc | 600 |
| cgggactgtg | gagggtgcgg | atgctcctgg | ggctgtggag | ggtgcggttc | actcccggga | 660 |
| ctgtggaggg | tgcggatcgc | tcctgggct | gtggagggtg | cggatcgctc | caggtgtgat | 720 |
| tttcatggga | atggaactgg | ctccctaggt | ggtgttcatt | tc | | 762 |

<210> SEQ ID NO 133
<211> LENGTH: 270
<212> TYPE: DNA
<213> ORGANISM: Homo sapiens

<400> SEQUENCE: 133

```
cgaacgccgg gggagggacg gtgggagggg tgcggtgagc gagggctgc cctgcatgta      60 aacagcctcg gggtcccaga cgagacaagt gggaccgctc aagcctgcag aaccccggt     120 ctcggtccag gcacaagagc ctcccgtagc cccgcctgat ctttctcagt ctttaggttc    180
caggacatcc aaaggagcgt aggtaaccga cgtctacgta gtatttctgt ccccggaaga    240
ctggatctca gggaattatt atggaagata                                     270
```

<210> SEQ ID NO 134
<211> LENGTH: 876
<212> TYPE: DNA
<213> ORGANISM: Homo sapiens

<400> SEQUENCE: 134

```
cggggcaagg gcgcgttccc tatcgcagga tcacttgcta tggtaagccg cccaccctgc     60
gcgctcctcc gcgcggggaa gaacctgcgc ggcaggacgt ggtgttggag ttggggcgcc    120
cggagcggga gtggggagac ctgatgcaga gagtctggag tcggagctgg gggtgctgca    180
ggtaggagca ggagcggggc ggagagggag gcccgaagaa gaccccacac aggttggcgc    240
agcggggctt gggaggctt cagcccagaa gtggagaggg ttgacagacg ccgcctgatt     300
agaaaaagcc gggagcttgg gaaggagacg ggattgaaga agccacccgg cagggaggcc    360
gaacggccca gagctctccg ggtaaaaccc gcctgcggtg atctgggaag tgtgtctcca    420
cctagccctg cgagcagcgg ccttcctccc gcccgttgaa gggcgctgtg ctggagtacg    480
aacccggccc agagaagcca ctcgcccttc tttgtcactt aaaaccctgt cccgacgcgg    540
atctcacgtc tagacctctg tctttaaagc ggatgtgagg cgcgttctaa ccgttccta    600 accattgtgt caccgcgaaa ggcgggctg tgtggaaccg tcccgcacgt gtgcgatgaa     660
tctggctccg ctgagaacgg atccgtgggc tgtctggcgc gggctgggc agcagccgag    720 agttagtcta cagagctagg gcccgagggt ggacctgcgt ccgcgtctcg tcacgaaagg    780
aagctctttt ggagaggcaa aacgtggtcg cccagatccg gcgcagctgt agccgtgggc    840
gctgtgcagt gacagccaca cccgccacct gtcacg                              876
```

<210> SEQ ID NO 135
<211> LENGTH: 309
<212> TYPE: DNA
<213> ORGANISM: Homo sapiens

<400> SEQUENCE: 135

```
tttctcatca ggatacagtt ccagcgtcgc acaaacccga aggaggagta ccaagagatg     60
aaaaacaggc agcccacgcc ggccatgccg gtgactgctc tcgcggagac agagaagaaa    120
ccgcaggctg gccggcagcc agggtgagaa tccccagcgc caggaactgg gtgtaacccc    180
agagctgcgc cctcagggcg gcgtccactt cggggggcct gcctgggtca cagtcgtttg    240
tgagcgtgaa gggcatgccg tagaaatagt caaatccgtg gttcaggggg tgtggcagtg    300
atccccgcg                                                            309
```

<210> SEQ ID NO 136
<211> LENGTH: 1209
<212> TYPE: DNA
<213> ORGANISM: Homo sapiens

<400> SEQUENCE: 136

```
aaaaaagaaa tgagtatcag agtcttatca tcattacagt tcttatggtt tttaaccgac     60
```

```
ctttaggagt tccaccgacg tgacccaagc agctggtagg agaatctggg ctggattcgg      120
aaggcgcgct acaggacgcc cgctgccccg gatcggaagg cgcagcacct caggccacaa      180
tctcagacac gccctcgggt cccgacaggt gttgcccgcc tcccacgggg ctccgggacc      240
ccggtccccg ggctgccccc tgccttctgg ggcgctggag cgcgcgcagt ggcggagctg      300
agccacccag tgcttcgcac gggcgcgctc cgcttctccg ggttttagcg gaagcctgcg      360
gggggcgggg taaccgcgga agccggcggc cgtgggcgcg cgggttgggg gctctcgcgc      420
cgctccgggc tctcccccccc cccggctgcg gttgccgaag agaggccgga ggcggcgccc      480
ggctgctcca cctggcgcgc tgagcaccgc gcggggagcc cccggggggcg ggcggtgggg      540 ggcgcggact gcgggaagaa ggcacgaggc gtcgccgcag ctcggtcagg ggccggggcc      600
ccgccgctcg ccgctgcact aacttgccgc ttggtctcgc ctcccgccgc ggctcgctgc      660
gctttgggtg gcggggggcg gggagagcgg ggagtcagag ggtctgcggt ggccgaggga      720
gggaccctac gacggggagc ccgcccggtg ccgctcttct tcccctcccc gcccctccgc      780
tccccccacc ccgtcccttc cgccgattcc gggaggacgg gcgcccgtga cctgcgaacg      840
ctgccaagtg acggtccccg agtctgaagc gcccgcgagg aagcgagcgc cagcgcgggc      900
cgccggcgat gacggccgcg aagcaggagc cgcagcccac ccgggggggcc agggcgagcc      960 aggcgcagcc ggcggaccag gtgagagcgg cagccgcggc caggccctcc cgggaggggt     1020
ggctccagtg cgcgctccgc ccgcctcccg cttcccaggc tgggctcccg cgcctccctc     1080 ttctcacccct ccccgcccc gccccagttc caggctctcc tgcttctcca cggactctgc     1140
gggaagttag agcctctgct gcgctccggg gcccggcgag aggatgcgca aggtggagag     1200
ccgcggggga                                                            1209

<210> SEQ ID NO 137
<211> LENGTH: 327
<212> TYPE: DNA
<213> ORGANISM: Homo sapiens

<400> SEQUENCE: 137
aaaattggtg catttaggaa ggaaatgcta taaacgccta attccttctc gttctttggg       60
gttgctgagc tgacctcgcc gcgaggggag agggggaaaa aaacgcgcac taatgattct      120
gtttattagt tatatatgta tatattccgt gttcgcttgt acaggaggat ttacatggct      180
gtataaagat ggctaggggc gccgcgctct tctgggcgcg tcacggtgac aggctggggt      240
taaaactggc tgccccagga gaagcggagg cctggaatta aatacgtttc ggcgcactga      300
tttaaataag tttcctgaat atacaaa                                          327

<210> SEQ ID NO 138
<211> LENGTH: 629
<212> TYPE: DNA
<213> ORGANISM: Homo sapiens

<400> SEQUENCE: 138
agagcttccc cctacaccag gcacaacccg attctaaaga aatgctgcgc ccgcgcctgc       60
agatttcgcc ttctctctcc agatccctct ttgccttcct gccagccagc cgcgacccga      120
gtcctgagtg aggtgagaag agaaggcctc gcctggcacg ttacctttttt ggtgaaagcc     180 tttgccgcaa aattcgcaga cgaagggctt gtagcccgcg tggatgcgga tatgcgtgtt      240
gagcgtggag ctgcggttga acgctttgcc gcactggttg catttatgtg cttttcctta     300
ggaaaggggc gagtgcacag taaggagagg ccacctcggg aacacctgga agggacatcc      360
```

```
ccccaccc cactcaaccc tagagggtaa gggataatct ttggccatcg tatcccggt      420 gttatcacta agattctggg ggttgcgcgc gggctaggcc cgacccgggg gcacgtacct    480
gggtgtggat aattttgtgc ctgcagagcg tgctggcctg gcgaaagcct ttgccgcaga   540 cttgcacac gaacggtctg gctccggtgt ggaccggcat gtggcgggtg agattatagt    600
gagcgttaaa cacctatgga aagacatgg                                     629
```

<210> SEQ ID NO 139
<211> LENGTH: 385
<212> TYPE: DNA
<213> ORGANISM: Homo sapiens

<400> SEQUENCE: 139

```
atcttttgct gctgaaatgc agatggtttg gacacttcat aaagagggca ttaataagcc    60
cgccgagtga gcgccagggc gggattctcc cacaaattca aggtctgtat ctccgcggaa   120
gccgtgctat cggtccccg agtgctgaag gctcccacga ggggcaggcc agcccggtgc    180
gccagggaag gagcttgatg gtgtgtacgg ctacgtagtg aacgtggagg tgtgcgcagc   240
ggagtcagag gggctagatc cccagcattt cccacgggt cccacctagc gcgtggatgg     300
agcaacttca tcactccacc gagggcaggg aaagaggagt aagcattgga gctcaaagaa    360
tgagcaattt ttcaaagctt tctcc                                        385
```

<210> SEQ ID NO 140
<211> LENGTH: 1209
<212> TYPE: DNA
<213> ORGANISM: Homo sapiens

<400> SEQUENCE: 140

```
cgggtggttg aaggcgtagt ggtgttccgg cttcaggtgg gcctcaggcg gcaggcccgg    60
gtggtggggc gggcccagca ggtgggccgc ggcctgctgc tgctgcccgg gagagggcgc   120
cggctctggg ggctcagcgc cgcagccggc gtccccttca gctctcccag gccccctcgc   180
ttgtgctcct ggcacgggga ggcgctcgag tgaggcgact cggtgcccgc cggagtctcg   240
gaggccggcc cggcggcctc cccgagttga gcctgtgagg cctgggctcc ggcggccgct   300
tcttgccgct gccggcggcg cctgcggcct ccttcagcgc cagctgcttc tcgcacttga   360
agcgcttctg gcgcgcagg tagcagccgt tctcgaacat gttgcccgag tcagggtgca    420
gggtccagaa ggagcccttg ccgggcttgt cgggcgagcg gggcaccttc agaaacagtc   480
gttgaaggag agcgagtggc ggatggagtt ctgccagccg tgctggttct gccggtagaa   540 gggggaagagg tccatgatcc actggtagat ctcgctcagc gtcagcatct tgttggggct   600
ctgctggatg gccatggtga tgagcgagat gtacgagtag ggcgctttgc gtgcgtgtag   660
ctgcgcctgt aggtcttggg gtcgcgggcg cggctcaggc ccgcctgccc gtacatgggg   720
ctcatggagt tcatgttggc gtaggggcc aggccgccca tggccccggc cgcctgcccc    780
ccgagcgggc tcaggctggg actcaagtgc ggcccatgcc cgccacgccg gccgcccgg    840 ccgagccgcc catgcccgcc atggcgcccg cgccggggga catccccgcc agggacgggc   900
tcatgccagc gcccacgtac gacgacatgt tcatggagcc cgcgctcatg ttgcccgagc    960
cgctgcccat ggcggccgcc gacatgccat gtacgtgttc atgccgttca tccccaggcc   1020
ggcgttcatg ttgctcacgg aggagtagcc ctgcggacag agcccgggga gggaggcgac    1080
agcgttagca ccgcggctgg agggtgccca gacctcccac ccaccgccca ggcctccgcg   1140
```

```
tccggggagg cctccggggg cccttcgtc cccgatggcc cagtctccgg actccgagtc    1200
tgtttcatt                                                          1209
```

<210> SEQ ID NO 141
<211> LENGTH: 1209
<212> TYPE: DNA
<213> ORGANISM: Homo sapiens

<400> SEQUENCE: 141

```
acagaggact tctcggggtt cccgaattcc cagggttaaa acaaacttgg tttgtgcggc     60
gacaccgcta cccttaccgg tccccagata gtcgcggatc cccgaagcta agagccaggg    120
caggactcag tcagtgttcc aggaacagct gagacaccca ggtcaccacg ggctcgcgcc    180
gctgcggctc cgaccggtg cgaaccgcca tacgcgccgc gcggtgggcc ggaggcagtc    240
cgcgtactgt tgcggaaact ctgtctcaca aggtgcgcaa cactcgccgc gcgcaacacc    300
accaggaagt tgatgtcggc cgggcgcact aggcggtagc tgcacgtcgc gcaatcctgg    360
ctgcattcgg cccgcacggt cgccaggagc ccggggccga gcaacagcag ccaagtgcaa    420
agtgtcagga accgcgccat ggactgcgag gagagaggga cgcgtgcttc ggcctgcctg    480
ggcgcagaac ggggtccctc ggcaggaccc tcgccgcgca agcctcagca ggggatcgtc    540
gagcaaaagc ccgcaggaat gctccttct ggggccccgc cctcccggcc gacagctttt    600
aggtagacgt ggaggcgact cagatcgcct cgcggttccc gggtggcgcg gtcgccccca    660
acgcgaggct gcctggggca cccggctctt ttcctgggcg tccgcggccc agggcaagat    720
tccgagagaa cgccgcaga ccaggggcga gagagcggga gccggggggag gcaggacatt    780 gactggggtc acaaagaaga accagggaac gctgtgggga acccatgcaa tgaaatgtga    840
agggaaagag ggcgggcaga cgtccccaaa cccgctcagc aaagacaagc ttcgggcaaa    900
ttcactcacg ttgacgctgt tcggatggag caggccaatt ggaaaagccg ggttcagaca    960
cgactctaga gggaagagaa gaaggcagtg tgaggagggc gggcgtcggg gagaagcggg   1020
cccgggtgtg ctggcggacg tagggcctca ccgtcgcggt cctcagcgtc tctgcgggt   1080 cacgggccag gctgcggggc tctgagcgcc tgcctcgccg tcccggggct taacggctgc   1140
tggagccact ttataattac cccaaaccga aggaggcgcg cgcgcccaa tcgccggcgg   1200 gctgcagct                                                          1209
```

<210> SEQ ID NO 142
<211> LENGTH: 476
<212> TYPE: DNA
<213> ORGANISM: Homo sapiens

<400> SEQUENCE: 142

```
gatctgctct tcaagaggaa gcctaaagtg gagagtttgt aatcctgaca acgcccagct     60
acctgcgtac cccggactcc aactcccagt ttgcaacgcc aaagggtcta aagggcgaac    120
gggggcgatt gcatcctggg agcaagaatc gcgataggtc tgatggattg tgggaactgt    180
agttccatgt gcgtgcgatg cactctatgg taggatagac ccggggaaga gtcatttgcc    240
ggccaggaag ggatactttt gagagcgtca gtgctgcatg ccgggatttg tagtctgagg    300
cccgcctcgc attctgggcg gggattcatg ctccttttca gggcgcccgc tcctccctt    360 ggtattgccg tcagagatgg gcggttggtt attgctgcct gatggtggat gaagcagtgg    420
aaaagagaat tgtatcgttg tgcttgacac taggggttta gttggaattg tgcttc       476
```

```
<210> SEQ ID NO 143
<211> LENGTH: 679
<212> TYPE: DNA
<213> ORGANISM: Homo sapiens

<400> SEQUENCE: 143
taggattact gcatgttcag ctacgacctc atcaacatgg ctgctggaag tcgtctacag      60
gaaaaagaaa gaaatgacac tgaaggatca cttccgcttc cgttggcgca agcgctttca     120
ttttttcgct accgtgacta agatggaagc gttttgggg tcgcggtccg gactttgggc     180 gggggtccg gccccaggac agttttaccg cattccgtcc actcccgatt ccttcatgga     240
tccggcgtct gcacttttaca gaggtccaat cacgcgacc cagtaagttc tcggcgcttc    300
gtttgcgtag cgggagggac cgtggggcct ggtgctgccg gctggttttg agagcccggg    360
aaggtgaggc ggggacccccg ggggcgcgcg aacggcaggg gagctcaggg cgcggagtcc    420
tggagaatgc agaataattg gaaggaatta tagaaaatca gaagcgcagc tagtgcgcgg    480
aaagagggcg cagtccatcc cccctctcag ctcccaccgt tctcactctt taggaacccc    540
atggtgaccg ggacctcagt cctcggcgtt aagttcgagg gcggagtggt gattgccgca    600
gacatgctgg gatcctacgg ctccttggct cgtttccgca acactctcgc attatgcgag    660
tcaacaacag taccatgct                                                   679

<210> SEQ ID NO 144
<211> LENGTH: 1209
<212> TYPE: DNA
<213> ORGANISM: Homo sapiens

<400> SEQUENCE: 144
tccttagtga caaggtctct gatctcctgc tgccactgca atagcctctc ccatcccgcg      60
gggaacggcc ggagttcttc ccttgatctc tcccgagtcg gcttccgctg gggatggatc     120
gcaggtagcg ccggcgcggc ctggggaaga acagttgcgg agcatctgaa gcggaaaatc    180
caagcagatg tgaggcgatc cgggcccgcc tcgttcctct tggggcctga atttcttcca    240
gataagtttc ctaatggaac atttctaaga ggtggggtac gaggcggctt gctcgcacgg    300
cagtgggaca gactgcgggt ggggacgtac tgagaggtcc ggacctcaat gcgtccgacc    360
cgtctccaca ccgcccttttt ccagccccca gtctcctttc attccctact cttcaggctc     420 cttgggcc agtgggtgaa ccgccattta gaacggtgcc tcggactcgg ggtcgtgcgc       480
tccatctctg cctccccct ggggcccgcg aggctggtcc gggctttctg agctgggcgt     540
tcggctttag gcccaatacc tggaccagga atttcttctc cccgcgccag aagggaaaga    600
cataggaggt gtcccaatct gcggtcaccg ccgatgctcc tgacactcta gtgagcacct    660
gcccggtact tttccattcc aacagagctt ccagcttcat actaactatc ccacatacgg    720
cctgtgggta ttagctctaa gtgtcctttt ccagggcc gaggctcccc ctccagcagg      780
gagagctccg ggacggcccc caccaagggt tgggttcttc cttcacaatt ccacagaggc    840
atccctgtcc ttcctacctg ggaaacctcg aggtgcggtg cccgtgtact tctggtactt    900
tgcgtggtgc catcagggac cccagagcca cagctgcgtg tgtgtgtgga tgtgtgtgtg    960
tgtgtgcgcg cgcgcgcgtg tacggcgaag gatgtgcttc ggggagccga gtacacaacg   1020
tctgcttggg cagctgctgg gcaggcgttg ggcctggagg tatctcacac ccacgtatct    1080
tccagtcttc aaacacggca ttgctctgcc tcccgtagcg cgcttcgaac ctgcctcgcg    1140
gacacgtgaa cagaggctgc cctgggaaga taagtgcgct ttcccgtaaa atccgggaaa   1200
``` tttgccttg                                                          1209

<210> SEQ ID NO 145
<211> LENGTH: 1209
<212> TYPE: DNA
<213> ORGANISM: Homo sapiens

<400> SEQUENCE: 145
aagtactgaa ctgggagcgg cagggtttga gtcaaaagag aagggtggag gagcgcgtcc      60
ggtgccccaa ggcttccagg cggagcgcgg gcgcgaggtg cgggctccgg ggcggagcgc     120
acgcccggag gcgggaagtg ggcagcagcg cccccgcctg gcccctgtgc gccccgaccc     180
gacgcctccc cgcccgacca ggtgcctcga gagcgcacag ctgggagggc tctcccggtc     240
gcggcgagac tcacgcctgc ggtgtgctag ggcggcggcg acggtgacgg gcgtgggggcc    300
ggcgctgcct cggctgccgg gtcgttgcgg cgagcgcgcg ggccggcctg gagtcaccgg     360
gctgaaccgc cgcgcctgca tcgtgccgca cgccgcggag gcgctcgggt acagaccgcg     420
cgggcgcgca caaagcggcc cggggcggcc ggcgcggcgc agaccctcgg tggcagcgca     480
ctccagtctt cccaggctag cggctgcagg gagctccggc ccgcggcccc tccgcctcaa     540
gtctgggagc tgccggtccc actctgtctt tgcctatggg gattcgagag tttcccagcg     600
gcgcacccag gggcaagagc attgccgtgt gagtagcgcc ccggcgtggg tgagcgagcc     660
ggcggggcggg aggccggagc gccggggtag ccctttgcag ctgggacact gggcagtctg     720
aggctcgggg aagggcggcg cgcgcggtgg agctgctcgg gaagtttcag tcattctttc     780
cctcgccact cgccccaacc cgcactgccc cgagagccca ggatagggca ctggggacag     840
ctgcccgggg aagtgggtga gtggcggcgg gaagggagga gcgcgggctc tgccgcggcg     900
ctcgcccccg gagggccccg gccgcgctct tgctctcgcc ctgggatctg ctcctcacga     960
atcccctcct ctctgtccat gctcccctgc ccacccacct gcccgtggcg cctgcgaccg    1020
cagtggcatg aggaggtcac cggacgtcag cccccgagaa ctgtccgaca tcagcccca     1080
gctccggcag ctcaagtact tggtggtgga cgaggcgatt aaggaggatc tgaaatggtc    1140
gcgctccgtg gaggatctcc cagcggggccg gtggggctca cgtccatcga ggagcggatc    1200
ctgcgcatc                                                            1209

<210> SEQ ID NO 146
<211> LENGTH: 475
<212> TYPE: DNA
<213> ORGANISM: Homo sapiens

<400> SEQUENCE: 146
tgcatcacca ccttggtttt gttttatttt gcttcttggt caagaaagga ggggagaacc      60
cagcgcaccc ctcccccccct ttttttaaac gcgtgatgaa gacagaaggc tccggggtga     120
cgaatttgcc gatggcagat gttttggggg aacgccggga ctgagagact ccacgcaggc     180
gaattcccgt ttgggctttt tttttcctcc ctcttttccc cttgcccccct ctgcagccgg     240
aggaggagat gttgagggga ggaggccagc cagtgtgacc ggcgctagga aatgacccgg     300
aaccccgttg gaagcgcagc agcgggagct aggggcgggg gcggaggagg acacgaactg     360
gaagggggtt cacggtcaaa ctgaaatgga tttgcacgtt ggggagctgg cggcggcggc     420
tgctgggcct ccgccttctt ttctacgtga aatcagtgag gtgagacttc cagac           475

<210> SEQ ID NO 147
<211> LENGTH: 551

<212> TYPE: DNA
<213> ORGANISM: Homo sapiens

<400> SEQUENCE: 147

```
ttggggttgt agtctatctg ggtcgtatag gaatactcat tctcgaacag cagcctgggg    60
acgatctgtg tgttggtgtg ggtgtcgaaa gcgtaggaga tgttggcatt ccgctggttg   120
tagctatcac ggcatacagc accccacaga tgacgaagca gttgccgtag aaattcctcc   180
ggagccccgt gcgccatgtg gtctccttct gtgtgctcag gtccgcggca ttgagcttgc   240
tcaggacaat gacctcctgg ctgaagccct catcgtccag ggccgggtag atgagccatg   300
gccattctcg tccacagcaa agtccacgtc tgagtggccc tgccatcgcc aggggggtggc   360
ctcctcgtag gccacgtcat gcagcatggc ccaggcagcc acgtagcgct gcttcaggtc   420
gtacttgatg atgttgcggg tgaaggcgcg attgtagtag aaggcgccat ttataccacg   480
tggcctgtgc cgatccagct gtacgggagc ttgtaggaat tgctccagcg acctgcaggt   540
ggggagaaaa c                                                         551
```

<210> SEQ ID NO 148
<211> LENGTH: 1209
<212> TYPE: DNA
<213> ORGANISM: Homo sapiens

<400> SEQUENCE: 148

```
tcacaggcca gctggaagtg ggcagaaacc ctgtgggtcc cagaccctcc ccaatcggcc    60
gctgctccca cctctcccgc cccaattttt cagcagctcg attcctgcgg atcctacatc   120
cgggaagaag cagacgggcc ctcctcccct ccctcgcctg gcgcgcggcg cctgggttct   180
catcaccacg ggcccagtgc tcaccgtgcg cggggctgta ggagacgcgc gcccgcgcgt   240
gagcggggtt ggcatagtag gggttgccct gcgagtcgag gtgattgaag aagacgtccc   300
ctcgtctgga ggcagcagct gcgcgggttc catgtagttg tgcgccaggc ccgggtggtg   360
tgagtcgggg tgctgcgcat tcagcacggc cgggtgcgcc atccagcgcg gctgctcggg   420
cgccacctcc atggccggcg gcggcggctc agggtctggg tgcagacggc acggccctgc   480
gcgaggaagg gggagtgagg cgtgccgcca gcgcctgaca ccccccaaag tcccaccacg   540
aggtgtcccg cacgccacgg agccccagcc cagatccggc gagaaagagc accagtcccg   600
ggtgggagga aagcccaagg ctcaaaacga aggaaggcg gggaggggt tcagccacgc   660
acactcacgt ggtgacccgc ggctccagaa tcacacaccc gtgcacatgg ggtcacgccc   720
ggggacgggt cccgacacca gtgaccccaa caaacgcaca gagcagcact tcagtcagac   780
actcacactg agccccccccg cccggtagac aaacaatgaa cacagactca aaagttggag   840
acaggcgccc gggcacccag tgtggcactt gatcccagcg acacgcacac cccacactt   900
ggcgccagat acacatactg atctcaaccc cgaaaacatg cacacgcagc ccctgagcg   960
cagtactaag cggcacaatc aggaccttca acaaagcaca ccaaagcagt cgcccgcagc  1020
ctggcccccc gccctaagtc cccccagagt cccctcaaag ctaggagcgc cccaggcccc  1080
cagccggctc tcaaaccccca aacttacaca cgcagccgtg gggaggggag ggactcggcc  1140
tctgagagtg aaggagttcg gcgggagccc cgagggcgac gggcccaggg acagcacgtc  1200
cggaggctg                                                          1209
```

<210> SEQ ID NO 149
<211> LENGTH: 601
<212> TYPE: DNA

<213> ORGANISM: Homo sapiens

<400> SEQUENCE: 149

| | | | | | |
|---|---|---|---|---|---|
| gtctgatctg | tgaagggtag | ggccagcagg | cagcaccaaa | gttcccgtat | gcgcgttttc | 60 |
| agtcttcatt | taggtccgaa | ttcccggcat | ataagaatac | taccgtcgct | tgttttcag | 120 |
| attttggc | tattttcgtt | ggtgtgttgg | tcatgtctgg | tcgcggcaaa | ggcggaaagg | 180 |
| gactgggtaa | aggaggcgct | aagcgtcacc | gtaaggtcct | gcgagataac | atccagggca | 240 |
| ttaccaagcc | tgccatccgg | cgccttgctc | gtcgcggggg | tgtcaagcgc | atttctggtt | 300 |
| catctacgag | gagactcgcg | gggttctgaa | ggtgtttctg | gaaaacgtga | ttcgtgatgc | 360 |
| tgtgacttac | acggagcacg | ccaaacgcaa | gacagtgaca | gcgatggatg | tggtctacgc | 420 |
| gctgaagaga | cagggacgca | ctctttacgg | cttcggcggc | taatgctacc | gttaaacgac | 480 |
| tcagcatctc | gacttcccaa | atcaaaggcc | cttttcaggg | ccgcccacag | ttttccgcaa | 540 |
| aagagctcat | gacttgttag | acgattggtt | ggtctcttta | taagttaatt | gttcctgtca | 600 |
| a | | | | | | 601 |

<210> SEQ ID NO 150
<211> LENGTH: 22
<212> TYPE: DNA
<213> ORGANISM: Artificial
<220> FEATURE:
<223> OTHER INFORMATION: primer

<400> SEQUENCE: 150
gggtttttag aggttagggg aa                                              22

<210> SEQ ID NO 151
<211> LENGTH: 25
<212> TYPE: DNA
<213> ORGANISM: Artificial
<220> FEATURE:
<223> OTHER INFORMATION: primer

<400> SEQUENCE: 151
caactaaata accaaacctc tcctc                                           25

<210> SEQ ID NO 152
<211> LENGTH: 24
<212> TYPE: DNA
<213> ORGANISM: Artificial
<220> FEATURE:
<223> OTHER INFORMATION: probe

<400> SEQUENCE: 152
ggagaggggg gttatgatgt tagg                                            24

<210> SEQ ID NO 153
<211> LENGTH: 20
<212> TYPE: DNA
<213> ORGANISM: Artificial
<220> FEATURE:
<223> OTHER INFORMATION: probe

<400> SEQUENCE: 153
gtttgtttgg ttttagagaa                                                 20

<210> SEQ ID NO 154
<211> LENGTH: 8077
<212> TYPE: DNA
<213> ORGANISM: Homo sapiens

<400> SEQUENCE: 154

```
cgggcaggcc caagctgcga tgtggagaat tcgatgtccg agcgacctcc tcggaggagt      60
gggtcgagtt aaatataacc gcgcgaatgg aatggcgcta aaaataaggc agcagctggc     120
ctgtccacag ccctgtcccg ggaggggcgg gggcccagt ggtcttgggc aggaaggccg     180
cgtccggccc aggggcgaga aggctgcggc gtccgcagcc agggctggaa ggcctgggag     240
gccgcgctct gtgggccccg gggcctccat tcggctgggg tcgcgggcct ggacggggac     300
tgtccagagg catccgaaag ccaggccaac ttgcctggac gtaacaagac ggaagggctg     360
ggcgctgagg tcctgccagc ccggccgcca gagggagctg agcgccagag gaggacaagc     420
cgaacccttc aggaggccgg gcgtctccgg agaccgaagc gccggaggac ccgaggaggt     480
ctgccccgcg cgctgctctg gagactcccg gggcgggtgg cgctcggcct ttccgctccc     540
ttccttccca caagtccctt cccgcgcgcg ccccacggcc ctgcccgccc tcccgcgtca     600
gcgcccaac cgtcaagcca gcaattgaaa cgtttccaaa acgtctatt tatttgctcc     660
caataaatcg atcggcggtg attaaagaat cgatgtggcc tgggtgggcg agtcgcttga     720
ggggagggat tgggggcttt cgcccggcgc ctgcagggag gccgagggcg ggcgcgggcc     780
tgagggaggc gtgtcccgcc cgggccacac ccgaggaccc gacacctggg ctggcaggcc     840
ccggcaggca gcgttccctc cggcggagag gggcgcgcgc ccgccgcctg ctttcctcgg     900
ccctctcgc ctttctcgcg cgccggggag gctgtggccg ccagtggctg cggagctgct     960
cagaggcttt tgttgctcct cggccggctg aatggggatt ttgtaaagcg ggacagataa    1020
aaatgagcag catcatattg tttgacagaa tgatctcgca tgatgaagtg tcggctccga    1080
aggggggtgaa aatggtgaat tcctaaaaac ccagccctgg gctcctcctc gagctgccgg    1140
tagcctggag ggacccagcg gacagccggg cctggccgca tcgctccaaa cggtgtcaga    1200
aagactccgg ctttcaatgc caagtcattt ttaagcccg atcctgtcca ggaccttcct    1260
cctcgtggat gaaaagaaca attttcgaga gaaaggctcg ttttattaa atccgacatg    1320
ctgctgataa ctccatgcta atgtgaaata attaacataa tagccataat taaaagcacg    1380
ctaacaatgc cataaattta tcacacaatt ttactagctt tctgcccta actgctctct    1440
catcgttaat taaacgtgtt gccttttaca gaatggatgt ttatatattt ccaatataaa    1500
taaattcgaa accatcctct ctctcttcct ctttctctcc tcctttcctt ttggtctctc    1560
gccatttaca ggcacgcctt ggcgtggacc ctgagtggca gacatcttga aaataaatga    1620
agttttgaga tgcaaatcca aacaagaaca ttaaaatagc ctctttttt ccaccccgaa    1680
aagatccgga gaggtataca aggggtagt ggtgggtaag agagttgaaa tcccccgct    1740
ttgggaaatg gaagtaatct gggtgggttg gggccttggg taccacctct gcccttccc    1800
accttccttg gtggcggcca tccagacaaa gaggccggta atagtttaac aaatctatga    1860
agattttcaa gaagcagcag actttgattg ttgcgggcgc ggggggtgttg gggagaaagg    1920
agggaattt ttctaatagt cccacccacg ttttgctccc tcttggacaa agagtaacta    1980
ctcttggtgg gggacgcgcc cttcactccg cggaacctgg tcccaactcc ccgtattgta    2040
agaaaagtgc acccgcgcgc gggcatgatg attctatctc acatcgcgcc aacgacttat    2100
tcaagccact ggcactgtct ctgacttaaa agaggagaaa agaggcatat gggttcactt    2160
gggcctggtg aggggtaggt gggcaattcc cgccttccgc actctaaccg tgcccctcct    2220
ccagtgttga ccacctaaga acccaaaatg agctgtaatt aattccctt tctccatcat    2280
```

```
aaatttttct atccatttct tccccccat cccccactg gacgcacaca ctaaatctcc    2340
cctcccctgg agacgtctca atttccttcc tatcgatccg gactccattc ttcttgcctc    2400
ctgttgctag aacctagatc cccactcccc gcaccctca ttcccaccgc gtccaggtgg    2460
ctttcccagc ggggtaccat gtactctgcc cgctccagag gaaccgaagg ggtttcattc    2520
cattctcctt tggttgaaac atttcaaaca tttgagcagg tgaggcagct ggctgccatc    2580 ttcctttta aatctctcct gggaagttcg cttgttgaga ctcaaagagt cactcaaact    2640
cataattgcg tgtgtgtgtc tactcattct ccctctatct ctccaataac cctttgagac    2700
tcagaaactt tttatccaca tacacccttt atcacatttt cttcccccca ctacatgtgt    2760
ctcactttct ctctgtatct gtctcgcttc ttccgtctct gtcctacagc ttggcggtaa    2820
ctgacgacct gtgagctttt agctgcaaac tgcaactacg cggcaaacaa tttatttagc    2880
ccgacatcta gccggtctcc ggcaggaccc tgcaccgcgt cgggatcgga cccttccgct    2940
ggggcggcct cctgcgtcaa ggccagcagg aaccttcctg tcgccctccc cggccgccgc    3000
ttcgcctcct tcccgccccc ggaggttgtg caggcgctat ggtccgcctg gagggagaaa    3060
gccggcggcc ggttcctgag ccgagagcgg ccgcggaaaa atcctctgcc tccgctggaa    3120
atcgatatta ggccggcgcg ggcgcgggac gtcggggccg cagccagtag ttgtgcacg    3180 tctcatcatt tagctaatcg agtcgaaaag tttctgtaag ggccggaccc agcatcagat    3240
ggtaacactg attgaacaag agattagcac aatagatctc taaccgaggg gaagcgttgc    3300
ttttcacgct acgcgccgta attaatggta tgaatcaatt aatttgactt ttattgtgtc    3360
gaaggaaaaa agcgcaacaa atggaaccgg cagctgggag ttgttcgtcc tccaccccct    3420
tccccaggga ggttccaagg agacaccggg gaatggacgg atcaggctgg gccgtggcag    3480
agggagggta ggaggcagcg accagcagcg tggagggagt ccagagagct agcctctgcg    3540
gacggcggaa tcgaaattag gctcatttgg agactacttc gagaccggtg aggggagccc    3600
tgtagccacc atcctccggc gcgcatccac acatactagt ccacgcgggc ccagccacca    3660
aggccgcggc agggccagcg ctgcgccccg ggccctgcc tttagggctg ggcaacccaa    3720
gcagagcaaa ggaggttcct gaatgtgtaa atttccgctt tttagctttt ttttttttt    3780 tttttggacc ttccgacact tcggttgctg aggcagttgc agacgcgacc tctgcagtcc    3840
tgggcgatgg ccagccagct cagctcgggt cggtttcgcg gaaagctgtc tagacggcat    3900
tgtaaacggt tcggagcctg cgggccacaa agctgtggag ctacggaaat caactctgag    3960
atgcgtttta gggccgtgtg caacctcggg atcatttaga taaagaaaaa ctgtggaggt    4020
tggcgggcgt ctcaggatag tgtcaccacc ccctaccctg ctcccagcct cagatgagta    4080
gtgttatatc ctgggaaact gtctaatggg gatgaaagtc aatctgtgtg tctcaatgcc    4140
tgtaatgaag caagtttaca gattttaaa ttttattt tattattg aattattttt    4200 ggtgtgtcta ggccaaggaa agaggagatc gtgggtgggg aaacagactg agggaatcag    4260
aagcaccact gtccatccgg aattaaatcc acatcccagc atcttctgca aatatttcac    4320 taattattc ctctcggaac tcctcccctc gtgctccttc ctctggtgag gccggcgctc    4380
ccctcccagg ccgcagcgga cagacaggga ttgggttccg tgtgcctgcc acaccaggca    4440
ggctcttgcg gctcccaact aggcggccta aatgagggag gaaagaggag gcgcatcgct    4500
gattcaccgc gtcaagagca ctgactttcc ttggaggtgt gaggtccacg caccccagcc    4560
acgcacttgg gggtcggttt gcggtgcctc ccctccagt cccagtgaaa tccccacagt    4620
ttttcctact atcactgact tgccttgcac tccgcgtgca ttggccacac atcctcgcct    4680
```

```
cctccacccg ctccgccgcc ggttttcttg gaagttaaat cttggaggat tgtccacac    4740 cttaagagaa gaaaatccac gttagctggc agcaacggag atcccagcat gctggcatgc    4800
ccaagtctgc ccaggttccc ccaaggccat gcccgccgcc cgggaagtca ctgcccgcac    4860
ccctcacgtt tcttcagccg cccctgggcg ctgcgtctaa cctgaagaca ccaggcctct    4920
tcccggatcc actcgactta cccaggccgc tgccaatccc agctccttcc ccagcgcctc    4980
atttccgatt ttttcatatg ctaagtcgtt taacaactcc aagtagccag ttatggcttc    5040
tttatttata ggttccctgc tattttacgt cgttttatt tctctcggca actattctag    5100
tagattaatc aatagccatt ttctgacctt cgggaacccc agctgatgct ttttgtggcc    5160
gcacgaaaaa atacatacag gaaaacacgc ccgcatcaag ccgggaaaga gcaggtagga    5220
cctgagtggt ttggttgggg gagggggaaa aagacatctc agcaggtgtc ttccccggaa    5280
tgagcactga ggccagaggg gaatctgaaa tctaattagc aggagggagc cgggtgcgct    5340
gctcttactc tttaaagcta aaacaatga aacaaaaagc aaaacagaga ctaagttttg    5400 cttttttaaaa cacgatatgg gaacctcgtt ctaggtcgcc cagtccctgt ctaaggagtg    5460
tgacaaagtg ggggggagaa gggcggaagg gagaggggggc ggggaaggca gggcagcgac    5520
agtcgcacag tcccgcggac gctcccaggc ccacgccctg actcgctcac acccacccac    5580
actcacaccc acccgctccc tgggcccag ggcccggatc cagcctgggt gggggggtct    5640
ccgggcgggc cgcagcgccc tccgtgcccc ggggatgctg gcgcacagtg cggagcggag    5700
ttgcgcgtct ctcgtccctt tgttgacaat tccctgaacc aacttgagtt tggccggctc    5760
ggccgcggcc ctgacgtcac gcacggtcac gtggccccgc ctcccgctgg atctttaagt    5820
agaaagtaat ctatcaggcc agtccttaaa acgggacttt cgactaccgg ggcttcggcg    5880
tccctgacac ccagccccct gcccccccgc tactgtccct gcccgcgccc tcccgagctg    5940
ctcggcgccc ggcgtcccgc gcccgcctgg accgctcctg cgcccacgc cagggccaga    6000 ggccgaggaa ggcgggctaa gtgagggggc gcggcgtgga gaaccgccgg ggccgggagc    6060
ggtagcgagc gcctagtacc gagcgccagg gacggcagga gttcgcggag cgcggccgct    6120
gggggcggac ggcagagccc gcgccacgcg atgcggggcc gccgagtgtg agctgagccc    6180
agcgggcccc aagccacctg cggcccctc ccctctccct gcccccate tttcggggc      6240 actcaaaccc tcttccctg agctccgtgg cagcccccga acaccctcat cgcccgctgc    6300 cccctcccg ccgccgctac caaccccgag gagggatgac cctctccggc ggcggcagcg    6360
ccagcgacat gtccggccag acggtgctga cggccgagga cgtggacatc gatgtggtgg    6420
gcgagggcga cgacgggctg gaagagaagg acagcgacgc aggttgcgat agccccgcgg    6480
ggccgccgga gctgcgcctg gacgaggcgg acgaggtgcc cccggcggca ccccatcacg    6540
gacagcctca gccgccccac cagcagcccc tgacattgcc caaggaggcg gccggagccg    6600
gggccggacc ggggggcgac gtgggcgcgc cggaggcgga cggctgcaag ggcggtgttg    6660
gcggcgagga gggcggcgcg agcggcggcg ggcctggcgc gggcagcggt tcggcgggag    6720
gcctggcccc gagcaagccc aagaacagcc tagtgaagcc gccttactcg tacatcgcgc    6780
tcatcaccat ggccatcctg cagagcccgc agaagaagct gacctgagc ggcatctgcg    6840 agttcatcag caaccgcttc cctactaca gggagaagtt cccgcctgg cagaacagca    6900 tccgccacaa cctctcactc aacgactgct tcgtcaagat cccccgcgag ccgggcaacc    6960
cgggcaaggg caactactgg accctggacc cgcagtccga ggacatgttc gacaacggca    7020
```

-continued

```
gcttcctgcg gcgccggaaa cgcttcaagc gccaccagca ggagcacctg cgcgagcaga    7080
cggcgctcat gatgcagagc ttcggcgctt acagcctggc ggcggcggcc ggcgccgcgg    7140
gaccctacgg ccgcccctac ggcctgcacc ctgcggcggc ggccggtgcc tattcgcacc    7200
cggcagcggc ggcggccgcg gctgctgcgg cggcgctcca gtacccgtac gcgctgccgc    7260
cggtggcacc ggtgctgcct cccgctgtgc cgctgctgcc ctcgggcgag ctgggccgca    7320
aagcggccgc cttcggctca cagctcggcc cgggcctgca gctgcagctc aatagcctgg    7380
gcgccgccgc ggccgctgcg ggcacagcgg gcgccgcggg caccaccgcg tcgctcatca    7440
agtccgagcc aagcgcgcgg ccgtcgttca gcatcgagaa catcataggt gggggccccg    7500
cggctcctgg gggctcggcg gtgggcgctg gggtcgccgg cggcactggg ggttcagggg    7560
gcggcagcac ggcgcagtcg tttctgcggc caccogggac cgtgcagtcg gcagcgctca    7620
tggccaccca ccaaccgctg tcgctgagcc ggacgactgc caccatcgcg cccattctta    7680
gcgtgccact ctccggacag tttctgcagc ccgcagcctc ggccgccgcc gctgctgcgg    7740
ccgccgctca agccaaatgg ccggcgcaat agggacgcgc caatggccgg gacccagggt    7800
ccggcggcgg cctcgagcaa caaatgcacc tccaggctgc gcgccctgtc ccaagcccgg    7860
tcccggtccc gctgcccaat cctggactct gcctctcccc aatttccttt ccctgagcc     7920 cccaacgcct accttccgcg gcctccatcc cctcgcgcac acctaagctg gtcgagcaaa    7980
ctcaccgcgc gcccgccggg gatagctttc catacaggta aaaccgaaaa ccgaattttc    8040
caaaaatgca ccccgacggc gcctgctctt agtaccg                             8077
```

<210> SEQ ID NO 155
<211> LENGTH: 348
<212> TYPE: DNA
<213> ORGANISM: Homo sapiens

<400> SEQUENCE: 155

```
cgcgtctgct accagatgcg gctccggggg ctccatggtg actgagatag gagaagaagg     60
cgccgtccct acggtatcaa tctccgaaca gggagatggg gtggcctgac tcctaaaatc    120
cgcggtcctg gcctcaccga gcgggcggaa atctccattc atcatgcctg gctgcctga    180 actggcactg gacaaaatcg tgtctattcc aaaactcgac ccgctggccc cttccattgt    240
cattgctaca tgaggtccac gccactccgc cgttcagcag ccgccccgaa ccagcgaaga    300
aagctatcga tcgtaaaaca aaataaacac caaacaatgt tgccgccg                348
```

<210> SEQ ID NO 156
<211> LENGTH: 325
<212> TYPE: DNA
<213> ORGANISM: Homo sapiens

<400> SEQUENCE: 156

```
cgagaggccc ggccaccggc tcgggagctg ggccggtcgc tttgggagcg gatgaggaag     60
gttaggagaa gcagcgagat agatcccaat tttacaattc tattttcttt cggtagggtc    120
tcggcgtcct gggccacgtt gagagcgaac gtgggccgag cggaggacac agagtaaaaa    180
gcgacgcccg ctgtatacat aaatccgcac ccgctgcccg cccgggtact gcctgctctg    240
gcttccgctc tcttccgagg ctgggcaagt ccaaaagttc ccgaaagggg ggttcaaaga    300
ggggcgctca gtgcacgtga tttcg                                          325
```

<210> SEQ ID NO 157
<211> LENGTH: 431

<212> TYPE: DNA
<213> ORGANISM: Homo sapiens

<400> SEQUENCE: 157

| | | | | | |
|---|---|---|---|---|---|
| cgcggaagag | ggcggaagga | gaacccctgg | actggtcctc | accgagcact | acaggtggca | 60 |
| gagccgtggg | ggacccgtgg | gttatgagat | tcagcggtga | ggggtagcgg | tgtggataaa | 120 |
| agtagaggcc | tgacctgctt | gaacgtccgc | agcagcgagc | ccagcatgaa | ggccgccatg | 180 |
| ttgtccgcta | caaactacaa | accgctgaaa | ctttattgac | actgccgaat | agcgcaggac | 240 |
| acgaggggcg | gggcctgggc | cgcctggggc | ggagctggga | ggtgggtggg | aatgtggcct | 300 |
| acaggaaagc | ggggttagtt | ttgggatcgg | agctctcgcg | atatttcacg | gaacttgggc | 360 |
| aaatgacaaa | tctgaaggcg | ccgcgttgat | gctgatggcg | cagccagacc | cgccccgtgt | 420 |
| gttgcagccc | g | | | | | 431 |

<210> SEQ ID NO 158
<211> LENGTH: 703
<212> TYPE: DNA
<213> ORGANISM: Homo sapiens

<400> SEQUENCE: 158

| | | | | | |
|---|---|---|---|---|---|
| cgtctggcca | aaggcgccca | gctcaacggc | cgcgacgcgg | taaggaaggg | ctccgccgcg | 60 |
| gcggtagccg | ggcacccctg | cgccctctgt | taaaccaagc | cgactccctg | gccggtggag | 120 |
| aaccggagcg | gcgggtcgta | gagacgtccg | cttgagggtg | gcgggtgagt | tttctcccgt | 180 |
| ccacctatgc | ctacagggct | aagaaacggt | cgttttttctg | aatcgaaatg | tctgcagctg | 240 |
| gctatcctcc | gtcgcagctg | attccgaaag | agcaggagga | ggaactggga | ggaggtggga | 300 |
| tgggggggtgg | tggcattctc | ttctacagac | ctcaaggttc | ccttgattcc | ggggcaggcg | 360 |
| tctccccggc | gaggatccgc | agctccgagg | gcaagctggg | cataagcaat | aggaggacgg | 420 |
| cgcgctgccg | aggcgtccga | gccaagcagg | agcccaggtg | gccttagtct | ctgggcctga | 480 |
| tgaccggacc | tgtggagtag | attccgacgc | gactgggtca | tttccagttc | tctagacgct | 540 |
| cggggcttgg | gaccctaac | cgagagaatc | tcagggtttc | tggcatcccg | actcagtccc | 600 |
| tctaaggaga | cagcactacg | tttagcgcca | ggacccggcg | ggtgtcatgt | gtaggggaa | 660 |
| atcaaataaa | acatacggag | gagcgcggca | cccagtcgaa | acg | | 703 |

<210> SEQ ID NO 159
<211> LENGTH: 416
<212> TYPE: DNA
<213> ORGANISM: Homo sapiens

<400> SEQUENCE: 159

| | | | | | |
|---|---|---|---|---|---|
| cggcggggt | cgctccaaag | acttgtattt | cgcgtttgcc | tccgggagct | gggagtaagg | 60 |
| ccttggatgg | cgccgacgcg | gttgcgagga | agctgaggcc | tgggagagca | aggggcgcgc | 120 |
| aggcgaagtt | gcaacttgca | ctccagccgc | gggcctggcg | gagaaaggga | ggctcgcggc | 180 |
| gccgcgagga | gtcggcgggc | ctcggggcct | cgctttcgcc | gcatctgccc | agcgctccgg | 240 |
| gccttgaatc | tcggcagatg | cgagttgtgg | gcacctaggg | aaccctgagg | actcgcattc | 300 |
| ccccgggtct | gtatcccgtg | cccacccccgg | agcgtcgcaa | accttggaaa | gggtgaaagc | 360 |
| tgataggga | gtcttatttc | ttaagagaga | gggtgagggc | gcgcggcgct | gcctcg | 416 |

<210> SEQ ID NO 160
<211> LENGTH: 332
<212> TYPE: DNA

<213> ORGANISM: Homo sapiens

<400> SEQUENCE: 160

| | | | | | |
|---|---|---|---|---|---|
| cggaagaggt | ggaccggctg | cggacccagg | tactgtgcag | aacgcggcgc | aggtgggagt | 60
| ccttgggcgg | gcgtctacag | gtggatcttt | tatgcacctc | aacaggccgg | ctttctcacg | 120
| gatcacatcg | gttagcagta | agctgggagg | gaggtcccga | agactgtgct | gggcacagtg | 180
| caggacccag | agaagcggag | ccatgggccc | gtcctggtga | gggagttaaa | gtccgtgcag | 240
| gtgaacagac | cccggcccgc | gaatcaacga | accacaccga | gtgccaagtt | gcgccgtgca | 300
| ggctgcggag | ggtgcgagag | cagggagaag | cg | | | 332

<210> SEQ ID NO 161
<211> LENGTH: 1475
<212> TYPE: DNA
<213> ORGANISM: Homo sapiens

<400> SEQUENCE: 161

| | | | | | |
|---|---|---|---|---|---|
| cgaacgcaac | atcaagggcg | aaaagaggct | gcacaaatca | cgtagaaaat | tagaccgcct | 60
| ctttccatgg | cgataatcga | attagcctca | aattaaacgt | gaaattggcc | ctctccggct | 120
| gtggagacaa | agcccctatt | gtcctgctcg | ggtagcggca | gcagcagtgc | ccaccccgcc | 180
| ccggccagcc | tggtcggtcc | ccgccgctgg | gaggatgagg | tccgggctgg | acccgggaag | 240
| agcctcagct | ggagaggacg | tggacgcgcc | cgaggctcgg | ctccctgggc | ggctgcgggg | 300
| ctccgggcag | gaggagaggg | cgggcgaagc | agagggagcg | ggcgggagtg | gggagggagg | 360
| agtgcggagg | gcggagggcg | tgcgggaggg | atcccgggag | tgcgcttgtg | tgtgtgtgcg | 420
| cgcgcgcccg | cccgcgcgc | tcctctcccc | gcccctcgcc | ccctcctgc | gagcgccctc | 480
| ctctcctcct | ccccccgccc | ccgcgctcc | cgcccagccc | ccggaatcag | tgccgctgtt | 540
| gccgtgcagg | ctgcggattc | ctccagtccc | tccctcggcc | gcctctcctc | ccggagcgag | 600
| cgcgcagccc | tgcgcagcag | cgcccactgg | tcccgtcctg | tgagccccgg | ccccagccgc | 660
| ggacagaccc | gcggagtcgc | ctcccggccc | accgcccgg | ccgccgagga | gcgggaggag | 720
| gacgggaccc | cggcgccccc | accccatccc | cgggaggtag | gtaggggggcc | cgaggcaggg | 780
| agatgccaac | tcactggggc | tgcctccccgg | gtgggctccg | cggcggcgga | cgggcgggag | 840
| gaggggcgcg | ggcccagggc | cggaggacgc | cgctgcccgc | ctgccctgcg | cccggggagc | 900
| cgcgtggggg | cagggaggct | gcaaagcccg | ggcggggggcg | gcgcggggag | cccgggtcgc | 960
| gggtgctcat | tggtactcgg | atgatgcggg | acgaggggcg | gcaggctctg | cggtgaggcg | 1020
| gcagcagacc | cgccgtgcgc | accgctgccg | tccggcccca | gccccggcgc | ggcgcggcga | 1080
| ttcctcctcc | ctgcctccgc | cggcgcctcc | ctgcagccgg | gcgcggcggc | ccctgacgcg | 1140
| gaggcccctg | gcgcggaggt | gggtgcggag | cggacagcgg | acagccggag | ggtctatttt | 1200
| caggtgccct | ctctgtggcc | ccgcggggtgg | ggagcggggg | cggcggtgac | agggccgggc | 1260
| tctgcgcgta | gcggtgcagg | ggatgcggcc | aggcgtggtc | ccggctgcgc | cgcgctgcag | 1320
| ctgagccgga | ggcggcggcc | ccgcgccccc | acctccgccc | catccctgcg | cttgctaccc | 1380
| tcgtgcgccc | gccccccccc | cgcccttctct | gccgtcccca | ctctcccagg | gctgggcgtg | 1440
| agccgcctcc | gggcgccgag | ccgccgctgc | gcccg | | | 1475

<210> SEQ ID NO 162
<211> LENGTH: 860
<212> TYPE: DNA
<213> ORGANISM: Homo sapiens

<400> SEQUENCE: 162

```
cgcgttcccc cgcggagtgg ctctcgagtg cggggaggtg ttgcggaggg gagtggactt        60
agggaagggg cggcaaaagg gcaaaggag aaatggcgtg tgtgtgcgtg tcaaggaatg       120
gagagggcag ggcgcttggg agcagggcgc gaggccaggc tctgttgggc cccggctcac       180
ggcgccctt ctctctgtct gtacctgcgt gtgttgccgt cggcggcggg gccgcagcca       240
gcgacgtgcc ccaggacggg ctgcttctgc acggcccctt cgcacgcaag cccaagcgga       300
tccgcacggc cttctcgccc tcgcagctgc tgcggctgga gcgcgccttc gagaagaacc       360
actacgtggt gggcgccgag cggaagcagc tggccgcag tctcagcctc tccgagacgc       420
aggtaatcac ccccggtcgc ggcctgccct gcgcccggag cccgggtgga ggtgagggtg       480
cgcgggtgca ggagaggccc tgagcccgcc ccagcccagc cctgctgggt tccaaaaggc       540
ccccattccc cgcggcgctg cggtcaagcc cgtctttaga gcctcttcct cgagactgcg       600
tgcagcctgc tgagcccgca ggactttttgt caagcgctaa agacctagca ggaggcagag       660
taaatgcaaa ctgtatcccg agcccggctc ccaaagctcc tcacgggggg accaggttcc       720
ctggaggaag cgggtcgcct cgggagcggg cagcgcaggc agcaccgagg ccactggagc       780
tggctccagc cctggcattc ctgcagccct tttcccgcca ctgtgtcggg gcgctcatag       840
tcctgcgggg agccggtccg                                                  860
```

<210> SEQ ID NO 163
<211> LENGTH: 2637
<212> TYPE: DNA
<213> ORGANISM: Homo sapiens

<400> SEQUENCE: 163

```
cggggggtcgc gttggaaccc cacaggaaaa aggcgcggaa agccgccggg cattttccgg        60
ggttccatag atgtccccag tgtcctagtc cgtgcatcag ctcgcgcact cggagggact       120
ctaggcaggg ggagggcccc gcggccagta tgtgcgtccg aggctttccc gcaggggca       180
gtgccgcccg cccgcgcgcc gatacgtgtg gagggggtgg gaacctgcgc ggagttctgg       240
aggttctttg ggagaaagtt aggggatgcg gaggggtggg cgcaagactt ccaggactcc       300
agggaggccg tgggagggc cgccgagggt gcagtgtgag gcgcaggagg gggttggggg       360
cggtgcacgt tgcagggaga cgcagcccct ggaagatgcg agtgtgaacg tgtgagtgtg       420
agtgcgtgtg tatgtgtgtg tgtgcgcgcg caccgcagct ctccgggttc cgcgaggcgc       480
gcgggtgtca gcttgcagcc ggggctcctc cctccggccc cctgcccag cccggcggtc       540
cctcctccct ccctccccgc tcgcccctcc ccggcgggcc aggggctggg acgccccggc       600
ggagcaggcg gcgcggtgg cgagttgggg agccctaggc tcggcgctgc cggaggggcc       660
cgagccgagc cgcctgcgcc ccggccgggc agcgccgggc ccgcttcccg cggggccacg       720
ccctgtcaaa ctttgttgcg gcggctagcc cagcgggccc gcaagcgggc gggaggggcg       780
ccgggccggg ccgggcaggg cgcgggcggc taggggctcc gagagcggcg ccccggccc       840
gcggccccac catgcccag ctcgcggcg ggggcggcgg cggcggcggc ggcagcgggg       900
gaggcggcg ctcagcgcc ggggcggccg gcggagggga cgacctcggg gcgaacgacg       960
agctgatccc cttccaggac gagggggcg aggagcagga gccgagcagc gatagcgcct      1020
cggcgcagcg ggacctagac gaggtcaagt cgtccctggt caacgagtcg gagaaccaga      1080
gcagcagctc ggactcggag gtaaggaagc accgcggcca ccccgggggg atcccggccc      1140
```

```
tgcgtccgct cacccgctct tgcctttgtg tctcctccgc aggcggagag gcgcccgcag    1200
cccgtccggg acactttcca gaagccgcgg gactatttcg ccgaaggtat gtgcccgctg    1260
ggacagcccc ccactctcga ttcccgctgc gctccgctgc tcagcccggg cggcccaccg    1320
tcccccttgc ttgggtggac gcaccccttgc cctccgcctt tattggcggc agcccccgtg   1380
gggcgcgcgt gggggggcgct ggggtcccca gctcccgcct cgagcccct gccgcggcgc    1440 tgtcagtccc gggggcctgg gcctcacctc gccttggtct tgttcgcagt gagaaggcct    1500
caggacagcg cgttctttaa aggaccccg taccctgggt acccttcct gatgatcccg      1560 gacctgagca gcccgtacct ctccaacgga ccctgtctc ccggaggagc gcgcaccgtg     1620
agtgcccgtc gggcgcgccg ggagggtgg gaggccgcgg cccgcaggat gcgccccgg      1680 gcttggccat ggagtggggg atggggcctt ctgcgccgat cccaagcaga acttgtttgc    1740
ggagttgaac tactctctgg cggccgagcg cgaggctgcg ctggccagtg cctggatgaa    1800
agtaaagtta ctttaacttt tccctcttg cgggttgagg ttttggagtc cacctctggg    1860
atcttccttg gcctccagaa ttcttcgcct gcaccgaagg aaacttggat ttgtgcccgc    1920 tttgggggg tctcgctttc cttcttggaa atcggtcagc tttctctggc agtggggcaa    1980
ggggcctagg gagctgggtt ggcgacgttg tcctccgact ccgggttcac tgggcggctg    2040
caggctggtt cctaagaaac ccagttttcg tggcgggtta ttcacagccc ccgttcccac    2100
ccccagccct cgcaccgggg cctcagcttt tctgcggagc tagctccgaa ttttaaactc    2160
gcgtagatga tttcgaggcg acccaaggca ttcttcaagt tgaggaactt ggcttttcc    2220 cccttttgtc gcctgctttt ctcatttaaa gcgagcgctg cgacacttta aacctgttaa    2280
tgggcgcgta ttgtgtgctg cccgctggca tttagagcgg tgattaagca aattgaccgg    2340
gccccagacg acgtgcaaat gagggcggat tccttcgccc cctctctctg gctctaaact    2400
cccgcccccc gcgttgcgag gggcgcagct gggggctggc gaggcctttg tgtcccccaa    2460
gccgccactc caccctagg ctccctgccc aggtgctggg tccgatgaca atgttgggt     2520 gaacgcctac ctactgtgtg ccaggttccc gcgtgctgct gcttgggcgc gatgtgaatc    2580
gtagtagttc tttgcttccc gcccagattc ccattgcctg ccacttcgct gtcgacg      2637
```

<210> SEQ ID NO 164
<211> LENGTH: 2534
<212> TYPE: DNA
<213> ORGANISM: Homo sapiens

<400> SEQUENCE: 164

```
cgaggaggct gcagggacgc gcatggaaga gccggtgcgt gggagggttt gcggggggga      60
catcgcgccc cctaggggtg acccccagtgg gtcccgtgtg ctctccgcgg agccggcgga   120
gccttgtcct ctgcacccgg cgcgcagcgg cccccttaaac agtggaaccg tgaggccgct   180
ctaagccgaa gggctggaat ctgggttct cgggttttat tttagaccat tcggcaccaa     240
gcccgagctc ccccgccgca ccgcttccag tccccctttct ttccatagag cgacccgaag   300
ccggcggtgg cgcagggagc cgagtctgat gagctcgcgg gcggctgaag gccggcttcc    360
ctgtggggaa cgcgccacct gtcggcgcca gtgagaactg cgtctgtgtg gcgccctcgg    420
ggtattcggg gctgcgggga gatgtgtgcc tgaagccctg cgcttgcggt ggggacgtcc    480
ggcctctttc ctggcaattg accctgagg cgggagagac aacggaattc ccacaaaggg     540
atccttctcg ggatctcccc acctcaagac agctaaagct ggaggaaaag cccctccggg    600
gggtgggggg tgcgggtttg ccctgcgatt ccgaaagcag aaaatacccg agccacacag    660
```

```
ggacgggcgc cgcgttggta gtcggggcta cgttcctact ccctctacct ccccccgcgct    720 gtgtgaccct gggcggaacc ccgctgctct ctgggcctca gtgttcttat tcgtaaactg    780
agggcgttgg atgagattgg tcctctccca actctgacct tgaaactgat actgaatctg    840
agcagcgtct gtagacacct gtgccttgcc ttctatttct agccttgaat aaatcctgga    900
cttttatgtg ccatttatat cctaatctca tatatattta atgtataact gctgccatta    960
ttgttttctc aattgtctag gttttcattt ggatgggggtt aggatggtcc aaattatccc   1020
gataagtgcc cattaactta aacctttta aaaaatgaaa ccagtaaaac ttcattcact   1080
ttgcagtgtg gacactgctg gagagcaccc atgtcgtggg tccagcgagg acacaaggag   1140
gggcttagag acatgcggga ggcttagatg agaagacagc acccgggcag cggtcagtgt   1200
tagagagagg acccgtaaga agggccgagg ctagagggag agcgaagact gagccaacga   1260
cgcacctgag ccctggggtg ggggtggaga cgtggctcct aacccaaatc tccctgccag   1320
gcagtgtccg acgagcatcg acggcaggcg tcgagaccag tgcagggtag ctcagacctc   1380
aagccacgct tgacctttcc atgaaatgaa taaaactcga agccaggga aggggacag    1440 tactttgatc cggagatcgc ttataacctc tgcttggagt tccgagttcg tgcggctcaa   1500
gggaggctac agtccagcaa gctctgggct ccaagcgtgg ggacggcagc ccccaagctt   1560
ggcgcacccc tcgggaagcc ccggaacggt cctcgccaga catagccggc tgtcctggtc   1620
cttagcttca ggctggcggc gcaaggccag agcggctgcc ttctaggcac ctgggtggag   1680
gtctcgcata gcattccctg agaagcgaaa ctgcccttgg ggccgcagcg agcctgccac   1740
atcgaactgg agaccctctg ctttcgggat agatgggacg tttctgctct gtccttcttg   1800
gagtcccgga atcgttctgg ggccgcgtgc tgcctggagg cggtgaattt cagggtcttg   1860
agaagccgcg cacacacggg attctgggcg agcgtcccgt ctcttaattc ctattaagag   1920
acggaaaaat cgagggactg gaggtcccat cattgtcgcg tgagcagcct cctgaacacc   1980
aagcgagacc tgagggttcc gctggggcct cgccctgaca cccgggccct ccgtgtggtc   2040
gagagtttgc gcccgctccc gctagggcag cgaggtccca cttgcggccg gctgggggcat   2100 ggtggcaccg gttgtctact ccccacttgt gacaccgaca gcttccaact cctcagaccc   2160
accccgtgga attctggact ttgtgagggc cgccggggtc ctggccctgg ggtcagctgc   2220
catctgacta agccaggacg gcggagctcc aggccttgct ccagcactgc cggtgcgtcg   2280
gggcccgcgg agagcccagg gcgggagctg tgggctgagc cgggtggccg cgtggacaca   2340
gatgcccggc cggactgagc ggcagccaag actctccgtc catcccgccg ctggactcga   2400
ctctcccaga cccgccacgg aacccagatt tgagcacgca agataaagac gccagaggcg   2460
agtgcgcggc ggagaactgg ccgcgacacg ggaagcttct ggggcgcaga acgctggctc   2520
cgactcgcgc ggcg                                                    2534
```

<210> SEQ ID NO 165
<211> LENGTH: 396
<212> TYPE: DNA
<213> ORGANISM: Homo sapiens

<400> SEQUENCE: 165

```
cgacggcgcg cttgtggccc ggccggagct tgcgtgcgcg ttctgacggc tgggtgctgt     60
gttacaggtc ggcgcagttc gagcacacgg ttctgatcac gtcgaggggc gcgcagatcc    120
tgaccaaact accccatgag gcctgaggag ccgcccgaag gtcgcggtga cctggtgcct    180
```

| | | |
|---|---|---|
| ttttaaataa attgctgaaa tttggctgga gaacttttag aagaaacagg gaaatgaccg | 240 | |
| gtggtgcggt aacctgcgtg gctcctgata gcgtttggaa gaacgcgggg gagactgaag | 300 | |
| agcaactggg aactcggatc tgaagccctg ctggggtcgc gcggctttgg aaaaacaaat | 360 | |
| cctggccctg gactcggttt cccagcgcgg tcaacg | 396 | |

<210> SEQ ID NO 166
<211> LENGTH: 3176
<212> TYPE: DNA
<213> ORGANISM: Homo sapiens

<400> SEQUENCE: 166

| | |
|---|---|
| cgccctcgcc ccccccccgc aagtatcccc cactactccc ccccaccccc gcggccctag | 60 |
| ctagctgact tgactggcac gcgccgggag cccgggctcg ggcccctcgg agcgtctgat | 120 |
| tggctgcggg gcagctccgg tctgctctgc ctgcgccctc attgggcgag aggcgcagcc | 180 |
| agcggcactt caaagcgggt gctcctcgca cttaggctga gtttagccgg cgggagcctg | 240 |
| gagtccgctc ggcacgagcg cggggacgcg ggagccgcgc gggacccaag cagttttcc | 300 |
| gagcagccgc caggctcagc cccgctccca gcctcgctgc gcagccagag acctgctatg | 360 |
| gccacgtcta tactcggggt aagtcgcaag gcgggcaacg catttgcttg ttttaaccgg | 420 |
| agtaattttt cgttatggct tctggggtct gcggctccgg agaaactgtt gctgctagac | 480 |
| tgcagcttca gcttctatta gcactttcca catttctggg actgattttt ccccaagttt | 540 |
| ttggaaccca gaaagatgcc tttgcaagaa aaggccttct taatcaagtc ctttttcatt | 600 |
| tggtttcaaa aaaagctag aggtttcttt tcttcccctc gtgatttata ccccatcccc | 660 |
| cgcattgctt tggggatttt gttgcaatta tgcgacaatg gtgtttccag aaaacagtct | 720 |
| taatcgtttt gcagtccatc tagtcacgct aataaacatt tacatttccg cggctccccca | 780 |
| attcgcccat gactttgaaa tctgtctctg gccgcttatc ctcggattat tgttttcata | 840 |
| atcgctgttt ttgtgtgtat gtaaacttta aaaccaaacg ttttctatta aaaaagaaaa | 900 |
| gtcaagtcgt agccaccctg ggagagctgc aagtttcgcc cgtccctggc agctgtttcg | 960 |
| gccgcctccg ccctcacccg tgtttgttg tctctggtct ctgtgtttac cttcgcgctt | 1020 |
| caccccgaag ggcgacttgg ggtcttctgg gagatgagcc ggtttacggc gacaacccaa | 1080 |
| gtccggttgt aggcagggtt gcagcgggga acacggaggc atctttgatt tatagcctca | 1140 |
| gcgaagtgca acttttccggc gcctggacct tcgcccgggt gatcgcccct gctccgcgcc | 1200 |
| cggtgcggcg actcctccgc gggcgcgtgg ggaggaggcg cgaggcgggg agccaggacc | 1260 |
| cccccgggagc agccgcaggg gacgaggctg ctcacgggtg cactttgttt cttccccac | 1320 |
| ttcctcttgc cctcctcctt cttgctccct cccccatccc acccactcta ggaagagccg | 1380 |
| cgcttcggaa cgaccccgtt ggccatgctg gcggcgacct gcaacaagat cggcaacacg | 1440 |
| agcccgctga cgacgctgcc agagtcgagc gccttcgcca aaggcggctt tcaccctgg | 1500 |
| aagcgctcct cgtccagctg caacctcggc tccagcctct cgggcttcgc ggtggccacc | 1560 |
| gggggccgtg gctcgggcgg cctggcgggc ggctcgggcg ccgccaacag cgccttctgc | 1620 |
| ctggcctcca cgtcgcccac gtcgtccgcc ttcagcagcg actacggcgg cctcttctcc | 1680 |
| aactcggcgg ctgccgcggc ggcagcggcc ggggtgtccc cgcaggaggc gggtggccag | 1740 |
| tcggccttca tttccaaggt gcacacgacg gcagccgacg ggctgtaccc gcgcgtgggc | 1800 |
| atggcgcacc cgtacgagtc ctggtacaag tcgggcttcc attcgacgct ggcggccggc | 1860 |
| gaggtgacca acggcgcggc gtcgtcgtgg tgggacgtgc acagcagccc gggctcgtgg | 1920 |

```
ctggaagtgc agaaccccgc tgggggctc cagagctcgc tgcactcggg cgcccccag    1980
gcctcgctgc actcgcagct gggcacctac aaccccgact tcagtcgct cacgcactcc    2040
gccttcagct ccacgggcct cggctcctcc gccgccgccg cctcccacct gctctccacc    2100
agccagcacc tgctggccca ggacggcttc aagccggtgt tgccctccta ttcggactcc    2160
agcgccgccg tggcagccgc cgccgccagc gccatgatat cgggcgccgc ggctgccgcc    2220
gccgggggga gctcggcacg ctctgcccgc cgctactcgg gccgcgccac ctgcgactgc    2280
cccaactgcc aggaggcgga gcggctgggc ccggccgggg cgagcctgcg gcgcaagggc    2340
ctgcacagct gccacattcc gggctgcggc aaggtgtacg ggaagacgtc gcacctgaag    2400
gcgcacctgc gctggcacac gggcgagcgg cccttcgtgt gcaactggct cttctgcggc    2460
aagcgcttca cgcgctcgga cgagctgcag cggcatctgc ggactcacac gggcgagaag    2520
cgcttcgcct gtccggtgtg caacaagcgc ttcatgcgca gcgaccacct gagcaaacac    2580
attaagacgc acaacggggg cggcggggc aaaaagggca gcgacagtga cacggacgcc    2640
agcaacctgg agacgccccg ttccgaatcc cccgacctca tcctgcatga ctccggcgtc    2700
agtgccgccc gggcggcggc agcggcggcg cggcagcgg cggcggcggc ggcggcggcc    2760
tccgcgggag gcaaggaagc agcgtctggc cccaacgact cttagaggcc gggcgagagg    2820
cgcgagcaca caagcgagta gagacaccga gaacgaacga gaggttcgga gggcgagcga    2880
gcgggaggcg ggagggcagg ggcttcagtg acgcccccag ggcccgggct gggcgcgagg    2940
tggagccgct cagggctccc gggctgcggt tcgcccgctg tgcgaggagc tccctctgc    3000
cttccgcgcc cggataagaa tcgaacgcgt ggtccggaaa caaaagcgaa ccatcctccg    3060
acacaaacac tttaaaaact gtactcccag acgtacacat acaccggaga cctacaacca    3120
caagcacgca cactcgcgcg cgcacacaca taccactcgc ccaaacttct cgagcg       3176
```

<210> SEQ ID NO 167
<211> LENGTH: 4359
<212> TYPE: DNA
<213> ORGANISM: Homo sapiens

<400> SEQUENCE: 167

```
cgaaaaggag gcggcgcaac ggccacccct tccagcacct cggctttgtc cttcccgggg     60
aaggcggcca catccctacc cgccttgctc ctgaacgtag taaacaatct cacaaacaac    120
caccgctgcc cacgctctcc atccgtcctc ccggccttat cagacctccg ttctcccgca    180
ctcttcgggc agggtcccta ataagctcag gctgaaagaa cgtttgccac ctcccccacc    240
ctcgttgaaa gaaaggaag aaaaacagca gcagcgagaa acctcgggg cgactcctcc     300
cccgccccca agcaccagcg cacagcatcc ccctctgtct ttgttgtggt tctccgttgc    360
ttcgggccac gccgttcagc caagcaaccc ggacctgaga gtgcacagcc aggactagct    420
taggggcga ggggttggtc tttgggaaac caagcgctca ggacagaggt ggaaagtggg    480
tcccgggagc cagaaaagag agagaagggc agacggctgg gtggcaaata caaaaataga    540
aataatttag ggggatgccc gccaggcttt tgcgcctgct ccttctcccc caattcggag    600
caggttccct tcggcctccc gcgccccggg gcgcccctg gcggcagcgg cagcagcggg    660
caacgcgcgg agggctcagg gggcgcacag gggactcccg gcacactca gagaggcggg    720
cgcgcccccc tggcggtggc gacgtagtta tctggtgagc ggagcctcgt ccctctggtc    780
cggcgggctc acggccgtct tactaagcac cgcggccgag tagggcagga agccgctctc    840
```

-continued

| | |
|---|---|
| ggaacgcggc gccgccgcgc tgcagccgaa gtccgagcct ccccggccc cggcgccccc | 900 |
| gccgccgccg ccaccaccac caccgccgcc gccaccgcca ccccgggaac ccagggctgc | 960 |
| ggcagctgct gccgcggctg ccgccgccga ctgactgctg tggcaactga ggcacgagca | 1020 |
| gggtgcagag ccgccgctgg ggggcgcgcc ggccgccgcc gccgaggagg ccgcagccgc | 1080 |
| tgcggctgcc gcggctgccg cggcagaggc cgcgctgttg agccccgcgg cggccgcggg | 1140 |
| agcctggtag agaccagggt ggcggaagct acacagcagc tccggccgag agtaggggtg | 1200 |
| cgagagggcg cggaaggtgt ccagtggccg gatggaagta gcgaagggcg acgaagccgc | 1260 |
| ggccgccgcg cctgaggctg cagccgcggc cgccgccgcc gtgacgccca cgtgcgggta | 1320 |
| gtagtgcagc ggcacgtgcg agtggaaggg gtagggcagg cttccggtgg cggccgcgtg | 1380 |
| cgtcatcatg taggtgtaga agctggggtc ggctgggtgc ggccaggaca tggccaggcg | 1440 |
| ctgccgcttg tccttcatgc gccggttctg gaaccacacc tgcggggaga gacgcgccgc | 1500 |
| agcctgggtt agggagcgcc ccgtgttccc agctcctgtc ccaggacctc tgccccttcc | 1560 |
| ggacctctga atggcttggt ctacttctct ccgaccaagc ccaaccccga gtaccctgtg | 1620 |
| gtctcccagc tgggaaagtg tggacggcag tgtgtggacc gccgtgggca caccgtcctc | 1680 |
| aacgaagagg gtcctctccc ccgcgtccgg ctgctgctgc tcctcaggct tttattccct | 1740 |
| tacttcttgc tgcactttttt tgtcccaatc caacctttcc tctccctccc gccacccacc | 1800 |
| agtgccggtc tcgctgagca cccgtctctc aatcccagga tttgtacggg gattctgggc | 1860 |
| agcctttgaa gagaggctgc cgctcagctt ttctgagagg tcgccgcgcg aagtcttgag | 1920 |
| ccctccgaac tgcaaggacc tgcccctagg ggcacgggtc cgattttgat attgaaggga | 1980 |
| tgattttgtt ggaatcgttt gccttaaatg agtgggtaga gcaatgtctc cataaacggg | 2040 |
| gaaggggacg tttccacccc tcccaacact atctaataaa gacatcattc gtcacaactc | 2100 |
| taaattaaag aaagcccgat caaaccagag ggagacttcc acactcctcc cctaccccgt | 2160 |
| ggagattttt tcttttttct gcagtgtcga acgctccatg aagggctcac caaatcgcct | 2220 |
| aacctcccgg ctatctctcc cagacgtata ataaaattaa taacctaaag ttatatataa | 2280 |
| ataaggacaa tttcgttgca ttttttcccg caggaggttg ccctttttttc gttgcccaag | 2340 |
| aggaaaatgt tcaggaaact actgtctcaa accaatcgat tttaaagata cagtatcctt | 2400 |
| ttctccgtgt aacgatttat gcggaaaata aatctccaag ctcaagagca aatgaaaagt | 2460 |
| ttcacctctg gttcctgctt gaggaacaaa gaccaactgg gcttgccgcc tagggggaaag | 2520 |
| tggggccgtg ggtatgggcg agggggcatc tggccaggcg ttgggcacaa tggagcaggg | 2580 |
| gcgagtgctt tcagcattgg agtcaccatt cgggggcctt cttagatccg tcaggccgga | 2640 |
| caaccgttcg gattcggtgg ccgggaaata aataagccaa ttcctttggt gactacccc | 2700 |
| cgcggatttc cagacccctta gctaaatcta gccacccaga aaggggaaag gggaaaaaga | 2760 |
| aacaatcaac ccagatgccc ccggggaggc cagagcaggc atgcactgga attgatacct | 2820 |
| tgatggtggt ttcgggcagg ttgagtgccg cggccagctc gcaccggcgg ggccgcgaca | 2880 |
| catagttctc ccggtagaac tccttctcca ggcgcgcgat ctgctcgcgg gtgaacgccg | 2940 |
| tacggtagcg ccgcacttga tccgcgccag agcggagcc acccagcgcc gcgctcccgc | 3000 |
| cgctgcctcc gctgcctcca tgcaggcttc cgaggcctga gcccgacgcc gacgtcgtgg | 3060 |
| tgccggcagc cgagccgctc tctgcgtacc ctggcaaaca aacgaccaac agcgcatgag | 3120 |
| tggctgtagg accaacagcc cggcgctggc gctgcgcgcg gatcggggaa gccccgtcag | 3180 |
| gaaggagagt cgctgccgga attgatgggg tctgtcatgc ttacaaattg ctgccgttaa | 3240 |

```
tggaatcaat aaagtttggg gagcccttca taagcaaata atagaaacgg aattaggaga      3300
tttctttttt aataattaga aattttcaac caaggaggaa aagtggccga gggaaaatgc      3360
ctacctctgg gcgcagtttg ggaagctctg ggtttcccat ggtctggaga ccgcagggca      3420
gctttttata cggcctctaa cctттtatctg agtcttcggg gtttcaaata ttttaagagt     3480
tccaacacag cagtagctca aacccaagcc aataggggt gaaatatact tttcaactct       3540

ttctcccgct gacctaaaca gagacgccgg cgaggcttcc tccgacttac ccagaagaat     3600
gccccctcca gccctgaggg cacaggggca ggggagttca gagtagttgc ccagggtacc     3660
tttcccaaaa gcaactcggc tgctgactag gggtctaccg gctcgctcgg gctcttagac    3720
acgagcgcag aaacattttc tcggactcag gagcgagggc gggtgggcct ggtgttccag    3780
gctccgcagg cctgagcctg gcgggaaagc tcaaggagca gaactggaag gcacggtccc   3840
agacatgcgt cccgcccccg cccgtgctag ctcggtgtag cttgcctgtg gagggtctga    3900
gaggggaaaa ggcaccggga aaggctggcg ggggccgcgg aggagcaaag aggatgggac   3960
tggagagcgc ggtgcggccg gcgcggttac ctttgccatt gttttcctta gctgagcgg    4020 cgccgaggcc cccgggggag cgaagcgcgg agcagcccac ctccacgtcg ctgctcatgt   4080
cggcctcagc ggccgcctct gaataatggc ccggcttctt gcggctctcg gcggcggagg   4140
agatttcgga ggagacggtg ctttcgctgc ccgtgtgctg caggttgaac aaagtgtcta    4200

tttcgaattt gcccttggcg gggagttctc ccagagcgct gtgcagggg gcagacggca    4260 ggcgcgggct taggcgagcc gggtgctgcg aattttccag ggcctcgagc acagcattgc   4320
cagccgagtt ggacaaattg gagaatctct tgcccgccg                          4359

<210> SEQ ID NO 168
<211> LENGTH: 304
<212> TYPE: DNA
<213> ORGANISM: Homo sapiens

<400> SEQUENCE: 168
cgccgctgta agtaccttcc cgcttcttcc gaatcgcgaa gagacggtac tgatcgcggg      60
gaagtggtgg gctaaggggc caagccagcg gagtgggcgg atagaagaaa ggccctgcct    120
cccccacccc acccccaccc tccacccccg gcctcgctct gcgaggttag cccgcttcgg   180
gaggtggagg cgctaaatcg aggtcccgga aagcttttct ggggcctggt tcacagacac    240
ctgcctgaga gaacggtccg cggggtctcg cccttgtctc cttgggcctc cctagacctt   300
cgcg                                                                 304

<210> SEQ ID NO 169
<211> LENGTH: 201
<212> TYPE: DNA
<213> ORGANISM: Homo sapiens

<400> SEQUENCE: 169
cgaatccagt cccggccggc gctttgaagc ctgtgctgtg cgattttctc agcagtgagg      60
taggaataga cgcggctaat gacaggaagg tcgcgcgggt gagctgacct gtgtgtggcg    120
cagccttggg ttccgcaaat agggcaccca cagtaacacg tgtggcgccg accccgccgt    180
gcgcaatcgg ggcтттtatac g                                            201

<210> SEQ ID NO 170
<211> LENGTH: 247
<212> TYPE: DNA
```

<213> ORGANISM: Homo sapiens

<400> SEQUENCE: 170

| cgatgggacc gcggcttgac acgcattaag gagccactga aaactccatc taagcagaaa | 60 |
|---|---|
| agcggcttag tcatccatgc gttctgggca agttatcctg gccgcaccac gtggaacgga | 120 |
| gtagatagag ctcgggaagc tgagcgcagg gcggacaacg ggaaggccag agccgtgggc | 180 |
| aagcacgcgg agggcagcga ggggcactgg caccggagcc gcggggaggc aggaaaacgc | 240 |
| agaggcg | 247 |

<210> SEQ ID NO 171
<211> LENGTH: 562
<212> TYPE: DNA
<213> ORGANISM: Homo sapiens

<400> SEQUENCE: 171

| cgctcctgtc ccaagggcgc gtctctctct cccacgcaca aactcgggtc ctgtttgctc | 60 |
|---|---|
| ttctctcacc caaacccaca gtctggcgga cgcaccccgc cccgcaggca gctttctctc | 120 |
| gcacgccggg cgcccggtcc cgacggtcac ccgcactccc gcacaggcat ccccacagcc | 180 |
| tgcgccagcc caccgctcag cacccgggaa ggccgctcgc cccgcgccgc gccctcaccc | 240 |
| gctgtcaagc tctagctcca gaagggactg gtcctctcc gagttgcagt gcaggcacca | 300 |
| catggcggcc gcagtgggag cgggccgggc cgggagccgg gacccaggcc cagcagaggc | 360 |
| cgccgactcc cgccagcgag ccgccggatc ccggggccga cacccggcca ccggagacc | 420 |
| cgaccacccg ccacgcgatc acgtcggggc tcctggtcca gcgtccgccg gctcccgcgg | 480 |
| ctccggcccc aagtccgagc cccaggccag ccaagcccgc ccctccgccg ccgcccgctt | 540 |
| ggcgcagcgc gaggccgggc cg | 562 |

<210> SEQ ID NO 172
<211> LENGTH: 1014
<212> TYPE: DNA
<213> ORGANISM: Homo sapiens

<400> SEQUENCE: 172

| cgcggggagc gggctggagg attctgcaag cacaggcccc tatggagcgc ccgttcgggg | 60 |
|---|---|
| gacgggattt ccctcccttt cccctccccc gcccgttcgg aattccgccc cgccgcggg | 120 |
| cccggaacaa tgcagccgcc cgtcccgggg accagccact taccacccag gtcagtgccc | 180 |
| cgttgccgcc gcccacgccg gctcccgcgc cgcagccacc cgacttggcc atggcgagtg | 240 |
| cctccagctc acaggccctg aggccgcagc cgccgctccc gcctccctgc gggccgctgg | 300 |
| gccccgccgc tccgcaccca ccgctccact cgccgcactc ctagccgcgc cgaccccgc | 360 |
| gccccatcgc gaagatccgg agcggacgtc cagccgagcc cgctgaggag ccgcgccgc | 420 |
| cggctgccct caaactcgag gcggcggcgtc cgcgtcgccc gggcctagcg cggcggctga | 480 |
| ggagaaagca gggagcgacc ggcggcggcc gagcggcggc gttgccttct cgcccgcccg | 540 |
| cgggcgccgc tgcaggccgg gctgaagccc gggcgtgcga gccgcgaggg cggccgggga | 600 |
| gcccgaggcg ctcggacgtg gcgaggacgc agaggtgcct tgtccttctc acactccgcg | 660 |
| aaggccagcc actcgagtcg ccagagtagt cgtcccggtc gccgccgctg cttcaaaggc | 720 |
| agccttagcc tcgctgcagc cccgatttcc tcacacacac acaccgagag gacaataaa | 780 |
| cagagccgcc gccgccgccg ccacggtcac ctccctcttg tccggcataa caccgcacac | 840 |
| acacatttgc acaccgggga gagagggagg gcgcggcggc cgcccccgct gtcagtcagc | 900 |

```
gccatgctgt ccaatccggg ccttgtcgcc acagcctctc ggccaatccc aaaattccaa      960 gcccctgga ggggcgggac ccgagggggg aaacgtcatt gcggtagca accg             1014

<210> SEQ ID NO 173
<211> LENGTH: 235
<212> TYPE: DNA
<213> ORGANISM: Homo sapiens

<400> SEQUENCE: 173
gaccggcgct tcgctaacag cagcgaccgc aagaagcaca tgcacgtgca cacgagcgac       60
aagccctatc tttgcaagat gtgcgacaag tcctacacgc atcccagttc gctgcgcaaa      120
cacatgaagg taatcgccgc actctcgtcg ccccctttga ggcaggagct ctcttggctc      180
tcggcttggg gtcgggcggc gagtggcaga caggcggtgg cgggagccag aggaa           235

<210> SEQ ID NO 174
<211> LENGTH: 559
<212> TYPE: DNA
<213> ORGANISM: Homo sapiens

<400> SEQUENCE: 174
cgggcaaacc tccggaggcc ccggtgcacc cgcgtccag ccggcccaac tcgagctaga       60
agccccaacc actgcccagt gcctgagttg cagtcttggg tcctttagaa acctggagat      120
gtgcgtaaaa ttcagatgcc ggtattcccg aacttcccca ggcctcagca tatctcggcg      180
gcctgtggac agatgggagg ctaccaatcg ctccggcgtc cgcagcccga ccctgccgc      240 cagaccccgg acgtcttccg gataataaag ttcccgctct aattcatttt ccctaatctg      300 gacgcccta atctacagct tttattcgc ccagttaaaa gtcgagggaa ttcgctgtcc       360
ctccgcgctc ggataattac ccctaaatgg ccacggcagc cccttgtgtt tcctggagat      420
tagaaccccg cagtcatcaa tggcagggc gagtgagccg ccaatcacct ccgctcactc      480
cctgagagcc gctggcctgg gccgcaggag gagaggccat aaagcgacag gcgcagaaaa      540
tggccaagcc ccgaccccg                                                   559

<210> SEQ ID NO 175
<211> LENGTH: 3638
<212> TYPE: DNA
<213> ORGANISM: Homo sapiens

<400> SEQUENCE: 175
cgagcgcggc ggctggctga cgctccctcc cgcctcctta tcccgggccc tcctccctcg       60
ctctctccta gtgtgtagtt tcggcggctc ggctgctact gccgccgccg ctgcagcagc      120
agcgtcaggg acaagcctga tccgtgagcg agcgagcacc cagcagcaac caccactttg      180
ggcaacttgc gggtttcctg ctcgcgggta gcgaacggga gattcccact agcggttcag      240
tgtctccgag ccgctgcagc ccgaggggcg cgggagcgc ccgcaccaga ctctcccaga      300
cgcgaaaagg gacgagacaa ctgcggaatt caccagccgt gccagggcac ttccgaggcc      360
acaaccgact gacactttt ctcccttgg caaactggat tttttttttt aagctacttg      420
gcagctgtct ctgactccac ctccccctcc accccgccc gaaagccttt ggcttttctt      480
cggaaatcca gacagaattg ggcatctttg ttaattgccg ttgggacgc ccggccgtgc      540 gctttcgccg gctaacgtcg cctgtgctcc gagcctggtt tgctcacctt tgaactgcaa      600
agggatcaag ttcagcttga gttccctgca ttgggaagga gagagagcgt gcaagagagc      660
```

```
gagtgggaga gggggaaagg ggaaaggaga ggagggagga gagagaggag ggaggagaga    720
gaaagggagg gagggagggg agggatcgag agagagcggg gagagagagg ctgcaatctc    780
ctccctgaat cgcgcacagc gctgcagatc ccactgctcc gacatgcggg ccgaatgcag    840
gtgagaaaag gcacggactc tgcggctgcg aacccaaact tgggcaccgc acggtgcgca    900
ctgctcagcc ttcgccccg tgggcgaaag gctgctgcgg tttcaggcgg ctgcttcgtg    960
actaatgacc ttgcgcagag ttgttaagaa aaagagaaa cccgcgctct ccggggtgag   1020
aagggactga ctctgggcgt ctctgaagat ggctcgggct tctctttggc gcgccggggg   1080
gaccctgaca ctgaccgctc tgtgacgcga gtagtctccc ctgcaccgtg cccgaagcga   1140
cgtgccgggg gattttcat tctcgatctg ttgactggct cccccgctgc atgagcagag   1200
tcggagttga gactggcttg ttgctggccc cagcgcctgg tgcaggaagc gactcacgtt   1260
tgtctgggtg gccggagccg gagcagagcc tgggtttgga gtgagtgcct ggaacgtgaa   1320
ttggactcaa ctcgagtagc agcaaagacc agcgggctgg caggcggggg aggctgcagg   1380
ctcattcccc acctcttccc agcccactg cccgtctgcc ggagcggttc tggccccttc   1440
cgacagagcg gggactagag ccggggattc tccgcccgct gaggggatga ctctgggttg   1500
ggggagcgcc gaacccgcgg cgcgcagtgt cccgtgaact gtgagtactg cgactgaacg   1560
gcggcaggcg agcgggcgat tagcacccat tgcatgaatt atgaaacaat aactttcgga   1620
agaagcagga ggaaaaaaag aagcatctat cgctgccctc ccacccccat tcccggccaa   1680
ctctccacgc cgcttttgcc ccctccctcc cctccctctc gctccttcct ttccgggaga   1740
ggggagagga ctcgggggag ggcaggcggc cggccccgga ggagggggc gccgaggggg   1800 ctgtggttag aaggagcagt agcagcagca gcaggagaag atgctgagga tgcggaccgc   1860
gggatgggcg cgcggctggt gcttgggctg ctgcctcctc ctgccgctct cgctcagcct   1920
ggcggccgcc aagcagctcc tccggtaccg gctggccgag gagggccccg ccgacgtccg   1980
catcggcaac gtggcttcag acctgggcat cgtgaccgga tcgggtgagg tgactttcag   2040
cctggagtcc ggttccgagt acctgaagat cgacaacctc actggcgagc tgagcacgag   2100
cgagcggcgc atcgaccgcg agaagctgcc ccagtgtcag atgatcttcg acgagaacga   2160
gtgcttcctg gacttcgagg tgtcggtgat cgggccctcg cagagctggg tggacctgtt   2220
tgagggtcag gtcatcgtgc ttgacatcaa cgacaacacg cccaccttcc cgtcgcccgt   2280
gctcacgctc acggtggagg agaatcggcc ggtgggcaca ctttacctgc tgcccacagc   2340
caccgaccgc gacttcggcc gcaacggcat cgagcgctac gagctgctcc aggagcccgg   2400
aggcggcggc agcggcggcg agagccggcg cgccggggcg gccgacagcg cccctaccc   2460 cggggcggc gggaacggcg cgagcggcgg cggctcggga ggctccaagc ggcggctgga   2520
cgcatcagag ggcggcggcg gcaccaaccc cggcggccgc agcagcgtgt tcgagctgca   2580
ggtggcggac accccggacg gcgagaagca gccgcagctg atcgtgaagg gggcgctgga   2640
ccgcgagcag cgcgactcct acgagctgac cctgcgagtg cgcgacggcg cgacccgcc   2700 tcgctcctcg caggccatcc tacgggtcct catcaccgac gtgaacgaca acagcccccg   2760
cttcgagaag agcgtgtacg aggccgactt ggctgagaac agcgcccgg ggaccccat   2820 cctgcaactg cgcgcagccg acttggacgt gggggtcaac gggcagatcg aatacgtgtt   2880 cgggcggcc accgagtcgg tgaggcggct gctgcgcctt gacgagacgt ccggctggct   2940
cagcgtcctg caccggatcg accgcgagga ggtgaaccag ctgcgcttca cggtcatggc   3000
ccgcgaccgc gggcagcccc ccaagaccga caaggccacc gtggtcctta acatcaaaga   3060
```

```
cgagaacgac aacgtgccgt ccattgaaat ccgcaagatt gggcgcatcc ccctcaagga    3120
cggggtggcc aacgtggccg aggacgttct ggtcgacacc cccatcgctc tggtgcaggt    3180
gtccgaccga gaccaaggcg agaacggggt ggtcacctgc accgtggtgg gcgacgtgcc    3240
cttccagctc aagccagcca gcgacaccga gggcgaccag aacaagaaaa agtacttctt    3300
gcacacctcg acccctctgg actatgaggc cacccgggag ttcaacgtgg tcatcgtggc    3360
ggtggactca ggcagcccca gcctctcgag caacaactcc ctgattgtca aggtgggaga    3420
caccaacgac aacccgccca tgttcggcca gtcggtggtg gaggtttact ccctgagaa     3480 caacatcccg ggcgagaggg tggccacggt gctggcgaca gacgcagaca gcggtaagaa    3540
cgccgagatc gcctactcgc tggactcctc tgtgatgggg atctttgcca tcgatcccga    3600
ttctggggac atcctggtca ataccgtgct ggaccgcg                            3638

<210> SEQ ID NO 176
<211> LENGTH: 261
<212> TYPE: DNA
<213> ORGANISM: Homo sapiens

<400> SEQUENCE: 176
cgtcaccagt tactcccgtt tagccaacga gctgcgtgtg agctgcatgg agcggaaaaa     60
ggtccaaatt cggagcttgg atccctcctc tttggcgagc gaccgattta acttcattct    120
ggcgagtacc aacagcgacc agctcttcgt agtgaaccag gtcgaagtcg aaggctccaa    180
gtacggcatc atcagcctgc gaactctgaa gatcccttcg ttccacgtgt acgtgctcag    240
aaacctctac gtccccaacc g                                              261

<210> SEQ ID NO 177
<211> LENGTH: 3140
<212> TYPE: DNA
<213> ORGANISM: Homo sapiens

<400> SEQUENCE: 177
cgcaacttcc cgcagttact gccgctcagc cgcactaagg aggtccggag acttggaaga     60
aacttcggag actcgctgaa aggcgaagaa ctgagcgaga aaaggacccc aggctgggcc    120
ctgaagtcca cctggaaggc tgggagcctc cgcggcgctg cggcctacta ccccgaagac    180
tagcgtgatc ttggggcaac tcagtttgcc tcaagcaagg tctttgcggg atggtacatt    240
ttccccaggc cgtgtccctt catctcactc ttctcctggc tcgctcttgt gttagggtgt    300
tgagctccac gatgtcccca aatgtgcccg gacgcagcgt gtgccagccc ccagagtgga    360
ggcaggtggg aaagcgcggg cccagcgctg gtgagcggct ggaagcgctc gccctgccct    420
ggggacgctg gactgtcttc aatgggctca cccaggccga gtgtactcgg gcggcgaggg    480
cgaagaggtg aggtggggac acccaggcg agacgtgca tgcaaataca ctcacttccc     540
gggcggtgga gggctcaccg ctgccgggcc tcactgcttc gaagagaggc agcgggttag    600
gctggcgaag gcggaatggg gcgctggacg acagggagga gccgggaaag cagagatgca    660
gtggcctctc ctcccctctc ctcccccatct ttctaatcca ggccaggcct gcggtcctgg    720
ccaggccgtt tcaggaacag ccagggcctc ggacgagaca cacgtccctc accgcgttgt    780
ggtccacacg aacacacaca caccggctca gcccaggcgt actcaagact tagagagagg    840
gaggcgcttg gatacagcca cgcgagctca gaaaagcgag aatccctttc tggaagccct    900
ggcccaacct aactggtgtg attccggcgc tgtcaaacta ctggggcggg ccacaggatg    960
```

```
gactgagcgg catgcacacc aggggccgcg acccgggagt gggcagaaca ggcacggcag    1020
gcaggcatcg gggcgcgggt ggtagtactc acgaggggta caggccaggc gtgcgtccct    1080
ccagggcggg ctctgcatca ctccgggcca gaagatgggc gtccggccag gcagctcagc    1140
cagcggcttg gggtaccggc ccacggcggc cacggccgcg gcgctggggc tgaagtagag    1200
cccgggcggc ggcggcggcg ggctcaggct gctaaagcgt ggcagtccgg ccagcagccc    1260
cgccggggat gaggcggcgg ctgcggccgc ggcagcagcc gcggcggcgg cagaggcgga    1320
ggaggcagag gcggacgagg aagaggagga ggaggaaccg gagggcgagg cggagggcag    1380
ggcggccccc gaggccacgg gcatggaggg ccggctcagg atatcgttga tgccgtgtgg    1440
ggtggcggcc gagagctgct gcgggggct gccgagggat gagagccccc ccgtggccgg    1500
gggcttcagg ccgcctgggt tgtgggtgcc cagaggcggg gagggcgacg aggaggacga    1560
cgacgaggac gaggaggagg gggggccggc aggcagcggg ggatacgcgg cagggtacag    1620
cggggtcttc atctcggcca tgctgtgcag ggcggccagg ggagggctgc tgagcaggaa    1680
tgcgctctgc cgggtgccct ccattgcccc caccgctaac atcccacggc cacgccggag    1740
accgtagcct tgcagcgagg gcgctggctg gtgccccccg cggggctcag aggagccgga    1800
agcgccgagg gcgcgagcgg agaggcactc ggcgcgcccg gaggcgagct gccaactgaa    1860
ccaaaaatgc cgctgccggg agttgctcgc ctagctgcgc agcagagatg tccaaaccct    1920
ccacgcggga ggcggcagct cgccgagaaa agcaggcgtc ccggcgggct aggcagtcct    1980
ttcgttccgc gagtcctaga ttcgatccct ggctattctc tcttcctcac ttttcctagc    2040
tgttcaaagt gcgctacttc tcatcttctg ccccgggaa ataagcaaaa caaaacccag    2100
gctggctccg gagagtttgt agcaaagtta gttgccgaat ctccactttg aagttggagg    2160
gtgggggtgg cttgctttct ttggggaggt tcaaaggacg ccttgtgcag cccgtggcgc    2220
tcctctgatc ttactgggat gctctgctct ttcggtcgcg cggctgattc gcattcgacg    2280
ctcactgtgc ccggggagaa agcgcatcca gcccgcggga gatctagcct ctgtgcgggc    2340
ttcctccgcc cacgctgccc cgggctgctg cgccagaaag ggcagtgcca cggatccccg    2400
cggctcccag gtcctcacct ccacccgcct tgccctctgg cccacggggc actggagttg    2460
caatattgaa aagaaaaagg gggaggaaaa acacagaaaa acaaaagact aagtgtgaaa    2520
agtctgacgg ctgggtttcg gcgccgctcg tcagtccact tctgcaaacg ggcccggcga    2580
cccccgcccc accccgctc cctctctccc tctcactctc agcctttgac tctcctctct    2640
ggcattttct tcgcggcttc ccaggcttcg gtcttctaag tcctgtcctc tggccaaact    2700
gaccctctcc gcggctcctc cgctctttct ctcctttcct ctctccctcc gggcctgaca    2760
gttcagatga agctctcaaa ggtaataaaa catttgcatc actccctacc cctctttagc    2820
tgggggacga aagggagggg gaagtggggg accaaaatga gaactttgag ggacgtcact    2880
ccgaggctgc gggggccggc gagccggggcg caggccgggg gcgtaaccac cgtgtccaat    2940
agctcgccgc ctcgatcctt gcgtcgcccc tgggctcgc ccactcgggg gcgccgcacc    3000
ctctgattgg ctgaggcggg ccaggcgtag ggccgcgccc gcctagtccc ctcccgctcc    3060
ctacttcttt ctcctgtggg cggggccagg aggggcggga gctggtgagt ggtgcggttc    3120
cgcgctgggg ccagtggccg                                               3140
```

<210> SEQ ID NO 178
<211> LENGTH: 524
<212> TYPE: DNA
<213> ORGANISM: Homo sapiens

<400> SEQUENCE: 178

```
cgcggtgcgg agcgtctgga gcggagcacg cgctgtcagc tggtgagcgc actctccttt      60
caggcagctc cccggggagc tgtgcggcca catttaacac catcatcacc cctccccggc     120
ctcctcaacc tcggcctcct cctcgtcgac agccttcctt ggccccccac cagcagagct     180
cacagtagcg agcgtctctc gccgtctccc gcactcggcc ggggcccctc tcctccccca     240
gctgcgcagc gggagccgcc actgccact gcacctccca gcaaccagcc cagcacgcaa      300
agaagctgcg caaagttaaa gccaagcaat gccaagggga ggggaagctg gaggcggcag     360
aggcggcggc gggagagctg tggggttgtt caggaaaagt tgggctgggg gctgaggcac     420
ctgaagcagt gaaccaggac taggtaggaa gcaagagcat cctcctgcgc aagcggagac     480
gcaaacgcgc tcctgaaccc atgcaaccgc ccggcccagc gccg                      524
```

<210> SEQ ID NO 179
<211> LENGTH: 1966
<212> TYPE: DNA
<213> ORGANISM: Homo sapiens

<400> SEQUENCE: 179

```
cggagccaga cctgacggtg gaaatctctg agagcgccac gccaggcact cgcttcccct      60
tggagagcgc attcgaccca gacgtgggca ccaactcctt gcgcgactac gagatcaccc     120
ccaacagcta cttctccctg gacgtgcaga cccaggggga tggcaaccga ttcgctgagc     180
tggtgctgga gaagccactg gaccgagagc agcaagcggt gcaccgctac gtgctgaccg     240
cggtggacgg aggaggtggg ggaggagtag agaaggagg gggaggtggc gggggagcag     300
gcctgccccc ccagcagcag cgcaccggca cggccctact caccatccga gtgctggact     360
ccaatgacaa tgtgcccgct ttcgaccaac ccgtctacac tgtgtcccta ccagagaact     420
ctccccagg cactctcgtg atccagctca acgccaccga cccggacgag ggccagaacg     480
gtgaggtcgt gtactccttc agcagccaca tttcgccccg ggcgcgggag cttttcggac     540
tctcgccgcg cactggcaga ctggaggtaa gcggcgagtt ggactatgaa gagagcccag     600
tgtaccaagt gtacgtgcaa gccaaggacc tgggccccaa cgccgtgcct gcgcactgca     660
aggtgctagt gcgagtactg gatgctaatg acaacgcgcc agagatcagc ttcagcaccg     720
tgaaggaagc ggtgagtgag ggcgcggcgc ccggcactgt ggtggccctt ttcagcgtga     780
ctgaccgcga ctcagaggag aatgggcagg tgcagtgcga gctactggga gacgtgcctt     840
tccgcctcaa gtcttccttt aagaattact acaccatcgt taccgaagcc ccctggacc      900
gagaggcggg ggactcctac accctgactg tagtggctcg ggaccggggc gagcctgcgc     960
tctccaccag taagtcgatc caggtacaag tgtcggatgt gaacgacaac gcgccgcgtt    1020
tcagccagcc ggtctacgac gtgtatgtga ctgaaaacaa cgtgcctggc gcctacatct    1080
acgcggtgag cgccaccgac cgggatgagg gcgccaacgc ccagcttgcc tactctatcc    1140
tcgagtgcca gatccagggc atgagcgtct tcacctacgt ttctatcaac tctgagaacg    1200
gctacttgta cgccctgcgc tccttcgact atgagcagct gaaggacttc agttttcagg    1260
tggaagcccg ggacgctggc agcccccagg cgctggctgg taacgccact gtcaacatcc    1320
tcatagtgga tcaaaatgac aacgcccctg ccatcgtggc cctctacca gggcgcaacg     1380
ggactccagc gcgtgaggtg ctgcccccgc tcggcggagcc gggttacctg ctcacccgcg    1440
tggccgccgt ggacgcggac gacggcgaga acgcccggct cacttacagc atcgtgcgtg    1500
```

| | |
|---|---|
| gcaacgaaat gaacctcttt cgcatggact ggcgcaccgg ggagctgcgc acagcacgcc | 1560 |
| gagtcccggc caagcgcgac ccccagcggc cttatgagct ggtgatcgag gtgcgcgacc | 1620 |
| atgggcagcc gccccttttcc tccaccgcca ccctggtggt tcagctggtg gatggcgccg | 1680 |
| tggagcccca gggcggggc gggagcggag cggagggtc aggagagcac cagcgcccca | 1740 |
| gtcgctctgg cggcggggaa acctcgctag acctcaccct catcctcatc atcgcgttgg | 1800 |
| gctcggtgtc cttcatcttc ctgctggcca tgatcgtgct ggccgtgcgt tgccaaaaag | 1860 |
| agaagaagct caacatctat acttgtctgg ccagcgattg ctgcctctgc tgctgctgct | 1920 |
| gcggtggcgg aggttcgacc tgctgtggcc gccaagcccg ggcgcg | 1966 |

<210> SEQ ID NO 180
<211> LENGTH: 3844
<212> TYPE: DNA
<213> ORGANISM: Homo sapiens

<400> SEQUENCE: 180

| | |
|---|---|
| cggattacgc agccacttct ccctgcaaag tgcacgctcc cgcgccgcgg ccgcacgccg | 60 |
| agcacggcaa gcggtgcccc gccgcgcgcc cctacacacc tgcctcggcc ggggtccgtc | 120 |
| tctcgccgtc tacctgttgc agcgcttgcc accgccacga aacccctgct gcggagcccc | 180 |
| cctaaatcca accacatcca ggccagcgag tgccgctctc cctgcagcgg gagagcccga | 240 |
| ggcagcaacg ctcttgcacc caggtgactg actgcacggg cttcctctga gcagcctgaa | 300 |
| gttggctccc gtctcccggg cccaatgaca ccccgggcgc ggaggggctg agaggagggg | 360 |
| gcaggggcag gggcagggcc agggcgggca aaaagggag ggagagaggg cgggcgaaag | 420 |
| cccggagggg gagtgggcca gctggagggc tggcccttt aaaagcgggt cacatgtcca | 480 |
| gataaagttc aggttgctat cccgcccccc tgaacccttc ctattggccc gaagagaagc | 540 |
| aaggctccac gccgcacggg tcaggcgggc ttcttattgg acaatccagg ctgtcagtca | 600 |
| ccaggcgggc gacatgactg atacaaagtt gctgcgacac agcctggact cggcagcttc | 660 |
| cttaaagccg cagccgcggc gggagcttgg ggtgccgggc ggtggctaca tcaggcggcc | 720 |
| tccgcacgct gcccccaccc ccatcgctcg gccgccccaa acttgcttac gtccaccctg | 780 |
| ctctccttct gaccgacccc aggatatctg agagatgtg aaaagtgtgc tgacgcggaa | 840 |
| gaagtcggtt tttccgcgag caaagtgtcg tcccctcacg ctctccacct gcagctccag | 900 |
| gtgagctgca gcccagaccc tggcgccgcc caacagcgtc cgcgcgcggg gaggactctg | 960 |
| ggtgggcttc acccgaccct cgaggttcct ctcccagccc cttccactg tctccagagt | 1020 |
| tacctctcag cagagcagca gcagccttcg ctgccagcga gcaagacgat cacgttcact | 1080 |
| cgatttgaat ttagttgttt taaccgtgct ggaaaaaccc tttaaacaca gctttcctcc | 1140 |
| catcccttag accctaaca ccaaaaaaaa aaaaaaaaa aaaaaaaaa aaagagaga | 1200 |
| gagagaaaga taaatgaaag aagtggcagg gtcaagagct gctcctctac ttccttataa | 1260 |
| ttttgtcact gtacttacta ctttagtatt ggatttttcc actagttcaa tttgaaagca | 1320 |
| agcttaccat cgaggatatt cacgttataa tgggtggagg gggtgggtca cataagtggg | 1380 |
| agaaacagac aggagggggg aaggaaccaa actgttttct aaggatcggt tgtctgcatg | 1440 |
| aagaaatttc ggtttccctc caaccgcccc ctcctcgatt ctcctcccgc ccacccaaat | 1500 |
| gctgcagtta ctaagcaaaa ggatgggggtt cctaactttg atttctaagg acttttaggc | 1560 |
| ttctcatgta aggccccgtt ttaggctccc cgctggcccg gagtcagcat cagtgacgta | 1620 |
| tacacctaaa tctggtcccc cggccctcgg cgacccgcag cccggcggcg gcagctgtgc | 1680 |

```
ggcctcccgc tcaccctcg cttcgcgccc gccaaagccc gaggcggggg accgggggac    1740
accctgtgcc caaaggcccc tcctctcctt aacagttagt taagctccgg gattccggac    1800
ccctaaccca gggctgagac ttgaactctc agccgctcca gtcaggaact ccctggagat    1860
aggggcgaca gcggcagcgc cgcgagctgg tcctgacccc agactctaat gcccctcggt    1920
ccccagcttg gagctgcccc cggcgtcccc gcagccagga gtccccgccg agcgtcccaa    1980 cttcccgcg gggcccaccg tcacgcgcac tctcccggcc cagcgaactg ggcatcgatc    2040
tcacgtcggc agagcgcggg cggcgggcgg gagcaagggg agtcccggac ctagagcctg    2100
ggcacgcgag gcggcggcgg ctccgcaagc gttgccgaat tattcattat taaaggaatg    2160
gacgtgtctc ttttactaag tttttatctc ctttgaggag ggccggtctt gccctggatc    2220
tcagcttctt gcaaaatcta ggttagaacc gtgcaggggc agccgccgcg atcactcgcc    2280
cgccacccag cacccttgcc ccagggccgc cagcgggcaa ctcgtctcct gcccgcatcc    2340
cacctccgct cgccaacccg cgccctctgc cctgggcgcg caacctgcct tgcccggggc    2400
cgcccctgcg ctctccggac cccctctcgc cgctgtcagc gcaaagtgac tgtcgctgca    2460 ctcaccttt ctaggacatg gtggggaggc tgggcgggg gaaggggaac ggctagactc    2520
ccgccgccgc tgctgccgcc gccaccagca agtccaatat tggctgatcg gcggtgagga    2580
tggagaggat gataatcccg gcagtggcag tcgccctgct gacggtgggt agagcaatag    2640
tgctgttacc ctacaagagg cggcgaggca gcggcgccaa atcgcgcaga gggggacgcg    2700
ggcacccgcc cgcccccagc ggcggcggcc gggcctctgg cgggcccctc tcccgggggct   2760 gcgcgtccgc tcggcgttga cagcggcgtc cctgggagcc gggaagtccg gcaggaggat    2820
cccgcgcccg ccgctccgca gcgccactct ccgcgccccc tccccgggcc ctgggtggcc    2880
ggtgacagct ccggcggccg agcgcgtgtg tgagggggcg gtcgcagggg gagcctgcgc    2940
ccccctcccc gggtcacgcc ctcacgagcg ggaggaggcg gcaccgcgtc cggccacccg    3000
cgggtgggaa acgggcaggg gcgccggcag ccgccctccc actacggcca ctgacaacct    3060
ggaggccaaa ggaaaactga gcccaaatgc acgcaccccc ttcagccctg ccgcagccc    3120 tccaaagtcc ggccctgacc tcgcgcccgg cttcaggtgc agttcccacc tgcgggggga    3180
ggcgagggct ggggacctcg cgcggggggc gggaggaaa agttttcttt tcctgctcct    3240
cggctgccca ccccgccagg ctgctcctct ccccgcccct ctcgggctcg ccgcgcctct    3300
gccccacccc cgccgtgggg gggcgccgag gagggagcgg gcgtctgtgc gcggaggcgt    3360
gcggggagct ggctggggcg ctgcggtcgc gaccggtccc ctcgctctga cggcggctca    3420
gacgcccgcg gaggcggctc ggcggggcaa gccgaggaag gggccgagag ccgggacccc    3480
tcctcctccg ctcgcggcgc gccgcgcgcc ccgcgtctc ctggcgcgcc ccgcgcgcct    3540
cgtgcccgct cgggcagaca cctacgcaga cgcgaaagtg aaaggggggc gactgggccc    3600
ggcaggcggg cggccggcgg cgcgcgggca gcggcaggg gacagaggat ggatgggtga    3660
acccggatcc cgggattctc ccgcgcccgc tgcccctctg cggagcctcc ccggagtccc    3720
acgcccccac cccggccacg gagatcacca cgtcaggaga tatgtatgcg tgtgcatgtg    3780
tgtgcgcgcg tgttcacgcg cgtgtgcgag gtacgcttct gccccagact cttccccgc    3840 accg                                                                 3844
```

<210> SEQ ID NO 181
<211> LENGTH: 623
<212> TYPE: DNA

<213> ORGANISM: Homo sapiens

<400> SEQUENCE: 181

| | | | | | |
|---|---|---|---|---|---|
| cgagaagctg | aacgagctgg | ccgaccagga | cttcccttg | cacccgcggg | agaacgacca | 60 |
| gctggatttc | atcgtggaaa | ccgaggggct | gaagaagtcc | atccacaacc | tcgggacgat | 120 |
| cttaaccacc | aacgccgttg | cctcagagac | agtggccacg | ggcgaggggc | tgcggcagac | 180 |
| catcatcggg | cagcccatgt | ccgtcaccat | caccaccaag | gacaaagacg | gtgagctgtg | 240 |
| caaaaccggc | aacgcctacc | tcaccgccga | actgagcacc | cccgacggga | gcgtggcaga | 300 |
| cggggagatc | ctggacaaca | gaacggcac | ctatgagttt | ttgtacactg | tccagaagga | 360 |
| aggggacttt | accctgtctc | tgagactcta | tgaccagcac | atccgaggca | gcccgtttaa | 420 |
| gctgaaagtg | atccgatccg | ctgatgtgtc | tcccaccaca | gaaggcgtga | agaggcgcgt | 480 |
| taagtccccg | gggagcggcc | acgtcaagca | gaaagctgtg | aaaagacccg | caagcatgta | 540 |
| cagcactgga | aaacgaaaag | agaatcccat | cgaagacgat | ttgatctttc | gagtgggtaa | 600 |
| ggagagggct | tctgtgcccg | acg | | | | 623 |

<210> SEQ ID NO 182
<211> LENGTH: 1423
<212> TYPE: DNA
<213> ORGANISM: Homo sapiens

<400> SEQUENCE: 182

| | | | | | |
|---|---|---|---|---|---|
| cggcgggtac | gttggggatg | cactcgcgca | gttcggcgaa | ggcgctgttg | atgctctgag | 60 |
| tcctgcgccg | ctccttgcgg | ttggcggtgc | ctcggcgctt | caccgggcgc | ggccccccca | 120 |
| ggcccggggg | cccggcgccc | ggcggcaccc | ccccgtaatg | ggagtggtcc | aggccggcgg | 180 |
| cgccgctggc | atactcgggg | ctgtaggaca | gggccatgct | gtagtcgggg | ggcgacatct | 240 |
| cggggtggcc | gatgagccag | ccatggaagt | aggggttctc | ctcatggctg | cagcggctgg | 300 |
| cggcggcggg | ggcagctgcg | gcggcggcgg | cggcaaacgg | gtagccctcg | tggtgcacca | 360 |
| ccgggtggtg | gggaaaacca | cctaccagac | tcatttcgcc | ctccgcgccc | ctccacgcgc | 420 |
| cccagcgtgc | gcgcagcccc | gccgcgccct | cggcccgggc | ccctgcctca | gcgctcggcg | 480 |
| tcctccccca | cccccaccc | cccagcccc | gggcgcccgg | gccgcccgg | cagccgcaga | 540 |
| gggggctgct | gcagcccggg | cccgtcccc | ccgcctggcc | agccgggccc | gcctcagcag | 600 |
| cgctgcggcc | gccggctccc | catggggcgc | ggcgagctgg | tcctggcacc | gtgcgcccct | 660 |
| ggccgccgcc | gccgccgcct | ccggttcccg | ccttgctcca | cggccgcgc | ttcggctcct | 720 |
| gcttcccggg | ctgctgcgcg | gaggcagaat | cctctcgtgc | tcatacaaag | gtgccggggc | 780 |
| tcccgcgagg | ctggtacgcg | gagtctcggg | aatccaagcc | cggccgcgg | tcctggcacc | 840 |
| gaagctaacc | cggaatccag | gggcgagtct | gagccgcggc | tggaggagcc | ggtccagctg | 900 |
| tgccgggggg | cggcggggtc | gactgctcac | tgcaaagcta | cctccgtgcg | accctccct | 960 |
| tcccgcctct | tccctcccc | ccaccagccc | gatctgggtt | cttgggcgct | tattgtttta | 1020 |
| atgaaatttt | tggttgttgt | tgttttggtc | cttaaatgtg | attttagctg | cgagtaacgt | 1080 |
| gtcctcgctc | ctctcgcgct | ctctcggagg | gttttcagag | aggtctcagt | gcatccattt | 1140 |
| tctcagatcc | tctcctttcg | gggcaaggat | ctggggccct | gaatgagcct | ggagctcga | 1200 |
| agaccgcggc | tcgggctctc | ggagggctct | gcgcggtggc | cgaggaagct | ccggggtgac | 1260 |
| ggcggtggtt | ctcctgggct | ggacgacgtg | agggagcaa | gcggattttc | ccagcaagat | 1320 |
| ctccatgtac | agctacatct | ttagggccgc | tcgggttaat | atatgtcgtc | agaggctcct | 1380 | cacgccaatc ccggggcggc aggggcggcg cctcgagctc tcg  1423

<210> SEQ ID NO 183
<211> LENGTH: 2549
<212> TYPE: DNA
<213> ORGANISM: Homo sapiens

<400> SEQUENCE: 183

| | | | | | |
|---|---|---|---|---|---|
| cgagattggc | cgcagatgcc | ccgacgggat | ggcctgggga | gccgaaagct | gtcccagcc | 60 |
| ccggacagct | actgcccacg | ccgcgcaggc | cagcctcaca | cagtagcgaa | tctccttcac | 120 |
| gcgacttcct | cgcaggcctg | tgaacccgca | ggggaggcgg | aggtcggttc | aaaccctgcg | 180 |
| agagcccctg | cccagcgcgg | agtcctgcac | acggtggaaa | gtccttacgc | attagcgggc | 240 |
| aggattaaac | gacttcacac | cacgaggtgc | aagactgggc | ttcggggcct | tcctcggtgt | 300 |
| tgctatttta | aaagaagctg | ctcagtaacc | cagaagaaga | tgacggggga | cggtggtgta | 360 |
| gacccggctg | gagaggagtc | cagggcctgg | gaggcgcccc | ctctgactga | ggggctgggg | 420 |
| accctgaagc | ttggcgtcca | ggccccgcca | gcgctgcacc | cggcattgtc | ccgcctgggg | 480 |
| caggcgtccg | gtccctcggc | agtgcgggcc | agcacgtacg | tagtagctgc | tgaataaata | 540 |
| aatgcctatg | caacagggaa | cgtcccggcc | caccccggcc | gggccagggc | ctaggaaggg | 600 |
| cgggcgtccg | cgccgccgt | gggtccctcc | ggcgtggccg | cccacacctc | ctggccacgg | 660 |
| cggggctgcg | gtgggggac | atcctgggc | gggcggctgg | acggaaggga | ctagagtcgg | 720 |
| ggcgcgtcca | cggccaaccg | ccccgaacca | agcaggggag | gccagggacc | aggagcttcc | 780 |
| ggggccccgc | ggctggagcg | cccggacgcg | aaggggcggc | gggtgacggg | gcgcggtgcg | 840 |
| ggcggctaca | gggccggacg | ggagttcctc | cgctttccgc | cgcgcggctc | gcggtctcag | 900 |
| ccgaggtcat | cgagggccag | gagccctggc | ggaggccccg | ccgtcccgga | cccaccgacg | 960 |
| cactcccagg | gcttggcgct | ttcccaccac | cccggaccgc | ccttggggtg | ccggaggggc | 1020 |
| tcggggcgcg | gcgtggggag | cctttgtgcc | ctctccgctt | gttgaggttt | tttctccgga | 1080 |
| ggagagctcc | ccgcccgcca | cccctttcct | ctcgaaagtt | ttgtggtttc | cctagaagac | 1140 |
| gaaagaggtt | gagaaggttg | cggagacttt | tgcaatcttc | cccgtccaga | aactctaaaa | 1200 |
| cctctcggcg | tttggcccag | gggagctatc | tggggtcaag | gggagggagc | tggccgcaca | 1260 |
| ttccttcgcc | cgccttcctc | ccacctggag | ccgcggcccc | cgggggcagt | gcgtccgagc | 1320 |
| tggtgcggcg | acgccggcag | cggcggggtt | aagctcagga | atgcggcgcg | aggaatgcgc | 1380 |
| atgcagatga | ggcgggcggg | cgcatgctaa | tcgcatgcaa | atgagggcc | cgccgctgcc | 1440 |
| gcggcagcgc | cgcagcttcc | cggatccgag | cccagacggc | ggcggctccg | gcagcctggg | 1500 |
| cgccgcgacc | ctcggcggcc | agaggggac | ggggcggagg | aggaggaaga | ggcggaggca | 1560 |
| gcggcggcga | gggggaggag | ggttcgctcg | ccggctccga | cgcagacatg | gtggactgat | 1620 |
| ccgcagcggg | gccgcgaaca | gcgtttcctg | aggcacctcc | cgcgcgtggt | tccgccgcgc | 1680 |
| cccgcgccct | gcgcccctca | gccccctcgcc | ggcgcccgcg | tcgcgggttg | gcagcctagc | 1740 |
| ccggcagccg | cgttcccgcc | gcgtcccgcg | cccggtacct | atggaggcgc | cgctcgccgg | 1800 |
| cgaggccgcc | gaccatgcct | aggagggccg | ggagcggtca | gctgccgctg | cccgggggct | 1860 |
| gggaggaggc | cagggactac | gacggcaagg | tcttctacat | tgaccacaac | accaggagga | 1920 |
| ccagctggat | cgaccccccgg | gacagtgggg | cgccggccgc | gggggcgcgg | gccgttcgg | 1980 |
| acacggcggc | tgttgtcccg | gagacccggc | cgcgcggggg | gctggggcgg | cgccggcccg | 2040 |

```
cggtgccccg aggggtcccg ggagggatgt ggggctggct gctccggcgg ggccgaggag    2100
ccgcccgtac ccgggctcct ccgcccaccg gcttcccgac gccccteegg ggacccggcc    2160 ccgaggcaag gctggagtcg ctgccccggg ccgacgccgc gcgccaggct aacggacccg    2220
aggggccacc tgagccctgt taggaacttc cctaggcttc gaggtgccca cgtggaggct    2280
gcaggacacc ttcggcctct gggcggcggg ggtgggctag ggcctcactg ccagttgggg    2340
aacgagccct ccgggccacc tgtggcatcc ctcaggccgt ccttggcgcg ggagcctggg    2400
ctgcgagctc ttggcggggg cgcccagact ggccggaggt cccgagctgg aaggggctc     2460 ccgcccccg ccgggccctg ctagtgggtg tgactgactt tgcccctcag agtttaaaaa     2520
cgcgcgtttg ggggtttcgc tgtctgtcg                                      2549
```

<210> SEQ ID NO 184
<211> LENGTH: 306
<212> TYPE: DNA
<213> ORGANISM: Homo sapiens

<400> SEQUENCE: 184

```
cgtgcgcctc agaagggcg ttaggcagaa cgcgtgccca ttctcaggtg tgctcggcgt      60
gtgtgtgctc ggcgtgtgtg tgctcggcgt gtgtgtgcac acgtgtgccg tgcgcctcag    120
aaggggcgtt aggcagaacg cgtgcccatt ctcaggtgtg ctcggcgtgt gtgtgctcgg    180
cgtgtgtgtg cacacgtgtg ccgtgcgcct cagaaggggc gttaggcaga acgcgtgccc    240
attctcaggt gcgctcagcg tgtgtgtgct tgacgcgtgt gcacacacac atgtgacggt    300
gtgccg                                                              306
```

<210> SEQ ID NO 185
<211> LENGTH: 249
<212> TYPE: DNA
<213> ORGANISM: Homo sapiens

<400> SEQUENCE: 185

```
cgaccggcgt gcaccgtctc gccattccca agggcagtgc agagcatggc acccagcacc     60
cgacaggcga ggacggccca ggacaaagcg gcagctctag ctgtcctcag attttgggag    120
ggggctccca acacggacac ggtaggtagt tggagcagga gggacgggca ggccactgac    180
cacgcaaccg ggcctctgtc agcggccagg ggcagaggga ggcaggaccg cccctggaca    240
accgacacg                                                           249
```

<210> SEQ ID NO 186
<211> LENGTH: 8587
<212> TYPE: DNA
<213> ORGANISM: Homo sapiens

<400> SEQUENCE: 186

```
cgaggctccg tgaagagagg gaagcgaggc aggggtgaa gggaccgcct ggccggtgtc      60
caggatacgg gtggctcaaa ccaccagcag aacagcatgc cgactctggc ccgatggccg    120
ccttcatccc gtagccccaa cccggcctaa agccgagaag acgccagagt gcgctgctga    180
aattcccgcg gagtccggtg tgctggagag ccgcagcggg gtgaactccc ggccccgtct    240
ctgcgtagga ggtggttcgc aaagtggccc cgggagccgg gactggtacc cggttcccca    300
cggcaccgtc cggagctctc cagccacgag gcgcagaagt ggcctgccag cgccttccca    360
ggctcaggga ggcgaggagg cccgtgcact tggcatcttc tcccgggagc cgcacggcca    420
gggccgcggc gaaacggagc ccatctcaag tgcgccgcgc ctggccgcgt cctgtagccc    480
```

-continued

```
gacgaggctg aggatggaga ggggagacgc agggagaaga gggacgcggg acttggaccc   540
aagaggccgc tccgttgccg gtctggcggc ggcgccgact cgggttcgcg cgttccacac   600
aagtttcctg tctgcctctg cacacctggt ggacaaaccg ggcgtccagg ccacaccgtc   660
ttcccccttc gcggggcgc ggggatgtt tccctccggc tgccagggg ctttctgggt      720
gaagagaaag ccctcccc cgcgtctccc ccaccctcc ctccgagaac ccgcggcgcc      780
gactgcgcct gcttccccg agctggcgac ttctccgcgg gatttgccct cgctcaaagt    840
ttgcacaatt gaaagagccc gcagagctcg gccgctcccc gcttccccaa gggcggcgag   900
gccggtcatt ggcagacgat cggttactac ccagtagggg cccacgggaa cccgcatctg   960
gagtcgggg tgtcacgcca cgccggttca gtggctcgcg gagagcgtcc gggtgcactt   1020
ctgccaaaga tgtccctgg aggccccggc gcgcgggac tcgggggaga ggccgctccc    1080
ccctcgctgt caccagcgtc caggccgccg gccccttccc cgctgcccaa acagtagaaa  1140
agcaggcgcc aagttgtttt tgttaaaaag gggacacacc tcggccgcga aactgcaaac  1200
ccggtgtcag acagctgtaa acccgtgtcg acaggttgtc agacagctgc ggggctggt   1260
cgggaaggag cccacggcct ccgggcccac acccgccgc cccgacgcgc gcgcccaccg   1320
cgagagtagc tggccgggcc ggcacggggc accacgtgct cgcgggaggg gcgggagcgg  1380
ccggcgaggg cgggcgggag gcagggaggg ggcgggaggg gagccagggg cggggcctgc  1440
gctcaagggg atgccaatca aagcatcaac ttcaaattgt gtctgaaagc cccgccgccg  1500
agcggagggc ggccgccgca gtcggcgcgc gattgcggat ccgggcgcag ccgggagccg  1560
ggcgcctgcg agcaccgggc agaggagccg cgaccggcct ccatctcccg gcccgcccga  1620
gcgcgcccgg ccggccgccc gctcctccct agacccctcg cggcgccccc tgcaaccccc  1680
tccggccggc ctccgcctcc ctccccgcgc ctttaatact cgcccgctgc ggcggtcgcc  1740
gagtccgcgg acatgtcctt cccgcagctg ggctacccgc agtacctgag cgccgcgggg  1800
ccgggcgcct acgcggcga gcgccgggg gtgctggccg cggccgctgc ggcggctgcc   1860
gccgcctcgt cgggccgacc gggggccgcg gagctgggcg gcggggcagg cgcggctgca  1920
gtcacctcgg tgctgggcat gtacgcgcg gcggggccgt acgcgggcgc gcccaactac   1980
agcgccttcc tgccctacgc cgcggatctc agcctcttct cgcagatggt gagtgcgccc  2040
ggcctccccc gcttctcctc tgtctcaccc gcgccagggc aagggtggcg ggtcgcccgg  2100
gagggagaga ctacgggtgg acctggtccg gaagaggaac tagaaaggtc cggggggcagg 2160
ttcccggtgg ccgaggccgc ggcccccggg gacgcaagag ggctgggagg ccgggcgggt  2220
gacggctggg ccatctcggc ctgggaaagc ggaaggcccg ggccagggag cgggtagcga  2280
gtgaattcag agaggccgca gaagcaggcc cgtggagcgg tgcccgcgct ggaggtcggg  2340
ggcaaactcg cctggctcgg ccagggcgcc cgggcaggcc cacggggttc ctgcaggtcg  2400
gcccggcgta gcgtagcagg acttcccttc ctggccgcgg gttccactcg cgcggcctct  2460
ttagttttcg aaccgagtct ggaaaacttg gttttctccc tctttagcag ctccgagata  2520
gttgtatccg agtttgccag acagacccct tctaagcctg gtagagtcaa tcaaaataat  2580
cttaacaata gaggtccaaa gggatggaga ggtctctcca cggcgtgagt gcgaatttga  2640
gattaaacaa aaattaagtt gcagtaatgt gctggtgtct gaaacggtgt tgattttac   2700
ttttgtaagt tgcccaagtt ttcatttcat ttgcacagaa agaaaagcac ttttcttcct  2760
gcgttacata atggaggatt aaagaaaaca gtgtcccttg gcttaaaaca aatggtgtcc  2820
```

-continued

```
tcttagtctc ccgtcccagt gggcgttaga tgtcggggca ggcggctgca cacttaattc    2880
tccgcggggg cattggcctg tctgccggtc caaatcatcc attttccttg gtctgactgc    2940
aaggtcggtg cttaaacttc ggacggctgg tgaattgtgc ggcgggcgcg gggccctggg    3000
aggcagcccc ctcctgggtc gctgcccgcg ggataaagca atttccaagc acccgcgata    3060
tctccccgct ccccgcagga gaagcgggga gtaaacgccc ctcaagtgtg cacaagcaaa    3120
gagcgggttt ccctgtaact tttcttgtag ttttgaaaga aagcggcccg gctgcctttc    3180
aggtctctta ctatcgaaaa agatcagccc ccattttgtt caggcggcgg ggaggccggg    3240
acgcgatgag agatttacaa ggtgtccttt caaaaagaat tcccagtgga gacgaggctg    3300
aaacgtcttc tttacaatta caaccaaaat aattagaaaa gcgcaaagta cattttggaa    3360
cgattgggca aaaacgaaat ctagccgcag aaatgttttc tctgcggcct cagtcaccaa    3420
actaattagt ccaagaaatc ttctggtctt tacaactttc tcagagtccg gaactcccett   3480 tgctaacatt gcaactagac cattttttca gaggatgaat attttttaca gaaattgcga    3540
atgcagttgt gtgccatttg ggaaccctgc ctgtgtttgc gggggaggga gagagcttca    3600
gtgtgaggac ctgcacccett tgtggagagc tggggaaggg agatgtttgc tgttctgagt    3660 tgttttccc acctagaggg ataatatgta aaaattattc ccacccaaaa ggtgtgtgtt     3720
tctccagctc tcccactggt tctgagagag taaactcaaa cccaaaccct gattctaggc    3780 ctaggttttcc aagccattat aattgggtgt ttggaagtca aaagataaaa ttgtatttga   3840
atgtctgtct gcgcaattta tggtaataat gaggcctaat gaggttgtta gaaagataaa    3900
atgttattta ccaaaaaacc tgatgggata atttgacttg ctgtgttttta ctactgatta   3960 taaaagaat atcgattgca aataaatcag cgcctctaaa tgcctgcaaa cagctagtgt     4020
ttgctccctc cagatcaaag tcaaacttaa gagatgaagt aactgagaag aggcctagga    4080
tactgaaccg gttcccctcc tggccgccgg tggctcccag cccttgcgtt aatatttttac   4140 aggctaagcc ttcctttgt attaaaaaaa aaatggtgt ttttgttatt gttgtcgatg      4200
atggccggga ttaaaatttt aaattacctg tcacctctaa agaccttta atgtgggtaa     4260 accattatat gcagattaat ttggaaggca aaggactgtg cttttcgttttt aaattgctgg  4320 cggatttaga ccggtagaaa acccgggatg gtttatttg attgagcccc ctctgggtgg    4380
cagagaggag gcttgggctc tgggcccttt acgtttggag aaatggcttt atcagctcag    4440
ttgaaaggtt tttccctcta gctagtgaaa gataaacttg gaaatgcagg tttctccagc    4500
ggttggtggt ggggacaggg gtcgcctagg gaacttgcag gggccgcggc ctctgttgtg    4560
ctcttctgga gagtgcactg tttgtggaac ttttctagag tggcaaaaac gatctccact    4620
gtcggtgaaa gggcagttcc tgaagtcagc tcatggtcct ggctcccctt ctccccagca    4680
gtgaactggg ggtgacttcc tgatctgccc agcacaggag agcccgcaa agcgcctggg     4740 aggccctcga gtccattgaa gcggctgctt cccactctcc cgtcttgggg actcatgtct    4800
ctctctctct ctccctttct ctctccactt ccctcctctc tctcctcgat ggatctgccc    4860
tgtggcttca gggctcgcag tatgaactga aggacaaccc tggggtgcac cccgccacct    4920
tcgcagccca cacggcgccg gcttattacc cctacgccca gttccaatac ggggaccccg    4980
ggcggcccaa gaacgccacc cgcgagagca ccagcacgct caaggcctgg ctcaacgagc    5040
accgcaagaa tccctacccc accaaggggcg agaagatcat gctggccatc atcaccaaga    5100
tgaccctcac gcaggtctcc acctggttcg ccaacgcgcg ccggcgcctc aagaaggaga    5160
acaaggtgac atggggagcg cgcagcaagg accaggaaga tggagcgctc ttcggcagcg    5220
```

```
acaccgaggg cgacccggag aaggccgagg acgacgagga gatcgacctg gaaagcatcg    5280
acattgacaa gatcgacgag cacgatggcg accagagcaa cgaggatgac gaggacaagg    5340
ccgaggctcc gcacgcgccc gcagcccctt ctgctcttgc ccgggaccaa ggctcgccgc    5400
tggcagcagc cgacgttctc aagcccagg actcgccctt gggcctggca aaggaggccc    5460
cagagccggg cagcacgcgc ctgctgagcc ccggcgctgc agcgggcggc ctgcagggtg    5520
cgccgcacgg caagcccaag atctggtcgc tggcggagac agccacgagc ccgacggtg    5580
cgcccaaggc ttcgccacca ccacccgcgg gccaccccgg cgcgcacggg ccctccgccg    5640
gggcgccgct gcaacacccc gccttcctgc ctagccacgg actgtacacc tgccacatcg    5700
gcaagttctc caactggacc aacagcgcat cctcgcaca gggctccctg ctcaacatgc    5760
gctccttcct gggcgttggc gctccccacg ccgcgcccca tgccctcac cttcctgcac    5820
ctccaccacc gcagccgccg gtcgctattg ccccgggggc actcaatgga gacaaggcct    5880
cggtccgcag cagccccacg ctcccaggta cagctccagg ccgcgtccac ctgtccccta    5940
gctgggaatg cagaggcctg gctaggtgtg gtagcgtggg gtgcagcatg agccgggagg    6000
gtaccaggca gtgccgctg agccctgggg ctgcgcttaa tccctgcttc aatttagaaa    6060
gccagacaag gccctagggc tctcccaaga gagctttgcc ctaccggcgg gcctgctacg    6120
gggtggtggt ggggtgaggg gtgacgtttt tcggcgaatc tgcctgggca gccggcagaa    6180
gttggtggga aggaggcctg ggacctctcc cgcccgtctc tccgtcctaa ctctgcctct    6240
tccgatctct cgcagagaga gacctcgtcc ccaggccaga ttcgccggca cagcagttaa    6300
agtcgccctt ccagccggta cgcgacaagt gagtgctgtt tgcttttgct atgggagaag    6360
gcggtgggga ggggggagga ggagtggtcg ggacccgggc ggagctggct gggtggcggt    6420
gggggtcgcg cagtcctagt tgaaggagcg ctccccgcca gccctgggcg ccgggcgagc    6480
cgaggagact ggagtttctc cccagccggg agccgcgctg gctgtcgacc ccgcccccag    6540
ggctccgcta ctggaaccgg cgtcgcccgg cgctgcgtcc cccactcaca gtgcccctgt    6600
cttcttgtct cgctgtgttt cccatgcagc tctctggccc cgcaggaggg aacgccgcgg    6660
atcctagcag ccctcccgtc cgcctgatta agggtcttct tttacttttg cggggggag    6720
ggggaggag ttggggaggg agggaatgtg ggaggaatta agacaaatat ttcagactgg    6780
tgtaaaggac aaatatgaca acgacgtcaa ggactcgcat ccgtcgcttt ctgcagaaag    6840
ggcttcttc ggtcccgagc tcgcgtccag gtggccaggc ctctgccggc ggctccagtg    6900
gctgcgatta tcgggttcgg taaatgcccc cacgtgcttg tgtctctttc cccccttttc    6960
tgtatataga gtggtttcag attgtaaata gcgcgtcagc gaacttgtct aaatcatata    7020
tttttgtcta ataaactaaa tgaaatgaca ccccctcccc gctcctgctg ctgtgtgcct    7080
gtccagcgtg tgtgtgagtg tgtgtttgtg tgtgaatgtg tgtgtgtgag tgtctgtgtg    7140
gcagaaacag agacagagag agagaagtgg gggatacagg gatcctggaa ccctgggtgg    7200
gacccaaggg tctgtggctg ggggagatgg gcttctcaat gggggccttt agagactgtt    7260
gccacccaag acgcaggtgc tttaaacatc tcttcgttgt ttgtggttgt tgttgaattt    7320
ttaaatattg tcactgtggc agtttcttgc tggcagttca attgctttca cgaacatttt    7380
tctgagacat aattttctca ggacataaat aagttcaatt tgaggcagtt ttacaaaacg    7440
atttttataac gtcggtaaaa acagaggaaa aagaattttt attgcgaccc cagaggagaa    7500
cttcggatta gaaaccagtt tacaactagt tgtctcaacg gcgcatcgtg gcgcctggtc    7560
```

```
gttttctgag ttgagtgtga aaataatgga gtatcgcttt gcatgtattt ttagtgattc    7620
ggttaaatca aacacgggaa gaaattggaa ggctcttta  aactccacag atgggccagc    7680
cgggatgcgg tgcggggctt ctctgcggtg tgaggtgtga acgaggggct gaggctgtgg    7740
tgggaagcga gaaagaggag gtggctttgg tctcccaggg aagccccttt acacttgggc    7800
tccacggact gcgtcctttg ccctcaggcg cgcgcaccgc gggagtccag agcaaattgc    7860
ccttagatgg ccgcggccgg gcagcgggga ggcagctggg agcagcgatg ttgggaaaca    7920
ctcgcagcgg ggctggcctc gggcgcgcgc gagtggggaa aggcctagga gcctggacat    7980
cgctgcggat ccgggacatc agcatcagtg ggttcggagc gggacgcgcg ccacgcgccg    8040
cagcaggcac cttcaggagg ctttgcggac ccggcgcggg gccttcaggg cgcaggcgac    8100
tcagcgttga atgcgtgaaa actgagccag caaacatttc caaaactgcc agcgaggatg    8160
tgggctgccg ggaaaaacgg tctagtgggg acagggccga gtcccgaagt cagagccgag    8220
tcccgaggtc agagcggccg tcctccgctc gcacccccag cctgtgaccc gcccttcccg    8280
gcttgctcga gacccactgg cgccagtgct gcgcgtgggg actccgtgca tggccgaagc    8340
gagggggaaa gtcggggcgc tggtgtcttt tcagaggttc caggaaagag ggaggctcgc    8400
gttaggacta ggaggtgcca gtccacggct cctacccgct cccgacgccc gcatccttct    8460
acagccctcc acccgttcc  tggtccctgt agaggggaag gtcctctccc tgccccgagg    8520
cgggaggaaa agcggcgaag aggaggctcg aagggcgccg cgtagggcaa gtgggccgag    8580
gacaccg                                                              8587

<210> SEQ ID NO 187
<211> LENGTH: 1500
<212> TYPE: DNA
<213> ORGANISM: Homo sapiens

<400> SEQUENCE: 187
cgtgtactcg cgcacacgca gtcaggtgtg gatgtacacc cgcgcacacc caggcacatg      60
tacacccgcg cgctcacaca ccccatccag ctacagcaga attctggcca ggctgttgac     120
cgcacacctg ctgcctcctt ggccaccctg tccacacagt agcccgatcg accccccgtgg    180 cggccgagac ccaggcccat ccgcagccct gagacctccc tagggattgc acccagcagc    240
cagtcaccgg cctccgcggc ctggccagtt gagggtggcc gtgaccgcgg ggccaggagc    300
gccgccacat ctcggggcaa atggcgcggg ggaagagttt cctcctcagc ctccccgtct    360
ccgatcgctc cgcaaaactcc agagcgaggc acgcgccttt aaaggcaggt ccgcggctct    420
cccacgtcct ggcgcccggt tttccgcacc cagtgtcccc acagctgtgc ccgggcacag    480
aggcgcggcc agaccgcact ccgcgggctg caggtgtccc ggcctctggc ggcgccggtg    540
cggcccggag gtgggagccc gcggagccac tgcagtagct ggagtcccgc cgagtcccca    600 gcccaaggc  agggcaggag cgcgcaccgg ccggaggtcc atgctgagca tcgcccgcgc    660
cggtgcccgg cagcctctcc aactgtgtgg tccccgcgcg ggcagagagg cacggactgc    720
aggccgtggg cagctccatc ttcccgcgtc ctcctcctct ggcgctgccc gctgtctccc    780
gccttccctc tgctccccgc tcgctccgc  ctcagcgccc cgctgacctc gcctcctccc    840
ctctgctctt tgtccctgca ctctccctc  ctcggtcctc tgaccccccc gccctcacct    900 cctccctcc  tctctccccct gccgccccac cgctctccca ccgctcccgc cgccccgcc    960 gccgcggctg ccactccgcc cccgcgccg cacggagctt cagtaataac cccggcgcgg    1020
cggcggagtc gctgtgggga atcctcccgc gctctgcctg ggtcgggtcc tccctgcccg    1080
```

```
ctcgcacgct gccggccggg gaccctccgg tggcccctag cccctcggag cgctcctgga   1140
tgaagccccg cgcgcgcgga tggcggggct tggcggcgct gtggatgctg ttggcgcagg   1200
tggccgagca ggtgagtccc gggcgctccc accagcgcgg aaaccgcggg tccggacagc   1260
tggaggcgag tccccgcgg ctcctctccc gcggaccccg ccgtctcacc gcgatgtcgc    1320
cgctgttttc cgcaggcacc tgcgtgcgcc atgggacccg cagcggcagc gcctgggagc   1380
ccgagcgtcc cgcgtcctcc tccacccgcg gagcggccgg gctggatgga aaagggcggt   1440
aagtccgtga ggtgggggct tctaatcctt gccatttagc agctcgtaat ctccgtgccg   1500
```

<210> SEQ ID NO 188
<211> LENGTH: 300
<212> TYPE: DNA
<213> ORGANISM: Homo sapiens

<400> SEQUENCE: 188

```
cggatcgaaa ctgtggtgaa agacctttgg ccgacggctg atgtgagtat gttctttgga    60
gttctgtgtc gcacgtcacg tgcgagtaaa tttaaatacc ctgtgatgat gatgtgtcgg   120
ctagatccac acagaccttt tctcgttggc ccgaggcagc agttctccaa gtgtgctttg   180
agaaggcctc cgttgcctgg aatgcatggc ccccggcgca cctgcacctg ctgtcttaga   240
cacctgcggt ggccgcacat cttcgtgatg ctggcgcgca ctcaagtgcg aagaccatcg   300
```

<210> SEQ ID NO 189
<211> LENGTH: 574
<212> TYPE: DNA
<213> ORGANISM: Homo sapiens

<400> SEQUENCE: 189

```
cgggctcggc ggcggtctgc tcgcacttac gtcgccagcc cagtctcgta cccgaaaatt    60
caagccccat ccgagacagg gaacccagca ggcttgcact gccacggtgg ggagcgggac   120
gcacggagca cgacactgac tgggggaagg gggcagcagt tcgcggctcc tgcagagcag   180
ctgcgtggcg ggaatgggtc cttccaccgg cggtgcggcg gccctgcgcc ggctccgggc   240
agccgagtag cccgccaccc accaactagc taagcagccg cctctgtgaa gctcggcggt   300
tccctgtgcg cctgcgaaat tttgactccg actcaccagc gaccggccac cgagccgccg   360
ctgtaggagc tgagagcacg tcttgaacac cggatctttc cacccaagac ccgacagcgt   420 gcagggggcct cgagcagtaa tttgaggccg cgtttcccgc caaggtttgg ccccagctaa   480
ccgccccacc catgcaaccg agcgggaaga aagctgtgat tcgaggggcc aggagaatac   540
gggaaaagct tctgttctgc gcacagccag tgcg                                574
```

<210> SEQ ID NO 190
<211> LENGTH: 1504
<212> TYPE: DNA
<213> ORGANISM: Homo sapiens

<400> SEQUENCE: 190

```
cgcgcacagg gagtcgagtg ctcctttgtg ccatcacctc ttctcgaagc tccaggcgca    60
gagggcaaac gctgacgccc tttcccgcct tctctccgtc tgcgagttcc ggagggcagt   120
gcactgtgca gcctccgtac ttcccgacac gttccgcctg caaaccactt aggagcttct   180
gccggcaatt tctcggatgc agcgcggagc ccagcctccc gcactgactc aggcccggca   240
ccaccccgcc tgctgagggc gtcgtcgcgg gcgccaccga cggcgccagc ctgcgttcct   300
```

```
aaaggctcca ggacaggtgt ggggctgaaa tcccgctcct ccagcatctt cccctcccta    360
ccaaaagaag gctgctttaa atattcccgg cctggagcag cagcagctaa ggacctggaa    420
agaggcccga aaaggccagg gcagggcgaa cgaacgtgct gtccctattt accggccaca    480
cgctctgact gcgggctgac cctgatcgca cacttcgagc ctgttcactc gctgggcgga    540
ccctccctcc acgctccgcg cccaggcagg cgaggtcacc cactcgaagt caccacgttt    600
gagtagccct ggttggtggg gcagcgcccc cttggccaac gccccgccct cctctccatc    660
ttccgacgct gggctctcgc ccttcggcgt ccgagagccc ctattgctgc ccagctggcc    720
ccaaaagcgt ccgaaagtcc cctcttggct tatttcagag atgccacgca ataaagaaaa    780
ggcggctact ttgcattccg cagctgctgg gacgcccggg ctgcgagcgc ggctcctgga    840
ttccagcctc ccgcccttcc caggcgctgg aatggacacg gacgcccaca gtggcgggcc    900
aggtagtgcc ggagtcgggg gcccaggccg cggcgccccg cgcctcatca cttaccttgc    960
ctttagctat caattccatg atgtagccaa attcactcat ctccccagac tccgacatgt   1020
ttacacccct tcacaaactc tggaggaccg acgcgggtgt atcgaatttg tcctttcttt   1080 tctcttttc tgttttagt ctgagttttg ccgagctccc cgcccataag ctgttaacca    1140
ggaaaagagg ggaagcgccg gggaaagcaa gaagcgggct tgggtgaaat gaaggccatc   1200
gagggctccc gggcagcctc gcccggcttg ctaggatccg ggtgcagcgg tcggggctgc   1260
gcgatctaac ggaacaaacg agggcggcgg cggcggcagc agaggccgtg aaaccctcac   1320
caggcggagc cgggcgcgcg gaggccccgc ctcctcgggg gtcgcggcag cggttcggac   1380
cgcagcggag acaaacaaac gcgcacacaa agcgggtccg cactcggctc agcgcggccc   1440
cagctagaca ttccccggcc tttatcgcat gccggcaggt tggccgtccc cggctctcgg   1500
cgcg                                                                1504

<210> SEQ ID NO 191
<211> LENGTH: 305
<212> TYPE: DNA
<213> ORGANISM: Homo sapiens

<400> SEQUENCE: 191
cgcgtcccga ttatcagtgc aatgtgatca cttgatttta aacgcaacta tgcgtccaaa     60
tggctgagtg caagaggtcg gccggagata gggccgagtg cgctgcccca agctgcgatc    120
cctgccaagc actcacggac aatgcactgg tttcctccag ggagcgtctt ccatccaggg    180
cagcagtagg agtggaatct ggagccgcac acgttgggcc tgtgatggac aagcgcggtc    240
acgtaacaga taggtagagg gatgcagcaa catataaacg gtcttcgtaa gcaatgcccc    300
gagcg                                                                305

<210> SEQ ID NO 192
<211> LENGTH: 645
<212> TYPE: DNA
<213> ORGANISM: Homo sapiens

<400> SEQUENCE: 192
cgccagtcct tgtaggcgt tcatgcgcga gcgcgagtgg ctgaaggagt ctttccgctg      60
tttctcggtg cactcattgc acttgcagaa gtagtcgtgg ggccgctcga tgcgggcgcc    120
cttgagcagc aggatgtgca cgatctcata ctcctggcag tgcgccgcca ggatgatggg    180
cgtgatgtcg tgggagaagc gcgtgccgtc ctcgtcgtag gcatagaagt cgtcgtcgcg    240
cagctcctgt tccagcgggc tgagcgtcag gcgctggccc tgcgcgaagg ccgggtggtt    300
```

```
gaggatggcc tccacgatgc gcacatagcc cttgctgatg ccagcagca gcgcgtcccc    360
cacccgtgcc aggttctcct tcttcagcag cagctccgtg acctctaggt gctcgttgcc    420
cacggccagc tgcagagcgt tctgccccat gtagtccaca cagttgaagt taagggtctt    480
ggactcctcc agcattttcc ggaccaccgg gatgttgcca tactcagccg agtccaggaa    540
gcgctcctcc tcgggcgtca gactggtgcc cttctcgttg aacatgtagg cgggaccccg    600
gatggcctgg cgacggccct tctccctcag cgttgtgtgc cggcg                    645
```

<210> SEQ ID NO 193
<211> LENGTH: 312
<212> TYPE: DNA
<213> ORGANISM: Homo sapiens

<400> SEQUENCE: 193

```
cgagaaaccg cggaatatcg gcttagagcc tgccatggcg aatcggctac agcgcgggga     60
ccgcagtcgg ctgctgctgc tgctgtgcat tttcctgggg acgctgcggg ggttccgggc    120
caggcagatc cgatattcgg tgccagaaga gaccgaaaag ggctccttcg tgggcaatat    180
ctccaaggac ctggggctgg agccccggga gctggcgaag gcggagtcc gcatcgtctc    240
cagagggaag acacagcttt tcgctgtgaa tccgcgaagc ggcagcttga tcacggcagg    300
caggatagac cg                                                        312
```

<210> SEQ ID NO 194
<211> LENGTH: 2404
<212> TYPE: DNA
<213> ORGANISM: Homo sapiens

<400> SEQUENCE: 194

```
cgcggcgtct tcctgcacga agcgacccaa gcagccccag tccgcaccgc cttggtcagc     60
gggcgctccc agcacacacc cagcgcgcgg agcgactcct cccagaggac gccgagtgtg    120
tgtgtgtgtt gcggagatta gggggtggcg gggggacgg cggcagtttc ttgggctctg    180
gcggccccac ccccaccccg gcagcgccca gcctccagga acccaaggca aggctagggc    240
gcggcgtggt gagaacgcgc ttcggctagt ggggggagcc cttgcgcccc cgcacccag    300
gccaccgcgg ggaatccctc ctccccggca tctccggcct cggcctaggg tccccgcaa    360
gccgagccg gcgcgagcgg cgcagcgggc gccaggaggg ggcggggagg gagccggcgc    420
cggaatcaca aagccgcgaa cccggctagg cggggacatt ctcataaaac cgaccctctc    480
gtggcgagca gaggggtttt tttgccctac gctcaatcct ccaaggcctc agtgccgccc    540
ccagtctttc ctggcagaag aaatagtagc cgaccactgt tggggaaact gaggccagaa    600
ttctgactta cagagggtag ctgggggaa ggggtgcgag accacctcgc ctacaaattc    660
tgctcctatg cctgccgcga tctccgttct ggctccaggg cctgcccgcg cacacactgg    720
cctacagcgg ggaccaggcg gaggggcgc tcagtgtga acgaaccca ggtgtgcggg    780
acccaccaag gtgtgtggga cccaggtgtg ctggagaccc aggtggctca gaaaactcag    840
ctaaatggct ggaagagggt cgcaatcacc gtcccaggct agcaccctct acaaaggaac    900
ctggggcccc agagctccgg ggaggcggga tggcttggcc agccaggtcc agcttgttcc    960
cggaacacca gccggttcgg cccgggagtg ggggttgggg aggcgccgac tgggaagccg   1020
gcaggccggc ccagccttcc cgctgtgccg atatttacaa taataatgtc gcgattaacg   1080
tggcggggcg cttgggctc gccgaacgac cccggcggct tctcctgcct gaatctggac   1140
```

```
tccgagagag aggaacggag tgtgtgtgtt tgtgtgtatg cgctgcaggg tgtaatgtaa    1200
tgtgacactg ttggtttaag gtgtgtgtga cacccagtgt taagatgggg gaagcagtgg    1260
attctgtgtt tgtgaccgtg aggcgctgct gtaggtgcca attcctgtgt tagagtgtgt    1320
gccatcaagc gtgtgctgag atactgggtt gtgtgtttgt gtgggtgcag tagagggtg     1380 caaggagacc tgtgctgtgt acctatgttc tggccaagaa gtgggtaaga tgatatatgc    1440
tagggtgtgt tccttaaagg aatgtggggg gtggctaggt tttgagggtt catctagtga    1500
actgtggctg tgacactcgt acatgagggc acgagattgt gtttgtgtgt ccacgtcgcg    1560
gggtgtcaca cccggttgtg ttattgctct gtaaagccac gggttgtgtg tcggtgctgc    1620
tgatcgtgca gacactgaag cggattctga gctggcgacg gtgccccagt gggcgctggt    1680
gtgcgggagg tatgtctgtg tgcacatatg cagggatgta tgtatgtgtg tatatatgtc    1740
cacggtctgg ccctctgggt gcccgcgaga agctggaagc ggctgagtga gccgaggtag    1800
ttgcccaaca agtgtgtatg tatgtgttgt ggacaacggt ccttgcttgc tccgtcctcc    1860
gggagacccc caccaaactg ggggccgcgc gcttccccaa acccatcctc cacgccgcgc    1920
gctcctggag tctccttatc cccgtctctc cgagcgcgcc caggtttggg acgcggggac    1980
tagggttctg ctcagcaccc cctccctcc ctcggcttct cgccgcggac ctgggaggac    2040
ggaatccctc agccgcatcc cctgctatgg gctcccagca gcccccacct cagccccctc    2100
gcgccgagct cgtgttgggc cccgcggcc tcgctccgcc gagcgcccct ccctcagctc    2160
ccgccggcca tgaccgcttc gggcccaag ccgctgctgc ctccaccgcc gccggatcct    2220
tacccgcctc cgggcagcgc cggccgcccg ccccgctgtc catgagccgc cgccggcccc    2280
ggcctgggct gcggctccgc acggctgggg ctggagctgc agttcgggct ccggctccgg    2340
ctccggctgg ctctgggcgc agcagcccgg cggctttgcg tccgcgccgc gctcccgctc    2400
cccg                                                                 2404

<210> SEQ ID NO 195
<211> LENGTH: 3468
<212> TYPE: DNA
<213> ORGANISM: Homo sapiens

<400> SEQUENCE: 195
cgccgcgcag agtcggccga atccagcttc tccaagggcg ggcgggtggg atgatttgtt     60
gatttgcttg ttttccacca aaccgcaggg cacctccagg agctccggga caacttacaa    120
atgaagacac agagccccg tcccttgctt cagagaacca aataacggaa ctgaatgatc     180
gtttcttcag caaagcctaa agacgcttgc gtcccgcgga gaggtgccca cgcgcgactc    240
ggctgccccc tcttcttgcg ggtccgggta gggtagggcg ggaacgcggg acgtgcccta    300
agcgggccag ccgagcgcga gacaggcgat gctgcagaag cctgcccgcc tgcgggtcac    360
acaccggccg gcctcggctg caggggttgc ggggccacgg gtcgcggggc gccgggagcc    420
gcgagcaggt gacggccgcg ccgggcagcc ccgcgggcc cgattcccga gagcctggcg    480 ccacccgcg gaagccggag gaactgcggc ttcttcccgc tcccgcgcgg aggggagagg    540
gaggcgcagc gcggaggga gagggaggcg cagcgcggag gggagaggga ggcgcagcgc    600
ggaggggaga gggaggcgca gcccgcaccg cgcaatcccg gggctctggc gggagggaag    660
gtgacttgcg tgggacgact ccaagaggcc aggcccggcc ttcgcagttc acccacgagg    720
ataccgcgac caagccacca aagcactctc tggccaggcc gagaccccttt ttcccccggg   780 ccccaagaga aaaagcact ttctcctaaa acacgaactc cccgcggagg ggcccggggc    840
```

-continued

```
tgcctggcac ggggcagggt gtgcggctgc cgtgcgggcg cgggccagag tcacgtggag      900
gcaggcggag agggcgaggg ggcccccgta aatcatcctg agggattttt ggcccaagtc      960 cctgttccg aaaggttgcg ggacggcttt gacgttgatt atgtagctgt tctctttca      1020 agtgcgcgcc cctccccacc gcagcccgtc tggtgtgcga ggattgtgtt tgaaagggag     1080
gaagcatcct tgaagtggtg ggtgatggat tgtctaaacc cttctgggac gttctgggtg     1140
ggggttttcg aggcagctca tcaataaaga ccccccctgga gagaaggggc ggctggagac    1200
cagcccccgc cgcgcagccc cgaggcccca ggcctggaac acagtcctcg gtgtggggca     1260
cagggcgtga gggaggatg agctcccct gagcagatgg agatttctcc ttgcctgggc      1320
cgtttgaccc ccaaagcctt gcagactggc cgcgtgggtg ccatgggcg atttcttggg     1380 aaaggagggc agcagaaagg cccgtgggct ctcagcgcct tggagtcagg ggagcaggaa    1440
ggggagtgga ggtgcggaca cgcctccagc caccgtgctc ccctaggagg atctcccttc    1500 agccctgta gaaccctgca tctcaaccac cctcgtgcat gtggtttacc ttggcataga    1560
tttccaagcc gctacagaaa acctgtccac ctcccccaag gtggaggcgg gagttgggag    1620
gcaggggtgc tggaaagggt cacctggctc aagccgaccc caggtctgac gggcggagag    1680
cctcgagggc cacgcccag gccagtggtg tcctctgagg ccgcaaagcc gactggcttc    1740
tggaggagca gcagcctcgg cctcagcctc ggctgggaaa agacgcagtc ggggccctcc    1800
gtgctccaaa cttgaactac tctgggtccc cacgaggagg aggctgccct ggggtcagaa    1860
actccgacgg aaatgaaggg gaggggcgt aggttccctg gcacagctcg gcctggagag    1920
gcagcctggg ggcccaaact catctagggc gcgcccggag cttccccggc ctctcttggc   1980
ccatcgcgaa cgagctcccc tccccgactg ggtcggcctc gggcgccttt cgccttcgca   2040
ggccgccggg gttccgcgga gggcttgtgt ccctccctcc cgccgccgca gcccgcccga   2100
aggtcaggcc gcatccgggg cccgggggcct ttggccaggc tgcggggagg ggtggggttg   2160
gggggctccc caaagcagct tctcggaggc ggcgtcgggg cgccctgagg tccctagtcg   2220
gcctctgggc gccgagcacg tttatttat ccccacagag gatgctggag acaaaagaa    2280 atatttggac gtcagagctg atttatattt ttggaagagc tacgtttcct tttctgaaga   2340
gaagcgagcg cgcccccatat cctgagctcg gcggggagga cgagagggga gttttgatgc  2400
gccaggaagt tcatctatcg cccaggcgct caggacccgg cgccccgccg agttcgccgc   2460
cctcggaaat atttatttat ttgggggaag ggagggcagc ggggaggaga ccagccagac    2520
gggagaagaa agccctgccc gggctgggtt ggacctcca gggcgcttcc ccgcgcggcc   2580
gcagccggcc agcctctggt ctcggttgga gggcatcgca ggcgcggcct ggcgacctcc   2640
gggcgccttt ggctggtgtc ttccgtagcc ctcggcgcgc accctcccgc gtgcagtgcc   2700
cggagtgacc tcttcaggcc ccgcgggcgc ctcctgggtg ggccccgcgg ccccctccaac   2760 cctgcccagc gtgtgtgcgc ggcctagcca tctttctccc cagcctggga aggcgggcgg   2820
gaggagggga tccgaggccg ggggccgcgg agcaaaaggc acgcggaccc ctaaacgacc    2880
cccgagcgtt gccacagccg ggagggcgga gggaaggtgt gcagagctcg ggggtctccc    2940
aggacgcagc ttggctccta ccggtttcca aggcatctgc aagctctgtc ctgcgaccta    3000
aagcatgggg acgtcccttc cagcagcatc agtgggcgaa aagttaacat gctgagggcc    3060
accggcaccc acacttgctt ccaggaatac ttgcggtaca ggcttcctga cttatttct    3120 ttagccgctg ggtgccccc cttcttcccc cgttgggaga cgcagaccga ctctgttcca   3180
```

-continued

| | | |
|---|---|---|
| acctaagccc cttctctctg cctttggac aaagcgggcc gcctctgctc tccactcact | 3240 | |
| ccccgcaacc ccgcaactcg ccaccccctaa acgcagcggg ctgtaggcga agtcgaagag | 3300 | |
| gtgctccgcc tggtaccgcg gcctgcgcac tgggatcggg gcctgcaggc cgctgggctg | 3360 | |
| gctcctggga tcatcccaag gttttggtct cgcaaccgag gggacccgcg cccggcaatt | 3420 | |
| tgggaagtgc ggaaatgggg tgaggccggt cttcgcttga gggtctcg | 3468 | |

<210> SEQ ID NO 196
<211> LENGTH: 2654
<212> TYPE: DNA
<213> ORGANISM: Homo sapiens

<400> SEQUENCE: 196

| | |
|---|---|
| cgatgcggat tcgcgctggc gctgaacgct gagcgcaggc ggggaggctc ggcactctcc | 60 |
| gacctcagta gcgcccccaa aaccgaagtc cagccggcca gagaggacac ttacgtgcac | 120 |
| acggtcttga tgttcgtctt gtcgtccagg ccctgcgggt agttggccat gctgtcgccc | 180 |
| agcttgagca aacagtccga aaagcccttg aagaccgcat cgcacttgcc cgctgctctc | 240 |
| acggcctgca ccagatacgc tgcggggagg agggaacacc ggtcagcagc gccacgaccc | 300 |
| cgccctgccg cccactgccc tttcctgcga gaccctggct ccgcgcgcc tcatcgcatc | 360 |
| gggcggcctc tcccagcgcc cagcctcggg gctcgccagt gttaaaggtg aatgaaagac | 420 |
| gtgacccagg aatgcccgac ctgcagctaa cgctgcgtct agtgcaaatt gtcggtgtgt | 480 |
| gagcaggtgt gggtgggtgg gaggtaggtg agtccattcc tttcctccag ctccctcccg | 540 |
| catctcgctc cgtatctttt tctgttccca tcgccccctc ttctcacctc cctcatccct | 600 |
| tttatttctc tttctcctcg ctccctcctt cgtctcccaa cacttcccca gcaagccctg | 660 |
| tcacagctct cgcaatgcga tcttccattt tgaggtgaca aaaggggtct cggctgcagc | 720 |
| gtgcggggc gagaacgggg tggggagacg acagggcgtg gggtcacgca gctgaaccca | 780 |
| acgccacatc acgagaataa gcctcaggct tggcgctctg tccttggtgg gcgctcagca | 840 |
| aacactgctg aatgaatgaa cgaatatagt ccctggaagc caccagcagt taccgaaatg | 900 |
| gattgtttca ttataaaacc gattgcctac cgtggactct gtattccgag tgagaccctc | 960 |
| ggatgcaccc tctcccgccc cgctggaaag agggcagcct ggacgtcctg agacctggcg | 1020 |
| cggatgatga gtggtctgga gaggagaagg ccagaggccg ggcggggtca cggatgagtc | 1080 |
| tgcctgggtc acctccgcaa aggccaaatc cacgaacctc gggcctcttt ctctcctcct | 1140 |
| ccctgtccg ccactcggct ccccagacac ccttaacaac ccaccgccc gccaaaaagc | 1200 |
| ccgcctacac tccggacggc agcggggaga ggctgttctt ctccaggtgc cagccctgct | 1260 |
| gctgaaagtg agctcgccgc ggcccggggc tcctggcccc agctcaggac tccctgcaga | 1320 |
| gagcaggcag ggataaaagc tgagcggcgg gaggaggagg aggaggagga aacacaggcc | 1380 |
| gcacgaaggt ccaagcccca agccccaag ccccggcct ctggacggcc aaaccccgag | 1440 |
| gcgcgggact ggaaggacag gtaccaggct gcggcgcgc ggctgtggcc atctcttcc | 1500 |
| gccctgaggc cgacgaaccc ggctggaagc tgagtgccta gcggcccaaa gcagcccggg | 1560 |
| cgccgggagg gcgccagaga agcacagcgt tagggcgggg aagaaagggt gaatctcaga | 1620 |
| atcgaaatcc gcactggcgc ccacgaccct gggcgccggc ctggtcctcg gcagctttct | 1680 |
| ggcggctgcg cttgtgtgtg aatgtgtccc gggaggaccg gacacctcaa tccccggcc | 1740 |
| cccaacgcgg gcgcctgtcc gcgagcgccg ggccagacgc cgaagaggaa ggtgaccgaa | 1800 |
| cccgtagcag cttccgagag cgtacccgtt tgcaaattgc tgcaggaaga gcgaggcggg | 1860 |

```
ccttgcgctt tttaatccgg aacgggaagc actggggaag ggaccgaggt taacttcgac   1920
ctccgctggg gcagatacgt aaaccttctc aaacctccga gttcaccttA cagcgaacat   1980
taaatacCct tgcgactaca atactaacaa atcgaacact gacgtaaaat cttaagaata   2040
aacgaatctt tgttctgata gagctcgttc aaaatggaaa tacactccac acatcttcct   2100
ctataacgca tgtcacaaat acagctttgc agagaagaaa cgaaataaaa taaagtccaa   2160
tctccccgtc cacgtctctc ccacccctt gcctacaccc ccaaaactca gtggcgaaag    2220
aagcccctaa aatgcattga cattttttaa ggggaattgg ggctcgccgg gggcgggagc   2280
gctcttgtca cgttatcttc ccaggcgctg ctggagaaga ccctgcacac cgcgcatgtg   2340
tgagtgtgtg ctgtgtaaaa taagtcgtga acatttctgt cttttaaaac tgtgactcct   2400
tggactctag ccttctctgg gaggccggga ggctgcgcgc gggacggatt ttgcaggcgc   2460
acgcgtccca gcaggtcgca gcccgtgggt ccctcgctgt ccttcctgaa ccccgcttag   2520
gcgagactct agcgggtgac cctggctcct tccctgtcct ctctgccgtc cccttcttgt   2580
gcggtttcca tccgttcatt cattcgttcg acctctcatt cattccgaac ttcctcctgc   2640
tgcgtcttct ttcg                                                    2654

<210> SEQ ID NO 197
<211> LENGTH: 527
<212> TYPE: DNA
<213> ORGANISM: Homo sapiens

<400> SEQUENCE: 197
cgtttcgggt gcggggtgct gatgctgctt ttttgttgtt cgtttgcgct cgcgctcgct     60
ctcgctctct ctctgcatcc ccctcacccc ctttctcgga gactgaacta agtgaaaagt   120
tgtttcaata atcgcagctc tctgctccgc cagggccgag ggaggcgggc ggaacacgga   180
gggtgttttg ttaaatgctc ccgtcgttcg caggggctgg gacttgataa aaggagacag   240
ttttctgaaa agatttgatt gaaatggcgt gtgccagggc tgatgggagc cagcgaggga   300
caaagcgccg agaatccatg gacactcgag caattatgcc tccacgctga aggtggatta   360
gcgcgctgga aagaagcata tgtttggccc ggggcgacac ttccccccgg ctgagcttag   420
agaatgggag cgcggagagc ggctggaccc ggaatatcaa ctatctgcga agccccccct   480
tctagcccaa ctccgccagc ctccccgccc ccgccgggga aaagtcg                527

<210> SEQ ID NO 198
<211> LENGTH: 1121
<212> TYPE: DNA
<213> ORGANISM: Homo sapiens

<400> SEQUENCE: 198
cgtccgaggg tgggtccaac gggcttcgag tgttcgggag ataatgcaca cttcgcagtg     60
gatcttctcg gggccccgag cgttgcccgc ccattaggtg gcgccggtcc cctcgaacag   120
gtcgctcaac aactcccgcc cagcagccgc ccttactgcg cgcgcgcaga cttcggcgtc   180
tacttccggt gtggcccagg cggggtccgc agaaccagct atgtcggcct acggcatgcc   240
catgtacaag agcggggacc tggtgtttgc caagttaaag ggctatgccc actggccggc   300
gaggatagag cacatgaccc agcccaaccg ctaccaggtg ttttttcttcg ggacccacga   360 gacggccttc ctgagtccca aacgcctgtt cccgtacaag gagtgcaagg agaagttcgg   420
caagcccaac aagaggcgcg gcttcagcgc ggggctgtgg gaaatcgaga acaacccac    480
```

```
ggtccaggcc tccgactgcc cattagcctc agagaagggc agcggagacg ggccttggcc      540
ggagcccgag gccgcagagg gcgacgagga caagccgacc cacgctggtg gcggcggcga      600
cgaattgggg aagccggacg acgacaagcc cactgaggag gagaagqggc cgctgaagag      660 gagcgcgggg gacccgccgg aggacgcccc caaacgaccc aaggaggcag ccccgacca      720 agaggaggag gcggaggcgg agagggcggc ggaagcggag agggcggcgg cggcggcggc      780
ggcgacggcc gtcgacgagg agagtccgtt cctcgtggcg gtggagaacg gcagcgcccc      840
tagcgagccg ggcctggtct gcgagccgcc tcagccagag gaggaggagc tccgggagga      900
agaagtcgcg gacgaggagg cctcccagga gtggcatgcc gaggcaccgg gcggcggaga      960
tcgcgacagc ctgtagttac cagcgttttcc agaagagccc ctgccccgtt cctgctgcgg     1020
cctggccgtt cttggggaat ctgaccacgg cgtgcaaact gggactgcct ttccctctcc     1080
tcagcccgtc ctcctccaac ccgcgctcct ttgccctgcc g                         1121

<210> SEQ ID NO 199
<211> LENGTH: 268
<212> TYPE: DNA
<213> ORGANISM: Homo sapiens

<400> SEQUENCE: 199
cgccgcccaa aagcttattg agttcctcat cattgcggat cgctagctgc aggtggcggg       60
gaataatgcg agttttttttg ttatcgcgag acgcattgcc tgccagctca aggatttctg     120
ctgtgagata ctctaacact gccgccaaat acactggtgc gcctgcccct atccgctctg     180
catagtttcc cttacgaagc agacgatgga tccggcctac gggaaactgc aaacccgctc     240
tagaagagcg agacttagac ttggcgcg                                         268

<210> SEQ ID NO 200
<211> LENGTH: 873
<212> TYPE: DNA
<213> ORGANISM: Homo sapiens

<400> SEQUENCE: 200
cggctttatc gtaggagcgt cttcgcctcc cccgtttcca gtagaaaaga cagctttgct       60
cctttgaaag cgcagaccgc cgcacctcca gccccttctc cccggggaag taggccccgc      120
taagaatgtg ggaaggtggt ggggcggcga ctgaagtcgc ttccgattgg cgttgtccca      180
aggaagcctg cgcggattga tcggcggcag gcctccaata gagcctgcta ggcggattgg      240
ctgctacgcg gctgggccct gtttccggta cctaggcggg cagccatggt gaccggcgag      300
cggcatgcga cgccgcctct gtggcctgtg gaggcccgct tggcggcgct gcttcccgac      360
ctactggtct ttcggaagcc tcggggatgg gaacccgagc tcgccacggc ccagggcgtc      420
ctcctaggcg tccatgtgac gggtgagggc gacggccggc acttgcactt aagtctcctg      480
gcctgcggga gaggcggccg ttgggtctaa gccctggag gctcgacgg ttacaggcct       540 agcctcccgc gagctaaggc acagtttaac ttcgtgctgc ggcttcctta ggaaactttg      600
agtatcttcg tttagcgtg ggaggacatc ttttgggatg aaccggctca gtccttgagc       660
tcaccccaaa gatgatgaaa ttgaaactca gaggaaagga ttttacagg accacgcccc       720 gggctttgaa cccgttttttc ccaaccccga gcattttcta ttaagcgttc tgtttcaatt      780 atttttattcg ttcagttaat tcgttcttgg cgtcataagt atatgcccgc cgttgttctg     840
gccgtagcta tctagcagcc actccgcgag tcg                                   873
```

<210> SEQ ID NO 201
<211> LENGTH: 805
<212> TYPE: DNA
<213> ORGANISM: Homo sapiens

<400> SEQUENCE: 201

| | | | | | |
|---|---|---|---|---|---|
| cgtccgaaca | gaaatcgcag | ccgcctcctg | tgtgggcatc | tttcacggaa | atttctgccc | 60 |
| acgttcaatg | cgtacgggtc | tctagcactg | aggctagctc | aactcttcgg | ggcaggagaa | 120 |
| gttgcgccca | gccaggagga | cgccagccgc | ctccggggcc | cggaccgcgc | tcgccaaagc | 180 |
| ccttttccgg | ctcgggcgag | ggctgacgcg | gccagacggc | tccgctactc | gcgggcgagg | 240 |
| cggactaggc | ggacgaggcg | gccgaggcgg | gcgaggtggg | agaggcgggc | gaggtgggag | 300 |
| aggcggccga | ggcgggcgag | gcgcggggcg | cgcggcgggc | caggctgggg | accgggaagc | 360 |
| ccgcggagcc | tcgcttttaa | gcggaatggt | ctgggacagc | cccaggtggt | tgccagggga | 420 |
| agggaggaag | ggaaggttct | gctgagacgt | cgaggttgga | aataaaaact | tcggaaaggc | 480 |
| gaagcggatt | tagaaaagga | gggaagtcga | ggcgggcgaa | gcgggccatg | agattgcta | 540 |
| agaggaaaag | ttgagagaa | aaggaaggaa | gagaagcaga | ctcccgggtg | gcgggcgcgg | 600 |
| gccgctaggt | cagacgaaag | gtggagggat | gcagaggctc | cccaaagagc | cgagaaagac | 660 |
| acgcgacccc | tccggatcgg | gacagctcct | gaaagcccgg | cgcagagccg | cctcgaagat | 720 |
| cctaagagtg | ggcgactcac | aggcgcggcc | ggcaagctcc | tgggggactc | gggctcggac | 780 |
| gagcgcccac | aggcagcgcc | tggcg | | | | 805 |

<210> SEQ ID NO 202
<211> LENGTH: 554
<212> TYPE: DNA
<213> ORGANISM: Homo sapiens

<400> SEQUENCE: 202

| | | | | | |
|---|---|---|---|---|---|
| cggcgccgtt | ttggaaaccc | atctcggagc | gccccactgc | ctccgcggga | aggtccgacg | 60 |
| cacccggctg | tccctgaggg | aggcaggatg | gagcaagggc | aggacactgg | aggtggtgcc | 120 |
| cagcaactcc | ggcgcgcgct | tgcttcccag | gctggaaacc | ttggcccagg | ctcaacctgt | 180 |
| ctgagctgga | ccagtccagg | ccacgcgcct | tggagccctg | ctaaccaaca | gggacagccg | 240 |
| cgaccctagg | tcgtgcgaac | acctggggtc | ccggatctcc | gcttgcctgc | catcatcccc | 300 |
| caggctgctt | ggctgctggc | tcatctgccc | gcaccgtccg | ccccgccgac | tgagctcccc | 360 |
| acaaagcaca | cagaggcgca | gagccagcgc | tgttggagtc | ttttattgtg | ttctgtcacc | 420 |
| gaggtcgcag | ccccgagcca | ggtggttggt | taccagccaa | gcgagcgagt | gcgcccgctc | 480 |
| ttcggggctc | ctgggtgcca | cccggaggtg | tcctgttggt | tgcgctgatt | agagccgtcg | 540 |
| cccctctcg | ggcg | | | | | 554 |

<210> SEQ ID NO 203
<211> LENGTH: 369
<212> TYPE: DNA
<213> ORGANISM: Homo sapiens

<400> SEQUENCE: 203

| | | | | | |
|---|---|---|---|---|---|
| cgccttttgt | gccgggctgt | ggctcgctat | cgacatctcg | tccgttacca | aggctgggtt | 60 |
| tcctactgat | ttccctcctc | ctctgctttc | acaggctcgc | gcggccggac | attgtgggtg | 120 |
| tgcgtgctgg | atttctcccg | gatgctctcc | gactaacatg | gatgtcccac | cattccttgc | 180 |
| agtggaaggt | tgttccttgg | cgcagtgagt | gaagaacatg | cagcgattgc | taatgggttt | 240 |

```
gggaagcgga gactccttcc tctctctatg accatgccgt gatcgtgtct gcggtcacca    300
ctcgacgcat cctcatttct acccgaaccc aggagccgaa cgctagatcg gggaagtggg    360
tgccgtgcg                                                            369

<210> SEQ ID NO 204
<211> LENGTH: 4868
<212> TYPE: DNA
<213> ORGANISM: Homo sapiens

<400> SEQUENCE: 204
cgccgagttc gagaaagcgc tacgccgccg gtcgggctag ctccacaagc ggctgtacaa     60
gttggctgtc aaaaaacgct gatttctcct cctgtcacct aataaacccc tacgcgctta    120
tggcctcgtc ccacaatccc ccaatctcgt cccaattcga aaaccgagg aggagggaat    180 aaactgagag ataaagatcc ccccatcttg ctctttcccc gggaccccag ccttggtcgc    240
ggcgccccac taaggaggac acaggctctg gtgtgtgtgg tgtgcgagac cccgagctcg    300
aggccgagcc aaggctgggc agaaagttgc aatcacgtgc tgtcggagcc cactggagcg    360
cacagcccgc tcccctggg acgcccaggc ggaggacctg ctgcgccctc ccagggctcg    420
ggggactcca gcattcactt gcacgcacag gcgaactctg attgaaagcc cgggatgaca    480
ccgagtctgg agaaagaggg accgggggt gggctggcgg aattgcagag cgccggccac    540
agctcccctc cccgcgaacg tcgagcgag gcgggaggt gtaacctctg acctctggcc    600
gggtccacgc cctgaggagg gactggcaag ctcttgttcg acaagttcaa gctgccgaga    660
gagcttaaat agaattaatc tcttagagat cggggatcat cgctccctcg gcatgcgctc    720
tcccagcgcc gcgcacagag caaggcgcga gagagctcag gaatcgcggg aaggcaagcg    780
gaatggggag gggtagggg atgagggcct ctcttcacta ttcctccgcc ggagagcgg    840 gagcccgcaa cgcccgccga ggacgagcgg cgggagggaa cgctctgccc tccagccgcc    900
ccggtgcaga taatggaggc gacaagagat tcgctcagcg tcggatgggc cagctctgct    960
tggggaagct ggcggcatcc tcccctcggc tggtgcccaa acccactgcg cgaaggccga   1020
aggaacgcgg aacctccaga agaccccatc ctcagccctg actttccgta gatatgtgca   1080
aaatgagtaa attactcacc tcgggccaga tccaagtttt acccaacaga aggggcaccg   1140
gaccaagaat gaaccaactc acatggccat gtccggcgcg cacaatcaca cgccagcaca   1200
cagccaccca atttcttccg cgaatctatc tggcactctg gagagagggg gaaaagcgtt   1260
ttgagaaagc cccgtcaccc ctccccttcc ttcttgccgt gaaatatacg aattcatttt   1320
tattacgagc cgcaccgtcc tcaccatcac gcacgcacag agccacactc ccatattcac   1380
actttctaac tcgtaagctc cgacagcgcc tgcattttct ttgggagccg cttggaggtt   1440
cattaatatc attagcattt aaccccctcc ctcttcccat cccctccccg cacatggctg   1500
acgtcagacc ccgccaggag ttgggggaaa agctaagtgg gccagggacg ccctattccc   1560
ctccccgcgg ctgcctgtca gagcgcttct ggagatatta caggggaccc agcccgcagc   1620
gacaggcaca aagtcacggg gtaatgaact tcggggaccc ttcgccgctg cgtgcgcggc   1680
tctccccgga aacccggacc tggccgcctc ttccctcgga agatttccca gcaatctagt   1740
tttcccactc tgcgcttggg ttcggcagc gcggagcccg tctgcctctg agactgcggt   1800
agtgttttcc ttctttcctt gggagaccag cggtcggcag agattgccca cactctgcat   1860
gcctatgtag agggagagat cgaagactga gtgacaggaa tggggaaaaa gagggatttc   1920
gctccgtagg aaggccattt tcgtgtctcc atctctgtct ttcaacatcc ctctcttgct   1980
```

```
gttcttcctt cttcctcagt cttcctgtcc atctctccat ctgtctgtcc atgtgtgtgt    2040
ccatatcaag cagcattccc agcagctgcg gttttgcaag agccgggaag aaacttaagg    2100
atgcttaaat ttccactgtt ggacgaattc tgagcgccca gggagcagcg cagcgcgcga    2160
ctgacaccca cctgtcccgc ccaggagcct tgcaggctgg agggcagctg gagagcggcg    2220
gcgcccggcg gcgaggcggg cgctgccggc cgggactcgg gcagcgccca ccaaccgctc    2280
cgccccggga cagccagcat gagcaagcca gccggatcaa caagtgggta cctctcgggc    2340
cgccgtgggg cctaggcgcg cagcctgggg cgagcgagcg gggaggctgg gggaggtcct    2400
gcctggagcg ctgcgaatct gagcccctga gagggattcc agcgggcgtg tgcgttcggc    2460
ccagacctgt agaccgtgag ttggagcatt tcgtggagag gggagagccg tttcgttgcc    2520
tctggattgc ttgatccccc ctgtctggtg cggtgagaag gttacgaccc cgcagccca    2580
ccagtcggat gagttgtctc catttagccg ccaggtgctg gatgggggg ccatgggggc    2640
gggaactggg ccgcagctcc aggcggtagc acaataacac actcgctcaa aactccgagc    2700
tccagcgcgc aaaagcaact ctgtgcaaag cggattttga atggaatgct ttgcaccccg    2760
tttctagcta tttcaaataa tcctgcaaac tgggaagcag aaacaattta aaagtcacat    2820
tttccttaat cctaaatccg cgtaggtcat aactgggaa tttaaagtat ggcgaaccac    2880
tctagcaaag agaggaccaa atccctaatc ccaaggactt ttcgagccgg agcccagcag    2940
aggcaggagt gcgcggcctg ctccctccgt gcgcttctct ccttcctcga acttccttag    3000
ctgccggctc tccgaacgcc aggccgcagc tgacctctca ccaccccgag actcacgagc    3060
gcagggctaa gtgtgtgtgc gagggcattt gcttgcaccc tgcctgcgga acccaagaat    3120
gtgcaggccc gagccagcgt tgagcaggcg cggtcacggt gctcagatct cccgggggca    3180
tttcagttcc cgccatccag tgcccacgg ctgcgggctc cagggtctga ggctggggac    3240
taccgttgcc gccgcagtcc ccatatcccg aagttgcctt gctgcttgtg ttgttttcgc    3300
agatagcatt tttggcgctc tgtgcgttcc ttccctcccc ctccccctt cactcgccct    3360
cattgtcctg agtctttgaa agttgggaga atcggagata cttctgagga ctggtaatga    3420
agtctcactt aagtgggatg caattcccgc cctcctaccc ccctccaaga aggaggttgt    3480
gttttcattt tgttttgctt tgggtgctga ccttaaaaa attagagcaa aatgaacgtg    3540
aacaaaaga aaaggagaaa tgtttcgagc tggggcagag ggagcagaga aggagccctc    3600
accgcggccg gaatgcagag cggaccctgg cccaggactg ggtttccctt taggctcggg    3660
cctaccctgg ccctcgctgt tggaatctcc aggaggtaaa gcgacctcga ttttgttgc    3720
ccgcattccc gggcgtgagt gtccttccca ggaggctcag gaggccgttt ctgttgcatt    3780
ctgagcctcc gttgcaaaaa ctgaagcccg tgggtctcgg caggcctcct agctcgctcg    3840
ccccgggaca ggccctcgcc tacaccctg gaagtaagga gccccgggct ctttcgtcct    3900
tttcggggtg tggagcccct ggggccctg aaaggtgagg cctcagaggc gagggagggg    3960
tgagcgggga gctctgcccg cctgcggctg cgccccgct gtggactagg aggcaggcca    4020
accctccgga ctttggggga aaaaccacag cgggctcctt gcggaaactt tggccgttct    4080
aacttgccaa gagcctgagt gaggccttgg aagcctccag ccccgctca ggtcgggacg    4140
cggctgctga gctttctcag gccccgcagga cagcggcccc cgccggtggc gccgctgcat    4200
ttaggccctt tccagaccgg tggcggcagc aaccccgaga cttgcgtccc tcgggcccgg    4260
ggcagctagg aggtcggcgc gcagcgggcc gggtcaggac tgggtcgagc agacagagct    4320
```

| | |
|---|---|
| gcagccccg ccttgccggg cttctcgcgg ctggagagca gagcgatgtc acccggagcc | 4380 |
| ccgcctgggt ggtaacgaga ccctggccag tcacccctgc agcccagact aacttctttc | 4440 |
| aacagcctct gatggtaatt acagtaatcg aagctgccat atatctttag gcaattatga | 4500 |
| cacacaaaaa gccccgaggg gaccccctgg cgagggaagt taagaacggt tttccagctt | 4560 |
| caggaaactc cggctcgcct cacgtcggag ctcgctcggc ttgctaaatg agaggagctt | 4620 |
| tgcaacgggg tcaaccagct tgtctcgtga ccccaagtca ccttaacgtg ctgggtggc | 4680 |
| ggagtctgag gcacaggccc gctatgcccc ggaattttcg cgtccctccc tcctgggccc | 4740 |
| cgccccagcc cggttgcctg tttctaatct gccccgggag ccgcggctca gaggtctgct | 4800 |
| cagaggcagg actcgcactg gtggtggcct agagggcaac agtccggaag ctcgggcggg | 4860 |
| ggaatccg | 4868 |

<210> SEQ ID NO 205
<211> LENGTH: 497
<212> TYPE: DNA
<213> ORGANISM: Homo sapiens

<400> SEQUENCE: 205

| | |
|---|---|
| cgcggtacct gagctccgtg gaaggcctgg actcctcgga tccgctgcgg gtgcggcttg | 60 |
| tgtctcatct cagcacttgc gccacccagc gggaggcggc ggccatgaca tcctccatgg | 120 |
| cccaccacca tcatccgctc cacccgcatc actgggccgc cgccttccac cacctgcccg | 180 |
| cagccctgct ccagcccaac ggcctccatg cctcagagtc aacccctttgt cgcctctcca | 240 |
| caacttcaga agtgcctcct gcccacggct ctgctctcct cacggccacg tttgcccatg | 300 |
| cggattcagc cctccgaatg ccatccacgg gcagcgtcgc ccctgcgtg ccacctctct | 360 |
| ccacctctct cttgtccctc tctgccaccg tccacgccgc agccgcagca gccaccgcgg | 420 |
| ctgcacacag cttccctctg tccttcgcgg gggcattccc catgcttccc ccaaacgcag | 480 |
| cagcagcagt ggccgcg | 497 |

<210> SEQ ID NO 206
<211> LENGTH: 3450
<212> TYPE: DNA
<213> ORGANISM: Homo sapiens

<400> SEQUENCE: 206

| | |
|---|---|
| cgtcgcctcc cgttcaagca gcgtcccttc ccacaacccc cgtgcagaag gcgcagcgcg | 60 |
| gcccctcct cgctggtccc agacctggcg ggctcctcac acctacctgg cccctccgt | 120 |
| tgagcttgtt ggtgagcttg actttgctga aggagacggg agccttcatc cagtgggccc | 180 |
| cgaagttggg cgagtcgggg tggatgtaga cgcagctggg cgcctgcggc tccggcttgc | 240 |
| ccccggcac ccattccccg ttcacgtact tccagcggtg gttgtccgcc gccacgaagt | 300 |
| ccagcaggaa ggagtacatg gcgttggggt ccaggccaga cacgttcacc ttcagcaccg | 360 |
| gaaacatcct cctggaaaac acggggcggg cgcaggagga ccccgacact gaccaggtag | 420 |
| gccggaggca gaagctgggc acagaggcct cagttatttc ggggcacaga ggagccccct | 480 |
| ggggaacgtc cgagggtgac tcccaagctc ccccttcccc gagccctgcc aggtccaggt | 540 |
| ggcctcctca ccatctccac ggcctcggga gggaggggag gagaggacct ggcgaagggt | 600 |
| ttcagtgcag gaggccacat cccgcgggga caggcgggga ccaggcgcg cctcgcgggt | 660 |
| cccgggatgc ctccgaggtc gggacaccga agtgcgcgtt cctcctcccc aagcttccgc | 720 |
| ggagaaagcc ccagaagagg ggcttgtaga aatgcactcg agggagttaa ccagagcggg | 780 |

```
aacaaacaca aagccctcct ccaggagaaa aagggttcga cctccgggaa cttgccaggt      840
cccccaggct gcccaggcgc tggagagcgc ggcgcgcgcg ggctccggac gcgcacccac      900
ctgccgttct tggtcacgat catctcattg gtgagctcct tgaagcgcag ccacagctcg      960
ctctcctcca ggcccacgcg cagttcgcgc tctgtggggt cgcccttctc gctgcccgcc     1020
tgcagctcat tctccacggc gctcagcagg tggtccactc ggtactgcag gctcttccc      1080 gcgctctcgg tgccagggga gctcatcctc ccgtccggct cccctccccg ccgtcccga      1140 agcccagact cgctacctga gatccacctt ccctgctctt ggccgccgcc cttccgagaa     1200
aaggggcccc ttggaccgag acctgcgacg gctcccgggt cccgggtccc ggcacagacc     1260
cgggaggagg gcgcggacca agacttgggg ggaggggacg ggggcagagg ggtggggaga     1320
agttattcca cttgaactcc ccaaggctct actagtgtag gtctctgggg accgaaattc     1380
agtgccctcc ccataaatag agccgcggcg gcagcgctgg ggtgctcggc ggattgggcc     1440
gcgcacgctt tgaagtgccg ggcagcctcc cattggccga gagcggccat atcagaccca     1500
gccgggcggg tctggaggc cggggggccaa caatgggctc ccgcacgcct gtttcatgta     1560
aatccggggc cccagccctg cgagccccgg cccagccct acaccccgc ccttctccaa       1620 atgtttgcac ctccatcaaa gcggcgggc aagccccgga ggaaggtaag ctggacgccc     1680
cggcctgccc cagcccgccc cagcccgccc cagcccgcac ttccgcgagg ggctgcccgg     1740
cagcctgcga tgctccctga ttcccgcgcg gggtcctcct cgctttccca gcgcgcccgg     1800
atcccgcagc cgcgccaggc tggaacgttc gcgcggcctc acctgtcccc gctccaggcg     1860
cgcctccctc ccctcccagg gacgagcgca tttggccggg ctttgggatg cgccgcgctc     1920
gtctcgccgc agtagtagtg ctgttctcgc gcctccgatg cctcaactct ccagtctggc     1980
agtttccggt gcacctgtcc ccacacgtcc ctcgcccacg gagccccagg cggcgttacg     2040
cacacccagg atcgtggatc agcctgcccc ggcgtcgggt gtccccgcgg ctctcaccat     2100
ctggaaaagg aaggtccgcg cgcagagagg gaaatggacg gaaataagca aaagcaaaac     2160
aaccccttct gagaagtgtc ctcctcgctc tcttataaaa acaggacttg ttgccgaggt     2220
cagcgcgcgc atcgagtgtg ccaggcgtgt gcgtggtttc tgctgtgtca ttgctttcac     2280
ggaaggtggg agaaggtcgg ggctggcggg gtggtccgga ctagtgggac tcggggcgct     2340
ttccccgccc ggcccagcgc caagcggtgt cggcagcggt tgtttatta cctttcggtg      2400 agaacttacg cgaggagagc gaaggagagg tgacaatgag caggaaatag ttcagtgggg     2460
tctctttaaa cagtaacatt cctcctaaaa cgggagccca ggaaggggga aggaggcaga     2520 agctcccct tccaaggcct ggctttgcgc ttctgcacac ctcgcccatt cgctggacga     2580
gggcctgcct cgggtagcag cctctgtttc ccggtctcct gagcgggcac cccagcccca    2640 accctctag agaaagcctg cgcatcgggt ggggcagcga gttcagagga gtcttgcgcc     2700
ctagcaaggg ggctttcccg cggacatggt atctgcgccc cgcgctaagt ctcccctgcc     2760
ccctgccccc tgcccctcgc ccctcgccca gccgggctcg ctccggggtc gggaattgct     2820
ggggaagccg aaggagggat ccccgcccgg gactcgaggg atcgaccgc ctcgcggtat     2880 gcggagggct gccaggagcc agtccggggg aagggtgcct gccgcccgtg ggggacaggg     2940
ctccttctct cccttctcca acttacaccg acgagtcagg aagccggagc gtctagtccc     3000
tgtccgcatt tctcagtgtc ttttgatgtc tgggatgcat ggatattccc aggggggctga    3060 cccgaggtgg ggaagtttcc ttctagaaag aggcaccaaa aggacctcat ttgctcctga     3120
```

```
cgccggaccc tcctgacacg ccttcactgg ctcatcgggt cctgggcttt ggggagagc    3180
gtggtgcgtg ttactctcct tactccgggt attaaaatgt ctaagaggtc atcgctttgg   3240
cccaaggcct cccgaggata agataaaagg gaaagtggga ggggaggtga aggaggaacg   3300
agggtgggtc ccaggcaatt gagggcctcg gaaccctagg cacggagcg aaacctctcc    3360
tgcggcttca gggcaaagga gtcccgaagg ctggatccct cccctgcgct cggacggcgt   3420
cgcggccgct tttcccacag tcgggaagcg                                    3450
```

<210> SEQ ID NO 207
<211> LENGTH: 349
<212> TYPE: DNA
<213> ORGANISM: Homo sapiens

<400> SEQUENCE: 207

```
cgcggccggg ttgatctcca acacggcaat cttcccgcca agagggagg ccagcaagca     60
cagcacctgc agggacgcgg tttcaacatc gttagcgaca ccacccagta aaagcagacg   120
aaacgtgcat ccgcacacgt atcctaacag ctgcttcatt tcatagcag cgacatcgcc    180
ctgtcactcc taaaacgttt ttacacacaa atcccgtttt actcagccag tcgttacagg   240
atcactctga agaaagaaga aatcagaggc acgtctcata gacagggagg gccgcgtctc   300
aggactgacc ttttgatccg cagtgcggtt cctcagggca cacgatccg                349
```

<210> SEQ ID NO 208
<211> LENGTH: 470
<212> TYPE: DNA
<213> ORGANISM: Homo sapiens

<400> SEQUENCE: 208

```
cgcatacgag tccagggggct gctacaaagc gcggcgacgt ctccgcggcg agctggccac    60
tccatggtcc cggcgcagac actggggcag gcgccggctc tgtcgtcgag gcgctcacag   120
gcaggcacac gtgagctcct ggaggacagg gagagcggcc gccccgcccc tgcggagcac   180
aggacgcttc ctgccacccc tgcagagcat gggacgcttc ctgccatggt gccgtggcaa   240
tgggtggcac ctgcctgtgg ccccttctca gaaggacgtt ttaaacgcgt gaggtctgat   300
gcacagccac agggagacac agacgagcag atgtgggcat ccgagtattt acaaggtctg   360
gtggctcctg cagccgcgac acgggctgag cgcaagtgat gtgtgaggtg tccccaacag   420
atggcacggg gagcgcccac acccgccacc gcggggtctg cggaagctcg                470
```

<210> SEQ ID NO 209
<211> LENGTH: 385
<212> TYPE: DNA
<213> ORGANISM: Homo sapiens

<400> SEQUENCE: 209

```
cgcttctaaa cccaatacgc ttttctggag tcctcggaac agctggccgg ggcttttagc     60
acacgggacg ggaccttcgc ctttgcctgt ttttttttcg accaggagaa gcaggtgcga   120
gagtctgggg cttaggaggt ggaaggcggg gaaagagaat ccactaggtc ctcgtgtaga   180
gaacaacagt cgctccttag atattactcc aggacgaaaa cctgattgca aaccgctgtt   240
ccttcgaaac ttgcaaaacc cggaacagaa aactcccgcc cagccaattt tagctctcgc   300
tgaactctcc cgcctgcgtt acgtttgcac agcaactctt tgtaaatgtc cgagtcctct   360
cggaggaaag atcgttaggg cgacg                                         385
```

<210> SEQ ID NO 210
<211> LENGTH: 2949
<212> TYPE: DNA
<213> ORGANISM: Homo sapiens

<400> SEQUENCE: 210

| | | | | | |
|---|---|---|---|---|---|
| cgagagccgc | gtccccgcgg | tcgcgtggat | ttagaaaaag | gctggcttta | ccatgactta | 60 |
| tgtgcagctt | gcgcatccag | gggtagatct | ggggttgggc | gggcggcgcc | gggctcggct | 120 |
| cgctctgcgc | actcgcctgc | tcgctgctgg | caggggcgtc | ctcctcggct | ccggacgccg | 180 |
| tgccaacccc | ctctctgctg | ctgatgtggg | tgctgccggc | gtcggccgag | gcgccgctgg | 240 |
| agttgcttag | ggagtttttc | ccgccgtggt | ggctgtcgct | gccgggcgag | ggggccacgg | 300 |
| cggagcaggg | cagcggatcg | ggctgaggag | agtgcgtgga | cgtggccggc | tggctgtacc | 360 |
| tgggctcggc | gggcgccgcg | ctggcgctgg | cagcgtagct | gcgggcgcgc | tctccggagc | 420 |
| caaagtggcc | ggagcccgag | cggccgacgc | tgagatccat | gccattgtag | ccgtagccgt | 480 |
| acctgccgga | gtgcatgctc | gccgagtccc | tgaattgctc | gctcacggaa | ctatgatctc | 540 |
| cataattatg | caactggtag | tccgggccat | ttggatagcg | accgcaaaat | gagtttacaa | 600 |
| aataagagct | catttgtttt | ttgatatgtg | tgcttgattt | gtggctcgcg | gtcgtttgtg | 660 |
| cgtctatagc | acccttgcac | aatttatgat | gaattatgga | aatgactggg | acatgtactt | 720 |
| ggttccctcc | tacgtaggca | cccaaatatg | gggtacgact | tcgaatcacg | tgcttttgtt | 780 |
| gtccagtcgt | aaatcctgcc | tgatgacctc | tagaggtaaa | ctcgtgcact | aataggggag | 840 |
| ttgggtggag | gcgaggggg | tggcgcgcgc | gccccgggcg | cgtgcccgcc | gccagttgcc | 900 |
| gccgttcagc | cggactcgag | cgccacccgc | tggaggcagg | gctcatcgcc | cagcttccga | 960 |
| ccggggctg | caagggccgg | ggtcgaattg | aggttacagc | ccattatggc | aaaattattg | 1020 |
| catttccctc | gcagttccat | taggatgtac | caattgttag | gccgtcagct | gccgatcgcg | 1080 |
| cgccccggcga | ggatgcagag | gattgggggg | aggtggtgac | ttgcatttta | tttacaacaa | 1140 |
| ctttatttcc | cccgttttgc | agcccctctt | attttttgtgt | cgaggttggg | gtcggtactg | 1200 |
| accgtcctgc | cagcagctct | gaattttgaa | aatacagata | tcaccttcgg | ggaaggggga | 1260 |
| aagccattta | gccaattgga | gaaataaatc | ctgcccgcag | cagcagcagc | tacaattacg | 1320 |
| gctctgtttt | tgcgagcgca | tgagggacag | tgtccctgcc | gctcttaaat | gacaggcgtc | 1380 |
| tattaaagat | agcttttgtg | tagtgtttct | ccaaggcgag | gtcaaattcc | atacactttt | 1440 |
| ataaccgtag | tcgatttttc | tttcgtgtga | atatggtttt | cgtgtcatta | gtttgcgatt | 1500 |
| tgatttgctt | acgtatccag | cctggaaaat | cttcatcaca | gggtccggtt | cctcgagcca | 1560 |
| gccgggcccc | aagtcggagg | gttctccttg | aacccagcga | gtgggcccag | gctccctgca | 1620 |
| gccacagagg | ctgcctgggg | tctggggatc | cgtggggcgg | gttactgggg | tcttgcttag | 1680 |
| acctccagga | gtaaaatgag | ggcgataatg | gaagcattcc | ttggcagtgc | ctagtatctc | 1740 |
| tgtagttatt | ttccacggct | ccgaaagact | caagtaaatc | acaaatatag | ctgagaggca | 1800 |
| agtggagtct | ccccgctgga | ggcccggcgt | tgcaggcgcc | cctggcacgt | ctggaagcca | 1860 |
| ggactctggc | ggctcccatg | gccctgggcc | cctcgttggg | tcctgaacgc | tgctgtggcg | 1920 |
| gcgacgcggg | cgctatcgga | ggctgggagc | gggaatccgg | agccgggagc | ctaccccggg | 1980 |
| ctgtaatgtt | ccaccgcgc | ccaggttaac | tcgcctcggc | tgaggctgct | tctcttccac | 2040 |
| tgacggttgc | acacgcggga | ccgagagact | gggctctgtt | ggggcccct | ttgttcctcg | 2100 |
| agcttccttc | ctgttctggg | aggcggcttg | ggaggccgcg | acaaggccgg | gctccagctc | 2160 |

| | |
|---|---|
| ttagaccccc tctttccact ggccagagat gatttgatga tgcccttcgg gacttactgg | 2220 |
| cgagggactt aggcagagac gcccagacac gaaacgggc tcggcccagg gctctttcct | 2280 |
| ccccagcagc cccgcgtccc gaggtcgggg agctcagaga cactagcaca ggagcccag | 2340 |
| acgcattcag ggcgcacccc agaactccgg agccggttg ggcatccttg tggagcggga | 2400 |
| ctgggtgtgt gcagtgcgcc ccgctccacc gctggtattg gctgtgtgtg aggttttgtt | 2460 |
| ttgttttgtt ttgttttgtt ttgttttgtt ttgttttgtt ttgtaagaaa taaatgcaca | 2520 |
| gacgcttgca aagctccggg ctcccctgaa gctgcggaag cccccagatg ggagcaggcg | 2580 |
| gggagaaaag ttggggaaca ggcgagggca aggggcaaa gccgaaggag gttgcagcgc | 2640 |
| tggcctggtc cctgcccagg catctactcg cccgccttg cctctgagtc ctccccgctg | 2700 |
| ggctgcgtgg aattgatgag cttgttttcc ttttccact tcatgcggcg gttctggaac | 2760 |
| cagatcttga tctggcgctc ggtgaggcag agcgcgttgg cgatctcgat gcggcggcgc | 2820 |
| cgtgtcaggt agcggttgaa gtggaactcc ttctccagct ccagtgtctg gtagcgcgtg | 2880 |
| taggtctggc ggcctcggcg cccatggctc ccatacacag cacctacgag cagaaacggc | 2940 |
| cgggcgccg | 2949 |

<210> SEQ ID NO 211
<211> LENGTH: 2547
<212> TYPE: DNA
<213> ORGANISM: Homo sapiens

<400> SEQUENCE: 211

| | |
|---|---|
| cggagctggg caagccgtca gggcgcccta aggccgctga tcacgtctgt ggcttatttg | 60 |
| aataatctgt catggggacc cttgtggccc gggtcgcccg cagcctcatc ttggcaggat | 120 |
| ttacgccgcc actggccgaa ggcaagaagt ggaaggaatc ggccgtctcc cccagcgtcc | 180 |
| cagctccggc tgccctggct gccgccgctc acggacaatc tagttgtaca aaaggctctc | 240 |
| tgggctgcac tgctttcgaa gaacggccca aagtatctcg gtcctgggcc tgggcagcca | 300 |
| aggagagggg cggccagtct tggctcgtcc cgaagtgccc gccccgcccc ctctcgctgc | 360 |
| agcagccgcc tcctctcccg tagccctgcg ggccgctctt cactgctctc cagacttggg | 420 |
| gccctatctg aggcgtccca aacaccaact tctggctcct ggccccaact cgagaggctt | 480 |
| ccagcgagga cgaaggcagg ctcgagagaa acctggcggg ccagcagatc cgggaggccg | 540 |
| gcgtggaggc ggcggcggat ttgaagggag gagacactta ctgggatcga tggggggctt | 600 |
| gtctccgccg ctctcattct cagcattgtt ttcagagaag gcgccttcgc tgggttgttt | 660 |
| ttctctatca actggaggag aaccacaagc atagtcagtc agggacaaag tgtgagtgtc | 720 |
| aagcgtggga cagtcacccc ttctggccga cagcggttca ggtttaatgc cataaggccg | 780 |
| gctggagggc aagcccgcga aggagagcgc accgggcgtg ggctccagcc aggagcgcat | 840 |
| gtacctgccg tccggcgccg ccgccgccac gggcgcctgg gggtgcacgt aggggtggtg | 900 |
| gtgatggtgg tggtacaccg cagcgggtac agcgttggcg cccgccgcgt gcactgggtt | 960 |
| ccacgaggcg ccaaacaccg tcgccttgga ctggaagctg cacgggctga agtcggggtg | 1020 |
| ctcggccagc gtcgccgcct gccggggagg ctggcccagg gtcccggcg catagcggcc | 1080 |
| aacgctcagc tcatccgcgg cgtcggcgcc cagcaggaac gagtccacgt agtagttgcc | 1140 |
| cagggcccca gtggtggcca tcaccgtgcc cagcgcctgg cccgcccggc cgacccacg | 1200 |
| gaaattgatga aactgcagat ttcatgtaac aacttggtgg caccggggg gaagtacagt | 1260 |
| cacctaataa gttgccggcg cccgcgcccc cattggccgt gcgcgtcacg tgcccgtcca | 1320 |

```
gcagaacaat aacgcgtaaa tcactccgca cgctattaat ggtccgatgt tttgcagtca    1380
taatttttat agcaaaagcc atatgttttt atgtaaaggg atcgtgccgc tctacgatgg    1440
ggtttgtttt aattgtggcc aacgacgatt aaaagatcaa atctagcctt gtctctgtac    1500
tctcccgtct ccccccccat acacacactt cttaagcgga ctattttata tcacaattaa    1560
tcacgccatc aagaaggcgc gggtcccgcg tgcgagtgcg ccagcggag ccctcacat     1620 aaaattagac aataattgaa gccataaaaa agcagccaaa tcgcattgtc gctctactgt    1680
atttaaatct atatttatga tatttcataa ggagttattg tttcagaagc cacacaggct    1740
ggcgggaagt cggaaacgac caacagattc gtttgcctcg ccgtggctcc cagctgtaaa    1800
aatttacgag gacttggaaa ggttagactg ttgtgtttgg ttggcgagct ccctgtaaat    1860 aatcccctgcg gtccccggga gaggcgagtt tacccgcggc cgccctcgaa aagtcaaatt   1920
caacgcagga tccgtcccaa acggagccgc cgccggccct accagggcac tccaggcagg    1980
gaccggccgc tcagggagta ccgcgggtgt aggtccccac agctaccgc ctggagcgag    2040 gggcgcccgg gcaacccta aattcgcctt tgctacgagg accccacgga ggagctggcc    2100
aggagggagc ggccagccgc caccagggcg aaggttttga gggcctggtt ggttgtgcgg    2160
cgcgctcggt ccccggccct cgaccccacg cacacgcgcg cccagcccgc ctttctcatc    2220
agctggcaat caggattccc aggcgcaggc ggctggcgac ccagccctgt gctccagcct    2280
cagaggctct aaccatgagc gctgcaagcc tggttgcgct ccgtgaatcc cagctgggga    2340
aaaaactaca agtggcatga atggaaggca agttcggttt gggaaaaggc agcctcgcct    2400
aagagacccc gcagctccgg aacctgggag gcccgcaccg atgtggcctg tcccggggcc    2460
gcgtgagcct ttcagggctc cttcctccct ttccagctgc tactccgggc ctcgccttgg    2520
ttacctacgg ggccccggaga ctcggcg                                       2547

<210> SEQ ID NO 212
<211> LENGTH: 1292
<212> TYPE: DNA
<213> ORGANISM: Homo sapiens

<400> SEQUENCE: 212
cggcggcagc gatcggccct gaccatagag gcggccgtgg cgcggaggac ttgaccttta     60
cggcacgaga ggagggcgct ggctgagccg cagggagggg gacgctgctc tctccagcct   120
cctccaccca atagcagtcc gctcgaccca cgccagctgc gcgctcaccc cctttccccc   180 tccatttgt gcagtgtccg cagacccgcg gccggaaaca aagcccccag ccctgctctc    240 accaccttc ttgcaagctg ctgtcgccaa ccccccagac cagaggctca gagctaacgc    300
taagcccctt aaggccctct ccagggccct cttctctcgc cagccgccct cagccagctc   360
ctgaccccag ccgccctcag ccagctcctg gtaccactc tgggtgccaa ccgggacctg    420
ccggtgccac ggtcccgtgc gccgggtccc ggcctcgggc tgcgggcggc ttcggggcct   480
acagcccagc ggcgcggagc gtggcagagg cgcggggcgc agcgcagccc gaggctgcct   540
cccgcccggg cggacggcgc ggccgctggg gtgcacagcg tagccccgcg tgccggctc    600 gctctccgtt ccctcggata gctcccaccg ctcggctccg ggctcagaaa gcggaagtat   660
ttggtagaga aaaacacggt ttcttttcag ctcgtctcaa atccctttt agagaaaatg    720 ctcctgtcaa gttttatttc ccgttgcaaa ccaccttcca cgctgccaag aattaagacc    780
gggagagatt aaatacccga ttattctcct ggggagggcg gggcggggcc gggaagtggg   840
```

| | |
|---|---|
| cacccacacc aaacattcct tgaagtaggc ttgtcctgat ccagccgcgc ccggggagcc | 900 |
| ccacgaaggc ccgcgcggcc tgcggtgacg tcagcctgca gttgcgggc cactcacccg | 960 |
| cacagacacg gcccttgctg ttccgcgccg ggacctccgc cagccgtcct gccgcagccc | 1020 |
| cgactggccc gcgtgccgtc agagggaggc ccgctttaca ccggcctgag cctccatttt | 1080 |
| gagtaggggg ttcttgtaga agcgtggagg gtttggggcc gcgcctctgt ccccgagggg | 1140 |
| cgcgacatca ggtagctctc cgagttcaca ccccagtacc tggggagga cctatgtcgc | 1200 |
| cgcataaccg cccgcagagg tttggaaatc tctgagaccc gttgtaatta tttctgccca | 1260 |
| gtggatccgg ctcttcagcg tcacgagagc cg | 1292 |

<210> SEQ ID NO 213
<211> LENGTH: 1297
<212> TYPE: DNA
<213> ORGANISM: Homo sapiens

<400> SEQUENCE: 213

| | |
|---|---|
| cggtttccgg cttttggaca atggtccctc gcttaacgaa tgctaacgaa tgctccctta | 60 |
| gctgggagct gcaggaccg gtcccggcag gtctaaccaa ccgtccgcag gcgccgtggt | 120 |
| cgagagcaga gccgagacgg cggggcaggg tgccaagcgg agggcacagc ctggcagcca | 180 |
| ccgttggcgg caggagagaa tgggagaagg gagaccgct tctcagcaca agggcatctg | 240 |
| tctactcccg aacatggccg gagattcctg tccacagcct ccctccagct ctttctggta | 300 |
| gacactttaa aagcgacatt aacgggcttc ggtgcctttg gattcctaaa ttaggtttac | 360 |
| ggaaaaggaa agacttccca agaacagtga gaagaggaac tgcagcccct ccaaggccgc | 420 |
| tgcggcgcgt tcccggggcg cgccgagagc agcgcgcggc tccgtgcccc gtggggagcg | 480 |
| cgcggcgcgg ccttggattt caccgcgagt cggagggcg ggtctgagcc ttgcctccca | 540 |
| ggatccttcc gacgaacacc ccgcgggttt tagtttatcg agccaaagtg gtcccggaga | 600 |
| agcgctccct cgcagccaag ctgcaagaag tggccgggaa cctacaggcc tcgggccgac | 660 |
| ccaggaagcc tccgcaccag aaagctcgag gagcccttac ccaagtcttg ctcgaagggc | 720 |
| aaagcaaaga gccagcaccc ctgagtgtca ctgaagttcc tggatggggt gtgagtgcgc | 780 |
| gcgttccgtc cgagacctca gtctcgccca gctatagagc cgataaaggg atgtcttgtg | 840 |
| ggcgtaaggc gcttcgcgcc catctccaag gccgatgtgg tcaggaggtg aggggaaatg | 900 |
| tccttctggc agaagcccgc ggtgctgcga cgttgacccg cctggcctca ggctcagggc | 960 |
| ggcgggcagc ccagggcaca tgtagtttca gcagccgcgc tacgtgggcg ggggacccca | 1020 |
| ggccacccca cgtgtccgcc ctgggcctcc tccgggtccc aaggcgcggc gcctccaggc | 1080 |
| cttgtagcgt cttccccggg tccccgcgcg ccaggcccg cagcctgctc acaggacagc | 1140 |
| cctcggggct gcgaccctct cgctcctccc cgcggccact cgctcccgt tcatccccca | 1200 |
| cgagctcact accgcaggga ccggccctca gagccccggg cctcctcccg gcagtggaag | 1260 |
| aatcagcgtg ctaacattgt gtgcaaaact cgcagcg | 1297 |

<210> SEQ ID NO 214
<211> LENGTH: 417
<212> TYPE: DNA
<213> ORGANISM: Homo sapiens

<400> SEQUENCE: 214

| | |
|---|---|
| cgagggcctt gccgccctc ctcctcccac ccgcaagggt tggcccgcgt tccctgcgg | 60 |
| gcgagacaaa gaagcaggag ccaggacccg gctggcgcct aacccggcgc cggggccttg | 120 |

```
agcccctgag gtgtgcgcct tcctgcaagg ccccaaagaa cccgagtttt tgccccttgc      180
tgaagggttg gaagtgcggg ctggactagt gcaaacaaga gtgactccaa ccgccttact      240
tcagctcatt accgtcaccc atgaaaacgg aatgaaggac tgggaagcca atctgccgcg      300
ttcaattgga gagaaatgac tgtcggaaga ggccctgcgg taaatagcct ctgagccgcg      360
aactctatgc gccgtggccg gtggcagagg ccacacctgg cagccactcg tggcgcg        417
```

<210> SEQ ID NO 215
<211> LENGTH: 423
<212> TYPE: DNA
<213> ORGANISM: Homo sapiens

<400> SEQUENCE: 215

```
cggaaatcat cggcgactgc tgttatgagg agtacaagga tcgcaggcga gagaacgccg       60
agcgcctgca ggacgacgcg gataccgaca ccgctgggga gagcgccttg cccaccatga      120
ctgcaaggca gagggtctgg agggccttcg agaaccccca caccagcacg atggccctgg      180
tgttctacta tgtcacgggg ttttcattg ccgtctctgt catcgcgaat gtggtggaaa       240
cagtgccgtg cggatcaagc ccaggtcaca ttaaagaact gccctgtgga gagcggtatg      300
ctgtggcctt cttctgcttg gacacggcct gcgtcatgat cttcacagtt gagtatttgc      360
ttcgcctggc tgcagcgcct agtcgttacc gttttgtgcg tagtgtcatg agtatcatcg      420
acg                                                                   423
```

<210> SEQ ID NO 216
<211> LENGTH: 454
<212> TYPE: DNA
<213> ORGANISM: Homo sapiens

<400> SEQUENCE: 216

```
cgtcctccga cgcgagatgg ctgtgtgcca ccgactgtcc aaatgccctg ccaatgccat       60
cgtgaagcat ccgtgtgaag gaaaaagtcc accttaccgt gcgctgtggc atcgatcagg      120
cgtgtggaca gtcgcaggca cgcagcggtc tcccaacatc agggcacacc gcgatcaggt      180
gtgtggacag tcgcaggcac gcagcggtcc tgcagcagca gggcgcaccg cgatcaggtg      240
tgtggacagt tgcaggcacg cagcggtctc ccagcatcag gcacaccgc gatcaggtgt       300 gtggacagtc gcaggcacga gcggtcctg cagcagcagg cgcaccgcg atcaggtgtg        360 tggacagttg caggcacgca gcggtctccc agcgtcaggg cgcaccgcga tcaggtgtgt      420
ggacagtcgg tgggcacgca gcggtctccc agcg                                 454
```

<210> SEQ ID NO 217
<211> LENGTH: 273
<212> TYPE: DNA
<213> ORGANISM: Homo sapiens

<400> SEQUENCE: 217

```
cgcaggaggg ctcggcctgg gaccccctct gcgggcctgc ggctttagcc agcagaaaga       60
ggggcgtcag tcctatcccc aaagttccgc ctcgggaaag agccctgagc tctgaactcc      120
gacgaaaaaa ggaagggctc tgttccggac cgggtgggt tgggaaggg tagagccggc        180 ctcgggtgcc cttcttacag ggcctgtctc ccgctgcgtg caccaagtgc tttgaaagtt      240
tttcgcggat taaaacgaat aaaaacctcg tcg                                   273
```

<210> SEQ ID NO 218

<211> LENGTH: 3360
<212> TYPE: DNA
<213> ORGANISM: Homo sapiens

<400> SEQUENCE: 218

| | | | | | |
|---|---|---|---|---|---|
| cgagggtgaa | ggatcgccgc | aaggcaccgc | acctcccgct | gcagcccatc | ccgcactact | 60 |
| aggagaagcc | ggcgtaggag | cgccgcctgt | gtccttggct | gtggggagga | cgtcagatgg | 120 |
| caccccgcca | gacactaagc | cccaagcccc | tggcttgttg | ctaagaaaat | tcactgcccg | 180 |
| gtccagactc | agccctttc | gccctttaag | ggtcgcgcgt | gggaggcagc | tctgagaccc | 240 |
| cgggtagcgc | tggagccaca | gatttcctcc | gagaaaagaa | aggccgggat | agcttcccgc | 300 |
| tcgcccaagc | ccagatttc | cactctccag | gaaggccttg | caggtccctg | ccgcaggcct | 360 |
| tggcttcgcg | cctctctcgc | tcgccccca | cgaagatgat | tgccggttc | aaaccgggag | 420 |
| cagggagtct | gcttccttct | ccgctgagtc | cgaaggatcg | cagattggag | cgtgctccgg | 480 |
| agaccgcttt | tccgcagcgc | cggcctccga | gatccccagc | accccttcag | ccttaagttc | 540 |
| ccacgtttcg | ggtccgtggc | gccaattctg | ctaagtagca | ggctaggaat | tgggggaagt | 600 |
| cggagaagaa | acccctaagtg | tgtcgccccc | agcttccggg | atgcaggccc | gccgggggtct | 660 |
| agaggggcgg | ctgccgtgcg | tccagcctgt | gcgcaggcct | ttcgccgctc | ggcgccccag | 720 |
| gcagcctcag | tttcctttcc | tctgtttgcg | ccccagtgaa | cctccgcacc | tctcattcag | 780 |
| ggaagagaat | tccccgcgca | gccgcgctcg | tttcttcctc | tgggattttc | ctgagaatcc | 840 |
| ccaggagttg | gccacgatcc | catgggggggt | ttccttctac | ccagcccgc | gtcctggcct | 900 |
| cgtccttaac | ccccggggttg | ccttcactca | ggctgggaat | ccacgattga | tttcctacta | 960 |
| cggaagcggg | tggcgttccc | agcctgcttt | cggagcagca | cgggtttcgt | gcagggtgtt | 1020 |
| atcccgaccc | cttccccccat | ccctctaatc | tggcttgaga | agcccgtgct | ggagagaaaa | 1080 |
| acgcggcctt | aaaaaaaaaa | aaaagtttaa | ccgaaagcgt | gagagccacc | cgccggctgt | 1140 |
| tatctggggc | tgaaggctgc | ggtaatcgat | gggttatttt | tacgcggtaa | tagggccctg | 1200 |
| tgattgctct | attaaccttt | agacctgtct | gagggactct | ccggctcgca | gccccgctgc | 1260 |
| gctgggggcct | ccaggctctg | acgccgactc | ccaactcagg | cctgacacat | tccctctccc | 1320 |
| catacccctgg | aagagccccc | tccatgaaga | agctcccctg | gaccgcctgg | ctccccagcc | 1380 |
| cttgccacgt | cccttggatt | ggtgcagagc | cgccgcaggc | tgcagaaaaa | agggggaaag | 1440 |
| attagaagag | aggaggccac | aggagatggg | aagtgtcgcc | aggaagggat | gcagattgca | 1500 |
| taaatacata | aaattgaggc | tgaggcctgg | gctcccgacc | atctccctgg | gattttggga | 1560 |
| aggcaaaagg | gaggcttcgg | tctctacgct | ctgattttag | gaggcagtct | gggtgtctcc | 1620 |
| tgaacctcca | aggaatccgg | ggctgggagg | atccccacta | cccctgccca | ggaactagca | 1680 |
| tccagccggg | caccccgggt | gacccagtgc | cccacacaag | atcgagagtt | gagcccaaga | 1740 |
| ggtcaccttc | ttctctactg | gccccgcccc | tcgcccgccg | ctgcgggatg | aggaccacag | 1800 |
| gaagggggggg | cggggaggga | gaaagggaac | tcattaataa | agctgaccct | gggcaccaca | 1860 |
| gcgaacccaa | tcgacctccg | gctgggttgc | gggtgattcc | ccgctccctg | gcggtagcac | 1920 |
| ttgggcatttt | tccgcggaga | ccccagagcc | tggactttgc | ctgctgggggg | agctttccgc | 1980 |
| acagtcccgc | agcctgcgcc | cagcggaggt | gtagccgggg | ccgcgcaccc | ccgccccgcc | 2040 |
| cttgcacgtg | actcccacag | gccagtcagc | gccctagggc | cgagttgctg | ggccggggac | 2100 |
| ccgagccgcg | agctggggac | ttggaggcgg | ccggcgcagg | ggccgcgaga | ggcttcgtcg | 2160 |
| ccgctgcagc | tccgggggct | cccaggggag | cgtgcgcgga | acctccaggc | ccagcaggta | 2220 |

```
gggcttttttt cttcccttc tttgctcctt cccgcggtcc cccaaactcg gagcttctcc    2280
gcctttgctt gtctggaggt agagaggtag ctagtgggag gaaaagagac gtgcgctact    2340
cacttcaccg aaattgccca acccctgctc tgcttttgac tttgccttag caacttcttt    2400
aagtcaaagt aagacttggg ggcaaaacag agaaatattg gaagcgcctt tggattcttt    2460
ccgtgtgaac ttgaacgctt tcaatccctg tccccgtgtg cacattctcc aacccttgtt    2520
tgcatatcgc aggccgggc ctgggtggtg atggtggccg cgtgaagtta ccggactga    2580 cgggcccggg acaggctgca cggcagctcg cacatggagg gaagtagacg gaggcttgtc    2640
gcccaccagc gactccgggg acgcaggtg gcagtgccag gcagctccgc tgggcctcag    2700 ggcccccgg gagccgctct gaggtgcgga gaggctgctg agtggcggaa ctattcatgc    2760
cctttctggc cggcctcctc gccctcgggg ctggggtcca gggactgaat gctcctctgg    2820
aagctcacca ccccacctgc ccgcgctgct tctacctgaa actggccaag ggcccgagcc    2880
cggaccggag ccgtgacttc cctccgccgg ccacggggct gcccggatcc gccgggttat    2940
gtcgcttggc tttgggctca ggggtcaccg tgggcagagg ggggtgccgg ggtcgcggac    3000
tgccaccagg ttgaggaaag gagggggcctt ttggctgggg aaagagcgtg gtgggggacc    3060
cgcggccgat ggaatccctg gggcagcgcg gcccgcaccg tggaggttgg ggaagcgcct    3120
cggggaagtg tttcctgtgt tcccagaaaa ggaagacaac cgagagcagg tttcaggctt    3180
ttaaagaaag cctggggtgt ggaggtgatg ctccgcacac gtctgtgtct cctcccctgc    3240
tgcggccggc ttggttgtgc cggctagcgt gcgaccgtcc tcctcgctgc aggccgagag    3300
cggaggcgta aacccaggcc agcgaggagt gtcctataaa gggacgggga cttttcggcg    3360

<210> SEQ ID NO 219
<211> LENGTH: 357
<212> TYPE: DNA
<213> ORGANISM: Homo sapiens

<400> SEQUENCE: 219
cgtttgctcc gccgtcagtc cataaccagg cgctactaag gcctccaggc tcggtgcgca      60
gagccgggag cgctcctcca gctccaggtt ggggagtcg gggtgggagg aggttcggga     120
aatcgactga tttagaggct gggggtgagt agcctcgatt tatcatccct gatggtgaga     180
gtggaaaagt gtcgcgagag tgacagatgg aatctttagt gcttcgcaag agggagttat     240
taggccgcgg ggtttggggg gtactttccg cttactttgt cattctccac aaagtccacg     300
aaggccgtcc gctcgatctc caccggctgg ccctgcctgt catagagcgc caggacg        357

<210> SEQ ID NO 220
<211> LENGTH: 2355
<212> TYPE: DNA
<213> ORGANISM: Homo sapiens

<400> SEQUENCE: 220
cgctcggtat gttcatctaa acgaccttgg gcaagtacgt cgattccaag gtacaatcag      60
ccctcccaga cggcttttcg agtctcccta accccggtgg gagaggacgc ggcgccagag     120
cccagctccg gctagttttc ccgggggcag gtgtagcctt gggcgcgggg ccggggagg     180 ggcaagggc gggcgtgggg ttggactggg acgtgggact cggaccacgg cctgggcgtg     240
ggcctaacga cgcgggaccg gcccgccctc gccgctccat ggccacatc tgtgcagaaa     300 aggccccgcg gcccaggggc gcccgcagtg tcactaggcc ggctgggggc cctgggtacg     360
```

| | | |
|---|---|---|
| ctgtagacca gaccgcgaca ggccagaaca cgggcggcgg cttcgggccg ggagacccgc | 420 | |
| gcagccctcg gggcatctca gtgcctcact ccccaccccc tcccccgggt cggggggaggc | 480 | |
| ggcgcgtccg gcggagggtt gaggggagcg gggcaggcct ggagcgccat gagcagcccg | 540 | |
| gatgcgggat acgccagtga cgaccagagc cagacccaga gcgcgctgcc cgcggtgatg | 600 | |
| gccgggctgg gcccctgccc ctgggccgag tcgctgagcc ccatcgggga catgaaggtg | 660 | |
| aagggcgagg cgccggcgaa cagcggagca ccggccgggg ccgcgggccg agccaagggc | 720 | |
| gagtcccgta tccggcggcc gatgaacgct ttcatggtgt gggctaagga cgagcgcaag | 780 | |
| cggctggcgc agcagaatcc agacctgcac aacgccgagt tgagcaagat gctgggtgag | 840 | |
| tccgagtcgc agacccaggc ggccgggcgc gctggcgcga atcgctaggc cgatttctta | 900 | |
| aaccccaaac tgttctttgc gagcctgacg cccaaaacca ggggtgtgta gcggccacgt | 960 | |
| cctttcttaa ggctctgggt tcccttcccg cttcccgccc tccgaccctc caaagcagct | 1020 | |
| ttccgccttg ctctccggct cccggattcc ccaggtggcc gggggcgcgg gtccaacggc | 1080 | |
| tctgggaagg cgacttcccg gcacctccgg gcggcgcgag agcacccttg ccctgaact | 1140 | |
| gggccggttg tgtccatccc tcgacccctt ccctagttag gtgtccttt ctgttttcg | 1200 | |
| aacgaccggg tgatgggtga gcggaaagcc gcttccagga gaccaaaaga aaggggtgcc | 1260 | |
| tttagaggac gggtgttccc caagggctcg gactcaggag tcccagatct ccctctttaa | 1320 | |
| cttcaccccg gttgcgcaat tcaaagtctg aggggggagg tgcgtccagg tggggccagg | 1380 | |
| tggggcctgg agcgggagcg cagccgataa gccctgcgcc cctctccccc ttccttccac | 1440 | |
| tgtgcaggca agtcgtggaa ggcgctgacg ctggcggaga gcggccctt cgtggaggag | 1500 | |
| gcagagcggc tgcgcgtgca gcacatgcag gaccacccca actacaagta ccggccgcgg | 1560 | |
| cggcgcaagc aggtgaagcg gctgaagcgg gtggagggcg gcttcctgca cggcctggct | 1620 | |
| gagccgcagg cggccgcgct gggccccgag ggcggccgcg tggccatgga cggcctgggc | 1680 | |
| ctccagttcc ccgagcaggg cttccccgcc ggcccgccgc tgctgcctcc gcacatgggc | 1740 | |
| ggccactacc gcgactgcca gagtctgggc gcgcctccgc tcgacggcta cccgttgccc | 1800 | |
| acgcccgaca cgtccccgct ggacggcgtg gaccccgacc cggctttctt cgccgccccg | 1860 | |
| atgcccgggg actgccccgg ggccggcacc tacagctacg cgcaggtctc ggactacgct | 1920 | |
| ggccccccgg agcctcccgc cggtcccatg cacccccgac tcggcccaga gcccgcgggt | 1980 | |
| ccctcgattc cgggcctcct ggcgccaccc agcgcccttc acgtgtacta cggcgcgatg | 2040 | |
| ggctcgcccg gggcgggcgg cgggcgcggc ttccagatgc agccgcaaca ccagcaccag | 2100 | |
| caccagcacc agcaccaccc cccgggcccc ggacagccgt cgccccctcc ggaggcactg | 2160 | |
| ccctgccggg acggcacgga ccccagtcag cccgccgagc cctcggggga ggtgaccgc | 2220 | |
| acggaatttg aacagtatct gcacttcgtg tgcaagcctg agatgggcct ccctaccag | 2280 | |
| gggcatgact ccggtgtgaa tctccccgac agccacgggg ccatttcctc ggtggtgtcc | 2340 | |
| gacgccagct ccgcg | 2355 | |

<210> SEQ ID NO 221
<211> LENGTH: 881
<212> TYPE: DNA
<213> ORGANISM: Homo sapiens

<400> SEQUENCE: 221

| | | |
|---|---|---|
| cggggcaagg gcgcgttccc tatcgcagga tcacttgcta tggtaagccg cccaccctgc | 60 | |
| gcgctcctcc gcgcggggaa gaacctgcgc ggcaggacgt ggtgttggag ttggggcgcc | 120 | |

```
cggagcgtgg agtggggaga cctgatgcag agagtctgga gtcggagctg ggggtgctgc    180
aggtaggagc aggagcgggg cggagaggga ggcccgaaga agaccccaca caggttggcg    240
cagcggggct tggggaggct tcagcccaga agtggagagg gttgacagac gcctgcctga    300
ttagaaaaag ccgggagctt gggaaggaga cgggattgaa gaagccaccc ggcagggagg    360
ccgaacggcc cagagctctc cgggtaaaac ccgcctgcgg tgatctggga agtgtgtctc    420
cacctagccc tgcgagcagc ggccttcctc ccgcccgtta gaagggcgct gtgctggagt    480
acgaacccgg cccagagaag ccactcgccc ttctttgtca cttaaaaccc tgtcccgacg    540
cggatctcac gtctagacct ctgtctttaa gcggatgta gagcgcgttc taaccgttcc     600
ctaaccattg tgtcaccgcg aaaggccggg gctgtgtgga accgtcccgc acgtgtgcga    660
tgaatctggc tccgctgaga acggatccgt gggctgtctg gcgcgggctg ggcagcagc    720 cgagagttag tctacagagc tagggcccga gggtggacct gcgtccgcgt ctcgtcacga    780
aaggaagctc tttttggaga ggcaaaacgt ggtcgcccag atccggcgca gctgtagccg    840
tgggcgctgt gcagtgacag ccacacccgc cacctgtcac g                       881
```

<210> SEQ ID NO 222
<211> LENGTH: 236
<212> TYPE: DNA
<213> ORGANISM: Homo sapiens

<400> SEQUENCE: 222

```
cggccgcccc gatgcacagc gtccccatgc aggagaagaa gcccacagtc accatgttct    60
ccatagacac gtcagtgttg cgcatgccac agcacttctt aatgcgcttc agcaggtagc   120
gcacgaaggt gttcatgcgc tcgcccaggc tctggaacat gaccagtgtc agcgggatgc   180
ccagcacggc gtagaacatg cagaaggcct tgcccgcatc ggtgccaggt gcagcg       236
```

<210> SEQ ID NO 223
<211> LENGTH: 288
<212> TYPE: DNA
<213> ORGANISM: Homo sapiens

<400> SEQUENCE: 223

```
cgctgaccac ctgccgcagg gccgcagccc tcccagaccg acagagtgcc accagctccc     60
gccgcttgtc agcgccaacg tattcggaga gcagcaggtc ccagagtgac acgctacacc   120 ccttaaaccct ccctgtgctg acgggcacct tcatggccct cagagccacc gcggtgtggt   180
cgtccacctc aagcactgtg tctgagggca gtggcaacag caacaatccg gtctcggagt   240
cgcacacgca gcgctcccctg agctgctggt aggtcacctg gtcccgcg               288
```

<210> SEQ ID NO 224
<211> LENGTH: 3747
<212> TYPE: DNA
<213> ORGANISM: Homo sapiens

<400> SEQUENCE: 224

```
cgtgtgccct tcggcgggcg gctgtagctg tagctgttgt gacggctacg gcggaggctg     60
cggccgcgcg gggaatggag ccggaccgcg gagtcgtcac ctccaaggtg tttctagtgg   120
cctcctggaa gatgatcccg cgcccacctt gccggcgtgt tcgcgggccc ctgcccactg   180
ccccccctct ttctttaggt ctggcttttg aggatcccgg agtcttgcag ctcccgccat   240
tccgcagata acctccgcac acttaattgt gaccgcggg gtggtcggag aagctccgca    300
```

```
cgcgtcctca gtgggaaagt gtccctctc agcactgccc ccttcagtcc ccctgcattt    360
ctggaaagtc aggcaaggcc caggtaggct gccagtgcac tctcagcctt gactgagcac    420
ctttcgggcc tctggtgagc cccgagagcc aggtttggct cggcagagcg ggcttgggct    480
gcgcaagcaa tgcgcatcgt ggccgcctgc accctgggaa ctaggcctgt ccagtgggca    540
gcatcctcat ttttgaaaag gcccttctaa acccaccggc ctcgcctaac gccgtttggt    600
gctgcatccg agcggcctca cgcggtcccc tggaagggcc actccagcg ggagggcggg    660
gcccgggacc tgcgctggcc acgcagggtc tcaagctgac cggaagaccc ggcttttggc    720
ctgtgtccaa tagccccaga agagaggggt ctggagcctt cctcccacgc gtagtgacgc    780
tcaggtgtcc tcgggttgtt agtcttgacc caggagagtg caagacaggc caaggcctg    840
gggggattgc gttatgaatg tccaattcta aacacaaggt agagcacaga cagtacatcc    900
tcacggctgg attttaaccg tattttaata aacacattcg aggggtgtc agtttcccca    960
agctctgccc ccttccgcgg gcgggatcca tggtgtgtgc agtgtaagag tgcgcagaac   1020
gcgtgtgttc aagtgtgggc gtggcaggcg tcgtgtgctc gccccgcgca ctgtgcggat   1080
cgcccagaca gccttgacag gttttttgcag atgtttgggt gctacggtgt ggggaaaccc   1140
aggcaggagc gccaggccta attctcctgg actcttggtg agcggccgct actccacgag   1200
gggctagaag caaaggggc acgcgctttt ccccaggccg cctcttgctg ccgcagtggc   1260
tgagggcgct gatgacccct ccccgcttcc agcggacttg acccgcgggc tgacaaccca   1320
ccgcgacaag caggcggctg ggttcgcgcc gccgccccgg ggcccttggc tcaaatttca   1380
cctcgagtcc tgcagaccct gcgccactga attgggccc aggacgccct tggtgacact   1440
cgccttcttg ctgccacaac caccgtcata cccgcagccg ggctccctc cgctaaccac   1500
gcttggagac cccaatcggg gacagaggtg ggagtcagac cccccctggc ctgcactgcc   1560
gtttccctcg attcttgcgg aaacaagact cccgcccaca cataaaaatg cagctcccgg   1620
ccaccgggcg ccgtggctc acgcctgtaa tcccaacacc ttgggaggcc gaggcgggcg   1680
gatcacttga ggtcaggagt tcgagagcag cctgaccgac tactaaaaat acaaaaatta   1740
gccaggagta gtggtgcatg cctgtaatcc cagctactcg ggaggctgag gcacaagaat   1800
cgtctgaacc cgggaagcgg agggaagcag cgagtcgaga tcgcgccact gcactccagc   1860
ctgggcgaca gaatgagatt ccgtctcaac aaataaatag aaataaaaat atgcagcccc   1920
ctccgctcca cttgaacttt aatgctgaac cggtttccca cgtatacgtg tatcgcaccg   1980
cattttgacg ctttgcatcg agtcgcatta atggcgcttt tgagaacgcg tcgtcgcgct   2040
ttacagagaa accctacggg cagcctgtgg aggggtaggg gatattcatt ggcttttccct   2100
gctgggcccc gtccgccggg cgggttaggg tcgtggcagc ctgcccgcgc gccgctgact   2160
ctggaatttt gtccgggaaa ctggcgtagg gccctggctc tcccttcgcc ctccgcgcac   2220
acgcggacga ggcctagat ccacagcctt ttctaggccc tgcgcctttg aagctgggcc   2280
actgccaacc gctcgcgatt ctcaccttca acagtcgccc ccttacccct cccccacccg   2340
cctgccctcg ggagcgggtc gcctccactc caccacctgt ttaagttcct cccctcggc   2400
gcccctccag tccccacccc ggcccggtc caaaaaacca gcaaacggaa cttttccaca   2460
gttgaaagcc gcggcccgcg aggccgggct gggaggggaa agcggggcgt gtctgggggg   2520
cggggccccg agcactccgg aagttgcccc gcccaggagg ctcctgggaa agtgaggaga   2580
gggcccgggc ctactttcgt cctggtgtgg cgccctcag cctcccctcc tcccagttcc   2640
cgcgcctccg cagggcgcct cggcctggcc tccaggcaaa gttcgcgccc cctgttcctg   2700
```

| | | |
|---|---|---|
| gggtgtcggc cgcgcgggcc gtttcccttc attactcccg ggcccctgaa tccgaacgct | | 2760 |
| ttcccagaag cgcgcaaatc cgcttgcttt ccccgcggct gggctttgtt cagggacagc | | 2820 |
| aaaggaggag gcgggaggct ggtgaggttt tctggaaaag gggcttgtcc cgaggaggaa | | 2880 |
| gtgccccaga tccctgagag ccaacgctct ggggagaaga aactttcctt ctcccttgaa | | 2940 |
| tgttgctcag attacctaaa attatttttt cagcccttgt gttctaaagt cgcagggtaa | | 3000 |
| aggttatctt aagacttaac atcagcgctg ctcatttgta cgttggtgga gacgtgcctt | | 3060 |
| ttttcctttg cacttaaggt ggacagggtc tgcgacgctc ccttccagga cggtgtgggg | | 3120 |
| aagcggccga cgtccccagc cggactcacg ccctcctact actgggcgtc ggctccgccg | | 3180 |
| cgggcgctcc cgacagggag ctggagtcgg acgagcggct gccccagggg cctccaggaa | | 3240 |
| ccgcggccca gcggggagcg ccccaggcta gcgcttttcc agttcccttc gaaagcgcgg | | 3300 |
| ggctgaggtc gcggcgctgg gccctcggat gaagccgtgc tgtagctaca cctgaaccccc | | 3360 |
| gcgaaaggct ggcgcggtcg tgtatccagg ctgggtctga ggaatccgca agcgggagag | | 3420 |
| cgctaactcc taggcgtgag ccgctgctgg cttcgagagt tcgagaacat gaaggacctg | | 3480 |
| gcttctcccg cccggtcggc ttagggccag cgaggtcaca ggccgttctg ctctccctgt | | 3540 |
| ttgtccccaa aggcctcggc acgtggggat ctggagcagg cctcaggctg cgaccgtct | | 3600 |
| cttcccctac caaaattatg tgggaacagc ggtccaggac cttcccctgt tcagcggtat | | 3660 |
| ccccgggccg gtgaccccgg ggttcagtcg tctcccccgac cccaagcggc ctctgctttc | | 3720 |
| caccccctcgc cccggagggc ggcttcg | | 3747 |

<210> SEQ ID NO 225
<211> LENGTH: 335
<212> TYPE: DNA
<213> ORGANISM: Homo sapiens

<400> SEQUENCE: 225

| | | |
|---|---|---|
| cgcggccagt gaaatcccaa tcgtcttcca cgtggaaccc caggtccgca gttatgataa | | 60 |
| cggatcacat cgctcctgcg gaaagtgcgc gcggtggagt gataattgga cctagcgtct | | 120 |
| aaattcttgt tggaggacct cgttccagct gccagttaag cctctgggat ccgcagcgtc | | 180 |
| tctaggaatt gagagagtgg ggaagttagg atccaggagg aggatggtgg gggctgagga | | 240 |
| gtggaggagc agcgtgcatc tcatctcttg tcgccgggcg ggcgctcttt cgggtccagg | | 300 |
| gcccttgcac ccccagcgtg gctccggagg cggcg | | 335 |

<210> SEQ ID NO 226
<211> LENGTH: 255
<212> TYPE: DNA
<213> ORGANISM: Homo sapiens

<400> SEQUENCE: 226

| | | |
|---|---|---|
| cgactatgca aacgcttgcc gctagccgca tccttctatc gcccccccaac tcaagacccg | | 60 |
| aaatggccaa ctcttcaccg agggggcgtc ccatcgctgc cttgccttgg cccgccccctt | | 120 |
| cgccaagctc aatccctttt ccccagaaaa acctgtgcct gtcctcagac ccggccccac | | 180 |
| ggctggaagt caaaacccac cccggagcca cgcggctgga gcacgttttt acacctgctc | | 240 |
| ggccgcttaa ttacg | | 255 |

<210> SEQ ID NO 227
<211> LENGTH: 4206
<212> TYPE: DNA

<213> ORGANISM: Homo sapiens

<400> SEQUENCE: 227

| | | | | | |
|---|---|---|---|---|---|
| cgctcacagg | tcggaataat | tcaagccttc | cgctcccccg | ccgagctggg | gtagctgatc | 60 |
| actgagctga | aactaaacgt | tttaggtgga | aaaaaagcgt | ccgaaggcac | cgtgaaatga | 120 |
| ttaaggaact | aaagagcttc | tcgccatgtg | agatcatgtc | ctgttctcgc | caacatcaca | 180 |
| agatgtcccc | agacacgccg | cgcccccagc | gcgccgcccc | acactgccgg | cccggagcga | 240 |
| ggaaagggta | ggcgctgcgc | ggccgggcct | gctcagcgcg | ccagacgtgg | cggacccggc | 300 |
| ccggccggag | tagagcggga | agccgggaga | gcagcagtgc | tgctgccgcg | ccgccccaga | 360 |
| ctttttatagg | ggttgggggg | agggaaggaa | ggcttcagcc | tgcgccgggc | gctagccagc | 420 |
| gcacctacgg | gaaggggcag | accgaagcgg | agcccgggag | cccgggtctt | ccagccgcac | 480 |
| cttctattaa | gacatgcgct | tggggggtcgc | ggccctctgc | gctgtgcgcg | gggcctgtga | 540 |
| catctccatg | tgcaaacccc | gctgcttaga | cgagcgcagg | ccgggttttt | gtttttgaag | 600 |
| aaattaactg | ctcggccaag | caggtgcttt | tgaaaggggt | tgcaaaggct | ggcagtgttg | 660 |
| ccaggcaccg | aggcgacgtt | ccggtttact | ccgattcacc | cctagggcgg | cgcccgaccc | 720 |
| cagggttccc | agccatccaa | ccccccacccc | aatttgttgg | ggtcctgact | attgctgggc | 780 |
| ccctgaccct | agggcagcgc | cagatcccta | aagcccccag | gtcccatcca | gtcttctagt | 840 |
| cccagaaccc | ctccccacat | caagttccat | tctggcccag | agcatggagg | ttaagctgtg | 900 |
| aaatactgga | gatgaaatcc | gggcttccgc | tttggagcac | ccgggcagag | cagaacatct | 960 |
| cagtagtttc | tggagattgg | cgggagttcc | agacacctta | ccccggccca | taagtggaat | 1020 |
| cgcattgccc | tcgagccctg | agacgttgtg | gagtcccaga | gccccaggac | ttgattccag | 1080 |
| agaggaaatc | agatccacag | agaccgagca | gaggtgtggc | atgtccagcc | ctctctcttc | 1140 |
| gggccagact | caagcctccc | ctccctgttc | ccctccccag | ccttgagtta | gttcagctgc | 1200 |
| tgggcctagc | cactgaaagc | ctgtggggcc | ctgcagcggg | gtggtcgcag | gggaaaggtt | 1260 |
| ctccagggcg | ggggagcgct | ccgtaggagg | actcctggcc | cgccggacaa | tggcagtttt | 1320 |
| ggagagtgaa | tcgtcctcag | caagagtgtt | gtttgttttt | tggaggggt | ggtcacgagg | 1380 |
| ctgggtcgca | acctaggggg | aagagcctag | agctcgagga | aagggggggcc | cccggcggca | 1440 |
| actggacatc | acatatccac | tgagcagatt | tcgccacaat | cggaaatgtg | gctgtggatt | 1500 |
| cccgggcggc | ccccccacca | agtggtctgc | gcagttcccc | agcgccgcct | cctccctgca | 1560 |
| gcctgcgggc | ccgtgtccct | accccgagat | ttgatttttg | gccatctccg | agtgctcgac | 1620 |
| tctttccctc | cgcagcccag | ccccagccca | ggcttcccgc | cctcccgcct | cgcccgcgcc | 1680 |
| gggaggcagc | gcctgggagg | agcggcctgt | ccgcgcctgg | agatcaaaag | ccctcccgga | 1740 |
| attgacattt | caccccgggc | tgggggcggg | gggtgttggt | gttttgttgt | tgttgttgtt | 1800 |
| tccatttaga | gggcttgttt | tgttttgtt | tgttttctgt | gagttttcat | ttttccatgg | 1860 |
| gatattcttt | tgtttcgggt | gttttgcgtg | ttgtttttc | gtgggattga | ttttagcggg | 1920 |
| ttttgctctg | taagtcctgg | tctttggggt | gagttttgat | tttgtgtaat | tttgtacttt | 1980 |
| gtccttgtag | gctgtctttt | tgtgtgtcgt | ttgtaaggct | tttccttctc | cgcggtgttt | 2040 |
| agatgtgttt | tgatttggtg | tgagtgggtg | tcgtctgtgt | gtgtgttgcc | ttagggaatt | 2100 |
| tcgtgttgtg | tgtgttttgt | ttccttcgat | ttgaatttta | ttttttttgaa | ctgtacgttt | 2160 |
| tggtggggga | tcgggttata | ttttcatgtg | ttgtctttag | tttttgtgtt | tgtgagatgc | 2220 |
| gctggtgaga | gtttgcgtgt | gtattttggc | ttttgtgggg | ctttgggatt | agggagggga | 2280 |

-continued

```
catcagccgc tactccgttc ctgcccgcac ccatgaaggg cagaggatta ggccaagcat    2340
cacgaatcgt aggttcgccg tgctccgccg cttcgcgctc tggacgctcg agaccagcgg    2400
gaaacaaatg tggttcccga gggggcgccc gctggtcgtc aaaacctcgc gggcccggag    2460
gcgccgctgc tgggtcagaa tcgcagagcc ccctcgcgg ggtaccgagg cccagccgcc     2520
gtccccttgc ccaccctctc ccctgtgagt cggtctcccc ttgcgcctgg ccagcatgct    2580
tcggaccgtc cggactcccg cagcgttggc ccaaggggcg ctcccctcg cggagcagg      2640 tgacgaacca cttcggagga cacggaattg acactgcggc cctagagata cgggacaagg    2700
ggccagaacg cggggagtct aggctcagat cggagtcggg atcccgggaa aatcccccat    2760
ctcccttgcc cgcagcccta gaatcccaga aacccaactc cgcgcagctt cggtttgga    2820 gagcccgccc tggtttgcaa gcacagatac atgtgcccac acccgaacac acgcagacac    2880
cgccagagag cgagacagcg agcgggcgcc tccgtagcag cggcctgcgg ggcggaaccg    2940
gagctggcgc cgcctcaagg ggaaaccgaa ctgtagtgac cggaaatgtc cccaggacag    3000
aataagccat tccttctgtc cacgttgcca ggacttctcc agctcaacac accttggttt    3060
gtttaatgtt acacgaggga gaagatttag aggcagagac acatgctggc tcaatcggcg    3120
aggaaatacg agcagagtct aaacagaaag aaatatggaa cgggggggaga ctagactgtg    3180 gggaaggcaa attggaggcc cagaaaaggg gctggtgcgg aagctcctcc aggcccctgg    3240
gcgctctggc attctgtgag aaggagaaag cagaagccga gaacagagag tgacaggaaa    3300
agaaaagaga cgcagaaggg gttggcctag gcacgctgcg agctgccctc cagctaagac    3360
gctgcgggca agggaggggg aggccgacat cgccaggcga ggggccaagg tcgggctctt    3420
taactcagcc aggaaacatc gttgggggct ccagggctcg tggagcccga actgggctc    3480 atttccggcc cgatgcccct cttccccaga cccctagccc ggaatccagc aaaggctggg    3540
ccatcgccgt ccgccactgg gcctccctct gtgcgagccc tggagaagc ctcaggggaac    3600 gactctggca ctgggctcg gccccggagc tagcgcagag cgtgggtggg agtcgacatc    3660
caggcaggag gcaaagaaga ggccccgccc taaagccgag ggcccagttc ttcgaaagcc    3720
tgtggccgga gctggactca caggattcgg ggtccgtaca gcgcgcacgt ggtaccgcat    3780
cttcggcagg cggcgcccct aatgcccagc cccgccctgc ttcgtttgcc gggcctgaac    3840
tgtgtcagca ttgagggtgg acgccgagtc gcggcgagtt ggtcccttgc ggtataaact    3900
tggggcttcc ctaggggcgg tgccgggatg gatgggggcg cctctccacc tgcaactccc    3960
ccagcgcaga gcgcaaaaag tgcacatcgc gggccagccg tcgcctcggg gtttcaggcg    4020
gcgcccgggg caaaaaggag ctgaggattg gtttgggtca aaacacccat ttcagttggc    4080 agtgggtcc tctgcgccta cagggcttcg agctccgggt gcgggctcac tggggcacca    4140
tgtgccagcg actcgccacc cggaaatact tgggttgcgc tagaatacgc aatgggtctg    4200
tgttcg                                                              4206
```

<210> SEQ ID NO 228
<211> LENGTH: 5770
<212> TYPE: DNA
<213> ORGANISM: Homo sapiens

<400> SEQUENCE: 228

```
cgggccgcca ccgccgcctc ggctcctccg tgacgtccgg gaagggtatc cccggcactc      60
aggaagtggt ggccgcgggc agctccgccc ccacgcgact cggggctggc cgagctgccg     120
```

```
ggtggtagaa ccgccgggcc ttccgcaggg cgggcgggga tcaccgtctc cccacctccg    180
tgcgcacaca catgcacggg cctcgcgccc cgctgtcgcc cgcgcctcgc cctgctcact    240
tctcacagcc cgcgccggac gaagagagcc gccagcgccc ccctctctc ccacggctcg     300 cacccactca ccccgacccc cggcgccgag cccggcccct cgtcgccggt caccagacct    360
ggtcgaaccg agtccaagat ggcgactccg ccccgcccc ctccgcactc ccggcggggt     420
cagggcgccc cctcacgcgg cgggctcgcg cccgagaccc ggctaaaaat agccaggccc    480
gactatattt ggttcggccg gatcctggcg cggccgcgcg ctccccgccc cgccccgccc    540
cgccccgcgc gccctgcccc gccccgcgcg gcgttgaatg gagaaggggc ggggtgacc    600 gaggggaacc tactccgcta tctgcggcgc gcgccggcgc cgggtccggg ccaaccgccg    660
aatttagtaa catcgcctgc gtcaatcacg cgcctcgcgt gcgtcagcgc cgcgcggctc    720
caggtcctgc tccccccctt caagcctttg aatggataca atgtagcagc gccctccttc    780
cttccgaggc tggattggaa cccgccgcag tgcagagact cggttgctct cggctgggtc    840
aactttcggg gcattctccc acgatcctct ccgcaccacc gtgtctgaat tggaagtgga    900
ggcgaagaaa gatatacatg ccatatttac ctatatgtag tttgttttca agtttctggt    960
cctagctcga accttcttcg attctgaaat gtgtgctgtc tacaaaggaa tcttgtatct   1020
cccctcggcg cagcgccccc cgccccgcc acacacacac aaattgggac aggtcaaaca    1080
tataaaacgg tatttgtgat tcaagcggac cacatgggga ccactctatc tgcattgttt   1140
cactcaaata ttttctcctg tccaaaaatt catttctgaa agagactgcg ttcactcagc   1200
agcaaccttt gggactaggg gtctttaact ctgataaatt ttgttttcat caagaaattt   1260
acacttaaat ttatcatttc caggaagaaa ttgctctcct tcatacagtc acccaggctt   1320
tcggcacacc atttcatgac aaatgtgtcc gaggagacca aagcaaatcc cctagcgagg   1380
gactgactaa taagtcctgt tgattgattt cgaaatgttt aatttgggag atgtgggcgg   1440
agggcatcta caaccatcaa aaagtgaaag tgctagttga gagttccatt tctgacccgg   1500
tgccggggag gaggaatgat ttgcaatagt cagacccgct cagctgttca acgtgtgt    1560 gtttgttta cacacagagt agtttctgct gcagcgcgcg tgtgcatgat ggatgtgcac    1620
ttcgctgggt tataacgtgt ccagttaaga acccacgcc gtacgtgtaa agaaatcaaa    1680
ccttatcccc ggaaccatct gcatccctgt gtgaaacacg cacccagtaa atgatgcggg   1740
gaggggggat tagcctgggc gcagaggacc ggagcaacgt aaacagcttt agaacctatg   1800
caagaggaaa gtgcagctgc acctcagggc gtcttcgggc tggtgccaga cgccttctgc   1860
accggctgcc aggtcactgg agctggtcag aagctggctg gcggagcctt cccttttcgga  1920 agagctgtcc tctcccttac ccccctcgcc ctggctccgt gcctcgggc agcctcggag    1980 gcgcgccagc agcactcctc caactctact ccacccgagc ctgacagctg gcggtcccg    2040 cctgacccgt gggcaggccg ctgcaccctc ccgcagacgc acgccctggc gagcggttcc   2100
gctgcaaaaa gagaagcccc caggccgggg ccggccgtgc ggcggagttt ccattgtgcg   2160
gccgtgcgac tggccgagga acgcgcgcgc gcgcgcgcgc acacgaacac acacaccctc   2220
cctcgcacac gcgaaccgg ctgggccagg ggagggagga ggaggtgac gtagcgtccc     2280 atggcgtcac attgacgtct cgcattccag gcactctatg gagaggccgc tagggctcct   2340
gtggcataaa tgacgtgccg agagagcgag cgaacgcgca gccgggagag cggagtctcc   2400
tgcctcccgc ccccaccccc tccagctcct gctcctcctc cgctcccat acacagacgc    2460 gctcacaccc gctccctcac tcgcacacac agacacaagc gcgcacacag gctccgcaca   2520
```

```
cacacttcgc tctcccgcgc gctcacaccc ctcttgccct gagcccttgc cggtgcagcg    2580
cggcgccgca gctggacgcc cctcccgggc tcactttgca acgctgacgg tgccggcagt    2640
ggccgtggag gtgggaacag cggcggcatc ctccccctg gtcacagccc aagccaggac     2700
gcccgcggaa cctctcggct gtgctctccc atgagtcggg atcgcagcat cccccaccag    2760
ccgctcaccg cctccgggag ccgctgggct tgtacaccgc agcccttccg ggacagcagc    2820
tgtgactccc ccccagtgca gatttcggga cagctctcta gaaactcgct ctaaagacgg    2880
aaccgccaca gcactcaagt acgtatgaga ttcgcccagt taataagggg acttgctaaa    2940
aaagttggct tgctgggaag cgtcgctcct gaaattgaca actttgagtg tggggttccc    3000 tccctgacc ttgccgcccg gctccggctt tgctagccca gcggcccgta ggttctgatc     3060
tgaaactttt cccctgtagt gggcccgcgg ggatctctgg agctcgtggg attcctcccc    3120
ccactcgaag aggcgaaaag cctctaacaa agaggaggac cgggatttgt gctatagcgg    3180
ctccagcgat gtaattcagg gtatttcggc tctagttgtc atggtaatga tgctctcggc    3240
ggcggcggcg gcggcggcag cggcagcggc agggagttgc agctccggtg atgaacggca    3300
gtaattttcc tgccttttaa gtaggattga aaataggagc tctggtgggt ccaagtaaat    3360
gttgctaatg gtggcaccga gctggttctc tggaaggaag cttaggaggg aagggcctag    3420
gcagcgacgg ccagagtttg cagacgcact cggaggacct caggaaagag ggcgtaattg    3480
taggaatgtg gcttattgta ttgaaatgag cctggggttc cactaggcac gtctgcctgt    3540
cgtcgctgac atgccggttt acactttcc cttaggaggt aaatcgggtg taattggcga    3600
ctcccgcaca ctgacacgtg tggggacggt gtccctctcc tctggacgtt ggctcggtgt    3660
gggaaaggca tgcttttttca cggacagaac tcgcgctttt ggagaagttg ctccgagtgt    3720
tttactctta gtagaaatga aagttctcgg tggtgagacg agagcggtca tgcgagcgca    3780
gcctgcggag actgacttcc aaaggcacct ctccaacctg ttggaagcct cggggcagtg    3840
gtgaggaaga acgcatttgt cccttgattt ccaaaaacgt tcttggagat tgccttttat    3900
ttatttatgc gtccggattc tccagaggga agagctgcga ggagttagta atcagaaatg    3960
tcgggctgtg atcccagggc cttgtggtgc tgggagagaa gaacagggag ccgtcattcc    4020
atcgcgagtc cagtgccgga tctccttttc ccacgaccgg gaaatatttt atagaatcaa    4080
gttagggaaa gaaaaagctg cctaacgtgg ctgatgggca caatgaatga agttacttta    4140
ttcgagttat tttcgctgaa caagatgctc gcagagttag tatcaaagcc tccttaggcc    4200
acagcaacct ccacgtccgc tccgcccccc acccccggc acccatccac ccctttgcct     4260
gggaccgtgc gctcacagaa attcttcccc gcggtttgtc tagtctccct cggtctttct    4320
gagaatctca gtctttccct ttctgtcagt ctctccctcg ctcctcttgc cccgcccaa     4380 cctccgcccc cgctccccag ggttggaaac tccgcagagg agcccggtc acaatggtgc     4440 gtttcacggt ttcctccaca cacttcacca ccggagggg aacacggggg tgttcctttc     4500
gtctgcccac gagaaagaaa ggggctttga cagaggtagt tatttcttcc taatttacaa    4560
ccccaaggct ctgtgctccc ggccccggcg gccgcaagca ggagcggcgg aacgtgtttc    4620
caggcactga ggctttgcct aggtaaccgg ccgcttgtgg ggtggagaga gcggcggggc    4680
gctgggctgg gctggaggaa aggctgtgtg gtccctcccc gcgaacgctg ggcgctcgag    4740
gggaactcct tcgttgggga gaggcggtcc ccgcccaccc gagttctgag gcctcctctc    4800
agagaacgac tccgcttgaa aggccctcag ggaatgcggg acgggaatgc gggcacccac    4860
```

| | |
|---|---:|
| tgaagggggcg ggtgggggat tgctggagac ccccattgaa gatgcgggga gacgggaagc | 4920 |
| acgtgctaca gccgtgggaa gatccgcttc tacccgcgct acatcgagcg caagcttttcc | 4980 |
| gtccgagcag ctccagctgg ggctgggggt ggcaagggaa tcccccattt cctggtcgtc | 5040 |
| gagggtttcc tggacctggg agccccgagt ccctttctct cttcctgcag gcaagccccg | 5100 |
| ggctcagggg cgccaggaga tgaccctcgt ggccccgcgc acctcggagg ttttttggttt | 5160 |
| ggtttgattt ggggttttttc ggtccctgtt cccactcttc gagctgcgcc caccccgggc | 5220 |
| aaagggggcg ctataggccg gagtttgggc acccagttcc ttccctgagg cctgctgagc | 5280 |
| tgcgctttca gctacaaagt ttcgctgagg ctgtgggctg agacgctggt cccggagctg | 5340 |
| cgctcggcgc cctcaggaat gtgccccgc taggccgctg ggtggccagg agcctccaag | 5400 |
| ccgcccaccc tcgaagacac cgccctctgg gtgcagggga cctgcctccg ctcgtcccat | 5460 |
| cagccgctaa cgccgtccgc ttcgtcccct tgcttccagc gccagccttc tcatcgctgt | 5520 |
| gccctttgt ttgcttgacc cctgcccctc gaaactcgcg gctaatagaa gcgaagctcc | 5580 |
| attagcattt agaatgaaaa gcgcagactt tcttaattcc tcggggcatt catgcattcg | 5640 |
| ttccggacct tgtgcatttc ctatgcaacg tgtaaaattt gtatttgagg ggtggggcg | 5700 |
| ggcggagctg gaaaatggct ttttttccgct ggtgaacact cactgacccc ccgtattcgg | 5760 |
| gcggagctcg | 5770 |

<210> SEQ ID NO 229
<211> LENGTH: 582
<212> TYPE: DNA
<213> ORGANISM: Homo sapiens

<400> SEQUENCE: 229

| | |
|---|---:|
| cgctgttaga tttcgggtca atatccatca tcgctgttag actcggggcc gacatccgtc | 60 |
| atcgctgtta gactcggggt cgacacccat catcgccgtt ggactcgggg ctgatacccg | 120 |
| tcatcgctgt tagatgcggg gtcgatatcc atcatcgctg ttaaatttgg ggtcgatatc | 180 |
| cgtcatgact gttagatttg ggtcgatat tcctcatgac tgttagactc ggggctgata | 240 |
| tctgtcatga ctgttagact cggggccgat atctgtcatc actgttagac tcgggtcaat | 300 |
| acccgtcatc actgttacac tcggggccga tacccgtcac cgctgttgga ctcgggtcga | 360 |
| tacccgtcac cgctgttgga ctcgggttga tacccgtcac cgctgttgga ctcgggtcga | 420 |
| tacccgtcac cgctgttgga ctcgggtcga tacccgtcat cgctgttgga ctcgggtcga | 480 |
| tacccgtcat cgctgttgga ctcggtcga tatccgtcat cagtgttggg ctcaggtcga | 540 |
| tacccgtcat cagtgttgga ctcgggtcga tacccatcat cg | 582 |

<210> SEQ ID NO 230
<211> LENGTH: 254
<212> TYPE: DNA
<213> ORGANISM: Homo sapiens

<400> SEQUENCE: 230

| | |
|---|---:|
| cgttagagca tagcgacatc acgtgcggtt tcttaatgtc cctggtggcg gatacgccga | 60 |
| gtcctcggaa ggcatctgg acaccacttt cagccacctc cttgcagggg cgacatccgc | 120 |
| caaagtcatc ctttattccg agtaataact ttaattcctt tctaacattt acacggcaaa | 180 |
| caggaatgca gtaaacgtcc acgtccgtcc cacggctggg ctgccgttcc gtttcctcca | 240 |
| cgaacgggta cgcg | 254 |

<210> SEQ ID NO 231
<211> LENGTH: 14472
<212> TYPE: DNA
<213> ORGANISM: Homo sapiens

<400> SEQUENCE: 231

| | | | | | |
|---|---|---|---|---|---|
| cgctcccaaa | gccacgcgaa | agtggaagcg | cggggcctcg | ggatgcccat | ccagccggct | 60 |
| gcccgcgcgc | tggccggggt | tccaggactc | cttcctgctc | cgccgggctc | tgcagcgccg | 120 |
| cctggtggac | acgcggcgct | ccgcccgggc | tccagccgcc | agccgcgcg | ccggggatcc | 180 |
| cgcggctgtt | cgggaaaaag | ctggagagag | tcggggggcg | cgccttgggg | aggggcattt | 240 |
| gtccctccga | ggaggctcgc | acctcggcct | ggacacgcag | cagatactgg | cacccaccct | 300 |
| tcacttaccg | cgcgcccggg | gtgactcgga | tccgtccaac | acgtcgggga | atcctttctg | 360 |
| tcctcacccc | cgggcgcccc | agcgccgaa | cgctgctgcc | tctgtgtagc | tgctcccgga | 420 |
| aggagtttca | tcaaactttt | aaggggcttt | ggttttgggt | tgtgttgata | aataccaag | 480 |
| aaggggcatg | aaggcacgaa | cgtcccgggt | tcgtctccct | gctggtccca | agcctgaatc | 540 |
| ccagggcggg | ggaatgtcta | ggtccttccg | ggccggcaag | gtgtggtcgc | tcagggaccc | 600 |
| ctgtccgaag | acgctaggga | aaagaggcac | agcctgtggg | tcgcagtggc | caggagcgcg | 660 |
| tggccgctgc | tggtgagaga | gtggtagacg | cctggctttc | aggtcctgag | ctgcgggcac | 720 |
| cggagcgtgg | gaccccggct | gcagcaccgc | cacgcgctcc | cgccctccca | cctgcagggc | 780 |
| gggggatgtc | tgtccaagag | gccggggcga | caagcccgcc | ggccaggatt | ctcaaggaac | 840 |
| caggcccagc | tcagcctctc | tcggcgggac | cagagtggga | ccggggccgc | ggcgtccgaa | 900 |
| gacgctgcgg | gccaggggtc | ctcctcggcg | ccagctccgt | ttcctggggt | ctcgcgacgt | 960 |
| ccggacatca | gggtcggggg | tgtggagacg | gcggcggagc | cagagtcccc | accaagtcag | 1020 |
| ttccaggagg | cggcccgcgc | gcttcccgca | gtgtccggga | ggtcgctggg | ggtggctttg | 1080 |
| cgtgcaaccc | gggtaaaggc | cctgcagccg | tgaggctggc | gctgggagga | gggtggaaaa | 1140 |
| tctcaaagtc | accaatcccg | gtgcaaatgg | cggcagggc | cgcgggctgt | cggacgcagg | 1200 |
| cgagaggcca | aaggctgact | tcgcgcggcc | gtgagtcccc | agaggcaaca | ggggtacctg | 1260 |
| agcgccgagg | ggatcccgag | actcggagaa | accggaagag | cctgacccca | gggagcggag | 1320 |
| agtttggggt | gcgctctcag | agctgtgact | ccacggtccc | ggaatccttg | gaaagggcgc | 1380 |
| tctgggctca | gagctcccaa | ctagccgag | gacctgggct | agcgcccagg | cctggagcgt | 1440 |
| ctggagggg | gcgctgggtc | tcggccccc | tcccccaaa | agggactgag | acttttttct | 1500 |
| gcgtgcttcc | ttcggcgctt | cgggcagctc | tgtcctgcgg | cccaagctgg | ggagaagaca | 1560 |
| gcggcccgcg | ccacagggag | ctgcgcccgg | acccagactc | ccgccgcgct | tctgcagagc | 1620 |
| ggagccctag | gtgccacct | ggtagcccca | gaaaggccgg | acctgggcgc | cgggacgctc | 1680 |
| gcggggccgc | acttggaggg | gctttccggg | tcctggccgg | gcgggctctc | ctgcggcgcg | 1740 |
| gaatggaata | gagcgccggc | tgcagagcca | cccgacggg | gaaagcagc | ggtgcgccg | 1800 |
| gccagccccg | ggtcccgact | ctggagggag | gaaggagcgg | gcgggtgggg | gtgggggtga | 1860 |
| gggcgagggt | tgcggggagc | gtttagaagg | ccctgggcag | ccagaagaag | aaaagaggac | 1920 |
| gcactctccc | ctagggacca | gagggtccct | gcgtactccc | ccaggcccg | ggacacaggt | 1980 |
| tcccccagcg | cccctccgcc | tccagtcta | ttcggcttgc | ccagcgcgc | tgccccacgt | 2040 |
| ccccgaggcc | ccgcccagg | cccagccggc | gagtcccggc | ctgctccact | ctgcacaaaa | 2100 |
| cgaaacccaa | atgcccaaaa | agctcaggag | ggaaatttaa | caaaaccct | gtcccccgcc | 2160 |

```
ccacaccccc tttcacttttt aacaagccag ctgccaagag aaaattgaaa taaaaacgaa      2220
atgatagata gcggaggaca ctattttcca aatggtgaaa tatcctctaa aaatatgttc      2280
cccaaggcca acttcgcggc tggtagcccc ttccgacgcc tttgcctccc agaaaatcac      2340
aacaaagcga tcggaaattc agccacggtc ccgggaagaa ggagtagcag tgaggccccg      2400
gaacccactg cggccgaaac tgccatgctc tctttaacca aaataaaaaa gataagaaga      2460
agaagtaaaa ccctttaata catcaaatat acggaatttt aatctttaaa gcgatacatt      2520
gtctattatt ttagtacatg acgtaaacct tgtccccttc tcagcgggtg gacttaaaaa      2580
ttaaaaatag ttaagtgttc cttttaaaga acaaaataag gcaaatgagg tttttggaata     2640 gaatttttc ttttttcttt ttttttttgtt gttttcttcc agaatacata caaaaaaata      2700
cccattctct tcgatggtat acaccttaaa aataattgca atttgaaatc agagctgaca      2760
aattgtgact ttttttttca tttttttttgt aacaaacatg catgtaaatt tgtgtttcaa      2820
tcagacatta ataacgtac aatacaatca tagcaatttt aaagtaacat taaagagaag       2880
acctctagtt ctgtggcggt tttgctttta tttataatct acaagggatg ggagggtttg      2940
ttttccacat ttttaccctc aagttttaaa attttttccca cctccttttt acctacagag     3000
ctcaaactaa ataatgcact tttgaaccac cggtccgctt ggagctaaca taaataaata     3060
ccagtgtcca ccgatgcagt cctcagatga acactttctc aattattttt tccttttttt      3120
ttctataaaa agtcaaatga tattttttca acttttataa agtttgggtg gggaggtgaa      3180
agtggggaga aggggagtgt cccaccgggt ctcggtcgct gctgtcgggt agatagatac      3240
ggtatacatt tctttccttt cgtggcccga gtcctcccca cgcgcgggtg tcagcagcct      3300
gggccgtgat cccgcctctc cctggactcc tcccctcccc ctctccctcc tctccctcgc      3360
tcgccctccc ggccgccctc actgataccc cagcgccgag gcggtggtca gtctctgtcc      3420
gtagagggcg tagggggagt agtacggtcc ggtggcggcg ggcaccggca cggggggcgcc     3480 aggcgtggga agcgggctct tggagtaggg gtggtagcgg ctgctgagtc ccagcgcgtg      3540
gtgggggctg cgcagcgcca gcgtcccagg gctgcccggt gcgcccgagg tggggatgtg      3600
catgtggcaa gccatggcgg ccgcggcagc gctggccaga gacgacgagc tggggtagcc      3660
cgacagcagt ttgtctgtcc cgggaaatgc cgtatgggtc cgcaagtggc tcagcagctc      3720 ttcgacgtg gcgaagcgct tgtcgcacgg cccgttggcc gacacccagt tgcagatgtg      3780
ggggagtggg tcgttaggga gcataaagcc gtaggggtag aggggtggc cggccaggga      3840 gggcggtgtg gcgccagcag ccgcggcggc cgttagcgag gagtgcacac cgtgcagcgg      3900
gtgcgtgggg tacaccagcg ggtatccgga cttcagcgcc gcagccgcag cagccggatc      3960
atgtgcgcaa gaagcgctgg cggccgccgc ccctgccagg tggctagcgc agtggtagct      4020
gaggcagtaa gggtcccggc acaaactggc tgtcatcacg gacggcggag acgctccggc      4080
caaagggctg gagccggccg gcttactgca gcccagagac ccggccgcgg ccgccgccag      4140
ctgcgccccc accaggctgc ccggcttggt ggggtcaagt gccacgccgt gtggcaggaa      4200
ctggggcggg tagccggcgt aggccccggc caggctgcct gggtaggtca tacccgcggg      4260
aggcagaggg aacactgtct ggcccggctt gtagggtgac acgggagcca ccagcccaga      4320
gcccaacact gaggaggagg tgggcgcgct ggggccggag ccggagctgg agcccgatga      4380
accgccgcag tccgagccca gagccttgcc tcccgggccc ccatccggat gctggttcac      4440
atccacatta atcccgccgc cgcagctaat ccggccgtgt gccagccccg tgggtccccc      4500
ttcggccgag gcgcccccgg tgcccttgcc accgccgccc acgtcggtgt ctttcttgtc      4560
```

```
gtccttgccc tccggggcac ccccggccga ggacagcata cctcccgccg agcaggccga    4620
ggcgctggag ctcgggctgc ctgtcctggg cgtgaatggc tggcaggtgg cgctcggtac    4680
ccggaatccc gacttctccg acgaaacacc cccgccgccg ccccgccac cgccaccgcc    4740 tccaccgccg cctcccggct ccttcttatc cgagccgggt tggagtacg gcttgaaact    4800 cgacttgtcc tccacgccga tgtcgctcag cttcaggggg cccgatttgg tgtccttgtc    4860
gcccgcagca ccgccgccgg caccgcccgc gccgcccccg ttggaggcaa ccgaggagag    4920
tttggaggag ggcgaggggt cgggcttccc gatctgcgaa catgtttgcg ccaacagcgc    4980
cagcgggctc ttcttggcat cgagctgcgg ggtcagacga tggggggga gcgtcacaca    5040 gagaaagaag tggaaaccct ttagaatcct ggcttctggg gttcaaatgc ctctccgcaa    5100
cagcccacga agatcctccc agccccaagg cgcaattcta ggcggcaccc cctcttcaac    5160
acccactcac aaacattctc gccgttggga aaggcagcag attgctcccc cgcccaacc    5220 accaccccca gcagcatctt tcctgccctc tctgagcgct aactagattt ttaaagagca    5280
aaatgttttg gttttcggtt cctagaccca gaactgtacc ccctcccac aaacactcct    5340 taattcttca gagtaagggc tcgggcggct ggcgcctcag aggctgtgtg cacacactgg    5400
cttctgcgga tacgaaggac ggcgactttg gaaccgtatt tcagacctcc gcctgccttc    5460
ggtgccgagt gaaggggcct gggtcggggt aggggctttc atatcgaaag gagaaacaag    5520
tattggcagc cttgctccct agcatgcacg ccccattcca cttcctcccc cttttccgcc    5580
ctagttttga ggtacggaag cagtagcctc ttcccccatt cgggagctga atcactccga    5640 ccccccacc tccgcccaga tcccgagaaa aagaaagccc tagggtggca gccagggtag    5700
tggtcccagt gcgatccaga gagggtcc ttacctcgat ggggctgacc ggcgtggaag    5760 gcagggggctg caggtactcg gggtgcaaaa tgtggccagt tcgtgccgtc agcatcttca    5820
gcaccttgat tggcaggcgg ttggcctggc gcaggggtc agaggggggc acggcgtgca    5880
caaaaggctt ggtgctgccg gccggggacg agcctgggcc ggggccggag ctatttccag    5940
agagcgcgct ggtccaggca gggtctgcac cgccgcctcc gcctccgccg ccgccgccgc    6000
cgctgtgctt actgcttctt agggcagaaa gcgagggcgc tgtgctcatg acccaccgc    6060 gcgcatggga gcagcggggg ggagggctcc gggaggcgcg gggcgggctc ggggctgcgc    6120
gctcgccccg ggagcaggag cagcgggagg aggaggagct ggcgcggcgg ccacgggcgc    6180
ccagcgcgcc ttctcggcgc ctggagccag acgcgagtaa tcctgggtgg cccgcagcgg    6240
agccgtggcc gggctagagg agccggctgg actgcgggag tgccgggcgg ctcgcggtgt    6300
ccgcctcggg ctgctcccct gcgctgcgtt ctcgcggccc cgccgccggcg ctgcgctctg    6360 cgatgcgagc cgctgcgtgt ccagccgggg ctctggcgga gaaactcact tcaaaagcag    6420
ctgcaccaag ggggagatta aagcctttgc cgccttccaa tcaaatggga gcccgaggtg    6480
attggagggt caaggggatg tgacgcgtcc cgcgccgccg ccgccgccgc tgccaggact    6540
ctcagtgccg gttttaatgg gcagctccct cttcgccgcc ccctgtgtg tccctccct    6600 cgatttcgct gggaggacga gatggacatt tattctacgt ttgccatccg ccgcctccct    6660 ctttttttcct cctcgtcgtt cttccttcc ccagctcgaa aataaactga aaccttcttt    6720
tgaagggggg tgcgcgtgag gaacagactg cgggggggtgt ccagaaggag caccggtggg    6780
agtgtggaca ccgccggac tgtcaactcc aggggcgaag ggaacctgca cacccagtgt    6840
tttttccttc gcagtaatcg agatcccgcg cggcgcagcg cagccaccag ggtaagaagg    6900
```

```
caaggtgggg agccggagct ggaagaagcc cgcccgcccg ctctaatttc ctcagattcc   6960
gcggcggaga aaccagaagc tagatgggca gtcgcagcgg cggcggctca acaccgcgag   7020
gagcgctggg ctctccgccc ttcccggcca cgtgacgccc ggggacgcgt agattggggc   7080
agcagcgggg gtcacatgtt tcctctgttt caccctcagt ctgtccccca accccccatt   7140
cttactctcc caccctgttt tcctccctcc cccccttctt tgggcatctc caccccctcca  7200
tcaattgtca atgttcctcg accgcaatca atcagttatt tgtcagctct tgtcaatcct   7260
cccgtgattt atgtcagctt ttgttgctga ttacaaggcg ggtgcgactt gaagggaaaa   7320
agagagaggg agagagagac ggagaggaag gaggagattg agaggaact ggaggagggg    7380
aaaagaggag cggcctcctg ggatgggggt ggggtggggg ctctaagaaa aagaatgaaa   7440
gaggcgcacg gtgtcaggaa aatgaatagc gagagtaaag tgcgcaggtg cgcccagggc   7500
gccgagaggg gcgcgcaggc ctggagtgtg cgcctgccct ctcggtgtcg gagagacgcc   7560
cttccacctc tgggagcctc ggtctgttgg ggtcgcggag ttcgggcgcg gctccgggta   7620
cccgagacca gcggcggcaa cttctaacac gggagatttc ccgccacccc accccgccgc   7680
cgcgagtcct cgcggggcgt gttgcgtgcg gaggtcaggc tgccaccctc tgtagttccc   7740
taaccccaaa ctcggagact tctaagagcc acaccaccaa ggaacttcta gtcctggagg   7800
tcaatggtgg ggcaaacctc gcctcaattc tttgacccc tcgggtcgta agcagggcta   7860
agaggctgcg aagaagaggc ctggccatgg gtgtatgggg gaagaaacat ctcaggctca   7920
ctcatgcccc ctccccgacc ttctcccacc tgccgccatc cccgcaggct ggggagccag   7980
ggtaactcgg ggctgctctc tcgaatttat tggaacgccg agtcggaatg agctgcgcta   8040
ggagagccga gggaaggagc gagagaggga ggggcggct gcctgtggga acgcgggttc   8100
ttccagggaa gcggagcggg actgccgcgt tcccctcgat ttgcaccgtc actcgggttg   8160
tttgggaaga aaaggggagg cgctgtgcgt gccaccgggt acctggacct ggatgcccag   8220
tgtgtatgca tgcctgtggc gctgcgtgag ttatcggggc tctgatagcg tccggagcgg   8280
gttcgagggt ctcctccagg aactcgcaga aattagaggg ggtggggagg aggacacacc   8340
cccttcctcg gaacgactta gaagactttg aatctcccct cctccgcttt tccgcccgg    8400
ctcttctttt gttgtcaagt cctttgata aatggtgggg ctgggagctc tgggagtcgg    8460
gagccagtct gtgcccgcgt ggggggcggg ggccgagcct ggagaccccgg tttcgaccgg   8520
cgcgcacctg gggctgagcc gggtgcgcgc ggggtcggg tctggaactg cccttggtat    8580
gctcgccctc tcctcttggc ccatctcact cccctccccc acctgactcc cctcccggc    8640
ttctttctct gtctcccact ccgcacgggt accgagaact ttccggggtg agttttagaa   8700
tttgctccta ggcattcttt ttctgcgttt ggattttatc ccttgattct ttgggttggt   8760
aaactttatg aaatggtaac ttgactgaag ctcatttgga gagaagaggg gagtgaggcg   8820
gtgtgtgctt gggctggtg tttgtcagtg tgagcgtgta agagcacacc tgcattcaag    8880
ggggtttgta gtgtccgtgc gacatctgag ggaggtgagt cggcgagcgg gtggcgaggc   8940
cccacgctga gggaggcggt tgtctggtct ccggggagca agtcccaggt gcgcgtttcg   9000
gagggcggga cagtcctacg ctgtctctgc ggggcagcgc gtctgtgaag cactcttatc   9060
cttcgggtgt gtccatgtgt gcctggttac tgagtgcgcg gccgtctagg tgtcgaccca   9120
accaatggta gtgctcctaa cgccgcgagc ccacctttgg gccgctatcg ccgcggcctc   9180
cccgcgaggc ccgggcactg aaattctggg gcctgcgaca gggccggggg ggacgcagcc   9240
aagggcgtcc ctccccagcc tccagactca gctcttcccc ctctcctcta attccagcag   9300
```

```
cttattacgc cggcggctca ggggaggcag cctcagcacc tgaagcctgg ggggccgtg      9360 gagtggctcc tgcgtccccc ggtgtggcca cacacgctcg tggggctgcg ctgtgctgcg      9420
tgggtgcggg tcgtggtcag cgtgcgttcg ctttcctcaa aactccactc cgagggtccg      9480
agcgcatggg ggcgcctggg ggcctgcgcg cccggggctt tgggaggcg ccagcgtccg      9540 agcctgcgca cctcgcgcag gaggccaaac ccccgaaggc cggcgcgggc ccgggagtgg      9600
gggccattaa ttactctgcg ccaggcctaa agcctccaac ccccagcagc agttggcgtg      9660
gatgtcctgc ggattttatt tgcaaacaat ggaaatgatt tgttttctct aaaaaggag      9720 tgggcaaggc agatattgga ggaggggtg ggaggaggag aaggaagggg aaagagctga      9780
ggaaaaaagt ttgaaaatgc cttgaactat tcactgtcga gatggctaat cagtattgag      9840
gccggagggc aggcgggccg cctttcaccg ccgcttccct ttcatctcgg gctcggcgga      9900
ggcgctcaat taaaagccta tcagtttgta agtaaatcaa cgcctatcag agttgtcaca      9960
tcaaacaaaa cgattattat tgcagcccgc ctcccctatt aatctccctc gaagataatc     10020
cgcctgacag gtcaggcccg gcgagctgga aagcctggcc cagagcaccc aaacagtccc     10080
ggactggcgc gcgccccccgg gggcctcccc accctgtcc tgccccgcct cgcggtccct     10140
gggagcgggg agagaaagcg cgcgcggagg cctctgcacc caggtccgcc ccacctgact     10200
gggagcaagg cccagattcg cggggccagt agggacagt cccgcgcggc cctcgccgct     10260
gctcggggca ggggagaagc ctggcgtgca ggagccgcgg cccggcccgg ggtctcgcca     10320
cggcctgcgc tctcctcggc tctcatttat ttttcttcctc ccttcttttt gttttctctc     10380
ccgcgtcttt ctgggctccc ccatctttt ccttcatttc cttttccttt tccctttttt     10440
ttacttgcca gggagtattt cccattctgg ctctctcttc ttggtgtgcc gtataaacct     10500
ttcttgcgca gccacactgc ctggagtagg atgttctcag gcccgggtt atttctcccg     10560 ggttgcccca ggagtgtgca gttcccagaa actcatggca aagtcctcta taatctcttt     10620
ccgagcaggg gctctgagaa gctctgcgcc tgtttaaggg ttgggtgggt ttggagggt     10680 gaagaggaaa aagagggaga gagactggtg gacagttgtc ctattctgga attagtattt     10740
tgccttggaa tttcatagct gtaacgttgc cgacctcgct gttggcgttg cccgggcttt     10800
tcaaatatgt agataagact caaggggca tccaggcctc agtagtgact atgtgtgtgt     10860
gggtgggtgc ctgatacaag taaatacacc cagataactg cctctgtggc ctcaagttag     10920
tgtcccaaga gtttgggtgg ggcctcgctt ctagaaggcg caaaaatcgt ggccttcttc     10980
ccagtggcct ccggcttcct gctttgggat gcctcggaat cgagccggac ccgcctttt      11040 ctgcgctctt cctccacatc tgtaggccca acggccact gccggagcca ggtggagcca     11100
ggattgaggg gtagctgaag tgtctgtgac gaaagggctg cccgagggag cccaggcctg     11160
ccacctcata tgtcgggttc agtgcgccgc gaaggctctc cgcgcctgta tctcggagga     11220
cccccagagc gctgcagtat tgggcgtcag ggccgagcct ctcgcagcag tcacgccgca     11280
gtccgaggcc acggacatcc aatagagccc acttcaactt gcatggtgca tggggtccag     11340
gaccggtggc cccacacag ggtttcccaa agcctctcca tttgtctgca ctctccactg     11400
ccgaccttgt aggaaattta tttccatgcc cagaaatatt gtttggacac agtggctcgg     11460
ttatcttcgc gcctgctttt cttaaataca tttatttcac ctctgccacg ctgcagatat     11520
ttaaagatct gtagataccg taaccctcag cgatgcggga ctcactctgg ttatagataa     11580
tattctctgg gtggttattt gaacataagt tctatctcca gcccagatga cacccaagca     11640
```

```
ggggctgtaa aggacacttg ctctagaatg ttttcaactg aaatatatgt ccacacacgg    11700
agaatttaag agtattttta tatttctctc tagatctaaa tattcagatg tgttaattac    11760
atgccctaga agctggaagc gatcagtggt gttcacactg gacgtggagc tgtttgtata    11820
attttcatct ccctgcactt aaacatgact ctcagtctaa taaattcaac cttgtcattt    11880
ttagaatcga cgggatttct ctggctgtcg tttgcgctgc atttatccga atacatccag    11940
ctcgcaggca tcctgcaaga aacggctccc ggctcgcgtg tacgccgaca cctcggccca    12000
acgcaggact cgaggtggtt tctagtgccc gggtggctgc aagtctgccc tccgagggag    12060
gctggacaag cggcgccccc aggtcgagcg gcctctcgct gcctggcagt gcctggcagc    12120
ccccacctct gccagtgctt cggaaacccg cctggccagg ttcgcccgcg gtgaaaaatg    12180
aaagcaaatt ccccaacaga ggtagccgga actttcctcg acgaaggctc cctcctgcgc    12240
ctgtgtctgg agaaccccca gagcgctgca agttagcaag agagattcga tggcggctct    12300
ggaaggcgca cgaagggtgg ggcgggggag caaagaggcc actgggtgac ccagcctggt    12360
ccggggtgaa acgctagaga aggcgcctcg ccttccttat ttcaatgcaa ctcctcggcc    12420
ccagacggta aaaatagttt ccaagctgcc gcggacgccc aggatgtgtt tgcagagatc    12480
aaactgggga ggaggcagct ttgtaaaagt tgcagaaaga ttagccgaga agcgtccgcc    12540
cggcggggct caagaaagct tggggacagc tccatgttcc ttggggcgga atggcccaag    12600
aattggcctg ggtaacccccc tgcccagttc tctgtcctca cttcgagcca gtgcttaaat    12660
aacttcccgc cgcctgccct gcaaacttcc cggcgcggcg ccgttgaggc caggacacag    12720
caaaggctag caaaaccccg ccgcggcgcg ctcggccccg gccctgagag ctgcgcgggg    12780
tgggaggacc agtgtggttt ctgctcccac tcggctgccc agaccctcaa gaccgatccc    12840
ccaactcctg ggagcgggtg cttccctctg ggagccgaga tcttgcgggg ccagcgaggg    12900
cgcaaagtgc gcgcgctggc ccgcgcgggg gcggccgcgc gtctctccgc ggggcctgtc    12960
gccaggccgg ccgcggcgcg tgagtgatga gggcagagaa gggcgcccat aaatcgcggg    13020
tgtcagggcg aaaaactctc tttattgtct gcgtgatgga tgggcccggg gacgagacac    13080
caaatacttc gtatcgccctt taaatgggaa cacattttcc gcggccataa ttcatgtttt    13140
ttaaatagaa agtttgaaat gttgcctata tttcaccagc cctgacatat ttatgaatcg    13200
ctccctgcat gcaaatatca ttacttaaag cgccggggag agcgcggggg aggggaggag    13260
gcgcggttcc cggggcgtgg gggtggtgaa ccggggaaat atcggtggag ggggggccatc    13320 tccctaaagg gcagagggtg aggtgcggtg aatagccgta tccggaaacc gagcgtgccc    13380
cgggcttctt tcccgccgcc agaccccgca cagccgccct gggacgtttt tcgaggcttg    13440
ggacctaaga cgggtccccg gaccctgctg ggaaaccagg gggcgttttt cgtccctctc    13500
tgaggccatt atccaagctg aaaccacctt ttataagaaa aaagtttaaa gaaaaaaaat    13560
ttaacaaaca caaataataa taataaccca acatgtttcg cgttctttgc cactgcatcg    13620
attttattga ttttcattct gcaaacctgg gaatgtgcgc gctcgggagg ggaggctgtc    13680
aaaacccagt catcgcgggg actggatggg ggacaattct ccgacgccgc ggcctggacc    13740
cgcccccacc caaccggcgc accacctccc aggcaccacg gagcctgcgc aagctgcggg    13800
gccgtaaagg aaccggcccc caatctccgg ggcttcagtc ccgcccctct ctcccccag    13860 tgccctgcag cgctcccagg gtccgtgtct gccctcccca agcccccact gtcaatacaa    13920
tccctgttaa aaaaaaaaaa tctttttaga gccaggcacg tgccgtcggc ctctcccctg    13980
cccgcctggc ccaggaggcg cccacacctg cgccctcact tgccgagact tttacctgtg    14040
```

```
cagtccccgg cggcgcctgc agccgcgcag gtaaccgaga aatggaaggg agggctgggg   14100
agtgagaagg acagagagca ccgcccgaca caaccagacg cgcggacccg gggcctcctc   14160
tctggaccgg tgctggggcc ctggtagaac cagctccggg agccgaaatt gagccatgaa   14220
gagtgggccg agggaggggc gagggaacgg ggcctcagga gggaggggcg ggcccggcgg   14280
cacttccgtt gggggtgggg ctgcgggctg ccgcgccggt cccgcccctc cgccgcgcgg   14340
gcccgcccgc tccaggccag gctccgcccc caccgactcg gagctggatc tcaggccacg   14400
gcgccccccc agtcgcgccc ccaaccccgg aggcctcggg ctgaaccggg tttcgcagga   14460
gggcacaggg cg                                                       14472

<210> SEQ ID NO 232
<211> LENGTH: 4440
<212> TYPE: DNA
<213> ORGANISM: Homo sapiens

<400> SEQUENCE: 232
cgtgaacgcc ctcgcctcgc acctgtggcg cctgccgcgg ggcccgaccg gaggcagtgg     60
ctgtggacaa gggcggcccc ggcgtaggcc aggatttccc cgcagccgga ccggcccagc    120
tccgctcctt tcctgggcga acagcgccca cctccggccc aggcggcggc gcctccgccc    180
gcggcgcgga cagcgagaga gaaaccggct cctccaaacc tggtggagga gcgctgcaga    240
gaagcgccgg gctgaggctc tgggggccgc ggggcgcgaa acgccgcgcc taccaggtta    300
tgcccgggag aaggagacag gtcgggctcc agccgctggg cgctcctcac ctcgaagcga    360
ggaaaacacc gggccactga gatcagggga ggtgcgcccg atacaggtac ccggcacgca    420
gacacgccca cccccaaaca ccgagaaaca aagactgccc cgagccacgc acgcctgcgc    480
ggccagcgct gggcgcacac ccgcgcccac acagcccgaa gggcgccacg caacccgcaa    540
gaacaccagc tccccgcgct cgcaggctct ccgtgccggc ccgcagcgca gagcagtccc    600
ggcgccgctg cctaggtggg ccggggaagg cgcgccaccg cgcatggcac cgcggctgcc    660
gaggaacaga gggtgccctg cgcagcccag ctcgtcccaa cccctccggt gcccactgct    720
gcgacgcctc gcaggccgtg tcccagtggg ccctgggcac agcggtcact caccttcctg    780
cacagcctgg aatgggttgt tggcctcgat gaccttgatg gagtaggtga tcttctcgct    840
ctgcaggatg tcatcgttga ggctcaggtc ggataccgcc aactggaaca ccctgtcgtc    900
cttggccgcg ttctcctcga agatggcacc tggaggagag aagggatcaa gaccggacct    960
ggacaagaac cctctccccg cttcccttgg cccgagggtc aaggcactcg cagaccgatg   1020
attgccgggt ggtgggaagt ctgaactggg atttcagctt ggcggggtag attaaggctc   1080
tccgatctcc acctgcacag gaatatgttc ccctcccccc accagccctc agcgcacacg   1140
tgcacacagt tgacatgagt tacacatgca catcccacag gctgccacca ggtcacacac   1200
gtgtctcaca accaaggcac cacatgtcct agccatgctc cacacaaggg actaagccaa   1260
gctggggtgg cccccaggcag cgcccaaatg ccttgacatg gttccataaa tcccatccca   1320
ggagccagga agttccccgg gagggtggtg tcccccaccc aaatcccagg acagaatgat   1380
gggtccttct ccatgcacgt cccctgctga gtggagctga gcgaagcagg tctacagttg   1440
gctttcctgc gcagaggggt cttccttagg caggggcttc ggatggcctg cagcttggat   1500
gactgtgacg ctgccggcc tggcgccctg agctcagcct cctactctcc atccttcccc   1560
actcccattt cctgtacgtc tgtcgagggg agtgggggaa gggggacttgt gtcctaggcg   1620
```

```
cctccacgtt cagatctagc ggagctgggg gtcccagaag gagctgctct tgaagggctt    1680
tctagaaccg cggacagctc ctccagggcg ccctccggct ggcgctttgt gcgcctagca    1740
cagcttccac ggaccctgcg cttccagccg agatcagtgc gaccagcccg agcctagtcc    1800
tgcaacctgg acagctctgg agtcagccac ccacatcccg cctcaccaag cctcgagggt    1860
ccctgaggtc ccggagctag gcccagtgat ccctcgagct gggggctggg taggaggagg    1920
gaggcccgga ttcctcacta cacccggagc cggcgccgca atgctgaccg cgagacccgc    1980 accccctccag ggcgggaagc aggtttggtc acgggcccct gaggaggaat cgtagctctc    2040
cgagcccagg cctagtcctc accacccac tccaccaccc accctcccgc cttgtcccgt    2100
cctcctcgcc ttcaacacct cccaaccccc agtttccctg tgctcgctgg tctttcccaa    2160
cttccggaaa gacgactgcg gagggactcc cccaaagcga ccgctgtcag cccccccaact    2220 cggcccaact tcccgagatt cctcccgtgt tgctcccaac tccaccccac tccccctcgg    2280
cgcgcccact cccctcggc gcgccccctc ctcctctgcg ctttcatctt ctctcccggt    2340
tctctctctc tatccatctc ttcccgctca gcatcccct accccgct gcccacgctt    2400 cttccctcgg ctcccaccac ccagaccgtc tgggcccca agacttggac cacgcaaaac    2460
tctaggactg tccaggatgg ggatgcagtc gccacaacca gatacacacg cactcacaca    2520
tacaccaagg gctacacaga cacacaccgg agaagcaggc agacactgtg tccactctaa    2580
caggctgaca gacagtcgtg cacgcaccaa cacacgctca gatggcccca cacacccaa    2640 caccctctca cagtaacacc gacaccgtgc caggcgcaca cagcgacaca cgctgacaac    2700
acgcacccac acacattcac acacggttcc ggtccggcct ctttgatctt gccctgccaa    2760
cttggcgagc cccccgctgt acctccccct gcccccgct gctctgagct gcgcagaagg    2820
gccctcccga cccgccgacg gcccgctaa gggcgcgggt ctcgacgcgc gtccatcccg    2880
gtgttccccg aagcgtcggc cctaagtgtc ggtagaggcc gcggcccc gcgcggagat    2940 cggagccccg gggagcggca agcagccagc gggagcgcgg cgcggccggt gcacagctcc    3000
tccgccgggc ggcgcggcgc ggcccttcgg gggagcaccg cccgccgagc ccctcggccc    3060
agggaaacgc caagtttgga cgccgcgcac ccctgccc gttggggccc ccgcccagcc    3120
tcggcccggc ctccagccgc gcttaccgat gtggatgatg gagtcggccc gcaccgacac    3180
gcactggcat atccagggga gaagccacag cgtcagcgct tccatgtccc ccgggcgcgc    3240
ggctcatcca cccgggcccg gggcgaggcc gagggcagcg cgaagcgggg aggcgctggt    3300
cccggtgcag tccgggccg ctccccggga gagccgagcc cgcccgtgcg tcttcccccg    3360
cgcgcccgcc cctgcgccct gcgcccgccc cagcccagcc cagcccagcc cagcgcggtc    3420
gggctcccgc tccggctccg gtggcggctg cggcggtgct ggcagcttga gcccaggccg    3480
gcgcggcggg ggcggcccgc ggctgtggca gcggcgcttc ccgcggctag agcggcttcg    3540
ggggaggctg aggcggtggc ggcggcggcc gggccggcgt ggcggctctg ggctggctgt    3600
gtgtctgagc cccggcgagg agcgaactgc ggaggacgcc ccctcccctc ccctccccc    3660 tcagctccgc tcccctccc ctccctgccc gcctccctcc cctccgcccg cctctctacc    3720
acgtgactgc ggagcctcag cctcgccgcg cggctctcgc ccgctcgcgg ctcggagggg    3780
gcgccgggtg ctccacgctc ccggctcggg ggacgctcgg agaccggcac agcggcgggg    3840
accggcctgg gctgcggcgc gccgagctct gacggttcgg gcctccttct ccggttcgcc    3900
aggggcggga gaatggagga gggccggccg ctaactgccc tcgaggggct cccgaagcgc    3960
cctggcgacc tcagcagccg cgcgtctcgg gtcatgtccc cggccgaaac agaccgttcc    4020
```

```
tcgtggagtg ggacctgggg agcaagaaga gagaccgggg cggggcgccg ggccaggccc     4080
caggacagct ggggagccag aggggccgg ccgccgcaag catctcagag tagagcccgg      4140
gccgtgggct cgaaccctgg ctggccgcgc ggacctcggc gggcgccat cccccgctcc      4200 atgggcagcc cgctcagccg ggagtcgggc aagaggctcg gactctgaag cccaattcat     4260
ggccggaaac cagcgcagcc gtgaccgcgg cgcctggacg tgaggagcct tccaagcggc     4320
cggcgggctc agactccgac cctgcacgga gctttcatgt gcgagccgg gcgaagagcc      4380 cgctcctcgc ggccacagcg gaacagggct ccctccgcct ccggtgcctg cctcgggccg     4440
```

<210> SEQ ID NO 233
<211> LENGTH: 408
<212> TYPE: DNA
<213> ORGANISM: Homo sapiens
<400> SEQUENCE: 233

```
cgagggtttg atgatgcggc ccgagcctgg ctgtggtcgc ctgtcggggc tggagcggga      60
ccctcagccg ggccgggcct gggggctaac gttttcacag tgcgccctga gtttccttgg     120
gttactgctg ggaccgcgca ggaggaagca aagagttttt cgagctagac caacaggaaa    180
cacattgacg gaaatgttgc catagcccat ggggtggctt taactggccg cccccgcggg     240
ctgggtgtga aatcagagga ggccgcggct ccccggcca ggattggagg ctcctcgcgc      300
aacctaatgc gggtgtccgg gcccgagcgc ttcccgcgca gccaggcctt gtcggtgcag     360
cagccccgct cctccccaac acgcacacac ccggtgttcg caagtgcg                  408
```

<210> SEQ ID NO 234
<211> LENGTH: 2237
<212> TYPE: DNA
<213> ORGANISM: Homo sapiens
<400> SEQUENCE: 234

```
cgcgcccgac tgcgggagcc aggatcaggt ccccagggcg cccttgcaga cagcaccctg      60
agcgaaggag ctcagaaggc agtccggctt cacccagacc cccaatccca cagaagcgcc     120 gtccccagc ggcacagcac cccctccccg gcgcggtggt agggcccgac gtgacgtcac       180
ccattgttta caaatcaacc cgagccggca ggattccggc tcccgcggct gcaggcgcgc     240
ggctagagtg cctggcgggc tccggcttcc gcgtccgccc cggccccggt ccagacttag     300
tcttcagctc cgcgcccgct ccgccgcggc ccaccgcgcc cgccggcagc cgagccccca    360
gcgacgcccg cacagctccg ggtgcccaga caggggccca tgccgtgccg gagggaggag     420
gaagaggaag ccggcgagga ggcggagggg gaggaagagg aggaggacag cttcctccta    480
ctgcagcagt cagtggcgct gggcagctcg ggcgaggtgg accggctggt ggcccagatc    540
ggcgagacgc tgcagctgga cgcggcgcag cacagcccgg cctcgccgtg cgggccccg      600 ggggcgccgc tgcgggcccc ggggcccctg gctgcggcgg tgccggcgga caaggccagg    660
tccccggcgg tgccgctgct gctgccgccc gcgttggcgg agactgtggg cccggcgccc    720
cctggggtcc tgcgctgcgc cctggggac gcggccgcg tgggggccg cgctgcgccc      780 tactgcgtgg ccgagctcgc cacaggcccc agcgcgctgt ccccactgcc ccctcaggcc    840
gaccttgatg ggcctccggg agctggcaag cagggcatcc cgcagccgct gtcgggtccg    900
tgccggcgag gatggctccg gggcgccgcc gcctccgcc gcctgcagca gcgacgcggg    960
tcccaaccag aaacccgcac aggcgacgac gaccccgcacc ggcttctgca gcagctagtg   1020
```

```
ctctctggaa acctcatcaa ggaggccgtg cgaaggcttc attcgcgacg gctgcagtta     1080
cgtgcaaagc ttccccaacg cccgctcctg ggacctctgt cggccccggt gcatgaaccc     1140
ccttcgcctc gcagccctcg cgcggcctgc agtgaccctg gcgcctccgg gagggcgcag     1200
ctcagaactg gcgacggcgt tcttgtgcct ggcagctaac acgcccgggg tggccacagc     1260
gccagcctca gactggaggg caaggggttc ccttgagggc tgcagttcta ctcaggctgg     1320
tggagaactc tggcttttgg aagcgagagt aaaaagctaa tgacgaggaa ccgaaaaatc     1380
gcgagtgttt cgcgggtaac tggggttgag ggccaaaata tttggaatga aggactttgg     1440
ccctatttaa ggcagatttt acagagcgca cctcaaacgt acaagtcagt aggactcctt     1500
atttggcgtg acccgacctg gccgcggagc ctgcatttcc tcgcagcctc tcagtgccct     1560
ccagccccgc gaccatgtgg ccacaatcca cgcttctccg gatcgcggtg cgccggaacc     1620
acggaggatg atgccagtta cttgctttac cttttcaggg ctggctcctg atccactttg     1680
ggggaggaga acatgagtag ataatttcag ggtgcagccc aatctgccag acttaaaaaa     1740
accatcttgt gtctttggag gtgctgctta ataccaaaca tgcggtgcca tgaagggacc     1800 ctttggggt tgaataggag ttaacccctg cgctctcttt gcaactgtct ctcttctcag      1860
agtggtgggg gaaggctgta cgacacgggt ggggaaggga ggtgggggcg gggagtattg     1920
aatggtggtg gaagggtaga gaggcgcgga gtgaacccca cgccctgtct aaagtgtatt     1980
ttcagagccg gcccgcctct cctcggttca aggtcactgt ttcctgggca cgcactgggt     2040
tgcgggacag agtagccagg ttctgccggt gctcggagaa gagcgcagtg ttttgcaagt     2100
gctggagtct cctgaggaca cgcgcgtcgc cgccaccgcg ggtgtgggaa agcgcggacg     2160
tgctgggcgg ctgtgcttcg gtaggcgacc accgcccctg gccgcgctcc gggctttcac     2220
ggaaactccc gagaccg                                                    2237

<210> SEQ ID NO 235
<211> LENGTH: 758
<212> TYPE: DNA
<213> ORGANISM: Homo sapiens

<400> SEQUENCE: 235
cgtgcacggg cttggagacg gggcgccagt accaggcagg gcacaatgag gcttggggcc       60
cttacagtcg ctgcaacctg gaggtaccga accggggact ccgacctgac atgcaggcga      120
ggctgcgagg tccagagcct ggacctggtt cctagggagc gccactcctt ctgaccctg      180 tggcgtgcgt cctggcgcgc cgcacccgcc tggtgcctcg gccctctctg ctgttccctg      240
gctgattctg agcaaggcca gcagcccacg gccccacccg accccacat ctccgcaggg      300 tcaggcgagc cgagcaggaa ctgcgccggg gcagtggtga tggctgggcg tccctgcagc      360
ttcaggggcc aagggcaatc gggggggctag gcccgcagac ctggccgtcc gctgacgcag      420
cgaaggtcta gcggaacctt ggggatcgct ctcccagtgc cgaccgaagg cccggacctc      480
caggctggac gcggcgaagg ccgcataaga cgttacttaa acatgttact taaacaagac      540
tgcagtaaac gtttctttcc aagtgagaaa ggtctttttc gttctcagac ggtttgaagg      600
tgtttgtgcc aacgtgaccc ccggggagat ttggaggaag cttttctacgt cctaggaggc      660 tgagatccca cggagccggt ttacggttga gagcagacag tttcgagtag atagcgctgg      720
aagagacacg aagaatctct cttgcttctt ggaacgcg                              758

<210> SEQ ID NO 236
<211> LENGTH: 5881
```

```
<212> TYPE: DNA
<213> ORGANISM: Homo sapiens

<400> SEQUENCE: 236
cgctttaact agacgggcgg ataaatggcc ccgtttctcc tcagcccga cgcgcctgct      60
tagctgcgcg ccccgcgggc gccgcagctc gggtgggctc agccctgggg ccgccgcccc    120
cagcccaaag ggacccagcg gggccaggcc cagggccgcg aagcagagag cggccggagg    180
tgccagggcc gcttcattgg gattcatgag cgtgttgggc gggcggcctg gggcttcggg    240
cgcggggcgg gggccgagtg gggggtgcg cacggcgggc gcagatgccc gggtgaccga     300
cccgccgtgt tccctgcgcc gcctttgtgc cgaggaggcg cgcgcgggga cctaatccat    360
caaattgtct acaaattgtg aagaaaattc aaaaaccata tggtcgccag cgccggcgcg    420
ctctgggctg cggagggccg cggccgtgcc cgcaccggga gccgcggggg gctgggcccg    480
gctattgtcg cctgtcagcg gccgcccagg cccattcgtc ccggccttca tggtccgcgc    540
tccgaattac agaccatcc atcctaagag agggcaattt ttgtcgcccg ggaggaacca     600
gccgcacgcc tgccccgctg ccctgccgtc tccttccttc tctgctcctt ctctctcttc    660
tcctctcttc ccattctttt tttctcccctc tgtctctgtc tcccttcttc cgtttctctg   720
tttctctctc ttttctctct ttttctccgt cctgtctctg tggctctccg cttctctct    780
ctgcttttgg agtgtctttc tgtgctccta tttttttttc ctgtttctct ctgtctcttc   840
gtttcctcct ggacacgcac gttcctggct cgggcccggg ggcccatcg ccgcccgaga    900
ccagatgcgc atttctcaca tcaattttgc ggagaaagag agcccagcgg cccggaggcg   960
ggacccccact ccggtgacag cggctactcg ccagcccagc gacaacaaaa gcccggagag 1020
aaacccgctc tgtccaggaa agtgaaagcg gcctcagccc ccgccccagc cggccttggg  1080
gcgccgcaga cccgagagag tccttgcaag atccataccct ctgcccccag cggtgtgccg 1140
gggtgtggag gcagaattgg ttaatgttgc cagaaattca caccagctcc cagacgcttg  1200
ggcttacagt tccaggtgcc cacattgaaa ttcagcctgg ccttgatgcc tttagccttt   1260
ggccccccgac tccccaagga tgaggccctc ggggctagaa tcgaaacttg ggaacccaag  1320
gctccacccc gcgtctgact gagtgatacc tgcagcgctc ccggggctca gccctgtttt  1380
cggggagtgc agggagaatg cccttgggtc tggggtggga tgcaggaaat gcagggcaag  1440
accccctccc acccttttgtt caacacaaat taatgttgta ctgtggtgtg ccccacata   1500
cacaggcatt ttctcccagc atttcacggc tcgttttta ccccgacctg gcgaagcccg   1560
cttctctccc gatttagcag ctgcctcagg tttatgggca agaggcgcct cctcctgctg  1620
cttccccctc gcccttcact cttaagcctg tcctgaaaat ccccccaaa tctccaaggc    1680
tagggcgacc ggcacgaaga gcggcaagaa gcccagcctg ccgctgcttc tcggaaacgg  1740
gcccaccact cagacacggt cgccgccggt tctagtaaaa tggcaaagac tttatttatt  1800
ggagaaagag gccttgggta cagtctaggg aggagagggg aagggaggag cagggaaggg  1860
gcactcgcag cccactcaca tccagccacc ctcctctggc caagtcgggt aggagtgggg  1920
tgttcgaagt ggcaagagag acccagagct gtggaggagg tgaggtgagg gcttgggtcg  1980
gcctcctctc tgtctctgtc acatgcaaaa aaattctaaa aagagtacaa ataattata   2040
gggctttggg ttctgttttc gatagttggt tggttggatt tccccctgca ttgtccctaa  2100
gagccggact ccaacagtca gtccgaggaa atgcgggagg gagggaggaa tcttaaaaac  2160
agcattagtg ggcattagga ggcagaaatg gcatcgaaaa cagactttc tctcagaggg    2220
```

```
tggggaggaa agatcgattt tgaaacttgc aagtcaggac ctgactgccc acctcttccc    2280
ctcccacatg aggaaaaaag gcccgaggaa atagaagtca actgcaataa ggccgaggga    2340
ggcgaggaag gagcgggccg gtgcattcgc cacatgcaga gaaaaatcaa aacagccgga    2400
gctgccactc ccctagaccg cagggttagt gttccccgcc ctggtttctg tctcgccctc    2460
agcaaacccg gcagcccgag agctttgaaa acatcgaaat ctccgagatt taaaaaataa    2520
taataaaaga aaggaaaaat caggctgcgg tgggaagaac ccgctatata ggtttaaata    2580
tttatataga agccatacag aattgcacgg cgagggcttc cggggcggcg gaggccgctg    2640
gtggcggccg gccggccgg ccagcctggg tttattgctt cgagagggaa gaggcggctg     2700
ccaggagccg agtccggggc cggggacagg ggaggaggcg ggagttggca gaggaggtcc    2760
cagctcccct cggcggtccg gtccggggag cgttgggctt cgagcgcta ggagcccagg     2820 gcggcggaag accggggcg ccgctcaatc gtccacgtcg atctcttcgt cttcctcgtc     2880
ctccgagcag tcctggctgc tggccggctg gtccgtgagc ggagaggcag gcgagagctg    2940
cagggcgcca gcgcccgggg ccttcggggc gcctggggg aggaccggag agccgggcct     3000
cgacttggcc ctgccgcagc cgccgccacc gccggctgtg gcctccgagt tctgctcgag    3060
ttcggccagc gccacgatgt ccatctgccc gctggggccc agtttcttgg cggactctac    3120
gtcggccttc atctcctcca ggtcccgctt gagcttagcg cgccgattct ggaaccaggt    3180
gatgacttgc gcgttggtga ggcccagctg ctgcgcgatt tggtcgcgat cggcggggga    3240
caggtacttc tggtatagaa agcgcttttc caattcatag atctggtggt tggtgaaggc    3300
cgtgcgcgac tttcgccgct tcttaggggt ctgccgctgc ccaaagatgg tcataccgtc    3360
gcggcctggg aggaaaggac agtgtaggct cgcgttggga gagaggaagc ccaccctggc    3420
tctcgccccc gtaactccgt aacccaccca ggcctgccg gcctgcagtc taccaatgtt     3480
cccttctcag atttaattca gcctccagga ccagggcaag tcttggctat ggcaaaccat    3540
ctcctgtctt tggtctccca gaagtcccta ggaaaaattg ttttggtctc tgcccccta     3600 ctaagagttg gtttgaaaga cccaaagtct ctaagggtat gagaaagcca gacagagaca    3660
ccctaattgc ggtgtgaatg ttggttctcc atcccttccc aatcacttca actctaccct    3720
acccataagg tccccggcaa aagactctcg attccccacg ccgagtagcc gggctaagag    3780
cgcccaggac actgggaacg caagggagcc cggcaaagca agcagactgc ggaaagagct    3840
tggccaccct tctcctgcca cccccagct ctggcctacc cagaggtccc tgggaaataa     3900
ggattgggtc ccgtcccaca tatcttcact cccataagca gctgctcagg ctggaaggcc    3960
ctggcggccg gagagggcag aggcgagcag aggcataggg gacgaagcgc gcagggcaca    4020
gggcgcgagg cgctgggtgc agggggaaccc agcagctgcg cctaccttcg gctgcctgca    4080
gaacgctgac ctccagcccc ttaaacgtct tgctggcgag ctcctccagc gcgcacagcg    4140
gcgaggtctg cgagagcagc gcgcggcccg ccaggggcaa gccgccctgc gcgtgcttgt    4200
ccgcggcggc cagcaggtgc gccgccccgc acagcgagta acttctccgc acagacggct    4260
tgttgaggat gtcctcgatg ctgaacggcg tcagtggctt gttggagttg gcaggcggag    4320
gcaggtggtc cagcggggctg cgccgccgct cctccccgg gccgccttg ccgtcctcct     4380 tggaagtcat ctcggccttg ttcggggtcc cggccggggc ggctcgggcc gcgggaccc     4440 agcccgcggg cagctcgggc gccggacggc gcggcaggc agcggcgggt ggaaaggagg     4500
ccgcactggg cagggcgcgg gccggggcgcg gggccgatta gcgcggcggc tgaggagggg    4560
agaacagcgc ggggcccggg gaagagggcg ctgacgcggg cgccgctgct gctgggggctt   4620
```

```
ccagcaatcc ggggccggag ccggggcgcg ctgcgcgggg ctccagtttc gccaaccccg    4680
gtgctattta aaggtgtcag gtggctcggc agtggctcct ggccccgggt cctggcggcc    4740
gcagttggaa gagccgaggc gagggcgccg atcccggact gcgagggagg cggagagacg    4800
gggcaattga ctattgctaa caagttagcc ttgatcgcgg tgtaatcaat tatctgcagc    4860
ggcacttctt tctcttctc tctcctttct ccctttttcc tctcttcttt gcctctgttc    4920
tctcctcctg ttctcgctct ccctccctcc ctctctcttc tctcttctct gctccccct    4980 tctctctcct tctctccctc tccctcgccc tctctttcac tctctgtctg tccaatgcag    5040
gcggctgtaa gttgggaagc tcattaatta gcgggccggg ggtaggagga gccggctgga    5100
attagcctgc ctaatgcgcc tgtcagtccg ggcgctgcgc tgcgttcggc ccgagctgtt    5160
tgtaaattac attagctgct cctttattgc acccgaacct cgggcgactg aaaagccacc    5220 gccccaccc caaactgcga gccgcgctcc tggcgcaccc gcctcccgcc ggcctagctg    5280
caatgaccgc accggcccga aggtctcggt ctctccgacc cggatgtgg agcccgaaag    5340 agtggtggga accccagccc gggagggacg cggccgccgc tcgggccagg taggaccagg    5400
agcccgggtg ggccccgctg ccacccagag tggactttgc ggagctgaga tcaagagccc    5460
agcgcctcta cctctgaccc tcttgcccct cacccccactg cctgggcgac gcgcctgggg    5520
agagggaatc tgaagcccctc ctgcgctggc ccgcaggagg tcagagccgg ctgcgcagcc    5580
ttgggtgggc gacgcgggaa gggggtggag gaccccaggg gttggggag ggggctagtc    5640 ggagagctca gccttctcca cgcggagagg cggaggaggg aattgttggc ggctctggac    5700
gcctctcccc ggcctgattc cgaagcggcc gccctacctc ctccggcaat cttgctcact    5760
ttcctccggc agccgctccc caggctggct ggggccacca acggcctgat gatgggcgtc    5820
tgaagagtag ccaggccagg tgccggggct aacggggccg gctccgtgcc tccctgctgc    5880
g                                                                   5881
```

<210> SEQ ID NO 237
<211> LENGTH: 3245
<212> TYPE: DNA
<213> ORGANISM: Homo sapiens

<400> SEQUENCE: 237

```
cggtcacgaa ggatctcagc tgcaccaagc gcgcaggcta cactcctgca gtagcggatt      60
ggggaccaga taagcccacg cggctcccgc ctgagtaccc tcttaactgg cggccgacac     120
tttgaaacaa ttgagtccgt tcagaaacgg actggggaga gtgagggcac gacctcaaaa     180
tcctaggcag caaaatgagg tctggatcct ccctggaaga acagacatct cgactactct     240
ctcgccccac ctctggccgg gaggtcgggg caaggagaat ccctcaaccg agaagatctg     300
gcaagtcccc gatcccaccg gggccttccg cctctttcc ctcatcccct aggaggcttt     360
atcaggttct aaccgcttgt agtggggcc gtgggtgctc ggggcgccaa gaggaggggg     420
ctgccgagag cggcctgcct agttctcagc attgcctctt tgaccactcg caggctcctg     480
gaaatgcaaa cacagcccgt gcgtgatccg cacgcgacca aaagccgagc gcacacctcc     540
cgcccccgcc ccacttgcca tcgctcacac taacgtgcac acatgctcgt gcaaacgcgc     600
acgcacggaa ccgcgcgccc cctcacaccc agccgcgctc ccggcccggc tcagccaggt     660
gcccccacgc ggcagcgccc ggtctgcccg ccggccccct gcgaacccct cgcctcacgc     720
ccgcctgcct gcgcgcacgc acgcgcacgc acgcattccc cacgccccg cgcggggcg      780
```

```
caggccttgg gtggcggggt ttggccggga gccggccggg ccagggagcg gcgagcagag    840
tccagggtgc atcccgcgct tggcttccgt gcgcagcctc cccgcgcgga ggcacctggc    900
tccctctcgg ctctagaacg cgaacagttg gcgttgagca cacaactcct cctccttctc    960
ccccgagacc cctgtaccct ccccgcgcgc catctcccgc ccctcataac aggcccgaag   1020
agtaaacccc caaacgcgtc cagaagcggc tcccaactct tcgccgggag cacgttggag   1080
gctggatttc ggagagactc gggattgggg tctattgccg gccccctcctg gatccggctt   1140
```

```
cagccaagca agaaaaggc gggggacagg ttcccaccat ctccccgact tccctccctc    3240
ccgcg                                                               3245

<210> SEQ ID NO 238
<211> LENGTH: 710
<212> TYPE: DNA
<213> ORGANISM: Homo sapiens

<400> SEQUENCE: 238
cgggcgctca ttctgagccg cgacgccccc tcaacaggct cccggcaccg cagagccaga     60
ggccacgcgg tgagaacccc agtgcgtgcg ctcttcttgt gtgagaggcc ggaggtagag    120
ttgggagaaa gaggagccgg cgaaaaggtt agtgggatct gctttccctt ctgcggcctt    180
ctgggccagc tagggcctgg gagatgggga ccagggtcgg aggcttgggg gcgggagggc    240
ggtgctgccg gctgcttcct gcaagcggtt tgaagaggca tcgcgttgtc cggccgcctg    300
cgcaagggcc acgcgctgct gctttcaccc ccttgcgccc gcggggcacc tggactcccc    360
ttaagagtcc ccgtggggcc tgagcttctg ctgggcgcta cgctgccctc cacgattcca    420
ttttgcccca tttactcggg tcgtccactt cccgcggctc agtgacccag ccaggggggcg   480 tcttccgcta gcggtccaaa tgtagactcc gcaaagaggc taagaagacc tgtctacccg    540
ggtgcgcgcg atggggtcag ggtgtaagaa ccaggagcct catagaaacc tctgcttggg    600
gtccaaagcc cagccgggca ctcccagagg acaacatccg ccccccgcatg tacacgtggc    660 cccgcaggac ccagccgcag ggctcccacg ctcggctccc cgccctctcg                710

<210> SEQ ID NO 239
<211> LENGTH: 474
<212> TYPE: DNA
<213> ORGANISM: Homo sapiens

<400> SEQUENCE: 239
cgaccacttc cgtatgaggc acgattcgtt ggcattcttc acctgcagca accgctgtgg     60
gactaggctg gttccccagc cccggcgggg tgtgagtctg cgacggctgc tcactacatt    120
cgggggacag gcactgcatc gggggtgagc aggccaggga gtttccgag ggcgcctgga    180 gcccgttgag atgtgtggct ctcctccgct cgtcatctgc cgggcagagt gaccactggc    240
tggcggctgc agagtctgac aaaccaggct cgggggccct ggcactgagg gcaggtgcgt    300
aaacggtggc aacctccgtt ttaaacaccc tcctgagggc aggtggagcg ggctcctcgg    360
agtttggcct cccccggtcc tgcttggccc tcccgagcag ctggtaatcg ggctcttcgg    420
atggaggccg agtggagttt tggagcgcag cttctccata gctgagcggc tccg          474

<210> SEQ ID NO 240
<211> LENGTH: 515
<212> TYPE: DNA
<213> ORGANISM: Homo sapiens

<400> SEQUENCE: 240
cgccgccgcc gcggccaagg gcacctgcag aatgtgagag agcctgggag gtcttgcagc     60
ttggtgtcac cccaccaccc taatcccgca gggtggggg aggtcgacgg ccctcctccc     120
aaccccgacg ggtcctgaaa atgggaatg ggtcagcatc gggggtacct aagccgccaa     180
gtccttgact cgcccctgct ctgccgcgca gggtgctgga gaagaagcaa gacaccgggg    240
agacaatcga gctgacggag gatgggaagc ccctagaggt gcccgagagg aaggcgccgc    300
```

```
tgtgcgactg cacgtgcttc ggcctgcccc gccgctacat tatcgccatc atgagcggcc    360
tgggcttctg catctccttc ggtatccgct gcaacctggg cgtggccatt gtggacatgg    420
tcaacaacag caccatccac cgcgggggca aggtcatcaa ggaggtgggc aacgtctggc    480
cgccctggct cctgcccttc ggccatgcgg cctcg                              515

<210> SEQ ID NO 241
<211> LENGTH: 1356
<212> TYPE: DNA
<213> ORGANISM: Homo sapiens

<400> SEQUENCE: 241
cgggaacgtg aagcgaagct caccaccggt gcccgctacc cccacgccgg caactctgtg    60
cttcgtttgg cccacgtgtc ctccccacgc aactagggc gacggtcctg tgcctgaggt    120
gacaatcacc ccccaaaaac ctcacttgcg ggtgggggg tggtgattgc cagttgaccc    180
agaattttct agcaactagg cgcgttaaag tgaaaagccc ctggactagc tccacctccg    240
gccccaacca tcacaggcgg accctagctg atttgactct cacttcccgc cctcagactg    300
ccggcgacga aaatccgccc gaatcgggcg ccacctctgg tggaagctgc tgtcctcggc    360
ttctgcccaa ctccaagaag cggaaggggg gtgtatcctg cgcccaagc tcatgggagc    420 ccacgcaccg gggagagccc ggagtggagg ctctgggctc agccctccca ggcctaggcc    480
accgtgccct gagtccctcc ccaagacttc tcggactaag tgggccagac tcttgtcagg    540
ggagggatca ccaggacctc agattgctgg gggcggaggg gtggacgctc gtgagtgcga    600
agttcgggtg tcacttgggt gtgtccagtg tctacaagtg ggaatcctac ggtttcaaaa    660
gtcaggcagg gatggggttg cctacactcg gtgggtcaa tcgctagtct caccagaggc    720
gggagcgggc ctgggggccc tctgagctcg cggaggcggc gggttcgggg ccgtgcggg    780 cggggtcgcc caggggagcc cgggccccgc gcgtcaggag gcctccgccg gccgagcggc    840
cgcgctggga aacaagaagc gagcgctttg ctccctatct tcccagtgtc cgtcctatat    900
tgttttctgc tcttaaaact gacatgtcta attggcaatt ggtgccgaat cgtgtccaga    960
ggtctcttgt ggaacatttc tacagctgtc tccttcaact agacgcttat tcatgtcgcc    1020
ttaatgagaa acaaaacgtt ctctaatgag caattacaga gcgacaggat tgttcccata    1080
acaaattctt gcgagtgaca gaagcatcct ttgtaccaga tatttcgcat actgttaccg    1140 attttcccctt ccctcgcccg actccatgga ggcgccgggc atccggagcc ggtccgagag    1200
ctcacggatg cgccggcagc ctcctcgcag tcccgcgcgc cgcccctggc cccgagcccc    1260
tcggctccgt tgtgctcctg ggagtgagac gccacgtccc attatcccgc atattatctc    1320
cttgtcacga ggacaacaaa taccgattaa tcttcg                              1356

<210> SEQ ID NO 242
<211> LENGTH: 512
<212> TYPE: DNA
<213> ORGANISM: Homo sapiens

<400> SEQUENCE: 242
cggacgcccg ggtgggaggc tccttccagg acccaggcgc caggggcaa caccgccggg    60 ctgcggtgcg cgggtagcag cgaggacagg aagtgcacgt tgcaggcggg cggctgcggg    120
gcctgcagga gcgcgacgtc ctccagcgcg ctgagctctg ggatcccggg gtactccccg    180
aggagctccc cgccgtcgct gtcgcccccc gcgagcttcg ccttgacctg gcccttgcag    240
tcggcgccca gcgcggggtt gaacgcgtgc aggacgggtt cctggggtc cgccgggccc    300
```

| | | | |
|---|---|---|---|
| aggtacgctt | ctttgaagac gtggaactcg tcctcctcgt acttcacggg ggccttcagg | 360 | |
| ccgatgttct | ccgaagcgaa cggaccctcg gggcttaaga gctccgtcac catcgcatcc | 420 | |
| tcggggctgg | gcagcccgcc cggcagaggg ccctcctcca tggcgcaggg cggcggggcg | 480 | |
| ggatggcggg | ggccgcgcac ctgcaacacg cg | 512 | |

<210> SEQ ID NO 243
<211> LENGTH: 3661
<212> TYPE: DNA
<213> ORGANISM: Homo sapiens

<400> SEQUENCE: 243

| | | |
|---|---|---|
| cggacgggac gggggacggg ggcggggact ggcgggaggg gggcgggaca ggctcgctct | 60 |
| cctcctactt agcgagctcc cggggaaaag caacggtgtc ctcctaagcc tgaggccacc | 120 |
| gcgaccgagc cgagccaggc taagggacca gtgtctccct gcccccccc cacctctagg | 180 |
| taagagcgcc ccgtcccact acacttgcgg gtcccattcg ctgcggtgct aggactggat | 240 |
| aaggggaagt ccccggggcc tggcgagagc cctgagatca gctctaggct agggagctcg | 300 |
| gcagaaaccc gtgggggaga gagggcaccc caggtgagtg cgtgggggcg aaaggagcgt | 360 |
| tatgggagt tttcctgtga gcctcttgct tttgccttcc tcggccgctg ccaacgccac | 420 |
| cgccagaggg ggccgtgacg ctctcccccc cttggagaaa ctctgatcct ggccctatcc | 480 |
| agactctccc gccggcaccc aggcggccgg gcggacactc gcggggtatc gggcggcgag | 540 |
| cgcgcgcgcg ggttttcgtc ctccagcgcc ccacacctcc ccctctccgc ccacagcagg | 600 |
| accttggggc gggggtatct cctgtgacgt ctccccgcct gtcccaggc cggccgcctt | 660 |
| gatggaccag gaagggattc ggagtccggc tcagagtctt gagcgtctag gagggctgcc | 720 |
| tgggggtgtc caggagatgg gaagcccgcc tggggcctcc caggcactcc caaggcccc | 780 |
| acgtcctcgg gggccgggga ggccgcctgg ggcgccttgc cacgcccgcg cggtccctat | 840 |
| tggaatccct agcggagttc cccgagcgga ggctgaccca agtcatccgg gctcccccgg | 900 |
| gatagggaag tgcgggcggg cggctgggta ggggcgccgg cgcagggtgg ccgagtcgcc | 960 |
| cgctagcgct tccgccgagg caggctcgag tggggacttg gccgggcgac cgcacagccc | 1020 |
| tgccggggac ccacggctct ggggcggggc tgcattctgg gccgttagct cagcggtcct | 1080 |
| ggagcctccc gaggctgact catcgggcgg cgggctcacc ccccagccgt caaacgcaaa | 1140 |
| cgcaggcgcc ccaccacgcc gggctcccac gcggcacaca cgcacgcctc cgcgacactt | 1200 |
| cgcacaccta cgtccctgcg tcacgccacc cagacacacc cggacccgcc cacacgccga | 1260 |
| ggccttccca cgcactccat gccttacgcc tcacaggaaa gcgccccgcg ctcacgcagc | 1320 |
| ccctcacacc cgcagcccg cttacacgcg cccagctca cacatgcacc ccagtcacac | 1380 |
| agcctacctc acacacgcac cccagtcaca cacacaaccc agctcacaca cgtacccgtc | 1440 |
| acacatgagg cccagctca cacacgaagc ccagctcaca cacgcagtcc cagctctcac | 1500 |
| acacacaccc cagtcaaaca cgaggcccca gctcacacac gaagcccagc tcacacacac | 1560 |
| tgccccagtt acacagccca gctcatgcaa gcagcccgtc acacacacag cccagctcac | 1620 |
| acacacagcc cagctcacac aagcagcccg tcacacacac agcccagctc acacacacag | 1680 |
| ccccagttat acacacacag cccagctcac acacgcagcc cgtcacacac acagctcagc | 1740 |
| tcaatacaca gccagctca cacacacagc cccagttaca cacacagccc agcttacaca | 1800 |
| cacagcccag ctcacacaca cagcccatca cacacagc ctatcacaca cacagctcag | 1860 |

```
ctcaatacac agcccagctg acacacgcag cccagctcac acatacactc cagctcacac    1920
acgcagcccg tcacacagcc ccagccacac acacagccca gctcacacac gcagcccagc    1980
tcacacatgc agcccctca cacatgcagc cccagtcaca cacacagccc agctcacacc    2040
gcagccccag ctcacacacg cggcccctca cacacattca gccgcccttc ccgcagctgc    2100
caggctcgga acgggcggtg tctgtggggg ccgccccgtt tccggccgc gcaaacaagc    2160
ggctccttct ctctgccccg ccaaagaaag gccgcttgtc aggggcgggc gggcaggcgg    2220
cagcggcagg cgcccaacac tgcggccttg tcccacgcgg gcagcctggg caggagcagg    2280
ccgaggggtg caaggggccg ctaccttgcg gaaacctccc tccctcggcc ctgcggaccg    2340
cggagaggca cctttccacc accggacacc caagcaacag ccctcgctcc atccgcgctc    2400
tcccggctcc ccctctcctc gggccgccca tctctcctct cttccgcctt tggggtcccg    2460
gtgggcccca gcctccctct ccttcgcccc atctccccgc ccgtcagcct cccctccgct    2520
gccctcgcgc atccccagtg ttcccgtctg tcgtcgcctc cacttgagga cccgcctgtc    2580
cttcttccc ccgaccccct cacctctgtg ttcttcagtc tccccgcatc ctctgccctc    2640
ggtcttcccc tccccagctt gcatttttc ccatctctta gtctgccttt catttttccc    2700
ttcacatccc ggtggctccc cttccccgcc ccgtccctct gcaccccc attcatctct    2760
gtcaggtttt tctcatcctt aagttctctc gtcccctcc ccactcgggc gtccccgct    2820
gggctccccg cctcagtttc cttcccttcc tgactccttc ctctgacggc ggccctttct    2880
cgagggcgga tgtgcgcctg gagggcgaag gcggcggccg agaggacccc agctcggcct    2940
ggcgggcctc tggccacagc catgcaccgc ttgggccgag gccgaggccg acccccaggg    3000
acacaggtga ggccgggcga cccgcggggc tccggggagc gcccgagcag tggccccgcg    3060
aagggccggg tctggtgctc tggggctggc tttggacctc tcgtcctggg actccgtggg    3120
agcccgggag ctgtgtcagt gcccgttggt gctggagcca gtcggcccctt ccttggcctc    3180
cttcaggcgg gggccaagac ccccgagagt tcactctggg tgctccactc ggcggagagg    3240
gcttcagact ggtgtcccgc gtggctgggg tgtcggcgca ttcccgcggg ggaggaggcc    3300
gagggcccgg gccggggtca cctgccgcg ccccggcctt gcgcacagag ggccttgcct    3360
gtcgctcgtc aaatccagac acctgggcct ccgccactcg gctgccgggg cggcactggg    3420
gcgtctgtac ccagcgtgcg ggagggcacc cagggccgga cgcgcaccgc agggtctttt    3480
ttttggccgc ggggccgggc gggcgggtaa tgacagccgg gttgctgggg agccgcgggc    3540
cagatggaag cggggccgca ggtgagggac gtccctcgcg tagcgccact cagccgccgg    3600
ggccagagcg ggagtcaagg tgagggcgcc cccaggtggc cgctctcggc cgcggcgatc    3660
g                                                                    3661
```

<210> SEQ ID NO 244
<211> LENGTH: 1219
<212> TYPE: DNA
<213> ORGANISM: Homo sapiens

<400> SEQUENCE: 244

```
cgtgcgggtg actcctcttc ctgccgacaa ggtgggcgat gagaacgagg aggcccagtc      60
ccaccagggc gccgccgacg gcgatgggga tcggcgtgtt gttctcgccc agcagacgct     120
cctccgcaga tccgaactgg ttgccttcca ccttgaaagc ctggcccac actgggaata     180
tgttgattga aaacgccttc gtgccgcgga cacgctccgc tccggctgta gaattgccga     240
tggctgcccg caatgctcgc agggagtcgt tggcagcttt aaaagtgggg tctctggggt     300
```

```
caggaagagt cgtattcagc tggattcctc gtaggaaaat ccggctagaa cctgcattca    360
tccccaaccg gaagcccagg accgtggtgc cctcgccgcg ccgctcccgg gtctccaggt    420
gggcgccgcg ctcccgctgg ctgaggtcat gcccaggtca ccgtcgcgtg gtccctcctc    480
tctgggtgag gttcagctgc agtcccgcgc tggccggcag gcaggccccg tgggtgccgc    540
tcacgctgta cctggccacg gaggggagaa ggggctctcg gcgccgtggc ggggaaggcg    600
cgtcttgctc gtggcgcgtc tctcccttgc tgaagctgct gttggaaatc taggcctgga    660
tcggggcacc gcggagcctg atggtctcgc tgttcgtgcg gacctggggg ccttgatatc    720
tggtagagat tccacagtcc tgatttcctt ggagcttgca ctgaggaaaa tgtgtgtgtc    780
tgacaagttg taaacaaaac tcatgagctg gacgctgtca cgtgtcgcac ttcttgtgaa    840
atggaaggtc agtgtctgtc ttcctccaaa gcacaatcgc gtgcctgggg tcggaagtgt    900
tctctttact gcaagagcca ctgtcaagca cttccgcatt ggatggcagg tcaaaggtca    960
cattcttaga gccactctta gagtcgtagt tcatcgagaa ggcagcgaag ctggccatta   1020
cgcaggctgt cccgttgccc tttttcaccg catccgctgc ggctgcacca cgcacgaggc   1080
ccagcagcag cagcagcacc aggggcagcc ggggctcca ccagatgcag cccggggcgg    1140
aggcgcgagg ggagccggtg tgtggggaac cggggcgcgg ggaggcggtt gcggggcgct   1200
ggcctgaagg acggtggcg                                                1219

<210> SEQ ID NO 245
<211> LENGTH: 210
<212> TYPE: DNA
<213> ORGANISM: Homo sapiens

<400> SEQUENCE: 245
cgacgggaca cggtacatca caaagagacc cgtgcgagac cgaatcctga aggaacgtgc     60
cttaaagatc aaggaagagc ggagtggcat gaccacagac gatgacacca tgagcgagat    120
gaaaatgggg cgctactgga gcaaagagga gagaaagcag cacctggtta gggccaaaga    180
gcagcgccgt cgccgtgagt tcatgatgcg                                    210

<210> SEQ ID NO 246
<211> LENGTH: 901
<212> TYPE: DNA
<213> ORGANISM: Homo sapiens

<400> SEQUENCE: 246
cgtgttcccg ggcggaggtg cgcgcagcca ccccaggctg ctgccaggtg cccgctgggg     60
ctgccagggc gaggaggcct ctgggctgtg gagcgaaagt cagatccacc gcctactgcg    120
gggtaggggc cgcagtgggg accgccagcc ctgtggtccc tctcgcgctg actggcgtaa    180
agttgtggcc gaattcgcat ctcttctggt gcttctcgcc cgccagcgca gggcccaggt    240
gtttgaggcg aagggctct agctcccgc aagcctggag ccaggcgtcg cgcttcctcc      300
gggcttaatc cagaccttc aacacacacc tcattcgggg gaggagaaaa gcacaggacc     360
gcggagagcc cagctttgag gccaggcctg aagggataac ccacacaggg aacgttttcc    420
tatcagagaa taatggagca caaaataatt cagaaagcga atgggcagga ccacagcctg    480
agagtcccgc gccgcgggc cgctgcagag ccggtctccc gagcaccgcg gcaggaccat     540
ttcgttggaa tgtagggcga ggccgaagcc cgccccggac ccaggccgcg aggtgcgcgc    600
cggccgccga ggggccgcct gtaaattaca gcccgccggg aggactcgga aatacacaaa    660
```

```
aggagccgaa agatttaaac agtcggaggc agaggcgtcc cgaggcggcc aaagcggaaa      720
tcaatcacgt aattaaaaca gggaggggac gaagcccaag gctggggtc ccgggttcgg       780 aggaggcggc caaggtgcag gccgaggctg gcgagcggct tagggacgtg gctcgcccgc      840
caggaccaga gcgcgcggag gggcttcggg gaagtttata acacatcgct attgattccc      900
g                                                                     901
```

```
<210> SEQ ID NO 247
<211> LENGTH: 401
<212> TYPE: DNA
<213> ORGANISM: Homo sapiens

<400> SEQUENCE: 247
cggagcgaca gactagggag ctccgcccgg gatttgccca tcggcggagg cgccaggctc       60
ccgtttctcc ccatccctct cgctgccgtc caggtgcacc gcctgcctct cagcaggatg      120
gacgtgatgg atggctgcca gttctcacct tctgagtact tctacgacgg ctcctgcata      180 ccgtccccg agggtgaatt tggggacgag tttgtgccgc gagtggctgc cttcggagcg       240
cacaaagcag agctgcaggg ctcagatgag gacgagcacg tgcgagcgcc taccggccac      300
caccaggctg gtcactgcct catgtgggcc tgcaaagcct gcaagaggaa gtccaccacc      360
atggatcggc ggaaggcagc cactatgcgc gagcggaggc g                          401
```

```
<210> SEQ ID NO 248
<211> LENGTH: 370
<212> TYPE: DNA
<213> ORGANISM: Homo sapiens

<400> SEQUENCE: 248
cgcggtggag atcagccggg agagccttct gctgcaggac agcgactgca aggcgtctcc       60
ggagggccgc gaggcccaca aacacggcct ggccgccctc agaagcacga gccgcaacga      120
atacatccac tcaggcctgt actcgtcctt caccattaat tccctgcaga acccaccaga      180
cgccttcaag gccatcaaga cggagaagct ggaggagccg cccgaagaca gccccccgt       240 ggaagaagtc aggactgtga tcaggtttgt gaccaataaa accgacaagc acgtcaccag      300
gccggtggtg tccctgcctt ccacgtcaga ggctgcggcg gcgtccgcct tcctggcctc      360
gtccgtctcg                                                            370
```

```
<210> SEQ ID NO 249
<211> LENGTH: 423
<212> TYPE: DNA
<213> ORGANISM: Homo sapiens

<400> SEQUENCE: 249
cgcgcgaagc agagaacgag aggaaagttt gcggggttcg aatcgaaaat gtcgacatct       60
tgctaatggt ctgcaaactt ccgccaatta tgactgacct cccagactcg gcccaggag       120 gctcgtatta ggcagggagg ccgccgtaat tctgggatca aaagcgggaa ggtgcgaact      180
cctctttgtc tctgcgtgcc cggcgcgccc ccctcccggt gggtgataaa cccactctgg      240
cgccggccat gcgctgggtg attaatttgc gaacaaacaa aagcggcctg gtggccactg      300
cattcgggtt aaacattggc cagcgtgttc cgaaggcttg tgctgggcct ggcctccagg      360
agaacccacg aggccagcgc tccccggacc ccggcattag gcgccagctg ccggctatct      420
gcg                                                                   423
```

<210> SEQ ID NO 250
<211> LENGTH: 1267
<212> TYPE: DNA
<213> ORGANISM: Homo sapiens

<400> SEQUENCE: 250

| | | | | | |
|---|---|---|---|---|---|
| cgcaataatg | ctgcgtcacg | aaactgcgca | ttccaagaga | aactttctc | aggcccagaa | 60 |
| ttaagtcgga | gggatccgcc | gcgcagctca | atccctagga | agcatgaaag | aatgtattgt | 120 |
| aaagagtaaa | atcacgcgca | atccatccca | atataaccgc | agttgttcgt | gggccttctt | 180 |
| gcagagaaag | gctgcccaac | cttgacgggg | ccatgggcgc | tgcgggaggg | caaaagacca | 240 |
| cagagatctg | cgaagccaaa | gtaaacaacg | gggttgggc | ggcgagaatg | atcaatagcg | 300 |
| atgctccgaa | aggactccgc | gataggaatc | gagcgggaag | gattccctcc | atcctaacag | 360 |
| tccatgggtt | aagaggccga | agcttcccta | aataccacac | tcccgcgaga | gaagggactg | 420 |
| agaacaactt | ctcaaactat | tctctctcga | aatcgctccc | ttcctcgaaa | attccatctc | 480 |
| tgagactcgg | atgaggtccc | caccccctcc | accccttgtcc | cgtgaccgtc | gcccgctcag | 540 |
| cctcccagcc | gagtccgcgg | ggcctggggc | gcccaccccg | cccacccaag | ggaccgcgca | 600 |
| ggggtgaact | cccccgcgcc | ccacctgcgc | cttccagacc | tcgggcgccc | cggcgttgcc | 660 |
| tcgagagctc | cctgcgcggc | cgccgcggca | cggaccagct | cccactccct | tacactgggc | 720 |
| gccgctgcgc | tcgccggggg | ccggtcccga | ggttcccaag | gcctcgcgcg | cgcgcttgcc | 780 |
| gtggcaacca | agacgttcca | cgacgcgcgc | tctcgaacgc | ttcgcgtcac | gcggccgcgc | 840 |
| ggccccgccc | gtcggcctcg | ctcccgccac | agagcccgca | gcacgccgcc | gccgcagcct | 900 |
| aggtcacgtg | agtacccacg | cgcgcgtctt | gccagcggat | tcatcaccgg | cctgctcaga | 960 |
| ctaggttctg | cccactctga | ccttctaaat | ggtacgtggg | aggacgtccg | tccccttcgg | 1020 |
| acccaagagt | caccgtaaca | ctctagaagg | ggagaaaagg | agcgagggcg | gcaggcgaca | 1080 |
| gagaacctcg | cgagtcagcg | gccccgcgca | gacccccca | ggcacggtcc | cctgcggcca | 1140 |
| cgtcggctgc | tcggcgcctg | cgcaatctct | ttctctccag | cgaaaccgag | gcctccggag | 1200 |
| agcctagtag | agagtgtggg | cagtgagcgc | ttgtagccgc | tagagggagc | gctgggcaca | 1260 |
| gtgcacg | | | | | | 1267 |

<210> SEQ ID NO 251
<211> LENGTH: 736
<212> TYPE: DNA
<213> ORGANISM: Homo sapiens

<400> SEQUENCE: 251

| | | | | | |
|---|---|---|---|---|---|
| cgcggcatgt | tcgtaccagc | gcgggcagaa | acgggctcac | gagcgccctc | gaattcacac | 60 |
| acactcaccg | aaatacacat | ctcagcccgt | ggaagcgcat | tcacacacac | ccacgtacac | 120 |
| tcctccgcac | ctcattcaga | tgggtccacg | cggagtcagg | gctgcgcttc | ccttggcatg | 180 |
| ggcgtgtgtg | cggcgagggc | gtgtgtcgt | gcgtgtgtga | gagtgtgtgt | agagaaaccc | 240 |
| tttaggcaga | ccgcagctac | gttattctgc | aagcatactg | cgattcccga | ttccgtgtat | 300 |
| gtaggaccac | aaaaaaatta | aatcgctgtt | aaacttttt | ttgtaaattc | tcttttccga | 360 |
| aggaaggcgc | tggaagagct | actcccggtg | gttaaaggcc | cggagacct | ggtggcgaat | 420 |
| cctggggcgc | gtccgctttg | gcggagcgct | gggctccgct | agccggactg | gttccccatc | 480 |
| taactgatct | aatcaatgac | tccgaagagc | cggggctcct | ggccccgccc | cgccatcct | 540 |
| cttctccgcc | tcccattgga | cgcgggccga | gaaggcaggg | ccttgctcct | cgctcggatt | 600 |

| | |
|---|---|
| ggctgacagg gaatcagtat caatgtttaa gcggcggcgt gaggtgaata gagtcagtca | 660 |
| gcaagagacg ctggggagag agcagggatc gcgagcccgg cggatgcggc agcggcggaa | 720 |
| ggcggctggg gagacg | 736 |

<210> SEQ ID NO 252
<211> LENGTH: 379
<212> TYPE: DNA
<213> ORGANISM: Homo sapiens

<400> SEQUENCE: 252

| | |
|---|---|
| cgccgggctc tgcgggggca tctcctggac gatgtacacc gggtgcccgt agtcgccgct | 60 |
| gaccttctcg tagtgagggc agaagacgct gtccgcagtc cttagcggga tgataatgtc | 120 |
| actgggctct gagccgttgt tgttgccgct gcgcttgggt gtggccagtg tgctgagcga | 180 |
| cagcgtggtc gtgtgctgcg gcgagtgctt cctgtgtctc ctccggtact tcagcaagag | 240 |
| gaccaccagc gtgatgatga tgacgatgaa gatgatgcat cctgaagcaa tccctgcaaa | 300 |
| taaggccact tcggaaccga ggatgttgtt ccccgaatgt ccggcgctgt tgccgtctgt | 360 |
| gctagaacct gcagacgcg | 379 |

<210> SEQ ID NO 253
<211> LENGTH: 875
<212> TYPE: DNA
<213> ORGANISM: Homo sapiens

<400> SEQUENCE: 253

| | |
|---|---|
| cgctcccagc cggcagccgc tctgggcgtg cacccgccac gcgaagccag aggttggacg | 60 |
| acgcagccgg ccaggcgcgg ctccggggg accccgaaac cgcctgtggc tcaggcccta | 120 |
| cttggcaaga agagactggg gagtgagagg aggggtcact cttgctctct cgcacaatag | 180 |
| acttcccgca ggcgagtgcg aacggccttt tgcttcctcc ttcttttcca ggacccttag | 240 |
| cgacaggaga ggaagagaag cggccggcg gtttaattgc caatttcctg atgcagccac | 300 |
| agggcccagc agcggctcag cctaggccac cgggtccagg cctctaggca ataggcccgg | 360 |
| cgccccctcc aagcaccgtt tcccgccgac cccgcagtca tcactgtgag ctcgagagta | 420 |
| tgggcagcct gtggtgccct gaggcgccgg gcgctcggcg catccgccgt gcccacagcg | 480 |
| ctgaggacca actagggctg ccctcggcca ggggcactgt gcccgtttga gtggcactcg | 540 |
| gacctggcga ggggtggaag cccaggtaga gctcgcgtct ttaagagcca cccgacagaa | 600 |
| ctgcgcgcta catctgcgcc agctgggctg ggtgggaaca gcgcagaaat actcccgtgc | 660 |
| cggggcgtac agggcaggta ggcccagcag agagtcttct cggaaagttt cccacaaaag | 720 |
| aagggccggg caggccgagc ggcaggaaaa gccggtgctc agcggcgagg cccgagaggt | 780 |
| ctggcatccg gcggcctccc agctttgctc gggtctcccg ccgcctctct ccagagccgc | 840 |
| ccgtagctcc gtggggcgga gggcgcaatg ccccg | 875 |

<210> SEQ ID NO 254
<211> LENGTH: 221
<212> TYPE: DNA
<213> ORGANISM: Homo sapiens

<400> SEQUENCE: 254

| | |
|---|---|
| cgattcctat cgaatcaaca cggccattaa ggacaaaaac gggcaggaca caaaagcaag | 60 |
| cctggatggc gcaccctaca aacgagttct gaaacaaagc gagtgccaga cgcgcgtggg | 120 |
| aaagacgcgc gtgggaaaga cgtgcatggg aaagtcgcgc gtgggaaagt cgcgcgtggg | 180 |

```
aaagtcgcgc gtgggaaaga cgtgcgtggg aaagacgcgc g                  221
```

<210> SEQ ID NO 255
<211> LENGTH: 1283
<212> TYPE: DNA
<213> ORGANISM: Homo sapiens

<400> SEQUENCE: 255

```
cgtgacgtaa gtccgccgcg ggttcgccag caccttgcca tcccgcacca cgcccacgcc    60
aatcttattg gcgctgcctt caaaacccag caccgccggc atggcggagg ctgggagaaa   120
acgccgacag gactcctggc aatgtcagga gctgtggagg tcctcactag tccgcgctgg   180
gccgcagctt tccggagcgc agaggaagct ggccagcctg cagatagcac tgggaaagac   240
accgcggaac tccgcgagc ggagaccgc caaggcccct ccaggacct gtcttcctaa      300
ctgccaggga cgccgagcca actctgtgcc ttacattcgt atccgttttc ctatctcttt   360
cccgtggtcc agcccagcct tctccactgt ttttttccct cttgcacata gttagaatct   420
taagtcagtg tcacacaatg tgctgtgcat ctggcacaac gataaacagc ccgagggagg   480
gttggggacc taagtgtcct agagaattag aggaggagg cgaggctaag cgtctccgtc    540
acgtggtgtc agacagacca atcacgcgca ttcttcggcc acgacaagcg cgcctctgat   600
cacgtgacca ggtccgctac ccacgtgggg gctcagcgtg cacccttctt tgtgctcggg   660
ttaggaggag ctaggctgcc atcgggccgg tgcagatacg gggttgctct tttgctcata   720
agaggggctt cgctggcagt ctgaacggca agcttgagtc aggacccta attaagatcc    780
tcaattggct ggagggcaga tctcgcgagt agggtacaag gcactatgaa atgatctagt   840
ttcgtgggtg aggggctgaa gggcctatga tgcacggagg cggggaaagg atttagagat   900
aacgtggttt gaaaggcggg acctggtgcg gggacgctct tgggaggagt cttctcccca   960
gccttagctg gtttcatgat ttctttgcgt ctgtaggcaa cgcggtaaaa atattgcttc  1020
ggtgggtgac gcggtacagc tgcccaaggg cgttcgtaac gggaatgccg aagcgtggga  1080
aaaagggagc ggtggcggaa gacggggatg agctcaggac aggtaaggga atgaaatcag  1140
cccttcttcc tagaagctgc ggcggggtg tttgtcattc ccttgatgta cggtaagtac   1200
gggccgactc attttttgcag gggtttgtga agaagtcgca ggaaccgtag ctttcgttg   1260
ggtctatagt taacgccgga tcg                                           1283
```

<210> SEQ ID NO 256
<211> LENGTH: 1167
<212> TYPE: DNA
<213> ORGANISM: Homo sapiens

<400> SEQUENCE: 256

```
cgcctgttac tagaggcgag aaccggagcc cattggtcgg aacacctcac aatggacccc    60
agcggcgcgc aaaatcctta tgattggttt gctggctgcc tcgggagacc ctgttgccag   120
gatacttggc gttcccgacc cgaccccgt tccccattgg ctgtcagggc aaaagccgcc    180
atctaatgag gagcgaggtg cggtgccccg aagcgctcgc ttcccgcggt gcgatctagt   240
cctgcagtag gcggcccggg gccacaccgc ggccgcccaa gccagtgcaa ggcccagggg   300
cctgacatcg ctcccagcgc tcgaggaccg aggcctgctg tggaggacac cgtgctccct   360
cgggacctgc tctggattcc ggcccggacg tccccttgga gctctgcatc tccaacctgg   420
aacccaaccc agaagtctca agtttgacgc atcacgtggc gtgcggatcc actgagggtc   480
```

```
cacagagagg ggcgcccatc tcctgcgtct cagttatcct ggtaattgtg tatctgccca      540
ttgttcgttg cctcattaac ttggctttct aggtgcaccc accttgccac cagagaagtc      600
caaatcctga cttctctcca aggtgttggg aattctgtgc cctaaagaat tccgactcag      660
atccgaacgg ggatctggtg gaatcgaggg tgaaagacca gagggacaat gttctactat      720
cccaacgtgc ttcagcgcca caccggctgc tttgccacca tctggtaagg gcggggcccg      780
ttggcgcgcg atggcggacg ctgcccggga tcccagcctg acagctcccc ctccatcccc      840
attctcccac cttccccacc cacttcaggc tggcggcgac tcgcggcagc cggttggtga      900
agcgcgaata cctgagggtg aatgtggtga aaacctggta aggcccagaa aagggaagga      960
gggcctggtg cgggggggtga gttaggggat ggggtggcca agactgtggg cccactcctg     1020
gacgcagcgg taatcagggc gcattgttcc ccagcgagga aatcctcaat tacgtgctgg     1080
tacgagtgca acccccgcag cccggcctgc cgcggccccg cttctccctc tatctctcag     1140
cccaacttca gatcggtgtg atccgcg                                         1167

<210> SEQ ID NO 257
<211> LENGTH: 300
<212> TYPE: DNA
<213> ORGANISM: Homo sapiens

<400> SEQUENCE: 257
cgtagcgacg acgtggtcct tgtaggacca agcattcttg gcattctgtc gagattgaga       60
ttccagagca tcggatgaac gggacttata gctaaggcgt actcacccac ccctcccttc      120 gtcttttac gcacgcagca actcgtcctc acgtgcatag gggtagtgga cagtgttgac       180
ttgaattgct gtccctcgtt ccaagccttt cctgtgaatg aacccgaaaa cactcgacag      240
gtcgtgaata tcgttttaa tgagtgtgca aagcgtgcga cggggtgcac cgagctgtcg       300

<210> SEQ ID NO 258
<211> LENGTH: 1492
<212> TYPE: DNA
<213> ORGANISM: Homo sapiens

<400> SEQUENCE: 258
cgagaactcc aagtccgacg agaaggggaa ccagtccgag aacagcgaag acccggagcc       60
cgaccggaag aagtcgggca acgcgtgtga caacgacatg aactgcaacg acgacggcca      120
cagctccagt aacccggaca gccgcgacag cgacgacagc ttcgagcact cggactttga      180
gaaccccaag gcgggcgagg acggcttcgg tgctctgggc gcgatgcaga tcaaggtgga      240
gcgctacgtg gagagcgagt cggacctgcg gctgcagaac tgcgagtcac tcacgtccga      300
cagcgccaag gactcggaca gcgcaggcga ggcgggcgcg caggcctcca gcaagcacca      360
gaagcgcaag aaaaggcgga aacggcaaaa gggcggcagc gccagccgcc ggcgcctgtc      420
cagcgcgtcg agcccaggcg gcctggacgc gggcctggtg gagcccccgc ggctgctgtc      480
ctcccccaac agtgcctcgg tgctcaagat caagacggag atctcagaac ccatcaattt      540
cgacaatgac agcagcatct ggaactaccc gcccaaccgg agatctccag gaacgagtc       600 cccctacagc atgaccaagc cccccagctc tgagcacttc ccgtccccgc agggcggcgg      660
cggtgggggt ggcggtggcg gggggctgca cgtggccatt cccgactcgg tcctcacccc      720 gccggcgcc gacggcgcgg ccgccgcaa gactcagttc ggcgcctcgg ccaccgcggc      780
cctggccccc gtcgcctccg accgctgtc accccgctc tcggcgtccc cgcgggacaa      840
gcaccccggg aacggcggcg ggggcggggg cggggcggc ggcgcgggg gcggcggccc      900
```

```
cagcgcgtcc aactccttgc tgtacactgg ggacctggag gcgctgcaga ggttgcaggc    960
gggcaacgtc gtgctcccgc tggtgcacag ggtgaccggg accctggccg ccaccagcac   1020
ggccgcgcag agggtctaca ccacgggcac catccgctac gcgcccgccg aggtgaccct   1080
ggccatgcag agcaacctgc tgcccaacgc gcacgctgtt aacttcgtgg acgttaacag   1140
ccccggcttt ggcctcgacc ccaagacgcc catggagatg ctctaccacc acgtgcaccg   1200
gctcaacatg tcaggaccgt tcggcggcgc agtgagcgca gctagcctga cgcagatgcc   1260
cgccggcaac gtgttcacca cggccgaggg actcttctcc acgctgccct tccccgtcta   1320
cagcaacggc atccacgcgg cacagactct ggagcgcaag gaggactgag cgccgcccg    1380 tcctgggccc ggccaggccc cgcttggagg aggcatcgtc ggcattttcg tttagacctt   1440
taattctagc actttgaatt cgagcaggtc agcgtcttct ctcgccacga cg           1492

<210> SEQ ID NO 259
<211> LENGTH: 301
<212> TYPE: DNA
<213> ORGANISM: Homo sapiens

<400> SEQUENCE: 259
cgcccggccg ctgccgatct cggagctcgg aggccgagct ccacaaattt gggtccaggc     60
ccgctttaga gccctgggc gggggcgctt ctcagggcat cctgtgaggg ctttgaggcc    120
tccttggagt cgccagatga actggtgccg cctgtgcgcc ttggccccat agcctcaacg    180
gcactctcac tgcctgggct ttggtctttg cccaggagcc tgcccatggc ctacgctccc    240
cgctcgcagc atggcagacc ctgacgaggc tgcccgcctt ggtccgggaa tggaccgatc    300
g                                                                   301

<210> SEQ ID NO 260
<211> LENGTH: 1761
<212> TYPE: DNA
<213> ORGANISM: Homo sapiens

<400> SEQUENCE: 260
cggggcaggg tacccgcgag ggcaggcacg tggcggctcc tgcggtgtcc cgggttaaac     60
ttgcctgtgt ttaagacggg tctgcgacag cttgggcgg tccaggtcgc ggggagggcg    120
ggctcctcaa gtgggggatc cgcggcagtg aggactgtag ggtgcgcggg tactccgggt    180
agccgccagc ggaggaagcg gctccgccct tcccggaagc tgcccttgct acacccgtgg    240
ggcctgctcc cggcgcagtc ccgcagtacc tgagcggcac tcggtccttt gaccacgctt    300
ggctgcctca gcttacactt cccagcagga tctggctggg agccccttcc tcagatattc    360
accaggcagg tagaagcaga gggagacgac ggcgaaaggt ggaaggagag gccgcggcct    420
cgggcctcgg gccccgggcc cagacggcgg cctctcgcgg cgacagggtc cttcctatt    480 agcaggaccg cagggttggc agacagcagg ggctgggccg gcggggctct gcggtgccca    540
ttcgagtctc tccagggctt ccctctgtgg ctgtccctcg cctgccccct ttccttgcct    600
acccttccct ggacggggtt gttgtcaggt gacggcttca gcaacccagc catgcttggt    660
gtggagtggt tcgagttcct ccgcgggccc ccaccccca cccagataag aagcttaagt    720
cctccttctg caggggagaa tcggatgcaa tgaaactaag acctgtggtc gttaacgcgg    780
ttcaaagccg accccaactg ggacacggct cagcttagaa gtgaggaagg cctgggacgc    840
tggaaacaag gggtcacacg tgcgtgtgcc tggccttcgc aggtggatgt gtgcgccgag    900
```

```
ctggggaagg ggccagggag ccgcgagact gcggtccccc gcgagagaga agtatgggcc    960
tggccagggt tcgaactccg ttccttcgct gccttccttt tattttcttt cctcatcttc   1020
cttcctctct cccttggttc catcattaaa tctttaaggg attaattcac aactctgtag   1080
taggtagggg ccctgggacc acttgacggg cctttgcagg cagttctgta cagagtccta   1140
acccgtaacg ggcctcaacc ccggctgtgt gtgcgtgtgc ttgtgtctgt gtgtctttgt   1200
gtgtaaaagc aacgcataaa catacccagg gctttcactt attttattga agcaaacaaa   1260
caaaaacagc cactgggttt gtcttttccc ctactcctgc ctgagcgccg ccgggtttct   1320
gagctgctcc gggcgcggac ctagctcacc cgcagccgga tgtcggagcc ggagctgctc   1380
cccacccggc ctcgcccgcg ggcgacaaaa ccgtccctct ggccacggga gagcatcgcc   1440
ttgccaaaat caactcgcat tttcatgtat tcaaatgaga aagactgaga agggcgattt   1500
cccctgctgg gcagtcgaca gcgttggaag gaagaagtgc cccctagggc ctcgcggaaa   1560
cgggaacaaa cctccctcga gggcccccgga accgatatgg cgaccccgcc cagacctggg   1620
tccccgcggc cgcgcgcgtc tcccgccgtt gtggcccccg agttactgac ttttgttcac   1680
accggtcagc gcctgttgga ggacgtgctc agccccagcc ggtccctcct catccagccg   1740
atccccctcc tggggagcgc g                                             1761

<210> SEQ ID NO 261
<211> LENGTH: 219
<212> TYPE: DNA
<213> ORGANISM: Homo sapiens

<400> SEQUENCE: 261
cgggcctcga ggatgcgagt gtgaggtcga caagatatcg tggaagagag cgaacgaggg    60
aggcccccgt tggaaacagt ttctgtgtta gaacaaacgc caccaaacga ccgacactgc   120
gaggcctgga gctacctggg ctggcgccgc ccgagccccg ggctgcgagc ccagaggctg   180
ggaagtgatg ggacctgggg gcccgagccg gagagtgcg                          219

<210> SEQ ID NO 262
<211> LENGTH: 2448
<212> TYPE: DNA
<213> ORGANISM: Homo sapiens

<400> SEQUENCE: 262
cggcgggcgc tgtcgagcac ggggaggtgc tgaaatagtc ctggcgtgct gattcaagct    60
ttgattggca gagccacccg gtgactgaca gggggtctcc atggcgcccg cgccgccaat   120
ccgcccaccc caatagcgga gccagctcgc ctgccggcgt gcctgagccg agccgagccc   180
gaaccccaag ccgcggagcc agcacctcct ccagtcgggg tcgtccgctc ccggccgttg   240
agccaccgcc gccacccggt agtgtgtccc gctgccccaa tccgcctcat caacaagcgc   300
ctggcacact cagccaggcc cgcgggcatc tgctgcgtgt cccgctccgg gctcagtgcc   360
ctcgccgccg ccggcactgc ctcgatgttc cagctgccca tcttgaattt cagcccccag   420
caagtggccg gggtatgtga ccctggaa gagagcggcg atgtggagcg cctgggtcgc   480
ttcctctggt cgctgcccgt ggcccctgcg gcctgcgagg ccctcaacaa gaatgagtcg   540
gtgctacgcg cacgagccat cgtggccttt cacggtggca actaccgcga gctctatcat   600
atcctggaaa accacaagtt caccaaggag tcgcacgcca agctgcaggc gctgtggctt   660
gaagcacact accaggaggc tgagaagctg cgtggaagac cctgggacc tgtggacaag   720
taccgagtaa ggaagaagtt cccgctgccg cgcaccattt gggacggcga acagaagaca   780
```

```
cactgcttca aggagcgcac gcggcacctg ctacgcgagt ggtacctgca ggatccatac     840
cctaacccca gcaaaaaacg tgagctcgcc caggcaaccg gactgacccc tacgcaggtg     900
ggcaactggt tcaaaaaccg ccgacaaagg gaccgagcgg ctgcagccaa gaacaggtcg     960
gtacctagag gcctccgcgc tttgagcgca ccggggagga ggcgggtgga ggcacctctg    1020
gcgcccttac ccagtccctg gcgactccaa ttcagcagga gttgggagcg cggtctgtct    1080
tgggttaaga gccctgcgtt ctgggctcct ggccgggagt tcccttgccg gctctgcttc    1140
cccacccgct ggctccccac gcctgcgggc agctgcagca gctggtcccg gtcaccaaac    1200
caaggcttca ctgggacgga gaggggaaga gaaataaaaa attaaaatcc tacaaacagt    1260
tagggacccc aagacccaaa gctaattctt gtcagcctgg gcacaggctc ctactattaa    1320
tcgaagcctg gcttattagc aatgtgtcgg tttcatgtta attatcattt tcaaagccca    1380
ggtatatccc tccctaatgc tttgaaaaca gttttcaatg gacttttgag aaatgggaag    1440
tcgagttttc ctcttcccat gcgctgcctg ccactcttgt ctcaaaacag caaactagtc    1500
cgtgggccga ggcttttcgt ttcccggagt gtggatctcg attagccaaa cattttgcgg    1560
aagagcccgg cctcatcccc caggcccaaa tgctccttac aatccttttt gcctttaggt    1620
cgggccgacc cgatccaacg cgatcgcggg agcacttgct caggcgtaag ccccaggcag    1680
acgcaccgtt agaaatggta tcccatgtcc ctgggaccga tctgtccttg tcacccacac    1740
ttcgtttatt tcctgacagt cctgtaaatc tcccaaaagt gcacaacaaa cagggaggac    1800
actgcaagcc cagtatataa aagacctggg agctgcggcg ctgagaaagg gcgcgaatca    1860
tggtggggca acagtagg gacccgcgga ggggcggccg cggactcctg cccgacctct    1920
gtcgccttgc cgagtaatcc tcgccttaac tgctggggtc ttcggaagaa cctctagccg    1980
ccgggctgga gggacgcagg aggtggtggg ggcgggcgac gggcggctgt gttacgagct    2040 gtgaccgtg ttcccttct tccccgtaga ctccagcagc aggtcctgtc acagggttcc    2100
gggcgggcac tacgggcgga gggcgacggc acgccagagg tgctgggcgt cgccaccagc    2160
ccggccgcca gtctatccag caaggcggcc acttcagcca tctccatcac gtccagcgac    2220
agcgagtgcg acatctgagt tgcccatcca ggatgctcag aagcagattc cagtgtaaaa    2280
acgagaaaaa caaatgaaa gagggggaaga agatgagaga cctgcaaatc cagcgccaca    2340
gaagccaggt gaccagggac ccgcgggctc gggttgccgt ttcccgcccc accccgcggc    2400
cggcctggct tcactggcgc cctttggccg cgaccacggg aaccagcg                 2448
```

<210> SEQ ID NO 263
<211> LENGTH: 685
<212> TYPE: DNA
<213> ORGANISM: Homo sapiens

<400> SEQUENCE: 263

```
cggctaggct gcgcctgcat caggcgtggt gattggcagg cgcctacggc ccacgcagag      60
atggccgcgt gggggtcgga gcgccaactt ctcagctccc cttctcccat gaccctcacc     120
ccccacacca tcttcagccg cccactggga gcttcctcca ccctacccc ccagtgccgg      180 cgaggccccc tggcagatgg aagctgctga ctgatgggc ctgccgagcg cgaggagct      240 gagtgaggcc cttgcgccct aggcggttgc accccggacc cctgcagctg tggacgccgg     300
agctgtgcga agtcatcctg agccagcccg cggggcccga tcggaaggga cgcctctcct     360
aagagctggc ctggagtcct ggagcctcca agcgggcaag taggggccgc aaaggctggg     420
```

| | |
|---|---|
| ctgggcctcc gctgaggccc tcgggggcct ctgggccctc atggcctgga ggccgcgcgg | 480 |
| cccaagcccc tagagcagag gccgcgctag cctgcagggg tcgacgcagg gccggaggca | 540 |
| gcggcttttc cttcccactc cgggttgacc ctaaagacac gatttaacgt ggcggcggca | 600 |
| gctgcccacg ctgtctggag gagcagggcg cctgggatgc ggcggcgaaa ctggcccgga | 660 |
| gggggggccca ggcctcacgc gcccg | 685 |

<210> SEQ ID NO 264
<211> LENGTH: 1592
<212> TYPE: DNA
<213> ORGANISM: Homo sapiens

<400> SEQUENCE: 264

| | |
|---|---|
| cggaggctcc ttccgtcccg gcctcacctg gatcccggga accgcccgct ctgtcccgcc | 60 |
| aaggtgggct gaggaagacg gcgccactca tcagggcaat ggcggcgggc ggaagaggga | 120 |
| tccccgtgcg cccccagcac ccgggacgaa tgccaccccg gcgaagcgac ccgaccggcg | 180 |
| cgcacggttt cggggagggg accacttcca cattccccat gcccgagaag gtcacccacc | 240 |
| cgggagagcg cccaagggcc agagaggagg cgactggtgg aggaggggcg gccccgtgcg | 300 |
| cacaaagggg cccggggccg gcaggctccc cgccttgac cttgggtctc cgcctccatc | 360 |
| catctccgcc ggctgccagg aaggggggct ggcccggggc cagaggcgtg ctcgctgggc | 420 |
| tgctgctggg ctggggaccg acgggggcgg ggggaaagg agccgggaaa aaagactcca | 480 |
| gggctgcaga gtgctccgag gaagcctgca ttccaccacc ttcaggagcc ggtcccgagg | 540 |
| cggctccgat tcactgcatg cccccccgccc ccaaagcaa aagttgcacg gatgcacgag | 600 |
| ggaaacccct tcccaaagct agcccttcga ctcgcccacc cccgccttc ctcggaccca | 660 |
| ggccgagtgg gggaggggag tgtcagggga ggaagaaagg agcgcgcctt cccagcgagg | 720 |
| ccagacgcgg gctgggtcag ctgcgcctcc gcccgcccct cgccgcccgg ctcaggcagc | 780 |
| tgctccatta agccccccgaa ttatgcatgg accttgagcc ctctcggccc tcccgcccca | 840 |
| ccaaggcaca atcaacgtgc gcagcgggcg cgggtcaaag agagagggaa ggaggtggac | 900 |
| gatgggcgca aggccgtggg cgaatcagag gccggcggcc aggcggggc caggcgcgcc | 960 |
| cgcaggcctg ggaacagtgc cgaggagcct cccgacccgg ccagggccag ccgggaaagg | 1020 |
| ggcaccgctc gcaggggagg ccccgcgca gttttgaagt tgccaaagtg tccgcgccgt | 1080 |
| gccgggtgcg gggtccggga gatgcagccg ccccgcgga gctctgcgcc cctggcctcg | 1140 |
| gggaaggcca ttgtgttctc ctgtgtggca atgaaggggg ctatggaccc caaccattga | 1200 |
| gcccttggag ggaggggcct gaagacccct cgggcagggc gggggaggct gtcttgcggg | 1260 |
| cggcggagag gatgggtatg atttgctcgg gataggcacc gtcgcgggga ggggaggagg | 1320 |
| ccaagcttga ggaggggctg ctggagatgg aaggaagtga gaggagactt gcaagttgca | 1380 |
| aacgtcgggg aaaccggaaa attgcagtag cggggaggca ggtggcgccc agaggttcga | 1440 |
| aagcagaatt gggaggactt cgatgtccac ctcgcagaca gtgacccagg ccccagaggg | 1500 |
| ctccgcagcc tggagcctcg cgtcccgcct ccccgcaaca cgctgttttc agcgttccag | 1560 |
| accacagcgc tgcagtctac gctgccctga cg | 1592 |

<210> SEQ ID NO 265
<211> LENGTH: 3241
<212> TYPE: DNA
<213> ORGANISM: Homo sapiens

<400> SEQUENCE: 265

```
cgccaaaaga atgagcgcgg gagggggtca cagcagccag ttcggccaaa catcgacgct    60
gctccggcac gctccagccc agcgcctggg atgtgtcaga ggtacctgcg aggaacattt   120
gcgtgcgatt ccacgcacgc gttgcatccc tcttcccaaa cccggatcgc tgaactgaga   180
ggtggcgcag agtgtctcac caggtgcggg gatttctctc cgcctcaggc cgtacgagct   240
tccctcgctg tccctgagcg caaatgagcc tcttcagtcg ccgaggcccg gccgcttagc   300
tctcggagcc ttccacagcc caacaccctg agccctggag taggcaattt gctcccacag   360
ccctgtgctg gcccttccag gcacaggag tcccccttct aggggtaggg gcgggcggga    420
tgaagcgcac ccagccctct ctcctaccct tcctcctttg gtcccttcgg ctttcgtgta   480
ccttatctcc cgcgcgccca gctccttggc cggctcacct gctaagcgga gcgcggacat   540
gcgctggaac tccggctcct gcagccactt ccacatcctc cggaaggtct cccggccgga   600
tttgagtttg ctccagggtt tggggttgcg cagcaggtcc gagagggtcc cctgggagcg   660
gcagagcacc ctctgcgcga agatggcctg tgggatgctg tagcgcttga gctcggtggt   720
gatacgctgc gccacctctt tggtattgat ctcttccatc tgccctgaat tacttccatt   780
gctgacctgc gcgccggtca ccgaagggtt gggctcccgg gctgtgccca ggagttgccc   840
gtggccctgg gcgttcaggt gggcgtgggg atggtgcgga ggaaggccgt tgatgggcac   900
catgccggcc gaggtgggcg tgaggtgctg ctccccgtgg cggccgagca tggccgggtg   960
gtgggcttcg aagccgttgg gggtgagcat cttgtcggtg gcatggcgg ccccegggtg   1020 ggcatagtgg gggagcccttt gctgggagtt gtggatgctg cccagaccgg agctggagag   1080
gggcgagagg ctctggccca tgccggccac gtccttgtgg taggggtat agaggttatt   1140 catggaggcc agcccgcgct catcccgcat gagcgtgaag ctaccgctca cgttgcccgc   1200
caggcgctgg tggtggtgcg ggtggtggtg gtgatggtgg tggtggtgat ggtggggaa    1260 cttgtccgag actgtggaga tgggaggcag cggctgcaga ggggtcaagg tggtgtaggt   1320
ggtgggcatg ctcatacctg ggggagtctc gcaggccatg gtcatggtgg gatgcagggg   1380
gccggccagg ctgtgctcag gggcccggtg gtggtggtgg taatctccgc cgccgctgcc   1440
gccgtccagc agggacgcca tgcccatgga gcgcgggtgc gcgggggca ggtggctgcc    1500 gcggtgcgcc acggagctgc gcgcgtgggg gctgccgccc agcaggtcgg caggggcggg   1560
caccggctca tggctcaccc cgtgcagctc gccgatcgct tccatggtca gctgcgcgtt   1620
catcgtgatc cgggcgagca ggcggcggac acaacatcga tgtggccagg cagaggcggc   1680
gaggggcgca cggagtccgg tcttcacatc ggctgctggc gactgttgcc ttccttcctc   1740
tcactgtggg gctctgtctc tctctctctc tctctccgtg tgtgtgtgtc cgtgtgtgcg   1800
tgtcgtgtgt tgtgtgtgtg tgtgtctcgc cttccctctt accccccacc ttcccctctg   1860
cgtcctcggc tttttttttt ttaatattaa tttccaaaga ggatccgcgc cgttgggaga   1920
gcgcagtgcc ccagcccgcc cgcctcggcc acctctcgcc cctctcttc ttaaaattct    1980 gaggtctccg gctcccctgc cgcggccgc gcgcctgccg cgtctgctgc ctgcccgccc    2040
cgctggccag cttgagccat ggctctgtta ctgttacaga ctctgtggcc gcggttcggt   2100
agccgccgcc gccgccgccg cagcggcccg ccctcacgcc cgccaggcgc agcgcgcatg   2160
cgcgaggccc gccccgccc cctaggtcgc ggcgcgccag gcccttggcg tccggtaca    2220 aatgaaggag gggccccagc gccttccctg cggcgctgga tggccaggga gctgcgggca   2280
cgtgcgaaag attggcgcag agcgcgacct ggggccgccg ctgcaatccc aggagactcg   2340
```

-continued

| | |
|---|---|
| cgcctggctc gctcgcctcc cttgcttgag tgggctctgt cctcccagcc cggggacgct | 2400 |
| cgtgtcgggc ttctagcggc tggagtgctg tgcttggaga catcgcccct ctctctccag | 2460 |
| ttgctgcttc ccggtgcagc ttgcccgggg agctggggac tgtgtcatca ccccttcggc | 2520 |
| tctagcccac taagctttat ttcccggggg gctgctggga gtgcgctttc ccacccttga | 2580 |
| attcacggcc tattggggga tgggggttgg ggtggggtgg ggtgcagatt gcttaaaggg | 2640 |
| ctgggtccgt ttggcggccg ttgacccggc accttcgtc ctcccagata catacttgcc | 2700 |
| cacccttcct catccatgcc ctggggagag gagtaatcag tgccaagaat cccagttcgg | 2760 |
| gccatacctc actgtccccc gccgcctggc tccttctccc gctcagctca taattaaggc | 2820 |
| tgtgcgtccg cttcgccgat gactcggcct gtggagggg gcgagggaga gcggagggag | 2880 |
| tgccctggag ggtacccatg ttaacttccg ggtgctggtg gggccgtgga ggctcgggcc | 2940 |
| gtccctgcgg ttactcccaa ggccctcctg ctaaagcacc cggaggcggt tgctttccag | 3000 |
| aagtactgac gcagacaggg tggacgccgg cgcgcgggtc tccgcttggc ccctagggac | 3060 |
| gccctttttcc cggcgtcccc gagagacgcc tccagatttg aaaatcaatt cagcttcggg | 3120 |
| agtaatttcg cccttcccac agtcacgctc caatctggaa tcgaacctgg tctttgggcc | 3180 |
| tggtggggac gtgtgcggag gccccagtt tgagacgtac accggccgc cacatgccgc | 3240 |
| g | 3241 |

<210> SEQ ID NO 266
<211> LENGTH: 2385
<212> TYPE: DNA
<213> ORGANISM: Homo sapiens

<400> SEQUENCE: 266

| | |
|---|---|
| cgcgcggctg ctccatctgt gaacgtgagt ggtcgcctgg ctccctcttc cgcggcggcc | 60 |
| gcttcctcat accttcacac ggcgcacacc ggccggcgcg tccagctgcc tgcccagtgg | 120 |
| ccgaggctct tcccccctcgc ccagtcttga gctggaagtg attcctattg gccaaggtgt | 180 |
| ccatgtaaat aggtgtgaaa gaaaccagag ctggccgggc tctcccttct cgctcagtcc | 240 |
| cctccctctg cagccccgc tcccctcct cttcctcctc ctcccaaggc gattgtcata | 300 |
| tgatagctaa gaagtggcac attaatgaag cgccgctaca ggggtctttt ctgctcctgt | 360 |
| caccgcttaa aactatcaga tggttcgagg gaggacatgg aggcagccac ctagctcagc | 420 |
| ggagacgcgg agcccacagc agcgccctcc ggagccctaa cacgtcgctg ccaccatccg | 480 |
| cgccgggact ccgcagccga gctcggccgc ccgcaggacg ctccaggagc gtcgcggacc | 540 |
| gggcggcacg ggacgctgcg gggctgagct caagagccca ggttcgcgcc gagtccaacc | 600 |
| ggacccggac gctgcgcgcg gagtgcgcgt cgagtgcgcg ccgagagaga agcggcgcgc | 660 |
| agcggcgtcc tcccggatgc ggacgcgcaa cttgaagcaa ctttaaggtg agcagctctc | 720 |
| tgttccgtcc ctgcccccta ttctggcccc agtaccgact tacttcccgg ctatcctcgc | 780 |
| gccgttcgcc ggcttcccct cccgcgccca ctaagcccgc aaagttgctg gcgaaagagt | 840 |
| ccgggcgctg gctgatcgag cgccgcaggc cccaccccg accccgaag tctgttactc | 900 |
| ggtctggctc accccgccgg tgtctctgtg catccatgct acctttccct attacccacc | 960 |
| cccttcccag atccgagcag tccgccggcc cgcgcggacc cagagcaaga agagggcgag | 1020 |
| gaagaagatg cctcggcccg gccgcaacac gtacagcgac cagaagccgc cctactcgta | 1080 |
| catctcgctg accgctatgg ccatccagag ctctcccgag aagatgctgc cgctgagcga | 1140 |
| gatctacaag ttcatcatgg accgcttccc ctactacagg gagaacacgc agcgctggca | 1200 |

```
gaacagtctg cgccacaacc tctccttcaa cgactgcttc atcaagatcc cgcggcggcc    1260
ggaccagcca ggcaagggca gcttctgggc gctgcaccca agctgcgggg acatgttcga    1320
gaacggcagc ttcctgcggc gccgcaagcg cttcaaggtg cttaagtccg accacctggc    1380
gcccagcaag ccagccgacg cggcgcagta cctgcagcag caggccaagc tgcggctcag    1440
cgcgctggcg gcctcgggca cgcacctgcc acagatgccc gccgccgcct acaacttggg    1500
cggcgtggcg cagccctcgg gcttcaagca ccccttcgcc atcgagaaca tcatcgcgcg    1560
ggaatacaag atgcctgggg ggctggcctt ctccgccatg cagccggtgc ccgctgccta    1620
cccgctcccc aaccagttga ctaccatggg cagctcgctg gcaccggct ggccacacgt     1680 gtatggctcc gccggcatga tcgactcggc cacccccatc tccatggcga gtggcgacta    1740
cagcgcctac ggcgtgccgt tgaagccgct gtgccacgcg gcgggccaaa cgctgcccgc    1800
catccccgtg cccattaagc ccacgccggc cgccgtgccc gcgctgcctg cgctgccagc    1860
gcccatcccc accttgctct cgaactcgcc gccctcgctc agcccacgt cctcgcaaac     1920 agccaccagc caaagcagcc ccgccacccc cagcgaaacg ctcaccagcc cggcctccgc    1980
cttgcactcg gtggcggtgc actgaccgc aggagcccac gccccctctc gttctcctcc     2040
ccaccacctc actcgccttc cctggctccc agtcctgccg gcccccacct gggaccgcca    2100
ccctaacttg ttcatttcac cttcggccaa cccgccttgc cccaagagaa ctttgttttg    2160
gacccaggag accaaacaca aacttgcaga tgggccgaga ggcgcgtggg agttgtcctc    2220
gcccccacat caaggaaggc cggggccacc tgagccgaac catcccctcc ctgaggcccc    2280
gaaaccccct cctatttgac cggcggggga aaccctgtca cccctcttc gccgagaaaa     2340 gcgcgtcttc cctccgccca gatcggcgga gccccgaact ctgcg                    2385

<210> SEQ ID NO 267
<211> LENGTH: 264
<212> TYPE: DNA
<213> ORGANISM: Homo sapiens

<400> SEQUENCE: 267
cgcgcccctc tggcctccat cactgtcgtg ccggtcgtgg ggacagatgg gagggaatta      60
cggtatttac agctgctctt cgccggctct tgctcccccg cgtgtcgaca accgaaactg     120
cagcgaggcc cagaggcctc tgcccactcc cctcggagtt ccaggaggac gctaagcgcg     180
agaagccagg ctcagggaaa ctgaacgccc atacgctcct agtccctctc acctggatcc     240
tctgcgtcag gttacgtgct tgcg                                           264

<210> SEQ ID NO 268
<211> LENGTH: 7090
<212> TYPE: DNA
<213> ORGANISM: Homo sapiens

<400> SEQUENCE: 268
cgggacgcag gtgcagggtg ctggacgcag gtgtgcggcc gcttacctgg ggcgtgcagg      60
ccttgggctg cggggaggcg gcgggcgccg cgcgtggccc gcgggcgggc ggacccgggg     120
agggcgctag cgactgcgcg ggcggtgggt gtggcgcccc ggctctcagc tgtcaggcgc     180
gcctgccccg ccactcgggc tgtgaccgcg ccgtccccgc cgccgcgcca tgcgctccag     240
gcttcggcct cttcttccgg ccagtccccg gcctcggggt caacggctca gggttcgcat     300
ctccgcgccc ggggtcccgg cgccccgtgc ccgctgagag cgggagggc cgcgggtggg     360
```

```
agcgcggaga accagggagc acggctgtgc gcgcgcgcgg ggaggggccg cgccgtcacc    420
cggagagccc ggcggatccc ggactcccgc ccgccgctcc tcccgccgcg cacctccgct    480
caccgctcgc ccggctccag ccgccgccgc actgtgagta cccacgtccg gtagcccgcc    540 gccccgcgc tctgctcctg cagctttttt ttcgtttagt tctgatttgg gctcctgtgg     600
ctgttgtttt tatgattata cctaaagaca ccaccgcctc gctcccacca ctgccagtct    660
cccgcttcgc tgccctcccc aagctcgtcc atctagctcc gggagccgac gggggttcct    720
caagctgctc tggctgctgc tccttgtcgc tgcatatggc tcttcgcctg tgctttccgc    780
tttggccccc gaaattccgt tccttttccta gggaccccct tcttctgact ccgggcccgg   840 accccctcc tctcactcag ggaaaaccgc gcagggaccc aggaccctca actggggtac     900
gctctcggct cgggcgctgt cttcactgta tgcgggccag gcatagttgc cgatttcgag    960
aaaccgagaa gctgtcattt cccagcgctg cgcgccctcc agccacctcc aggagggcgc    1020
gaggcttgtc agccggggag ttaggacagt gttttttgcct cctacaatga tataaaggac   1080
ttcaacgcga aataagggtc aacttatttt agttcgatcc tcggagataa agatgaaaca   1140
gacagataat acataaatag cttgatactt gaagaaggta caaaacagat gagagaaaga   1200
ggaacgagcc ggcagagaca gctcaggac agataagatc gacaaatgag ggtctcctag    1260
acaaatagag aagaagggag agagacagat aaacagaaga ttccagtctc cttgctgaag   1320
gcttttgaac tgggatcccc tgtctggagc tgccccctctg aaaacggagt tacattcagg   1380
gccgactgca ggggaggagc cctcagggtt gggctgccct ggccgcagga gcgcctgcag    1440
ccttgggccg gatgggagcc tggcttgtct gaggacatgt ggctgggtca ggcgacctag    1500
agggccccaa acatcagtcc ccaagtaccc ccgctgctga ggtctgcctg cacagctccc    1560
tccctgcctc agccagaaag caaagtgcaa ggaccagcag caacttgtgt gcctggagcc    1620
ttgcaatggc tacgaagatg gctgagattc cttctagccc atatgagccg ggacagcgag    1680
gcatgaagga tactcagaga ggtgatgccc ctcaaagagg aagcccagag ccccgaatcc    1740
tgcagttggc ccgagtggga aacgtatatc tgaaggagga aagctcaagg agtgggcgac    1800
tggaagctaa gaagtggatc ccaacaaagt tccttgagaa cctctctgtc ccacacgttg    1860
acctcggtgg aaaccagctt tggtctggaa tacagctaaa aatgcagaaa atgtggttag    1920
aactgcagga tcctggtctc actaatagct ggaaagaaaa cggtttatat atccagccga    1980
aatctttctg ctcaacgaac gcgggcgcca gccgtgagag gagaagctcg ggtttgtgga    2040
aactggcaat gttgtcccct gaagccggct cgggcaccaa gctgggtgcg gtgggggccg    2100
cgctaggtcc gggtgcgcac cgagcgcttt ggagagggtc aggttcagca ccgcgaacag    2160
cggtagcctc cgcctctctc cttccctggc agacacggtt ccctcctcct tctcctcacc    2220 ccctccttc tcttcacccc cctctacccc ctgctgtctg gagatgggca gtgaccgccc     2280 ctccccctc cccacccctc cttgcactgc cccgcccgc ccgcgtgcat gcgcgactga      2340
gcagaggggc ggccgatccc cgaagtccgg gcttcaggac ccgggccggc agcaccggct    2400
gcgagggttg ccgaaggcgc acggatctgg gcgctgaaaa agccaggatt tggcaatggc    2460
tttgctgtgt ggccttgggc aagtcactct gcgtatctgg gtttcacttc cttcccaatc    2520
cgaaaacggg attgggttcc ttgcagcccg ggcattcctg aggtctcctt tacccccttct   2580 cctccccaa gccccggggg ctgttgttaa cggcgccaac atgggtctga gtaacaaaag    2640
acgcctgtcc aggggggtgaa tgagtttgga ctccccactg ccaagtatcc cccgcgcgcc   2700
caactcggag cgccctgctg ggcgggcccg agcctcggcg gcggcgctga aaatggctca    2760
```

-continued

| | |
|---|---|
| tctgctctct gctttctcta tttcgcagga gcggcggcat ggaggctctc accactcagc | 2820 |
| tggggccggg gcgcgagggc agttcctcgc ccaactccaa gcaggagctg cagccgtact | 2880 |
| cgggctccag cgctctcaaa cccaaccagg tgggcgagac gtcgctgtac ggggtgccca | 2940 |
| ttgtgtcgct ggtcatcgac ggccaggagc gcctatgcct ggcgcagatc tccaacaccc | 3000 |
| tcctcaagaa ctacagctat aatgagatcc acaaccgccg cgtggccctg gcatcacgt | 3060 |
| gcgtgcagtg cacgccggta cagctggaga ttctgcgtcg ggccggggcc atgcccatct | 3120 |
| cgtcgcgccg ctgcggcatg atcactaagc gagaggccga acgcctgtgc aagtcgttcc | 3180 |
| tgggcgagca caaaccaccc aagctgcccg agaacttcgc cttcgatgtg gtgcacgagt | 3240 |
| gcgcgtgggg ctcgcgtggt agcttcatcc ctgcgcgtta caacagctct cgtgccaagt | 3300 |
| gcatcaagtg cggctactgc agcatgtact tctcgcccaa caagttcatc ttccactcgc | 3360 |
| accgaacacc cgacgccaag tacacgcagc ccgatgccgc caacttcaac tcctggcgtc | 3420 |
| gtcacctcaa actcagtgac aagtcggcca cagacgaact gagccatgct tgggaggacg | 3480 |
| tcaaggccat gtttaatggc ggcacgcgca agcggacctt ctccctacaa ggaggcggcg | 3540 |
| gaggcggtgc caatggcggg tcgggtgggc aggggaaggg tggtgctggc ggcggtggcg | 3600 |
| gcggtggccc agggtgcggt gcagagatgg ccccaggccc gccgccccac aaaagcctgc | 3660 |
| gctgtgcga agatgaggct gccgggcctc cggggccacc tccacccac cgcagcgcg | 3720 |
| gacttggcct ggcgactgga gctagtggcc cggcgggccc aggagggccc ggtggcggcg | 3780 |
| ccggcgtacg aagctacccg gtgatcccgg tgcccagcaa aggctttggg ctcctgcaaa | 3840 |
| agctgccccc accactttc ccccatcctt acggcttccc tacggccttc ggcctatgcc | 3900 |
| ccaaaaagga cgaccggtt ttaggcgcgg gcgagccaaa gggcggtcct ggcactggga | 3960 |
| gcggcggcg cggcgcgggg acaggcgggg gtgcggggg cccgggagcc agccacttgc | 4020 |
| ccccggggc aggggcggc ccggcggcg cgccatgtt ctgggggcat caaccctccg | 4080 |
| gggcagccaa ggacgcagcg gcagtggctg cagcggccgc cgccgccact gtgtacccga | 4140 |
| cgtttcccat gttctggcca gcagcaggca gcctcccggt accgtcctac cccgctgctc | 4200 |
| agagccaagc caaggccgtg gcggcagccg tggcggcggc agcggcggcg gcagcggcag | 4260 |
| ctgctggcag cggtgcccca gagcccctgg acggtgccga ccagccaaa gagagtggcc | 4320 |
| tcggcgcgga ggagcgctgc ccgagcgctc tgtcccgcgg gccctggac gaagacggca | 4380 |
| cggacgaggc gctgccaccg ccctggcc cgttgcccc ccgccccg ccgcccgcac | 4440 |
| gcaaaggctc ctacgtgtcg gccttccggc cggtggtcaa ggacaccgag agcatcgcta | 4500 |
| agctctacgg gagcgcccgg gaggcgtacg gcgcggggcc tgctcggggg ccgggacccg | 4560 |
| gcgctgggag cggcggctac gtgagcccgg actttctgag cgaggcagc tccagctaca | 4620 |
| attccgcctc gcccgacgtg gacaccgcgg acgagcccga ggtggacgtg gaatccaacc | 4680 |
| gcttccccga cgacgaggac gcccaagagg agaccgagcc cagcgcaccc agcgcagggg | 4740 |
| gcggcccaga cggtgaacag cccactggac ccccttccgc cacctcctct ggcgcggacg | 4800 |
| gtcccgcaaa ctctccccgac ggcggcagcc ccgccccccg cgccgcctc gggcaccccc | 4860 |
| cagctggccg gccccgcattt ggggacttgg cagccgaaga cttggtgcgg agacctgaga | 4920 |
| ggagcccgcc aagcggcggc ggcggctacg agctgcgaga gccttgcggg cccctaggag | 4980 |
| gccccgcgcc ggccaaggtg agcccgcgc ccgccccgcc agtggcgcct tcccacctac | 5040 |
| cctgtgcgcg gcagggctgc ggggccgggc ggagaacggg aattttgttc cgcgcaggcg | 5100 |

```
tgggagcagc aggcctcggc cactctccgc aggcccagcc ttgggcgcgc tgcgaaactg    5160
ggcccacccg caccctccag tgagggtttc gaagggaagg gaagctgggg gcggcgggag    5220
gactggggaa cttgtgtgct ttgttttttgt tgatgggaat ggggaggaga ccggctgaga    5280
ctgccagaca cagagacaga aaaggggtgt ggagaaagaa agaggaggta agaaaggaac    5340
ccagagccag agaaaagcgc tcgcccgggt gggcatcaga gccccaagga agaggagaag    5400
agaggacagt gtggcctctc cctgagtcgg gccccagcag taccgggtcc ccggaatctc    5460
ccaccacccc aactcgcagt tttccgagtc tcttcgcact cccgccttgg gaaccacagg    5520
gttcgttgct gggaagctgt ctcgggaccg cgtgcggagc gggaggggggg ctctcaagct    5580 ggcagggccg gggcttgagg ggcaggatgc agccaggctg gagtcgttgg ccattttgaa    5640
agtgagtgcg catacctgta cattcggttc attaaaacac gaatcattaa ccggatgcga    5700
aaggcgtcat ttatgccgcg gacggggcac tggcgggagg gaaaatgcct aaaaggaggc    5760
gggtgcagag ggtggaggac actttgaacg cccctcggct tgggagccgc tttgtgttta    5820
gagtaatttt cccgagggcg ctaacaatta ccctgaatct acaaggggc aagggtgcgc    5880 cgcgtgcgtc actgtgcccg ctcaagtcca gcgggcgcac caacctttgc cactccgtcg    5940
gctttccctc ttggccgcgg ggtagggctg ggcgtctttg ggccgccgca gggcgccacc    6000
ctaatcgcct gtcatttctc ggccgtcgca ggtgttcgcg cccgagaggg atgagcacgt    6060
gaagagcgcg gcggtggcgc tggggcccgc ggcctcctac gtctgcaccc ccgaggccca    6120
cggtaacgcc tgtcgcggcc gctggccact gtaatggggg aaccgcagac agagggccgg    6180
ggtcaaggaa ggcctgcgaa ggaagacaag gagagagacg cagagaaaga gggagaggga    6240
aagaaaaata atgaaaacaa ggaagctaag ctagtactcc caacaacttc caatctttag    6300
ttacttaaaa acaacagtga caacgccctc tccaccacac gcacacacat gctgcagtac    6360
acccagacac ggcgttaaac ccttaacaaa atcacgcccg acacggcctt caaatcctct    6420
catttattca gcaagtgtgt ttggccgcgg ggtccccttt ggctaggccg gatcggggcg    6480
gaggatgggg gcacatggcc gcgcgcttgg gtaccccaga agcgccaggg tagctgaggc    6540
ccatcgcggg gtggtggggg ccgccctgca cttgcgcgcc ttaccaggtt cctcacagag    6600
gaggggttgg gggcagcgga aaatcgggca ggtcgaggca gccgaacccc ggacgatgtc    6660
cccccaccca ccccgaaggt cgcagcctgg gccgcgttct cagcaggagt cgggcggaca    6720
gacccggcgg ccacgcgcgc tcgcggtgcc ccagtatctg cgcgcgatgt aggtcgctcg    6780
tccctggtgg gctcggctgc tcgcctagct cttttccaag gggctggggc gggggcctga    6840
agcccggaga tgagcagacc aggcgcgggg gtgggggtg cccggcccaa agcctcaggg    6900
cgcgctcctg ggcgcacagc cgggaaccag aggcggccac gacgctttta attagggctg    6960
gggcgccccg accgcggcag ctccggcagt atccgggtca cggtttcttt gcctctcttg    7020
aaattcggtt tgttgccttc aagagccaga taaggaagac aatcactcgc ccgccgatga    7080
tttggaaacg                                                          7090

<210> SEQ ID NO 269
<211> LENGTH: 3174
<212> TYPE: DNA
<213> ORGANISM: Homo sapiens

<400> SEQUENCE: 269
cgggaagtaa agcctcggga ctttggttaa gcgcgcccca ctggcgtatc gcgccgcggg      60
actgcagagc cgtgagcagc ggtcgccttg gtgcagggtt ccagccacat cttcctcgcc     120
```

-continued

```
cagccagcac cctctgccgt tgacccgcct ctgcgcccgg caagcggctt ccagcagggg      180
gcgcgcgcgg accaggcttg ggccctagaa cagcgcggat ggagtcgctg gagcaagtcc      240
ccagatccaa ccggtttcaa ccctccccac cctcccgacg ctccgggttc gcgacgttga      300
agttaagggt cgatccgcag aaagcggcca ggggctccag ctctccattc ctgggtctgt      360
ctggggtcgg ctccagcctg gttagaagcc ttagtctgga ttcggcagat tctgaatctg      420
ggaccctctg cgctagcggc ttggaacctt gtcaccctcc cctcccccac ccctacttcc      480
acacacctga ttagttgtct gtttctttaa tgatcaaaga cgtgggcggc ggcgggatga      540
ggtcttggtt cccggctcca cagccctccc taactgtcat tattaacgtt ataaacatta      600
gacccgcttc tgcgcgccgg acggcgccgg acagggtgcg cgcagtcttc tagctgagct      660
cggaggcaga tccagaagtc gcggctccca ccccaggcct cggcggactc tgcctggggc      720
gactcgggct ccagccctgc ccgggcgggc actgggctct ccagggtcga aggcaggggt      780
aaggggcgtc tttcccccag ggcagcctcc gggaacaaaa gcatttgctg tagagtgagc      840
tagagcctcc gggcccgcgg gagtcagctc ccgcccaggg gtggtcaccg cgtccttaac      900
caccccagga gccccgtctc cctgccgaac tccttggctt ctgcaaccct gtcaagacag      960
caaggaaagg gggtcttccc tggtcctcgg gccccgaagt ttcggggttg cttataggac     1020
gggttcctgc agtccaggga agctctgggc agatagcgag cccattctcc cttccattac     1080
ccagattctg cctccctgcg gaaggcaaaa aagaaagaaa gaaataggt aaaaaccggc      1140 ggagggcctt gagcctcccc gcctggcgcc cctcactcag tcccgaaaag tccctggac      1200 acgccatgcc ggaccggact cagctcccgc tgctgggccc ctgcctccaa atatccttcc     1260
caggcacagg ctcccaagac cgcccctca gggttcccaa cacccggaca actgcccaag      1320
acgccgctcc ccgcccccac ccccaccttg ttcggcagac aaagaagggt gtgctggccc     1380
cgccgtctgc ctccttctcc cgaccccaca aggcctagaa acctcaggga ctcaccccgg     1440
gctagggacc caatcctggc tgtcccacca caggatcccc ggcagggacg ggtcacagtg     1500
ctctcacccc tcgaccattt tcgaagacac cttccctgaa aggcgccttg cgccctcccc     1560
atgggtcggc gggggggac tccaggcccg agcaggcggt gtgaagttct gtgttctgaa      1620
ctggggctga gcaagatgcg atggtctcag cccgctgggc cgcccgtagc gacggcagga     1680
gtaggggaga gggagggacg cttggagtgt gagcgcacca gtctgttcat atttaattta     1740
caaagcagcc tcggaacccc gggccgggtg gtctctttag acgctgcgct cttagcctgt     1800
ctctcttccc cacccccctcc cctagctcat taagatgctc aacactcaaa tcggggtatt    1860
gatctccacg gaagccccaa accctcgcca tcgagagacc cccatggccc ggggtgatgg     1920 ctgtgggct tggtgctccc agagagctca gtggctacaa aatgggtggg gattctgcgt      1980
gtctcccgga gcctgaaccc ctttcctggt tatggccggt agctgtctcc agggctaacg     2040
tgggcagcgc agggggcgg aaaccgggtt ttagccaaat gcctcgacat cgccgcgcct      2100
ccgcctcctc gtcgctgaaa gaaatgtcgg ggtttcatca gagctaggga gcgacagtcg     2160
ggaacagcga gtctgccgaa gccggctgtt gtgtgagggt gtgagacggc ggggcggtga     2220
ggggccaccg cggcttgggg gatagtgcgt gtggggttga ccgtgtgtct gcttgagagg     2280
ctgtgaagat atgggggca gatatgggag aaatgctcgg gcctgaagtc cccagcccac      2340
cgtgctcaag agtagcggac gttttgccac catccttgtc tgtgctactg tctgctgcag     2400
cttccgtgcc ccgttctcct ggagcaggca agacctggag tgaggtgctt gggtgcgctc     2460
```

```
gagagagctt cccctgctc cacctgtccc gcggtgcgcg caggccaacg cgtcgggcag    2520
tgggcttcaa gcgctggttt agccacaaaa gaccagaagt aaagagttcc ggcttaagag    2580
gctgggcagg gctgcggtgg gctggggagg ggggtgtccc ttcccagcac gccctgcagg    2640
gctgtgcgtt ctggtgtcgg gttagactag caggcgggc ggggggttg gggcggcggg      2700 gcggggaga ctagggctta tatcagccca gatccaggca aaaatggtag ggagggtgcg     2760
gcgctctgct aacactatca attatgcatc atgttgaacg tggcttcggg gaggaggcgg    2820
ctagcagcgg ggggtgcggg agggaagggt ccgcgcgagc tcggctgcgc gcagctcagc   2880
gggtcccgct cgaagtctgt cggtgccacc gcctgcattt gcaaaaagag tttaaaggca    2940
aagacacgcc ttccccccc acttcagccg cgcgcctttc cttcccccaa attcctcaaa    3000
gatggtttgt ctcacgtgtt gcagggcgta aaagcggctt gcattcaatt agcagcgaag   3060
ctcgcgggcg ctggcgggac aggcgcgtga gggtgagttc gcgtgaatgt gtgtatgcgt   3120
gtgcgagagg agaacggtaa gtgtcccggg tgcaggtgtg cccgtgaaaa tgcg           3174

<210> SEQ ID NO 270
<211> LENGTH: 315
<212> TYPE: DNA
<213> ORGANISM: Homo sapiens

<400> SEQUENCE: 270
cggagctcaa aagccggacg ctactggacg aggcttaaag cgctcgcccc agcgcggggc       60
cggtgaggaa cgttcaccgt ggaccatggt cgaataatgt tagcgtgcac tcggggcctc     120
gccctagcct tctgcaaagc ctcggcctgc ccctcggct gcatccgttt cgacgccaac      180
caacctcatg ctcttagtag aacggcagta gcgaccgcgc cctcaggccc acaagcccga    240
aggtctgggc agggtctgga atggcggtgg agacacttta ccgcaggcg tttcacctcg     300 cgccccaccc aggcg                                                          315

<210> SEQ ID NO 271
<211> LENGTH: 1171
<212> TYPE: DNA
<213> ORGANISM: Homo sapiens

<400> SEQUENCE: 271
cggcatcttg gccgggttgt aggagcgagg gagaacgcga ctgtaacgcg ggcgttgagc       60
acctagagtt cccccttcctc ttcactgaga gctgcggcgg aggctttaga ccgaggagcg    120
agatctaagg ttaaagaaag ggcctctgag cccagtgttg gccagagacc cacaggcgg     180 gccgggttcg ccctttgcct tcggccgcgc cccacccacc agggacagag tggccgcggc   240
cgagccgggt ccaccgccg cagcttagct ccgctccgcc gccctccccg tccgtcctcc    300
ccaggctccc gtcgccctcg cccaccctgg gccccctcc ccagatggga gccctccga    360 cccctgcgag gcccgctggg gacccacttg accgcgagat cgtagtggga gctcggccaa   420
aagaattctt cgctttccct ggccctcagt ttacccatct gggaagaggg gcgtcgcggc   480
cgcagaagtc cagctccgca cgcgccaagc gctgggtctg cagctccctc ggttcccgcg   540
cacccaactg ccccacgacc cctacccgcg cccgcagccc ccgccctccc gccccacttg   600
cctgggccgc cgggcgctgg aacctggacc ctggaccctg gcgggttccg agctgcgccg   660 cgccgtcc tgcccctcca gcactggact cctcctttcc cgtcttttta aagggaagta     720 accgacccg accactactc cacccgattc acccctagcg ggccgcccgc ccgcagctcc    780
gcccgggctc ctccccgtc cgcccgcggc ttcccgggag cccccaggg ctcctccgct    840
```

```
cctccgacgg cccggccttc ccccggggc ctgggatgca ccagggctcc tgctgccccc      900 gacgggtcc ctgtcgccgc agcccgcggg acccgccggc cacatctgga cggcatctgc      960 cgcggggag gggctcagag cctcgccctg agtgtcccgc agggagcctt gtgcatccgg     1020
ggcaggaagc cagcgcatcc cgtgcagacg ggtggtgcaa ataacggacc cgccacagca    1080
cgcaattcaa ctttcttggt acctgggact cgtagttcag aaggcgcagt agcacgacct    1140
tgcgaaaaag caccggagtc gggaacacgc g                                    1171

<210> SEQ ID NO 272
<211> LENGTH: 257
<212> TYPE: DNA
<213> ORGANISM: Homo sapiens

<400> SEQUENCE: 272
cgccacccgc acgacggacg tcggcaccac acagctgcc cttggcaaaa cgcgttgtcg      60
gctgctggga tggatttcag gttaaagcag agtcaccagg ccgaccactg cttaccttgt    120
tagcatctag aaccttcttc agctcctcgt ggctctgctg ggtgataagc acggtctctg    180
cggaggtgat gcagccgctg cacgccaggc agtcgtttag cgagaccttg gccttctcca    240
gcctccgggt cccgccg                                                    257

<210> SEQ ID NO 273
<211> LENGTH: 895
<212> TYPE: DNA
<213> ORGANISM: Homo sapiens

<400> SEQUENCE: 273
cgggtccact cctcactcgc gaagtcccta tctatctctg tgggtcccgg aggcacaggg     60
ctgcaagggc gcccgctaga gctgctccac ggcttaccgg attgcatgcg gagaagaaac    120
gggcccgggt ttcaacagag gccccgtgct ccgtgaattt ctaactcgaa ccagccgctg    180
ggataaatcc gagaaacgtt gtttattgtg ctattattaa ctttcccttc tccccacgcc    240
cctagaggaa ataaaattca ttcctgaata ttgggccagg aaaacgtttc tctgaaagga    300
accacaactg cagggaccca cccggctgca gctcccagcc cccggccctt cgccctaggc    360
tgcccactcg ctccggctcc cgacctcccc gctgccgaag caactgggtc agcctttcag    420
acttaaaacg aagtcgttta tttcattttt gctttcacat tatgttccga tacaatcaaa    480
actcctggac gaacctcttg aataaagtcc tgtgaatgag cggaatcata ggtcctgggc    540
gcccgagtat gcgcgggtg gactccggat tcagaggcg tgtataaaac atacgctgct      600
tcgggaactg cgaggggac gcggtggag acatccgggg acagaaggcc tgaggagtct      660
gccgctccag gcagggtcgt ttgggtcctc aaactggac tattcctgat gcatttggaa     720
tgcaaagaaa aaaatcaaac ttcgctcctg ggccggcgc cgcgcctggc ctagcaagat     780
ttcggccaca tttcttacgt ttccgccaaa gctgtgaaca caggcgaatg cagtgctggt    840
ccccggcctg gcgcaggaag gagcgcaagg ccggctttgc aaggaagccc tcgcg         895

<210> SEQ ID NO 274
<211> LENGTH: 2545
<212> TYPE: DNA
<213> ORGANISM: Homo sapiens

<400> SEQUENCE: 274
cgcgaaggct cggggctgcg agccgaatgc ccgccgagct gcctgggaac gggaaccgcg     60
```

-continued

| | |
|---|---|
| cacccgggaa cgccaggcgt ttctcttcat ccaggaacgg cgcggagagc ctccggctgg | 120 |
| ggagctaaac cgctggggac tccgcggctg ctgcctgagt cgctgtccgc tgcccgcatc | 180 |
| ccttccgccc tgggcctctg cacggtctgc ggttttctgt gcgcacttgg tcttcagtac | 240 |
| tagcacccaa ttacgtctgg gttttctc tttacagagc tgggtttcgg tggccaccag | 300 |
| cttttctggt gtttagtgac tctgagtttg gaggtggcct accaggcaaa cggggattca | 360 |
| gggcatttag gaaacgtctt ccgcgcttaa tcccagaagt ggttgcgtgt ccgtacgatc | 420 |
| ccaagttcct cccggagcct cttctttgct gcgtctcggg ccctccagca ggcgaagcct | 480 |
| cttagacgcg ctggggaaac ttccggcgtg ttcggggctc agggtttctt ctcaggcatg | 540 |
| gattgggcg cagaagttgc gcgaggcagc gcctaaggtc ccgaggtgct gagactgtgc | 600 |
| tggcgtttgc cacctgcccc tggctaggcc gtttctgggc cccaagaaac gcctaccttg | 660 |
| gcacttaggg accagaagcc tctggatgtc tagcaacagg ggtcacggga tcactgcgtg | 720 |
| gggtctctgt aagcagtccc ctgaggcagt gcaaaaccgg aaacctgctc tgtgcggggc | 780 |
| cgaatcagtt catgggattt gggagtcagg agagacgtct ttctcctccc agctcctaca | 840 |
| ctccggggtac caaggcccga aatgccgttc ccccagcccg ggtgcggggt ctgcagcaag | 900 |
| gcctcctgat ttgcaaaccc ctccgggctg cttattcctg gtgccatgcg cagcccttgg | 960 |
| gacctagaag attgtggggg agggaaggtc gcacgtgcgg ttttggcacc gaccgtgcct | 1020 |
| cctagtccac ctgtccccca cagctagctg ccaactcgga cggaagcgcg aacagcgca | 1080 |
| atgcaaaccg cccaaagtga aaggaatgta attgcgctcc catgacagag ccagacgcgg | 1140 |
| atgcagttta ggaagggcgc cgcctaccgg cccctgggag ccatgcgatt cgaagggagg | 1200 |
| gggacctaga ggagaccccc gctatccccc cacccaccgt ggggccttag ctttgaactc | 1260 |
| cggcccggac aaacttaaac tgcttcgcca ccccaacgcg ccacagccct ggacctaaga | 1320 |
| cccagttagc attgggaatt tggggagcag ggcccacgac tagaacaaag ttaaccctac | 1380 |
| cggttcccgc cacggcttcg gcacatttca aaaaaccagg cgcaggcaat tgagaaatac | 1440 |
| gctgccggct gaaacagcct gcgggtgggg gctgcagccg tgcgcgcccg gcagttcccg | 1500 |
| tcccgcatca ggtgtacgca cttccactcc tgcgggccct tccacgctcc aactctggac | 1560 |
| cccgcgcagt tttaatctgc ggtttgggaa atgggggtgc taccgtgcaa ccgcgccctg | 1620 |
| aaagaccgtt ttggtcttaa gagcttttgg cctgtgggt ggacatctgt agaaaaagga | 1680 |
| aaaacaaaac aaaagtaacc tcccattgcg tcgaaccctc ctattccgaa aagaacttta | 1740 |
| atgaggttgg cttggcaagg cctgcggtgc ttacctcggc ttcgccctac cccgccagaa | 1800 |
| gccctcatag gttgtatcca ctggtctccc ccaggtgcag ggttattagg ggaaaggggg | 1860 |
| gcgcgccctc gggctggatc tttgtttccc tcgtcgcccg gtcatcaaac aggagggaaa | 1920 |
| tcgggcccga ctgggacctt gctgcccgcc ttcccttaa actggctaaa gcttcaggac | 1980 |
| tgtccctaga cccaccccgc gggtcttcct tgtgtccag gcatagccg atctcctttt | 2040 |
| cgttttcacg agaactgcga cttgggcctc ggcactagg cgagcccagg ttgtggccta | 2100 |
| acagcagatc gcctcgggag cttggctgca gctctgcccg cacctccagc gctgggcggc | 2160 |
| ctctcggggc cagtggggat ctctggcctc gtgtaggcca cgggcccag ccctgggtcc | 2220 |
| ccaaggccgc tcgccgggca gcgctcgttt ccggcaccgg gacgagccca gcgcgctcag | 2280 |
| acaccacttt cccggtgaaa tctgctttta tttgctccga gcaaacctcg ggctctcagc | 2340 |
| gctcccgcct gatggatgca aatgtaaatg tgcacttatt taattggatc aggccccaag | 2400 |
| ataaaagaga taaacggctc cccgcttgct aacttatttt cctaggcatg cagcgccgcg | 2460 |

| | |
|---|---|
| tggaggggaa gctaatgaag gagcagcgcg gtgctgggca ctcgagctct ccgcagccgt | 2520 |
| ggcacgctgg ccggccggcc ccgcg | 2545 |

<210> SEQ ID NO 275
<211> LENGTH: 947
<212> TYPE: DNA
<213> ORGANISM: Homo sapiens

<400> SEQUENCE: 275

| | |
|---|---|
| cgcaggccaa cgcgaagaca cgatgatccc aaagacctta gtgtcttggc ggggggaggg | 60 |
| ggaagaggtg ggggacttttt ccgcttagct tccctaaggg ttgctacgcg acagctctcg | 120 |
| ggctacgtca gggtaaagag gtttgtatgg ccacacctcg caccgaccaa ctaccccga | 180 |
| aacaccccct cctcccaaac tgcagggtga gcacagcgag agaaaaggtg gcccaagcag | 240 |
| aggcgaacaa ctgcggttct taaagccttg tttgagtttg ggcccgcgcc gagccacagc | 300 |
| tagaggtaga tcccgctcct gcgcgtccgc tatcagcccc aggattccca gagaggcctc | 360 |
| tcaggcccttt caagaccccc ccttccggct tcccggccta cacctctgaa ccctcaggcc | 420 |
| ccggacagcc tctatccccg cctttcgcgg ccccggctca ccctctagcg tctcgcactg | 480 |
| caccaggttg aggtagtcgg cctggctgag caccccggcc ttcaggccgc gcaccagtcc | 540 |
| ctccaagtag ccattgtcca cgttaaagta aagctccggg aagaacgaca tggctgctgc | 600 |
| gggagcggcg ggaccggaga accaggaccg gccggcacga atcgcgactc cccaggtcag | 660 |
| ctgacgctgc gtcctcagcg ggctgtcaag tgcgtcaggt gacgcgcaag cgcctcacgt | 720 |
| gaccataagg gggcgtggct ctgagcggtg cccggcttcc gggtggctgc gcggaagcgc | 780 |
| ggtgcaggcg tgggctggcc ctgcggcgcc tgcgcgctaa aaagaggaag tttgaggccg | 840 |
| gccgcttggt ggcgcctgtg gccgcaggga tttgactggg ccttctctag cttttcccgg | 900 |
| tttgctgcac ttgacgctgc agggcgggcg gggtaaagaa gggagcg | 947 |

<210> SEQ ID NO 276
<211> LENGTH: 536
<212> TYPE: DNA
<213> ORGANISM: Homo sapiens

<400> SEQUENCE: 276

| | |
|---|---|
| cgggggttgg gggcacggaa ggggaagctt cggtcgctaa gtgggccggc ctttggaagg | 60 |
| gtctgggagg ggccagcgct gactaacagt cggtttccct accctagacg gctgcgacga | 120 |
| ggagctggtg ggtcccctgt atgcacgctc cctgggcgcc tcctcctact acagtctcct | 180 |
| tactgcgccg agattcgcca ggctgcacgg tgagctccgc ggaacatcag ctgccaactg | 240 |
| gcagcgcacc gcggaagggt gggggcctcc ggaggacttc ggggagaggg atagccggtt | 300 |
| aaagctcctg tcctttctat aggcataagc gggtggtcac cacggattgg ggatccgaat | 360 |
| ccctggctcc agatagactt aatgaagaag caccggatcc gggccgtggc cacacagggc | 420 |
| tcctttaatt cttgggactg ggtcacacgt tacatgctac tctacggcga ccgagtggac | 480 |
| agctggacac cgttctacca gcgagggcac aactcggtac tctgggcgcc aaggcg | 536 |

<210> SEQ ID NO 277
<211> LENGTH: 874
<212> TYPE: DNA
<213> ORGANISM: Homo sapiens

<400> SEQUENCE: 277

```
cggcgctggc gcaggcggcc aggagagagc agatgaaccg ttcgttagga gcagcgaggt      60
agtcgtgagc gctgagatcc agagactagg acccactccc tctctgagca gcaaattggg     120
aagaagatgc tcactcggta agggcgaggg agcccggcat ggcgcccac cacgggctcg      180 gtctatctgc gcgccaagat cccgcttggg gcgaggcgtt gggtcagcgt ttagagccac     240
tccctgcgct ggtggctgga catagcctcc ctatcccacc tcatcttccc ccatccccga     300
cagaggaggt tgtgaatcta caggcccttg acgttgaggc gtcggagggc gcaccttgt      360 aattgcggcc tcccttcgcc ccttaagtgc cgcttctggg cgcctaggct ggatatgaaa     420
gccccgttcc taatcctctg ctctggtccc ctcctctgga ctgctgggac tctaagctag     480
gccctcccca ggttccatca ctgcggcgcc aacccgcggc tgggctgtcc gcaagaggga     540
gttgaaggcg cgcggaatcc cgaggtgcag ctgaccctcc tctcaacgcc gactctgccg     600 ctccccgcccg gccacctccc tgtcgggcag acttcctgtt ctcctgctca cagcagggag     660
gcagtcgccg agccggtcag cagcgtgcac ggagatcttc actctgcgcc cagcccccggg    720 acacaggtgc agatctccag cggagcactg cggagtgcgc gccgtcgagc actagggaat     780
cctagacgga ggacttggtc cattccacgc agtcccaggc aggtccgcag cggagggacg     840
cagcggtctc caactcctgg tcacgacttc ggcg                                  874

<210> SEQ ID NO 278
<211> LENGTH: 3724
<212> TYPE: DNA
<213> ORGANISM: Homo sapiens

<400> SEQUENCE: 278
cgactcggct gacgttttg acccggccag gaggcaaaga ccaaaacgtc agagcagtag       60
ccctgttact gaggagcgtc ggcagggtcg cgggtagagg gggctggaga atgacttgtc     120
agagctcaag gtcgatgtgg cgcggggcgg cctcgagagc gccgggctcc tgcgtggcca     180
cggccgccgc tgccaacctt cgcggggact tagctttgct ttccattgac tcccttgca      240 aaagcgcagc agaatcctga ccagccgcac cagccccggc gaacccgagc atgttaatct     300
atttatatgg attattacgg aggaacagcg ggcgttgagt caccaaaaca tttgcttcaa     360
aagactattt ctaagcactt ttgcaggcag gcaggctcgc tccaggcgcg taaactcggc     420
tacgcattaa gaagcggctg cttttcgaat actgcaaact ccagctaagt ccccggtgcc     480
gcggagagag cagtgaaaag aaatgtcgga ggtgggggta gatcctagtc tagacacaca     540
cacttgcgcg cacacacaca cacacacaca caagattcgc gcggagaagg cactaaaatt     600
ctggcattcc gagagtacga caaacttaca cacttggaag tcccgggtcc ccgccttcc      660 ccgcagcacc ccccgccccc ccaccctacc gtccgcccct tggctgcgat cccctccct      720 ctcctcccct cccgcctcgt cacccagccc agtgccacaa tcctcctccc tcccaaaat      780 cgggtccaat cagctgcctg ccaacccggg gactgctgtg ctgtgattgg cgggtggctc     840
taaggtgagg cggagtattt attaaagaga ccctgggctg ggagttggag agccgaaagc     900
ggagctcgaa actgactgga aacttcagtg gcgcggagac tcgccagttt caaccccgga     960
aactttcttt tgcaggagga gaagagaagg ggtgcaagcg ccccactttt gctctttttt    1020
cctcccctcc tcctcctctc caattcgcct cccccacttt ggagcgggca gctgtgaact    1080
ggccaccccg cgccttccta agtgctcgcc gcggtagccg gccgacgcgc cagcttcccc    1140
gggagccgct tgctccgcat ccgggcagcc gaggggagag gagcccgcgc tcgagtccc     1200 cgagccgccg cggcttctcg ccttttcccgg ccaccagccc cctgccccgg gcccgcgtat   1260
```

-continued

```
gaatctcctg gaccccttca tgaagatgac cgacgagcag gagaagggcc tgtccggcgc   1320
ccccagcccc accatgtccg aggactccgc gggctcgccc tgcccgtcgg gctccggctc   1380
ggacaccgag aacacgcggc cccaggagaa cacgttcccc aagggcgagc ccgatctgaa   1440
gaaggagagc gaggaggaca agttccccgt gtgcatccgc gaggcggtca gccaggtgct   1500
caaaggctac gactggacgc tggtgcccat gccggtgcgc gtcaacggct ccagcaagaa   1560
caagccgcac gtcaagcggc ccatgaacgc cttcatggtg tgggcgcagg cggcgcgcag   1620
gaagctcgcg gaccagtacc cgcacttgca caacgccgag ctcagcaaga cgctgggcaa   1680
gctctggagg taggacccgg cggggcggc gcggcagggt gggcatcgcg gcggctgggg   1740
gcgctggtca gggctgattt gccccgcccc gcctcccatc gcccgggagt tgccgttccg   1800
ggagccggcg ggatggggtt gggagtggga atggggtgta actgtggctc agagtttgac   1860
aaagttcttg ggctgctcgc ggggacgcgg aggaggggg tggtaagtgg aagaggtgag    1920
ggaggtagct ggaggatgga cgaagactgg tgggagacgg aaggaggggg ctgccagcct   1980
gctctccagt cgcctggaag ctcaatcggg gcggggaagt gaaacttgcc tccctcctac   2040
ccggcctctt aaaactgcac tctctcgtgc agccccactg tccacggaga tggggcaagg   2100
gagaaaccga ggttggagga gacccttggc aggaactggg aggcgggagg agggaggcta   2160
ctggaaatag gtgggagtgt atggtggggg gtgagaattg gggaccttct tgcagcttaa   2220
gtaatttggg ggaaagtttt caaaggggt tggggttggg ggcggtaagt cgagcagcaa    2280
aggcgtttag ggggcagcac cgggagtcgt tttcatctcc agcgtttcca aaatagaaat   2340
agaaggggag gggagggagg gggcgggag tgaccgctca ggtcagactg caataactta    2400
tttatttatt tattttaag aaaagttatg agctgtggtt gcaggcagga gggaagatgg    2460
agttgtgtgc agaggaagcc gagtggtctg ggtcgccgcc tcctcccgc cgacctgaca    2520 gtttggcgga tttcactgac ccctctccct cttttctct gtgccccccg ccccgccccg    2580
agcagacttc tgaacgagag cgagaagcgg cccttcgtgg aggaggcgga gcggctgcgc   2640
gtgcagcaca agaaggacca cccggattac aagtaccagc cgcggcggag gaagtcggtg   2700
aagaacgggc aggcggaggc agaggaggcc acggagcaga cgcacatctc ccccaacgcc   2760
atcttcaagg cgctgcaggc cgactcgcca cactcctcct ccggcatgag cgaggtgcac   2820
tcccccggcg agcactcggg tgagtcgccc ctcgacccca ccggacaagc tatctccgtc   2880
ccgcctggca caccccctgc cctccgcctg ggagattctt cgtggggact ttatgcttcc   2940
cgggagggac acactgccct tgcgcccgt cccgctcccc tctctaccca gagcctaaga    3000
ggcatccaaa caacacacac acaaacacac acccccaac tcaatcccag catccgaaga    3060
gattaacttt tttattggga ggtaaaatgc ccttaacagc cttacaagac ctctcccttc   3120
ttctctgctc ccccacccca aaagcacaca cagggctctt acacaagtag caattaggtc   3180
ttccggaccc tccgggcccc agaccctccc ctgataaaag gggctgtcc agtgtgtacc    3240 ggcgggttaa tcattgggcg acttatctcc ggtgcagcgc gcctcttgcg cgggtgcggg   3300
cccttattac actttagcag cgagggaggg tccccggagg gtgcctaaga ctagggcgtc   3360
tgcacagccc ttgttgattt tctcgtgctt gttcttttat tgtccacagg gcaatcccag   3420
ggcccaccga ccccacccac cacccccaaa accgacgtgc agccgggcaa ggctgacctg   3480
aagcgagagg ggcgccccctt gccagagggg ggcagacagc ccctatcga cttccgcgac   3540 gtggacatcg gcgagctgag cagcgacgtc atctccaaca tcgagacctt cgatgtcaac   3600
```

```
gagtttgacc agtacctgcc gcccaacggc cacccggggg tgccggccac gcacggccag    3660
gtcacctaca cgggcagcta cggcatcagc agcaccgcgg ccaccccggc gagcgcgggc    3720
cacg                                                                 3724

<210> SEQ ID NO 279
<211> LENGTH: 3126
<212> TYPE: DNA
<213> ORGANISM: Homo sapiens

<400> SEQUENCE: 279
cgcctccgcc ccgcgtttcc tcccccgat ctcccagggg tcctcttttg agggcacccc      60
agcccctcga cggtcccggg atatcctgca cccctgccag gctgcaggga agcgccgagg    120
cgcgcggagt gcgaggtccg tgctccctgc ggcgcggcgc acacgcaggg tccgggtcg     180 accctccac cgctccggcg tctgccgggg aagtcagtcc gcctggtcag cccagaaccc     240
ccgactgcgg gggctggagc tcggaagcag gtacaagcgc cactctccgc ctgcgccgtg    300
gaatgcgcgc cggaccact ccgcagccct tcccccagcg ccgccggccg ctgctgggga    360
caacctcgcc ctcctgtctc ttgctcctcc tcctgacccc agcgcacccc catccccgcc    420
ccagatgagg caaggctccc tccgccttca gcccggcaga gtcgcactag gagttgcagc    480
ggccgcagcc ccgggagctt cccgctcgcg gagacccaga cggctgcagg agcccgggca    540
gcctcggggt cagcggcacc atgaacgtct cgggctgccc aggggccggg aacgcgagcc    600
aggcgggcgg cggggaggc tggcaccccg aggcggtcat cgtgcccctg ctcttcgcgc      660
tcatcttcct cgtgggcacc gtgggcaaca cgctggtgct ggcggtgctg ctgcgcggcg    720
gccaggcggt cagcactacc aacctgttca tccttaacct gggcgtggcc gacctgtgtt    780
tcatcctgtg ctgcgtgccc ttccaggcca ccatctacac cctggacggc tgggtgttcg    840
gctcgctgct gtgcaaggcg gtgcacttcc tcatcttcct caccatgcac gccagcagct    900
tcacgctggc cgccgtctcc ctggacaggt gagccagcgc cttggcctcc ctgggagatg    960
ggcatccacg cggggatgg agcgggaggc gggactgggg accaagaagg gacgcgcaga   1020
gtgggacagg acactaagaa ggcagtggaa gacaagcggg cgcggaggag gaaaaagagg   1080
aataagaatg ggggaccgtg gtgtccctcg gttagatgcg tcctggggcc tggaagcctg   1140
gagaatgtgg ctctccagcg ccgcccgtgc ctgacaacgc gcagcgtttc ccagtacgac   1200
gcgtttgtgc gcgttcatct cgcttgagct taatgccctc cgtgagggtg ggataggaca   1260
aagtgcccaa tatacagaag agttgagttc ctaagtaact cgctcagagt cgccagccag   1320
ggatcgggtg cgtgaagtga ccgtctgtct cctgcagcca acttcaggcg cctccactgc   1380
gctcgcctcc aagccacggt ttggttggtt ggtgcagctg gctcaggtcc aggctgtgga   1440
tcttgggtcc tttgcaagga tccactccgg agtcccagcg agcgtgccta aaggtcccta   1500
gctcagtccc agcccactct gcctctcgcc tccaaacaaa acaaaacaaa ataaaatcca   1560
aaacaagtcg gggccgggag aggagcgtgc cctggggttc ttcctcccca gccagaggag   1620
agcgagagac gcacattcgg gagagcgcgg gactcaggtg gagcttgaaa ggacactggg   1680
atggttcctg gggaggaaat ccgggtattt ccctctcca tcctctggaa aaacagagag   1740
gcgaggccag actgccccca cacctcctgt agccactgag cgcgaagtgc gttggttccg   1800
agcgcgctgg tgggatccac aaagctcgca ttctctcagg aatccctga gaaattaact    1860 gtcccttgcc caacatgtct tctccaggct gtctgctaga gcctcaggcg cctccgcct    1920 ccctcccgcg gcaccgtcac cagtgggtag tcacagcctc ccggagccca tagccggttc   1980
```

```
tccaaccttt agtcttcagt ggctttgggg tgccctctca gtggagactg tggttgcagt    2040 ccccggggc agcgggagaa tggcttgaag gcacaccttt cctgctgccg ggcccgcccc    2100
atttccaggc tccgctgagt gtctgggaca cgctgggagg ccccaccctc cgccctcacg    2160
ccgagcctca ccccaccctc ctctgtgtgc ggtgtaacca tgcgctaagg accttcctcg    2220
agagcagcct tgggaccgag gtgcaggggt cgcggccctc cagcatgaat gtgcccgctc    2280
agccgacgtc tcccttcccg gtctgaccgc aggtatctgg ccatccgcta cccgctgcac    2340
tcccgcgagc tgcgcacgcc tcgaaacgcg ctggcagcca tcgggctcat ctgggggctg    2400
tcgctgctct tctccgggcc ctacctgagc tactaccgcc agtcgcagct ggccaacctg    2460
accgtgtgcc atcccgcgtg gagcgcccct cgccgccgcg ccatggacat ctgcaccttc    2520
gtcttcagct acctgcttcc tgtgctggtt ctcggcctga cctacgcgcg caccttgcgc    2580
tacctctggc gcgccgtcga cccggtggcc gcgggctcgg gtgcccggcg cgccaagcgc    2640
aaggtgacac gcatgatcct catcgtggcc gcgctcttct gcctctgctg gatgccccac    2700
cacgcgctca tcctctgcgt gtggttcggc cagttcccgc tcacgcgcgc cacttatgcg    2760
cttcgcatcc tctcgcacct ggtctcctac gccaactcct gcgtcaaccc catcgtttac    2820
gcgctggtct ccaagcactt ccgcaaaggc ttccgcacga tctgcgcggg cctgctgggc    2880
cgtgccccag gccgagcctc gggccgtgtg tgcgctgccg cgcggggcac ccacagtggc    2940
agcgtgttgg agcgcgagtc cagcgacctg ttgcacatga gcgaggcggc gggggccctt    3000
cgtccctgcc ccggcgcttc ccagccatgc atcctgagc cctgtcctgg cccgtcctgg    3060
cagggcccaa aggcaggcga cagcatcctg acggttgatg tggcctgaaa gcacttagcg    3120
ggcgcg                                                                3126

<210> SEQ ID NO 280
<211> LENGTH: 526
<212> TYPE: DNA
<213> ORGANISM: Homo sapiens

<400> SEQUENCE: 280
cgagagcctc tacgacgcac tcaaccagta ctacgtccac ctcggcggcc agaagtacgt     60
ggacctcggt ctggggaccc accgcgtcaa atgtcgggtt cacccccaact tccgcctgat   120 tgtcattgaa gagaaagacg tcgtgtacaa acactttccc atcccctca ttaaccggct    180 ggagaagcac tatctggata tcaacacggt gctggagaaa tggcagaaga gcatcgtgga    240
ggagctctgt gcgtgggtgg agaagttcat caatgtcaaa gcacatcatt tccagaagag    300
gcacaaatac agccctctg acgtcttcat cggctaccac tcggacgcct gcgcgtctgt    360
ggtgctgcag gtcatagaga ggcagggtcc ccgggccttg acgaggaac ttcaccagaa    420 ggtgtctgag gaggccaaat cgatcctgct gaactgcgct acgcccgatg ccgtggtccg    480
gctgagcgcc tactcgctgg gcgggttcgc agcggagtgg ctgtcg                    526

<210> SEQ ID NO 281
<211> LENGTH: 242
<212> TYPE: DNA
<213> ORGANISM: Homo sapiens

<400> SEQUENCE: 281
cgtcacgtgc agagcatcct cccgactggc gaggtggctt ccacgtgccc cgtcaatcag     60
ggctggacag tccgtcacgt gcagagcatc ctcccgactg gcgaggtggc ttccacgtgc    120
```

| | |
|---|---:|
| cccgtcaatc agggctggac agtccatcac gtgcagagca tcctcccgac tggcgaggtg | 180 |
| gcttccacgg agcgattctc gagacccgag gggcgtggac acagcttcta cgcaggcagt | 240 |
| cg | 242 |

<210> SEQ ID NO 282
<211> LENGTH: 724
<212> TYPE: DNA
<213> ORGANISM: Homo sapiens

<400> SEQUENCE: 282

| | |
|---|---:|
| cgcgcgtcgg gcgctgggaa ggtgactgtg cgttgggcgc gcttggtggc cccagggctg | 60 |
| ggcctgctcc cgtctgacag tagtgccgcg ctgcatggca cgggtgttgc gttcgtgggt | 120 |
| gagagcgctg aggtctgcac gtcgggtctc agtggtcatg gggatggaag ccacccagt | 180 |
| ggctgtcggg gtgaatggag gcccctggag atggcagcgg gttaagcacg agcacggaat | 240 |
| tctccctccc aaaacggaac tcagacaaca gtgacggagc ctaagagcaa agccaaagcc | 300 |
| acgggcaggg gtgagcggga cccgaggcag gagatgacga gcctaagag caaagcgaag | 360 |
| ccacgggcag gggtgagcgg gacccgaggc aggaggtgac agagcctaag agcaaagcga | 420 |
| agccacgggc aggggtgagc gggacccgag gcaggagatg acgagcctg agagcaaagc | 480 |
| gaagccacgg gcaggggtga gcgggacccg agccaggagt ggcgccgggc agggaggcag | 540 |
| gcagccccag gcgctgtgtg ggcactgggt gagaagcagg atcccggcg ccctggctct | 600 |
| gtgctgcttc ctgagacgag agtggcagag ggcaagaaga aaaccaaaca gcgcggggaa | 660 |
| cagaagtcag gaaagatgaa cgtctggaag gaaatgcccc tgggccgggc ggtgcccccg | 720 |
| ggcg | 724 |

<210> SEQ ID NO 283
<211> LENGTH: 4996
<212> TYPE: DNA
<213> ORGANISM: Homo sapiens

<400> SEQUENCE: 283

| | |
|---|---:|
| cggagagacc tcggagcaga gaaggcgccg ccgaccctcg cggctgcctg gcccgcggct | 60 |
| cctacaaagg cgggctagcc gcccgccctc tcccttgcct tcctcccctt cttttctgac | 120 |
| tttccctctt tcccttaatc gcctgcttct tcctccgggt ggacttacgg ccaccttgct | 180 |
| cctccgcgct tcacctcatc gcccctctt tctttcttct gcctctctct ctgcgccccc | 240 |
| ttctctccgt gtcacgctcc ctcctggttc tgcgcgtcta caaactttg agcagaacac | 300 |
| gagcctcggc aaacgagtcc cgcagctcct cctgctgctc ccgctggttc ctgcggcttc | 360 |
| tgctcagaca ccaacgccag acggcgatgc ctctcgggtg gtgactccag cgcaggaact | 420 |
| tgaagaagcg ctttgcccgc cgtcctacct ggcagctctc ctggcagcgg gaggagttga | 480 |
| agggtaaggg agggaaaatc ttaccaaagc gaccggctca ctcgactgct gattctttcg | 540 |
| cttggcatcg cgtcagggga gttagctttc cttcagccgg gtctggctag ttattgggcg | 600 |
| ccgggtagat gcatatatat atattttttt ctaactatag caagcaagaa gtggcagggc | 660 |
| gcgcaccggc tgtcgccaag tgctgttcaa ctcaggagc cggggcttcg ctccgtccct | 720 |
| ccccggctt ccagagcttt tgggggttgg agggtgggag gccaggggcg ttctcacagc | 780 |
| tgtgtgtcct cttcccatc ctgcgcagaa tgaccatgtg tagcggagcg aggctggccc | 840 |
| tgctggtcta tgggataatc atgcacagca gcgtctacag ctcacctgcc gccgccggac | 900 |
| tccggttccc cgggatcagg taggtgctgg ctgcctggcc caagcaggag ctggggcttc | 960 |

```
ccaggcacag acgcttcctc acggtctcct tcctgcagtc ctttgggtcc agactactag   1020
catcgccctc tgcgccccg gtgcgcctcc gccagcctcg gctggacagc gggtccccat    1080
tctagccgag ggtctggcag gctccgcgac tgctcggacg cctcccccag ccctaggcag   1140
ctcagggtcc cgggtagagc cagtgagctt ctggccgctg gagaacccccc ctcccccaa   1200 cccggcccac aggatggggg cagggcacgg cccctagctt ggtttctttt acctattctt   1260
gggacgagtt aggagaactt cagctctgga gcctggccgg gggttgagcg tgaagctccc   1320
tcggactttg ctttgttact gcttgttctg gactatccgg gtgggtctc tctctctcct    1380 ccacccttc ttttcatttc attccaattc tttcccctga agagctttct ttcaagtgat    1440
ccgtgttcca actgcatttt gaatcccagg ctgtcttggg gggcgtgcgg tggggagggt   1500
gttggcccgg tgtgattgag gaaaagcgac ttaagagagg gaagaacaag gacgagactg   1560
cgaaggaggg ggaaaaacag gcgcaaagga ggaggaaggg aaagccagca ggcaggcagg   1620
accgggagag cagccctgcc tggcccggga tggaggaacc ttggcttttt tcttaaccccc  1680 gggtttctaa ccggcaggcg cggcccaggt tcccggaggc agccccagag tcgcggaccg   1740
atgtgccagc tgtggatga gccctgggta gggaggggtt cgtaccagcg cgcctggg     1800 cagcgaggag cgcgcgttct gcctgcgaag ctgccttctc cgagccccgc ccaggaacat   1860
tagctctggg gggccgctga tcattgattt ggacggagag atgggttctg ggttctgtat   1920
taggattcca gcatctgggc tcgaggcagg gcaatatcca gaaagacccc agggttcggg   1980
gtacccgggc cagggctgag gcgcatcgcc gagcaaaggc tgggtgcgag gcgtgcggaa   2040
tgatgcgctt gccttgcccg ggcctctcca aggatggaga aaaggcgagt gaagcagcga   2100
agtacgactc caacccccgcc cagagagtgc tactagcgct ggctgcacgc caagtctctc   2160 cagggggtcca aagcgagagg gatttgtttt aacccatctc tacccgtcct gtgtcaagaa   2220
cggaggctgt agagggcgac tgcgaagtcg ccaggcactc gctggatctc ggtcccctc    2280 ctcgtgctct ggggttgaga tggggcaccg ccatcgataa cagatcagcg cgaactattc   2340
gtttagtggc cttaaaacac cctggtttca ccctcagcta ttttcaagtt cccgtgtgcc   2400
tggcactttc tccgtgcgag aagcaccgga gggtgcggac gcgccacagt ctgagccgcc   2460
gccgaactgg ctaagtttag gggcatttat tattcatgtt cctgccagat cctcgcctgc   2520
ccaaaataga aaccgaggtt ctccgtgacc tacatctgct cggagaaggg ctcccctggg   2580
ctcggaggct ggggtggggg tggctgagga gttggccccc gcacgcccca cgcatcctct   2640
cctttgcttt ctgggcctcc ccattcgggt cttcgcgtgg gtcagcgccc ggtctcccag   2700
ggcctttctc gtccccgccc gttgctgctt tggggaggct cgggagccag gcggggaggg   2760
gggcggtcct tttccgtaga caggtgtgcg cgatcgcgg agacgcctcg gtttcccagc    2820
gcttgttgag gccgtggccc gcaggacgac ccttaccccg cgaaggggg gtgggcgggc    2880 cgcccggcgg ggtaggagtg gttgggtgtc gttgcctcct ccttacctct gctcccaccc   2940
ccagtcctgg gagaagagac aattctcagc ggaggacttt tatcacctgt gaaaatccgc   3000
gcgagcccct tactttggat cctcgccgag ctggggagga acttgcactg accacacctt   3060
ctgtccccgg ccacccccgca ggccagagga agaggcgtac ggcgaggacg gaaacccgct   3120
gccagacttc gatggctcgg agccgccggg cgcaggagc cccgcctccg cgccgcgcgc    3180
cgccgccgcc tggtaccgcc cggccgggag aaggtgagat tcgcgcggcc tcgcgcacac   3240
ccgcggctgg gagctcggga ctgcggtgac gggaggggca gtgtggtgac ccacccagga   3300
```

```
tttttttttt tttcccgtga agtcctcaa gcctgtcctc tccctggccc gatcctattg   3360
cagcgacaga aaatcagcag cgggcgggtc tgtgtggacc tgagggccgc gtggggaccg   3420
aggggggctg tggcccaaag agtggcagtg agtggcgtca aggaacccac actccgcatc   3480
tgccactcct agagccggga ctagctcccg atcctagcag ttgctctcga gatcatcccg   3540
ggagttattg gcgagttctg ggcctctgga ggtttccctg tcagcctccc cggccgccga   3600
gggggcgcgc gcccaacaag ggggtctcta gcggccacct ggggacagaa acagtgaccc   3660
tgggcgcgca ctttgcctcc ccgttagaga tgtcgcccac gggatcctta acgaggccta   3720
ccgcaaagtg ctggaccagc tgtccgccgg aagcacctg cagtcgctcg tggcccgggg   3780
cgtggggtaa gagtttgtgg aaggattaac ctgcgcgcgc cggggtgggt gcctgtgcgg   3840
ggcgcgcggg gcgggcggcg gtgggtgccc gtggggccca gggtgagtct gcgcccctgg   3900
gtctggggtg ggcatccgcc acgggtcgca gttggagatt ttgaagtggc actttaaatt   3960
tgcccagaga gctctggaag aggcaaaaag ggaacgcgag ccaggagtt tgatccgttt   4020 tgaatgaaaa gaaagagaaa ccaaaccaaa cctctcagtc atccaaaacc ttcaggcttc   4080
cagggaggtt ttgctataat tttctctaag catgactgtt tctggggag gggaaagggg   4140 tggttgtatt tactgaaaat tcaaatcgaa ataataaatg ccaaatgtg gacacttatg   4200 gacccaaaca gttttgctca cgccagagaa actgagagca cagggcttgt gtgaagccta   4260
tctcggcaga aggcaacatt ctaataaagc ccgtgggaaa acagattaca ttttcgccat   4320
gaataagtca tgcagtgaaa atattgcct acagcctgtc gacttatatt attatcacgt   4380
ttttcaactc ggcgtgagga gggagaggag tgttcatatt tgactaggaa ttgcaggatc   4440
gatgcaaact ccagggcagc agccagactg gcatatgtag ggctctccgg ttactttctc   4500
tgtatgtcgc gggtgagagg aacagcgagg acaatttagc gcaaacacac gaagggtcgg   4560
atctcaaggg ggcagcgctg ggagaaaggt taggcttgaa gcgcgcgtcg cctgcccgga   4620
tcttatcccg ggccccctcc gcaggggtttg gtgccaggag atcctgcgtg gggagggggg   4680
catcgagggg ctgccgtctc ggccctcccc acggctgctt ccaggcagag gcgggcgacg   4740
cggtgggcag tgcgagcccc gggccctccc cgaaggctcc cgcgtggggt ggggcccgcc   4800
tgctccccgc ggcgattgaa cctgtgtctc ccgcccgcc accctcttcc cgacccottt   4860 gcttgcagtg ggagcctcgg cggcggcgcg gggacgacg cggagccgct ctccaagcgc   4920
cactcggacg ggatcttcac ggacagctac agccgctacc ggaaacaaat ggctgtcaag   4980
aaatacttgg cggccg                                                   4996
```

<210> SEQ ID NO 284
<211> LENGTH: 4239
<212> TYPE: DNA
<213> ORGANISM: Homo sapiens

<400> SEQUENCE: 284

```
cgcagaaatt actcgtgcgc accatttccg ctgtgggggc attcgtacaa gtttccgctg     60
cacacacagc ctcccgggcc ctctcctcca aggctctgcc ggatcttcca acgaaatccc    120
agagcagcct cgcgctggga gcccgcaagt ctctccagat ctctgcaccc cgcaccgccc    180
ggaatctggg acggcgccca cgcagggctg gccaagggc agagctcgca ccctgccttc    240
acgcccggtt cacttgcgtc cacgaaagca gcgtgccggc ctcctccatc ttcccactcg    300
cgcaacgcac ggcgacccgc gcgacacttc tgcaatctga aggcttgctt cttacaaata    360
aagggccaga gtctcacact tgccttcgtt ggagggactt agaagatcct ccccacgtcc    420
```

```
acaccttgta ggaaatgcaa aacagatcga tgaaattaaa cagttgcatt tggaagcccc      480
agaaagacct aaagacatcg tgccggtttg ttggagagag ggttgcggga caggggagc       540 gggccttacg caacagaaaa ggtgggcaca gcgcgctcaa aatgacccag tgaggagttg      600
gtgccgccgg gccagaggct gcgagtccag ctggctctgg acttgctccg caggcgtcag     660
acgccgtggg aacctgtgtc tgcttcttct ctccaaagtg tatcggttaa aaaaaaataa     720
aagtagtagt agtagtagtg gtaaggaaaa aaataaaaat aaaaaggaga cacaattaac     780
caggtcataa aagctagggc accttcgacc agggctctgg ccctccagcg atcgttttgc     840
gttgtttctc ttctcaaaag tagtctcaga cccctgcctt tccgctgcag ctctgcgact     900
tccccaaact ccttaatcct gtaaattctg caagaaactc ccatcctgca agctgctttt     960 cccctcccc cctgcgttcc ttttttctct ccccacccgc gccgcctctc tatgcccctc     1020
tcttctcaga aaaattcctg cccccgcgc gccccaaagc ccgggctgca aacttttccc     1080
cgccgggcgc ctctgcgcca gatgccggag cgtctccaca aagcctgagc atctgcacaa     1140
gttcgcagcc taactgcggg ataaagacgt ttccccgta gcttaactag aaaagcgcca     1200
tcgatgggtg tgttaaacgg gataactaga gatttcaaac acctttatt tgcctgtctt     1260 gaaaaaaaaa tctaaatgaa tacgcccgct accaaaaggc aaaataaaac caaccttaag     1320 ggttttgtt gtttttttt tttttcaaaa gtggcgatag ggactgtttg gacctgactc     1380
caacctgcgc cctcccttcc tctatgaccc tcctgcgctt ttcctggaac ccaaagctct     1440
gacttcgtca aacttacaca attaaaggca ggcggaagaa gcgggctgg gaagcaagcg     1500 ggaagattct agaatggaag ggagcccgcc gagcgccgcg agccgcgcca ggcccgggtcc   1560 gatggagcag gcggggattc ctcccccagg cggaccccccg ccaccagccc tgccgggagc    1620
tcgcggcctg cggagcgccc gggctggccg ctcaccgccc gcttccccca gcgaacgact   1680
cggggaagct ccaggaggcc atctgtgctg acggttcaca ccagacagga ccacttgcaa     1740
ggacaaaaat aagaaattta ggaaacgaaa aaagacgtac tggggcgagg ggcgcgggcg     1800
cggcgacgac ggggccgggg gcacatcctg gcggccgctc ggggagagag gacacgcgcg     1860
ggaaggagcg cggcgggtgc acggccgcgg gtgggagtac gcgcctgtgc gcgcggggcg     1920
agggcgaggg cgcgtgcgtg tgaccgcggg gaggggggcgg gcgcgtgtgc ggggagcgcg     1980
ccgcgccagg ggccgagtgt gtggggccga tccagaagtg cgcagccccc tcacctggcc     2040
cccgtgtcat ccccgaaatc ccgggaaagg gtgggccgcg cgcgggagtt tggtggagtt     2100
ggaactttcg gtcgcgctcg ctgcccactc cgctggcgcc cggtgccccg tggtgaaggg     2160
ggactagggt ggggaacacc ggggccctgc ggtccccctcc ctttcctgta tttaagaagc   2220
cgccggcggc gcagaggccc aggcgggctg gcgcgggggc gaggcggccc ggtggcagca     2280
gcgggcgggg cgggcgctcc ggagtcggtg gggcccgcgg gttgggggc gggagaggg       2340 gggagtggaa gggaggggga acgcagggga gggagaggag gggaggagcc gcgcggcccg     2400
cgccgcttcc gaaccggaaa gttggtcttg ccgaagtcct gccacccgg cgtgcgcact     2460 ccgctccgct ccggccgcga gcctccgagc ccggccggcc gcggggggaa gcccgcggag     2520
gggacgcggg gccgggcgag aaggtccgga gagcggggg cacctgagcc cgggcgggcc     2580
cgccgcgctg agcggcgctg agagccgcgg cggagcagcg aaggcggccg gccgaccccg     2640
cgcgcccgga acaggaggcg cggcgcccga cgggcccggg cgagacaaag gcgccgggtc     2700
ggagccctgc ccgcggccgc tcgctccggg aggggccgcc cggcggcggc ggcggggggg     2760
```

```
gcgcgggcgg cggcgcagac actctataaa ggggcgagcc cggcgcgccg gcggagacgg    2820
cgccgcgcgg acgccgccaa agtttgctgc ctgcgccctg cggagggacg gccaccgcgg    2880
cccgcgccgc acccgggccc cgccacagcc gcacccgggg cggccgagga gcgcggcgcc    2940
ggagcccgcg atgtgaggcg gcgccggggca gcgcgcgccc cggtcccgag gcgccgcggc    3000
cccctcctcg tcggcgcggc cgctaattgc gagcgcggcc tcatttgcat aggccgccgg    3060
agtccgctgg agcccggcca atcggcgcgg ccctccgcta atggccatgc attattcacc    3120
agcctaattg ctcagcccca tgcgcggccc gcgcagccgc cgccgccccg cgcccgcgc    3180 cgcgcgcccg ccaggccgcc ccgcgccgtc ccgccggcc gccccgctga tgccgctgcc    3240
ccgcgcgggg cccgagcgcc gctagcagca tgtctcggcg caagcaggcc aagccccagc    3300
acctcaagtc ggacgaggag ctgctgccgc ctgacggggc tcccgagcac ggtgagggcc    3360
ggggctgcgg ggtggccggg gggtctgggg ctgccgtcc gggctgggga agcgcgtgcg    3420
gcgggagcgg atgcgcgcgt ccgggagcgg gagaaagttc cctgcttcct gcgggcaagc    3480
gtccgccccg cgccaggccg gccgcggggc cccgggtact tcgccggagc gcgcgcggcc    3540
gccgagagag ttgtgggcga agtaaacttg gctcctctcc tcggagtcgg ggagctgccc    3600
gcgaagggcg ccgaggccgc ggccggctcg aggacggctc ggaggccggg gcgggaggga    3660
gtccacggtg cctccgccgc cgcgccgccc cccaggg tct ctgcgccagg acgctgaggc    3720
cggcggcggc ggggaaggcg accgcagccc acctaccgct ggacgcgggt tggggacccc    3780
gccgcccggc cagctttgtt cgggggcccg cggcccctcc cgggcccccg caccgcctcg    3840
ggtgaccccg ggtgtcccag cgcgttgacg cagcctgtga tccctcgcga ggcgaggaga    3900
aggtcggggg cttggctctg cctaatggcc gcccggggaa ttaagctggg ggtgagcgca    3960 gcggcggcg cctgggcctg gcccctgctc gcggcgtgtt tccggggcgt tcgttgcagc    4020
gtctgcgcgg gcctttttctc tcccgtcttt ttggatccgc cgaggccggg cgctggagac    4080
ctcggctttg cagtcatttc gctggtagga gcgtcctctt cgaaacatcc aagagcaaag    4140
ggcaggcgcc gcgaaagtta agagactggc aaagggctgg acttcccaga gtggcgcctt    4200
agccccgcaa agtttggggc gccccacccc ccttcgtcg                           4239
```

<210> SEQ ID NO 285
<211> LENGTH: 621
<212> TYPE: DNA
<213> ORGANISM: Homo sapiens

<400> SEQUENCE: 285

```
cgggtgcaaa cgcatcctct gtcccacgtg gagtggtgtg tccacacgca tgtcctctgt     60
cccatgccca cgtggagggg cgtgtacaca cgcatgtcct ctgtcccgtg tggaggggcg    120
tgtacacgca cacgtgtcct ctgtcccgtg tggaggggcg tgtacatgct cacatgtgtc    180
ctctgtcccg tgtggagggg cgtgtacatg caaacgtgta tcctctgtcc catgtggagg    240
gatgggcaca tgtgtgtctt caggacgcct gtctcaggca cccgtgtgtc ttcaggacgc    300
ctgtcgggca cacgcgtgtc ttcagaacgc ttgtctgggg cacacgtgtg ttctcaggat    360
gcctgtctcg ggcacacagg ttgcggggc ggccggggct cctcaggcct tttctcccga    420
ctgttgctac tattcttttt agggcatctt tcacttccag ctgggccggg gtgagcccat    480
gctgcacacg cgcctgcgtc cacactgcaa ggacttcctg gagaagatcg ccaagctgta    540
cgagctgcac gtcttcacct tcggcagccg gctgtacgca cacaccatcg caggtcagtc    600
aagccgcagc cgaagaggcc g                                              621
```

```
<210> SEQ ID NO 286
<211> LENGTH: 434
<212> TYPE: DNA
<213> ORGANISM: Homo sapiens

<400> SEQUENCE: 286
cgggaccgtt tcacagatga aagaccgag gtgccagggt ggcgatcgca cgaagggccc      60
gtcacgggag aatgaggagg gtctggcgtc agcaagctcc cccggaatct cgtgatctgg    120
aaatccacag agaagcacct tcaccacgcc agcttcccgg gccgcgcttc attgtcattt    180
ctggagagtg ttattaatat ccgccccgtg ggtgcggcgc tgtgtatttc cagagagggg    240
actcggggcc catcagggcc gggggagtgg agccggcaga tgttcggccc tgcccagaat    300
cacttcccca atttccccac gcccggcggg gctctcagca tctgcatccg ccgaggcctg    360
gctgtgctga cgggaattga aaggacctcg tggcttaggc aggcggggga gcccccggc     420
tggtcaggtg cacg                                                      434

<210> SEQ ID NO 287
<211> LENGTH: 1012
<212> TYPE: DNA
<213> ORGANISM: Homo sapiens

<400> SEQUENCE: 287
cgccgcgact atggggtagc gttcaagggc aggccgcacc tcactcagca catgagcatg     60
tacgacggga gaaaaatgca tgaatgtcat cagtgccaaa aagccttcac cacgagcgcg    120
tccctcacac ggcacaggag aatccacacc ggggagaagc cttacgagtg cagcgactgc    180
gggaaagcct tcaacgaccc ttcagccctt aggagccacg caagaactca cctcaaagag    240
aagccctttg actgcagtca gtgtggaaat gcattccgga ccctctcggc cctgaaaatc    300
cacatgcgag ttcacactgg cgagaggcct acaagtgtg atcagtgcgg gaaggcttac    360
ggccggagct gccacctcat cgcacacaag agaacgcaca ccggagagag gccctacgag    420
tgtcacgact gtgggaaagc tttccagcac ccctcccacc tcaaagagca cgtgaggaat    480
cacacggggg agaagcccta cgcgtgcacg cagtgcggca aagccttccg ctggaagtcc    540
aactttaatt tgcacaagaa gaaccacatg gtggagaaga cctacgaatg taagaatgc     600
gggaaatcct ttggcgatct cgtgtcccgg aggaaacaca tgaggattca catcgtcaag    660
aaacccgtgg aatgtcggca gtgcgggaag accttccgaa accagtccat ccttaagact    720
cacatgaact ctcacactgg agagaaacca tacgggtgcg atctctgcgg gaaagctttc    780
agcgcgagtt caaacctcac cgcacacagg aagatacaca cgcaagagag acgctacgaa    840
tgcgccgcct gcgggaaagt cttcggtgac tatttatccc ggcggaggca catgagcgtt    900
cacccttgtaa agaaacgagt tgagtgtagg cagtgtggca aggccttcag gaaccagtca    960
acgctgaaga cgcacatgcg aagccacacg ggggagaaac cgtacgaatg cg           1012

<210> SEQ ID NO 288
<211> LENGTH: 300
<212> TYPE: DNA
<213> ORGANISM: Homo sapiens

<400> SEQUENCE: 288
cggaaagcgc gctttcggc agagctggtt agttttaaat gcgggctttt ttttctcac       60
ccgccgttcc ctccgctccg gtctgattcg caaatcccca aactggcaca aaccgggaaa    120
```

| | |
|---|---|
| cttgcggccg gccgttcttc tccccgagtt ggagacagcc ctctcctctt ccctccccg | 180 |
| cctctgggcc ctgacccact gcctggtttg cgctagagcc gttaaaaaa gaaagaaagg | 240 |
| aagaaaggag ccgggctctg gtaccccgat gccagccgag ggcgcgtttc ccaggcggcg | 300 |

<210> SEQ ID NO 289
<211> LENGTH: 310
<212> TYPE: DNA
<213> ORGANISM: Homo sapiens

<400> SEQUENCE: 289

| | |
|---|---|
| cgcgaccacc cgctgcgcat gcgcttcact tgggcgtcac ccggggaact gcgcctgcgc | 60 |
| agtctctccc catccgaggt ccgctccgcg agtgcgagcg cgcgccaggc ccacccgggc | 120 |
| gctgctcttc atgtccccgc ggtcgaagac ggccacatac gtccccaaga agacgtcacc | 180 |
| gaggatccag aagggccctg caggcggagg gacatccagg gcctggaaac cggacaagca | 240 |
| gaggcggacg ccatttcgag tagtctgcaa ggcaacaaga cgacaactgg gtgtcgcggc | 300 |
| cacaaggacg | 310 |

<210> SEQ ID NO 290
<211> LENGTH: 527
<212> TYPE: DNA
<213> ORGANISM: Homo sapiens

<400> SEQUENCE: 290

| | |
|---|---|
| cgattcgctt ccccaccacg acgccctagc gctactgtgc aacgaagacc tcccaagcac | 60 |
| tggttccaat gcggagacca tgggctccca gactctggga actccaacac gactgcgaaa | 120 |
| cgaactccga gcgaggactc cccgagagct ccccgcaaca cggacctcac gcgctagcga | 180 |
| acaacagaaa aaaaaagcg cgctctccct gcccctgaaa cattcccaga agcccacgca | 240 |
| gaccagaccg atgacctgtc tccactgctg gaggcgagtc agggacccga agtctctaaa | 300 |
| cactcgcctc tacccgccgc cccgcgaacc ccacacactg cagacgcgac actcgcaagt | 360 |
| ttcggggatg gcggccggcg agggccatac tgcgtctttc cggagacacg gaatacggca | 420 |
| ccagccgtcc ctttatgatg caatatgtct gcgcccaggg gacgcttgct gggagcagcc | 480 |
| attttcaacc ctactgccgt agagcaggcg gagtccctct tttcgcg | 527 |

<210> SEQ ID NO 291
<211> LENGTH: 2075
<212> TYPE: DNA
<213> ORGANISM: Homo sapiens

<400> SEQUENCE: 291

| | |
|---|---|
| cgaggtgggg gcgaggaacc acccggactg ggtctccatg ggcggggtcg tggcttaggg | 60 |
| cagggacagg tgtagggcga ggggtgagtt cggggcgtgg acgtgcgtgg gttcacaggt | 120 |
| gtgaacggta gccgcacgtg ggctgggact gagctgaaaa atcggccagg ggcgaggccc | 180 |
| gggtaggaag tgggtgcggc gtggggaggc gtggcctgac ggtgtgattg gcaggcggag | 240 |
| ctgatccgag aggacatcca gggggctctg cacaattacc gctcgggccg cggggagcgc | 300 |
| agggcggcgg cgctcaggtg agagggaaga agttggcagg gtctctggga agccggtttc | 360 |
| ccctccttgt gcctcagtct acaacaccag cctggaacag aacaagagtt ttgcatggag | 420 |
| tcaagcacac cctagtcgag tcttgtctgt acctcccaga cgagctgacc ccttctccag | 480 |
| aactctgctt cttttctctg ttccctgtcc aggccctcag tttcactcta gagaggtgct | 540 |
| atccctccgt atatcggatt tctccctacc tcgttgaact tgttcactcc ctttgagcct | 600 |

```
tttgagcctg tgtgtctcgt tctgcgccct ggatttcccc ctccctggac ccctcagtgg      660
acccagtctt ggtgtccccg tcgccctccg cagggccacg caggaggagt tgcagcgcga      720
ccgctcgccc gccgctgaga ccccgcccct gcagcgccgc ccgtcagtcc gcgcagtgat      780
cagcaccgta gagcggggcg cgggccgcgg acgaccccag gcgaagccca ttcccgaggc      840
agaggaggcg cagaggcctg agccggtggg gacctcgagc aacgctgact cggcctcccc      900
ggacctgggt ccccggggtc ctgacctggc ggttctgcag gcggagcggg aagtggtgag      960
ccgctaagga aggggtctgg gggcagggcc aggcgactgg aggcggggct agggcgtgga     1020
agggcggggc cggctgcggg acgggcgttc tctggtcaga cttctgcgtt atggaagagg     1080
ggctgggtcg ggggcggggc ttggttgtgg ggcgtggcca ggtgtttggg gcgtggcctg     1140
atctggggaa gtgtataggt gctcaggttc agggcttcga cggggatggt tttggaactc     1200
gggagccctg agcgtccccc tcctctgtcc cctaggacat cctgaaccac gtgttcgacg     1260
acgtagagag ctttgtatcg aggctgcaga agtcggcgga ggcggccagg gtgctggagc     1320
accgggaacg cggccgcagg agccggcgcc gggcggctgg gggtaagggg caccctggcg     1380
tgggatctga acccctccc gatctcttcc aaatgtcccc gctctcccca ggctctcccc      1440
tcccgccact tgccagggct gacctcaccg ccatcttaac cgggtgtcca cctctctctg     1500
cctgcctggt gctggcccg cgtcccatc gccgcgcccg tctgctcccc tcagagggct      1560
tgctgacgct gcgggccaag ccgccctcgg aggccgagta caccgacgtg ctgcagaaga     1620
tcaagtacgc cttcagcctg ctggtgagga cgcgcccgcc cctgggccgg ggcgcgggca     1680
cgacgaacct gtcccgtccc cgcacccacg ccaaccacct ccctcccac gccccaggcc      1740 cggctgcgcg gcaacatcgc cgaccctcc tctccggagc tgttgcactt ccttttcggg      1800
cctctgcaga tggtgagacc cgcccaggc cctcgggccc cctgcagcg ggaggaatcg       1860 ggttcgactt gtagaaggtg tggcggcaca gcctgcccct cctgctcccc tgacagattg     1920
tgaacacgtc gggggggccg gagttcgcga gcagtgtgcg gcggccgcat ctgacatcgg     1980
atgccgtggc gctgctgcgg gacaacgtca ctccacgtga aaacgagctc tggacctcgc     2040
tgggggactc gtggacccgc cccgggtgag gggcg                                2075

<210> SEQ ID NO 292
<211> LENGTH: 347
<212> TYPE: DNA
<213> ORGANISM: Homo sapiens

<400> SEQUENCE: 292
cgctcccctg cgtttcggct gctggcccag cagagggcgc cggagagcgg acggagccgc       60
aggcggggtt gtgggaagac gctgggatcc cgtgcgcgct tgtgctcctt ccttctgggc      120
cagcgcgcag actatcaacc gaggtattca gtccctcgga aacccagttc ctccgtttcc      180
aggcttctcg cccacacgga gacagtcgct ctcacacgta cctctcgcgg gctcttactc      240
gtggtcccgg tctcctcctg gtccccacct tccagcccag cgcgcacact agacggcacg      300
tgctctccac gctctttctc cagcgcccct tgctcacccg ccccccg                    347

<210> SEQ ID NO 293
<211> LENGTH: 712
<212> TYPE: DNA
<213> ORGANISM: Homo sapiens

<400> SEQUENCE: 293
```

```
cgcagcaagc tcagccgcc cttatttaag ataccgcccg agagggcggg gaaagaaaac    60
ccctacaggc aggacagccc ttcgcccctc ccaccaccac tgcggcaaac aagccccgcc   120
cccagagggt agccgggcac gccggcgccg cgaggccgat ggcaccccgc aggaagggc   180 attttcgcag cccccagacc cagcccagga ggcccagggc tcccgagagc cgcattccgc   240
cgtggcaaca gggatagcat tggtgtcgac cttgctggac ttgccgtggc agagccccg    300 gctgtctgcc ctaatgcccc cggtttgctg cggtggcccc cggccagtca gaaaggcgcg   360
gagaccctgc agcagcccct cagaccccgg actgcaagat ggcggcacca acgcagcagc   420
ccgggctgcg cccaccctg ccccaaaaag gcaccaacca tccacagcct ggccgccact    480
gtgcccactc tcggactggg cagcggggcgg ccaagtacca tgtccgccag cccgccctgc   540
cacaagggtc gctggcttgc cgcggggtct tgggcttgcg gcaagacggc cactctggcc   600
cagagccgtc gcgacaccaa ggtcccgcgg gcaggaggcg cgcggggcgg ccgaaggcgc   660
actcacctca cctcagtgct gcgcagcctc gggcacgaac agccgcctag cg           712

<210> SEQ ID NO 294
<211> LENGTH: 932
<212> TYPE: DNA
<213> ORGANISM: Homo sapiens

<400> SEQUENCE: 294
cgcccaacga agaggaggga gtaggggtcc gcgcccacc acgaaaggag agtagagggc     60
tcgcgccctg cggggagagg cgttaggggg tccgcgcccg gcgaggagat gcgcgtacca   120
gccccgcacg ccaaggggag aagacacgcg ggacggtccg cgcctggcgg agagagttcc   180
tcacgcccgc cccgccggga accacaagcc agcgcccta acaagcccct gcccagagca    240
gggctgccgc gtaccctcac agacagaaag agcgaccacg cagccaccgc ccagccccag   300
ccgctctgga gtccttgacc ccaccctcac taggccttgg ctccgcgacc ggtgggcggg   360
aacggaggaa acagacccga gaggccgcga gaggacggaa ctcacttccc gccgccgtag   420
cgtcctcgtc agctcgccct ccgactctcc gcatgggcgc gcagagttcc cggatgcgat   480
attccggtga caccggacgc tggggcgggg gcctagtgcg acgagggcgg ggccggggcc   540
ggccccgggc ggggccgtgg ccgcagctgc ctggcagcca gaacctggga gcgctcgcag   600
tgctgccttt cggggttctt tgtccttcgc ttctgctggt aggtgaggtt taacagacgg   660
aaagacgccg ggagcgcacg tgggctgcct tgagccgctg cggacgagca ccttgtctct   720
caggttgacc agccgtatat ccgcttgcga gcctgcacca ccctgggcgc gcgtggtctc   780
ggcagaatct cgttcacacg ggtcccactc gtaggctgct gtgtctcctt cctctcacgg   840
cgtcggggac tggggcctgg agtcactcct ctacagggt gtggaacgcg ccaatggacg    900
ctgacacctt catgcggtcg tttaacgctc cg                                 932

<210> SEQ ID NO 295
<211> LENGTH: 422
<212> TYPE: DNA
<213> ORGANISM: Homo sapiens

<400> SEQUENCE: 295
cgcttcccta tcggggctgc acgtagagca tctaaccgca tgttcccgga acctgggatg    60
cgcgcgcgca aaggagcgcc caagcgtgca acccagagtt tggacgcgcc gcccttaca    120 gccccgccc cggggccggg cgagctgagg gggcgcgggg cgtctgtgtt cccagctgat   180
cacagaacag gccgatatcg cattgacccg gggagctgag gtgaagggcc gctgtggcca   240
```

| | |
|---|---|
| cagccagtcg gagctgcaag tgttctgggt ggatcgcgca tatgcactca aaatgctctt | 300 |
| tgtaaaggta actccgagcc cagcgggcag aggggccgca ggctccgcgt gggtgtggga | 360 |
| agtggcggcc cctaggttta agaacccaga cgctgcgggg acgattgaag cgcacctccc | 420 |
| cg | 422 |

<210> SEQ ID NO 296
<211> LENGTH: 10782
<212> TYPE: DNA
<213> ORGANISM: Homo sapiens

<400> SEQUENCE: 296

| | |
|---|---|
| cgcggagaca tctcgagtcc cgcaggtgtc tgagctgcgc tgcgcgcccc agccgggaag | 60 |
| ccttttctta tccaaccgcg ccgccccgcg gaaagcctgg gtactgcaga cgccctcacc | 120 |
| ggcccaccga cagctggttt tgaagcgggg gcttagaaaa gtaaagggga cagtgtttgg | 180 |
| agccacgatg cctttgatgt gaggcggttc cacccaacaa tcaacgaatc aagctggaac | 240 |
| tgcaggccct acttttgttg gggggaggac cttaaggaat gtcacccccct tgtccctac | 300 |
| cctctgcccc acgccagcc tctcagaagg caccaggcgt gagtagagtg cgaggcgtcc | 360 |
| acaccctcgt gtcccttcca ttcccggaca cctttgcacc ctagccgagg cctcagcacg | 420 |
| gagtgagggt tgcctggggt gcccgctgt gtgtggggcg ttcttgcctc ccgggccctg | 480 |
| accccacggt ctgggtcggc gaggcgtctc tccctggcgt ctggactgtg cgcctgcccc | 540 |
| gcttccaggc gacgaacggc aggagccggg ggtccggcgg gacccggatc cagggcgggc | 600 |
| ggaaggcgag ggtctctcct tcccggaacc ccgcccccgg aaacctgcaa ccaaaccggg | 660 |
| tccctcctcc gcatcgctcc cgcgctcccg ggccgcctcc ccacgcgggc acccactctc | 720 |
| cgggccctcg cagcaccgcc ctctccgcgt ccacccgcgc ggccgacgcc gccaggggcc | 780 |
| ctgagatcgc ggagacagcg cgccctggcg cctggtgggg ccctcccagt ggccagagcg | 840 |
| ctcctggacc agtcggctgt ggtctgtgcc caaacacgat ggaaaccggg gctgggacgg | 900 |
| gcggtggtac gcacgtggag gagaagaggc atggcgggaa aaccacagcc gaacacaggt | 960 |
| cgactcgcac ctcccaggca cccgccgccg tctgactcgc ggctctcccc aaggttccga | 1020 |
| ctcgccgcca cctcttggca ccactcaccg ggctccgacc cgggccgcga gtccgctgat | 1080 |
| gcgcagctgc ctccggcggc tcccgggctc tgcccgacc cgcgcgcaga gacgctcggg | 1140 |
| aacgctgggc tcgggcgcct cctggcggcg gcagcacgcg gcacacgctc ggttctccgg | 1200 |
| cccgaggggg cgcgtggagc gtacgcggga tccgcgcgcg ggcctgggct gctggcccac | 1260 |
| atttccccgc ttgctcggat ggcggcgctg aggcctattc gcctctttat taataacgat | 1320 |
| gcctcgggag ggaaaaaata gagcctttaa aaatcagagt gcgagagagg agtgtgtgtg | 1380 |
| tgtgtgtgtg tgtgtgtgtg tgtgtgtgtc tcgggcgtt ggtgaaagca ataaaactca | 1440 |
| gatcgcttcc ttggcgagat agcggcggct ataatgcgcc gggggggatca gggtttatt | 1500 |
| tgcagatcct ggataaaaga tgatatatcg acacggttta gagtgtcact gcgcttggcc | 1560 |
| tctcagggag ccacaagtac atatttcctg aaataccgcc cagcacagta tctaatccgc | 1620 |
| ccgccactta acaccgggag gggaacttca gcagcgcaca agcgcgctcc cggtttcctg | 1680 |
| gttctgggtg gggagagccc aaatgagaag gatctggtat gcctagacgc cccctcccct | 1740 |
| ggcctttgtc ttcagtccaa gtaatcactt agcgatgggc cttaataaat acgtctgaga | 1800 |
| actgtcctta tgctcggtaa atattggatt agcttttcaa tgaccaggct cttgaaaagg | 1860 |

-continued

```
ctcgagaaat acacaccagg tctcaactaa gcccaacagt caataggtaa ggaaataagt      1920
tatttcccca tctgaggtgg ggaatgttgg gaaggggggac ttccactctt accaaattat     1980
ctgattctac taaatatgac cgttgtacta aataggaaag ggggcgcatc caagtttccc      2040
attagtcgga atttccacca gctcagttct gctcattaag ggccgagtga ctttgtgggg     2100
aacatatctg ggttccagtt tttatttcca cagagctcag cataaactat ttttgtttag     2160
tacatatggt ttatttgggg actgcttatg ggagttttga cctggcaatt gcaggggaga    2220
aggcatgacc caaattattt ccgactgcct cgcgccaatt tggaccgctt agaggaggca    2280
aaaaatgggc aaattccttg gaagccctgc tgtgtctccc tggtactgaa ttttgtaagc    2340
acgcgataca ggagacattg aaaattaaag aggaagtatc tccctcctcc aacatgggga    2400
gagacgctgt tggaagaagt ttctgaagtg gtttcccatc gcaccaagag gccagtggga    2460
tggatccccg cgcataattc aaaggaacgc gcgcgtcttt agctcttcgg ggttggtaac    2520
caagtggtcc ggccgggcgc aagtcgcctt ggaaccggct gcagcccaag tctagctggg    2580
cccgggactg agcggcaccc ttggcctctc agaaccttc tcgcggtgag tggaagggcg     2640
gctccgcgcg cgggcgcttc ggggccggtc ggttgcgaaa tcaggggtg gattttcatc    2700 tacccaggag ccgctaagcc cgtaggggac cgagcatcac ccaggccctg gtaccctga    2760 gttgcctcct gagccccagg acggtccgat ggtgcagagc tcccaggcag aagttagttt    2820
cctgatacac acacagcagt gagcaaagtg cgcacaagtg agccaaaccc tgaagacgca    2880
ggttcgcgga ctcccatccc agcgttagag tcaaggagac agaagagagg aaggagagaa    2940
gtgaggaagg gagagagatt atgagaaaaa gagattatga aagtagagaa agagattatg     3000
agagcgagat tatgagaaga gagaaaaaga gagattttga gagagagaga cagaatgaga    3060
gagatccaac tttcagtgtc acggggccta ggcggggcaa gcgccctccg aagccatcaa    3120 agacagggt ggcttttct cccctcctcc agcctcctcc ccaatagata tagcacgaat     3180
ttttaatgcg tcttcctttc acagacaaca atacagggtt tgaaagccgg acacaattta    3240
ggttttgtgc gggtccctcc tcgcgctccc tcggcccagc tggccatatg gaatccagca    3300
tggagcccgt ggatgacaaa gggacccagt gacaggccca acaaaacccc aaggagactt    3360
ctgcctgact ccgggattca ctgccggcga taagcgcgct gaatggtgcg gggtggggcg   3420
gggggtgggg ggcgggcccc ttctccttct tcccctctct ctgtccccgc gatccttct     3480 ctgtcccttt ttaatatgca cgcctctaac atctccggct cccagctttc ccattgtgcg    3540
gttttgtacc gcccgctgta gattgggcga agatagactg ctgaagcgga ccccgcgccg    3600
ggtgcgctcc cagggcgctg gggttagggc cacacagggc tccgcaggcg cttttattga    3660
ctccatgggg acccgaggac agagagaggc gggcgccggg tccacctccc gggctcccgg   3720
ccggccacag gagcgcacac ccagattgca ggcccgcggt cctggccaca gctccaaatt    3780
tgtcctcaat gagcaagtgg tggaagcctg ccagggtgag gaccttccac gcttccccct    3840
tcctctctgg aaacctgagg gtctcttgtg atcattctca ccctggaagc cctggggcct    3900
ggaaaagtca aaatggcctc aggccttctg acagctccgc tccaagagac ttgaaaccct    3960 caccttttcct cccaagagga ttttgggatt aggggaagtt gcaagtggat gttgagtggt    4020
tagtaccagg gcaggttggg cgttcaatta ttgcacaaca aactatttgg gagaaattcg    4080
ttggccttta aaaacagtaa gacataagcc cccaaacatt gccaagctag tgtggagaac    4140
aaagggagac cttttagcat ttagaaaaac tgccctttcc ccgaggatga gcccggagat    4200
gggaaaggac ctttactggg gtattagaaa gacttccgag ccctcaatta tccaggggcg    4260
```

```
gtgtggaacg cgggaataaa gtgtcatcgc gtccctgggc tgctgcgcag agtgctatcg    4320
acgcacagat ttggtcgcac ggataatcat gtttgcttta gatattgaat taaacctgat    4380
catcaactac agggagcgag aaagtcagct gggaccgctc cttttgcccg gcctcctcac    4440
tgccacccaa cccccagcc ttgatggtgc agcttcggag agaacagaga tacaatttcc     4500
aaatgcgccg acgttcagtc cctcagcgtc tgcagcaccc gctgggctct gagctagagt    4560
cccaagtatt tttagaaacc cgcgagatag aggagaaagg ctcatcctcc agttggccag    4620
gcttcctaag acgctccccc gcgtggccaa gtgtgcgcca gcatctgcca aggagatctt    4680
cctccagcaa caagggtggg acggaatccg ttccccgccg gaaagatgga tgcgcccttc    4740
ccgggcgtgc ccggggctgt gtgcccactt cccatccggg gagctcaccc cacccccaaa    4800
cctctacttc ctagcaatcc acccagttcc acgctcaagg gctgacctgg ggggaccgca    4860
caccctggtt cggaccgccg aacgctggag ggaaggaggc ccgggatcca gtccccggag    4920
agaggcctgg aagcccggaa aggatgggag cgtaagggaa gggagaggca tggtttgctg    4980
ggattgccaa agattctcgc tccctggctt cctggggcca aagatcctag ggagggctgc    5040
agtatcccct ccctcccccg agcccagaac cccgcgtact tcccccaagc cccctaagcc    5100
aaagcctcgc gcgccctgac cgttcccacc cccagcctta gcggtctcct aggtcagcac    5160
cagcccgcag attttgaaaa ggagtgggga gtggggagaa ggcagccagt cttaacctca    5220 gaccccccacc cacccacttt cttagcgtga ggtaagtcaa atgtaacaaa gtgaaagtca    5280
tcgagtgtag tggcttcaac agcttctcag gctgaaggag ccactcatag atttgggcca    5340
gcgagggggg tttgctctcc tcgcctttgc ggctcccgaa gtcacttttc ctcccgtagc    5400
cggacgctgc cgcccggggt tcagacagcg cgcgagacca ggggagatgc ggggagggt     5460 gggcggccct gggcttccgg ccgaccgctc gcaggccgga ggccgagcgt tctcctcccc    5520
gccccaatcc taggcgcggg gtgcagcctg tggtcggagg ggcctgcacc gggagccccg    5580 cccgcccag ggccccggta cccccggcct cccgcccga gaggaaccgc ctgtgggagc      5640
cccgcgggcg gccgggcccg gctcccagge ccaggcctcc ggcccggcgc agtaggacaa    5700
acgggagggc agggattttt tctttttttc tttttaaac acaggatttt tattaaaatt     5760
cttatttaaa aaatcgaaag ctttctgcgc ccggcgctgt tggggaaccg cgccgaatag    5820
ctgagctcca agttcgggc tgaaggcccg gaggacaggg cagagggctc cctgcctaca     5880
gggttttctt ttccatattt gagaaatgtt tgcacaataa aataaaaaga gaaaggaaga    5940
aagcagggga aaacgcaaaa acaaaaacaa aacaaaaaac aaacccaaac aagccacaaa    6000
gaaaggagtt ggacccagac gggaaacagg ccggtcctga aggtcatttt ggcaacaatc    6060
accaccgata tttacaacga aaagcgaaat ctgccaccag ttgtcagaac gtttacatgg    6120
ccataaatat ttagcatttt cttatttttt tttaaaaaaa ggaagaaatt ctctgtattt    6180
ttaaagtgtt ctccacttgc tttagaagac ggctgacaat atcgctactc acacaaacat    6240
attttacaaa atgcacgaaa gcaggggtgg ggggtcggtc ttttttctcgt tttcaagtga   6300 cgacattaac gctgggacgg tttggtcccc ccggggagag gcaaagaagc gaagctgcgc    6360
aaacattctg taaacacggc gtagagttca gccctctccc aaggttcaga aggagaggca    6420
tgggcagagc tgggtgggtg gaatctgcca ctccaaggag acgcaggcaa cctcccggcg    6480
cctccctagt ggaccgagag gtcaactcga ctccataata ataattataa taataataat    6540
aaccaccata aggaccgagg cctcctcgcc gccaccgccg ccggggtggg gctgggcct     6600
```

```
ggggccgcga gtctcgttgg ggcggcgctc accaagtcca ctgctgggcc tggaccaggg    6660
ggtgtgctgt cgggtactgg ggggtgctgg ccgagctgta ctgggcgttg tactgcatgt    6720
gctgcagcga ctgcgcgctg taggcagaaa agggaatgcc cgcctggaag gtggcggctg    6780
ccaggtcctg ggctttgagc gcgtgacatg gtttgccgtc cctgaccaag acgggcacgg    6840
ccacccggcg cggcgagggc aggggcgtca cctccatacc tttctcggcc cgggcgcgct    6900
tcatcttgta gcggtggttc tggaaccaga tcttgacctg cgtgggcgtg aggcggatga    6960
ggctggccag gtgttcgcgc tcgggcgccg acaggtaccg ctgctgccga aagcgccgct    7020
ccagctcgta ggtctgcgcc ttggagaaaa gcactcgccg cttcgcttc ttgccggcgt    7080 cccccccgcc gcccggggtc tccttgtcat tgtccggtga ctcgtcggcc gagggctccg    7140
gggacttgga gcttgagtcc tgaggggcg ccccggcagc cagaccgtgc actggggga    7200 gggggagaga gaagcgcgtc aggcgtctgg aggccgcgcg cagcctgcac cagactcgga    7260
gcaccctgga tcctccgtgc gaccctggac ctccgcgcct ggcagccag ccccgctgcc    7320 tttgccatga cccctgcctt cctctacgcc tgacgaagac gtcggaccct cccagggtaa    7380
agagggaaat ccgtaggagt gggggctagg ggctcgcctt tcaaggggct cacatagtgt    7440
gggtgagaat ttggggggg aagtggcact gaagatcatc gcgggttaag ggctccggcg    7500
cccttaagcg gtttcctctc cggcgagacg tgggcagatt tttaaaagaa atccccaca    7560 atcccagcat tgatcggctc ggccatttaa ggcaggtttt tggggcttt cgtttctgct    7620 ttcgggcctt ctagacaccc ctgcactgc acaaagcgtc ctctatgatc gcgcaggggg    7680
cagggtgagc tatttatacc cgggccaccc gaagcctccc cacccctccac ccgtacccgg    7740 acgaggctcg ctggctacct ccagggcgcc aggccagtcc ctcccagcgg ccggagtccg    7800
ggggctgcgg ctggagccat cggtccgggt tgacatcata taccagcccc tgggaggtat    7860
agcccttctc cctctttctc cttaacttct cgcattgaaa aaattttggg agaccaagtt    7920
ctttcccgga actaaggagg cttgaagagg agggcagagg acatcctata caggtgttaa    7980
aaatctttct acggatccga gtgaggggt ccgggcttac atggccctt ccctttcac    8040 tcccagcgtc caacccggc tgcggctgca ggaatggagg ggaccacggc ctcggcagcc    8100
aagttttgct acttacggga gtactgaagg ccctcggtgc tggccagcca gcgcgtgtac    8160
gggttgtcgc tgctgtcgta aagggggttc ttcaggggca ggctctgcac cgcgtccagg    8220
gcgccctgcc ccagcggccc ggccctcttg gctggctcgg gcccctcgtt ctcttcctcc    8280
ggaccttcgg ccacagagcc ctcctcatcg ttggtgtccg gcaggtctaa gatgtccttg    8340
accgaaaacc ccgtctttgt gttggtcagc gacatggttc gagaccccaa aatttatgtc    8400
gcaaagttgt agcttcactt ggtcaattcg tggcgctccc ctgccccggc gggcggggga    8460
ggggggagtt ggggggaggg actggggag gggaggggg aattggcttt aattattggg    8520
ataattatta tttttaaaaa gagaaagaaa ctggggatgg ggaggaaaaa aatgaagccc    8580
aacccagtgc ctctctctgt cttctttgaa agcacgcgga aatggacgca ggaagccggg    8640
cggcctgcgc gccgagcgcc gcgggccccg gccttagttt ctaactccag gagggtgcc    8700 aaggcggcgt cagctcgggc tccggcgcc gctcggcgcg cggtggcggc tggtggcgag    8760
gaaaaaatgg gccattgccc gagcgatcag tccatataag gctgggctcc actcacgaac    8820
ctggggaggc ggggagaggg ggagaaagag agggagggag ggaaagaaag agggagggag    8880
gggagcgcga gagggagcg ggagaagggt ggaaaaaagg gggaagagac attaaaaacg    8940
caaaggttgg ccacgtgtgg gcgggtcttg ggagtcaagt ggatgaagac agtatttgca    9000
```

```
gatgtgaaat tgtgggtttt ggggagctcc gcgctcccag ccaacggccc tctagagcaa      9060
gatgagaggt gtaacgtgtc aattaattgc aaagacgggg cgagcctttt ttttttttaaa     9120 cccagtattt acatacaaag ggccaccgcg tcgctcgcga gtccacacac ttgaaagggc      9180
cgttttaaca aattgcatct taaaaaaggt gggggtgggg aggaggaggg gagaaaacaa      9240
aacagaaacc aggaggaggg aaaaaatcct ctttaacatt caccggttcc tacctccccg      9300
cccccgcgcg cccaccccg gcaagccgga aaattggcga tttgtggcgc ctttggaaaa      9360 ggggagggg gcgaaggccg agctgcggaa atctctcctt tccatcgttg gtggttgcct      9420
aaacaagatc cggttcaaat ggcaagagcc caacttctgt aagcctccta ggtcaatatt      9480
ttggttgagg cttaaggatg agtgctagaa atgacaaggc aagtaattga ttccagttaa      9540
ccgcgagaga gcccaaaacc caggagagag ctccgctccg ggccggccag agccaccacc     9600
aagcgacccg ccccccttcca gccgcccttt atttgctaaa gactcattta tttccttcac     9660
tccgcctccc cccacctccc accccaacc ccccgcctcc acctctctgc ggccaaggag      9720
gacgcgcagt tcactttctg ctttgcgggc ggtcccgggg agggcggggt aagagtgagg      9780
agctccaact tcgtctgggg tcggaccctg gccctgctgc ctctgggctc tgcgggcctc      9840
tttccccggg tggaggaaag ggcagacggc cctgctcttt cctgccctct attatccctc     9900
cctctccggc cccctccctc tccagcctct ggctagaggt ggagcagcgg gaaggcggcg     9960
gggcgggatt gcggggtgg gggtgggggt tgtgtctcca gcctgggtga agacccagaa     10020
agctgcgggg gaggggggtc gctggtggc ccgacgatgc ctcgttttct ccccagtttt      10080
cttctcccac gcgagttctt tagtgtggtc tcttttttgga cgccttgggt gcgttcggag    10140
tacgcgctcc acgtttccag gttaagtcag gttagtgtga agtttccagc cactctcggc    10200
tctgggaact gaactttccc gggacttgca cttcctcctc ggcgctgggg ttggaaaaga   10260
ccacgccgca tttgccaccc cttcttctag ttaaaacttt tttggggggg gggtgcaggg    10320
gtgtagattg gctacctgat gctcgttcgc cccagaggag tgtcaggaag gagctttgtc   10380
tgggggcggg gaggggcaca gaaggccacc cctgcggggt ccaggtctag tcttcccaca   10440
acctgggctc ctccgcgcgg gccaagctga gcgcgcgggc accgggtcct cctcgcgcgc   10500
agctgcagcg gacgccgccg cgccccagct gccccgggt tgccagcgct gggtgagggc    10560
acctctcccc gagccgctcg gcggcttcct gcagccctag ctgcctcgcc cccagtatgt    10620
gacgtgggtg acaatggccc aggttagagc aagcccctcg tcggcgcgtc ctgggtggtc   10680
ggacccgggc aaacacaaat acaaaccgat tgctaagctg cggacaatga gcgaaatgta    10740
gacaaatgtc ccgctcccgt tggaagcctt tgtcccggct cg                       10782

<210> SEQ ID NO 297
<211> LENGTH: 616
<212> TYPE: DNA
<213> ORGANISM: Homo sapiens

<400> SEQUENCE: 297
cgccacggcg tggccaccga ggtggtgtac cgctgcgaca cctgcggcca gaccttcgcc         60
aaccgctgca acctgaagag ccaccagcgc cacgtgcaca gcagcgagcg ccatttccca       120
tgcgagctgt gcgggaagaa gttcaagcgc aagaaggacg tgaagcggca cgtgctgcag       180
gtgcatgagg gcggcggcga gcggcaccgc tgcggccagt gcggcaaggg cctgagttcc       240
aagacagcgc tgcggctgca cgagcgcaca cacacgggag accggcccta cggctgcacc       300
```

| | |
|---|---|
| gagtgcggcg ccaggttctc gcagccgtcc gcgctcaaga cgcacatgag gtacgcgggg | 360 |
| agccgtccgg aggggtccct gcgcactgga agggtgtgtc aagcactgag gtcgtcctgg | 420 |
| gatttgatgt ctcactgctt aatttctccg ctccaaacct gggggcttat ttcgagacag | 480 |
| cgtttagttc tctgtcaagg tacagggggct gcgagtgatg gctctgctcc cttgttctga | 540 |
| gaccctggg gcgcccctgc tggccgggac gtccctctgg tgggaccgcg acagcggccg | 600 |
| cgggctcgcc ccaccg | 616 |

<210> SEQ ID NO 298
<211> LENGTH: 1687
<212> TYPE: DNA
<213> ORGANISM: Homo sapiens

<400> SEQUENCE: 298

| | |
|---|---|
| cgcgctttga acccaaccag ccctcatcgc tcggagccct gcgtccccg cttcccaatc | 60 |
| ccagaacccc ggaagcagat ctcctcagtc ccactccctg agggtcctac agtccgaggt | 120 |
| cccgcagcga ggggaggagca aacgcctgag ctccgcggga accggcgcg gctgcctgcg | 180 |
| cgcacgcagg gaccggagcc cgagcctggg ccctgcaaag tgggtctccc actcgctgcg | 240 |
| cgttcgagtg gggcctccgc taaacatgca gattaaacaa ggggcttccg ataaggataa | 300 |
| ttacaggagg ctgcgcattg actttccgtt actaaaggaa gacccaaatc tcccccttgc | 360 |
| aagctgttcc cggattacc aaaacaatca cttttctttg agatcattgt cttttgaacc | 420 |
| actccagctc ggggcagaac gctttagacg ctggcgttgt tttccgctcc gcgaggaatt | 480 |
| tccccccaga tttatctctg ggtttaggga aggcgttggg cattcgggac tgcgtagtcg | 540 |
| tttgtaaatc cgaatttggg gtagcagtta agtgagatac ctacgcttcc acacagtttg | 600 |
| tagcccgaga ccagtcaggc aggcagggta gtcgattcta aggtggcccg accggggtcg | 660 |
| cccgcgaatg gaaagcctaa ggggcgaggg cggacgcggg cgccgtgcct gcagccccgg | 720 |
| gtgccgacca agtggcctca cctgggacag gtcttgggt ctccctcccc taggtctccc | 780 |
| tggaaggtag gcgatcacgg gagtgacaga ccccgagtag atagccagtg atccaaagac | 840 |
| accaaaaggc caggcggtag gagcccagcc tcagacactc tctatagtga ccgcggcgcc | 900 |
| tcgggaagga tcgtcttaaa ctcattttgc aggtgagagc aactgggact tattaaccca | 960 |
| gtcacatcgg acacagagac gtggcgaggg cgacacagag caggagactc aatcaaggag | 1020 |
| cccgtattgg agctctaagg ggactcagag atgcagaagg aacgaacttc taagggggtct | 1080 |
| tgcaattcct ggactggggc gttcctaatg catcccggga ccccaatgcc agggagggc | 1140 |
| ctgcaggacc ccagcggtgg gcgagttgtg tcctgggtca ccttgtgttt cgcagcgtgg | 1200 |
| cggtggcagg agcccagcgc gggaggacat tttcatagcc tcctacagtg agaaacgccc | 1260 |
| cccacccgac gctgcgctca tctgtgtccc cgctgttgcc ggggctctgg tatccacttg | 1320 |
| cgcgccctat gtggtgggga tccacccaga gcccagcgtc aagttatacg ggcgcttcac | 1380 |
| tcagcgtcag ccaagaccag ggaagcgctt cttgccgttt aggagacgtc tgcaagagat | 1440 |
| aaaaagctag cccacgatcc acccacaatc ctcgtgtccc cggggtgccc tcgcagttgc | 1500 |
| caaacctacg ggccgcgttt aggggaagcc tccgcgtcct ggcggccaaa gaatgggct | 1560 |
| ccttccagct tcccctacc ggataccacc tgcaaatcta ttgccagagg cgcagctccc | 1620 |
| gcgaacgttc ccgccccggg cggcccccag gagtcgtttt gggtccctaa atccgttgag | 1680 |
| ggttccg | 1687 |

<210> SEQ ID NO 299
<211> LENGTH: 5242
<212> TYPE: DNA
<213> ORGANISM: Homo sapiens

<400> SEQUENCE: 299

| | | | | | |
|---|---|---|---|---|---|
| cggccgtcgg | agcagggccc | cagcgcaccg | cgagcctctg | cttcctccgc | cttgcagcgc | 60 |
| cgcgagccct | tctttcctcc | gcgcctggcc | ccgtctgcgc | ccctctcggc | gtgggcattc | 120 |
| gcagacccgc | taggaggctg | acgagaggtg | tcctcataga | gtcctgcctt | cttccagacc | 180 |
| cccaaacgaa | aagaaagaga | aaagccaacc | tttcgcctcc | attctgcacg | catttggaga | 240 |
| gcggctggtg | gcgagcgatc | cgcacaatcg | cttccctcgc | ggcgtccctg | gacgggcgga | 300 |
| gagaacccgg | gtgactgagc | ctgaggctga | gcttccttgg | gagcgatcca | tgccagccac | 360 |
| ttctaccttc | aagggggact | cgcggccggg | tttacgcgcg | aaggatgggt | gccagggaaa | 420 |
| ctgacttata | gacgacccgc | tccgcgagag | actgacaact | cagtcctgcg | ggctttcggg | 480 |
| gcgcccagac | cagtccttag | ccagaggatc | tggggctgca | cagctcccgg | accctggagg | 540 |
| gggtggtccg | ggggtgggag | actgcgagca | tcagcccacg | ccggccccct | cccaccctgc | 600 |
| ggcggcgagg | tgggaagggc | caggatgcga | gcttagcacc | tcccctagaa | atgcagcact | 660 |
| tcgccccccc | acctcccctg | ccctcggcgc | tccctctttc | acgcgctccc | tcccgcctcc | 720 |
| ttcccaaggg | cgcccttctt | ctgcccccag | ctcacgtctg | aatccctcgg | cgcccccttt | 780 |
| ctcttctcct | agccccttcc | tcacgtcccc | tgcctccggg | tatttcctct | ctccaatccc | 840 |
| ccacccccgc | accgcctgat | tccgaggggc | gggagcgcat | tgggctgcgc | acgggtgggg | 900 |
| gcgccgcgcc | agcttcgcgt | agctgctctg | acgccgctgc | cgccgccgcc | gccgccgccg | 960 |
| ccctccgcag | cccagctcgc | gcccgcggc | agctccgcag | tgcactagcc | accaccgccg | 1020 |
| ccgccgccgc | tccgccagac | ctgctgccag | cttgcccggt | ccagccctga | gagagcctcg | 1080 |
| aacgccagct | gcgagggtca | tgagccgagag | agccccgggg | cgccgcgcgg | agagcaagcg | 1140 |
| gagatagcga | ctttgcgccc | cccagccctc | gccttcttgc | atcgcgttcc | ccgcatcctc | 1200 |
| gggtccttct | gtcctttccg | ctgtccccac | cgccgccatg | gccaccttgc | tccgcagcaa | 1260 |
| gctgtccaac | gtgccacgt | ccgtgtccaa | caagtcccag | gccaagatga | gcggcatgtt | 1320 |
| cgccaggatg | ggttttcagg | cggccacgga | tgaggaggcg | gtgggcttcg | cgcattgcga | 1380 |
| cgacctcgac | tttgagcacc | gccagggcct | gcagatggaa | atcctgaaag | ccgagggaga | 1440 |
| gccctgcggg | gacgagggcg | ctgaagcgcc | cgtcgaggga | gacatccatt | atcagcgagg | 1500 |
| cagcggagct | cctctgccgc | cctccggctc | caaggaccag | gtgggaggtg | gtggcgaatt | 1560 |
| cgggggccac | gacaagccca | aaatcacggc | gtgggaggca | ggctggaacg | tgaccaacgc | 1620 |
| catccaggta | agcgcgggat | tcccagttct | gcctgtcctc | ccccctccca | gctcagcgtg | 1680 |
| ccgggctctg | cccccgacag | tcgcccggtg | atctcggcct | ggagaccccc | tcctgtaccc | 1740 |
| aggaatctcc | ctttctccat | ccctcccagc | cctgcgcggg | gacctacgcc | cccaggcggt | 1800 |
| gttttccgcc | ctaacccacg | ctccctccca | acggcaccag | ctgcaagacc | gctaggctga | 1860 |
| agttcggtct | gagacacctg | tccggagaca | ctgcaaaagt | gaaggaaatg | ggggaggga | 1920 |
| gcaggaagcg | atgagaaaga | aagaaaatca | ggattggagg | gcacggtttg | gtcttggact | 1980 |
| ctggaacgga | ttcacagctg | cattttggg | aggaaagaag | aagggaaat | cgctgaggtc | 2040 |
| ggagtctcct | ccccccgcac | acacgcatag | acacgcacac | gtatataggc | aggcacacca | 2100 |
| catgcccaca | gccccccttc | ccacgaacaa | aggcgcaggc | acaggcgcac | acgacatgta | 2160 |

-continued

```
tctatatata gaccacagta ctatccccaa atgcacctgc gtacacccct acagctccac    2220
aaacaaaagc atatacctgc acataccaaa cacacgaata ttcgtttgaa catatgcaca    2280
cacacatgca cagatgcatg cagacaggaa ccagcctgct cccttgggtg cggccctgtt    2340
ggagacatac aggtatacac acacgaaagc acacacatgc tcccacacaa acacatttag    2400
tccgcaataa tccagcatta cctgtgcaca gactcgcccc tctcgcccga aatcccggct    2460
gcaccgcaaa gaggcggcca gctcctcccc gtgtgaccct ggcgaagccc tctcagagg    2520 ctaagaatgg cccctgctct ctaggccctc tccccttatt cctaaccccc cactcccac    2580 caggcggcgc aggactccta catagggagc aggtttggag tcttggcaac gacctccgag    2640
ctagcagggg ctggcaggcc gcagctttct gggccgaagg agacttcagc tctaggcaac    2700
cccggtccct tacagcttgg ccccgcgcg tccctggagc gcactatcac tggggccacg    2760
gaaggcaggt tttctgggag cagaggcctc ccaggggttg ttccatgtat cggggtaagc    2820
aggactccac cggccccga acaccagatg gcccgaccca aggcgctttc cgctccgggg    2880
cccggcgaga cggccttgct ggatcacgga cccgggctg ctcccgcctt cgctgtgccc    2940
cgcgacttcc cggggcgtct ttcaaggctc cgtttgatag gccccaaggg aggccagggc    3000
aggaggctgg aggctcgtag gcctccggga ccctggattt cgttagctct tagtcccgt    3060 gtggattcta aaccctacag ccctgtccgc ctgaccctga agcttctggt tctagactct    3120
tgctcggttc ggctttctgg cctccctggc gccttcccgc caagctcctc ctcctgcttg    3180
cctccccagc ctccacttag tccccttcct taggtctcgc cctcgcctca ctctaactcc    3240
agccttgtcc taagactctc aatttccagc cctgcttcct cctcccgcg cgctgctccc    3300 caagcgtctt cacattgtct ctgttcttgc ctcccagggg cttgtcccca ccttcagccc    3360
ctctccctct ctaccctatt tccttttcgc ctcacaactg cagcctttaa cgtttcctcc    3420
tctggtctga gcctgagacg cccgagtttt cctctttagc tcccgtgccc cattccagcc    3480
ccaccacaaa tcccgtgccc actctttcca ctggcccagg cccagctcac tacctttctt    3540
agagcccctt tccgactacg ctcccttctg tcccttctca tctcctcccc caactcctca    3600
ttctgttcct gtccccagaa accatcccga agtatctccc ttccctcctg tggcttctcc    3660
ctattctcag ccctctccca ccctagccct ctcgctatca ccagccatta gcgcacctt    3720 ccttctcaga tccgtccata catccctccc tctccatctc tggctcgaca cccgggctca    3780
ctattagttc ccctacatcc accccgcagc ctgctcttaa cctctcctcc ccggcggctc    3840
agacccaatt ctcagtgtcc ttagcgcccc cttcgggcca cagcgttaag ccacgccccc    3900
cgggcccctc atccgttgcc aagttcgctg agcgtccgcg tctggttgcc tctccgcccc    3960
acagggcatg ttcgtgctgg gcctacccta cgccatcctg cacggcggct acctgggggtt    4020 gtttctcatc atcttcgccg ccgttgtgtg ctgctacacc ggcaagatcc tcatcgcgtg    4080
cctgtacgag gagaatgaag acggcgaggt ggtgcgcgtg cgggactcgt acgtggccat    4140
agccaacgcc tgctgcgccc cgcgcttccc aacgctgggc ggccgagtgg tgaacgtagc    4200
gcagatcatc gagctggtga tgacgtgcat cctgtacgtg gtggtgagtg caacctcat    4260 gtacaacagc ttcccggggc tgcccgtgtc gcagaagtcc tggtccatta tcgccacggc    4320
cgtgctgctg ccttgcgcct tccttaagaa cctcaaggcc gtgtccaagt tcagtctgct    4380
gtgcactctg gcccacttcg tcatcaatat cctggtcata gcctactgtc tatcgcgggc    4440
gcgcgactgg gcctgggaga aggtcaagtt ctacatcgac gtcaagaagt tccccatctc    4500
cattggcatc atcgtgttca gctacacgtc tcagatcttc ctgccttcgc tggagggcaa    4560
```

| | |
|---|---:|
| tatgcagcag cccagcgagt tccactgcat gatgaactgg acgcacatcg cagcctgcgt | 4620 |
| gctcaagggc ctcttcgcgc tcgtcgccta cctcacctgg gccgacgaga ccaaggaggt | 4680 |
| catcacggat aacctgcccg gctccatccg cgccgtggtc aacatctttc tggtggccaa | 4740 |
| ggcgctgttg tcctatcctc tgccattctt tgccgctgtc gaggtgctgg agaagtcgct | 4800 |
| cttccaggaa ggcagccgcg ccttttccc ggcctgctac agcggcgacg ggcgcctgaa | 4860 |
| gtcctggggg ctgacgctgc gctgcgcgct cgtcgtcttc acgctgctca tggccattta | 4920 |
| tgtgccgcac ttcgcgctgc tcatgggcct caccggcagc ctcacgggcg ccggcctctg | 4980 |
| tttcttgctg cccagcctct ttcacctgcg cctgctctgg cgcaagctgc tgtggcacca | 5040 |
| agtcttcttc gacgtcgcca tcttcgtcat cggcggcatc tgcagcgtgt ccggcttcgt | 5100 |
| gcactccctc gagggcctca tcgaagccta ccgaaccaac gcggaggact agggcgcaag | 5160 |
| ggcgagcccc cgccgcgctt ctgcgctctc tcccttctcc cctcaccccg cccccaccag | 5220 |
| cccagtgcgc cctgccgccg cg | 5242 |

<210> SEQ ID NO 300
<211> LENGTH: 3437
<212> TYPE: DNA
<213> ORGANISM: Homo sapiens

<400> SEQUENCE: 300

| | |
|---|---:|
| cgctggtgga gcccgcctcc ctgaagccgg agttggcgag tttctcgcac ttgaccttgt | 60 |
| aggcgtctct ctcgcgggcc agccgggaca cctcctgctt aagctgctcc acctgctgaa | 120 |
| tgagctgcgt cttctcattc tccaggtggt gcttctgctg gacgcgttta tacctgcaag | 180 |
| actgggcgta gccccggttc ttcagggtcc gccgcttctg cttcaggcgg atcacctcgt | 240 |
| ccttggtgaa gccccgcagg tggcggttca gctcgcgcac ggacatggac acgagctggt | 300 |
| cgtcggagaa gcgtcctcc acgctgccgt tgccgcccgc cgccgtcgcc gaggccgtcg | 360 |
| cgtgcggccc gggcccgggg tggctagtgg gcagctgttg cgccgggcta gcggcgctgg | 420 |
| acggcggcgg cgacgcttgg tgatgatggt gatggtgcgg gtgagcgtgc gggcccagct | 480 |
| cgtcgtgggc cacgccggcg cccgggtacg cgtggtgcgg gtgagggtgg tggtgatggt | 540 |
| ggtggtggtg agcgccgcga aagctgtcga agctttgcag cggctgtggc actgggtgcg | 600 |
| agccgatgag cgcttccacc gcgtcctcgg gcgtcaggtt gagcgcctcg gggttcatct | 660 |
| gctggtagtt gctcgccatc cagtacagat cctcgaggtg tgtcttctgt tcggtcgggc | 720 |
| tgaagctggg cgacgagggc acggagctac acggagtgct gagcggtgtg gaggacaccg | 780 |
| agccggctgg ctgcaggcgt gtgcagggcc tgcccggacg ctccgcgcgc cccagtggct | 840 |
| ccttcttcac gtcgaacttg agcaggtcga agtcgttgac atactccatg gccagcgggc | 900 |
| tggtgggcag ctctggcccc atgctcagct ccgcggccat cgctgaagcg aggcgcagcc | 960 |
| gccgctgccg cccgggaaac tttgcggccg gccgagcgc gccgagccaa gcgcgggggg | 1020 |
| gaagagcgga gaagagctgg ggaggcgggg agcgagggcg cagcgggccg ggccgccgg | 1080 |
| ccaagccttt gtctgggac gcggcggcgc gccggagagt cccgaggctg cctgcaccgc | 1140 |
| cccagagctc tgggctgtgc ccgcgcaggg accgggccgg gtagagtcgg gcggggtgga | 1200 |
| gaggcaagcg gagcgcgcgg tggggctgag gggaggcgtg gggcgagtgc ccgttgctcg | 1260 |
| ctctctagct ctcttgctct tacgctctct cgctcgcagc cgctcgcagc tcggcggtgc | 1320 |
| agctgtgctg gatccggcgg cgccgcagcc ttttatcgcc tcctgatgtc actggggtgc | 1380 |

-continued

```
ggggccccgg gcggcccggt gcgcgggcca atagctgcac ggcctccgcg gcccagcggc      1440
gcagggcggg gcgcgcctga cagctccccc gcccccgcg tcagctgact ggcggcccga       1500 gcggcccgg agcggcggag gcctggcgga gcgctggagc ggagtgggac ggccagcctg       1560
ggcccacccc cgtaccctgc aggtcccggc cacgcacgc tcgcctggag tgcgcgcccc       1620
acctctaggc caaatcaccg ctttcccctc ctcgcgcact ctcctccctc agttcccttt     1680
gcaccccacc cccatcccgt gtcaccccca aggaggctca gaatgagcgc cgggacaacg     1740
cctcctgggc cctttgttcc caagcggccc ccgcccagtg ggcgacgctc tgtgtgtcct     1800
cgcggcttct ggccgtgtgt gtcgtgcgtt cctgtttctg gagatctgcg cgtatttgta     1860
tgttggggag ggcgggctcg aggctccgag agttgtgttc agacccaact cttaacctca    1920 ggggacccttt ctcaggccaa gcagggccc ctcctggcgg gtgcagtcgc agagccctga    1980
ggttcgactc cactggcccc gccgctcccc gcgttcaccc caccgcacaa tgttcacagt    2040
gaaggcgacg ggaaaagcag cagcccaaag gctctgaatt cctcttcccc gccacacgca    2100
cggaatcctg agccccggga gcctcggggc cgaggccggc ccgggacggt gctccgagta    2160
gctctccact gctggggagc cggccctgtt tttgtttgaa cgttttgtaa cgattaagca    2220
gatcccggcg tcagcccgcc gcggagaggc tcaaacagga ataaagtgcg accccaagtg    2280
gccactgtgc gcaaaggcgc gcgaccgcc cggcccacgg ccggaaggct tggacggcgc     2340
ctcgtaccca gccaggtctc ccctacctgg cccaacccaa gccagcccag aacgcatact    2400
atgtgtgcac cagagcccag acaggttcc cctcgagcga tgtacaggtc ctcgggtccc     2460
gtcttcgtac tcaccgcga gcctcgagcc gcgagctccg ctctggtcgc cccgttgaaa    2520
ttccgtgccc cagcgttcgg gggtgcccgt cggctgctcc ctgggccgga aggtcctggg    2580
cggaggaagg ccggtagcca aaagtggaag cgccacagtg aagcggccca gggccaccgg    2640
gtgagaaacc tccccggagg gcagacgggg agaccgaagc acaccgcact aggcatccag    2700
actgggcttg ggagccgcgc accctcccta cccagatcca ggatggctag aattaacggg    2760
ttctttctga gacctcggct caggcgccga aaccggatag atcgcgaatt cgctggaccc    2820
ggagacccga cccgcctccc gcgtcacctt cttctttcta gctttgggcg cgcgcagcga    2880
aaggcaggag aggcgcgcac tgggtgagtg agtcccggcc gctgtctgcg ctggaccagc    2940
ccgactgacc tcgcgcgtag gggtcgcgtg agccacaccg gtgcagacgc gcctagatta    3000 ttttttaaatg ttagaaggta aaatatttgc ctccaattaa tctgaaaact ctctattctc   3060
ttgcgccctc ggagaggctg gggtacgcg tggtattggg ccgcctattt ttaataaaat     3120
gagtgtattt taactaaaac ttaactcaat cttgtggggt ggcaaattaa atgctggaag    3180
agcgcgtcta caaccctctt cgagaagcgt gctctccgca gaaatgagtc ggccgcctgg    3240
agagagagcc tgggcggtgc cgctgcgcag cccctgccag tagctggggg ttggggactc    3300
gcaccttgta aatgtcctcg tcttgtttga acgcagtgag agcacactcg tttccagatc    3360
actcgggacc gggtgtctcg gatctgtgca gactatgtat ggctccggcc tcaggcggcc    3420
agggcgggac aagcacg                                                    3437
```

<210> SEQ ID NO 301
<211> LENGTH: 661
<212> TYPE: DNA
<213> ORGANISM: Homo sapiens

<400> SEQUENCE: 301

```
cgctggcacc accgagcccc gccgcacccc gccgctattc tcaggacgac ctgggcagcc      60
```

```
cccagcttc tagaaaagac acagaggaga ctgcgcaatc aacaggcagg agtgtgcgtg      120
agtgcggcat gacatgggca cgccacccca gagaagtggg cgcctgctgc gctaaacgtc      180
atccgtcatc ctttcgctga aaagttggaa aacaaacaac aaaaacccg cccagcctca       240 tttaatgcga accaaacaca aaagccacag gggaaagctt ttcctctctg tgcttccctt      300
ttccggccga ggaacaccac cagccaagat aaggggactg tgcggggccc tctgcgcggc      360
ttcaaagggc tggcacccgc ccgggcccgc tcccactccc actggctaat gggctccccg      420
ctccagccct tggggagcag gaggcggccg gggctccatg ccaggcgact tggaagaggt      480
ttaaggctca cgccacacaa gggaggaagc tcggcctgtc aagaggcgtg ataaagcagc      540
cccttatcgc agttttcctt tcaactgcct ccaagtgagc gccggccggg gctgggcctg      600
tcaaggccaa gcgtgttcct ttcatgtcgc cctgggttcc tcggtcagcg acgtatccac      660
g                                                                     661

<210> SEQ ID NO 302
<211> LENGTH: 247
<212> TYPE: DNA
<213> ORGANISM: Homo sapiens

<400> SEQUENCE: 302
cgcgggttta agtggacgcc aggtgcaccg gacacaggct gtgtttaacc acaccgagga       60
ctatgtgttg ctgcccgacg agaggacgat cagtctttgc tgctgggact cgaggacagc      120
cgagcggaga aacctgctgt cgttggggca caacaatatt gtacgctgca tagtgcactc      180
ccccaccaac cccgggttca tgacgtgcag cgatgacttc agagcgcggt tttggtaccg      240
gagatcg                                                              247

<210> SEQ ID NO 303
<211> LENGTH: 402
<212> TYPE: DNA
<213> ORGANISM: Homo sapiens

<400> SEQUENCE: 303
cgcacgcgca cgtgtgtgcc tgcatgcact cacatgtgtg tttccaaccg gccgacagtg       60
acgcacgtat gccctcgcca ctcggcaagc acctcgtgct ccttggtaac cagcagatgt      120
ttctctcaat tactgatttt caagagcctg tgtttcctg acatgagcca ggatggcggg       180
cggcgcccag gggaggggaa gtgaaccggg gctccgtttc caaggctctt ggacaaaaag      240
cgaagccctg gatcaggaag cacaatgcgg ctggtattta gccgcttctc aatagtgcct      300
cattcaatcc ccggggcctc attgatgccc gccgcgtgct ggagagcctc tgagggtcag      360
tcggcgacgg gcaccgtctg gaggggtctc gccgctaacc cg                        402

<210> SEQ ID NO 304
<211> LENGTH: 318
<212> TYPE: DNA
<213> ORGANISM: Homo sapiens

<400> SEQUENCE: 304
cgcagcatgg tagcgggagc gcagctgcgc gggcaaccgc cgggtttgtg gccggttggc       60
gggctcagtg ccgcctcagt gggctctagc agtagaaaag taaagcgact accctaagat      120
acccagagcg agaggagagg ggctagaagg gtgctggagg caggctgtag tggggctaaa      180
ggagctgact gaccagcgct gcggccggtg cccgaagcag cgagcagcgc acctcagctc      240
```

```
cggttgccgc gcggcatggt atttatctgt gggttcagtg cgcacagcgt tgtccagtct    300
cgaaaccacc ctaaaccg                                                  318

<210> SEQ ID NO 305
<211> LENGTH: 215
<212> TYPE: DNA
<213> ORGANISM: Homo sapiens

<400> SEQUENCE: 305
cgtgagtgag ggcgtgcacg gtgtggggtc ctgtgagtgc gggtgtgcac ggtgtggggt     60
cgtaagttca ggcgtgcacg gtatgggtt gtgtgagtgc atggcgtggg gtcttgtgag    120
tgcgggcgtg cacggtgtgg ggtcttgagt tcaggcgtgc acggtatggg gtcgtgtgag    180
tgcatggtgt ggggtcgtca gtgcgggcat gcacg                               215

<210> SEQ ID NO 306
<211> LENGTH: 214
<212> TYPE: DNA
<213> ORGANISM: Homo sapiens

<400> SEQUENCE: 306
cgcagggccc acgctcccgg cctctgggac gctcacggca gccccacgag aatgatcaca     60
cgagggccca cgctcccggc ctcggggacg ctcacggcag ccccacaaga acgatcacac    120
gagggcccat gctcccagcc ttggggacgc tcatggcagc cccacgagaa tgatcacacg    180
agggcccacg ctcccggcct cggggacgct cacg                                214

<210> SEQ ID NO 307
<211> LENGTH: 291
<212> TYPE: DNA
<213> ORGANISM: Homo sapiens

<400> SEQUENCE: 307
cgcggcctag agcggtgagt ggggtctcga gcgcatcccg ggtgtttgtg ccgaggctgg     60
tgacgtccga ggtggcctct gagtgtgctg acttgtgacc ctgagctgtt ggggggctcac    120 cggtgactcc atggtcttgt tgagcaccct gcacgtgggg ctcagggtcg gtaaaatagc    180
agtgcgtgga gaccgcgtgc tagaggccgt ggcgcccgcg tacaatgagt cgcagacagc    240
acagacggga gtagggcaga atagacaata tcccgtgaat tgcgtggggc g            291

<210> SEQ ID NO 308
<211> LENGTH: 568
<212> TYPE: DNA
<213> ORGANISM: Homo sapiens

<400> SEQUENCE: 308
cgccagcgca cagcgcggca ggacgcgccc gggtctcagc ggacttgtgc atgttagctg     60
tgtagattta tgtgagggct tgtaaaactc tggtcttgta aactagtctt aagcgctttt    120
aatatggaga cagatgagag cccctctccg ctcccgtgtg ggcccgcagg agaagcggtg    180
atggagagcc gagctcgccc cttccaagcg ctgccccgtg agcagtctcc accacctccc    240
ctgcaaacgt ccagtggtgc agaggtaatg gacgttggct ctggtggtga tggacagtcc    300
gaactccctg ctgaggaccc cttcaacttc tacggagctt ctcttctctc caaggatcc    360 ttctctaagg gccgcctcct catagacccg aactgtagtg ccacagccc gcgcaccgcc    420 cggcacgcac ctgcggtccg gaagttctcc cctgaccta agttgcttaa ggatgtaaag    480
attagcgtga gctttaccga gagctgcagg agtaaggaca ggaaggtgct gtacacagga    540
```

```
gcagagcgcg acgtgcgggc ggagtgcg                                        568
```

<210> SEQ ID NO 309
<211> LENGTH: 386
<212> TYPE: DNA
<213> ORGANISM: Homo sapiens

<400> SEQUENCE: 309

```
cgtgcggggc tggggcggcg gttacctggg cgtcctggta gccctggagc agcaggaagt     60
aggggcggtt gctggggcc tggatgaggc actgagtcaa ctgatcgaag tccccggggt    120
ctgcagttcc gatttgggcg tcggctgccc ctggggccat gctaagtgcc tgctgtctcc    180
gctcctgctg ccgccgccgc cgcccctgaa ggctaagctc cgacacgctg cgccgcaaag    240
acaagttttc tgagcgctcc ttgcctccag acccagctgg ggccctgat ccggtccccg    300
ggccaggact ggccagcgct gccccacccg acgccgcccg ggagcggttc ttctgtggcc    360
gccacgaagg ggcgccggtg cctgcg                                         386
```

<210> SEQ ID NO 310
<211> LENGTH: 611
<212> TYPE: DNA
<213> ORGANISM: Homo sapiens

<400> SEQUENCE: 310

```
cgaacgttaa gtccgtcccc agcgcttgga atcctacggc ccccacagcc ggatcccctc     60
agccttccag gtcctcaact cccgtggacg ctgaacaatg cctccatgg ggctacaggt    120
aatgggcatc gcgctggccg tcctgggctg gctggccgtc atgctgtgct gcgcgctgcc    180
catgtggcgc gtgacggcct tcatcggcag caacattgtc acctcgcaga ccatctggga    240
gggcctatgg atgaactgcg tggtgcagag caccggccag atgcagtgca aggtgtacga    300
ctcgctgctg gcactgccgc aggacctgca ggcggcccgc gccctcgtca tcatcagcat    360
catcgtggct gctctgggcg tgctgctgtc cgtggtgggg ggcaagtgta ccaactgcct    420
ggaggatgaa agcgccaagg ccaagaccat gatcgtggcg ggcgtggtgt tcctgttggc    480
cggccttatg gtgatagtgc cggtgtcctg gacggcccac aacatcatcc aagacttcta    540
caatccgctg gtggcctccg ggcagaagcg ggagatgggt gcctcgctct acgtcggctg    600
ggccgcctcc g                                                         611
```

<210> SEQ ID NO 311
<211> LENGTH: 5799
<212> TYPE: DNA
<213> ORGANISM: Homo sapiens

<400> SEQUENCE: 311

```
cgccaacgtc ttgtcgtcgt ccgcgctgtc caccagggcc ttgtcagcgg gcatgtacca     60
ggcagcgctg tgctctgcca tcagcgagtc caggtcaatg gtgctcatgg cgctcttgac    120
cgcctcggag cagcagctgc ccagctcgct gtcgccattc tgcgcccctg aggccccgac    180
ggcgcactca cccttcttgc caccccttcag ccccagaggc tggtcctcgg agatgctgaa    240
ctgctgcctc tgtagctgga tctgcgcctg aaggatctcc aggggtgga tctcgtcggg    300
tggcggggcg ccgctgctgc tcgtcggggt gcggacctgc tccaggcccg gagtgcccgg    360
atggcccggg cccccaccgc cgccgtagct gtcagggtc gaggtagagt tagacatgat    420
gcccaggccg agggcgggcg ggggcgcctt cggtccgtgt tccccggcgc ctaccccacg    480
```

-continued

```
gggagggagt ttgggcgagc cggtcaccag gggactcctg ctcgctttaa ctagtgcctg    540
ggggttgtca gagctggacg acacctcgtc ctcattggcg tagctcgtgc tcacctcgtc    600
cgaggcgaac tcacccacgt ttggcgaact actgtccgac ttggccccgc cgtccaggga    660
cccaatgagg tccggctgat cccccaggag caactcagcc cccttccccc aggatggcga    720
cgtgagcgcc ttttcgtggg gcgtcggtgc cccgcgcgtc tcgcctgcgg agcttccccc    780
gacggctgcg cctgacgctt gctgctgccc tgggctcacc ccaggtgcgc cccgctgtc     840
cggagccgcc gagtacttgt caaagaaggt gccagggctc acgtgaccac tgtcccttt     900
tctgcgaccc cgtccccggc cgccgccccc ggagaccggc ttgccgtcat tcccgacgt     960
ggattccagg gtgtagttgg gggagaggct ggtgccgtcc ccctgggctg gagggttggg   1020
cggcccgag gctttggagc cgctgctact ggtcccggac gggcctccgg gtcctggggc    1080
cccaggagca gtccctcctg ggaagtaatc cgagcccggg ttgccggcca ctgccgcgcc   1140
gtcggtctcg ttctggctca gtttcctctt gccctctggc gggttcttct tgttgaaggt   1200
cacgttgagg ttggggggccc cgaggctggc gatcatgttc tggcaagcgg tggagagcgc  1260
agccaggcag ctctggccga acaggttgtc cttggagctg gcttgttga aggagcccag    1320
cgagagcgcg cccaatttac tggccgaggt gcgctggctg gctggaaat caggctgcgg    1380
cgggtaggca cccccgccac cgccgccacc agagctgcca ccgcccctc ccgcgctggg    1440
gggcgagttc acgcctggac cgctgtgcgg cgtggactgc cggccggctg caccaaacgg   1500
aaagcccggc tggcccccga cgcagacgt agcaaagtcc ggcggcgggg gccggcgctc    1560
cgaagcagcg ctggggagcc ccacgcccgc cccgggcgac tgcagctgac ccaggcctcc   1620
cagactgccc ccgaactgca ggcccggtga aggcagcgcg ggcacgtggc cctctccggg   1680
catcctcatc ggctcctgca gagggccccg gaacagcacc cccgagccac caggcggagg   1740
agggggcgcc aggctggggt cgtgcgggcc acagtcagcg ggcagacccg agccgcccat   1800
cctacgggc agcaggtctc cgggcggcgg atgcggacct gagaaccacg cgctctcttg    1860
cgccaagtgc ggcgcctgct gctcgaaggt gcccagacgc ccggcgcccg tgctgccgcc   1920
ttcgcgctca aagttcggct gggccaagcc gcccaccggg ccgccatgca ccaggccgcc   1980
ctggcccacg tccccggggt ggcctagctg agccaggttg ggctggcgca ccgctgctg    2040
ctgattccgc gacgccatct gcttaatcat gagggccgcg ttttggcgct gctgctgctg   2100
ctgctgttgc tgttgctgtt gctgctgctg ctgctgctgt tgctgctgct gctgctgctg   2160
ctgctgctgt tgcagggact ggtggtccgg ggcggatgc tgcaggggcg gccccgaagg    2220
gaagctgtcg ggcacaggcg gtgtgaactc gccgggtagg cctgggtagg cggaagggga   2280
gaggtgatta tccagagcgc cgttgtgcat gctgccgttc cacgaagcgc agcggtccac   2340
tcccgcgctg cccggaaagt cgaagcgcgg cctcttggcc acgttcatgt aggggggcgc   2400
gtcgaaatgc tgcagccgct ggttgggcgc ctgctgcgga ggaggatgct gcatgctgaa   2460
aacaggctcg gaataagggt gcatgctccg gttctccagc cggtggatgg gatactcgaa   2520
ttgcgcgtgc tggctgggca gcatggggcc tccgtcctgc aggccgccgc tgggcgtgcc   2580
cgcctcgccc tgctggggcc gagggagcgc aggcgggcac gaattttgtc ggactagaag   2640
cccgggtggc ggcggcggct gctgctgtgg cggctgctgc ggggctgct gctgagggg     2700
tggcgggggcc tgctggggag gctgcattaa cgggtgcctg gagcccactg agggctccag   2760
acccacaggc atctttctgg ccccactgaa cctctcaaag aacacaccat gctgctgctg   2820
ctgctgctgg ggctgctgct gctgctgggg ctgctgctgc ggtggctggg cgtgcatttt   2880
```

```
ggacaagccc accatgcccg cagctctggg catggccgag gcgcccggga aagcgccccc    2940
aggaacctgg cgacccgctg cataatgagg cagctgccct tcggagtcag agggcgaaaa    3000
catgtcaaaa tgtcccgagg gcgcctcgcc cgggtaattg tattccagcg agtcgacggc    3060
tccttggttc gtcaccctcc gtggctccag actgtgggaa tcggagccgc tggaggacgg    3120
caggccgtgg aaggaggcgg ctcggttagg gctctggtcc agcggcaggc atggggccgg    3180
cacggcgtgg ctggaggcac ctgaactgtg gaagtccggg aggttccccg gtcgctgcgg    3240
gccgaagctc tcaggcccct ggctctccgc catgtgctca tagccctcgg cgaagggcgg    3300
ctggctgccc aggcctccgg ctgcgccgcc gtagccgagc aggcgacccc cgtgcaggca    3360
cgaggccccg ggtccgggc accgaagtt gccccaaag tggggtgat gctggtgggg        3420
atgatgactt cccgggtggc cgtggtgagg ctgctggccg ccaaagaagc cgtgcacagg    3480
ctgcgcttgc agccccctg cgtgcaactc cgagtggccg cgcgcgtgga agccgtaggg     3540
ctccatgttc atgcccaaga tcggggttc gcccagcgcg ctcatagcag atccacagg      3600
gccaggggc ccccagtgt ggaaagccgg ggccttaaag tgggtgttca tgctcagtcc      3660
ggtctcgtta aagttcctct cgccctggcc agcgttcctg ctgttgacct ggggctcgaa    3720
ttggtccagc ccaaacatac ttggcggggg gcagaggggg atcaataggg catgacagcc    3780
ggctctccgc ggcgcgcctc cggccagcta ctcgttccag cccaggattg ggcgctccgg    3840
gacgctcagc accgcggggg ctcagcgcgc acctccaccc cgcctgatgt gagggacggg    3900
gggcggggta ttagctcctc tcctgaagct ccgattctgc ccggggaggg cctctcacat    3960
cttgcgaggc cgcggggcct ctaggagccg tgttgggggg cccatgcccc gggcggttgt    4020
cacagccgcg ggtgggtctg cggggagggg acgaagccgc ggatgaacgg agacaaaaag    4080
ttaagtgggg ggaatgggga gggaaggggg ttgggagagc agagcgatca ccttctcaag    4140
tccgattggg tctgctgggg agccctcagg acgccgcccg cagcctcccg gagtccgtgg    4200
cagagctgct aagggcaggg gagggagacc cttcaaagcc gcggctggcg ccgggcaccg    4260
acagagcggt ccctccccc gccccccgga gtccccgcgc cccgcagccc gagcctccac     4320
cgagcacgat ccgctcgcac aatccccgta ggctccgggc gagcggctgc tgcttcttca    4380
gcgggtcgga ggactggagg ctccgctcgg catcgccggt gccggccccc gagccgagga    4440
cgcagagggg ctgcgaggcg gcaggcgccg ggggctggag ccgagggtcg gggaaaggcg    4500
cggctcctct gctcggcagc gggtgcgctg cgttcggcgc gcagcttcgc ggccacgtcc    4560
gccgcctgcc gcttctgttc tccgccgttg ggtgtctgag ttcgccggag tctccgcgca    4620
ccgttgcagg cgcgggaggg cagcgagacg aggggttggg tcgctccaag gctccggttc    4680
cctgcctccg cgctgaggtg cttcgcgagt ccctctcgga cctgagggag ggggcgtac    4740
gcgggtcggg gggccacgcc gggcgagcag gctaaggcgt tcccgctgcg ctctcagagc    4800
ccggaatggg gggagggggg cgcggggggca gctctggggg gtctgcgcac ccctctcccg    4860
actagcgggg gggctctgcg tggggcgttc cgagggtctc ggctcccctc tctgtgtctg    4920
cctctcgccc agcgccggga gaagcagcaa caagttttgc atttcagcaa tcaatttcag    4980
ccattacatt tgcaccaatc agcgccgccc aagttccggg ctcggggcgg ggctcgctct    5040
taaggtggtc cggggtcctg gctgccgaag cccccgccac gaacccgcac taccccagct    5100
ctggggtccc ctgcgcccgc ctctcctcgg ggtccggcgt cagtgcgctg ggggcgcgcc    5160
ccggcctccg ggcgcatcga gctggagagg gtgcaggcgg aggagaatgg cgggagcttg    5220
```

```
gctttgttca ccccttccc attcacactg ttcccaactc cccaccccca actggagcga      5280
gacccaccgg gtgggcaggg ggcggggagg tgggcggtga gcggtacggg gcgctcagac      5340
aatgaggtcg ccaggcaaag accctagact cgccacggaa agtcgctaag tgtctactgc      5400
acttcggctc cggggtgaac actccgttct ccgctagcgg cgcccaagtt agccggccct      5460
gggatttct tggagggtaa agcagacggg gaacctcgaa gttagggttc tcctcgagag       5520
acctgggcgc ttgctcactc ctccgtcact agggcgttca caattgttcc ccttccccac      5580
tgcctgggggt tcccggttct caccggccgg cgtgggctcc aaggagtcac agtcactcag    5640
ccactttatg ggggagcaca tcggttgagc ccagtaaccg gagcgacttg cgaggcggct      5700
gggaaccccg agaagacacg cacgaagagg gcgcacccgc cgggccgcac accttgccct     5760
gggccacccg gtccaagacc cagaccctct gcgggtgcg                            5799
```

```
<210> SEQ ID NO 312
<211> LENGTH: 327
<212> TYPE: DNA
<213> ORGANISM: Homo sapiens

<400> SEQUENCE: 312
cgcctaccac gtggccgaga ttcccgaggc tgcagccaat gagcagcata gtccgatggg        60
ggaggctgga agggccgttc acgagatctc tcgggaggaa tcggtaggag ctgcccaact      120
gaaagggacg ggggaataac ccggggcgag ggacctgccc aggccctgcc ctctgggggg     180
aagccaggcc aggggccggg ggcatctctg gggtcccagg tgagatgcgg gtcgagggag     240
ccaggccacg gttctccaga ctcgcgtgga ggccacgagc gtcttctgga ggagcgggca     300
ctgcgcggac cggcagactc tggggcg                                        327
```

```
<210> SEQ ID NO 313
<211> LENGTH: 1949
<212> TYPE: DNA
<213> ORGANISM: Homo sapiens

<400> SEQUENCE: 313
cgtcctaacg tactgtcgtt cctgaatctc gcaggcaccg acactgccct ggacactgtg        60
aggggggtgct ccgtggggggg atggatgacc ggcagggcgg actggagggc gggacgggga     120
gggctcggtc ccccgcgggg tgtagccaac agcctccccc cgcagctctt cgcagcggta     180
tcccgaggct gctgcaccag ccttacccac ctcgacgctt cgaggaacgt cttctcccgc      240
acgtaagggg gacctgtcgg ggccggggga ggctgctgga agccgcctcc ttgcggcccc     300
aggcccacct tcccacttcc cccaggaagt cccgcgccgc gccggccgcg ctgcagctct      360
tcctcagccg cgcgcggacg ctgcggcacc tgggcctggc gggctgcaag ctgccgcccg     420
acgcgctcag gtcagtgtcg gaccccggcc acgccccgc gggcgctccc accctgccct      480
ggccttcgcc cctccccgct cctgcttctg tcgctcccac aacctccccc agatcctggc     540
cctgcctcct tcgttcgcac cctggagccc cctgtcccag ctcccgccac ccgtgtaac      600
gtcctctccc agagcccttt tggatggcct cgcgctcaac acgcacctcc gcgacctgca    660
cctggacctc agcgcttgcg aggtgagcgc cggccccag aagagaccac acattgggag     720
aggcgctggg aggcggaagg gcagggccgt gggccgcctg cccctcccca ctcgcggcct     780
aagtgggtcc cacttcccac ctcccaccct ccacatacag ctgcgctcgg ccggcgccca     840
ggtgatacaa gacttagtgt gcgacgcagg cgctgtgagc tccctggatc tggcggataa     900
cggtgaggct gcaggagagc ccatcctcgc atcatccact cgattcccaa tccccaccct    960
```

```
accccttgcaa cttcgcctcg tgcgtgaccc gagtcacccc caggcttcgg ctcagacatg   1020
gtgactctgg tgctggccat cgggagaagc cggtccctga cacatgtggc gcttggaagg   1080
aacttcaacg tccggtgcaa gtgagccccc accctactcc tgggcctccc agacaacacc   1140
ccaccacccc tgtcccccac aactgcggcc cctgcccaca gggagaccct ggacgacgtc   1200
ctgcaccgga ttgtccagct catgcaggac gacgattgtg tgagttcacg ggaccttgca   1260
gggcctcggc aattagacc actttggtcc tcctttctct tgttccctca gaccctgtga   1320
cctgccctca ctgaccctg actccagcca tcaatggctt tctcttaacc ccagcctctt   1380
cagtctctgt cggtggctga gtctcggctg aagctgggtg ccagcgtcct actccgggcc   1440
ctagccacca atcctaacct gaccgcgctg gatatcagcg gcaacgccat ggggacgcg   1500 ggcgccaagt tgctggccaa ggcgctgcgg gtcaactcga ggctccggtg gcgggtca   1560 gaggggtggg accagcgggc aggggcgcg gtggagagga gggcaccggg ctaaggggag   1620
ggactgaatg aggcggagca aatggagcag gctgacgagg cgaatggact aggccgaggg   1680
ttgggtgggg cgttgggaag ctccgtcccc gactgaagcc aggcccggcc caggtctgtg   1740
gtctgggacc ggaaccacac atctgctttg ggtctgctgg acgtggcgca ggcgctggag   1800
cagaaccaca gcctgaaggc catgcctctg ccactgaacg acgtggccca ggcgcagcgc   1860
agccgcccgg aactgacagc acgtgcagtc catcaggtgg gcgtccccct cttcccttgc   1920
ccttctctgc acggtaactc cgtccctcg                                      1949

<210> SEQ ID NO 314
<211> LENGTH: 319
<212> TYPE: DNA
<213> ORGANISM: Homo sapiens

<400> SEQUENCE: 314
cggatgccgg cctcctgcct cggccaccgc cctcctcttc aaggatgctg ttttgcctct     60
ggtcgctcta tcttatcttt tttctccgca ctcctggacg tctctcggac ctttcgctct    120
gacagtggct tgagcctcgg ccgccacttc cgccctgct acttcggggc cacgtctcgg    180
tccgacgctg agggtgctg ccaaccgtgt ctttctctgtg aacgtcctca cgatgaacgc    240
ccccgttcca cttcccaccc tggagctgct gcttccgtga ctcacattcc ggccatttcc    300
gtggtgtgag gtacgggcg                                                319

<210> SEQ ID NO 315
<211> LENGTH: 776
<212> TYPE: DNA
<213> ORGANISM: Homo sapiens

<400> SEQUENCE: 315
cgttacattg cgattcattc aggaacccac gagacctctc ccgcagcgtc cccgctgctc     60
accgggctgc agacgagtgc gtcgcggtac ccccgaagga gcaggcctg ggctttgagg    120 aagagacggg acacccttc cccgggggcc agggcgacct tcctgagccg agcctcagc     180 agggacacct gaagcacaag ggagtggccc tgagtgggca ggtgtgggcc cctcgcctcc    240
cggggcagga aggtgggagg ggcgacactg accacgtctg gaggcagcgc ctgcacgtcg    300
ttaaaggtcg tctccaaggt attggcgtcc acgttcagca ccacgacgtc ctccagggct    360
ttttctcgta ctctctgcgg aaaagcgggg tcggccgctc agagcccggg agtccttggc    420
agaggagggc atctggggat gtagaggaag ggggaaccct cacgtccccg tcgtctgggt    480
```

```
agatccacgc tcacctcggc gagactggcg tgcactccaa tgaggtaggg catgggcgcg      540
ctgcggaccg aggggacggg gtcatgcagg caccgccccc agggcctgcc cacaggccct      600
gcccctccca gctgccctcg ctcaccagca gtagtccagc aggtgtgggg gcagcgtggg      660
gatcagcacg tgctcccagc gcatggggta caggagcgcg caggacgcgt ggacgcacga      720
ggtcagctgg ggagcgatgg cggggcgtgg agtcagggcc tggaccctct agcgcg          776

<210> SEQ ID NO 316
<211> LENGTH: 288
<212> TYPE: DNA
<213> ORGANISM: Homo sapiens

<400> SEQUENCE: 316
cgtgaaatcg ccgttcgtgg gcccacggct gcaccccgag atagaagcgg aataaaggga      60
cgacgttacc ttcaccagcc tgagtctctt gggccgcgcc cgcctgcccc gactccaagc     120
cctacaggaa ccggtttccc tggttaggag gtatccaccc ggctcaacca gggtctcgac     180
ttccttggaa aagaccaagg cagccgtacg ctgctggaac gccggagtgc aaaggctttt     240
agggctacat tgcaaccctc gggctcgatt tcgccctttg ggctgtcg                  288

<210> SEQ ID NO 317
<211> LENGTH: 482
<212> TYPE: DNA
<213> ORGANISM: Homo sapiens

<400> SEQUENCE: 317
cgttgccgcc ttttcgtac tgagcgcgca gggcactacg cccaccactc cccttgaccc       60
actcctcaag ccctgatacc ggggcgaggc cccttccttt tctagtcctt ctacgcgcca     120
ggtgggtggg tttcgcggtg acgaggcgac acctcttttcc cctctggcga gcacgttaac   180
tggggaagct accaaattct cacgccttag ctgccctgcc tccacctccc gcaagtccgg     240
ttgcccctct aggcttctgc gcctgcagtg gttccgaccc tcgcctttag aactctgccg     300
cttccgcctc ttatttcgcg cctttgtttt tagttttgga aggggcggag ttgaaatggc     360
tgcgccgcgg ttgccgaagc aacgctttgg ttacttccgt tggtttcaat gcttccgggt    420
tggcgctgca gtggcgtttc cgactgtggg agcctcagct tcccagtcgt ccgatgagcc    480
cg                                                                    482

<210> SEQ ID NO 318
<211> LENGTH: 3343
<212> TYPE: DNA
<213> ORGANISM: Homo sapiens

<400> SEQUENCE: 318
cgaggcccag gcgagtggcc aagacgcggc aggacaggag gatgcgcctg gctgctctcg      60
gctgctggac gcggcctgca gtagggagag cgcagcccgg ggtaatccca ctcagggctc     120
cgggtgccca gttctcccac ttcccatcct ggcggcctaa aggcaaggcc tagaccctgg     180
agaggccaaa gtcgggccaa acaacagcg aagctgggac tggaacaggc gctggggcc       240 tgcgcatgac cccaggctca gaatgcgaca ctccagtgac gccggggaat gagttgagat     300
ggagccggag acagaggttg gggttcagga cgaggcgctt gggtatggga tcggatctga     360
gacggttgcg gcgctggtgc tttgggctgg accagactcg aacccagagc ggagcgaggg     420
tcagagccag ggcaagagtc cgaagcccag ctcagcgtcc agcccgcgag agaccccacc     480
atgaatgacg tccgagtagg gttggaactc gaagcccgaa cgcactggaa atgcagccgg     540
```

-continued

```
acgacggctg ggatccgagt gggtccgggc cagaaatggg gacctcagag ctccaccgag    600
gcgctcgagg tcagaactga agcctgagac ttaggcagga cccagacag agccagagac     660 gataccgaaa cccaatggac cgcgaggacc gaaggcagat ccggggcgca aacctgtgca    720
ggcactggcg cgctgcctgg agctctgggt tcgcgccgct gagcgccggc aggttggacc    780
agcgctgcgc gccggaagtg cactcggac gccggggttc tggaggagag accacacgcc     840 gcaaagtgg cctccgaatg cgcccggggc ctgccctcgg cgacactgct ggctcggcgg     900
ccgcagccta cctgaagtag tccatcttgc agaagatctc cttgttcttg atgtagcagc    960
tgttctgctg cctcagcgac gtgcgacaca cggagcactc gaggcaccgc acgtgccaga   1020
tgaggttgtt gacctgggga cggggcgggg acggaggtcg gctcagcgcg ggcctctttc   1080
actccgggcc ccagccttcc cggtctcatt tacagtcaga ggcgctgaag ctcagaaggt   1140
gcatgcgatt cccctatttt tctcccgtaa tactgagact cagggaaatg gaaataaact   1200
cttcttattt ttcagacgga acccgggggc tcaggcagac cctaagtctt gcccaaagct   1260
tcgcagtcgg gcagcagtgg agccaggatt tggaagtaag aggacctgcg gtgcttccct   1320
gcagtctcct gcgctgcgtc ccacgcccg acaacacgca cgcaacacct accctgtct    1380 caccttgagc agatatcggt ccaggatctc gaggccgcag ctggagcaga tgttcttgcc   1440
tgcagacggc acgaggagg cggcagaggg cggtgagcag acagatggcg tgctgggcgt    1500
acatggggag gcctgaccct cgtccttgtc cagagctcct gccagggcct cggcgtcaga   1560
ctgagcctgc ggcgggggag agaaggagag gagcgctgat ccgggcaccc agagttgggg   1620
ctgccttgga gacaaatctg ggcccccga gcaccaattg acaacgaaat ctccccagga    1680
caatgcgccg tagactgaag gacagggatg gaagggccta ttggagagga agggacggcc   1740 ccaacttta acacgcgcat tctgggtgct gggagcggtt aaagccaaca ttccctgccg    1800
gaaaaccgag gctcagagag gggcggcgcc cgcggggagt ccccagagc gtgagcagca    1860 gttcgtggcc ggaaaacctg gccaggtccc cagggccggg ccgctggagg actgggcacc   1920
gcaggcaggg ccaaacggac tcaccatggc gggcggcgcg gtcccttcaa gacagcgggt   1980
ggtcgctttg cagccggacc ctggctggc catcacctgg gggagggggg gagggaacgc    2040
aggcggcggc ggctgctgaa ctggctccgc acagcctgag cccagcgcct ccccgcgcct   2100
gttatataaa ccggcgccga acaatgagtc ctaactttgt agtgggcatt taaagcccttt   2160 ccccacaaaa gcggtgtctc tctaatgaag caatttgaat ttggattgga ttttttccct   2220
ctctctcccc ctctccctgc acttaacccg tggctcttga agtaatcgct tagttccctt   2280
gcaatccaag cctctgaggg gggaagaaaa acacgcgcac acacacacaa actacctgca   2340
attagaaatt gtcgtgaatg cccaagataa gaggtagcca gagtgtcaat tccaactgtc   2400
aatcagtgag atccatcagg ccgcccaaag aattgcaaat ttgattttt aatggtagta    2460 attaaaaatc gaattttttc tctctccacc cgcccccca ccccactccc cttcctcgct    2520
cccttctcct ctcggcacaa aatgcaaaaa ggagaaaaga gagaaagaaa gaaaataaaa   2580
aagagatggg tgaggggcgg agggtggttg aagaaaagaa accccgagc gcggtgagca    2640 cccgcccgcc cgcccgcctg acacgcgcgg cgaaattgaa gcagctatat tgacacggat   2700
tcaggcgcct ttcgagggcc agtcggaggg aaacccggag caaaagaga gcgagatcgg    2760 ggcgaaacgg gaccaaaaag agaaagaga ggcgctcaag gggaggaaaa agcaccctcc    2820
agcccctcgg cgcgccgggt accggccccg cgtcgggatt ctcagcgctg cgccggcaca   2880
```

```
accccccggcg catcggcgct atcagcgcct attcagacgg acaataccgg cctcgcctcc    2940
tcttgattcg cctgtgtctt tactaaatcg cttttgaga aattcctcca acatttgcat      3000
aatgtgttcc cgctttccgc gaccccccc ccccgctcgc gcgcgcgctc ccacactcac      3060
aagcacacac tcacaggcgc accctcgtac ccctccttcc tgcaaccgcc cgccaccctg    3120
ctcggcccgg ctgggtcccg gaccctgccc gaccccggcc cgggccgctc acccagtcgt    3180
tcgccggctc acctggtcgg tggcggggcc ccctcggcc ggcagccggc agccctcggg     3240
caacgccggg gcggcgttct catgcttcca gtacatgggc cggggaaccct cgggctcagc   3300 gggcgcgcag cgcggagagc tgcgccgagg gggaccacag ccg                      3343
```

<210> SEQ ID NO 319
<211> LENGTH: 2956
<212> TYPE: DNA
<213> ORGANISM: Homo sapiens

<400> SEQUENCE: 319

```
cgcctctttc gcacaggtgc ccgactcgga gtccgggagg cgggccctct ttccaggtac     60
ccagcccagc gtcagcctgg gtccatcctc cgccacccca cagcgcgggg agcaggggag   120
gccgaaagcc gggcagcttg gggggccggg ataacccggg ctgcagcaac cccgggcggc   180
agcaggactg gagagctggt gtcggacgca ctgcagagac gtccctgttt cggcgcgtc    240 ctccgacacc cagcagagag cttggcgctc tccgctctgc gcgcccgagg tcacagcgcg   300
gagaaacctg gcggggcccc ggactccccg gcttgggaaa agcgatgact gccctgaact   360
gctggggcgt tcgaaatttc cagggtcccg accctccgtg gggtacgcgc gacttcggcg   420
cagatgtcag tccgctgcct tccgggttga gggagcgagg actccagacg accccagggc   480
cgctgtccag gccagcccc gcgttctcca cctcgccacc tcgctctgcg gctccagcct    540
ggagatctac ggacttcatt gcgatctctt gcgcagtgta gtcgccctct atccctagcc   600
ccgagtcccg ggtaacccag gggccccggc gaggcgagtt tctttgggc gagatgtccc    660 gagccgagca aggggccgc gcattggacg gggctcccaa gccacagccc tgggggcctt    720
gaggagtcgt ggtacggtcc agggcagtcg ggctgcggg gcccgtgaag ccagacgagg    780
ctacggactt agggtccctg caaccaagac cgcgagcgac tgtggactcg gacggatcg    840 cacaaaggag gaaggggaa tcagagggg gtccggtcca ggacgtgtca ggcctgggcg     900
gggcggaaaa ctgacaccag ggcgaggaca aggatttcgc tcctccaggg ctgccagggg   960 agggggctcgc caccgtcact ctccatgggc tctggccccg acggtgttta aagggcggag 1020
ggctgggccg ggctggtcgc accccggcgc tgctggcggc caagctggat gggtcgccag   1080
tgagtttcgg tgcggcaccg ctggcccagg cccgggcgcg gctggacatg gccacctact 1140
gcgacgacct gggcccctcc tcggccccgc ccggccaggc ccaggccacc gcgcacccc    1200 cgggctatga gccaggggat ctgggcgcgg tgggcggggg cccctcctg tgggtgaacg    1260 cgccagcgct cagccccaag tcctacgctt cgggtcccgg gcctgcgccg ccctacgcgg   1320
ccccgagcta cggggctccc ggccgctcc tcgcgcccc gggcggcctg gcgggcgccg   1380
acctcgcctg gctgagcctc tccggccagc aggagctgct gaggctggtg cggccgccct   1440
actcctactc ggcgctcatc gccatggcca tccagagcgc gccgctgcgg aagctgacgc   1500
tcagccagat ctaccagtac gtggctggta acttcccttt ctacaagcgc agcaaggcgg   1560
gctggcagaa ctccatccgc cacaacctgt cgctcaacga ctgcttcaag aaggtgcccc   1620
gcgacgagga cgacccaggt aacagcggcg cgccggctcg ctccgtccag gactccccat   1680
```

```
cttcccgccg ggccgcgggc actccggggg tgggagcacc ttagacaacc taatttctcc    1740
ctgcgcggtt ggggataccc ggggaggagg gagaaggggga agaagtgctt gggcatggac    1800
aggttctcag acagcggctg agcccaccac aggcccgcgt ttacagtgcg gcggtcccgg    1860
ggctctcaat ctctgtgcgc tccttcggag aagaagcgg gagagccagc aagctgggtg      1920
accttgggag tgactcaact tccctgggcc tcagtgccct acctggtaaa atggggaaga    1980
cagcgcctac cccaaggatg ggcaaaacaa ataggatgcc cgtttggaaa gctctggagc    2040
ctacctgggg gcctggcgtg gtctgcgctg tccttggcag agcggctggc ggagtcccac    2100
cattagcatc tcgcaggcct tccttcacct taacgggggc cggccttttcc cagggctccc    2160
ttcctcctcc tttctggatt gtcactttct cccagtcct gctgtggagg cccatcgggt     2220
acagagtgcc cgtcaagggt ggaatggggg cgaggactca gaccctctgt aagggccagc    2280
agggatcttt tctgaagctg acctcctcgc tggctcacac cacggcccgt caaagctcga    2340
accttctgaa ctgggctgtt tcttcttctg caggtaaagg caattactgg accctggacc    2400
ccaactgcga gaagatgttt gacaacggga acttccgaag gaagaggaag aggagagctg    2460
aagccagcgc ggccgtgcgc tcgggagcca ggagcgtggg aggggccgag cgccagcgc     2520
tggagccccc gagcgcggct tgcctggacc tgcaggcctc gccctctcca tccgcacccg    2580
aggccgccac ctgcttctcc ggtttcgctt ctgctatgag cgctctggct ggcggccttg    2640
gcaccttccc cgggggcctg gcgggcgact tttctttcgg gaggcggcca ccgacagtcg    2700
ccacccacgc tccccagacc cttaaccct cccctggctt cgcccctggc caccagaccg     2760
cggccgccgg cttccgcctc agtcacctcc tctacagccg ggaagggacc gaagtttgaa    2820
gggaggctgg aggctagccg ggtgcgggtc cagaggtgct gagctcaggc ctccggtttc    2880
ccctggtgac agccccacgt gttggcgttg aaggccttgg tgccctggga ggaagcgcag    2940
agccgggggc ggctcg                                                   2956
```

<210> SEQ ID NO 320
<211> LENGTH: 791
<212> TYPE: DNA
<213> ORGANISM: Homo sapiens

<400> SEQUENCE: 320

```
cggggtgcgg ggaggttgag agcgcggcgg ccgctgccag caatcgagga gccagcggcg     60
cgtgtgctga gggcccagct agcaaaataa agagggtttt cagcggagcg gcggctcagg    120
cgaggctggg ggagccgggg agcgcgtccc gccattttc cagccgaggt cagcagcggg     180
tgaaggggcg gagtccgtgg tgttcccaac tgcccaggcg ggcggtgaga tggggcaggc    240
ggttccgcaa cgcggctcag gccccagcgc cctgcctgca ggaggccgct tctttctctg    300
ttgccatcgg gcgccggttt cctcttccgg ggatgcaggg cagctggggg ggctctgcct    360
ctgtgcggct cttccgtggt tccacgctgg gctccgggt gaccacagtc ctcagcagcc    420
cacaccctca gcccgaaggg ggcccaggcc ccgtgcccag aggatccaga gagacagccg    480
ggagcccagc agctgtggca gctgccccca ccaccaccc ggggctggcc aggtcccacc     540
tcctgacgcc acacggtatg actgggccct cctggtcagt gcgtcgcatg taacgccttc    600
aactattggg gccggtgttg gagcatccgt ctctgcgtcc ccacctgatg acaagctccg    660
gggagcagga gtgctggcca agcccacgca cggaccaagc ccacgtcaga ctccgccaga    720
aaggcaagaa gggcctccgc atggcgtgac ggatgggttt atgggggcat tccatcccac    780
```

```
ccggacgctc g                                                      791
```

<210> SEQ ID NO 321
<211> LENGTH: 4184
<212> TYPE: DNA
<213> ORGANISM: Homo sapiens

<400> SEQUENCE: 321

```
cggagcttga gcgccagaac cacgcactga ggtcgcccag ggtggggaag tgggggggccg    60
ggggagggc ggggcatccg gcggggaggt ctcccccacc gcatgcaaga ccctttgccc    120
ccccacaaca tacactgagg ctaaaacggg gatgagagtc acacagagca ggagcgaaat   180
ctttcgctct ccgacccgaa cggcgcgttg ctcgaccccc ccttcctgg agccaggggc   240
tggccgagga aggtggctcc gttcttcccc cgtggccagt gcggggtctg cggctgcccg   300
gcgaggttcc ggcttccccg ggactggcag ggggagcccc gagaactgca ggcccgcccc   360
cccttcctcc tcctccttcc cctcctcccc cacgtgtcct ccctgagccc agcagcctga   420
tcccagcacc ccccgccacc tccctcctcc cgcttcgccc gcttcccgg cggcgtggag    480
aagagcaaag ttgcgacagc ggccgggggc tctgcccagg taaagggggc gccgtgaggc   540
gggggtggtg ggggaacggt gcggccctgc ggcgggggcg ggggaggat aaagaaactt    600
gcttcccgcg gccccaccc cgcgtgggtt ccgatcttgc gtggaacgag cccgcgtggc    660
gagtcgcggc aacactgccg ggaccgaggc cggcacctgg acccggaccc ggaccgcgcg   720
cttgggccgg ctcggcgggc gcaggcagcg ggccaggcca gcacccaggc aagggcgggg   780
tgggtggccg tacaccggac cgaatcgggg actccggtgg cgtgggcgcg ggccgaaccc   840
cgaccgggcc gagttgggtg gcgaagtagg acgtggattc ggggcgggg cgcggcggga    900
ggggaaacc aggcctggcc agactggcct gggcgtgggg gcggggggcg agttcggggc    960
acttgctggg ctctggaccg agcggtaggg cggggcggcg ctagggctg gccggaccc    1020
gcagggagag ggcgagggga gggagagccg ggggtggagt agggggcgtgg agttgtgagc   1080
ggggtctggc ctcggccggg ggcgaaggta gatcggcggg gccgcgagcg gagggaggga   1140
ggcccgcggc ggcgcggcgg cagcgaaggc cagcttccgc ggagtttgtg cccgggcttc   1200
ccgggctctg gccgcctcac gcgcacaaat ggggctaggg gactgagtgg taagcaactc   1260
cgagtgttag acggtgatcg ggcggcgatt ccggaaaag cgaggaaaga cacagtctgc   1320
gattgtgccg caccccccac ccacctctta gcatctggat tctgctctcg tagtgggggc   1380
cgcggaccct ccccgccaca gtccttttac tctccagcac tcccaccgcc ttccccttc    1440
ttcagccatc tgactctcct aggggtatgt gttttttggg gtggacggcg acggggtgg    1500
gggatacttt ccttcccgtg gcggcaacct agttcgtatc ttattcctac aaggtagcgt   1560
cgcttcgagt cgcatggaca ttgggtttta gataatttac ccccacccca agcgatttaa   1620
tggcttttaa gcaaaaggcg aatacctgga tttccatggg agggatgagg tttgaagatt   1680
gggattcacc cctagctcac ttccactacc aaccctctt tcttgtgagc cacttccacg   1740
ggtattcaaa tctgggggg agggggacg ggagtattaa tatgcttctc tatttctaca    1800
cagggtcggc gtggcgaagg acggctagcc ttggagggaa agtagccacc agtccaactc   1860
gggtcgcccc caccattatt tcggtgaggg ggcaacgcta agaagggat actggtgggt    1920
aggggcccag tataagggag gggctgggt agtcgtcccc agaaggactc cgtgtcttgg   1980
cggggagaga gagaggcgag ccccggcttc agggagggg ttccggggag ggagatgggg   2040
gggtggcgac gacggtgggg ggggagcgg gaagaagggg gagtcacgcc ctgcctgcaa    2100
```

```
ggggagcctc cctcaggccc ctgggagaag gggactgaat gcgtctgttc tccgctgccc   2160
ggcagaggag atctggggtc tcgagatttg cacactggat cggcaccagt ggcctgagaa   2220
agtcaggtcg gggcataagg tggagaacgt tggaagaaag agagagaacc ctttggccgc   2280
ggctcactga ccctctccct tcctcaacct ccccccttcga ggggcgtcga ggtgggggg   2340
gacgtggggc tcctgcagcc ccgcagattg agcgcctccg cctctcccag gagtctagct   2400
ttttgcccgg cttgctgcag ccactgctgc ctccctctcc ggaatccgct cggtcctctc   2460
agcgatcccc tcctcctctc ctcccctccc agtgtcaccg gggctgcttg gctctgcccc   2520
cttcgccgcc gcttgctccc tgctttcgtc cctccctctc ttgctcgctc cctcccttcg   2580
cctcctcctc cccattcccc cccacccgcg taggccgcat tctgggagtt gtagtccggt   2640
ggagcggggg ttggcgccgc ccgcggaccc agccggactc cacttcccgt cgagccctgc   2700
gaccggcacc cactccacca ggcttcgctc gcacacagac acacacacac accgctctcc   2760
ccctcactct ttcgctcgcc gcggctgctg ccagtgtgtg gctctgtctc tcctccgctt   2820
tgctgagccc tcccttcttc ctctcagttc ctagagtccg accgccgccg ccgccgagag   2880
agaggagaag gaggtcggtg gcgataaggg gcggaggggg gcatcagatc ggggcagtat   2940
taggcgggtg gcggttaaga gggagtaaga gggagcccgg gtggcggcct gagcctcccc   3000
gcggagccga cccgggaaca ggtgcgtctt ttttctctct cccccaatcc ctccacccct   3060
tttgactccc cggcttttt c gtatcccccc acccgcttct ttctatctta agcctttctc   3120
caaccctgtt ccttcttttc cctgcggccg ctcggcttgc ccccgggggg cgccgtcctc   3180
ttcgtgtccc cggacgtagc gctccctgga gctgggtatg tcttcgcccc tcccttcggg   3240
acagctccct tccacttccc accttcgtac cccatcccct gacttgccct acccccttct   3300
cgacccccctt ctctcttagc caggtgagac tcgttcgcca cgatccaaga gagtcttctt   3360
cccggctggg cggggggtctc catggaaacg ggggtcggtt gatcctgggg gggaaaccat   3420
aggaattacc ccactcctcg gaaagggagg tggaggctat ggtcttgtta actacctgac   3480
tccaaccccc gatccaagga tccgacgatc cgaaggagg ctggctagca gggcagggcg   3540
agaaaaggct tttttttggg gggggggggt gtccgtgatg aagtgttgaa gagaccggga   3600
gaaaatgccc tccaacctca gaggggaggt gcgacgggtg ctcttcaggg ctgctttctt   3660
cccggcgctg gggtgcggga atcgtagggt aaggggtacc cctaggtggc ggcggggcct   3720
gggttcggga gtgggagtgc tgtgatgggg gcagggcaa ttatccgagt ccctggaaaa   3780
aaggcggggg atgacttcgg agcgccctgg ctccgctgcc ctcgctctag gggcggggc   3840
cgccgggccg ggcgcggcgg ggaggggct taaattgaag gaagatgaga tcggggcaa   3900
ttcatactag caccggcaag ccagagggga gatccggcgt gcaagccctc cacccgcttc   3960
gcgccaggcc tggaggcaag gggtcggcga gcgaagccga gggctggaag gagggaggct   4020
ccggttacgg ggccgggttt cgggatcagg gcaatcccc cggcccttgg agaaggaggg   4080
agagggatgg ccgcgaaccc cagggctccc ccaccccggg tcctaagggg cgtgagggac   4140
ggacagcagg cccagcggag ctggattcga gcggatcgcg gccg             4184
```

<210> SEQ ID NO 322
<211> LENGTH: 514
<212> TYPE: DNA
<213> ORGANISM: Homo sapiens

<400> SEQUENCE: 322

```
cgagttggtg cgggacgtgc cgcacggcgt gcttctgctg acaccttcc  acaggcttgc    60 ctcccgcgag gtgcggctgc cccgcggctt cctcggcttc ccgtcccgcg tgctttcctg   120
gagtccctcc ttccggaggc cctcctgcct ccacgtgtgc ccttctccat gtccagcatt   180
cgggcgcctc ttgtctttct tctgttccct ggcttcggcg tccccgggag tgtgactccc   240 gcagcgggt gcagctttcc tctgggatga gtgaccggag ggaacccgcc ttcccgggca   300
cgtcgccagc ctcttcctct tcttccctag gctatcaagc ggacttatga caagaaggcg   360
gtggatctct acatgctgtt caatagcgag ctggccctgg tgaaccgtga acggaacaag   420
aaatggccag acctggagcc ctacgtggcc cagtattccg aaaggcgcg ctgggtgcac    480 atcctccggc gtcgcatcga cagagtcatg accg                               514
```

<210> SEQ ID NO 323
<211> LENGTH: 2097
<212> TYPE: DNA
<213> ORGANISM: Homo sapiens

<400> SEQUENCE: 323

```
cgaggaggct gacccggagc tggagcccgc gtcgggggga gagcaggagc cgcggcccca    60
gcaagcccag gtaggcggga gtgggcccgtg gctgctctca acatccggag cggactccgg   120
gcggggagcg ctcctgccca gggctgcgag ccgcccgcga cccagggcgc tcgggggcagg   180 ggtgggaaa aagggggcgc cccgtcactt gccccctctg cagaccaagg ccgcgtccca    240
gatcctggag aatggggagg aggccccggg gcccgacccc tctctcgacc gcatgctcag   300
cagcagctcc tcggtgtcca gccttaactc ctccacggtg aggcgggagg aggggaccc   360 gggcggccgg ggggtggacc cgttccgatg cgtagcccct gcctgcccct ccctcgccgc   420
gggacccacc gctgcagccc ccagcctgc cacctatgac ccgggtctga gcctccgcg    480 ctgcccgcgg ccccgacgtg agcctgcga gcggccctga ctcccaccca ctcccgtccg    540
cagctgagcg gcagccagat gagcctgtca ggcgacgcgg aggcggtgca ggtccgcggc    600
tccgtgcact tcgcgctgca ctacgagccg ggcgccgccg agctgcgcgt gcacgtgatc    660
cagtgccagg gcctggccgc cgcccggcgc cgccgctcgg accgtgagt gccccgccgg    720 ccaagcgggg cgcggctgtc acagcccagc ccaccattca cagggtctcg gcctcctcgt    780
cctcatcttc aaaatgggaa caacagcgtt attgggaggc gtgcgattaa gcagacaat    840 ccctgtaaag cgcttagcac gaggcctggc acgtgttcgg gatggtggct gggggagccc    900
acaggcaggg gagaaggctc tgggagggcc cctcctcacc tcgggttctc acctccccag   960
ctacgtcaaa agctacctcc tcccggataa gcagagcaag cgcaagacgg cggtgaagaa  1020
acggaatctg aatccggttt tcaacgagac tctccgggtg aggctgtgac cacgatgcgg  1080
ttccccgtta atgaactgga cgccccccttc ctgcggggct aggtggcaag ggcagccagt  1140
aacgtcattg cccggaggat cggcggaggg ggcccattaa ctcgttatcc agtgttgtca  1200
gcctcgtggt gggcgtggtg atagtgcagg tccccattaa tgcccttagg ggctccccag  1260
aattccatca tggtaggaac gcggtaggac ctgcctcagc caactcgcgc agcatctacg  1320
cgggccacca gcagtgctcc actaaagctc acctcctgtc ctcagtactc cgtcccgcag  1380
gccgagcttc agggccgcgt gctgagcctg tctgtgtggc accgcaaag cctgggtcgc  1440 aacatctttc tggcgaagt tgaagtgccc ctggacacgt gggactgggg ctctgagccc  1500
acctggctcc cctgcagcc ccgggtgagg cagccaggcc gcgtggggag acctgcggcc  1560
cgggtctcct gcatttaccc caccaggctc tcccgcagcc ccctcacacc ccgccttcga  1620
```

```
cagaacctcc cctcaacctc ttaacctcat ggccccaggc gaagcccggc cggccacggc   1680
cccttccccg agggcgctag gaccccctagg ttctgcccct gcaggcccct ccgtctcttc   1740
tagccgcacc ccatccgggt ctgcagaccc caccctcctg aggccccttt ccattagccc   1800
ctgctccacg ataagcccgc ctctcgcagg tcccaccctc tcccgacgac cttccgagcc   1860
gcgggttact cgccctgtcc ctcaagtacg tccccgccgg ctccgagggt gagtgacagc   1920
cggagaggcc aagctggaca cgccctgaaa agcgggagac tccagtcccc gggtttgggg   1980
gcggtggact ccatccgtgt gcgggcctga ccgagcctc tccgcaggcg caggactgcc   2040
cccgagcggg gagctgcact tctgggtgaa ggaggctcgg gacctcctgc cgctgcg      2097
```

<210> SEQ ID NO 324
<211> LENGTH: 2334
<212> TYPE: DNA
<213> ORGANISM: Homo sapiens

<400> SEQUENCE: 324

```
cgccccccttc cattccccgc ccgcttccat cacttggtgt cgcccaagcc tgtggtcgcc    60
cctagcaacg ccctccctca cttcgcagtc ggtttcccct ttcatcatcg ccccccacg    120 tcccgctctt ggtctctccc gatcccgcgt ggatccggtg cttgggcgcc cccgccaacg   180 accccgcgc acctcagcgt tggtgtcgcc cggttccccc cgcgcacgcg caccgtggta    240
tttcccgcca cgctcctaca ccgccccccc caatacctgg ttggtcacgt cccccgggag    300
gccccggatc agtatcttgc ggcggttacg gaactggcgc tcggtgtgtt ccaggcgttt    360
ccggatctct tctggatcta gaggcggcag ctcttcttcc ggcgcccggc gctccgcggc    420
atcgccggct tcgacttcgg ccccagactt agggctcagc gggggccggt gagtaacgga    480
cacgtccgcc gccatcttgg gaaacccggc gccttctggg accagcgagc cggggcggag    540
cggcatagag cggcaacgag ggcgcgcccg tcgattggct gggagaaacc ccacctcctt    600
cccgcccccc ttgccccgtt ggctaagccc cagcccacct ctcaagagtt caagctgcgt    660
ctgcgcgcca caggccccgc ccccttccgt cgcagcgacg ctactcagtg gatgtgcacc    720
tgggtgggag agacttgcag cgcgggtgga atcaaaccac agattaggga gtttgaaggc    780
tttattggtg cggaatctga gggcacagcc aagccccgc caactttgat cccggatccc    840
agcgtcactc agctctggac ggttcttccc ccattgcttc tgtcggctgc atagacgtga   900
ggggcagata ggtgctctcc tccctaacat ggtaactgcc gctccgttgg tgctccctga   960
agacgtacat taaggccagt acgatagtca ccacgcccag ggtcagtaac accgccacga   1020
agacggggac aaagtgggag ctcccagctg tgcagagaaa gcgctaagtc aatatgcgtc   1080
ccttctgtct ccaaccccc cgcccccggg cttaccggtc cagacccgca gcccgtgtt    1140 agctcaccct caatgtccat caccacgacc agggtgtatt tgcctcgtga gctggacgct   1200
tggcactgat aagtaccatt atgtgttacg ttgacgaaga acgggatccc caccggcacc   1260
tcccggctgg agccttcctt caaacaccgc agctcggggt acgggttgcc cctggcttgg   1320
cactgcagga cgtgtctcgt tttatctttc catttcaagt gctgggggca tgtggctcgg   1380
tcaattttgg gaccatctgt ggaaccacca tgtgtgatca gacacccaac acacccgagg   1440
cacagtggtg cagaggagcg tctaatcttt ccagggcagg ggtggaggga ttaaaggtca   1500
gggtgaccga ctcacacagg actcgcagct ggacgctact gttcctgtgc aagaactcgc   1560
cgtccacctc gagagtggca ctgcagaaga agctgcgtcc gtcgtcactc tcggtagcat   1620
```

| | |
|---|---|
| ttagctgaag ttgagctggc tgccccgggg ccgcggccgg aactccgtcc agcgtgacct | 1680 |
| ggactcgagc cccagccatg caactcacgg tcactgtgga cccctcatgg gcggtgggct | 1740 |
| cgctgaggtt cacaatgggt cctaggaagc ctaaaggcgg ggcattgccc aggagcttaa | 1800 |
| tgaacaggac cttcctgtgg gtcaagccgc tccctccgcc ctccccttt ctctcgggat | 1860 |
| atccgggcca cgctttcggc cgttcaagcc tcgcctctt tccgcgctgt gtccagcttc | 1920 |
| gggcactcag gcccaaccca cgttgcaact gctattgggg caagccaggc ccacccttt | 1980 |
| cggctagtct ccgcccctc tgccacgccc ccagactgct gaggccgcgc ccccttccca | 2040 |
| cgcctcctct tactaaagac cgtcaagttc tcccggcct cccgtctctc gcccctagg | 2100 |
| gtcacgttgc agacgatctc ccgggcaccc tcctgatccg cgcgcgccgt ggctgtggct | 2160 |
| gtggccgtta gcgtgtcccc gtggttcatg actgtcgcat tcagcatctg gtcccccagc | 2220 |
| gccaggtaga cctgggcctc tgaggctgga aaaagcccgt ctagggtgca gtccaccggc | 2280 |
| cacgacgttt ccacctccaa gaaccggggg gccacgaggc gcggggggt cacg | 2334 |

<210> SEQ ID NO 325
<211> LENGTH: 1481
<212> TYPE: DNA
<213> ORGANISM: Homo sapiens
<400> SEQUENCE: 325

| | |
|---|---|
| cgcggcgggc cttccccatt ggccagccaa acacaaccga ctgcggcagc caataggagc | 60 |
| cgctctcctg aacattcaga ggatgggtgc gcgtggtgtg ataaggggat gttggcgcct | 120 |
| ggtacgcgcc cccctacatc tggcaagtct gtaacagaaa cagttacacc ccctacacac | 180 |
| gcacacgcgt gcccgctggc tccctcctct cagctgtaca ggccccggac aacccactgc | 240 |
| gtgtcttggc agcggcctcc caggctgcct ggggcccgcg agtgcacctg ctcactcatt | 300 |
| aagacagagc atccctttat cccaaggcgc gggtcgggta gagggtgggg gtagagggga | 360 |
| cggggtagcg gggaccggga aggcgcggct cagctgcccg ctgctcccga ggtgaaagag | 420 |
| gtgcctccgc ccccacccca tccccgcaga gttgcgttgc tccagggagg ccgaagtgat | 480 |
| ccagtgatgt cttaaggtgc agctctttgt cctcccagc tgtgctccct gcccgctgac | 540 |
| cccgtgcgct cgagccagtg ggggtgggga gcccgaaacc tataacataa acgggggcaa | 600 |
| ggagaaagaa gtctatcccg gggtggcgtg tgccgctgtc cccacccgt ctctttcctc | 660 |
| ctgaggcttc ttccctcggg tccgtcccgg gaatgcaggc aggggagggt gtgggccgag | 720 |
| gcgcggcggc ggctggagca gcgcggtagg gtccttcgcc agagcatccg gtccgagggc | 780 |
| gcacacaggc agaaggctcg cggctcgtcc actctcctcc ctctctcctc ctctccctgg | 840 |
| cttttgtgtt ggtgcctccg agctgcaagg agggtgcgct ggaggaggag gagggggcc | 900 |
| cggagtgaga ggcaccccct tcacgcgcgc gcgcgcacac ggtgccggcg cacgcacaca | 960 |
| cgggcggaca cacacacacg cgcgcacaca cacgcgcaca gagctcgctc gcctcgagcg | 1020 |
| cacgaacgtg gacgttctct ttgtgtggag ccctcaaggg gggttgggc cccggttcgg | 1080 |
| tccgggggag atggcgcagc ccatcctggg ccatgggagc ctgcagcccg cctcggccgc | 1140 |
| tggcctggcg tccctggagc tcgactcgtc gctggaccag tacgtgcaga ttcgcatctt | 1200 |
| caaaataatc gtgattgggg actccaacgt gggcaagacc tgcctgacct tccgcttctg | 1260 |
| cgggggtacc ttcccagaca agactgaagc caccatcggc gtggacttca gggagaagac | 1320 |
| cgtggaaatc gagggcgaga agatcaaggt gatccagggg gtcaggtcca ggaagggtgg | 1380 |
| gacccgggag gggacctcgc ccgaggcata gctctagcgg ttgtcgtcgt ccagcgtcca | 1440 |

```
gcgcgtggcg gtttcgcctc ttgctgagcc gaggaccctc g                  1481
```

<210> SEQ ID NO 326
<211> LENGTH: 1703
<212> TYPE: DNA
<213> ORGANISM: Homo sapiens

<400> SEQUENCE: 326

```
cgcacgcccc tcctgtctcg cgtccgtccc tccgtgcagc cggggcagga ccctgcaggg    60
gccttgcggg ccggaggtgc cggcttcctc ctccgtcccg tcccccccgc ggtgactcta   120
ttcaaatctc cccccttccc gctgcccac cggactcagg gctgggtc gtagcccggc    180
gggcagcggt gttcaccttc cgcataaacc tgggcttcct cgcggggcag ccccgggcc   240
ctgtgctggg tcgcagcctc gggcggttcc ctcggggcgg gacgtgtccc cgtccgtcct   300
cgcccgtccc cgccgccccc gggtcccggc ccgccccgtc ctcgcagccg caggtccgct   360
gcggcgcccg cccccctctc ccctcccccgg gccttgccct gctcgtcgct ccgcccctg   420
cccggccct gccccggcccc gcccgcgcc cgcccctgc ccgcgcccgc ccgcccccct   480
gcccggcccc tgcccggccc ctgcccgccc cctgcccggc ctcccagcgg cggcggctgc   540
agcgcggcgg tccgagcggg tgcaccgcgg cggaggaggc agcatcccgc ggcgctgacg   600
gtcctgggga gagcatggcg ccgaggtgag gccggggctg cgggcagggg ttggggacg   660
ccaagatgcg gctgcggggg tcgcgggggt cgcgggcctc ggccgggtcc tgcgggggtc   720
gcggggtcc tgcggggtct gaccgtgcc tgtcccgcgc aggtgcccct ggccatggcc   780
gcggcggcgg cgcctcctgg acgtgctcgc gcccctggtc ctgctgctcg ggtccgcgc   840
ggcctccgcg gagccaggta agacccgggc gggacgggaa ggttcgcgcc ggtgcccgcc   900
ggcctcgccg cctggctgg ggtccccgcc cggctccctc accccgccc cggccgctct    960
gggttcagcc ccggccctgc ccacgcgcgc aggaggcgcc ggagccggac ggagcggggc   1020
ggggtggccg gagtcccgcc cattcattct ccccgcgggg tccgggccgg gagggtgcg   1080
cggtgcgagc ggccggagtc cccgcgcggg gaccgaacct ccgcggccgg cggggtcgtc   1140
ggtgccggga gggctcgggg cggggccgcg gggtctcggg agacgcggcc tctgtcgccg   1200
tcacggcctc gtccccgcag cgccgggtcc cgggactgac cgcgggcgga aggcggcga   1260
gcgcggggcg tcgtctccgc gtttccaacc tgttgaggct cctcgccgcg ggccgggcct   1320
tgtgcgcctc tgtccccgcc gccctcaggc ctctgtcccc gcgcccgccg tggtgtcggg   1380
ttgcgcggtc cccttgatg ccaaccgagc gccgcgcggt ccgagaacaa tgcccagaag   1440
ccgctgcccc gccggcctcg ccgcttcccg tgcgcggcaa acggtgcgcg ggccccgtgg   1500
ggaccttcct gcctccaacc ccgggaccca gttccccacc acctgctaac cggggcctcc   1560
tgcctccagc cagcccagca gaggcccggg ggaggcggcg gggacgcgga ccccagggga   1620
gccccgccca aagggcctgg gtgccttgtc gcgggtggaa tcccaccccgg gggtccacgc   1680
agccagcgcc tgcctccgac tcg                                          1703
```

<210> SEQ ID NO 327
<211> LENGTH: 699
<212> TYPE: DNA
<213> ORGANISM: Homo sapiens

<400> SEQUENCE: 327

```
cgaggacagg gcccggcccc acccggggc gagtacgagt ttggaagcag tgagggcgca    60
```

```
gagtggggct ccatctgggg agaggcctct ctctgtcacc cggccccgtg cggcagttca    120
gggtcccagc atctcccctg cactggggag cggcagccgt gcccggggggg cgcccgtggt    180
gggcgggtgc aagagagaag ggcgtcgggt gtgcaagcac caccggcctc ccattaacag    240
cctgcccggg ctccgcccac aggagccact gtccacgtaa cctgcgtctc tttcttccaa    300
ggaaaagaga agccagccat ggccaggacc agcagcaggg cccctgctc acccacctcg    360
gtgtcggatg tggactcgga cgcactgtca cggggaaact tcgaggtggg gtttcggcct    420
cagaggtccg taaaagccga gagagcgcag cagcctgagg ctggcgagga cagacggcca    480
gctggcgggg cctcagacgt ggaggcagtg acccgactgg ccaggtccaa aggggtcggc    540
ccagccttgt cccccggccc agccggattc cagagctgca gccccggctg gtgcagcgcc    600
ttctacgagg ccgactgctt cggggccgac gtccacaact acgtgaagga cctggggcgg    660
cagcaggcgg acgggccct gcccgacgcc cagagcccg                            699

<210> SEQ ID NO 328
<211> LENGTH: 1442
<212> TYPE: DNA
<213> ORGANISM: Homo sapiens

<400> SEQUENCE: 328
cgaatgcagc atccctgcgc tcggcgcccct gctattggcc agagatgatc tcaccgcctc    60
ccggcctgcg cgcgcctgat tggccggtgc ggggatgctg cgctccgccg ccggcggggc   120
agtccttcag gcgggctccg cgagcgtgtg tgagcctggg ggagcgaaga gccgacgcgc   180
ctggcatctc ccagggggct caggggggcag gagcgcggag accccggac agggtcttaa    240
ccccttcccg ccagcccgag cccagcatcc cctccagctc cctcggcgt cccaaccccca    300
agcaaagcca tccccaaagg atgctccgca gagaggcggg gtccgggtcc tcccctccac    360
cccccttccgt ttaaccctct caccgccgcg gcgccgtcct gcactgcccg ccagctggg    420
ctgggagaga cccgcgcccc aggcatgtcc aagcccacct agagggcggg agggtggcgg    480
gcgctctggc cccaaccctg gcatccgaag catcccccgc gtttcctgct cctcactcag    540
tcttcagatc ccagtccggc gccccccgta caatggggag ccagggtgcc caggtcagcc    600
gcaagggcca gcgtaccagg cggaggaccg gcaggacgcc ggagacccca tctcccagtc    660
cccccctgccc cagctctctc cctcctgcgg aggaggcaga aacggaccgg catctaccgc    720
agcccagagt cccaggagtg gccgccgaac cctcacccccg cggagcgcct gggcgcccag    780
aggtgaggct ggggtgaccc cgccccctcc ccgggtcggc cgggcccagc ccagcccgac    840
cctgccgggc gccgctgagc tgcagctccc cggctggctc tagggccccg ggcggagcgg    900
ccggggggtcc cagcccggcg cgcgtggcgg gggccgagcc gcccctcac ctgcacctgc    960
acgaaggagc cgcggtagaa gcagcaggcg gcggccgaca gggcactcca caggctgcac   1020
cgctcggtca tggtggggcc aggctgccgg ggcgggacg tgtgggggg gcggtggccg   1080
gcggggcagg ggcgcaggga ccaaccggct aggcaccggc tgcgcgtgcc tctcagcggc   1140
gcgattacct catcgccttg tcggggggagg agcggggagg cggggcgggg agacccccacc   1200
ctccagccgg ccaggggagg ggagggggcc attgttcctc cctccgcccg ccccccgctc   1260
ccagcccctc gcccccgcc ctccagttcc gcgcgctcgg gctgcctgga gctgcgggcg   1320
cggagcggag gacctgccaa ggagggtatt accgggggca gcgggatcgg gtggggaccc   1380
atgggccagc gaggggaggt tctgcctccc ccactcgccg cacctctaac agaccgggag   1440
cg                                                                 1442
```

```
<210> SEQ ID NO 329
<211> LENGTH: 690
<212> TYPE: DNA
<213> ORGANISM: Homo sapiens

<400> SEQUENCE: 329
cgcctgcgcg agtcaggacg agcgcttgcc ccagatcttg acgtttcagg cggcccctcc      60
taatccggaa cacgactcac attccgttgg tcttgccttg acagacgtga ccctgaccca     120
ataagggtgg aaggctgagt cccgcagagc caataacgag agtccgagag gcgacggagg     180
cggactctgt gaggaaacaa gaagagaggc ccaagatgga gacggcggcg gctgtagcgg     240
cgtgacaggt gagggcgggc ccgggagggc tcggtttctg gagcggctgc cgggcacggg     300
cagggagccc ggaccgaaag ctcagctcca ggatggctgc gcttgggccc cggcgttccc     360
tgcccggaac cggaggagtg gtttgacccg gggcgagacc atcgtcgaca gcggggtgg      420 ggtgggtaac aggaataggc gggcaaggct gcgggtgatg gtttcgcccg ctgctagtgg     480
tggtgcgcct gcgcagagcc ggaagccctt tggtaggcgg gacccgaccg agtggtgccg     540
ggattccgtc ttaaccccccg ctaaggtgtc caatgacctt tccttaccaa ctgcggggag    600
tgtgtggaaa cgcggttcac tccccggttt ccttattctg gatcagtgtc tgaccgcccc    660
cgccgggaga atgtcaggat tctcgcctct                                     690
```